(12) United States Patent
Bandarage et al.

(10) Patent No.: US 12,331,057 B2
(45) Date of Patent: *Jun. 17, 2025

(54) MODULATORS OF ALPHA-1 ANTITRYPSIN

(71) Applicant: Vertex Pharmaceuticals Incorporated, Boston, MA (US)

(72) Inventors: Upul Keerthi Bandarage, Lexington, MA (US); Cavan McKeon Bligh, Melrose, MA (US); Diane Boucher, South Hamilton, MA (US); Michael John Boyd, Sharon, MA (US); Michael Aaron Brodney, Newton, MA (US); Michael Philip Clark, Concord, MA (US); Veronique Damagnez, Boston, MA (US); Lev Tyler Dewey Fanning, San Marcos, CA (US); Robert Francis Fimognari, Brookline, MA (US); Gabrielle Simone Fleming, Boston, MA (US); Kevin James Gagnon, Burlington, MA (US); Pedro Manuel Garcia Barrantes, Melrose, MA (US); Robert Daniel Giacometti, Malden, MA (US); Simon Giroux, Cambridge, MA (US); Ronald Lee Grey, Jr., Mansfield, MA (US); Samantha Guido, Quincy, MA (US); Amy Beth Hall, Wellesley Hills, MA (US); Sarah Carol Hood, Worcester, MA (US); Dennis James Hurley, San Marcos, CA (US); Mac Arthur Johnson, Jr., Derry, NH (US); Peter Jones, Sharon, MA (US); Sarathy Kesavan, Quincy, MA (US); Mei-Hsiu Lai, Waltham, MA (US); Siying Liu, Malden, MA (US); Adam Looker, Newtonville, MA (US); Brad Maxwell, Holliston, MA (US); John Patrick Maxwell, Hingham, MA (US); Ales Medek, Winchester, MA (US); Philippe Marcel Nuhant, Dorchester, MA (US); Kirk Alan Overhoff, Lynn, MA (US); Setu Roday, Arlington, MA (US); Stefanie Roeper, Medford, MA (US); Steven M. Ronkin, Watertown, MA (US); Rupa Sawant, Wayland, MA (US); Yi Shi, Natick, MA (US); Muna Shrestha, Belmont, MA (US); Marisa Sposato, Cambridge, MA (US); Kathy Stavropoulos, Quincy, MA (US); Rebecca Jane Swett, Somerville, MA (US); Timothy Lewis Tapley, Cardiff, CA (US); Qing Tang, Boxborough, MA (US); Stephen Thomson, Del Mar, CA (US); Jinwang Xu, Framingham, MA (US); Mariam Zaky, Boston, MA (US); Kevin Michael Cottrell, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,690

(22) Filed: Oct. 16, 2023

(65) Prior Publication Data
US 2024/0336614 A1    Oct. 10, 2024

Related U.S. Application Data

(63) Continuation of application No. 15/931,256, filed on May 13, 2020, now Pat. No. 11,884,672.
(Continued)

(51) Int. Cl.
*C07D 487/04* (2006.01)
*A61K 9/16* (2006.01)
(Continued)

(52) U.S. Cl.
CPC .......... *C07D 487/04* (2013.01); *A61K 9/1635* (2013.01); *A61K 9/1652* (2013.01);
(Continued)

(58) Field of Classification Search
CPC .. C07D 487/04; C07D 491/18; C07D 513/04; C07D 519/00; A61K 9/1635;
(Continued)

(56) References Cited

U.S. PATENT DOCUMENTS

| 4,198,415 A | 4/1980 | Kornfeld et al. |
| 4,647,667 A | 3/1987 | Schaus et al. |

(Continued)

FOREIGN PATENT DOCUMENTS

| CN | 1704404 A | 7/2001 |
| CN | 107698505 A | 2/2018 |

(Continued)

OTHER PUBLICATIONS

Akhapkina, V.I. et al. (2012) "Fundamental bases of modulatory concept and classification of modulatory drugs", Russian Medical Journal, 19: 933-951.
(Continued)

*Primary Examiner* — Yih-Horng Shiao
(74) *Attorney, Agent, or Firm* — Finnegan, Henderson, Farabow, Garrett & Dunner, LLP

(57) ABSTRACT

The disclosure provides compounds useful for treating alpha-1 antitrypsin deficiency (AATD), according to formula (I):
(Continued)

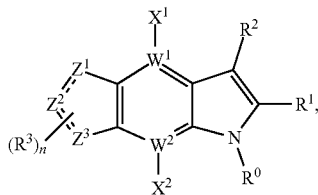

(I)

tautomers thereof, pharmaceutically acceptable salts of the compounds, pharmaceutically acceptable salts of the tautomers, deuterated derivatives of the compounds, deuterated derivatives of the tautomers, and deuterated derivatives of the salts, solid forms of those compounds and processes for making those compounds.

11 Claims, 95 Drawing Sheets

Related U.S. Application Data

(60) Provisional application No. 63/004,813, filed on Apr. 3, 2020, provisional application No. 62/847,562, filed on May 14, 2019.

(51) Int. Cl.
```
A61K 31/4162    (2006.01)
C07D 491/18     (2006.01)
C07D 513/04     (2006.01)
C07D 519/00     (2006.01)
C07F 9/6561     (2006.01)
C07H 15/26      (2006.01)
```
(52) U.S. Cl.
CPC ........ *A61K 31/4162* (2013.01); *C07D 491/18* (2013.01); *C07D 513/04* (2013.01); *C07D 519/00* (2013.01); *C07F 9/6561* (2013.01); *C07H 15/26* (2013.01); *C07B 2200/13* (2013.01)

(58) Field of Classification Search
CPC . A61K 9/1652; A61K 31/4162; C07F 9/6561; C07H 15/26; C07B 2200/13
USPC ........................................................ 514/25
See application file for complete search history.

(56) References Cited

U.S. PATENT DOCUMENTS

| | | | |
|---|---|---|---|
| 4,778,894 | A | 10/1988 | Schaus et al. |
| 5,216,001 | A | 6/1993 | Perregaard et al. |
| 11,623,924 | B2 | 4/2023 | Bandarage et al. |
| 11,884,672 | B2 * | 1/2024 | Bandarage ........... A61K 9/1652 |
| 2001/0051620 | A1 | 12/2001 | Berger et al. |
| 2003/0212085 | A1 | 1/2003 | McCall et al. |
| 2003/0097000 | A1 | 5/2003 | Bovy et al. |
| 2003/0165712 | A1 | 9/2003 | Lin et al. |
| 2004/0077865 | A1 | 4/2004 | Zhao et al. |
| 2005/0009754 | A1 | 1/2005 | Pan et al. |
| 2005/0043381 | A1 | 2/2005 | Johnson et al. |
| 2007/0232682 | A1 | 10/2007 | Beard et al. |
| 2008/0021056 | A1 | 1/2008 | Konradi et al. |
| 2010/0076018 | A1 | 3/2010 | Liu et al. |
| 2011/0118221 | A1 | 5/2011 | Nussbaum et al. |
| 2013/0167932 | A1 | 7/2013 | Maeda et al. |
| 2013/0319530 | A1 | 12/2013 | Maeda et al. |
| 2014/0341899 | A1 | 11/2014 | Dinarello et al. |
| 2016/0083363 | A1 | 3/2016 | Hamm et al. |
| 2016/0145271 | A1 | 5/2016 | Vakalopoulos et al. |
| 2018/0251460 | A1 | 9/2018 | Aktoudianakis et al. |
| 2023/0157999 | A1 | 5/2023 | Clark et al. |
| 2023/0159502 | A1 | 5/2023 | Giroux et al. |
| 2023/0159504 | A1 | 5/2023 | Giroux et al. |
| 2023/0159521 | A1 | 5/2023 | Giroux et al. |
| 2023/0159580 | A1 | 5/2023 | Giroux et al. |
| 2023/0265080 | A1 | 8/2023 | Bandarage et al. |
| 2023/0279010 | A1 | 9/2023 | Bligh et al. |
| 2023/0339915 | A1 | 10/2023 | Giroux et al. |
| 2024/0002386 | A1 | 1/2024 | Shi et al. |
| 2024/0012010 | A1 | 1/2024 | Penney et al. |
| 2024/0158404 | A1 | 5/2024 | Grey, Jr. et al. |

FOREIGN PATENT DOCUMENTS

| | | |
|---|---|---|
| CN | 109414596 A | 3/2019 |
| CN | 110776459 A | 2/2020 |
| EP | 0 465 398 A2 | 1/1992 |
| EP | 1 396 488 A1 | 3/2004 |
| EP | 3 699 179 A1 | 8/2020 |
| ES | 323287 A1 | 3/1967 |
| JP | 4856667 A | 8/1973 |
| JP | 2000-072751 A | 3/2000 |
| JP | 2000-281654 A | 10/2000 |
| JP | 5107589 B2 | 12/2012 |
| RU | 2617405 C2 | 4/2017 |
| SG | 11201810138 | 12/2017 |
| WO | WO 1996/037467 A1 | 11/1996 |
| WO | WO 2000/075114 A1 | 12/2000 |
| WO | WO 2001/044197 A2 | 6/2001 |
| WO | WO 2002/008224 A1 | 1/2002 |
| WO | WO 2002/094790 A1 | 11/2002 |
| WO | WO 2003/099824 A1 | 12/2003 |
| WO | WO 2004/108120 A1 | 12/2004 |
| WO | WO 2006/019831 A1 | 2/2006 |
| WO | WO 2006/093823 A1 | 9/2006 |
| WO | WO 2009/127686 A1 | 10/2009 |
| WO | WO 2011/056222 A1 | 5/2011 |
| WO | WO 2011/110852 A1 | 9/2011 |
| WO | WO 2012/016695 A2 | 2/2012 |
| WO | WO 2012/038820 A2 | 3/2012 |
| WO | WO 2016/154051 A1 | 9/2016 |
| WO | WO 2017/035418 A1 | 3/2017 |
| WO | WO 2017/117304 A1 | 7/2017 |
| WO | WO 2017/197240 A1 | 11/2017 |
| WO | WO 2019/076336 A1 | 4/2019 |
| WO | WO 2019/089667 A1 | 5/2019 |
| WO | WO 2019/116302 A1 | 6/2019 |
| WO | WO 2019/149522 A1 | 8/2019 |
| WO | WO 2019/243841 A1 | 12/2019 |
| WO | WO 2020/033288 A1 | 2/2020 |
| WO | WO 2020/081257 A1 | 4/2020 |
| WO | WO 2020/247160 A1 | 12/2020 |
| WO | WO 2021/067584 A1 | 4/2021 |
| WO | WO 2021/155087 A1 | 8/2021 |
| WO | WO 2021/203007 A1 | 10/2021 |
| WO | WO 2021/203010 A1 | 10/2021 |
| WO | WO 2021/203014 A1 | 10/2021 |
| WO | WO 2021/203023 A1 | 10/2021 |
| WO | WO 2021/203025 A1 | 10/2021 |
| WO | WO 2021/203028 A1 | 10/2021 |
| WO | WO 2022/026372 A2 | 2/2022 |
| WO | WO 2022/104353 A1 | 5/2022 |
| WO | WO 2022/109553 A2 | 5/2022 |
| WO | WO 2024/054624 A1 | 3/2024 |

OTHER PUBLICATIONS

Aldonyte, R. et al. (2004) "Analysis of systemic biomarkers in COPD patients", Journal of Chronic Obstructive Pulmonarydisease, 1(2):155-164.

American Thoracic Society & European Respiratory Society (2003) "American Thoracic Society/European Respiratory Society Statement: Standards for the Diagnosis and Management of Individuals with Alpha-1 Antitrypsin Deficiency," *Am J Respir Crit Care Med.*, 168:818-900.

(56) References Cited

OTHER PUBLICATIONS

Balle, T. et al. (2003) "Synthesis and Structure-Affinity Relationship Investigations of 5-Aminomethyl and 5-Carbamoyl Analogues of the Antipsychotic Sertindole. A New Class of Selective $\alpha_1$ Adrenoceptor Antagonists," *Bioorg. Med. Chem.*, 11:1065-1078.

Belikov, V.G. (2007) "Pharmaceutical Chemistry", textbook, Moscow, MEDpress-inform, pp. 27-29.

Bergin, D.A. et al. (2014) "The circulating proteinase inhibitor alpha-1 antitrypsin regulates neutrophil degranulation and autoimmunity," *Sci Transl Med.*, 6(217):217ra1 (70 pages).

Chemical Abstracts Service, CAS Registry No. 1516110-75-0. CA Index Name: Pyrrolo[2,3-f]benzimidazole-7-methanamine, 6-ethyl-3,5-dihydro-2-methyl-6-Ethyl-3,5-dihydro-2-methylpyrrolo[2,3-f]benzimidazole-7-methanamine Date: Jan. 10, 2014.

Chemical Abstracts Service, CAS Registry No. 2103889-64-9. CA Index Name: Pyrrolo[2,3-f]benzimidazole-7-carbonitrile, 3,5-dihydro-2,5,6-trimethyl Date: Jul. 27, 2017.

Chemical Abstracts Service, CAS Registry No. RN 2106364-27-4. Index Name: Pyrrolo[2,3-f]benzimidazole-7-carboxylic acid, 3,5-dihydro-2,5,6-trimethyl-, ethyl ester Date: Aug. 1, 2017.

Chou, T.-C. (2010) "Drug Combination Studies and Their Synergy Quantification Using the Chou-Talalay Method", Cancer Res; 70(2):440-446.

Dafforn, T. R. et al. (1999) "A kinetic mechanism for the polymerization of alpha1-antitrypsin", The Journal of Biological Chemistry, 274 (4): 9548-9555.

Donawade, D.S. et al. (2007) "Synthesis and antimicrobial activity of novel linearly fused 5-substituted-7-acetyl-2,6-dimethyloxazolo[4,5-f] indoles," *Indian Journal of Chemistry*, 46B, pp. 690-693.

Eggenschwiler, R. et al. (2013) "Sustained Knockdown of a Disease-Causing Gene in Patient-Specific Induced Pluripotent Stem Cells Using Lentiviral Vector-Based Gene Therapy", Stem Cells Translational Medicine, 2 (9): 641-654.

Ferrarotti, I. et al. (2020) "Quantification of circulating alpha-1-antitrypsin polymers in dried blood spots", Molecular Pathology and Funct. Genomics, 56, p. 326.

Forbes, I.T. et al. (1996) "Synthesis, Biological Activity, and Molecular Modeling Studies of Selective 5-HT*2C/2B* Receptor Antagonists," *J. Med. Chem.*, 39, pp. 4966-4977.

Fregonese, F. & J. Stolk (2008) "Hereditary alpha-1-antitrypsin deficiency and its clinical consequences," *Orphanet J. Rare Dis.*, 3:16 (9 pages).

Fujisawa, T. (1959) "Studies on the Utilisation of Safrole as Medicinal Raw Materials XII. Synthesis of Indole Derivatives" Journal of the Pharmaceutical Society of Japan, 79(6): 778-783.

Gadaginamath, G.S. et al. (2000) "Chemoselective Reaction of 3,6-Diacetylindole Towards Hydroxylamine: Synthesis and Antimicrobial Activity of Novel Isoxazolo[4,5-f]indole Derivatives," *Rev. Roum. Chim.*, 45(10):929-933.

Geraghty, P. et al. (2014), "$\alpha_1$-Antitrypsin Activates Protein Phosphatase 2A to Counter Lung Inflammatory Responses," *Am J Respir Crit Care Med*, 190(11):1229-1242.

Ghorai, J. et al. (2016) "Cobalt(III)-Catalyzed Intramolecular Cross-Dehydrogenative C—H/X-H Coupling: Efficient Synthesis of Indoles and Benzofurans," *Chem. Eur. J.*, 22:16042-16046.

Ghorai, J. et al. (2018) "Divergent Functionalization of N-Alkyl-2-alkenylanilines: Efficient Synthesis of Substituted Indoles and Quinolines," *Chem. Asian J.*, 13(17):2499-2504.

Gosai, S. et al. (2010) "Automated High-Content Live Animal Drug Screening Using C. elegans Expressing the Aggregation Prone Serpin $\alpha$1-antitrypsin Z," *PLoS One*, 5(11):e15460 (16 pages).

Grant & Hackh's Chemical Dictionary (5th ed. 1987), at p. 148.

Grinev, A.N. et al. (1975), "Synthesis of Aldehydes and Nitriles in the 5-Hydroxyindole Series," *Chem. Heterocycl. Compd.*, 11:1087-1090.

Harkevich, D.A. (2010) Pharmacology/Textbook, 10th edition, pp. 72-82.

He, L. et al. (2014) "Transition-metal-free synthesis of multisubstituted N-arylindoles via reaction of arynes and $\alpha$-amino ketones," *Tetrahedron*, 70:2400-2405.

International Search Report and Written Opinion for International Application No. PCT/US2020/032832, mailed Oct. 27, 2020 (17 pages).

Jafarpour, F. et al. (2019) "A Fast Track to Indoles and Annulated Indoles through ortho- vs ipso-Amination of Aryl Halides," *Org. Lett.*, 21:10143-10148.

Jiang, H. et al. (2016) "Multiple Roles of the Pyrimidyl Group in the Rhodium-Catalyzed Regioselective Synthesis and Functionalization of Indole-3-carboxylic Acid Esters," *Advanced Synthesis & Catalysis*, 358:188-194.

Kamat, A.G. et al. (1994), "Synthesis and Antimicrobial Activity of Furoindole Derivatives," *Indian J. Chem. Sect. B*, 33B(3): 255-259.

Kapetanovic IM. (2008). Computer-aided drug discovery and development (CADDD): in silico-chemico-biological approach. Chem Biol Interact. 30;171(2):165-76.

Kummerer, K. (2010) "Pharmaceuticals in the environment", Annual Review of Environment and Resources, 35:57-75.

Kuznetsova, G.A. (2005) "Methodological instructions", Irkutsk State University, Department of General Physics, pp. 2-3.

Laffranchi, M. et al. (2018) "Heteropolymerization of [alpha]-1-antitrypsin mutants in cell models mimicking heterozygosity", Human Molecular Genetics, 27 (10): 1785-1793.

Maity, S. et al. (2012) "A Visible-Light-Mediated Oxidative C—N Bond Formation/Aromatization Cascade: A New Photocatalytic Preparation of N-Arylindoles," *Angew Chem Int Ed Engl.*, 51(38):9562-9566. NIH Public Access Author Manuscript; available in PMC Sep. 17, 2013 (11 pages).

Mali, R.S. et al. (1994) "Useful Syntheses of Pyrano- and Pyridoindoles," *Organic Preparations and Procedures International: The New Journal for Organic Synthesis*, 26(5):573-577.

Mashkovsky (2001) M.D. Drugs, 14th edition, Moscow, 1:11.

Meti, P. et al. (2017) "Regioselective synthesis of dipyrrolopyrazine (DPP) derivatives via metal free and metal catalyzed amination and investigation of their optical and thermal properties," *RSC Adv.*, 7:18120-18131.

Ogushi, F. et al. (1987) "Z-type $\alpha$1-antitrypsin is less competent than M1-type $\alpha$1-antitrypsin as an inhibitor of neutrophil elastase," *J Clin Invest.*, 80(5):1366-1374.

Piitulainen, E. & H.A. Tanash (2015), "The Clinical Profile of Subjects Included in the Swedish National Register on Individuals with Severe Alpha 1-Antitrypsin deficiency," *COPD*, 12(S1):36-41.

Saccarello, M.L. et al. (1979) "A New Synthesis of 1-Alkyl-3-aminoindoles," *Synthesis*, 1979(9):727-729.

Song, X. et al. (2018) "Regioselective Synthesis of 2-Alkenylindoles and 2-Alkenylindole-3-carboxylates through the Cascade Reactions of N-Nitrosoanilines with Propargyl Alcohols," *J. Org. Chem.*, 83:8509-8521.

Tanash, H.A. et al. (2016) "Cause-specific mortality in individuals with severe alpha 1-antitrypsin deficiency in comparison with the general population in Sweden," *International Journal of COPD*, 2016(11):1663-1669.

Tidwell, R.R. et al. (1978) "Diarylamidine Derivatives with One or Both of the Aryl Moieties Consisting of an Indole or Indole-like Ring. Inhibitors of Arginine-Specific Esteroproteases," *J Med Chem*, vol. 21, No. 7:613-623.

U.S. Appl. No. 17/060,945, filed Oct. 1, 2020, by Bozic et al.

U.S. Appl. No. 18/630,559, filed Apr. 9, 2024, by Bozic et al.

*Vertex Announces Primary Endpoint Achieved in Phase 2 Study of VX-864 in Alpha-1 Antitrypsin Deficiency*, Vertex (Jun. 10, 2021), https://news.vrtx.com/press-release/vertex-announces-primary-endpoint-achieved-phase-2-study-vx-864-alpha-1-antitrypsin (5 pages).

*Vertex Provides Update on its Clinical Programs Targeting Alpha-1 Antitrypsin Deficiency*, Vertex (Oct. 14, 2020), https://news.vrtx.com/press-release/vertex-provides-update-its-clinical-programs-targeting-alpha-1-antitrypsin-deficiency (4 pages).

Wen, W. et al. (2014) "Substituted indoles as selective protease activated receptor 4 (PAR-4) antagonists: Discovery and SAR of ML354," Bioorg. Med. Chem, Lett.,24 (19): 4708-4713.

Yu-liang, L. et al. (2017) "Diagnosis and Treatment of $\alpha$1-Antitrypsin Deficiency," *Practical Clinical Medicine*, 18 (2): 104-107.

(56) References Cited

OTHER PUBLICATIONS

Xu, M. et al., Facile Assembly of 11H-Indolo[3,2-c]quinoline by a Two-Step Protocol Involving a Regioselective 6-endo-Cyclization Promoted by the Hendrickson Reagent, Synthesis 2011, No. 4, pp. 0626-0634.

Zorgdrager, J. et al. (1989) "Synthesis of indoles using (N-arylaminomethyl)diphenylphosphine oxides," *Recueil des Travaux Chimiques des Pays-Bas*, 108 (12): 441-444.

* cited by examiner

MODULATORS OF ALPHA-1 ANTITRYPSIN

This application is a continuation of U.S. application Ser. No. 15/931,256, filed on May 13, 2020, which claims the benefit of U.S. Provisional Application No. 62/847,562, filed on May 14, 2019, and U.S. Provisional Application No. 63/004,813, filed Apr. 3, 2020, the contents of which are incorporated by reference in their entirety.

The disclosure provides compounds that are capable of modulating alpha-1 antitrypsin (AAT) activity and methods of treating alpha-1 antitrypsin deficiency (AATD) by administering one or more such compounds.

AATD is a genetic disorder characterized by low circulating levels of AAT. While treatments for AATD exist, there is currently no cure. AAT is produced primarily in liver cells and secreted into the blood, but it is also made by other cell types including lung epithelial cells and certain white blood cells. AAT inhibits several serine proteases secreted by inflammatory cells (most notably neutrophil elastase [NE], proteinase 3, and cathepsin G) and thus protects organs such as the lung from protease-induced damage, especially during periods of inflammation.

The mutation most commonly associated with AATD involves a substitution of lysine for glutamic acid (E342K) in the SERPINA1 gene that encodes the AAT protein. This mutation, known as the Z mutation or the Z allele, leads to misfolding of the translated protein, which is therefore not secreted into the bloodstream and can polymerize within the producing cell. Consequently, circulating AAT levels in individuals homozygous for the Z allele (PiZZ) are markedly reduced; only approximately 15% of mutant Z-AAT protein folds correctly and is secreted by the cell. An additional consequence of the Z mutation is that the secreted Z-AAT has reduced activity compared to wild-type protein, with 40% to 80% of normal antiprotease activity (American thoracic society/European respiratory society, Am J Respir Crit Care Med. 2003; 168(7):818-900; and Ogushi et al. J Clin Invest. 1987; 80(5):1366-74.

The accumulation of polymerized Z-AAT protein within hepatocytes results in a gain-of-function cytotoxicity that can result in cirrhosis or liver cancer later in life and neonatal liver disease in 12% of patients. This accumulation may spontaneously remit but can be fatal in a small number of children. The deficiency of circulating AAT results in unregulated protease activity that degrades lung tissue over time, resulting in emphysema, a form of chronic obstructive pulmonary disease (COPD). This effect is severe in PiZZ individuals and typically manifests in middle age, resulting in a decline in quality of life and shortened lifespan (mean 68 years of age) (Tanash et al. Int J Chron Obstruct Pulm Dis. 2016; 11:1663-9). The effect is more pronounced in PiZZ individuals who smoke, resulting in an even further shortened lifespan (58 years). Piitulainen and Tanash, COPD 2015; 12(1):36-41. PiZZ individuals account for the majority of those with clinically relevant AATD lung disease. Accordingly, there is a need for additional and effective treatments for AATD.

A milder form of AATD is associated with the SZ genotype in which the Z-allele is combined with an S-allele. The S allele is associated with somewhat reduced levels of circulating AAT but causes no cytotoxicity in liver cells. The result is clinically significant lung disease but not liver disease. Fregonese and Stolk, Orphanet J Rare Dis. 2008; 33:16. As with the ZZ genotype, the deficiency of circulating AAT in subjects with the SZ genotype results in unregulated protease activity that degrades lung tissue overtime and can result in emphysema, particularly in smokers.

The current standard of care for AAT deficient individuals who have or show signs of developing significant lung or liver disease is augmentation therapy or protein replacement therapy. Augmentation therapy involves administration of a human AAT protein concentrate purified from pooled donor plasma to augment the missing AAT. Although infusions of the plasma protein have been shown to improve survival or slow the rate of emphysema progression, augmentation therapy is often not sufficient under challenging conditions such as during an active lung infection. Similarly, although protein replacement therapy shows promise in delaying progression of disease, augmentation does not restore the normal physiological regulation of AAT in patients and efficacy has been difficult to demonstrate. In addition, augmentation therapy requires weekly visits for treatment and augmentation therapy cannot address liver disease, which is driven by the toxic gain-of-function of the Z allele. Thus, there is a continuing need for new and more effective treatments for AATD.

One aspect of the invention provides compounds of Formulae I, I-A, I-B, I-C, I-D, I-E, I-F, I-G, and I-H as well as tautomers of those compounds, pharmaceutically acceptable salts of those compounds and their tautomers, and deuterated derivatives of any of the foregoing that can be employed in the treatment of AATD. For example, compounds of Formula I can be depicted as:

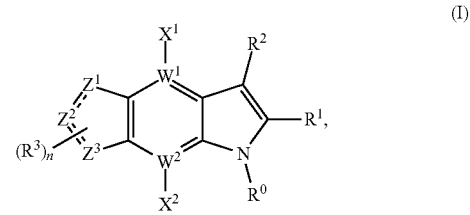

wherein:
(i) $R^0$ is chosen from
   (a) $C_1$-$C_8$ linear, branched, and cyclic groups, wherein the $C_1$-$C_8$ linear, branched, and cyclic groups are independently chosen from alkyl and alkoxy groups, and wherein the $C_1$-$C_8$ linear, branched, and cyclic groups are optionally substituted with 1-4 $R^A$; and
   (b) 5- to 14-membered aromatic rings optionally substituted with 1-4 $R^A$;
      wherein each $R^A$ is independently chosen from halogens, cyano, hydroxy, thiol, sulfonic acid, sulfonamide, sulfinamide, amino, amide, carboxylic acid, 5- to 10-membered aromatic rings, and $C_1$-$C_6$ linear, branched, and cyclic groups,
      wherein the amide nitrogen atom in the amide of $R^A$ is optionally substituted with a heterocyclyl group that is optionally further substituted with oxo,
         wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide,
      wherein the 5- to 10-membered aromatic rings and $C_1$-$C_6$ linear, branched, and cyclic groups are optionally substituted with 1-4 substituents selected from halogens, $C_1$-$C_6$ linear, branched, and cyclic groups, and methoxy, and wherein an $R^A$ group is optionally linked to an $R^B$ group on an $R^2$ group;
(ii) $R^1$ is chosen from
  (a) hydrogen,
  (b) $C_1$-$C_8$ linear, branched, and cyclic alkyl groups, wherein the alkyl group is optionally substituted with 1-4 substituents independently chosen from
    halogens,
    cyano,
    cyanoalkyl,
    hydroxy,
    alkylsulfonyl, and
    $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
      halogens,
      hydroxy, and
      $C_1$-$C_6$ linear, branched, and cyclic alkoxy groups,
  (c) $C_1$-$C_8$ linear, branched, and cyclic alkoxy or cyclic thioalkyl groups optionally substituted with 1-4 substituents independently chosen from
    halogens,
    cyano,
    cyanoalkyl,
    sulfone,
    sulfonamide,
    hydroxy, and
    $C_1$-$C_6$ linear, branched, and cyclic alkyl groups that are optionally substituted with 1-4 halogens or alkoxy groups;
  (d)

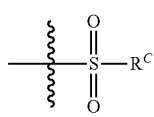

groups, wherein $R^C$ is chosen from:
    (aa) hydroxy,
    (bb) $C_1$-$C_8$ linear, branched, and cyclic alkyl groups, wherein the alkyl group is optionally substituted with 1-4 substituents independently chosen from
      halogens,
      cyano,
      hydroxy, and
      $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
        halogens,
        hydroxy, and
        $C_1$-$C_6$ linear, branched, and cyclic alkoxy groups, and
    (cc) $C_1$-$C_8$ linear, branched, and cyclic alkoxy groups optionally substituted with 1-4 substituents independently chosen from
      halogens,
      cyano,
      hydroxy, and
      $C_1$-$C_6$ linear, branched, and cyclic alkyl groups that are optionally substituted with 1-4 halogens;
  (e)

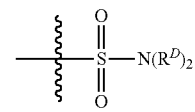

groups, wherein each $R^D$ is independently chosen from
    (aa) hydrogen,
    (bb) $C_1$-$C_8$ linear, branched, and cyclic alkyl groups, wherein the alkyl group is optionally substituted with 1-4 substituents independently chosen from
      halogens,
      cyano,
      hydroxy, and
      $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
        halogens,
        hydroxy, and
        $C_1$-$C_6$ linear, branched, and cyclic alkoxy groups, and
    (cc) $C_1$-$C_8$ linear, branched, and cyclic alkoxy groups optionally substituted with 1-4 substituents independently chosen from
      halogens,
      cyano,
      hydroxy, and
      $C_1$-$C_6$ linear, branched, and cyclic alkyl groups that are optionally substituted with 1-4 halogens,
  or two $R^D$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
    halogens,
    cyano,
    hydroxy, and
    $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
      halogens,
      hydroxy, and
      $C_1$-$C_6$ linear, branched, and cyclic alkoxy groups;
  (f)

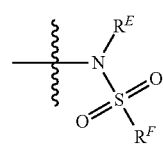

groups, wherein $R^E$ is chosen from:
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(dd) 5- to 10-membered aromatic rings optionally substituted with 1-4 $R^A$, and
(ee) $C_1$-$C_8$ linear, branched, and cyclic aminoalkyl groups,
and $R^F$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(g)

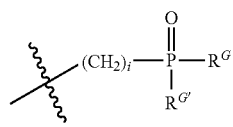

groups, wherein i is an integer ranging from 0 to 3 and each of $R^G$ and $R^{G'}$ is independently chosen from
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(dd) amino groups
(ee) $C_1$-$C_8$ linear, branched, and cyclic aminoalkyl groups,
or $R^G$ and $R^{G'}$ together with the phosphorous atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups; and
(h)

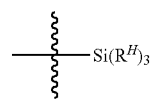

wherein each of $R^H$ is independently chosen from
(aa) $C_1$-$C_8$ linear, branched, and cyclic alkyl groups, wherein the alkyl group is optionally substituted with 1-4 substituents independently chosen from
halogens,
cyano,
hydroxy, and $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(bb) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(i) $C_1$-$C_6$ alkylamide;
(iii) $R^2$ is chosen from 5- and 6-membered heterocyclic rings (optionally substituted with oxo and/or $C_1$-$C_6$ linear and branched alkyl groups) and 5- to 6-membered aromatic rings comprising 0-4 heteroatoms chosen from O, N, and S, wherein the 5-membered aromatic ring is optionally substituted with 1-4 $R^B$ groups and the 6-membered aromatic ring is optionally substituted with 1-5 $R^B$ groups, wherein the $R^B$ groups are independently chosen from:
(a) amides, optionally substituted with 1-3 groups selected from $C_1$-$C_6$ linear, branched, and cyclic alkyl groups (optionally substituted with heteroaryl), 4- to 6-membered heterocyclyl (optionally substituted with oxo, $C_1$-$C_6$ linear, branched, and cyclic alkyl groups, hydroxyalkyl, amide, alkylsulfonyl, and acetamide); or wherein the amide nitrogen atom forms part of a 3- to 8-membered heterocyclyl ring (optionally substituted with alkylsulfonyl or $C_1$-$C_6$ linear, branched, and cyclic alkyl groups),
(b) imidazolidine-2,4-dione,
(c) heterocyclyls optionally substituted with one more groups independently chosen from oxo, acyl, and $C_1$-$C_6$ linear, branched, and cyclic alkyl groups (which is optionally further substituted with 1-3 groups independently chosen from oxo, hydroxy, and acyl),
(d) phosphorous acid optionally esterified with a $C_1$-$C_6$ linear, branched, or cyclic alkyl group,
(e) di($C_1$-$C_6$)alkylphosphine oxides,
(f) ($C_1$-$C_6$)alkylphosphinic acids optionally esterified with a $C_1$-$C_6$ linear, branched, or cyclic alkyl group,
(g) halogens,
(h) cyano,
(i) hydroxy,
(j) carboxylic acids optionally esterified with a uronic acid or a $C_1$-$C_6$ linear, branched, or cyclic alkyl group,
(k) oxo,
(l) —B(OR$^I$)$_2$ groups, wherein each R$^I$ is independently chosen from hydrogen and $C_1$-$C_6$ linear, branched, and cyclic alkyl groups, or two OR$^I$ groups together with the boron atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(m) 5- and 6-membered aromatic rings comprising 0-4 heteroatoms independently chosen from O, N, and S, optionally substituted with 1 or 2 substituents independently chosen from $C_1$-$C_6$ linear, branched, and cyclic alkyl groups that are optionally substituted with 1-4 substituents independently chosen from
hydroxy,
carboxylic acids,
pyrrolidin-2-one,
$C_1$-$C_6$ linear, branched, and cyclic alkyl groups, and
$C_1$-$C_6$ linear, branched, and cyclic alkylsulfonyl groups, and
$C_1$-$C_6$ linear, branched, and cyclic alkoxy groups,
(n) sulfonic acid,
(o)

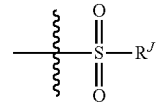

groups, wherein R$^J$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy,
$C_1$-$C_6$ linear, branched, and cyclic alkoxy groups,
heterocyclyl optionally substituted with oxo, and
amide
(cc) $C_1$-$C_8$ linear, branched, and cyclic alkoxy groups optionally substituted with 1-4 substituents independently chosen from
halogens,
cyano,
hydroxy, and $C_1$-$C_6$ linear, branched, and cyclic alkyl groups that are optionally substituted with 1-4 halogens (dd) 5- to 10-membered aromatic rings optionally substituted with 1-4 $R^A$, and (ee) $C_1$-$C_8$ linear, branched, and cyclic aminoalkyl groups, (p)

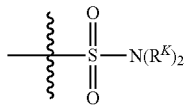

groups, wherein each $R^K$ is independently chosen from:

(aa) hydrogen, (bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and (cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens, or two $R^K$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups (q)

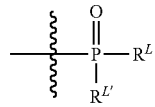

groups, wherein each of $R^L$ and $R^{L'}$ is independently chosen from (aa) hydroxy, (bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and (cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens, (dd) amino groups (ee) $C_1$-$C_8$ linear, branched, and cyclic aminoalkyl groups, or $R^L$ and $R^{L'}$ together with the phosphorous atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, (r) $C_1$-$C_6$ linear, branched, and cyclic alkyl groups that are optionally substituted with 1-4 substituents independently chosen from
halogens,
hydroxy,
carboxylic acid,
$C_1$-$C_6$ linear, branched, and cyclic alkoxy groups,
heterocyclyl optionally substituted with oxo, and
amide, (s) $C_1$-$C_6$ linear, branched, and cyclic alkoxy groups that are optionally substituted with 1-4 substituents independently chosen from
halogens,
hydroxy,
carboxylic acid,
$C_1$-$C_6$ linear, branched, and cyclic alkyl groups, and
$C_1$-$C_6$ linear, branched, and cyclic alkoxy groups, and
(t)

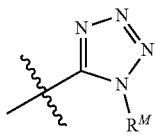

groups, wherein $R^M$ is chosen from:
(aa) hydrogen,
(bb) carboxylic acid,
(cc) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(dd) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens
(ee) 5- to 10-membered aromatic rings optionally substituted with 1-4 $R^A$
(ff) halogens
(gg) hydroxy
(u) O—$R^N$ wherein $R^N$ is chosen from
(aa) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(bb) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(v)

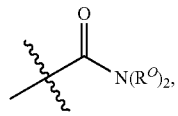

wherein each $R^O$ is independently chosen from hydrogen and a $C_1$-$C_8$ linear, branched, and cyclic alkyl group, wherein the alkyl group is optionally substituted with 1-4 substituents independently chosen from
alkylsulfonyl,
alkylamide,
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
or two $R^O$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(w)

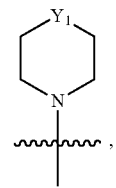

wherein $Y_1$ is chosen from oxygen, $N-R^P$, and

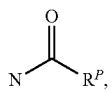

wherein $R^P$ is chosen from a $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
wherein 2 adjacent hydrogens on the 5- or 6-membered aromatic ring can be replaced by attachments to a second 5- or 6-membered aromatic ring comprising 0-4 heteroatoms independently chosen from O, N, and S to form a bicyclic $R^2$ group that is optionally substituted with 1-6 $R^B$ groups;

(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are independently chosen from alkyl, alkoxy, thioalkyl, and aminoalkyl groups, and wherein the $C_1$-$C_6$ linear, branched, and cyclic groups are optionally substituted by 1-4 independently chosen halogens;

(v) each of $W^1$ and $W^2$ is independently selected from C and N;

(vi) each ==== represents a single or double bond, provided that no more than one ==== is a double bond;

(vii) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the $C_1$-$C_6$ linear, branched, and cyclic alkyl groups and the $C_1$-$C_6$ linear, branched, and cyclic alkoxy groups are optionally substituted with 1-4 substituents independently chosen from halogens, hydroxy groups, and carboxylic acid;

(viii) n is an integer chosen from 0, 1, 2, and 3; and (ix) $Z^1$, $Z^2$, and $Z^3$ are independently chosen from carbon, boron, nitrogen, sulfur, and oxygen, wherein when $Z^1$, $Z^2$, and/or $Z^3$ are carbon or nitrogen, the valences of carbon and nitrogen are completed with hydrogen atoms, halogen, $C_1$-$C_6$ linear, branched, and cyclic alkyl groups, and $C_1$-$C_6$ linear, branched, and cyclic alkoxy groups, wherein the $C_1$-$C_6$ linear, branched, and cyclic alkyl groups and the $C_1$-$C_6$ linear, branched, and cyclic alkoxy groups are optionally substituted with 1-4 substituents independently chosen from halogens, hydroxy groups, and carboxylic acid, and wherein when $Z^1$, $Z^2$, or $Z^3$ is boron, the valence of boron is completed with a hydrogen atom or a hydroxy group.

In one aspect of the invention the compounds of Formula I are selected from Compounds 1-342, as well as tautomers of those compounds, pharmaceutically acceptable salts of those compounds and their tautomers, and deuterated derivatives of any of the foregoing that can be employed in the treatment of AATD.

In some embodiments, the invention provides pharmaceutical compositions comprising at least one compound of selected from compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing. In specific embodiments, the pharmaceutical compositions may comprise a compound selected from Compounds 1-342, tautomers of those compounds, pharmaceutically acceptable salts of those compounds and their tautomers, and deuterated derivatives of any of the foregoing. These compositions may further include at least one additional active pharmaceutical ingredient and/or at least one carrier.

Another aspect of the invention provides methods of treating AATD comprising administering to a subject in need thereof, at least one compound of selected from compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing or a pharmaceutical composition comprising the at least one compound. In specific embodiments, the methods comprise administering a compound selected from Compounds 1-342, tautomers of those compounds, pharmaceutically acceptable salts of those compounds and their tautomers, and deuterated derivatives of any of the foregoing.

In some embodiments, the methods of treatment include administration of at least one additional active agent to the subject in need thereof, either in the same pharmaceutical composition as the at least one compound of selected from compounds of Formulae I, I-A, I-B, I-C, I-D, I-E, I-F, I-G, and I-H tautomers of those compounds, pharmaceutically acceptable salts of those compounds and their tautomers, and deuterated derivatives of any of the foregoing, or as separate compositions. In specific embodiments, the methods comprise administering a compound selected from Compounds 1-342, tautomers of those compounds, pharmaceutically acceptable salts of those compounds and their tautomers, and deuterated derivatives of any of the foregoing with at least one additional active agent either in the same pharmaceutical composition or in a separate composition. In some embodiments, the subject in need of treatment carries the ZZ mutation. In some embodiments, the subject in need of treatment carries the SZ mutation.

Also provided are methods of modulating AAT, comprising administering to a subject in need thereof, at least one compound of selected from compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing or a pharmaceutical composition comprising the at least one compound, tautomer, salt, or deuterated derivative. In specific embodiments, the methods of modulating AAT comprise administering at least one compound selected from Compounds 1-342, tautomers of those compounds, pharmaceutically acceptable salts of those compounds and their tautomers, and deuterated derivatives of any of the foregoing or a pharmaceutical composition comprising the at least one compound, tautomer, salt, or deuterated derivative.

DETAILED DESCRIPTION

I. Definitions

Figure 1A:
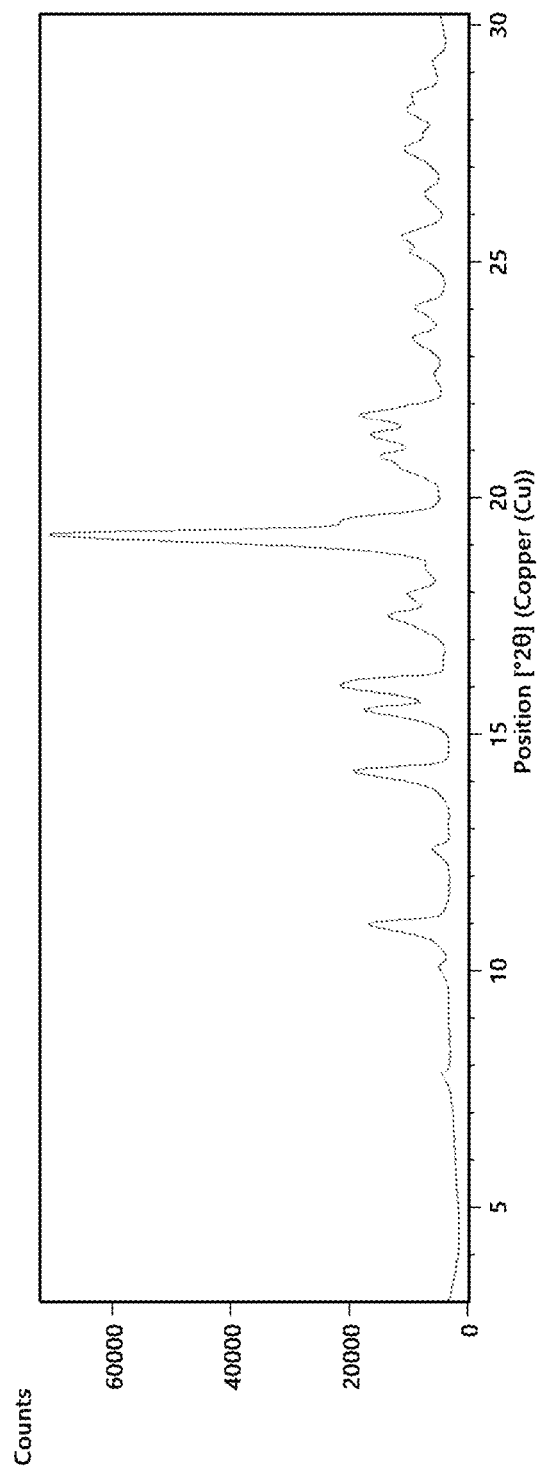
FIG. 1A shows an XRPD diffractogram of Compound 33 Form A.

The term "AAT" as used herein means alpha-1 antitrypsin or a mutation thereof, including, but not limited to, the AAT gene mutations such as Z mutations. As used herein, "Z-AAT" means AAT mutants which have the Z mutation.

The term "AATD" as used herein means alpha-1 antitrypsin deficiency, which is a genetic disorder characterized by low circulating levels of AAT.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

Compounds of the invention may optionally be substituted with one or more substituents. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C or $^{14}$C are within the scope of this disclosure.

Unless otherwise indicated, structures depicted herein are also meant to include all isomeric forms of the structure, e.g., racemic mixtures, atropisomers, diastereomeric mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of a compound that exist together in equilibrium and are readily interchanged by migration of an atom or group within the molecule.

"Stereoisomer" refers to both enantiomers and diastereomers.

As used herein, "deuterated derivative" refers to a compound having the same chemical structure as a reference compound, but with one or more hydrogen atoms replaced by a deuterium atom ("D"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the invention, at least one hydrogen is replaced with deuterium at well above its natural isotopic abundance (which is typically about 0.015%). In some embodiments, the deuterated derivatives of the invention have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at lease 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl," or "aliphatic" as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic that has a single point of attachment to the rest of the molecule. Unless otherwise specified, alkyl groups contain 1-20 alkyl carbon atoms. In some embodiments, alkyl groups contain 1-10 aliphatic carbon atoms. In other embodiments, alkyl groups contain 1-8 aliphatic carbon atoms. In still other embodiments, alkyl groups contain 1-6 alkyl carbon atoms, in other embodiments alkyl groups contain 1-4 alkyl carbon atoms, and in yet other embodiments alkyl groups contain 1-3 alkyl carbon atoms. Nonlimiting examples of alkyl groups include, but are not limited to, linear or branched, substituted or unsubstituted alkyl, alkenyl, alkynyl groups and hybrids thereof, such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The terms "cycloalkyl," "carbocycle," "cycloaliphatic," or "cyclic alkyl" refer to a spirocyclic or monocyclic $C_{3-8}$ hydrocarbon or a spirocyclic, bicyclic, bridged bicyclic, tricyclic, or bridged tricyclic $C_{8-14}$ hydrocarbon that is completely saturated or that contains one or more units of unsaturation, but which is not aromatic, wherein any individual ring in said bicyclic ring system has 3-7 members.

The term "heteroalkyl," or "heteroaliphatic" as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "alkenyl" as used herein, means a straight-chain (i.e., unbranched), branched, substituted or unsubstituted hydrocarbon chain that contains one or more units of saturation, or a monocyclic hydrocarbon or bicyclic hydrocarbon that contains one or more units of unsaturation, but which is not aromatic (referred to herein as, "cyclic alkenyl").

The term "heterocycle", "heterocyclyl", "heterocycloaliphatic", or "heterocyclic" as used herein means non-aromatic, monocyclic, bicyclic, or tricyclic ring systems in which one or more ring members is an independently chosen heteroatom. In some embodiments, the "heterocycle", "heterocyclyl", "heterocycloaliphatic", or "heterocyclic" group has three to fourteen ring members in which one or more ring members is a heteroatom independently chosen from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, wherein one carbon of the alkyl group is replaced by an oxygen ("alkoxy") or sulfur ("thioalkyl") atom, respectively, provided that the oxygen and sulfur atoms are linked between two carbon atoms. A "cyclic alkoxy" refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl. A "cyclic thioalkyl" refers to a monocyclic, spirocyclic, bicyclic, bridged bicyclic, tricyclic, or bridged tricyclic hydrocarbon that contains at least one thioalkyl group, but is not aromatic.

The terms "haloalkyl" and "haloalkoxy" means an alkyl or alkoxy, as the case may be, which is substituted with one or more halogen atoms. The term "halogen" or means F, Cl, Br, or I. Examples of haloalkyls include —CHF$_2$, —CH$_2$F, —CF$_3$, —CF$_2$—, or perhaloalkyl, such as, —CF$_2$CF$_3$.

The term "aminoalkyl" means an alkyl group which is substituted with or contains an amino group. As used herein, an "amino" refers to a group which is a primary, secondary, or tertiary amine.

The term "alkylsulfoxide" means an alkyl group in which a carbon of said alkyl group is replaced by or substituted with a sulfoxide group. A "cyclic alkylsulfoxide" refers to a monocyclic hydrocarbon or bicyclic hydrocarbon that contains one or more alkylsulfoxides, but is not aromatic. As used herein, "sulfoxide" means a sulfinyl (i.e., —S(O)—) which is attached to two carbon atoms.

The term "alkylsulfinamide" means an alkyl group in which a carbon of said alkyl group is replaced by or substituted with a sulfinamide group. As used herein, "sulfinamide" refers to —S(O)—, in which the sulfur atom is independently attached to an amine group and attached to carbon.

The term "alkylsulfonyl" means an alkyl group in which a carbon of said alkyl group is replaced by or substituted with a sulfonyl group. As used herein, "sulfonyl" refers to —S(O)$_2$—, wherein the sulfur is attached to a carbon and also attached to a different carbon.

The term "alkylsulfonamide" means an alkyl group in which a carbon of said alkyl group is replaced by or substituted with a sulfonamide group. As used herein, a "sulfonamide" refers to a —S(O)$_2$— wherein the sulfur is attached to an amine group and also attached to carbon.

The term "alkylamide" means an alkyl group in which a carbon of said alkyl group is replaced with an amide. As used herein, "amide" refers to a carbonyl (i.e., —C(O)—) that is attached to an amine group and also attached to carbon. An optionally substituted amide may be mono- or di-substituted at the amide nitrogen. Alternatively, or in addition, an optionally substituted amide may be substituted at the carbonyl carbon.

As used herein, an "oxo" group refers to =O.

As used herein, a "cyano" or "nitrile" groups refers to —C≡N.

As used herein, a "hydroxy" group refers to —OH.

"Tert" and "t-" each refer to tertiary.

As used herein, "aromatic groups" or "aromatic rings" refer to chemical groups that contain conjugated, planar ring systems with delocalized pi electron orbitals comprised of [4n+2] p orbital electrons, wherein n is an integer ranging from 0 to 6. Nonlimiting examples of aromatic groups include aryl and heteroaryl groups.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" also refers to heteroaryl ring systems as defined herein below. Nonlimiting examples of aryl groups include phenyl rings.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members.

An aryl (including arylalkyl, arylalkoxy, aryloxyalkyl and the like) or heteroaryl (including heteroarylalkyl and heteroarylalkoxy and the like) group may contain one or more substituents.

An alkyl group, or a non-aromatic heterocyclic ring may contain one or more substituents.

Examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999).

Examples of suitable solvents that may be used in this disclosure include, but not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Examples of suitable bases that may be used in this disclosure include, but not limited to, 1,8-diazabicyclo[5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the compounds of the invention. A salt of a compound of is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences*, 1977, 66, 1-19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The terms "patient" and "subject" are used interchangeably and refer to an animal including a human.

The terms "effective dose" and "effective amount" are used interchangeably herein and refer to that amount of a compound that produces the desired effect for which it is administered (e.g., improvement in AATD or a symptom of AATD, lessening the severity of AATD or a symptom of AATD, and/or reducing the rate of onset or incidence of AATD or a symptom of AATD). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the term "treatment" and its cognates refer to improving AATD or its symptoms in a subject, delaying the onset of AATD or its symptoms in a subject, or lessening the severity of AATD or its symptoms in a subject. "Treatment" and its cognates as used herein, include, but are not limited to the following: improved liver and/or spleen function, lessened jaundice, improved lung function, lessened lung diseases and/or pulmonary exacerbations (e.g., emphysema), lessened skin disease (e.g., necrotizing panniculitis), increased growth in children, improved appetite, and reduced fatigue. Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. In some embodiments, the term "about" reflects a variation of ±10% of a stated value. In some embodiments, the term "about" reflects a variation of ±5% of a stated value. In some embodiments, the term "about" reflects a variation of ±2% of a stated value.

Any one or more of the compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing may be administered once daily, twice daily, or three times daily for the treatment of AATD. In specific embodiments, the any one or more compounds are selected from Compounds 1-342, tautomers of those compounds, pharmaceutically acceptable salts of those compounds and their tautomers, and deuterated derivatives of any of the foregoing. In some embodiments, at least one compound chosen from compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing is administered once daily. In specific embodiments, a compound selected from Compounds 1-342, tautomers of those compounds, pharmaceutically acceptable salts of those compounds and their tautomers, and deuterated derivatives of any of the foregoing is administered once daily. In some embodiments, at least one compound chosen from compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing are administered twice daily. In specific embodiments, a compound selected from Compounds 1-342, tautomers of those compounds, pharmaceutically acceptable salts of those compounds and their tautomers, and deuterated derivatives of any of the foregoing is administered twice daily. In some embodiments, at least one compound chosen from compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing are administered three times daily. In specific embodiments, a compound selected from Compounds 1-342, tautomers of those compounds, pharmaceutically acceptable salts of those compounds and their tautomers, and deuterated derivatives of any of the foregoing is administered three times daily.

Any one or more of the compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing may be administered in combination with AAT augmentation therapy or AAT replacement therapy for the treatment of AATD. In specific embodiments, the any one or more compounds are selected from Compounds 1-342, tautomers of those compounds, pharmaceutically acceptable salts of those compounds and their tautomers, and deuterated derivatives of any of the foregoing.

As used herein, "AAT augmentation therapy" refers to the use of alpha-1 antitrypsin protein (AAT) from the blood plasma of healthy human donors to augment (increase) the alpha-1 antitrypsin levels circulating in the blood. "AAT replacement therapy" refers to administration of recombinant AAT.

In some embodiments, 10 mg to 1,500 mg, 100 mg to 1800 mg, 100 mg to 500 mg, 200 mg to 600 mg, 200 mg to 800 mg, 400 mg to 2,000 mg, 400 mg to 2,500 mg or 400 mg to 600 mg of a compound of Formulae I, I-A, I-B, I-C, I-D, I-E, I-F, I-G, and I-H and tautomers of those compounds, pharmaceutically acceptable salts of those compounds and their tautomers, or deuterated derivatives of such compound, tautomer, or salt are administered once daily, twice daily, or three times daily. In specific embodiments, 10 mg to 1,500 mg, 100 mg to 1800 mg, 100 mg to 500 mg, 200 mg to 600 mg, 200 mg to 800 mg, 400 mg to 2000 mg, or 400 mg to 600 mg of a compound selected from Compounds 1-342, tautomers of those compounds, pharmaceutically acceptable salts of those compounds and their tautomers, or deuterated derivatives of such compound, tautomer, or salt are administered once daily, twice daily, or three times daily.

One of ordinary skill in the art would recognize that, when an amount of a compound is disclosed, the relevant amount of a pharmaceutically acceptable salt form of the compound is an amount equivalent to the concentration of the free base of the compound. It is noted that the disclosed amounts of the compounds, tautomers, pharmaceutically acceptable salts, and deuterated derivatives are based upon the free base form of the reference compound. For example, "10 mg of at least one compound chosen from compounds of Formula (I) and pharmaceutically acceptable salts thereof" includes 10 mg of a compound of Formula (I) and a concentration of a pharmaceutically acceptable salt of compounds of Formula (I) equivalent to 10 mg of compounds of Formula (I).

As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), and/or thermogravimetric analysis (TGA). Accordingly, as used herein, the terms "crystalline Form [X] of Compound ([Y])" and "crystalline Form [C] of a [pharmaceutically acceptable] salt of Compound ([Y])" refer to unique crystalline forms that can be identified and distinguished from each other by one or more characterization techniques including, for example, X-ray powder diffraction (XRPD), single crystal X-ray diffraction, SSNMR, differential scanning calorimetry (DSC), and/or thermogravimetric analysis (TGA). In some embodiments, the novel crystalline forms are characterized by an X-ray powder diffractogram having one or more signals at one or more specified two-theta values (° 2θ).

As used herein, a crystalline form is "substantially pure" when it accounts for an amount by weight equal to or greater than 90% of the sum of all solid form(s) of that compound in a sample as determined by a method in accordance with the art, such as quantitative ssNMR and/or XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, a compound is "substantially crystalline" when it accounts for an amount by weight equal to or greater than 70% of the sum of all the solid forms of that compound in a sample as determined by a method in accordance with the art, such as quantitative ssNMR and/or XRPD. In some embodiments, the solid form is "substantially crystalline" when it accounts for an amount by weight equal to or greater than 75% of the sum of all solid form(s) in a sample. In some embodiments, the solid form is "substantially pure" when it accounts for an amount by weight equal to or greater than 80% of the sum of all solid form(s) in a sample. In some embodiments, the solid form is "substantially pure" when it accounts for an amount by weight equal to or greater than 85% of the sum of all solid form(s) in a sample.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. For example, an amorphous material is a solid material having no sharp characteristic signal(s) in its X-ray power diffractogram (i.e., is not crystalline as determined by XRPD). Instead, one or more broad peaks (e.g., halos) appear in its diffractogram. Broad peaks are characteristic of an amorphous solid. See, e.g., US 2004/0006237 for a comparison of diffractograms of an amorphous material and crystalline material. In addition, the widths of signals in $^{13}$C NMR and $^{19}$F NMR spectra of amorphous material are typically substantially broader than those in $^{13}$C NMR and $^{19}$F NMR spectra of crystalline material.

As used herein, a compound is "substantially amorphous" when it accounts for an amount by weight equal to or greater than 70% of the sum of all the solid forms of that compound in a sample as determined by a method in accordance with the art, such as quantitative ssNMR and/or XRPD. In some embodiments, a compound that is substantially amorphous accounts for an amount by weight equal to or greater than 75% of the sum of all the solid forms of that compound in a sample. In some embodiments, a compound that is substantially amorphous accounts for an amount by weight equal to or greater than 80% of the sum of all the solid forms of that compound in a sample. In some embodiments, a compound that is substantially amorphous accounts for an amount by weight equal to or greater than 85% of the sum of all the solid forms of that compound in a sample. In some embodiments, a compound that is substantially amorphous accounts for an amount by weight equal to or greater than 90% of the sum of all the solid forms of that compound in a sample. In some embodiments, a compound that is substantially amorphous accounts for an amount by weight equal to or greater than 95% of the sum of all the solid forms of that compound in a sample.

As used herein, a "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase), or alternatively, an amorphous drug (dispersed phase) in an amorphous polymer (continuous phase). In some embodiments an amorphous solid dispersion includes the polymer constituting the dispersed phase, and the drug constitutes the continuous phase. In some embodiments, the dispersion includes amorphous Compound 33 or substantially amorphous Compound 33.

The term "solid amorphous dispersion" generally refers to a solid dispersion of two or more components, usually a drug and polymer, but possibly containing other components such as surfactants or other pharmaceutical excipients, where Compound 33 is amorphous or substantially amorphous (e.g., substantially free of crystalline Compound 33), and the physical stability and/or dissolution and/or solubility of the amorphous drug is enhanced by the other components.

As used herein, the term "solvate" refers to a crystal form comprising one or more molecules of a compound of the present disclosure and, incorporated into the crystal lattice, one or more molecules of a solvent or solvents in stoichiometric or nonstoichiometric amounts. When the solvent is water, the solvate is referred to as a "hydrate". The term "solvate/hydrate" refers to a crystal form comprising one or more molecules of a compound of the present disclosure and, incorporated into the crystal lattice, one or more molecules of a non-water solvent and 0-50% water in stoichiometric or nonstoichiometric amounts, such as 0-5%, 0-10%, 5-10%, 0-20%, 10-20%, 10-15%, 15-20%, 5-20%, 0-25%, 20-25%, 10-25%, 15-25%, 5-25%, 0-30%, 5-30%, 10-30%, 15-30%, 20-30%, 25-30%, 30-45%, 35-40%, 40-50%, and 45-50%.

As used herein, the term "XRPD" refers to X-Ray Power Diffraction XRPD patterns can be recorded at ambient conditions in transmission or reflection geometry using a diffractometer.

As used herein, the terms "X-ray powder diffractogram," "X-ray powder diffraction pattern," "XRPD pattern" interchangeably refer to an experimentally obtained pattern plotting signal positions (on the abscissa) versus signal intensities on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . ." and/or "a signal at at least . . . two-theta value(s) chosen from . . . ."

The term "X-ray powder diffractogram having a signal at . . . two-theta values" as used herein refers to an XRPD pattern that contains X-ray reflection positions as measured and observed in X-ray powder diffraction experiments (° 2θ).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance.

As used herein, the term "ambient conditions" means room temperature, open air condition and uncontrolled humidity condition.

A "signal" or "peak" as used herein refers to a point in the XRPD pattern where the intensity as measured in counts is at a local. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value[ ] of . . . " and/or "a signal at at least . . . two-theta value(s) chosen from . . . " refer to X-ray reflection positions as measured and observed in X-ray powder diffraction experiments (° 2θ).

The repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, the term "SSNMR" refers to the analytical characterization method of solid state nuclear magnetic resonance. SSNMR spectra can be recorded at ambient conditions on any magnetically active isotope present in the sample. The typical examples of active isotopes for small molecule active pharmaceutical ingredients include $^1$H, $^2$H, $^{13}$C, $^{19}$F, $^{31}$P, $^{15}$N, $^{14}$N, $^{35}$Cl, $^{11}$B, $^7$Li, $^{17}$O, $^{23}$Na, $^{79}$Br, and $^{195}$Pt.

As used herein, an SSNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the signal maximum values in SSNMR spectra (in ppm) referred to herein generally mean that value reported ±0.2 ppm of the reported value, an art-recognized variance.

As used herein, the term "DSC" refers to the analytical method of Differential Scanning Calorimetry.

As used herein, the term "TGA" refers to the analytical method of Thermo Gravimetric (or thermogravimetric) Analysis.

II. Compounds and Compositions

In some embodiments, a compound of the invention is a compound of Formula I:

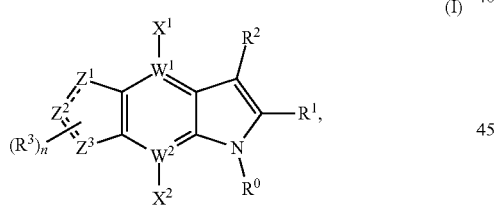

(I)

wherein:
(i) $R^0$ is chosen from
  (a) $C_1$-$C_8$ linear, branched, and cyclic groups, wherein the $C_1$-$C_8$ linear, branched, and cyclic groups are independently chosen from alkyl and alkoxy groups, and wherein the $C_1$-$C_8$ linear, branched, and cyclic groups are optionally substituted with 1-4 $R^A$; and
  (b) 5- to 14-membered aromatic rings optionally substituted with 1-4 $R^A$;
    wherein each $R^A$ is independently chosen from halogens, cyano, hydroxy, thiol, sulfonic acid, sulfonamide, sulfinamide, amino, amide, carboxylic acid, 5- to 10-membered aromatic rings, and $C_1$-$C_6$ linear, branched, and cyclic groups,
      wherein the amide nitrogen atom in the amide of $R^A$ is optionally substituted with a heterocyclyl group that is optionally further substituted with oxo,
      wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide,
      wherein the 5- to 10-membered aromatic rings and $C_1$-$C_6$ linear, branched, and cyclic groups are optionally substituted with 1-4 substituents selected from halogens, $C_1$-$C_6$ linear, branched, and cyclic groups, and methoxy, and
    wherein an $R^A$ group is optionally linked to an $R^B$ group on an $R^2$ group;
(ii) $R^1$ is chosen from
  (a) hydrogen,
  (b) $C_1$-$C_8$ linear, branched, and cyclic alkyl groups, wherein the alkyl group is optionally substituted with 1-4 substituents independently chosen from
    halogens,
    cyano,
    cyanoalkyl,
    hydroxy,
    alkylsulfonyl, and
    $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
      halogens,
      hydroxy, and
      $C_1$-$C_6$ linear, branched, and cyclic alkoxy groups,
  (c) $C_1$-$C_8$ linear, branched, and cyclic alkoxy or cyclic thioalkyl groups optionally substituted with 1-4 substituents independently chosen from
    halogens,
    cyano,
    cyanoalkyl,
    sulfone,
    sulfonamide,
    hydroxy, and
    $C_1$-$C_6$ linear, branched, and cyclic alkyl groups that are optionally substituted with 1-4 halogens or alkoxy groups;
  (d)

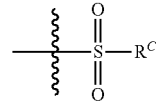

groups, wherein $R^C$ is chosen from:
  (aa) hydroxy,
  (bb) $C_1$-$C_8$ linear, branched, and cyclic alkyl groups, wherein the alkyl group is optionally substituted with 1-4 substituents independently chosen from
    halogens,
    cyano,
    hydroxy, and
    $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;

(e)

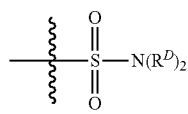

groups, wherein each $R^D$ is independently chosen from
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
or two $R^D$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups;

(f)

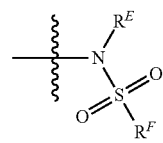

groups, wherein $R^E$ is chosen from:
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(dd) 5- to 10-membered aromatic rings optionally substituted with 1-4 $R^4$, and
(ee) $C_1$-$C_8$ linear, branched, and cyclic aminoalkyl groups,
and $R^F$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and (cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;

(g)

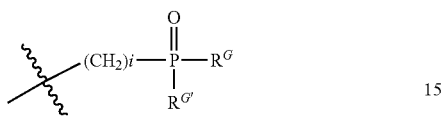

groups, wherein i is an integer ranging from 0 to 3 and each of $R^G$ and $R^{G'}$ is independently chosen from
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(dd) amino groups
(ee) $C_1$-$C_8$ linear, branched, and cyclic aminoalkyl groups, or $R^G$ and $R^{G'}$ together with the phosphorous atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups; and (h)

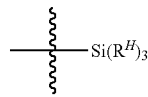

wherein each of $R^H$ is independently chosen from
(aa) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(bb) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(i) $C_1$-$C_6$ alkylamide;
(iii) $R^2$ is chosen from 5- and 6-membered heterocyclic rings (optionally substituted with oxo and/or $C_1$-$C_6$ linear and branched alkyl groups) and 5- to 6-membered aromatic rings comprising 0-4 heteroatoms chosen from O, N, and S, wherein the 5-membered aromatic ring is optionally substituted with 1-4 $R^B$ groups and the 6-membered aromatic ring is optionally substituted with 1-5 $R^B$ groups, wherein the $R^B$ groups are independently chosen from:
(a) amides, optionally substituted with 1-3 groups selected from $C_1$-$C_6$ linear, branched, and cyclic alkyl groups (optionally substituted with heteroaryl), 4- to 6-membered heterocyclyl (optionally substituted with oxo, $C_1$-$C_6$ linear, branched, and cyclic alkyl groups, hydroxyalkyl, amide, alkylsulfonyl, and acetamide); or wherein the amide nitrogen atom forms part of a 3- to 8-membered heterocyclyl ring (optionally
substituted with alkylsulfonyl or $C_1$-$C_6$ linear, branched, and cyclic alkyl groups),
(b) imidazolidine-2,4-dione,
(c) heterocyclyls optionally substituted with one more groups independently chosen from oxo, acyl, and $C_1$-$C_6$ linear, branched, and cyclic alkyl groups (which is optionally further substituted with 1-3 groups independently chosen from oxo, hydroxy, and acyl),
(d) phosphorous acid optionally esterified with a $C_1$-$C_6$ linear, branched, or cyclic alkyl group,
(e) di($C_1$-$C_6$)alkylphosphine oxides, (f) ($C_1$-$C_6$)alkylphosphinic acids optionally esterified with a $C_1$-$C_6$ linear, branched, or cyclic alkyl group,
(g) halogens,
(h) cyano,
(i) hydroxy,
(j) carboxylic acids optionally esterified with a uronic acid or a $C_1$-$C_6$ linear, branched, or cyclic alkyl group,
(k) oxo,
(l) —B(OR$^I$)$_2$ groups, wherein each R$^I$ is independently chosen from hydrogen and $C_1$-$C_6$ linear, branched, and cyclic alkyl groups, or two OR$^I$ groups together with the boron atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(m) 5- and 6-membered aromatic rings comprising 0-4 heteroatoms independently chosen from O, N, and S, optionally substituted with 1 or 2 substituents independently chosen from $C_1$-$C_6$ linear, branched, and cyclic alkyl groups that are optionally substituted with 1-4 substituents independently chosen from
hydroxy,
carboxylic acids,
pyrrolidin-2-one,
$C_1$-$C_6$ linear, branched, and cyclic alkyl groups, and
$C_1$-$C_6$ linear, branched, and cyclic alkylsulfonyl groups, and
$C_1$-$C_6$ linear, branched, and cyclic alkoxy groups,
(n) sulfonic acid,
(o)

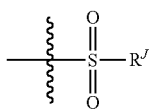

groups, wherein R$^J$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy,
$C_1$-$C_6$ linear, branched, and cyclic alkoxy groups,
heterocyclyl optionally substituted with oxo, and
amide
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens
(dd) 5- to 10-membered aromatic rings optionally substituted with 1-4 R$^A$, and
(ee) $C_1$-$C_8$ linear, branched, and cyclic aminoalkyl groups,
(p)

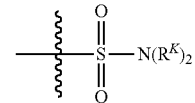

groups, wherein each R$^K$ is independently chosen from:
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
or two R$^K$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups
(q)

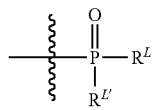

groups, wherein each of $R^L$ and $R^{L'}$ is independently chosen from
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(dd) amino groups
(ee) $C_1$-$C_8$ linear, branched, and cyclic aminoalkyl groups,
or $R^L$ and $R^{L'}$ together with the phosphorous atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, (r) $C_1$-$C_6$ linear, branched, and cyclic alkyl groups that are optionally substituted with 1-4 substituents independently chosen from
halogens,
hydroxy,
carboxylic acid,
$C_1$-$C_6$ linear, branched, and cyclic alkoxy groups, heterocyclyl optionally substituted with oxo, and amide,
(s) $C_1$-$C_6$ linear, branched, and cyclic alkoxy groups that are optionally substituted with 1-4 substituents independently chosen from
halogens,
hydroxy,
carboxylic acid,
$C_1$-$C_6$ linear, branched, and cyclic alkyl groups, and
$C_1$-$C_6$ linear, branched, and cyclic alkoxy groups, and
(t)

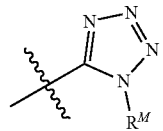

groups, wherein $R^M$ is chosen from:
(aa) hydrogen,
(bb) carboxylic acid,
(cc) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(dd) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens
(ee) 5- to 10-membered aromatic rings optionally substituted with 1-4 $R^A$
(ff) halogens
(gg) hydroxy
(u) O—$R^N$ wherein $R^N$ is chosen from
(aa) $C_1$-$C_8$ linear, branched, and cyclic alkyl groups, wherein the alkyl group is optionally substituted with 1-4 substituents independently chosen from
halogens,
cyano,
hydroxy, and C$_1$-C$_6$ linear, branched, and cyclic groups, wherein the C$_1$-C$_6$ linear, branched, and cyclic groups are independently chosen from alkyl and alkoxy groups, and wherein the C$_1$-C$_6$ linear, branched, and cyclic groups are optionally substituted with 1-4 substituents independently chosen from
halogens,
hydroxy, and
C$_1$-C$_6$ linear, branched, and cyclic alkoxy groups, and
(bb) C$_1$-C$_8$ linear, branched, and cyclic alkoxy groups optionally substituted with 1-4 substituents independently chosen from
halogens,
cyano,
hydroxy, and
C$_1$-C$_6$ linear, branched, and cyclic alkyl groups that are optionally substituted with 1-4 halogens, (v)

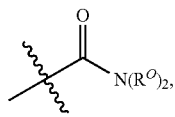

wherein each R$^O$ is independently chosen from hydrogen and a C$_1$-C$_8$ linear, branched, and cyclic alkyl group, wherein the alkyl group is optionally substituted with 1-4 substituents independently chosen from
alkylsulfonyl,
alkylamide,
halogens,
cyano,
hydroxy, and
C$_1$-C$_6$ linear, branched, and cyclic groups, wherein the C$_1$-C$_6$ linear, branched, and cyclic groups are independently chosen from alkyl and alkoxy groups, and wherein the C$_1$-C$_6$ linear, branched, and cyclic groups are optionally substituted with 1-4 substituents independently chosen from
halogens,
hydroxy, and
C$_1$-C$_6$ linear, branched, and cyclic alkoxy groups,
or two R$^O$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
C$_1$-C$_6$ linear, branched, and cyclic groups, wherein the C$_1$-C$_6$ linear, branched, and cyclic groups are independently chosen from alkyl and alkoxy groups, and wherein the C$_1$-C$_6$ linear, branched, and cyclic groups are optionally substituted with 1-4 substituents independently chosen from
halogens,
hydroxy, and
C$_1$-C$_6$ linear, branched, and cyclic alkoxy groups, and (w)

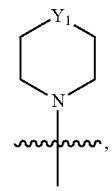

wherein Y$_1$ is chosen from oxygen, N—R$^P$, and

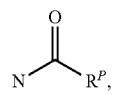

wherein R$^P$ is chosen from a C$_1$-C$_8$ linear, branched, and cyclic alkyl groups, wherein the alkyl group is optionally substituted with 1-4 substituents independently chosen from
halogens,
cyano,
hydroxy, and
C$_1$-C$_6$ linear, branched, and cyclic groups, wherein the C$_1$-C$_6$ linear, branched, and cyclic groups are independently chosen from alkyl and alkoxy groups, and wherein the C$_1$-C$_6$ linear, branched, and cyclic groups are optionally substituted with 1-4 substituents independently chosen from
halogens,
hydroxy, and
C$_1$-C$_6$ linear, branched, and cyclic alkoxy groups,
wherein 2 adjacent hydrogens on the 5- or 6-membered aromatic ring can be replaced by attachments to a second 5- or 6-membered aromatic ring comprising 0-4 heteroatoms independently chosen from O, N, and S to form a bicyclic R$^2$ group that is optionally substituted with 1-6 R$^B$ groups;
(iv) X$^1$ and X$^2$ are independently chosen from hydrogen, halogens, cyano, hydroxy, C$_1$-C$_6$ linear, branched, and cyclic groups wherein the C$_1$-C$_6$ linear, branched, and cyclic groups are independently chosen from alkyl, alkoxy, thioalkyl, and aminoalkyl groups, and wherein the C$_1$-C$_6$ linear, branched, and cyclic groups are optionally substituted by 1-4 independently chosen halogens;
(v) each of W$^1$ and W$^2$ is independently selected from C and N;
(vi) each ▬▬ represents a single or double bond, provided that no more than one ▬▬ is a double bond;
(vii) each R$^3$ is independently chosen from hydrogen, halogens, cyano, C$_1$-C$_6$ linear, branched, and cyclic alkyl groups, and C$_1$-C$_6$ linear, branched, and cyclic alkoxy groups, wherein the C$_1$-C$_6$ linear, branched, and cyclic alkyl groups and the C$_1$-C$_6$ linear, branched, and cyclic alkoxy groups are optionally substituted with 1-4 substituents independently chosen from halogens, hydroxy groups, and carboxylic acid;
(viii) n is an integer chosen from 0, 1, 2, and 3; and
(ix) Z$^1$, Z$^2$, and Z$^3$ are independently chosen from carbon, boron, nitrogen, sulfur, and oxygen, wherein when Z$^1$, Z$^2$, and/or Z$^3$ are carbon or nitrogen, the valences of carbon and nitrogen are completed with hydrogen atoms, halogen, C$_1$-C$_6$ linear, branched, and cyclic alkyl groups, and $C_1$-$C_6$ linear, branched, and cyclic alkyl groups, wherein the $C_1$-$C_6$ linear, branched, and cyclic alkyl groups and the $C_1$-$C_6$ linear, branched, and cyclic alkoxy groups are optionally substituted with 1-4 substituents independently chosen from halogens, hydroxy groups, and carboxylic acid, and wherein when $Z^1$, $Z^2$, or $Z^3$ is boron, the valence of boron is completed with a hydrogen atom or a hydroxy group.

In some embodiments, $R^0$ is chosen from heteroaryl rings.

In some embodiments, $R^0$ is phenyl.

In some embodiments, $R^0$ is unsubstituted.

In some embodiments, $R^0$ is substituted with 1-2 substituents.

In some embodiments, $R^0$ is substituted with 1-2 substituents that are independently chosen from halogens, cyano, $C_1$-$C_4$ alkyl groups, and $C_1$-$C_4$ alkoxy groups.

In some embodiments, $R^0$ is substituted with 1-2 substituents that are independently chosen from fluorine, chlorine, methyl, and methoxy.

In some embodiments, $R^1$ is chosen from $C_1$-$C_6$ linear and branched alkyl groups and $C_3$-$C_6$ cyclic alkyl groups.

In some embodiments, $R^1$ is chosen from $C_3$ branched alkyl groups and $C_6$ cyclic alkyl groups.

In some embodiments, $R^1$ is chosen from $C_4$-$C_6$ cyclic alkyl groups wherein one carbon atom is replaced by a heteroatom.

In some embodiments, $R^1$ is chosen from $C_6$ cyclic alkyl groups wherein one carbon atom is replaced by a heteroatom.

In some embodiments, $R^1$ is chosen from $C_1$-$C_4$ linear and branched alkyl groups and $C_4$-$C_6$ cyclic alkyl groups, wherein an alkyl group is substituted with a methyl, ethyl, methoxy, isopropoxy, cyano, cyanoalkyl, alkylsulfonyl, and/or hydroxy substituent.

In some embodiments, $R^1$ is chosen from

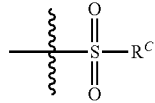

groups, wherein $R^C$ is chosen from $C_1$-$C_6$ linear, branched, and cyclic alkyl groups.

In some embodiments, $R^1$ is chosen from

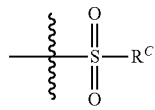

groups, wherein $R^C$ is chosen from $C_1$-$C_6$ linear, branched, and cyclic alkyl groups substituted with 1 or 2 substituents independently chosen from $C_1$-$C_6$ linear alkyl groups.

In some embodiments, $R^1$ is chosen from

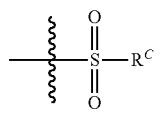

groups, wherein $R^C$ is chosen from $C_1$-$C_6$ linear alkyl groups.

In some embodiments, $R^1$ is chosen from

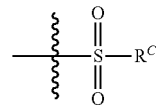

groups, wherein $R^C$ is chosen from $C_1$-$C_6$ linear alkyl groups substituted with 1 or 2 substituents independently chosen from $C_1$-$C_6$ linear alkyl groups.

In some embodiments, $R^1$ is chosen from

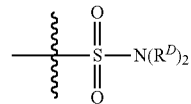

groups, wherein each $R^D$ is independently chosen from hydrogen and $C_1$-$C_8$ linear, branched, and cyclic alkyl groups.

In some embodiments, $R^1$ is chosen from

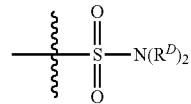

groups, wherein each $R^D$ is independently chosen from hydrogen and $C_1$-$C_8$ linear, branched, and cyclic alkyl groups substituted with 1 or 2 substituents independently chosen from $C_1$-$C_6$ linear alkyl groups.

In some embodiments, $R^1$ is chosen from

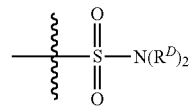

groups, wherein each $R^D$ is independently chosen from hydrogen and $C_1$-$C_8$ linear alkyl groups.

In some embodiments, $R^1$ is chosen from

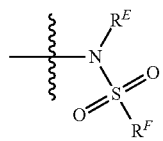

groups, wherein $R^E$ is chosen from hydrogen and $C_1$-$C_8$ linear, branched, and cyclic alkyl groups.

In some embodiments, $R^1$ is chosen from

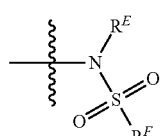

groups, wherein $R^E$ is chosen from hydrogen and $C_1$-$C_8$ linear, branched, and cyclic alkyl groups substituted with 1 or 2 substituents independently chosen from $C_1$-$C_6$ linear alkyl groups.

In some embodiments, $R^1$ is chosen from

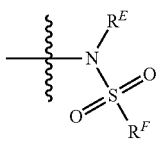

groups, wherein $R^E$ is chosen from hydrogen and $C_1$-$C_8$ linear alkyl groups.

In some embodiments, $R^1$ is chosen from

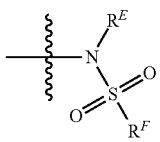

groups, wherein $R^F$ is chosen from hydroxy and $C_1$-$C_8$ linear, branched, and cyclic alkyl groups.

In some embodiments, $R^1$ is chosen from

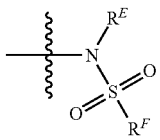

groups, wherein $R^F$ is chosen from hydroxy and $C_1$-$C_8$ linear, branched, and cyclic alkyl groups substituted with 1 or 2 substituents independently chosen from $C_1$-$C_6$ linear alkyl groups.

In some embodiments, $R^1$ is chosen from

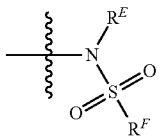

groups, wherein $R^F$ is chosen from hydroxy and $C_1$-$C_8$ linear alkyl groups.

In some embodiments, $R^1$ is chosen from

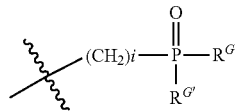

groups, wherein each of $R^G$ and $R^{G'}$ is independently chosen from $C_1$-$C_8$ linear, branched, and cyclic alkyl groups.

In some embodiments, $R^1$ is chosen from

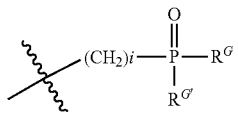

groups, wherein each of $R^G$ and $R^{G'}$ is independently chosen from $C_1$-$C_8$ linear, branched, and cyclic alkyl groups substituted with 1 or 2 substituents independently chosen from $C_1$-$C_6$ linear alkyl groups.

In some embodiments, $R^1$ is chosen from

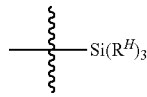

wherein each $R^H$ is independently chosen from $C_1$-$C_8$ linear, branched, and cyclic alkyl groups.

In some embodiments, $R^1$ is chosen from

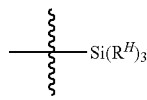

wherein each $R^H$ is independently chosen from $C_1$-$C_8$ linear, branched, and cyclic alkyl groups substituted with 1 or 2 substituents independently chosen from $C_1$-$C_6$ linear alkyl groups.

In some embodiments, $R^1$ is chosen from

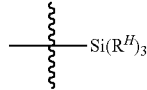

wherein each $R^H$ is independently chosen from $C_1$-$C_8$ linear alkyl groups.

In some embodiments, $R^1$ is chosen from hydrogen, methyl, trimethylsilyl, trifluoromethyl,

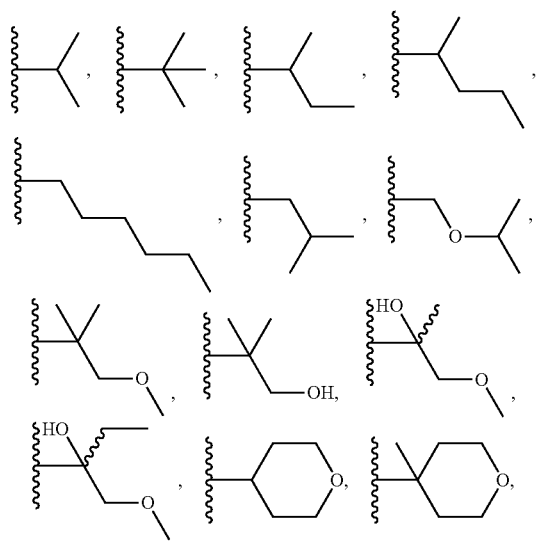

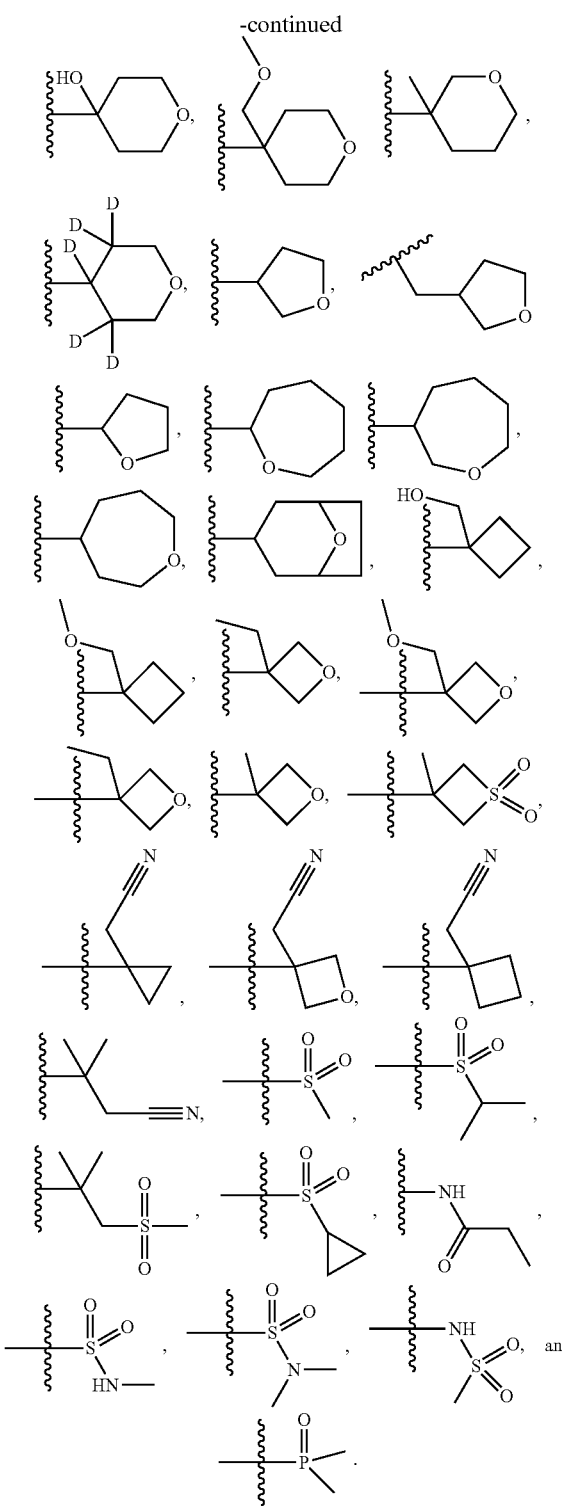

In some embodiments, $R^2$ is chosen from 5-membered aromatic rings comprising 0-4 heteroatoms chosen from O, N, and S, wherein the ring is optionally substituted with 1-4 $R^B$ groups. In some embodiments, $R^2$ is chosen from 6-membered aromatic rings comprising 0-4 heteroatoms chosen from O, N, and S, wherein the ring is optionally substituted with 1-5 $R^B$ groups.

In some embodiments, $R^2$ is chosen from 5-membered aromatic rings comprising 1 or 2 nitrogen heteroatoms, wherein the ring is optionally substituted with 1-4 $R^B$ groups. In some embodiments, $R^2$ is chosen from 6-membered aromatic rings comprising 1 or 2 nitrogen heteroatoms, wherein the ring is optionally substituted with 1-5 $R^B$ groups.

In some embodiments, $R^B$ groups are independent chosen from halogens, cyano, hydroxy, carboxylic acid, $C_1$-$C_6$ linear, branched, and cyclic alkyl groups, and $C_1$-$C_6$ linear, branched, and cyclic alkoxy groups.

In some embodiments, $R^B$ groups are independent chosen from halogens, hydroxy, carboxylic acid, $C_1$-$C_6$ linear alkyl groups, and $C_1$-$C_6$ linear alkoxy groups.

In some embodiments, $R^B$ groups are independent chosen from fluorine, chlorine, methyl, methoxy, hydroxy, and carboxylic acid.

In some embodiments, $Z^1$, $Z^2$, and $Z^3$ are independently chosen from carbon, nitrogen, sulfur, and oxygen.

In some embodiments, when $Z^1$, $Z^2$, and/or $Z^3$ are carbon or nitrogen, the valences of carbon and nitrogen are completed with hydrogen atoms.

In some embodiments, $Z^1$, $Z^2$, or $Z^3$ is boron, and the valence of boron is completed with a hydrogen atom or a hydroxy group.

In some embodiments, at least one of $Z^1$, $Z^2$, and $Z^3$ is nitrogen. In some embodiments, two of $Z^1$, $Z^2$, and $Z^3$ are nitrogen and the other is chosen from carbon and nitrogen.

In some embodiments, each $R^3$ is independently chosen from hydrogen, $C_1$-$C_6$ linear alkyl groups, and heterocyclyl groups.

In some embodiments, $X^1$ and $X^2$ are independently chosen from hydrogen and halogen.

In some embodiments, $X^1$ and $X^2$ are each hydrogen.

In some embodiments, the compound of the invention is a compound of any one of Formulae I-A, I-B, I-C, I-D, I-E, I-F, I-G, and I-H

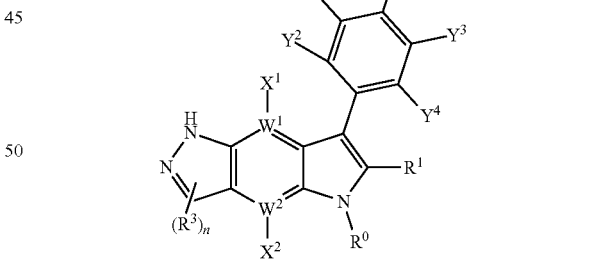

I-A

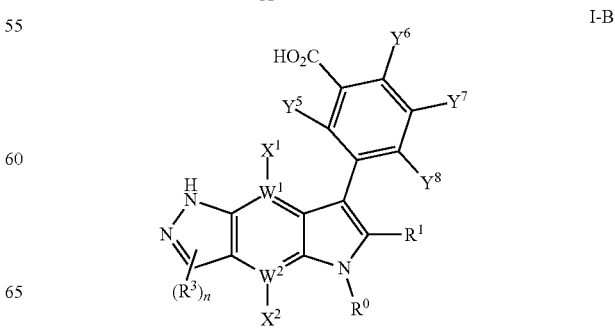

I-B

-continued

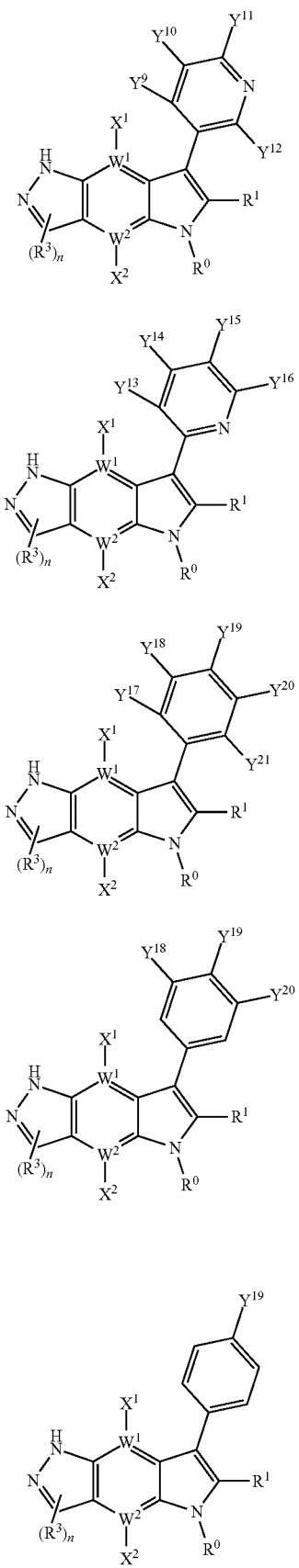

I-C

I-D

I-E

I-F

I-G

-continued

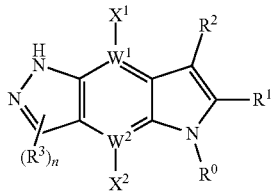

I-H a tautomer thereof, a pharmaceutically acceptable salts of such compound or tautomer, or a deuterated derivative of any of the foregoing, wherein:

$R^0$, $R^1$, $R^2$, $R^3$, and n are defined for compounds of Formula (I)

$X^1$ and $X^2$ are independently chosen from hydrogen and fluorine, or $X^1$ is fluorine and $X^2$ is hydrogen, or $X^2$ is fluorine and $X^1$ is hydrogen, or $X^1$ and $X^2$ are each hydrogen, each of $W^1$ and $W^2$ is independently selected from C and N, $Y^1$, $Y^2$, $Y^3$, and $Y^4$ are independently chosen from
hydrogen,
cyano,
halogen groups,
$C_1$-$C_6$ linear, branched, and cyclic alkyl groups,
$C_1$-$C_6$ linear, branched, and cyclic alkoxy groups that are optionally substituted with 1-4 substituents independently chosen from
hydroxy,
$C_1$-$C_6$ linear, branched, and cyclic alkyl groups, and
$C_1$-$C_6$ linear, branched, and cyclic alkoxy groups;

$Y^5$, $Y^6$, $Y^7$, and $Y^8$ are independently chosen from
hydrogen,
halogen groups
hydroxy,
$C_1$-$C_6$ linear, branched, and cyclic alkyl groups optionally substituted with 1-4 independently chosen halogen substituents, and
$C_1$-$C_6$ linear, branched, and cyclic alkoxy groups, $Y^9$, $Y^{10}$, $Y^{11}$, $Y^{12}$, $Y^{13}$, $Y^{14}$, $Y^{15}$, and $Y^{16}$ are independently chosen from
carboxylic acid,
hydrogen,
halogen groups,
$C_1$-$C_6$ linear, branched, and cyclic alkylsulfonyl groups,
$C_1$-$C_6$ linear, branched, and cyclic alkyl groups optionally substituted with 1-4 independently chosen halogen substituents, and
$C_1$-$C_6$ linear, branched, and cyclic alkoxy groups, $Y^{17}$, $Y^{18}$, $Y^{19}$, $Y^{20}$ and $Y^{21}$ are independently chosen from
hydrogen,
carboxylic acid,
halogen groups,
cyano,
hydroxy,
$C_1$-$C_6$ linear, branched, and cyclic alkyl groups that are optionally substituted with 1-4 substituents independently chosen from
halogens,
hydroxy, and
carboxylic acid,
$C_1$-$C_6$ linear, branched, and cyclic alkoxy groups that are optionally substituted with a carboxylic acid group, dihydroxyboryl,
sulfonic acid,
carboxylic acid optionally esterified with a uronic acid,
tetrazolyl groups,
aminosulfonyl groups, optionally substituted with 1 or 2 substituents independently chosen from
$C_1$-$C_6$ linear, branched, and cyclic alkyl groups, and
$C_1$-$C_6$ linear, branched, and cyclic alkylsulfonyl groups
with the proviso that, in Formula I-E, at least one of $Y^{17}$, $Y^{18}$, $Y^{19}$, $Y^{20}$, and $Y^{21}$ is hydrogen.

In some embodiments, in a compound of any one of Formulae I-A, I-B, I-C, I-D, I-E, I-F, I-G, and I-H, one or more of $Y^{17}$, $Y^{18}$, $Y^{19}$, $Y^{20}$, and $Y^{21}$ is chosen from methyl, methoxy, cyano, fluorine, hydroxy, —$CF_3$, —$B(OH)_2$, —$SO_2NHMe$, —$SO_2Me$, —$SO_2H$, —$CH_2CO_2H$,

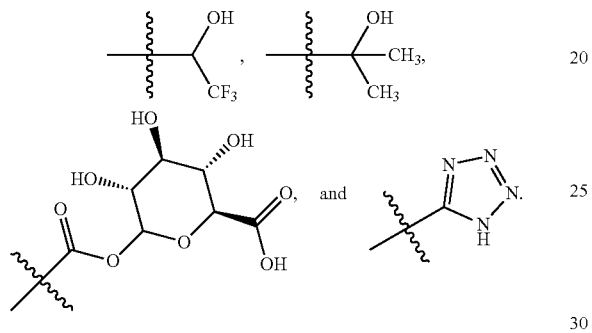

In some embodiments, a compound of the invention is a compound of Formula I':

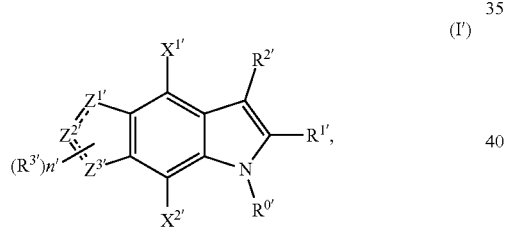

wherein:
(i) $R^{0'}$ is chosen from
(a) $C_1$-$C_8$ linear, branched, and cyclic groups, wherein the $C_1$-$C_8$ linear, branched, and cyclic groups are independently chosen from alkyl and alkoxy groups, and wherein the $C_1$-$C_8$ linear, branched, and cyclic groups are optionally substituted with 1-4 $R^{A'}$; and
(b) 5- to 14-membered aromatic rings optionally substituted with 1-4 $R^{A'}$,
wherein each $R^{A'}$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy, and wherein an $R^{A'}$ group is optionally linked to an $R^{B'}$ group on an $R^{2'}$ group;
(ii) $R^{1'}$ is chosen from
(a) hydrogen,
(b) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(c) $C_1$-$C_8$ linear, branched, and cyclic alkoxy or cyclic thioalkyl groups optionally substituted with 1-4 substituents independently chosen from
halogens,
cyano,
sulfone,
sulfonamide,
hydroxy, and
$C_1$-$C_6$ linear, branched, and cyclic alkyl groups that are optionally substituted with 1-4 halogens;
(d)

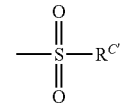

groups, wherein $R^{C'}$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;

(e)

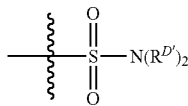

groups, wherein each $R^{D'}$ is independently chosen from
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
or two $R^{D'}$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups;

(f)

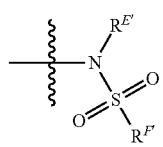

groups, wherein $R^{E'}$ is chosen from:
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(dd) 5- to 10-membered aromatic rings optionally substituted with 1-4 $R^{A'}$, and
(ee) $C_1$-$C_8$ linear, branched, and cyclic aminoalkyl groups,
and $R^{F'}$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;

(g)

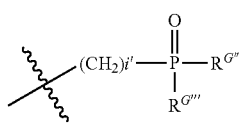

groups, wherein i' is an integer ranging from 0 to 3 and each of $R^{G''}$ and $R^{G'''}$ is independently chosen from
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(dd) amino groups
(ee) $C_1$-$C_8$ linear, branched, and cyclic aminoalkyl groups,
or $R^{G''}$ and $R^{G'''}$ together with the phosphorous atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups; and
(h)

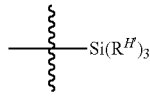

wherein each of $R^{H'}$ is independently chosen from
(aa) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(bb) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens;
(iii) $R^{2'}$ is chosen from 5- and 6-membered aromatic rings comprising 0-4 heteroatoms chosen from O, N, and S, wherein the 5-membered ring is optionally substituted with 1-4 $R^{B'}$ groups and the 6-membered ring is optionally substituted with 1-5 $R^{B'}$ groups, wherein the $R^{B'}$ groups are independently chosen from
(a) optionally substituted amides,
(b) imidazolidine-2,4-dione,
(c) optionally substituted heterocyclyls,
(d) phosphorous acid optionally esterified with a $C_1$-$C_6$ linear, branched, or cyclic alkyl group,
(e) di($C_1$-$C_6$)alkylphosphine oxides,
(f) ($C_1$-$C_6$)alkylphosphinic acids optionally esterified with a $C_1$-$C_6$ linear, branched, or cyclic alkyl group,
(g) halogens,
(h) cyano,
(i) hydroxy,
(j) carboxylic acid optionally esterified with a uronic acid or a $C_1$-$C_6$ linear, branched, or cyclic alkyl group,
(k) oxo,
(l) —B(OR$^{I'}$)$_2$ groups, wherein each $R^{I'}$ is independently chosen from hydrogen and $C_1$-$C_6$ linear, branched, and cyclic alkyl groups, or two OR$^{I'}$ groups together with the boron atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(m) 5- and 6-membered aromatic rings comprising 0-4 heteroatoms independently chosen from O, N, and S, optionally substituted with 1 or 2 substituents independently chosen from $C_1$-$C_6$ linear, branched, and cyclic alkyl groups that are optionally substituted with 1-4 substituents independently chosen from
hydroxy,
carboxylic acids,
pyrrolidin-2-one,
$C_1$-$C_6$ linear, branched, and cyclic alkyl groups, and
$C_1$-$C_6$ linear, branched, and cyclic alkylsulfonyl groups, and
$C_1$-$C_6$ linear, branched, and cyclic alkoxy groups,
(n) sulfonic acid,
(o)

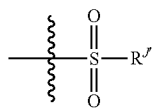

groups, wherein $R^{J'}$ is chosen from:
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens
(dd) 5- to 10-membered aromatic rings optionally substituted with 1-4 $R^{A'}$, and
(ee) $C_1$-$C_8$ linear, branched, and cyclic aminoalkyl groups,
(p)

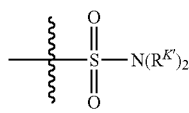

groups, wherein each $R^{K'}$ is independently chosen from:
(aa) hydrogen,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
or two $R^{K'}$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups
(q)

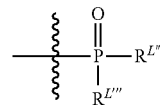

groups, wherein each of $R^{L''}$ and $R^{L'''}$ is independently chosen from
(aa) hydroxy,
(bb) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and (cc) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(dd) amino groups
(ee) $C_1$-$C_8$ linear, branched, and cyclic aminoalkyl groups,
or $R^{L''}$ and $R^{L'''}$ together with the phosphorous atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(r) $C_1$-$C_6$ linear, branched, and cyclic alkyl groups that are optionally substituted with 1-4 substituents independently chosen from
halogens,
hydroxy,
carboxylic acid, and
$C_1$-$C_6$ linear, branched, and cyclic alkoxy groups,
(s) $C_1$-$C_6$ linear, branched, and cyclic alkoxy groups that are optionally substituted with 1-4 substituents independently chosen from
halogens,
hydroxy,
carboxylic acid,
$C_1$-$C_6$ linear, branched, and cyclic alkyl groups, and
$C_1$-$C_6$ linear, branched, and cyclic alkoxy groups, and
(t)

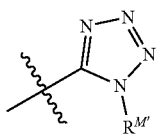

groups, wherein $R^{M'}$ is chosen from:
(aa) hydrogen,
(bb) carboxylic acid,
(cc) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
(dd) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens
(ee) 5- to 10-membered aromatic rings optionally substituted with 1-4 $R^{A'}$
(u) O—$R^{N'}$ wherein $R^{N'}$ is chosen from
(aa) $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, and
(bb) $C_1$-$C_8$ linear, branched, and cyclic alkoxy groups optionally substituted with 1-4 substituents independently chosen from
halogens,
cyano,
hydroxy, and
$C_1$-$C_6$ linear, branched, and cyclic alkyl groups that are optionally substituted with 1-4 halogens,
(v)

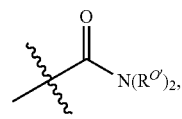

wherein each $R^{O'}$ is independently chosen from hydrogen and a $C_1$-$C_8$ linear, branched, and cyclic alkyl group, wherein the alkyl group is optionally substituted with 1-4 substituents independently chosen from
alkylsulfonyl,
alkylamide,
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
or two $R^{O'}$ groups together with the nitrogen atom to which they are bonded may form a 4-8 membered ring, optionally comprising one or two heteroatoms in addition to the nitrogen to which they are attached, and which ring is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups,
and
(w)

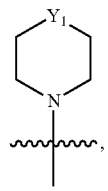

wherein $Y_1'$ is chosen from oxygen, N—$R^{P'}$, and

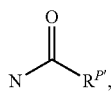

wherein $R^{P'}$ is chosen from a $C_1$-$C_8$ linear, branched, and cyclic alkyl groups, wherein the alkyl group is optionally substituted with 1-4 substituents independently chosen from
halogens,
cyano,
hydroxy, and
$C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
halogens,
hydroxy, and
$C_1$-$C_6$ linear, branched, and cyclic alkoxy groups, wherein 2 adjacent hydrogens on the 5- or 6-membered aromatic ring can be replaced by attachments to a second 5- or 6-membered aromatic ring comprising 0-4 heteroatoms independently chosen from O, N, and S to form a bicyclic $R^{2'}$ group that is optionally substituted with 1-6 $R^{B'}$ groups;

(iv) $X^{1'}$ and $X^{2'}$ are independently chosen from hydrogen, halogens, cyano, hydroxy, $C_1$-$C_6$ linear, branched, and cyclic groups wherein the $C_1$-$C_6$ linear, branched, and cyclic groups are independently chosen from alkyl, alkoxy, thioalkyl, and aminoalkyl groups, and wherein the $C_1$-$C_6$ linear, branched, and cyclic groups are optionally substituted by 1-4 independently chosen halogens;

(v) each ═══ represents a single or double bond, provided that no more than one ═══ is a double bond;

(vi) each $R^{3'}$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 independently chosen halogens;

(vii) n' is an integer chosen from 0, 1, 2, and 3; and (viii) $Z^{1'}$, $Z^{2'}$, and $Z^{3'}$ are independently chosen from carbon, boron, nitrogen, sulfur, and oxygen, wherein when $Z^{1'}$, $Z^{2'}$, and/or $Z^{3'}$ are carbon or nitrogen, the valences of carbon and nitrogen are completed with hydrogen atoms, and wherein when $Z^{1'}$, $Z^{2'}$, or $Z^{3'}$ is boron, the valence of boron is completed with a hydrogen atom or a hydroxy group.

In some embodiments, the compound of the invention is selected from Compounds 1-342 depicted in Table 1. A wavy line in a compound in Table 1 (i.e., ⌇ ) depicts a bond between two atoms and indicates a position of mixed stereochemistry for a ⌇ collection of molecules, such as a racemic mixture, cis/trans isomers, or (E)/(Z) isomers. An asterisk adjacent to an atom (e.g.,

in a compound in Table 1, indicates a stereogenic center of an unassigned, single stereoisomer in the molecule.

TABLE 1

Compounds 1-342

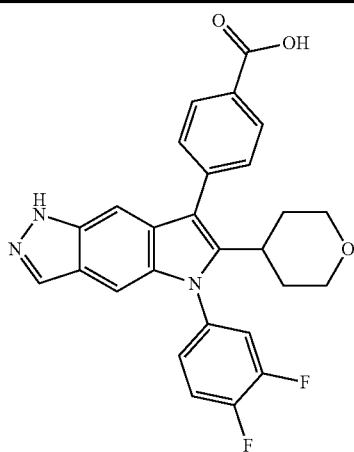

1

TABLE 1-continued
Compounds 1-342
| | |
|---|---|
| 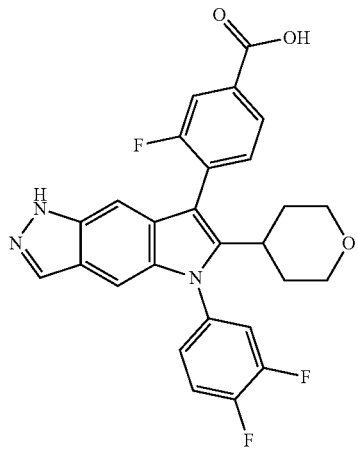 | 2 |
| 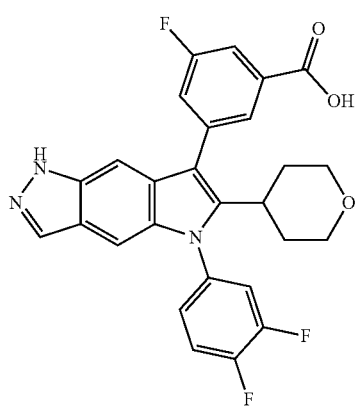 [SMILES: O=C(O)c1cc(F)cc(-c2c(C3CCOCC3)n(-c3ccc(F)c(F)c3)c3cc4cn[nH]c4cc23)c1] | 3 |
| 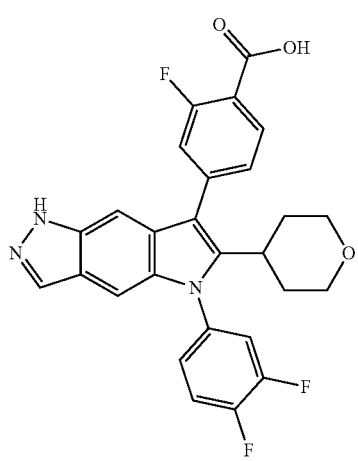 [SMILES: O=C(O)c1ccc(-c2c(C3CCOCC3)n(-c3ccc(F)c(F)c3)c3cc4cn[nH]c4cc23)cc1F] | 4 |
| 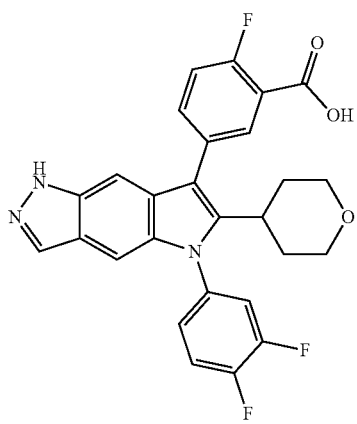 [SMILES: O=C(O)c1cc(-c2c(C3CCOCC3)n(-c3ccc(F)c(F)c3)c3cc4cn[nH]c4cc23)ccc1F] | 5 |
| 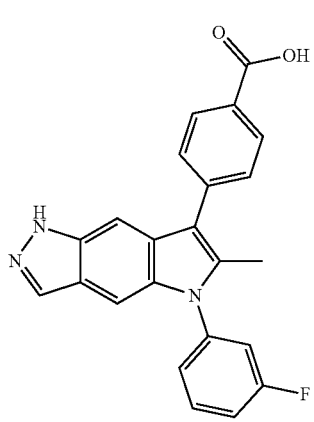 [SMILES: Cc1c(-c2ccc(C(=O)O)cc2)c2cc3[nH]ncc3cc2n1-c1cccc(F)c1] | 6 |
| 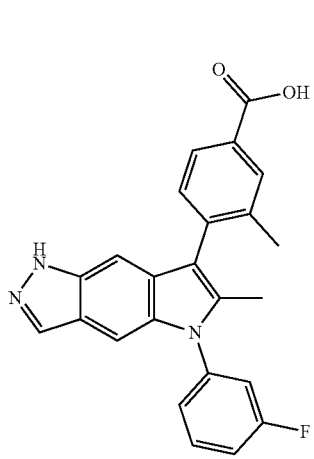 [SMILES: Cc1cc(C(=O)O)ccc1-c1c(C)n(-c2cccc(F)c2)c2cc3cn[nH]c3cc12] | 7 |

TABLE 1-continued
Compounds 1-342
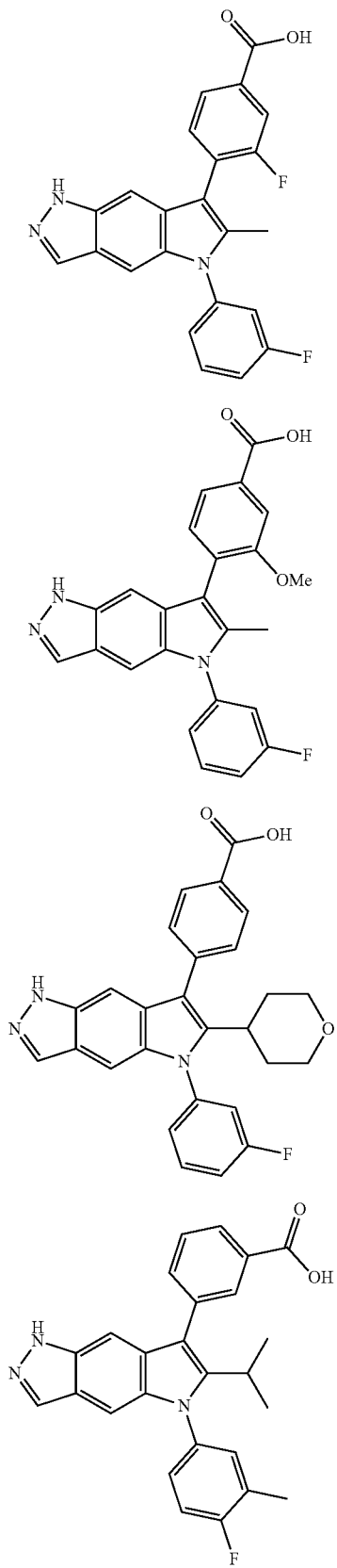
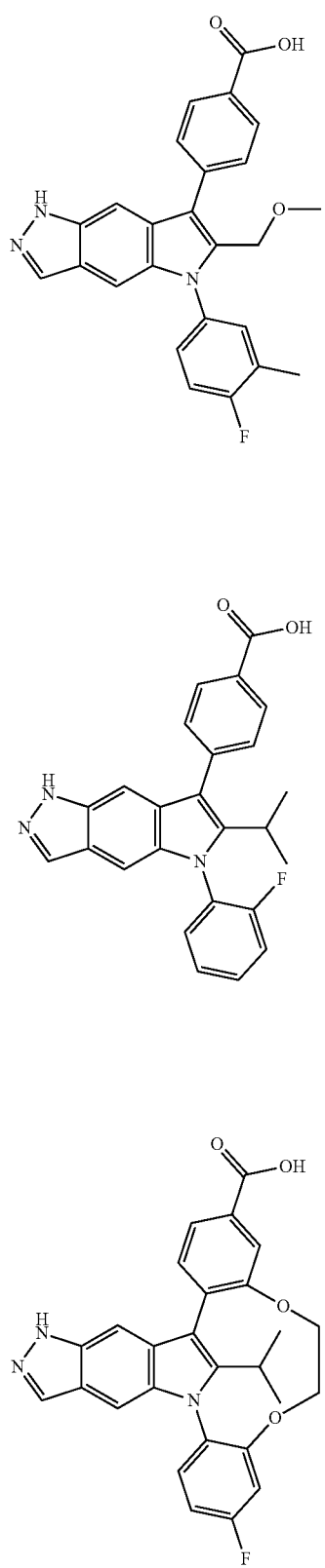

TABLE 1-continued
Compounds 1-342
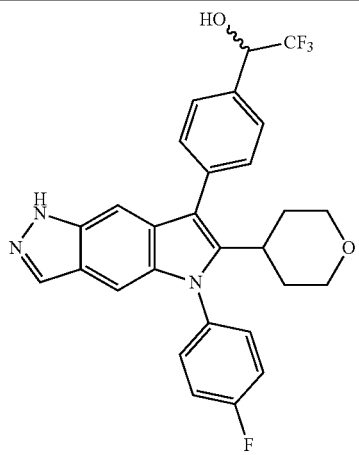
15
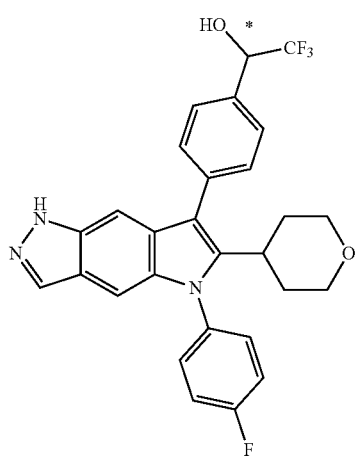
16
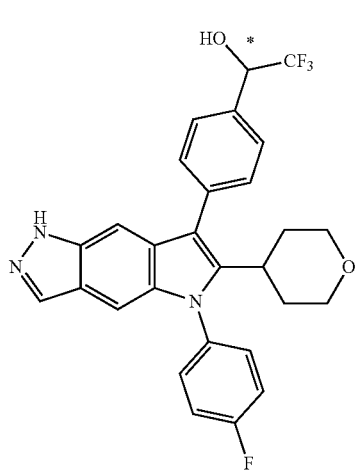 [SMILES: OC(c1ccc(-c2c(C3CCOCC3)n(-c3ccc(F)cc3)c3cc4cn[nH]c4cc23)cc1)C(F)(F)F]
17
TABLE 1-continued
Compounds 1-342
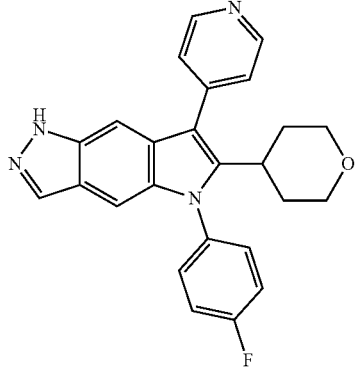 [SMILES: Fc1ccc(-n2c(C3CCOCC3)c(-c3ccncc3)c3cc4[nH]ncc4cc32)cc1]
18
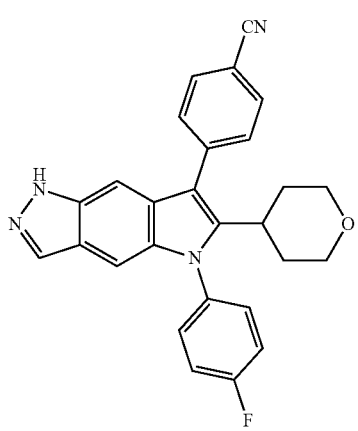 [SMILES: N#Cc1ccc(-c2c(C3CCOCC3)n(-c3ccc(F)cc3)c3cc4cn[nH]c4cc23)cc1]
19
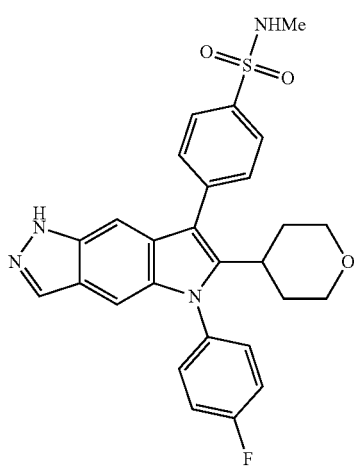 [SMILES: CNS(=O)(=O)c1ccc(-c2c(C3CCOCC3)n(-c3ccc(F)cc3)c3cc4cn[nH]c4cc23)cc1]
20

TABLE 1-continued
Compounds 1-342
21 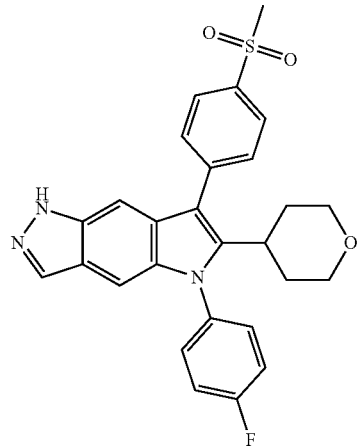 [SMILES: CS(=O)(=O)c1ccc(-c2c(C3CCOCC3)n(-c3ccc(F)cc3)c3cc4cn[nH]c4cc23)cc1]
22 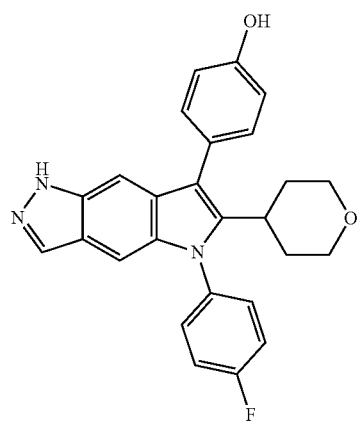
23 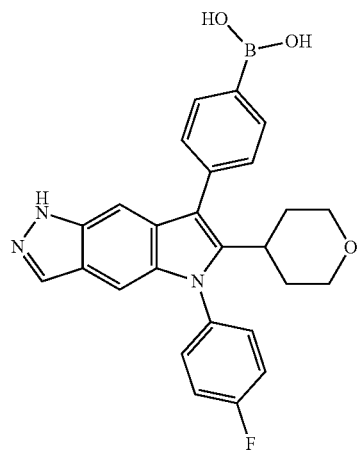 [SMILES: OB(O)c1ccc(-c2c(C3CCOCC3)n(-c3ccc(F)cc3)c3cc4cn[nH]c4cc23)cc1]
TABLE 1-continued
Compounds 1-342
24 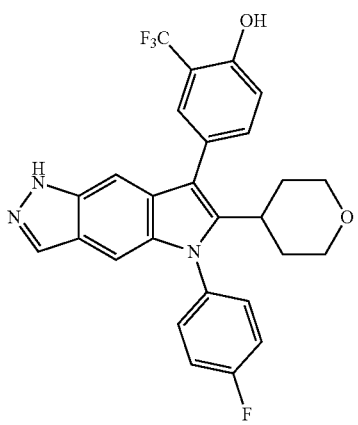 [SMILES: Oc1ccc(-c2c(C3CCOCC3)n(-c3ccc(F)cc3)c3cc4cn[nH]c4cc23)cc1C(F)(F)F]
25 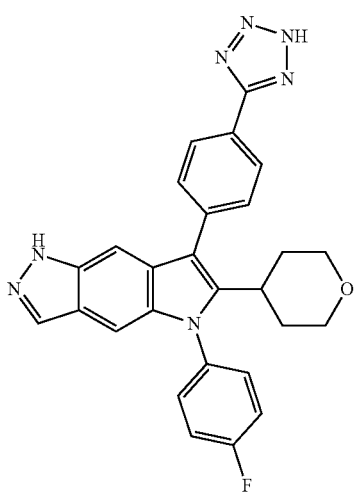 [SMILES: Fc1ccc(-n2c(C3CCOCC3)c(-c3ccc(-c4nn[nH]n4)cc3)c3cc4[nH]ncc4cc32)cc1]
26 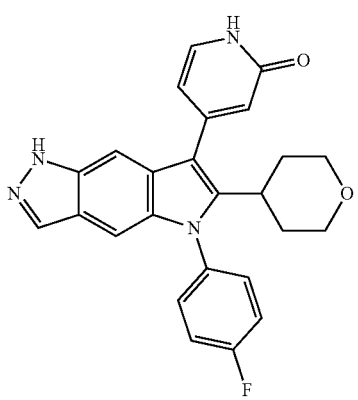

TABLE 1-continued
Compounds 1-342
27 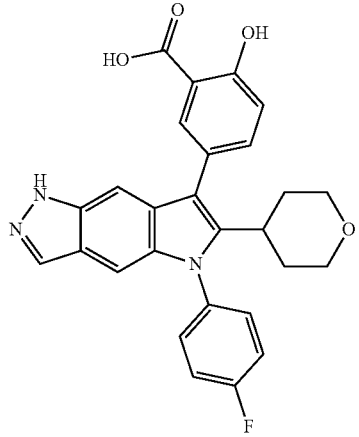
28 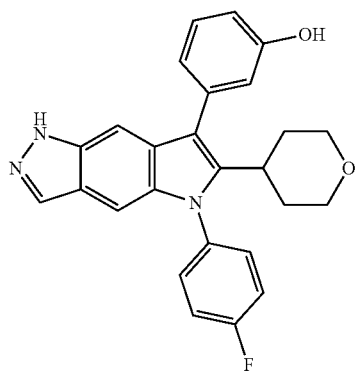
29 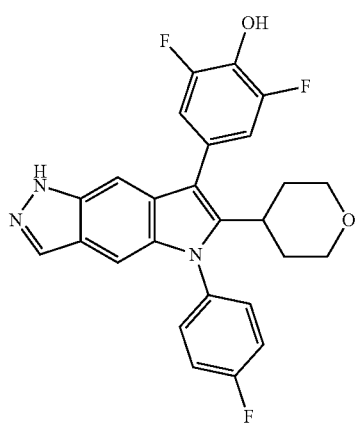 [SMILES: Oc1c(F)cc(-c2c(C3CCOCC3)n(-c3ccc(F)cc3)c3cc4cn[nH]c4cc23)cc1F]
30 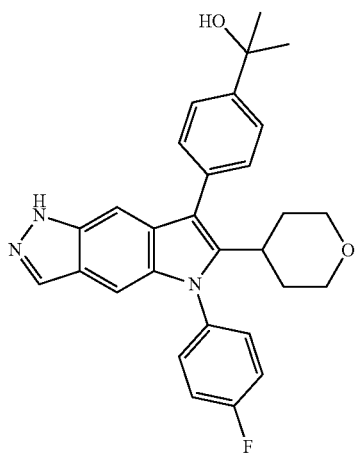 [SMILES: CC(C)(O)c1ccc(-c2c(C3CCOCC3)n(-c3ccc(F)cc3)c3cc4cn[nH]c4cc23)cc1]
31 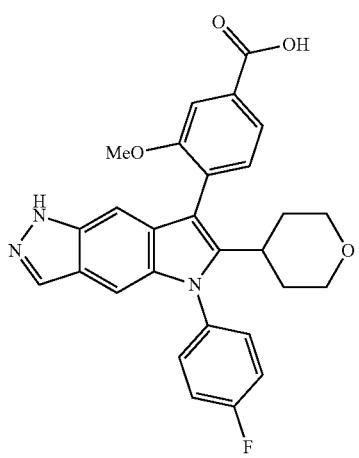 [SMILES: COc1cc(C(=O)O)ccc1-c1c(C2CCOCC2)n(-c2ccc(F)cc2)c2cc3cn[nH]c3cc12]
32 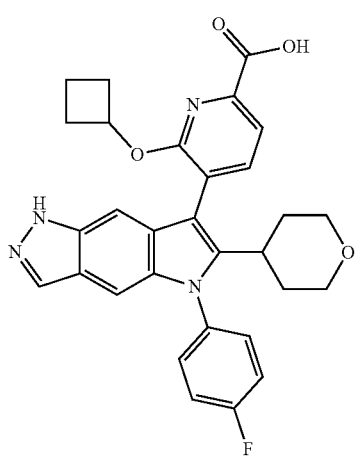 [SMILES: O=C(O)c1ccc(-c2c(C3CCOCC3)n(-c3ccc(F)cc3)c3cc4cn[nH]c4cc23)c(OC2CCC2)n1]

TABLE 1-continued
Compounds 1-342
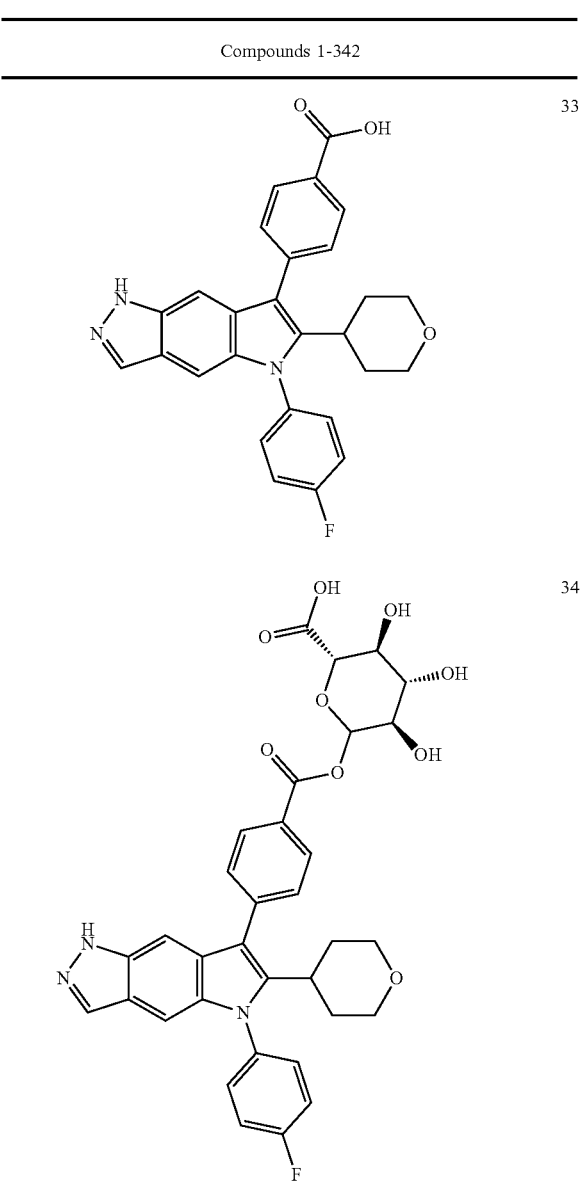
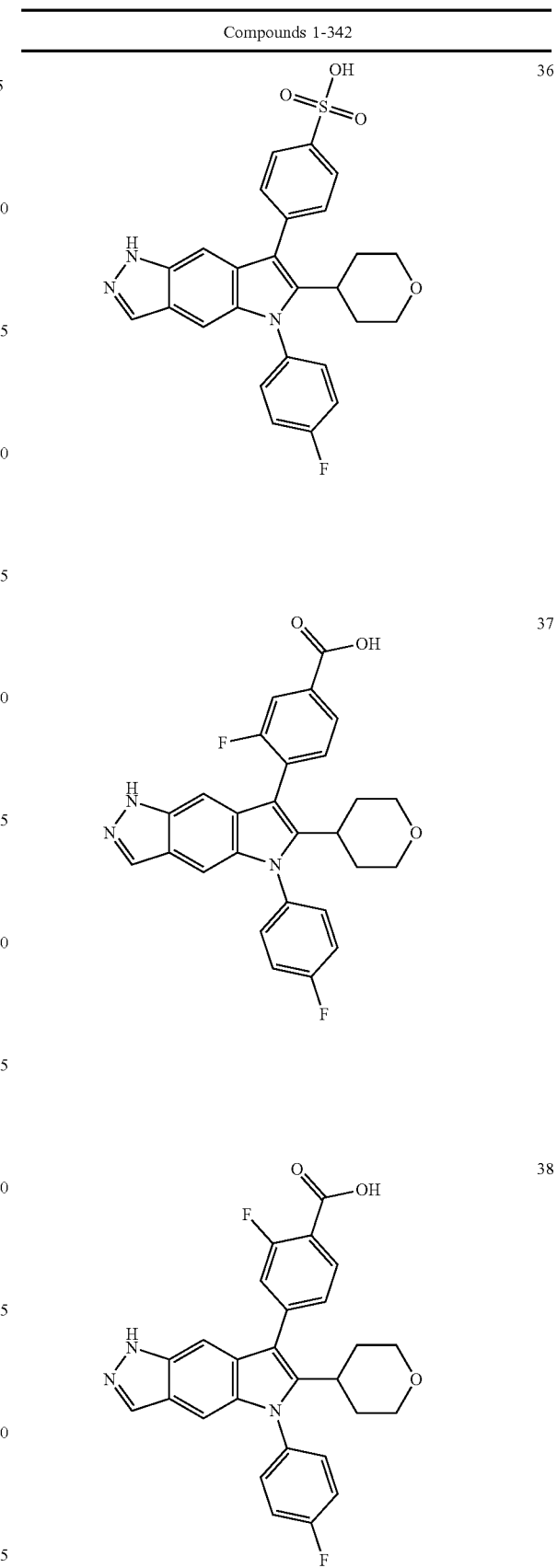

TABLE 1-continued
Compounds 1-342
39 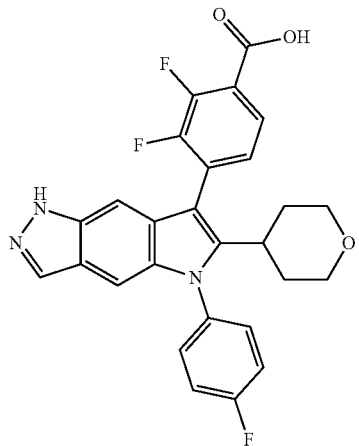 [SMILES: O=C(O)c1ccc(-c2c(C3CCOCC3)n(-c3ccc(F)cc3)c3cc4cn[nH]c4cc23)c(F)c1F]
40 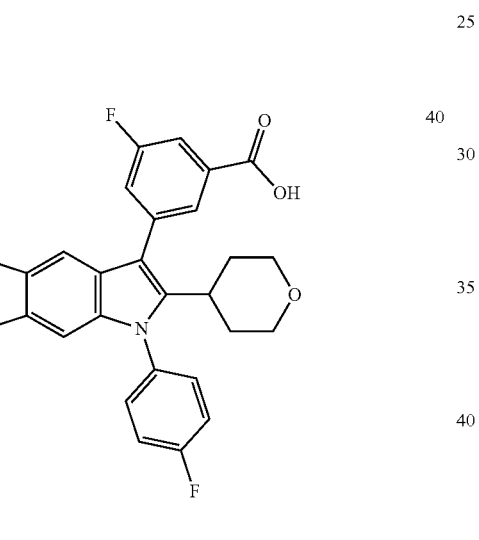
41 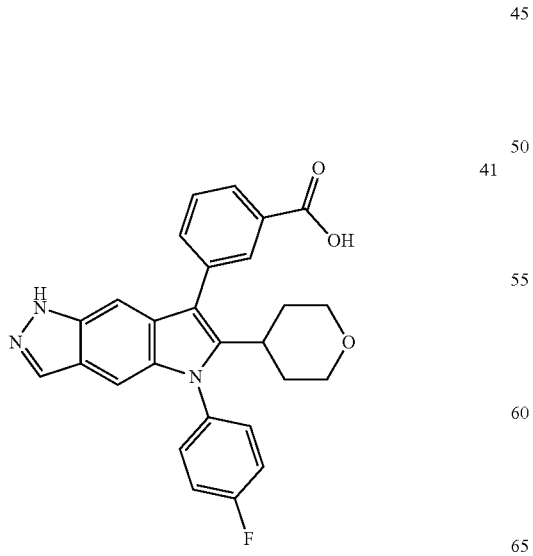
TABLE 1-continued
Compounds 1-342
42 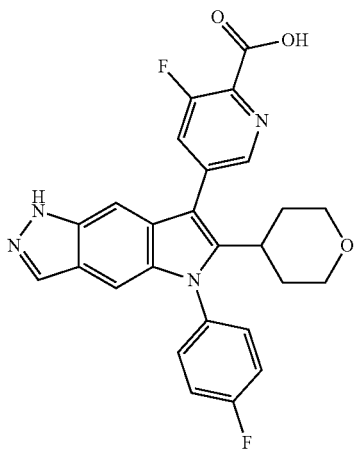
43 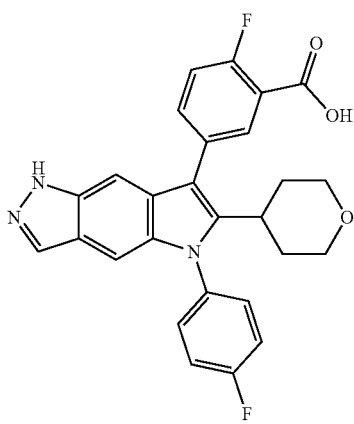 [SMILES: O=C(O)c1cc(-c2c(C3CCOCC3)n(-c3ccc(F)cc3)c3cc4cn[nH]c4cc23)ccc1F]
44 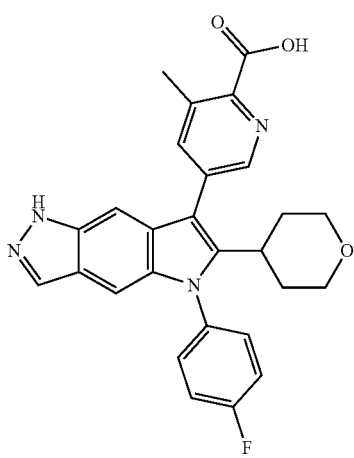 [SMILES: Cc1cc(-c2c(C3CCOCC3)n(-c3ccc(F)cc3)c3cc4cn[nH]c4cc23)cnc1C(=O)O]

TABLE 1-continued
Compounds 1-342
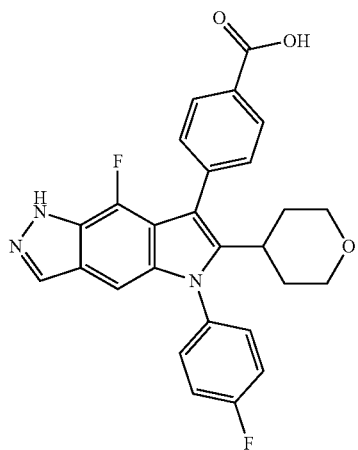
45
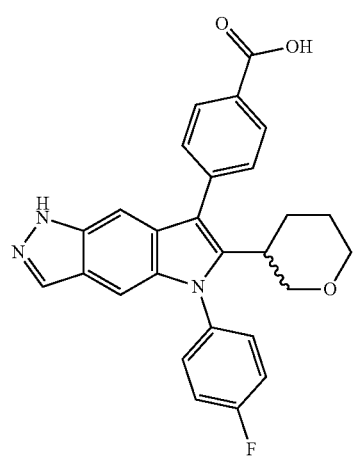 [SMILES: O=C(O)c1ccc(-c2c(C3CCCOC3)n(-c3ccc(F)cc3)c3cc4cn[nH]c4cc23)cc1]
46
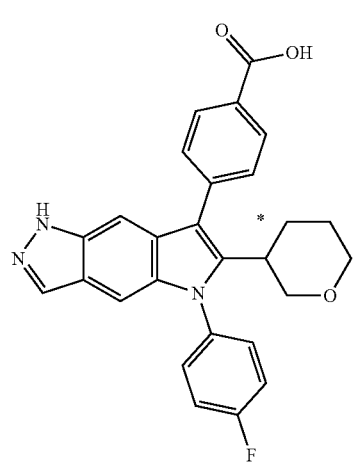 [SMILES: O=C(O)c1ccc(-c2c(C3CCCOC3)n(-c3ccc(F)cc3)c3cc4cn[nH]c4cc23)cc1]
47
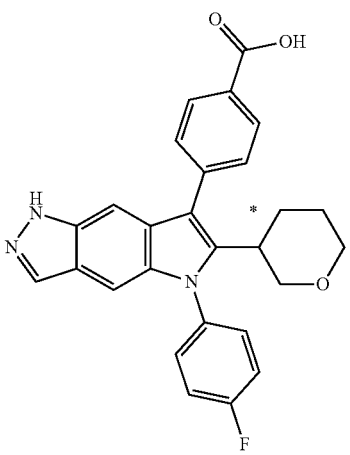 [SMILES: O=C(O)c1ccc(-c2c(C3CCCOC3)n(-c3ccc(F)cc3)c3cc4cn[nH]c4cc23)cc1]
48
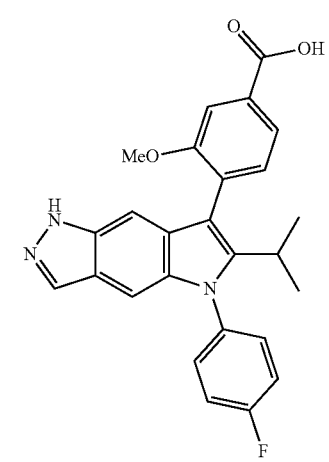 [SMILES: COc1cc(C(=O)O)ccc1-c1c(C(C)C)n(-c2ccc(F)cc2)c2cc3cn[nH]c3cc12]
49
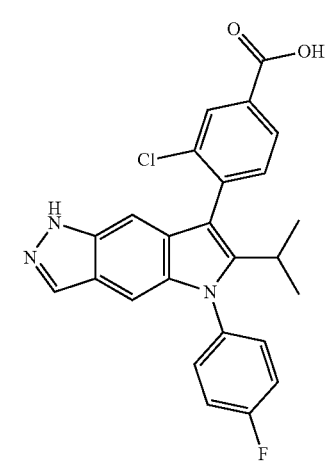
50

TABLE 1-continued
Compounds 1-342
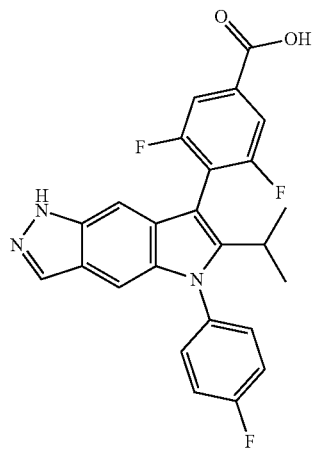 [SMILES: CC(C)c1c(-c2c(F)cc(C(=O)O)cc2F)c2cc3[nH]ncc3cc2n1-c1ccc(F)cc1] 51
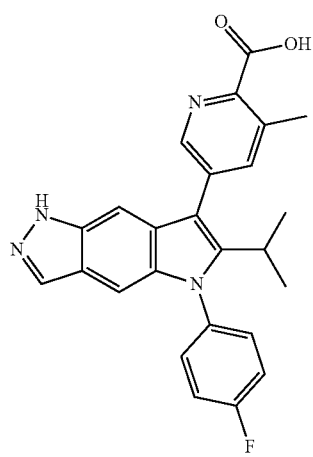 [SMILES: Cc1cc(-c2c(C(C)C)n(-c3ccc(F)cc3)c3cc4cn[nH]c4cc23)cnc1C(=O)O] 52
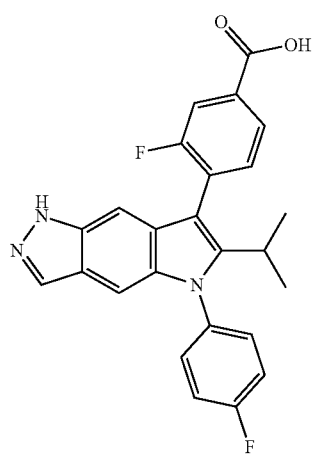 [SMILES: CC(C)c1c(-c2ccc(C(=O)O)cc2F)c2cc3[nH]ncc3cc2n1-c1ccc(F)cc1] 53
TABLE 1-continued
Compounds 1-342
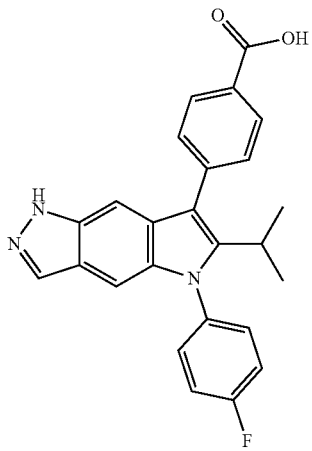 [SMILES: CC(C)c1c(-c2ccc(C(=O)O)cc2)c2cc3[nH]ncc3cc2n1-c1ccc(F)cc1] 54
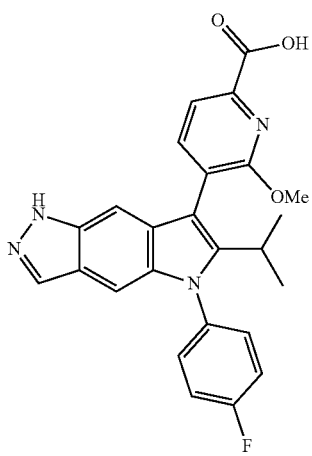 55
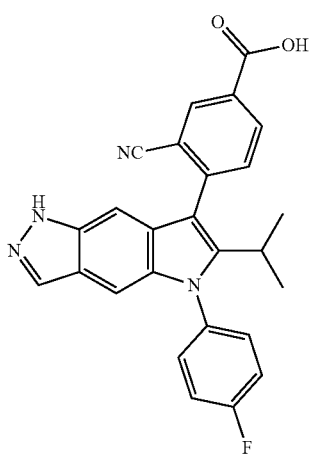 [SMILES: CC(C)c1c(-c2ccc(C(=O)O)cc2C#N)c2cc3[nH]ncc3cc2n1-c1ccc(F)cc1] 56

TABLE 1-continued
Compounds 1-342
| | |
|---|---|
| 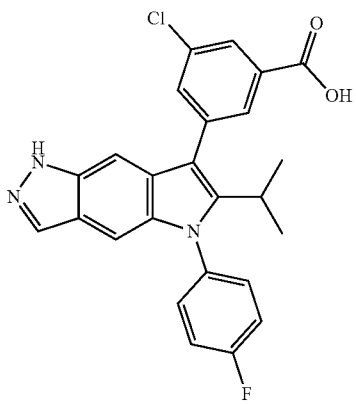 [SMILES: CC(C)c1c(-c2cc(Cl)cc(C(=O)O)c2)c2cc3[nH]ncc3cc2n1-c1ccc(F)cc1] | 57 |
| 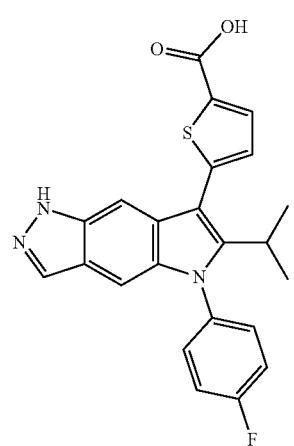 [SMILES: CC(C)c1c(-c2ccc(C(=O)O)s2)c2cc3[nH]ncc3cc2n1-c1ccc(F)cc1] | 58 |
| 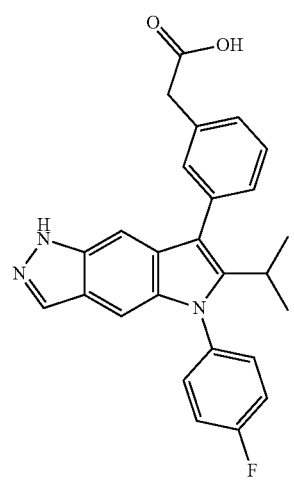 [SMILES: CC(C)c1c(-c2cccc(CC(=O)O)c2)c2cc3[nH]ncc3cc2n1-c1ccc(F)cc1] | 59 |
| 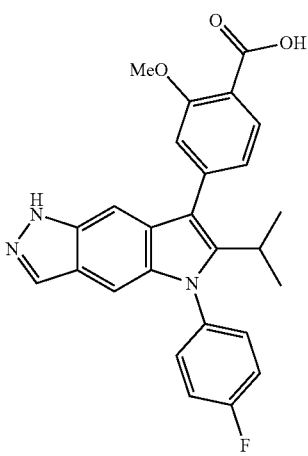 [SMILES: COc1cc(-c2c(C(C)C)n(-c3ccc(F)cc3)c3cc4cn[nH]c4cc23)ccc1C(=O)O] | 60 |
| 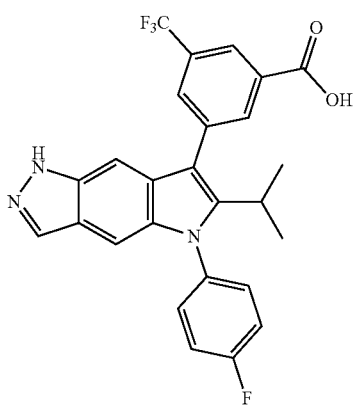 [SMILES: CC(C)c1c(-c2cc(C(=O)O)cc(C(F)(F)F)c2)c2cc3[nH]ncc3cc2n1-c1ccc(F)cc1] | 61 |
| 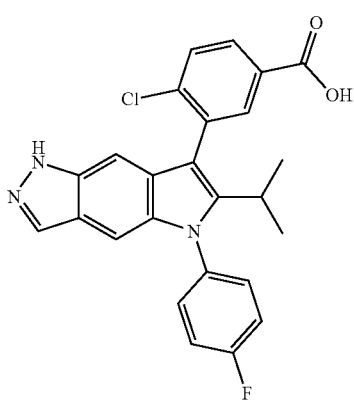 [SMILES: CC(C)c1c(-c2cc(C(=O)O)ccc2Cl)c2cc3[nH]ncc3cc2n1-c1ccc(F)cc1] | 62 |

TABLE 1-continued
Compounds 1-342
63 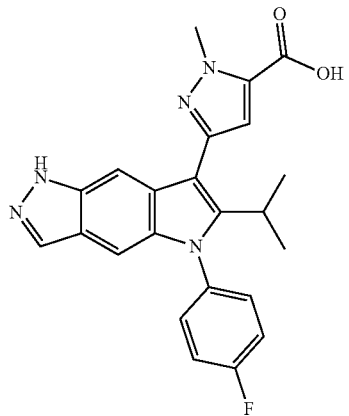 [SMILES: CC(C)c1c(-c2cc(C(=O)O)n(C)n2)c2cc3[nH]ncc3cc2n1-c1ccc(F)cc1]
64 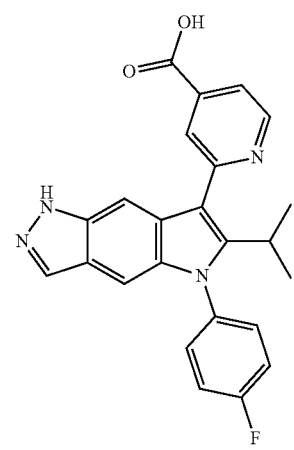 [SMILES: CC(C)c1c(-c2cc(C(=O)O)ccn2)c2cc3[nH]ncc3cc2n1-c1ccc(F)cc1]
65 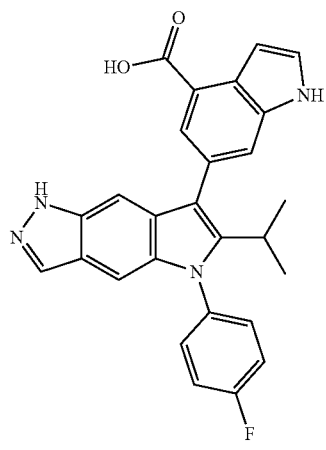 [SMILES: CC(C)c1c(-c2cc(C(=O)O)c3cc[nH]c3c2)c2cc3[nH]ncc3cc2n1-c1ccc(F)cc1]
66 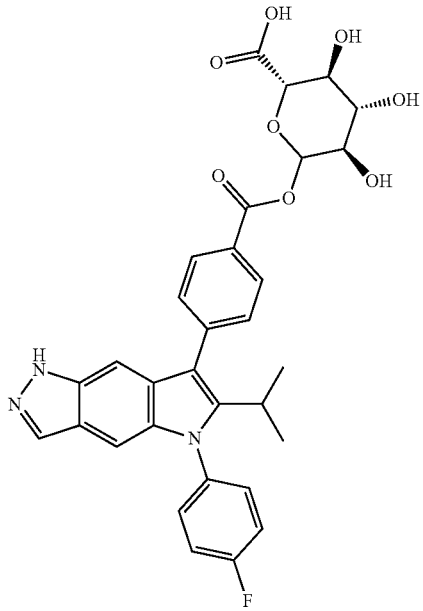 [SMILES: CC(C)c1c(-c2ccc(C(=O)OC3O[C@H](C(=O)O)[C@@H](O)[C@H](O)[C@H]3O)cc2)c2cc3[nH]ncc3cc2n1-c1ccc(F)cc1]
67 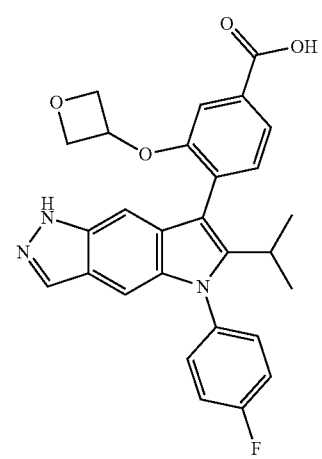 [SMILES: CC(C)c1c(-c2ccc(C(=O)O)cc2OC2COC2)c2cc3[nH]ncc3cc2n1-c1ccc(F)cc1]
68 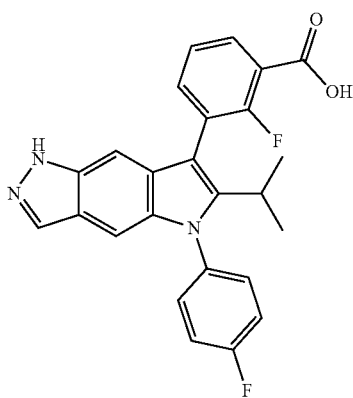 [SMILES: CC(C)c1c(-c2cccc(C(=O)O)c2F)c2cc3[nH]ncc3cc2n1-c1ccc(F)cc1]

TABLE 1-continued
Compounds 1-342
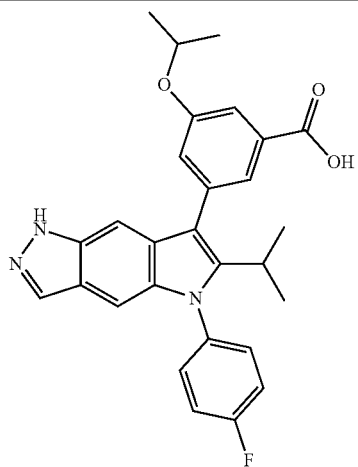
69
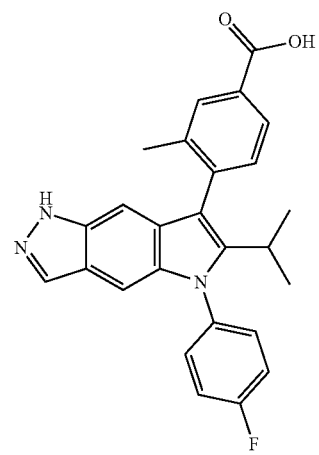 [SMILES: Cc1cc(C(=O)O)ccc1-c1c(C(C)C)n(-c2ccc(F)cc2)c2cc3cn[nH]c3cc12]
70
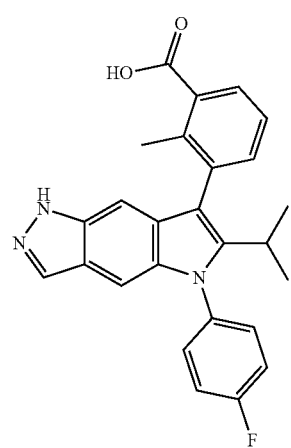 [SMILES: Cc1c(C(=O)O)cccc1-c1c(C(C)C)n(-c2ccc(F)cc2)c2cc3cn[nH]c3cc12]
71
TABLE 1-continued
Compounds 1-342
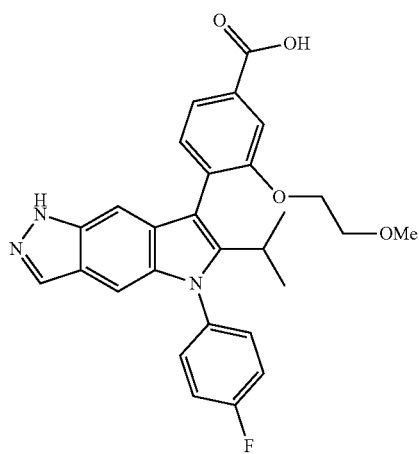 [SMILES: COCCOc1cc(C(=O)O)ccc1-c1c(C(C)C)n(-c2ccc(F)cc2)c2cc3cn[nH]c3cc12]
72
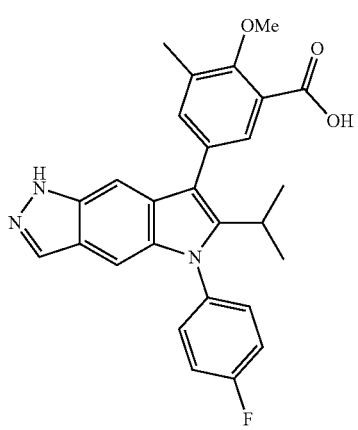 [SMILES: COc1c(C)cc(-c2c(C(C)C)n(-c3ccc(F)cc3)c3cc4cn[nH]c4cc23)cc1C(=O)O]
73
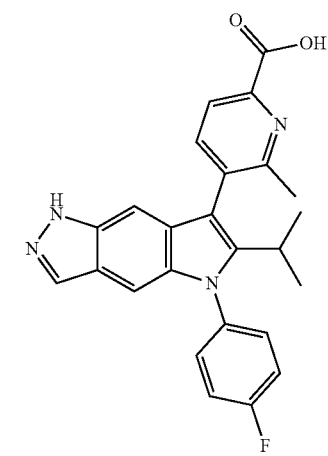 [SMILES: Cc1nc(C(=O)O)ccc1-c1c(C(C)C)n(-c2ccc(F)cc2)c2cc3cn[nH]c3cc12]
74

TABLE 1-continued
Compounds 1-342
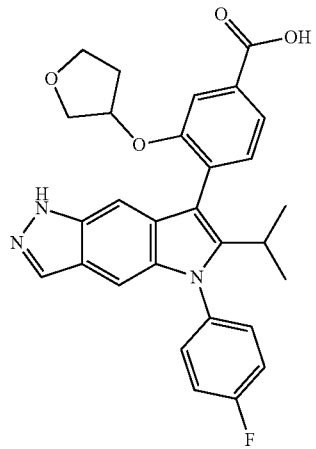 [SMILES: CC(C)c1c(-c2ccc(C(=O)O)cc2OC2CCOC2)c2cc3[nH]ncc3cc2n1-c1ccc(F)cc1]
75
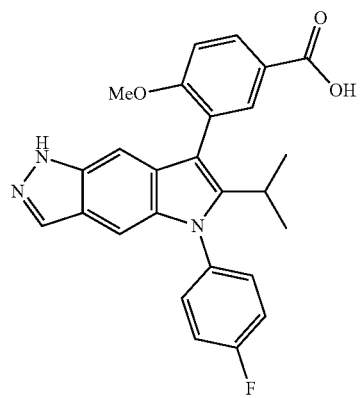
76
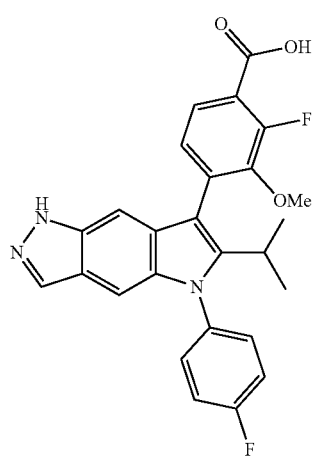 [SMILES: COc1c(-c2c(C(C)C)n(-c3ccc(F)cc3)c3cc4cn[nH]c4cc23)ccc(C(=O)O)c1F]
77
TABLE 1-continued
Compounds 1-342
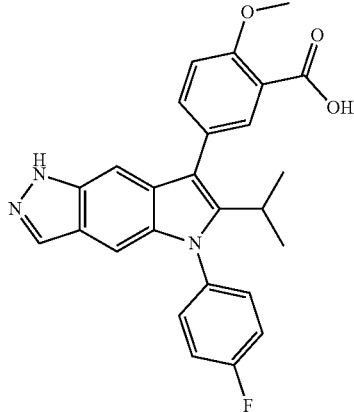 [SMILES: COc1ccc(-c2c(C(C)C)n(-c3ccc(F)cc3)c3cc4cn[nH]c4cc23)cc1C(=O)O]
78
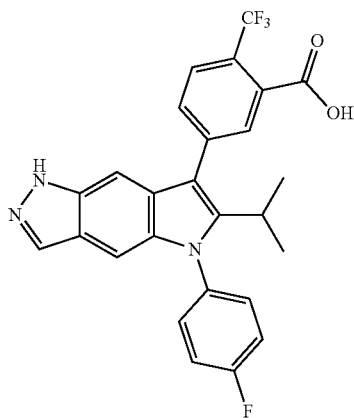 [SMILES: CC(C)c1c(-c2ccc(C(F)(F)F)c(C(=O)O)c2)c2cc3[nH]ncc3cc2n1-c1ccc(F)cc1]
79
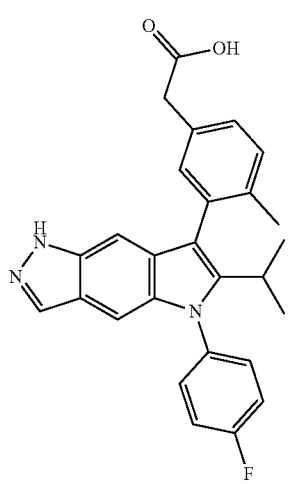 [SMILES: Cc1ccc(CC(=O)O)cc1-c1c(C(C)C)n(-c2ccc(F)cc2)c2cc3cn[nH]c3cc12]
80

TABLE 1-continued
Compounds 1-342
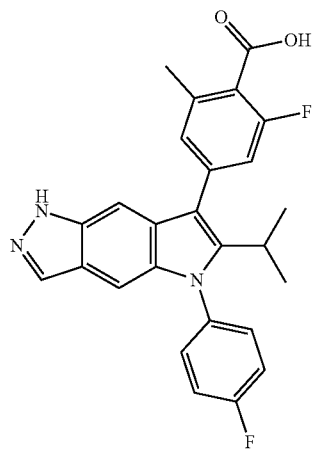 [SMILES: Cc1cc(-c2c(C(C)C)n(-c3ccc(F)cc3)c3cc4cn[nH]c4cc23)cc(F)c1C(=O)O] 81
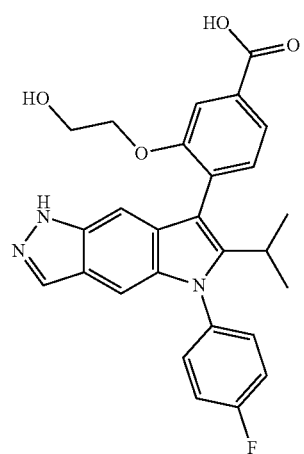 [SMILES: CC(C)c1c(-c2ccc(C(=O)O)cc2OCCO)c2cc3[nH]ncc3cc2n1-c1ccc(F)cc1] 82
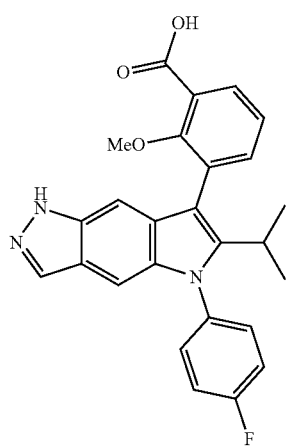 [SMILES: COc1c(C(=O)O)cccc1-c1c(C(C)C)n(-c2ccc(F)cc2)c2cc3cn[nH]c3cc12] 83
TABLE 1-continued
Compounds 1-342
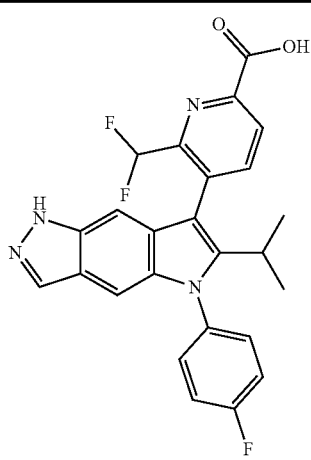 84
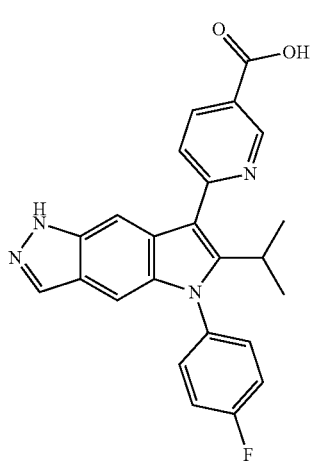 [SMILES: CC(C)c1c(-c2ccc(C(=O)O)cn2)c2cc3[nH]ncc3cc2n1-c1ccc(F)cc1] 85
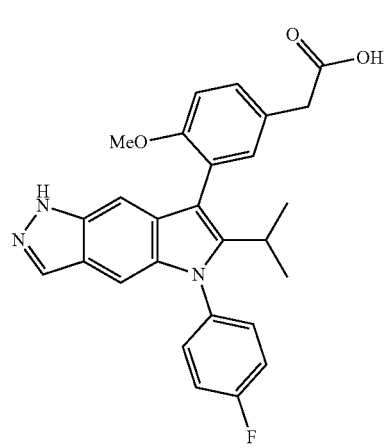 [SMILES: COc1ccc(CC(=O)O)cc1-c1c(C(C)C)n(-c2ccc(F)cc2)c2cc3cn[nH]c3cc12] 86

TABLE 1-continued
Compounds 1-342
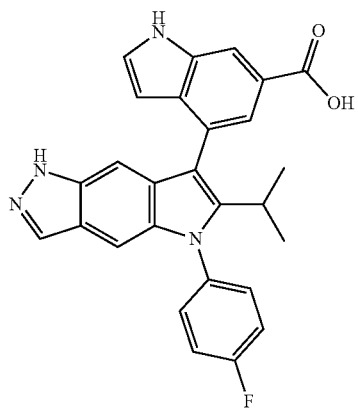 [SMILES: CC(C)c1c(-c2cc(C(=O)O)cc3[nH]ccc23)c2cc3[nH]ncc3cc2n1-c1ccc(F)cc1]
87
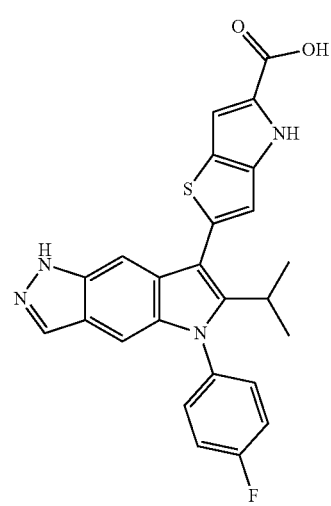 [SMILES: CC(C)c1c(-c2cc3[nH]c(C(=O)O)cc3s2)c2cc3[nH]ncc3cc2n1-c1ccc(F)cc1]
88
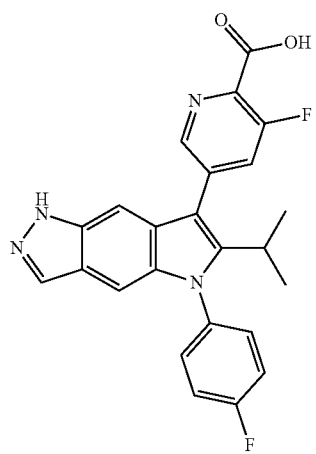 [SMILES: CC(C)c1c(-c2cnc(C(=O)O)c(F)c2)c2cc3[nH]ncc3cc2n1-c1ccc(F)cc1]
89
TABLE 1-continued
Compounds 1-342
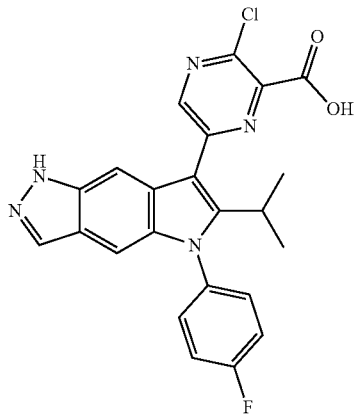 [SMILES: CC(C)c1c(-c2cnc(Cl)c(C(=O)O)n2)c2cc3[nH]ncc3cc2n1-c1ccc(F)cc1]
90
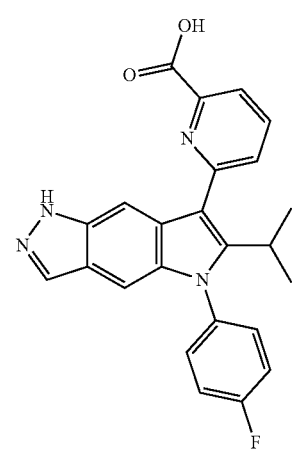 [SMILES: CC(C)c1c(-c2cccc(C(=O)O)n2)c2cc3[nH]ncc3cc2n1-c1ccc(F)cc1]
91
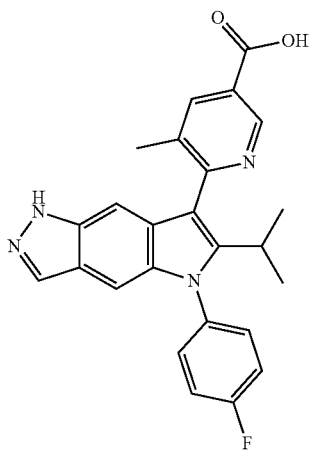 [SMILES: Cc1cc(C(=O)O)cnc1-c1c(C(C)C)n(-c2ccc(F)cc2)c2cc3cn[nH]c3cc12]
92

TABLE 1-continued
Compounds 1-342
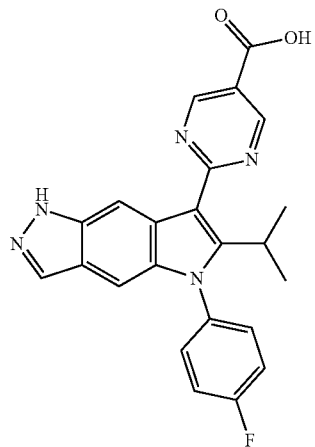 [SMILES: CC(C)c1c(-c2ncc(C(=O)O)cn2)c2cc3[nH]ncc3cc2n1-c1ccc(F)cc1]
93
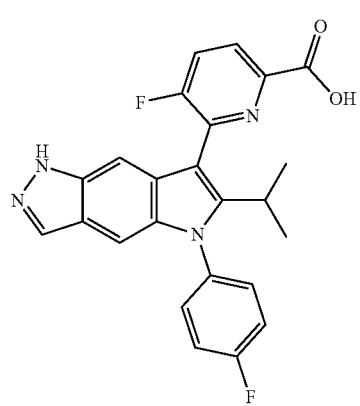 [SMILES: CC(C)c1c(-c2nc(C(=O)O)ccc2F)c2cc3[nH]ncc3cc2n1-c1ccc(F)cc1]
94
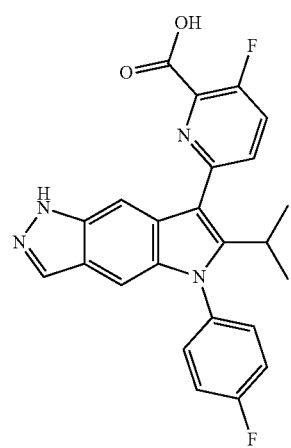 [SMILES: CC(C)c1c(-c2ccc(F)c(C(=O)O)n2)c2cc3[nH]ncc3cc2n1-c1ccc(F)cc1]
95
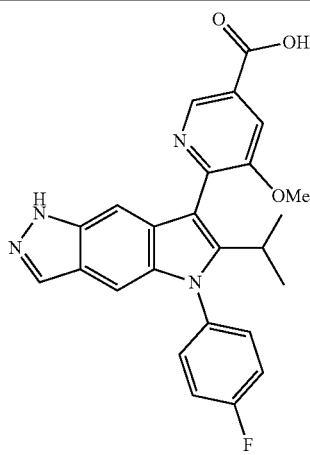
96
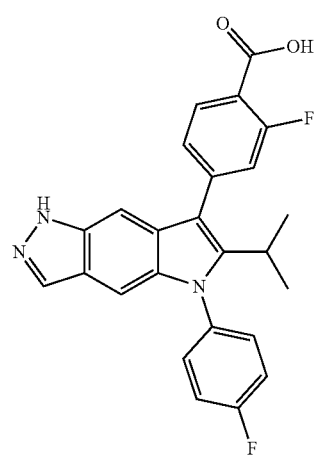 [SMILES: CC(C)c1c(-c2ccc(C(=O)O)c(F)c2)c2cc3[nH]ncc3cc2n1-c1ccc(F)cc1]
97
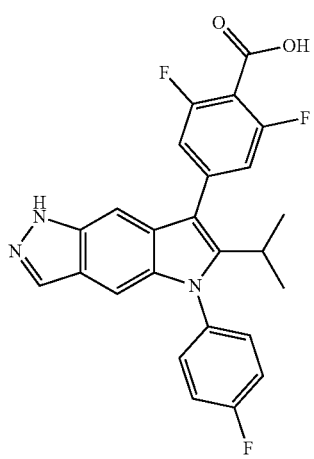 [SMILES: CC(C)c1c(-c2cc(F)c(C(=O)O)c(F)c2)c2cc3[nH]ncc3cc2n1-c1ccc(F)cc1]
98

TABLE 1-continued
Compounds 1-342
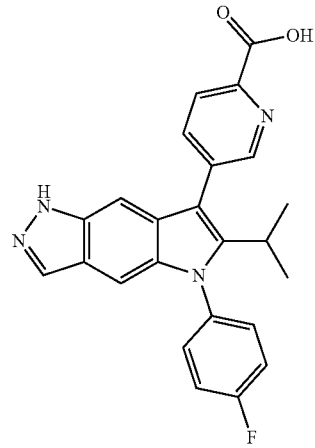 [SMILES: CC(C)c1c(-c2ccc(C(=O)O)nc2)c2cc3[nH]ncc3cc2n1-c1ccc(F)cc1]
99
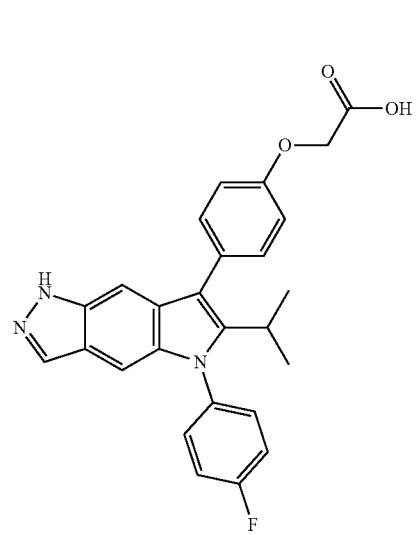 [SMILES: CC(C)c1c(-c2ccc(OCC(=O)O)cc2)c2cc3[nH]ncc3cc2n1-c1ccc(F)cc1]
100
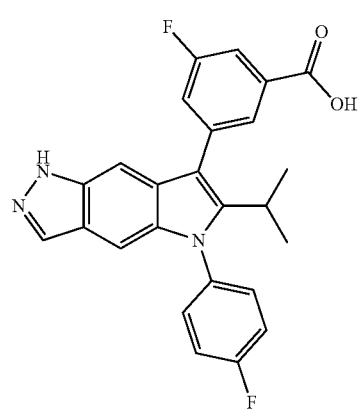 [SMILES: CC(C)c1c(-c2cc(F)cc(C(=O)O)c2)c2cc3[nH]ncc3cc2n1-c1ccc(F)cc1]
101
TABLE 1-continued
Compounds 1-342
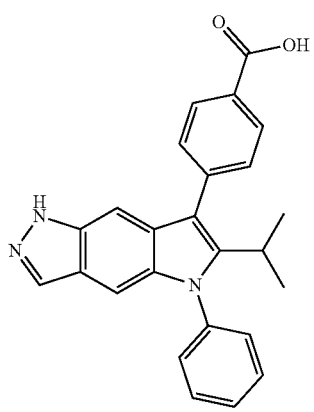 [SMILES: CC(C)c1c(-c2ccc(C(=O)O)cc2)c2cc3[nH]ncc3cc2n1-c1ccccc1]
102
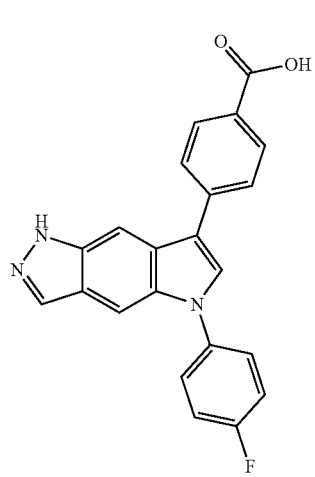 [SMILES: O=C(O)c1ccc(-c2cn(-c3ccc(F)cc3)c3cc4cn[nH]c4cc23)cc1]
103
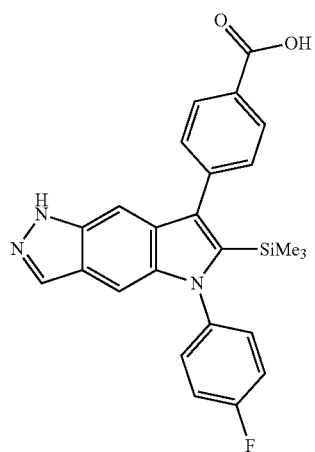 [SMILES: C[Si](C)(C)c1c(-c2ccc(C(=O)O)cc2)c2cc3[nH]ncc3cc2n1-c1ccc(F)cc1]
104

TABLE 1-continued
Compounds 1-342
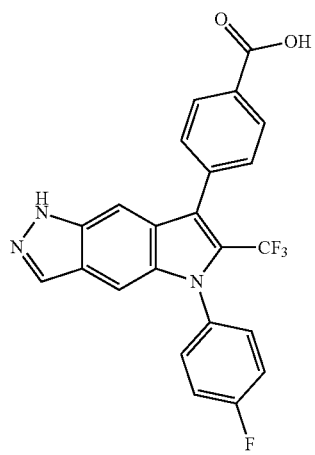 [SMILES: O=C(O)c1ccc(-c2c(C(F)(F)F)n(-c3ccc(F)cc3)c3cc4cn[nH]c4cc23)cc1] 105
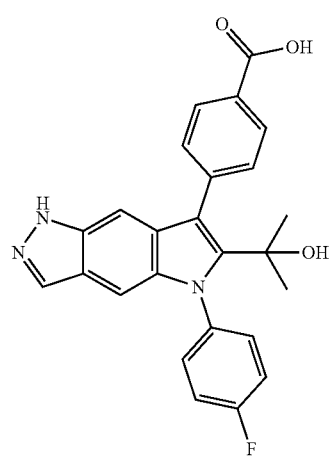 [SMILES: CC(C)(O)c1c(-c2ccc(C(=O)O)cc2)c2cc3[nH]ncc3cc2n1-c1ccc(F)cc1] 106
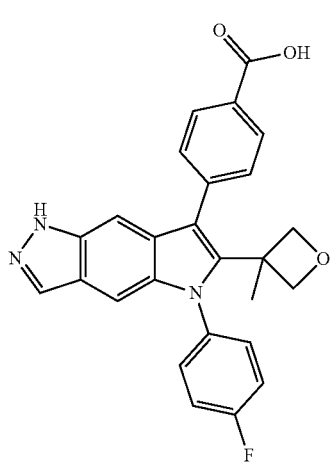 [SMILES: CC1(c2c(-c3ccc(C(=O)O)cc3)c3cc4[nH]ncc4cc3n2-c2ccc(F)cc2)COC1] 107
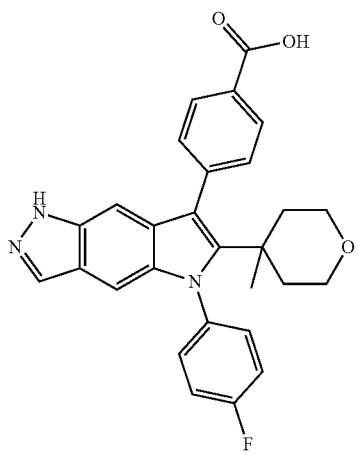 [SMILES: CC1(c2c(-c3ccc(C(=O)O)cc3)c3cc4[nH]ncc4cc3n2-c2ccc(F)cc2)CCOCC1] 108
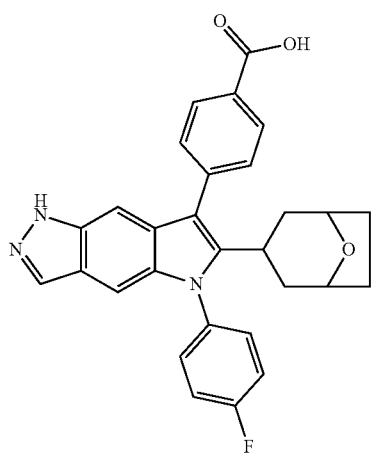 [SMILES: O=C(O)c1ccc(-c2c(C3CC4CCC(C3)O4)n(-c3ccc(F)cc3)c3cc4cn[nH]c4cc23)cc1] 109
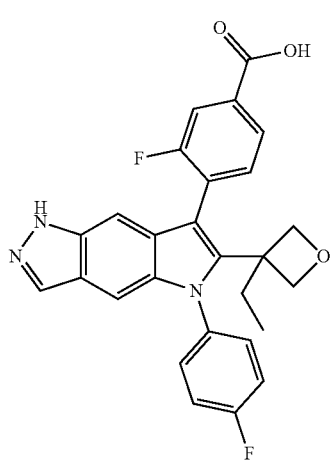 [SMILES: CCC1(c2c(-c3ccc(C(=O)O)cc3F)c3cc4[nH]ncc4cc3n2-c2ccc(F)cc2)COC1] 110

TABLE 1-continued
Compounds 1-342
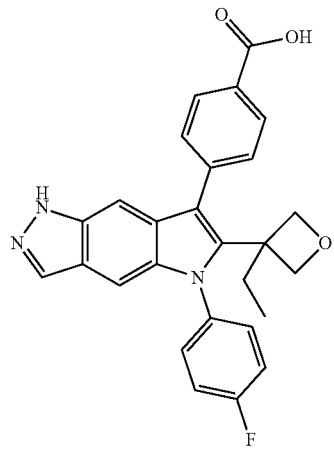 [SMILES: CCC1(c2c(-c3ccc(C(=O)O)cc3)c3cc4[nH]ncc4cc3n2-c2ccc(F)cc2)COC1]
111
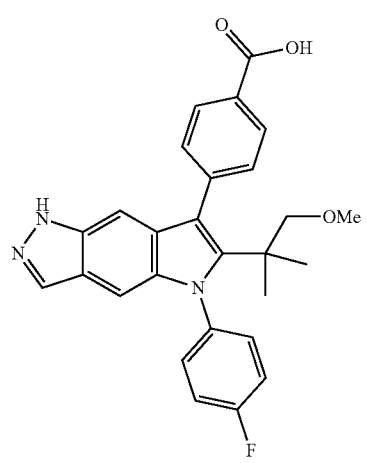 [SMILES: COCC(C)(C)c1c(-c2ccc(C(=O)O)cc2)c2cc3[nH]ncc3cc2n1-c1ccc(F)cc1]
112
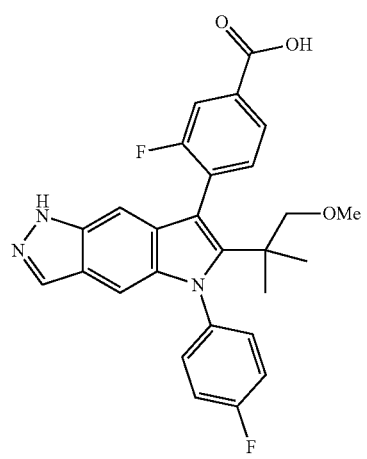 [SMILES: COCC(C)(C)c1c(-c2ccc(C(=O)O)cc2F)c2cc3[nH]ncc3cc2n1-c1ccc(F)cc1]
113
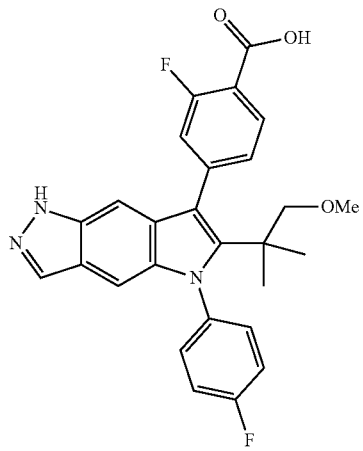 [SMILES: COCC(C)(C)c1c(-c2ccc(C(=O)O)c(F)c2)c2cc3[nH]ncc3cc2n1-c1ccc(F)cc1]
114
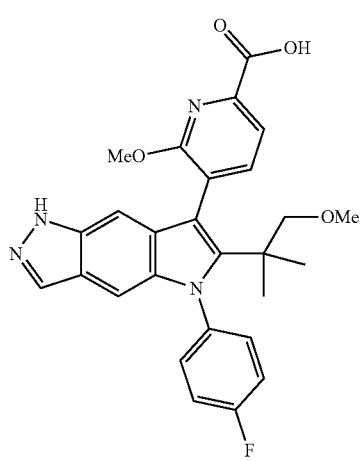 [SMILES: COCC(C)(C)c1c(-c2ccc(C(=O)O)nc2OC)c2cc3[nH]ncc3cc2n1-c1ccc(F)cc1]
115
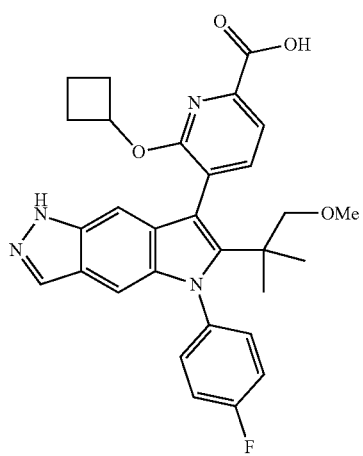 [SMILES: COCC(C)(C)c1c(-c2ccc(C(=O)O)nc2OC2CCC2)c2cc3[nH]ncc3cc2n1-c1ccc(F)cc1]
116

TABLE 1-continued
Compounds 1-342
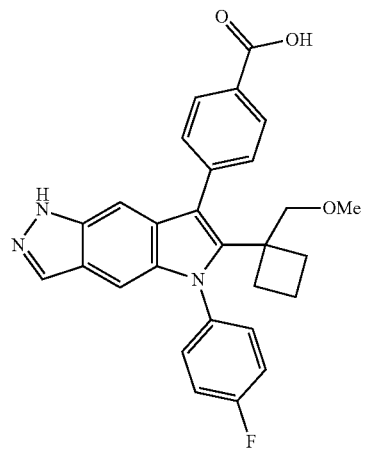 [SMILES: COCC1(c2c(-c3ccc(C(=O)O)cc3)c3cc4[nH]ncc4cc3n2-c2ccc(F)cc2)CCC1]
117
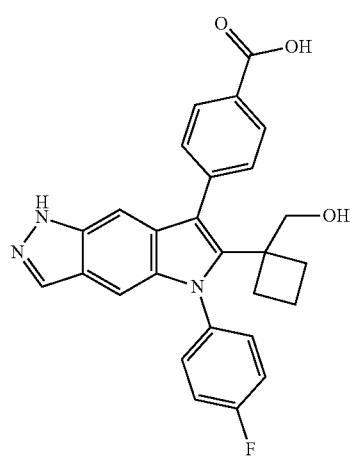 [SMILES: O=C(O)c1ccc(-c2c(C3(CO)CCC3)n(-c3ccc(F)cc3)c3cc4cn[nH]c4cc23)cc1]
118
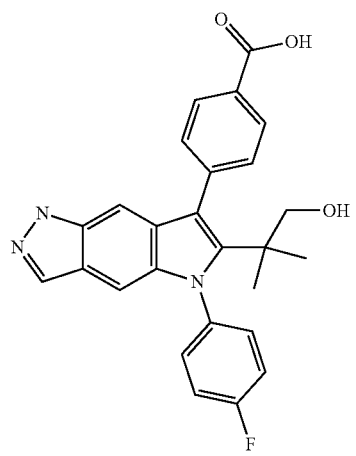 [SMILES: CC(C)(CO)c1c(-c2ccc(C(=O)O)cc2)c2cc3[nH]ncc3cc2n1-c1ccc(F)cc1]
119
TABLE 1-continued
Compounds 1-342
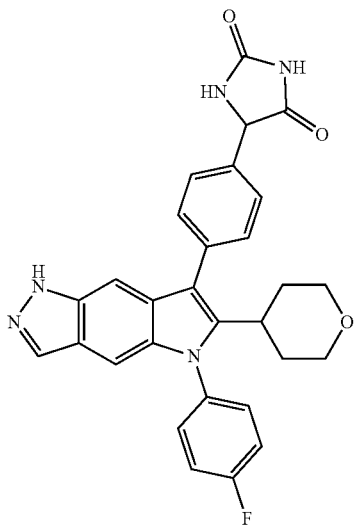 [SMILES: O=C1NC(=O)C(c2ccc(-c3c(C4CCOCC4)n(-c4ccc(F)cc4)c4cc5cn[nH]c5cc34)cc2)N1]
120
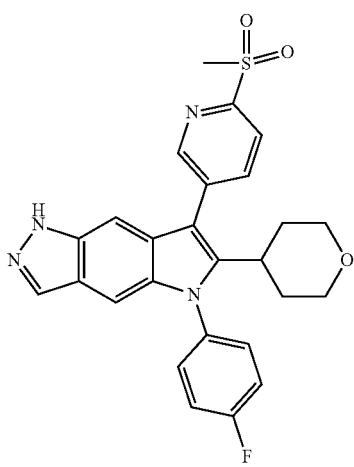 [SMILES: CS(=O)(=O)c1ccc(-c2c(C3CCOCC3)n(-c3ccc(F)cc3)c3cc4cn[nH]c4cc23)cn1]
121
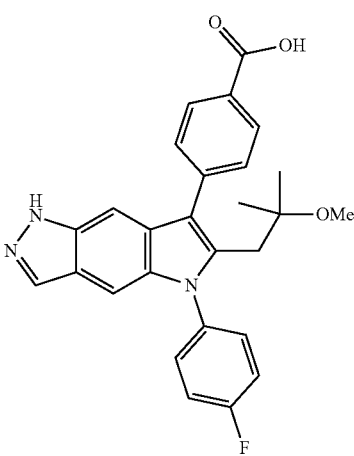 [SMILES: COC(C)(C)Cc1c(-c2ccc(C(=O)O)cc2)c2cc3[nH]ncc3cc2n1-c1ccc(F)cc1]
122

TABLE 1-continued
Compounds 1-342
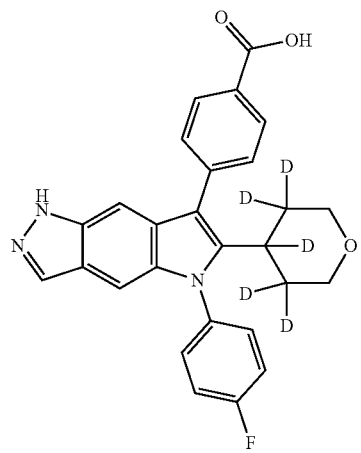
123
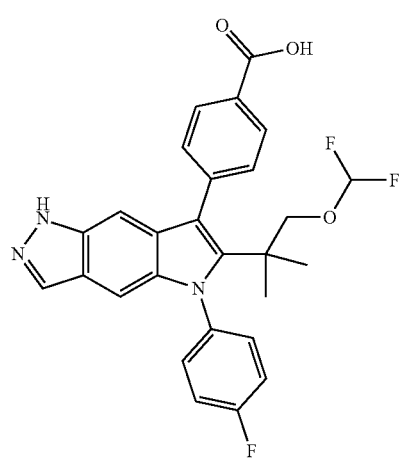 [SMILES: CC(C)(COC(F)F)c1c(-c2ccc(C(=O)O)cc2)c2cc3[nH]ncc3cc2n1-c1ccc(F)cc1]
124
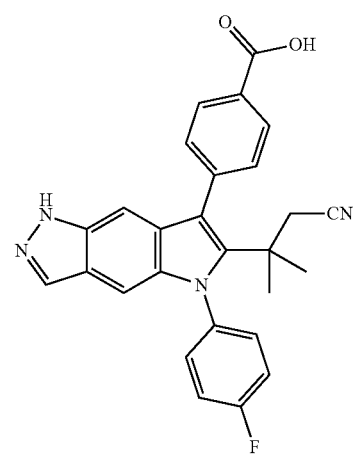 [SMILES: CC(C)(CC#N)c1c(-c2ccc(C(=O)O)cc2)c2cc3[nH]ncc3cc2n1-c1ccc(F)cc1]
125
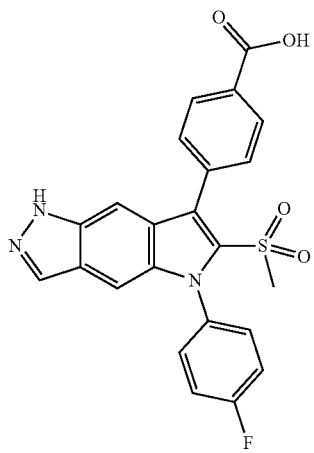 [SMILES: CS(=O)(=O)c1c(-c2ccc(C(=O)O)cc2)c2cc3[nH]ncc3cc2n1-c1ccc(F)cc1]
126
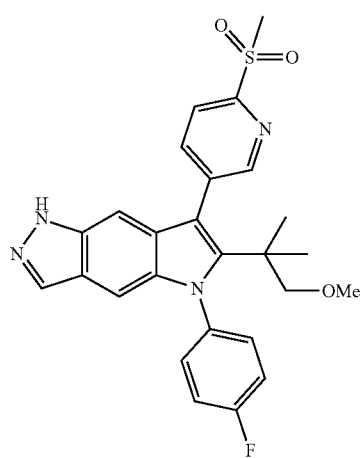 [SMILES: COCC(C)(C)c1c(-c2ccc(S(C)(=O)=O)nc2)c2cc3[nH]ncc3cc2n1-c1ccc(F)cc1]
127
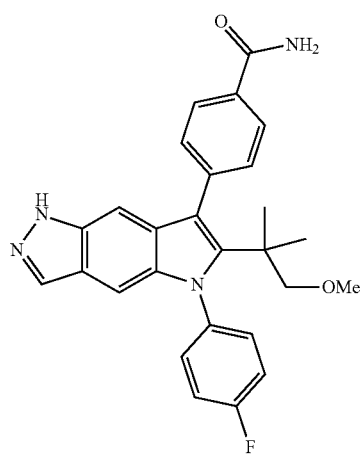 [SMILES: COCC(C)(C)c1c(-c2ccc(C(N)=O)cc2)c2cc3[nH]ncc3cc2n1-c1ccc(F)cc1]
128

TABLE 1-continued
Compounds 1-342
| 129 | 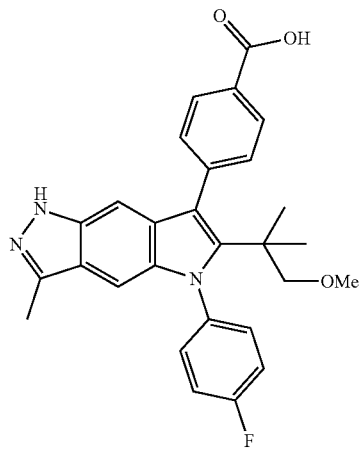 [SMILES: COCC(C)(C)c1c(-c2ccc(C(=O)O)cc2)c2cc3[nH]nc(C)c3cc2n1-c1ccc(F)cc1] |
| 130 | 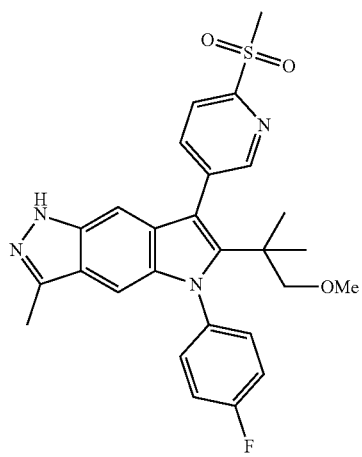 [SMILES: COCC(C)(C)c1c(-c2ccc(S(C)(=O)=O)nc2)c2cc3[nH]nc(C)c3cc2n1-c1ccc(F)cc1] |
| 131 |  |
| 132 | 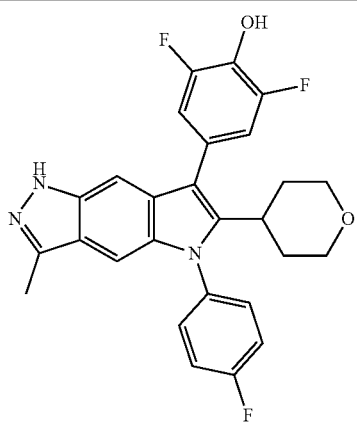 [SMILES: Cc1n[nH]c2cc3c(-c4cc(F)c(O)c(F)c4)c(C4CCOCC4)n(-c4ccc(F)cc4)c3cc12] |
| 133 | 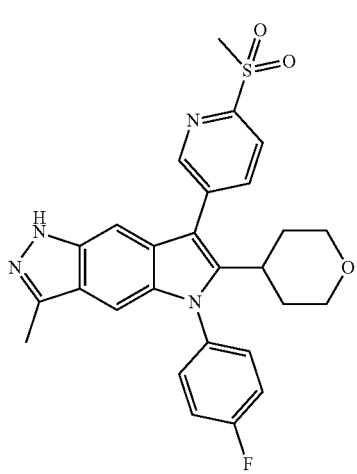 [SMILES: Cc1n[nH]c2cc3c(-c4ccc(S(C)(=O)=O)nc4)c(C4CCOCC4)n(-c4ccc(F)cc4)c3cc12] |
| 134 | 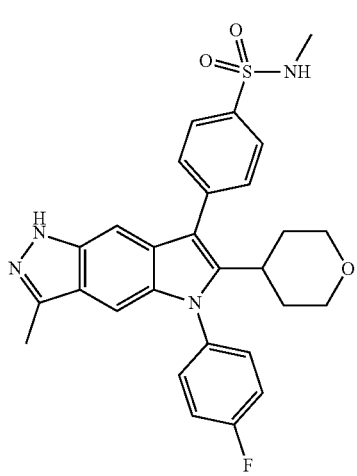 [SMILES: CNS(=O)(=O)c1ccc(-c2c(C3CCOCC3)n(-c3ccc(F)cc3)c3cc4c(C)n[nH]c4cc23)cc1] |

TABLE 1-continued
Compounds 1-342
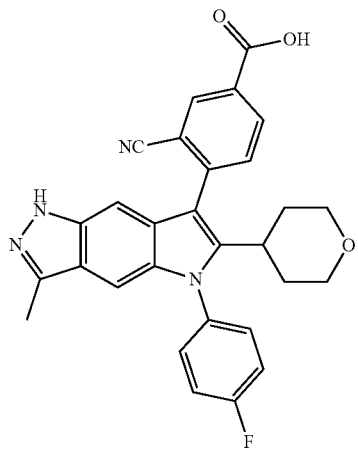 135
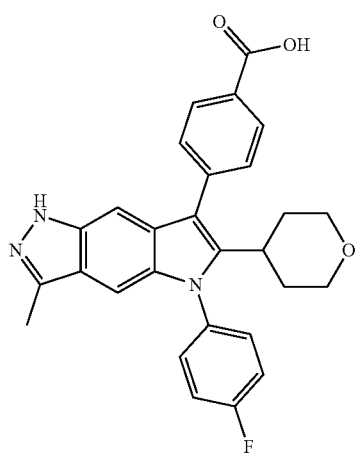 136
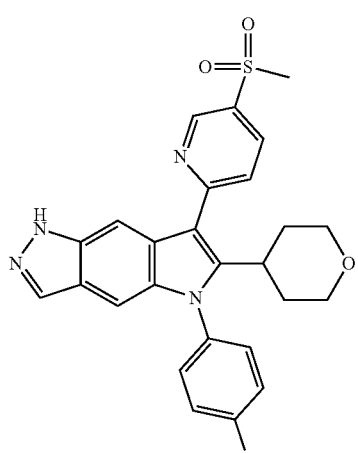 137
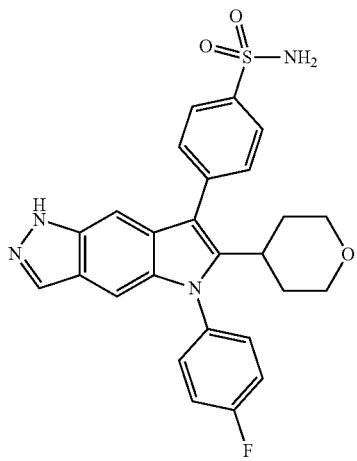 [SMILES: NS(=O)(=O)c1ccc(-c2c(C3CCOCC3)n(-c3ccc(F)cc3)c3cc4cn[nH]c4cc23)cc1] 138
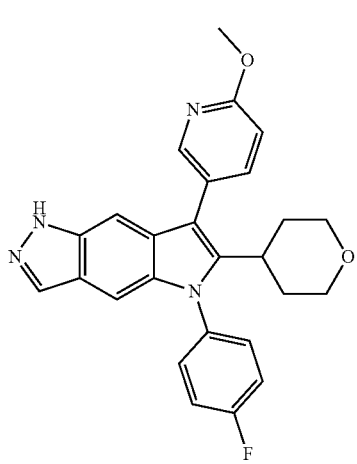 [SMILES: COc1ccc(-c2c(C3CCOCC3)n(-c3ccc(F)cc3)c3cc4cn[nH]c4cc23)cn1] 139
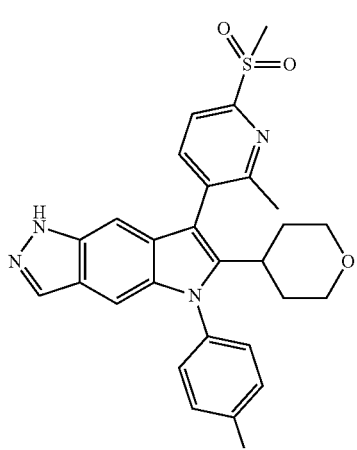 140

TABLE 1-continued
Compounds 1-342
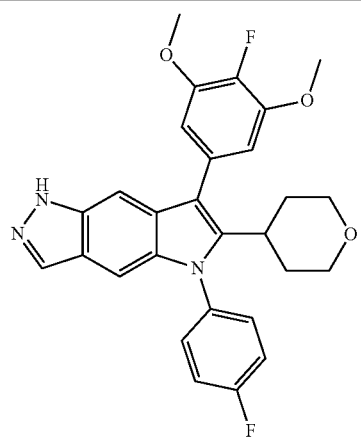 [SMILES: COc1cc(-c2c(C3CCOCC3)n(-c3ccc(F)cc3)c3cc4cn[nH]c4cc23)cc(OC)c1F] 141
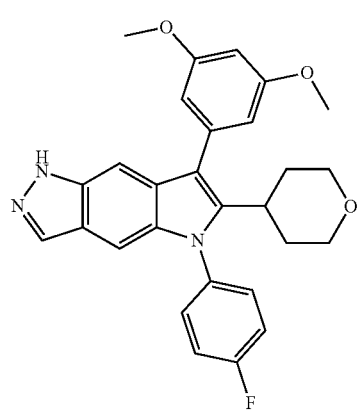 [SMILES: COc1cc(OC)cc(-c2c(C3CCOCC3)n(-c3ccc(F)cc3)c3cc4cn[nH]c4cc23)c1] 142
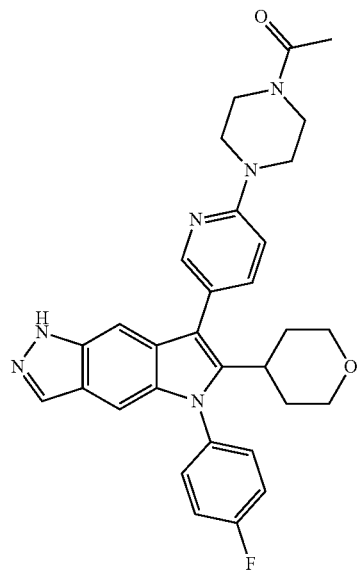 [SMILES: CC(=O)N1CCN(c2ccc(-c3c(C4CCOCC4)n(-c4ccc(F)cc4)c4cc5cn[nH]c5cc34)cn2)CC1] 143
TABLE 1-continued
Compounds 1-342
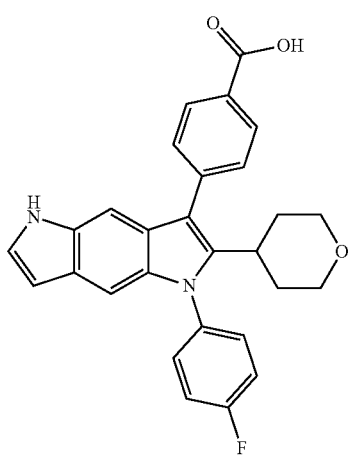 [SMILES: O=C(O)c1ccc(-c2c(C3CCOCC3)n(-c3ccc(F)cc3)c3cc4cc[nH]c4cc23)cc1] 144
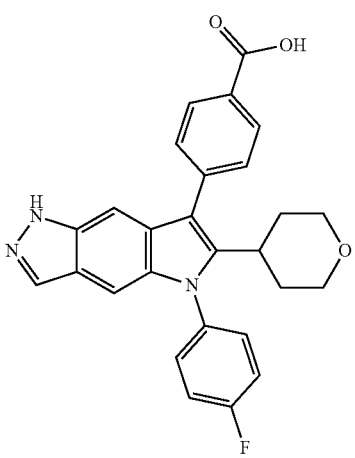 145
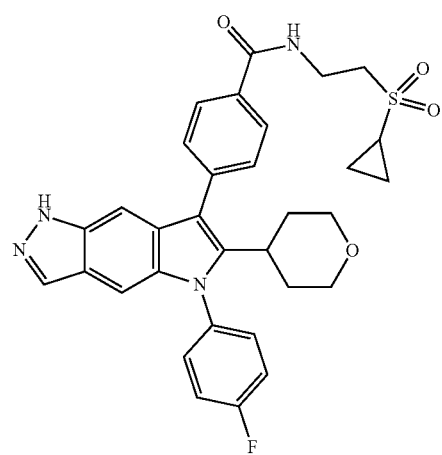 [SMILES: O=C(NCCS(=O)(=O)C1CC1)c1ccc(-c2c(C3CCOCC3)n(-c3ccc(F)cc3)c3cc4cn[nH]c4cc23)cc1] 146

TABLE 1-continued
Compounds 1-342
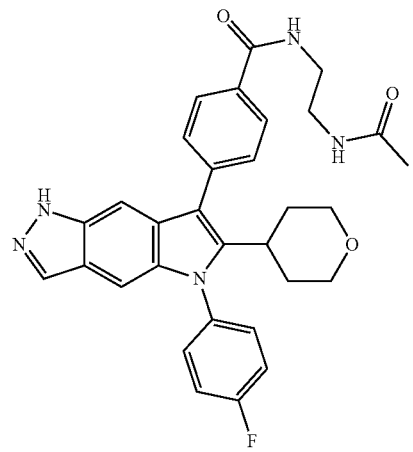 [SMILES: CC(=O)NCCNC(=O)c1ccc(-c2c(C3CCOCC3)n(-c3ccc(F)cc3)c3cc4cn[nH]c4cc23)cc1]
147
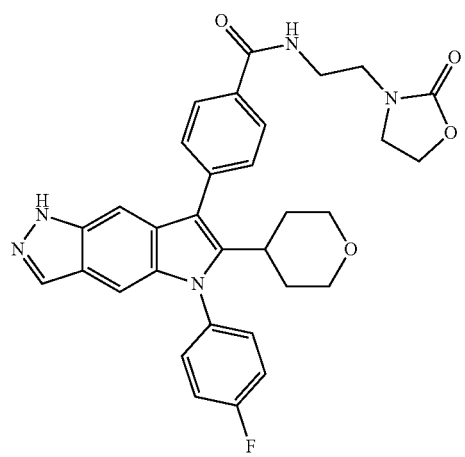 [SMILES: O=C(NCCN1CCOC1=O)c1ccc(-c2c(C3CCOCC3)n(-c3ccc(F)cc3)c3cc4cn[nH]c4cc23)cc1]
148
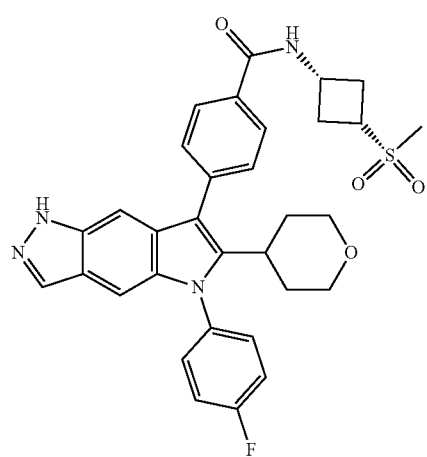
149
TABLE 1-continued
Compounds 1-342
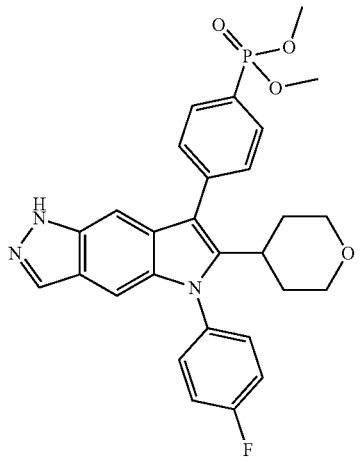 [SMILES: COP(=O)(OC)c1ccc(-c2c(C3CCOCC3)n(-c3ccc(F)cc3)c3cc4cn[nH]c4cc23)cc1]
150
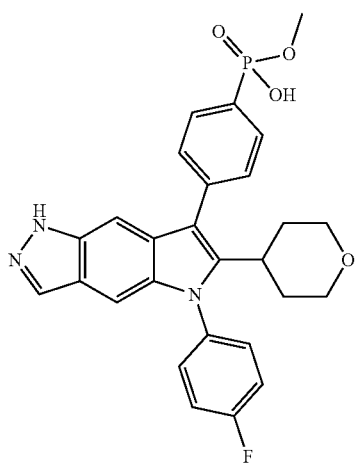 [SMILES: COP(=O)(O)c1ccc(-c2c(C3CCOCC3)n(-c3ccc(F)cc3)c3cc4cn[nH]c4cc23)cc1]
151
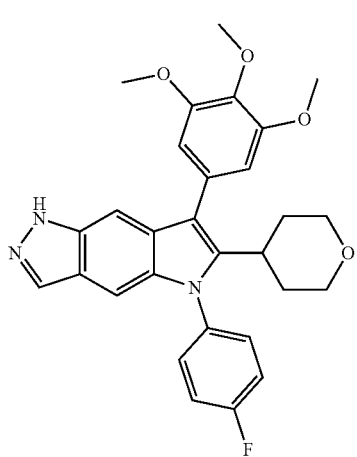 [SMILES: COc1cc(-c2c(C3CCOCC3)n(-c3ccc(F)cc3)c3cc4cn[nH]c4cc23)cc(OC)c1OC]
152

TABLE 1-continued
Compounds 1-342
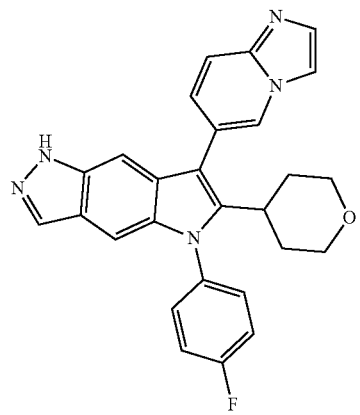 [SMILES: Fc1ccc(-n2c(C3CCOCC3)c(-c3ccc4nccn4c3)c3cc4[nH]ncc4cc32)cc1]
153
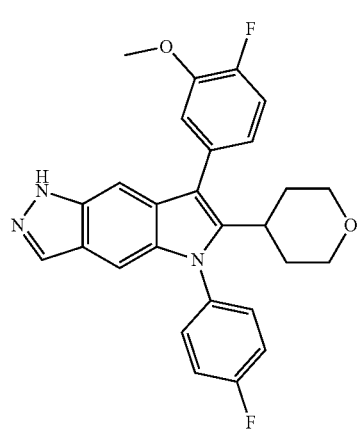
154
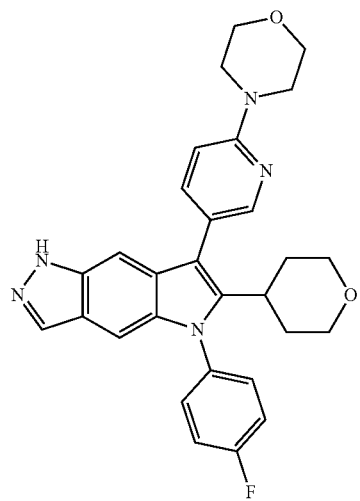
155
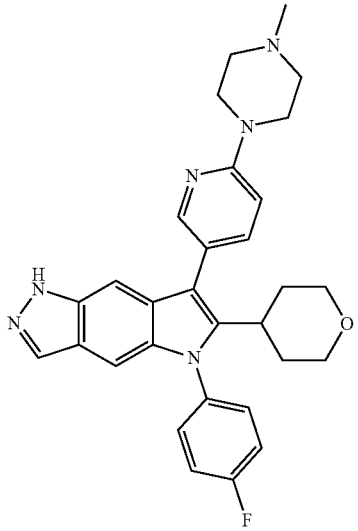 [SMILES: CN1CCN(c2ccc(-c3c(C4CCOCC4)n(-c4ccc(F)cc4)c4cc5cn[nH]c5cc34)cn2)CC1]
156
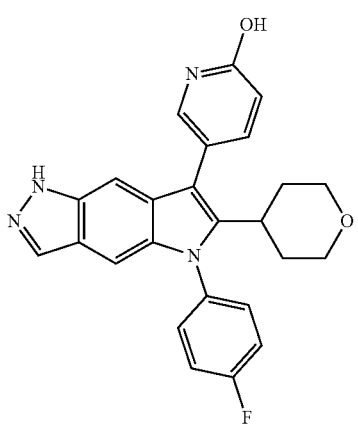 [SMILES: Oc1ccc(-c2c(C3CCOCC3)n(-c3ccc(F)cc3)c3cc4cn[nH]c4cc23)cn1]
157
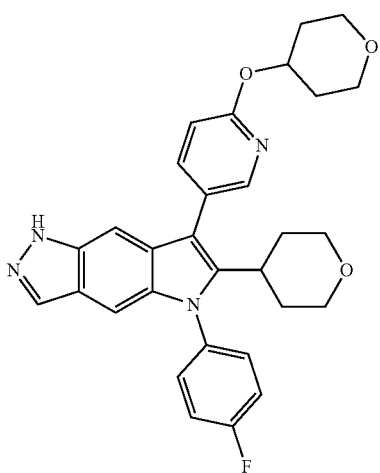 [SMILES: Fc1ccc(-n2c(C3CCOCC3)c(-c3ccc(OC4CCOCC4)nc3)c3cc4[nH]ncc4cc32)cc1]
158

TABLE 1-continued
Compounds 1-342
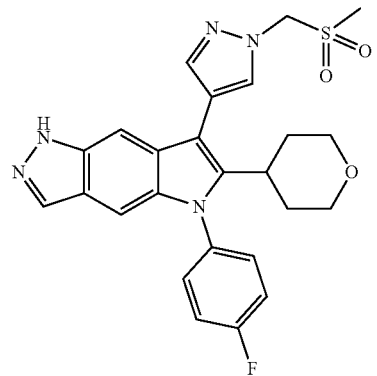 [SMILES: CS(=O)(=O)Cn1cc(-c2c(C3CCOCC3)n(-c3ccc(F)cc3)c3cc4cn[nH]c4cc23)cn1]
159
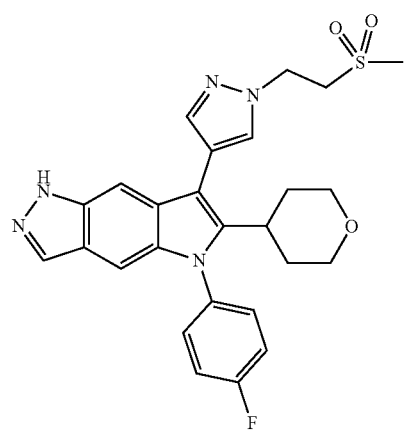 [SMILES: CS(=O)(=O)CCn1cc(-c2c(C3CCOCC3)n(-c3ccc(F)cc3)c3cc4cn[nH]c4cc23)cn1]
160
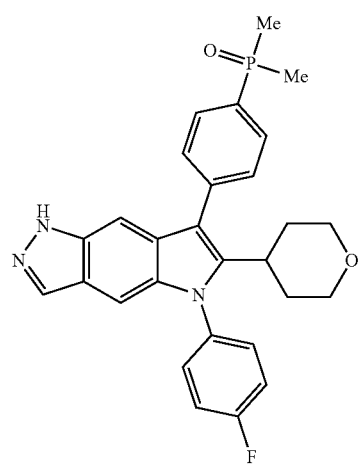
161
TABLE 1-continued
Compounds 1-342
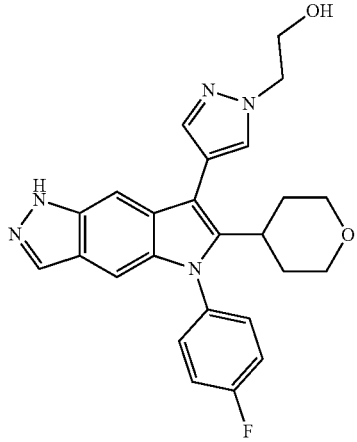 [SMILES: OCCn1cc(-c2c(C3CCOCC3)n(-c3ccc(F)cc3)c3cc4cn[nH]c4cc23)cn1]
162
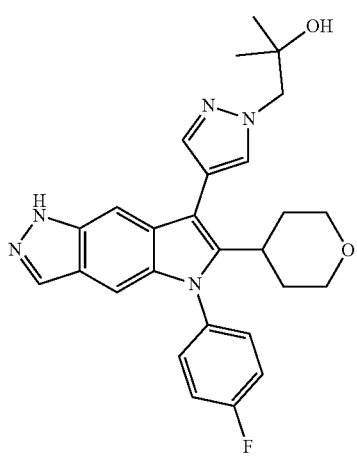 [SMILES: CC(C)(O)Cn1cc(-c2c(C3CCOCC3)n(-c3ccc(F)cc3)c3cc4cn[nH]c4cc23)cn1]
163
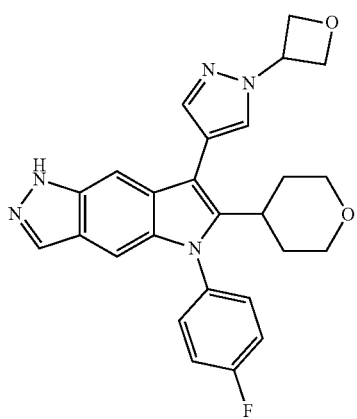 [SMILES: Fc1ccc(-n2c(C3CCOCC3)c(-c3cnn(C4COC4)c3)c3cc4[nH]ncc4cc32)cc1]
164

TABLE 1-continued
Compounds 1-342
165 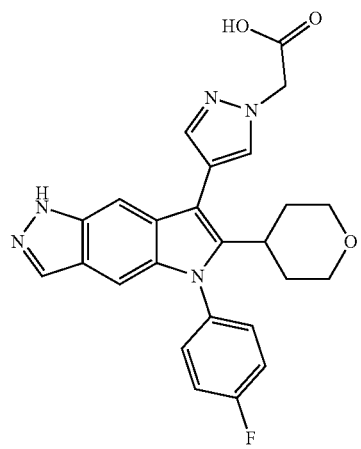 [SMILES: O=C(O)Cn1cc(-c2c(C3CCOCC3)n(-c3ccc(F)cc3)c3cc4cn[nH]c4cc23)cn1]
166 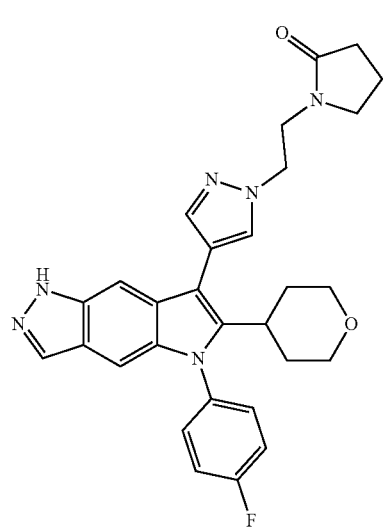 [SMILES: O=C1CCCN1CCn1cc(-c2c(C3CCOCC3)n(-c3ccc(F)cc3)c3cc4cn[nH]c4cc23)cn1]
167 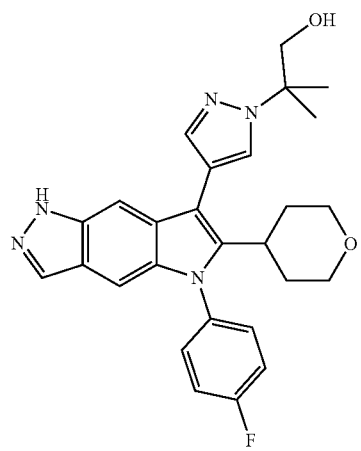 [SMILES: CC(C)(CO)n1cc(-c2c(C3CCOCC3)n(-c3ccc(F)cc3)c3cc4cn[nH]c4cc23)cn1]
168 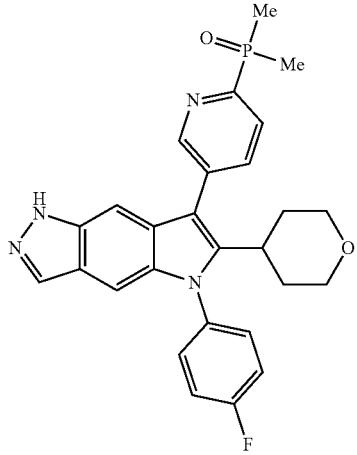 [SMILES: CP(C)(=O)c1ccc(-c2c(C3CCOCC3)n(-c3ccc(F)cc3)c3cc4cn[nH]c4cc23)cn1]
169 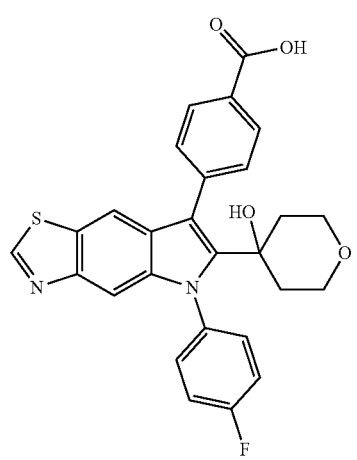 [SMILES: O=C(O)c1ccc(-c2c(C3(O)CCOCC3)n(-c3ccc(F)cc3)c3cc4ncsc4cc23)cc1]
170 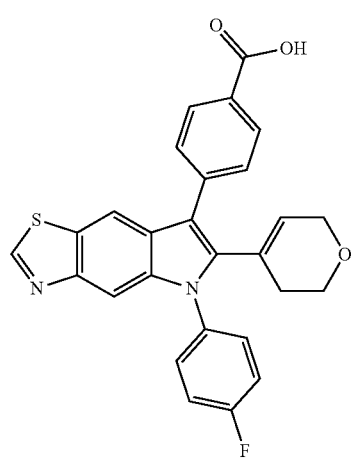 [SMILES: O=C(O)c1ccc(-c2c(C3=CCOCC3)n(-c3ccc(F)cc3)c3cc4ncsc4cc23)cc1]

TABLE 1-continued
Compounds 1-342
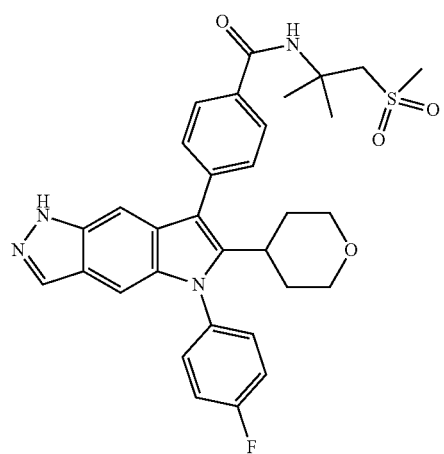 [SMILES: CC(C)(CS(C)(=O)=O)NC(=O)c1ccc(-c2c(C3CCOCC3)n(-c3ccc(F)cc3)c3cc4cn[nH]c4cc23)cc1]
171
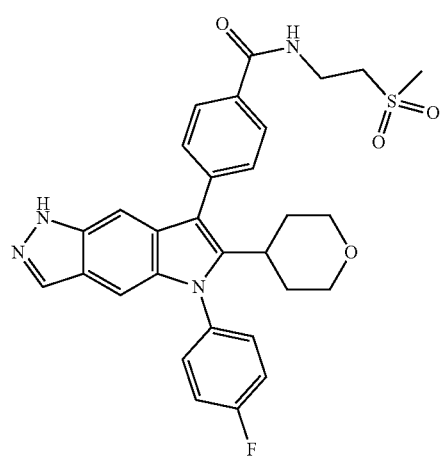 [SMILES: CS(=O)(=O)CCNC(=O)c1ccc(-c2c(C3CCOCC3)n(-c3ccc(F)cc3)c3cc4cn[nH]c4cc23)cc1]
172
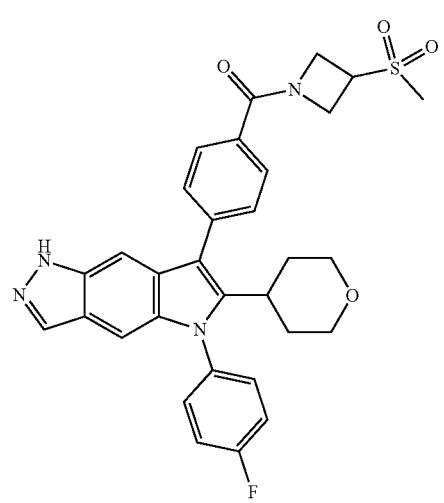 [SMILES: CS(=O)(=O)C1CN(C(=O)c2ccc(-c3c(C4CCOCC4)n(-c4ccc(F)cc4)c4cc5cn[nH]c5cc34)cc2)C1]
173
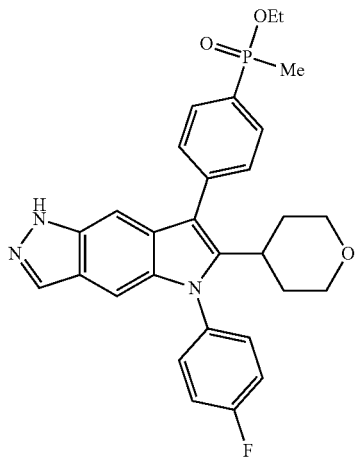 [SMILES: CCOP(C)(=O)c1ccc(-c2c(C3CCOCC3)n(-c3ccc(F)cc3)c3cc4cn[nH]c4cc23)cc1]
174
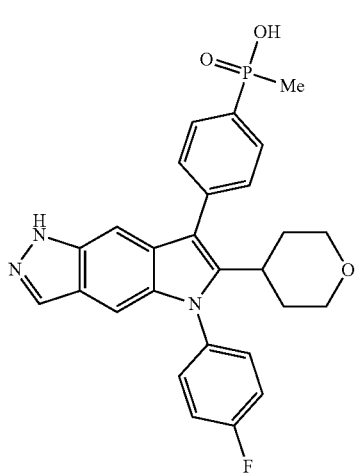 [SMILES: CP(=O)(O)c1ccc(-c2c(C3CCOCC3)n(-c3ccc(F)cc3)c3cc4cn[nH]c4cc23)cc1]
175
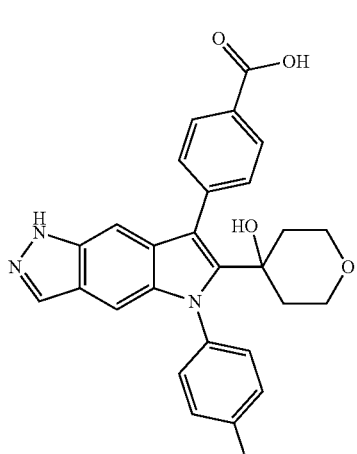
176

TABLE 1-continued
Compounds 1-342
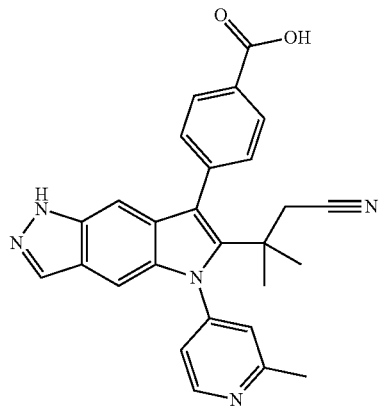 [SMILES: Cc1cc(-n2c(C(C)(C)CC#N)c(-c3ccc(C(=O)O)cc3)c3cc4[nH]ncc4cc32)ccn1]
177
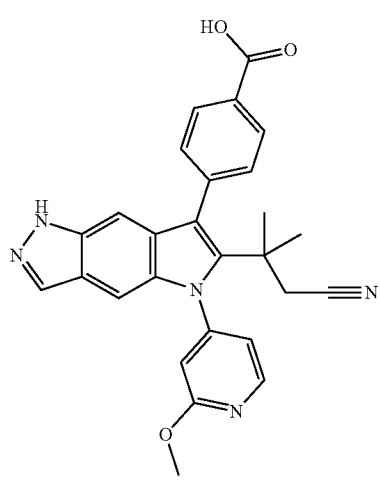 [SMILES: COc1cc(-n2c(C(C)(C)CC#N)c(-c3ccc(C(=O)O)cc3)c3cc4[nH]ncc4cc32)ccn1]
178
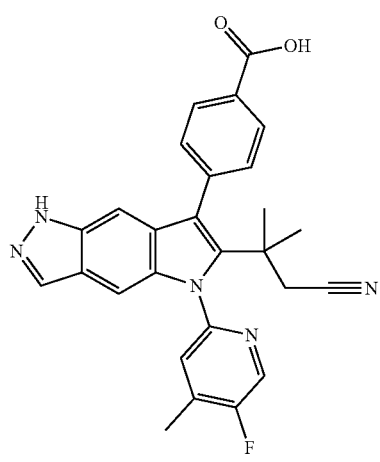
179
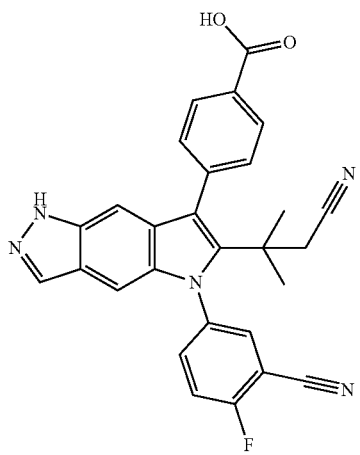 [SMILES: CC(C)(CC#N)c1c(-c2ccc(C(=O)O)cc2)c2cc3[nH]ncc3cc2n1-c1ccc(F)c(C#N)c1]
180
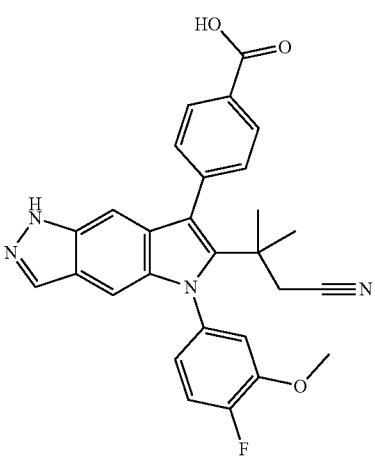 [SMILES: COc1cc(-n2c(C(C)(C)CC#N)c(-c3ccc(C(=O)O)cc3)c3cc4[nH]ncc4cc32)ccc1F]
181
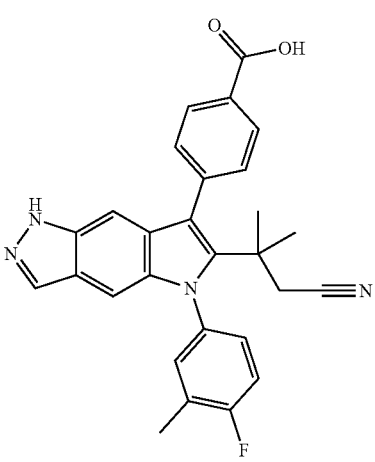 [SMILES: Cc1cc(-n2c(C(C)(C)CC#N)c(-c3ccc(C(=O)O)cc3)c3cc4[nH]ncc4cc32)ccc1F]
182

TABLE 1-continued
Compounds 1-342
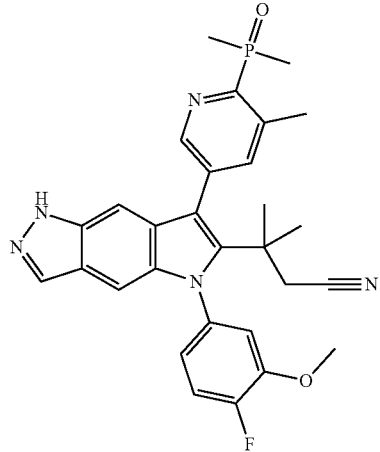 [SMILES: COc1cc(-n2c(C(C)(C)CC#N)c(-c3cnc(P(C)(C)=O)c(C)c3)c3cc4[nH]ncc4cc32)ccc1F]
183
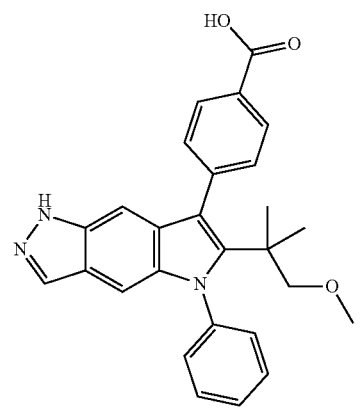 [SMILES: COCC(C)(C)c1c(-c2ccc(C(=O)O)cc2)c2cc3[nH]ncc3cc2n1-c1ccccc1]
184
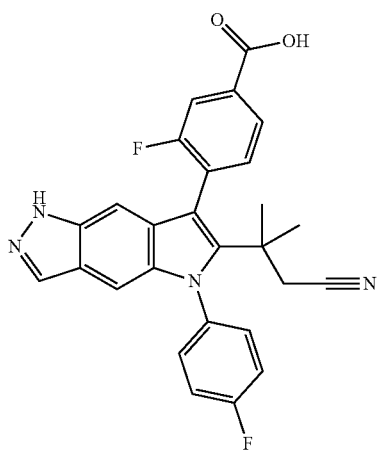 [SMILES: CC(C)(CC#N)c1c(-c2ccc(C(=O)O)cc2F)c2cc3[nH]ncc3cc2n1-c1ccc(F)cc1]
186
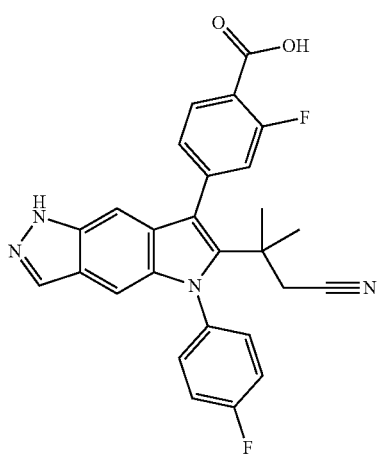 [SMILES: CC(C)(CC#N)c1c(-c2ccc(C(=O)O)c(F)c2)c2cc3[nH]ncc3cc2n1-c1ccc(F)cc1]
187
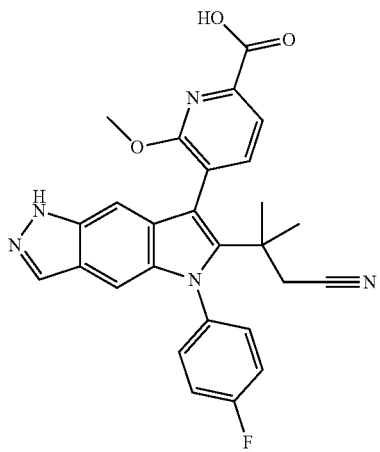 [SMILES: COc1nc(C(=O)O)ccc1-c1c(C(C)(C)CC#N)n(-c2ccc(F)cc2)c2cc3cn[nH]c3cc12]
188

TABLE 1-continued
Compounds 1-342
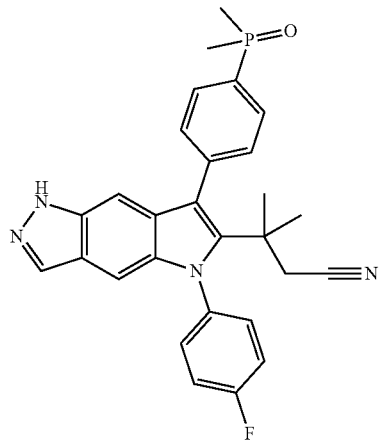 [SMILES: CC(C)(CC#N)c1c(-c2ccc(P(C)(C)=O)cc2)c2cc3[nH]ncc3cc2n1-c1ccc(F)cc1]
189
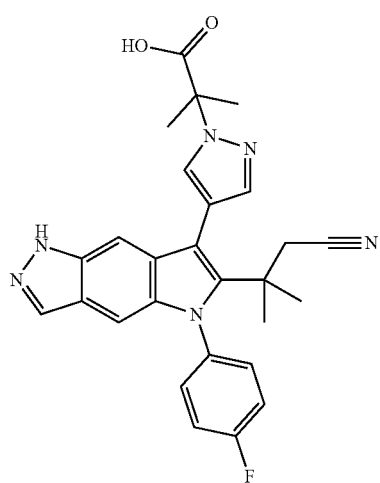 [SMILES: CC(C)(CC#N)c1c(-c2cnn(C(C)(C)C(=O)O)c2)c2cc3[nH]ncc3cc2n1-c1ccc(F)cc1]
190
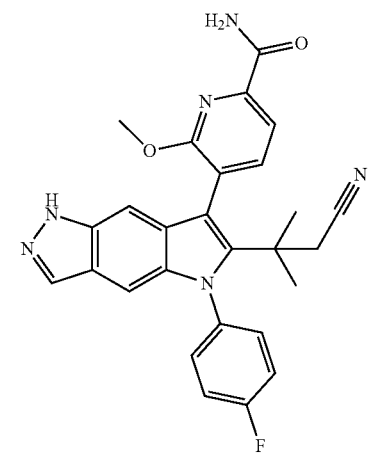 [SMILES: COc1nc(C(N)=O)ccc1-c1c(C(C)(C)CC#N)n(-c2ccc(F)cc2)c2cc3cn[nH]c3cc12]
191
TABLE 1-continued
Compounds 1-342
192
193
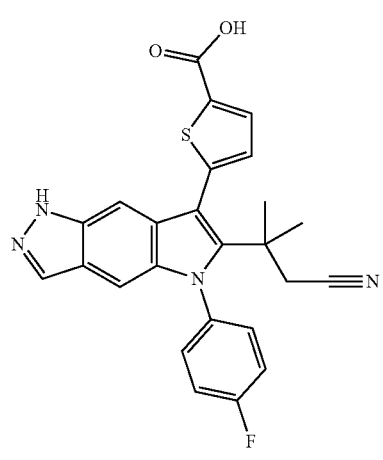 [SMILES: CC(C)(CC#N)c1c(-c2ccc(C(=O)O)s2)c2cc3[nH]ncc3cc2n1-c1ccc(F)cc1]
194

TABLE 1-continued
Compounds 1-342
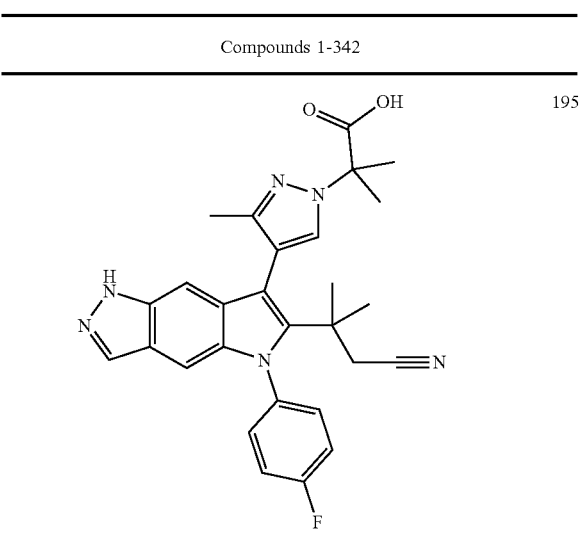
195
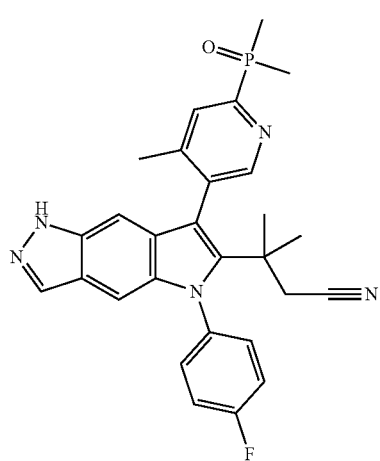 [SMILES: Cc1cc(P(C)(C)=O)ncc1-c1c(C(C)(C)CC#N)n(-c2ccc(F)cc2)c2cc3cn[nH]c3cc12]
196
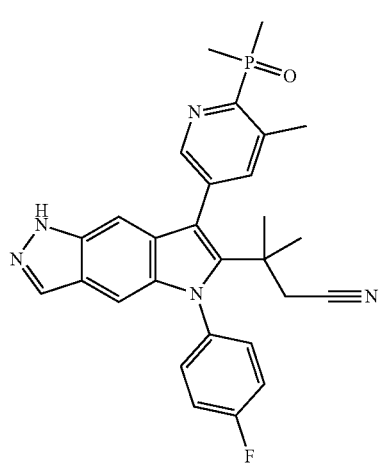 [SMILES: Cc1cc(-c2c(C(C)(C)CC#N)n(-c3ccc(F)cc3)c3cc4cn[nH]c4cc23)cnc1P(C)(C)=O]
197
TABLE 1-continued
Compounds 1-342
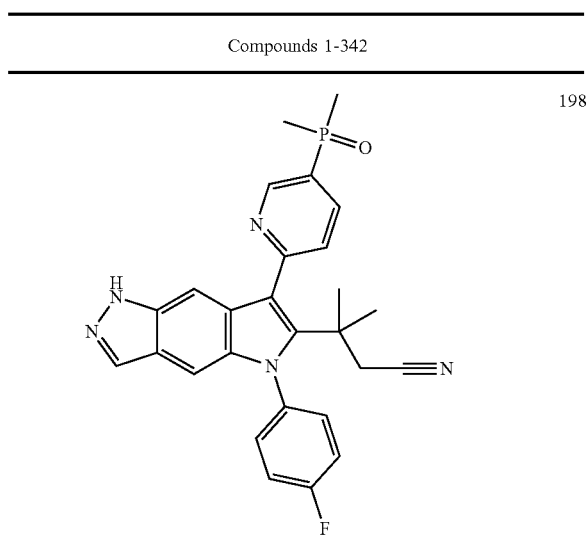
198
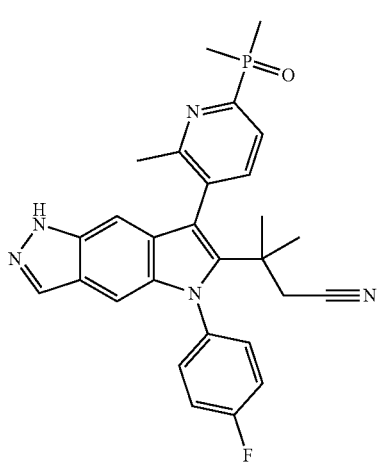 [SMILES: Cc1nc(P(C)(C)=O)ccc1-c1c(C(C)(C)CC#N)n(-c2ccc(F)cc2)c2cc3cn[nH]c3cc12]
199
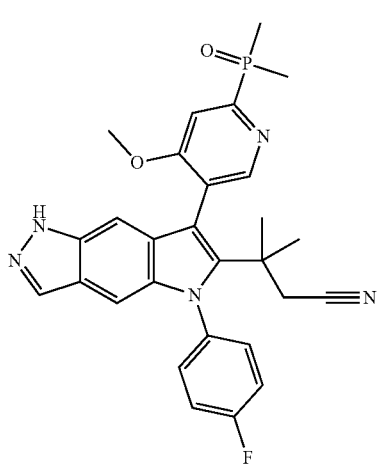 [SMILES: COc1cc(P(C)(C)=O)ncc1-c1c(C(C)(C)CC#N)n(-c2ccc(F)cc2)c2cc3cn[nH]c3cc12]
200

TABLE 1-continued
Compounds 1-342
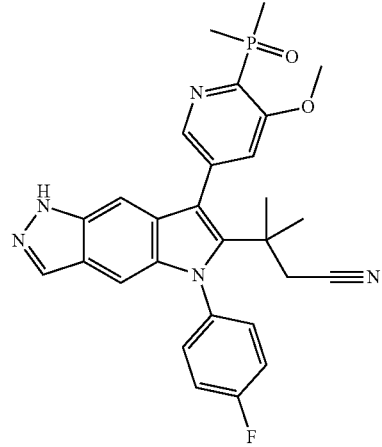 [SMILES: COc1cc(-c2c(C(C)(C)CC#N)n(-c3ccc(F)cc3)c3cc4cn[nH]c4cc23)cnc1P(C)(C)=O]
201
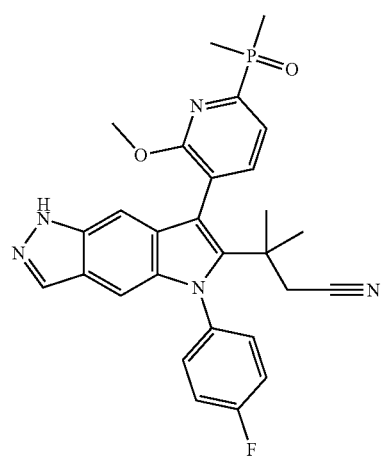 [SMILES: COc1nc(P(C)(C)=O)ccc1-c1c(C(C)(C)CC#N)n(-c2ccc(F)cc2)c2cc3cn[nH]c3cc12]
202
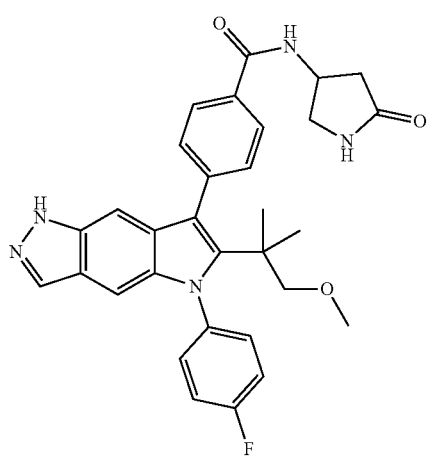 [SMILES: COCC(C)(C)c1c(-c2ccc(C(=O)NC3CNC(=O)C3)cc2)c2cc3[nH]ncc3cc2n1-c1ccc(F)cc1]
203
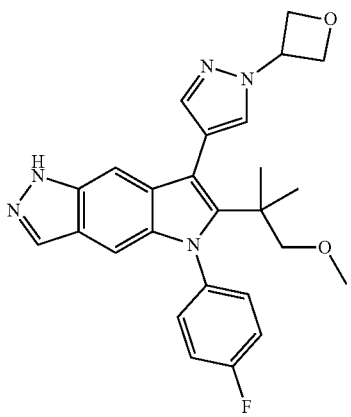
204
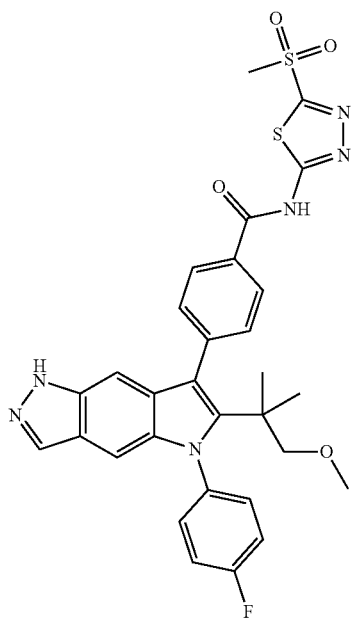 [SMILES: COCC(C)(C)c1c(-c2ccc(C(=O)Nc3nnc(S(C)(=O)=O)s3)cc2)c2cc3[nH]ncc3cc2n1-c1ccc(F)cc1]
205
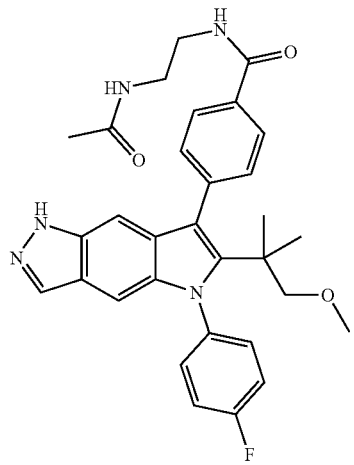
206

TABLE 1-continued
Compounds 1-342
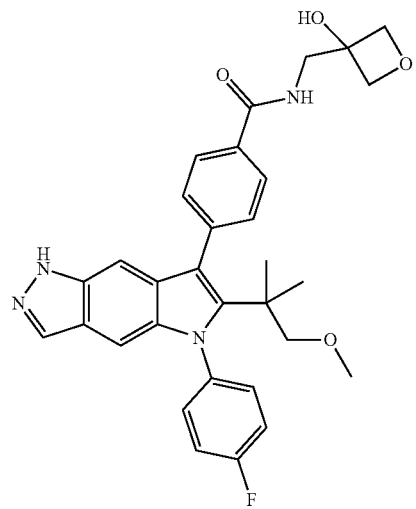 [SMILES: COCC(C)(C)c1c(-c2ccc(C(=O)NCC3(O)COC3)cc2)c2cc3[nH]ncc3cc2n1-c1ccc(F)cc1]
207
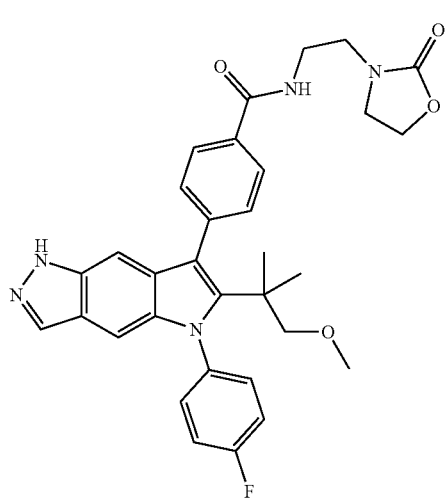 [SMILES: COCC(C)(C)c1c(-c2ccc(C(=O)NCCN3CCOC3=O)cc2)c2cc3[nH]ncc3cc2n1-c1ccc(F)cc1]
208
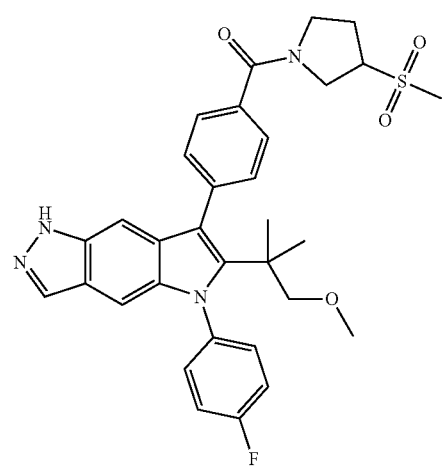 [SMILES: COCC(C)(C)c1c(-c2ccc(C(=O)N3CCC(S(C)(=O)=O)C3)cc2)c2cc3[nH]ncc3cc2n1-c1ccc(F)cc1]
209
TABLE 1-continued
Compounds 1-342
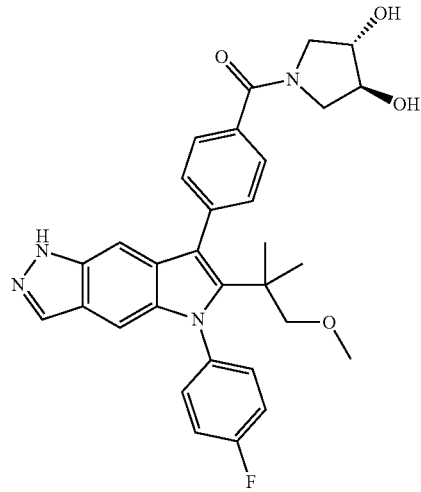 [SMILES: COCC(C)(C)c1c(-c2ccc(C(=O)N3C[C@H](O)[C@@H](O)C3)cc2)c2cc3[nH]ncc3cc2n1-c1ccc(F)cc1]
210
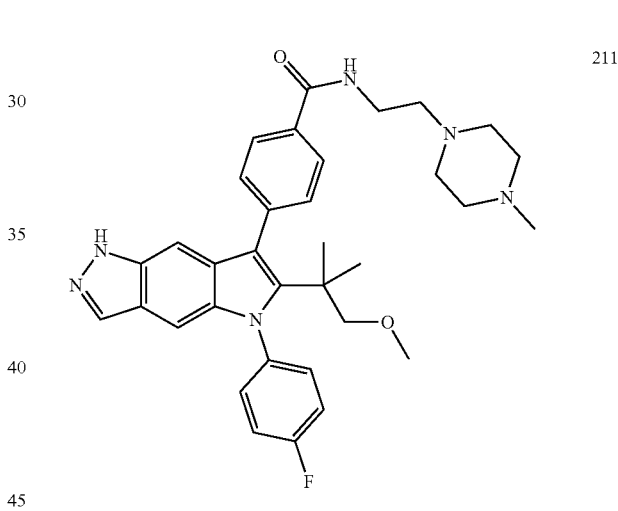
211
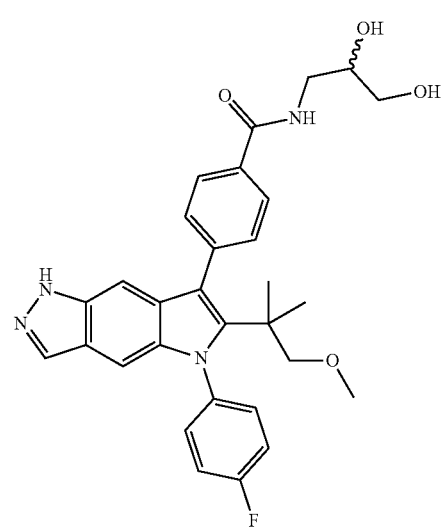 [SMILES: COCC(C)(C)c1c(-c2ccc(C(=O)NCC(O)CO)cc2)c2cc3[nH]ncc3cc2n1-c1ccc(F)cc1]
212

TABLE 1-continued
Compounds 1-342
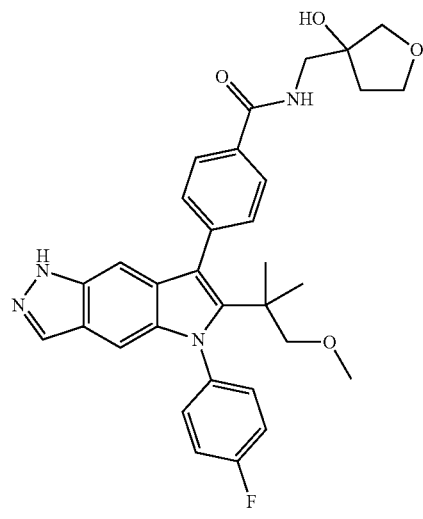 [SMILES: COCC(C)(C)c1c(-c2ccc(C(=O)NCC3(O)CCOC3)cc2)c2cc3[nH]ncc3cc2n1-c1ccc(F)cc1]
213
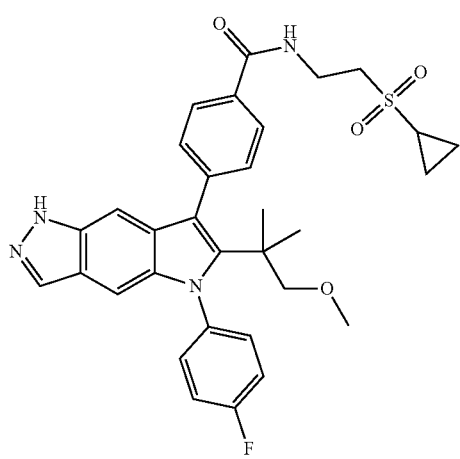 [SMILES: COCC(C)(C)c1c(-c2ccc(C(=O)NCCS(=O)(=O)C3CC3)cc2)c2cc3[nH]ncc3cc2n1-c1ccc(F)cc1]
214
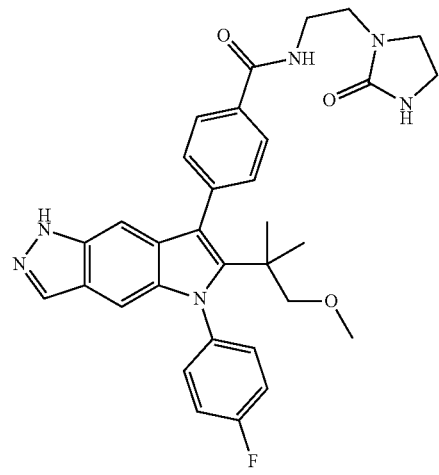 [SMILES: COCC(C)(C)c1c(-c2ccc(C(=O)NCCN3CCNC3=O)cc2)c2cc3[nH]ncc3cc2n1-c1ccc(F)cc1]
215
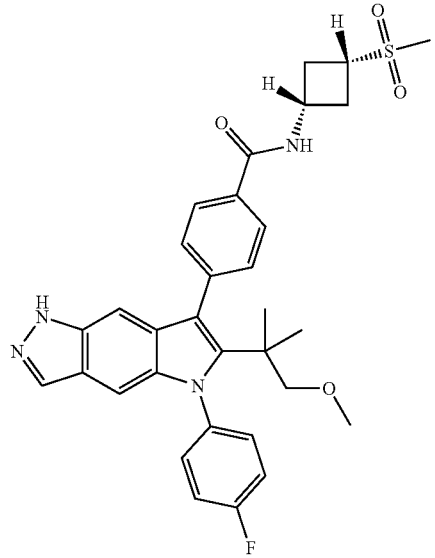 [SMILES: COCC(C)(C)c1c(-c2ccc(C(=O)N[C@H]3C[C@@H](S(C)(=O)=O)C3)cc2)c2cc3[nH]ncc3cc2n1-c1ccc(F)cc1]
216
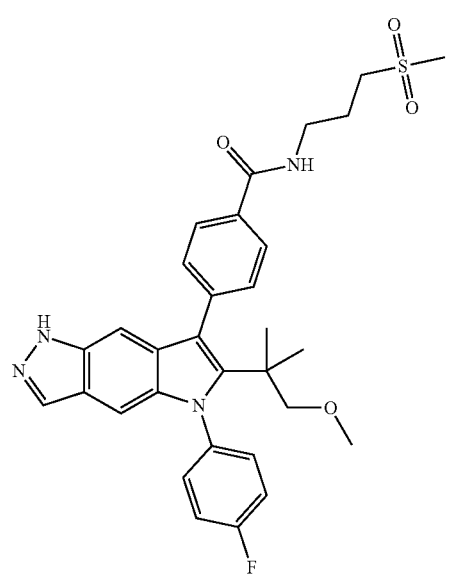 [SMILES: COCC(C)(C)c1c(-c2ccc(C(=O)NCCCS(C)(=O)=O)cc2)c2cc3[nH]ncc3cc2n1-c1ccc(F)cc1]
217
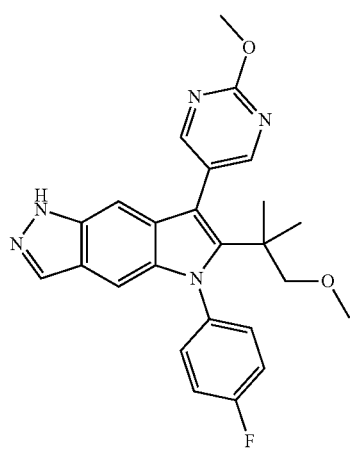 [SMILES: COCC(C)(C)c1c(-c2cnc(OC)nc2)c2cc3[nH]ncc3cc2n1-c1ccc(F)cc1]
218

TABLE 1-continued
Compounds 1-342
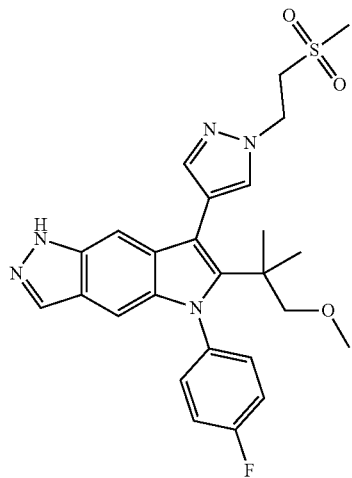 [SMILES: COCC(C)(C)c1c(-c2cnn(CCS(C)(=O)=O)c2)c2cc3[nH]ncc3cc2n1-c1ccc(F)cc1] 219
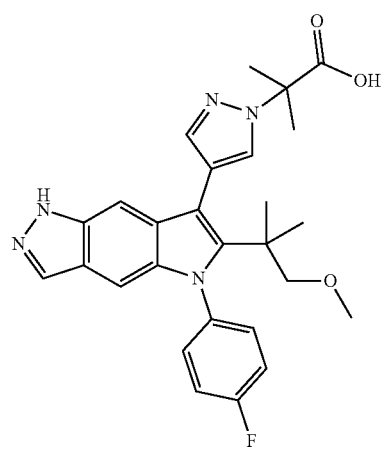 [SMILES: COCC(C)(C)c1c(-c2cnn(C(C)(C)C(=O)O)c2)c2cc3[nH]ncc3cc2n1-c1ccc(F)cc1] 220
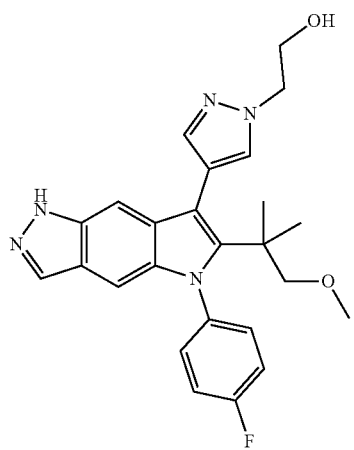 [SMILES: COCC(C)(C)c1c(-c2cnn(CCO)c2)c2cc3[nH]ncc3cc2n1-c1ccc(F)cc1] 221
TABLE 1-continued
Compounds 1-342
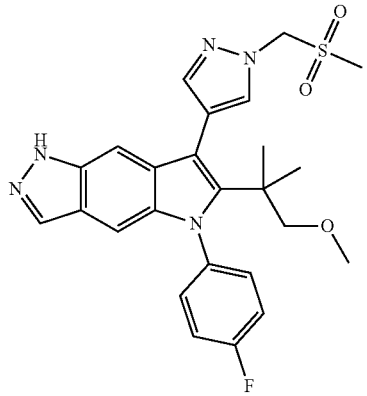 [SMILES: COCC(C)(C)c1c(-c2cnn(CS(C)(=O)=O)c2)c2cc3[nH]ncc3cc2n1-c1ccc(F)cc1] 222
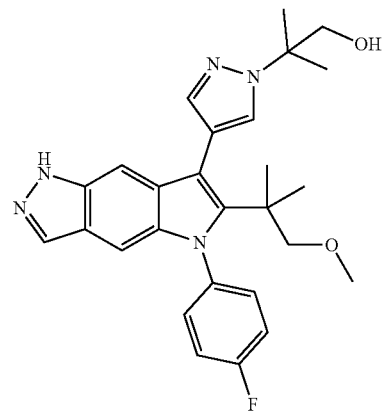 [SMILES: COCC(C)(C)c1c(-c2cnn(C(C)(C)CO)c2)c2cc3[nH]ncc3cc2n1-c1ccc(F)cc1] 223
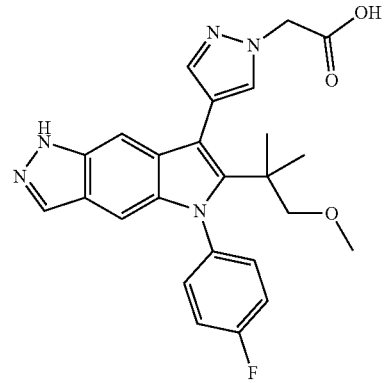 [SMILES: COCC(C)(C)c1c(-c2cnn(CC(=O)O)c2)c2cc3[nH]ncc3cc2n1-c1ccc(F)cc1] 224

TABLE 1-continued
Compounds 1-342
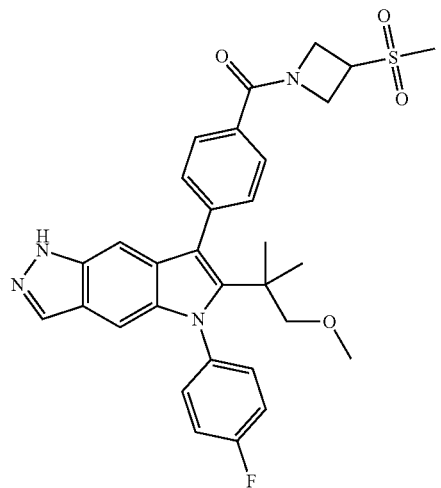 [SMILES: COCC(C)(C)c1c(-c2ccc(C(=O)N3CC(S(C)(=O)=O)C3)cc2)c2cc3[nH]ncc3cc2n1-c1ccc(F)cc1]
225
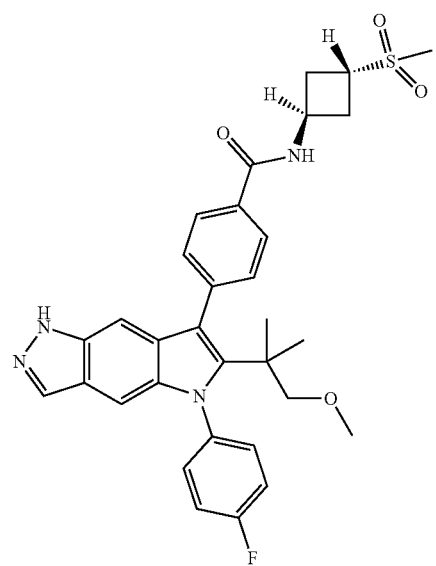 [SMILES: COCC(C)(C)c1c(-c2ccc(C(=O)N[C@H]3C[C@H](S(C)(=O)=O)C3)cc2)c2cc3[nH]ncc3cc2n1-c1ccc(F)cc1]
226
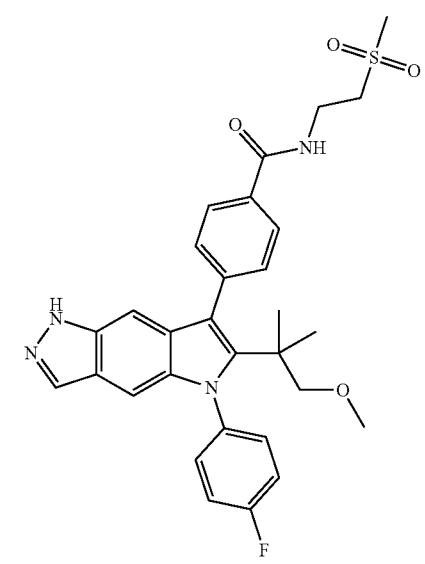 [SMILES: COCC(C)(C)c1c(-c2ccc(C(=O)NCCS(C)(=O)=O)cc2)c2cc3[nH]ncc3cc2n1-c1ccc(F)cc1]
227
TABLE 1-continued
Compounds 1-342
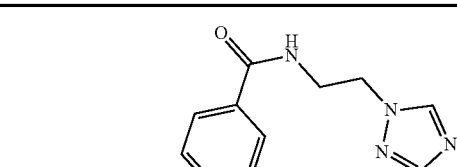
228
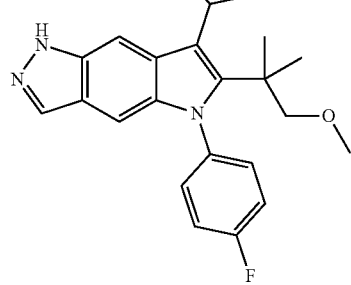
229
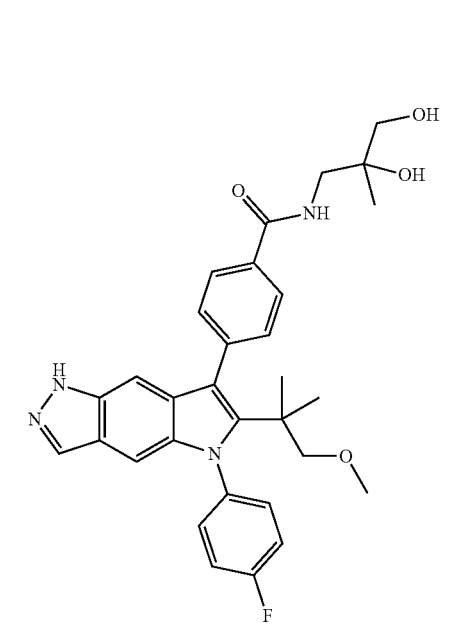 [SMILES: COCC(C)(C)c1c(-c2ccc(C(=O)NCC(C)(O)CO)cc2)c2cc3[nH]ncc3cc2n1-c1ccc(F)cc1]
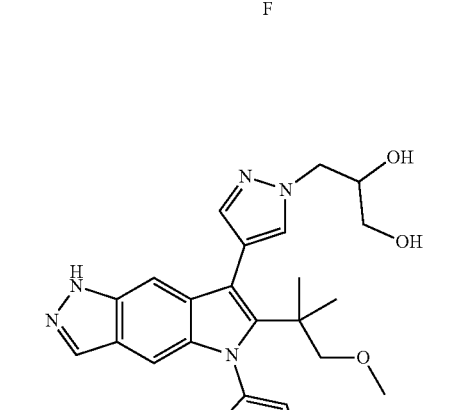
230

TABLE 1-continued
Compounds 1-342
231 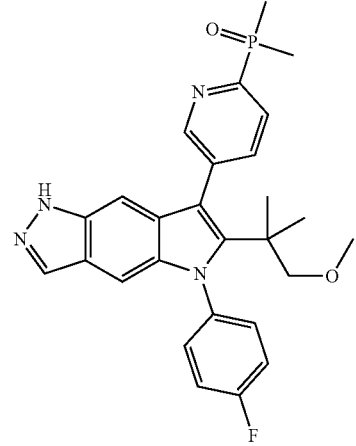 [SMILES: COCC(C)(C)c1c(-c2ccc(P(C)(C)=O)cc2)c2cc3[nH]ncc3cc2n1-c1ccc(F)cc1]
232 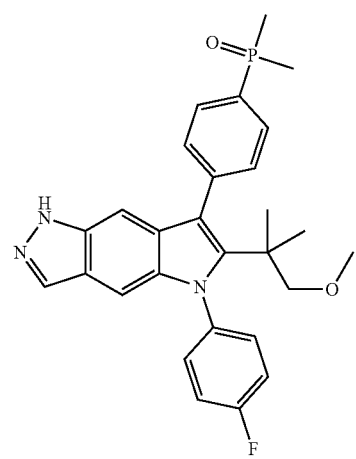
233 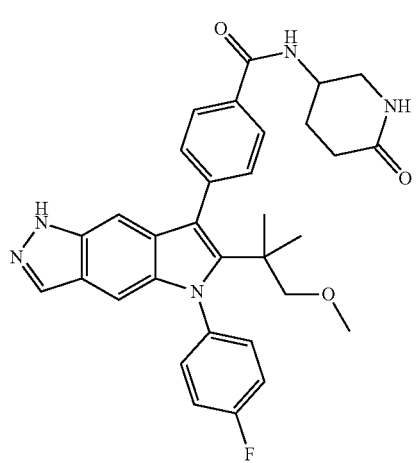 [SMILES: COCC(C)(C)c1c(-c2ccc(C(=O)NC3CCC(=O)NC3)cc2)c2cc3[nH]ncc3cc2n1-c1ccc(F)cc1]
TABLE 1-continued
Compounds 1-342
234 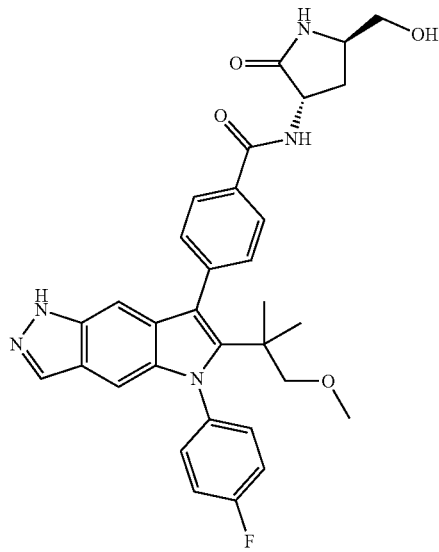 [SMILES: COCC(C)(C)c1c(-c2ccc(C(=O)N[C@H]3C[C@H](CO)NC3=O)cc2)c2cc3[nH]ncc3cc2n1-c1ccc(F)cc1]
235 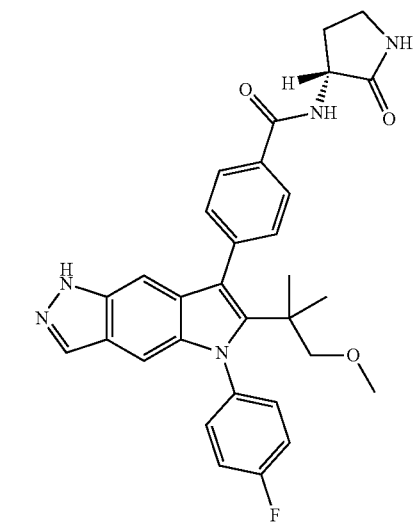 [SMILES: COCC(C)(C)c1c(-c2ccc(C(=O)N[C@@H]3CCNC3=O)cc2)c2cc3[nH]ncc3cc2n1-c1ccc(F)cc1]

TABLE 1-continued
Compounds 1-342
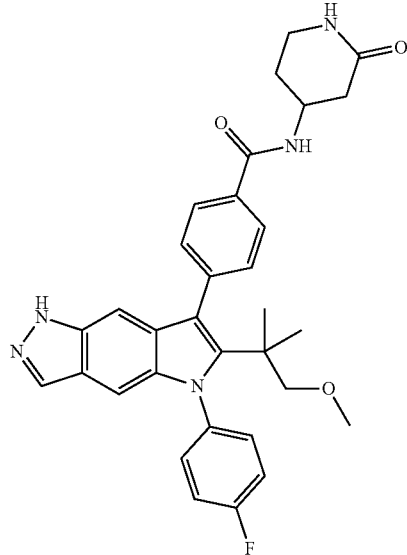 [SMILES: COCC(C)(C)c1c(-c2ccc(C(=O)NC3CCNC(=O)C3)cc2)c2cc3[nH]ncc3cc2n1-c1ccc(F)cc1]
236
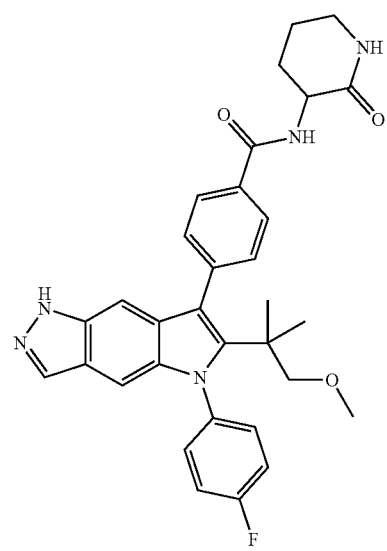 [SMILES: COCC(C)(C)c1c(-c2ccc(C(=O)NC3CCCNC3=O)cc2)c2cc3[nH]ncc3cc2n1-c1ccc(F)cc1]
237
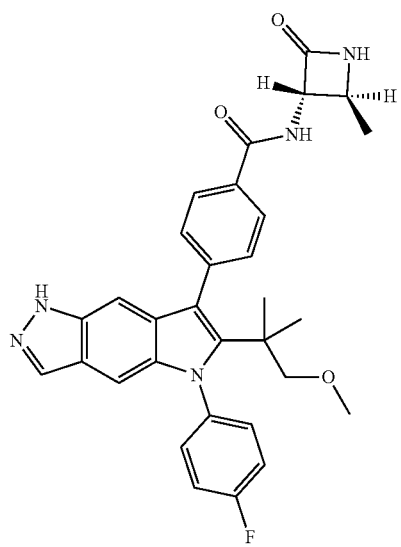 [SMILES: COCC(C)(C)c1c(-c2ccc(C(=O)N[C@@H]3C(=O)N[C@H]3C)cc2)c2cc3[nH]ncc3cc2n1-c1ccc(F)cc1]
238
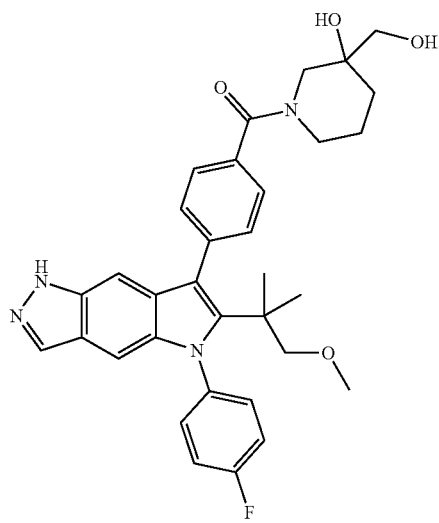 [SMILES: COCC(C)(C)c1c(-c2ccc(C(=O)N3CCCC(O)(CO)C3)cc2)c2cc3[nH]ncc3cc2n1-c1ccc(F)cc1]
239
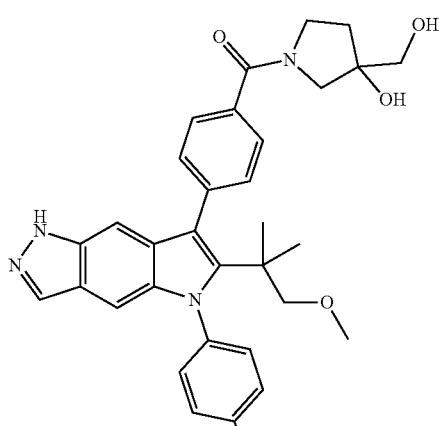
240

TABLE 1-continued
Compounds 1-342
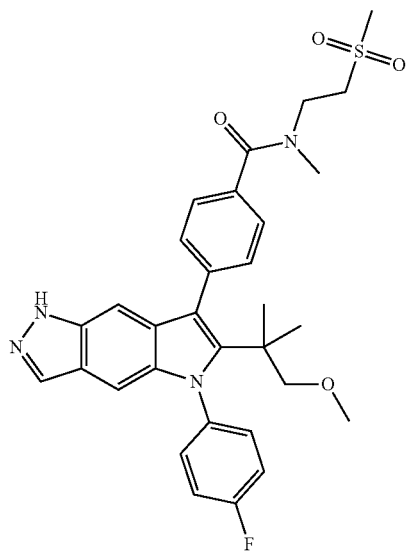 [SMILES: COCC(C)(C)c1c(-c2ccc(C(=O)N(C)CCS(C)(=O)=O)cc2)c2cc3[nH]ncc3cc2n1-c1ccc(F)cc1]
241
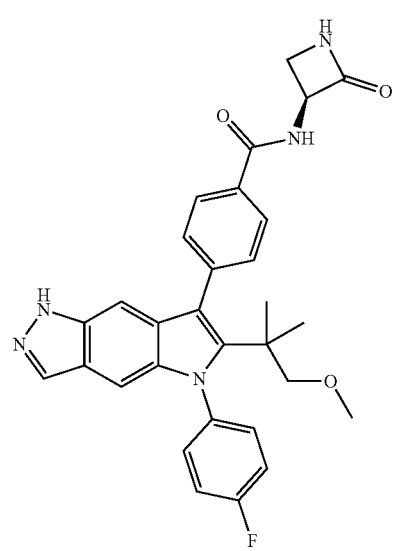 [SMILES: COCC(C)(C)c1c(-c2ccc(C(=O)N[C@H]3CNC3=O)cc2)c2cc3[nH]ncc3cc2n1-c1ccc(F)cc1]
242
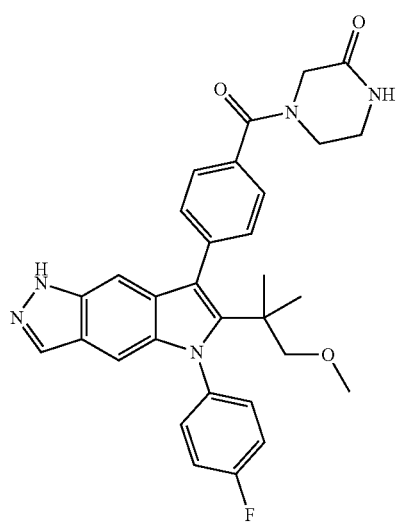 [SMILES: COCC(C)(C)c1c(-c2ccc(C(=O)N3CCNC(=O)C3)cc2)c2cc3[nH]ncc3cc2n1-c1ccc(F)cc1]
243
TABLE 1-continued
Compounds 1-342
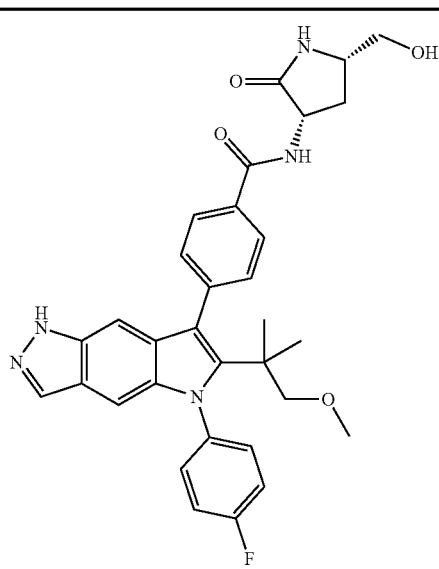
244
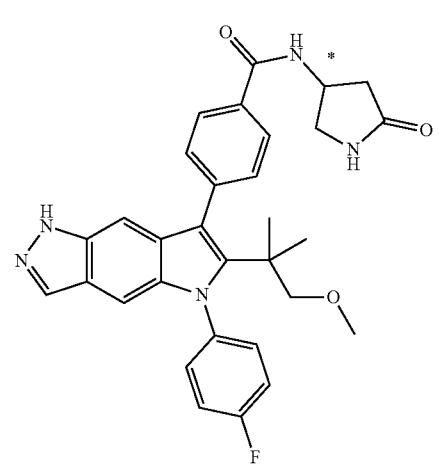 [SMILES: COCC(C)(C)c1c(-c2ccc(C(=O)NC3CNC(=O)C3)cc2)c2cc3[nH]ncc3cc2n1-c1ccc(F)cc1]
245
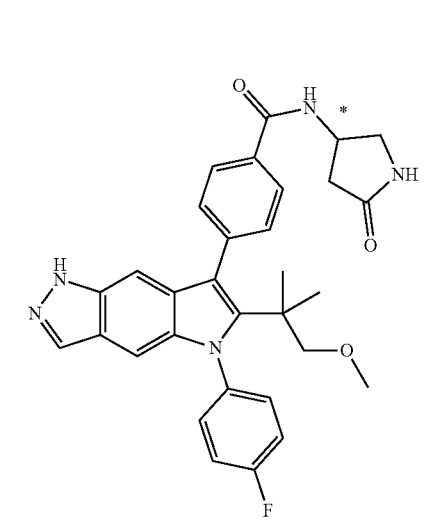 [SMILES: COCC(C)(C)c1c(-c2ccc(C(=O)NC3CNC(=O)C3)cc2)c2cc3[nH]ncc3cc2n1-c1ccc(F)cc1]
246

TABLE 1-continued
Compounds 1-342
247 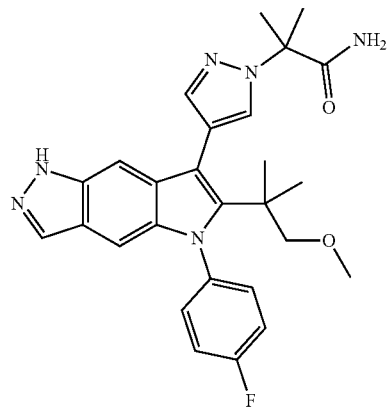 [SMILES: COCC(C)(C)c1c(-c2cnn(C(C)(C)C(N)=O)c2)c2cc3[nH]ncc3cc2n1-c1ccc(F)cc1]
248 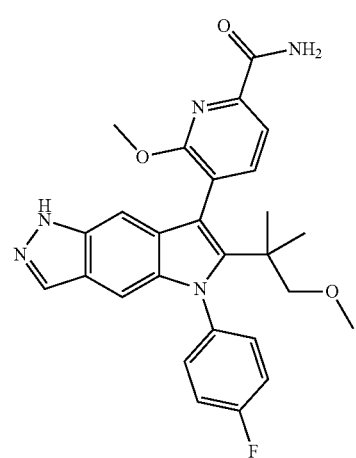 [SMILES: COCC(C)(C)c1c(-c2ccc(C(N)=O)nc2OC)c2cc3[nH]ncc3cc2n1-c1ccc(F)cc1]
249 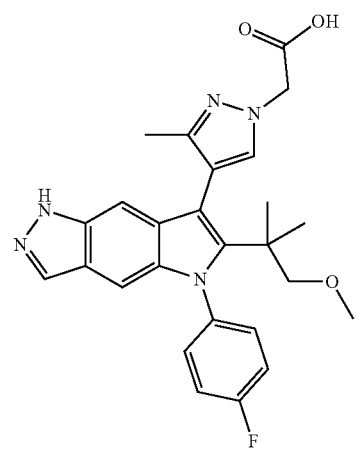 [SMILES: COCC(C)(C)c1c(-c2cn(CC(=O)O)nc2C)c2cc3[nH]ncc3cc2n1-c1ccc(F)cc1]
250 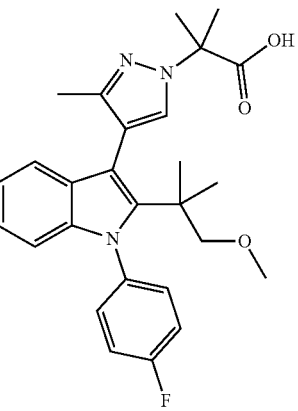
251 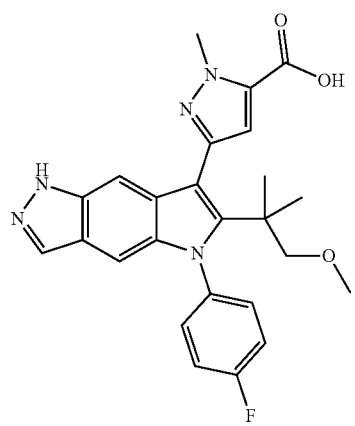 [SMILES: COCC(C)(C)c1c(-c2cc(C(=O)O)n(C)n2)c2cc3[nH]ncc3cc2n1-c1ccc(F)cc1]
252 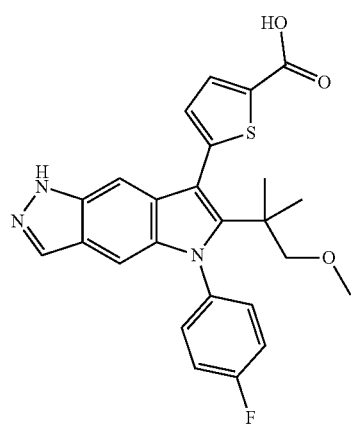 [SMILES: COCC(C)(C)c1c(-c2ccc(C(=O)O)s2)c2cc3[nH]ncc3cc2n1-c1ccc(F)cc1]

TABLE 1-continued
Compounds 1-342
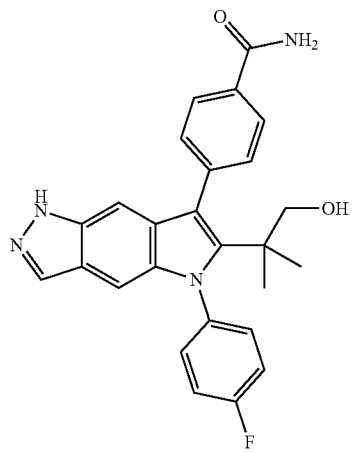
253
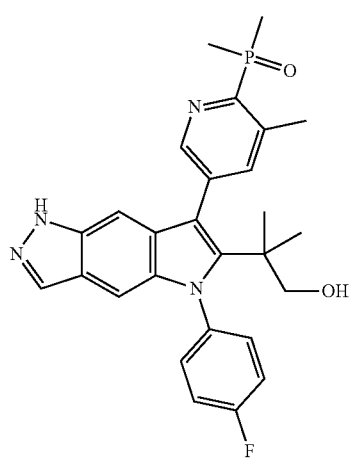 [SMILES: Cc1cc(-c2c(C(C)(C)CO)n(-c3ccc(F)cc3)c3cc4cn[nH]c4cc23)cnc1P(C)(C)=O]
254
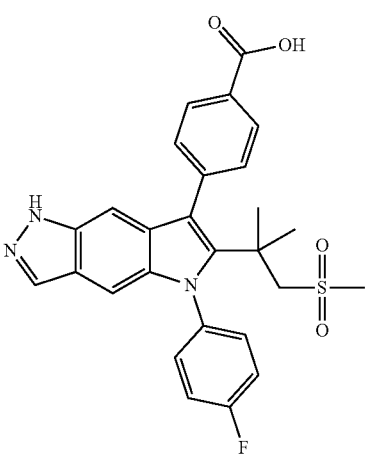 [SMILES: CC(C)(CS(C)(=O)=O)c1c(-c2ccc(C(=O)O)cc2)c2cc3[nH]ncc3cc2n1-c1ccc(F)cc1]
255
TABLE 1-continued
Compounds 1-342
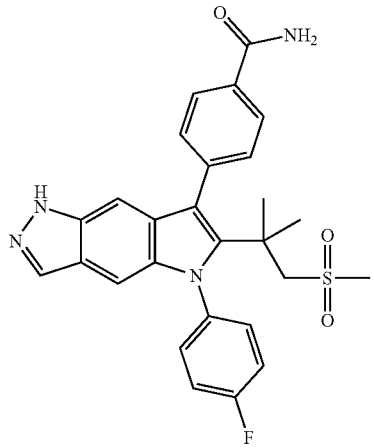 [SMILES: CC(C)(CS(C)(=O)=O)c1c(-c2ccc(C(N)=O)cc2)c2cc3[nH]ncc3cc2n1-c1ccc(F)cc1]
256
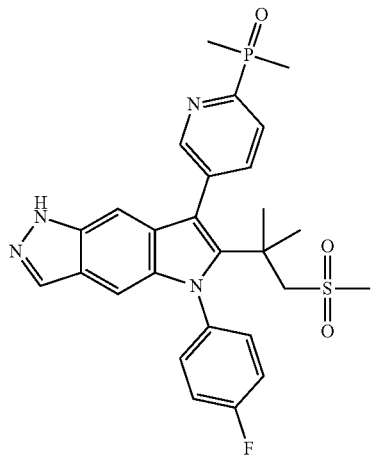 [SMILES: CC(C)(CS(C)(=O)=O)c1c(-c2ccc(P(C)(C)=O)nc2)c2cc3[nH]ncc3cc2n1-c1ccc(F)cc1]
257
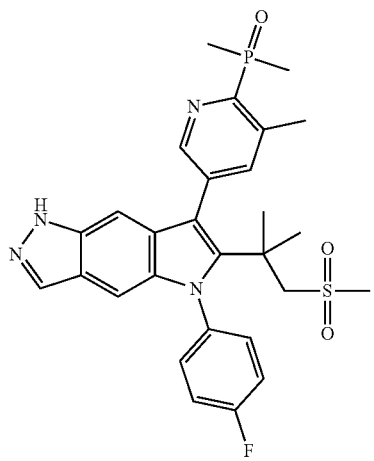 [SMILES: Cc1cc(-c2c(C(C)(C)CS(C)(=O)=O)n(-c3ccc(F)cc3)c3cc4cn[nH]c4cc23)cnc1P(C)(C)=O]
258

TABLE 1-continued
Compounds 1-342
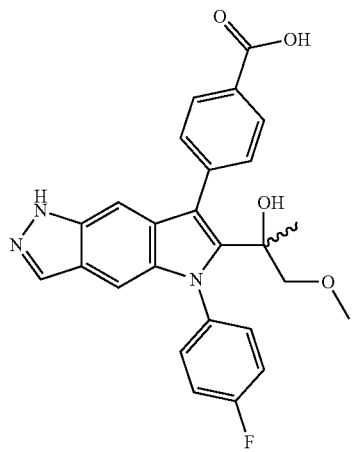 [SMILES: COCC(C)(O)c1c(-c2ccc(C(=O)O)cc2)c2cc3[nH]ncc3cc2n1-c1ccc(F)cc1]
259
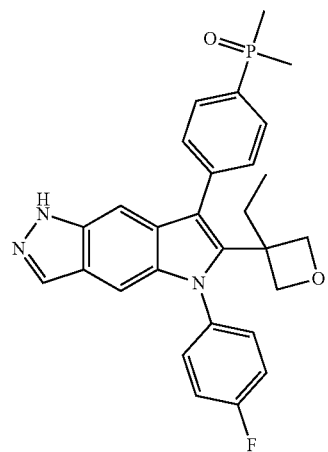 [SMILES: CCC1(c2c(-c3ccc(P(C)(C)=O)cc3)c3cc4[nH]ncc4cc3n2-c2ccc(F)cc2)COC1]
260
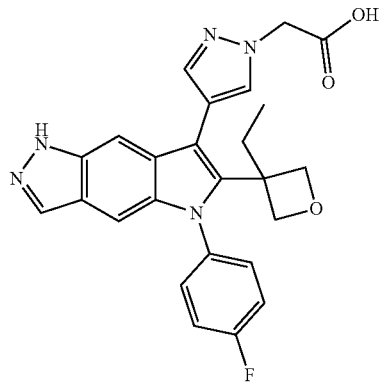 [SMILES: CCC1(c2c(-c3cnn(CC(=O)O)c3)c3cc4[nH]ncc4cc3n2-c2ccc(F)cc2)COC1]
261
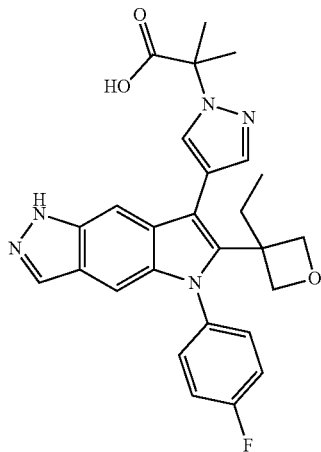 [SMILES: CCC1(c2c(-c3cnn(C(C)(C)C(=O)O)c3)c3cc4[nH]ncc4cc3n2-c2ccc(F)cc2)COC1]
262
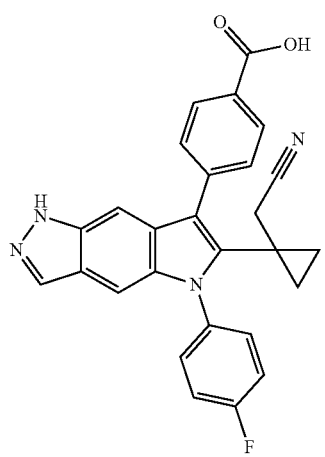 [SMILES: N#CCC1(c2c(-c3ccc(C(=O)O)cc3)c3cc4[nH]ncc4cc3n2-c2ccc(F)cc2)CC1]
263
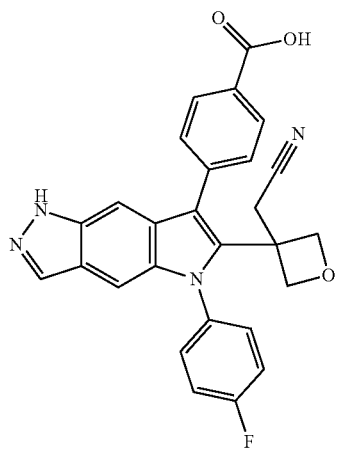 [SMILES: N#CCC1(c2c(-c3ccc(C(=O)O)cc3)c3cc4[nH]ncc4cc3n2-c2ccc(F)cc2)COC1]
264

TABLE 1-continued
Compounds 1-342
265 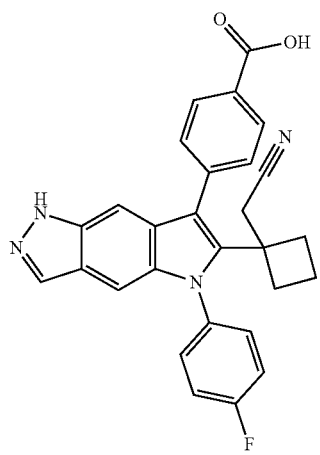 [SMILES: N#CCC1(c2c(-c3ccc(C(=O)O)cc3)c3cc4[nH]ncc4cc3n2-c2ccc(F)cc2)CCC1]
266 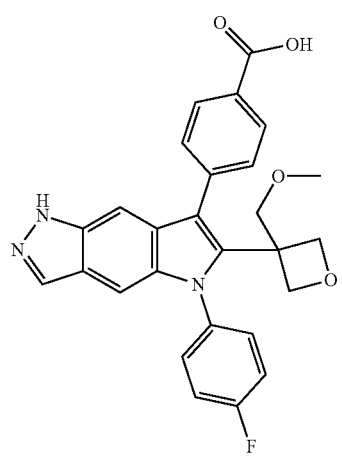 [SMILES: COCC1(c2c(-c3ccc(C(=O)O)cc3)c3cc4[nH]ncc4cc3n2-c2ccc(F)cc2)COC1]
267 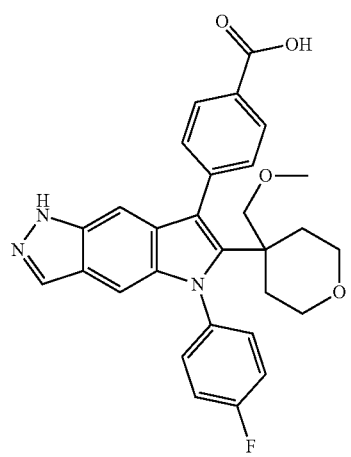 [SMILES: COCC1(c2c(-c3ccc(C(=O)O)cc3)c3cc4[nH]ncc4cc3n2-c2ccc(F)cc2)CCOCC1]
TABLE 1-continued
Compounds 1-342
268 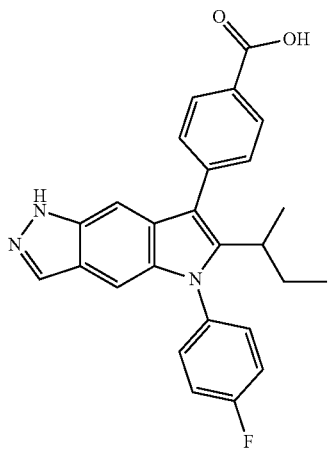 [SMILES: CCC(C)c1c(-c2ccc(C(=O)O)cc2)c2cc3[nH]ncc3cc2n1-c1ccc(F)cc1]
269 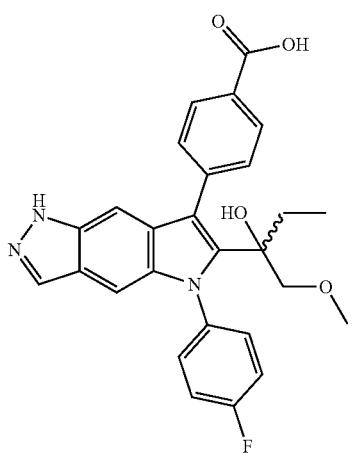 [SMILES: CCC(O)(COC)c1c(-c2ccc(C(=O)O)cc2)c2cc3[nH]ncc3cc2n1-c1ccc(F)cc1]
270 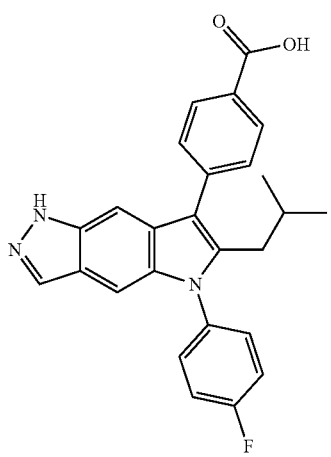 [SMILES: CC(C)Cc1c(-c2ccc(C(=O)O)cc2)c2cc3[nH]ncc3cc2n1-c1ccc(F)cc1]

TABLE 1-continued
Compounds 1-342
| | |
|---|---|
| 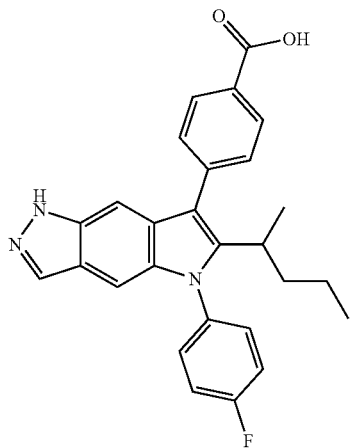 271 | 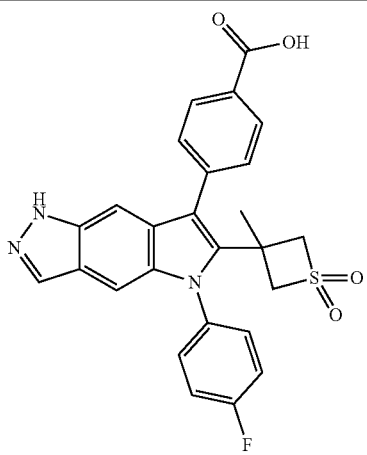 274 |
| 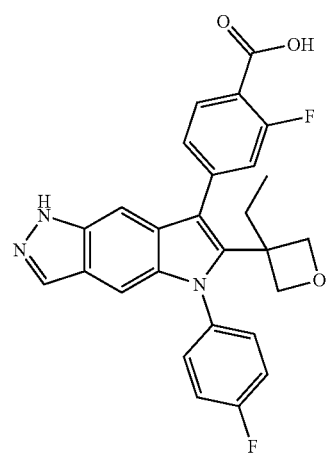 272 | 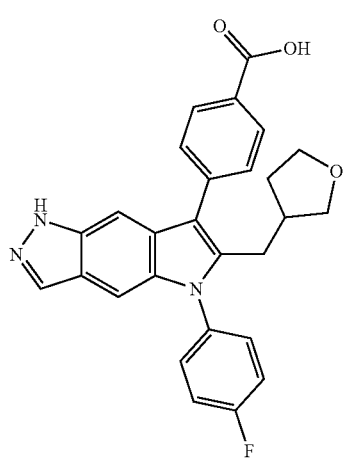 275 |
| 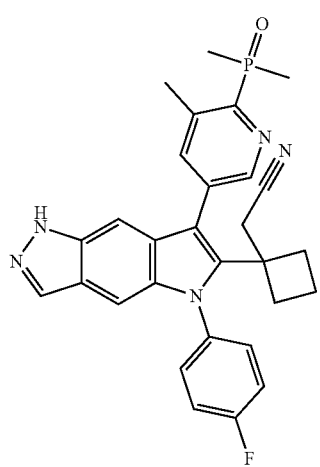 273 | 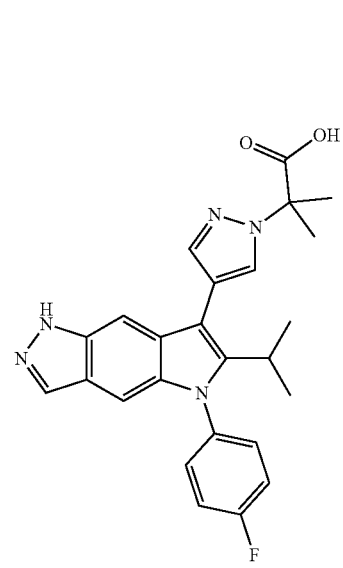 276 |

TABLE 1-continued
Compounds 1-342
277 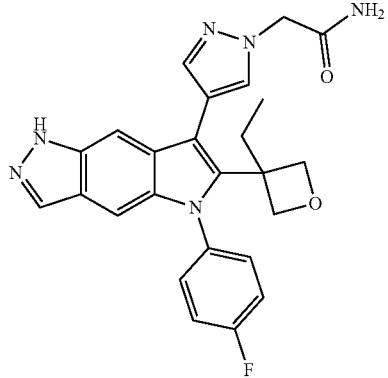
278 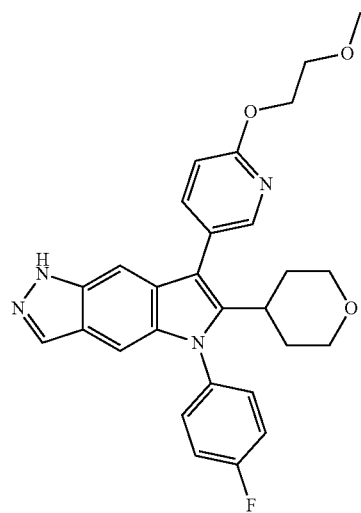
279 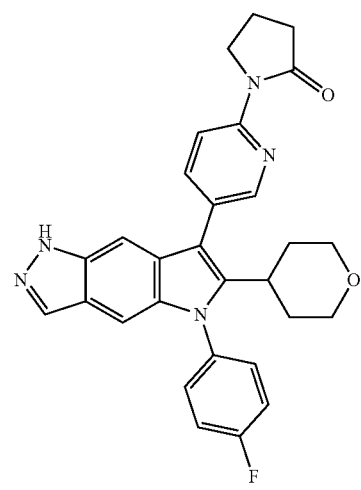
TABLE 1-continued
Compounds 1-342
280 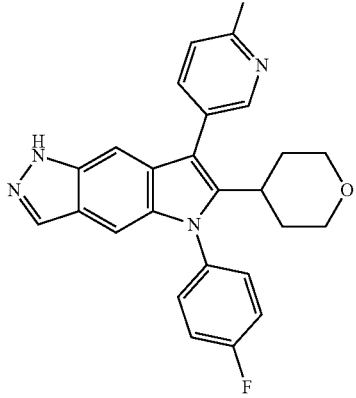
281 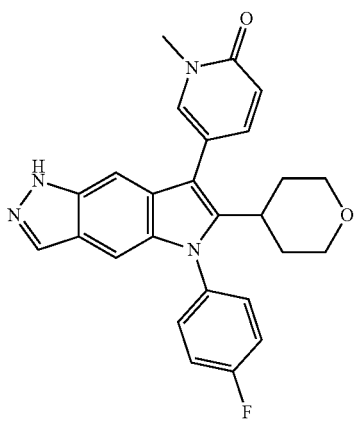
282 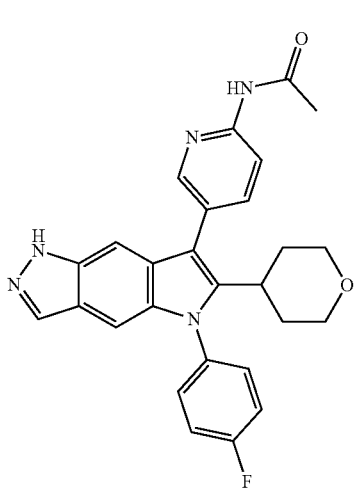

TABLE 1-continued
Compounds 1-342
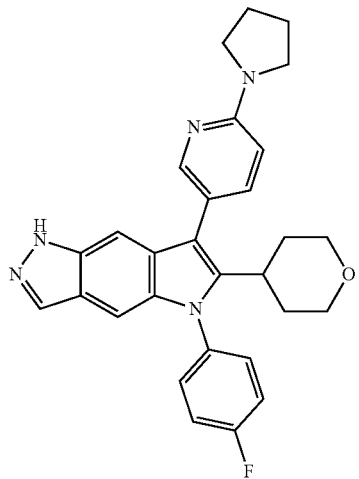
283
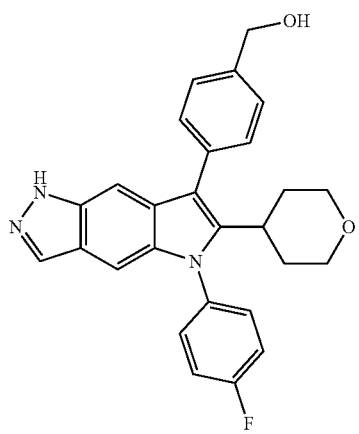
284
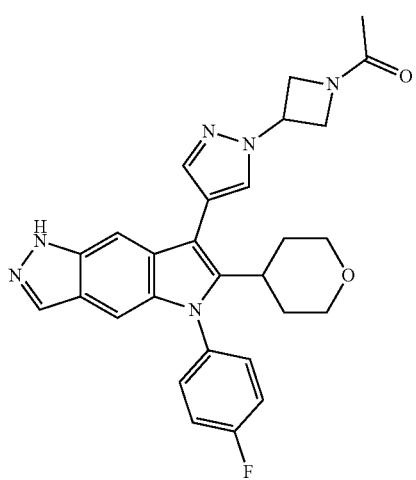
285
TABLE 1-continued
Compounds 1-342
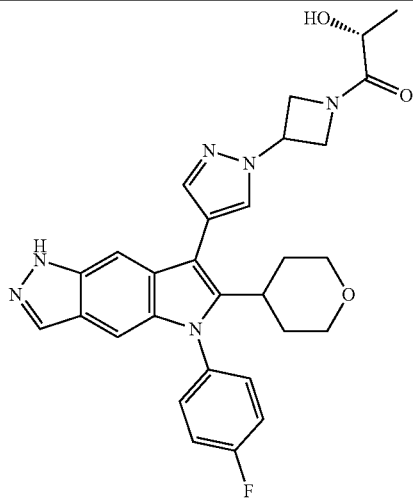
286
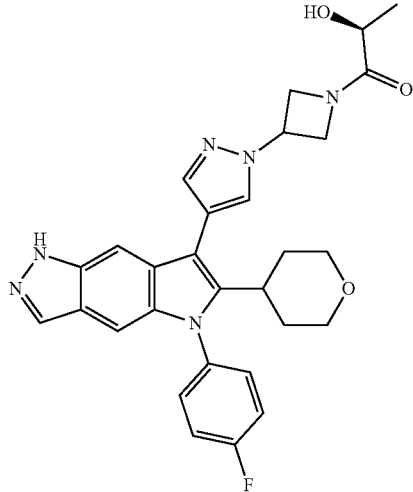
287
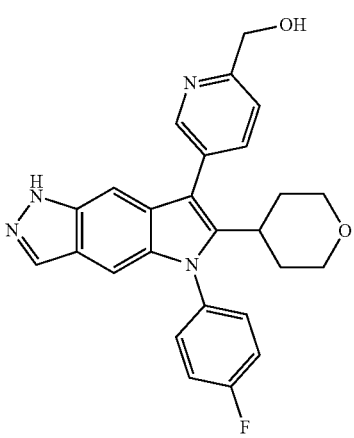
288

TABLE 1-continued
Compounds 1-342
289
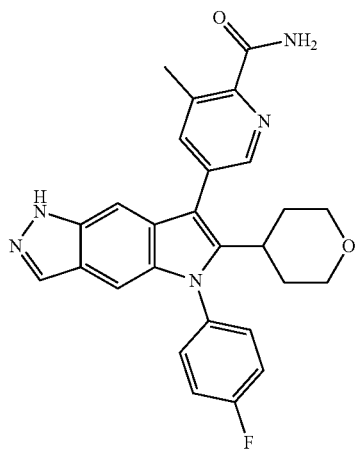
290
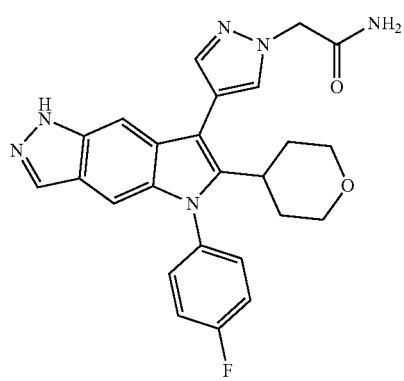
291
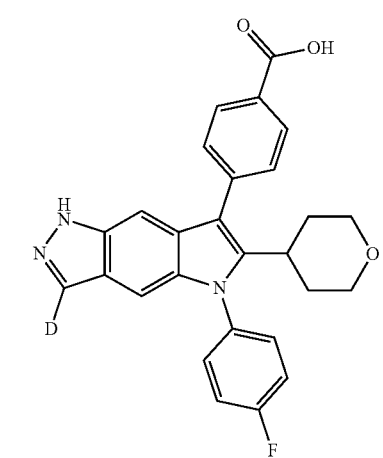
TABLE 1-continued
Compounds 1-342
292
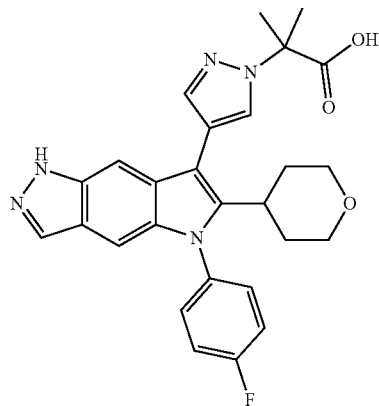
293
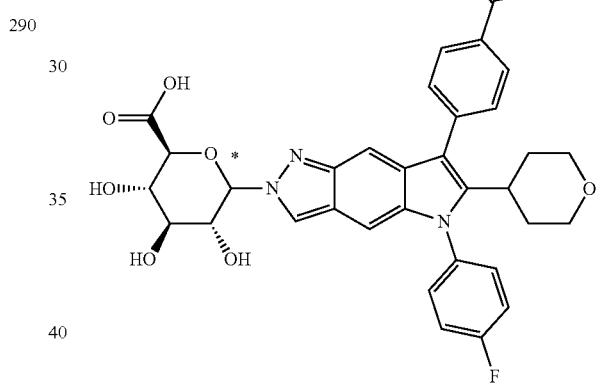
294
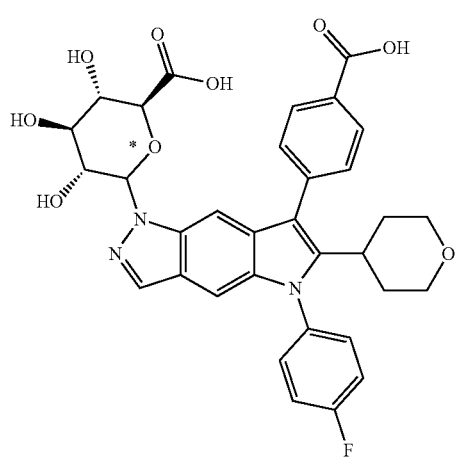

TABLE 1-continued
Compounds 1-342
| 295 | 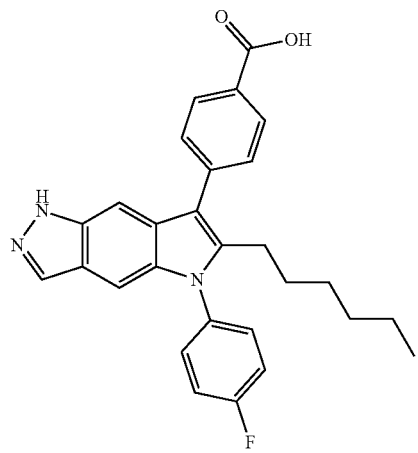 |
| 296 | 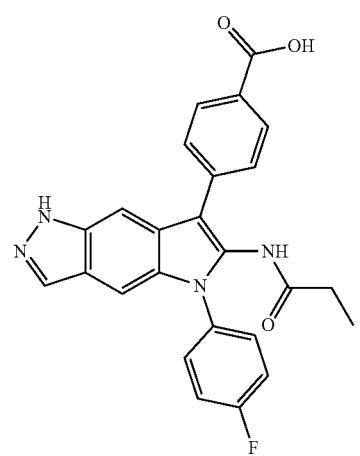 |
| 297 | 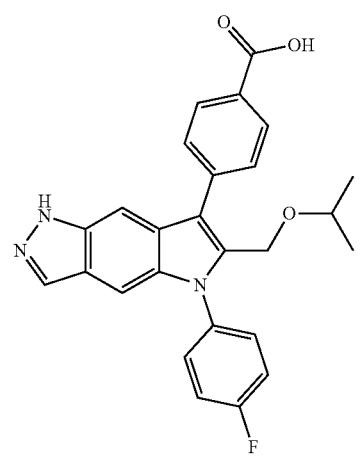 |
| 298 | 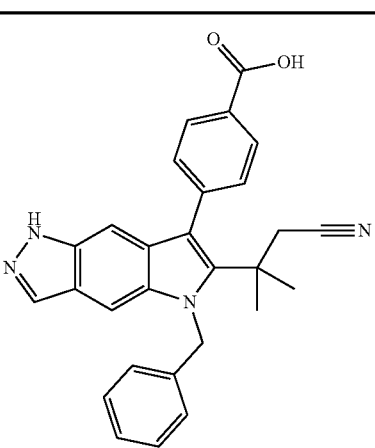 |
| 299 | 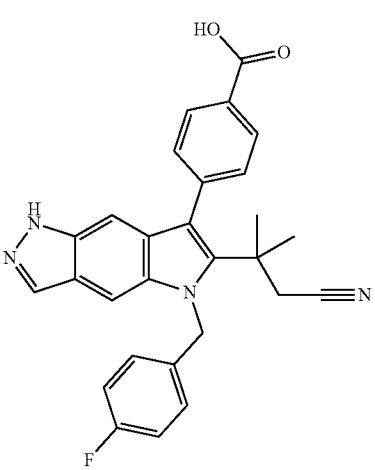 |
| 300 | 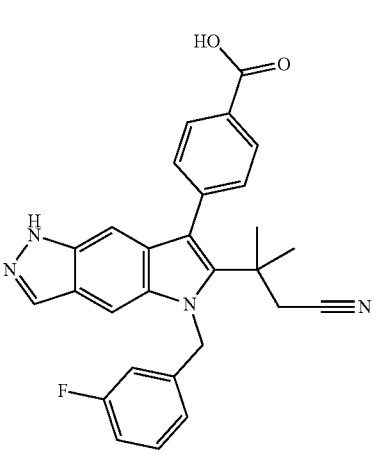 |

TABLE 1-continued
Compounds 1-342
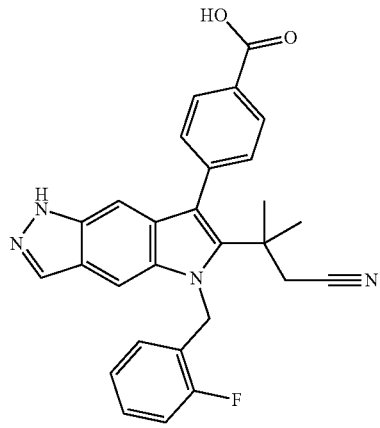
301
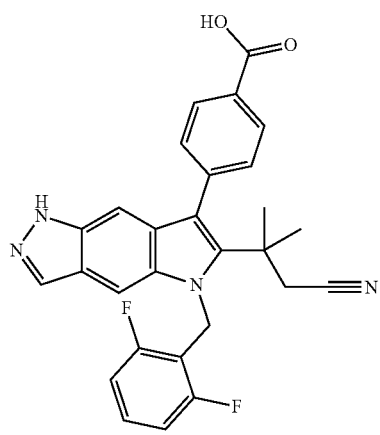
302
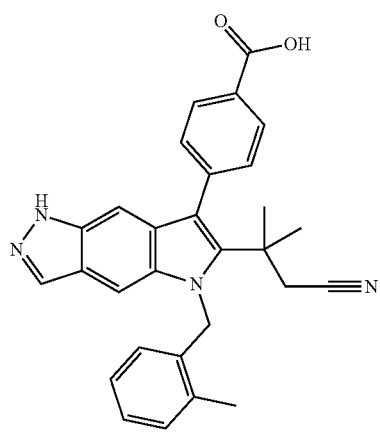
303
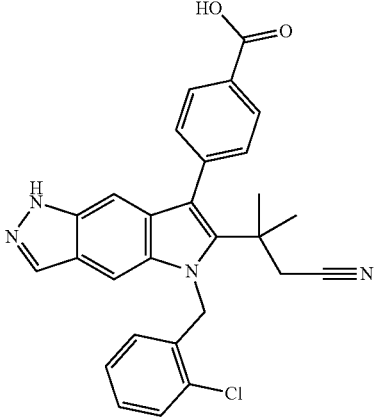
304
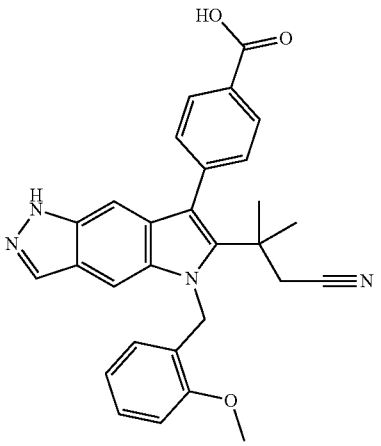
305
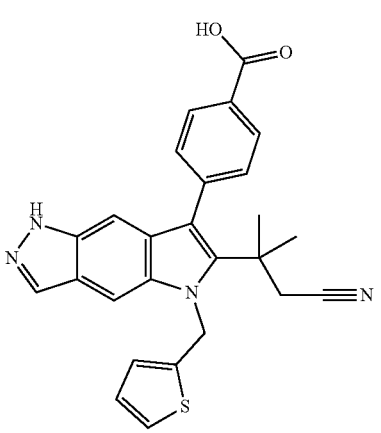
306

TABLE 1-continued
Compounds 1-342
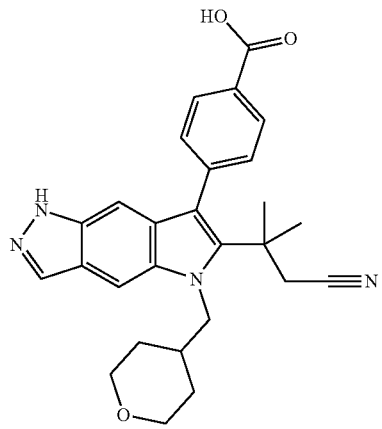 307
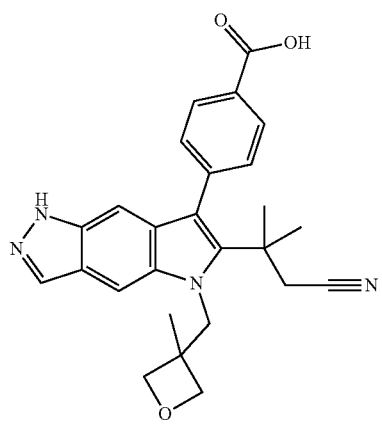 308
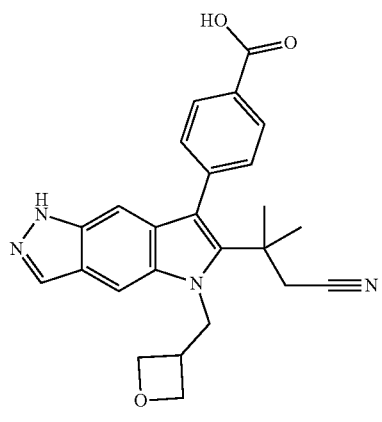 309
TABLE 1-continued
Compounds 1-342
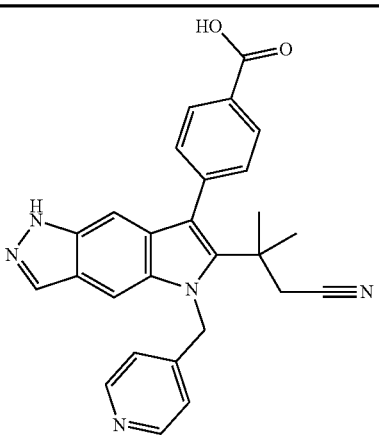 310
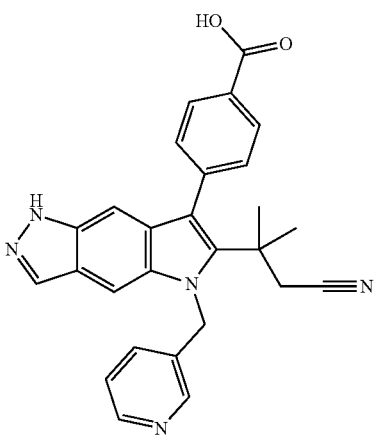 311
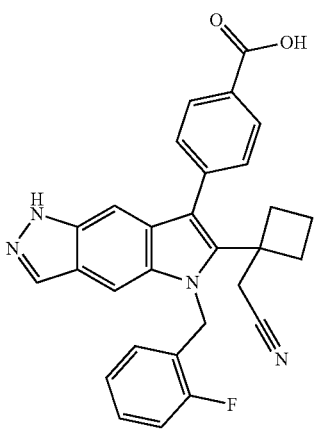 312

TABLE 1-continued
Compounds 1-342
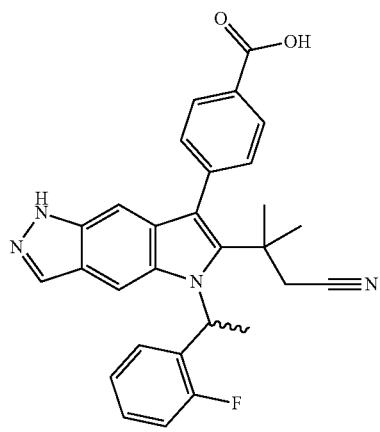
313
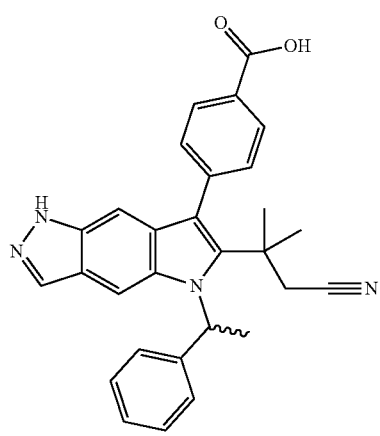
314
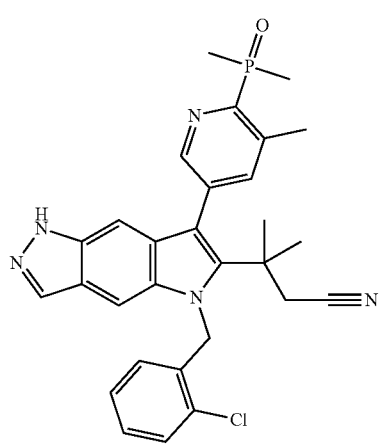
315
TABLE 1-continued
Compounds 1-342
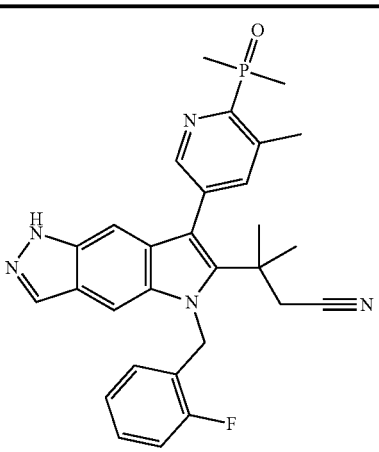
316
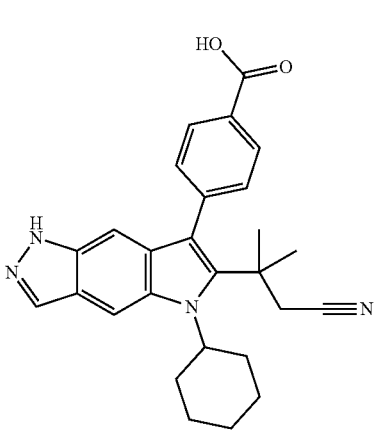
317
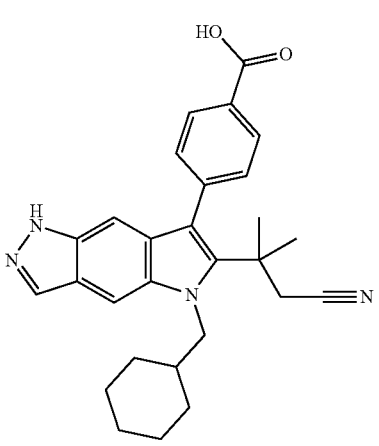
318

TABLE 1-continued
Compounds 1-342
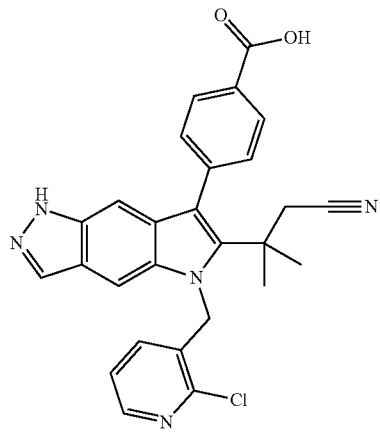
319
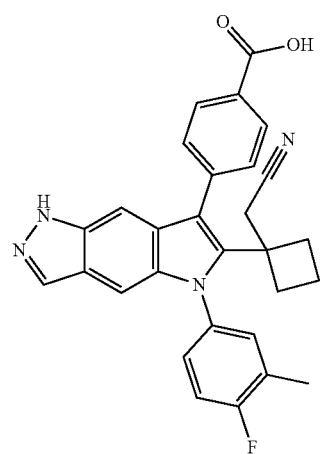
320
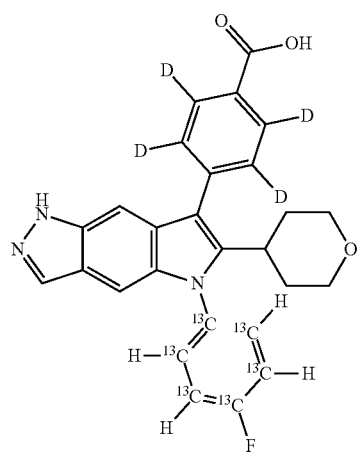
321
TABLE 1-continued
Compounds 1-342
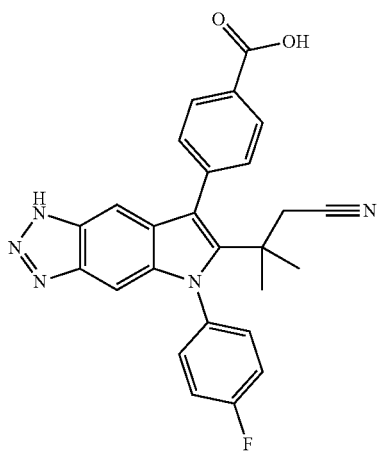
322
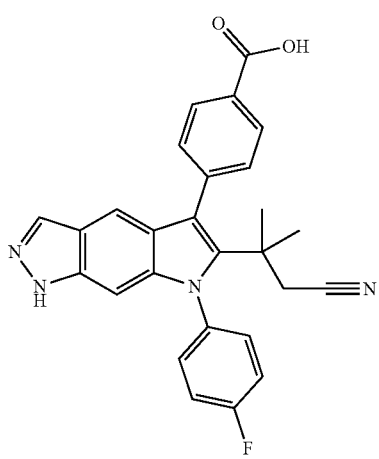
323
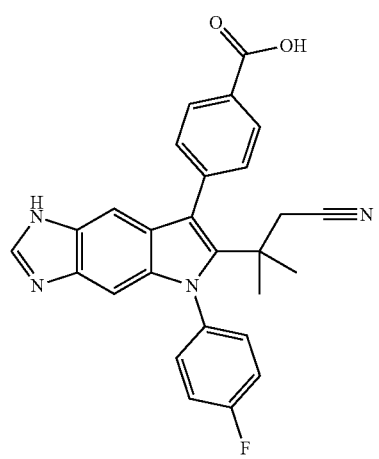
324

TABLE 1-continued
Compounds 1-342
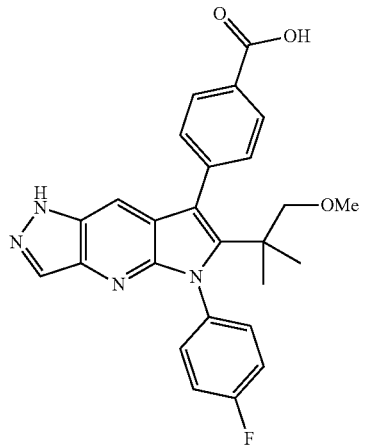
325
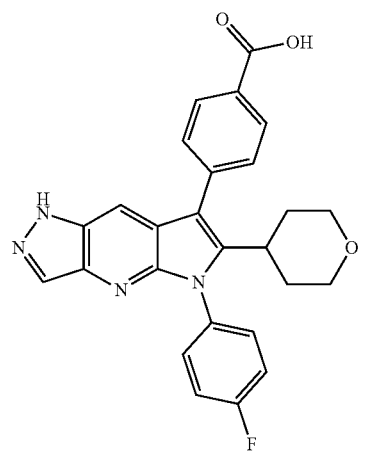
326
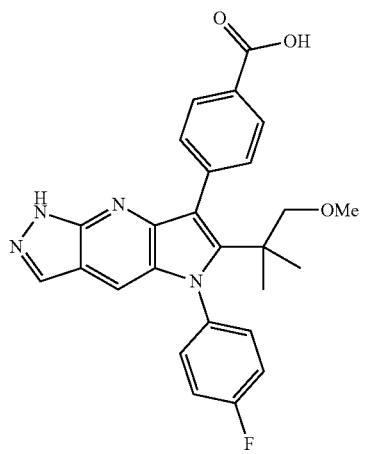
327
TABLE 1-continued
Compounds 1-342
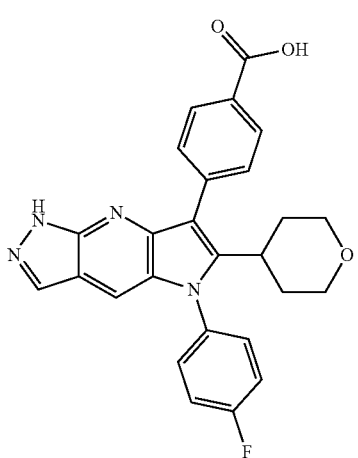
328
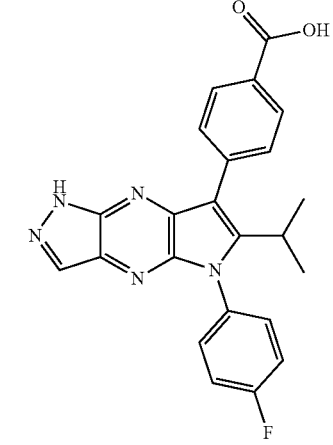
329

330

TABLE 1-continued
Compounds 1-342
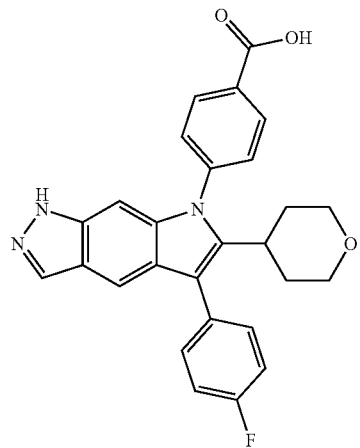
331
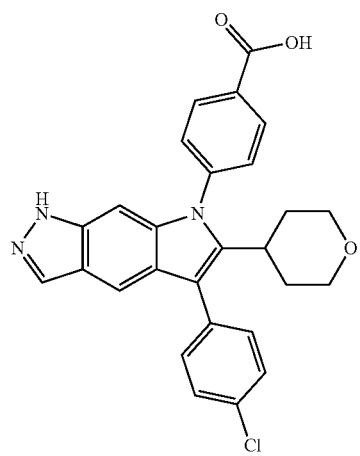
332
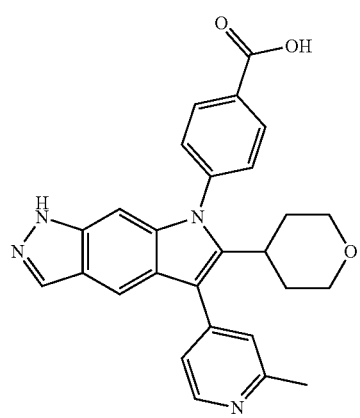
333
TABLE 1-continued
Compounds 1-342
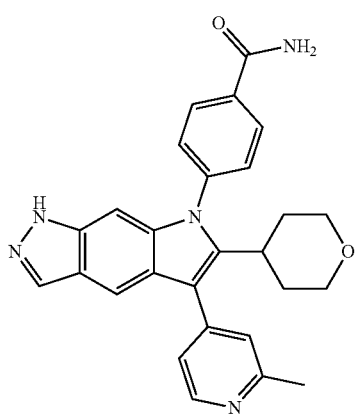
334
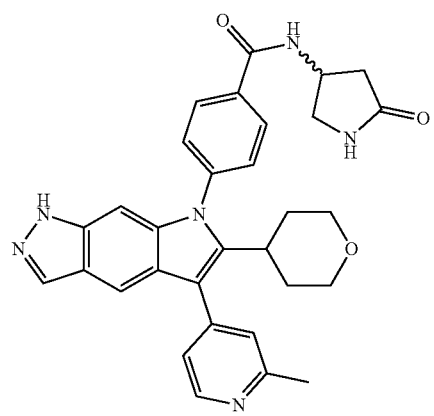
335
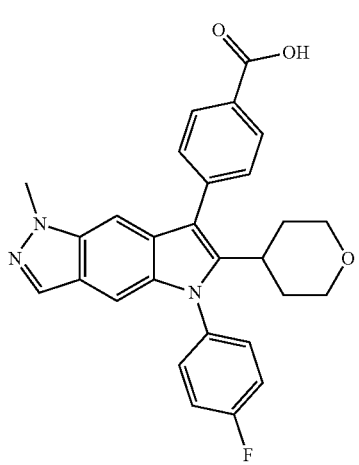
336

TABLE 1-continued

Compounds 1-342

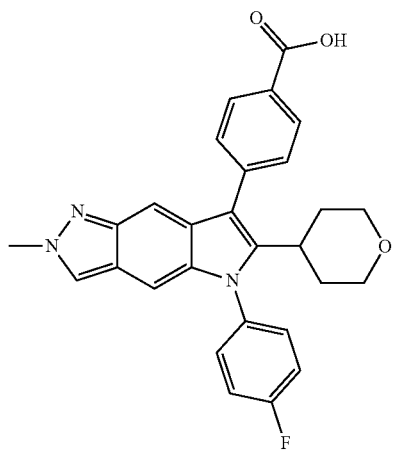
337

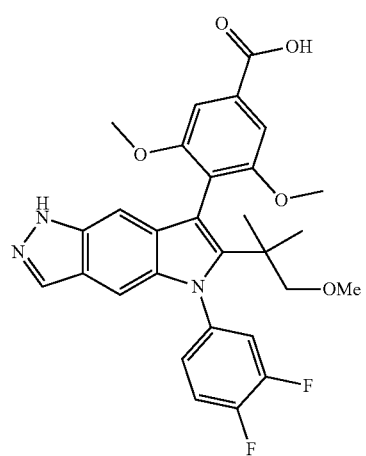
338

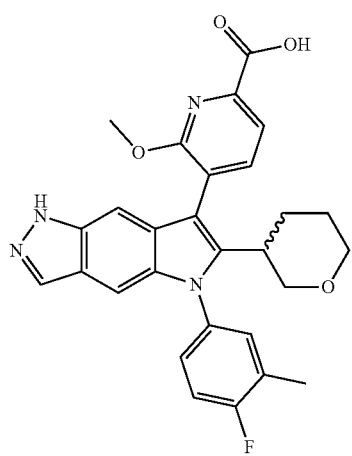
339

TABLE 1-continued

Compounds 1-342

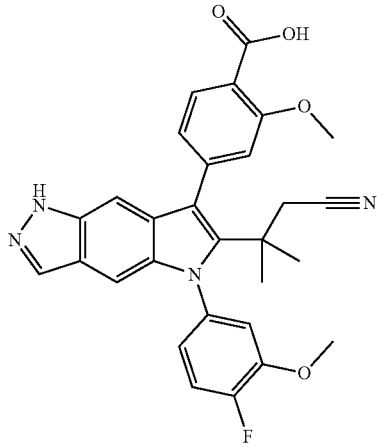
340

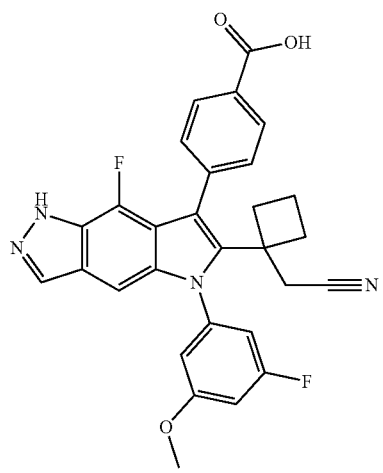
341

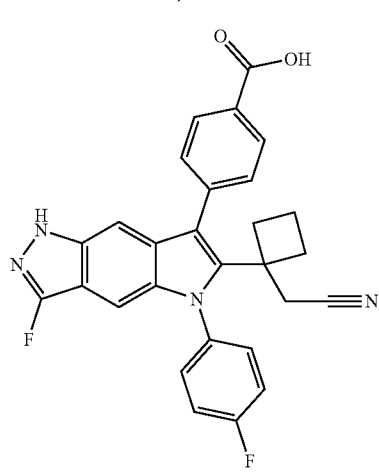
342

Some embodiments of the invention include derivatives of Compounds 1-342 or compounds of Formulae I, I-A, I-B, I-C, I-D, I-E, I-F, I-G, and I-H. In some embodiments, the derivatives are silicon derivatives in which at least one carbon atom in a compound selected from Compounds 1-342 or compounds of Formulae I, I-A, I-B, I-C, I-D, I-E, I-F, I-G, and I-H has been replaced by silicon. In some embodiments, the derivatives are boron derivatives, in which at least one carbon atom in a compound selected from Compounds 1-342 or compounds of Formulae I, I-A, I-B, I-C, I-D, I-E, I-F, I-G, and I-H has been replaced by boron. In other embodiments, the derivatives are phosphate derivatives, in which at least one carbon atom in a compound selected from Compounds 1-342 or compounds of Formulae I, I-A, I-B, I-C, I-D, I-E, I-F, I-G, and I-H has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom in a compound selected from Compounds 1-342 or compounds of Formulae I, I-A, I-B, I-C, I-D, I-E, I-F, I-G, and I-H has been replaced by silicon. In other embodiments, two carbon atoms have been replaced by silicon. The carbon replaced by silicon may be a non-aromatic carbon. In some embodiments a quaternary carbon atom of a tert-butyl moiety may be replaced by silicon. In certain embodiments, the silicon derivatives of the invention may include one or more hydrogen atoms replaced by deuterium. For example, one or more hydrogens of a tert-butyl moiety in which the carbon has been replaced by silicon, may be replaced by deuterium. In other embodiments, a silicon derivative of a compound selected from Compounds 1-342 or compounds of Formulae I, I-A, I-B, I-C, I-D, I-E, I-F, I-G, and I-H may have silicon incorporated into a heterocycle ring.

Solid Forms of Compound 33

In some embodiments, Compound 33 is an amorphous solid. In some embodiments, Compound 33 is a crystalline solid. In some embodiments, Compound 33 is in the form of Compound 33 Form A. In some embodiments, Compound 33 is in the form of Compound 33 Form B. In some embodiments, Compound 33 is in the form of Compound 33 dichloromethane (DCM) solvate Form A. In some embodiments, Compound 33 is in the form of Compound 33 hydrate Form A. In some embodiments, Compound 33 is in the form of Compound 33 methanol (MeOH)/H$_2$O solvate Form A. In some embodiments, Compound 33 is in the form of Compound 33 Form C. In some embodiments, Compound 33 is in the form of Compound 33 Form D. In some embodiments, Compound 33 is in the form of Compound 33 Form E. In some embodiments, Compound 33 is in the form of Compound 33 Form F. In some embodiments, Compound 33 is in the form of Compound 33 Form G. In some embodiments, Compound 33 is in the form of Compound 33 Form H. In some embodiments, Compound 33 is in the form of Compound 33 Form I. In some embodiments, Compound 33 is in the form of Compound 33 tetrahydrofuran (THF) solvate Form A. In some embodiments, Compound 33 is in the form of Compound 33 Form J. In some embodiments, Compound 33 is in the form of Compound 33 Form K. In some embodiments, Compound 33 is in the form of Compound 33 Form L. In some embodiments, Compound 33 is in the form of Compound 33 2-methyltetrahydrofuran (Me-THF) solvate Form A. In some embodiments, Compound 33 is in the form of Compound 33 Form M. In some embodiments, Compound 33 is in the form of Compound 33 Form N. In some embodiments, Compound 33 is in the form of Compound 33 Form O. In some embodiments, Compound 33 is in the form of Compound 33 potassium salt Form A. In some embodiments, Compound 33 is in the form of Compound 33 potassium salt Form B. In some embodiments, Compound 33 is in the form of Compound 33 potassium salt Form C. In some embodiments, Compound 33 is a mixture of any two or more of the foregoing.

1. Compound 33 Form A

In some embodiments, Compound 33 is a crystalline solid comprising of crystalline Form A. In some embodiments, the crystalline solid comprises of 30% to 99% crystalline Compound 33 Form A relative to the total weight of solid Compound 33. In some embodiments, the crystalline solid comprises of 40% to 99% Compound 33 Form A relative to the total weight of solid Compound 33. In some embodiments, the crystalline solid comprises of 50% to 99% Compound 33 Form A relative to the total weight of solid Compound 33. In some embodiments, the crystalline solid comprises of 60% to 99% Compound 33 Form A relative to the total weight of solid Compound 33. In some embodiments, the crystalline solid comprises of 70% to 99% Compound 33 Form A relative to the total weight of solid Compound 33. In some embodiments, the crystalline solid comprises of 75% to 99% Compound 33 Form A relative to the total weight of solid Compound 33. In some embodiments, the crystalline solid comprises of 80% to 99% Compound 33 Form A relative to the total weight of solid Compound 33. In some embodiments, the crystalline solid comprises of 85% to 99% Compound 33 Form A relative to the total weight of solid Compound 33. In some embodiments, the crystalline solid comprises of 90% to 99% Compound 33 Form A relative to the total weight of solid Compound 33. In some embodiments, the crystalline solid comprises of 95% to 99% Compound 33 Form A relative to the total weight of solid Compound 33.

Thus, in some embodiments, Compound 33 Form A is substantially crystalline. In some embodiments, Compound 33 Form A is substantially pure crystalline. In some embodiments, Compound 33 Form A is characterized by an X-ray powder diffractogram generated by an X-ray powder diffraction analysis with an incident beam of Cu Kα radiation. FIG. 1A provides an X-ray powder diffractogram of Compound 33 Form A at room temperature.

In some embodiments, Compound 33 Form A is characterized by an X-ray powder diffractogram having signals at one or more of 15.5±0.2 degrees two-theta, 17.5±0.2 degrees two-theta, 19.2±0.2 degrees two-theta, and 19.5±0.2 degrees two-theta. In some embodiments, Compound 33 Form A is characterized by an X-ray powder diffractogram having signals at 15.5±0.2 degrees two-theta, 17.5±0.2 degrees two-theta, 19.2±0.2 degrees two-theta, and 19.5±0.2 degrees two-theta. In some embodiments, Compound 33 Form A is characterized by an X-ray powder diffractogram having (a) signals at 19.2±0.2 degrees two-theta, 19.5±0.2 degrees two-theta, 15.5±0.2 degrees two-theta, and 17.5±0.2 degrees two-theta; and (b) at least one, at least two, at least three, at least four, or at least five signals selected from 11.0±0.2 degrees two-theta, 14.2±0.2 degrees two-theta, 16.0±0.2 degrees two-theta, 16.2±0.2 degrees two-theta, 20.9±0.2 degrees two-theta, 21.3±0.2 degrees two-theta, 21.8±0.2 degrees two-theta, and 25.5±0.2 degrees two-theta. In some embodiments, Compound 33 Form A is characterized by an X-ray powder diffractogram having signals at 11.0±0.2 degrees two-theta, 14.2±0.2 degrees two-theta, 15.5±0.2 degrees two-theta, 16.0±0.2 degrees two-theta, 16.2±0.2 degrees two-theta, 17.5±0.2 degrees two-theta, 19.2±0.2 degrees two-theta, 19.5±0.2 degrees two-theta, 20.9±0.2 degrees two-theta, 21.3±0.2 degrees two-theta, 21.8±0.2 degrees two-theta, and 25.5±0.2 degrees two-theta.

In some embodiments Compound 33 Form A is characterized by an X-ray powder diffractogram substantially similar to FIG. 1A.

In some embodiments, Compound 33 Form A is characterized as having a $^{13}$C ssNMR spectrum with at least one peak selected from: 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound I sodium salt hydrate Form A is characterized as having a $^{13}$C ssNMR spectrum with at least two peaks selected from: 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound 33 Form A is characterized as having a $^{13}$C ssNMR spectrum with at least three peaks selected from: 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound 33 Form A is characterized as having a $^{13}$C ssNMR spectrum with at least four peaks selected from: 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound 33 Form A is characterized as having a $^{13}$C ssNMR spectrum with at least five peaks selected from: 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound 33 Form A is characterized as having a $^{13}$C ssNMR spectrum with at least six, at least seven, or at least eight peaks selected from: 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound 33 Form A is characterized as having a $^{13}$C ssNMR spectrum with peaks at 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm. In some embodiments, Compound 33 Form A is characterized by a $^{13}$C ssNMR spectrum substantially similar to FIG. 1B.

In some embodiments, Compound 33 Form A is characterized as having a $^{19}$F ssNMR spectrum with a peak at −109.3±0.2 ppm. In some embodiments, Compound 33 Form A is characterized by a $^{19}$F ssNMR spectrum substantially similar to FIG. 1C.

Another aspect of the invention provides a composition comprising Compound 33 Form A. In some embodiments, the composition of the invention comprises substantially pure crystalline Compound 33 Form A. In some embodiments, the composition consists essentially of Compound 33 Form A.

Another aspect of the invention provides a method of making Compound 33 Form A. In some embodiments, Compound 33, Form A is prepared by:
(a) contacting methyl 4-(5-(4-fluorophenyl)-1-pivaloyl-6-(tetrahydro-2H-pyran-4-yl)-1,5-dihydropyrrolo[2,3-f]indazol-7-yl)benzoate with a first organic solvent and a first base to form a first reaction mixture;
(b) adding water and a first acid to the first reaction mixture;
(c) isolating an organic portion from step (b), adding an alcohol and optionally adding water to the organic portion, and concentrating the mixture by distillation; and
(d) isolating the compound 4-[5-(4-fluorophenyl)-6-tetrahydropyran-4-yl-1H-pyrrolo[2,3-f]indazol-7-yl]benzoic acid from the mixture from step (c) and drying the material to remove all water content.

2. Compound 33 Form B

In some embodiments, Compound 33 is a crystalline solid comprising of crystalline Form B. In some embodiments, the crystalline solid comprises of 30% to 99% crystalline Compound 33 Form B relative to the total weight of solid Compound 33. In some embodiments, the crystalline solid comprises of 40% to 99% Compound 33 Form B relative to the total weight of solid Compound 33. In some embodiments, the crystalline solid comprises of 50% to 99% Compound 33 Form B relative to the total weight of solid Compound 33. In some embodiments, the crystalline solid comprises of 60% to 99% Compound 33 Form B relative to the total weight of solid Compound 33. In some embodiments, the crystalline solid comprises of 70% to 99% Compound 33 Form B relative to the total weight of solid Compound 33. In some embodiments, the crystalline solid comprises of 75% to 99% Compound 33 Form B relative to the total weight of solid Compound 33. In some embodiments, the crystalline solid comprises of 80% to 99% Compound 33 Form B relative to the total weight of solid Compound 33. In some embodiments, the crystalline solid comprises of 85% to 99% Compound 33 Form B relative to the total weight of solid Compound 33. In some embodiments, the crystalline solid comprises of 90% to 99% Compound 33 Form B relative to the total weight of solid Compound 33. In some embodiments, the crystalline solid comprises of 95% to 99% Compound 33 Form B relative to the total weight of solid Compound 33.

Figure 2A:
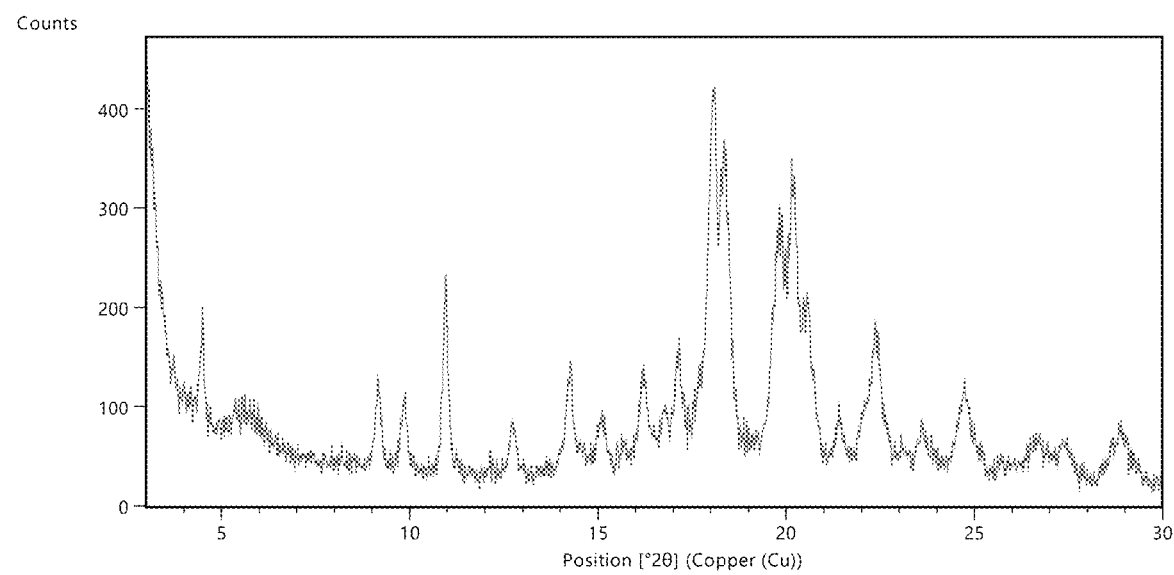
FIG. 2A shows an XRPD diffractogram of Compound 33 Form B.

Thus, in some embodiments, Compound 33 Form B is substantially crystalline. In some embodiments, Compound 33 Form B is substantially pure crystalline. In some embodiments, Compound 33 Form B is characterized by an X-ray powder diffractogram generated by an X-ray powder diffraction analysis with an incident beam of Cu Kα radiation. FIG. 2A provides an X-ray powder diffractogram of Compound 33 Form B at room temperature.

In some embodiments, Compound 33 Form B is characterized by an X-ray powder diffractogram having signals at one or more of 20.2±0.2 degrees two-theta, 9.2±0.2 degrees two-theta, 4.5±0.2 degrees two-theta, and 15.1±0.2 degrees two-theta. In some embodiments, Compound 33 Form B is characterized by an X-ray powder diffractogram having signals at 20.2±0.2 degrees two-theta, 9.2±0.2 degrees two-theta, 4.5±0.2 degrees two-theta, and 15.1±0.2. In some embodiments, Compound 33 Form B is characterized by an X-ray powder diffractogram having (a) signals at 20.2±0.2 degrees two-theta, 9.2±0.2 degrees two-theta, 4.5±0.2 degrees two-theta, and 15.1±0.2; and (b) at least one, at least two, at least three, at least four, at least five, at least six, at least eight, or at least ten signals selected from 9.9±0.2 degrees two-theta, 11.0±0.2 degrees two-theta, 12.7±0.2 degrees two-theta, 14.3±0.2 degrees two-theta, 16.2±0.2 degrees two-theta, 16.8±0.2 degrees two-theta, 17.1±0.2 degrees two-theta, 18.1±0.2 degrees two-theta, 18.4±0.2 degrees two-theta, 19.8±0.2 degrees two-theta, 20.6±0.2 degrees two-theta, 21.4±0.2 degrees two-theta, 22.3±0.2 degrees two-theta, 23.6±0.2 degrees two-theta, 24.7±0.2 degrees two-theta, 26.6±0.2 degrees two-theta, 27.4±0.2 degrees two-theta, and 28.9±0.2 degrees two-theta.

In some embodiments Compound 33 Form B is characterized by an X-ray powder diffractogram substantially similar to FIG. 2A.

In some embodiments, Compound 33 Form B is characterized as having a $^{13}$C ssNMR spectrum with at least one peak selected from: 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound I sodium salt hydrate Form B is characterized as having a $^{13}$C ssNMR spectrum with at least two peaks selected from: 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound 33 Form B is characterized as having a $^{13}$C ssNMR spectrum with at least three peaks selected from: 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound 33 Form B is characterized as having a $^{13}$C ssNMR spectrum with at least four peaks selected from: 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound 33 Form B is characterized as having a $^{13}$C ssNMR spectrum with at least five peaks selected from: 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound 33 Form B is characterized as having a $^{13}$C ssNMR spectrum with at least six, or at least seven peaks selected from: 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound 33 Form B is characterized as having a $^{13}$C ssNMR spectrum with peaks at 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm. In some embodiments, Compound 33 Form B is characterized by a $^{13}$C ssNMR spectrum substantially similar to FIG. 2B.

In some embodiments, Compound 33 Form B is characterized as having a $^{19}$F ssNMR spectrum with a peak at one or more of −110.2±0.2 ppm, 111.6±0.2 ppm, and −115.6±0.2 ppm. In some embodiments, Compound 33 Form B is characterized as having a $^{19}$F ssNMR spectrum with peaks at −110.2±0.2 ppm, 111.6±0.2 ppm, and −115.6±0.2 ppm. In some embodiments, Compound 33 Form B is characterized by a $^{19}$F ssNMR spectrum substantially similar to FIG. 2C.

Another aspect of the invention provides a composition comprising Compound 33 Form B. In some embodiments, the composition of the invention comprises substantially pure crystalline Compound 33 Form B. In some embodiments, the composition consists essentially of Compound 33 Form B.

Another aspect of the invention provides a method of making Compound 33 Form B. In some embodiments, Compound 33, Form B is prepared by suspending Compound 33 Form A in DCM, stirring, and isolating air-dried solids.

3. Compound 33 DCM Solvate Form A

In some embodiments, Compound 33 is a crystalline solid comprising of crystalline DCM Solvate Form A. In some embodiments, the crystalline solid comprises of 30% to 99% crystalline Compound 33 DCM Solvate Form A relative to the total weight of solid Compound 33. In some embodiments, the crystalline solid comprises of 40% to 99% Compound 33 DCM Solvate Form A relative to the total weight of solid Compound 33. In some embodiments, the crystalline solid comprises of 50% to 99% Compound 33 DCM Solvate Form A relative to the total weight of solid Compound 33. In some embodiments, the crystalline solid comprises of 60% to 99% Compound 33 DCM Solvate Form A relative to the total weight of solid Compound 33. In some embodiments, the crystalline solid comprises of 70% to 99% Compound 33 DCM Solvate Form A relative to the total weight of solid Compound 33. In some embodiments, the crystalline solid comprises of 75% to 99% Compound 33 DCM Solvate Form A relative to the total weight of solid Compound 33. In some embodiments, the crystalline solid comprises of 80% to 99% Compound 33 DCM Solvate Form A relative to the total weight of solid Compound 33. In some embodiments, the crystalline solid comprises of 85% to 99% Compound 33 DCM Solvate Form A relative to the total weight of solid Compound 33. In some embodiments, the crystalline solid comprises of 90% to 99% Compound 33 DCM Solvate Form A relative to the total weight of solid Compound 33. In some embodiments, the crystalline solid comprises of 95% to 99% Compound 33 DCM Solvate Form A relative to the total weight of solid Compound 33.

Figure 3A:
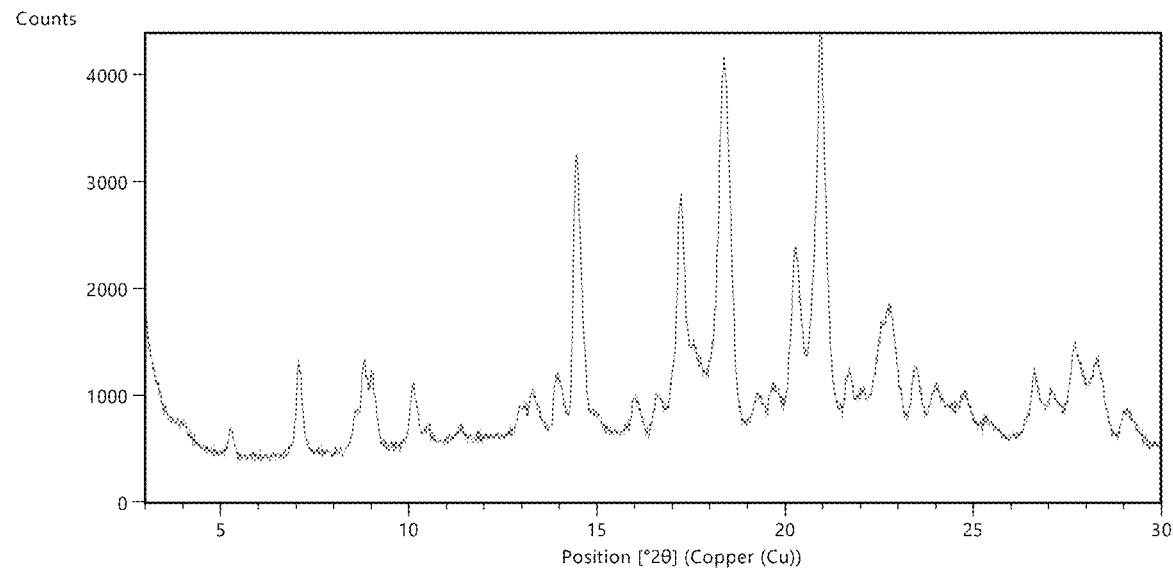
FIG. 3A shows an XRPD diffractogram of Compound 33 DCM solvate Form A.

Thus, in some embodiments, Compound 33 DCM Solvate Form A is substantially crystalline. In some embodiments, Compound 33 DCM Solvate Form A is substantially pure crystalline. In some embodiments, Compound 33 Form A is characterized by an X-ray powder diffractogram generated by an X-ray powder diffraction analysis with an incident beam of Cu Kα radiation. FIG. 3A provides an X-ray powder diffractogram of Compound 33 DCM Solvate Form A at room temperature.

In some embodiments, Compound 33 DCM Solvate Form A is characterized by an X-ray powder diffractogram having signals at one or more of 20.9±0.2 degrees two-theta, 18.3±0.2 degrees two-theta, and 14.4±0.2 degrees two-theta. In some embodiments, Compound 33 DCM Solvate Form A is characterized by an X-ray powder diffractogram having signals at 20.9±0.2 degrees two-theta, 18.3±0.2 degrees two-theta, and 14.4±0.2 degrees two-theta. In some embodiments, Compound 33 DCM Solvate Form A is characterized by an X-ray powder diffractogram having (a) signals at 20.9±0.2 degrees two-theta, 18.3±0.2 degrees two-theta, and 14.4±0.2 degrees two-theta; and (b) at least one, at least two, at least three, at least four, at least five, at least six, at least eight, or at least ten signals selected from 7.1±0.2 degrees two-theta, 8.8±0.2 degrees two-theta, 9.0±0.2 degrees two-theta, 10.1±0.2 degrees two-theta, 13.3±0.2 degrees two-theta, 13.9±0.2 degrees two-theta, 17.2±0.2 degrees two-theta, 20.3±0.2 degrees two-theta, 21.7±0.2 degrees two-theta, 22.6±0.2 degrees two-theta, 22.8±0.2 degrees two-theta, 23.4±0.2 degrees two-theta, 24.0±0.2 degrees two-theta, 26.6±0.2 degrees two-theta, 27.1±0.2 degrees two-theta, 27.7±0.2 degrees two-theta, 28.3±0.2 degrees two-theta.

In some embodiments Compound 33 DCM Solvate Form A is characterized by an X-ray powder diffractogram substantially similar to FIG. 3A.

Another aspect of the invention provides a composition comprising Compound 33 DCM Solvate Form A. In some embodiments, the composition of the invention comprises substantially pure crystalline Compound 33 DCM Solvate Form A. In some embodiments, the composition consists essentially of Compound 33 DCM Solvate Form A.

Another aspect of the invention provides a method of making Compound 33 DCM Solvate Form A. In some embodiments, Compound 33 DCM Solvate Form A is prepared by suspending Compound 33 Form A in a mixture of DCM, EtOH, and THF (about 54:36:10 by volume), stirring, and then isolating the solid.

4. Compound 33 Hydrate Form A

In some embodiments, Compound 33 is a crystalline solid comprising of crystalline Hydrate Form A. In some embodiments, the crystalline solid comprises of 30% to 99% crystalline Compound 33 Hydrate Form A relative to the total weight of solid Compound 33. In some embodiments, the crystalline solid comprises of 40% to 99% Compound 33 Hydrate Form A relative to the total weight of solid Compound 33. In some embodiments, the crystalline solid comprises of 50% to 99% Compound 33 Hydrate Form A relative to the total weight of solid Compound 33. In some embodiments, the crystalline solid comprises of 60% to 99%

Compound 33 Hydrate Form A relative to the total weight of solid Compound 33. In some embodiments, the crystalline solid comprises of 70% to 99% Compound 33 Hydrate Form A relative to the total weight of solid Compound 33. In some embodiments, the crystalline solid comprises of 75% to 99% Compound 33 Hydrate Form A relative to the total weight of solid Compound 33. In some embodiments, the crystalline solid comprises of 80% to 99% Compound 33 Hydrate Form A relative to the total weight of solid Compound 33. In some embodiments, the crystalline solid comprises of 85% to 99% Compound 33 Hydrate Form A relative to the total weight of solid Compound 33. In some embodiments, the crystalline solid comprises of 90% to 99% Compound 33 Hydrate Form A relative to the total weight of solid Compound 33. In some embodiments, the crystalline solid comprises of 95% to 99% Compound 33 Hydrate Form A relative to the total weight of solid Compound 33.

Figure 4A:
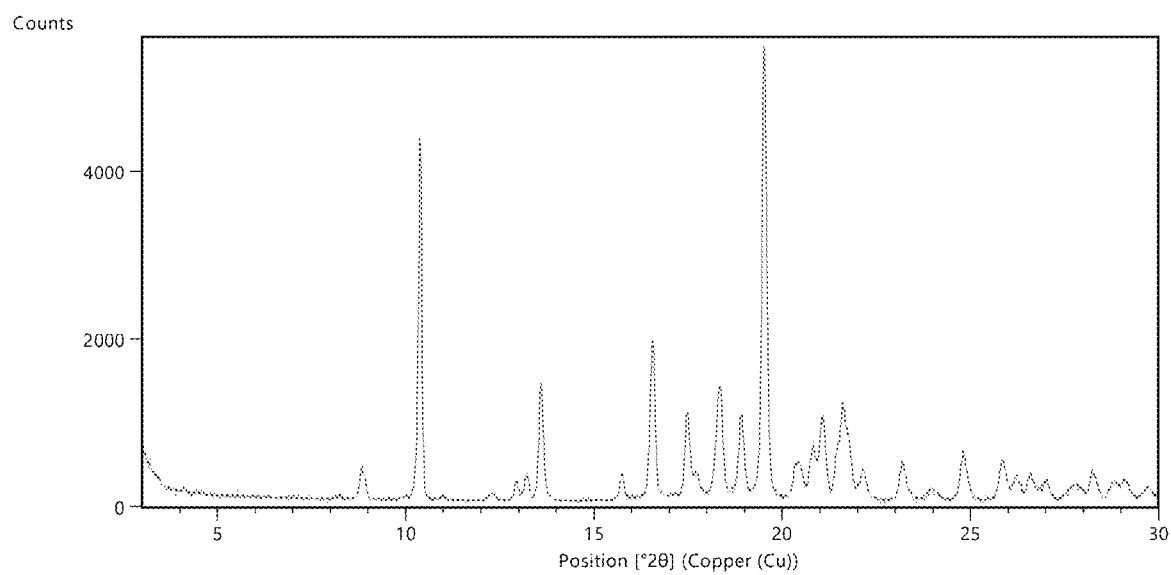
FIG. 4A shows an XRPD diffractogram of Compound 33 hydrate Form A.

Thus, in some embodiments, Compound 33 Hydrate Form A is substantially crystalline. In some embodiments, Compound 33 Hydrate Form A is substantially pure crystalline. In some embodiments, Compound 33 Hydrate Form A is characterized by an X-ray powder diffractogram generated by an X-ray powder diffraction analysis with an incident beam of Cu Kα radiation. FIG. 4A provides an X-ray powder diffractogram of Compound 33 Hydrate Form A at room temperature.

In some embodiments, Compound 33 Hydrate Form A is characterized by an X-ray powder diffractogram having signals at one or more of 19.5±0.2 degrees two-theta, 10.4±0.2 degrees two-theta, and 16.6±0.2 degrees two-theta. In some embodiments, Compound 33 Hydrate Form A is characterized by an X-ray powder diffractogram having signals at 19.5±0.2 degrees two-theta, 10.4±0.2 degrees two-theta, and 16.6±0.2 degrees two-theta. In some embodiments, Compound 33 Hydrate Form A is characterized by an X-ray powder diffractogram having (a) signals at 19.5±0.2 degrees two-theta, 10.4±0.2 degrees two-theta, and 16.6±0.2 degrees two-theta; and (b) at at least three, at least four, at least five, at least six, at least seven, at least eight, at least nine, or ten signals selected from 13.6±0.2 degrees two-theta, 18.4±0.2 degrees two-theta, 17.5±0.2 degrees two-theta, 18.9±0.2 degrees two-theta, 20.8±0.2 degrees two-theta, 21.1±0.2 degrees two-theta, 21.4±0.2 degrees two-theta, 21.6±0.2 degrees two-theta, 21.8±0.2 degrees two-theta, and 24.8±0.2 degrees two-theta. In some embodiments, Compound 33 Hydrate Form A is characterized by an X-ray powder diffractogram substantially similar to FIG. 4A.

In some embodiments, Compound 33 Hydrate Form A is characterized by a triclinic crystal system, a P-1 space group, and the following unit cell dimensions measured at 100 K on a Bruker diffractometer equipped with Cu K$_\alpha$ radiation (λ=1.54178 Å) and a CMOS detector:

| | |
|---|---|
| a (Å) | 9.98 ± .01 |
| b (Å) | 10.42 ± .01 |
| c (Å) | 11.30 ± .01 |
| α (°) | 74.06 ± .02 |
| β (°) | 78.91 ± .02 |
| γ (°) | 84.14 ± .02 |
| V (Å3) | 1107.3 ± 1.8 |
| Z/Z' | 2/1 |

In some embodiments, Compound 33 Hydrate Form A is characterized as having a $^{13}$C ssNMR spectrum with at least one peak selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized as having a $^{13}$C ssNMR spectrum with at least two peaks selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized as having a $^{13}$C ssNMR spectrum with at least three peaks selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized as having a $^{13}$C ssNMR spectrum with at least four peaks selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized as having a $^{13}$C ssNMR spectrum with at least five peaks selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized as having a $^{13}$C ssNMR spectrum with at least six peaks selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized as having a $^{13}$C ssNMR spectrum with at least seven peaks selected from: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A characterized as having a $^{13}$C ssNMR spectrum with peaks at: 172.3±0.2, 141.6±0.2, 134.8±0.2, 132.4±0.2, 129.6±0.2, 123.1±0.2, 32.8±0.2, and 28.4±0.2 ppm. In some embodiments, Compound 33 Hydrate Form A is characterized by a $^{13}$C NMR spectrum having a signal at at least at least four, at least six, at least eight, at least ten, at least twelve, or at least fifteen ppm values chosen from 172.3±0.2, 163.8±0.2, 161.3±0.2, 144.4±0.2, 141.6±0.2, 139.0±0.2, 136.8±0.2, 134.8±0.2, 132.4±0.2, 129.6±0.2, 128.9±0.2, 123.1±0.2, 117.2±0.2, 116.5±0.2, 112.1±0.2, 97.7±0.2, 67.9±0.2, 36.1±0.2, 32.8±0.2, 29.4±0.2, and 28.4±0.2 ppm. In some embodiments, Compound 33 Hydrate Form A is characterized by a $^{13}$C ssNMR spectrum substantially similar to FIG. 4B.

In some embodiments, Compound 33 Hydrate Form A is characterized by a $^{19}$F NMR spectrum having a signal at −103.1±0.2 ppm. In some embodiments, Compound 33 Hydrate Form A is characterized by a $^{19}$F ssNMR spectrum substantially similar to FIG. 4C.

Another aspect of the invention provides a composition comprising Compound 33 Hydrate Form A. In some embodiments, the composition of the invention comprises substantially pure crystalline Compound 33 Hydrate Form A. In some embodiments, the composition consists essentially of Compound 33 Hydrate Form A.

Another aspect of the invention provides a method of making Compound 33 Hydrate Form A. In some embodiments, Compound 33 Hydrate A is prepared by adding water to Compound 33 Form A, stirring for about two weeks and isolating the solid form.

5. Compound MeOH/H$_2$O Solvate/Hydrate Form A

In some embodiments, Compound 33 is a crystalline solid comprising of crystalline MeOH/H$_2$O Solvate/Hydrate Form A. In some embodiments, the crystalline solid comprises of 30% to 99% crystalline Compound 33 Form A relative to the total weight of solid Compound 33. In some embodiments, the crystalline solid comprises of 40% to 99% Compound 33 MeOH/H$_2$O Solvate/Hydrate Form A relative to the total weight of solid Compound 33. In some embodiments, the crystalline solid comprises of 50% to 99% Compound 33 MeOH/H$_2$O Solvate/Hydrate Form A relative to the total weight of solid Compound 33. In some embodiments, the crystalline solid comprises of 60% to 99% Compound 33 MeOH/H$_2$O Solvate/Hydrate Form A relative to the total weight of solid Compound 33. In some embodiments, the crystalline solid comprises of 70% to 99% Compound 33 MeOH/H$_2$O Solvate/Hydrate Form A relative to the total weight of solid Compound 33. In some embodiments, the crystalline solid comprises of 75% to 99% Compound 33 MeOH/H$_2$O Solvate/Hydrate Form A relative to the total weight of solid Compound 33. In some embodiments, the crystalline solid comprises of 80% to 99% Compound 33 MeOH/H$_2$O Solvate/Hydrate Form A relative to the total weight of solid Compound 33. In some embodiments, the crystalline solid comprises of 85% to 99% Compound 33 MeOH/H$_2$O Solvate/Hydrate Form A relative to the total weight of solid Compound 33. In some embodiments, the crystalline solid comprises of 90% to 99% Compound 33 MeOH/H$_2$O Solvate/Hydrate Form A relative to the total weight of solid Compound 33. In some embodiments, the crystalline solid comprises of 95% to 99% Compound 33 MeOH/H$_2$O Solvate/Hydrate Form A relative to the total weight of solid Compound 33.

Figure 5A:
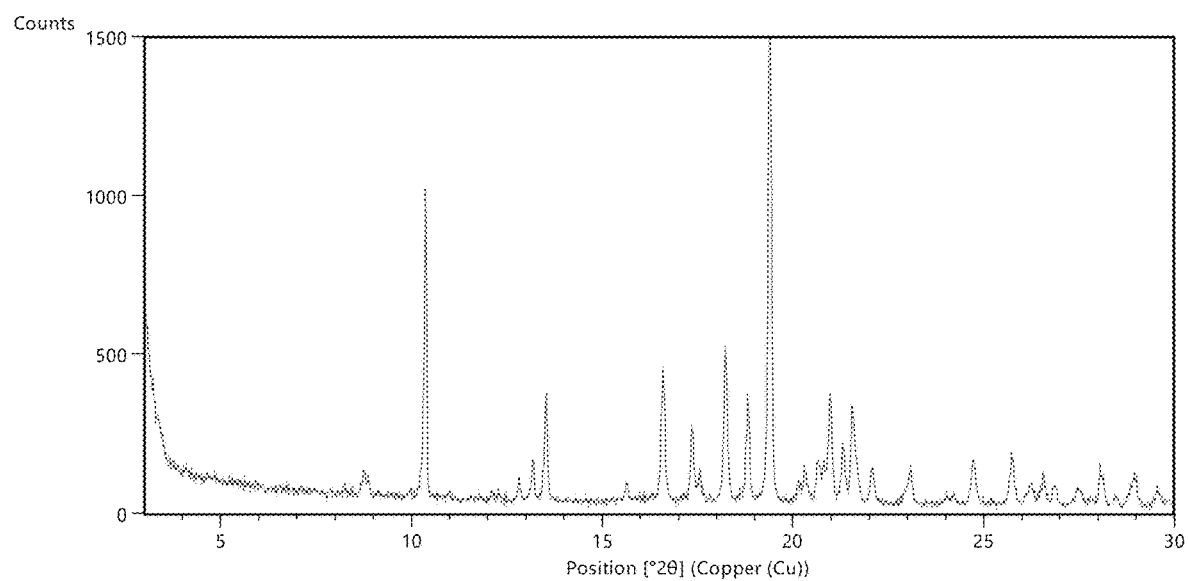
FIG. 5A shows an XRPD diffractogram of Compound 33 MeOH/H$_2$O solvate/hydrate Form A.

Thus, in some embodiments, Compound 33 MeOH/H$_2$O Solvate/Hydrate Form A is substantially crystalline. In some embodiments, Compound 33 MeOH/H$_2$O Solvate/Hydrate Form A is substantially pure crystalline. In some embodiments, Compound 33 MeOH/H$_2$O Solvate/Hydrate Form A is characterized by an X-ray powder diffractogram generated by an X-ray powder diffraction analysis with an incident beam of Cu Kα radiation. FIG. 5A provides an X-ray powder diffractogram of Compound 33 MeOH/H$_2$O Solvate/Hydrate Form A at room temperature.

In some embodiments, Compound 33 MeOH/H$_2$O Solvate/Hydrate Form A is characterized by an X-ray powder diffractogram having signals at 16.6±0.2 degrees two-theta and 17.4±0.2 degrees two-theta. In some embodiments, Compound 33 MeOH/H$_2$O Solvate/Hydrate Form A is characterized by an X-ray powder diffractogram having signals at (a) 16.6±0.2 degrees two-theta and 17.4±0.2 degrees two-theta and (b) one or more of 10.4±0.2 degrees two-theta, 18.2±0.2 degrees two-theta, and 19.4±0.2 degrees two-theta. In some embodiments, Compound 33 MeOH/H$_2$O Solvate/Hydrate Form A is characterized by an X-ray powder diffractogram having signals at 10.4±0.2 degrees two-theta, 16.6±0.2 degrees two-theta, 17.4±0.2 degrees two-theta, 18.2±0.2 degrees two-theta, and 19.4±0.2 degrees two-theta.

In some embodiments, Compound 33 MeOH/H$_2$O Solvate/Hydrate Form A is characterized by an X-ray powder diffractogram having a signal at at least four, at least six, at least eight, or at least ten two-theta values chosen from 19.4±0.2, 10.4±0.2, 18.2±0.2, 16.6±0.2, 13.5±0.2, 21.0±0.2, 21.6±0.2, 18.8±0.2, 17.4±0.2, 21.3±0.2, 21.7±0.2, and 24.0±0.2. In some embodiments, Compound 33 MeOH/H$_2$O Solvate/Hydrate Form A is characterized by an X-ray powder diffractogram substantially similar to FIG. 5A.

In some embodiments, Compound 33 MeOH/H$_2$O Solvate/Hydrate Form A is characterized by a triclinic crystal system, a P-1 space group, and the following unit cell dimensions measured at 100 K on a Bruker diffractometer equipped with Cu K$_\alpha$ radiation (λ=1.54178 Å) and a CMOS detector:

| | |
|---|---|
| a (Å) | 10.02 ± .01 |
| b (Å) | 10.43 ± .01 |
| c (Å) | 11.25 ± .01 |
| α (°) | 74.50 ± .01 |
| β (°) | 79.62 ± .01 |
| γ (°) | 84.98 ± .01 |
| V (Å3) | 1113.5 ± 1.8 |
| Z/Z' | 2/1 |

Another aspect of the invention provides a composition comprising Compound 33 MeOH/H$_2$O Solvate/Hydrate Form A. In some embodiments, the composition of the invention comprises substantially pure crystalline Compound 33 MeOH/H$_2$O Solvate/Hydrate Form A. In some embodiments, the composition consists essentially of Compound 33 MeOH/H$_2$O Solvate/Hydrate Form A.

Another aspect of the invention provides a method of making Compound 33 MeOH/H$_2$O Solvate/Hydrate Form A. In some embodiments, Compound 33 MeOH/H$_2$O Solvate/Hydrate A is prepared by adding MeOH to Compound 33 Form A, stirring for about two weeks at ambient temperature, and isolating the solid form.

6. Compound 33 Form C

In some embodiments, Compound 33 is a crystalline solid comprising of crystalline Form C. In some embodiments, the crystalline solid comprises of 30% to 99% crystalline Compound 33 Form C relative to the total weight of solid Compound 33. In some embodiments, the crystalline solid comprises of 40% to 99% Compound 33 Form C relative to the total weight of solid Compound 33. In some embodiments, the crystalline solid comprises of 50% to 99% Compound 33 Form C relative to the total weight of solid Compound 33. In some embodiments, the crystalline solid comprises of 60% to 99% Compound 33 Form C relative to the total weight of solid Compound 33. In some embodiments, the crystalline solid comprises of 70% to 99% Compound 33 Form C relative to the total weight of solid Compound 33. In some embodiments, the crystalline solid comprises of 75% to 99% Compound 33 Form C relative to the total weight of solid Compound 33. In some embodiments, the crystalline solid comprises of 80% to 99% Compound 33 Form C relative to the total weight of solid Compound 33. In some embodiments, the crystalline solid comprises of 85% to 99% Compound 33 Form C relative to the total weight of solid Compound 33. In some embodiments, the crystalline solid comprises of 90% to 99% Compound 33 Form C relative to the total weight of solid Compound 33. In some embodiments, the crystalline solid comprises of 95% to 99% Compound 33 Form C relative to the total weight of solid Compound 33.

Figure 6A:
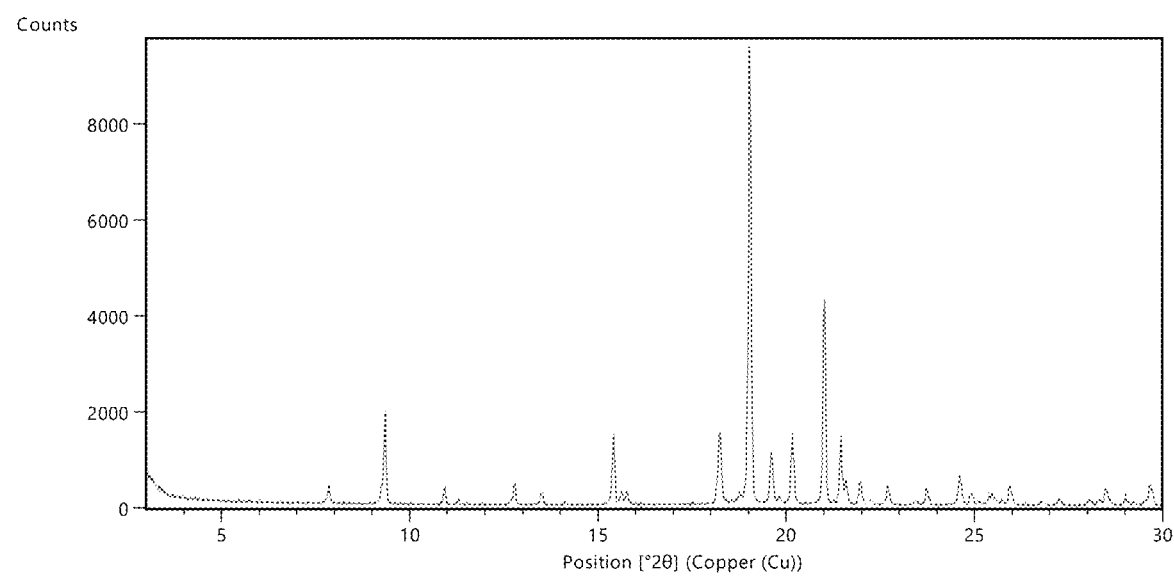
FIG. 6A shows an XRPD diffractogram of Compound 33 Form C.

Thus, in some embodiments, Compound 33 Form C is substantially crystalline. In some embodiments, Compound 33 Form C is substantially pure crystalline. In some embodiments, Compound 33 Form C is characterized by an X-ray powder diffractogram generated by an X-ray powder diffraction analysis with an incident beam of Cu Kα radiation. FIG. 6A provides an X-ray powder diffractogram of Compound Form C at room temperature.

In some embodiments, Compound 33 Form C is characterized by an X-ray powder diffractogram having signals at 9.4±0.2 degrees two-theta and 15.4±0.2 degrees two-theta. In some embodiments, Compound 33 Form C is characterized by an X-ray powder diffractogram having signals at (a) 9.4±0.2 degrees two-theta and 15.4±0.2 degrees two-theta and (b) 19.0±0.2 degrees two-theta and/or 21.0±0.2 degrees two-theta. In some embodiments, Compound 33 Form C is characterized by an X-ray powder diffractogram having signals at 9.4±0.2 degrees two-theta, 15.4±0.2 degrees two-theta, 19.0±0.2 degrees two-theta, and 21.0±0.2 degrees two-theta. In some embodiments, Compound 33 Form C is characterized by an X-ray powder diffractogram having a signal at at least four, at least six, or eight two-theta values chosen from 9.4±0.2 degrees two-theta, 15.4±0.2 degrees two-theta, 18.2±0.2 degrees two-theta, 19.0±0.2 degrees two-theta, 19.6±0.2 degrees two-theta, 20.2±0.2 degrees two-theta, 21.0±0.2 degrees two-theta, and 21.5±0.2 degrees two-theta. In some embodiments, Compound 33 Form C is characterized by an X-ray powder diffractogram substantially similar to FIG. 6A.

Another aspect of the invention provides a composition comprising Compound 33 Form C. In some embodiments, the composition of the invention comprises substantially pure crystalline Compound 33 Form C. In some embodiments, the composition consists essentially of Compound 33 Form C.

Another aspect of the invention provides a method of making Compound 33 Form C. In some embodiments, Compound 33 Form C is prepared by mixing a sample of stock solution (prepared by dissolving Compound 33 Form A in MeOH, warming to about 45° C. and then about 50° C.) in MeOH/H2O (2:1 by volume) and stirring at about 45° C. for about 3 days and isolating the solid form.

7. Compound 33 Form D

In some embodiments, Compound 33 is a crystalline solid comprising of crystalline Form D. In some embodiments, the crystalline solid comprises of 30% to 99% crystalline Compound 33 Form D relative to the total weight of solid Compound 33. In some embodiments, the crystalline solid comprises of 40% to 99% Compound 33 Form D relative to the total weight of solid Compound 33. In some embodiments, the crystalline solid comprises of 50% to 99% Compound 33 Form D relative to the total weight of solid Compound 33. In some embodiments, the crystalline solid comprises of 60% to 99% Compound 33 Form D relative to the total weight of solid Compound 33. In some embodiments, the crystalline solid comprises of 70% to 99% Compound 33 Form D relative to the total weight of solid Compound 33. In some embodiments, the crystalline solid comprises of 75% to 99% Compound 33 Form D relative to the total weight of solid Compound 33. In some embodiments, the crystalline solid comprises of 80% to 99% Compound 33 Form D relative to the total weight of solid Compound 33. In some embodiments, the crystalline solid comprises of 85% to 99% Compound 33 Form D relative to the total weight of solid Compound 33. In some embodiments, the crystalline solid comprises of 90% to 99% Compound 33 Form D relative to the total weight of solid Compound 33. In some embodiments, the crystalline solid comprises of 95% to 99% Compound 33 Form D relative to the total weight of solid Compound 33.

Figure 7A:
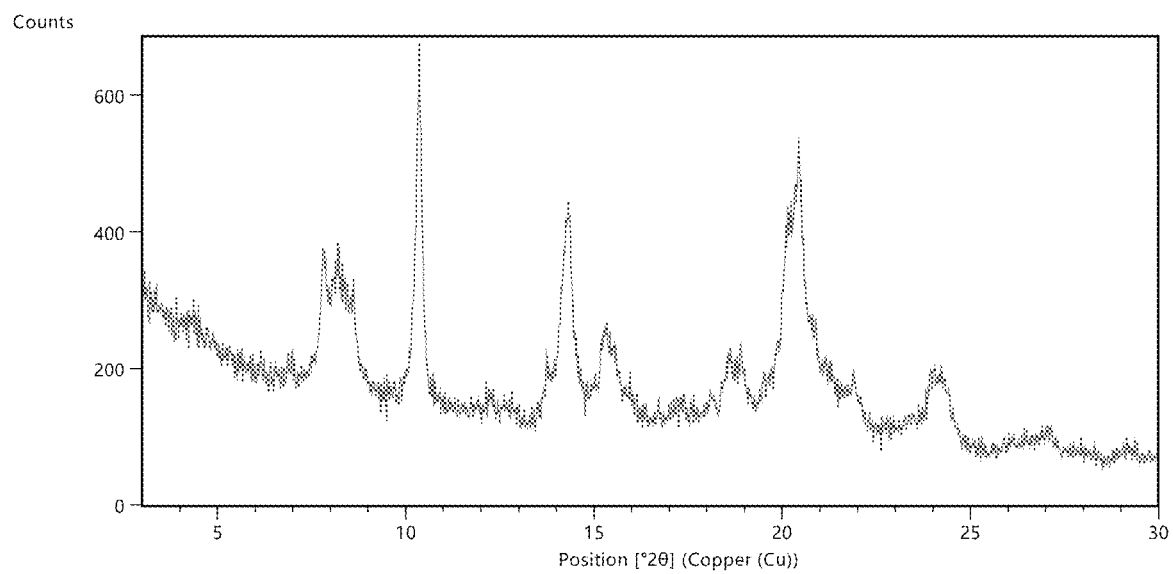
FIG. 7A shows an XRPD diffractogram of Compound 33 Form D.

Thus, in some embodiments, Compound 33 Form D is substantially crystalline. In some embodiments, Compound 33 Form D is substantially pure crystalline. In some embodiments, Compound 33 Form D is characterized by an X-ray powder diffractogram generated by an X-ray powder diffraction analysis with an incident beam of Cu Kα radiation. FIG. 7A provides an X-ray powder diffractogram of Compound Form D at room temperature.

In some embodiments, Compound 33 Form D is characterized by an X-ray powder diffractogram having signals at 14.4±0.2 degrees two-theta and 24.0±0.2 degrees two-theta. In some embodiments, Compound 33 Form D is characterized by an X-ray powder diffractogram having signals at (a) 14.4±0.2 degrees two-theta and 24.0±0.2 degrees two-theta and (b) 10.4±0.2 degrees two-theta and/or 20.5±0.2 degrees two-theta. In some embodiments, Compound 33 Form D is characterized by an X-ray powder diffractogram having signals at 10.4±0.2 degrees two-theta, 14.4±0.2 degrees two-theta, 20.5±0.2 degrees two-theta, and 24.0±0.2 degrees two-theta. In some embodiments, Compound 33 Form D is characterized by an X-ray powder diffractogram having a signal at at least four, at least six, at least eight, or at least ten two-theta values chosen from 7.8±0.2 degrees two-theta, 8.2±0.2 degrees two-theta, 8.6±0.2 degrees two-theta, 10.4±0.2 degrees two-theta, 13.7±0.2 degrees two-theta, 14.4±0.2 degrees two-theta, 15.3±0.2 degrees two-theta, 18.6±0.2 degrees two-theta, 18.9±0.2 degrees two-theta, 20.1±0.2 degrees two-theta, 20.5±0.2 degrees two-theta, 21.9±0.2 degrees two-theta, 24.0±0.2 degrees two-theta, and 24.3±0.2 degrees two-theta. In some embodiments, Compound 33 Form D is characterized by an X-ray powder diffractogram substantially similar to FIG. 7A.

Another aspect of the invention provides a composition comprising Compound 33 Form D. In some embodiments, the composition of the invention comprises substantially pure crystalline Compound 33 Form D. In some embodiments, the composition consists essentially of Compound 33 Form D.

Another aspect of the invention provides a method of making Compound 33 Form D. In some embodiments, Compound 33 Form D is prepared by adding Compound 33 THF solvate Form A to MeOH vapor in a container, sealing the container and storing at room temperature for about 10 days, and isolating the solid form.

8. Compound 33 Form E

In some embodiments, Compound 33 is a crystalline solid comprising of crystalline Form E. In some embodiments, the crystalline solid comprises of 30% to 99% crystalline Compound 33 Form E relative to the total weight of solid Compound 33. In some embodiments, the crystalline solid comprises of 40% to 99% Compound 33 Form E relative to the total weight of solid Compound 33. In some embodiments, the crystalline solid comprises of 50% to 99% Compound 33 Form E relative to the total weight of solid Compound 33. In some embodiments, the crystalline solid comprises of 60% to 99% Compound 33 Form E relative to the total weight of solid Compound 33. In some embodiments, the crystalline solid comprises of 70% to 99% Compound 33 Form E relative to the total weight of solid Compound 33. In some embodiments, the crystalline solid comprises of 75% to 99% Compound 33 Form E relative to the total weight of solid Compound 33. In some embodiments, the crystalline solid comprises of 80% to 99% Compound 33 Form E relative to the total weight of solid Compound 33. In some embodiments, the crystalline solid comprises of 85% to 99% Compound 33 Form E relative to the total weight of solid Compound 33. In some embodiments, the crystalline solid comprises of 90% to 99% Compound 33 Form E relative to the total weight of solid Compound 33. In some embodiments, the crystalline solid comprises of 95% to 99% Compound 33 Form E relative to the total weight of solid Compound 33.

Figure 8A:
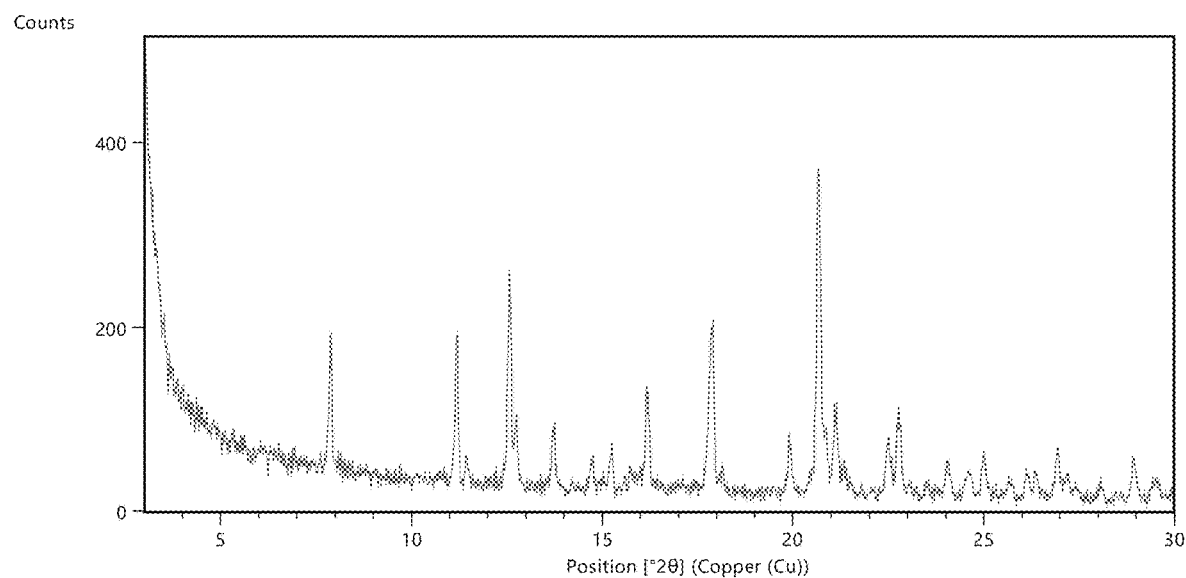
FIG. 8A shows an XRPD diffractogram of Compound 33 Form E.

Thus, in some embodiments, Compound 33 Form E is substantially crystalline. In some embodiments, Compound 33 Form E is substantially pure crystalline. In some embodiments, Compound 33 Form E is characterized by an X-ray powder diffractogram generated by an X-ray powder diffraction analysis with an incident beam of Cu Kα radiation. FIG. 8A provides an X-ray powder diffractogram of Compound Form E at room temperature.

In some embodiments, Compound 33 Form E is characterized by an X-ray powder diffractogram having signals at 16.2±0.2 degrees two-theta and 17.9±0.2 degrees two-theta. In some embodiments, Compound 33 Form E is characterized by an X-ray powder diffractogram having signals at (a) 16.2±0.2 degrees two-theta and 17.9±0.2 degrees two-theta and (b) 12.6±0.2 degrees two-theta and/or 20.7±0.2 degrees two-theta. In some embodiments, Compound 33 Form E is characterized by an X-ray powder diffractogram having signals at 12.6±0.2 degrees two-theta, 16.2±0.2 degrees two-theta, 17.9±0.2 degrees two-theta, and 20.7±0.2 degrees two-theta. In some embodiments, Compound 33 Form E is characterized by an X-ray powder diffractogram having a signal at at least four, at least six, at least eight, at least ten, or at least twelve two-theta values chosen from 7.9±0.2 degrees two-theta, 11.2±0.2 degrees two-theta, 12.6±0.2 degrees two-theta, 12.8±0.2 degrees two-theta, 13.7±0.2 degrees two-theta, 15.3±0.2 degrees two-theta, 16.2±0.2 degrees two-theta, 17.9±0.2 degrees two-theta, 19.9±0.2 degrees two-theta, 20.7±0.2 degrees two-theta, 21.1±0.2 degrees two-theta, 22.5±0.2 degrees two-theta, 22.8±0.2 degrees two-theta, 24.1±0.2 degrees two-theta, 25.0±0.2 degrees two-theta, 27.0±0.2 degrees two-theta, and 28.9±0.2 degrees two-theta. In some embodiments, Compound 33 Form E is characterized by an X-ray powder diffractogram substantially similar to FIG. 8A.

Another aspect of the invention provides a composition comprising Compound 33 Form E. In some embodiments, the composition of the invention comprises substantially pure crystalline Compound 33 Form E. In some embodiments, the composition consists essentially of Compound 33 Form E.

Another aspect of the invention provides a method of making Compound 33 Form E. In some embodiments, Compound 33 Form E is prepared by dissolving Compound 33 Form A in MeOH after warming to 45° C. and then 50° C., cooling solution and stirring in cold room for about 3 days, and isolating the solid form.

9. Compound 33 Form F

In some embodiments, Compound 33 is a crystalline solid comprising of crystalline Form F. In some embodiments, the crystalline solid comprises of 30% to 99% crystalline Compound 33 Form F relative to the total weight of solid Compound 33. In some embodiments, the crystalline solid comprises of 40% to 99% Compound 33 Form F relative to the total weight of solid Compound 33. In some embodiments, the crystalline solid comprises of 50% to 99% Compound 33 Form F relative to the total weight of solid Compound 33. In some embodiments, the crystalline solid comprises of 60% to 99% Compound 33 Form F relative to the total weight of solid Compound 33. In some embodiments, the crystalline solid comprises of 70% to 99% Compound 33 Form F relative to the total weight of solid Compound 33. In some embodiments, the crystalline solid comprises of 75% to 99% Compound 33 Form F relative to the total weight of solid Compound 33. In some embodiments, the crystalline solid comprises of 80% to 99% Compound 33 Form F relative to the total weight of solid Compound 33. In some embodiments, the crystalline solid comprises of 85% to 99% Compound 33 Form F relative to the total weight of solid Compound 33. In some embodiments, the crystalline solid comprises of 90% to 99% Compound 33 Form F relative to the total weight of solid Compound 33. In some embodiments, the crystalline solid comprises of 95% to 99% Compound 33 Form F relative to the total weight of solid Compound 33.

Figure 9A:
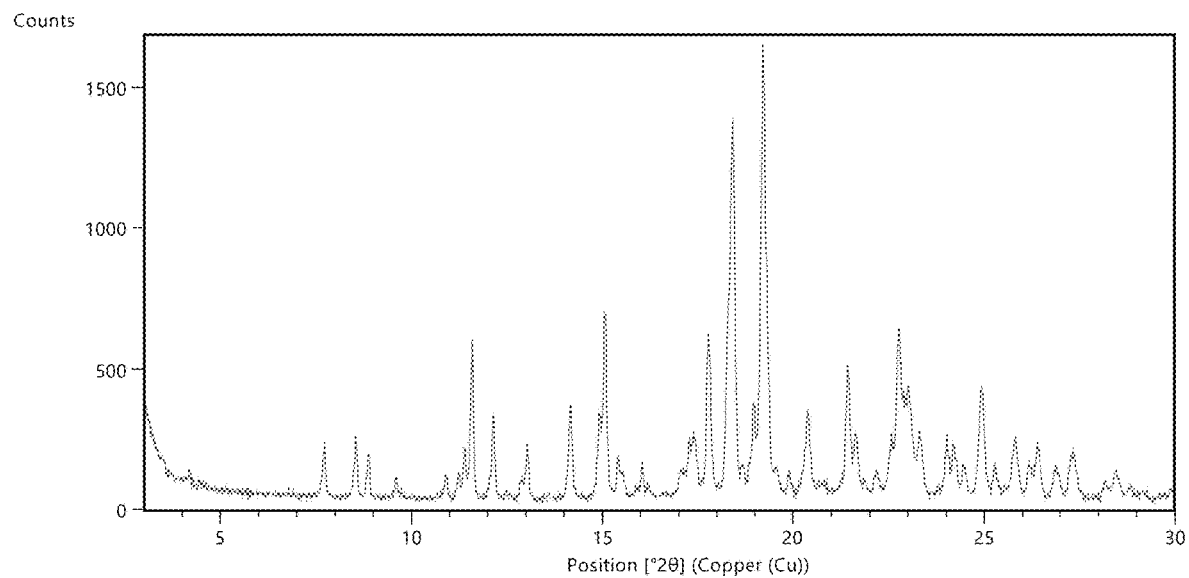
FIG. 9A shows an XRPD diffractogram of Compound 33 Form F.

Thus, in some embodiments, Compound 33 Form F is substantially crystalline. In some embodiments, Compound 33 Form F is substantially pure crystalline. In some embodiments, Compound 33 Form F is characterized by an X-ray powder diffractogram generated by an X-ray powder diffraction analysis with an incident beam of Cu Kα radiation. FIG. 9A provides an X-ray powder diffractogram of Compound Form F at room temperature.

In some embodiments, Compound 33 Form F is characterized by an X-ray powder diffractogram having a signal at one or more two-theta values selected from 8.6±0.2 degrees two-theta, 13.0±0.2 degrees two-theta, and 23.0±0.2 degrees two-theta. In some embodiments, Compound 33 Form F is characterized by an X-ray powder diffractogram having signals at 8.6±0.2 degrees two-theta, 13.0±0.2 degrees two-theta, and 23.0±0.2 degrees two-theta. In some embodiments, Compound 33 Form F is characterized by an X-ray powder diffractogram having a signal at at least four, at least six, at least eight, at least ten, or at least twelve two-theta values chosen from 7.7±0.2 degrees two-theta, 8.6±0.2 degrees two-theta, 11.4±0.2 degrees two-theta, 11.6±0.2 degrees two-theta, 12.2±0.2 degrees two-theta, 13.0±0.2 degrees two-theta, 14.2±0.2 degrees two-theta, 14.9±0.2 degrees two-theta, 17.3±0.2 degrees two-theta, 17.4±0.2 degrees two-theta, 17.8±0.2 degrees two-theta, 18.3±0.2 degrees two-theta, 19.0±0.2 degrees two-theta, 20.4±0.2 degrees two-theta, 21.4±0.2 degrees two-theta, 21.6±0.2 degrees two-theta, 22.6±0.2 degrees two-theta, 22.8±0.2 degrees two-theta, 23.0±0.2 degrees two-theta, 23.3±0.2 degrees two-theta, 24.0±0.2 degrees two-theta, 24.2±0.2 degrees two-theta, 24.9±0.2 degrees two-theta, 25.8±0.2 degrees two-theta, and 26.4±0.2 degrees two-theta. In some embodiments, Compound 33 Form F is characterized by an X-ray powder diffractogram substantially similar to FIG. 9A.

Another aspect of the invention provides a composition comprising Compound 33 Form F. In some embodiments, the composition of the invention comprises substantially pure crystalline Compound 33 Form F. In some embodiments, the composition consists essentially of Compound 33 Form F.

Another aspect of the invention provides a method of making Compound 33 Form F. In some embodiments, Compound 33 Form F is prepared by adding Compound 33 THF Solvate Form A to EtOH, stirring and slurrifying at about 20° C. overnight, and isolating the solid form.

10. Compound 33 Form G

In some embodiments, Compound 33 is a crystalline solid comprising of crystalline Form G. In some embodiments, the crystalline solid comprises of 30% to 99% crystalline Compound 33 Form G relative to the total weight of solid Compound 33. In some embodiments, the crystalline solid comprises of 40% to 99% Compound 33 Form G relative to the total weight of solid Compound 33. In some embodiments, the crystalline solid comprises of 50% to 99% Compound 33 Form G relative to the total weight of solid Compound 33. In some embodiments, the crystalline solid comprises of 60% to 99% Compound 33 Form G relative to the total weight of solid Compound 33. In some embodiments, the crystalline solid comprises of 70% to 99% Compound 33 Form G relative to the total weight of solid Compound 33. In some embodiments, the crystalline solid comprises of 75% to 99% Compound 33 Form G relative to the total weight of solid Compound 33. In some embodiments, the crystalline solid comprises of 80% to 99% Compound 33 Form G relative to the total weight of solid Compound 33. In some embodiments, the crystalline solid comprises of 85% to 99% Compound 33 Form G relative to the total weight of solid Compound 33. In some embodiments, the crystalline solid comprises of 90% to 99% Compound 33 Form G relative to the total weight of solid Compound 33. In some embodiments, the crystalline solid comprises of 95% to 99% Compound 33 Form G relative to the total weight of solid Compound 33.

Figure 10A:
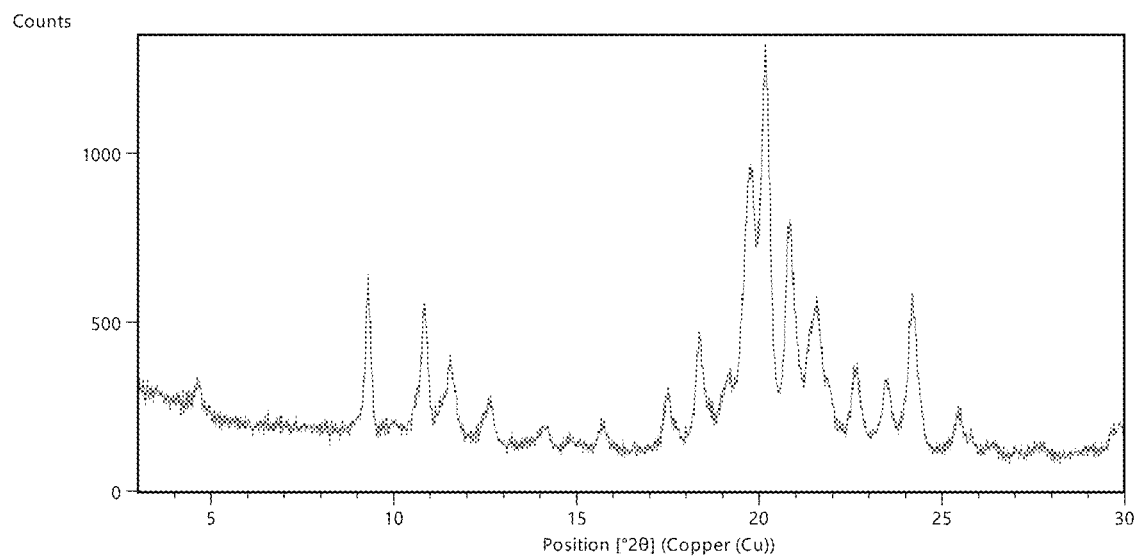
FIG. 10A shows an XRPD diffractogram of Compound 33 Form G.

Thus, in some embodiments, Compound 33 Form G is substantially crystalline. In some embodiments, Compound 33 Form G is substantially pure crystalline. In some embodiments, Compound 33 Form G is characterized by an X-ray powder diffractogram generated by an X-ray powder diffraction analysis with an incident beam of Cu Kα radiation. FIG. 10A provides an X-ray powder diffractogram of Compound Form G at room temperature.

In some embodiments, Compound 33 Form G is characterized by an X-ray powder diffractogram having a signal at one or more two-theta values selected from 19.8±0.2 degrees two-theta, 20.2±0.2 degrees two-theta, and 20.8±0.2 degrees two-theta. In some embodiments, Compound 33 Form G is characterized by an X-ray powder diffractogram having signals at 19.8±0.2 degrees two-theta, 20.2±0.2 degrees two-theta, and 20.8±0.2 degrees two-theta. In some embodiments, Compound 33 Form G is characterized by an X-ray powder diffractogram having a signal at at least four, at least six, at least eight, at least ten, or at least twelve two-theta values chosen from 9.3±0.2 degrees two-theta, 10.8±0.2 degrees two-theta, 11.5±0.2 degrees two-theta, 12.6±0.2 degrees two-theta, 17.5±0.2 degrees two-theta, 18.4±0.2 degrees two-theta, 19.1±0.2 degrees two-theta, 19.8±0.2 degrees two-theta, 20.2±0.2 degrees two-theta, 20.8±0.2 degrees two-theta, 21.6±0.2 degrees two-theta, 22.6±0.2 degrees two-theta, 23.4±0.2 degrees two-theta, 24.2±0.2 degrees two-theta and 25.5±0.2 degrees two-theta. In some embodiments, Compound 33 Form G is characterized by an X-ray powder diffractogram substantially similar to FIG. 10A.

Another aspect of the invention provides a composition comprising Compound 33 Form G. In some embodiments, the composition of the invention comprises substantially pure crystalline Compound 33 Form G. In some embodiments, the composition consists essentially of Compound 33 Form G.

Another aspect of the invention provides a method of making Compound 33 Form G. In some embodiments, Compound 33 Form G is prepared by adding Compound 33 Form A to EtOH, stirring for about one day at about 5° C., and isolating the solid form.

11. Compound 33 Form H

In some embodiments, Compound 33 is a crystalline solid comprising of crystalline Form H. In some embodiments, the crystalline solid comprises of 30% to 99% crystalline Compound 33 Form H relative to the total weight of solid Compound 33. In some embodiments, the crystalline solid comprises of 40% to 99% Compound 33 Form H relative to the total weight of solid Compound 33. In some embodiments, the crystalline solid comprises of 50% to 99% Compound 33 Form H relative to the total weight of solid Compound 33. In some embodiments, the crystalline solid comprises of 60% to 99% Compound 33 Form H relative to the total weight of solid Compound 33. In some embodiments, the crystalline solid comprises of 70% to 99% Compound 33 Form H relative to the total weight of solid Compound 33. In some embodiments, the crystalline solid comprises of 75% to 99% Compound 33 Form H relative to the total weight of solid Compound 33. In some embodiments, the crystalline solid comprises of 80% to 99% Compound 33 Form H relative to the total weight of solid Compound 33. In some embodiments, the crystalline solid comprises of 85% to 99% Compound 33 Form H relative to the total weight of solid Compound 33. In some embodiments, the crystalline solid comprises of 90% to 99% Compound 33 Form H relative to the total weight of solid Compound 33. In some embodiments, the crystalline solid comprises of 95% to 99% Compound 33 Form H relative to the total weight of solid Compound 33.

Figure 11A:
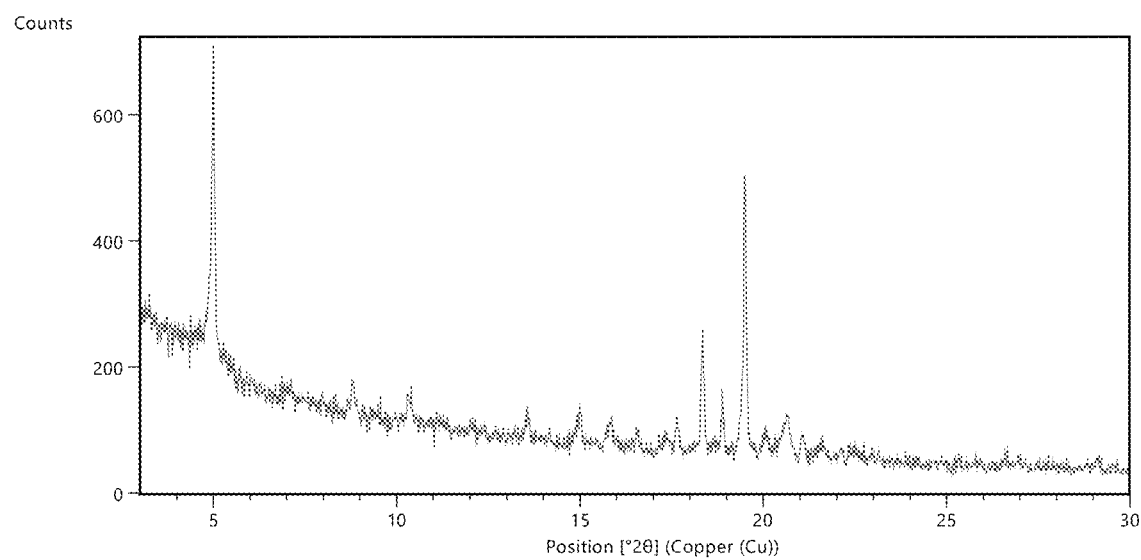
FIG. 11A shows an XRPD diffractogram of Compound 33 Form H.

Thus, in some embodiments, Compound 33 Form H is substantially crystalline. In some embodiments, Compound 33 Form H is substantially pure crystalline. In some embodiments, Compound 33 Form H is characterized by an X-ray powder diffractogram generated by an X-ray powder diffraction analysis with an incident beam of Cu Kα radiation. FIG. 11A provides an X-ray powder diffractogram of Compound Form H at room temperature.

In some embodiments, Compound 33 Form H is characterized by an X-ray powder diffractogram having a signal at one or more two-theta values selected from 5.0±0.2 degrees two-theta, 18.3±0.2 degrees two-theta, and 19.5±0.2 degrees two-theta. In some embodiments, Compound 33 Form H is characterized by an X-ray powder diffractogram having signals at 5.0±0.2 degrees two-theta, 18.3±0.2 degrees two-theta, and 19.5±0.2 degrees two-theta. In some embodiments, Compound 33 Form H is characterized by an X-ray powder diffractogram having a signal at at least four, at least five, at least six, or at least seven two-theta values chosen 5.0±0.2 degrees two-theta, 8.8 degrees two-theta, 15.0 degrees two-theta, 17.6 degrees two-theta, 18.3±0.2 degrees two-theta, 18.9 degrees two-theta, 19.5±0.2 degrees two-theta, and 20.7 degrees two-theta. In some embodiments, Compound 33 Form H is characterized by an X-ray powder diffractogram having signals at 5.0±0.2 degrees two-theta, 8.8 degrees two-theta, 15.0 degrees two-theta, 17.6 degrees two-theta, 18.3±0.2 degrees two-theta, 18.9 degrees two-theta, 19.5±0.2 degrees two-theta, and 20.7 degrees two-theta. In some embodiments, Compound 33 Form H is characterized by an X-ray powder diffractogram substantially similar to FIG. 11A.

Another aspect of the invention provides a composition comprising Compound 33 Form H. In some embodiments, the composition of the invention comprises substantially pure crystalline Compound 33 Form H. In some embodiments, the composition consists essentially of Compound 33 Form H.

Another aspect of the invention provides a method of making Compound 33 Form H. In some embodiments, Compound 33 Form H is prepared by dissolving Compound 33 Form A in EtOH, placing the solution in a water bath at room temperature for enough time to allow water vapor to interact with solution, and isolating the solid form.

12. Compound 33 Form I

In some embodiments, Compound 33 is a crystalline solid comprising of crystalline Form I. In some embodiments, the crystalline solid comprises of 30% to 99% crystalline Compound 33 Form I relative to the total weight of solid Compound 33. In some embodiments, the crystalline solid comprises of 40% to 99% Compound 33 Form I relative to the total weight of solid Compound 33. In some embodiments, the crystalline solid comprises of 50% to 99% Compound 33 Form I relative to the total weight of solid Compound 33. In some embodiments, the crystalline solid comprises of 60% to 99% Compound 33 Form I relative to the total weight of solid Compound 33. In some embodiments, the crystalline solid comprises of 70% to 99% Compound 33 Form I relative to the total weight of solid Compound 33. In some embodiments, the crystalline solid comprises of 75% to 99% Compound 33 Form I relative to the total weight of solid Compound 33. In some embodiments, the crystalline solid comprises of 80% to 99% Compound 33 Form I relative to the total weight of solid Compound 33. In some embodiments, the crystalline solid comprises of 85% to 99% Compound 33 Form I relative to the total weight of solid Compound 33. In some embodiments, the crystalline solid comprises of 90% to 99% Compound 33 Form I relative to the total weight of solid Compound 33. In some embodiments, the crystalline solid comprises of 95% to 99% Compound 33 Form I relative to the total weight of solid Compound 33.

Figure 12A:
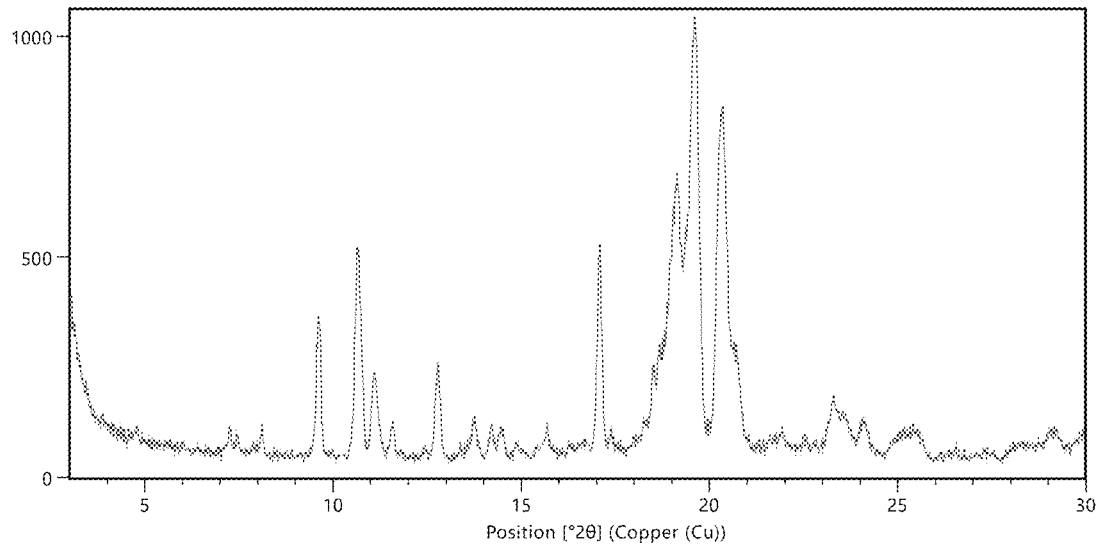
FIG. 12A shows an XRPD diffractogram of Compound 33 having been initially reacted with EtOH.
Figure 12B:
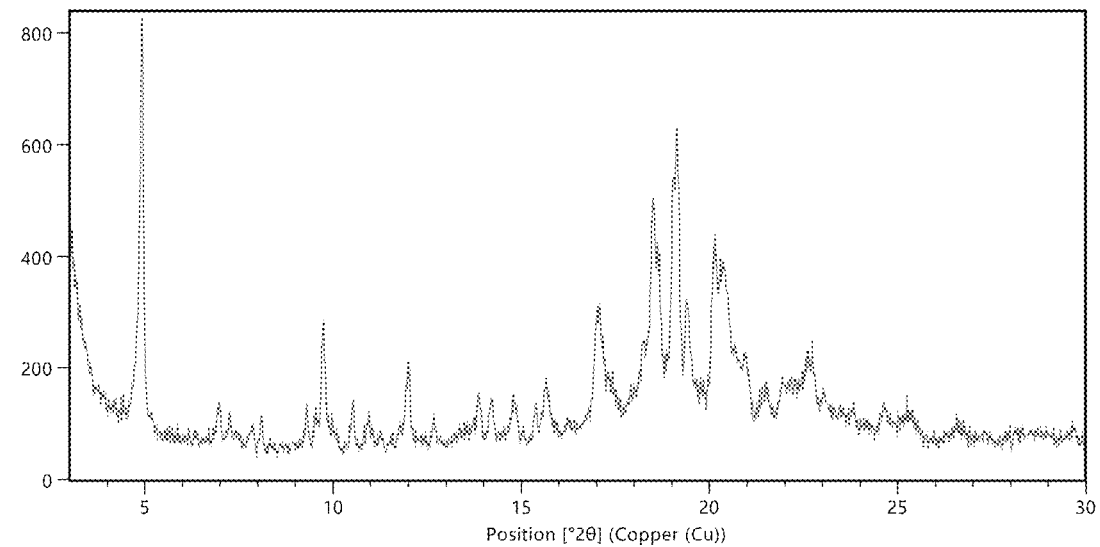
FIG. 12B shows an XRPD diffractogram of Compound 33 having been reacted with EtOH overnight.
Figure 12C:
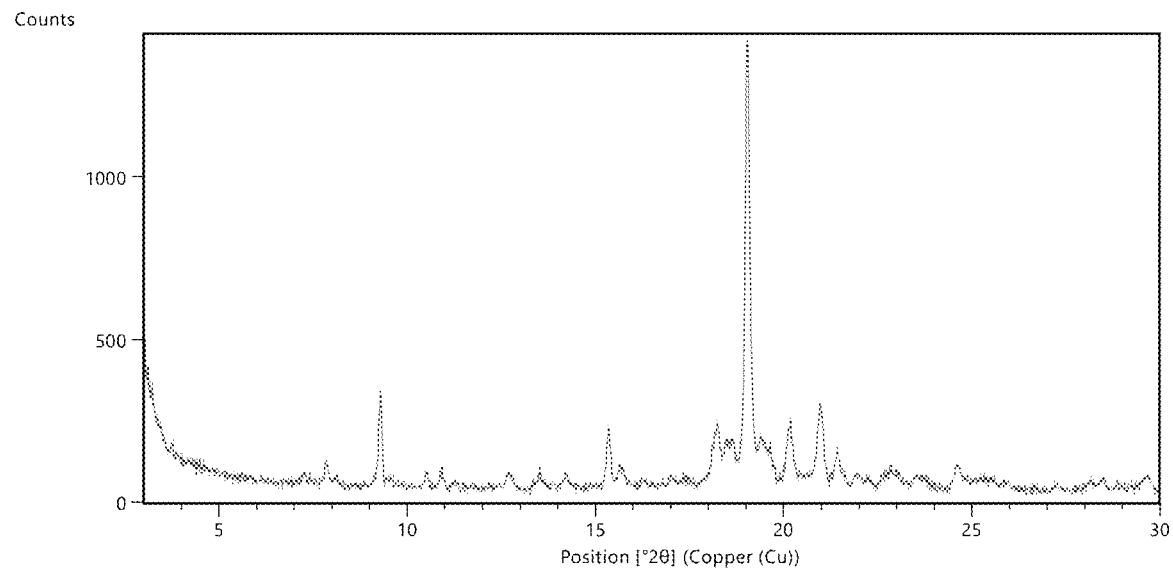
FIG. 12C shows an XRPD diffractogram of Compound 33 Form I.

Thus, in some embodiments, Compound 33 Form I is substantially crystalline. In some embodiments, Compound 33 Form I is substantially pure crystalline. In some embodiments, Compound 33 Form I is characterized by an X-ray powder diffractogram generated by an X-ray powder diffraction analysis with an incident beam of Cu Kα radiation. FIG. 12C provides an X-ray powder diffractogram of Compound Form I at room temperature.

In some embodiments, Compound 33 Form I is characterized by an X-ray powder diffractogram having a signal at one or more two-theta values selected from 9.3±0.2 degrees two-theta, 19.0±0.2 degrees two-theta, and 21.0±0.2 degrees two-theta. In some embodiments, Compound 33 Form I is characterized by an X-ray powder diffractogram having signals at 9.3±0.2 degrees two-theta, 19.0±0.2 degrees two-theta, and 21.0±0.2 degrees two-theta. In some embodiments, Compound 33 Form I is characterized by an X-ray powder diffractogram having a signal at at least four, at least five, or at least six two-theta values chosen from 9.3±0.2 degrees two-theta, 15.4±0.2 degrees two-theta, 18.3±0.2 degrees two-theta, 18.6±0.2 degrees two-theta, 19.0±0.2 degrees two-theta, 20.2±0.2 degrees two-theta, and 21.0±0.2 degrees two-theta. In some embodiments, Compound 33 Form I is characterized by an X-ray powder diffractogram having signals at 9.3±0.2 degrees two-theta, 15.4±0.2 degrees two-theta, 18.3±0.2 degrees two-theta, 18.6±0.2 degrees two-theta, 19.0±0.2 degrees two-theta, 20.2±0.2 degrees two-theta, and 21.0±0.2 degrees two-theta. In some embodiments, Compound 33 Form I is characterized by an X-ray powder diffractogram substantially similar to FIG. 12C.

Another aspect of the invention provides a composition comprising Compound 33 Form I. In some embodiments, the composition of the invention comprises substantially pure crystalline Compound 33 Form I. In some embodiments, the composition consists essentially of Compound 33 Form I.

Another aspect of the invention provides a method of making Compound 33 Form I. In some embodiments, Compound 33 Form I is prepared by distillative crystallization of Compound 33 from 2 Me-THF/THF to EtOH/H₂O, stirring overnight, drying in a vacuum oven with nitrogen at about 66° C. overnight, and isolating the solid form.

13. Compound 33 THF Solvate Form A

In some embodiments, Compound 33 is a crystalline solid comprising of crystalline THF Solvate Form A. In some embodiments, the crystalline solid comprises of 30% to 99% crystalline Compound 33 THF Solvate Form A relative to the total weight of solid Compound 33. In some embodiments, the crystalline solid comprises of 40% to 99% Compound 33 THF Solvate Form A relative to the total weight of solid Compound 33. In some embodiments, the crystalline solid comprises of 50% to 99% Compound 33 THF Solvate Form A relative to the total weight of solid Compound 33. In some embodiments, the crystalline solid comprises of 60% to 99% Compound 33 THF Solvate Form A relative to the total weight of solid Compound 33. In some embodiments, the crystalline solid comprises of 70% to 99% Compound 33 THF Solvate Form A relative to the total weight of solid Compound 33. In some embodiments, the crystalline solid comprises of 75% to 99% Compound 33 THF Solvate Form A relative to the total weight of solid Compound 33. In some embodiments, the crystalline solid comprises of 80% to 99% Compound 33 THF Solvate Form A relative to the total weight of solid Compound 33. In some embodiments, the crystalline solid comprises of 85% to 99% Compound 33 THF Solvate Form A relative to the total weight of solid Compound 33. In some embodiments, the crystalline solid comprises of 90% to 99% Compound 33 THF Solvate Form A relative to the total weight of solid Compound 33. In some embodiments, the crystalline solid comprises of 95% to 99% Compound 33 THF Solvate Form A relative to the total weight of solid Compound 33.

Figure 13A:
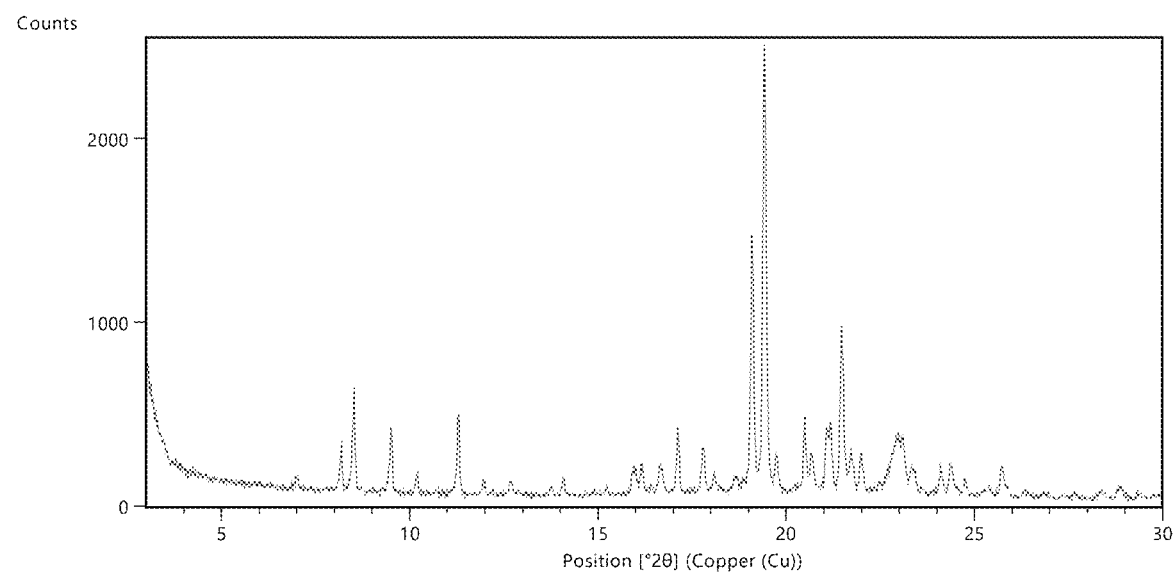
FIG. 13A shows an XRPD diffractogram of Compound 33 THF solvate Form A.

Thus, in some embodiments, Compound 33 THF Solvate Form A is substantially crystalline. In some embodiments, Compound 33 THF Solvate Form A is substantially pure crystalline. In some embodiments, Compound 33 THF Solvate Form A is characterized by an X-ray powder diffractogram generated by an X-ray powder diffraction analysis with an incident beam of Cu Kα radiation. FIG. 13A provides an X-ray powder diffractogram of Compound THF Solvate Form A at room temperature.

In some embodiments, Compound 33 THF Solvate Form A is characterized by an X-ray powder diffractogram having a signal at 8.2±0.2 degrees two-theta and/or 8.5±0.2 degrees two-theta. In some embodiments, Compound 33 THF Solvate Form A is characterized by an X-ray powder diffractogram having a signal at 19.1±0.2 degrees two-theta and/or 19.4±0.2 degrees two-theta. In some embodiments, Compound 33 THF Solvate Form A is characterized by an X-ray powder diffractogram having signals at 8.2±0.2 degrees two-theta, 8.5±0.2 degrees two-theta, 19.1±0.2 degrees two-theta, and 19.4±0.2 degrees two-theta. In some embodiments, Compound 33 THF Solvate Form A is characterized by an X-ray powder diffractogram having a signal at at least four, at least six, at least eight, or at least ten two-theta values chosen from 8.2±0.2 degrees two-theta, 8.5±0.2 degrees two-theta, 9.5±0.2 degrees two-theta, 11.3±0.2 degrees two-theta, 17.1±0.2 degrees two-theta, 17.8±0.2 degrees two-theta, 19.1±0.2 degrees two-theta, 19.4±0.2 degrees two-theta, 20.5±0.2 degrees two-theta, 21.1±0.2 degrees two-theta, 21.2±0.2 degrees two-theta, 21.5±0.2 degrees two-theta, 22.9±0.2 degrees two-theta, and 23.1±0.2 degrees two-theta. In some embodiments, Compound 33 THF Solvate Form A is characterized by an X-ray powder diffractogram substantially similar to FIG. 13A.

In some embodiments, Compound 33 THF Solvate Form A is characterized by a orthorhombic crystal system, a Pca2₁ space group, and the following unit cell dimensions measured at 100 K on a Bruker diffractometer equipped with Cu K$_\alpha$ radiation (λ=1.54178 Å) and a CMOS detector:

| | |
|---|---|
| a (Å) | 25.12 ± .01 |
| b (Å) | 11.98 ± .01 |
| c (Å) | 17.7 ± 0.1 |
| α (°) | 90 |
| β (°) | 90 |
| γ (°) | 90 |
| V (Å3) | 5327 ± 30 |
| Z/Z' | 4/2 |

In some embodiments, Compound 33 THF Solvate Form A is characterized as having a $^{13}$C ssNMR spectrum with at least one peak selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized as having a $^{13}C$ ssNMR spectrum with at least two peaks selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized as having a $^{13}C$ ssNMR spectrum with at least three peaks selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized as having a $^{13}C$ ssNMR spectrum with at least four peaks selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized as having a $^{13}C$ ssNMR spectrum with at least five peaks selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized as having a $^{13}C$ ssNMR spectrum with at least six peaks selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized as having a $^{13}C$ ssNMR spectrum with at least seven peaks selected from: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A characterized as having a $^{13}C$ ssNMR spectrum with peaks at: 165.8±0.2, 140.0±0.2, 133.9±0.2, 121.2±0.2, 114.3±0.2, 96.1±0.2, 69.0±0.2, 25.7±0.2 ppm and 25.3±0.2 ppm. In some embodiments, Compound 33 THF Solvate Form A is characterized by a $^{13}C$ ssNMR spectrum substantially similar to FIG. 13B.

In some embodiments, Compound 33 THF Solvate Form A is characterized by a $^{19}F$ NMR spectrum having a peak at −110.5±0.2 ppm and/or −113.0±0.2 ppm. In some embodiments, Compound 33 THF Solvate Form A is characterized by a $^{19}F$ ssNMR spectrum substantially similar to FIG. 13C.

Another aspect of the invention provides a composition comprising Compound 33 THF Solvate Form A. In some embodiments, the composition of the invention comprises substantially pure crystalline Compound 33 THF Solvate Form A. In some embodiments, the composition consists essentially of Compound 33 THF Solvate Form A.

Another aspect of the invention provides methods of making Compound 33 THF Solvate Form A. In some embodiments, Compound 33 THF Solvate Form A is prepared by adding Compound 33 Form A to THF in a container, sealing the container and storing at room temperature for about 2 weeks, and isolating the solid form.

14. Compound 33 Form J

In some embodiments, Compound 33 is a crystalline solid comprising of crystalline Form J. In some embodiments, the crystalline solid comprises of 30% to 99% crystalline Compound 33 Form J relative to the total weight of solid Compound 33. In some embodiments, the crystalline solid comprises of 40% to 99% Compound 33 Form J relative to the total weight of solid Compound 33. In some embodiments, the crystalline solid comprises of 50% to 99% Compound 33 Form J relative to the total weight of solid Compound 33. In some embodiments, the crystalline solid comprises of 60% to 99% Compound 33 Form J relative to the total weight of solid Compound 33. In some embodiments, the crystalline solid comprises of 70% to 99% Compound 33 Form J relative to the total weight of solid Compound 33. In some embodiments, the crystalline solid comprises of 75% to 99% Compound 33 Form J relative to the total weight of solid Compound 33. In some embodiments, the crystalline solid comprises of 80% to 99% Compound 33 Form J relative to the total weight of solid Compound 33. In some embodiments, the crystalline solid comprises of 85% to 99% Compound 33 Form J relative to the total weight of solid Compound 33. In some embodiments, the crystalline solid comprises of 90% to 99% Compound 33 Form J relative to the total weight of solid Compound 33. In some embodiments, the crystalline solid comprises of 95% to 99% Compound 33 Form J relative to the total weight of solid Compound 33.

Figure 14A:
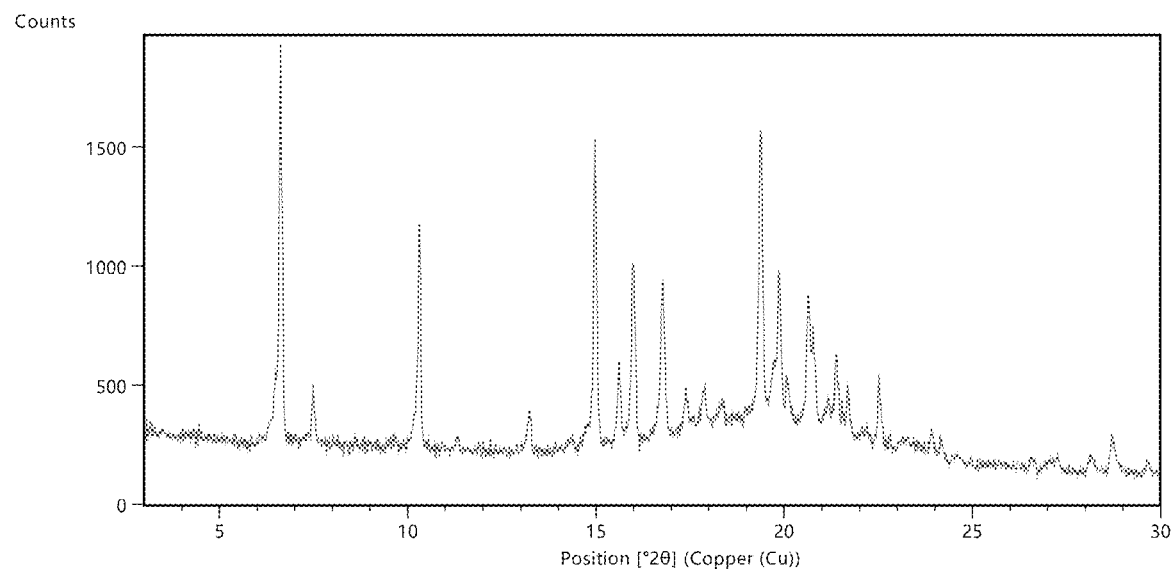
FIG. 14A shows an XRPD diffractogram of Compound 33 Form J.

Thus, in some embodiments, Compound 33 Form J is substantially crystalline. In some embodiments, Compound 33 Form J is substantially pure crystalline. In some embodiments, Compound 33 Form J is characterized by an X-ray powder diffractogram generated by an X-ray powder diffraction analysis with an incident beam of Cu Kα radiation. FIG. 14A provides an X-ray powder diffractogram of Compound Form J at room temperature.

In some embodiments, Compound 33 Form J is characterized by an X-ray powder diffractogram having signals at one or more of 6.6±0.2 degrees two-theta, 7.5±0.2 degrees two-theta, and 15.0±0.2 degrees two-theta. In some embodiments, Compound 33 Form J is characterized by an X-ray powder diffractogram having signals at 6.6±0.2 degrees two-theta, 7.5±0.2 degrees two-theta, and 15.0±0.2 degrees two-theta. In some embodiments, Compound 33 Form J is characterized by an X-ray powder diffractogram having (a) signals at 6.6±0.2 degrees two-theta, 7.5±0.2 degrees two-theta, and 15.0±0.2 degrees two-theta; and (b) a signal at at least one, at least two, at least three, at least four, at least six, at least eight, or at least ten two-theta values chosen from 10.3±0.2 degrees two-theta, 15.6±0.2 degrees two-theta, 16.0±0.2 degrees two-theta, 16.8±0.2 degrees two-theta, 17.9±0.2 degrees two-theta, 19.4±0.2 degrees two-theta, 19.9±0.2 degrees two-theta, 20.1±0.2 degrees two-theta, 20.6±0.2 degrees two-theta, 20.8±0.2 degrees two-theta, 21.4±0.2 degrees two-theta, 21.7±0.2 degrees two-theta, and 22.5±0.2 degrees two-theta. In some embodiments, Compound 33 Form J is characterized by an X-ray powder diffractogram substantially similar to FIG. 14A.

Another aspect of the invention provides a composition comprising Compound 33 Form J. In some embodiments, the composition of the invention comprises substantially pure crystalline Compound 33 Form J. In some embodiments, the composition consists essentially of Compound 33 Form J.

Another aspect of the invention provides methods of making Compound 33 Form J. In some embodiments, Compound 33 Form J is prepared by adding Compound 33 Form A to THF:EtOH:Water (6:1:1 by volume) in a container, slurrying for about 1 hour, filtering, and then adding a polymer mixture comprising one or more polymers selected from polyvinyl pyrrolidone (PVP), polyvinyl alcohol (PVA), polyvinylchloride (PVC), hypromellose (HPMC), methyl cellulose (MC), stirring at room temperature for about a day, and isolating the solid form.

15. Compound 33 Form K

In some embodiments, Compound 33 is a crystalline solid comprising of crystalline Form K. In some embodiments, the crystalline solid comprises of 30% to 99% crystalline Compound 33 Form K relative to the total weight of solid Compound 33. In some embodiments, the crystalline solid comprises of 40% to 99% Compound 33 Form K relative to the total weight of solid Compound 33. In some embodiments, the crystalline solid comprises of 50% to 99%

Compound 33 Form K relative to the total weight of solid Compound 33. In some embodiments, the crystalline solid comprises of 60% to 99% Compound 33 Form K relative to the total weight of solid Compound 33. In some embodiments, the crystalline solid comprises of 70% to 99% Compound 33 Form K relative to the total weight of solid Compound 33. In some embodiments, the crystalline solid comprises of 75% to 99% Compound 33 Form K relative to the total weight of solid Compound 33. In some embodiments, the crystalline solid comprises of 80% to 99% Compound 33 Form K relative to the total weight of solid Compound 33. In some embodiments, the crystalline solid comprises of 85% to 99% Compound 33 Form K relative to the total weight of solid Compound 33. In some embodiments, the crystalline solid comprises of 90% to 99% Compound 33 Form K relative to the total weight of solid Compound 33. In some embodiments, the crystalline solid comprises of 95% to 99% Compound 33 Form K relative to the total weight of solid Compound 33.

Figure 15A:
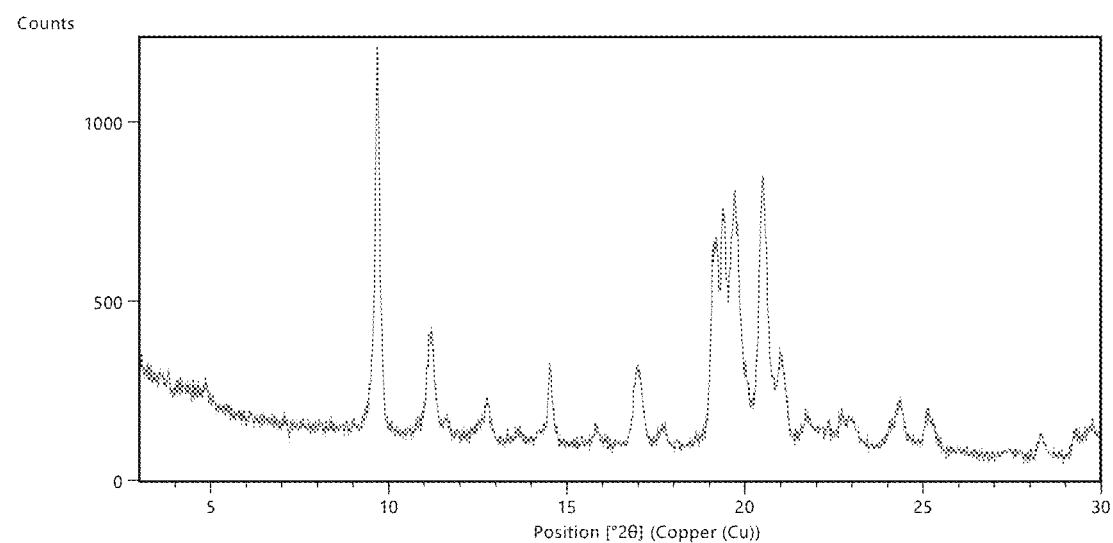
FIG. 15A shows an XRPD diffractogram of Compound 33 Form K.

Thus, in some embodiments, Compound 33 Form K is substantially crystalline. In some embodiments, Compound 33 Form K is substantially pure crystalline. In some embodiments, Compound 33 Form K is characterized by an X-ray powder diffractogram generated by an X-ray powder diffraction analysis with an incident beam of Cu Kα radiation. FIG. 15A provides an X-ray powder diffractogram of Compound Form K at room temperature.

In some embodiments, Compound 33 Form K is characterized by an X-ray powder diffractogram having a signal at 14.5±0.2 degrees two-theta. In some embodiments, Compound 33 Form K is characterized by an X-ray powder diffractogram having signals at 14.5±0.2 degrees two-theta and at one or more of 9.7±0.2 degrees two-theta, 19.7±0.2 degrees two-theta, and 20.5±0.2 degrees two-theta. In some embodiments, Compound 33 Form K is characterized by an X-ray powder diffractogram having signals at 9.7±0.2 degrees two-theta, 14.5±0.2 degrees two-theta, 19.7±0.2 degrees two-theta, and 20.5±0.2 degrees two-theta. In some embodiments, Compound 33 Form K is characterized by an X-ray powder diffractogram having (a) signals at signals at 9.7±0.2 degrees two-theta, 14.5±0.2 degrees two-theta, 19.7±0.2 degrees two-theta, and 20.5±0.2 degrees two-theta, and a signal at at least one, at least two, at least three, at least four, at least five, or at least six, two-theta values chosen from 11.2±0.2 degrees two-theta, 14.5±0.2 degrees two-theta, 17.0±0.2 degrees two-theta, 19.1±0.2 degrees two-theta, 19.4±0.2 degrees two-theta, 21.0±0.2 degrees two-theta, and 24.4±0.2 degrees two-theta. In some embodiments, Compound 33 Form K is characterized by an X-ray powder diffractogram substantially similar to FIG. 15A.

Another aspect of the invention provides a composition comprising Compound 33 Form K. In some embodiments, the composition of the invention comprises substantially pure crystalline Compound 33 Form K. In some embodiments, the composition consists essentially of Compound 33 Form K.

Another aspect of the invention provides methods of making Compound 33 Form K. In some embodiments, Compound 33 Form K is prepared by dissolving Compound 33 Form A in THF in a container, adding water, sealing the container, and storing at room temperature for enough time to allow the water vapor to interact with the solution, and isolating the precipitated solid.

16. Compound 33 2 Me-THF Solvate Form A

In some embodiments, Compound 33 is a crystalline solid comprising of crystalline 2 Me-THF Solvate Form A. In some embodiments, the crystalline solid comprises of 30% to 99% crystalline Compound 33 2 Me-THF Solvate Form A relative to the total weight of solid Compound 33. In some embodiments, the crystalline solid comprises of 40% to 99% Compound 33 2 Me-THF Solvate Form A relative to the total weight of solid Compound 33. In some embodiments, the crystalline solid comprises of 50% to 99% Compound 33 2 Me-THF Solvate Form A relative to the total weight of solid Compound 33. In some embodiments, the crystalline solid comprises of 60% to 99% Compound 33 2 Me-THF Solvate Form A relative to the total weight of solid Compound 33. In some embodiments, the crystalline solid comprises of 70% to 99% Compound 33 2 Me-THF Solvate Form A relative to the total weight of solid Compound 33. In some embodiments, the crystalline solid comprises of 75% to 99% Compound 33 2 Me-THF Solvate Form A relative to the total weight of solid Compound 33. In some embodiments, the crystalline solid comprises of 80% to 99% Compound 33 2 Me-THF Solvate Form A relative to the total weight of solid Compound 33. In some embodiments, the crystalline solid comprises of 85% to 99% Compound 33 2 Me-THF Solvate Form A relative to the total weight of solid Compound 33. In some embodiments, the crystalline solid comprises of 90% to 99% Compound 33 2 Me-THF Solvate Form A relative to the total weight of solid Compound 33. In some embodiments, the crystalline solid comprises of 95% to 99% Compound 33 2 Me-THF Solvate Form A relative to the total weight of solid Compound 33.

Figure 16A:
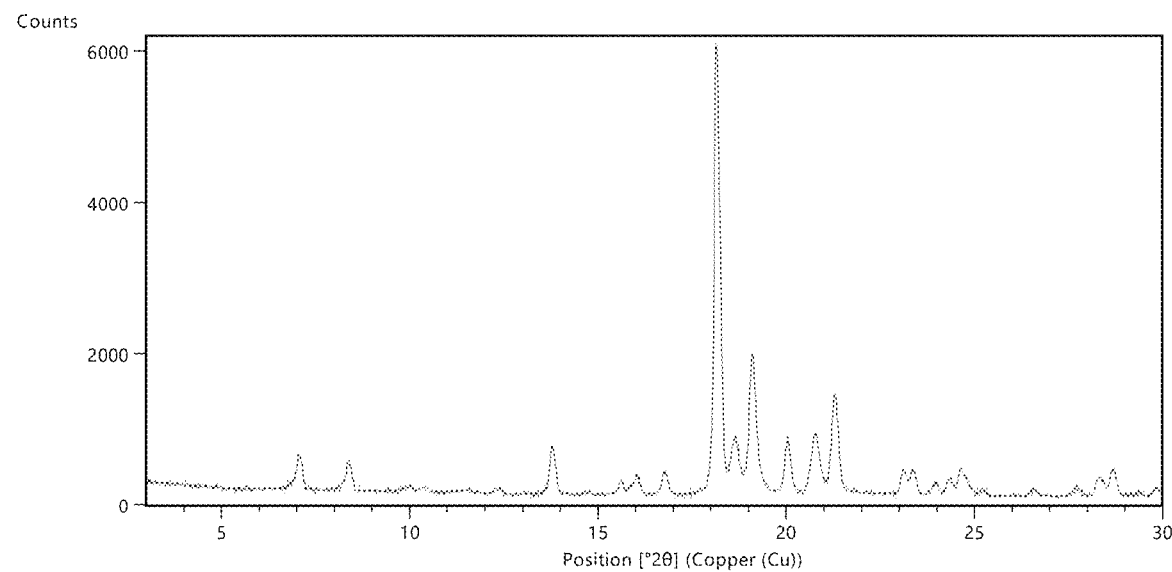
FIG. 16A shows an XRPD diffractogram of Compound 33 2-MeTHF solvate Form A.

Thus, in some embodiments, Compound 33 2 Me-THF Solvate Form A is substantially crystalline. In some embodiments, Compound 33 2 Me-THF Solvate Form A is substantially pure crystalline. In some embodiments, Compound 33 2 Me-THF Solvate Form A is characterized by an X-ray powder diffractogram generated by an X-ray powder diffraction analysis with an incident beam of Cu Kα radiation. FIG. 16A provides an X-ray powder diffractogram of Compound 33 2 Me-THF Solvate Form A at room temperature.

In some embodiments, Compound 33 2 Me-THF Solvate Form A is characterized by an X-ray powder diffractogram having a signal at 18.1±0.2 degrees two-theta, 19.0±0.2 degrees two-theta, and/or 21.3±0.2 degrees two-theta. In some embodiments, Compound 33 2 Me-THF Solvate Form A is characterized by an X-ray powder diffractogram having (a) signals at 18.1±0.2 degrees two-theta, 19.0±0.2 degrees two-theta, and 21.3±0.2 degrees two-theta; and (b) a signal at at least one, at least two, at least three, or at four two-theta values chosen from 13.8±0.2 degrees two-theta, 18.7±0.2 degrees two-theta, 20.0±0.2 degrees two-theta, and 20.8±0.2 degrees two-theta. In some embodiments, Compound 33 2 Me-THF Solvate Form A is characterized by an X-ray powder diffractogram substantially similar to FIG. 16A.

Another aspect of the invention provides a composition comprising Compound 33 2 Me-THF Solvate Form A. In some embodiments, the composition of the invention comprises substantially pure crystalline Compound 33 2 Me-THF Solvate Form A. In some embodiments, the composition consists essentially of Compound 33 2 Me-THF Solvate Form A.

Another aspect of the invention provides methods of making Compound 33 2 Me-THF Solvate Form A. In some embodiments, Compound 33 2 Me-THF Solvate Form A is prepared by dissolving Compound 33 Form A in 2 Me-THF, stirring the slurry for about two days at room temperature or one day at 5° C., and isolating the solid form.

17. Compound 33 Form L

In some embodiments, Compound 33 is a crystalline solid comprising of crystalline Form L. In some embodiments, the crystalline solid comprises of 30% to 99% crystalline Compound 33 Form L relative to the total weight of solid Compound 33. In some embodiments, the crystalline solid comprises of 40% to 99% Compound 33 Form L relative to the total weight of solid Compound 33. In some embodiments, the crystalline solid comprises of 50% to 99% Compound 33 Form L relative to the total weight of solid Compound 33. In some embodiments, the crystalline solid comprises of 60% to 99% Compound 33 Form L relative to the total weight of solid Compound 33. In some embodiments, the crystalline solid comprises of 70% to 99% Compound 33 Form L relative to the total weight of solid Compound 33. In some embodiments, the crystalline solid comprises of 75% to 99% Compound 33 Form L relative to the total weight of solid Compound 33. In some embodiments, the crystalline solid comprises of 80% to 99% Compound 33 Form L relative to the total weight of solid Compound 33. In some embodiments, the crystalline solid comprises of 85% to 99% Compound 33 Form L relative to the total weight of solid Compound 33. In some embodiments, the crystalline solid comprises of 90% to 99% Compound 33 Form L relative to the total weight of solid Compound 33. In some embodiments, the crystalline solid comprises of 95% to 99% Compound 33 Form L relative to the total weight of solid Compound 33.

Figure 17A:
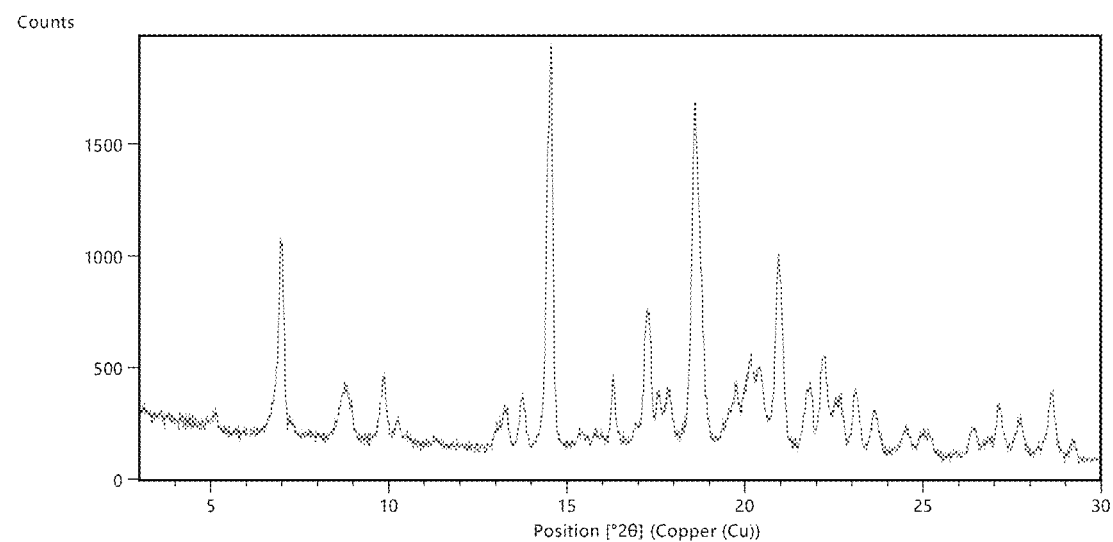
FIG. 17A shows an XRPD diffractogram of Compound 33 Form L.

Thus, in some embodiments, Compound 33 Form L is substantially crystalline. In some embodiments, Compound 33 Form L is substantially pure crystalline. In some embodiments, Compound 33 Form L is characterized by an X-ray powder diffractogram generated by an X-ray powder diffraction analysis with an incident beam of Cu Kα radiation. FIG. 17A provides an X-ray powder diffractogram of Compound Form L at room temperature.

Thus, in some embodiments, Compound 33 Form L is substantially crystalline. In some embodiments, Compound 33 Form L is substantially pure crystalline. In some embodiments, Compound 33 Form L is characterized by an X-ray powder diffractogram generated by an X-ray powder diffraction analysis with an incident beam of Cu Kα radiation. FIG. 17A provides an X-ray powder diffractogram of Compound 33 Form L at room temperature.

In some embodiments, Compound 33 Form L is characterized by an X-ray powder diffractogram having signals at one or more of 14.5±0.2 degrees two-theta, 14.6±0.2 degrees two-theta, 16.3±0.2 degrees two-theta, and 17.3±0.2 degrees two-theta. In some embodiments, Compound 33 Form L is characterized by an X-ray powder diffractogram having signals at 14.5±0.2 degrees two-theta, 14.6±0.2 degrees two-theta, 16.3±0.2 degrees two-theta, and 17.3±0.2 degrees two-theta. In some embodiments, Compound 33 Form L is characterized by an X-ray powder diffractogram having (a) signals at 14.5±0.2 degrees two-theta, 14.6±0.2 degrees two-theta, 16.3±0.2 degrees two-theta, and 17.3±0.2 degrees two-theta; and (b) a signal at at least one, at least two, at least four, at least six, at least eight, or at least ten two-theta values chosen from 7.0±0.2 degrees two-theta, 8.8±0.2 degrees two-theta, 9.9±0.2 degrees two-theta, 13.7±0.2 degrees two-theta, 17.6±0.2 degrees two-theta, 17.9±0.2 degrees two-theta, 18.6±0.2 degrees two-theta, 18.8±0.2 degrees two-theta, 19.7±0.2 degrees two-theta, 20.2±0.2 degrees two-theta, 20.4±0.2 degrees two-theta, 20.7±0.2 degrees two-theta, 20.9±0.2 degrees two-theta, 21.0±0.2 degrees two-theta, 21.9±0.2 degrees two-theta, 22.2±0.2 degrees two-theta, 23.1±0.2 degrees two-theta, 23.6±0.2 degrees two-theta, 27.1±0.2 degrees two-theta, 28.6±0.2 degrees two-theta, and 31.7±0.2 degrees two-theta. In some embodiments, Compound 33 Form L is characterized by an X-ray powder diffractogram substantially similar to FIG. 17A.

Another aspect of the invention provides a composition comprising Compound 33 Form L. In some embodiments, the composition of the invention comprises substantially pure crystalline Compound 33 Form L. In some embodiments, the composition consists essentially of Compound 33 Form L.

Another aspect of the invention provides methods of making Compound Form L. In some embodiments, Compound 33 Form L is prepared by dissolving Compound 33 Form A in 2-MeTHF, allowing a slow evaporation at room temperature, and isolating the solid form. In some embodiments, Compound 33 Form L is prepared by adding Compound 33 Form A to 2-MeTHF/Heptane (1:1 by volume), heating and stirring the mixture at about 50° C. for about two hours until equilibrium is reached, filtering the mixture, slowly cooling to about 5° C., and isolating the solid form.

18. Compound 33 Form M

In some embodiments, Compound 33 is a crystalline solid comprising of Form M. In some embodiments, the crystalline solid comprises of 30% to 99% crystalline Compound 33 Form M relative to the total weight of solid Compound 33. In some embodiments, the crystalline solid comprises of 40% to 99% Compound 33 Form M relative to the total weight of solid Compound 33. In some embodiments, the crystalline solid comprises of 50% to 99% Compound 33 Form M relative to the total weight of solid Compound 33. In some embodiments, the crystalline solid comprises of 60% to 99% Compound 33 Form M relative to the total weight of solid Compound 33. In some embodiments, the crystalline solid comprises of 70% to 99% Compound 33 Form M relative to the total weight of solid Compound 33. In some embodiments, the crystalline solid comprises of 75% to 99% Compound 33 Form M relative to the total weight of solid Compound 33. In some embodiments, the crystalline solid comprises of 80% to 99% Compound 33 Form M relative to the total weight of solid Compound 33. In some embodiments, the crystalline solid comprises of 85% to 99% Compound 33 Form M relative to the total weight of solid Compound 33. In some embodiments, the crystalline solid comprises of 90% to 99% Compound 33 Form M relative to the total weight of solid Compound 33. In some embodiments, the crystalline solid comprises of 95% to 99% Compound 33 Form M relative to the total weight of solid Compound 33.

Figure 18A:
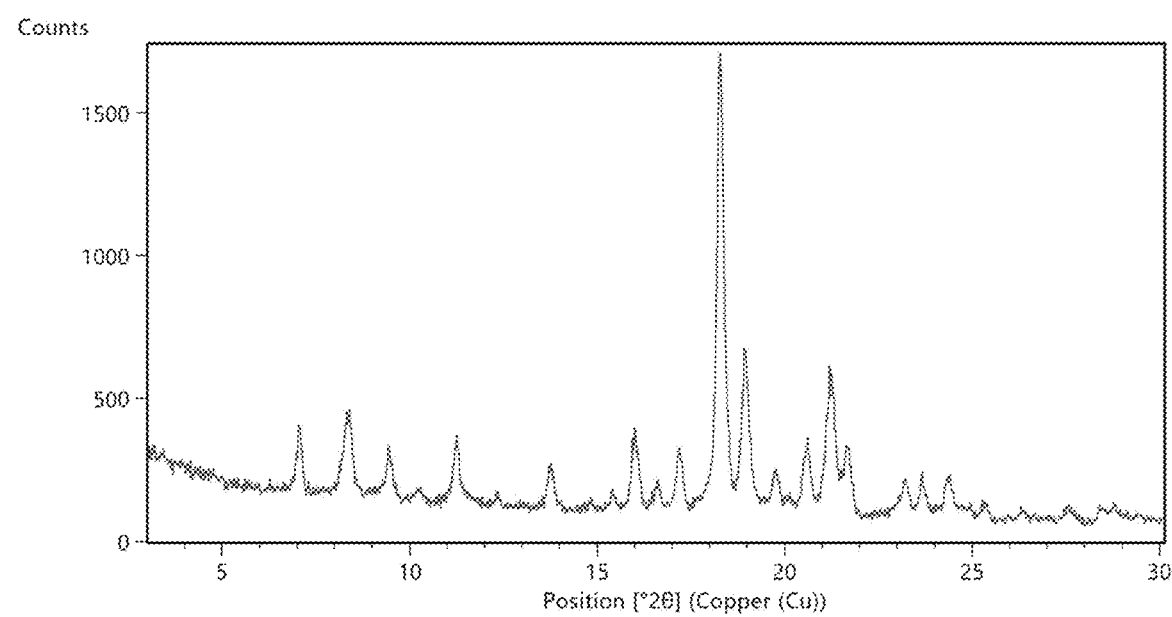
FIG. 18A shows an XRPD diffractogram of Compound 33 Form M.

Thus, in some embodiments, Compound 33 Form M is substantially crystalline. In some embodiments, Compound 33 Form M is substantially pure crystalline. In some embodiments, Compound 33 Form M is characterized by an X-ray powder diffractogram generated by an X-ray powder diffraction analysis with an incident beam of Cu Kα radiation. FIG. 18A provides an X-ray powder diffractogram of Compound 33 Form M at room temperature.

In some embodiments, Compound 33 Form M is characterized by an X-ray powder diffractogram having signals at one or more of 18.3±0.2 degrees two-theta, 18.9±0.2 degrees two-theta, and 21.2±0.2 degrees two-theta. In some embodiments, Compound 33 Form M is characterized by an X-ray powder diffractogram having signals at of 18.3±0.2 degrees two-theta, 18.9±0.2 degrees two-theta, and 21.2±0.2 degrees two-theta. In some embodiments, Compound 33 Form M is characterized by an X-ray powder diffractogram having (a) signals at of 18.3±0.2 degrees two-theta, 18.9±0.2 degrees two-theta, and 21.2±0.2 degrees two-theta; and (b) a signal at at least one, at least two, at least three, or at least four two-theta values chosen from 7.0±0.2 degrees two-theta, 8.4±0.2 degrees two-theta, 11.3±0.2 degrees two-theta, 13.8±0.2 degrees two-theta, 16.0±0.2 degrees two-theta, 17.2±0.2 degrees two-theta, 9.4±0.2 degrees two-theta, 20.6±0.2 degrees two-theta, and 21.7±0.2 degrees two-theta. In some embodiments, Compound 33 Form M is characterized by an X-ray powder diffractogram substantially similar to FIG. 18A.

Another aspect of the invention provides a composition comprising Compound 33 Form M. In some embodiments, the composition of the invention comprises substantially pure crystalline Compound 33 Form M. In some embodiments, the composition consists essentially of Compound 33 Form M.

Another aspect of the invention provides methods of making Compound 33 Form M. In some embodiments, Compound 33 Form M is prepared by adding Compound 33 THF Solvate Form A to methyl tert-butyl ether (MTBE) vapor in a container, sealing the container, storing at room temperature for about ten days, and isolating the solid form.

19. Compound 33 Form N

In some embodiments, Compound 33 is a crystalline solid comprising of Form N. In some embodiments, the crystalline solid comprises of 30% to 99% crystalline Compound 33 Form N relative to the total weight of solid Compound 33. In some embodiments, the crystalline solid comprises of 40% to 99% Compound 33 Form N relative to the total weight of solid Compound 33. In some embodiments, the crystalline solid comprises of 50% to 99% Compound 33 Form N relative to the total weight of solid Compound 33. In some embodiments, the crystalline solid comprises of 60% to 99% Compound 33 Form N relative to the total weight of solid Compound 33. In some embodiments, the crystalline solid comprises of 70% to 99% Compound 33 Form N relative to the total weight of solid Compound 33. In some embodiments, the crystalline solid comprises of 75% to 99% Compound 33 Form N relative to the total weight of solid Compound 33. In some embodiments, the crystalline solid comprises of 80% to 99% Compound 33 Form N relative to the total weight of solid Compound 33. In some embodiments, the crystalline solid comprises of 85% to 99% Compound 33 Form N relative to the total weight of solid Compound 33. In some embodiments, the crystalline solid comprises of 90% to 99% Compound 33 Form N relative to the total weight of solid Compound 33. In some embodiments, the crystalline solid comprises of 95% to 99% Compound 33 Form N relative to the total weight of solid Compound 33.

Figure 19A:
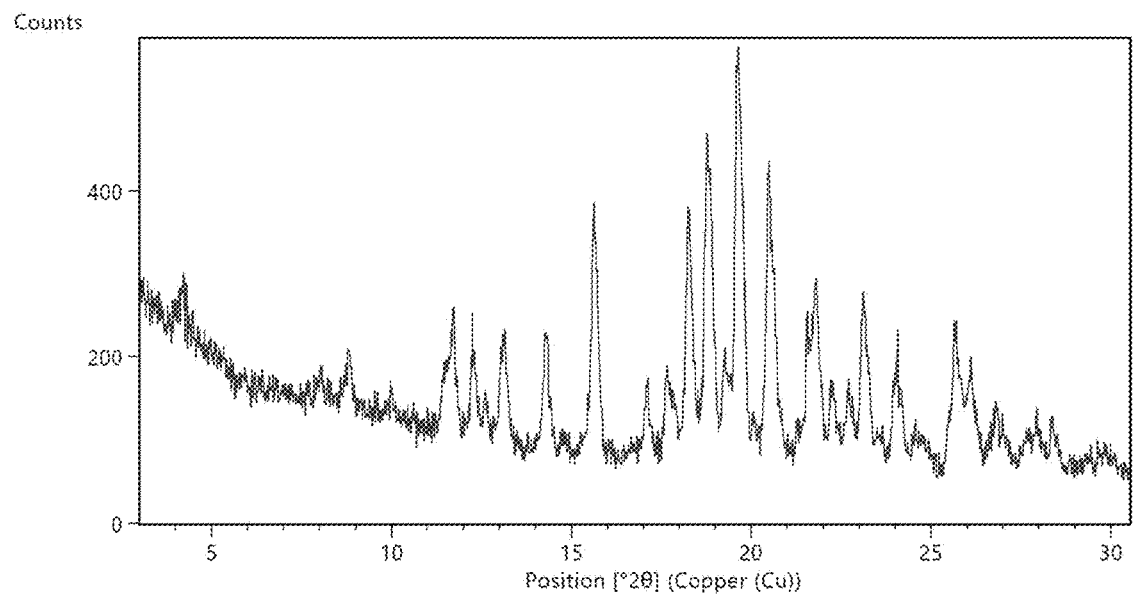
FIG. 19A shows an XRPD diffractogram of Compound 33 Form N.

Thus, in some embodiments, Compound 33 Form N is substantially crystalline. In some embodiments, Compound 33 Form N is substantially pure crystalline. In some embodiments, Compound 33 Form N is characterized by an X-ray powder diffractogram generated by an X-ray powder diffraction analysis with an incident beam of Cu Kα radiation. FIG. 19A provides an X-ray powder diffractogram of Compound 33 Form N at room temperature.

In some embodiments, Compound 33 Form N is characterized by an X-ray powder diffractogram having signals at one or more of 13.0±0.2 degrees two-theta, 14.3±0.2 degrees two-theta, and 18.2±0.2 degrees two-theta. In some embodiments, Compound 33 Form N is characterized by an X-ray powder diffractogram having signals at 13.0±0.2 degrees two-theta, 14.3±0.2 degrees two-theta, and 18.2±0.2 degrees two-theta. In some embodiments, Compound 33 Form N is characterized by an X-ray powder diffractogram having (a) signals at 13.0±0.2 degrees two-theta, 14.3±0.2 degrees two-theta, and 18.2±0.2 degrees two-theta; and (b) a signal at at least two, at least four, at least six, at least eight, or at least ten two-theta values chosen from 4.2±0.2 degrees two-theta, 8.8±0.2 degrees two-theta, 11.7±0.2 degrees two-theta, 12.3±0.2 degrees two-theta, 12.6±0.2 degrees two-theta, 15.6±0.2 degrees two-theta, 17.1±0.2 degrees two-theta, 17.6±0.2 degrees two-theta, 18.7±0.2 degrees two-theta, 19.2±0.2 degrees two-theta, 19.6±0.2 degrees two-theta, 20.5±0.2 degrees two-theta, 21.5±0.2 degrees two-theta, 21.8±0.2 degrees two-theta, 22.2±0.2 degrees two-theta, 22.7±0.2 degrees two-theta, 23.1±0.2 degrees two-theta, 24.0±0.2 degrees two-theta, 25.6±0.2 degrees two-theta, 26.1±0.2 degrees two-theta, 26.8±0.2 degrees two-theta, 28.0±0.2 degrees two-theta, and 28.4±0.2 degrees two-theta. In some embodiments, Compound 33 Form N is characterized by an X-ray powder diffractogram substantially similar to FIG. 19A.

Another aspect of the invention provides a composition comprising Compound 33 Form N. In some embodiments, the composition of the invention comprises substantially pure crystalline Compound 33 Form N. In some embodiments, the composition consists essentially of Compound 33 Form N.

Another aspect of the invention provides methods of making Compound 33 Form N. In some embodiments, Compound 33 Form N is prepared by adding Compound 33 Form A to ethyl acetate (EtOAc), stirring at room temperature, and isolating the solid form.

20. Compound 33 Form O

In some embodiments, Compound 33 is a crystalline solid comprising of Form O. In some embodiments, the crystalline solid comprises of 30% to 99% crystalline Compound 33 Form O relative to the total weight of solid Compound 33. In some embodiments, the crystalline solid comprises of 40% to 99% Compound 33 Form O relative to the total weight of solid Compound 33. In some embodiments, the crystalline solid comprises of 50% to 99% Compound 33 Form O relative to the total weight of solid Compound 33. In some embodiments, the crystalline solid comprises of 60% to 99% Compound 33 Form O relative to the total weight of solid Compound 33. In some embodiments, the crystalline solid comprises of 70% to 99% Compound 33 Form O relative to the total weight of solid Compound 33. In some embodiments, the crystalline solid comprises of 75% to 99% Compound 33 Form O relative to the total weight of solid Compound 33. In some embodiments, the crystalline solid comprises of 80% to 99% Compound 33 Form O relative to the total weight of solid Compound 33. In some embodiments, the crystalline solid comprises of 85% to 99% Compound 33 Form O relative to the total weight of solid Compound 33. In some embodiments, the crystalline solid comprises of 90% to 99% Compound 33 Form O relative to the total weight of solid Compound 33. In some embodiments, the crystalline solid comprises of 95% to 99% Compound 33 Form O relative to the total weight of solid Compound 33.

Figure 20A:
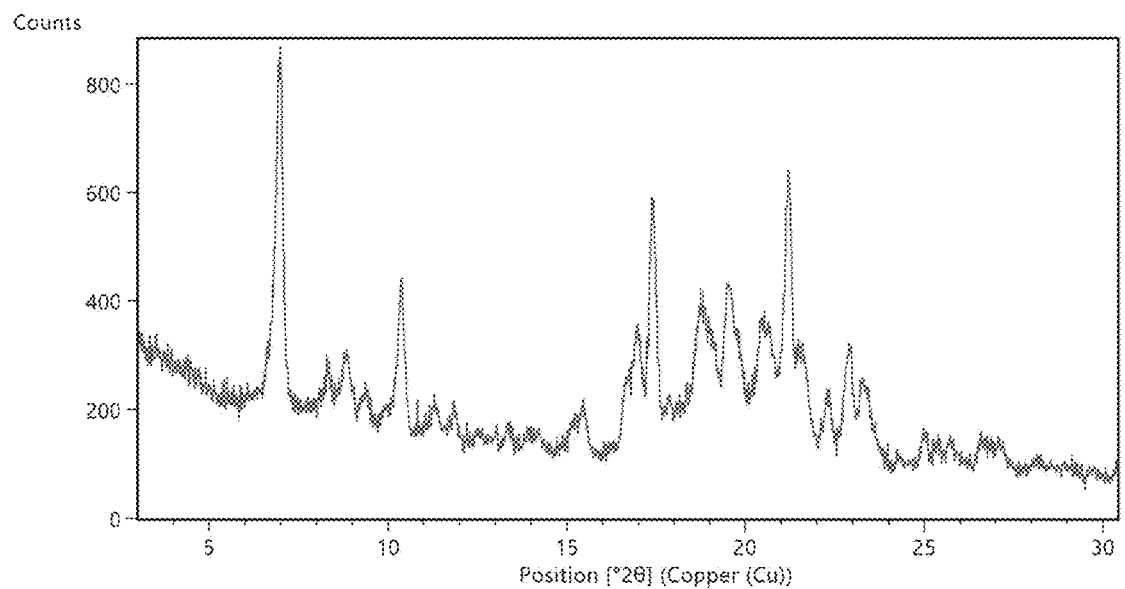
FIG. 20A shows an XRPD diffractogram of Compound 33 Form O.

Thus, in some embodiments, Compound 33 Form O is substantially crystalline. In some embodiments, Compound 33 Form O is substantially pure crystalline. In some embodiments, Compound 33 Form O is characterized by an X-ray powder diffractogram generated by an X-ray powder diffraction analysis with an incident beam of Cu Kα radiation. FIG. 20A provides an X-ray powder diffractogram of Compound 33 Form O at room temperature.

In some embodiments, Compound 33 Form O is characterized by an X-ray powder diffractogram having signals at one or more of 7.0±0.2 degrees two-theta, 10.4±0.2 degrees two-theta, 17.4±0.2 degrees two-theta, and 21.2±0.2 degrees two-theta. In some embodiments, Compound 33 Form O is characterized by an X-ray powder diffractogram having signals at 7.0±0.2 degrees two-theta, 10.4±0.2 degrees two-theta, 17.4±0.2 degrees two-theta, and 21.2±0.2 degrees two-theta. In some embodiments, Compound 33 Form O is characterized by an X-ray powder diffractogram having (a) diffractogram having signals at 7.0±0.2 degrees two-theta, 10.4±0.2 degrees two-theta, 17.4±0.2 degrees two-theta, and 21.2±0.2 degrees two-theta; and (b) a signal at at least one, at least two, at least four, or at least six two-theta values chosen from 8.3±0.2 degrees two-theta, 8.8±0.2 degrees two-theta, 15.5±0.2 degrees two-theta, 16.6±0.2 degrees two-theta, 16.9±0.2 degrees two-theta, 18.8±0.2 degrees two-theta, 19.5±0.2 degrees two-theta, 20.4±0.2 degrees two-theta, 21.6±0.2 degrees two-theta, 22.3±0.2 degrees two-theta, 22.9±0.2 degrees two-theta, and 23.3±0.2 degrees two-theta. In some embodiments, Compound 33 Form O is characterized by an X-ray powder diffractogram substantially similar to FIG. 20A.

Another aspect of the invention provides a composition comprising Compound 33 Form O. In some embodiments, the composition of the invention comprises substantially pure crystalline Compound 33 Form O. In some embodiments, the composition consists essentially of Compound 33 Form O.

Another aspect of the invention provides methods of making Compound 33 Form O. In some embodiments, Compound 33 Form O is prepared by suspending Compound 33 THF Solvate Form A in ethyl acetate (EtOAc), stirring the suspension at room temperature for about two days, and isolating the solid form.

21. Compound 33 Potassium Salt Form A

In some embodiments, Compound 33 is a crystalline solid comprising of Potassium Salt Form A. In some embodiments, the crystalline solid comprises of 30% to 99% crystalline Compound 33 Potassium Salt Form A relative to the total weight of solid Compound 33. In some embodiments, the crystalline solid comprises of 40% to 99% Compound 33 Potassium Salt Form A relative to the total weight of solid Compound 33. In some embodiments, the crystalline solid comprises of 50% to 99% Compound 33 Potassium Salt Form A relative to the total weight of solid Compound 33. In some embodiments, the crystalline solid comprises of 60% to 99% Compound 33 Potassium Salt Form A relative to the total weight of solid Compound 33. In some embodiments, the crystalline solid comprises of 70% to 99% Compound 33 Potassium Salt Form A relative to the total weight of solid Compound 33. In some embodiments, the crystalline solid comprises of 75% to 99% Compound 33 Potassium Salt Form A relative to the total weight of solid Compound 33. In some embodiments, the crystalline solid comprises of 80% to 99% Compound 33 Potassium Salt Form A relative to the total weight of solid Compound 33. In some embodiments, the crystalline solid comprises of 85% to 99% Compound 33 Potassium Salt Form A relative to the total weight of solid Compound 33. In some embodiments, the crystalline solid comprises of 90% to 99% Compound 33 Potassium Salt Form A relative to the total weight of solid Compound 33. In some embodiments, the crystalline solid comprises of 95% to 99% Compound 33 Potassium Salt Form A relative to the total weight of solid Compound 33.

Figure 21A:
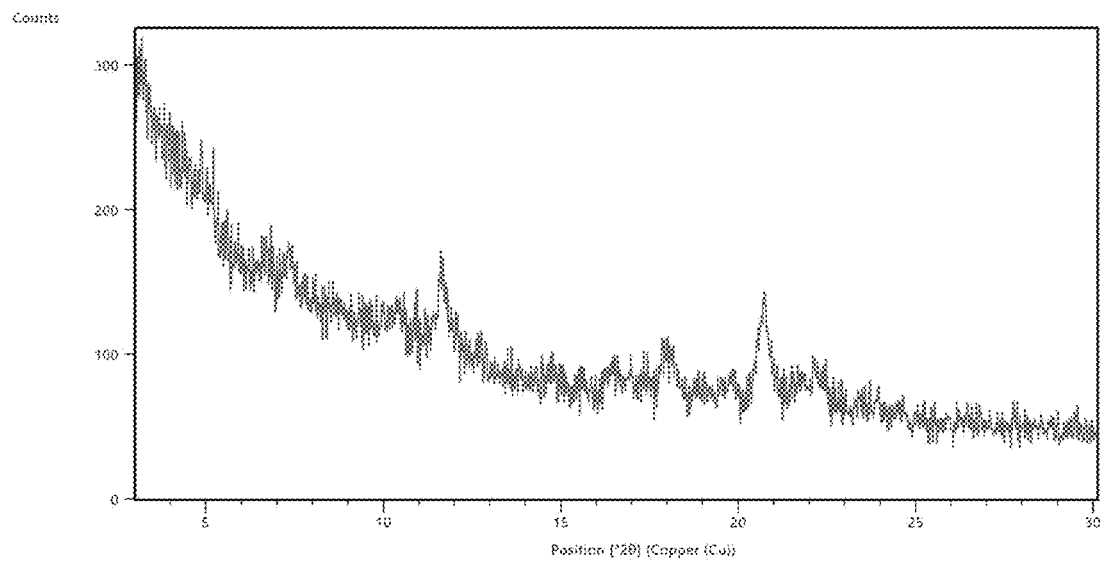
FIG. 21A shows an XRPD diffractogram of Compound 33 K salt Form A.

Thus, in some embodiments, Compound 33 Potassium Salt Form A is substantially crystalline. In some embodiments, Compound 33 Potassium Salt Form A is substantially pure crystalline. In some embodiments, Compound 33 Potassium Salt Form A is characterized by an X-ray powder diffractogram generated by an X-ray powder diffraction analysis with an incident beam of Cu Kα radiation. FIG. 21A provides an X-ray powder diffractogram of Compound 33 Potassium Salt Form A at room temperature.

In some embodiments, Compound 33 Potassium Salt Form A is characterized by an X-ray powder diffractogram having signals at one or more of 11.7±0.2 degrees two-theta, 18.0±0.2 degrees two-theta, and 20.7±0.2 degrees two-theta. In some embodiments, Compound 33 Potassium Salt Form A is characterized by an X-ray powder diffractogram having signals at 11.7±0.2 degrees two-theta, 18.0±0.2 degrees two-theta, and 20.7±0.2 degrees two-theta. In some embodiments, Compound 33 Potassium Salt Form A is characterized by an X-ray powder diffractogram substantially similar to FIG. 21A.

Another aspect of the invention provides a composition comprising Compound 33 Potassium Salt Form A. In some embodiments, the composition of the invention comprises substantially pure crystalline Compound 33 Potassium Salt Form A. In some embodiments, the composition consists essentially of Compound 33 Potassium Salt Form A.

Another aspect of the invention provides methods of making Compound 33 Potassium Salt Form A. In some embodiments, Compound 33 Potassium Salt Form A is prepared by dissolving Compound 33 Form A into acetone at about 50° C., dispensing the Compound 33 Form A acetone solution into a container at room temperature, adding KOH aqueous solution, and obtaining Compound 33 Potassium Salt Form A via evaporation at room temperature.

22. Compound 33 Potassium Salt Form B

In some embodiments, Compound 33 is a crystalline solid comprising of Potassium Salt Form B. In some embodiments, the crystalline solid comprises of 30% to 99% crystalline Compound 33 Potassium Salt Form B relative to the total weight of solid Compound 33. In some embodiments, the crystalline solid comprises of 40% to 99% Compound 33 Potassium Salt Form B relative to the total weight of solid Compound 33. In some embodiments, the crystalline solid comprises of 50% to 99% Compound 33 Potassium Salt Form B relative to the total weight of solid Compound 33. In some embodiments, the crystalline solid comprises of 60% to 99% Compound 33 Potassium Salt Form B relative to the total weight of solid Compound 33. In some embodiments, the crystalline solid comprises of 70% to 99% Compound 33 Potassium Salt Form B relative to the total weight of solid Compound 33. In some embodiments, the crystalline solid comprises of 75% to 99% Compound 33 Potassium Salt Form B relative to the total weight of solid Compound 33. In some embodiments, the crystalline solid comprises of 80% to 99% Compound 33 Potassium Salt Form B relative to the total weight of solid Compound 33. In some embodiments, the crystalline solid comprises of 85% to 99% Compound 33 Potassium Salt Form B relative to the total weight of solid Compound 33. In some embodiments, the crystalline solid comprises of 90% to 99% Compound 33 Potassium Salt Form B relative to the total weight of solid Compound 33. In some embodiments, the crystalline solid comprises of 95% to 99% Compound 33 Potassium Salt Form B relative to the total weight of solid Compound 33.

Thus, in some embodiments, Compound 33 Potassium Salt Form B is substantially crystalline. In some embodiments, Compound 33 Potassium Salt Form B is substantially pure crystalline. In some embodiments, Compound 33 Potassium Salt Form B is characterized by an X-ray powder diffractogram generated by an X-ray powder diffraction analysis with an incident beam of Cu Kα radiation. FIG.

22A provides an X-ray powder diffractogram of Compound 33 Form B at room temperature.

In some embodiments, Compound 33 Potassium Salt Form B is characterized by an X-ray powder diffractogram having signals at one or more of 9.1±0.2 degrees two-theta, 13.7±0.2 degrees two-theta, 15.3±0.2 degrees two-theta, 17.5±0.2 degrees two-theta, and 21.7±0.2 degrees two-theta. In some embodiments, Compound 33 Potassium Salt Form B is characterized by an X-ray powder diffractogram having signals at two or more of 9.1±0.2 degrees two-theta, 13.7±0.2 degrees two-theta, 15.3±0.2 degrees two-theta, 17.5±0.2 degrees two-theta, and 21.7±0.2 degrees two-theta. In some embodiments, Compound 33 Potassium Salt Form B is characterized by an X-ray powder diffractogram having signals at three or more of 9.1±0.2 degrees two-theta, 13.7±0.2 degrees two-theta, 15.3±0.2 degrees two-theta, 17.5±0.2 degrees two-theta, and 21.7±0.2 degrees two-theta. In some embodiments, Compound 33 Potassium Salt Form B is characterized by an X-ray powder diffractogram having signals at 9.1±0.2 degrees two-theta, 13.7±0.2 degrees two-theta, 15.3±0.2 degrees two-theta, 17.5±0.2 degrees two-theta, and 21.7±0.2 degrees two-theta. In some embodiments, Compound 33 Potassium Salt Form B is characterized by an X-ray powder diffractogram having (a) signals at three or more of 9.1±0.2 degrees two-theta, 13.7±0.2 degrees two-theta, 15.3±0.2 degrees two-theta, 17.5±0.2 degrees two-theta, and 21.7±0.2 degrees two-theta; and (b) a signal at at least one, at least two, or at least three two-theta values chosen from 6.9±0.2 degrees two-theta, 10.8±0.2 degrees two-theta, 20.0±0.2 degrees two-theta, and 20.6±0.2 degrees two-theta. In some embodiments, Compound 33 Potassium Salt Form B is characterized by an X-ray powder diffractogram substantially similar to FIG. 22A.

Another aspect of the invention provides a composition comprising Compound 33 Potassium Salt Form B. In some embodiments, the composition of the invention comprises substantially pure crystalline Compound 33 Potassium Salt Form B. In some embodiments, the composition consists essentially of Compound 33 Potassium Salt Form B.

Another aspect of the invention provides methods of making Compound 33 Potassium Salt Form B. In some embodiments, Compound 33 Potassium Salt Form B is prepared by dissolving Compound 33 Form A into 1,4-dioxane at about 50° C. with sonication, dispensing the Compound 33 1,4-dioxane solution into a container at room temperature, adding KOH aqueous solution, and isolating Compound 33 Potassium Salt Form B at room temperature.

23. Compound 33 Potassium Salt Form C

In some embodiments, Compound 33 is a crystalline solid comprising of Potassium Salt Form C. In some embodiments, the crystalline solid comprises of 30% to 99% crystalline Compound 33 Potassium Salt Form C relative to the total weight of solid Compound 33. In some embodiments, the crystalline solid comprises of 40% to 99% Compound 33 Potassium Salt Form C relative to the total weight of solid Compound 33. In some embodiments, the crystalline solid comprises of 50% to 99% Compound 33 Potassium Salt Form C relative to the total weight of solid Compound 33. In some embodiments, the crystalline solid comprises of 60% to 99% Compound 33 Potassium Salt Form C relative to the total weight of solid Compound 33. In some embodiments, the crystalline solid comprises of 70% to 99% Compound 33 Potassium Salt Form C relative to the total weight of solid Compound 33. In some embodiments, the crystalline solid comprises of 75% to 99% Compound 33 Potassium Salt Form C relative to the total weight of solid Compound 33. In some embodiments, the crystalline solid comprises of 80% to 99% Compound 33 Potassium Salt Form C relative to the total weight of solid Compound 33. In some embodiments, the crystalline solid comprises of 85% to 99% Compound 33 Potassium Salt Form C relative to the total weight of solid Compound 33. In some embodiments, the crystalline solid comprises of 90% to 99% Compound 33 Potassium Salt Form C relative to the total weight of solid Compound 33. In some embodiments, the crystalline solid comprises of 95% to 99% Compound 33 Potassium Salt Form C relative to the total weight of solid Compound 33.

Figure 23A:
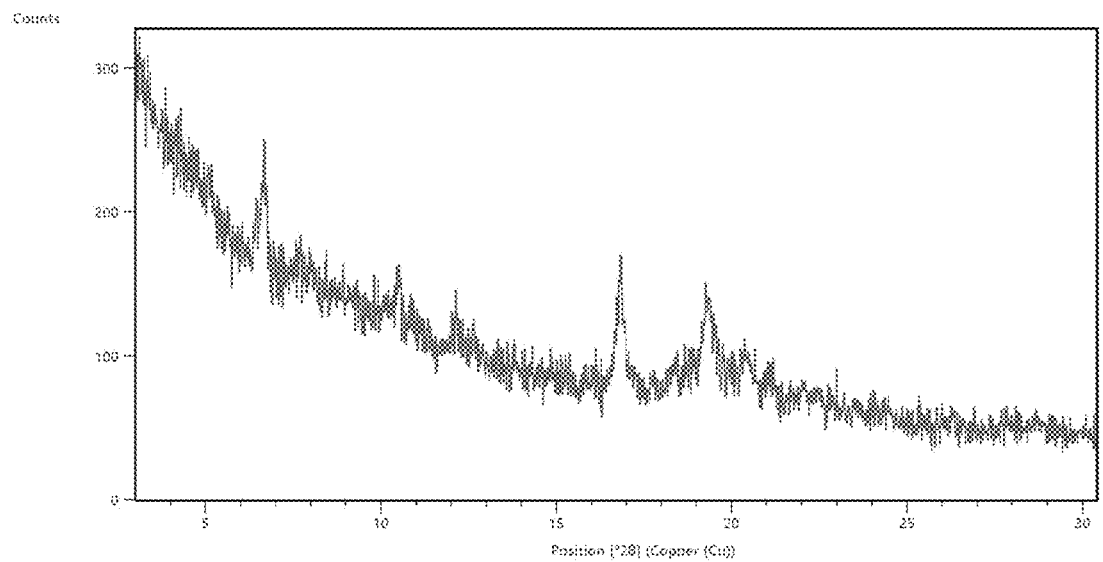
FIG. 23A shows an XRPD diffractogram of Compound 33 K salt Form C.

Thus, in some embodiments, Compound 33 Potassium Salt Form C is substantially crystalline. In some embodiments, Compound 33 Potassium Salt Form C is substantially pure crystalline. In some embodiments, Compound 33 Potassium Salt Form C is characterized by an X-ray powder diffractogram generated by an X-ray powder diffraction analysis with an incident beam of Cu Kα radiation. FIG. 23A provides an X-ray powder diffractogram of Compound 33 Potassium Salt Form C at room temperature.

In some embodiments, Compound 33 Potassium Salt Form C is characterized by an X-ray powder diffractogram having signals at 16.8±0.2 degrees two-theta and 19.3±0.2 degrees two-theta. In some embodiments, Compound 33 Potassium Salt Form C is characterized by an X-ray powder diffractogram having signals at (a) 16.8±0.2 degrees two-theta and 19.3±0.2 degrees two-theta and (b) 6.7±0.2 degrees two-theta, and/or 10.5±0.2 degrees two-theta. In some embodiments, Compound 33 Potassium Salt Form C is characterized by an X-ray powder diffractogram having a signal at 6.7±0.2 degrees two-theta, 10.5±0.2 degrees two-theta. 16.8±0.2 degrees two-theta, and 19.3±0.2 degrees two-theta. In some embodiments, Compound 33 Potassium Salt Form C is characterized by an X-ray powder diffractogram substantially similar to FIG. 23A.

Another aspect of the invention provides a composition comprising Compound 33 Potassium Salt Form C. In some embodiments, the composition of the invention comprises substantially pure crystalline Compound 33 Potassium Salt Form C. In some embodiments, the composition consists essentially of Compound 33 Potassium Salt Form C.

Another aspect of the invention provides methods of making Compound 33 Potassium Salt Form C. In some embodiments, Compound 33 Potassium Salt Form C is prepared by dissolving Compound 33 Form A in an acetone/water solution (e.g., v/v 9:1) at about 50° C., dispensing the Compound 33 4-dioxane solution into a container at room temperature, adding KOH aqueous solution (e.g., at K/Compound 33 molar ratio of about 1:1), obtaining Compound 33 Potassium Salt Form C via evaporation at room temperature.

Solid Dispersions Comprising Amorphous Compound 33

In another aspect, the invention features a solid dispersion comprising the amorphous Compound 33 and a polymer. In one embodiment, the polymer is hydroxypropylmethylcellulose acetate succinate (HPMCAS). In another embodiment, the polymer is polyvinylpyrrolidone/vinyl acetate PVPVA. In another embodiment, the polymer is hydroxypropylmethylcellulose (HPMC). Other suitable exemplary polymers are as described in WO 2011/119984, which is incorporated herein by reference in its entirety.

In one embodiment, the polymer is present in an amount from about 0.10% by weight to about 10% by weight based on the total weight of the dispersion (prior to drying or solidifying). In another embodiment, the polymer is present in an amount from about 0.2% by weight to about 7.5% by weight based on the total weight of the dispersion (prior to drying or solidifying). In another embodiment, the polymer is present in an amount from about 0.2% by weight to about 5.0% by weight based on the total weight of the dispersion (prior to drying or solidifying).

In another embodiment, Compound 33 is present in an amount from about 30% by weight to about 80% by weight of the solid dispersion. In another embodiment, Compound 33 is present in an amount of about 50% by weight of the solid dispersion. In another embodiment, Compound 33 is present in an amount of about 80% by weight of the solid dispersion.

Some embodiments provide spray dried neat amorphous Compound 33 without polymer.

In another aspect, the invention features a pharmaceutical composition comprising the solid dispersion and a pharmaceutically acceptable carrier. In some embodiments, the invention features a pharmaceutical composition comprising spray-dried, neat substantially amorphous Compound 33 without polymer.

Methods of Preparing Amorphous Compound and Solid Dispersions

Amorphous forms of any of the compounds disclosed herein and solid dispersions comprising those amorphous compounds can be prepared. Starting from a compound of the invention or a salt, solvate or hydrate of that compound, the amorphous form of of the compound may be prepared by rotary evaporation or by spray dry methods. In some embodiments, the amorphous Compound of the invention is Compound 33 or a pharmaceutically acceptable salt or deuterated derivative thereof. Some embodiments of the invention provide a pharmaceutical composition comprising amorphous Compound 33 or a pharmaceutically acceptable salt or deuterated derivative thereof. In some embodiments, the composition comprising amorphous Compound 33 or a pharmaceutically acceptable salt or deuterated derivative thereof is a spray-dried dispersion.

Dissolving a compound, a salt, solvate or hydrate of the invention in an appropriate solvent like methanol and rotary evaporating the methanol to leave a foam produces the amorphous form. In some embodiments, a warm water bath is used to expedite the evaporation.

Amorphous form may also be prepared from any of the compounds, salts, solvates or hydrates described herein, including, e.g., Compound 33 and salts, solvates and hydrates of Compound 33, using spray dry methods. Spray drying is a process that converts a liquid feed to a dried particulate form. Optionally, a secondary drying process such as fluidized bed drying or vacuum drying, may be used to reduce residual solvents to pharmaceutically acceptable levels. Typically, spray drying involves contacting a highly dispersed liquid suspension or solution, and a sufficient volume of hot air to produce evaporation and drying of the liquid droplets. The preparation to be spray dried can be any solution, coarse suspension, slurry, colloidal dispersion, or paste that may be atomized using the selected spray drying apparatus. In a standard procedure, the preparation is sprayed into a current of warm filtered air that evaporates the solvent and conveys the dried product to a collector (e.g. a cyclone). The spent air is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; us 2003/0144257).

Spray drying typically employs solid loads of material from about 3% to about 30% by weight, (i.e., drug and excipients), for example about 4% to about 20% by weight, preferably at least about 10%. In general, the upper limit of solid loads is governed by the viscosity of (e.g., the ability to pump) the resulting solution and the solubility of the components in the solution. Generally, the viscosity of the solution can determine the size of the particle in the resulting powder product.

Techniques and methods for spray drying may be found in Perry's Chemical Engineering Handbook, 6th Ed., R. H. Perry, D. W. Green & J. 0. Maloney, eds.), McGraw-Hill book co. (1984); and Marshall "Atomization and Spray-Drying" 50, Chem. Eng. Prog. Monogr. Series 2 (1954). In general, the spray drying is conducted with an inlet temperature of from about 60° C. to about 200° C., for example, from about 95° C. to about 185° C., from about 110° C. to about 182° C., from about 96° C. to about 180° C., e.g., about 145° C. The spray drying is generally conducted with an outlet temperature of from about 30° C. to about 90° C., for example from about 40° C. to about 80° C., about 45° C. to about 80° C. e.g., about 75° C. The atomization flow rate is generally from about 4 kg/h to about 12 kg/h, for example, from about 4.3 kg/h to about 10.5 kg/h, e.g., about 6 kg/h or about 10.5 kg/h. The feed flow rate is generally from about 3 kg/h to about 10 kg/h, for example, from about 3.5 kg/h to about 9.0 kg/h, e.g., about 8 kg/h or about 7.1 kg/h. The atomization ratio is generally from about 0.3 to 1.7, e.g., from about 0.5 to 1.5, e.g., about 0.8 or about 1.5.

Removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In another aspect, the invention features a process of preparing amorphous Compound 33 comprising spray drying the compound. In another embodiment, the process comprises combining Compound 33 (or a salt, solvate, or hydrate thereof) and a suitable solvent or a mixture of solvents and then spray drying the mixture to obtain amorphous Compound 33. In another embodiment, the solvent is an organic solvent or a mixture of organic solvents. In another embodiment, the solvent is an organic solvent or a mixture of organic solvents selected from dichloromethane (DCM), ethanol (EtOH), tetrahydrofuran (THF), and 2-methyltetrahydrofuran (Me-THF). In another embodiment, the mixture of solvents comprises one or more organic solvents in combination with water, such as about 1% water, about 2% water, about 3% water, about 5% water, about 10% water, about 12.5% water, about 15% water, or about 20% water based on the total volume of the solvent mixture. In one embodiment, the solvent mixture comprises DCM, EtOH and about 10% water. In one embodiment, the solvent mixture comprises about 70% DCM, about 29% EtOH, and about 1% water. In another embodiment, the solvent mixture comprises about 65.98% water, about 27.17% EtOH, and about 0.87% water. In another embodiment the solvent mixture comprises about 59% DCM, about 40% EtOH, and about 1% water. In one embodiment, the solvent mixture comprises THF and water. In another embodiment, the solvent mixture comprises Me-THF, EtOH, and water. Other suitable exemplary solvents are as described in WO 2011/119984, which is incorporated herein by reference in its entirety.

In another embodiment, the process comprises: a) forming a mixture comprising Compound 33 (or a salt, solvate, or hydrate thereof), a polymer, and a solvent or a mixture of solvents; and b) spray drying the mixture to form a solid dispersion.

Another aspect of the invention provides pharmaceutical compositions comprising a compound according to any one formula chosen from Formulae I, I-A, I-B, I-C, I-D, I-E, I-F, I-G, and I-H and Compounds 1-342, tautomers of those compounds, pharmaceutically acceptable salts of those compounds and their tautomers, and deuterated derivatives of any of the foregoing. In some embodiments, the pharmaceutical composition comprising at least one compound chosen from Formulae I, I-A, I-B, I-C, I-D, I-E, I-F, I-G, and I-H and Compounds 1-342, tautomers of those compounds, pharmaceutically acceptable salts of those compounds and their tautomers, and deuterated derivatives of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include another active therapeutic agent. Alternatively, a pharmaceutical composition comprising at least one compound of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing can be administered as a separate composition concurrently with, prior to, or subsequent to, a composition comprising at least one other active therapeutic agent. In specific embodiments, a pharmaceutical composition comprising at least one compound selected from Compounds 1-342 tautomers of those compounds, pharmaceutically acceptable salts of those compounds and their tautomers, and deuterated derivatives of any of the foregoing can be administered as a separate composition concurrently with, prior to, or subsequent to, a composition comprising at least one other active therapeutic agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In another aspect of the invention, the compounds and the pharmaceutical compositions, described herein, are used to treat AATD. In some embodiments, the subject in need of treatment with the compounds and compositions of the invention carries the ZZ mutation. In some embodiments, the subject in need of treatment with the compounds and compositions of the invention carries the SZ mutation.

In some embodiments, the methods of the invention comprise administering to a patient in need thereof at least one compound chosen from any of the compounds of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing. In some embodiments, the compound of Formula I is selected from Compounds 1-342, tautomers of those compounds, pharmaceutically acceptable salts of those compounds and their tautomers, and deuterated derivatives of any of the foregoing. In some embodiments, said patient in need thereof has a Z mutation in the alpha-1 antitrypsin gene. In some embodiments said patient in need thereof is homozygous for the Z-mutation in the alpha-1 antitrypsin gene.

Another aspect of the invention provides methods of modulating alpha-1 antitrypsin activity comprising the step of contacting said alpha-1-antitrypsin with at least one compound of Formulae I, I-A, I-B, I-C, I-D, I-E, I-F, I-G, and I-H and tautomers of those compounds, pharmaceutically acceptable salts of those compounds and their tautomers, and deuterated derivatives of any of the foregoing. In specific embodiments, the methods of modulating alpha-1 antitrypsin activity comprising the step of contacting said alpha-1-antitrypsin with at least one compound selected from Compounds 1-342, tautomers of those compounds, pharmaceutically acceptable salts of those compounds and their tautomers, and deuterated derivatives of any of the foregoing.

Some embodiments of the invention provide spray-dried dispersions of compounds of the invention, pharmaceutically acceptable salts, and deuterated derivatives thereof. In some embodiments, the spray-dried dispersion comprises 30-50% Compound 33 (or a salt, or deuterated derivative thereof) and a polymer. In some embodiments, the spray-dried dispersion comprises 30-50% Compound 33 (or a salt or deuterated derivative thereof) and polyvinylpyrrolidone/vinyl acetate (PVPVA). In some embodiments, the spray-dried dispersion comprises 30-50% Compound 33 (or a salt or deuterated derivative thereof) and hydroxypropylmethylcellulose (HPMC). In some embodiments, the spray-dried dispersion comprises 30-50% Compound 33 (or a salt or deuterated derivative thereof) and HPMCAS. In some embodiments, the spray-dried dispersion comprises 50-80% Compound 33 (or a salt or deuterated derivative thereof) and a polymer. In some embodiments, the spray-dried dispersion comprises 50-80% Compound 33 (or a salt or deuterated derivative thereof) and polyvinylpyrrolidone/vinyl acetate (PVPVA). In some embodiments, the spray-dried dispersion comprises 50-80% Compound 33 (or a salt or deuterated derivative thereof) and hydroxypropylmethylcellulose (HPMC). In some embodiments, the spray-dried dispersion comprises 50-80% Compound 33 (or a salt or deuterated derivative thereof) and HPMCAS.

III. Preparation of Compounds

All the generic, subgeneric, and specific compound formulae disclosed herein are considered part of the invention.

A. Compounds of Formula I

The compounds of the invention may be made according to standard chemical practices or as described herein. Throughout the following synthetic schemes and in the descriptions for preparing compounds of Formulae I, I-A, I-B, I-C, I-D, I-E, I-F, I-G, and I-H, Compounds 1-342, tautomers of those compounds, pharmaceutically acceptable salts of those compounds and their tautomers, and deuterated derivatives of any of the foregoing, the following abbreviations are used:

Abbreviations 18-crown-6=1,4,7,10,13,16-hexaoxacyclooctadecane
BrettPhos Pd G1=chloro[2-(dicyclohexylphosphino)-3,6-dimethoxy-2',4',6'-triisopropyl-1,1'-biphenyl][2-(2-aminoethyl)phenyl]palladium(II) or (BrettPhos) palladium(II) phenethylamine chloride
BrettPhos Pd G4=dicyclohexyl-[3,6-dimethoxy-2-[2,4,6-tri(propan-2-yl)phenyl]phenyl]phosphane; methanesulfonic acid; N-methyl-2-phenylaniline; palladium
CBzCl=benzyl chloroformate
Cphos=2-dicyclohexylphosphino-2',6'-bis(N,N-dimethylamino)biphenyl
$Cs_2CO_3$=cesium carbonate
DCE=1,2-dichloroethane
DIPEA=N,N-diisopropylethylamine or N-ethyl-N-isopropyl-propan-2-amine
DMAP=dimethylamino pyridine
DMF=dimethylformamide
DMSO=dimethyl sulfoxide
Dppf=1,1'-ferrocenediyl-bis(diphenylphosphine)
DTBPF=1,1'-bis(di-tert-butylphosphino)ferrocene
EtOAc=ethyl acetate
HATU=[dimethylamino(triazolo[4,5-b]pyridin-3-yloxy)methylene]-dimethyl-ammonium (Phosphorus Hexafluoride Ion)
IPA=isopropyl alcohol
KOtBu=potassium tert-butoxide
$K_3PO_4$=potassium phosphate tribasic
MeOH=methanol MP-TMT scavenger resin=a macroporous polystyrene-bound trimercaptotriazine, a resin bound equivalent of 2,4,6-trimercaptotriazine (TMT).
MTBE=methyl tert-butyl ether
$NaCNBH_3$=sodium cyanoborohydride
NMM=N-methyl morpholine
NaOtBu=sodium tert-butoxide
$Pd_2(dba)_3$=tris(dibenzylideneacetone)dipalladium (0)
$Pd(dppf)_2Cl_2$=[1,1'-Bis(diphenylphosphino)ferrocene]dichloropalladium(II)
$PdCl_2(PPh_3)_2$=bis(triphenylphosphine)palladium(II) dichloride
$Pd(OAc)_2$=palladium(II) acetate
$Pd(tBu_3P)_2$=bis(tri-tert-butylphosphine)palladium(0)
PivCl=pivaloyl chloride
PTSA=p-toluenesulfonic acid monohydrate
rac-BINAP=(±)-2,2'-bis(diphenylphosphino)-1,1'-binaphthalene
[Rh(COD)Cl]2=chloro(1,5-cyclooctadiene)rhodium (I) dimer
SEMCl=2-(trimethylsilyl)ethoxymethyl chloride
SFC=super critical fluid chromatography
SPhos=2-dicyclohexylphosphino-2',6'-dimethoxybiphenyl
SPhos Pd G4=dicyclohexyl-[2-(2,6-dimethoxyphenyl)phenyl]phosphane; methanesulfonic acid; N-methyl-2-phenylaniline; palladium
SPM32=3-mercaptopropyl ethyl sulfide Silica
TBAB=tetrabutylammonium bromide
TBAF=tetrabutylammonium fluoride
tBuXPhos Pd G1=chloro[2-(di-tert-butylphosphino)-2',4',6'-triisopropyl-1,1'-biphenyl][2-(2-aminoethyl)phenyl)]palladium(II) or t-BuXPhos palladium(II) phenethylamine chloride
tBuXPhos Pd G3=[(2-di-tert-butylphosphino-2',4',6'-triisopropyl-1,1'-biphenyl)-2-(2'-amino-1,1'-biphenyl)]palladium(II) methanesulfonate
tBuXPhos Pd G4=methanesulfonato(2-di-t-butylphosphino-2',4',6'-tri-1-propyl-1,1'-biphenyl)(2'-methylamino-1,1'-biphenyl-2-yl)palladium(II) dichloromethane
TEA=triethylamine
TFA=trifluoroacetic acid
THF=tetrahydrofuran
THP=tetrahydropyran
TMSI=iodotrimethylsilane
XantPhos Pd G3=[(4,5-bis(diphenylphosphino)-9,9-dimethylxanthene)-2-(2'-amino-1,1'-biphenyl)]palladium (II) methanesulfonate
XPhos Pd G1=(2-dicyclohexylphosphino-2',4',6'-triisopropyl-1,1'-biphenyl)[2-(2-aminoethyl)phenyl)]palladium(II) chloride or (XPhos) palladium(II) phenethylamine chloride
XPhos Pd G3=(2-dicyclohexylphosphino-2',4',6'-triisopropyl-1,1'-biphenyl)[2-(2'-amino-1,1'-biphenyl)]palladium(II) methanesulfonate In some embodiments, processes for preparing compounds of Formula I, tautomers, pharmaceutically acceptable salts of those compounds or tautomers, or deuterated derivatives of any of the foregoing, comprise reactions depicted in Schemes 1-9 below:

Scheme 1 provides methods for preparation of compounds of Formula I, tautomers, salts or derivatives thereof, from a compound of Formula 1-1, wherein variables $X^1$, $X^2$, $R^0$, $R^1$, $R^2$, $R^3$, $Z^1$, $Z^2$, $Z^3$, and n are defined as above in Formula I. When at least one of $Z^1$, $Z^2$, or $Z^3$ is a nitrogen atom, a protecting group ($PG^1$) is used. In some embodiments, PG$^1$ is chosen from p-toluenesulfonamide (Tosyl), pivaloyl (Piv), trimethylsilyl ethoxymethyl (SEM), tetrahydropyranyl (THP), phenyl sulfonyl, benzyl carbamate (Cbz), Benzyl (Bn), p-methoxybenzyl (PMB), t-butyl carbamate (Boc), allyloxycarbamate (Alloc), 9-fluorenylmethyl carbamate (FMOC), methoxymethyl (MOM), Benzyloxymethyl (BOM), 2-methoxyethoxyethyl (MEM), trifluoroacetamide or any other suitable protecting group. Any suitable conditions known in the art, such as those for a deprotection reaction of a nitrogen atom, can be used for preparation of compounds of Formula I from compounds of Formula 1-1. In some embodiments, the reaction depicted in scheme 1 is performed in the presence of a base, such as a metal hydroxide (e.g. an aqueous solution of NaOH or KOH). The reaction may be performed at elevated temperature (e.g. 60° C.). A solvent mixture such as MeOH and THF may be used. Alternative conditions known in the art may be used as appropriate for the deprotection of PG$^1$.

Scheme 1

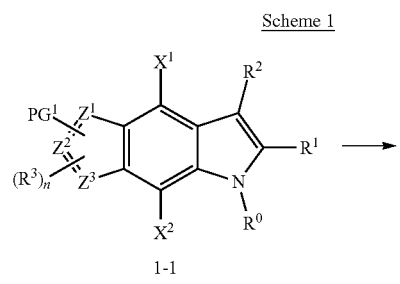

1-1

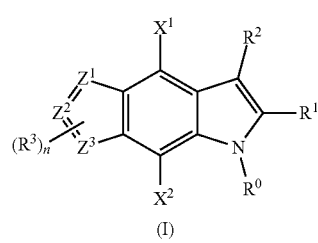

(I)

In some embodiments, as shown in Scheme 2, processes for the preparation of compounds of Formula 1-1, comprise reacting a compound of Formula 2-1, (wherein $X^1$, $X^2$ $R^0$, $R^1$, $R^2$, $R^3$, $Z^1$, $Z^2$, $Z^3$, and n are defined as above in Formula I), with a boronic acid or ester of Formula 2-3, a boronic ester of formula 2-4, or a boronic ester of formula 2-5. $R^{11}$ may be hydrogen, or a suitable alkyl such as Me, Et, propyl, isopropyl, or isobutyl. Each $R^{12}$ may independently be hydrogen, methyl, or any other suitable alkyl group. $X^3$ is any suitable halide (e.g. I, Br or Cl). Variable p may be 1 or 2. In some embodiments, the reactions generating a compound 1-1 are performed in the presence of any suitable coupling reagent, such as palladium a catalyst (e.g. Pd(dppf)Cl$_2$, Pd(OAc)$_2$, Pd(PPh$_3$)$_4$, or XPhos Pd G3) in the presence of a base (Na$_2$CO$_3$, Cs$_2$CO$_3$, K$_3$PO$_4$). In some embodiments, the reaction may be performed in a polar solvent (1,4-dioxane) in the presence of added heat (>80° C.).

Scheme 2

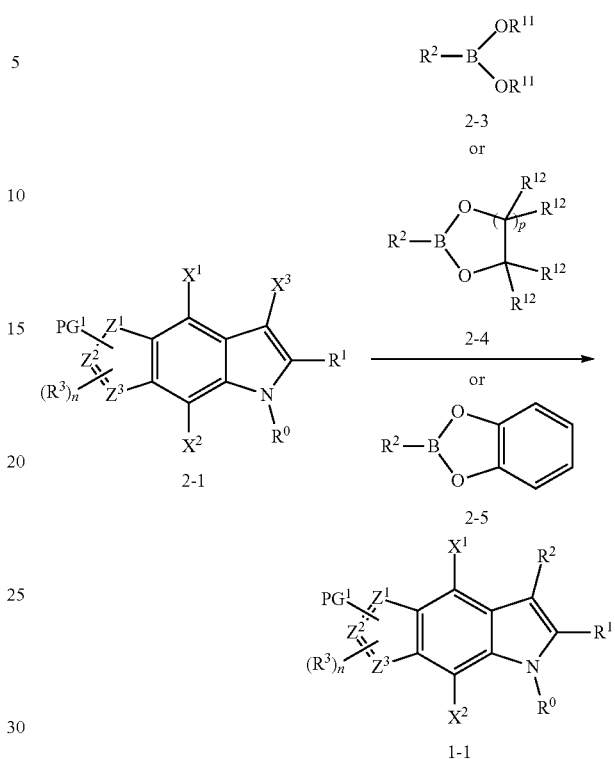

Scheme 3 refers to an additional process for the preparation of compounds of Formula 1-1 from compounds of Formula 2-1 wherein, variables depicted in scheme 3 are defined as above. $R^{13}$ is a hydrogen atom or any suitable alkyl group (e.g. Me, Et). $X^4$ is any suitable halogen (e.g. I, Br, or Cl). A compound of Formula 3-1 may be prepared from a compound of Formula 2-1 using any suitable conditions for formation of a boronate ester from an aryl halide. In some embodiments, 4,4,5,5-tetramethyl-1,3,2-dioxaborolane in the presence of a catalyst (e.g. Pd(dppf)Cl$_2$) and an organic base (triethylamine) may be used. A compound of Formula 3-1 may be converted to compound of Formula 1-1 via a cross-coupling reaction with a halide of Formula 3-2, in the presence of a suitable catalyst and base. For example, in some embodiments, the coupling reaction is performed in the presence of a catalyst such as Pd(dppf)Cl$_2$, base (e.g. Na$_2$CO$_3$). The reaction may be performed in polar solvent (1,4-dioxane), at elevated temperature (e.g. >90° C.).

Scheme 3

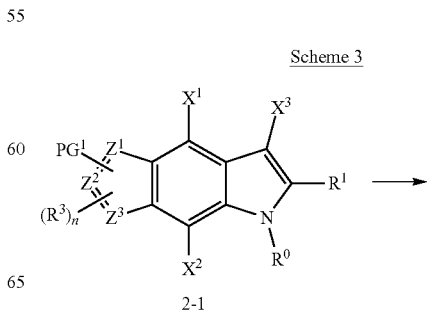

2-1

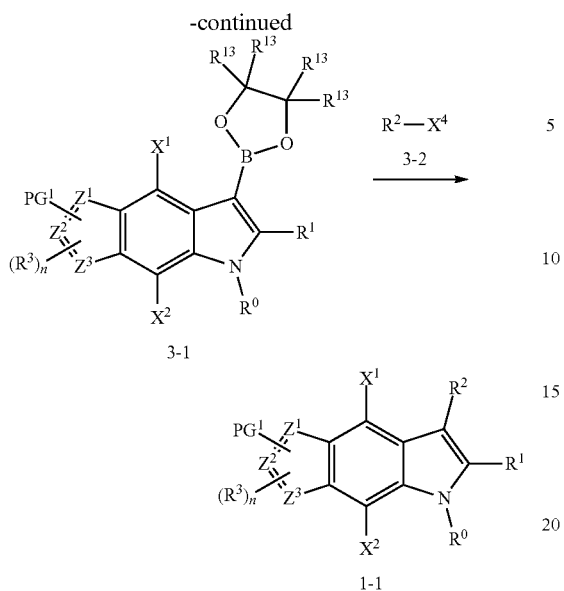

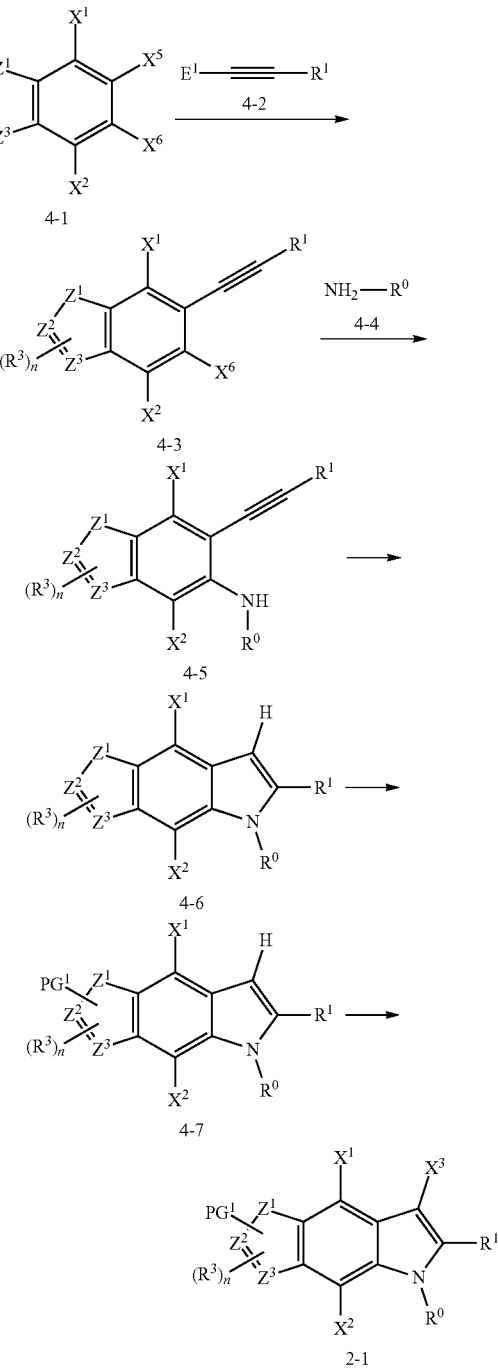

Scheme 4

Scheme 4 provides processed for the preparation of compounds of Formula 2-1. $X^5$ and $X^6$ are any suitable halogen (e.g. Cl, Br or I). $E^1$ is hydrogen, $SiMe_3$ or $SnBu_4$. All other variables are defined as above. Compounds of Formula 2-1 may be used in scheme 2 and scheme 3 above. Any suitable conditions, for alkyne coupling known in the art (e.g. Sonogashira coupling) may be used to prepare a compound of Formula 4-3 from a compound of Formula 2-1 and alkynes of Formula 4-2. In some embodiments, the reaction may be performed in the presence of CuI and $Pd(PPh_3)_2Cl_2$. In some embodiments, a base such as triethylamine or DIPEA may be used. In some additional embodiments, KOH or CsF may be present. Compounds of Formula 4-3 and amines of Formula 4-4 may be converted to compounds of Formula 4-5 using any amine coupling conditions known in the art. For example, in some embodiments, the reaction is performed in the presence of a catalyst (e.g. BrettPhos Pd G1, tBuXPhos Pd G1, BrettPhos Pd G4 or tBuXPhos Pd G1). The reaction may be performed in the presence of a suitable base (e.g. NaOtBu), and a solvent such as THF, tBuOH or ethanol. In some embodiments the reaction may be performed with added heat (70° C.). A compound of Formula 4-5 may be converted to a compound of Formula 4-6 using any suitable condition for the intramolecular reaction of an amine with an alkyne. The reaction may be performed in the presence of a polar solvent (DMSO, EtOH or AcOH) with added heat (e.g. 60° C. or 150° C.). In some embodiments, the reaction is performed in the presence of CuI. Any suitable condition known to those skilled in the art, such as those used for the protection of a nitrogen atom, may be used to generate a compound of Formula 4-7 from compounds of Formula 4-6. In some embodiments, the reaction is performed in the presence of pivaloyl chloride (Piv-Cl) or p-toluenesulfonyl chloride (Ts-Cl). The reaction may be performed in the presences of a base (e.g. KOtBu). A suitable halogenating agent (e.g. N-iodosuccinimide) may be used in the conversion of a compound of Formula 4-7 to a compound of Formula 2-1.

Scheme 5 provides processes for preparing compounds of Formula 5-6 from compounds of Formula 5-1. $X^7$ is any suitable halogen (e.g. Cl, Br or I). $X^8$ is a suitable halogen (e.g. Cl, Br or I). Other variables are defined as in Formula I. Compounds of Formula 5-6 may be used as a compound of Formula 1-1 in scheme 1. A compound of Formula 5-3 may be prepared by reacting a compound of Formula 5-1 and a compound of Formula 5-2. The reaction may be performed in the presence of a catalyst system (e.g. tBuXPhos Pd G4) and a base (e.g. NaOtBu). The reaction may be performed in a solvent such as tBuOH. Compounds of Formula 5-4 may be prepared from compounds of Formula 5-3 using any reagent appropriate for the protection of a nitrogen atom. In some embodiments, pivaloyl chloride (Piv-Cl) in the presence of a base (e.g. KOtBu) may be used. Compounds of Formula 5-6 may be prepared by reacting compounds of Formula 5-4 with alkynes of Formula 5-5 in the presence of a catalyst (e.g. Pd(PtBu$_3$)$_2$) and an amine base (e.g. N-methyldicyclohexylamine). In some embodiments, the reaction may be performed in a polar solvent such as 1,4-dioxane, with added heat (110° C.).

Phos Pd G4 or tBuXPhos Pd G1), a suitable base (e.g. NaOtBu), and a solvent such as THF, tBuOH or ethanol. In some embodiments the reaction may be performed with added heat (70° C.). Compounds of Formula 6-6 may be prepared from compounds of Formula 6-5 using any suitable condition for the intramolecular addition of an amine to an alkyne. In some embodiments, the reaction may be performed by heating a compound of Formula 6-5 in a suitable solvent (e.g. DMSO at 150° C.). In an alternative embodiment, compounds of Formula 6-5 may be heated (60° C.) in a solvent such as EtOH, in the presence of AcOH. Compounds of Formula 6-7 may be prepared from 6-6 using a suitable protecting group reagent. For example, PivCl, SEM-Cl or PhSO$_2$—Cl may be used. The reaction may be performed in the presence of any suitable base (e.g. KOtBu or KOH). Compounds of Formula 6-8 may be prepared by reaction of compounds of Formula 6-7 with a halogenating agent (e.g N-iodosuccinimide or N-bromosuccinimide) in a solvent such as dichloromethane.

Scheme 5

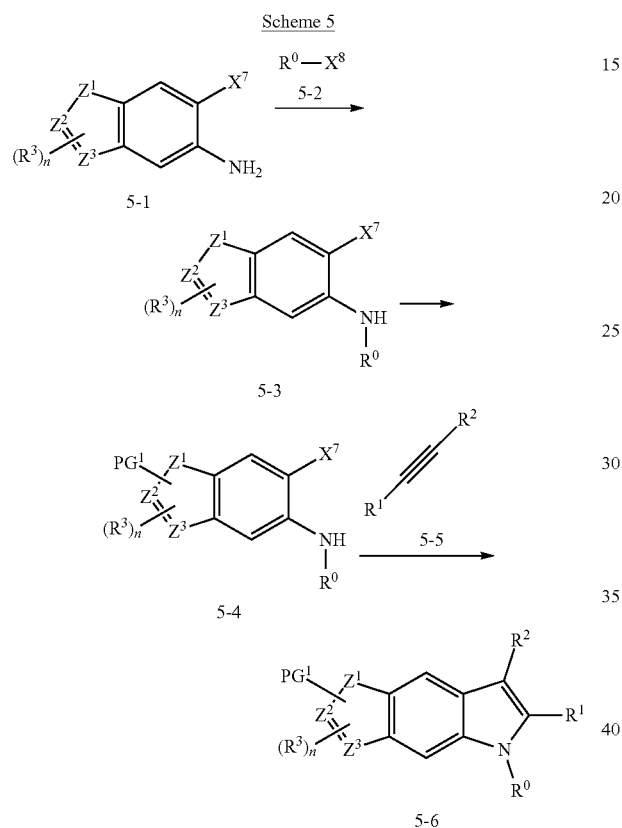

Scheme 6 depicts processes for the preparation of compounds of Formula 6-8. Compounds of Formula 6-8 may be used as a compound of Formula 2-1 above. X$^9$ and X$^{10}$ are independently selected halogens (e.g. Cl, Br, or I). X$^{11}$ is a halogen (e.g. Br or I). E$^2$ is a hydrogen atom, SnBu$_4$ or SiMe$_3$. All other variables are as defined in Formula I.

Compounds of Formula 6-1 may be coupled to alkynes of Formula 6-2 using any suitable conditions for aryl halide to alkyne coupling known to those skilled in the art (e.g. Sonogashira coupling). In some embodiments, the reaction may be performed in the presence of CuI and Pd(PPh$_3$)$_2$Cl$_2$. In some embodiments, a base such as triethylamine or DIPEA may be used. In some alternative embodiments, bases such as KOH or CsF may be used. Any suitable condition, such as those for performing amination reactions may be used to react compounds of Formula 6-3 and amines of Formula 6-4 to give a compound of Formula 6-5. For example, the reaction may be performed in the presence of a catalyst (e.g. BrettPhos Pd G1, tBuXPhos Pd G1, Brett- Scheme 6

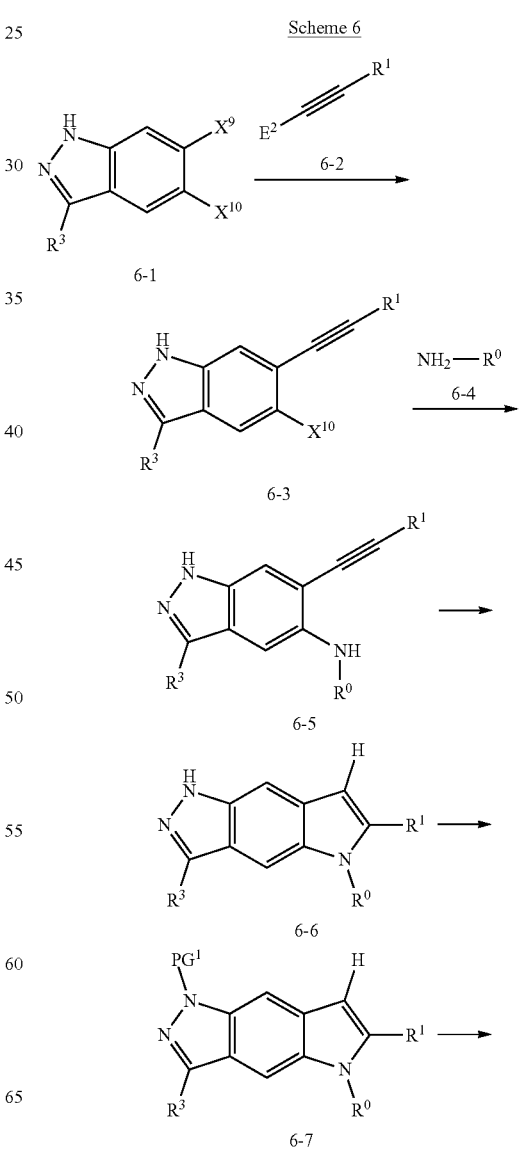

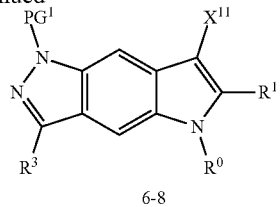

Scheme 7 provides processes for preparation of compounds of Formula 7-3. $X^{11}$ is a suitable halide (e.g. Cl, Br, I). $R^{14}$ is a hydrogen atom, or any suitable alkyl group (e.g. Me or Et). $R^{14}$ groups may also be linked through a single carbon-carbon bond to form a cyclic boronate ester. $R^{15}$ is any suitable alkyl (e.g. Me or Et). Ar is any suitable 5 or 6 membered aromatic group, such that a compound of Formula 7-3 may be also a compound of Formula I. Any suitable condition known to those in the art may be used for coupling of a compound of Formula 6-8 with a boronic acid or boronic ester of Formula 7-1. In some embodiments, the coupling reaction is performed in the presence of a palladium based catalyst (e.g. Pd(dppf)Cl$_2$, Pd(PPh$_3$)$_4$, XPhos Pd G3, or Pd$_2$(dba)$_3$) and a base (e.g. Na$_2$CO$_3$ or K$_3$PO$_4$). The reaction may be performed in polar solvent (1,4-dioxane or DMF), at elevated temperature (e.g. 70° C.). Any suitable reagents known in the art, such as those suitable for the hydrolysis of an ester and appropriate for removal of a protecting group PG$^1$ from a nitrogen atom, may be used to prepare compounds of Formula 7-3 from compounds of Formula 7-2. In some embodiments, an aqueous solution of base (e.g. NaOH or KOH) in a polar solvent (e.g. a THF and MeOH mixture) may be used. The reaction may be performed with added heat (e.g. 55° C.). In alternative embodiments, the reaction may be performed in the presence of an amine (e.g. piperidine).

Scheme 8 shows an alternative process for the preparation of compounds of Formula 7-3 from 6-8. $X^{11}$ is a suitable halide (e.g. Cl, Br, I). $R^{16}$ is any suitable alkyl (e.g Me). $X^{12}$ is any suitable halide (e.g. Cl, Br, I). $R^{17}$ is any suitable alkyl that forms an ester group (e.g Me, Et, tBu). A compound of formula 8-1 may be prepared from 7-3 using any suitable conditions known to those skilled in the art for the preparation of aryl boronic esters. In some embodiments, 4,4,5,5-tetramethyl-1,3,2-dioxaborolane in the presence of a catalyst (e.g. Pd(dppf)Cl$_2$) and an organic base (triethylamine) may be used. The reaction may be performed in a solvent such as xylene with added heat (150° C.). A compound of Formula 8-1 may react with an aryl halide of Formula 8-2 using any suitable condition known to those skilled in the art, such as those for a Suzuki coupling reaction. In some embodiments, a catalyst such as Pd(dppf)Cl$_2$ is used. In some embodiments, the reaction may be performed in the presence of a base (e.g. Na$_2$CO$_3$) in a polar solvent (e.g. 1,4-dioxane) at elevated temperature (95° C.). Any suitable condition for the hydrolysis of an ester, and removal of a nitrogen protecting group, may be used in the conversion of compounds of Formula 8-3 to compounds of Formula 7-3. In some embodiments, an aqueous solution of base (e.g. NaOH or KOH) in a polar solvent (e.g. a THF and MeOH mixture) may be used. The reaction may be performed with added heat (e.g. 55° C.). In alternative embodiments, the reaction may be performed in the presence of an amine (e.g. piperidine).

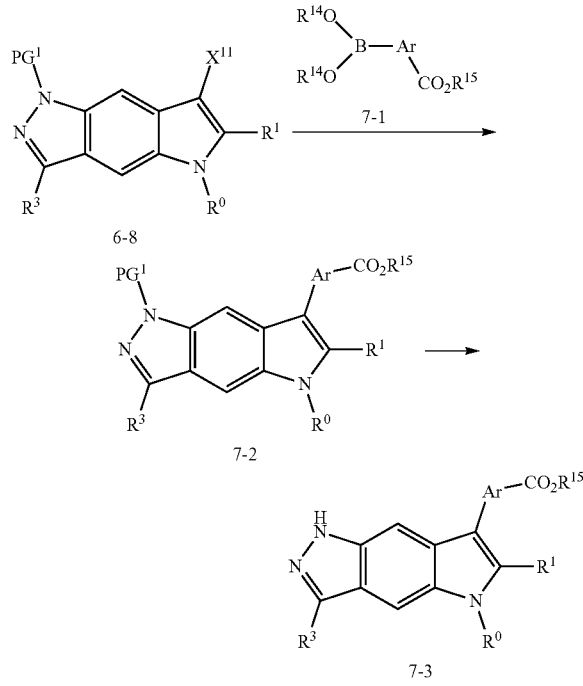

Scheme 7

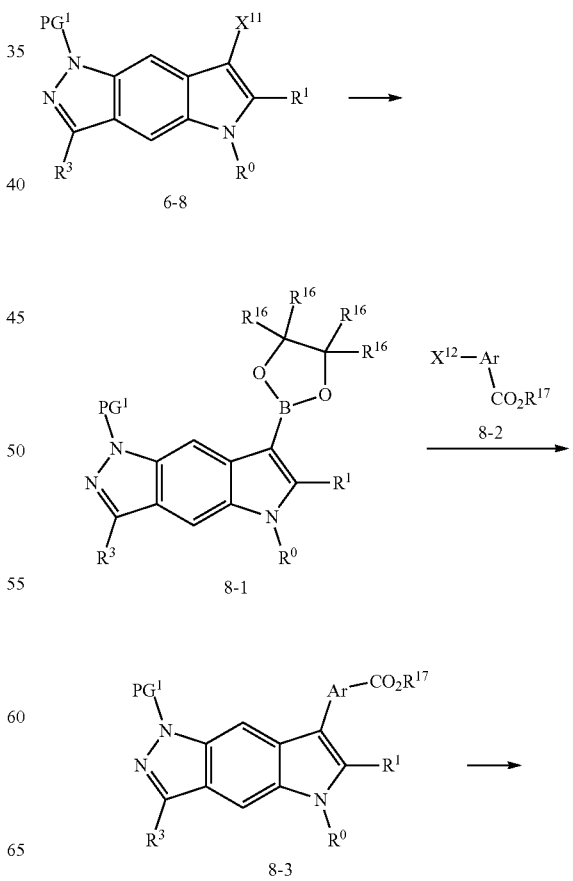

Scheme 8

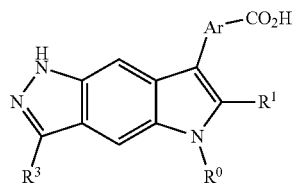

7-3

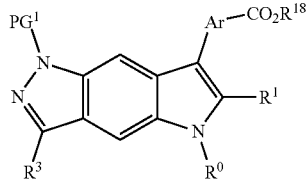

9-6

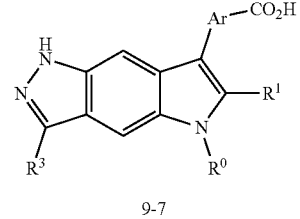

9-7

Scheme 9 depicts an alternative process for the preparation of compounds of Formula 7-3. $X^{13}$ is any suitable halogen (e.g. I, Br or Cl). $X^{14}$ is any suitable halogen (e.g. I, Br or Cl). $R^{18}$ is any suitable alkyl group that forms an ester (e.g. Me or Et). Other variables are as defined in Formula I. In some embodiments, a compound of Formula 9-3 may be prepared by reaction of compounds of Formula 9-1 with compounds of Formula 9-2. Any suitable conditions for coupling of an amine and aryl halide may be used. For example, a palladium catalyst system (e.g. tBuXPhos Pd G4) and a base (e.g. NaOtBu) may be used. Compounds of Formula 9-4 may be prepared from 9-3 using any suitable reagent for the protection of a nitrogen atom. A compound of formula 9-4 may react with an alkyne of Formula 9-5 under suitable conditions to give a compound of Formula 9-6. For example, in the presence of a catalyst system (e.g. Pd(PtBu$_3$)$_2$, or Pd(OAc)$_2$ with a ligand such as DTBPF). In some embodiments, the reaction is performed in the presence of a base (e.g. N-methyldicyclohexylamine, KHCO$_3$ or K$_2$CO$_3$). A compound of Formula 7-3 may be prepared from 9-6 using any suitable conditions for the removal of a nitrogen protecting group such as PG$^1$, and the simultaneous hydrolysis of an ester group. For example, in some embodiments the reaction may be performed in the presence of a base (e.g. NaOH, KOH or NaOH and piperidine). The reaction may be performed in a polar solvent system (THF, MeOH, EtOH, water) with added heat (70° C.).

Scheme 9

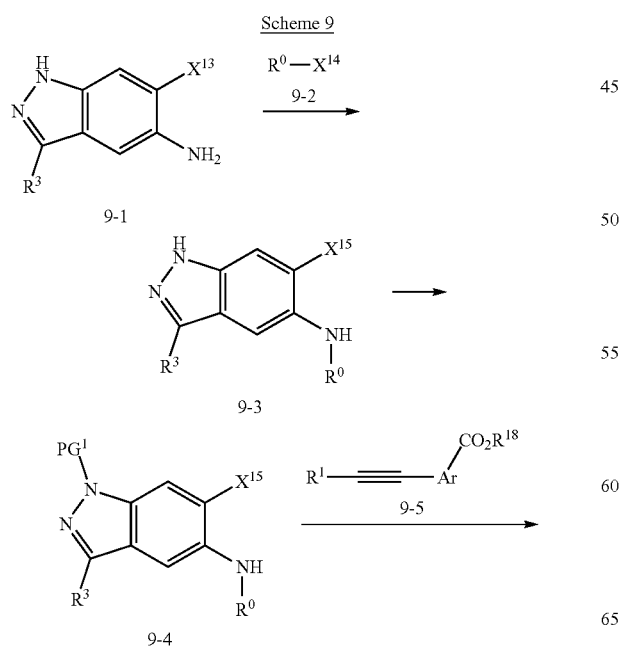

Non-limiting exemplary embodiments include:
1. A compound of formula (I):

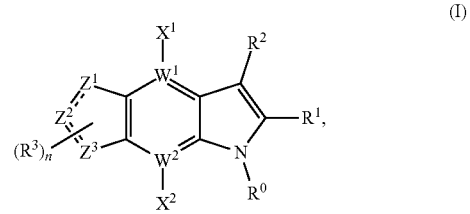

(I)

a tautomer thereof, a pharmaceutically acceptable salt of any of the foregoing, and/or a deuterated derivative of any of the foregoing;

wherein:
(i) $R^0$ is chosen from
   (a) $C_1$-$C_8$ linear, branched, and cyclic alkyl groups, wherein the alkyl group is optionally substituted with 1-4 $R^A$; and
   (b) 5- to 14-membered aromatic rings optionally substituted with 1-4 $R^A$;
      wherein each $R^A$ is independently chosen from halogens, cyano, hydroxy, thiol, sulfonic acid, sulfonamide, sulfinamide, amino, amide, carboxylic acid, 5- to 10-membered aromatic rings, and $C_1$-$C_6$ linear, branched, and cyclic groups,
      wherein the amide nitrogen atom in the amide of $R^A$ is optionally substituted with a heterocyclyl group that is optionally further substituted with oxo,
      wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide,
      wherein the 5- to 10-membered aromatic rings and $C_1$-$C_6$ linear, branched, and cyclic groups are optionally substituted with 1-4 substituents selected from halogens, $C_1$-$C_6$ linear, branched, and cyclic groups and methoxy, and
      wherein an $R^A$ group is optionally linked to an $R^B$ group on an $R^2$ group;

(ii) $R^1$ is chosen from
  (a) hydrogen,
  (b) $C_1$-$C_8$ linear, branched, and cyclic alkyl groups, wherein the alkyl group is optionally substituted with 1-4 substituents independently chosen from
    halogens,
    cyano,
    cyanoalkyl,
    hydroxy,
    alkylsulfonyl, and
    $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
      halogens,
      hydroxy, and
      $C_1$-$C_6$ linear, branched, and cyclic alkoxy groups,
  (c) $C_1$-$C_8$ linear, branched, and cyclic alkoxy or cyclic thioalkyl groups optionally substituted with 1-4 substituents independently chosen from
    halogens,
    cyano,
    cyanoalkyl;
    sulfone,
    sulfonamide,
    hydroxy, and
    $C_1$-$C_6$ linear, branched, and cyclic alkyl groups that are optionally substituted with 1-4 halogens or alkoxy groups
  (d) $C_1$-$C_6$ linear, branched, and cyclic alkylsulfonyl groups optionally substituted with $C_1$-$C_6$ linear or branched alkyl groups;
  (e) aminosulfonyl groups, optionally substituted with 1 or 2 substituents independently chosen from
    $C_1$-$C_6$ linear, branched, and cyclic alkyl groups;
  (f) $C_1$-$C_6$ linear, branched, and cyclic alkylsulfonyl amino groups; and
  (g) phosphine oxide groups, optionally substituted with 1 or 2 substituents independently chosen from
    $C_1$-$C_6$ linear, branched, and cyclic alkyl groups;
  (h) $C_1$-$C_6$ linear, branched, and cyclic trialkylsilyl groups;
  (i) $C_1$-$C_6$ alkylamide;
(iii) $R^2$ is chosen from 5- and 6-membered heterocyclic rings (optionally substituted with oxo and/or $C_1$-$C_6$ linear and branched alkyl groups) and 5- to 6-membered aromatic rings comprising 0-4 heteroatoms chosen from O, N, and S, wherein the 5-membered aromatic ring is optionally substituted with 1-4 $R^B$ groups and the 6-membered aromatic ring is optionally substituted with 1-5 $R^B$ groups, wherein the $R^B$ groups are independently chosen from:
  amides, optionally substituted with 1-3 groups selected from $C_1$-$C_6$ linear, branched, and cyclic alkyl groups (optionally substituted with heteroaryl), 4- to 6-membered heterocyclyl (optionally substituted with oxo, $C_1$-$C_6$ linear, branched, and cyclic alkyl groups, hydroxyalkyl, amide, alkylsulfonyl, and acetamide); or wherein the amide nitrogen atom forms part of a 3- to 8-membered heterocyclyl ring (optionally substituted with alkylsulfonyl or $C_1$-$C_6$ linear, branched, and cyclic alkyl group),
  imidazolidine-2,4-dione,
  heterocyclyls, optionally substituted with one more groups independently chosen from oxo, acyl, and $C_1$-$C_6$ linear, branched, and cyclic alkyl group (which is optionally further substituted with 1-3 groups independently chosen from oxo, hydroxy, and acyl),
  phosphorous acid optionally esterified with a $C_1$-$C_6$ linear, branched, or cyclic alkyl group,
  di($C_1$-$C_6$)alkylphosphine oxides,
  ($C_1$-$C_6$)alkylphosphinic acids optionally esterified with a $C_1$-$C_6$ linear, branched, or cyclic alkyl group,
  halogens,
  cyano,
  hydroxy,
  carboxylic acids optionally esterified with a uronic acid or a $C_1$-$C_6$ linear, branched, or cyclic alkyl group,
  oxo,
  dihydroxylboryl,
  5- and 6-membered aromatic rings comprising 0-4 heteroatoms independently chosen from O, N, and S, optionally substituted with 1 or 2 substituents independently chosen from $C_1$-$C_6$ linear, branched, and cyclic alkyl groups that are optionally substituted with 1-4 substituents independently chosen from
    hydroxy,
    carboxylic acids,
    pyrrolidin-2-one,
    $C_1$-$C_6$ linear, branched, and cyclic alkyl groups, and
    $C_1$-$C_6$ linear, branched, and cyclic alkylsulfonyl groups, and
  $C_1$-$C_6$ linear, branched, and cyclic alkoxy groups,
  sulfonic acid,
  alkylsulfonamide,
  $C_1$-$C_6$ linear, branched, and cyclic alkylsulfonyl groups,
  aminosulfonyl groups, optionally substituted with 1 or 2 substituents independently chosen from
    $C_1$-$C_6$ linear, branched, and cyclic alkyl groups,
  $C_1$-$C_6$ linear, branched, and cyclic alkyl groups that are optionally substituted with 1-4 substituents independently chosen from
    halogens,
    hydroxy,
    carboxylic acid,
    $C_1$-$C_6$ linear, branched, and cyclic alkoxy groups,
    heterocyclyl optionally substituted with oxo, and
    amide,
  $C_1$-$C_6$ linear, branched, and cyclic alkoxy groups that are optionally substituted with 1-4 substituents independently chosen from
    halogens,
    hydroxy,
    carboxylic acid,
    $C_1$-$C_6$ linear, branched, and cyclic alkyl groups, and
    $C_1$-$C_6$ linear, branched, and cyclic alkoxy groups, and
  tetrazolyl groups that are optionally substituted with substituents chosen from
    halogens,
    hydroxy,
    carboxylic acid,
    $C_1$-$C_6$ linear, branched, and cyclic alkyl groups, and
    $C_1$-$C_6$ linear, branched, and cyclic alkoxy groups,
  wherein 2 adjacent hydrogens on the 5- or 6-membered aromatic ring can be replaced by attachments to a second 5- or 6-membered aromatic ring comprising 0-4 heteroatoms independently chosen from O, N, and S to form a bicyclic $R^2$ group that is optionally substituted with 1-6 $R^B$ groups;

(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are independently chosen from alkyl, alkoxy, thioalkyl, and aminoalkyl groups, and wherein the $C_1$-$C_6$ linear, branched, and cyclic groups are optionally substituted by 1-4 independently chosen halogens;

(v) each of $W^1$ and $W^2$ is independently selected from C and N;

(vi) each ⸺ represents a single or double bond, provided that no more than one ⸺ is a double bond;

(vii) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the $C_1$-$C_6$ linear, branched, and cyclic alkyl groups and the $C_1$-$C_6$ linear, branched, and cyclic alkoxy groups are optionally substituted with 1-4 substituents independently chosen from halogens, hydroxy groups, and carboxylic acid;

(viii) n is an integer chosen from 0, 1, 2, and 3; and (ix) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, halogen, $C_1$-$C_6$ linear, branched, and cyclic alkyl groups, and $C_1$-$C_6$ linear, branched, and cyclic alkoxy groups, wherein the $C_1$-$C_6$ linear, branched, and cyclic alkyl groups and the $C_1$-$C_6$ linear, branched, and cyclic alkoxy groups are optionally substituted with 1-4 substituents independently chosen from halogens, hydroxy groups, and carboxylic acid.

2. The compound according to embodiment 1, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^0$ is chosen from aryl rings, heteroaryl rings, and $C_1$-$C_8$ linear, branched, and cyclic alkyl groups, each of which is optionally substituted with 1-2 substituents independently chosen from halogen, carboxylic acid, $C_1$-$C_6$ linear, branched, and cyclic alkyl groups, $C_1$-$C_6$ linear, branched, and cyclic alkoxy groups, aryl rings, and heteroaryl rings.

3. The compound according to embodiment 1 or 2, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^0$ is chosen from:

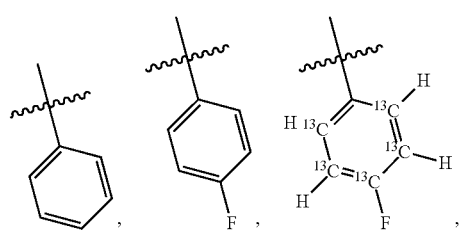

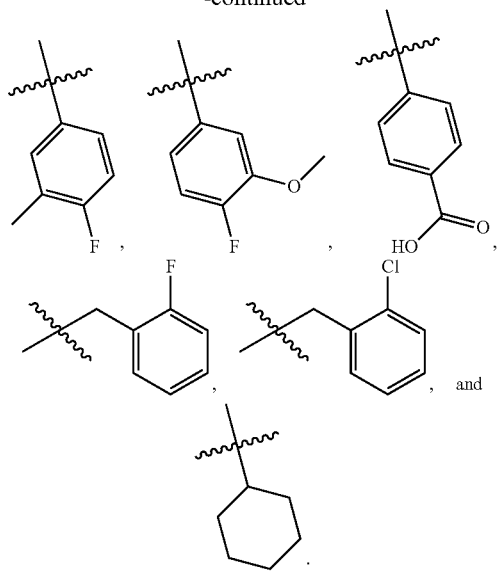

4. The compound according to any one of embodiments 1 to 3, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^1$ is chosen from:

hydrogen, methyl, trimethylsilyl, trifluoromethyl,

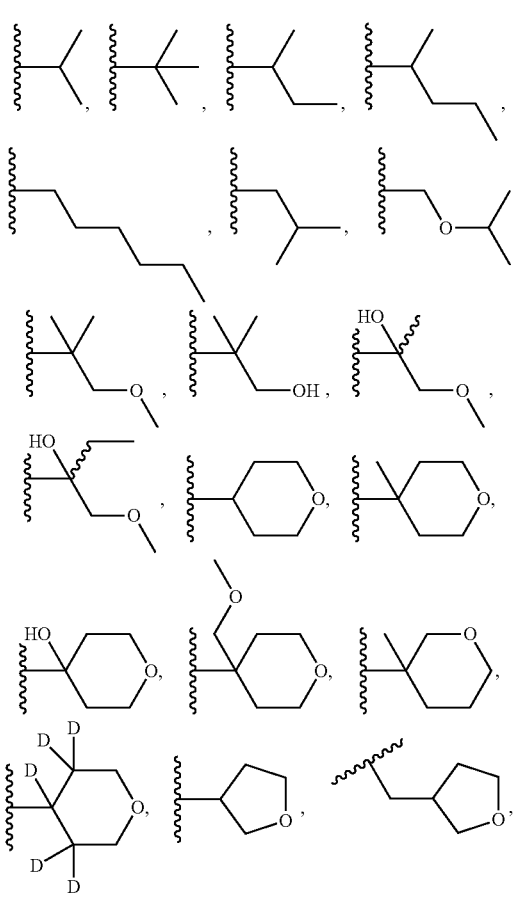

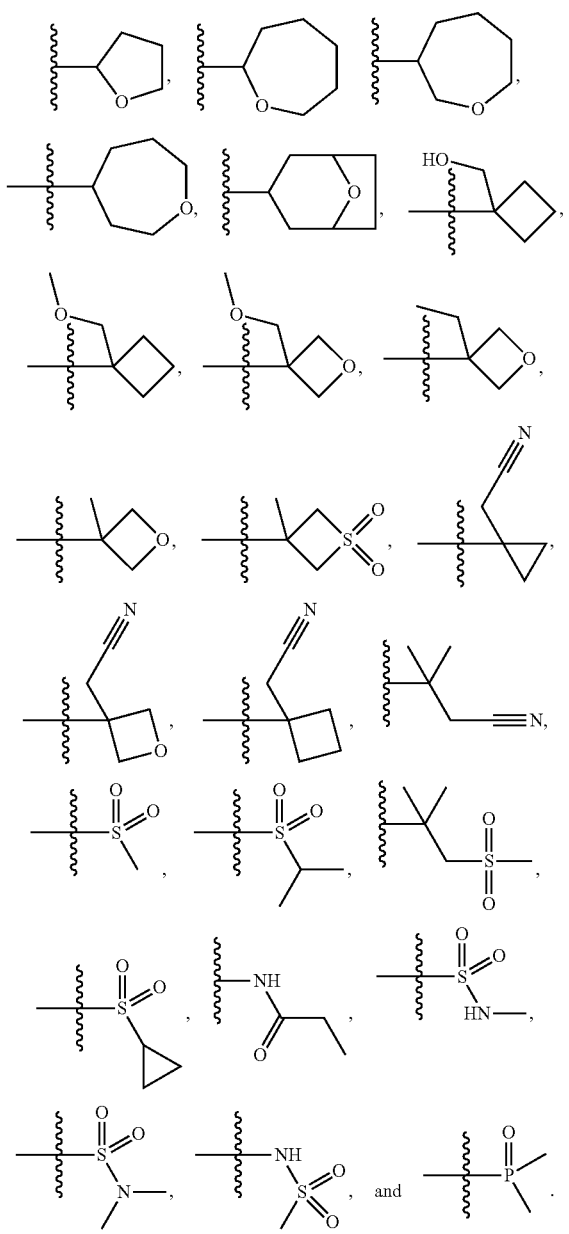

5. The compound according to any one of embodiments 1 to 4, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^2$ is chosen from:

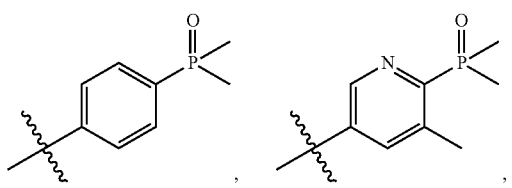

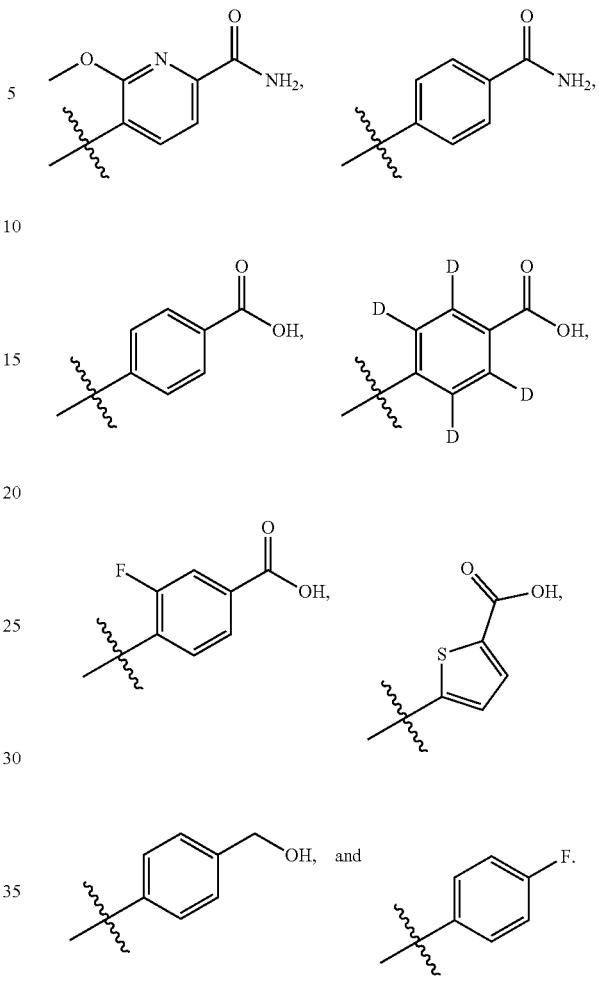

6. The compound according to any one of embodiments 1 to 5, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein two of $Z^1$, $Z^2$, and $Z^3$ are nitrogen and the other is chosen from carbon and nitrogen.

7. The compound according to any one of embodiments 1 to 6, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein each $R^3$ is independently chosen from hydrogen, deuterium, halogen, $C_1$-$C_6$ linear alkyl groups, and heterocyclyl groups.

8. The compound according to any one of embodiments 1 to 7, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $X^1$ and $X^2$ are independently chosen from hydrogen and halogen.

9. The compound according to embodiment 1 chosen from compounds of Formula I-A, I-B, I-C, I-D, I-E, I-F, I-G, and I-H:

I-A

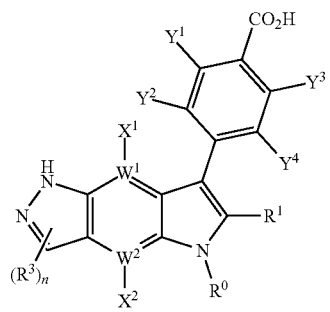

I-B

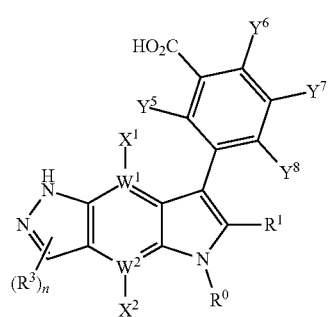

I-C

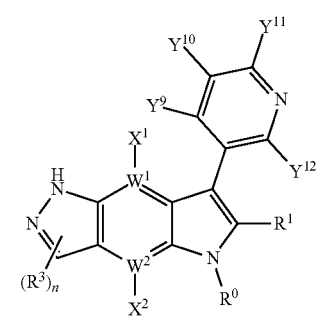

I-D

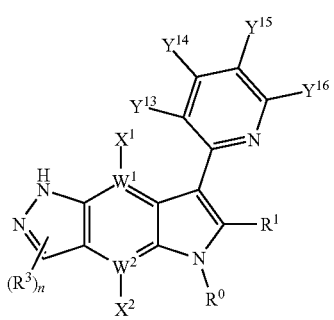

I-E

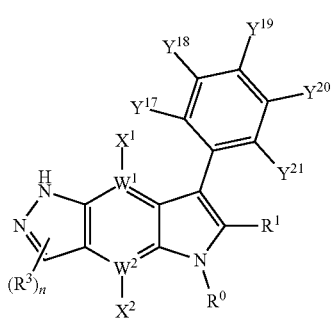

I-F

I-G

I-H a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein:

$R^0$, $R^1$, $R^2$, $R^3$, and n are defined for compounds of Formula (I)

$X^1$ and $X^2$ are independently chosen from hydrogen and fluorine, or $X^1$ is fluorine and $X^2$ is hydrogen, or $X^2$ is fluorine and $X^1$ is hydrogen, or $X^1$ and $X^2$ are each hydrogen, each of $W^1$ and $W^2$ is independently selected from C and N, $Y^1$, $Y^2$, $Y^3$, and $Y^4$ are independently chosen from
hydrogen,
cyano,
halogen groups,
$C_1$-$C_6$ linear, branched, and cyclic alkyl groups,
$C_1$-$C_6$ linear, branched, and cyclic alkoxy groups that are optionally substituted with 1-4 substituents independently chosen from
hydroxy,
$C_1$-$C_6$ linear, branched, and cyclic alkyl groups, and
$C_1$-$C_6$ linear, branched, and cyclic alkoxy groups;

$Y^5$, $Y^6$, $Y^7$, and $Y^8$ are independently chosen from
hydrogen,
halogen groups,
hydroxy,
$C_1$-$C_6$ linear, branched, and cyclic alkyl groups optionally substituted with 1-4 independently chosen halogen substituents, and
$C_1$-$C_6$ linear, branched, and cyclic alkoxy groups, $Y^9$, $Y^{10}$, $Y^{11}$, $Y^{12}$, $Y^{13}$, $Y^{14}$, $Y^{15}$, and $Y^{16}$ are independently chosen from
carboxylic acid,
hydrogen,
halogen groups,
$C_1$-$C_6$ linear, branched, and cyclic alkylsulfonyl groups,
$C_1$-$C_6$ linear, branched, and cyclic alkyl groups optionally substituted with 1-4 independently chosen halogen substituents, and
$C_1$-$C_6$ linear, branched, and cyclic alkoxy groups,
$Y^{17}$, $Y^{18}$, $Y^{19}$, $Y^{20}$, and $Y^{21}$ are independently chosen from
hydrogen,
carboxylic acid,
halogen groups,
cyano,
hydroxy,
$C_1$-$C_6$ linear, branched, and cyclic alkyl groups that are optionally substituted with 1-4 substituents independently chosen from
halogens,
hydroxy, and
carboxylic acid,
$C_1$-$C_6$ linear, branched, and cyclic alkoxy groups that are optionally substituted with a carboxylic acid group,
dihydroxyboryl,
sulfonic acid,
carboxylic acid optionally esterified with a uronic acid,
tetrazolyl groups,
aminosulfonyl groups, optionally substituted with 1 or 2 substituents independently chosen from
$C_1$-$C_6$ linear, branched, and cyclic alkyl groups, and
$C_1$-$C_6$ linear, branched, and cyclic alkylsulfonyl groups
with the proviso that, in Formula I-E, at least one of $Y^{17}$, $Y^{18}$, $Y^{19}$, $Y^{20}$, and $Y^{21}$ is hydrogen.

10. The compound according to embodiment 9, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein one or more of $Y^{17}$, $Y^{18}$, $Y^{19}$, $Y^{20}$, and $Y^{21}$ is chosen from methyl, methoxy, cyano, fluorine, hydroxy, —$CF_3$, —$B(OH)_2$, —$SO_2NHMe$, —$SO_2Me$, —$SO_2H$, —$CH_2CO_2H$,

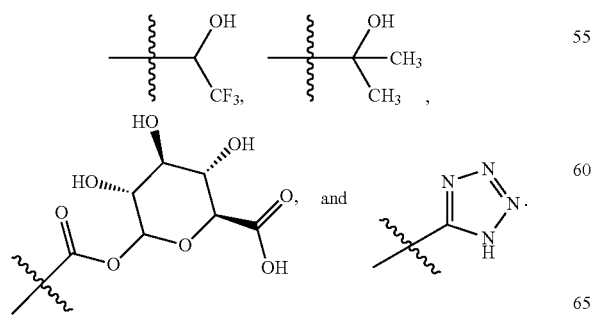

11. A compound chosen from:

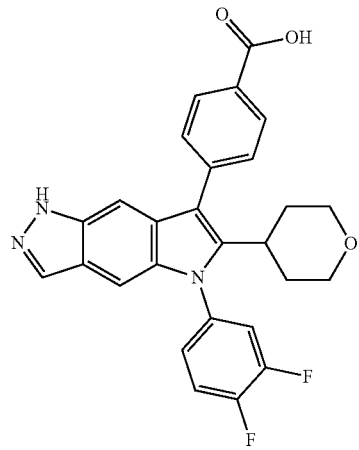

1

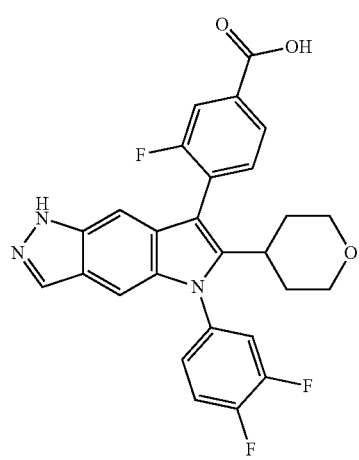

2

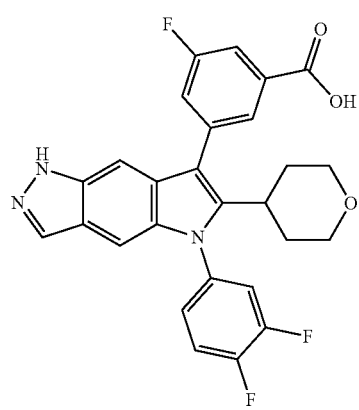

3

4
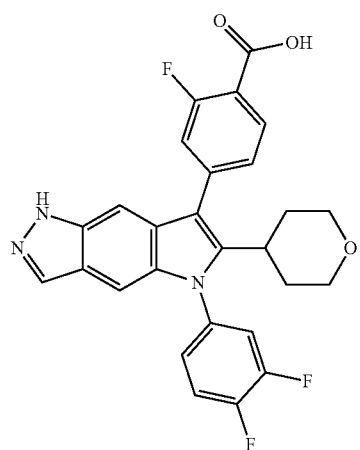
5
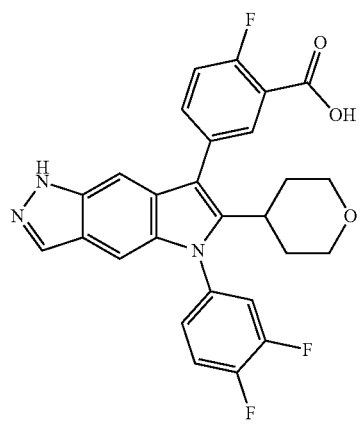
6
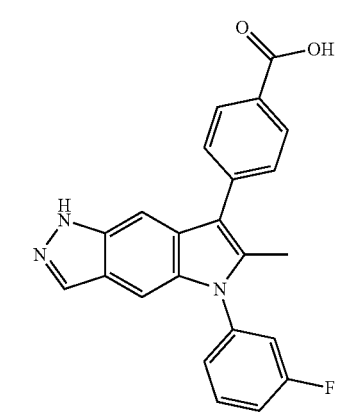
7
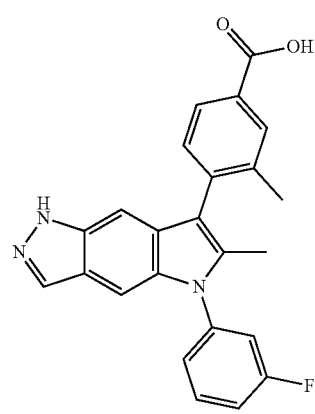
8
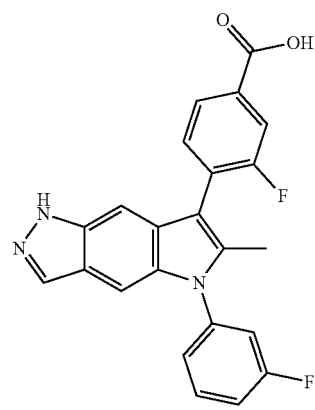
9
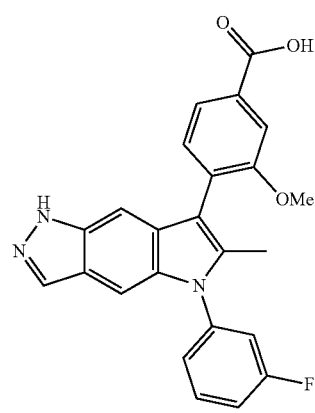
10
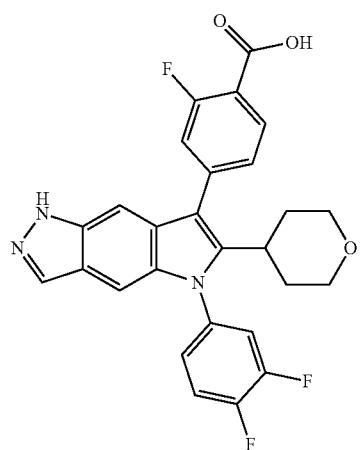

-continued
11
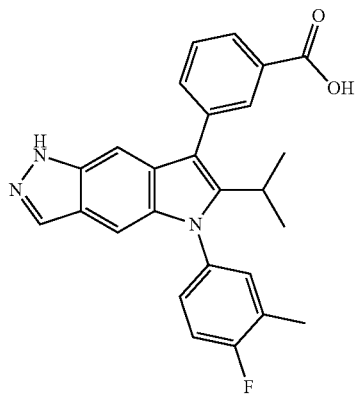
12
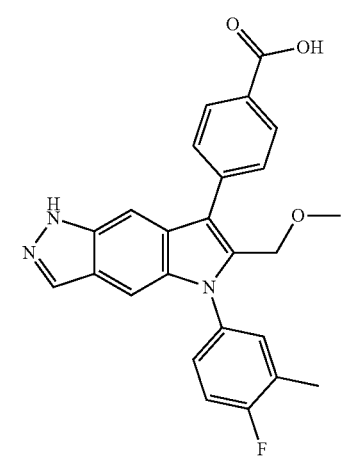
13
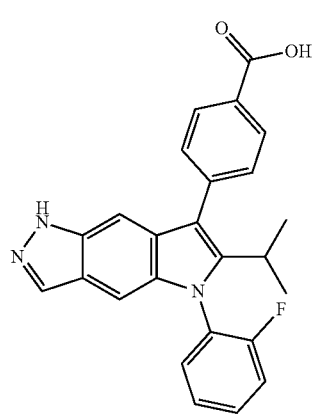
-continued
14
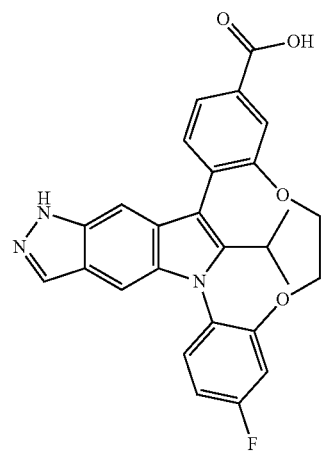
15
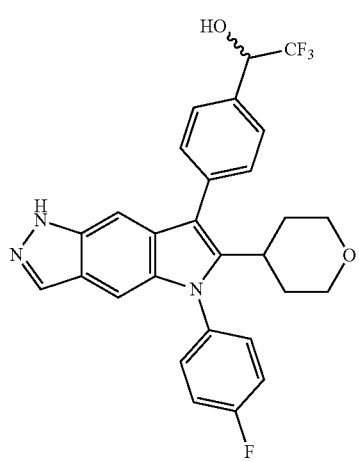
16
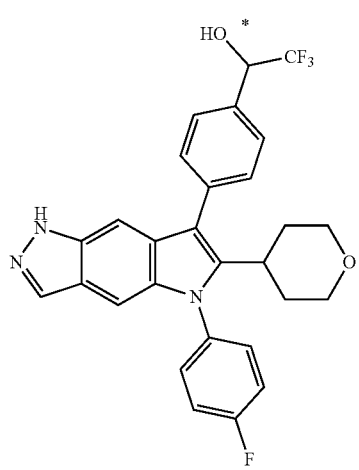

| | |
|---|---|
| 17 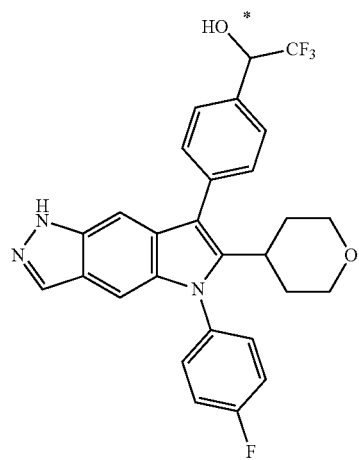 | 20 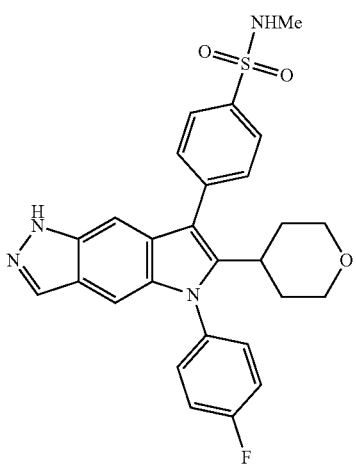 |
| 18 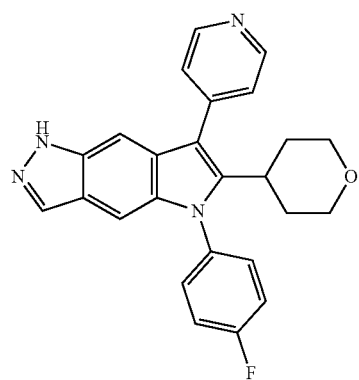 | 21 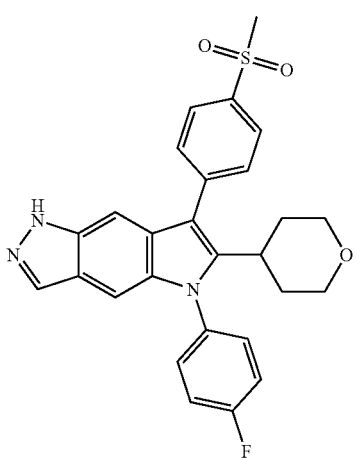 |
| 19 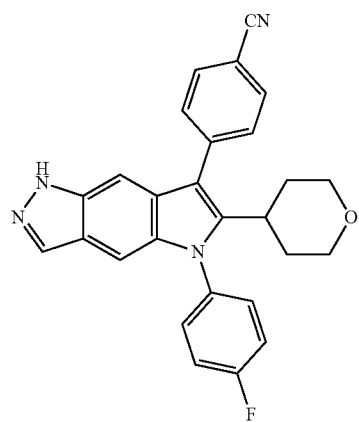 | 22 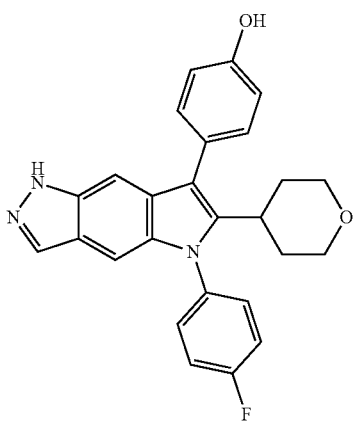 |

23
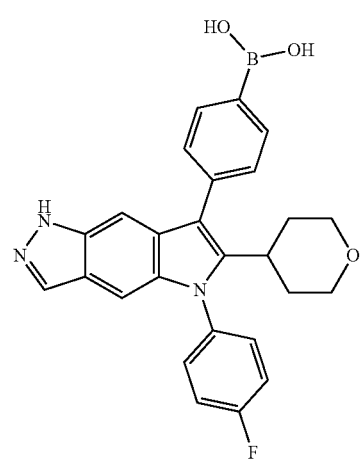
24
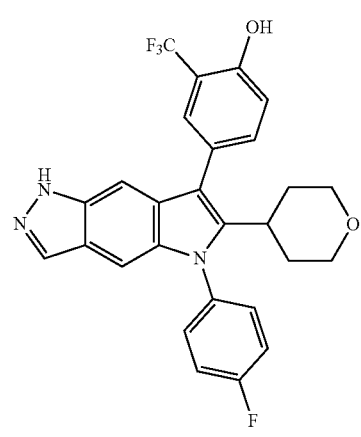
25
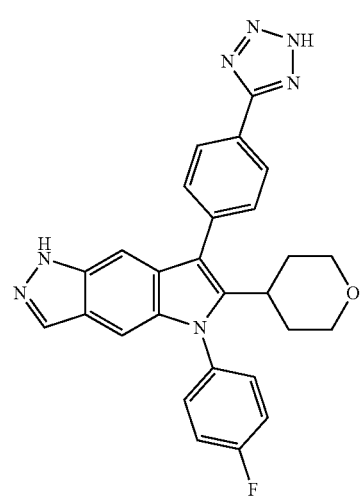
26
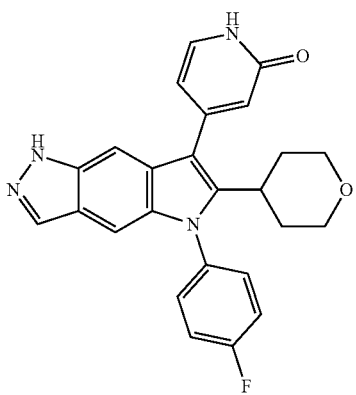
27
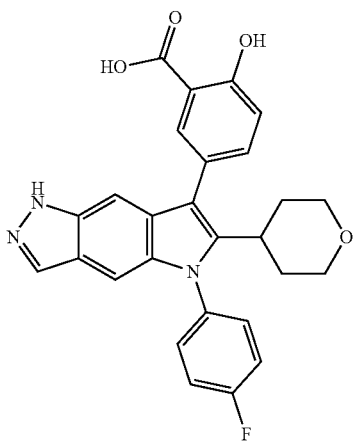
28
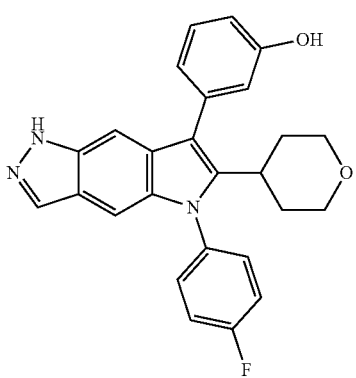
29
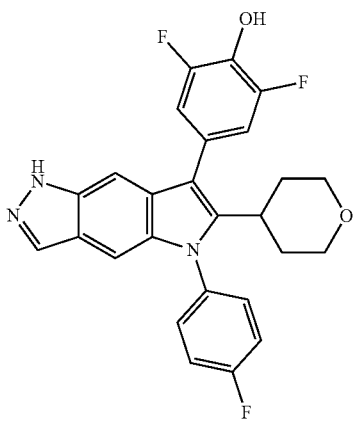

| 30 | 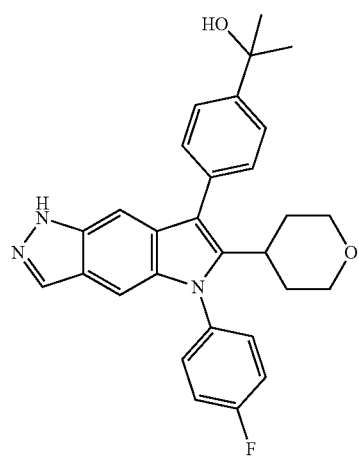 | 33 | 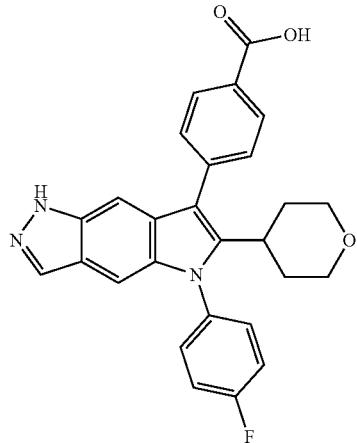 |
| --- | --- | --- | --- |
| 31 | 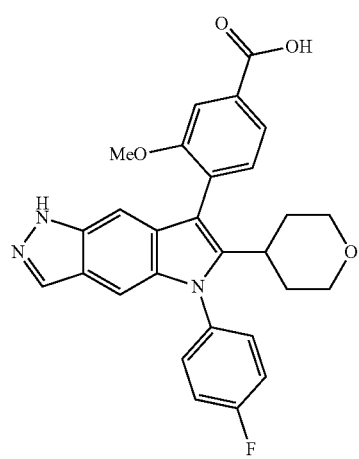 | 34 | 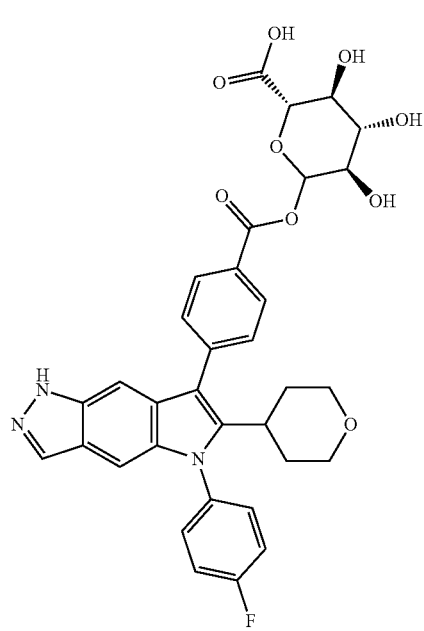 |
| 32 | 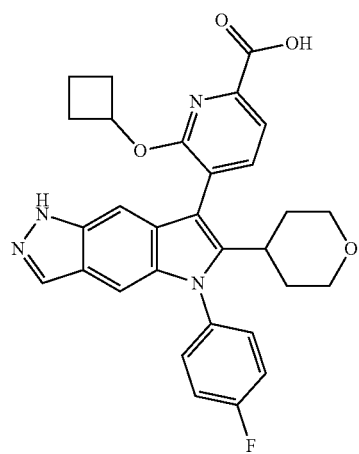 | 35 | 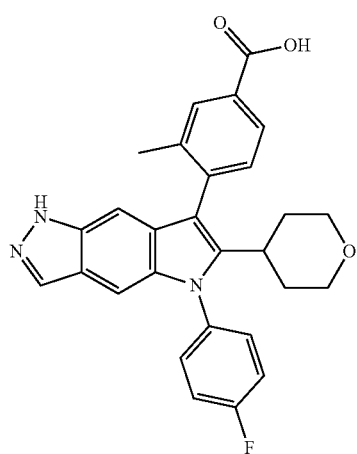 |

36
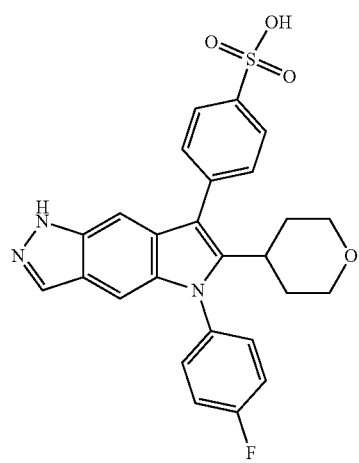
37
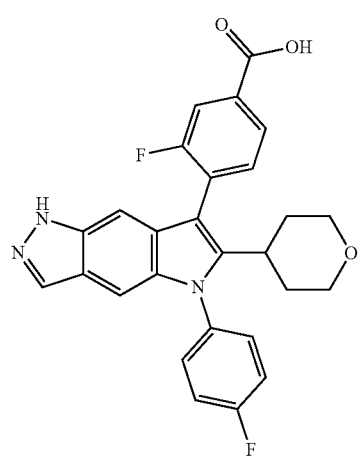
38
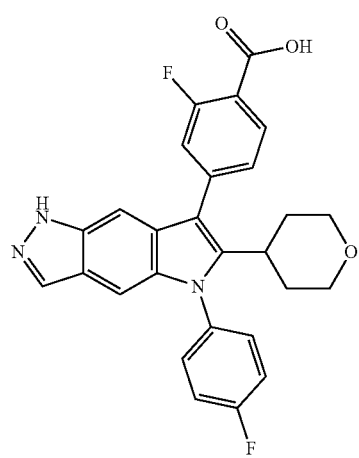
39
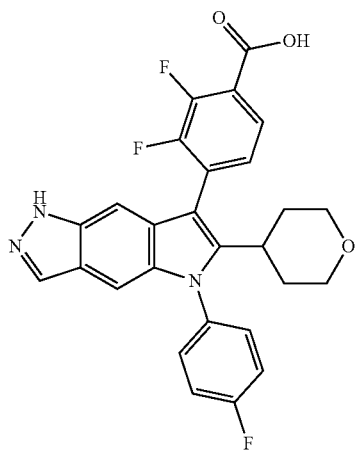
40
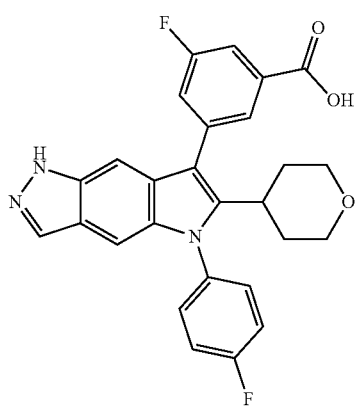
41
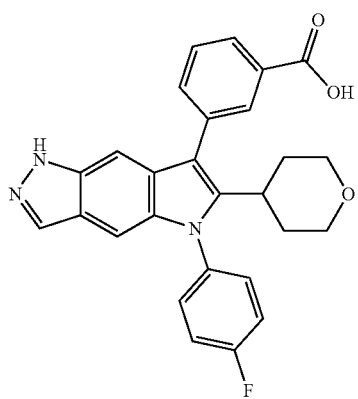

-continued
42
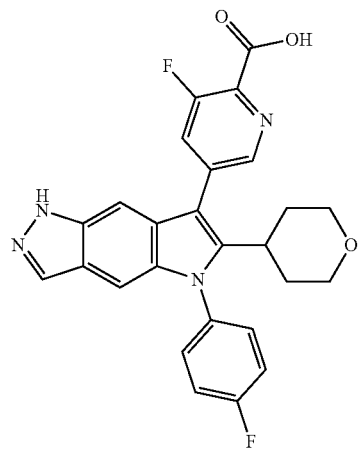
43
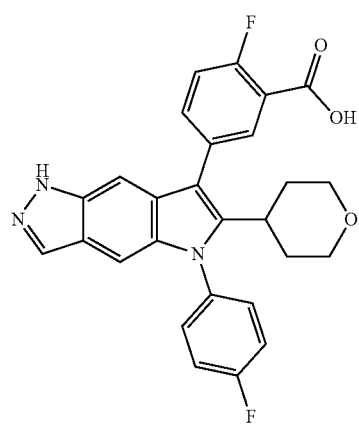
44
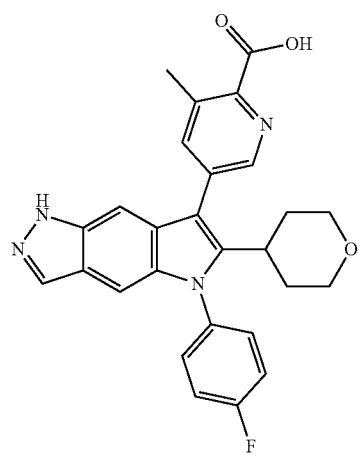
-continued
45
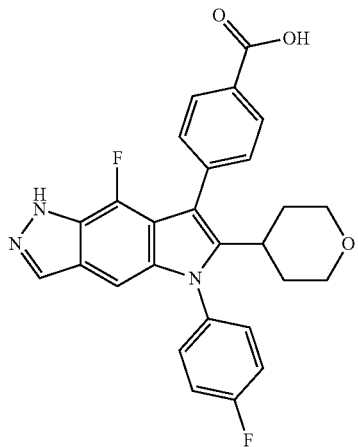
46
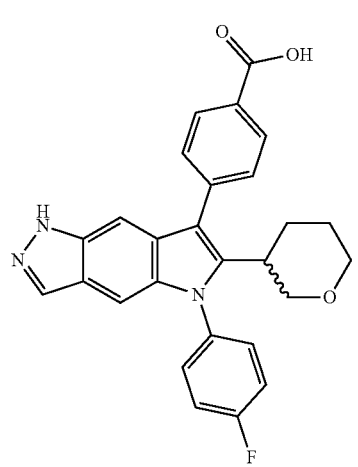
47
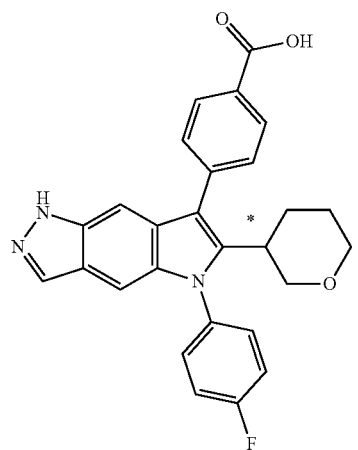

48
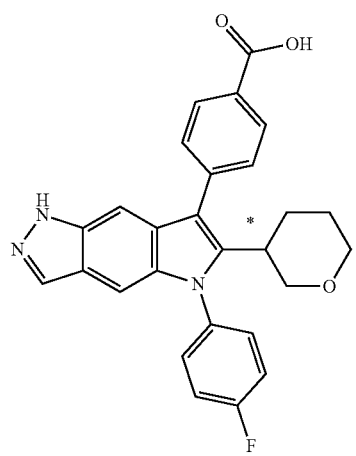
49
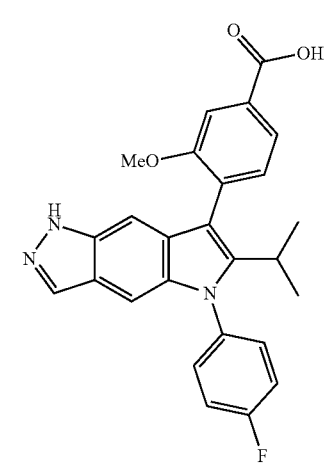
50
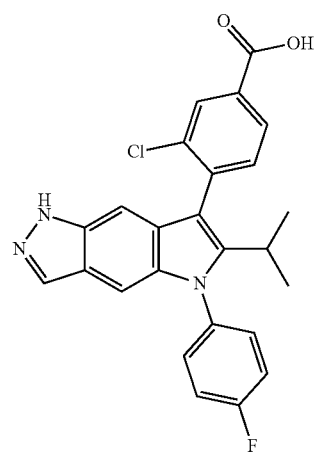
51
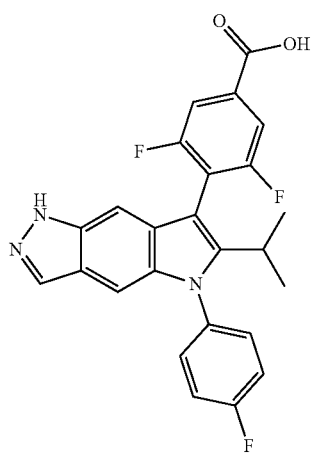
52
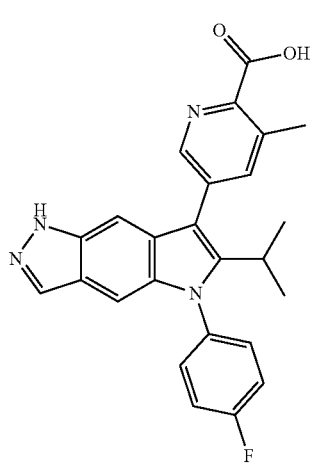
53
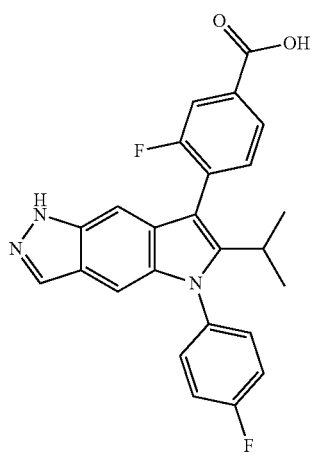

247
-continued
54
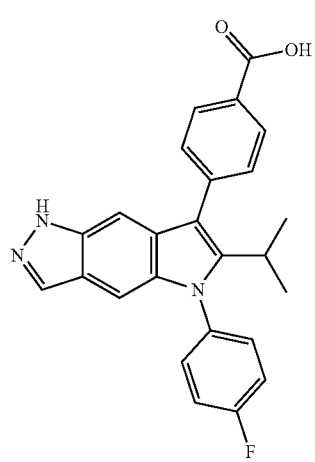
55
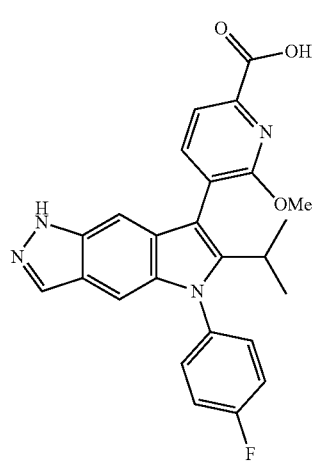
56
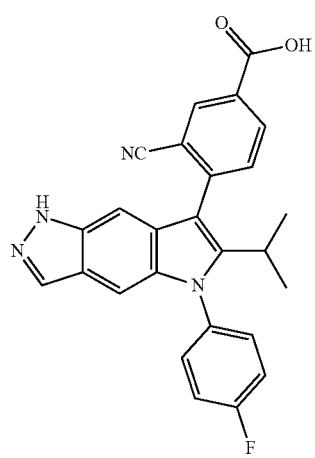
248
-continued
57
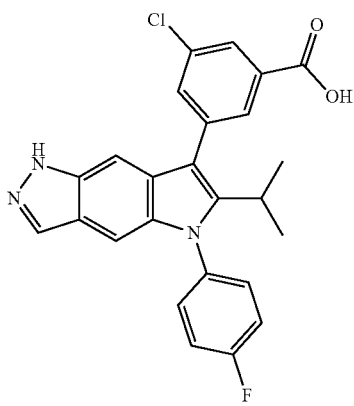
58
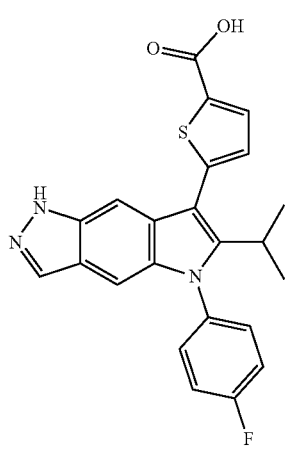
59
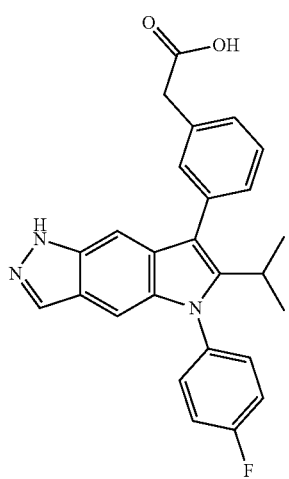

249
-continued
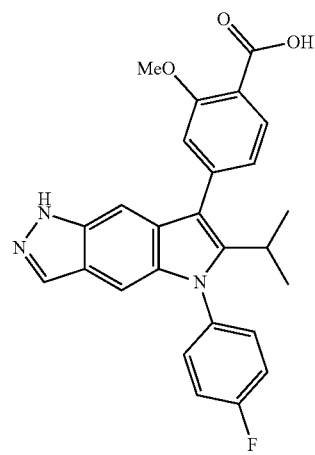
60
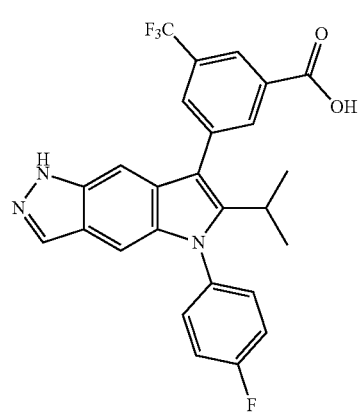
61
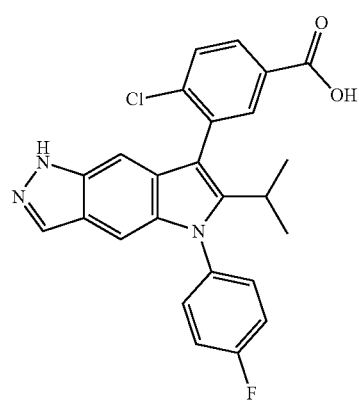
62
250
-continued
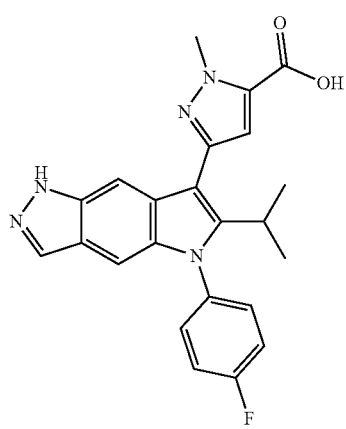
63
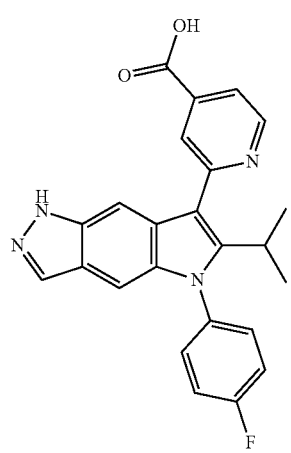
64
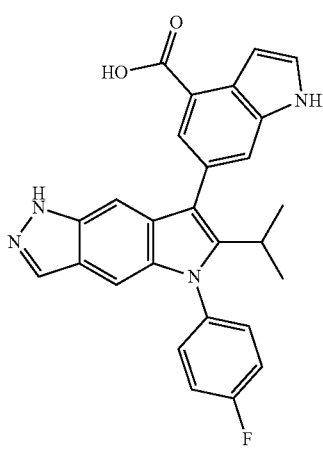
65

251
-continued
66
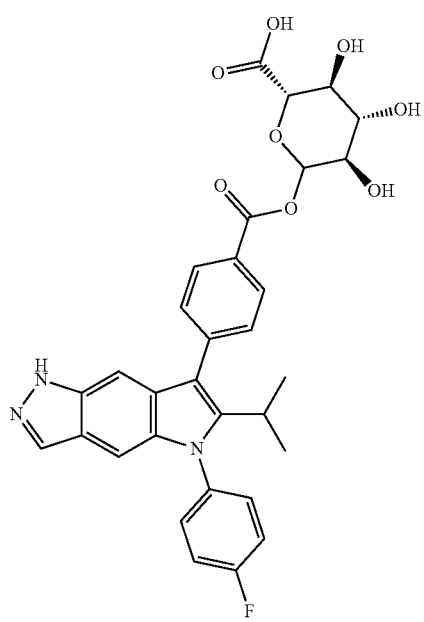
67
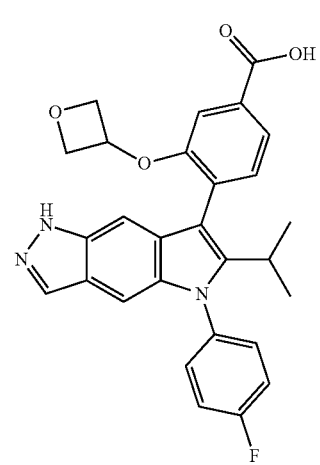
68
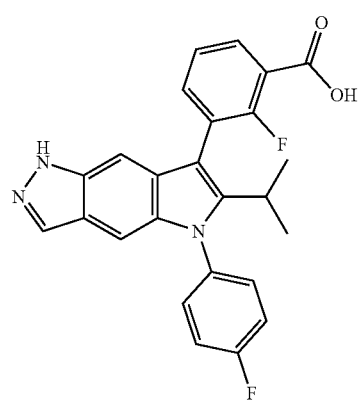
252
-continued
69
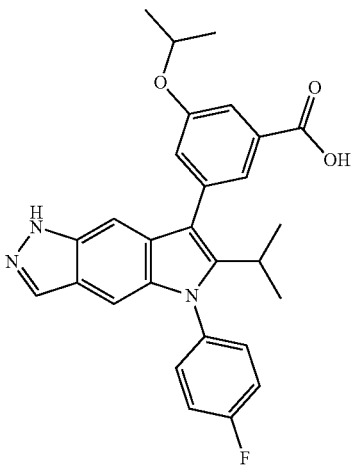
70
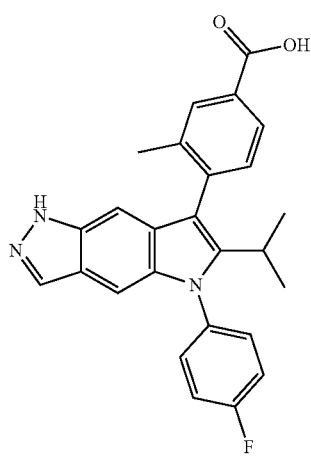
71
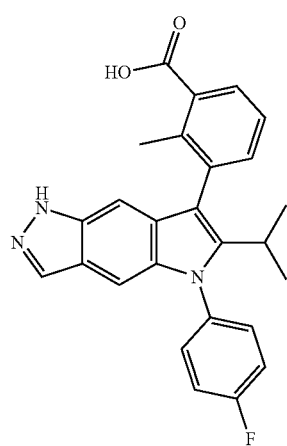

72
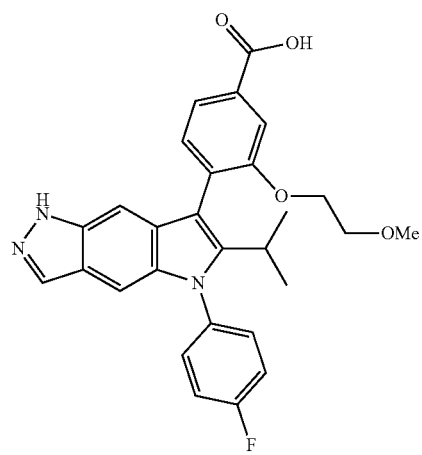
75
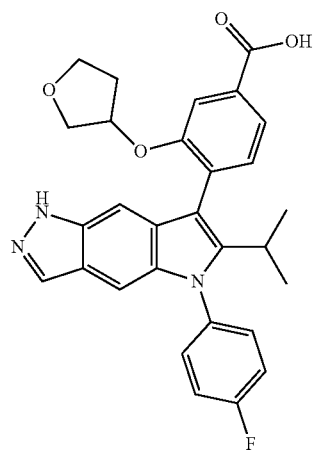
73
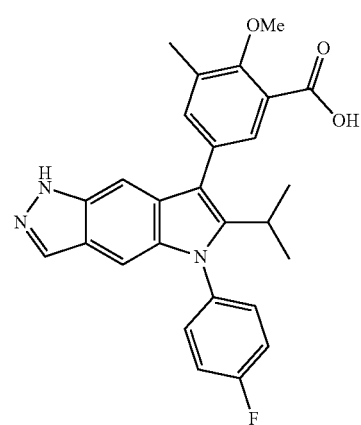
76
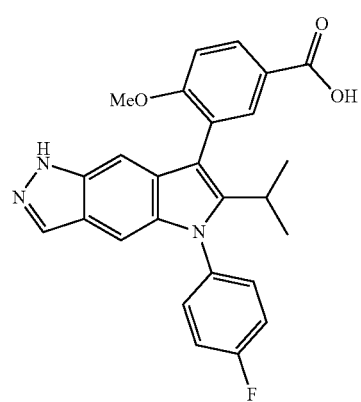
74
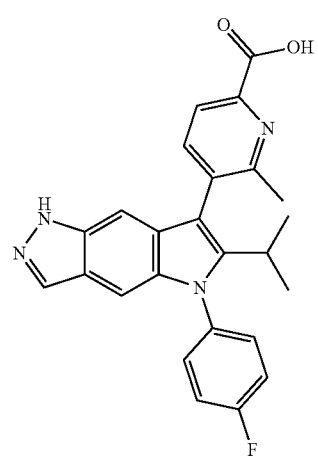
77
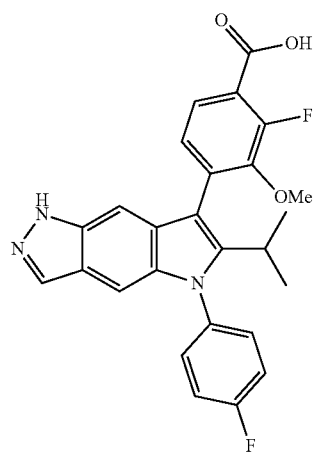

78
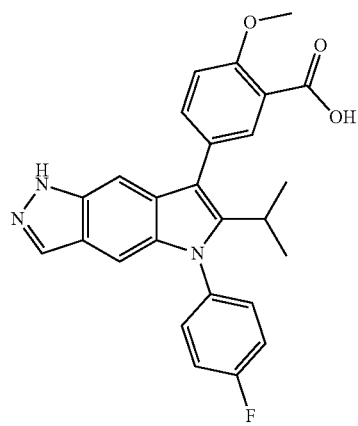
79
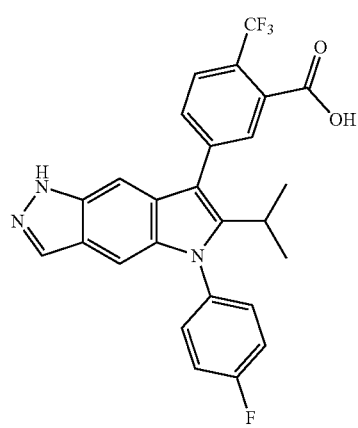
80
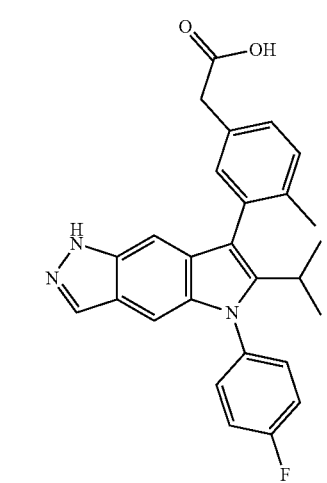
81
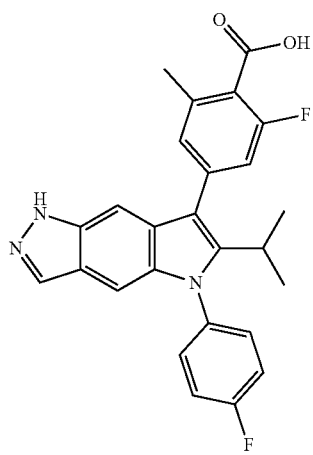
82
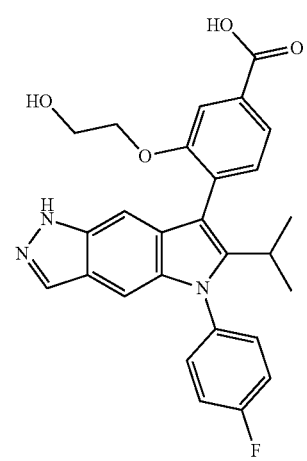
83
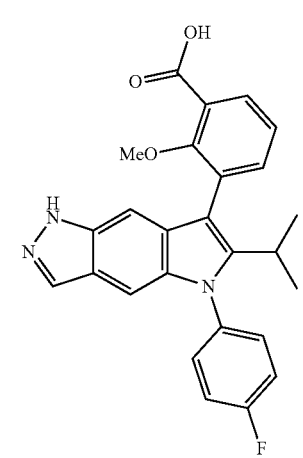

84
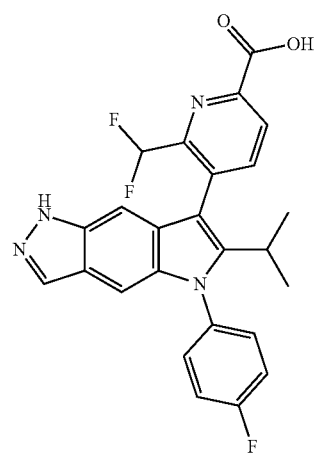
85
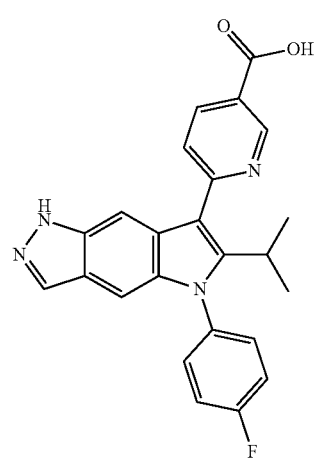
86
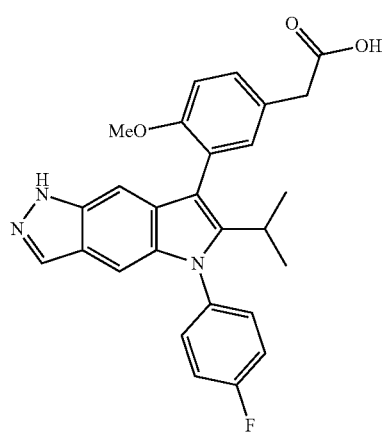
87
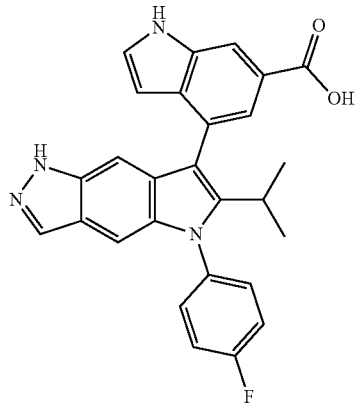
88
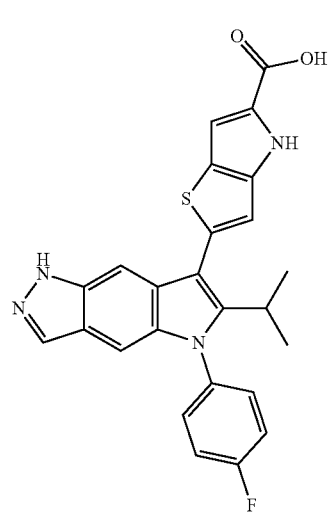
89
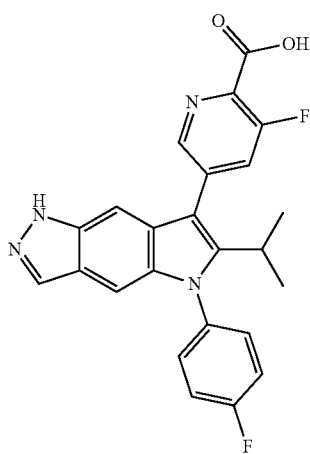

259
-continued
90 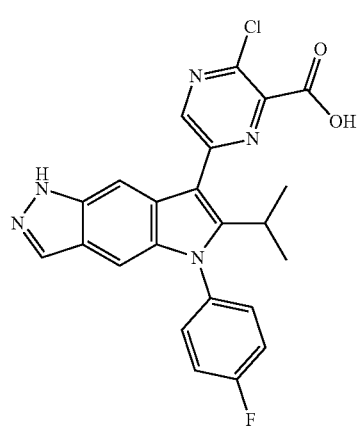
91 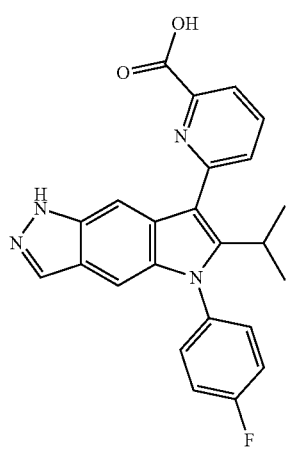
92 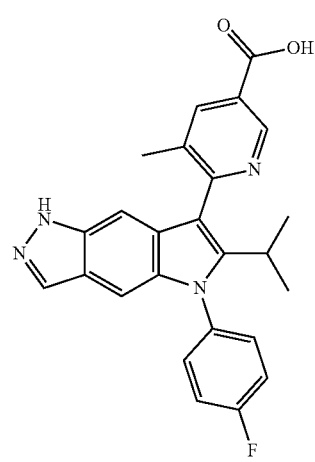
260
-continued
93 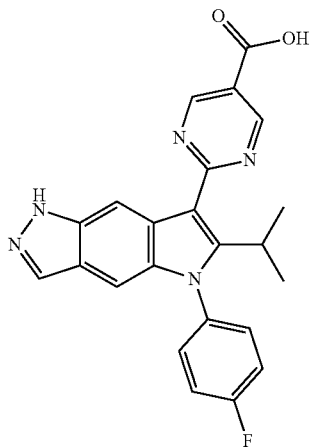
94 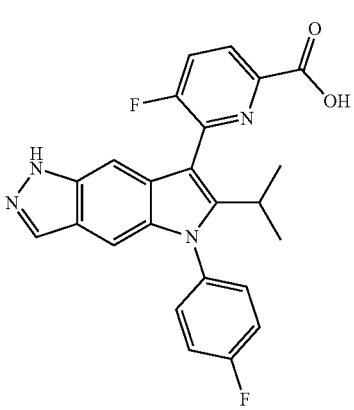
95 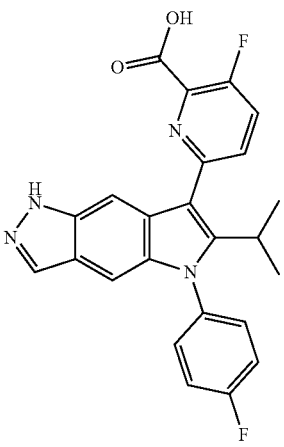

96
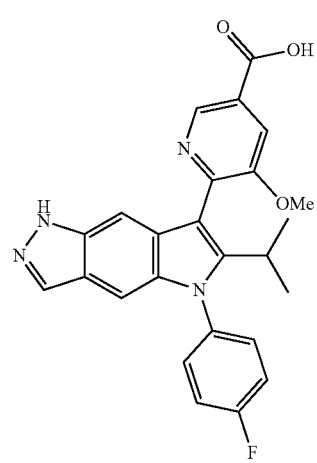
97
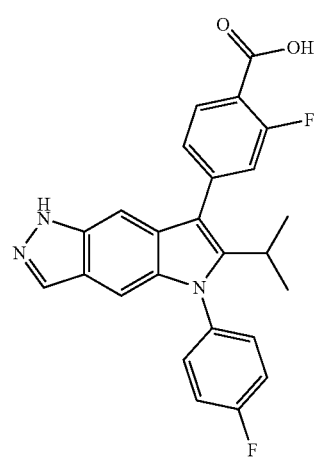
98
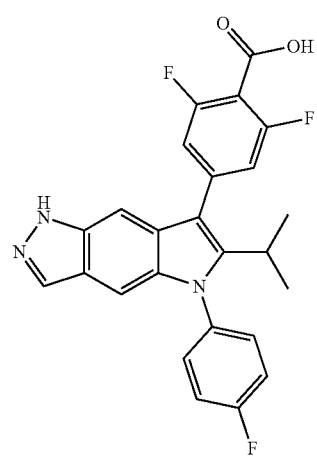
99
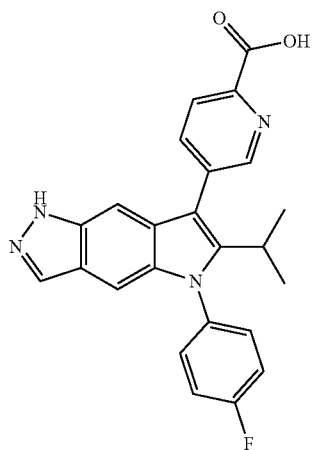
100
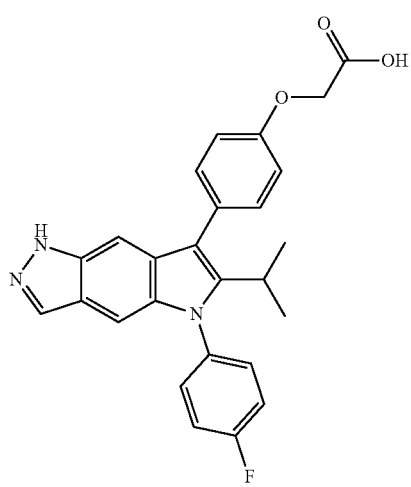
101
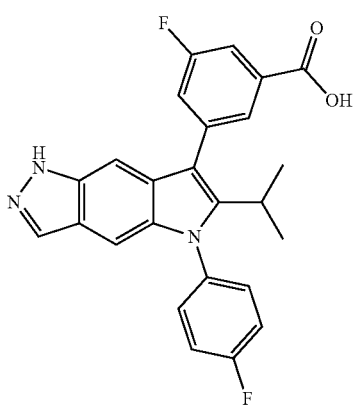

| 102 | 105 |
|---|---|
| 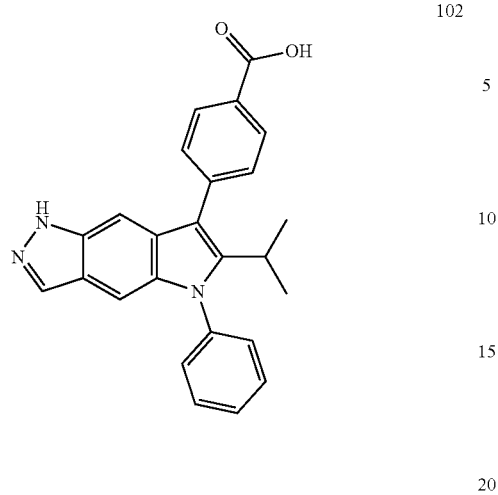 | 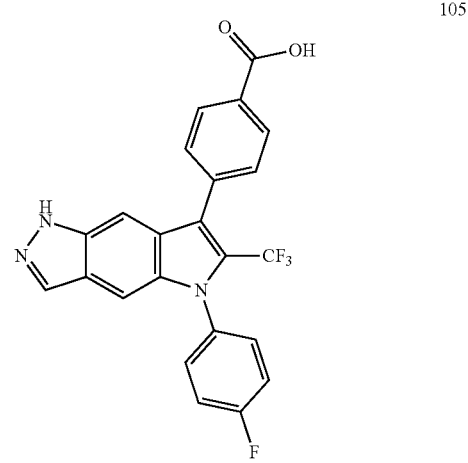 |
| 103 | 106 |
|---|---|
| 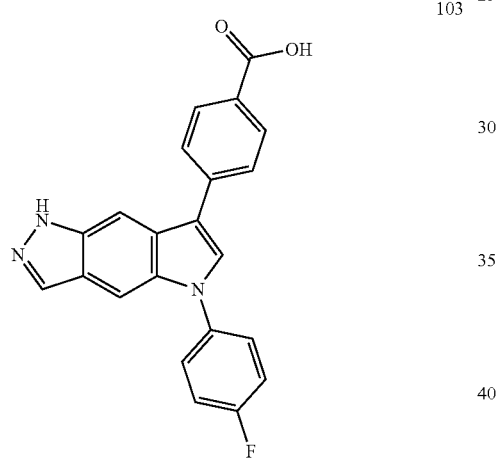 | 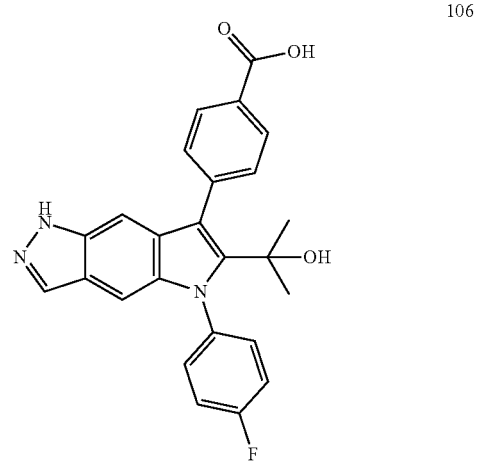 |
| 104 | 107 |
|---|---|
| 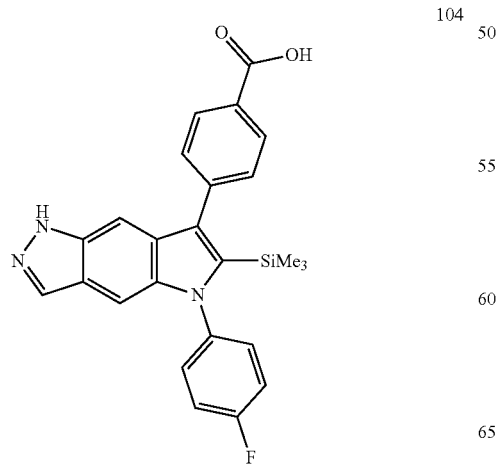 | 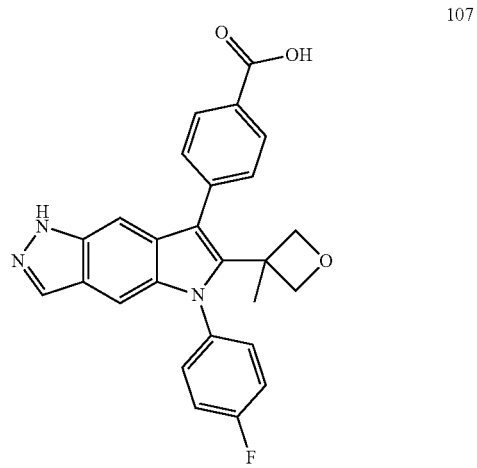 |

-continued
108
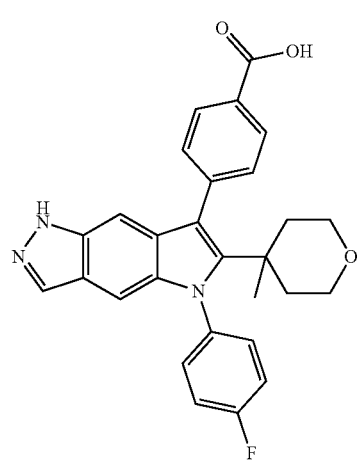
109
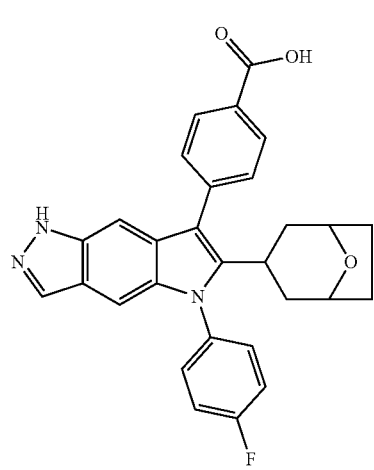
110
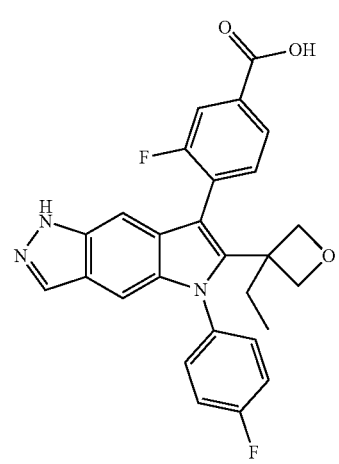
-continued
111
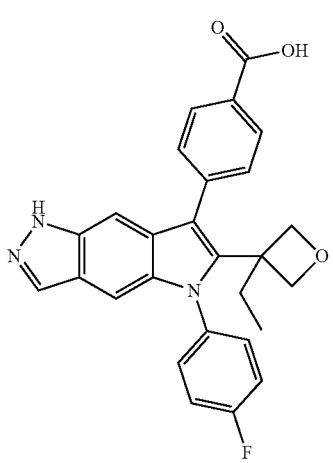
112
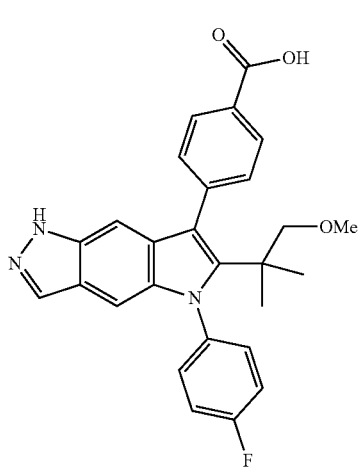
113
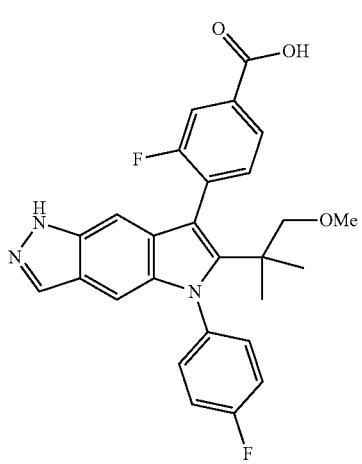

114 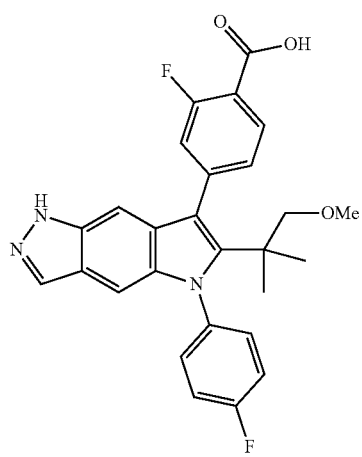
115 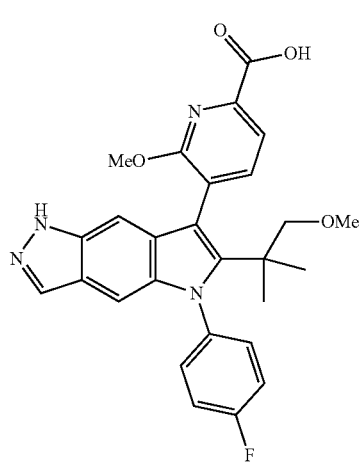
116 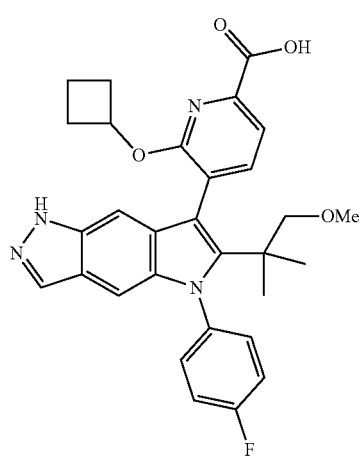
117 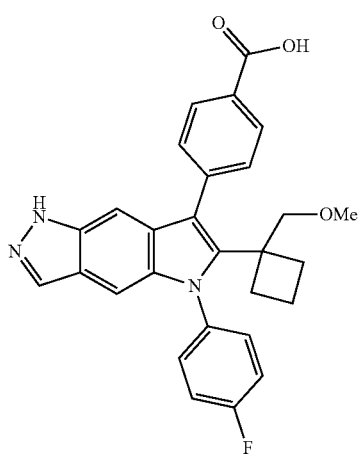
118 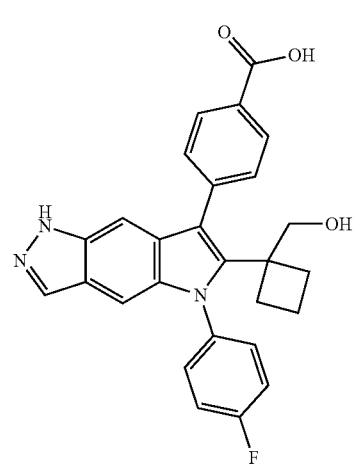
119 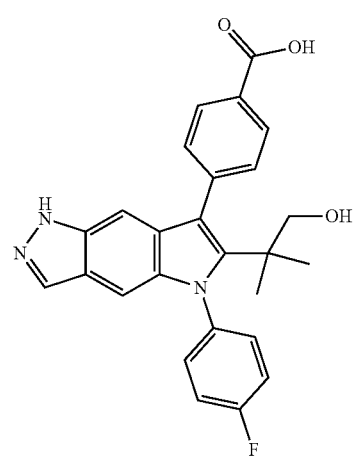

269
-continued
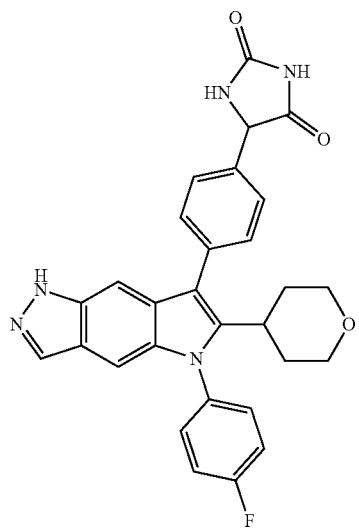
120
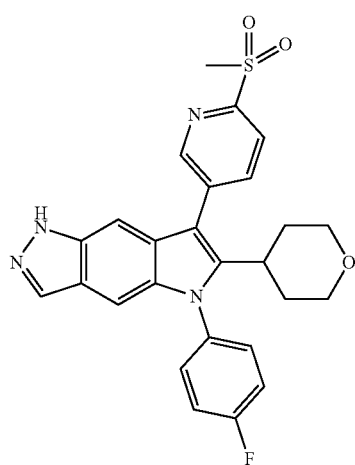
121
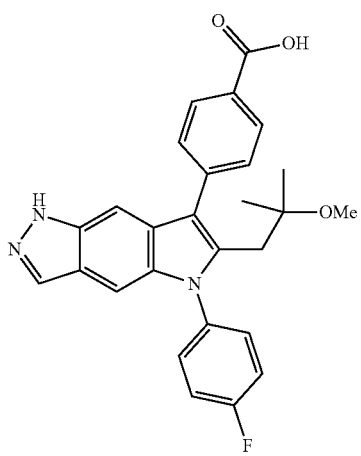
122
270
-continued
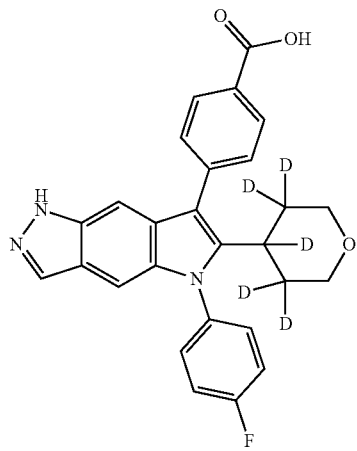
123
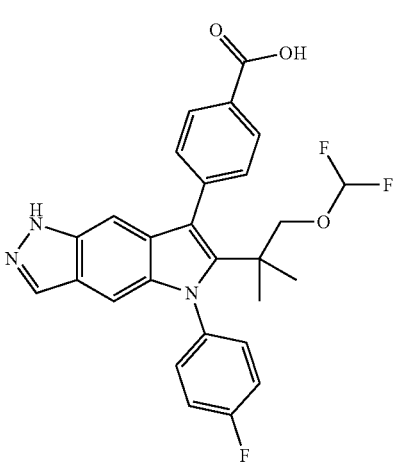
124
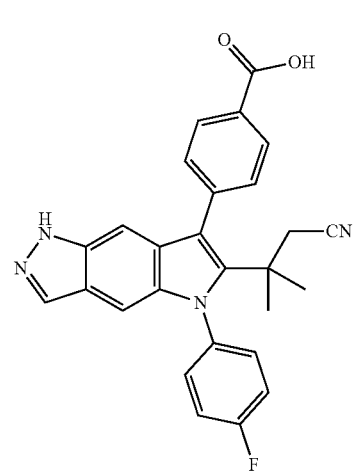
125

-continued
| 126 | 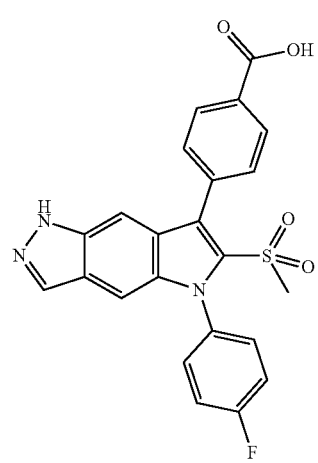 |
| 127 | 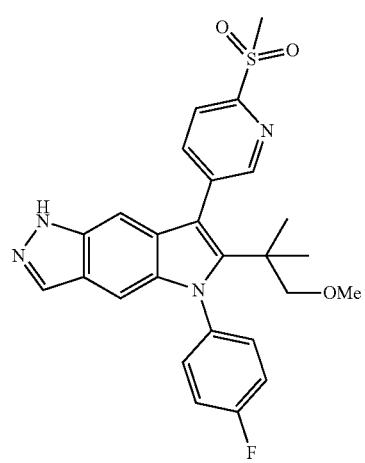 |
| 128 | 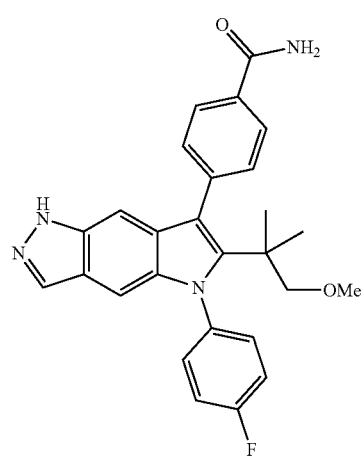 |
-continued
| 129 | 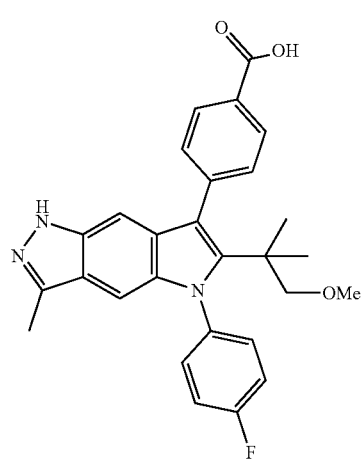 |
| 130 | 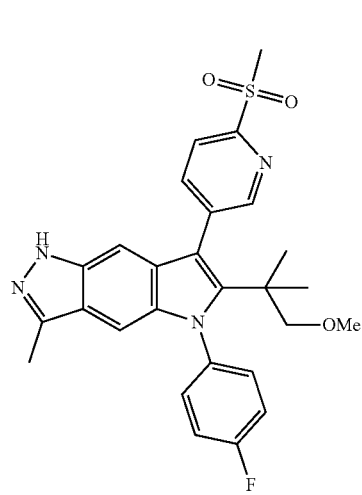 |
| 131 | 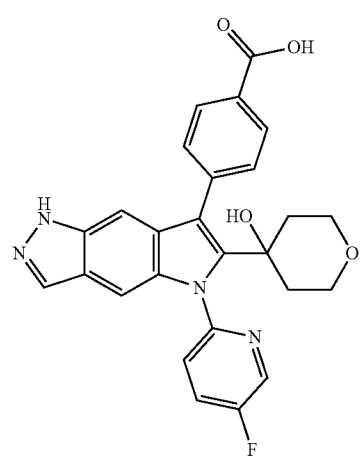 |

273
-continued
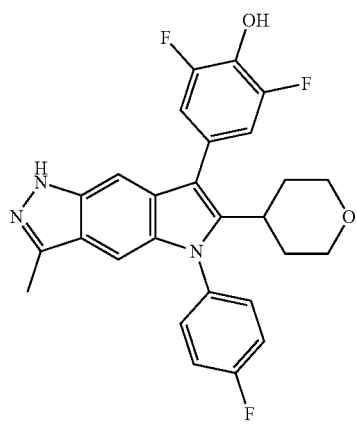
132
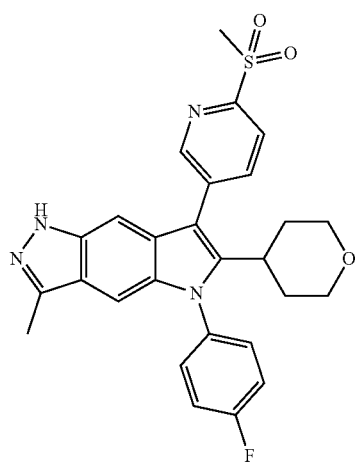
133
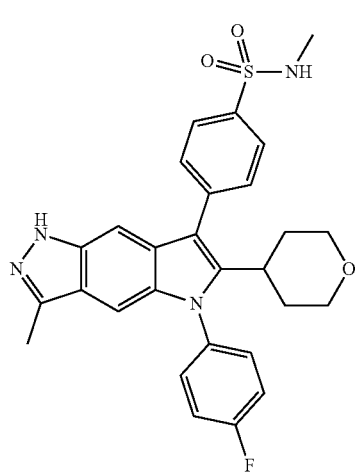
134
274
-continued
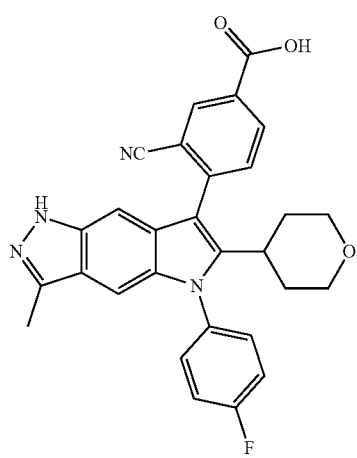
135
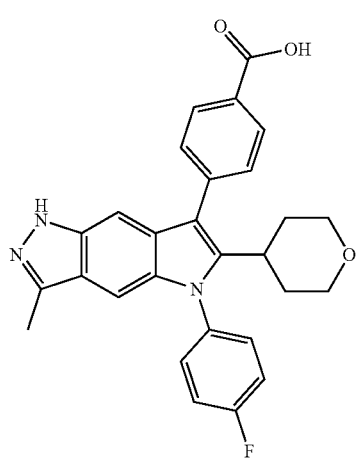
136
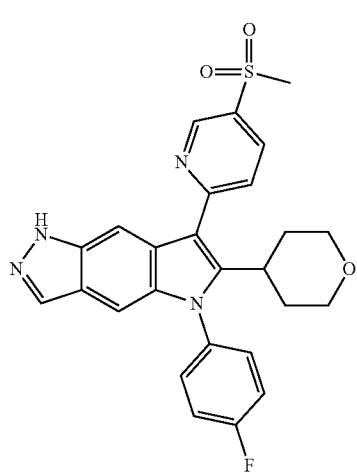
137

138
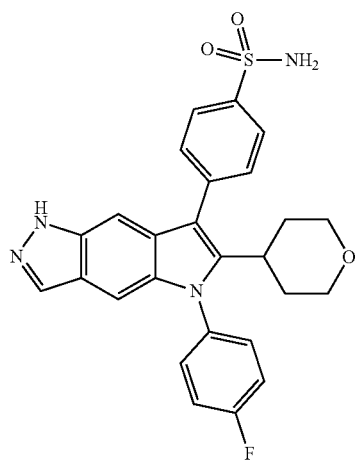
139
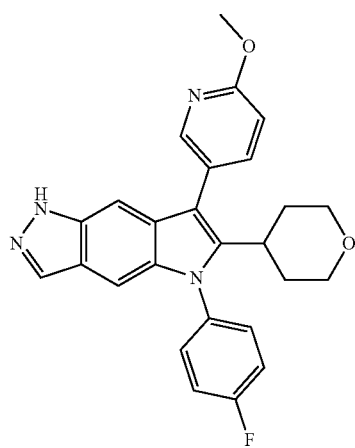
140
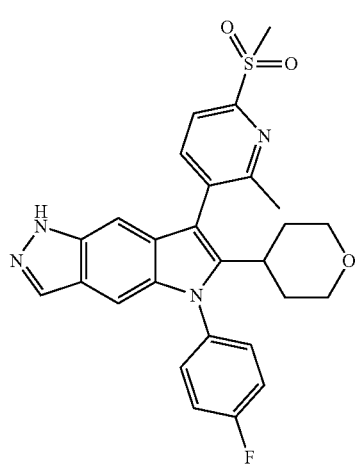
141
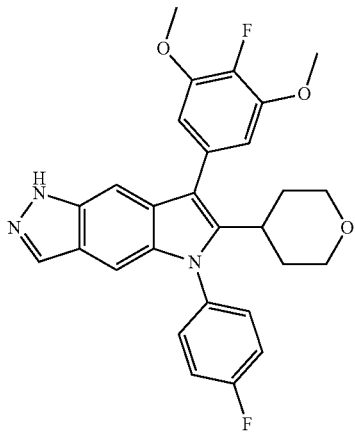
142
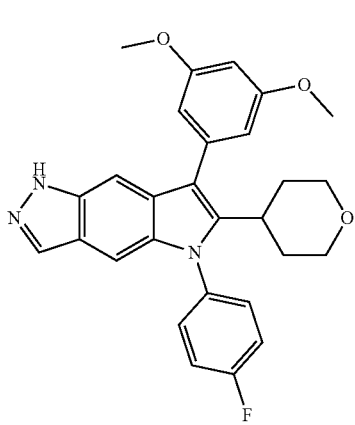
143
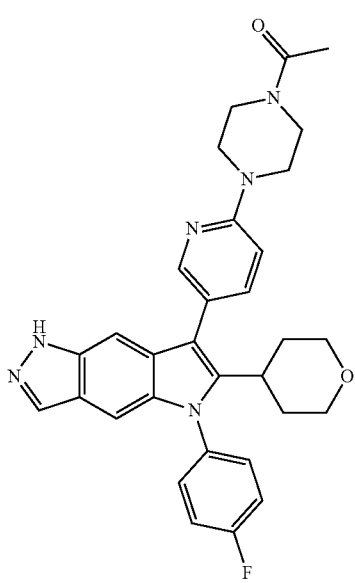

144
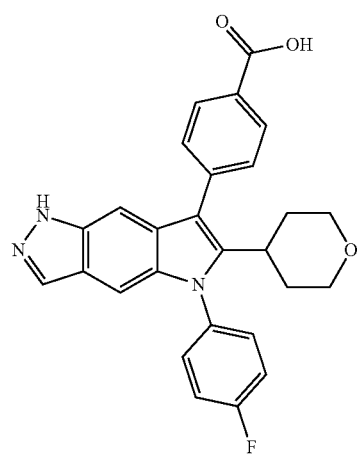
145
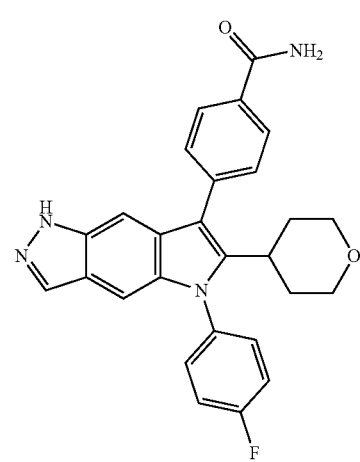
146
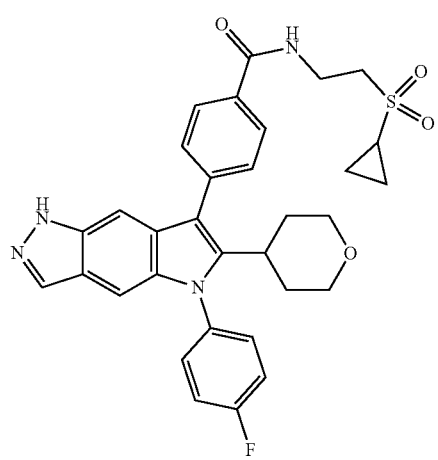
147
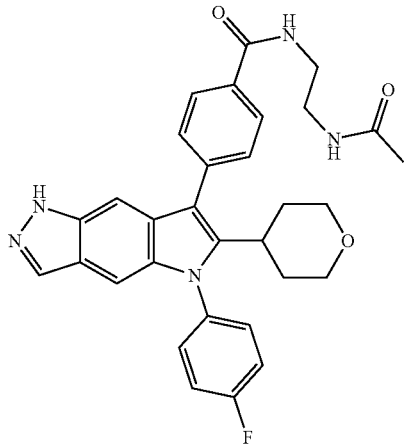
148
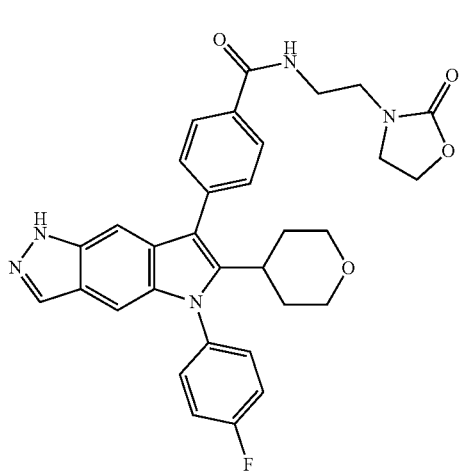
149
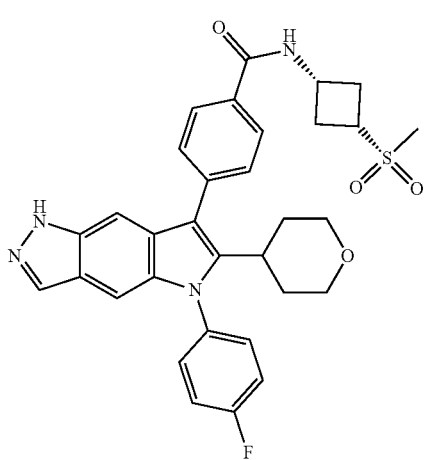

150
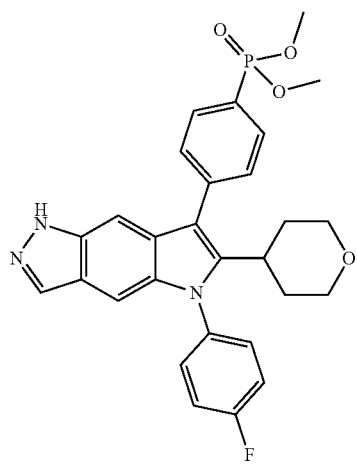
151
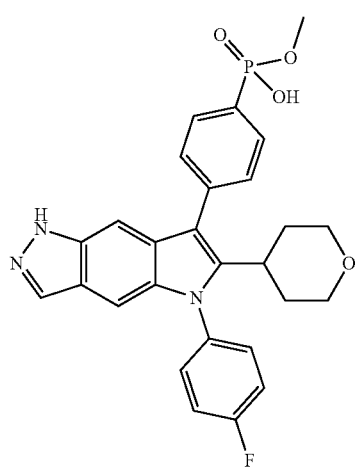
152
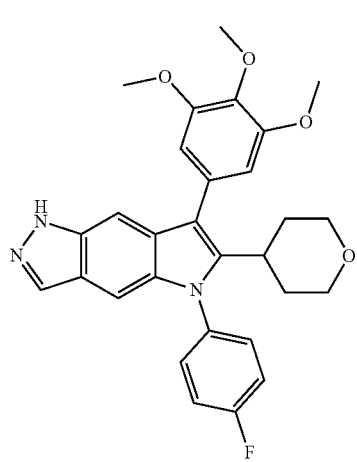
153
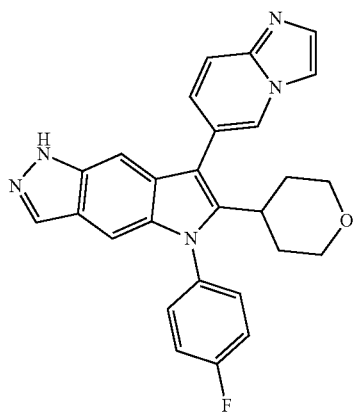
154
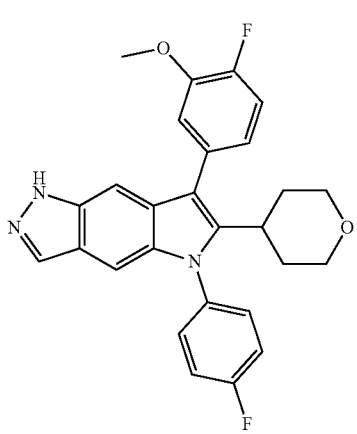
155
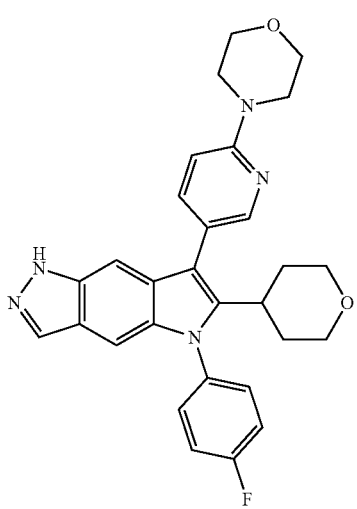

281
-continued
156
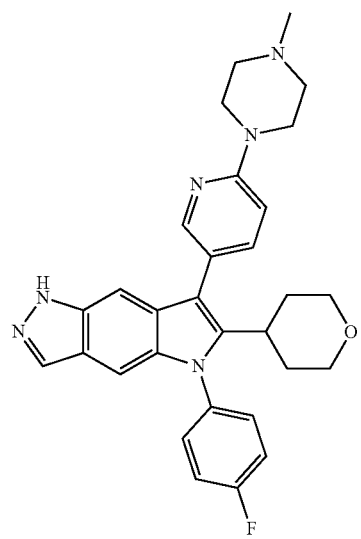
157
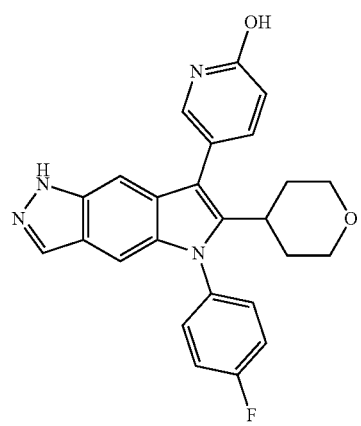
158
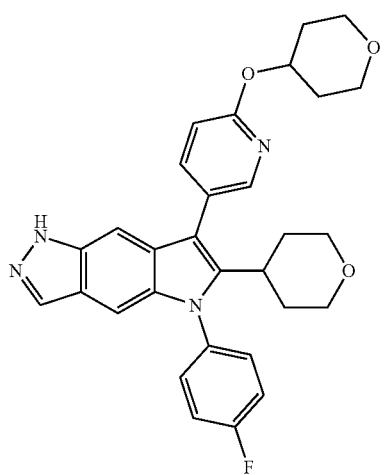
282
-continued
159
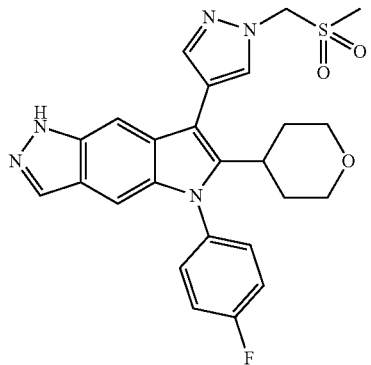
160
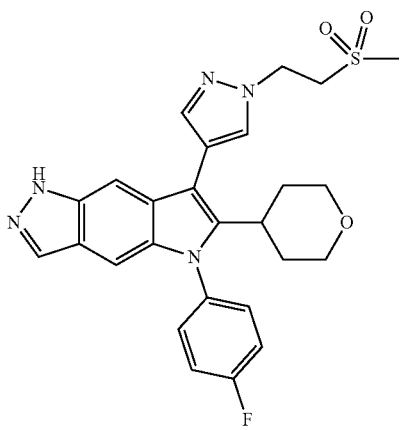
161
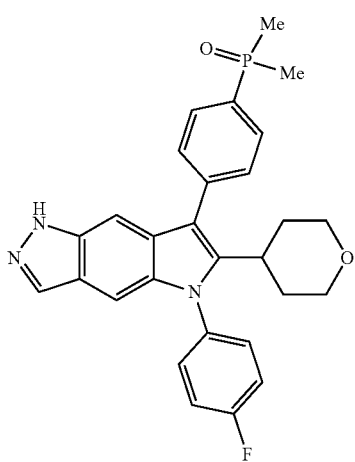

283
-continued
162
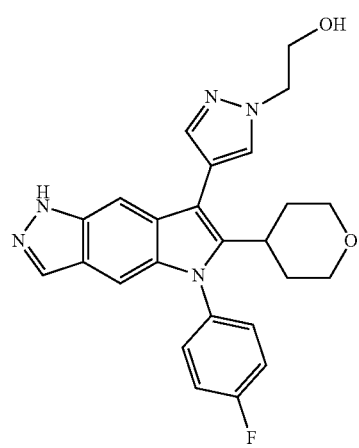
163
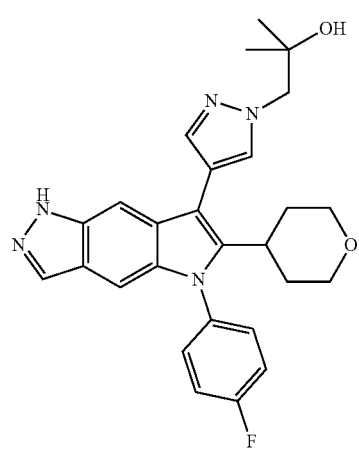
164
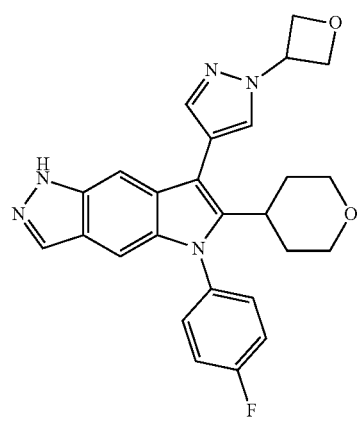
284
-continued
165
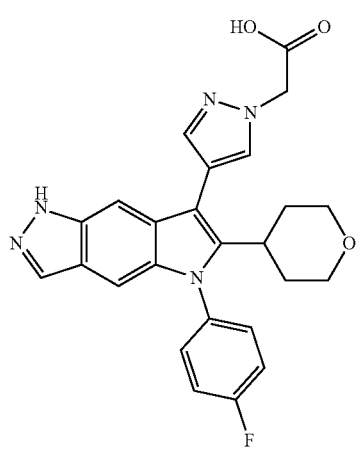
166
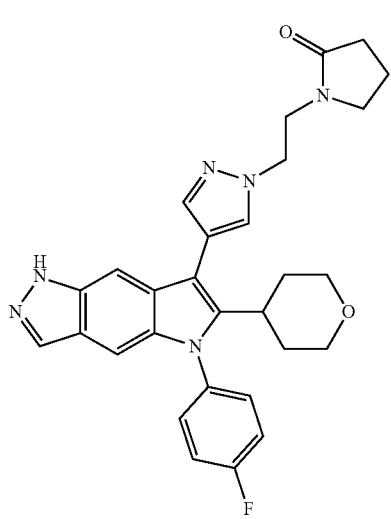
167
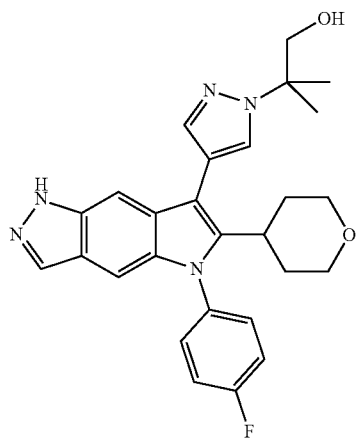

168
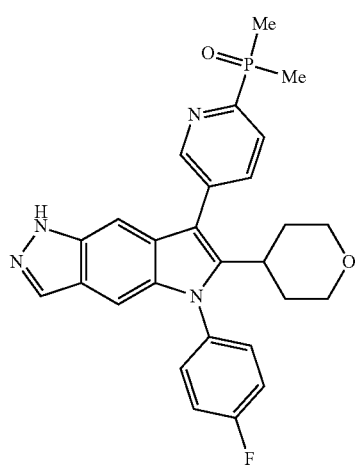
169
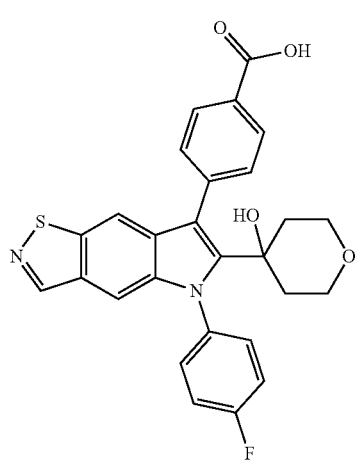
170
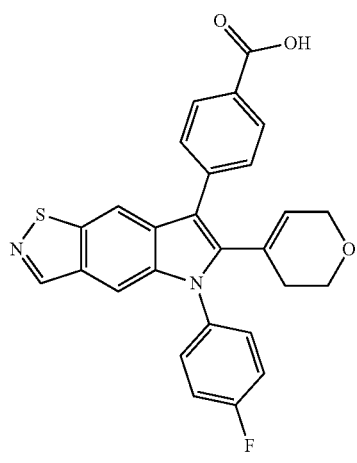
171
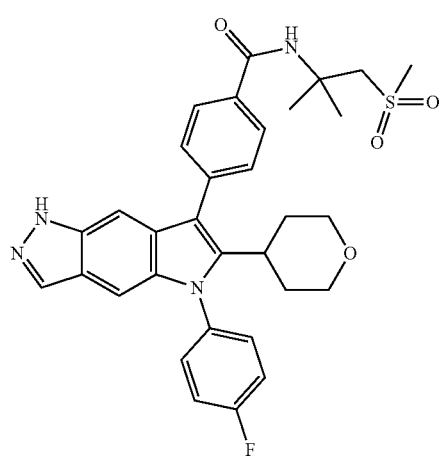
172
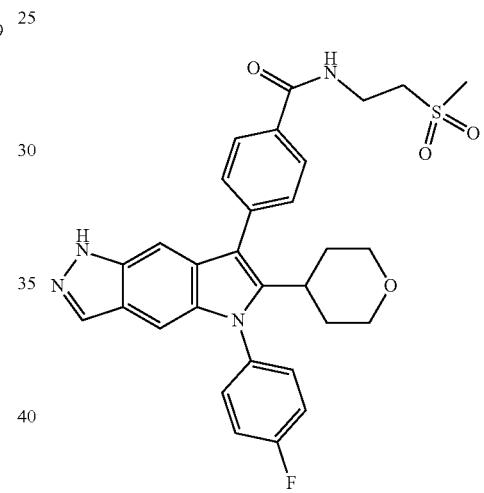
173
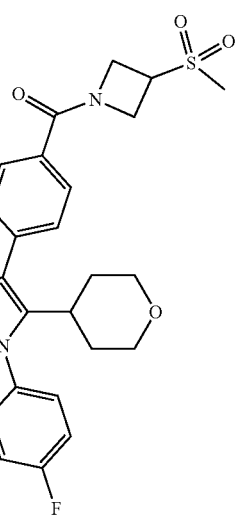

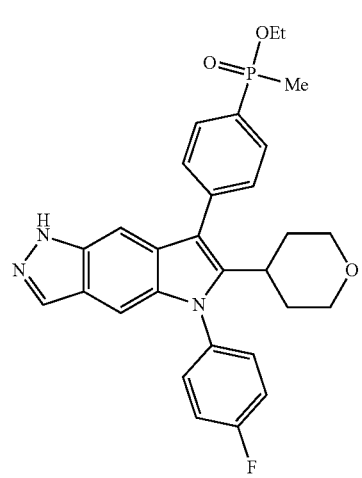
174
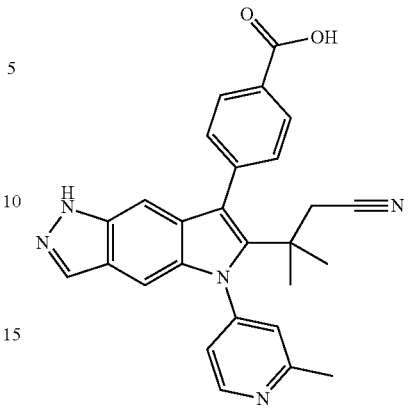
177
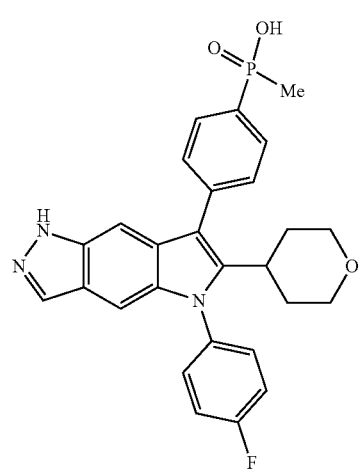
175
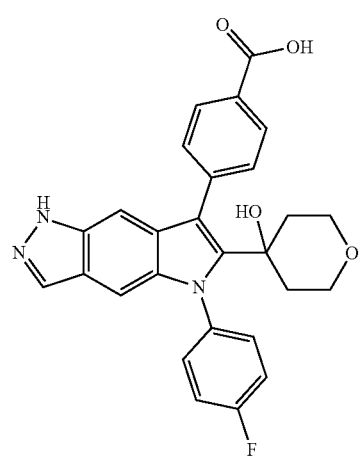
176
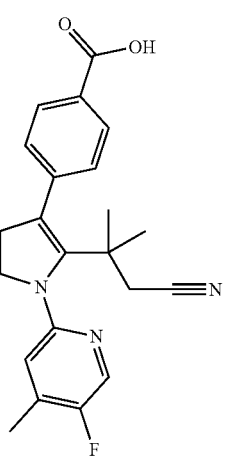
179

289
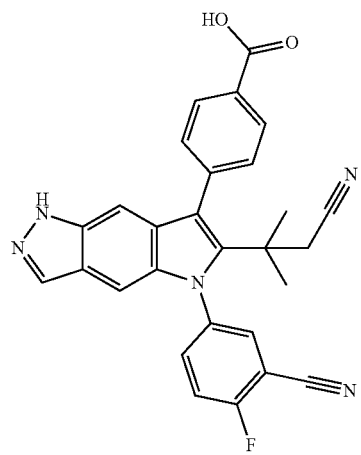
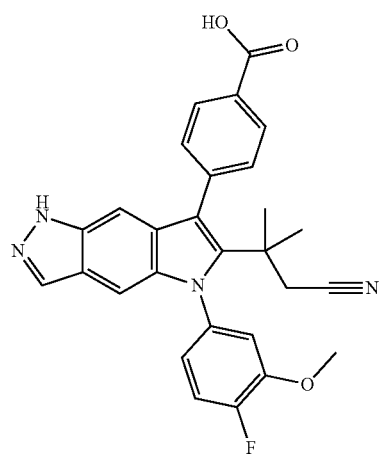
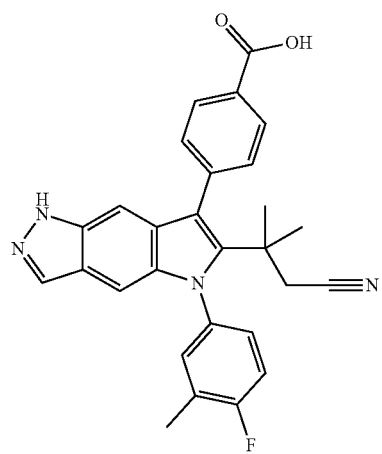
290
180
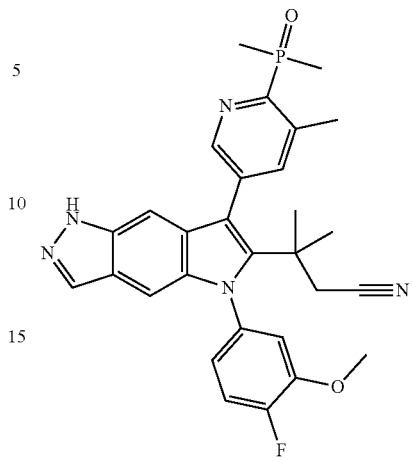
181
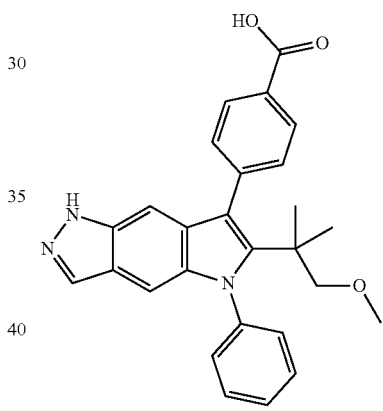
182
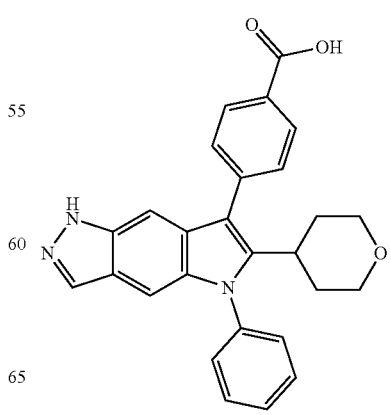
183
184
185

291
-continued
186
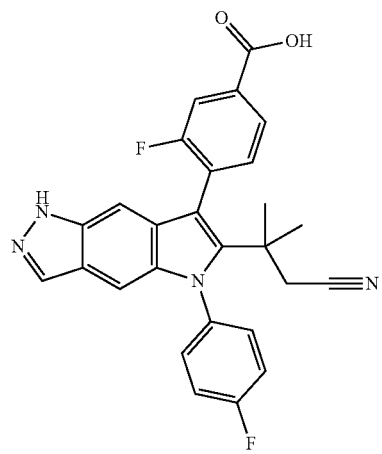
187
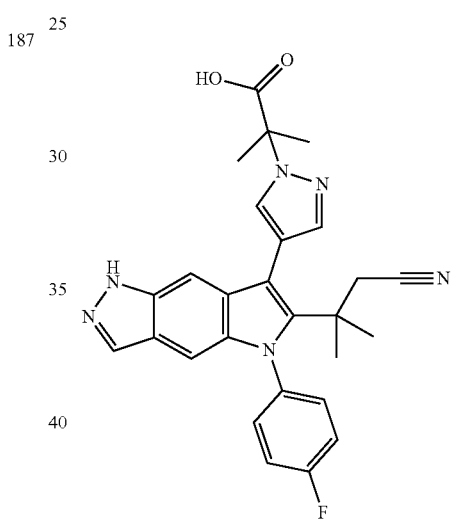
188
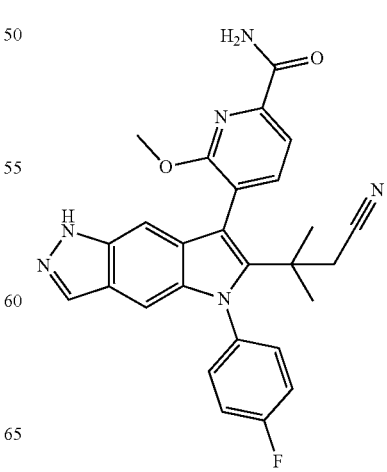
292
-continued
189
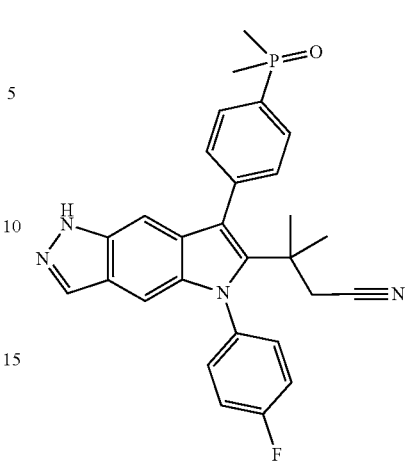
190
191

293
-continued
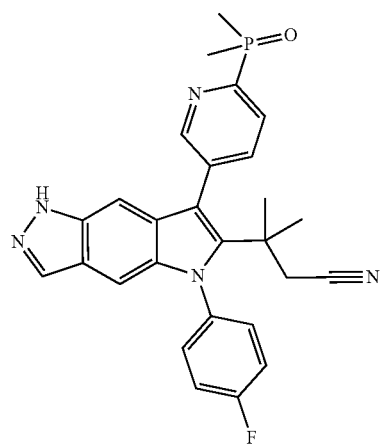
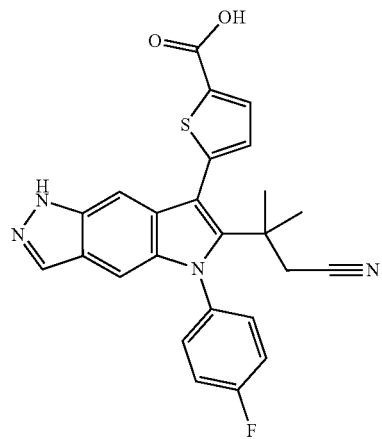
294
-continued
192
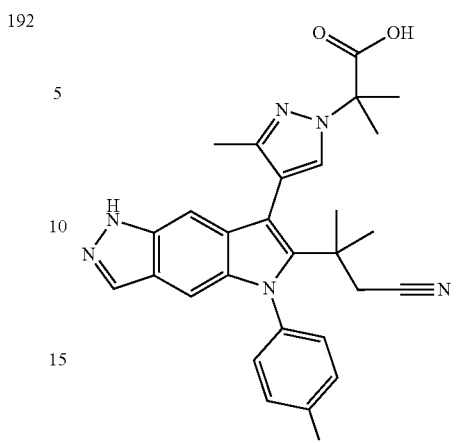
193
194
195
196
197

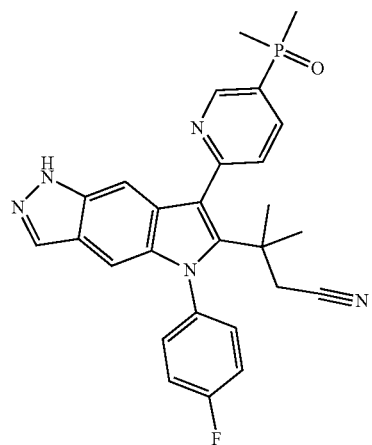
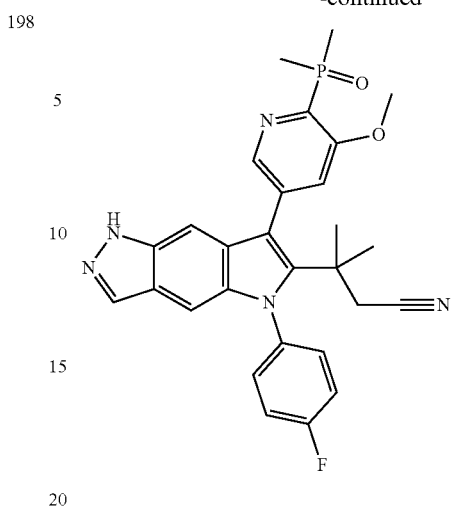

| | |
|---|---|
| 204 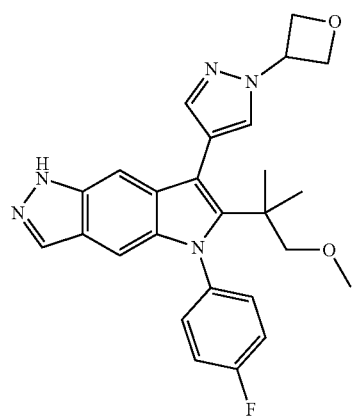 | 207 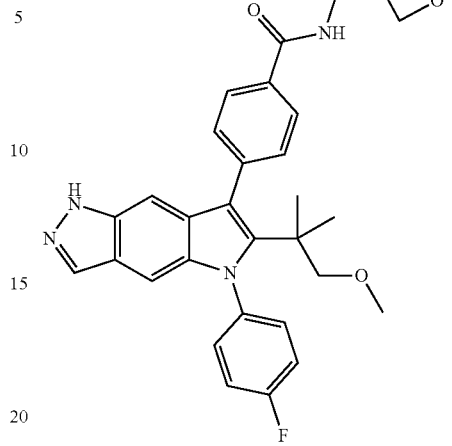 |
| 205 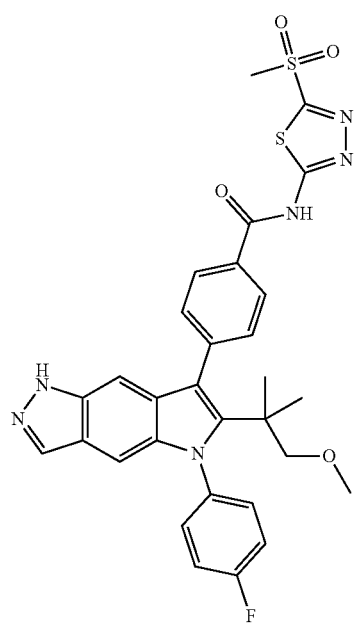 | 208 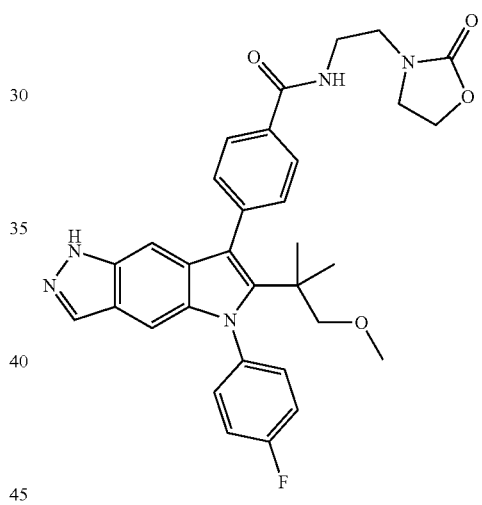 |
| 206 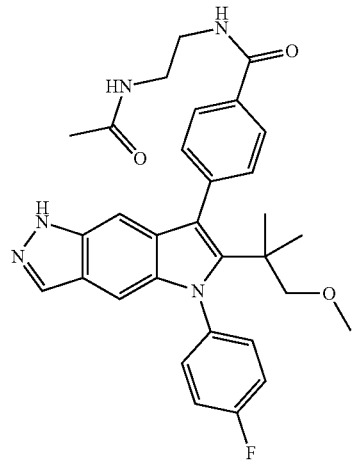 | 209 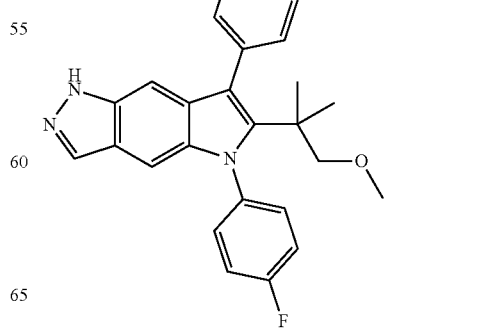 |

299
-continued
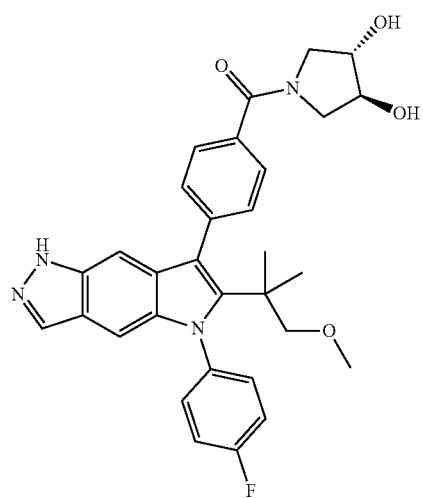
210
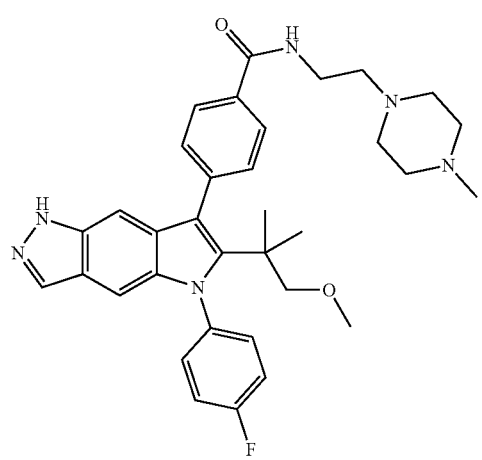
211
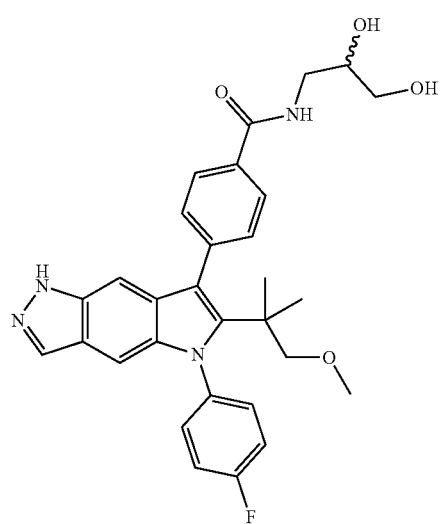
212
300
-continued
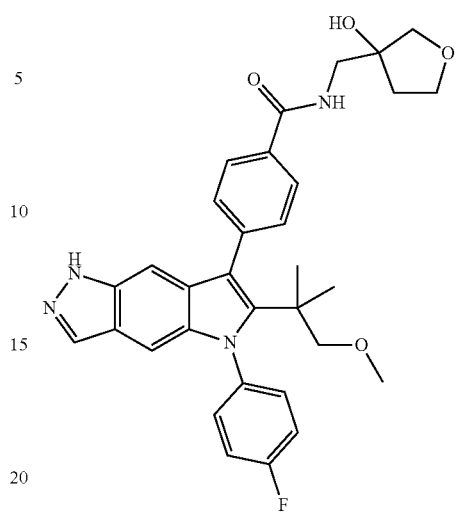
213
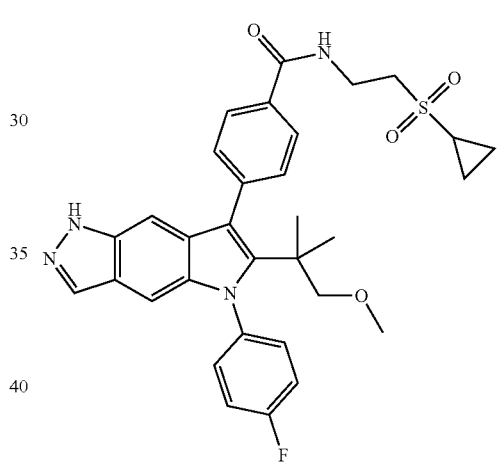
214
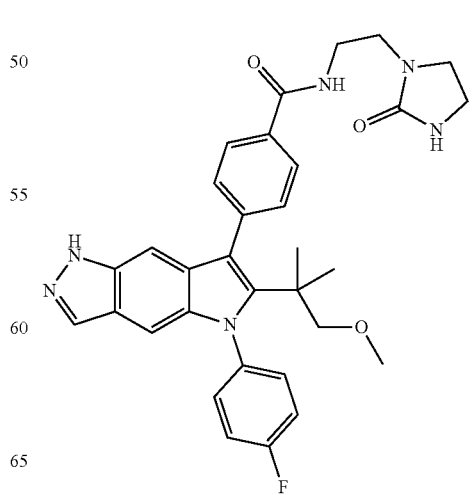
215

301
216
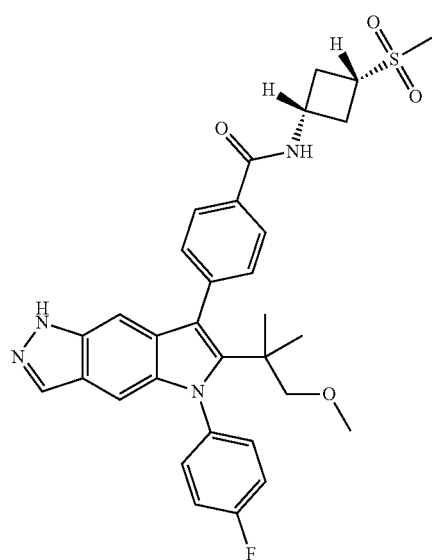
217
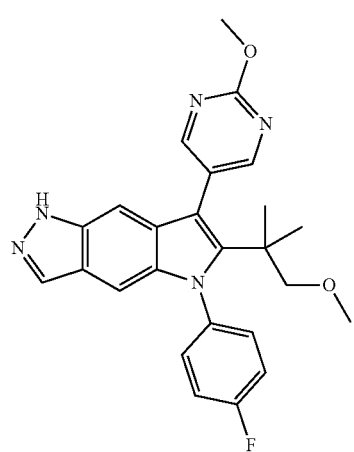
218
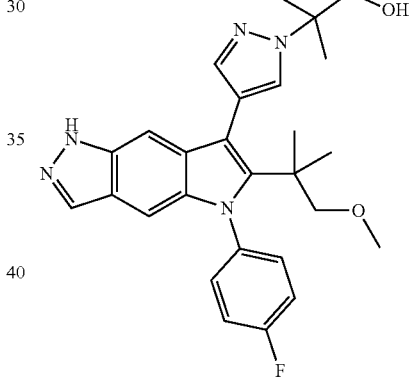
302
219
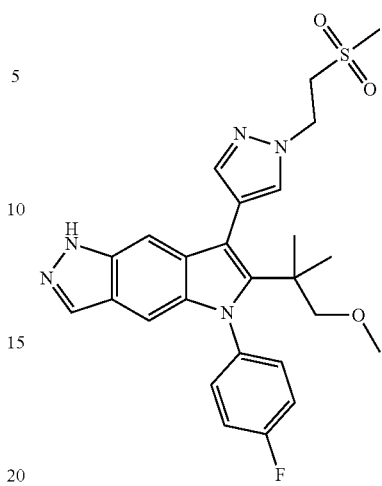
220
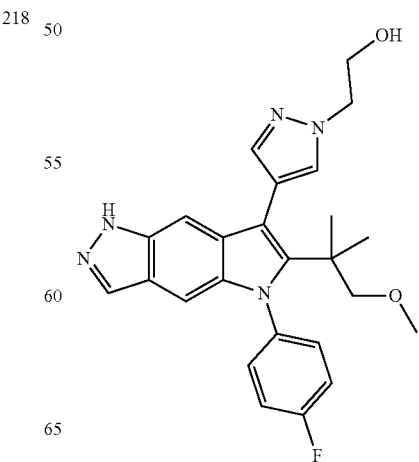
221

| | |
|---|---|
| 222 | 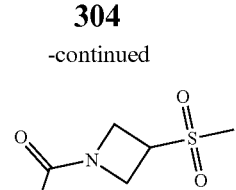 |
| 223 | 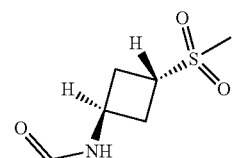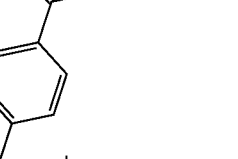 |
| 224 | 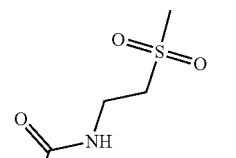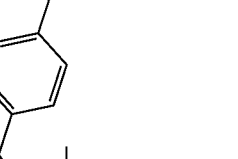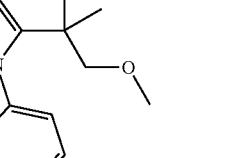 |
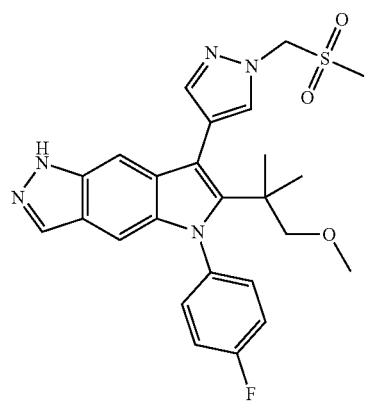
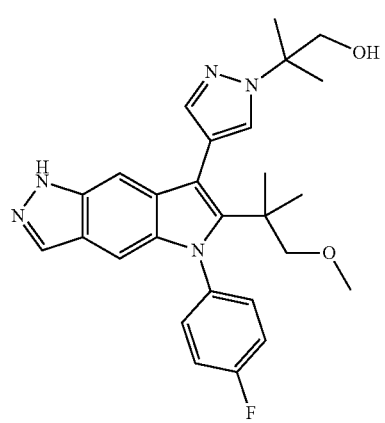
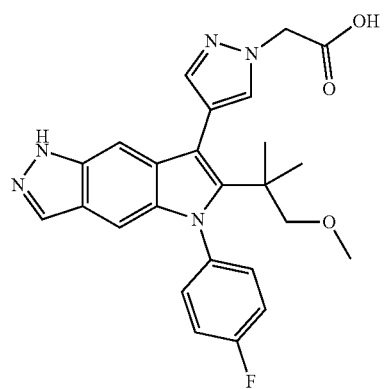
225
226
227

228
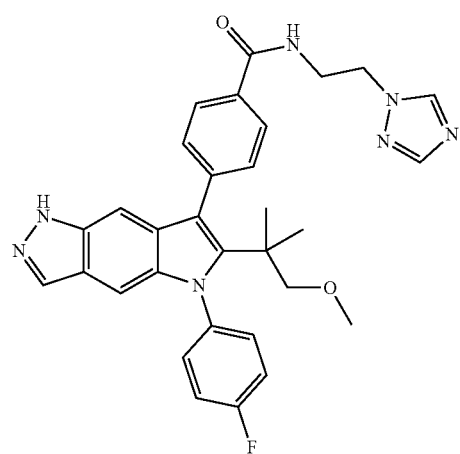
229
231
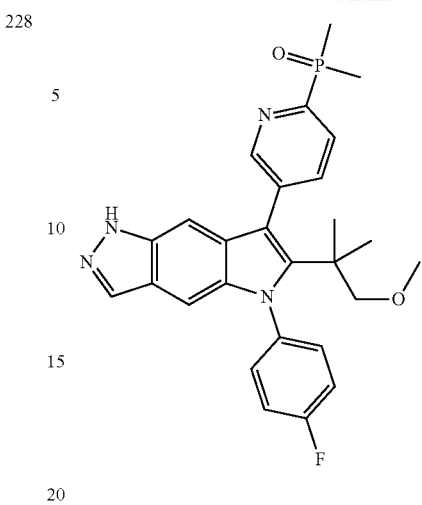
232
230
233

307
-continued
234
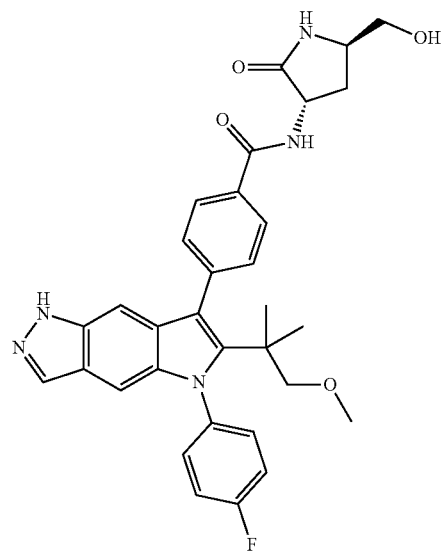
235
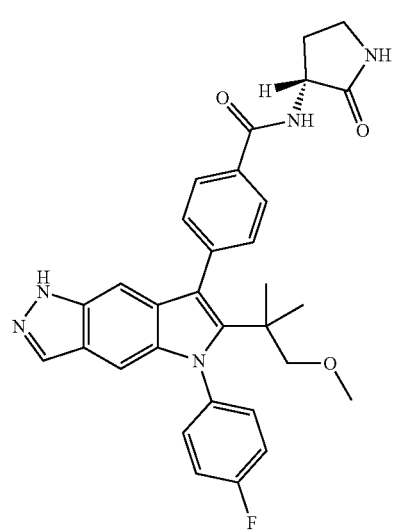
236
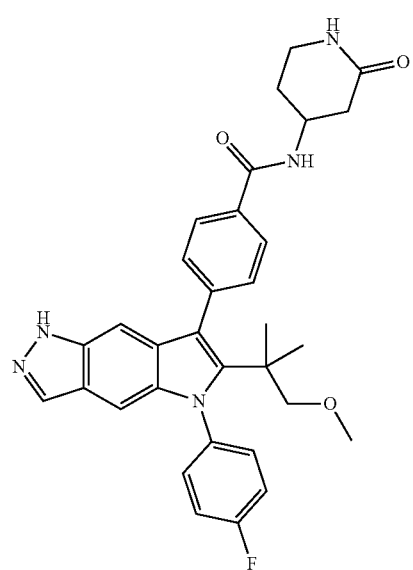
308
-continued
237
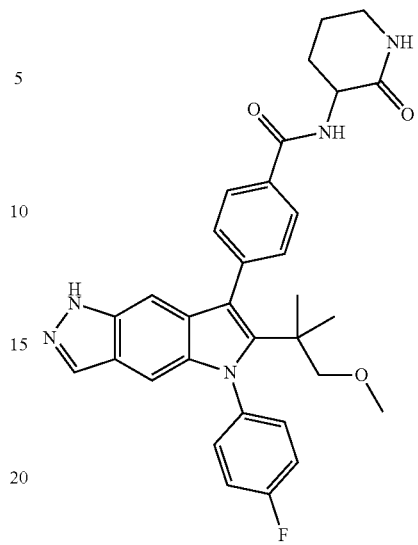
238
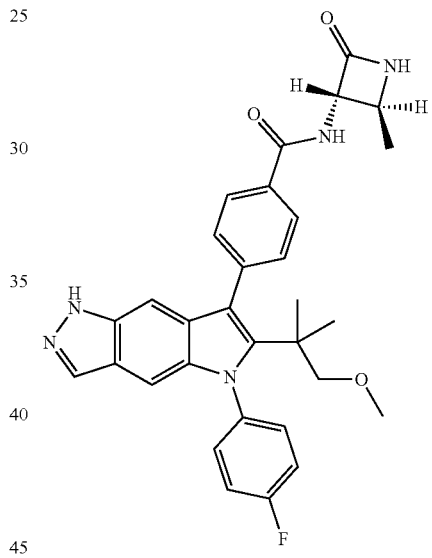
239
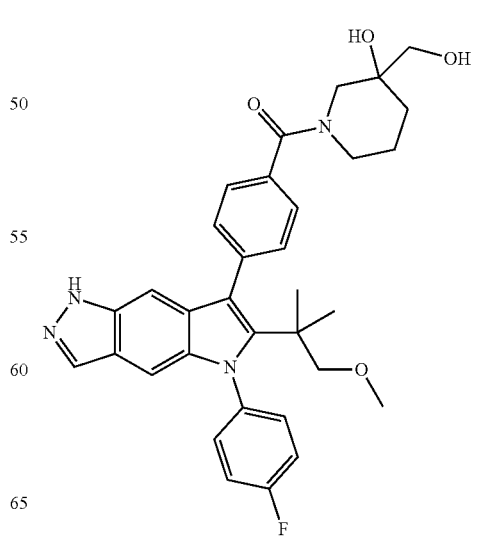

| 309 -continued | 240 | 310 -continued | 243 |
|---|---|---|---|
| 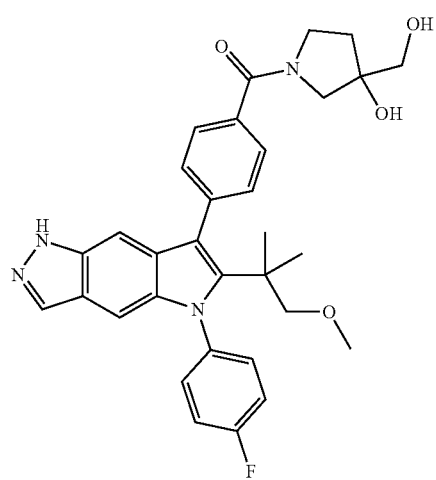 | | 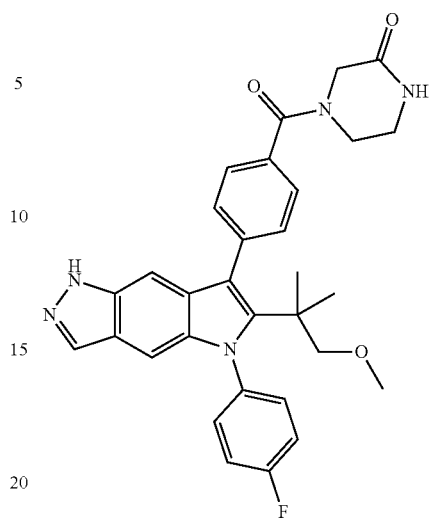 | |
| | 241 | | 244 |
| 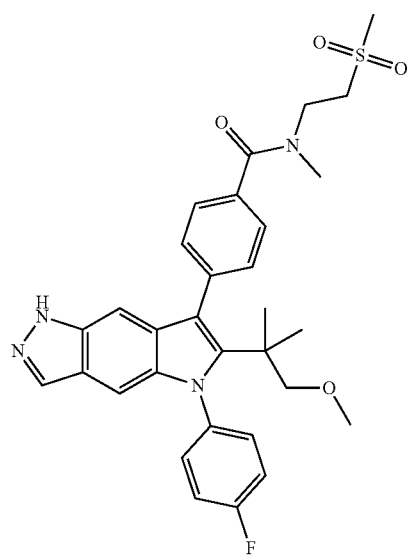 | | 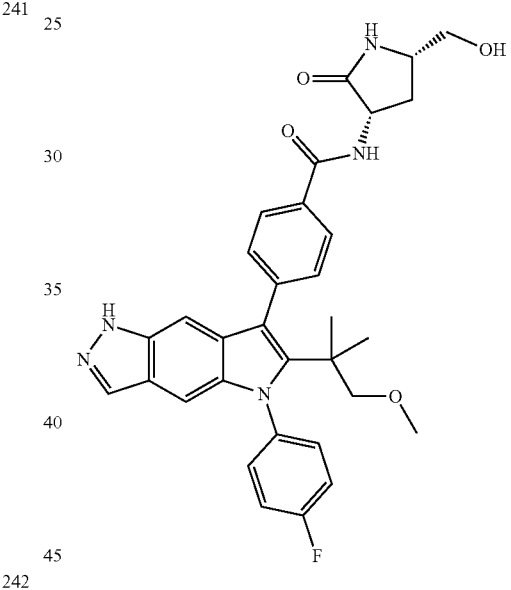 | |
| | 242 | | 245 |
| 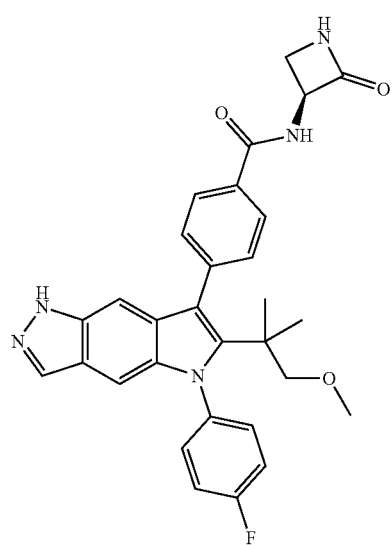 | | 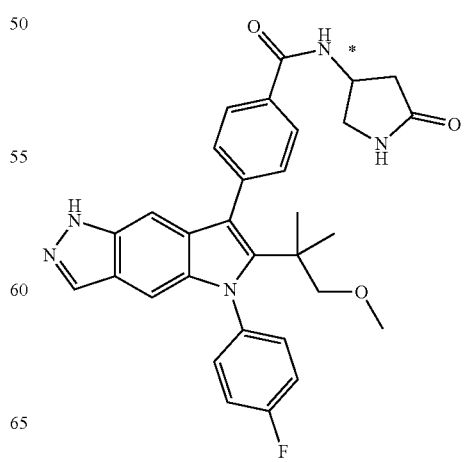 | |

311
-continued
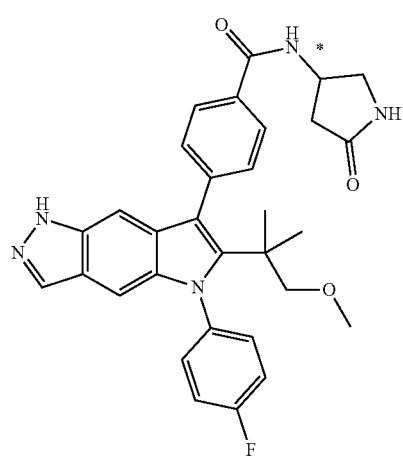
247
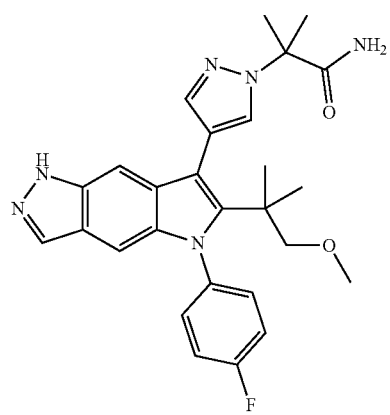
248
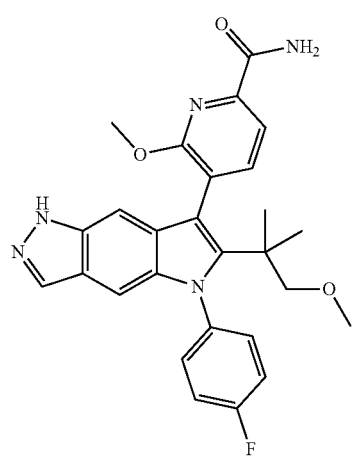
312
-continued
246
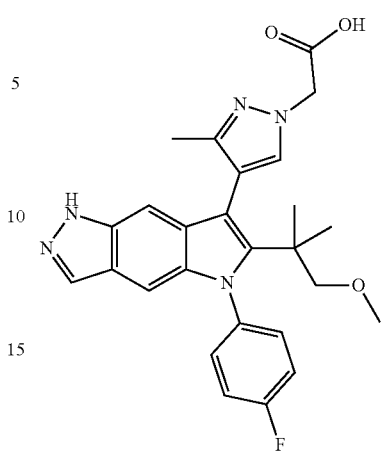
249
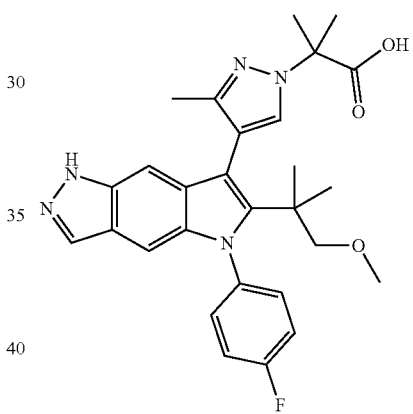
250
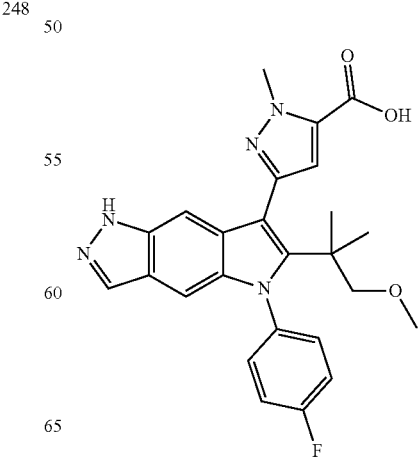
251

252
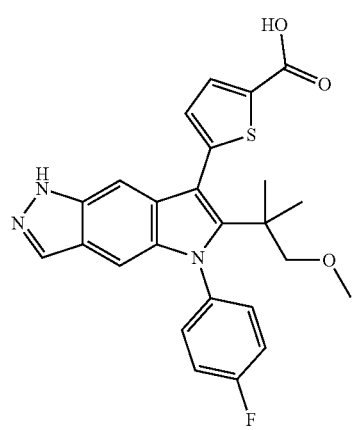
255
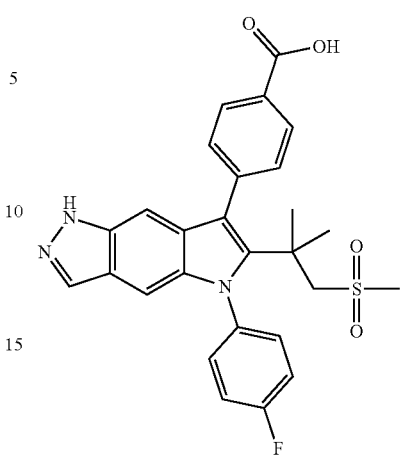
253
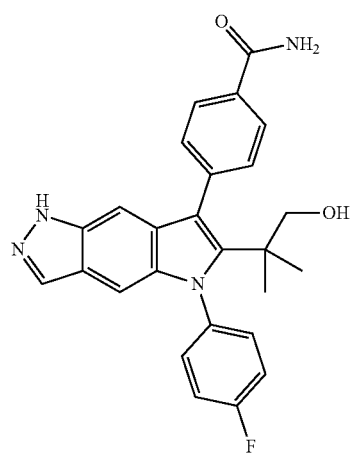
256
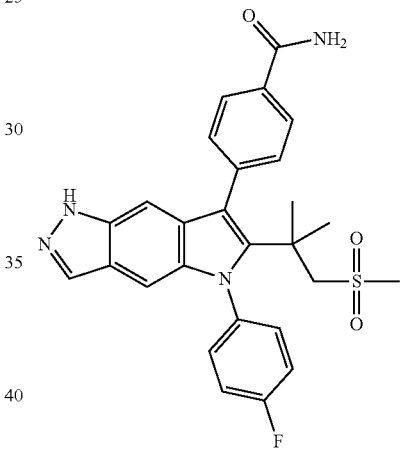
254
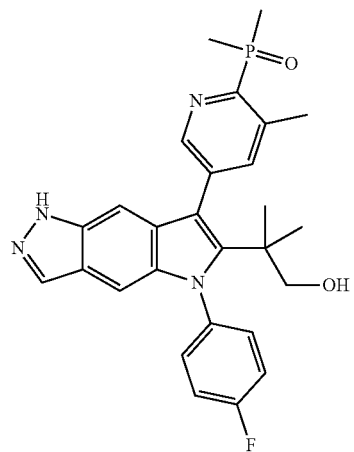
257
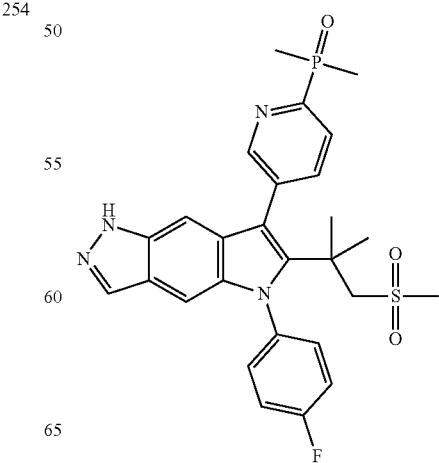

258
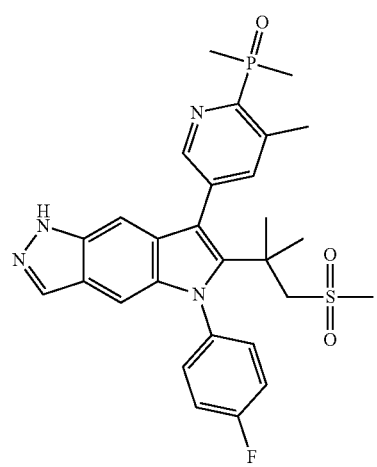
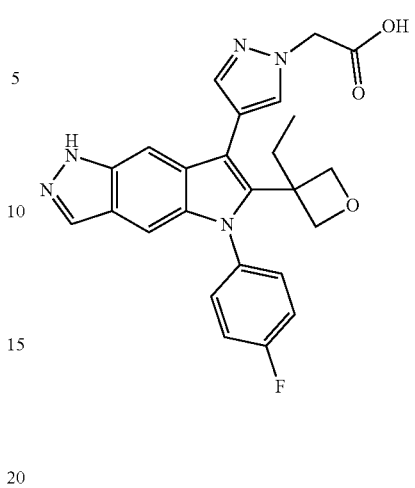
261
259
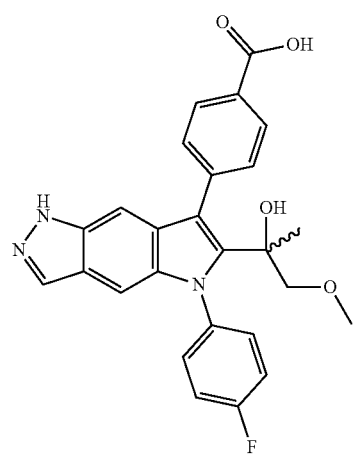
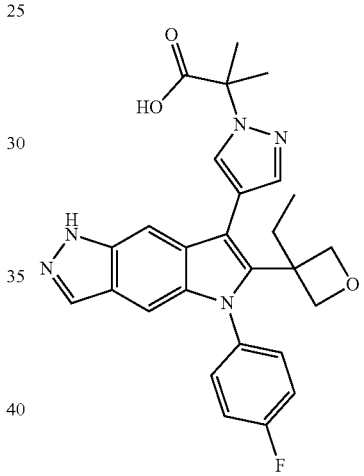
262
260
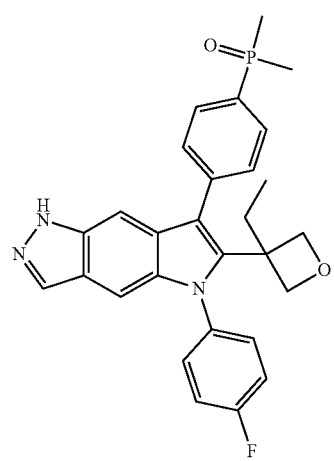
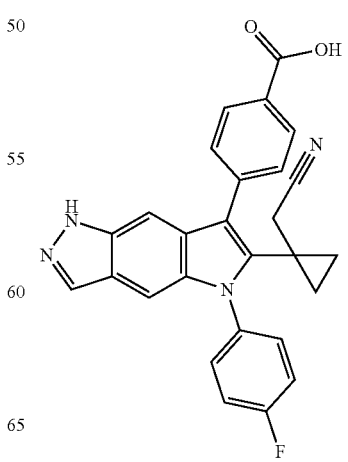
263

264 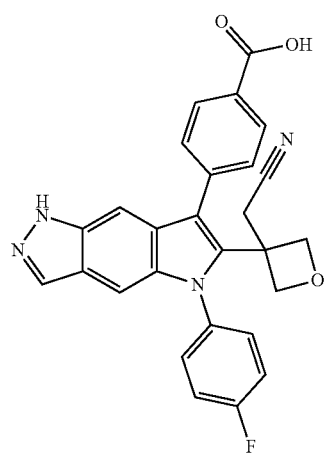 267 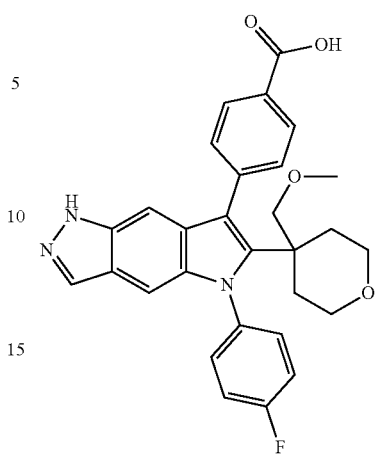
265 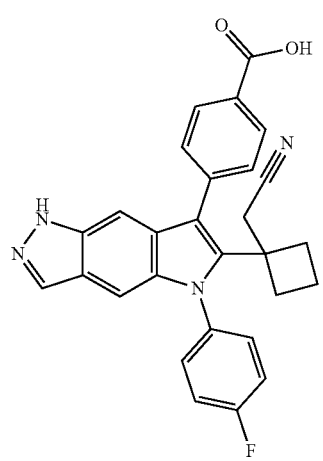 268 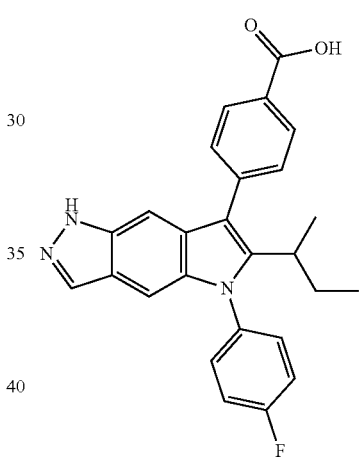
266 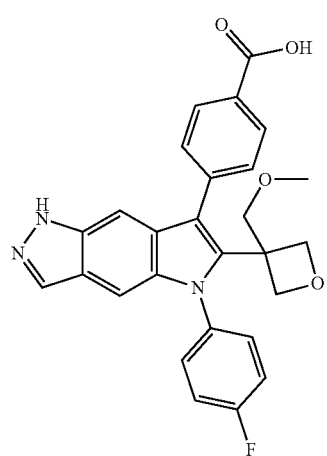 269 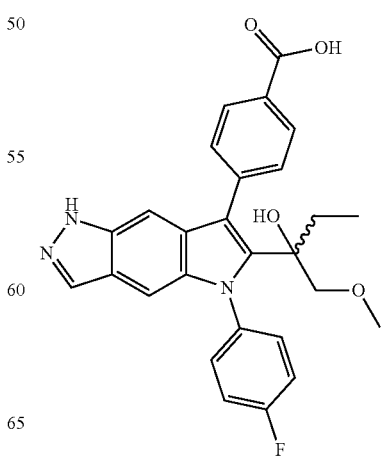

319
-continued
270
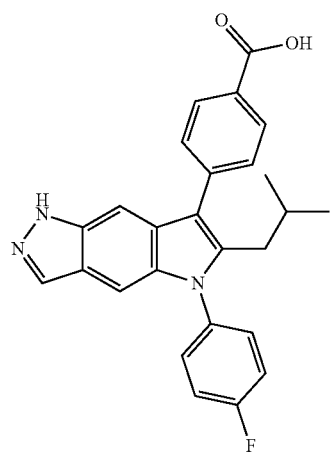
271
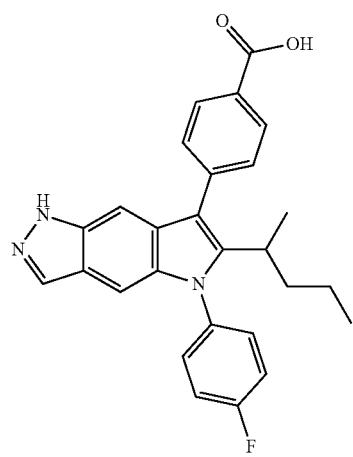 [SMILES: CCCC(C)c1c(-c2ccc(C(=O)O)cc2)c2cc3[nH]ncc3cc2n1-c1ccc(F)cc1]
272
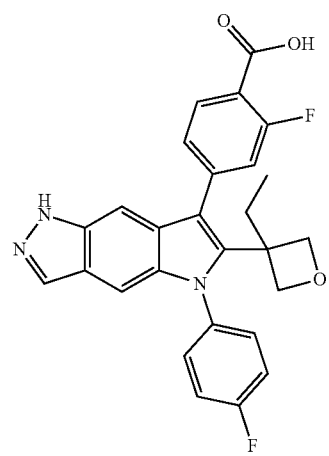 [SMILES: CCC1(c2c(-c3ccc(C(=O)O)c(F)c3)c3cc4[nH]ncc4cc3n2-c2ccc(F)cc2)COC1]
320
-continued
273
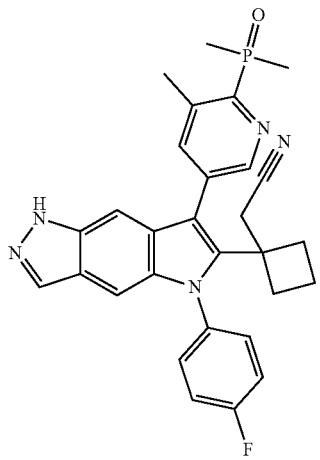 [SMILES: Cc1cc(-c2c(C3(CC#N)CCC3)n(-c3ccc(F)cc3)c3cc4cn[nH]c4cc23)cnc1P(C)(C)=O]
274
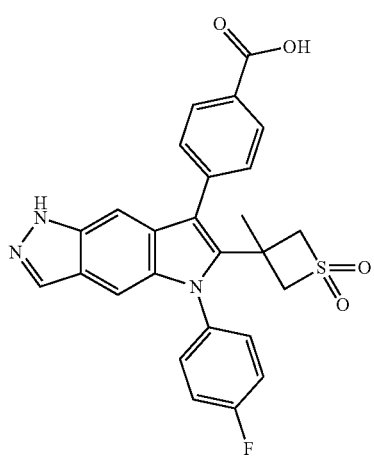
275
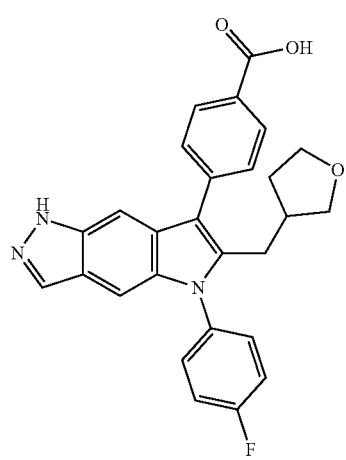 [SMILES: O=C(O)c1ccc(-c2c(CC3CCOC3)n(-c3ccc(F)cc3)c3cc4cn[nH]c4cc23)cc1]

276 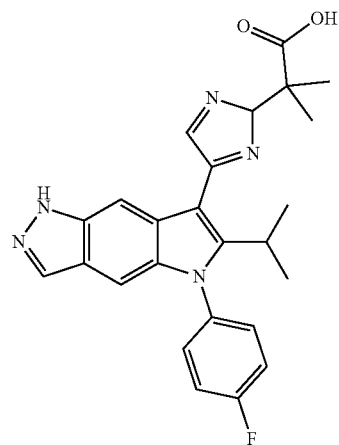 [SMILES: CC(C)c1c(-c2cnn(C(C)(C)C(=O)O)c2)c2cc3[nH]ncc3cc2n1-c1ccc(F)cc1]
277 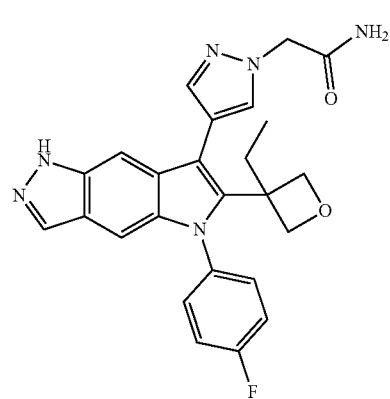
278 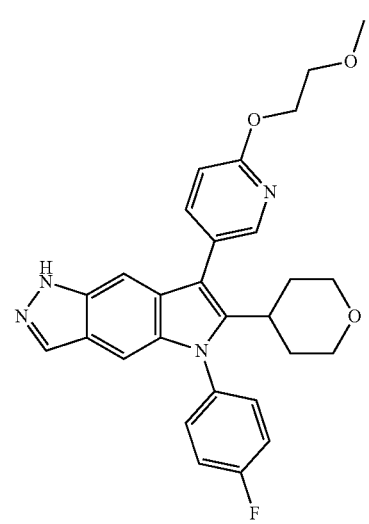 [SMILES: COCCOc1ccc(-c2c(C3CCOCC3)n(-c3ccc(F)cc3)c3cc4cn[nH]c4cc23)cn1]
279 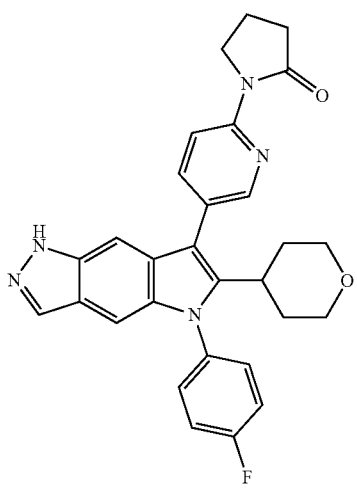 [SMILES: O=C1CCCN1c1ccc(-c2c(C3CCOCC3)n(-c3ccc(F)cc3)c3cc4cn[nH]c4cc23)cn1]
280 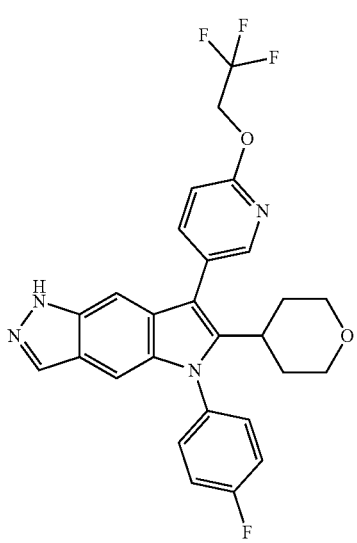 [SMILES: Fc1ccc(-n2c(C3CCOCC3)c(-c3ccc(OCC(F)(F)F)nc3)c3cc4[nH]ncc4cc32)cc1]
281 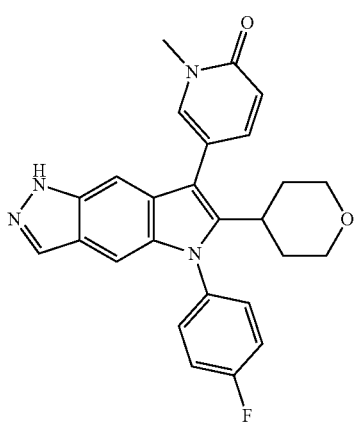 [SMILES: Cn1cc(-c2c(C3CCOCC3)n(-c3ccc(F)cc3)c3cc4cn[nH]c4cc23)ccc1=O]

-continued
282
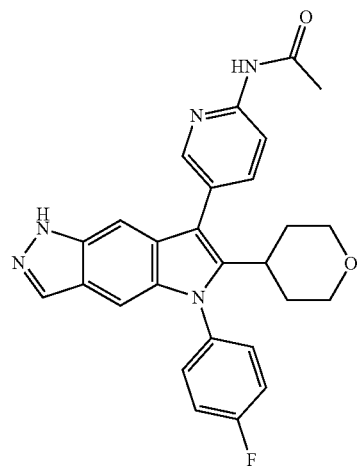 [SMILES: CC(=O)Nc1ccc(-c2c(C3CCOCC3)n(-c3ccc(F)cc3)c3cc4cn[nH]c4cc23)cn1]
283
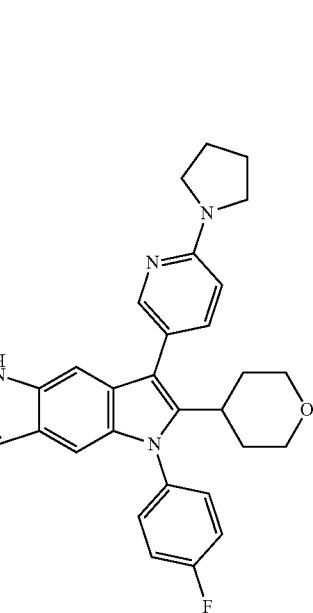
284
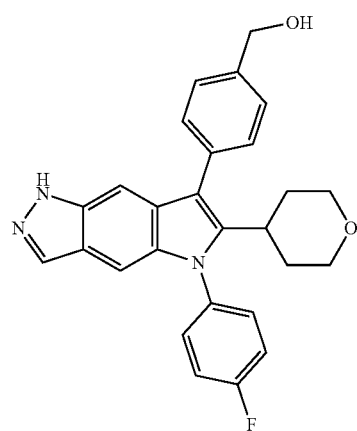
-continued
285
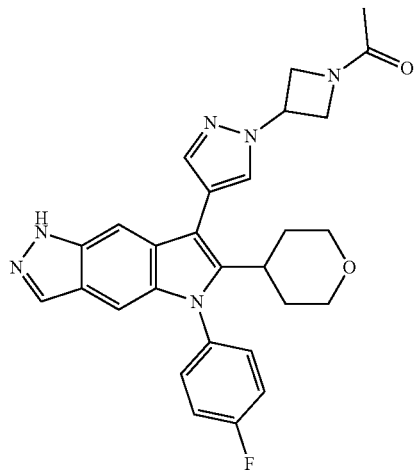 [SMILES: CC(=O)N1CC(n2cc(-c3c(C4CCOCC4)n(-c4ccc(F)cc4)c4cc5cn[nH]c5cc34)cn2)C1]
286
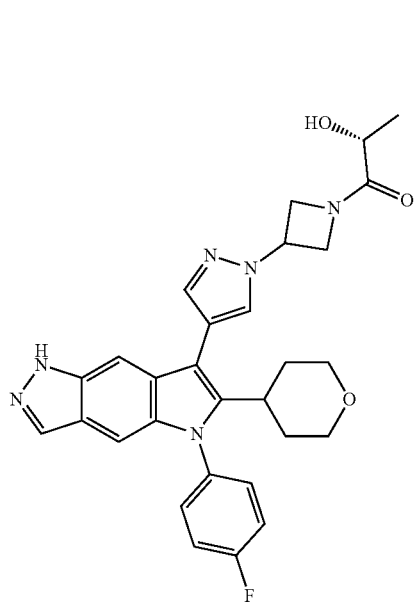 [SMILES: C[C@@H](O)C(=O)N1CC(n2cc(-c3c(C4CCOCC4)n(-c4ccc(F)cc4)c4cc5cn[nH]c5cc34)cn2)C1]
287
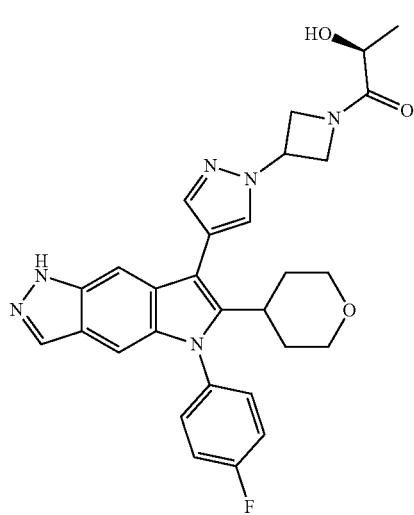 [SMILES: C[C@H](O)C(=O)N1CC(n2cc(-c3c(C4CCOCC4)n(-c4ccc(F)cc4)c4cc5cn[nH]c5cc34)cn2)C1]

288
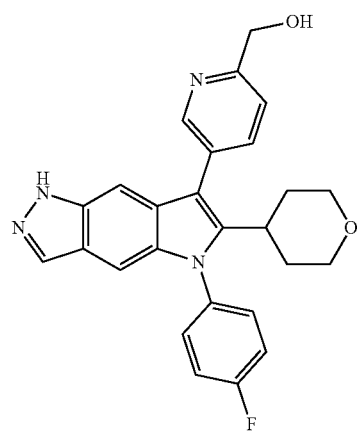 [SMILES: OCc1ccc(-c2c(C3CCOCC3)n(-c3ccc(F)cc3)c3cc4cn[nH]c4cc23)cn1]
289
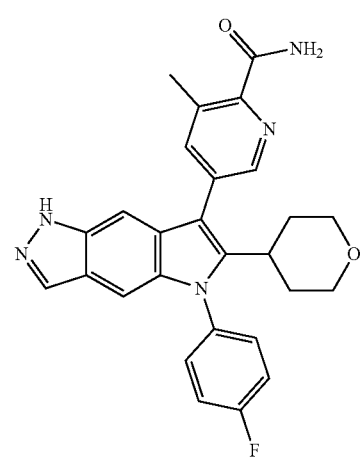 [SMILES: Cc1cc(-c2c(C3CCOCC3)n(-c3ccc(F)cc3)c3cc4cn[nH]c4cc23)cnc1C(N)=O]
290
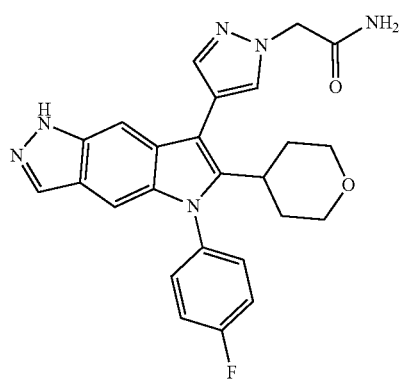
291
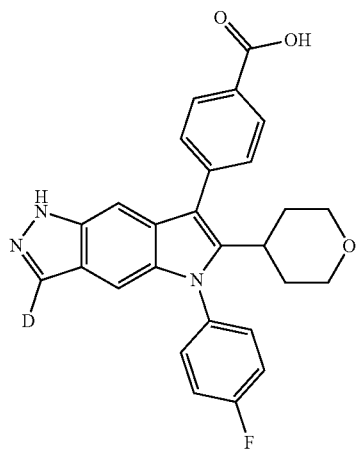 [SMILES: [2H]c1n[nH]c2cc3c(-c4ccc(C(=O)O)cc4)c(C4CCOCC4)n(-c4ccc(F)cc4)c3cc12]
292
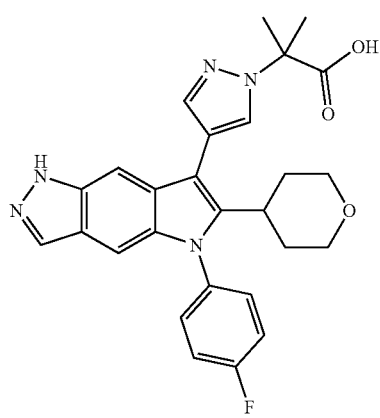
293
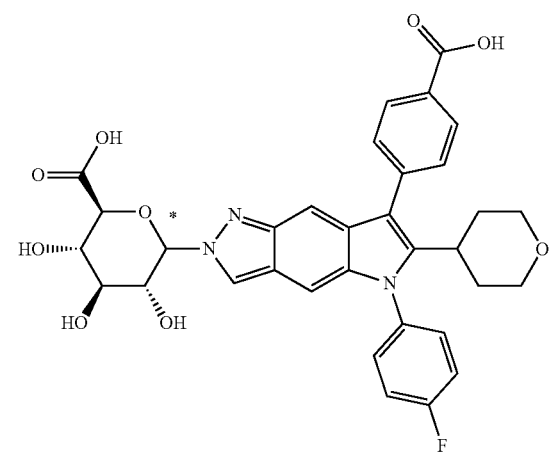 [SMILES: O=C(O)c1ccc(-c2c(C3CCOCC3)n(-c3ccc(F)cc3)c3cc4cn(C5O[C@H](C(=O)O)[C@@H](O)[C@H](O)[C@H]5O)nc4cc23)cc1]

327
-continued
294
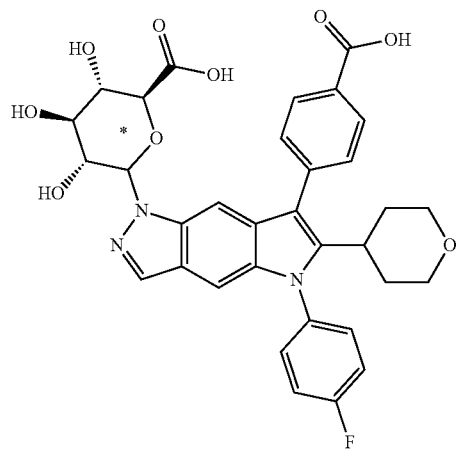 [SMILES: O=C(O)c1ccc(-c2c(C3CCOCC3)n(-c3ccc(F)cc3)c3cc4cnn(C5O[C@H](C(=O)O)[C@@H](O)[C@H](O)[C@H]5O)c4cc23)cc1]
295
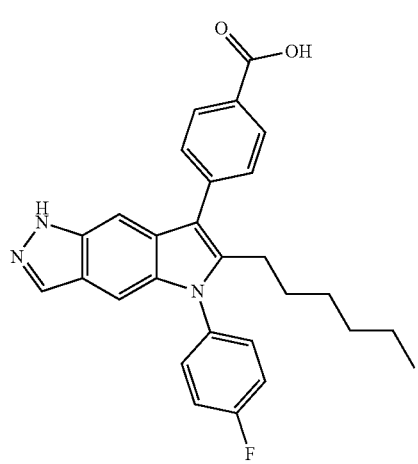 [SMILES: CCCCCCc1c(-c2ccc(C(=O)O)cc2)c2cc3[nH]ncc3cc2n1-c1ccc(F)cc1]
296
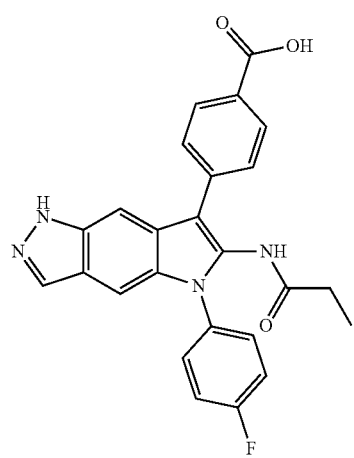 [SMILES: CCC(=O)Nc1c(-c2ccc(C(=O)O)cc2)c2cc3[nH]ncc3cc2n1-c1ccc(F)cc1]
328
-continued
297
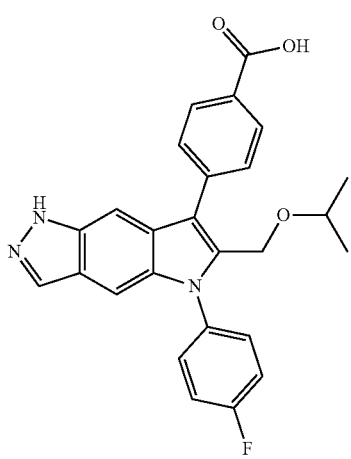 [SMILES: CC(C)OCc1c(-c2ccc(C(=O)O)cc2)c2cc3[nH]ncc3cc2n1-c1ccc(F)cc1]
298
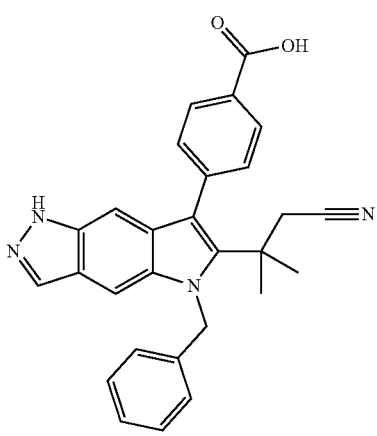 [SMILES: CC(C)(CC#N)c1c(-c2ccc(C(=O)O)cc2)c2cc3[nH]ncc3cc2n1Cc1ccccc1]
299
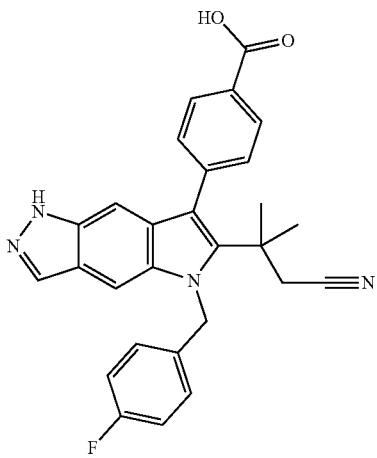 [SMILES: CC(C)(CC#N)c1c(-c2ccc(C(=O)O)cc2)c2cc3[nH]ncc3cc2n1Cc1ccc(F)cc1]

-continued
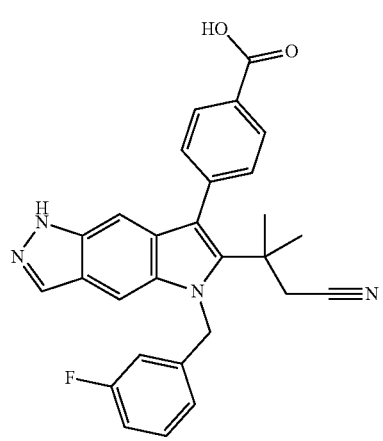 [SMILES: CC(C)(CC#N)c1c(-c2ccc(C(=O)O)cc2)c2cc3[nH]ncc3cc2n1Cc1cccc(F)c1]
300
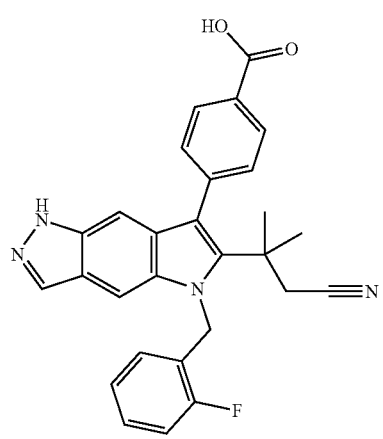
301
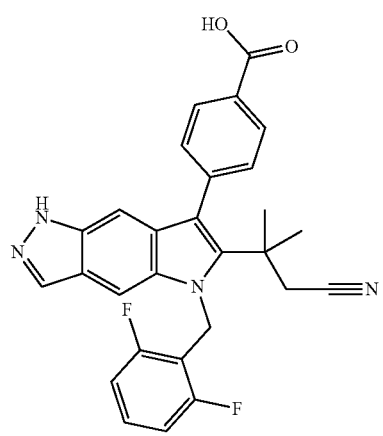 [SMILES: CC(C)(CC#N)c1c(-c2ccc(C(=O)O)cc2)c2cc3[nH]ncc3cc2n1Cc1c(F)cccc1F]
302
-continued
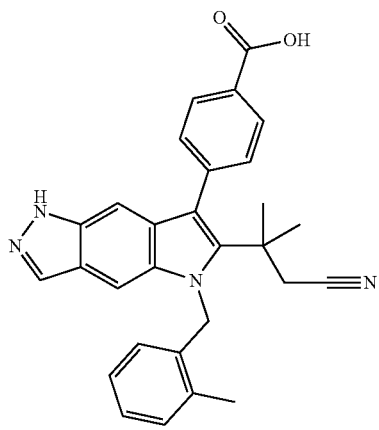 [SMILES: Cc1ccccc1Cn1c(C(C)(C)CC#N)c(-c2ccc(C(=O)O)cc2)c2cc3[nH]ncc3cc21]
303
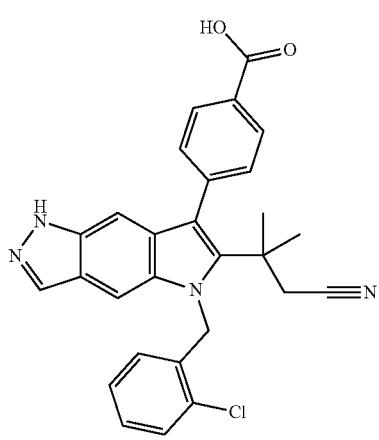
304
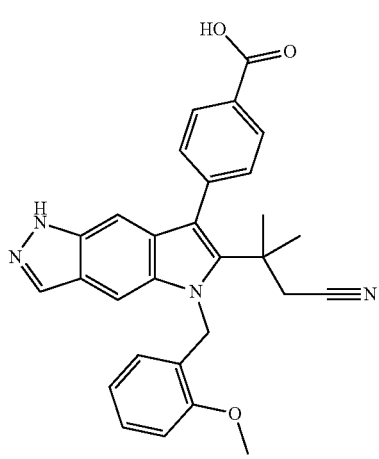 [SMILES: COc1ccccc1Cn1c(C(C)(C)CC#N)c(-c2ccc(C(=O)O)cc2)c2cc3[nH]ncc3cc21]
305

331
-continued
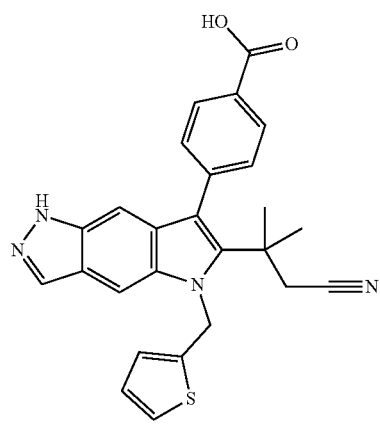 [SMILES: CC(C)(CC#N)c1c(-c2ccc(C(=O)O)cc2)c2cc3[nH]ncc3cc2n1Cc1cccs1]
306
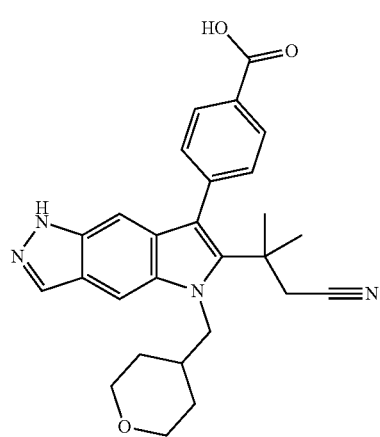
307
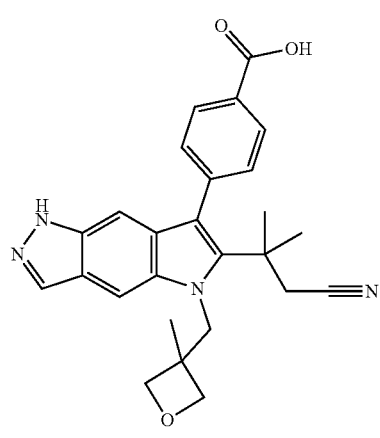 [SMILES: CC1(Cn2c(C(C)(C)CC#N)c(-c3ccc(C(=O)O)cc3)c3cc4[nH]ncc4cc32)COC1]
308
332
-continued
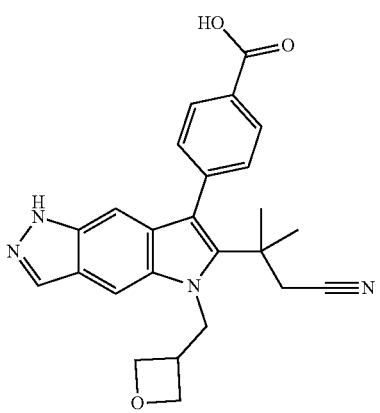 [SMILES: CC(C)(CC#N)c1c(-c2ccc(C(=O)O)cc2)c2cc3[nH]ncc3cc2n1CC1COC1]
309
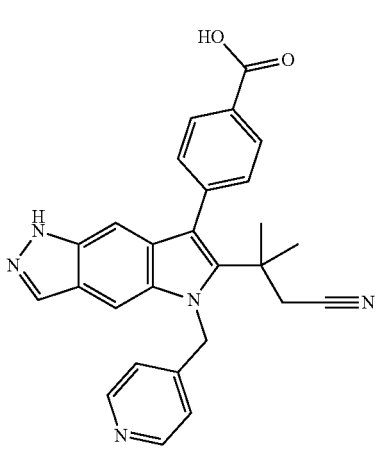 [SMILES: CC(C)(CC#N)c1c(-c2ccc(C(=O)O)cc2)c2cc3[nH]ncc3cc2n1Cc1ccncc1]
310
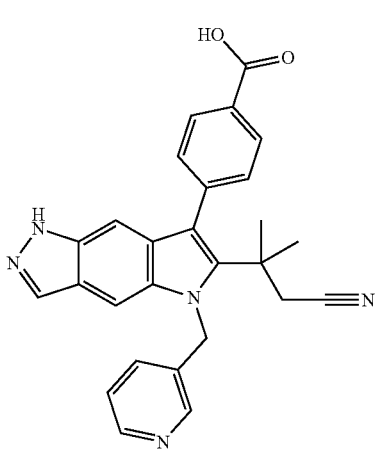 [SMILES: CC(C)(CC#N)c1c(-c2ccc(C(=O)O)cc2)c2cc3[nH]ncc3cc2n1Cc1cccnc1]
311

312
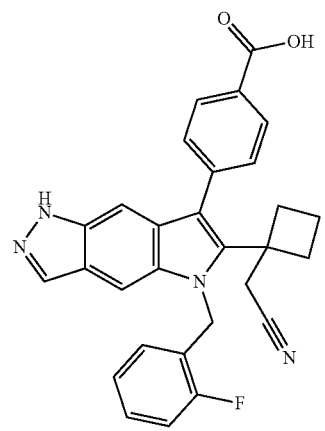 [SMILES: N#CCC1(c2c(-c3ccc(C(=O)O)cc3)c3cc4[nH]ncc4cc3n2Cc2ccccc2F)CCC1]
313
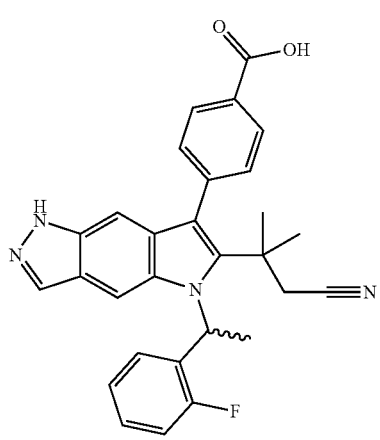 [SMILES: CC(c1ccccc1F)n1c(C(C)(C)CC#N)c(-c2ccc(C(=O)O)cc2)c2cc3[nH]ncc3cc21]
314
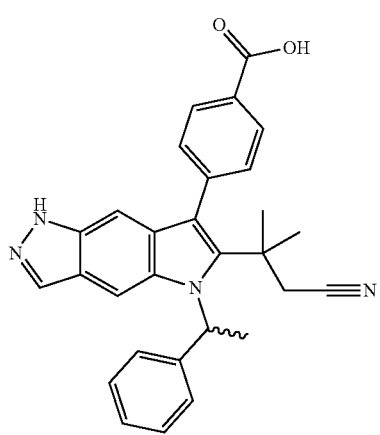 [SMILES: CC(c1ccccc1)n1c(C(C)(C)CC#N)c(-c2ccc(C(=O)O)cc2)c2cc3[nH]ncc3cc21]
315
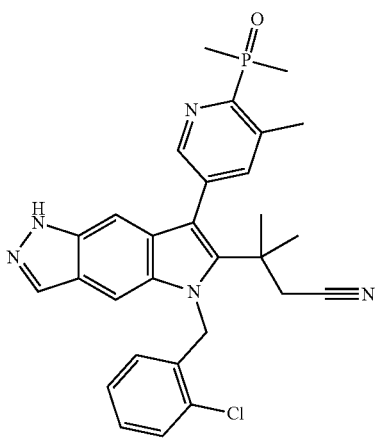
316
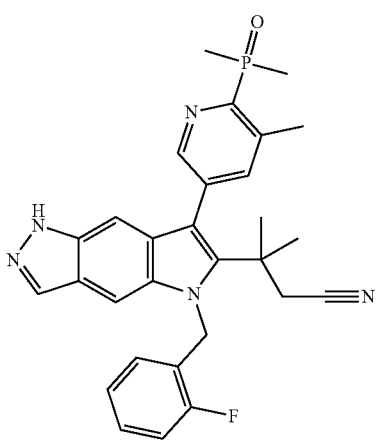 [SMILES: Cc1cc(-c2c(C(C)(C)CC#N)n(Cc3ccccc3F)c3cc4cn[nH]c4cc23)cnc1P(C)(C)=O]
317
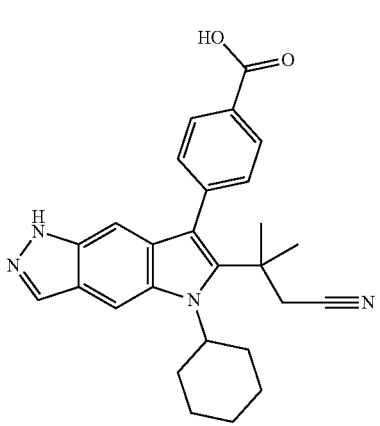 [SMILES: CC(C)(CC#N)c1c(-c2ccc(C(=O)O)cc2)c2cc3[nH]ncc3cc2n1C1CCCCC1]

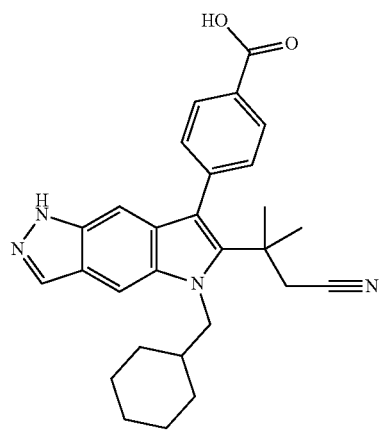
318
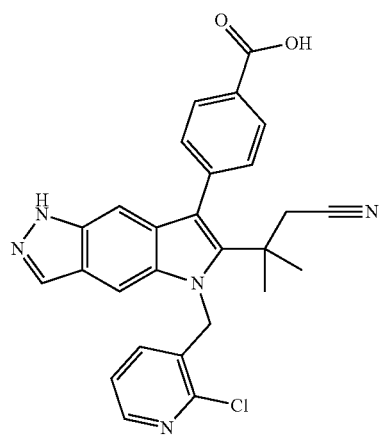 [SMILES: CC(C)(CC#N)c1c(-c2ccc(C(=O)O)cc2)c2cc3[nH]ncc3cc2n1Cc1cccnc1Cl]
319
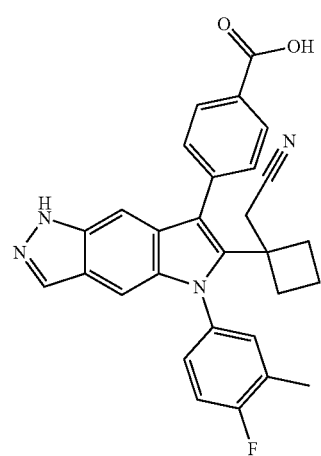 [SMILES: Cc1cc(-n2c(C3(CC#N)CCC3)c(-c3ccc(C(=O)O)cc3)c3cc4[nH]ncc4cc32)ccc1F]
320
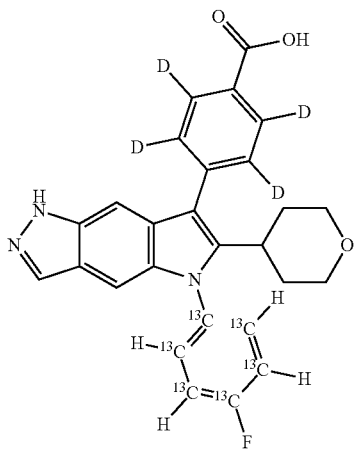 [SMILES: [H]/[13CH]=[13CH]/[13C](F)=[13CH]\[13CH]=[13CH]\n1c(C2CCOCC2)c(-c2c([2H])c([2H])c(C(=O)O)c([2H])c2[2H])c2cc3[nH]ncc3cc21]
321
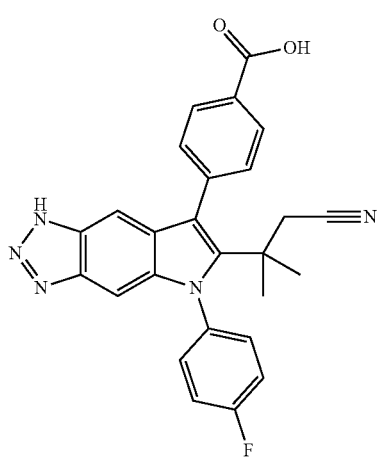 [SMILES: CC(C)(CC#N)c1c(-c2ccc(C(=O)O)cc2)c2cc3[nH]nnc3cc2n1-c1ccc(F)cc1]
322
323

| 324 | 327 |
|---|---|
| 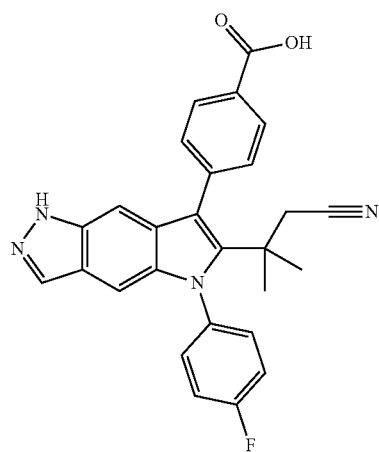 | 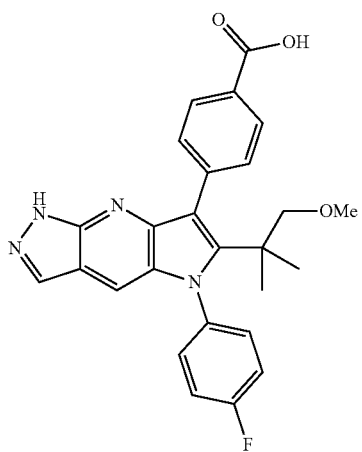 |
| 325 | 328 |
|---|---|
| 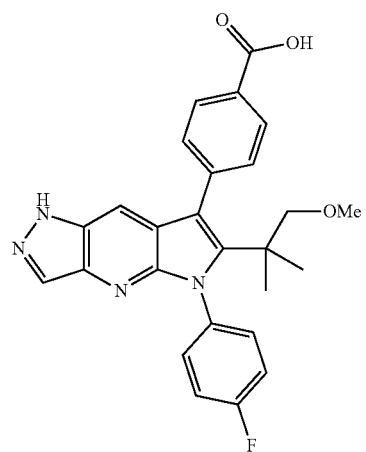 [SMILES: COCC(C)(C)c1c(-c2ccc(C(=O)O)cc2)c2cc3[nH]ncc3nc2n1-c1ccc(F)cc1] | 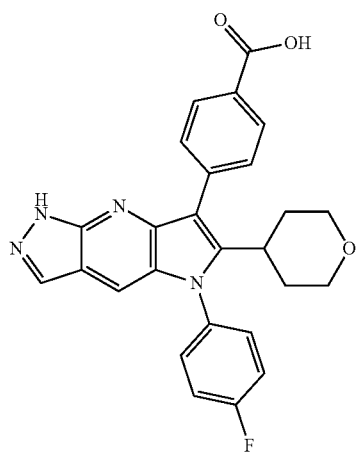 |
| 326 | 329 |
|---|---|
| 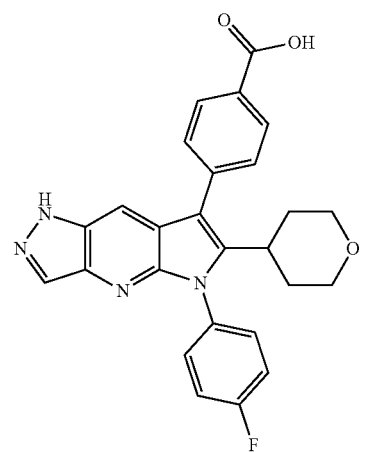 [SMILES: O=C(O)c1ccc(-c2c(C3CCOCC3)n(-c3ccc(F)cc3)c3nc4cn[nH]c4cc23)cc1] | 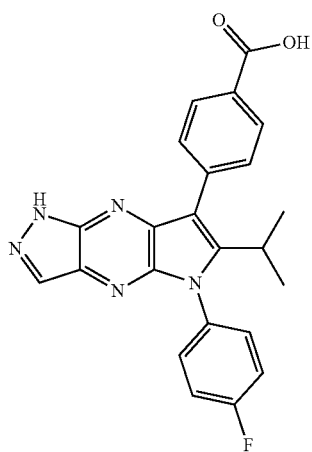 [SMILES: CC(C)c1c(-c2ccc(C(=O)O)cc2)c2nc3[nH]ncc3nc2n1-c1ccc(F)cc1] |

339
-continued
330
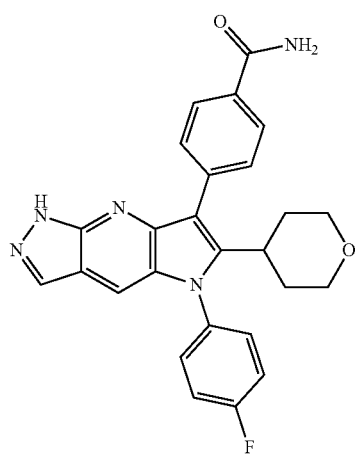 [SMILES: NC(=O)c1ccc(-c2c(C3CCOCC3)n(-c3ccc(F)cc3)c3cc4cn[nH]c4nc23)cc1]
331
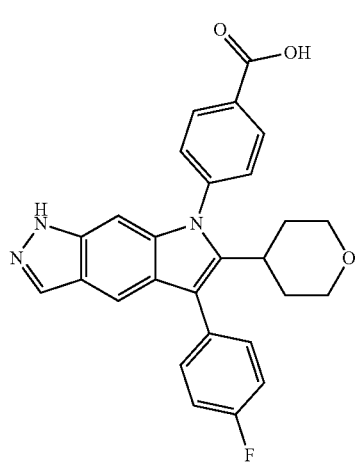
332
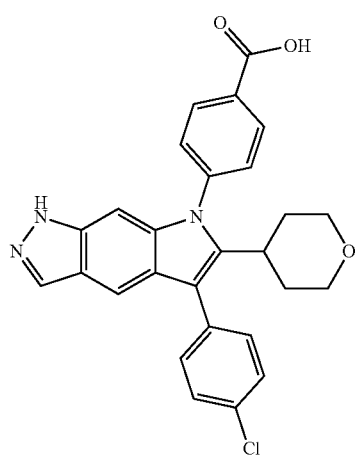
340
-continued
333
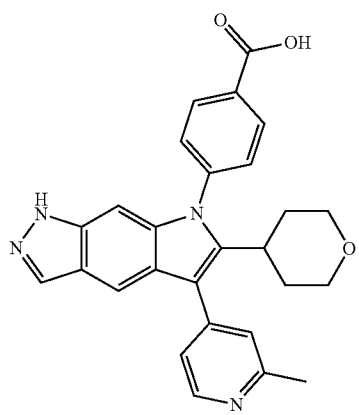
334
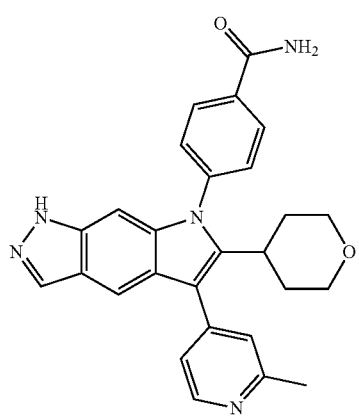
335
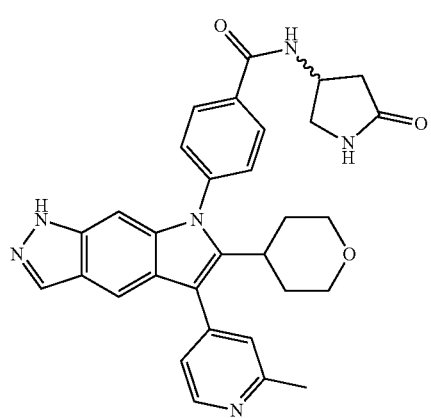 [SMILES: Cc1cc(-c2c(C3CCOCC3)n(-c3ccc(C(=O)NC4CNC(=O)C4)cc3)c3cc4[nH]ncc4cc23)ccn1]

336 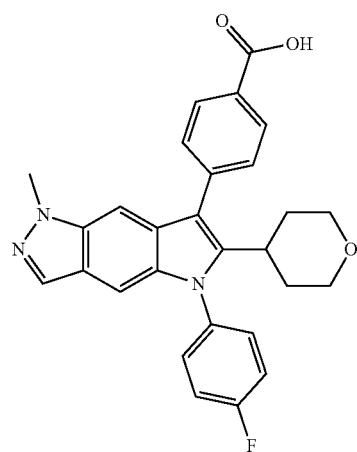
337 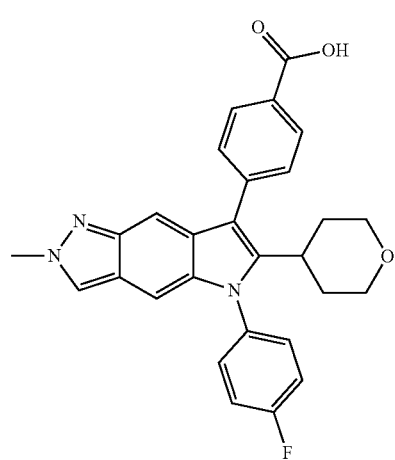 [SMILES: Cn1cc2cc3c(cc2n1)c(-c1ccc(C(=O)O)cc1)c(C1CCOCC1)n3-c1ccc(F)cc1]
338 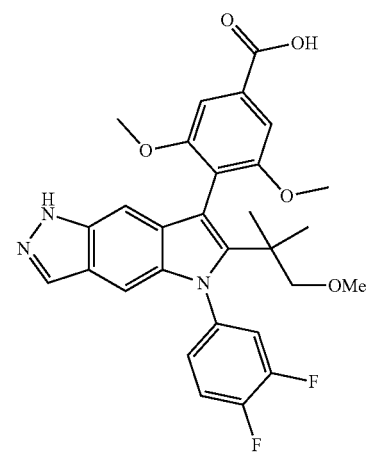 [SMILES: COCC(C)(C)c1c(-c2c(OC)cc(C(=O)O)cc2OC)c2cc3[nH]ncc3cc2n1-c1ccc(F)c(F)c1]
339 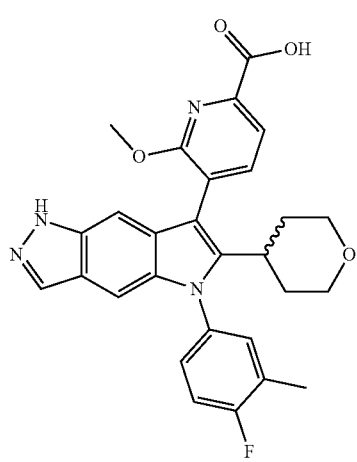
340 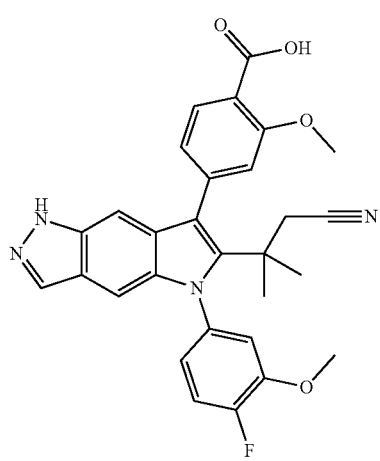 [SMILES: COc1cc(-n2c(C(C)(C)CC#N)c(-c3ccc(C(=O)O)c(OC)c3)c3cc4[nH]ncc4cc32)ccc1F]
341 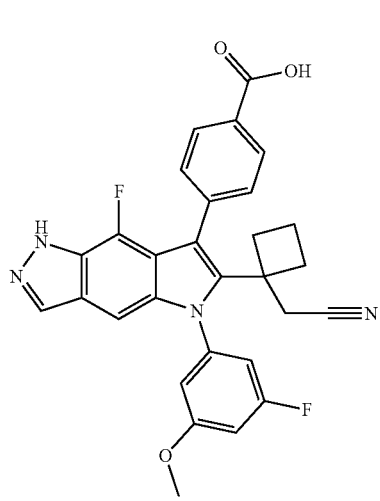 [SMILES: COc1cc(F)cc(-n2c(C3(CC#N)CCC3)c(-c3ccc(C(=O)O)cc3)c3c(F)c4[nH]ncc4cc32)c1]

-continued (342)

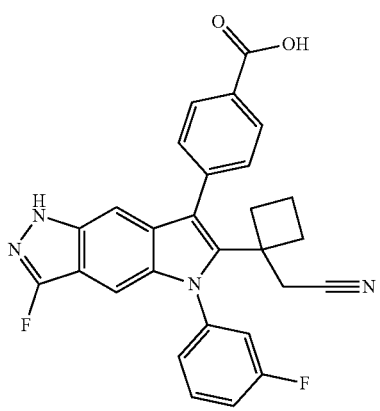

a tautomer thereof, a pharmaceutically acceptable salt of the compound, a pharmaceutically acceptable salt of the tautomer, a deuterated derivative of the compound, a deuterated derivative of the tautomer, and a deuterated derivative of the salt.

12. A pharmaceutical composition comprising a compound according to any one of embodiments 1 to 11, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, and a pharmaceutically acceptable carrier.

13. A method of treating alpha-1 antitrypsin deficiency comprising administering to a patient in need thereof at least one compound chosen from the compounds, the tautomers, pharmaceutically acceptable salts, and the deuterated derivatives according to any one of embodiments 1 to 11, or comprising administering to a patient in need thereof a pharmaceutical composition according to embodiment 12.

14. The method according to embodiment 13, wherein the patient has a Z mutation in alpha-1 antitrypsin.

15. The method according to embodiment 14, wherein the patient has an SZ mutation in alpha-1 antitrypsin.

16. The method according to embodiment 14, wherein the patient is homozygous for Z-mutations in alpha-1 antitrypsin.

17. A method of modulating alpha-1 antitrypsin activity comprising contacting said alpha-1-antitrypsin with at least one compound chosen from the compounds, the tautomers, pharmaceutically acceptable salts, and the deuterated derivatives according to any one of embodiments 1 to 11, or contacting said alpha-1-antitrypsin with a pharmaceutical composition according to embodiment 12.

18. A compound of formula (I'):

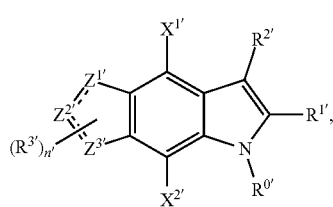

a tautomer thereof, a pharmaceutically acceptable salt of any of the foregoing, and/or a deuterated derivative of any of the foregoing;

wherein:
(i) $R^{0'}$ is chosen from
  (a) $C_1$-$C_8$ linear, branched, and cyclic alkyl groups, wherein the alkyl group is optionally substituted with 1-4 $R^{A'}$; and
  (b) 5- to 14-membered aromatic rings optionally substituted with 1-4 $R^{A'}$,
    wherein each $R^{A'}$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy, and
    wherein an $R^{A'}$ group is optionally linked to an $R^{B'}$ group on an $R^{2'}$ group;
(ii) $R^{1'}$ is chosen from
  (a) hydrogen,
  (b) $C_1$-$C_8$ linear, branched, and cyclic alkyl groups, wherein the alkyl group is optionally substituted with 1-4 substituents independently chosen from
    halogens,
    cyano,
    hydroxy, and
    $C_1$-$C_6$ linear, branched, and cyclic groups, wherein the $C_1$-$C_6$ linear, branched, and cyclic groups are independently chosen from alkyl and alkoxy groups, and wherein the $C_1$-$C_6$ linear, branched, and cyclic groups are optionally substituted with 1-4 substituents independently chosen from
    halogens,
    hydroxy, and
    $C_1$-$C_6$ linear, branched, and cyclic alkoxy groups,
  (c) $C_1$-$C_8$ linear, branched, and cyclic alkoxy or cyclic thioalkyl groups optionally substituted with 1-4 substituents independently chosen from
    halogens,
    cyano,
    sulfone,
    sulfonamide,
    hydroxy, and
    $C_1$-$C_6$ linear, branched, and cyclic alkyl groups that are optionally substituted with 1-4 halogens;
  (d) $C_1$-$C_6$ linear, branched, and cyclic alkylsulfonyl groups;
  (e) aminosulfonyl groups, optionally substituted with 1 or 2 substituents independently chosen from
    $C_1$-$C_6$ linear, branched, and cyclic alkyl groups;
  (f) $C_1$-$C_6$ linear, branched, and cyclic alkylsulfonyl amino groups;
  (g) phosphine oxide groups, optionally substituted with 1 or 2 substituents independently chosen from
    $C_1$-$C_6$ linear, branched, and cyclic alkyl groups; and
  (h) $C_1$-$C_6$ linear, branched, and cyclic trialkylsilyl groups;
(iii) $R^{2'}$ is chosen from 5- and 6-membered aromatic rings comprising 0-4 heteroatoms chosen from O, N, and S, wherein the 5-membered ring is optionally substituted with 1-4 $R^{B'}$ groups and the 6-membered ring is optionally substituted with 1-5 $R^{B'}$ groups, wherein the $R^{B'}$ groups are independently chosen from optionally substituted amides,
imidazolidine-2,4-dione,
optionally substituted heterocyclyls,
phosphorous acid optionally esterified with a $C_1$-$C_6$ linear, branched, or cyclic alkyl group,
di($C_1$-$C_6$)alkylphosphine oxides,
($C_1$-$C_6$)alkylphosphinic acids optionally esterified with a $C_1$-$C_6$ linear, branched, or cyclic alkyl group,
halogens,
cyano,
hydroxy,
carboxylic acids optionally esterified with a uronic acid or a $C_1$-$C_6$ linear, branched, or cyclic alkyl group,
oxo,
dihydroxylboryl,
5- and 6-membered aromatic rings comprising 0-4 heteroatoms independently chosen from O, N, and S, optionally substituted with 1 or 2 substituents independently chosen from $C_1$-$C_6$ linear, branched, and cyclic alkyl groups that are optionally substituted with 1-4 substituents independently chosen from
hydroxy,
carboxylic acids,
pyrrolidin-2-one,
$C_1$-$C_6$ linear, branched, and cyclic alkyl groups, and $C_1$-$C_6$ linear, branched, and cyclic alkylsulfonyl groups, and $C_1$-$C_6$ linear, branched, and cyclic alkoxy groups,
sulfonic acid,
$C_1$-$C_6$ linear, branched, and cyclic alkylsulfonyl groups,
aminosulfonyl groups, optionally substituted with 1 or 2 substituents independently chosen from
$C_1$-$C_6$ linear, branched, and cyclic alkyl groups,
$C_1$-$C_6$ linear, branched, and cyclic alkyl groups that are optionally substituted with 1-4 substituents independently chosen from
halogens,
hydroxy,
carboxylic acid, and
$C_1$-$C_6$ linear, branched, and cyclic alkoxy groups,
$C_1$-$C_6$ linear, branched, and cyclic alkoxy groups that are optionally substituted with 1-4 substituents independently chosen from
halogens,
hydroxy,
carboxylic acid,
$C_1$-$C_6$ linear, branched, and cyclic alkyl groups, and
$C_1$-$C_6$ linear, branched, and cyclic alkoxy groups, and
tetrazolyl groups that are optionally substituted with substituents chosen from
halogens,
hydroxy,
carboxylic acid,
$C_1$-$C_6$ linear, branched, and cyclic alkyl groups, and
$C_1$-$C_6$ linear, branched, and cyclic alkoxy groups,
wherein 2 adjacent hydrogens on the 5- or 6-membered aromatic ring can be replaced by attachments to a second 5- or 6-membered aromatic ring comprising 0-4 heteroatoms independently chosen from O, N, and S to form a bicyclic $R^{2\prime}$ group that is optionally substituted with 1-6 $R^{B\prime}$ groups;
(iv) $X^{1\prime}$ and $X^{2\prime}$ are independently chosen from hydrogen, halogens, cyano, hydroxy, $C_1$-$C_6$ linear, branched, and cyclic groups wherein the $C_1$-$C_6$ linear, branched, and cyclic groups are independently chosen from alkyl, alkoxy, thioalkyl, and aminoalkyl groups, and wherein the $C_1$-$C_6$ linear, branched, and cyclic groups are optionally substituted by 1-4 independently chosen halogens;
(v) each $=$ represents a single or double bond, provided that no more than one $=$ is a double bond;
(vi) each $R^{3\prime}$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 independently chosen halogens;
(vii) n' is an integer chosen from 0, 1, 2, and 3; and
(viii) $Z^{1\prime}$, $Z^{2\prime}$, and $Z^{3\prime}$ are independently chosen from carbon, nitrogen, sulfur, and oxygen, wherein when $Z^{1\prime}$, $Z^{2\prime}$, and/or $Z^{3\prime}$ are carbon or nitrogen, the valences of carbon and nitrogen are completed with hydrogen atoms.

19. The compound according to embodiment 18, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^{0\prime}$ is chosen from heteroaryl rings.

20. The compound of embodiment 18, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^{0\prime}$ is phenyl.

21. The compound according to any one of embodiments 17 to 20, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^{0\prime}$ is unsubstituted.

22. The compound according to any one of embodiments 17 to 20, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^{0\prime}$ is substituted with 1-2 substituents.

23. The compound according to embodiment 22, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein the 1-2 substituents are independently chosen from halogens, $C_1$-$C_4$ alkyl groups, and $C_1$-$C_4$ alkoxy groups.

24. The compound according to embodiment 23, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein the 1-2 substituents are independently chosen from fluorine, methyl, and methoxy.

25. The compound according to embodiment 18, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $R^{1\prime}$ is chosen from $C_1$-$C_4$ linear and branched alkyl groups and $C_4$-$C_6$ cyclic alkyl groups.

26. The compound according to embodiment 25, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein R$^{1\prime}$ is chosen from C$_3$ branched alkyl groups and C$_6$ cyclic alkyl groups.

27. The compound according to embodiment 26, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein R$^{1\prime}$ is chosen from C$_4$-C$_6$ cyclic alkyl groups wherein 1 carbon atom is replaced by a heteroatom.

28. The compound according to embodiment 27, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein R$^{1\prime}$ is chosen from C$_6$ cyclic alkyl groups wherein 1 carbon atom is replaced by a heteroatom.

29. The compound according to any one of embodiments 25-28, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein the alkyl group is substituted with a methyl, ethyl, methoxy, and/or hydroxy substituent.

30. The compound according to embodiment 18, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein R$^{1\prime}$ is chosen from

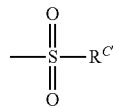

groups, wherein R$^{C\prime}$ is chosen from (a) C$_1$-C$_6$ linear, branched, and cyclic alkyl groups, (b) C$_1$-C$_6$ linear, branched, and cyclic alkyl groups substituted with 1 or 2 substituents independently chosen from C$_1$-C$_6$ linear alkyl groups, (c) C$_1$-C$_6$ linear alkyl groups, and (d) C$_1$-C$_6$ linear alkyl groups substituted with 1 or 2 substituents independently chosen from C$_1$-C$_6$ linear alkyl groups, or wherein R$^{1\prime}$ is chosen from

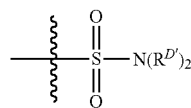

groups, wherein each R$^{D\prime}$ is independently chosen from (e) C$_1$-C$_8$ linear, branched, and cyclic alkyl groups and (f) C$_1$-C$_8$ linear, branched, and cyclic alkyl groups substituted with 1 or 2 substituents independently chosen from C$_1$-C$_6$ linear alkyl groups, or wherein R$^{1\prime}$ is chosen from

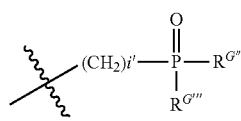

groups, wherein each of R$^{G\prime\prime}$ and R$^{G\prime\prime\prime}$ is independently chosen from (g) C$_1$-C$_8$ linear, branched, and cyclic alkyl groups and (h) C$_1$-C$_8$ linear, branched, and cyclic alkyl groups substituted with 1 or 2 substituents independently chosen from C$_1$-C$_6$ linear alkyl groups.

31. The compound according to any one of embodiments 25-30, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein R$^{1\prime}$ is chosen from:

hydrogen, methyl, trimethylsilyl, trifluoromethyl,

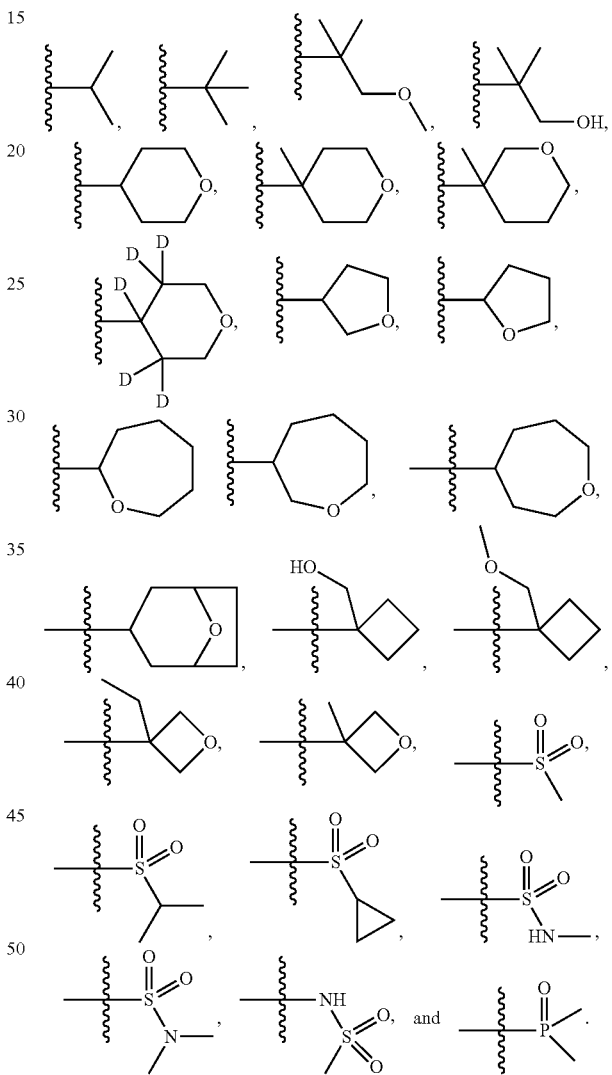

32. The compound according to embodiment 18, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein at least one of Z$^{1\prime}$, Z$^{2\prime}$, and Z$^{3\prime}$ is nitrogen.

33. The compound according to embodiment 32, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein two of $Z^{1'}$, $Z^{2'}$, and $Z^{3'}$ are nitrogen and the other is chosen from carbon and nitrogen.

34. The compound according to any one of embodiments 18 to 33, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein each $R^{3'}$ is independently chosen from hydrogen and $C_1$-$C_6$ linear alkyl groups.

35. The compound according to any one of embodiments 18 to 35, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $X^{1'}$ and $X^{2'}$ are independently chosen from hydrogen and halogen.

36. The compound according to embodiment 35, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein $X^{1'}$ and $X^{2'}$ are each hydrogen.

37. The compound according to embodiment 18 chosen from compounds of Formula I-A', I-B', I-C', I-D', I-E', I-F', I-G', and I-H'

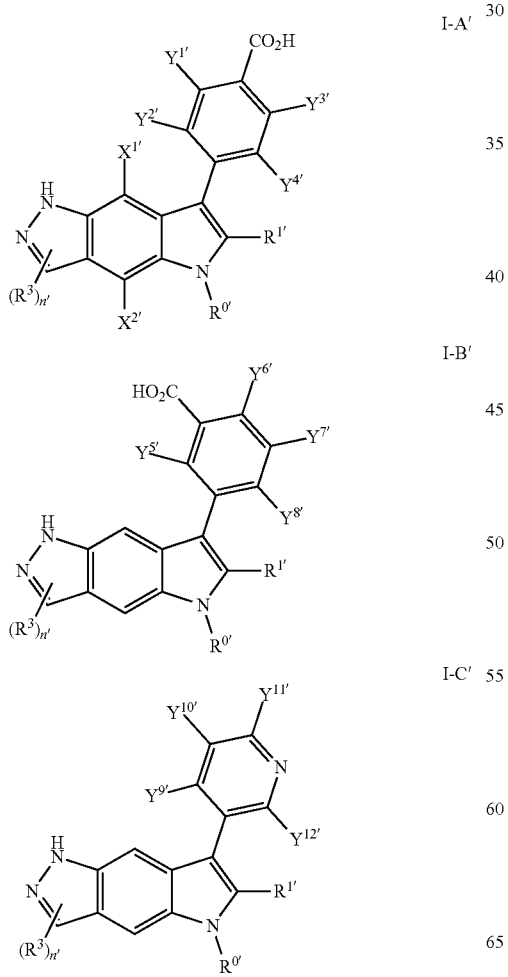

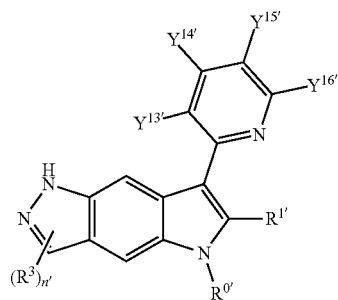

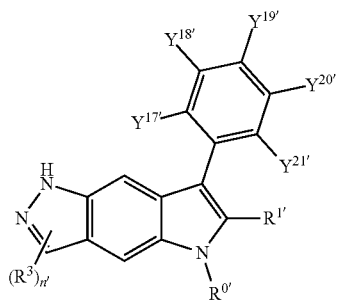

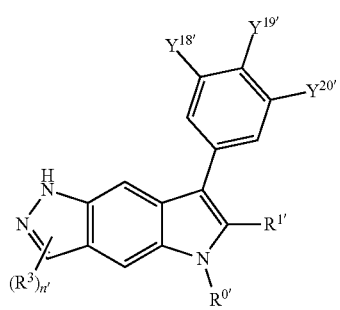

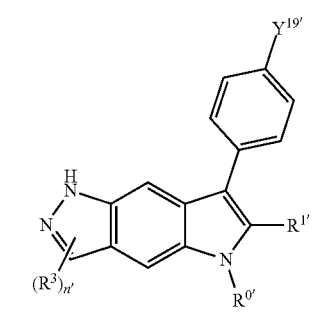

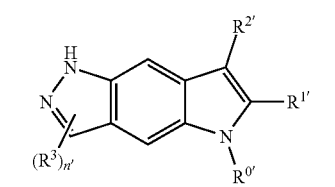

a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, wherein:

$R^{0'}$, $R^{1'}$, $R^{2'}$, $R^{3'}$, and n' are defined for compounds of Formula (I')

$X^{1'}$ and $X^{2'}$ are independently chosen from hydrogen and fluorine, or $X^{1'}$ is fluorine and $X^{2'}$ is hydrogen, or $X^{2'}$ is fluorine and $X^{1'}$ is hydrogen, or $X^{1'}$ and $X^{2'}$ are each hydrogen, $Y^{1'}$, $Y^{2'}$, $Y^{3'}$, and $Y^{4'}$ are independently chosen from
hydrogen,
cyano,
halogen groups,
$C_1$-$C_6$ linear, branched, and cyclic alkyl groups,
$C_1$-$C_6$ linear, branched, and cyclic alkoxy groups that are optionally substituted with 1-4 substituents independently chosen from
hydroxy,
$C_1$-$C_6$ linear, branched, and cyclic alkyl groups, and
$C_1$-$C_6$ linear, branched, and cyclic alkoxy groups;

$Y^{5'}$, $Y^{6'}$, $Y^{7'}$, and $Y^{8'}$ are independently chosen from
hydrogen,
halogen groups
hydroxy,
$C_1$-$C_6$ linear, branched, and cyclic alkyl groups optionally substituted with 1-4 independently chosen halogen substituents, and
$C_1$-$C_6$ linear, branched, and cyclic alkoxy groups, $Y^{9'}$, $Y^{10'}$, $Y^{11'}$, $Y^{12'}$, $Y^{13'}$, $Y^{14'}$, $Y^{15'}$, and $Y^{16'}$ are independently chosen from
carboxylic acid,
hydrogen,
halogen groups,
$C_1$-$C_6$ linear, branched, and cyclic alkylsulfonyl groups,
$C_1$-$C_6$ linear, branched, and cyclic alkyl groups optionally substituted with 1-4 independently chosen halogen substituents, and
$C_1$-$C_6$ linear, branched, and cyclic alkoxy groups, $Y^{17'}$, $Y^{18'}$, $Y^{19'}$, $Y^{20'}$, and $Y^{21'}$ are independently chosen from
hydrogen,
carboxylic acid,
halogen groups,
cyano,
hydroxy,
$C_1$-$C_6$ linear, branched, and cyclic alkyl groups that are optionally substituted with 1-4 substituents independently chosen from
halogens,
hydroxy, and
carboxylic acid,
$C_1$-$C_6$ linear, branched, and cyclic alkoxy groups that are optionally substituted with a carboxylic acid group,
dihydroxyboryl,
sulfonic acid,
carboxylic acid optionally esterified with a uronic acid,
tetrazolyl groups,
aminosulfonyl groups, optionally substituted with 1 or 2 substituents independently chosen from
$C_1$-$C_6$ linear, branched, and cyclic alkyl groups, and
$C_1$-$C_6$ linear, branched, and cyclic alkylsulfonyl groups
with the proviso that, in Formula I-E', at least one of $Y^{17'}$, $Y^{18'}$, $Y^{19'}$, $Y^{20'}$, and $Y^{21'}$ is hydrogen.

38. The compound according to embodiment 37, a tautomer thereof, a pharmaceutically acceptable salt of the compound, a pharmaceutically acceptable salt of the tautomer, a deu-terated derivative of the compound, a deuterated derivative of the tautomer, and/or a deuterated derivative of the salt, wherein one or more of $Y^{17'}$, $Y^{18'}$, $Y^{19'}$, $Y^{20'}$, and $Y^{21'}$ is chosen from methyl, methoxy, cyano, fluorine, hydroxy, —$CF_3$, —$B(OH)_2$, —$SO_2NHMe$, —$SO_2Me$, —$SO_2H$, —$CH_2CO_2H$,

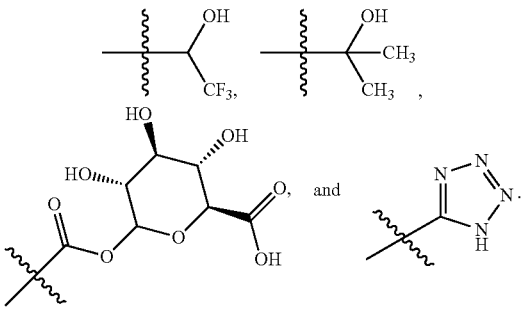

39. A pharmaceutical composition comprising a compound according to embodiment 18, a tautomer thereof, a pharmaceutically acceptable salt of the compound, a pharmaceutically acceptable salt of the tautomer, a deuterated derivative of the compound, a deuterated derivative of the tautomer, and/or a deuterated derivative of the salt, and a pharmaceutically acceptable carrier.

40. A method of treating alpha-1 antitrypsin deficiency comprising administering to a patient in need thereof at least one compound chosen from the compounds, the tautomers, pharmaceutically acceptable salts, and the deuterated derivatives according to any one of embodiments 18 to 38 or a pharmaceutical composition according to embodiment 39.

41. The method according to embodiment 40, wherein the patient has a Z mutation in alpha-1 antitrypsin.

42. The method according to embodiment 41, wherein the patient has an SZ mutation in alpha-1 antitrypsin.

43. The method according to embodiment 41, wherein the patient is homozygous for Z-mutations in alpha-1 antitrypsin.

44. A method of modulating alpha-1 antitrypsin activity comprising contacting said alpha-1-antitrypsin with at least one compound chosen from the compounds, the tautomers, pharmaceutically acceptable salts, and the deuterated derivatives according to any one of embodiments 18 to 38 or a pharmaceutical composition according to embodiment 39.

45. Substantially crystalline Compound 33 Form A (Compound 33)

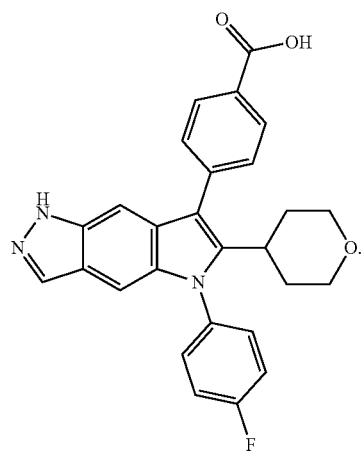

46. The Compound 33 Form A according to Embodiment 45, wherein Compound 33 is substantially pure crystalline Compound 33 Form A.

47. The Compound 33 Form A according to Embodiment 45 or Embodiment 46, wherein Compound 33 Form A is characterized by an X-ray powder diffractogram having signals at one or more of 19.2±0.2 degrees two-theta, 19.5±0.2 degrees two-theta, 15.5±0.2 degrees two-theta, and 17.5±0.2 degrees two-theta.

48. The Compound 33 Form A according to Embodiment 45 or Embodiment 46, wherein Compound 33 Form A is characterized by an X-ray powder diffractogram having signals at 19.2±0.2 degrees two-theta, 19.5±0.2 degrees two-theta, 15.5±0.2 degrees two-theta, and 17.5±0.2 degrees two-theta.

49. The Compound 33 Form A according to Embodiment 45 or Embodiment 46, wherein Compound 33 Form A is characterized by an X-ray powder diffractogram having signals at (a) 19.2±0.2 degrees two-theta, 19.5±0.2 degrees two-theta, 15.5±0.2 degrees two-theta, and 17.5±0.2 degrees two-theta; and (b) at least one, at least two, at least three, at least four, or at least five signals selected from 11.0±0.2 degrees two-theta, 14.2±0.2 degrees two-theta, 16.0±0.2 degrees two-theta, 16.2±0.2 degrees two-theta, 20.9±0.2 degrees two-theta, 21.3±0.2 degrees two-theta, 21.8±0.2 degrees two-theta, and 25.5±0.2 degrees two-theta.

50. The Compound 33 Form A according to Embodiment 45 or Embodiment 46, wherein Compound 33 Form A is characterized by an X-ray powder diffractogram having signals at 11.0±0.2 degrees two-theta, 14.2±0.2 degrees two-theta, 15.5±0.2 degrees two-theta, 16.0±0.2 degrees two-theta, 16.2±0.2 degrees two-theta, 17.5±0.2 degrees two-theta, 19.2±0.2 degrees two-theta, 19.5±0.2 degrees two-theta, 20.9±0.2 degrees two-theta, 21.3±0.2 degrees two-theta, 21.8±0.2 degrees two-theta, and 25.5±0.2 degrees two-theta.

51. The Compound 33 Form A according to Embodiment 45 or Embodiment 46, wherein Compound 33 Form A is characterized by an X-ray powder diffractogram substantially similar to FIG. 1A.

52. The Compound 33 Form A according to any one of Embodiments 45-51, wherein Compound 33 Form A is characterized by a $^{13}C$ solid state nuclear magnetic resonance ($^{13}C$ ssNMR) spectrum with one, two, three, four, five, six, seven, or more peaks selected from 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm.

53. The Compound 33 Form A according to any one of Embodiments 45-51, wherein Compound 33 Form A is characterized by a $^{13}C$ ssNMR spectrum with peaks at 173.5±0.2 ppm, 142.9±0.2 ppm, 136.5±0.2 ppm, 131.8±0.2 ppm, 127.9±0.2 ppm, 112.8±0.2 ppm, 95.0±0.2 ppm, 67.4±0.2 ppm, and 30.8±0.2 ppm.

54. The Compound 33 Form A according to any one of Embodiments 45-51, wherein Compound 33 Form A is characterized by a $^{13}C$ ssNMR spectrum substantially similar to FIG. 1B.

55. The Compound 33 Form A according to any one of Embodiments 45-54, wherein Compound 33 Form A is characterized by a $^{19}F$ solid state nuclear magnetic resonance ($^{19}F$ ssNMR) spectrum having a peak at −109.3±0.2 ppm.

56. The Compound 33 Form A according to any one of Embodiments 45-54, wherein Compound 33 Form A is characterized by a $^{19}F$ ssNMR spectrum substantially similar to FIG. 1C.

57. A pharmaceutical composition comprising the Compound 33 Form A according to any one of Embodiments 45-56 and a pharmaceutically acceptable carrier.

58. A method of treating alpha-1 antitrypsin deficiency comprising administering to a patient in need thereof the Compound 33 Form A according to any one of Embodiments 45-56, or a pharmaceutical composition according to Embodiment 57.

59. The method according to Embodiment 58, wherein the patient has a Z mutation in alpha-1 antitrypsin.

60. The method according to Embodiment 58, wherein the patient has an SZ mutation in alpha-1 antitrypsin.

61. The method according to Embodiment 58, wherein the patient is homozygous for Z-mutations in alpha-1 antitrypsin.

62. Use of the Compound 33 Form A according to any one of Embodiments 45-56 in the manufacture of a medicament for treating alpha-1 antitrypsin deficiency.

63. Substantially crystalline Compound 33 Form B.

64. The Compound 33 Form B according to Embodiment 63, wherein Compound 33 is substantially pure crystalline Compound 33 Form B.

65. The Compound 33 Form B according to Embodiment 63 or Embodiment 64, wherein Compound 33 Form B is characterized by an X-ray powder diffractogram having signals at one or more of 20.2±0.2 degrees two-theta, 9.2±0.2 degrees two-theta, 4.5±0.2 degrees two-theta, and 15.1±0.2 degrees two-theta.

66. The Compound 33 Form B according to Embodiment 63 or Embodiment 64, wherein Compound 33 Form B is characterized by an X-ray powder diffractogram having signals at 20.2±0.2 degrees two-theta, 9.2±0.2 degrees two-theta, 4.5±0.2 degrees two-theta, and 15.1±0.2 degrees two-theta.

67. The Compound 33 Form B according to Embodiment 63 or Embodiment 64, wherein Compound 33 Form B is characterized by an X-ray powder diffractogram having signals (a) at 20.2±0.2 degrees two-theta, 9.2±0.2 degrees two-theta, 4.5±0.2 degrees two-theta, and 15.1±0.2; and (b) at least one, at least two, at least three, at least four, at least five, at least six, at least eight, or at least ten signals selected from 9.9±0.2 degrees two-theta, 11.0±0.2 degrees two-theta, 12.7±0.2 degrees two-theta, 14.3±0.2 degrees two-theta, 16.2±0.2 degrees two-theta, 16.8±0.2 degrees two-theta, 17.1±0.2 degrees two-theta, 18.1±0.2 degrees two-theta, 18.4±0.2 degrees two-theta, 19.8±0.2 degrees two-theta, 20.6±0.2 degrees two-theta, 21.4±0.2 degrees two-theta, 22.3±0.2 degrees two-theta, 23.6±0.2 degrees two-theta, 24.7±0.2 degrees two-theta, 26.6±0.2 degrees two-theta, 27.4±0.2 degrees two-theta, and 28.9±0.2 degrees two-theta.

68. The Compound 33 Form B according to Embodiment 63 or Embodiment 64, wherein Compound 33 Form B is characterized by an X-ray powder diffractogram having signals at 4.5±0.2 degrees two-theta, 9.2±0.2 degrees two-theta, 15.1±0.2 degrees two-theta, 17.1±0.2 degrees two-theta, 18.1±0.2 degrees two-theta, 20.2±0.2 degrees two-theta, 22.3±0.2 degrees two-theta, 26.6±0.2 degrees two-theta, and 27.4±0.2 degrees two-theta.

69. The Compound 33 Form B according to Embodiment 63 or Embodiment 64, wherein Compound 33 Form B is characterized by an X-ray powder diffractogram substantially similar to FIG. 2A.

70. The Compound 33 Form B according to any one of Embodiments 63-69, wherein Compound 33 Form B is characterized by a $^{13}C$ solid state nuclear magnetic resonance ($^{13}C$ ssNMR) spectrum with one, two, three, four, five, six, seven, or more peaks selected from 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm.

71. The Compound 33 Form B according to any one of Embodiments 63-69, wherein Compound 33 Form B is characterized by a $^{13}$C ssNMR spectrum with peaks at 167.9±0.2 ppm, 143.9±0.2 ppm, 133.1±0.2 ppm, 130.1±0.2 ppm, 120.4±0.2 ppm, 100.9±0.2 ppm, 34.1±0.2 ppm, and 31.9±0.2 ppm.

72. The Compound 33 Form B according to any one of Embodiments 63-69, wherein Compound 33 Form B is characterized by a $^{13}$C ssNMR spectrum substantially similar to FIG. 2B.

73. The Compound 33 Form B according to any one of Embodiments 63-72, wherein Compound 33 Form B is characterized by a $^{19}$F solid state nuclear magnetic resonance ($^{19}$F ssNMR) spectrum having a peak at one or more of −110.2±0.2 ppm, 111.6±0.2 ppm, and −115.6±0.2 ppm.

74. The Compound 33 Form B according to any one of Embodiments 63-72, wherein Compound 33 Form B is characterized by a $^{19}$F ssNMR spectrum substantially similar to FIG. 2C.

75. A pharmaceutical composition comprising the Compound 33 Form B according to any one of Embodiments 63-74 and a pharmaceutically acceptable carrier.

76. A method of treating alpha-1 antitrypsin deficiency comprising administering to a patient in need thereof the Compound 33 Form B according to any one of Embodiments 63-74, or a pharmaceutical composition according to Embodiment 75.

77. The method according to Embodiment 76, wherein the patient has a Z mutation in alpha-1 antitrypsin.

78. The method according to Embodiment 76, wherein the patient has an SZ mutation in alpha-1 antitrypsin.

79. The method according to Embodiment 76, wherein the patient is homozygous for Z-mutations in alpha-1 antitrypsin.

80. Use of the Compound 33 Form B according to any one of Embodiments 63-74 in the manufacture of a medicament for treating alpha-1 antitrypsin deficiency.

81. Substantially crystalline Compound 33 Dichloromethane (DCM) Solvate Form A.

82. The Compound 33 DCM Solvate Form A according to Embodiment 81, wherein Compound 33 is substantially pure crystalline Compound 33 DCM Solvate Form A.

83. The Compound 33 DCM Solvate Form A according to Embodiment 81 or Embodiment 82, wherein Compound 33 DCM Solvate Form A is characterized by an X-ray powder diffractogram having signals at one or more of 20.9±0.2 degrees two-theta, 18.3±0.2 degrees two-theta, and 14.4±0.2 degrees two-theta.

84. The Compound 33 DCM Solvate Form A according to Embodiment 81 or Embodiment 82, wherein Compound 33 DCM Solvate Form A is characterized by an X-ray powder diffractogram having signals at 20.9±0.2 degrees two-theta, 18.3±0.2 degrees two-theta, and 14.4±0.2 degrees two-theta.

85. The Compound 33 DCM Solvate Form A according to Embodiment 81 or Embodiment 82, wherein Compound 33 DCM Solvate Form A is characterized by an X-ray powder diffractogram having signals (a) at 20.9±0.2 degrees two-theta, 18.3±0.2 degrees two-theta, and 14.4±0.2 degrees two-theta; and (b) at least one, at least two, at least three, at least four, at least five, at least six, at least eight, or at least ten signals selected from 7.1±0.2 degrees two-theta, 8.8±0.2 degrees two-theta, 9.0±0.2 degrees two-theta, 10.1±0.2 degrees two-theta, 13.3±0.2 degrees two-theta, 13.9±0.2 degrees two-theta, 17.2±0.2 degrees two-theta, 20.3±0.2 degrees two-theta, 21.7±0.2 degrees two-theta, 22.6±0.2 degrees two-theta, 22.8±0.2 degrees two-theta, 23.4±0.2 degrees two-theta, 24.0±0.2 degrees two-theta, 26.6±0.2 degrees two-theta, 27.1±0.2 degrees two-theta, 27.7±0.2 degrees two-theta, 28.3±0.2 degrees two-theta.

86. The Compound 33 DCM Solvate Form A according to Embodiment 81 or Embodiment 82, wherein Compound 33 DCM Solvate Form A is characterized by an X-ray powder diffractogram substantially similar to FIG. 3A.

87. A pharmaceutical composition comprising the Compound 33 DCM Solvate Form A according to any one of Embodiments 81-86 and a pharmaceutically acceptable carrier.

88. A method of treating alpha-1 antitrypsin deficiency comprising administering to a patient in need thereof the Compound 33 DCM Solvate Form A according to any one of Embodiments 81-86, or a pharmaceutical composition according to Embodiment 87.

89. The method according to Embodiment 88, wherein the patient has a Z mutation in alpha-1 antitrypsin.

90. The method according to Embodiment 88, wherein the patient has an SZ mutation in alpha-1 antitrypsin.

91. The method according to Embodiment 88, wherein the patient is homozygous for Z-mutations in alpha-1 antitrypsin.

92. Use of the Compound 33 DCM Solvate Form A according to any one of Embodiments 81-86 in the manufacture of a medicament for treating alpha-1 antitrypsin deficiency.

93. Substantially crystalline Compound 33 Hydrate Form A.

94. The Compound 33 Hydrate Form A according to Embodiment 93, wherein Compound 33 is substantially pure crystalline Compound 33 Hydrate Form A.

95. The Compound 33 Hydrate Form A according to Embodiment 93 or Embodiment 94, wherein Compound 33 Hydrate Form A is characterized by an X-ray powder diffractogram having signals at one or more of 19.5±0.2 degrees two-theta, 10.4±0.2 degrees two-theta, and 16.6±0.2 degrees two-theta.

96. The Compound 33 Hydrate Form A according to Embodiment 93 or Embodiment 94, wherein Compound 33 Hydrate Form A is characterized by an X-ray powder diffractogram having signals at 19.5±0.2 degrees two-theta, 10.4±0.2 degrees two-theta, and 16.6±0.2 degrees two-theta.

97. The Compound 33 Hydrate Form A according to Embodiment 93 or Embodiment 94, wherein Compound 33 Hydrate Form A is characterized by an X-ray powder diffractogram having (a) signals at 19.5±0.2 degrees two-theta, 10.4±0.2 degrees two-theta, and 16.6±0.2 degrees two-theta; and (b) at at least three, at least four, at least five, at least six, at least seven, at least eight, at least nine, or ten signals selected from 13.6±0.2 degrees two-theta, 18.4±0.2 degrees two-theta, 17.5±0.2 degrees two-theta, 18.9±0.2 degrees two-theta, 20.8±0.2 degrees two-theta, 21.1±0.2 degrees two-theta, 21.4±0.2 degrees two-theta, 21.6±0.2 degrees two-theta, 21.8±0.2 degrees two-theta, and 24.8±0.2 degrees two-theta.

98. The Compound 33 Hydrate Form A according to Embodiment 63 or Embodiment 64, wherein Compound 33 Hydrate Form A is characterized by an X-ray powder diffractogram substantially similar to FIG. 4A.

99. The Compound Hydrate Form A according to Embodiment 93 or Embodiment 94, wherein Compound 33 Hydrate Form A is characterized by a triclinic crystal system, a P-1 space group, and the following unit cell dimensions measured at 100 K on a Bruker diffractometer equipped with Cu K$_\alpha$ radiation ($\lambda$=1.54178 Å) and a CMOS detector:

| | |
|---|---|
| a (Å) | 9.98 ± .01 |
| b (Å) | 10.42 ± .01 |
| c (Å) | 11.30 ± .01 |
| α (°) | 74.06 ± .02 |
| β (°) | 78.91 ± .02 |
| γ (°) | 84.14 ± .02 |
| V (Å3) | 1107.3 ± 1.8 |
| Z/Z' | 2/1 |

100. The Compound 33 Hydrate Form A according to any one of Embodiments 93-99, wherein Compound 33 Hydrate Form A is characterized by a $^{13}C$ solid state nuclear magnetic resonance ($^{13}C$ ssNMR) spectrum with one, two, three, four, five, six, seven, or more peaks selected from 172.3±0.2 ppm, 141.6±0.2 ppm, 134.8±0.2 ppm, 132.4±0.2 ppm, 129.6±0.2 ppm, 123.1±0.2 ppm, 32.8±0.2 ppm, and 28.4±0.2 ppm.

101. The Compound 33 Hydrate Form A according to any one of Embodiments 93-99, wherein Compound 33 Hydrate Form A is characterized by a $^{13}C$ ssNMR spectrum with peaks at 172.3±0.2 ppm, 141.6±0.2 ppm, 134.8±0.2 ppm, 132.4±0.2 ppm, 129.6±0.2 ppm, 123.1±0.2 ppm, 32.8±0.2 ppm, and 28.4±0.2 ppm.

102. The Compound 33 Hydrate Form A according to any one of Embodiments 93-99, wherein Compound 33 Hydrate Form A is characterized by a $^{13}C$ ssNMR spectrum substantially similar to FIG. 4B.

103. The Compound 33 Hydrate Form A according to any one of Embodiments 93-102, wherein Compound 33 Hydrate Form A is characterized by a $^{19}F$ solid state nuclear magnetic resonance ($^{19}F$ ssNMR) spectrum having a peak at −103.1±0.2 ppm.

104. The Compound 33 Hydrate Form A according to any one of Embodiments 93-102, wherein Compound 33 Hydrate Form A is characterized by a $^{19}F$ ssNMR spectrum substantially similar to FIG. 4C.

105. A pharmaceutical composition comprising the Compound 33 Hydrate Form A according to any one of Embodiments 93-104 and a pharmaceutically acceptable carrier.

106. A method of treating alpha-1 antitrypsin deficiency comprising administering to a patient in need thereof the Compound 33 Hydrate Form A according to any one of Embodiments 93-104, or a pharmaceutical composition according to Embodiment 105.

107. The method according to Embodiment 106, wherein the patient has a Z mutation in alpha-1 antitrypsin.

108. The method according to Embodiment 106, wherein the patient has an SZ mutation in alpha-1 antitrypsin.

109. The method according to Embodiment 106, wherein the patient is homozygous for Z-mutations in alpha-1 antitrypsin.

110. Use of the Compound 33 Hydrate Form A according to any one of Embodiments 94-104 in the manufacture of a medicament for treating alpha-1 antitrypsin deficiency.

111. Substantially crystalline Compound 33 MeOH/H$_2$O Solvate/Hydrate Form A.

112. The Compound 33 MeOH/H$_2$O Solvate/Hydrate Form A according to Embodiment 111, wherein Compound 33 is substantially pure crystalline Compound 33 MeOH/H$_2$O Solvate/Hydrate Form A.

113. The Compound 33 MeOH/H$_2$O Solvate/Hydrate Form A according to Embodiment 111 or Embodiment 112, wherein Compound 33 MeOH/H$_2$O Solvate/Hydrate Form A is characterized by an X-ray powder diffractogram having signals at one or more of 16.6±0.2 degrees two-theta and 17.4±0.2 degrees two-theta.

114. The Compound 33 MeOH/H$_2$O Solvate/Hydrate Form A according to Embodiment 111 or Embodiment 112, wherein Compound 33 MeOH/H$_2$O Solvate/Hydrate Form A is characterized by an X-ray powder diffractogram having signals at 16.6±0.2 degrees two-theta and 17.4±0.2 degrees two-theta.

115. The Compound 33 MeOH/H$_2$O Solvate/Hydrate Form A according to Embodiment 111 or Embodiment 112, wherein Compound 33 MeOH/H$_2$O Solvate/Hydrate Form A is characterized by an X-ray powder diffractogram having a signal at (a) 16.6±0.2 degrees two-theta and 17.4±0.2 degrees two-theta and (b) one or more of 10.4±0.2 degrees two-theta, 18.2±0.2 degrees two-theta, and 19.4±0.2 degrees two-theta.

116. The Compound 33 MeOH/H$_2$O Solvate/Hydrate Form A according to Embodiment 111 or Embodiment 112, wherein Compound 33 MeOH/H$_2$O Solvate/Hydrate Form A is characterized by an X-ray powder diffractogram having signals at 10.4±0.2 degrees two-theta, 16.6±0.2 degrees two-theta, 17.4±0.2 degrees two-theta, 18.2±0.2 degrees two-theta, and 19.4±0.2 degrees two-theta.

117. The Compound 33 MeOH/H$_2$O Solvate/Hydrate Form A according to Embodiment 111 or Embodiment 112, wherein Compound 33 MeOH/H$_2$O Solvate/Hydrate Form A is characterized by an X-ray powder diffractogram substantially similar to FIG. 5A.

118. The Compound MeOH/H$_2$O Solvate/Hydrate Form A according to Embodiment 111 or Embodiment 112, wherein Compound 33 MeOH/H$_2$O Solvate/Hydrate Form A characterized by a triclinic crystal system, a P-1 space group, and the following unit cell dimensions measured at 100 K on a Bruker diffractometer equipped with Cu K$_\alpha$ radiation (λ=1.54178 Å) and a CMOS detector:

| | |
|---|---|
| a (Å) | 10.02 ± .01 |
| b (Å) | 10.43 ± .01 |
| c (Å) | 11.25 ± .01 |
| α (°) | 74.50 ± .01 |
| β (°) | 79.62 ± .01 |
| γ (°) | 84.98 ± .01 |
| V (Å3) | 1113.5 ± 1.8 |
| Z/Z' | 2/1 |

119. A pharmaceutical composition comprising the Compound 33 MeOH/H$_2$O Solvate/Hydrate Form A according to any one of Embodiments 111-118 and a pharmaceutically acceptable carrier.

120. A method of treating alpha-1 antitrypsin deficiency comprising administering to a patient in need thereof the Compound 33 MeOH/H$_2$O Solvate/Hydrate Form A according to any one of Embodiments 111-118, or a pharmaceutical composition according to Embodiment 119.

121. The method according to Embodiment 120, wherein the patient has a Z mutation in alpha-1 antitrypsin.

122. The method according to Embodiment 120, wherein the patient has an SZ mutation in alpha-1 antitrypsin.

123. The method according to Embodiment 120, wherein the patient is homozygous for Z-mutations in alpha-1 antitrypsin.

124. Use of the Compound 33 MeOH/H$_2$O Solvate/Hydrate Form A according to any one of Embodiments 111-118 in the manufacture of a medicament for treating alpha-1 antitrypsin deficiency.

125. Substantially crystalline Compound 33 Form C.

126. The Compound 33 Form C according to Embodiment 125, wherein Compound 33 is substantially pure crystalline Compound 33 Form C.

127. The Compound 33 Form C according to Embodiment 125 or Embodiment 126, wherein Compound 33 Form C is characterized by an X-ray powder diffractogram having signals at 9.4±0.2 degrees two-theta and 15.4±0.2 degrees two-theta.

128. The Compound 33 Form C according to Embodiment 125 or Embodiment 126, wherein Compound 33 Form C is characterized by an X-ray powder diffractogram having a signal at (a) 9.4±0.2 degrees two-theta and 15.4±0.2 degrees two-theta and (b) 19.0±0.2 degrees two-theta and/or 21.0±0.2 degrees two-theta.

129. The Compound 33 Form C according to Embodiment 125 or Embodiment 126, wherein Compound 33 Form C is characterized by an X-ray powder diffractogram having signals at 9.4±0.2 degrees two-theta, 15.4±0.2 degrees two-theta, 19.0±0.2 degrees two-theta, and 21.0±0.2 degrees two-theta.

130. The Compound 33 Form C according to Embodiment 125 or Embodiment 126, wherein Compound 33 Form C is characterized by an X-ray powder diffractogram having signals at at least four, at least six, or eight two-theta values chosen from 9.4±0.2 degrees two-theta, 15.4±0.2 degrees two-theta, 18.2±0.2 degrees two-theta, 19.0±0.2 degrees two-theta, 19.6±0.2 degrees two-theta, 20.2±0.2 degrees two-theta, 21.0±0.2 degrees two-theta, and 21.5±0.2 degrees two-theta.

131. The Compound 33 Form C according to Embodiment 125 or Embodiment 126, wherein Compound 33 Form C is characterized by an X-ray powder diffractogram substantially similar to FIG. 6A.

132. A pharmaceutical composition comprising the Compound 33 Form C according to any one of Embodiments 125-131 and a pharmaceutically acceptable carrier.

133. A method of treating alpha-1 antitrypsin deficiency comprising administering to a patient in need thereof the Compound 33 Form C according to any one of Embodiments 125-131, or a pharmaceutical composition according to Embodiment 132.

134. The method according to Embodiment 133, wherein the patient has a Z mutation in alpha-1 antitrypsin.

135. The method according to Embodiment 133, wherein the patient has an SZ mutation in alpha-1 antitrypsin.

136. The method according to Embodiment 133, wherein the patient is homozygous for Z-mutations in alpha-1 antitrypsin.

137. Use of the Compound 33 Form C according to any one of Embodiments 125-131 in the manufacture of a medicament for treating alpha-1 antitrypsin deficiency.

138. Substantially crystalline Compound 33 Form D.

139. The Compound 33 Form D according to Embodiment 138, wherein Compound 33 is substantially pure crystalline Compound 33 Form D.

140. The Compound 33 Form D according to Embodiment 138 or Embodiment 139, wherein Compound 33 Form D is characterized by an X-ray powder diffractogram having signals at 14.4±0.2 degrees two-theta and 24.0±0.2 degrees two-theta.

141. The Compound 33 Form D according to Embodiment 138 or Embodiment 139, wherein Compound 33 Form D is characterized by an X-ray powder diffractogram having signals at (a) 14.4±0.2 degrees two-theta and 24.0±0.2 degrees two-theta and (b) 10.4±0.2 degrees two-theta and/or 20.5±0.2 degrees two-theta.

142. The Compound 33 Form D according to Embodiment 138 or Embodiment 139, wherein Compound 33 Form D is characterized by an X-ray powder diffractogram having signals at 10.4±0.2 degrees two-theta, 14.4±0.2 degrees two-theta, 20.5±0.2 degrees two-theta, and 24.0±0.2 degrees two-theta.

143. The Compound 33 Form D according to Embodiment 138 or Embodiment 139, wherein Compound 33 Form D is characterized by an X-ray powder diffractogram having signals at at least four, at least six, at least eight, or at least ten two-theta values chosen from 7.8±0.2 degrees two-theta, 8.2±0.2 degrees two-theta, 8.6±0.2 degrees two-theta, 10.4±0.2 degrees two-theta, 13.7±0.2 degrees two-theta, 14.4±0.2 degrees two-theta, 15.3±0.2 degrees two-theta, 18.6±0.2 degrees two-theta, 18.9±0.2 degrees two-theta, 20.1±0.2 degrees two-theta, 20.5±0.2 degrees two-theta, 21.9±0.2 degrees two-theta, 24.0±0.2 degrees two-theta, and 24.3±0.2 degrees two-theta.

144. The Compound 33 Form D according to Embodiment 137 or Embodiment 138, wherein Compound 33 Form D is characterized by an X-ray powder diffractogram substantially similar to FIG. 7A.

145. A pharmaceutical composition comprising the Compound 33 Form D according to any one of Embodiments 138-144 and a pharmaceutically acceptable carrier.

146. A method of treating alpha-1 antitrypsin deficiency comprising administering to a patient in need thereof the Compound 33 Form D according to any one of Embodiments 138-144, or a pharmaceutical composition according to Embodiment 145.

147. The method according to Embodiment 146, wherein the patient has a Z mutation in alpha-1 antitrypsin.

148. The method according to Embodiment 146, wherein the patient has an SZ mutation in alpha-1 antitrypsin.

149. The method according to Embodiment 146, wherein the patient is homozygous for Z-mutations in alpha-1 antitrypsin.

150. Use of the Compound 33 Form D according to any one of Embodiments 138-144 in the manufacture of a medicament for treating alpha-1 antitrypsin deficiency.

151. Substantially crystalline Compound 33 Form E.

152. The Compound 33 Form E according to Embodiment 151, wherein Compound 33 is substantially pure crystalline Compound 33 Form E.

153. The Compound 33 Form E according to Embodiment 151 or Embodiment 152, wherein Compound 33 Form E is characterized by an X-ray powder diffractogram having signals at 16.2±0.2 degrees two-theta and 17.9±0.2 degrees two-theta.

154. The Compound 33 Form E according to Embodiment 151 or Embodiment 152, wherein Compound 33 Form E is characterized by an X-ray powder diffractogram having signals at (a) 16.2±0.2 degrees two-theta and 17.9±0.2 degrees two-theta and (b) 12.6±0.2 degrees two-theta and/or 20.7±0.2 degrees two-theta.

155. The Compound 33 Form E according to Embodiment 151 or Embodiment 152, wherein Compound 33 Form E is characterized by an X-ray powder diffractogram having signals at 12.6±0.2 degrees two-theta, 16.2±0.2 degrees two-theta, 17.9±0.2 degrees two-theta, and 20.7±0.2 degrees two-theta.

156. The Compound 33 Form E according to Embodiment 151 or Embodiment 152, wherein Compound 33 Form E is characterized by an X-ray powder diffractogram having signals at at least four, at least six, at least eight, at least ten, or at least twelve two-theta values chosen from 7.9±0.2 degrees two-theta, 11.2±0.2 degrees two-theta, 12.6±0.2 degrees two-theta, 12.8±0.2 degrees two-theta, 13.7±0.2 degrees two-theta, 15.3±0.2 degrees two-theta, 16.2±0.2 degrees two-theta, 17.9±0.2 degrees two-theta, 19.9±0.2 degrees two-theta, 20.7±0.2 degrees two-theta, 21.1±0.2 degrees two-theta, 22.5±0.2 degrees two-theta, 22.8±0.2 degrees two-theta, 24.1±0.2 degrees two-theta, 25.0±0.2 degrees two-theta, 27.0±0.2 degrees two-theta, and 28.9±0.2 degrees two-theta.

157. The Compound 33 Form E according to Embodiment 150 or Embodiment 151, wherein Compound 33 Form E is characterized by an X-ray powder diffractogram substantially similar to FIG. 8A.

158. A pharmaceutical composition comprising the Compound 33 Form E according to any one of Embodiments 151-157 and a pharmaceutically acceptable carrier.

159. A method of treating alpha-1 antitrypsin deficiency comprising administering to a patient in need thereof the Compound 33 Form E according to any one of Embodiments 151-157, or a pharmaceutical composition according to Embodiment 143.

160. The method according to Embodiment 159, wherein the patient has a Z mutation in alpha-1 antitrypsin.

161. The method according to Embodiment 159, wherein the patient has an SZ mutation in alpha-1 antitrypsin.

162. The method according to Embodiment 159, wherein the patient is homozygous for Z-mutations in alpha-1 antitrypsin.

163. Use of the Compound 33 Form E according to any one of Embodiments 151-157 in the manufacture of a medicament for treating alpha-1 antitrypsin deficiency.

164. Substantially crystalline Compound 33 Form F.

165. The Compound 33 Form F according to Embodiment 164, wherein Compound 33 is substantially pure crystalline Compound 33 Form F.

166. The Compound 33 Form F according to Embodiment 164 or Embodiment 165, wherein Compound 33 Form F is characterized by an X-ray powder diffractogram having a signal at one or more two-theta values selected from 8.6±0.2 degrees two-theta, 13.0±0.2 degrees two-theta, and 23.0±0.2 degrees two-theta.

167. The Compound 33 Form F according to Embodiment 164 or Embodiment 165, wherein Compound 33 Form F is characterized by an X-ray powder diffractogram having signals at 8.6±0.2 degrees two-theta, 13.0±0.2 degrees two-theta, and 23.0±0.2 degrees two-theta.

168. The Compound 33 Form F according to Embodiment 151 or Embodiment 152, wherein Compound 33 Form F is characterized by an X-ray powder diffractogram having signals at at least four, at least six, at least eight, at least ten, or at least twelve two-theta values chosen from 7.7±0.2 degrees two-theta, 8.6±0.2 degrees two-theta, 11.4±0.2 degrees two-theta, 11.6±0.2 degrees two-theta, 12.2±0.2 degrees two-theta, 13.0±0.2 degrees two-theta, 14.2±0.2 degrees two-theta, 14.9±0.2 degrees two-theta, 17.3±0.2 degrees two-theta, 17.4±0.2 degrees two-theta, 17.8±0.2 degrees two-theta, 18.3±0.2 degrees two-theta, 19.0±0.2 degrees two-theta, 20.4±0.2 degrees two-theta, 21.4±0.2 degrees two-theta, 21.6±0.2 degrees two-theta, 22.6±0.2 degrees two-theta, 22.8±0.2 degrees two-theta, 23.0±0.2 degrees two-theta, 23.3±0.2 degrees two-theta, 24.0±0.2 degrees two-theta, 24.2±0.2 degrees two-theta, 24.9±0.2 degrees two-theta, 25.8±0.2 degrees two-theta, and 26.4±0.2 degrees two-theta.

169. The Compound 33 Form F according to Embodiment 150 or Embodiment 151, wherein Compound 33 Form F is characterized by an X-ray powder diffractogram substantially similar to FIG. 9A.

170. A pharmaceutical composition comprising the Compound 33 Form F according to any one of Embodiments 164-169 and a pharmaceutically acceptable carrier.

171. A method of treating alpha-1 antitrypsin deficiency comprising administering to a patient in need thereof the Compound 33 Form F according to any one of Embodiments 164-169, or a pharmaceutical composition according to Embodiment 170.

172. The method according to Embodiment 171, wherein the patient has a Z mutation in alpha-1 antitrypsin.

173. The method according to Embodiment 171, wherein the patient has an SZ mutation in alpha-1 antitrypsin.

174. The method according to Embodiment 171, wherein the patient is homozygous for Z-mutations in alpha-1 antitrypsin.

175. Use of the Compound 33 Form F according to any one of Embodiments 164-169 in the manufacture of a medicament for treating alpha-1 antitrypsin deficiency.

176. Substantially crystalline Compound 33 Form G.

177. The Compound 33 Form G according to Embodiment 176, wherein Compound 33 is substantially pure crystalline Compound 33 Form G.

178. The Compound 33 Form G according to Embodiment 176 or Embodiment 177, wherein Compound 33 Form G is characterized by an X-ray powder diffractogram having a signal at one or more two-theta values selected from 19.8±0.2 degrees two-theta, 20.2±0.2 degrees two-theta, and 20.8±0.2 degrees two-theta.

179. The Compound 33 Form G according to Embodiment 176 or Embodiment 177, wherein Compound 33 Form G is characterized by an X-ray powder diffractogram signals at 19.8±0.2 degrees two-theta, 20.2±0.2 degrees two-theta, and 20.8±0.2 degrees two-theta.

180. The Compound 33 Form G according to Embodiment 176 or Embodiment 177, wherein Compound 33 Form G is characterized by an X-ray powder diffractogram having signals at at least four, at least six, at least eight, at least ten, or at least twelve two-theta values chosen from 9.3±0.2 degrees two-theta, 10.8±0.2 degrees two-theta, 11.5±0.2 degrees two-theta, 12.6±0.2 degrees two-theta, 17.5±0.2 degrees two-theta, 18.4±0.2 degrees two-theta, 19.1±0.2 degrees two-theta, 19.8±0.2 degrees two-theta, 20.2±0.2 degrees two-theta, 20.8±0.2 degrees two-theta, 21.6±0.2 degrees two-theta, 22.6±0.2 degrees two-theta, 23.4±0.2 degrees two-theta, 24.2±0.2 degrees two-theta and 25.5±0.2 degrees two-theta.

181. The Compound 33 Form G according to Embodiment 176 or Embodiment 177, wherein Compound 33 Form G is characterized by an X-ray powder diffractogram substantially similar to FIG. 10A.

182. A pharmaceutical composition comprising the Compound 33 Form G according to any one of Embodiments 176-181 and a pharmaceutically acceptable carrier.

183. A method of treating alpha-1 antitrypsin deficiency comprising administering to a patient in need thereof the Compound 33 Form G according to any one of Embodiments 176-181, or a pharmaceutical composition according to Embodiment 182.

184. The method according to Embodiment 183, wherein the patient has a Z mutation in alpha-1 antitrypsin.

185. The method according to Embodiment 183, wherein the patient has an SZ mutation in alpha-1 antitrypsin.

186. The method according to Embodiment 183, wherein the patient is homozygous for Z-mutations in alpha-1 antitrypsin.

187. Use of the Compound 33 Form G according to any one of Embodiments 176-181 in the manufacture of a medicament for treating alpha-1 antitrypsin deficiency.

188. Substantially crystalline Compound 33 Form H.

189. The Compound 33 Form H according to Embodiment 188, wherein Compound 33 is substantially pure crystalline Compound 33 Form H.
190. The Compound 33 Form H according to Embodiment 188 or Embodiment 189, wherein Compound 33 Form H is characterized by an X-ray powder diffractogram having a signal at one or more two-theta values selected from 5.0±0.2 degrees two-theta, 18.3±0.2 degrees two-theta, and 19.5±0.2 degrees two-theta.
191. The Compound 33 Form H according to Embodiment 188 or Embodiment 189, wherein Compound 33 Form H is characterized by an X-ray powder diffractogram signals at 5.0±0.2 degrees two-theta, 18.3±0.2 degrees two-theta, and 19.5±0.2 degrees two-theta.
192. The Compound 33 Form H according to Embodiment 188 or Embodiment 189, wherein Compound 33 Form H is characterized by an X-ray powder diffractogram having signals at at least four, at least six, at least eight, at least ten, or at least twelve two-theta values chosen from 5.0±0.2 degrees two-theta, 8.8 degrees two-theta, 15.0 degrees two-theta, 17.6 degrees two-theta, 18.3±0.2 degrees two-theta, 18.9 degrees two-theta, 19.5±0.2 degrees two-theta, and 20.7 degrees two-theta.
193. The Compound 33 Form H according to Embodiment 188 or Embodiment 189, wherein Compound 33 Form H is characterized by an X-ray powder diffractogram having signals at 5.0±0.2 degrees two-theta, 8.8 degrees two-theta, 15.0 degrees two-theta, 17.6 degrees two-theta, 18.3±0.2 degrees two-theta, 18.9 degrees two-theta, 19.5±0.2 degrees two-theta, and 20.7 degrees two-theta.
194. The Compound 33 Form H according to Embodiment 188 or Embodiment 189, wherein Compound 33 Form H is characterized by an X-ray powder diffractogram substantially similar to FIG. 11A.
195. A pharmaceutical composition comprising the Compound 33 Form H according to any one of Embodiments 188-194 and a pharmaceutically acceptable carrier.
196. A method of treating alpha-1 antitrypsin deficiency comprising administering to a patient in need thereof the Compound 33 Form H according to any one of Embodiments 188-194, or a pharmaceutical composition according to Embodiment 195.
197. The method according to Embodiment 196, wherein the patient has a Z mutation in alpha-1 antitrypsin.
198. The method according to Embodiment 196, wherein the patient has an SZ mutation in alpha-1 antitrypsin.
199. The method according to Embodiment 196, wherein the patient is homozygous for Z-mutations in alpha-1 antitrypsin.
200. Use of the Compound 33 Form H according to any one of Embodiments 188-194 in the manufacture of a medicament for treating alpha-1 antitrypsin deficiency.
214. Substantially crystalline Compound 33 Form I.
215. The Compound 33 Form I according to Embodiment 214, wherein Compound 33 is substantially pure crystalline Compound 33 Form I.
216. The Compound 33 Form I according to Embodiment 214 or Embodiment 215, wherein Compound 33 Form I is characterized by an X-ray powder diffractogram having signals at 9.3±0.2 degrees two-theta, 19.0±0.2 degrees two-theta, and 21.0±0.2 degrees two-theta.
217. The Compound 33 Form I according to Embodiment 214 or Embodiment 215, wherein Compound 33 Form I is characterized by an X-ray powder diffractogram having signals at at least four, at least five, or at least six two-theta values chosen from 9.3±0.2 degrees two-theta, 15.4±0.2 degrees two-theta, 18.3±0.2 degrees two-theta, 18.6±0.2 degrees two-theta, 19.0±0.2 degrees two-theta, 20.2±0.2 degrees two-theta, and 21.0±0.2 degrees two-theta.
218. The Compound 33 Form I according to Embodiment 214 or Embodiment 215, wherein Compound 33 Form I is characterized by an X-ray powder diffractogram having signals at 9.3±0.2 degrees two-theta, 15.4±0.2 degrees two-theta, 18.3±0.2 degrees two-theta, 18.6±0.2 degrees two-theta, 19.0±0.2 degrees two-theta, 20.2±0.2 degrees two-theta, and 21.0±0.2 degrees two-theta.
219. The Compound 33 Form I according to Embodiment 214 or Embodiment 215, wherein Compound 33 Form I is characterized by an X-ray powder diffractogram substantially similar to FIG. 12C.
220. A pharmaceutical composition comprising the Compound 33 Form I according to any one of Embodiments 214-219 and a pharmaceutically acceptable carrier.
221. A method of treating alpha-1 antitrypsin deficiency comprising administering to a patient in need thereof the Compound 33 Form I according to any one of Embodiments 214-219, or a pharmaceutical composition according to Embodiment 220.
222. The method according to Embodiment 221, wherein the patient has a Z mutation in alpha-1 antitrypsin.
223. The method according to Embodiment 221, wherein the patient has an SZ mutation in alpha-1 antitrypsin.
224. The method according to Embodiment 221, wherein the patient is homozygous for Z-mutations in alpha-1 antitrypsin.
225. Use of the Compound 33 Form I according to any one of Embodiments 214-219 in the manufacture of a medicament for treating alpha-1 antitrypsin deficiency.
226. Substantially crystalline Compound 33 Tetrahydrofuran (THF) Solvate Form A.
227. The Compound 33 THF Solvate Form A according to Embodiment 226, wherein Compound 33 is substantially pure crystalline Compound 33 THF Solvate Form A.
228. The Compound 33 THF Solvate Form A according to Embodiment 226 or Embodiment 227, wherein Compound 33 THF Solvate Form A is characterized by an X-ray powder diffractogram having a signal at 8.2±0.2 degrees two-theta and/or 8.5±0.2 degrees two-theta.
229. The Compound 33 THF Solvate Form A according to Embodiment 226 or Embodiment 227, wherein Compound 33 THF Solvate Form A is characterized by an X-ray powder diffractogram having a signal at 19.1±0.2 degrees two-theta and/or 19.4±0.2 degrees two-theta.
230. The Compound 33 THF Solvate Form A according to Embodiment 226 or Embodiment 227, wherein Compound 33 THF Solvate Form A is characterized by an X-ray powder diffractogram having signals at 8.2±0.2 degrees two-theta, 8.5±0.2 degrees two-theta, 19.1±0.2 degrees two-theta, and 19.4±0.2 degrees two-theta.
231. The Compound 33 THF Solvate Form A according to Embodiment 226 or Embodiment 227, wherein Compound 33 THF Solvate Form A is characterized by an X-ray powder diffractogram having a signal at at least four, at least six, at least eight, or at least ten two-theta values chosen from 8.2±0.2 degrees two-theta, 8.5±0.2 degrees two-theta, 9.5±0.2 degrees two-theta, 11.3±0.2 degrees two-theta, 17.1±0.2 degrees two-theta, 17.8±0.2 degrees two-theta, 19.1±0.2 degrees two-theta, 19.4±0.2 degrees two-theta, 20.5±0.2 degrees two-theta, 21.1±0.2 degrees two-theta, 21.2±0.2 degrees two-theta, 21.5±0.2 degrees two-theta, 22.9±0.2 degrees two-theta, and 23.1±0.2 degrees two-theta.
232. The Compound 33 THF Solvate Form A according to Embodiment 226 or Embodiment 227, wherein Compound 33 THF Solvate Form A is characterized by an X-ray powder diffractogram substantially similar to FIG. 13A.

233. The Compound 33 THF Solvate Form A according to Embodiment 226 or Embodiment 227, wherein Compound 33 THF Solvate Form A is characterized by a orthorhombic crystal system, a Pca21 space group, and the following unit cell dimensions measured at 100° K on a Bruker diffractometer equipped with Cu $K_\alpha$ radiation ($\lambda$=1.54178 Å) and a CMOS detector:

| | |
|---|---|
| a (Å) | 25.12 ± .01 |
| b (Å) | 11.98 ± .01 |
| c (Å) | 17.7 ± 0.1 |
| $\alpha$ (°) | 90 |
| $\beta$ (°) | 90 |
| $\gamma$ (°) | 90 |
| V (Å3) | 5327 ± 30 |
| Z/Z' | 4/2 |

234. The Compound 33 THF Solvate Form A according to any one of Embodiments 226-233, wherein Compound 33 THF Solvate Form A is characterized as having a $^{13}$C solid state nuclear magnetic resonance ($^{13}$C ssNMR) spectrum with one, two, three, four, five, six, seven, or more peaks selected from 165.8±0.2 ppm, 140.0±0.2 ppm, 133.9±0.2 ppm, 121.2±0.2 ppm, 114.3±0.2 ppm, 96.1±0.2 ppm, 69.0±0.2 ppm, 25.7±0.2 ppm, and 25.3±0.2 ppm.

235. The Compound 33 THF Solvate Form A according to any one of Embodiments 226-233, wherein Compound 33 THF Solvate Form A is characterized as having a $^{13}$C ssNMR spectrum substantially similar to FIG. 13B.

236. The Compound 33 THF Solvate Form A according to any one of Embodiments 226-235, wherein Compound 33 THF Solvate Form A is characterized by a $^{19}$F solid state nuclear magnetic resonance ($^{19}$F ssNMR) spectrum having a peak at −110.5±0.2 ppm and/or −113.0±0.2 ppm.

237. The Compound 33 THF Solvate Form A according to any one of Embodiments 226-236, wherein Compound 33 THF Solvate Form A is characterized by a $^{19}$F ssNMR spectrum substantially similar to FIG. 13C.

238. A pharmaceutical composition comprising the Compound 33 THF Solvate Form A according to any one of Embodiments 226-237 and a pharmaceutically acceptable carrier.

239. A method of treating alpha-1 antitrypsin deficiency comprising administering to a patient in need thereof the Compound 33 THF Solvate Form A according to any one of Embodiments 201-206, or a pharmaceutical composition according to Embodiment 238.

240. The method according to Embodiment 239, wherein the patient has a Z mutation in alpha-1 antitrypsin.

241. The method according to Embodiment 239, wherein the patient has an SZ mutation in alpha-1 antitrypsin.

242. The method according to Embodiment 239, wherein the patient is homozygous for Z-mutations in alpha-1 antitrypsin.

243. Use of the Compound 33 THF Solvate Form A according to any one of Embodiments 226-237 in the manufacture of a medicament for treating alpha-1 antitrypsin deficiency.

244. Substantially crystalline Compound 33 Form J.

245. The Compound 33 Form J according to Embodiment 244, wherein Compound 33 is substantially pure crystalline Compound 33 Form J.

246. The Compound 33 Form J according to Embodiment 244 or Embodiment 245, wherein Compound 33 Form J is characterized by an X-ray powder diffractogram having signals at one or more of 6.6±0.2 degrees two-theta, 7.5±0.2 degrees two-theta, and 15.0±0.2 degrees two-theta.

247. The Compound 33 Form J according to Embodiment 244 or Embodiment 245, wherein Compound 33 Form J is characterized by an X-ray powder diffractogram having signals at 6.6±0.2 degrees two-theta, 7.5±0.2 degrees two-theta, and 15.0±0.2 degrees two-theta.

248. The Compound 33 Form J according to Embodiment 244 or Embodiment 245, wherein Compound 33 Form J is characterized by an X-ray powder diffractogram having (a) signals at 6.6±0.2 degrees two-theta, 7.5±0.2 degrees two-theta, and 15.0±0.2 degrees two-theta; and (b) a signal at at least one, at least two, at least three, at least four, at least six, at least eight, or at least ten two-theta values chosen from 10.3±0.2 degrees two-theta, 15.6±0.2 degrees two-theta, 16.0±0.2 degrees two-theta, 16.8±0.2 degrees two-theta, 17.9±0.2 degrees two-theta, 19.4±0.2 degrees two-theta, 19.9±0.2 degrees two-theta, 20.1±0.2 degrees two-theta, 20.6±0.2 degrees two-theta, 20.8±0.2 degrees two-theta, 21.4±0.2 degrees two-theta, 21.7±0.2 degrees two-theta, and 22.5±0.2 degrees two-theta.

249. The Compound 33 Form J according to Embodiment 244 or Embodiment 245, wherein Compound 33 Form J is characterized by an X-ray powder diffractogram substantially similar to FIG. 14A.

250. A pharmaceutical composition comprising the Compound 33 Form J according to any one of Embodiments 244-249 and a pharmaceutically acceptable carrier.

251. A method of treating alpha-1 antitrypsin deficiency comprising administering to a patient in need thereof the Compound 33 Form J according to any one of Embodiments 244-249, or a pharmaceutical composition according to Embodiment 250.

252. The method according to Embodiment 251, wherein the patient has a Z mutation in alpha-1 antitrypsin.

253. The method according to Embodiment 251, wherein the patient has an SZ mutation in alpha-1 antitrypsin.

254. The method according to Embodiment 252, wherein the patient is homozygous for Z-mutations in alpha-1 antitrypsin.

255. Use of the Compound 33 Form J according to any one of Embodiments 244-249 in the manufacture of a medicament for treating alpha-1 antitrypsin deficiency.

256. Substantially crystalline Compound 33 Form K.

257. The Compound 33 Form K according to Embodiment 256, wherein Compound 33 is substantially pure crystalline Compound 33 Form K.

258. The Compound 33 Form K according to Embodiment 256 or Embodiment 257, wherein Compound 33 Form K is characterized by an X-ray powder diffractogram having a signal at 14.5±0.2 degrees two-theta.

259. The Compound 33 Form K according to Embodiment 256 or Embodiment 257, wherein Compound 33 Form K is characterized by an X-ray powder diffractogram having signals at 14.5±0.2 degrees two-theta and at one or more of 9.7±0.2 degrees two-theta, 19.7±0.2 degrees two-theta, and 20.5±0.2 degrees two-theta.

260. The Compound 33 Form K according to Embodiment 256 or Embodiment 257, wherein Compound 33 Form K is characterized by an X-ray powder diffractogram having signals at 9.7±0.2 degrees two-theta, 14.5±0.2 degrees two-theta, 19.7±0.2 degrees two-theta, and 20.5±0.2 degrees two-theta.

261. The Compound 33 Form K according to Embodiment 256 or Embodiment 257, wherein Compound 33 Form K is characterized by an X-ray powder diffractogram having (a) signals at signals at 9.7±0.2 degrees two-theta, 14.5±0.2 degrees two-theta, 19.7±0.2 degrees two-theta, and 20.5±0.2 degrees two-theta, and a signal at at least one, at least two, at least three, at least four, at least five, or at least six, two-theta values chosen from 11.2±0.2 degrees two-theta, 14.5±0.2 degrees two-theta, 17.0±0.2 degrees two-theta, 19.1±0.2 degrees two-theta, 19.4±0.2 degrees two-theta, 21.0±0.2 degrees two-theta, and 24.4±0.2 degrees two-theta.

262. The Compound 33 Form K according to Embodiment 256 or Embodiment 257, wherein Compound 33 Form K is characterized by an X-ray powder diffractogram substantially similar to FIG. 15A.

263. A pharmaceutical composition comprising the Compound 33 Form K according to any one of Embodiments 256-262 and a pharmaceutically acceptable carrier.

264. A method of treating alpha-1 antitrypsin deficiency comprising administering to a patient in need thereof the Compound 33 Form K according to any one of Embodiments 256-262, or a pharmaceutical composition according to Embodiment 263.

265. The method according to Embodiment 264, wherein the patient has a Z mutation in alpha-1 antitrypsin.

266. The method according to Embodiment 264, wherein the patient has an SZ mutation in alpha-1 antitrypsin.

267. The method according to Embodiment 264, wherein the patient is homozygous for Z-mutations in alpha-1 antitrypsin.

268. Use of the Compound 33 Form K according to any one of Embodiments 256-262 in the manufacture of a medicament for treating alpha-1 antitrypsin deficiency.

269. Substantially crystalline Compound 33 2-Methyltetrahydrofuran (2-MeTHF) Solvate Form A.

270. The Compound 33 2-MeTHF Solvate Form A according to Embodiment 269, wherein Compound 33 is substantially pure crystalline Compound 33 2-MeTHF Solvate Form A.

271. The Compound 33 2-MeTHF Solvate Form A according to Embodiment 269 or Embodiment 270, wherein Compound 33 2-MeTHF Solvate Form A is characterized by an X-ray powder diffractogram having a signal a signal at 18.1±0.2 degrees two-theta, 19.0±0.2 degrees two-theta, and/or 21.3±0.2 degrees two-theta.

272. The Compound 33 2-MeTHF Solvate Form A according to Embodiment 269 or Embodiment 270, wherein Compound 33 2-MeTHF Solvate Form A is characterized by an X-ray powder diffractogram having having (a) signals at 18.1±0.2 degrees two-theta, 19.0±0.2 degrees two-theta, and 21.3±0.2 degrees two-theta; and (b) a signal at at least one, at least two, at least three, or at four two-theta values chosen from 13.8±0.2 degrees two-theta, 18.7±0.2 degrees two-theta, 20.0±0.2 degrees two-theta, and 20.8±0.2 degrees two-theta.

273. The Compound 33 2-MeTHF Solvate Form A according to Embodiment 269 or Embodiment 270, wherein Compound 33 2-MeTHF Solvate Form A is characterized by an X-ray powder diffractogram substantially similar to FIG. 16A.

274. A pharmaceutical composition comprising the Compound 33 2-MeTHF Solvate Form A according to any one of Embodiments 256-262 and a pharmaceutically acceptable carrier.

275. A method of treating alpha-1 antitrypsin deficiency comprising administering to a patient in need thereof the Compound 33 2-MeTHF Solvate Form A according to any one of Embodiments 269-273, or a pharmaceutical composition according to Embodiment 274.

276. The method according to Embodiment 275, wherein the patient has a Z mutation in alpha-1 antitrypsin.

277. The method according to Embodiment 275, wherein the patient has an SZ mutation in alpha-1 antitrypsin.

278. The method according to Embodiment 275, wherein the patient is homozygous for Z-mutations in alpha-1 antitrypsin.

279. Use of the Compound 33 2-MeTHF Solvate Form A according to any one of Embodiments 269-273 in the manufacture of a medicament for treating alpha-1 antitrypsin deficiency.

280. Substantially crystalline Compound 33 Form L.

281. The Compound 33 Form L according to Embodiment 280, wherein Compound 33 is substantially pure crystalline Compound 33 Form L.

282. The Compound 33 Form L according to Embodiment 280 or Embodiment 281, wherein Compound 33 Form L is characterized by an X-ray powder diffractogram having a signal at 14.5±0.2 degrees two-theta.

283. The Compound 33 Form L according to Embodiment 280 or Embodiment 281, wherein Compound 33 Form L is characterized by an X-ray powder diffractogram having signals at one or more of 14.5±0.2 degrees two-theta, 14.6±0.2 degrees two-theta, 16.3±0.2 degrees two-theta, and 17.3±0.2 degrees two-theta.

284. The Compound 33 Form L according to Embodiment 280 or Embodiment 281, wherein Compound 33 Form L is characterized by an X-ray powder diffractogram having signals at 14.5±0.2 degrees two-theta, 14.6±0.2 degrees two-theta, 16.3±0.2 degrees two-theta, and 17.3±0.2 degrees two-theta.

285. The Compound 33 Form L according to Embodiment 280 or Embodiment 281, wherein Compound 33 Form L is characterized by an X-ray powder diffractogram having (a) signals at 14.5±0.2 degrees two-theta, 14.6±0.2 degrees two-theta, 16.3±0.2 degrees two-theta, and 17.3±0.2 degrees two-theta; and (b) a signal at at least one, at least two, at least four, at least six, at least eight, or at least ten two-theta values chosen from 7.0±0.2 degrees two-theta, 8.8±0.2 degrees two-theta, 9.9±0.2 degrees two-theta, 13.7±0.2 degrees two-theta, 17.6±0.2 degrees two-theta, 17.9±0.2 degrees two-theta, 18.6±0.2 degrees two-theta, 18.8±0.2 degrees two-theta, 19.7±0.2 degrees two-theta, 20.2±0.2 degrees two-theta, 20.4±0.2 degrees two-theta, 20.7±0.2 degrees two-theta, 20.9±0.2 degrees two-theta, 21.0±0.2 degrees two-theta, 21.9±0.2 degrees two-theta, 22.2±0.2 degrees two-theta, 23.1±0.2 degrees two-theta, 23.6±0.2 degrees two-theta, 27.1±0.2 degrees two-theta, 28.6±0.2 degrees two-theta, and 31.7±0.2 degrees two-theta.

286. The Compound 33 Form L according to Embodiment 280 or Embodiment 281, wherein Compound 33 Form L is characterized by an X-ray powder diffractogram substantially similar to FIG. 17A.

287. A pharmaceutical composition comprising the Compound 33 Form L according to any one of Embodiments 281-286 and a pharmaceutically acceptable carrier.

288. A method of treating alpha-1 antitrypsin deficiency comprising administering to a patient in need thereof the Compound 33 Form L according to any one of Embodiments 281-286, or a pharmaceutical composition according to Embodiment 287.

289. The method according to Embodiment 288, wherein the patient has a Z mutation in alpha-1 antitrypsin.

290. The method according to Embodiment 288, wherein the patient has an SZ mutation in alpha-1 antitrypsin.

291. The method according to Embodiment 288, wherein the patient is homozygous for Z-mutations in alpha-1 antitrypsin.

292. Use of the Compound 33 Form L according to any one of Embodiments 281-286 in the manufacture of a medicament for treating alpha-1 antitrypsin deficiency.

293. Substantially crystalline Compound 33 Form M.

294. The Compound 33 Form M according to Embodiment 293, wherein Compound 33 is substantially pure crystalline Compound 33 Form M.

295. The Compound 33 Form M according to Embodiment 292 or Embodiment 293, wherein Compound 33 Form M is characterized by an X-ray powder diffractogram having a signal at one or more of 18.3±0.2 degrees two-theta, 18.9±0.2 degrees two-theta, and 21.2±0.2 degrees two-theta.

296. The Compound 33 Form M according to Embodiment 292 or Embodiment 293, wherein Compound 33 Form M is characterized by an X-ray powder diffractogram having signals at 18.3±0.2 degrees two-theta, 18.9±0.2 degrees two-theta, and 21.2±0.2 degrees two-theta.

297. The Compound 33 Form M according to Embodiment 292 or Embodiment 293, wherein Compound 33 Form M is characterized by an X-ray powder diffractogram having (a) signals at of 18.3±0.2 degrees two-theta, 18.9±0.2 degrees two-theta, and 21.2±0.2 degrees two-theta; and (b) a signal at at least one, at least two, at least three, or at least four two-theta values chosen from 7.0±0.2 degrees two-theta, 8.4±0.2 degrees two-theta, 11.3±0.2 degrees two-theta, 13.8±0.2 degrees two-theta, 16.0±0.2 degrees two-theta, 17.2±0.2 degrees two-theta, 9.4±0.2 degrees two-theta, 20.6±0.2 degrees two-theta, and 21.7±0.2 degrees two-theta.

298. The Compound 33 Form M according to Embodiment 292 or Embodiment 293, wherein Compound 33 Form M is characterized by an X-ray powder diffractogram substantially similar to FIG. 18A.

299. A pharmaceutical composition comprising the Compound 33 Form M according to any one of Embodiments 293-298 and a pharmaceutically acceptable carrier.

300. A method of treating alpha-1 antitrypsin deficiency comprising administering to a patient in need thereof the Compound 33 Form M according to any one of Embodiments 293-298, or a pharmaceutical composition according to Embodiment 299.

301. The method according to Embodiment 300, wherein the patient has a Z mutation in alpha-1 antitrypsin.

302. The method according to Embodiment 300, wherein the patient has an SZ mutation in alpha-1 antitrypsin.

303. The method according to Embodiment 300, wherein the patient is homozygous for Z-mutations in alpha-1 antitrypsin.

304. Use of the Compound 33 Form M according to any one of Embodiments 293-298 in the manufacture of a medicament for treating alpha-1 antitrypsin deficiency.

305. Substantially crystalline Compound 33 Form N.

306. The Compound 33 Form N according to Embodiment 305, wherein Compound 33 is substantially pure crystalline Compound 33 Form N.

307. The Compound 33 Form N according to Embodiment 305 or Embodiment 306, wherein Compound 33 Form N is characterized by an X-ray powder diffractogram having a signal at one or more of 13.0±0.2 degrees two-theta, 14.3±0.2 degrees two-theta, and 18.2±0.2 degrees two-theta.

308. The Compound 33 Form N according to Embodiment 305 or Embodiment 306, wherein Compound 33 Form N is characterized by an X-ray powder diffractogram having signals at 13.0±0.2 degrees two-theta, 14.3±0.2 degrees two-theta, and 18.2±0.2 degrees two-theta.

309. The Compound 33 Form N according to Embodiment 305 or Embodiment 306, wherein Compound 33 Form N is characterized by an X-ray powder diffractogram having (a) signals at 13.0±0.2 degrees two-theta, 14.3±0.2 degrees two-theta, and 18.2±0.2 degrees two-theta; and (b) a signal at at least two, at least four, at least six, at least eight, or at least ten two-theta values chosen from 4.2±0.2 degrees two-theta, 8.8±0.2 degrees two-theta, 11.7±0.2 degrees two-theta, 12.3±0.2 degrees two-theta, 12.6±0.2 degrees two-theta, 15.6±0.2 degrees two-theta, 17.1±0.2 degrees two-theta, 17.6±0.2 degrees two-theta, 18.7±0.2 degrees two-theta, 19.2±0.2 degrees two-theta, 19.6±0.2 degrees two-theta, 20.5±0.2 degrees two-theta, 21.5±0.2 degrees two-theta, 21.8±0.2 degrees two-theta, 22.2±0.2 degrees two-theta, 22.7±0.2 degrees two-theta, 23.1±0.2 degrees two-theta, 24.0±0.2 degrees two-theta, 25.6±0.2 degrees two-theta, 26.1±0.2 degrees two-theta, 26.8±0.2 degrees two-theta, 28.0±0.2 degrees two-theta, and 28.4±0.2 degrees two-theta.

310. The Compound 33 Form N according to Embodiment 305 or Embodiment 306, wherein Compound 33 Form N is characterized by an X-ray powder diffractogram substantially similar to FIG. 19A.

311. A pharmaceutical composition comprising the Compound 33 Form N according to any one of Embodiments 305-309 and a pharmaceutically acceptable carrier.

312. A method of treating alpha-1 antitrypsin deficiency comprising administering to a patient in need thereof the Compound 33 Form N according to any one of Embodiments 305-310, or a pharmaceutical composition according to Embodiment 311.

313. The method according to Embodiment 312, wherein the patient has a Z mutation in alpha-1 antitrypsin.

314. The method according to Embodiment 312, wherein the patient has an SZ mutation in alpha-1 antitrypsin.

315. The method according to Embodiment 312, wherein the patient is homozygous for Z-mutations in alpha-1 antitrypsin.

316. Use of the Compound 33 Form N according to any one of Embodiments 305-310 in the manufacture of a medicament for treating alpha-1 antitrypsin deficiency.

317. Substantially crystalline Compound 33 Form O.

318. The Compound 33 Form N according to Embodiment 317, wherein Compound 33 is substantially pure crystalline Compound 33 Form O.

319. The Compound 33 Form O according to Embodiment 317 or Embodiment 318, wherein Compound 33 Form O is characterized by an X-ray powder diffractogram having a signal at one or more of 7.0±0.2 degrees two-theta, 10.4±0.2 degrees two-theta, 17.4±0.2 degrees two-theta, and 21.2±0.2 degrees two-theta.

320. The Compound 33 Form O according to Embodiment 317 or Embodiment 318, wherein Compound 33 Form O is characterized by an X-ray powder diffractogram having signals at 7.0±0.2 degrees two-theta, 10.4±0.2 degrees two-theta, 17.4±0.2 degrees two-theta, and 21.2±0.2 degrees two-theta.

321. The Compound 33 Form O according to Embodiment 317 or Embodiment 318, wherein Compound 33 Form O is characterized by an X-ray powder having (a) diffractogram having signals at 7.0±0.2 degrees two-theta, 10.4±0.2 degrees two-theta, 17.4±0.2 degrees two-theta, and 21.2±0.2 degrees two-theta; and (b) a signal at at least one, at least two, at least four, or at least six two-theta values chosen from 8.3±0.2 degrees two-theta, 8.8±0.2 degrees two-theta, 15.5±0.2 degrees two-theta, 16.6±0.2 degrees two-theta, 16.9±0.2 degrees two-theta, 18.8±0.2 degrees two-theta, 19.5±0.2 degrees two-theta, 20.4±0.2 degrees two-theta, 21.6±0.2 degrees two-theta, 22.3±0.2 degrees two-theta, 22.9±0.2 degrees two-theta, and 23.3±0.2 degrees two-theta.

322. The Compound 33 Form O according to Embodiment 317 or Embodiment 318, wherein Compound 33 Form O is characterized by an X-ray powder diffractogram substantially similar to FIG. 20A.

323. A pharmaceutical composition comprising the Compound 33 Form O according to any one of Embodiments 317-322 and a pharmaceutically acceptable carrier.

324. A method of treating alpha-1 antitrypsin deficiency comprising administering to a patient in need thereof the Compound 33 Form O according to any one of Embodiments 317-322, or a pharmaceutical composition according to Embodiment 323.

325. The method according to Embodiment 324, wherein the patient has a Z mutation in alpha-1 antitrypsin.

326. The method according to Embodiment 324, wherein the patient has an SZ mutation in alpha-1 antitrypsin.

327. The method according to Embodiment 326, wherein the patient is homozygous for Z-mutations in alpha-1 antitrypsin.

328. Use of the Compound 33 Form O according to any one of Embodiments 305-309 in the manufacture of a medicament for treating alpha-1 antitrypsin deficiency.

329. Substantially crystalline Compound 33 Potassium Salt Form A.

330. The Compound 33 Potassium Salt Form A according to Embodiment 329, wherein Compound 33 is substantially pure crystalline Compound 33 Potassium Salt Form A.

331. The Compound 33 Potassium Salt Form A according to Embodiment 329 or Embodiment 330, wherein Compound 33 Potassium Salt Form A is characterized by an X-ray powder diffractogram having a signal at one or more of 11.7±0.2 degrees two-theta, 18.0±0.2 degrees two-theta, and 20.7±0.2 degrees two-theta.

332. The Compound 33 Potassium Salt Form A according to Embodiment 317 or Embodiment 318, wherein Compound 33 Potassium Salt Form A is characterized by an X-ray powder diffractogram having signals at 11.7±0.2 degrees two-theta, 18.0±0.2 degrees two-theta, and 20.7±0.2 degrees two-theta.

333. The Compound 33 Potassium Salt Form A according to Embodiment 317 or Embodiment 318, wherein Compound 33 Potassium Salt Form A is characterized by an X-ray powder diffractogram substantially similar to FIG. 21A.

334. A pharmaceutical composition comprising the Compound 33 Potassium Salt Form A according to any one of Embodiments 329-333 and a pharmaceutically acceptable carrier.

335. A method of treating alpha-1 antitrypsin deficiency comprising administering to a patient in need thereof the Compound 33 Potassium Salt Form A according to any one of Embodiments 329-333, or a pharmaceutical composition according to Embodiment 334.

336. The method according to Embodiment 335, wherein the patient has a Z mutation in alpha-1 antitrypsin.

337. The method according to Embodiment 335, wherein the patient has an SZ mutation in alpha-1 antitrypsin.

338. The method according to Embodiment 335, wherein the patient is homozygous for Z-mutations in alpha-1 antitrypsin.

339. Use of the Compound 33 Potassium Salt Form A according to any one of Embodiments 329-333 in the manufacture of a medicament for treating alpha-1 antitrypsin deficiency.

340. Substantially crystalline Compound 33 Potassium Salt Form B.

341. The Compound 33 Potassium Salt Form B according to Embodiment 340, wherein Compound 33 is substantially pure crystalline Compound 33 Potassium Salt Form B.

342. The Compound 33 Potassium Salt Form B according to Embodiment 340 or Embodiment 341, wherein Compound 33 Potassium Salt Form B is characterized by an X-ray powder diffractogram having a signal at one or more of 9.1±0.2 degrees two-theta, 13.7±0.2 degrees two-theta, 15.3±0.2 degrees two-theta, 17.5±0.2 degrees two-theta, and 21.7±0.2 degrees two-theta.

343. The Compound 33 Potassium Salt Form B according to Embodiment 340 or Embodiment 341, wherein Compound 33 Potassium Salt Form B is characterized by an X-ray powder diffractogram having a signal at two or more of 9.1±0.2 degrees two-theta, 13.7±0.2 degrees two-theta, 15.3±0.2 degrees two-theta, 17.5±0.2 degrees two-theta, and 21.7±0.2 degrees two-theta.

344. The Compound 33 Potassium Salt Form B according to Embodiment 340 or Embodiment 341, wherein Compound 33 Potassium Salt Form B is characterized by an X-ray powder diffractogram having a signal at three or more of 9.1±0.2 degrees two-theta, 13.7±0.2 degrees two-theta, 15.3±0.2 degrees two-theta, 17.5±0.2 degrees two-theta, and 21.7±0.2 degrees two-theta.

345. The Compound 33 Potassium Salt Form B according to Embodiment 340 or Embodiment 341, wherein Compound 33 Potassium Salt Form B is characterized by an X-ray powder diffractogram having signals at 9.1±0.2 degrees two-theta, 13.7±0.2 degrees two-theta, 15.3±0.2 degrees two-theta, 17.5±0.2 degrees two-theta, and 21.7±0.2 degrees two-theta.

346. The Compound 33 Potassium Salt Form B according to Embodiment 340 or Embodiment 341, wherein Compound 33 Potassium Salt Form B is characterized by an X-ray powder diffractogram having (a) signals at three or more of 9.1±0.2 degrees two-theta, 13.7±0.2 degrees two-theta, 15.3±0.2 degrees two-theta, 17.5±0.2 degrees two-theta, and 21.7±0.2 degrees two-theta; and (b) a signal at at least one, at least two, or at least three two-theta values chosen from 6.9±0.2 degrees two-theta, 10.8±0.2 degrees two-theta, 20.0±0.2 degrees two-theta, and 20.6±0.2 degrees two-theta.

347. The Compound 33 Potassium Salt Form B according to Embodiment 340 or Embodiment 341, wherein Compound 33 Potassium Salt Form B is characterized by an X-ray powder diffractogram substantially similar to FIG. 22A.

348. A pharmaceutical composition comprising the Compound 33 Potassium Salt Form B according to any one of Embodiments 340-347 and a pharmaceutically acceptable carrier.

349. A method of treating alpha-1 antitrypsin deficiency comprising administering to a patient in need thereof the Compound 33 Potassium Salt Form B according to any one of Embodiments 340-347, or a pharmaceutical composition according to Embodiment 348.

350. The method according to Embodiment 349, wherein the patient has a Z mutation in alpha-1 antitrypsin.

351. The method according to Embodiment 349, wherein the patient has an SZ mutation in alpha-1 antitrypsin.

352. The method according to Embodiment 349, wherein the patient is homozygous for Z-mutations in alpha-1 antitrypsin.

353. Use of the Compound 33 Potassium Salt Form B according to any one of Embodiments 340-347 in the manufacture of a medicament for treating alpha-1 antitrypsin deficiency.

354. Substantially crystalline Compound 33 Potassium Salt Form C.

355. The Compound 33 Potassium Salt Form C according to Embodiment 354, wherein Compound 33 is substantially pure crystalline Compound 33 Potassium Salt Form C.

356. The Compound 33 Potassium Salt Form C according to Embodiment 354 or Embodiment 355, wherein Compound 33 Potassium Salt Form C is characterized by an X-ray powder diffractogram having signals at 16.8±0.2 degrees two-theta and 19.3±0.2 degrees two-theta.

357. The Compound 33 Potassium Salt Form C according to Embodiment 354 or Embodiment 355, wherein Compound 33 Potassium Salt Form C is characterized by an X-ray powder diffractogram having signals at (a) 16.8±0.2 degrees two-theta and 19.3±0.2 degrees two-theta and (b) 6.7±0.2 degrees two-theta, and/or 10.5±0.2 degrees two-theta. In some Embodiments, Compound 33 Potassium Salt Form C is characterized by an X-ray powder diffractogram having a signal at 6.7±0.2 degrees two-theta, 10.5±0.2 degrees two-theta. 16.8±0.2 degrees two-theta, and 19.3±0.2 degrees two-theta.

358. The Compound 33 Potassium Salt Form C according to Embodiment 354 or Embodiment 355, wherein Compound 33 Potassium Salt Form C is characterized by an X-ray powder diffractogram substantially similar to FIG. 23A.

359. A pharmaceutical composition comprising the Compound 33 Potassium Salt Form C according to any one of Embodiments 354-358 and a pharmaceutically acceptable carrier.

360. A method of treating alpha-1 antitrypsin deficiency comprising administering to a patient in need thereof the Compound 33 Potassium Salt Form B according to any one of Embodiments 354-358, or a pharmaceutical composition according to Embodiment 359.

361. The method according to Embodiment 360, wherein the patient has a Z mutation in alpha-1 antitrypsin.

362. The method according to Embodiment 360, wherein the patient has an SZ mutation in alpha-1 antitrypsin.

363. The method according to Embodiment 360, wherein the patient is homozygous for Z-mutations in alpha-1 antitrypsin.

364. Use of the Compound 33 Potassium Salt Form C according to any one of Embodiments 354-358 in the manufacture of a medicament for treating alpha-1 antitrypsin deficiency.

365-370. (omitted)

371. A method for preparing the compound 4-[5-(4-fluorophenyl)-6-tetrahydropyran-4-yl-1H-pyrrolo[2,3-f]indazol-7-yl]benzoic acid, the method comprising:
(a) contacting methyl 4-(5-(4-fluorophenyl)-1-pivaloyl-6-(tetrahydro-2H-pyran-4-yl)-1,5-dihydropyrrolo[2,3-f]indazol-7-yl)benzoate with a first organic solvent and a first base to form a first reaction mixture;
(b) adding water and a first acid to the first reaction mixture;
(c) isolating an organic portion from step (b), adding an alcohol and optionally adding water to the organic portion, and concentrating the mixture by distillation; and
(d) isolating the compound 4-[5-(4-fluorophenyl)-6-tetrahydropyran-4-yl-1H-pyrrolo[2,3-f]indazol-7-yl]benzoic acid from the mixture from step (c) and drying the material to remove all water content.

372. The method of Embodiment 371, wherein step (a) comprises heating methyl 4-(5-(4-fluorophenyl)-1-pivaloyl-6-(tetrahydro-2H-pyran-4-yl)-1,5-dihydropyrrolo[2,3-f]indazol-7-yl)benzoate with the first organic solvent and the first base to about 50-65° C.

373. The method of Embodiment 372, wherein step (a) comprises heating methyl 4-(5-(4-fluorophenyl)-1-pivaloyl-6-(tetrahydro-2H-pyran-4-yl)-1,5-dihydropyrrolo[2,3-f]indazol-7-yl)benzoate with the first organic solvent and the first base to about 55-60° C.

374. The method of Embodiment 373, wherein step (a) comprises heating methyl 4-(5-(4-fluorophenyl)-1-pivaloyl-6-(tetrahydro-2H-pyran-4-yl)-1,5-dihydropyrrolo[2,3-f]indazol-7-yl)benzoate with the first organic solvent and the first base to about 58° C.

375. The method of any one of Embodiments 371-374, wherein the first organic solvent is selected from THF, 2-MeTHF, EtOH, MeOH, and IPA.

376. The method of Embodiment 375, wherein the first organic solvent is THF.

377. The method of any one of Embodiments 371-376, wherein the first base is selected from LiOH, NaOH, and KOH.

378. The method of Embodiment 377, wherein the first base is NaOH.

379. The method of any one of Embodiments 371-378, wherein step (b) comprises adding water and the first acid to the first reaction mixture at about 15-25° C.

380. The method of Embodiment 379, wherein step (b) comprises adding water and the first acid to the first reaction mixture at about 20° C.

381. The method of any one of Embodiments 371-380, wherein step (b) further comprises adding a second organic solvent to the first reaction mixture.

382. The method of Embodiment 381, wherein the second organic solvent is 2-MeTHF.

383 The method of any one of Embodiments 371-382, wherein step (c) comprises washing the organic portion with a NaCl aqueous solution prior to adding alcohol and/or water.

384. The method of any one of Embodiments 371-383, wherein the first acid is an organic acid or a strong acid.

385. The method of Embodiment 384, wherein the first acid is acetic acid or HCl.

386. The method of Embodiment 385, wherein the first acid is acetic acid.

387. The method of any one of Embodiments 371-386, wherein step (c) comprises 2 to 10 cycles of adding an alcohol, optionally adding water, and concentrating the mixture by distillation.

388. The method of any one of Embodiments 371-387, wherein step (c) comprises concentrating the mixture by distillation at about 20-40° C.

389. The method of any one of Embodiments 371-388, wherein the alcohol is selected from EtOH, MeOH, IPA, TBA, and n-butanol.

390. The method of Embodiment 389, wherein the alcohol is EtOH.

391. The method of any one of Embodiments 371-390, wherein step (d) comprises filtering the mixture from step (c) to form a wet cake and drying the wet cake.

392. The method of Embodiment 391, wherein the drying comprises drying the wet cake under vacuum at about 60-70° C.

393. The method of Embodiment 392, wherein the wet cake is dried at about 66° C.

394. The method of any one of Embodiments 371-393, wherein the method further comprises reacting 1-(5-(4-fluorophenyl)-7-iodo-6-(tetrahydro-2H-pyran-4-yl)pyrrolo[2,3-f]indazol-1(5H)-yl)-2,2-dimethylpropan-1-one with 4-(methoxycarbonyl)phenyl)boronic acid to form methyl 4-(5-(4-fluorophenyl)-1-pivaloyl-6-(tetrahydro-2H-pyran-4-yl)-1,5-dihydropyrrolo[2,3-f]indazol-7-yl)benzoate.

395. The method of Embodiment 394, wherein reacting 1-(5-(4-fluorophenyl)-7-iodo-6-(tetrahydro-2H-pyran-4-yl)pyrrolo[2,3-f]indazol-1(5H)-yl)-2,2-dimethylpropan-1-one with 4-(methoxycarbonyl)phenyl)boronic acid to form methyl 4-(5-(4-fluorophenyl)-1-pivaloyl-6-(tetrahydro-2H-pyran-4-yl)-1,5-dihydropyrrolo[2,3-f]indazol-7-yl)benzoate takes place at about 60-70° C.

396. The method of Embodiment 395, wherein reacting 1-(5-(4-fluorophenyl)-7-iodo-6-(tetrahydro-2H-pyran-4-yl)pyrrolo[2,3-f]indazol-1(5H)-yl)-2,2-dimethylpropan-1-one with 4-(methoxycarbonyl)phenyl)boronic acid to form methyl 4-(5-(4-fluorophenyl)-1-pivaloyl-6-(tetrahydro-2H-pyran-4-yl)-1,5-dihydropyrrolo[2,3-f]indazol-7-yl)benzoate takes place at about 65° C.

397. The method of any one of Embodiments 394-396, wherein reacting 1-(5-(4-fluorophenyl)-7-iodo-6-(tetrahydro-2H-pyran-4-yl)pyrrolo[2,3-f]indazol-1(5H)-yl)-2,2-dimethylpropan-1-one with 4-(methoxycarbonyl)phenyl)boronic acid to form methyl 4-(5-(4-fluorophenyl)-1-pivaloyl-6-(tetrahydro-2H-pyran-4-yl)-1,5-dihydropyrrolo[2,3-f]indazol-7-yl)benzoate takes place in the presence of a first catalyst, triethylamine, water, a third organic solvent, and a second base.

398. The method of Embodiment 397, wherein the first catalyst is selected from $PCy_3P(tBu)_3$, DavePhos, SPhos $Pd(PPh_3)_2Cl_2$, Xphos, CataCXium; $Pd(AmPhos)Cl_2$, RuPhos, $Pd(dippf)Cl_2$, $Pd(dtbpf)Cl_2$, $Pd(DPEPhos)Cl_2$, $Pd(dppf)Cl_2 \cdot CH_2Cl_2$, $Pd(Xantphos)Cl_2$, and $Pd(dppb)Cl_2$.

399. The method of Embodiment 398, wherein the first catalyst is selected $Pd(dppf)Cl_2 \cdot CH_2Cl_2$.

400. The method of any one of Embodiments 397-399, wherein the third organic solvent is selected from 1,4-dioxane, THF, 2-MeTHF, IPA, toluene, ACN, DMSO, EtOH.

401. The method of Embodiment 400, wherein the third organic solvent is THF.

402. The method of any one of Embodiments 397-401, wherein the second base is selected from $K_2CO_3$, $Na_2CO_3$, and $K_3PO_4$.

403. The method of Embodiment 402, wherein the second base is $K_2CO_3$.

404. The method of any one of Embodiments 397-403, further comprising removing aryl dimer impurities by charging methyl 4-(5-(4-fluorophenyl)-1-pivaloyl-6-(tetrahydro-2H-pyran-4-yl)-1,5-dihydropyrrolo[2,3-f]indazol-7-yl)benzoate with THF and heating the mixture; adding EtOH to the mixture to form a slurry; stirring the slurry; cooling the slurry and filtering the slurry to form a wet cake; and rinsing and drying the wet cake.

405. The method of any one Embodiments 394-404, wherein the method further comprises reacting 1-(5-(4-fluorophenyl)-6-(tetrahydro-2H-pyran-4-yl)pyrrolo[2,3-f]indazol-1(5H)-yl)-2,2-dimethylpropan-1-one with N-iodosuccinimide to form 1-(5-(4-fluorophenyl)-7-iodo-6-(tetrahydro-2H-pyran-4-yl)pyrrolo[2,3-f]indazol-1(5H)-yl)-2,2-dimethylpropan-1-one.

406. The method of Embodiment 405, wherein reacting 1-(5-(4-fluorophenyl)-6-(tetrahydro-2H-pyran-4-yl)pyrrolo[2,3-f]indazol-1(5H)-yl)-2,2-dimethylpropan-1-one with N-iodosuccinimide to form 1-(5-(4-fluorophenyl)-7-iodo-6-(tetrahydro-2H-pyran-4-yl)pyrrolo[2,3-f]indazol-1(5H)-yl)-2,2-dimethylpropan-1-one takes place at about −5.0 to 0° C. for about 20-45 minutes.

407. The method of Embodiment 405, wherein reacting 1-(5-(4-fluorophenyl)-6-(tetrahydro-2H-pyran-4-yl)pyrrolo[2,3-f]indazol-1(5H)-yl)-2,2-dimethylpropan-1-one with N-iodosuccinimide to form 1-(5-(4-fluorophenyl)-7-iodo-6-(tetrahydro-2H-pyran-4-yl)pyrrolo[2,3-f]indazol-1(5H)-yl)-2,2-dimethylpropan-1-one takes place at about −5.0° C. for about 30 minutes.

408. The method of any one of Embodiments 405-407, wherein reacting 1-(5-(4-fluorophenyl)-6-(tetrahydro-2H-pyran-4-yl)pyrrolo[2,3-f]indazol-1(5H)-yl)-2,2-dimethylpropan-1-one with N-iodosuccinimide to form 1-(5-(4-fluorophenyl)-7-iodo-6-(tetrahydro-2H-pyran-4-yl)pyrrolo[2,3-f]indazol-1(5H)-yl)-2,2-dimethylpropan-1-one takes place in the presence of a fourth organic solvent selected from THF, MeTHF, ACN, EtOAc, DMF, and DCM.

409. The method of Embodiment 408, wherein the fourth organic solvent is DCM.

410. The method of any one of Embodiments 405-409, wherein the method further comprises reacting 5-(4-fluorophenyl)-6-(tetrahydro-2H-pyran-4-yl)-1,5-dihydropyrrolo[2,3-f]indazole with trimethylacetyl chloride to form 1-(5-(4-fluorophenyl)-6-(tetrahydro-2H-pyran-4-yl)pyrrolo[2,3-f]indazol-1(5H)-yl)-2,2-dimethylpropan-1-one.

411. The method of Embodiment 410, wherein reacting 5-(4-fluorophenyl)-6-(tetrahydro-2H-pyran-4-yl)-1,5-dihydropyrrolo[2,3-f]indazole with trimethylacetyl chloride to form 1-(5-(4-fluorophenyl)-6-(tetrahydro-2H-pyran-4-yl)pyrrolo[2,3-f]indazol-1(5H)-yl)-2,2-dimethylpropan-1-one takes place at about −6 to 0° C. for about an hour.

412. The method of any one of Embodiments 410 and 411, wherein reacting 5-(4-fluorophenyl)-6-(tetrahydro-2H-pyran-4-yl)-1,5-dihydropyrrolo[2,3-f]indazole with trimethylacetyl chloride to form 1-(5-(4-fluorophenyl)-6-(tetrahydro-2H-pyran-4-yl)pyrrolo[2,3-f]indazol-1(5H)-yl)-2,2-dimethylpropan-1-one takes place in the presence of a fifth organic solvent and a third base.

413. The method of Embodiment 412, wherein the fifth organic solvent is selected from 2-MeTHF, THF, and DCM.

414. The method of Embodiment 413, wherein the fifth organic solvent is THF.

415. The method of any one of Embodiments 412-414, wherein the third base is selected from LiOtBu, NaOtBu, KOtBu, LiOtAm, NaOtAm, and KOtAm.

416. The method of Embodiment 415, wherein the third base is KOtBu.

417. The method of any one of Embodiments 410-416, wherein the method further comprises reacting N-(4-fluorophenyl)-6-((tetrahydro-2H-pyran-4-yl)ethynyl)-1H-indazol-5-amine with a second acid to form 5-(4-fluorophenyl)-6-(tetrahydro-2H-pyran-4-yl)-1,5-dihydropyrrolo[2,3-f]indazole.

418. The method of Embodiment 417, wherein reacting N-(4-fluorophenyl)-6-((tetrahydro-2H-pyran-4-yl)ethynyl)-1H-indazol-5-amine with a second acid to form 5-(4-fluorophenyl)-6-(tetrahydro-2H-pyran-4-yl)-1,5-dihydropyrrolo[2,3-f]indazole takes place at about 55-65° C. for no less than 3 hours.

419. The method of Embodiment 418, wherein reacting N-(4-fluorophenyl)-6-((tetrahydro-2H-pyran-4-yl)ethynyl)-1H-indazol-5-amine with a second acid to form 5-(4-fluorophenyl)-6-(tetrahydro-2H-pyran-4-yl)-1,5-dihydropyrrolo[2,3-f]indazole takes place at about 60° C.

420. The method of any one of Embodiments 417-419, wherein the second acid is an organic acid, a strong acid, or a Lewis acid.

421. The method of Embodiment 420, wherein the second acid is acetic acid or NaHSO3.

422. The method of any one of Embodiments 417-421, wherein the method further comprises reacting 5-bromo-6-

((tetrahydro-2H-pyran-4-yl)ethynyl)-1H-indazole with 4-fluoroaniline to form N-(4-fluorophenyl)-6-((tetrahydro-2H-pyran-4-yl)ethynyl)-1H-indazol-5-amine.

423. The method of Embodiment 422, wherein reacting 5-bromo-6-((tetrahydro-2H-pyran-4-yl)ethynyl)-1H-indazole with 4-fluoroaniline to form N-(4-fluorophenyl)-6-((tetrahydro-2H-pyran-4-yl)ethynyl)-1H-indazol-5-amine takes place at about 60-70° C.

424. The method of Embodiment 423, wherein reacting 5-bromo-6-((tetrahydro-2H-pyran-4-yl)ethynyl)-1H-indazole with 4-fluoroaniline to form N-(4-fluorophenyl)-6-((tetrahydro-2H-pyran-4-yl)ethynyl)-1H-indazol-5-amine takes place at about 65° C.

425. The method of any one of Embodiments 422-424, wherein reacting 5-bromo-6-((tetrahydro-2H-pyran-4-yl)ethynyl)-1H-indazole with 4-fluoroaniline to form N-(4-fluorophenyl)-6-((tetrahydro-2H-pyran-4-yl)ethynyl)-1H-indazol-5-amine takes place in the presence of a second catalyst, a sixth organic solvent, and a fourth base.

426. The method of Embodiment 425, wherein the second catalyst is selected from PdtBuXPhos G1-4; (PdOAc)₂, Pd(cinnamyl)Cl₂ with ligands, BrettPhos, SPHos, XPhos, XantPhos, Pd(dppf)Cl₂·CH₂Cl₂, JosiPhos, and cataCXium® A.

427. The method of Embodiment 426, wherein the second catalyst is PdtBuXPhos.

428. The method of any one of Embodiments 425-427, wherein the sixth organic solvent is selected from EtOH, MeOH, 1-butanol, tert-butanol, isopropyl alcohol (IPA), tAmOH, THF, 2-MeTHF, CPMe, Toluene, DMF, ACN, DMA, and diglyme.

429. The method of Embodiment 428, wherein the sixth organic solvent is EtOH.

430. The method of any one of Embodiments 425-429, wherein the fourth base is selected from NaOH, K₃PO₄, K₂CO₃, NaOtBu, KOtBu, and NaOEt.

431. The method of Embodiment 430, wherein the fourth base is NaOtBu.

432. The method of any one of Embodiments 422-431, wherein the method further comprises reacting 5-bromo-6-iodo-1H-indazole with trimethyl((tetrahydro-2H-pyran-4-yl)ethnyl)silane to form 5-bromo-6-((tetrahydro-2H-pyran-4-yl)ethynyl)-1H-indazole.

433. The method of Embodiment 432, wherein reacting 5-bromo-6-iodo-1H-indazole with trimethyl((tetrahydro-2H-pyran-4-yl)ethnyl)silane to form 5-bromo-6-((tetrahydro-2H-pyran-4-yl)ethynyl)-1H-indazole takes place at about 70-80° C.

434. The method of Embodiment 433, wherein reacting 5-bromo-6-iodo-1H-indazole with trimethyl((tetrahydro-2H-pyran-4-yl)ethnyl)silane to form 5-bromo-6-((tetrahydro-2H-pyran-4-yl)ethynyl)-1H-indazole takes place at about 75° C.

435. The method of any one of Embodiments 432-434, wherein reacting 5-bromo-6-iodo-1H-indazole with trimethyl((tetrahydro-2H-pyran-4-yl)ethnyl)silane to form 5-bromo-6-((tetrahydro-2H-pyran-4-yl)ethynyl)-1H-indazole takes place in the presence of a seventh organic solvent, a fifth base, and a third catalyst.

436. The method of Embodiment 435, wherein the seventh organic solvent is selected from DMF, EtOH, MeOH, 1-butanol, tert-butanol, isopropyl alcohol (IPA), tAmOH, a THF/alcohol mixture, and a 2-MeTHF alcohol mixture.

437. The method of Embodiment 436, wherein the seventh organic solvent is EtOH.

438. The method of any one of Embodiments 435-437, wherein the fifth base is selected from NaOH, KOH, K₂CO₃, Na₂CO₃, Cs₂CO₃ NaOtBu, KOtBu, and DBU (1,8-Diazabicyclo(5.4.0)undec-7-ene).

439. The method of Embodiment 438, wherein the fifth base is KOH.

440. The method of any one of Embodiment 435-439, wherein third catalyst is selected from Pd(PPh₃)₄, CuI, CuI/PPh₃, and water.

441. The method of Embodiment 70, wherein the third catalyst is Pd(PPh₃)₄.

442. A compound selected from:

5-bromo-6-((tetrahydro-2H-pyran-4-yl)ethynyl)-1H-indazole (C2)

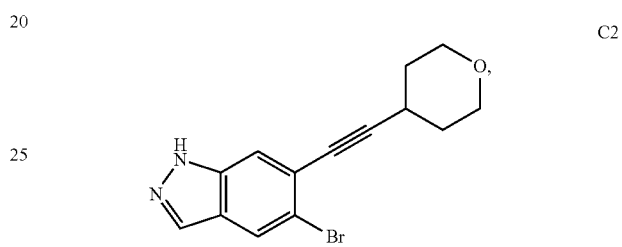

N-(4-fluorophenyl)-6-((tetrahydro-2H-pyran-4-yl)ethynyl-1H-indazole-5-amine (C12)

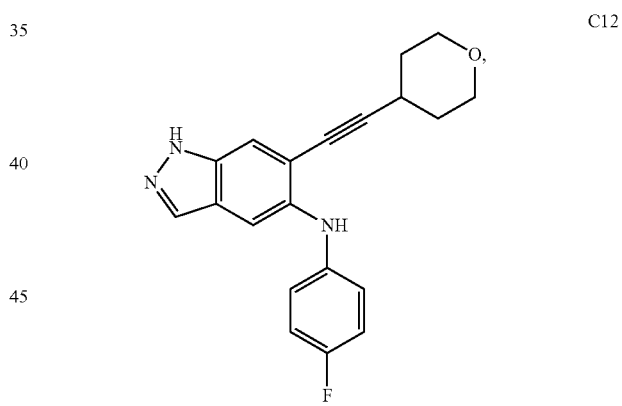

5-(4-fluorophenyl)-6-(tetrahydro-2H-pyran-4-yl)-1,5-dihydropyrrolo[2,3-f]indazole (C13)

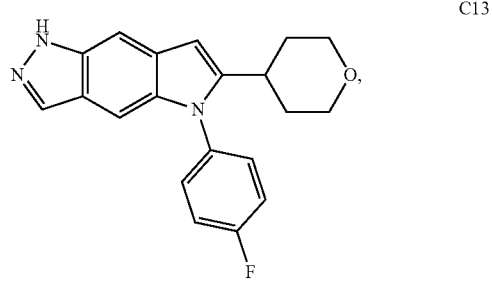 [SMILES: Fc1ccc(-n2c(C3CCOCC3)cc3cc4[nH]ncc4cc32)cc1]

1-(5-(4-fluorophenyl)-6-(tetrahydro-2H-pyran-4-yl)pyrrolo[2,3-f]indazol-1(5H)-yl)-2,2-dimethylpropan-1-one (C14)

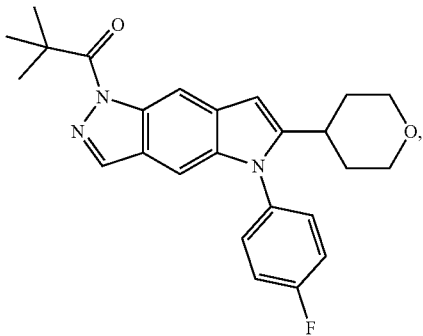

C14

1-(5-(4-fluorophenyl)-7-iodo-6-(tetrahydro-2H-pyran-4-yl)pyrrolo[2,3-f]indazol-1(5H)-yl)-2,2-dimethylpropan-1-one (S4)

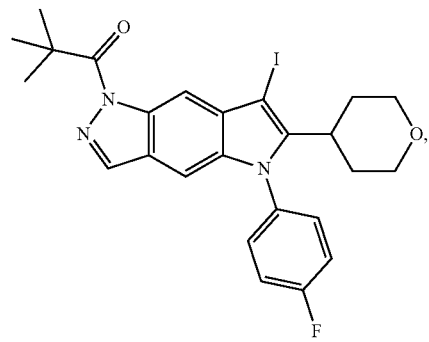

S4 and
methyl 4-(5-(4-fluorophenyl)-1-pivaloyl-6-(tetrahydro-2H-pyran-4-yl)-1,5-dihydropyrrolo[2,3-f]indazol-7-yl)benzoate (C58)

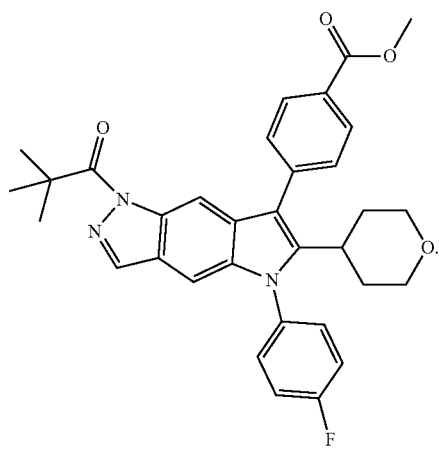

C58

443. Neat amorphous Compound 33.
444. The neat amorphous Compound 33 according to Embodiment 443, characterized as having a $^{13}$C solid state nuclear magnetic resonance ($^{13}$C ssNMR) spectrum with peaks at 161.6±0.2 ppm, 130.7±0.2 ppm, 121.4±0.2 ppm, and 115.7±0.2 ppm.
445. The neat amorphous Compound 33 according to Embodiment 443, characterized as having a $^{13}$C ssNMR spectrum with (a) peaks at 161.6±0.2 ppm, 130.7±0.2 ppm, 121.4±0.2 ppm, and 115.7±0.2 ppm; and (b) one, two, three, four, five, six, seven, or more peaks selected from 172.5±0.2 ppm, 170.1±0.2 ppm, 167.0±0.2 ppm, 163.7±0.2 ppm, 144.5±0.2 ppm, 140.8±0.2 ppm, 137.4±0.2 ppm, 97.6±0.2 ppm, 67.9±0.2 ppm, 35.3±0.2 ppm, and 31.5±0.2 ppm.
446. The neat amorphous Compound 33 according to Embodiment 443, characterized as having a $^{13}$C ssNMR spectrum with (a) peaks at 161.6±0.2 ppm, 130.7±0.2 ppm, 121.4±0.2 ppm, and 115.7±0.2 ppm; and (b) two or more peaks selected from 172.5±0.2 ppm, 170.1±0.2 ppm, 167.0±0.2 ppm, 163.7±0.2 ppm, 144.5±0.2 ppm, 140.8±0.2 ppm, 137.4±0.2 ppm, 97.6±0.2 ppm, 67.9±0.2 ppm, 35.3±0.2 ppm, and 31.5±0.2 ppm.
447. The neat amorphous Compound 33 according to Embodiment 443, characterized as having a $^{13}$C ssNMR spectrum with (a) peaks at 161.6±0.2 ppm, 130.7±0.2 ppm, 121.4±0.2 ppm, and 115.7±0.2 ppm; and (b) three or more peaks selected from 172.5±0.2 ppm, 170.1±0.2 ppm, 167.0±0.2 ppm, 163.7±0.2 ppm, 144.5±0.2 ppm, 140.8±0.2 ppm, 137.4±0.2 ppm, 97.6±0.2 ppm, 67.9±0.2 ppm, 35.3±0.2 ppm, and 31.5±0.2 ppm.
448. The neat amorphous Compound 33 according to Embodiment 443, characterized as having a $^{13}$C ssNMR spectrum with (a) peaks at 161.6±0.2 ppm, 130.7±0.2 ppm, 121.4±0.2 ppm, and 115.7±0.2 ppm; and (b) four, five, six, seven or more peaks selected from 172.5±0.2 ppm, 170.1±0.2 ppm, 167.0±0.2 ppm, 163.7±0.2 ppm, 144.5±0.2 ppm, 140.8±0.2 ppm, 137.4±0.2 ppm, 97.6±0.2 ppm, 67.9±0.2 ppm, 35.3±0.2 ppm, and 31.5±0.2 ppm.
449. The neat amorphous Compound 33 according to Embodiment 443, characterized as having a $^{13}$C ssNMR spectrum substantially similar to FIG. 38C.
450. The neat amorphous Compound 33 according to any one of Embodiments 443-449, characterized as having a $^{19}$F solid state nuclear magnetic resonance ($^{19}$F ssNMR) spectrum with a peak at −112.8±0.2 ppm.
451. The neat amorphous Compound 33 according to any one of Embodiments 443-449, characterized as having $^{19}$F ssNMR spectrum substantially similar to FIG. 38D.
452. A spray dried neat amorphous Compound 33 according to any one of Embodiments 443-451.
453. A pharmaceutical composition comprising spray-dried neat amorphous Compound 33 according to any one of Embodiments 443-451.
454. A solid dispersion comprising substantially amorphous Compound 33 and a polymer.
455. The solid dispersion comprising substantially amorphous Compound 33 according to Embodiment 454, wherein the polymer is selected from polyvinylpyrrolidone/vinyl acetate (PVPVA), hydroxypropylmethylcellulose (HPMC), and hydroxypropylmethylcellulose acetate succinate (HPMCAS).
456. The solid dispersion comprising substantially amorphous Compound 33 according to Embodiment 454 or Embodiment 455, wherein substantially amorphous Compound 33 is present in an amount from 30-50%.
457. The solid dispersion comprising substantially amorphous Compound 33 according to Embodiment 454 or Embodiment 455, wherein substantially amorphous Compound 33 is present in an amount from 50-80%.

458. The solid dispersion comprising substantially amorphous Compound 33 according to any one of Embodiments 454-457 prepared as a spray-dried dispersion.

459. A solid dispersion comprising 50% amorphous Compound 33 and HPMCAS, characterized as having a $^{13}$C ssNMR spectrum with at least 5, at least six, at least 8, at least 10, or at least 12 peaks selected from 173.1±0.2 ppm, 170.0±0.2 ppm, 167.2±0.2 ppm, 163.9±0.2 ppm, 161.5±0.2 ppm, 144.4±0.2 ppm, 141.2±0.2 ppm, 137.8±0.2 ppm, 130.9±0.2 ppm, 121.7±0.2 ppm, 116.5±0.2 ppm, 103.0±0.2 ppm, 98.4±0.2 ppm, 83.5±0.2 ppm, 74.1±0.2 ppm, 68.5±0.2 ppm, 60.5±0.2 ppm, 35.8±0.2 ppm, 30.7±0.2 ppm, 20.6±0.2 ppm, and 16.5±0.2 ppm.

460. The solid dispersion comprising 50% amorphous Compound 33 and HPMCAS, according to Embodiment 459, characterized as having a $^{13}$C ssNMR spectrum substantially similar to FIG. 30D.

461. The solid dispersion comprising 50% amorphous Compound 33 and HPMCAS, according to Embodiment 459 or Embodiment 460, characterized as having a $^{19}$F ssNMR spectrum with a peak at −112.6±0.2 ppm.

462. The solid dispersion comprising 50% amorphous Compound 33 and HPMCAS, according to any one of Embodiments 459-461, characterized as having $^{19}$F ssNMR spectrum substantially similar to FIG. 30E.

463. A solid dispersion comprising 80% amorphous Compound 33 and HPMCAS, characterized as having a $^{13}$C ssNMR spectrum with at least 5, at least six, at least 8, at least 10, or at least 12 peaks selected from 173.0±0.2 ppm, 169.6±0.2 ppm, 163.8±0.2 ppm, 161.2±0.2 ppm, 144.1±0.2 ppm, 140.9±0.2 ppm, 137.6±0.2 ppm, 130.9±0.2 ppm, 121.6±0.2 ppm, 116.3±0.2 ppm, 103.2±0.2 ppm, 98.1±0.2 ppm, 82.9±0.2 ppm, 74.6±0.2 ppm, 68.2±0.2 ppm, 60.5±0.2 ppm, 35.6±0.2 ppm, 31.5±0.2 ppm, and 20.1±0.2 ppm.

464. The solid dispersion comprising 80% amorphous Compound 33 and HPMCAS, according to Embodiment 463, characterized as having a $^{13}$C ssNMR spectrum substantially similar to FIG. 34C.

465. The solid dispersion comprising 80% amorphous Compound 33 and HPMCAS, according to Embodiment 463 or Embodiment 464, characterized as having a $^{19}$F ssNMR spectrum with a peak at −112.6±0.2 ppm.

466. The solid dispersion comprising 50% amorphous Compound 33 and HPMCAS, according to any one of Embodiments 463-465, characterized as having $^{19}$F ssNMR spectrum substantially similar to FIG. 34D.

EXAMPLES

In order that the disclosure described herein may be more fully understood, the following examples are set forth. It should be understood that these examples are for illustrative purposes only and are not to be construed as limiting this disclosure in any manner.

Example 1. Synthesis of Compounds

All the specific and generic compounds, and the intermediates disclosed for making those compounds, are considered to be part of the invention disclosed herein.

Preparation S1

5-(3,4-difluorophenyl)-7-iodo-1-(phenylsulfonyl)-6-(tetrahydro-2H-pyran-4-yl)-1,5-dihydropyrrolo[2,3-f]indazole (S1)

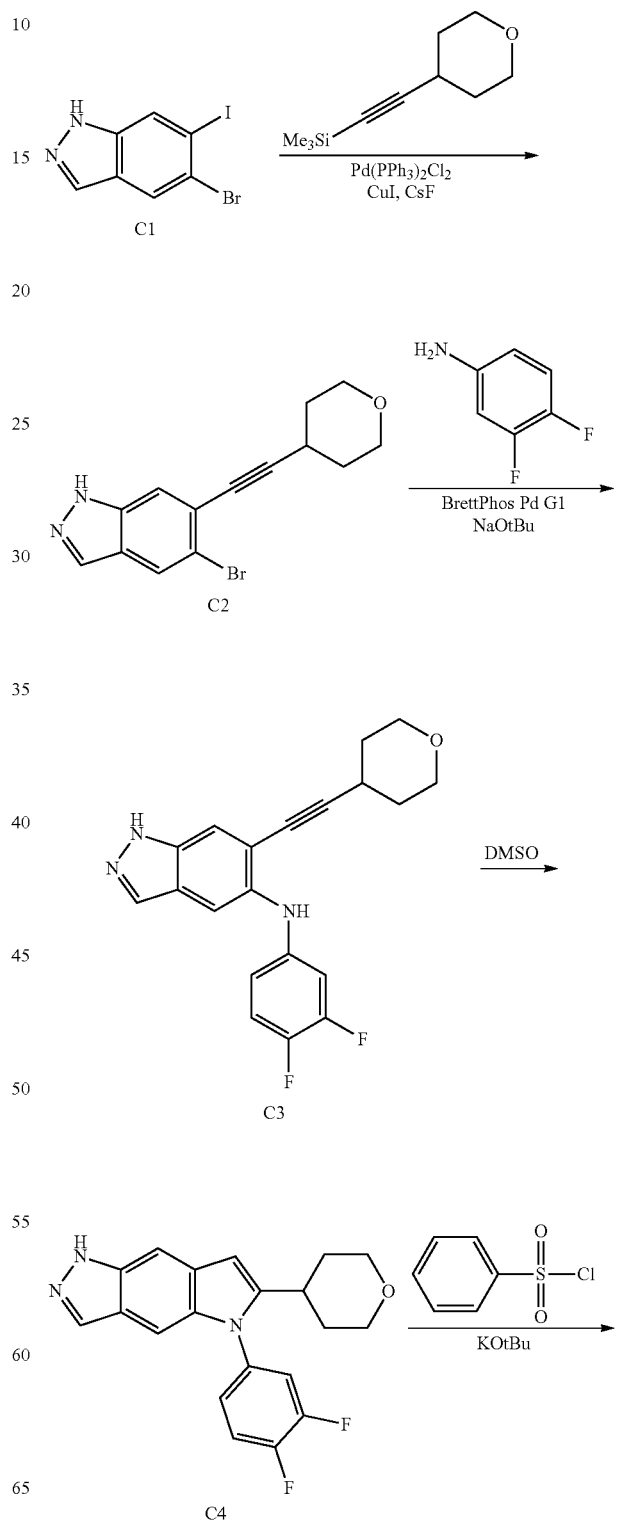

-continued

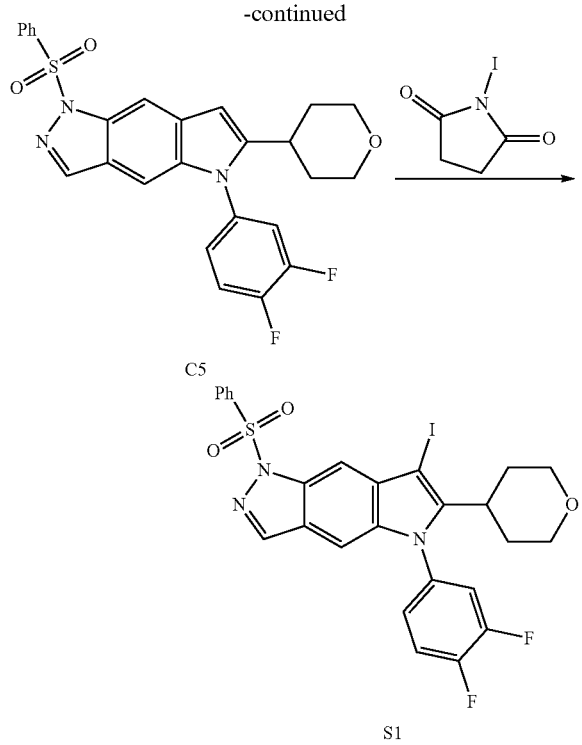

Step 1. Synthesis of 5-bromo-6-(2-tetrahydropyran-4-ylethynyl)-1H-indazole (C2)

To a solution of 5-bromo-6-iodo-1H-indazole C1 (100 g, 294.2 mmol) in 1,4-dioxane (500 mL) was added Et₃N (500 mL, 3.6 mol), copper iodide (3.4 g, 17.9 mmol), CsF (89.4 g, 588.5 mmol), H₂O (10.6 mL, 588.4 mmol), and Pd(PPh₃)₂Cl₂ (6.2 g, 8.8 mmol). Trimethyl((tetrahydro-2H-pyran-4-yl)ethynyl)silane (67 g, 367.5 mmol) was added, and the reaction mixture was purged with nitrogen for 15 min, then heated to 80° C. overnight. Upon cooling, Et₃N and 1,4-dioxane were removed by concentration in vacuo. Water (200 mL) and brine (200 mL) were added and the mixture was extracted with EtOAc (1.4 L). The combined organic layers were dried and concentration in vacuo. Ethyl acetate (120 mL) was added, and the mixture stirred for 1 h. The resulting solid which formed was filtered, and washed with EtOAc (×2) to afford the desired product as a solid (43 g). The filtrate was concentrated and purified by silica gel chromatography (Column: 800 g Silica Gel. Eluent: 25% CH₂Cl₂ in heptane, followed by a gradient of 0-90% CH₂Cl₂ in heptane) to afford additional product as a brown solid (29 g). The product batches were combined to afford the product as a brown solid (72 g, 80%). ¹H NMR (300 MHz, Chloroform-d) δ 10.43 (s, 1H), 8.00 (dd, J=3.0, 0.9 Hz, 2H), 7.62 (t, J=0.8 Hz, 1H), 4.02 (ddd, J=11.6, 6.5, 3.5 Hz, 2H), 3.62 (ddd, J=11.3, 7.7, 3.2 Hz, 2H), 2.98 (tt, J=8.0, 4.2 Hz, 1H), 2.02-1.89 (m, 2H), 1.82 (dtd, J=13.4, 7.7, 3.5 Hz, 2H). LCMS m/z 306.8 [M+H]⁺.

Step 2. Synthesis of N-(3,4-difluorophenyl)-6-(2-tetrahydropyran-4-ylethynyl)-1H-indazol-5-amine (C3)

5-bromo-6-(2-tetrahydropyran-4-ylethynyl)-1H-indazole C2 (51.9 g, 170.1 mmol), 3,4-difluoroaniline (25.3 mL, 255.1 mmol), and NaOtBu (49 g, 509.9 mmol) were added to a Parr bottle. THF (625 mL) was added, and the mixture was then degassed with nitrogen for a ~10 min. BrettPhos Pd G1 (6.8 g, 8.5 mmol) was added, and the mixture degassed further. The reaction was allowed to stir at 70° C. for 120 min. The mixture was concentrated in vacuo, then diluted with CH₂Cl₂ (1 L). The organic layer was washed with 50% saturated sodium bicarbonate (~700 mL). The organic layer was dried with sodium sulfate, filtered and concentrated in vacuo. Two additional 50 g batches of C2 were processed as described. The combined products were purified by silica gel chromatography (Column: 3 kg Silica. Gradient: 0-100% EtOAc in heptane) to afford the product (155.2 g, 83%). ¹H NMR (300 MHz, DMSO-d₆) δ 13.06 (s, 1H), 8.00 (t, J=1.2 Hz, 1H), 7.72 (s, 1H), 7.64-7.58 (m, 1H), 7.55 (s, 1H), 7.26-7.08 (m, 1H), 6.69 (ddd, J=13.4, 7.0, 2.7 Hz, 1H), 6.62-6.52 (m, 1H), 3.72-3.61 (m, 2H), 3.43-3.35 (m, 2H), 2.88-2.76 (m, 1H), 1.76-1.64 (m, 2H), 1.50-1.34 (m, 2H). LCMS m/z 354.2 [M+H]⁺.

Step 3. Synthesis of 5-(3,4-difluorophenyl)-6-tetrahydropyran-4-yl-1H-pyrrolo[2,3-f]indazole (C4)

N-(3,4-difluorophenyl)-6-(2-tetrahydropyran-4-ylethynyl)-1H-indazol-5-amine C3 (155.2 g, 439.2 mmol) was dissolved in DMSO (650 mL) and placed in a 2 L Parr bottle. The reaction was sealed and heated at 150-160° C. for 120 min, and then cooled to room temperature. 25% saturated sodium bicarbonate (6.5 L) was added to the reaction mixture. Upon stirring for 1 h, the mixture was filtered, the filter cake washed with additional water, and dried under vacuum at 50° C. for 2 days to afford the product (146 g, 89%). ¹H NMR (300 MHz, DMSO-d₆) δ 12.63 (s, 1H), 7.98 (s, 1H), 7.81-7.63 (m, 2H), 7.57 (t, J=1.1 Hz, 1H), 7.44-7.33 (m, 1H), 7.25 (t, J=0.9 Hz, 1H), 6.52 (d, J=0.8 Hz, 1H), 3.85 (dt, J=11.5, 3.2 Hz, 2H), 3.28 (td, J=11.3, 3.5 Hz, 2H), 2.88 (tt, J=10.0, 4.9 Hz, 1H), 1.78-1.58 (m, 4H). LCMS m/z 354.2 [M+H]⁺.

Step 4. Synthesis of 1-(benzenesulfonyl)-5-(3,4-difluorophenyl)-6-tetrahydropyran-4-yl-pyrrolo[2,3-f]indazole (C5)

To a solution of 5-(3,4-difluorophenyl)-6-tetrahydropyran-4-yl-1H-pyrrolo[2,3-f]indazole C4 (15 g, 40.8 mmol) in THF (175 mL) was added KOtBu (5.9 g, 52.6 mmol) and the mixture was stirred at room temperature for 10 min. The reaction was cooled to 0° C. in an ice bath, then benzenesulfonyl chloride (6.7 mL, 52.5 mmol) was added dropwise over 2 h. The mixture was allowed to stir at 0° C. for an additional 2 h. Aqueous NH₄Cl₍sat.₎, water and CH₂Cl₂ was added. The organic phase was separated on a phase separator and purified by silica gel chromatography (Eluent: Ethyl acetate/CH₂Cl₂) to afford the product (15.2 g, 73%). ¹H NMR (400 MHz, DMSO-d₆) δ 8.47 (s, 1H), 8.24 (s, 1H), 7.84 (t, J=8.7 Hz, 3H), 7.68 (dt, J=26.0, 8.4 Hz, 2H), 7.53 (t, J=7.7 Hz, 2H), 7.47-7.28 (m, 2H), 6.75 (s, 1H), 3.86 (d, J=11.4 Hz, 2H), 3.33-3.16 (m, ~2H), 2.89 (d, J=5.8 Hz, 1H), 1.71 (t, J=5.6 Hz, 4H). LCMS m/z 494.3 [M+H]⁺.

Step 5. Synthesis of 1-(benzenesulfonyl)-5-(3,4-difluorophenyl)-7-iodo-6-tetrahydropyran-4-yl-pyrrolo[2,3-f]indazole (S1)

1-iodopyrrolidine-2,5-dione (1.1 g, 4.4 mmol) was added to a solution of 1-(benzenesulfonyl)-5-(3,4-difluorophenyl)-6-tetrahydropyran-4-yl-pyrrolo[2,3-f]indazole C5 (2.2 g, 4.5 mmol) in CH$_2$Cl$_2$ (25 mL) at room temperature over 1 h. The mixture was allowed to stir overnight and then purified by silica gel chromatography (Eluent: Ethyl acetate/CH$_2$Cl$_2$) to afford the product (2.33 g, 84%). $^1$H NMR (400 MHz, DMSO-d$_6$) δ 8.51 (s, 1H), 8.05 (s, 1H), 7.82 (d, J=7.9 Hz, 3H), 7.80-7.62 (m, 2H), 7.56 (t, J=7.7 Hz, 2H), 7.43 (d, J=8.9 Hz, 1H), 7.33 (s, 1H), 5.76 (s, 3H), 3.97-3.73 (m, 2H), 3.32-3.17 (m, 1H), 2.92 (t, J=12.3 Hz, 1H), 2.30 (dd, J=16.3, 10.0 Hz, 2H), 1.66 (d, J=13.0 Hz, 2H). LCMS m/z 620.2 [M+1]$^+$.

Preparation S2

1-(5-(3-fluorophenyl)-7-iodo-6-methylpyrrolo[2,3-f]indazol-1(5H)-yl)-2,2-dimethylpropan-1-one (S2)

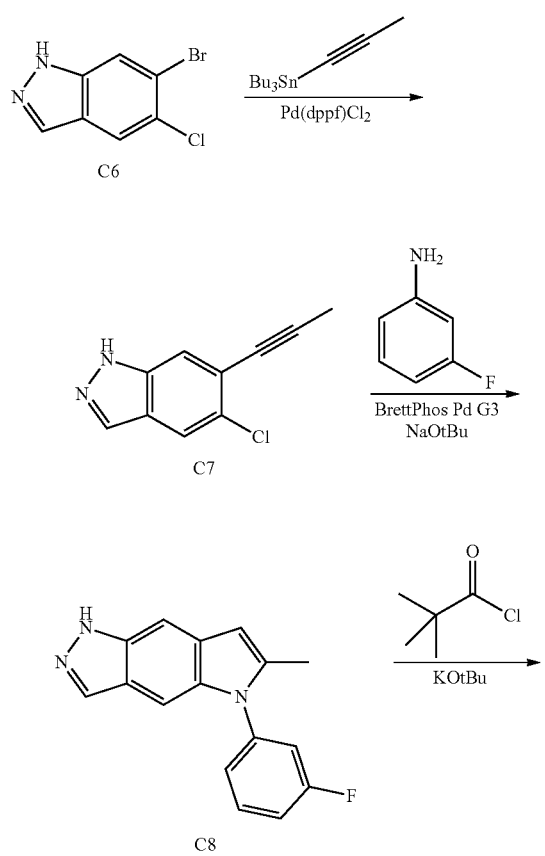

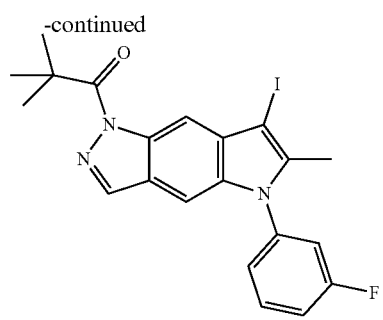

S2

Step 1. Synthesis of 5-chloro-6-prop-1-ynyl-1H-indazole (C7)

6-bromo-5-chloro-1H-indazole C6 (1.5 g, 6.5 mmol) and Pd(dpppf)$_2$Cl$_2$ (550 mg, 0.67 mmol) were added to a Parr bottle. 1,4-dioxane (50 mL) was added and the vessel flushed with nitrogen. tributyl(prop-1-ynyl)stannane (3 mL, 9.9 mmol) was added, and the reaction heated to 115° C. overnight. The reaction mixture was adsorbed onto Celite® and purified by silica gel chromatography (Gradient: 0-100% ethyl acetate in heptane) to afford the product (0.77 g, 56%). LCMS m/z 191.1 [M+H]$^+$.

Step 2. Synthesis of 5-(3-fluorophenyl)-6-methyl-1H-pyrrolo[2,3-f]indazole (C8)

5-chloro-6-prop-1-ynyl-1H-indazole C7 (770 mg, 3.7 mmol), 3-fluoroaniline (600 µL, 6.2 mmol), sodium t-butoxide (1.1 g, 11.0 mmol), and BrettPhos Pd G3 (160 mg, 0.18 mmol) were added to a vial. m-Xylene (13 mL) was added and the mixture purged with nitrogen. The reaction was allowed to stir at 115° C. overnight. The mixture was then concentrated in vacuo, diluted with ethyl acetate (20 mL) and washed with 50% saturated sodium bicarbonate (20 mL). The organic layer was dried sodium sulfate, filtered and concentrated in vacuo. Purification by silica gel chromatography (Gradient: 0-100% ethyl acetate in heptane) afforded the product (179 mg, 18%). $^1$H NMR (300 MHz, DMSO-d$_6$) δ 12.62 (s, 1H), 7.99 (t, J=1.3 Hz, 1H), 7.72-7.61 (m, 1H), 7.55-7.49 (m, 1H), 7.45 (dt, J=10.0, 2.3 Hz, 1H), 7.40-7.30 (m, 3H), 6.48 (t, J=1.0 Hz, 1H), 2.33 (d, J=1.0 Hz, 3H). LCMS m/z 266.2 [M+H]$^+$.

Step 3. Synthesis of 1-[5-(3-fluorophenyl)-6-methyl-pyrrolo[2,3-f]indazol-1-yl]-2,2-dimethyl-propan-1-one (C9)

To a solution of 5-(3-fluorophenyl)-6-methyl-1H-pyrrolo[2,3-f]indazole C8 (177 mg, 0.65 mmol) in THF (3.5 mL) at 1° C. (ice-water bath) was added KOtBu (881 µL of 1 M, 0.9 mmol). After ~10 min, 2,2-dimethylpropanoyl chloride (108 µL, 0.9 mmol) was added and the mixture allowed to stir for 30 min. An additional 25 µl of 2,2-dimethylpropanoyl chloride was added and the mixture stirred for an additional ~30 min in an ice bath. The reaction was quenched with water (3 mL), stirred for 5 min and concentrated to in vacuo. The residue was partitioned between CH$_2$Cl$_2$ (10 mL) and water (10 mL). The organic layer was isolated, washed with water, passed through a phase separator and concentrated in vacuo. Silica gel chromatography (Gradient: 0-50% ethyl acetate in heptane) afforded the product (151 mg, 64%). $^1$H NMR (400

MHz, DMSO-d$_6$) δ 8.48 (s, 1H), 8.40 (d, J=0.8 Hz, 1H), 7.73-7.64 (m, 1H), 7.54-7.47 (m, 2H), 7.45-7.36 (m, 2H), 6.68-6.63 (m, 1H), 2.37 (d, J=1.0 Hz, 3H), 1.52 (s, 9H). LCMS m/z 350.3 [M+H]$^+$.

Step 4. Synthesis of 1-[5-(3-fluorophenyl)-7-iodo-6-methyl-pyrrolo[2,3-f]indazol-1-yl]-2,2-dimethyl-propan-1-one (S2)

1-iodopyrrolidine-2,5-dione (97 mg, 0.41 mmol) was added portion-wise to a solution of 1-[5-(3-fluorophenyl)-6-methyl-pyrrolo[2,3-f]indazol-1-yl]-2,2-dimethyl-propan-1-one C9 (148 mg, 0.41 mmol) in CH$_2$Cl$_2$ (2 mL) at room temperature. The mixture was stirred for 1 h, and diluted with CH$_2$Cl$_2$ (5 mL). The mixture was washed with 50% saturated sodium bicarbonate (5 mL). The organic layer was separated on a phase separator and then concentrated in vacuo to afford the product (195 mg, 97%). $^1$H NMR (400 MHz, DMSO-d$_6$) δ 8.46 (d, J=0.8 Hz, 1H), 8.34-8.30 (m, 1H), 7.70 (td, J=8.2, 6.5 Hz, 1H), 7.58-7.53 (m, 2H), 7.48-7.40 (m, 2H), 2.42 (s, 3H), 1.53 (s, 9H). LCMS m/z 476.3 [M+H]$^+$.

Preparation S3

1-(5-(3-fluorophenyl)-7-iodo-6-(tetrahydro-2H-pyran-4-yl)pyrrolo[2,3-f]indazol-1(5H)-yl)-2,2-dimethylpropan-1-one (S3)

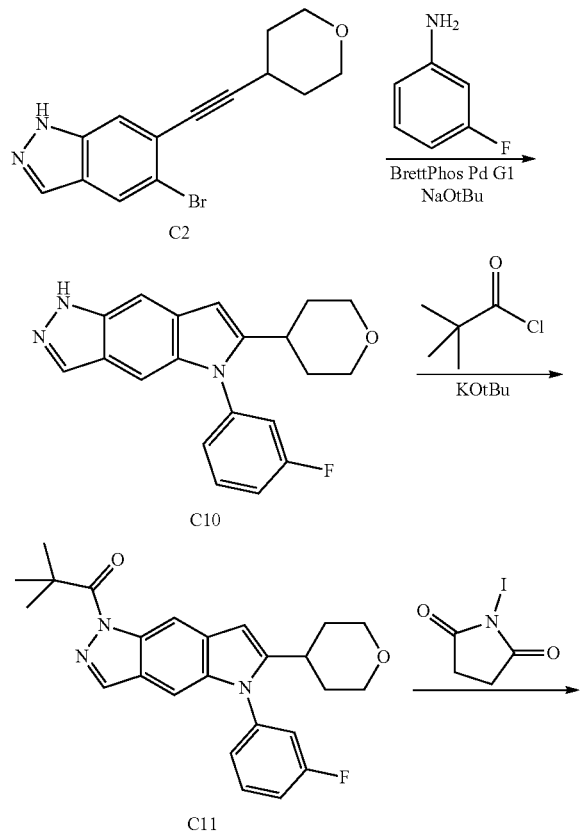

C2

C10

C11

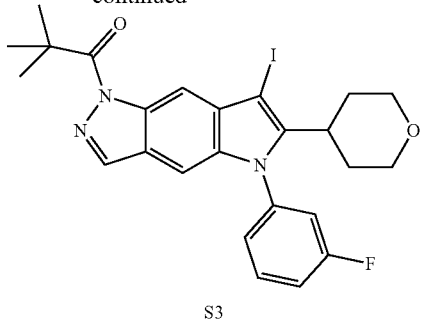

S3

Step 1. Synthesis of 5-(3-fluorophenyl)-6-tetrahydropyran-4-yl-1H-pyrrolo[2,3-f]indazole (C10)

5-bromo-6-(2-tetrahydropyran-4-ylethynyl)-1H-indazole C2 (3 g, 9.8 mmol), 3-fluoroaniline (1.5 mL, 15.6 mmol), and NaOtBu (2.8 g, 29.1 mmol) were added to a Parr bottle. THF (65 mL) was added, and the mixture purged with nitrogen for ~10 min. BrettPhos (388 mg, 0.49 mmol) was added, and the mixture further purged with nitrogen. The reaction was heated at 50° C. overnight, then diluted with EtOAc (150 mL). The mixture was then washed with 50% saturated sodium bicarbonate (100 mL). The organic layer was dried over sodium sulfate, filtered and concentrated in vacuo. Purification by silica gel chromatography (Gradient: 0-100% ethyl acetate in heptane) afforded the product (3.06 g, 91%). $^1$H NMR (300 MHz, DMSO-d$_6$) δ 13.05 (s, 1H), 8.04-7.92 (m, 1H), 7.78 (s, 1H), 7.60 (d, J=6.1 Hz, 2H), 7.19-7.05 (m, 1H), 6.60 (ddd, J=8.2, 2.0, 0.9 Hz, 1H), 6.52-6.36 (m, 2H), 3.72-3.59 (m, 2H), 3.42-3.32 (m, 2H), 2.87-2.75 (m, 1H), 1.75-1.61 (m, 2H), 1.49-1.34 (m, 2H).

Step 2. Synthesis of 1-[5-(3-fluorophenyl)-6-tetrahydropyran-4-yl-pyrrolo[2,3-f]indazol-1-yl]-2,2-dimethyl-propan-1-one (C11)

To a suspension of 5-(3-fluorophenyl)-6-tetrahydropyran-4-yl-1H-pyrrolo[2,3-f]indazole C10 (1.65 g, 4.9 mmol) in THF (40 mL) at 1° C. (ice-water bath) was added KOtBu (6.5 mL of 1 M, 6.5 mmol). After ~10 min, 2,2-dimethylpropanoyl chloride (806 µL, 6.6 mmol) was added, and the reaction was allowed to stir for 30 min. An additional 80 µL of 2,2-dimethylpropanoyl chloride was added, and the mixture allowed to stir for an additional ~30 min. The reaction mixture was quenched with water (5 mL), stirred for 5 min, and then concentrated to dryness under reduced pressure. The mixture was partitioned between CH$_2$Cl$_2$ (100 mL) and water (50 mL). The organic layer was washed with water, passed through a phase separator and concentrated in vacuo. Silica gel chromatography (Gradient: 0-50% ethyl acetate in heptane) afforded the product (1.75 g, 84%). $^1$H NMR (400 MHz, DMSO-d$_6$) δ 8.40 (d, J=0.8 Hz, 1H), 8.37-8.33 (m, 1H), 7.97 (s, 1H), 7.70 (s, 1H), 7.27-7.19 (m, 1H), 6.82 (ddd, J=8.2, 2.2, 0.8 Hz, 1H), 6.74 (dt, J=11.8, 2.3 Hz, 1H), 6.64-6.57 (m, 1H), 3.76-3.65 (m, 2H), 3.45-3.36 (m, 2H), 2.95-2.84 (m, 1H), 1.81-1.71 (m, 2H), 1.54-1.44 (m, 11H). LCMS m/z 420.3 [M+H]$^+$.

Step 3. Synthesis of 1-[5-(3-fluorophenyl)-7-iodo-6-tetrahydropyran-4-yl-pyrrolo[2,3-f]indazol-1-yl]-2,2-dimethyl-propan-1-one (S3)

1-iodopyrrolidine-2,5-dione (112 mg, 0.5 mmol) was added portion-wise to a solution of 1-[5-(3-fluorophenyl)-

6-tetrahydropyran-4-yl-pyrrolo[2,3-f]indazol-1-yl]-2,2-dimethyl-propan-1-one C11 (202 mg, 0.5 mmol) in CH$_2$Cl$_2$ (3 mL), and the reaction allowed to stir at room temperature for 1 h. The mixture was diluted with CH$_2$Cl$_2$ (5 mL), washed with 50% saturated sodium bicarbonate (5 mL). The organic layer was passed through a phase separator, and concentrated to dryness under reduced pressure. The resulting solid was dried under vacuum for 2 h to afford the product (237 mg, 87%). $^1$H NMR (300 MHz, DMSO-d$_6$) δ 8.44 (d, J=0.8 Hz, 1H), 8.39 (t, J=0.9 Hz, 1H), 7.77-7.68 (m, 1H), 7.58-7.51 (m, 2H), 7.42-7.36 (m, 1H), 7.34 (d, J=1.0 Hz, 1H), 3.96-3.88 (m, 2H), 3.23 (t, J=12.1 Hz, 2H), 2.96 (t, J=12.6 Hz, 1H), 2.38-2.26 (m, 2H), 1.67 (d, J=12.7 Hz, 2H), 1.52 (s, 9H). LCMS m/z 546.4 [M+H]$^+$.

Preparation S4

1-(5-(4-fluorophenyl)-7-iodo-6-(tetrahydro-2H-pyran-4-yl)pyrrolo[2,3-f]indazol-1(5H)-yl)-2,2-dimethylpropan-1-one (S4)

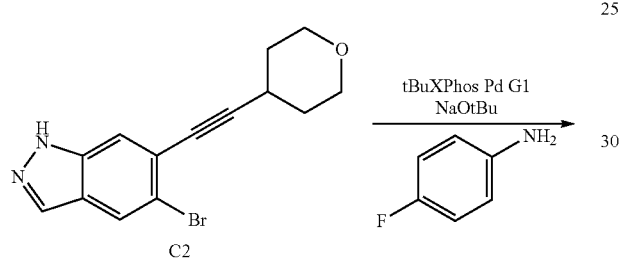

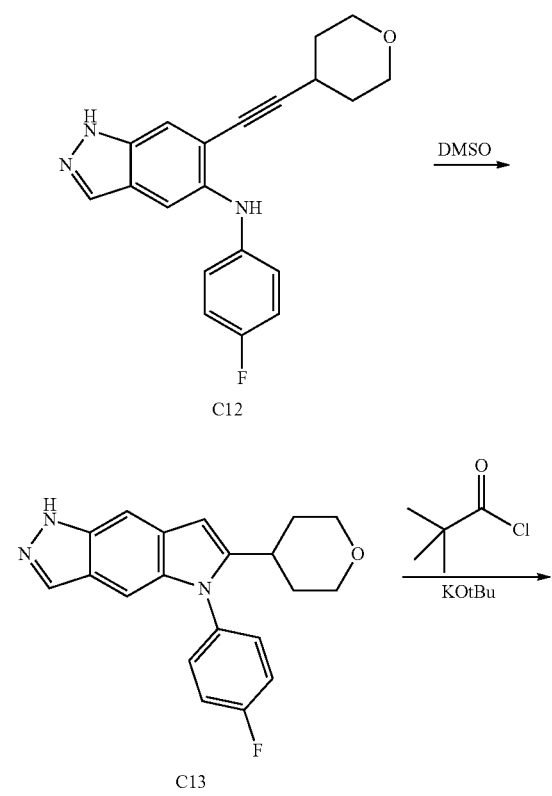

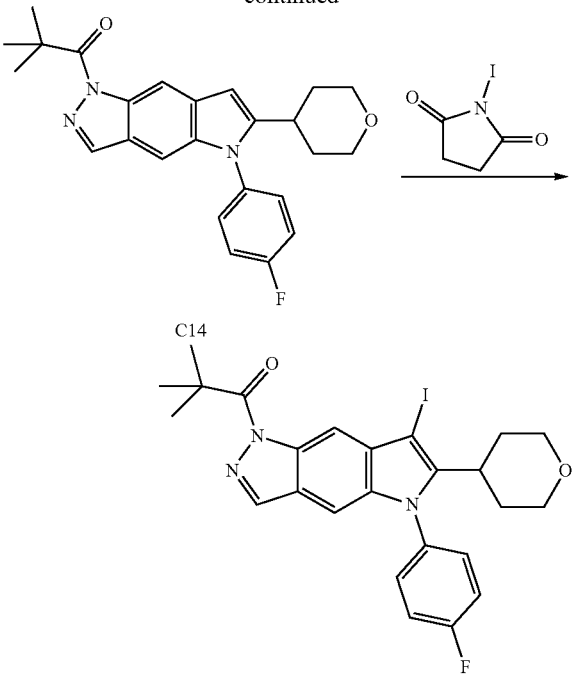

Steps 1 & 2. Synthesis of 5-(4-fluorophenyl)-6-tetrahydropyran-4-yl-1H-pyrrolo[2,3-f]indazole (C13)

A mixture of 5-bromo-6-(2-tetrahydropyran-4-ylethynyl)-1H-indazole C2 (160 g, 524.3 mmol), 4-fluoroaniline (75 mL, 791.7 mmol), NaOtBu (90 g, 936.5 mmol) in tBuOH (2.1 L) at 40° C. was purged with nitrogen for 10 min. tBuXPhos Pd G1 (10.8 g, 15.7 mmol) was added, and the mixture purged with nitrogen for an additional 10 min. The mixture was heated to 80° C. for 1 h, and then concentrated in vacuo. CH$_2$Cl$_2$ (1.5 L), saturated NH$_4$Cl (1 L), and HCl (62 mL of 6 M, 372.0 mmol) were added. The organic layer was dried with Na$_2$SO$_4$, concentrated in vacuo, and re-dissolved in CH$_2$Cl$_2$ (160 mL). The mixture was filtered to remove the white inorganic solid. The filtrate was then purified by silica chromatography (Column: 3 kg Silica gel. Gradient: 0-90% EtOAc in heptane) to afford the product contaminated with 4-fluoroaniline. The mixture was dissolved in EtOAc (1.5 L), a washed with 1N HCl (2×250 mL), then brine. The organic layer was dried, and concentrated in vacuo to afford the product as a sticky solid, which was used without further purification (160 g, 91%). LCMS m/z 336.1 [M+H]$^+$.

A solution of N-(4-fluorophenyl)-6-(2-tetrahydropyran-4-ylethynyl)-1H-indazol-5-amine C12 in DMSO (550 mL) was heated to 160° C. for 1.5 h. The mixture was cooled, and sat. Na$_2$CO$_3$ (500 mL) and water (1.5 L) were added. The mixture was allowed to stir overnight. The resulting grey solid suspension was filtered, and the filter cake was washed with water (×3), then heptane (×3). The filter cake was suspended in TBME (300 mL) and stirred. Solvent was then removed by concentration in vacuo. The resulting solid was dried under vacuum overnight to afford the product (134 g, 76%). $^1$H NMR (300 MHz, DMSO-d$_6$) δ 12.62 (s, 1H), 7.97 (s, 1H), 7.66-7.35 (m, 5H), 7.17 (s, 1H), 6.51 (s, 1H), 3.93-3.75 (m, 2H), 3.24 (td, J=11.3, 5.2 Hz, 2H), 2.82 (dt, J=10.4, 6.3 Hz, 1H), 1.70 (dt, J=10.1, 4.8 Hz, 4H). LCMS m/z 336.1 [M+H]⁺.

Step 3. Synthesis of 1-[5-(4-fluorophenyl)-6-tetrahydropyran-4-yl-pyrrolo[2,3-f]indazol-1-yl]-2,2-dimethyl-propan-1-one (C14)

To a solution of 5-(4-fluorophenyl)-6-tetrahydropyran-4-yl-1H-pyrrolo[2,3-f]indazole C13 (10 g, 29.8 mmol) in THF (320 mL) at 0° C. was added KOtBu (7.4 g, 65.7 mmol) and the mixture allowed to stir for 5 min. 2,2-dimethylpropanoyl chloride (14.5 mL, 117.9 mmol) was added and the mixture allowed to stir for 1 h. Water (200 mL) and CH₂Cl₂ (250 mL) were added and the mixture extracted with additional dichloromethane (2×50 mL). The organic layer was dried over Na₂SO₄ and concentrated in vacuo. Purification by silica gel chromatography (Gradient: 0-5% EtOAc in Heptane) afforded the product as light yellow solid. 1-[5-(4-fluorophenyl)-6-tetrahydropyran-4-yl-pyrrolo[2,3-f]indazol-1-yl]-2,2-dimethyl-propan-1-one (10.7 g, 83%). ¹H NMR (400 MHz, Chloroform-d) δ 8.69 (s, 1H), 8.07 (s, 1H), 7.39 (dd, J=8.4, 4.9 Hz, 2H), 7.32 (d, J=8.3 Hz, 2H), 7.21 (s, 1H), 6.59 (s, 1H), 4.01 (dd, J=12.0, 4.1 Hz, 2H), 3.37 (t, J=11.7 Hz, 2H), 2.89-2.80 (m, 1H), 1.89 (qd, J=12.2, 4.1 Hz, 2H), 1.78 (d, J=13.0 Hz, 2H), 1.61 (d, J=1.3 Hz, 9H). LCMS m/z 420.3 [M+H]⁺.

Step 4. Synthesis of 1-[5-(4-fluorophenyl)-7-iodo-6-tetrahydropyran-4-yl-pyrrolo[2,3-f]indazol-1-yl]-2,2-dimethyl-propan-1-one (S4)

1-iodopyrrolidine-2,5-dione (7.4 g, 31.2 mmol) was added portion-wise over 30 min to a solution of 1-[5-(4-fluorophenyl)-6-tetrahydropyran-4-yl-pyrrolo[2,3-f]indazol-1-yl]-2,2-dimethyl-propan-1-one C14 (10.7 g, 25.4 mmol) in CH₂Cl₂ (110 mL). The reaction was stirred at room temperature for 30 min. Purification by silica gel chromatography (Gradient: 0-5% EtOAc in Dichloromethane) resulted in an orange solid, which was triturated with heptane. Water (250 mL) was then added, and the mixture stirred vigorously for 30 min. The solid was filtered, washed with excess water then dissolved in CH₂Cl₂ (250 mL). The solution was washed with water (250 mL) and the organic phase dried (phase separator) and concentrated in vacuo to afford the product as a light tan solid (11.7 g, 84%). ¹H NMR (400 MHz, Chloroform-d) δ 8.63 (s, 1H), 8.08 (s, 1H), 7.37-7.30 (m, 4H), 7.08 (s, 1H), 4.04 (dd, J=11.7, 4.2 Hz, 2H), 3.38 (t, J=11.8 Hz, 2H), 3.07 (t, J=12.6 Hz, 1H), 2.43 (qd, J=12.5, 4.3 Hz, 2H), 1.62 (s, 9H). LCMS m/z 546.33 [M+H]⁺.

Alternative Preparation of 1-[5-(4-fluorophenyl)-7-iodo-6-tetrahydropyran-4-yl-pyrrolo[2,3-f]indazol-1-yl]-2,2-dimethyl-propan-1-one (S4)

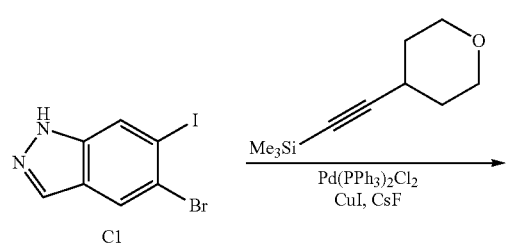

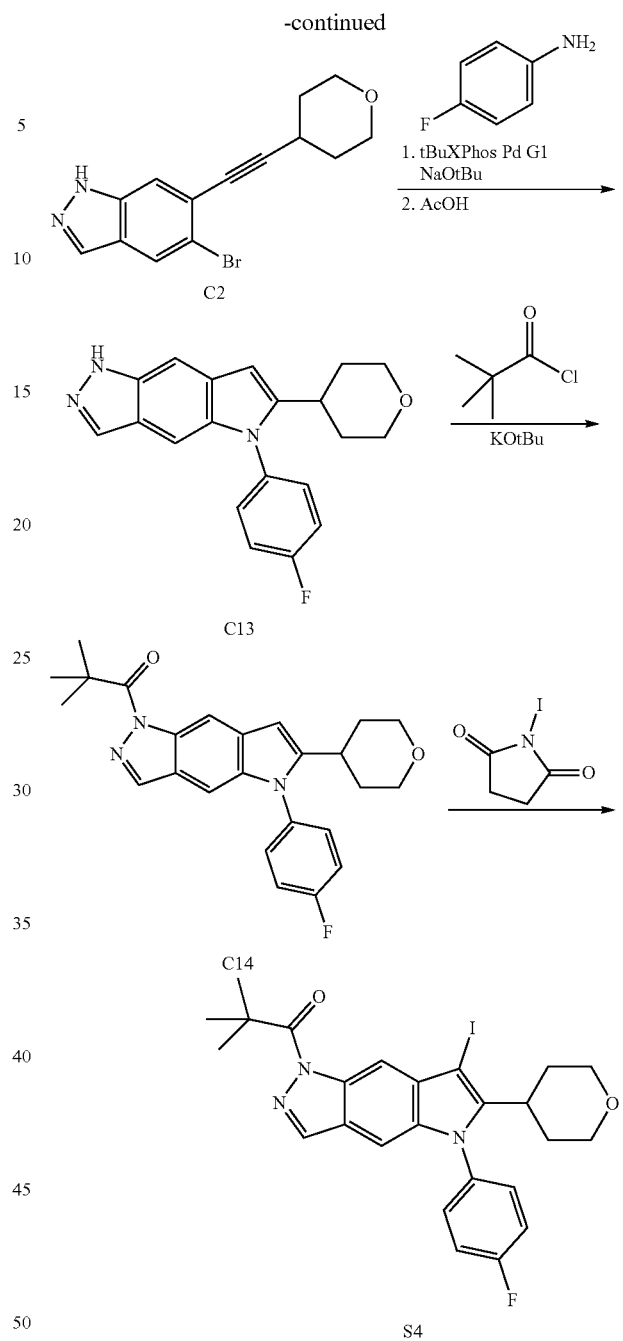

Step 1. Synthesis of 5-bromo-6-(2-tetrahydropyran-4-ylethynyl)-1H-indazole (C2)

To reactor A under N₂ was charged 5-bromo-6-(2-tetrahydropyran-4-ylethynyl)-1H-indazole C1 (12.0 kg), PdCl₂(PPh₃)₂, (0.26 kg), and CuI (0.35 kg). Reactor A was degassed (vacuum/nitrogen purges×2). To reactor B was charged EtOH (52.1 kg) (to aid in the transfer of trimethyl ((tetrahydro-2H-pyran-4-yl)ethynyl)silane), and degassed with (vacuum/nitrogen purges×2). To reactor A was charged trimethyl((tetrahydro-2H-pyran-4-yl)ethynyl)silane (7.42 kg) and EtOH (4.7 kg). To reactor A was charged 45 wt % KOH (9.72 kg) and EtOH (4.6 kg) (to aid in the transfer of the 45 wt % KOH). The agitator was started in Reactor A, the vessel was then degassed (vacuum/nitrogen purges×4), and the contents of Reactor A were heated to 75±5° C. The reaction was held at 76.5 to 77.0° C. for 2 h, and then cooled to 40.1° C. over 20 min. The contents of reactor A were concentrated to a volume of 24 L by vacuum distilled with the maximum temperature of 35.1° C. The contents of reactor A were adjusted to 13.5° C. To a drum was added water (73.9 kg) and concentrated HCl (4.1 kg). The HCl transfer line was rinsed with water (4.7 kg) and charged to the drum. The contents of the drum were mixed (0.5 M HCl soln). The 0.5 M HCl solution (73.9 kg) was transferred to Reactor A over 21 min to cause precipitation of 5-bromo-6-(2-tetrahydropyran-4-ylethynyl)-1H-indazole C2 and a maximum temperature of 20.9° C. (spec. 20±5° C.) during the addition. An aliquot of the slurry was taken and the pH was measured to be 2.0 with a calibrated pH probe. KOH (45 wt %, 0.3 kg) was charged to Reactor A to give a reaction temperature of 15.4° C. An aliquot of the slurry was taken and the pH was measured to be 10.3 with a calibrated pH probe. HCl (0.5 M, 1.2 kg) was transferred over 2 min to reactor A with a maximum temperature of 13.8° C. An aliquot of the slurry was taken and the pH was measured to be 6.03 with a calibrated pH probe. The contents of reactor A were adjusted to 22.1° C. and held for 1 h at 22.1° C. The contents of reactor A were filtered (filtration time 27 min) and washed with water (2×36 kg). The solids were dried on the filter for 50 min, then dried on trays at 50-55° C. for 16 h to afford the product C2.

Step 2. Synthesis of 5-(4-fluorophenyl)-6-tetrahydropyran-4-yl-1H-pyrrolo[2,3-f]indazole (C13)

NaOtBu, 97% (39.2 g, 407.4 mmol, 2.1 equiv.) was added to a reactor. Ethanol (355.2 mL, 6 vols) was added (Note: exothermic reaction) and the mixture was purged with nitrogen. 5-bromo-6-[2-(oxan-4-yl)ethynyl]-1H-indazole C2 (59.2 g, 194 mmol, 1 equiv.) was added at 20° C. to the reactor. 4-fluoroaniline (23.71 g, 20.3 mL, 213.4 mmol, 1.1 equiv.) was then added and the mixture degassed (vacuum and nitrogen purge cycles×3). t-BuXPhos Pd G1 (4.0 g, 5.82 mmol, 0.03 equiv.) at 20° C. was added and the mixture degassed again (vacuum and nitrogen purge cycles×3). The reactor was heated to 65° C. internal temperature for 2 h, then cooled to 60° C. AcOH (55.3 g, 52.8 mL, 921.5 mmol, 4.75 equiv.) at 60° C. was added (Note exothermic reaction, solids precipitate during addition) and the reaction allowed to stir at 60-63° C. for 2 h. The mixture was then cooled to 25° C. Dichloromethane (8 vol) was added to the mixture. 0.5 M NaOH (5 vol) was added and the phases were stirred vigorously for 20 minutes. Additional 0.5 M NaOH was added to adjust the pH to pH 6-7. The phases were separated, and the aqueous phase was separated and extracted with dichlormethane (4 vol). The organic phases were combined, and distilled to ~3 vol. Additional dichloromethane (6 vol) was added and the distillation to 3 vol. repeated. Addition of dichloromethane, then distillation was repeated until the residual EtOH was reduced to below 1% by NMR. The residual solution of 3 vol dichloromethane was heated to 38° C. Heptane (3 vol) was added and the mixture was stirred for 1 h, then cooled to 20° C. over 3 h. The resulting slurry was filtered and the filter cake washed with 1:1 v/v dichloromethane:heptane. The product was dried under vacuum at 45° C. to afford the product as a white solid (75% yield).

Step 3. Synthesis of 1-[5-(4-fluorophenyl)-6-tetrahydropyran-4-yl-pyrrolo[2,3-f]indazol-1-yl]-2,2-dimethyl-propan-1-one (C14)

To reactor A under nitrogen was charged 5-(4-fluorophenyl)-6-tetrahydropyran-4-yl-1H-pyrrolo[2,3-f]indazole C13 (8.3 kg) and THF (99.4 kg). The agitator was started in Reactor A. Compound C13 dissolved and the solution was cooled to 1.7° C. KOtBu in THF (15.9 kg) was charged to reactor A over 9 min (temp. range during addition 0.2° C. to 1.6° C.). The transfer line was rinsed with THF (1.0 kg) and transferred to reactor A. The contents of reactor A were stirred for 10 min at 1.6° C. Pivaloyl chloride (3.3 kg) was charged over 32 min to reactor A with the maximum temperature reaching 2.3° C. The transfer line was rinsed with THF (0.5 kg) and transferred to reactor A. The contents of reactor A were held at 0.7° C. to 2.1° C. for 1 h. To a drum was charged NaHCO$_3$ (2.3 kg) and water (32.0 kg). The contents were briefly mixed to dissolve the NaHCO$_3$. The contents of reactor A were warmed to 19.0° C. over 2 h 10 min. The NaHCO$_3$ solution was charged to reactor A over 10 min (max. temp. during addition 19.4° C.). MTBE (29.3 kg) was charged to reactor A. The contents of reactor A were stirred at 25±5° C. for 15 min. The agitator was stopped and the phases separated for 33 min. The aqueous phase was removed. The agitator in reactor A was started. To a drum was added sodium chloride (6.2 kg) and water (26.1 kg). The drum was stirred to give a solution. The brine solution was transferred to reactor A. The contents were stirred for 19 min at 25±5° C. The agitator in reactor A was stopped and the phases settled for 20 min. The aqueous phase was removed. The agitator was started and the organic phase was concentrated by vacuum distillation to 30 L with the maximum distillation temperature of 26.2° C. To reactor A was charged n-heptane (21.9 kg). The contents of reactor A were concentrated to 30 L by vacuum distillation (maximum temperature 25.8° C.). To reactor A was charged n-heptane (21.8 kg) over 17 min. The contents of reactor A were concentrated to 30 L by vacuum distillation (maximum temperature 29.3° C.). To reactor A was charged n-heptane (23.0 kg) over 16 min. The contents of reactor A were stirred at 20±5° C. for 1 h. The slurry was filtered. To reactor A was charged n-heptane (11.2 kg) and transferred to the filter. This was repeated with another n-heptane (11.2 kg) rinse. The cake was dried under nitrogen pressure for 5 h and then loaded into trays and dried for 3 days to afford the product 1-[5-(4-fluorophenyl)-6-tetrahydropyran-4-yl-pyrrolo[2,3-f]indazol-1-yl]-2,2-dimethyl-propan-1-one (C14) as a solvate with THF (5 wt %) by $^1$H NMR (6.9 kg, 68%, brown solid).

Step 4. Synthesis of 1-[5-(4-fluorophenyl)-7-iodo-6-tetrahydropyran-4-yl-pyrrolo[2,3-f]indazol-1-yl]-2,2-dimethyl-propan-1-one (S4)

To reactor A under nitrogen was added 1-[5-(4-fluorophenyl)-6-tetrahydropyran-4-yl-pyrrolo[2,3-f]indazol-1-yl]-2,2-dimethyl-propan-1-one C14 (4.75 kg) and CH$_2$Cl$_2$ (29 L). The agitator was started and the jacket was set at −10° C. The solution was cooled to <5.0° C. and N-iodosuccinimide (2.73 kg) was added in three equal portions. At 3.0° C. the 1$^{st}$ portion was added and gave an exotherm to 4.1° C. After 19 min the reaction temperature had cooled to 0.9° C. The 2$^{nd}$ portion was added at 0.9° C. with an exotherm to 2.3° C. After 15 min, the reaction temperature had cooled to 1.4° C. The 3$^{rd}$ portion was added at 1.4° C. with an exotherm to 2.1° C. CH$_2$Cl$_2$ (1 L) was charged to reactor A to rinse the N-iodosuccinimide. The jacket temperature was set at 0° C. and the reaction was stirred for 50 min with a final reaction temperature of 3.2° C. To a container was charged sodium thiosulfate pentahydrate (0.85 kg) and water (14.5 L). The contents were mixed to give a solution. The sodium thiosulfate solution (room temperature) was charged in portions to the reaction solution (3.4° C., jacket temperature 0° C.)

over 8 min to give an exotherm to 11.6° C. The mixture was warmed to 20° C. stirred for 15 min. The agitator was stopped to let the phases separate for 35 min. The aqueous phase was removed and back extracted with $CH_2Cl_2$ (5 L). The mixture was stirred 10 min at 20° C. and the agitator was stopped. The phases settled for 10 min and the aqueous phase was removed. The organic phases were combined and charged back to reactor A. The agitator was started. To a container was charged $KHCO_3$ (0.90 kg) and water (14.1 L). The contents were mixed to give a solution. The $KHCO_3$ aq. solution was added to reactor A and stirred for 10 min at 20° C. The agitator was stopped and an emulsion had formed. The phases separated overnight and the aqueous phase was removed. The organic phase was charged back to the reactor and rinsed in with $CH_2Cl_2$ (1 L). A container was charged NaCl (3.0 kg) and potable water (12.0 L). The contents were mixed to dissolve and the brine solution was transferred to reactor A. The contents of reactor A were mixed for 10 min at 20° C. The agitator was stopped and an emulsion had formed. After settling for 2 h the majority of the organic $CH_2Cl_2$ bottom phase was removed leaving behind about 18 L of emulsion. Water (7.5 L) was added to reactor A with slow stirring (50 rpm) this diluted the brine wash from 20 wt % to approximately 12 wt %. The phases separated in 20 min and the $CH_2Cl_2$ bottom layer was removed. The organic phase was split in half and concentrated in two flasks. Each flask was concentrated to 5 volumes. To each flask was charged MeOH (10 L) in portions and distilled to 4 volumes. To each flask was charged MeOH (4 L) and distilled to 2 volumes. The contents of each flask were cooled to 0-5° C. and stirred for 1.5 h. Contents of the two flasks were combined into one filter and filtered quickly. The filter cake was washed with 0-10° C. MeOH (2×5 L) and filtered fast. The cake was deliquored for 1 h under vacuum filtration and then loaded into drying trays. The solid was dried overnight at 45° C. in drying trays to afford S4 as a brown solid (5.75 kg, 8.98 wt % solvate).

Preparation S5

1-(5-(4-fluorophenyl)-6-(tetrahydro-2H-pyran-4-yl)-7-(4,4,5,5-tetramethyl-1,3,2-dioxaborolan-2-yl)pyrrolo[2,3-f]indazol-1(5H)-yl)-2,2-dimethylpropan-1-one (S5)

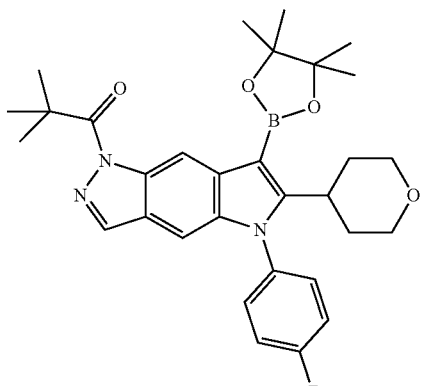

S5

Synthesis of 1-(5-(4-fluorophenyl)-6-(tetrahydro-2H-pyran-4-yl)-7-(4,4,5,5-tetramethyl-1,3,2-dioxaborolan-2-yl)pyrrolo[2,3-f]indazol-1(5H)-yl)-2,2-dimethylpropan-1-one (S5)

A flask containing 1-[5-(4-fluorophenyl)-7-iodo-6-tetrahydropyran-4-yl-pyrrolo[2,3-f]indazol-1-yl]-2,2-dimethylpropan-1-one S4 (0.99 g, 1.83 mmol) and Pd(dppf)Cl$_2$ (57 mg, 0.078 mmol) was evacuated and purged with nitrogen (×3). m-Xylene (7.8 mL) was added and the mixture degassed. Triethylamine (830 μL) and 4,4,5,5-tetramethyl-1,3,2-dioxaborolane (550 μL, 3.8 mmol) were added, and the reaction heated at 150° C. for 1 h. The mixture was cooled, and filtered, washing with $CH_2Cl_2$. The filtrate was concentrated and the crude product mixture was purified by silica gel chromatography (Gradient: 0-5% EtOAc in $CH_2Cl_2$) to afford the product as an off-white solid (788.9 mg, 65%). $^1$H NMR (400 MHz, Chloroform-d) δ 9.14 (s, 1H), 8.03 (s, 1H), 7.35-7.30 (m, 4H), 7.05 (s, 1H), 4.01 (dd, J=10.9, 3.4 Hz, 2H), 3.33 (t, J=11.7 Hz, 2H), 3.26-3.15 (m, 1H), 2.38 (qd, J=12.6, 4.0 Hz, 2H), 1.61 (s, 9H), 1.48 (s, 12H). LCMS m/z 546.5 [M+H]$^+$.

Preparation S6

5-(4-fluorophenyl)-7-iodo-1-(phenylsulfonyl)-6-(tetrahydro-2H-pyran-4-yl)-1,5-dihydropyrrolo[2,3-f]indazole (S6)

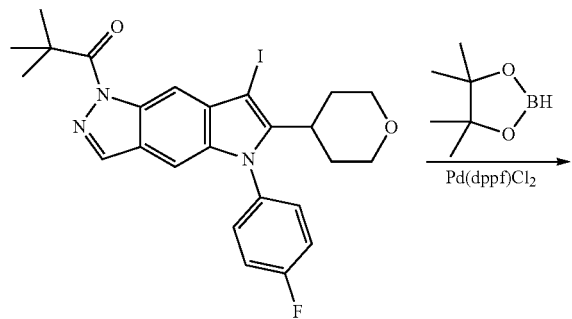

S4

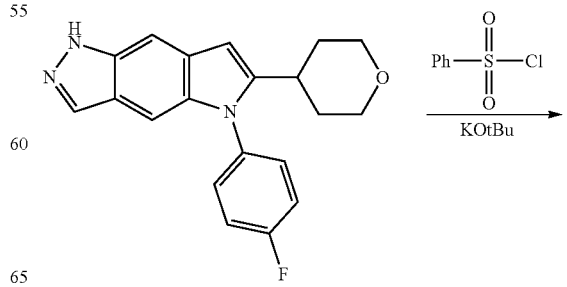

C13

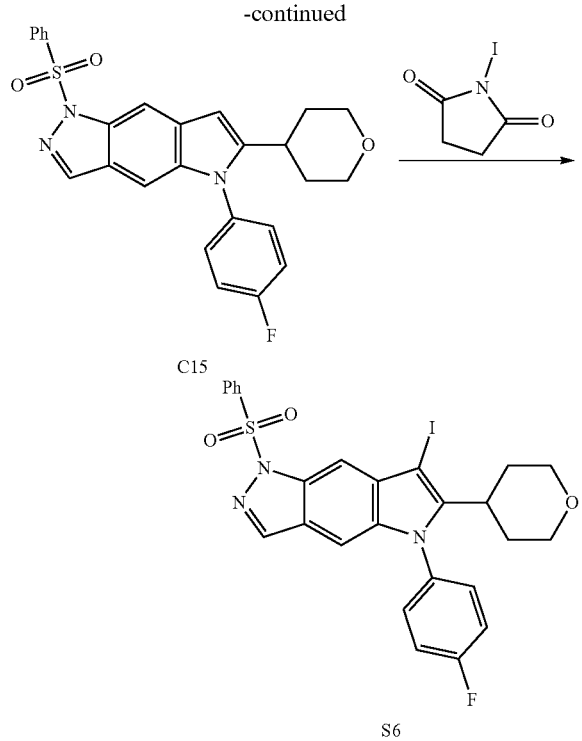

Step 1. Synthesis of 1-(benzenesulfonyl)-5-(4-fluorophenyl)-6-tetrahydropyran-4-yl-pyrrolo[2,3-f]indazole (C15)

To a solution of 5-(4-fluorophenyl)-6-tetrahydropyran-4-yl-1H-pyrrolo[2,3-f]indazole C13 (10 g, 29.8 mmol) in THF (120 mL) at 0° C. was added KOtBu (4.2 g, 37.3 mmol) and the mixture stirred for 10 min. Benzene sulfonyl chloride (4.4 mL, 34.5 mmol) was added, and the mixture stirred for 1 h at 0° C., then for an additional 1 h at room temperature. The mixture was concentrated in vacuo, and then saturated NH$_4$Cl and CH$_2$Cl$_2$ were added. The organic layer was separated, and dried. Purification by silica gel chromatography (Gradient: 0-60% CH$_2$Cl$_2$ in EtOAc) afforded the product as a white solid, containing around 5% of C13 (11.8 g, 83%). $^1$H NMR (300 MHz, Chloroform-d) δ 8.38 (t, J=1.0 Hz, 1H), 8.14 (d, J=0.9 Hz, 1H), 8.04-7.93 (m, 2H), 7.57-7.47 (m, 1H), 7.46-7.38 (m, 2H), 7.38-7.30 (m, 3H), 7.15 (t, J=0.9 Hz, 1H), 6.62 (d, J=0.8 Hz, 1H), 4.08-3.94 (m, 2H), 3.37 (td, J=11.8, 2.3 Hz, 2H), 2.82 (ddt, J=11.5, 8.0, 3.9 Hz, 1H), 1.98-1.70 (m, 5H). LCMS m/z 476.2 [M+H]$^+$.

Step 2. Synthesis of 1-(benzenesulfonyl)-5-(4-fluorophenyl)-7-iodo-6-tetrahydropyran-4-yl-pyrrolo[2,3-f]indazole (S6)

To a solution of 1-(benzenesulfonyl)-5-(4-fluorophenyl)-6-tetrahydropyran-4-yl-pyrrolo[2,3-f]indazole C15 (151.8 g, 319.2 mmol) in CH$_2$Cl$_2$ (1.52 L) cooled to 0° C. was added 1-iodopyrrolidine-2,5-dione (74.5 g, 321.2 mmol), in 4 approximately equal portions over 45 min, additions were 15 min apart. After each addition a slight exotherm was observed, the internal temp. rose to −2° C. The reaction mixture was warmed to room temperature and stirred overnight. CH$_2$Cl$_2$ (500 mL) was added, and the reaction was stirred for 15 min. Water (1 L) was added, followed by 1 M aqueous sodium thiosulfate (200 mL). The mixture was stirred for 20 min, then the organic layer was separated, and the aqueous layer was extracted with CH$_2$Cl$_2$ (50 mL). Combined organic layers were washed successively with water, saturated aqueous sodium bicarbonate, and brine (1.5 L each). The organic layer was then dried (MgSO$_4$), filtered and concentrated to afford a solid residue. The residue was treated with MTBE (500 mL), then stirred for 90 min. The resulting solid was isolated via filtration, washing with MTBE (2×200 mL) and dried under suction for 30 min. The solid was further dried under vacuum (2 mbar, 75° C.) for 30 min, to afford the product as pale, cream-colored crystals. 1-(benzenesulfonyl)-5-(4-fluorophenyl)-7-iodo-6-tetrahydropyran-4-yl-pyrrolo[2,3-f]indazole (181.4 g, 94%). $^1$H NMR (400 MHz, DMSO-d$_6$) δ 8.51 (d, J=0.9 Hz, 1H), 8.06 (t, J=0.9 Hz, 1H), 7.87-7.80 (m, 2H), 7.71-7.63 (m, 1H), 7.62-7.45 (m, 6H), 7.25 (d, J=1.0 Hz, 1H), 3.96-3.85 (m, 2H), 3.22 (td, J=11.8, 1.9 Hz, 2H), 2.93 (tt, J=12.4, 3.6 Hz, 1H), 2.29 (qd, J=12.6, 4.4 Hz, 2H), 1.63 (dd, J=13.5, 3.5 Hz, 2H). 19F NMR (376 MHz, DMSO-d$_6$) δ −111.78. LCMS m/z 602.1 [M+H]$^+$.

Preparation S7

1-(5-(4-fluorophenyl)-7-iodo-6-isopropylpyrrolo[2,3-f]indazol-(5H)-yl)-2,2-dimethylpropan-1-one (S7)

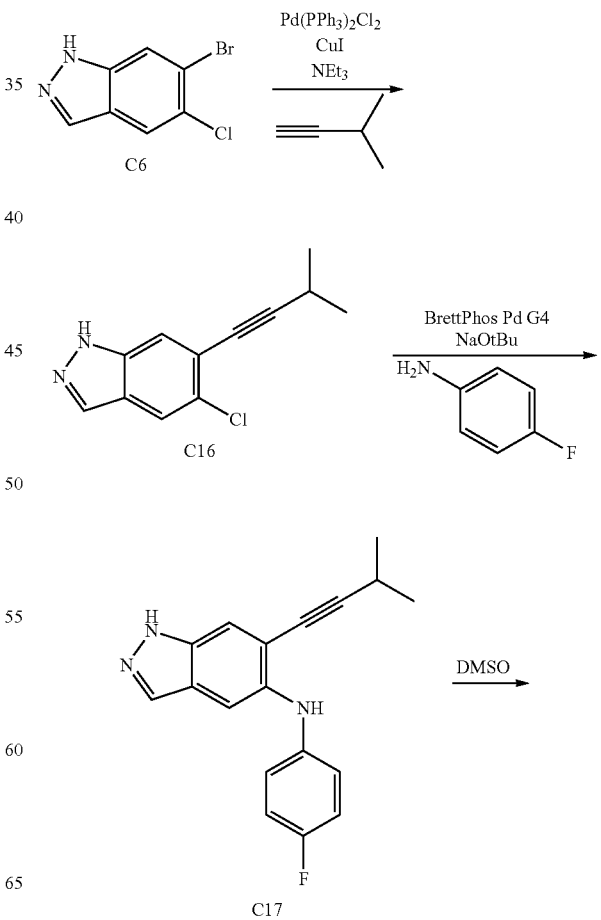

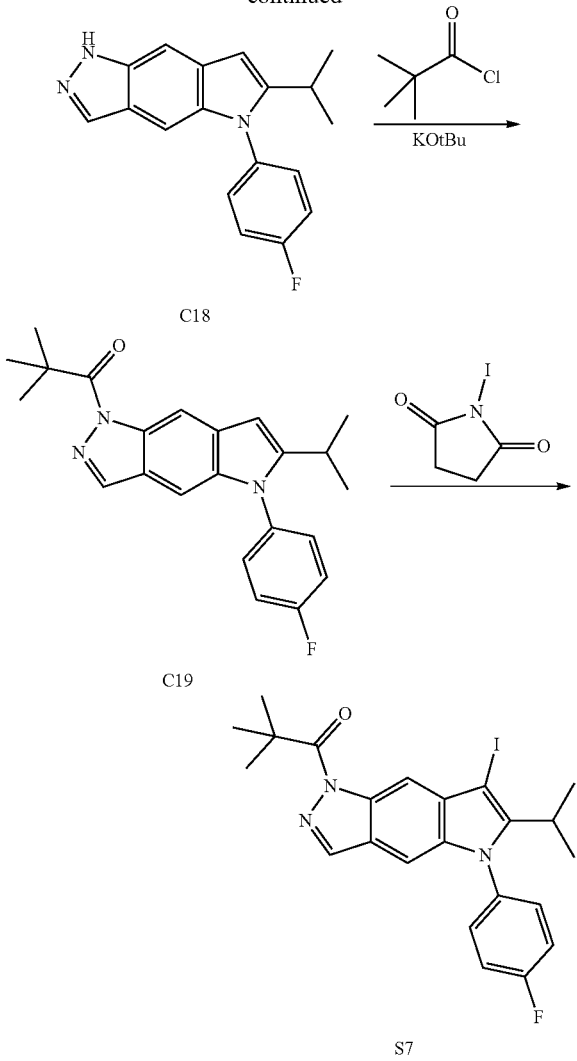

Step 1. Synthesis of 5-chloro-6-(3-methylbut-1-yn-1-yl)-1H-indazole (C16)

Pd(PPh₃)₂Cl₂ (1.7 g, 2.4 mmol) was added to a nitrogen purged solution of 3-methylbut-1-yne (10.7 mL, 104.6 mmol), 6-bromo-5-chloro-1H-indazole C6 (10.4 g, 44.9 mmol) and CuI (497 mg, 2.6 mmol) in Et₃N (100 mL) and 1,4-dioxane (100 mL). The solution was stirred at 90° C. overnight in a Parr bottle, whereupon Celite® and methanol were added, and the mixture concentrated in vacuo. Purification of the Celite® adsorbed mixture by silica gel chromatography (Gradient: 0-100% EtOAc in heptanes) afforded the product (7.0 g, 71%). ¹H NMR (300 MHz, Chloroform-d) δ 10.17 (s, 1H), 8.02 (d, J=1.1 Hz, 1H), 7.80 (d, J=0.7 Hz, 1H), 7.62 (t, J=0.9 Hz, 1H), 2.88 (hept, J=6.9 Hz, 1H), 1.34 (d, J=6.9 Hz, 6H). LCMS m/z 219.04 [M+H]⁺.

Step 2. Synthesis of N-(4-fluoro-3-methylphenyl)-6-(3-methylbut-1-yn-1-yl)-1H-indazol-5-amine (C17)

t-Butanol (45 mL) and 1,4-dioxane (15 mL) were added to a flask containing 4-fluoro-3-methyl-aniline (2.1 g, 16.8 mmol), 5-chloro-6-(3-methylbut-1-ynyl)-1H-indazole C16 (2.3 g, 10.5 mmol), sodium t-butoxide (3.9 g, 40.6 mmol), and BrettPhos Pd G4 catalyst (280 mg, 0.3 mmol). The mixture was degassed and stirred under N₂ at 100° C. overnight. The mixture was concentrated under reduced pressure, re-dissolved in dichloromethane, and washed with water. The organic layer was dried by passing through a phase separator and concentrated in vacuo. Silica gel chromatography (Gradient: 0-100% EtOAc in heptanes) afforded the product (1.9 g, 58%). ¹H NMR (300 MHz, DMSO-d₆) δ 12.93 (s, 1H), 7.92 (s, 1H), 7.52 (s, 1H), 7.40 (s, 1H), 7.16 (s, 1H), 7.02-6.91 (m, 1H), 6.87-6.71 (m, 2H), 2.75 (m, 1H), 2.15 (d, J=1.9 Hz, 3H), 1.11 (d, J=6.9 Hz, 6H). LCMS m/z 308.2 [M+H]⁺.

Step 3. Synthesis of 5-(4-fluoro-3-methylphenyl)-6-isopropyl-1,5-dihydropyrrolo[2,3-f]indazole (C18)

A solution of N-(4-fluoro-3-methyl-phenyl)-6-(3-methylbut-1-ynyl)-1H-indazol-5-amine C17 (254 mg, 0.83 mmol) in DMSO (2.3 mL) was heated under microwave conditions at 150° C. for 30 min. The reaction mixture was poured into water (30 mL) and stirred for 4 h. The resulting solid was filtered and dried under vacuum at 50° C. to afford the product (143 mg, 53%). ¹H NMR (300 MHz, DMSO-d₆) δ 12.58 (s, 1H), 7.96 (d, J=1.3 Hz, 1H), 7.53 (d, J=1.1 Hz, 1H), 7.45-7.27 (m, 3H), 7.16 (d, J=1.0 Hz, 1H), 6.46 (d, J=0.9 Hz, 1H), 3.03-2.83 (m, 1H), 2.34 (d, J=2.0 Hz, 3H), 1.18 (d, J=6.8 Hz, 6H). LCMS m/z 308.2 [M+H]⁺.

Step 4. Synthesis of 1-[5-(4-fluorophenyl)-6-isopropyl-pyrrolo[2,3-f]indazol-1-yl]-2,2-dimethyl-propan-1-one (C19)

A solution of 5-(4-fluorophenyl)-6-isopropyl-1H-pyrrolo[2,3-f]indazole C18 (60 g, 204.5 mmol) in THF (600 mL) was cooled to 0° C. KOtBu (29.8 g, 265.9 mmol) was added and the mixture allowed to stir at 0° C. for 10 min. 2,2-dimethylpropanoyl chloride (34 mL, 276.3 mmol) was added and the mixture allowed to stir at room temperature for 1 h. saturated NH₄Cl (640 mL) and EtOAc was added. The aqueous layer was isolated and further extracted with EtOAc. Combined organic layers were dried, and concentrated in vacuo. Purification by silica gel chromatography (Column: 1.5 kg silica gel. Gradient: 0-30% EtOAc/Heptane) afforded the product as a yellow solid (64 g, 83%). ¹H NMR (300 MHz, Chloroform-d) δ 8.67 (t, J=0.9 Hz, 1H), 8.05 (d, J=0.8 Hz, 1H), 7.44-7.32 (m, 2H), 7.32-7.26 (m, 2H), 7.19 (t, J=0.9 Hz, 1H), 6.56 (t, J=0.8 Hz, 1H), 3.04-2.88 (m, 1H), 1.60 (s, 9H), 1.26 (d, J=6.8 Hz, 6H). LCMS m/z 378.17 [M+H]⁺.

Step 5. Synthesis of 1-[5-(4-fluorophenyl)-7-iodo-6-isopropyl-pyrrolo[2,3-f]indazol-1-yl]-2,2-dimethyl-propan-1-one (S7)

To a solution of 1-[5-(4-fluorophenyl)-6-isopropyl-pyrrolo[2,3-f]indazol-1-yl]-2,2-dimethyl-propan-1-one C19 (71 g, 188.1 mmol) in CH₂Cl₂ (710 mL) cooled to 0° C. was added 1-iodopyrrolidine-2,5-dione (49 g, 206.9 mmol) over 15 min. The mixture was then allowed to stir at room temperature for 0.5 h. An additional 500 mL of CH₂Cl₂ was added. 1M Na₂S₃O₄ solution (100 mL) and a saturated NaHCO₃ solution (300 mL) were also added. The organic layer was separated, washed with additional sat. NaHCO₃ (300 mL), and then dried over sodium sulfate to afford the product as a brown solid (93 g, 98%). ¹H NMR (300 MHz, Chloroform-d) δ 8.60 (t, J=0.9 Hz, 1H), 8.06 (d, J=0.8 Hz, 1H), 7.40-7.30 (m, 3H), 7.29 (d, J=4.1 Hz, 1H), 7.07 (d, J=0.9 Hz, 1H), 3.18 (p, J=7.2 Hz, 1H), 1.61 (s, 9H), 1.39 (d, J=7.2 Hz, 6H). LCMS m/z 504.2 [M+H]$^+$.

Alternative Preparation of C18

5-(4-fluorophenyl)-6-isopropyl-1,5-dihydropyrrolo[2,3-f]indazole (C18)

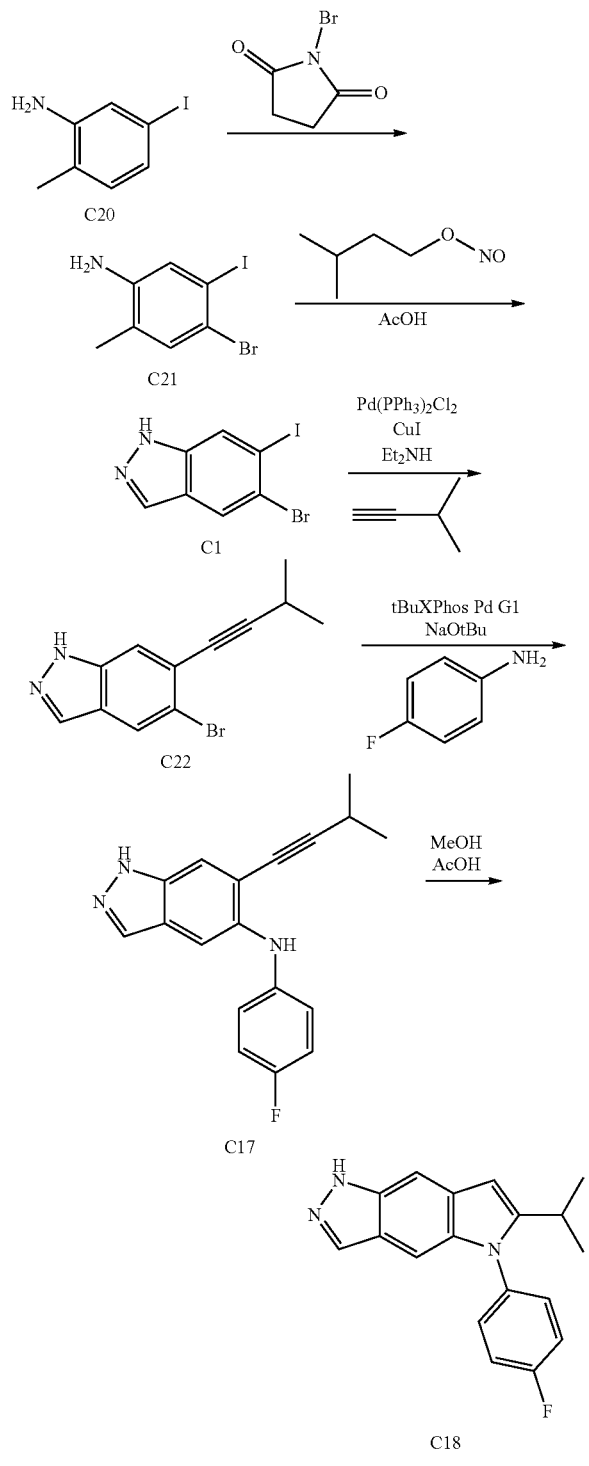

Step 1. Synthesis of 4-bromo-5-iodo-2-methylaniline (C21)

To a solution of 5-iodo-2-methylaniline C20 (600 g, 2.6 mol) in DMF (3 L) at −6° C. was added N-bromosuccinimide (460 g, 2.6 mol) in 5 portions over ~45 min (maintaining the temperature between −3 to −7° C.). The mixture was stirred at −5 to −8° C. for 55 min. The mixture was quenched by addition of 0.5M $Na_2S_2O_3$ (200 mL) then added to ice/water (4.8 kg) over 4 min. A slurry formed, and an exotherm to +10° C. was observed. The mixture was diluted with additional cold water (1 L), stirred for 1 h at −10° C., filtered and washed with water (1.5 L). The solids were dried at 45° C. under vacuum to afford the product as an off-white solid (779 g, 97%). $^1$H NMR (500 MHz, Chloroform-d) δ 7.25 (s, 1H), 7.14 (s, 1H), 3.60 (2H, s), 2.05 (3H, s).

Step 2. Synthesis of 5-bromo-6-iodo-1H-indazole (C)

To a solution of C21 (791 g, 2.5 mol) in AcOH (4.2 L) at 44° C. was added isopentyl nitrite (333 g, 2.8 mol) over 1 h. The reaction was allowed to exotherm to 55° C., then held between 55-64° C. The mixture was stirred at 55° C. for 30 min, then cooled to 50° C. Ice-cold water (4.2 L) was added over 15 min while continuing to cool to 20° C. The slurry was stirred for 25 min at 20° C., filtered and washed with water (2 L). The crude orange solid was dried at 50° C. under vacuum. The solid was then triturated at room temperature in MeCN (2.25 L) for 30 min, filtered, and washed with MeCN (~750 mL) to afford the product as an orange solid (679 g, 83%). $^1$H NMR (500 MHz, DMSO-d$_6$) δ 13.25 (1H, s), 8.22 (1H, s), 8.20 (1H, s), 8.05 (1H, s).

Step 3. Synthesis of 5-bromo-6-(3-methylbut-1-yn-1-yl)-1H-indazole (C22)

A solution of C1 (2738 g, 8.5 mol) in DMF (10 L) was de-oxygenated with 4× vacuum/nitrogen cycles. The mixture was cooled to 6° C. and then diethylamine (1.54 kg, 21.1 mol) and 3-methyl-1-butyne (652 g, 9.57 mol) were added. The mixture was transferred using nitrogen pressure to an inert 20-L autoclave containing copper (I) iodide (32 g, 168 mmol) and PdCl$_2$(PPh$_3$)$_2$ (115 g, 164 mmol). The autoclave was sealed, pressurized to 5 psi using nitrogen and then heated to 85° C. for 15 h. The pressure increased to 23 psi initially and then gradually decreased to 15 psi as the 3-methyl-1-butyne was consumed (the pressure stopped dropping after about 8 h, presumably indicating complete reaction). The mixture was cooled to 20° C. and then added to a mixture of 37% hydrochloric acid (1.5 kg, 14.9 mol), water (13.7 L) and MTBE (8.7 L) at 5° C. [exotherm to 26° ]. The layers were separated, and the organic layer was washed with a mixture of water (8 L) and saturated brine (2 L), and then with saturated brine (3 L). The aqueous layers were sequentially re-extracted with MTBE (5 L then 3 L). The combined organics were dried over magnesium sulfate, filtered and concentrated to dryness in vacuo. The residue was triturated in dichloromethane (2 L) at 35° C., gradually diluted with hexane (2 L) and cooled to 20° C. The slurry was filtered, washed with 1:1 dichloromethane:hexane (1.5 L) and dried under vacuum at 40° C. to afford the product as a pale tan solid (1492 g, 67%). $^1$H NMR (500 MHz, Chloroform-d) δ 10.6 (s, 1H), 8.01 (s, 1H), 7.98 (s, 1H), 2.85 (m, 1H), 1.32 (d, 9H).

Steps 4 and 5. Synthesis of C17 and 5-(4-fluorophenyl)-6-isopropyl-1H-pyrrolo[2,3-f]indazole (C18)

To a 50 L glass reactor was added C22 (2973 g, 11.3 mol), 4-fluoroaniline (1419 g, 12.8 mol) and THF (29 L). The solution was vacuum purged with nitrogen (5×) and cooled to 3° C. Sodium t-butoxide (3.47 kg, 36 mol) was added in 1 kg portions over 20 min with a resulting heat rise to 16° C. The solution was vacuum purged with nitrogen (5×) and cooled to 11° C. tBuXPhos Pd G1 MTBE catalyst (200 g, 0.2 mol) was added in 3 portions over 1 h. An exotherm to 33° C. over 2 h was observed. The contents were stirred overnight—cooling to room temperature. HPLC analysis indicated conversion to C17. The solution was diluted with hexanes (4 L) and cooled to 3° C. Acetic acid was added over 1 h (exotherm to 20° C.). Water (8 L) was added and the contents stirred, then settled. The lower layer was removed, and the upper layer concentrated by vacuum distillation to approx. 10 L. The solution was diluted with methanol (25 L) and heated overnight to about 55° C. The solution was concentrated by vacuum distillation to about 10 L and cooled to 16° C. The solids were collected by filtration and washed with cool methanol (4 L) and dried in a vacuum oven to provide the product C18 as a brown solid. (2.52 kg, 76% yield).

Preparation S8

1-(5-(4-fluorophenyl)-6-isopropyl-7-(4,4,5,5-tetramethyl-1,3,2-dioxaborolan-2-yl)pyrrolo[2,3-f]indazol-1(5H)-yl)-2,2-dimethylpropan-1-one (S8)

Synthesis of 1-(5-(4-fluorophenyl)-6-isopropyl-7-(4,4,5,5-tetramethyl-1,3,2-dioxaborolan-2-yl)pyrrolo[2,3-f]indazol-1(5H)-yl)-2,2-dimethylpropan-1-one (S8)

A flask containing 1-[5-(4-fluorophenyl)-7-iodo-6-isopropyl-pyrrolo[2,3-f]indazol-1-yl]-2,2-dimethyl-propan-1-one S7 (3.95 g, 7.7 mmol) and Pd(dppf)Cl$_2$ (230 mg, 0.31 mmol) was evacuated and purged with nitrogen. m-Xylene (31 mL) was added and the mixture degassed. Triethylamine (3.4 mL) and 4,4,5,5-tetramethyl-1,3,2-dioxaborolane (2.4 mL, 16.5 mmol) were added and the mixture heated at 150° C. for 3 h. The solution was cooled and filtered, washing with dichloromethane, then purified by silica gel chromatography (Gradient: 25-100% dichloromethane in Heptane) to afford the product as a pale orange solid (3.03 g, 77%). $^1$H NMR (400 MHz, Chloroform-d) δ 9.15 (s, 1H), 8.02 (d, J=1.3 Hz, 1H), 7.37-7.26 (m, 4H), 7.05 (s, 1H), 3.23 (hept, J=5.9 Hz, 1H), 1.61 (s, 9H), 1.47 (s, 12H), 1.39 (dd, J=7.1, 1.5 Hz, 6H). LCMS m/z 504.4 [M+H]$^+$.

Preparation S9

5-(4-fluorophenyl)-7-iodo-6-isopropyl-1-tosyl-1,5-dihydropyrrolo[2,3-f]indazole (S9)

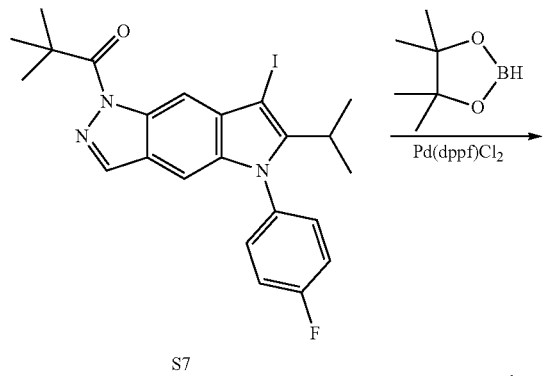

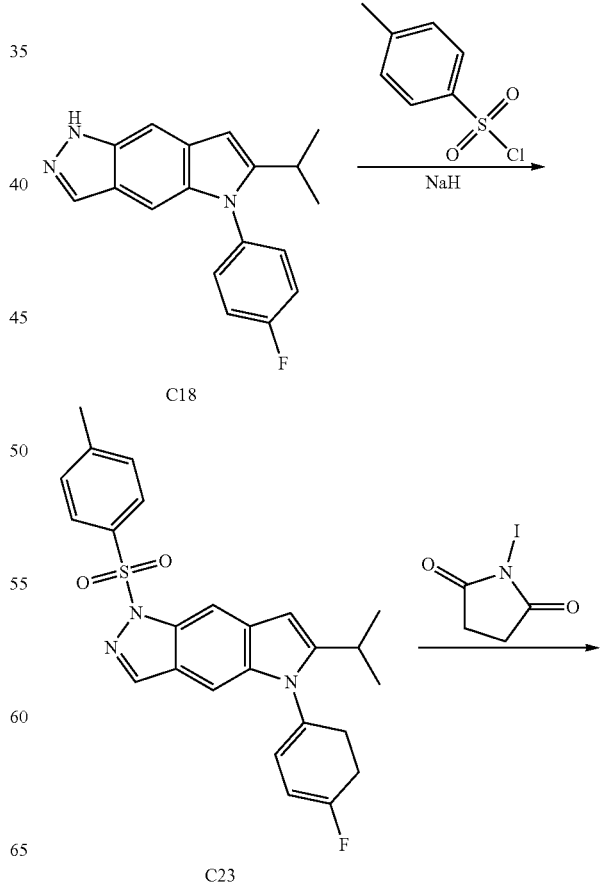

-continued

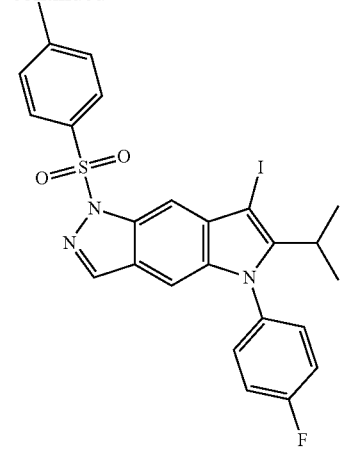

S9

Step 1. Synthesis of 5-(4-fluorophenyl)-6-isopropyl-1-(p-tolylsulfonyl)pyrrolo[2,3-f]indazole (C23)

To a solution of 5-(4-fluorophenyl)-6-isopropyl-1H-pyrrolo[2,3-f]indazole C18 (5.13 g, 17.5 mmol) in DMF (55 mL) was cooled to 0° C. under $N_2$. NaH (1.05 g of 60% w/w, 26.3 mmol in mineral oil) was added. Upon stirring for 1 h at room temperature, 4-methylbenzenesulfonyl chloride (5.0 g, 26.2 mmol) was added and the mixture was allowed to stir at 0° C. for 1 h. Water was added (~100 mL) and the mixture was allowed to stir at room temperature. The resulting precipitate was collected via filtration, washed with water, then heptane. The solid was dissolved in $CH_2Cl_2$, and filtered through a phase separator. The solution of product in $CH_2Cl_2$ was dried over $Na_2SO_4$, filtered and concentrated in vacuo. Purification by silica gel chromatography (Gradient: 0-50% EtOAc/heptane) followed by a second silica gel chromatography (Gradient: 0-20% EtOAc/$CH_2Cl_2$) afforded the product as a pale yellow solid (5.52 g, 68%). $^1$H NMR (300 MHz, Chloroform-d) δ 8.34 (s, 1H), 8.13 (d, J=0.9 Hz, 1H), 7.85 (d, J=8.4 Hz, 2H), 7.44-7.23 (m, 4H), 7.22-7.16 (m, 2H), 7.13 (d, J=0.9 Hz, 1H), 6.59 (d, J=0.8 Hz, 1H), 2.95 (p, J=6.8 Hz, 1H), 2.33 (s, 3H), 1.26 (d, J=6.8 Hz, 6H). LCMS m/z 448.36 [M+H]$^+$.

Step 2. Synthesis of 5-(4-fluorophenyl)-7-iodo-6-isopropyl-1-(p-tolylsulfonyl)pyrrolo[2,3-f]indazole (S9)

To a solution of 5-(4-fluorophenyl)-6-isopropyl-1-(p-tolylsulfonyl)pyrrolo[2,3-f]indazole C23 (5.52 g, 11.8 mmol) in $CH_2Cl_2$ (55 mL) was added iodopyrrolidine-2,5-dione (2.92 g, 12.9 mmol) and allowed to stir at room temperature for 2 h. The mixture was then purified by silica gel chromatography (Gradient: 0-20% EtOAc in $CH_2Cl_2$). The product fractions were combined, concentrated and dissolved in $CH_2Cl_2$. The solution was washed with 1 M sodium thiosulfate, dried over $Na_2SO_4$, filtered and evaporated to afford the product as a pale yellow solid (5.80 g, 83%). $^1$H NMR (300 MHz, Chloroform-d) δ 8.32-8.22 (m, 1H), 8.14 (d, J=0.9 Hz, 1H), 7.89 (d, J=8.3 Hz, 2H), 7.27 (m, 4H), 7.26-7.13 (m, 2H), 7.02 (d, J=0.9 Hz, 1H), 3.17 (p, J=7.2 Hz, 1H), 2.34 (s, 3H), 1.39 (d, J=7.1 Hz, 6H). LCMS m/z 574.3 [M+H]$^+$.

Preparation S10

5-(4-fluorophenyl)-7-iodo-6-isopropyl-1-((2-(trimethylsilyl)ethoxy)methyl)-1,5-dihydropyrrolo[2,3-f]indazole (S10)

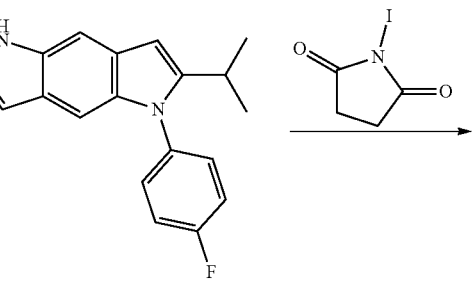

C17

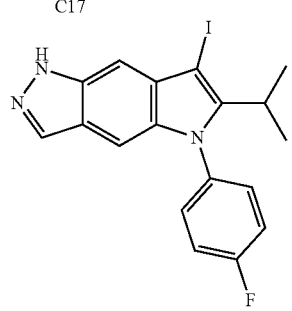

C24

Step 1. 5-(4-fluorophenyl)-7-iodo-6-isopropyl-1H-pyrrolo[2,3-f]indazole (C24)

1-iodopyrrolidine-2,5-dione (3.4 g, 15 mmol) in $CH_2Cl_2$ (104 mL) was added dropwise to a solution of 5-(4-fluorophenyl)-6-isopropyl-1H-pyrrolo[2,3-f]indazole C17 (4.0 g, 13.6 mmol) in $CH_2Cl_2$ (104 mL) at 0° C. The mixture was stirred at room temperature for 60 min. The reaction mixture was then quenched with 1 M sodium thiosulfite. Water was added and the mixture was extracted with $CH_2Cl_2$ (3×). The organic phases were combined, filtered through a phase separator and concentrated in vacuo. Silica gel chromatography (Gradient: 0-20% of EtOAc in $CH_2Cl_2$) afforded the product as a yellow solid (4.17 g, 73%). $^1$H NMR (400 MHz, Chloroform-d) δ 8.05 (d, J=1.1 Hz, 1H), 7.50 (t, J=1.1 Hz, 1H), 7.38-7.31 (m, 2H), 7.31-7.24 (m, 2H), 7.11 (d, J=1.1 Hz, 1H), 3.15 (hept, J=7.2 Hz, 1H), 1.38 (d, J=7.2 Hz, 6H). LCMS m/z 420.1 [M+H]$^+$.

407

Step 2. 2-[[5-(4-fluorophenyl)-7-iodo-6-isopropyl-pyrrolo[2,3-f]indazol-1-yl]methoxy]ethyl-trimethyl-silane (S10)

To a solution of 5-(4-fluorophenyl)-7-iodo-6-isopropyl-1H-pyrrolo[2,3-f]indazole C24 (1.08 g, 2.6 mmol) and nBu₄NBr (41 mg, 0.13 mmol) in CH₂Cl₂ (5 mL) at 0° C. was added KOH (4.5 mL, 163.9 mmol) and SEM-C₁ (510 μL, 2.9 mmol). The mixture was allowed to stir at room temperature overnight. Water and CH₂Cl₂ were added and phases were separated on a phase separator. Silica gel chromatography (Eluent: Ethyl acetate/heptanes) afforded the product (1.2 g, 86%). LCMS m/z 550.2 [M+H]⁺.

Preparation S11

1-(5-(4-fluorophenyl)-7-iodo-6-(I-methoxy-2-methylpropan-2-yl)pyrrolo[2,3-f]indazol-1(5H)-yl)-2,2-dimethylpropan-1-one (S11)

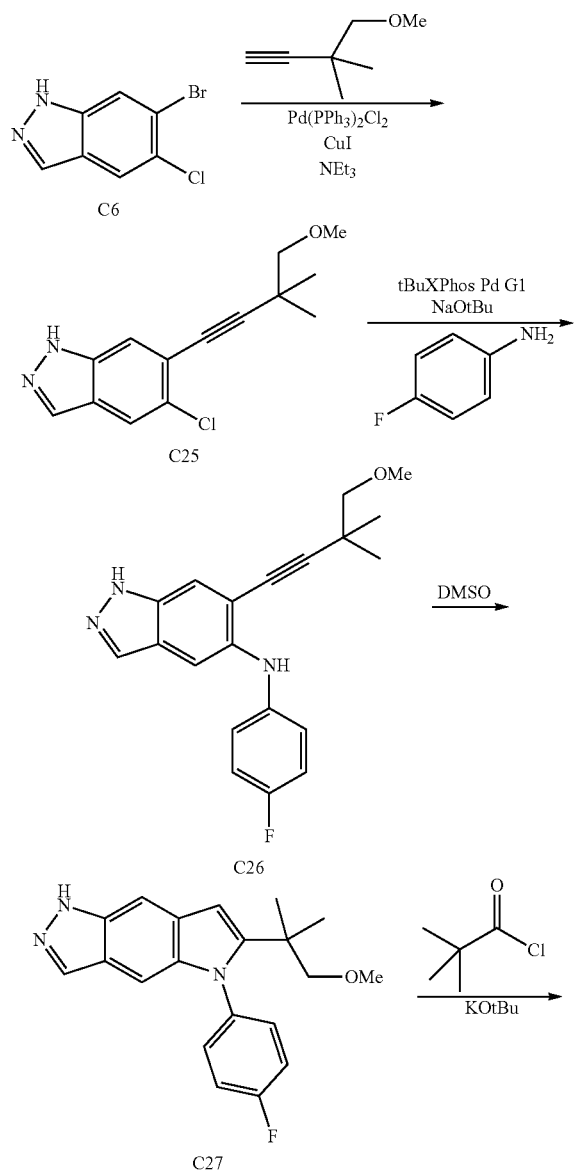

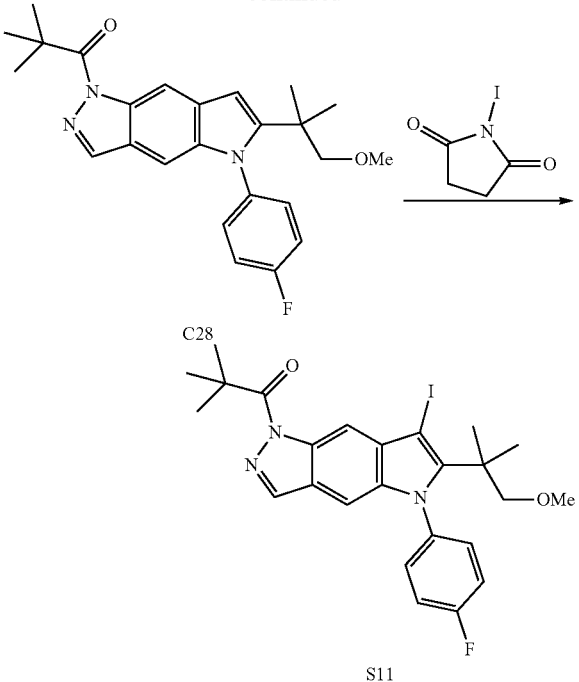

Step 1. Synthesis of 5-chloro-6-(4-methoxy-3,3-dimethyl-but-1-ynyl)-1H-indazole (C25)

A solution of 6-bromo-5-chloro-1H-indazole C6 (5.2 g, 22.46 mmol), PPh₃ (355 mg, 1.4 mmol), Pd(PPh₃)₂Cl₂ (473 mg, 0.67 mmol), CuI (257 mg, 1.3 mmol) and Et₃N (40 mL) in 1,4-dioxane (40 mL) was purged with nitrogen. 4-methoxy-3,3-dimethyl-but-1-yne (3.5 g, 31.5 mmol) was added and the reaction was heated at 110° C. for 1.5 h. A white solid precipitated upon cooling. The reaction was filtered through Celite®, washing with EtOAc. The filtrate was concentrated and purified by silica gel chromatography (Gradient: 0-80% EtOAc/heptane) to afford the product as a brown solid (3.5 g, 59%). ¹H NMR (300 MHz, Chloroform-d) δ 10.27 (s, 1H), 8.00 (s, 1H), 7.78 (d, J=0.5 Hz, 1H), 7.63 (s, 1H), 3.49 (s, 3H), 3.42 (s, 2H), 1.38 (s, 6H). LCMS m/z 263.1 [M+H]⁺.

Step 2. Synthesis of N-(4-fluorophenyl)-6-(4-methoxy-3,3-dimethyl-but-1-ynyl)-1H-indazol-5-amine (C26)

A suspension of 5-chloro-6-(4-methoxy-3,3-dimethyl-but-1-ynyl)-1H-indazole C25 (4.3 g, 16.37 mmol), 4-fluoroaniline (2.5 mL, 26.4 mmol), NaOtBu (4.09 g, 42.6 mmol) in tBuOH (60 mL) were purged with nitrogen. tBuXPhos Pd G1 (563 mg, 0.82 mmol) was added and the mixture purged with nitrogen for an additional 10 min. The mixture was heated at 90° C. for 1 h. An additional 1.4% of tBuXPhos Pd G1 catalyst (~150 mg) was added, and the mixture heated to reflux for another 1 h. Then a further portion of tBuXPhos Pd G1 (80 mg) catalyst was added, and the mixture heated to reflux for 1.5 h. The mixture was concentrated in vacuo, and then saturated NH₄Cl and EtOAc were added. The layers were separated and the aqueous layer extracted with further EtOAc. Combined organic layers dried, and concentrated in vacuo. Purification by silica gel chromatography (Gradient: 0-80% EtOAc/heptane) afforded the product. LCMS m/z 338.0 [M+H]⁺.

Step 3. Synthesis of 5-(4-fluorophenyl)-6-(2-methoxy-1,1-dimethyl-ethyl)-1H-pyrrolo[2,3-f]indazole (C27)

A solution of C26 in DMSO (26 mL) was heated at 160° C. for 2 h. Upon cooling, 50% saturated NaHCO₃ solution (120 mL) was added. The mixture was extracted with EtOAc (×2). The organic layer was concentrated to afford the product as a grey solid which was used without further purification (5 g, 91%). ¹H NMR (300 MHz, Chloroform-d) δ 9.89 (s, 1H), 7.99 (s, 1H), 7.54 (t, J=1.1 Hz, 1H), 7.47-7.36 (m, 2H), 7.28-7.19 (m, 2H), 6.88 (s, 1H), 6.57 (d, J=0.7 Hz, 1H), 3.27 (s, 3H), 3.23 (s, 2H), 1.33 (s, 6H). LCMS m/z 422.3 [M+H]⁺.

Step 4. -[5-(4-fluorophenyl)-6-(2-methoxy-1,1-dimethyl-ethyl)pyrrolo[2,3-f]indazol-1-yl]-2,2-dimethyl-propan-1-one (C28)

To a solution of 5-(4-fluorophenyl)-6-(2-methoxy-1,1-dimethyl-ethyl)-1H-pyrrolo[2,3-f]indazole C27 (6 g, 17.8 mmol) in THF (70 mL) cooled to 0° C. was added KOtBu (2.7 g, 24.1 mmol) and the mixture stirred for 10 min. 2,2-dimethylpropanoyl chloride (2.9 mL, 23.6 mmol) was added and the reaction allowed to stir for an additional 1 h. Sat. NH₄Cl and EtOAc were added. The layers were separated, and the aqueous layer extracted with additional EtOAc. Combined EtOAc layers were dried, and concentrated. Silica gel chromatography (Gradient: 0-40% EtOAc in heptanes) afforded the product as a bright yellow solid (5.2 g, 69%). ¹H NMR (300 MHz, Chloroform-d) δ 8.64 (t, J=0.8 Hz, 1H), 8.01 (d, J=0.7 Hz, 1H), 7.47-7.36 (m, 2H), 7.32-7.23 (m, 2H), 6.86 (s, 1H), 6.65 (d, J=0.7 Hz, 1H), 3.27 (s, 3H), 3.23 (s, 2H), 1.59 (d, J=2.9 Hz, 9H), 1.33 (s, 6H). LCMS m/z 422.3[M+1]+.

Step 5. Synthesis of 1-[5-(4-fluorophenyl)-7-iodo-6-(2-methoxy-1,1-dimethyl ethyl)pyrrolo[2,3-f]indazol-1-yl]-2,2-dimethyl-propan-1-one (S11)

To a solution of 1-[5-(4-fluorophenyl)-6-(2-methoxy-1,1-dimethyl-ethyl)pyrrolo[2,3-f]indazol-1-yl]-2,2-dimethyl-propan-1-one C28 (4.2 g, 9.96 mmol) in CH₂Cl₂ (42 mL) at 0° C. was added 1-iodopyrrolidine-2,5-dione (2.47 g, 10.98 mmol). The mixture was allowed to stir for 1 h at room temperature. CH₂Cl₂ (100 mL) was added, followed by 1N Na₂S₃O₄ and NaHCO₃. The organic layer was washed with additional NaHCO₃, dried and concentrated down to afford the product as a yellow solid (5.2 g, 95%). ¹H NMR (300 MHz, Chloroform-d) δ 8.67 (t, J=0.8 Hz, 1H), 8.03 (d, J=0.8 Hz, 1H), 7.42-7.32 (m, 2H), 7.27-7.17 (m, 2H), 6.82 (d, J=0.9 Hz, 1H), 3.67 (s, 2H), 3.26 (s, 3H), 1.60 (s, 9H), 1.42 (s, 6H). LCMS m/z 548.1 [M+H]⁺.

Compound 1

4-[5-(3,4-difluorophenyl)-6-tetrahydropyran-4-yl-1H-pyrrolo[2,3-f]indazol-7-yl]benzoic Acid (1)

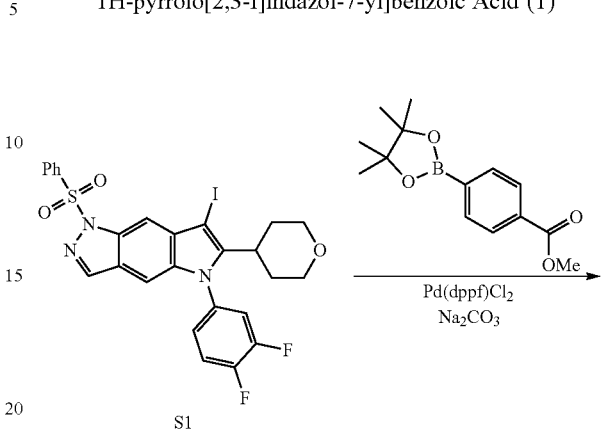

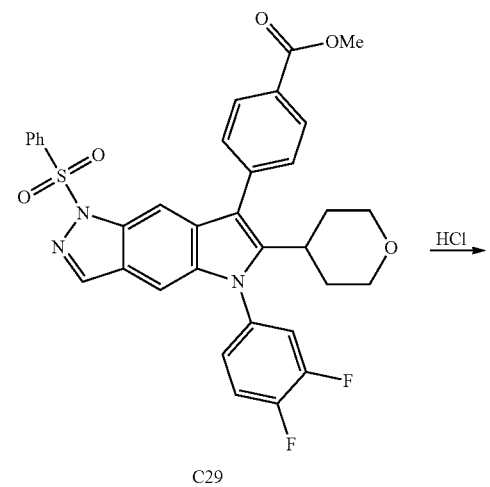

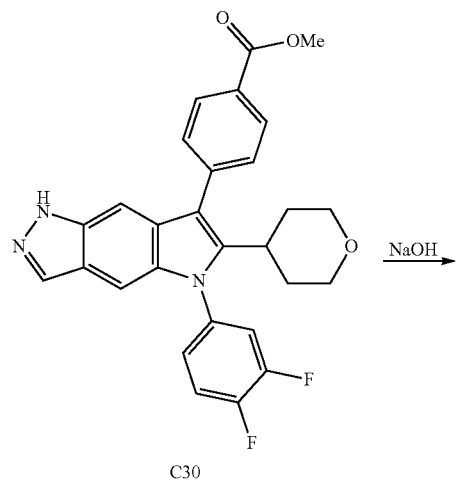

-continued

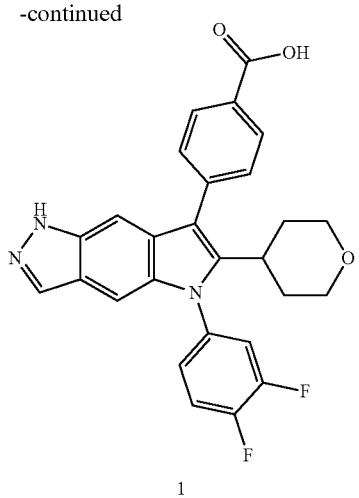

1

Step 1. Synthesis of methyl 4-[1-(benzenesulfonyl)-5-(3,4-difluorophenyl)-6-tetrahydropyran-4-yl-pyrrolo[2,3-f]indazol-7-yl]benzoate (C29)

A mixture of 1-(benzenesulfonyl)-5-(3,4-difluorophenyl)-7-iodo-6-tetrahydropyran-4-yl-pyrrolo[2,3-f]indazole S1 (5000 mg, 7.6 mmol), methyl 4-(4,4,5,5-tetramethyl-1,3,2-dioxaborolan-2-yl)benzoate (4 g, 15.3 mmol) and PdCl$_2$(dppf)$_2$ (300 mg, 0.37 mmol) was placed in a vial and purged with nitrogen. 1,4-dioxane (30 mL) and sodium carbonate (11 mL of 2 M, 22.0 mmol) were added and the mixture purged with nitrogen for 10 min. The mixture was then heated at 90° C. under microwave conditioned for 60 min. Water and CH$_2$Cl$_2$ were added and the aqueous and organic layers separated. The organic layer was concentrated in vacuo and the crude product mixture was purified by silica gel chromatography (Eluent: Ethyl acetate/CH$_2$Cl$_2$) to afford the product as a beige solid (4 g, 83%). $^1$H NMR (400 MHz, DMSO) δ 8.49 (s, 1H), 8.22 (d, J=7.7 Hz, 2H), 7.91 (d, J=10.3 Hz, 2H), 7.71 (qt, J=15.0, 8.4 Hz, 6H), 7.53 (t, J=8.1 Hz, 3H), 7.33 (s, 1H), 3.94 (s, 3H), 3.73 (d, J=10.7 Hz, 2H), 3.14 (d, J=12.1 Hz, 2H), 3.01 (dt, J=10.9, 6.6 Hz, 1H), 1.73-1.53 (m, 4H).

Step 2. Synthesis of methyl 4-[5-(3,4-difluorophenyl)-6-tetrahydropyran-4-yl-1H-pyrrolo[2,3-f]indazol-7-yl]benzoate (C30)

To a solution of methyl 4-[1-(benzenesulfonyl)-5-(3,4-difluorophenyl)-6-tetrahydropyran-4-yl-pyrrolo[2,3-f]indazol-7-yl]benzoate C29 (405 mg, 0.65 mmol) in MeCN (3.6 mL) was added HCl (1.6 mL of 4 M, 6.4 mmol) in 1,4-dioxane. The mixture was heated to 70° C. overnight. Water (1.1 mL) was added and the mixture heated to 70° C. for an additional 30 min. Water and CH$_2$Cl$_2$ were added and the phases were separated on a phase separator. The organic layer was concentrated in vacuo. Purification by reversed-phase chromatography (Column: C18. Gradient: 0-100% MeCN in water with 0.1% formic acid) afforded the product, which was used in the subsequent step without further purification. (175 mg, 56%). LCMS m/z 488.4 [M+H]$^+$.

Step 3. Synthesis of 4-[5-(3,4-difluorophenyl)-6-tetrahydropyran-4-yl-1H-pyrrolo[2,3-f]indazol-7-yl]benzoic Acid (1)

A solution of methyl 4-[5-(3,4-difluorophenyl)-6-tetrahydropyran-4-yl-1H-pyrrolo[2,3-f]indazol-7-yl]benzoate C30 (291 mg, 0.6 mmol) in THF (7.5 mL) and MeOH (3.8 mL) was treated with NaOH (3 mL of 1 M, 3.0 mmol) and heated to 50° C. for 30 min. The reaction mixture was cooled and the pH adjusted to 3 by addition of 2 N HCl. Water and CH$_2$Cl$_2$ were added and the phases were separated on a phase separator. The organic layer was concentrated in vacuo and the mixture purified by reversed-phase chromatography (Column: C18. Gradient: 0-100% MeCN in water with 0.1% formic acid). The product was triturated with MBTE, then dissolved in CH$_2$Cl$_2$/MeOH. 200 mg MP-TMT resin (Pd scavenger) was added and the mixture stirred for 3 h. The mixture was filtered, and washed with CH$_2$Cl$_2$ and MeOH, followed by flushing with heptanes and MBTE. An additional purification by reversed-phase chromatography (Column: C18. Gradient: 0-100% MeCN in water with 0.1% formic acid), then drying under vacuum afforded the product (125.4 mg, 44%). $^1$H NMR (400 MHz, DMSO-d$_6$) δ 13.02 (s, 1H), 12.61 (s, 1H), 8.12 (d, J=7.8 Hz, 2H), 8.01 (s, 1H), 7.88 (t, J=9.6 Hz, 1H), 7.75 (q, J=9.3 Hz, 1H), 7.63 (d, J=8.0 Hz, 2H), 7.48 (d, J=8.9 Hz, 1H), 7.24 (s, 1H), 7.17 (s, 1H), 3.84-3.59 (m, 2H), 3.13 (s, 2H), 3.00 (s, 1H), 1.68 (d, J=7.6 Hz, 4H). LCMS m/z 474.4 [M+H]$^+$.

Compound 2-5

Compounds 2-5 (Table 2) were prepared in two or three steps from intermediate S1 from the appropriate boronic ester or boronic acid according to the method described for compound 1. Any modifications to methods are noted in Table 2 and accompanying footnotes. In some cases, the Suzuki coupling reaction is performed using XPhos Pd G3 as the catalyst and K$_3$PO$_4$ as the base.

TABLE 2

Method of preparation, structure, physicochemical data for compounds 2-5

| Compound | Method/Product | Boronic acid or ester | $^1$H NMR; LCMS m/z [M + H]$^+$ |
|---|---|---|---|
| 2 | 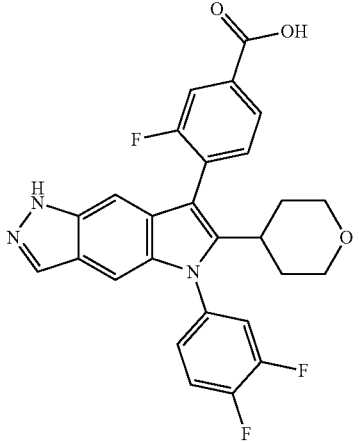<br>Compound 1$^1$ from S1 | 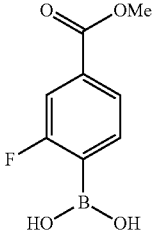 [SMILES: COC(=O)c1ccc(B(O)O)c(F)c1] | $^1$H NMR (400 MHz, DMSO-d$_6$) δ 13.38 (s, 1H), 12.61 (s, 1H), 8.02 (s, 1H), 7.95 (d, J = 8.1 Hz, 1H), 7.87 (d, J = 10.0 Hz, 1H), 7.79-7.62 (m, 2H), 7.55-7.43 (m, 1H), 7.21 (s, 1H), 7.06 (s, 1H), 3.78-3.67 (m, 2H), 3.12 (t, J = 11.9 Hz, 2H), 2.91 (t, J = 12.2 Hz, 1H), 1.76-1.50 (m, 4H). LCMS m/z 492.2 [M + H]$^+$. |
| 3 | 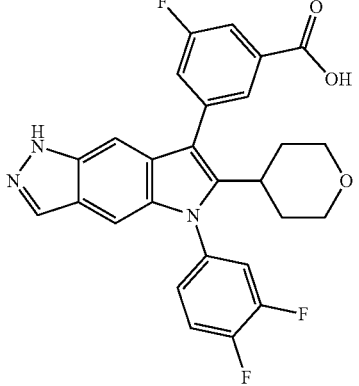<br>Compound 1$^1$ from S1 | 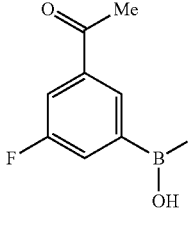 | $^1$H NMR (400 MHz, DMSO-d$_6$) δ 13.45 (s, 1H), 12.61 (s, 1H), 8.02 (s, 1H), 7.91-7.83 (m, 2H), 7.81-7.71 (m, 2H), 7.64-7.58 (m, 1H), 7.52-7.45 (m, 1H), 7.21 (d, J = 16.2 Hz, 2H), 3.80-3.71 (m, 2H), 3.16-3.07 (m, 2H), 2.98 (t, J = 12.2 Hz, 1H), 1.74-1.56 (m, 4H). LCMS m/z 492.4 [M + H]$^+$. |
| 4 | 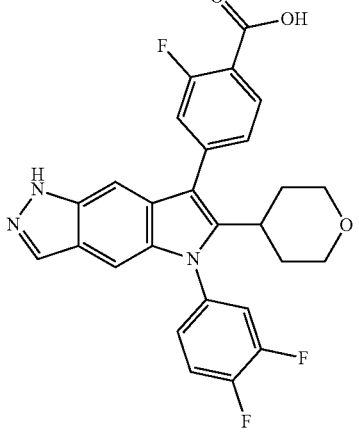<br>Compound 1$^2$ from S1 | 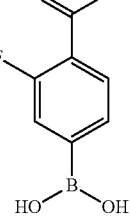 | $^1$H NMR (400 MHz, DMSO-d$_6$) δ 13.30 (s, 1H), 12.64 (s, 1H), 8.08-7.99 (m, 2H), 7.86 (t, J = 9.2 Hz, 1H), 7.76 (q, J = 9.3 Hz, 1H), 7.50-7.39 (m, 3H), 7.29 (s, 1H), 7.17 (s, 1H), 3.75 (d, J = 11.2 Hz, 2H), 3.20-3.09 (m, 2H), 3.08-2.96 (m, 1H), 1.76-1.57 (m, 4H). LCMS m/z 492.3 [M + H]$^+$. |

TABLE 2-continued

Method of preparation, structure, physicochemical data for compounds 2-5

| Compound | Method/Product | Boronic acid or ester | $^1$H NMR; LCMS m/z [M + H]$^+$ |
|---|---|---|---|
| 5 | 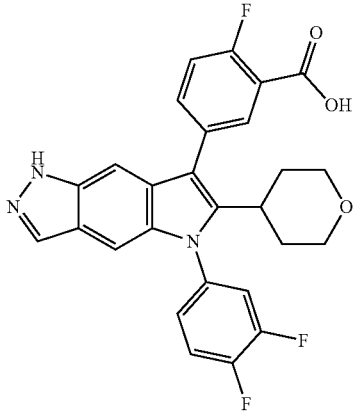<br>Compound 1[1] from S1 | 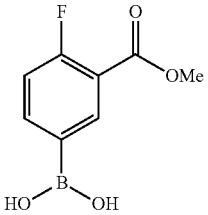 [SMILES: COC(=O)c1cc(B(O)O)ccc1F] | $^1$H NMR (400 MHz, DMSO-$d_6$) δ 13.41 (s, 1H), 12.60 (s, 1H), 8.01 (s, 1H), 7.93 (d, J = 6.9 Hz, 1H), 7.89-7.82 (m, 1H), 7.79-7.69 (m, 2H), 7.53-7.44 (m, 2H), 7.18 (d, J = 5.8 Hz, 2H), 3.78-3.69 (m, 2H), 3.12 (t, J = 11.2 Hz, 2H), 2.94 (t, J = 12.4 Hz, 1H), 1.74-1.55 (m, 4H), LCMS m/z 492.4 [M + H]$^+$. |

[1] Step 1. XPhos Pd G3, K$_3$PO$_4$ in 1,4-dioxane at 85° C. for 1 h. Step 2. 4M HCl, MeCN at 70° C.; Step 3. 2M NaOH in THF/MeOH at 55° C.

[2] Ester hydrolysis and sulfonamide de-protection performed in a single step with 2M NaOH in MeOH/THF at 55° C.

Compound 6

4-[5-(3-fluorophenyl)-6-methyl-1H-pyrrolo[2,3-f]indazol-7-yl]benzoic Acid (6)

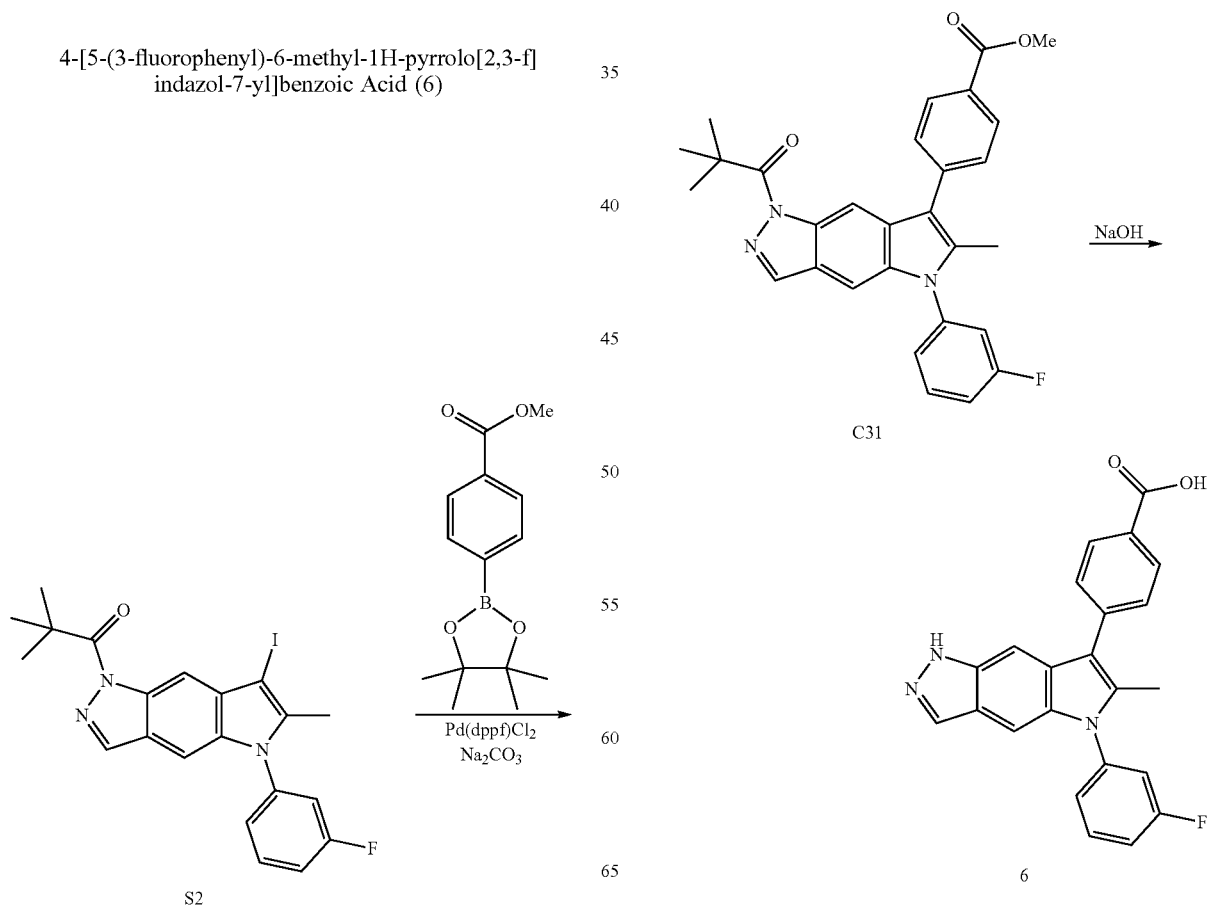

Step 1. Synthesis of methyl 4-[1-(2,2-dimethylpropanoyl)-5-(3-fluorophenyl)-6-methyl-pyrrolo[2,3-f]indazol-7-yl]benzoate (C31)

A mixture of 1-[5-(3-fluorophenyl)-7-iodo-6-methyl-pyrrolo[2,3-f]indazol-1-yl]-2,2-dimethyl-propan-1-one S2 (38 mg, 0.08 mmol), methyl 4-(4,4,5,5-tetramethyl-1,3,2-dioxaborolan-2-yl)benzoate (41 mg, 0.16 mmol) and Pd(dppf)Cl₂ (3 mg, 0.004 mmol) in a reaction vial were placed under a nitrogen atmosphere. 1,4-Dioxane (500 µL) and sodium carbonate (25 mg, 0.24 mmol) were added and the mixture purged with nitrogen. The reaction was heated at 90° C. for 60 min. Water and CH₂Cl₂ were added. The organic layer was passed through a phase separator and concentrated in vacuo to afford the crude product which was used in the subsequent step without further purification (37.4 mg, 100%). LCMS m/z 484.5 [M+H]⁺.

Step 2. Synthesis of 4-[5-(3-fluorophenyl)-6-methyl-1H-pyrrolo[2,3-f]indazol-7-yl]benzoic Acid (6)

Sodium hydroxide (1000 µL of 1 M, 1.0 mmol) was added to a solution of methyl 4-[1-(2,2-dimethylpropanoyl)-5-(3-fluorophenyl)-6-methyl-pyrrolo[2,3-f]indazol-7-yl]benzoate C31 (37.4 mg, 100%) in methanol (2 mL) and THF (2 mL). The mixture was heated at 50° C. for 2 h. The reaction mixture was concentrated in vacuo, acidified with acetic acid and diluted with DMSO (2 mL). Purification by reversed-phase HPLC (Method: C18 Waters Sunfire column (30×150 mm, 5 micron). Gradient: 10-100% MeCN in H₂O with 0.2% formic acid) afforded the product (19.3 mg, 62%). ¹H NMR (300 MHz, DMSO-d₆) δ 12.92 (s, 1H), 12.69 (s, 1H), 8.15-8.07 (m, 2H), 8.05 (d, J=1.0 Hz, 1H), 7.78-7.66 (m, 3H), 7.64 (t, J=1.1 Hz, 1H), 7.56 (dt, J=10.0, 2.3 Hz, 1H), 7.49-7.37 (m, 3H), 2.40 (s, 3H). LCMS m/z 386.3 [M+H]⁺.

Compounds 7-10

Compounds 7-10 were prepared in two steps from S2 or S3 and the appropriate boronic acid or boronic ester as described for compound 6.

TABLE 3

Method of preparation, structure, physicochemical data for compounds 7-10

| Compound | Method/Product | Boronic acid or ester | ¹H NMR; LCMS m/z [M + H]⁺ |
|---|---|---|---|
| 7 | 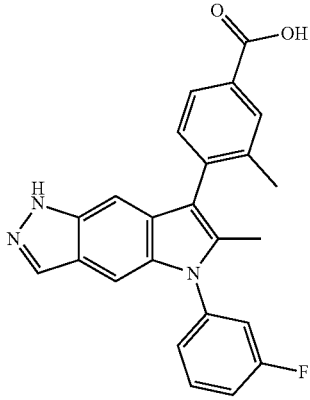<br>Compound 6¹ from S2 | 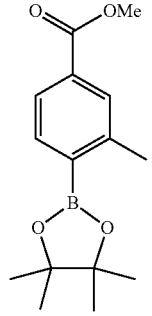 | ¹H NMR (300 MHz, DMSO-d₆) δ 12.95 (s, 1H), 12.60 (s, 1H), 8.04 (d, J = 1.0 Hz, 1H), 8.01 (d, J = 1.8 Hz, 1H), 7.89 (dd, J = 7.9, 1.8 Hz, 1H), 7.75-7.61 (m, 1H), 7.57 (dt, J = 10.0, 2.3 Hz, 1H), 7.52-7.44 (m, 3H), 7.44-7.34 (m, 1H), 7.13-7.04 (m, 1H), 2.27 (s, 3H), 2.18 (s, 3H). LCMS m/z 400.3 [M + H]⁺. |
| 8 | 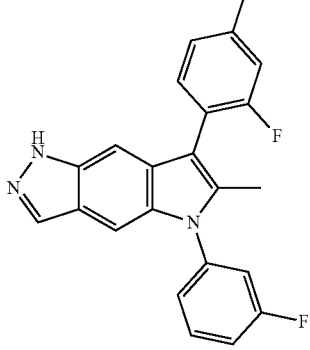<br>Compound 6¹ from S2 | 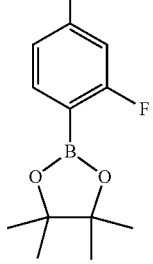 | ¹H NMR (300 MHz, DMSO-d₆) δ 13.27 (s, 1H), 12.68 (s, 1H), 8.05 (d, J = 1.0 Hz, 1H), 7.94 (dd, J = 7.9, 1.7 Hz, 1H), 7.87 (dd, J = 10.7, 1.6 Hz, 1H), 7.80-7.66 (m, 2H), 7.58 (dt, J = 9.9, 2.2 Hz, 1H), 7.49-7.38 (m, 4H), 2.30 (d, J = 1.4 Hz, 3H). LCMS m/z 404.11 [M + H]⁺. |

TABLE 3-continued

Method of preparation, structure, physicochemical data for compounds 7-10

| Compound | Method/Product | Boronic acid or ester | ¹H NMR; LCMS m/z [M + H]⁺ |
|---|---|---|---|
| 9 | 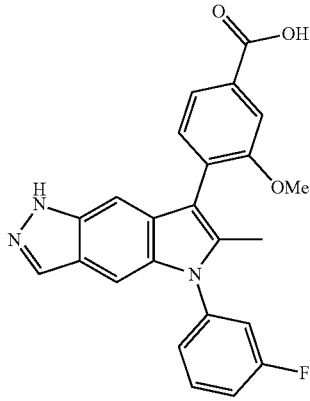<br>Compound 6[1] from S2 | 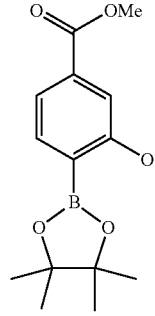 | ¹H NMR (300 MHz, DMSO-d₆) δ 13.02 (s, 1H), 12.61 (s, 1H), 8.02 (d, J = 1.0 Hz, 1H), 7.74-7.65 (m, 3H), 7.59-7.51 (m, 2H), 7.47-7.36 (m, 3H), 7.29-7.25 (m, 1H), 3.85 (s, 3H), 2.22 (s, 3H). LCMS m/z 416.37 [M + H]⁺. |
| 10 | 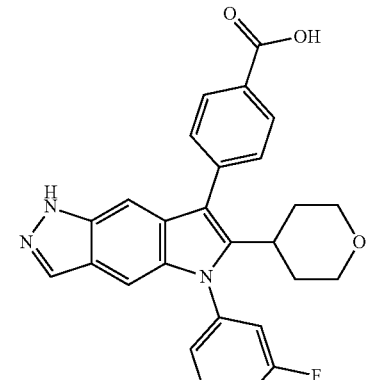<br>Compound 6[1] from S3 | 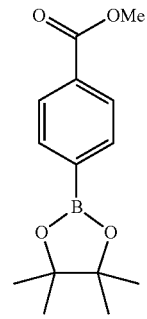 | ¹H NMR (300 MHz, DMSO-d₆) δ 13.00 (s, 1H), 12.60 (s, 1H), 8.16-8.05 (1H, 2H), 8.01 (d, J = 1.0 Hz, 1H), 7.78-7.68 (m, 1H), 7.68-7.60 (m, 2H), 7.60-7.46 (m, 2H), 7.46-7.40 (m, 1H), 7.24 (t, J = 1.1 Hz, 1H), 7.15 (d, J = 1.1 Hz, 1H), 3.73 (d, J= 11.3 Hz, 2H), 3.18-2.94 (m, 3H), 1.75-1.57 (m, 4H). LCMS m/z 456.37 [M + H]⁺. |

[1]Purification by reversed-phase HPLC (Method: C18 Waters Sunfire column (30 × 150 mm, 5 micron). Gradient: 10-100% MeCN in H₂O with 0.2% formic acid)

Compound 11

3-[5-(4-fluoro-3-methyl-phenyl)-6-isopropyl-1H-pyrrolo[2,3-f]indazol-7-yl]benzoic Acid (11)

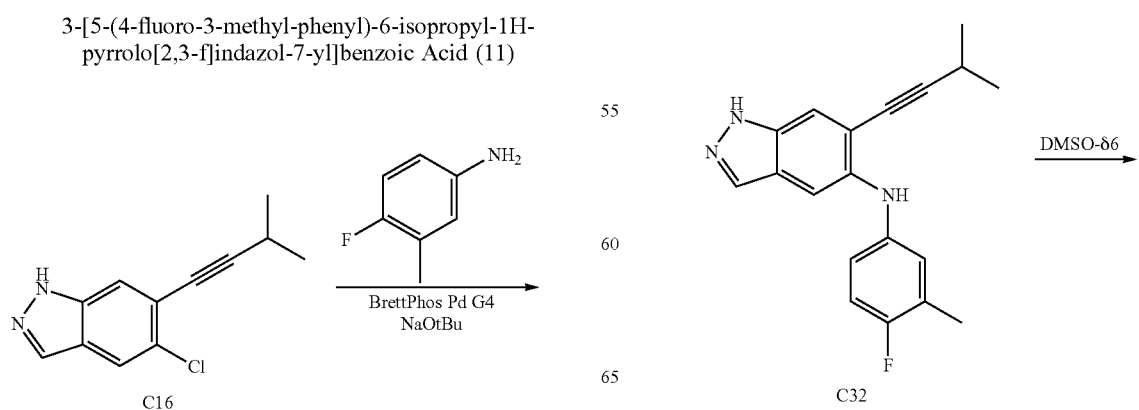

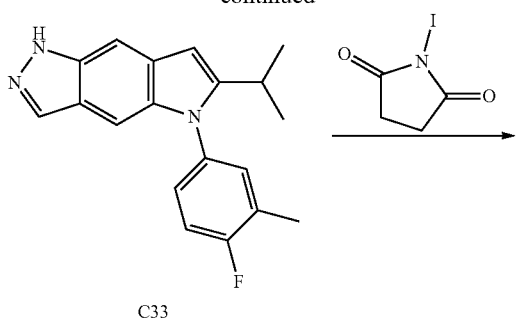

C33

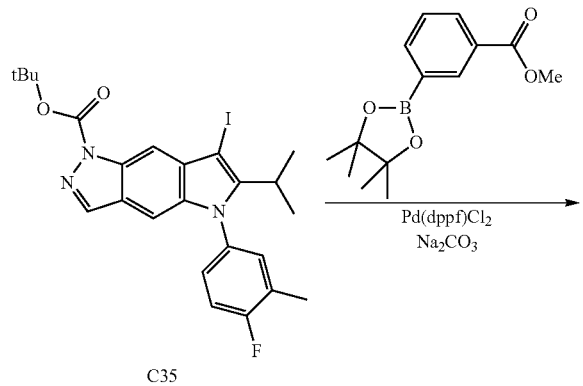

C34

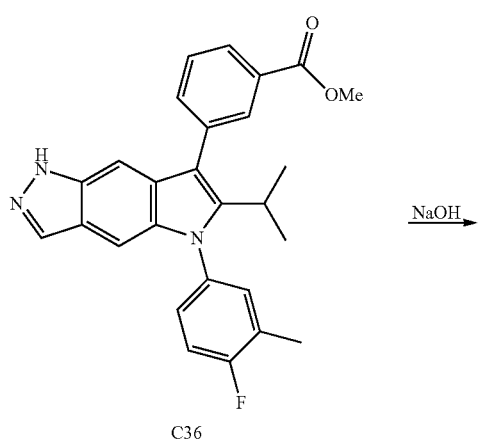

C35

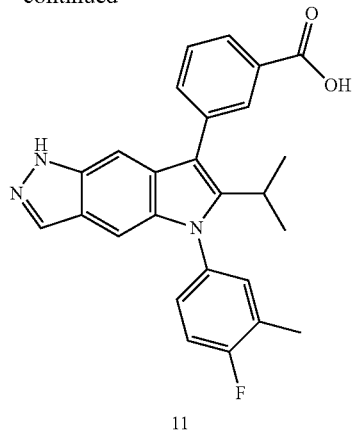

11

Step 1. Synthesis of 5-chloro-6-(3-methylbut-1-yn-1-yl)-1H-indazole (C32)

t-Butanol (45 mL) and 1,4-dioxane (15 mL) were added to a flask containing 4-fluoro-3-methyl-aniline (2.1 g, 16.8 mmol), 5-chloro-6-(3-methylbut-1-ynyl)-1H-indazole C16 (2.3 g, 10.5 mmol), sodium t-butoxide (3.9 g, 40.6 mmol), and BrettPhos Pd G4 catalyst (280 mg, 0.3 mmol). The mixture was degassed and stirred under $N_2$ at 100° C. overnight. The mixture was concentrated under reduced pressure, re-dissolved in dichloromethane, and washed with water. The organic layer was dried by passing through a phase separator and concentrated in vacuo. Silica gel chromatography (Gradient: 0-100% EtOAc in heptanes) afforded the product (1.9 g, 58%). $^1$H NMR (300 MHz, DMSO-$d_6$) δ 12.93 (s, 1H), 7.92 (s, 1H), 7.52 (s, 1H), 7.40 (s, 1H), 7.16 (s, 1H), 7.02-6.91 (m, 1H), 6.87-6.71 (m, 2H), 2.75 (m, 1H), 2.15 (d, J=1.9 Hz, 3H), 1.11 (d, J=6.9 Hz, 6H). LCMS m/z 308.2 [M+H]$^+$.

Step 2. Synthesis of 5-(4-fluoro-3-methylphenyl)-6-isopropyl-1,5-dihydropyrrolo[2,3-f]indazole (C33)

A solution of N-(4-fluoro-3-methyl-phenyl)-6-(3-methyl-but-1-ynyl)-1H-indazol-5-amine C32 (254 mg, 0.83 mmol) in DMSO (2.3 mL) was heated at 150° C. under microwave conditions for 30 min. The reaction mixture was poured into water (30 mL) and stirred for 4 h. The resulting solid was filtered and dried under vacuum at 50° C. to afford the product (143 mg, 53%). $^1$H NMR (300 MHz, DMSO-$d_6$) δ 12.58 (s, 1H), 7.96 (d, J=1.3 Hz, 1H), 7.53 (d, J=1.1 Hz, 1H), 7.45-7.27 (m, 3H), 7.16 (d, J=1.0 Hz, 1H), 6.46 (d, J=0.9 Hz, 1H), 3.03-2.83 (m, 1H), 2.34 (d, J=2.0 Hz, 3H), 1.18 (d, J=6.8 Hz, 6H). LCMS m/z 308.2 [M+H]$^+$.

Step 3. Synthesis of 5-(4-fluoro-3-methyl-phenyl)-7-iodo-6-isopropyl-1H-pyrrolo[2,3-f]indazole (C34)

1-iodopyrrolidine-2,5-dione (285 mg, 1.267 mmol) and 5-(4-fluoro-3-methyl-phenyl)-6-isopropyl-1H-pyrrolo[2,3-f]indazole C33 (420 mg, 1.31 mmol) were diluted with dichloroethane (12.6 mL) and the mixture was flushed with nitrogen. The mixture was allowed to stir at room temperature for 30 min. Celite® was added and the mixture was concentrated in vacuo. Purification of the Celite® adsorbed crude mixture by silica gel chromatography (Gradient: 0-50% EtOAc in heptane) afforded the product (194.6 mg, 34%). $^1$H NMR (300 MHz, DMSO-d$_6$) δ 12.73 (s, 1H), 8.02 (t, J=1.3 Hz, 1H), 7.48-7.29 (m, 4H), 7.09 (t, J=0.8 Hz, 1H), 3.04 (p, J=7.1 Hz, 1H), 2.33 (d, J=2.0 Hz, 3H), 1.34 (dd, J=7.1, 1.3 Hz, 6H). LCMS m/z 434.1 [M+H]$^+$.

Step 4. Synthesis of tert-butyl 5-(4-fluoro-3-methyl-phenyl)-7-iodo-6-isopropyl-pyrrolo[2,3-f]indazole-1-carboxylate (C35)

To a solution of 5-(4-fluoro-3-methyl-phenyl)-7-iodo-6-isopropyl-1H-pyrrolo[2,3-f]indazole C34 (200 mg, 0.5 mmol) in CH$_2$Cl$_2$ (6 mL) was Boc$_2$O (150 mg, 0.7 mmol), DIPEA (180 μL, 1.0 mmol) and DMAP (13.0 mg, 0.11 mmol). The mixture was allowed to stir at 25° C. for 16 h. Silica gel chromatography (Gradient: 0-40% EtOAc in heptane) afforded the product (240 mg, 97%) as mixture of regioisomers which were used in the subsequent step without separating.

$^1$H NMR (400 MHz, Chloroform-d) Minor: δ 8.39 (d, J=1.2 Hz, 1H), 7.52 (t, J=1.3 Hz, 1H), 7.02-6.87 (m, 3H), 6.62 (d, J=1.3 Hz, 1H), 2.14 (dd, J=4.9, 2.0 Hz, 3H), 1.50 (s, 9H), 1.15 (ddd, J=10.3, 7.2, 3.4 Hz, 6H). Major: δ 7.99 (s, 1H), 7.90 (d, J=0.9 Hz, 1H), 7.02-6.87 (m, 3H), 6.62 (d, J=1.3 Hz, 1H), 2.93 (p, J=7.2 Hz, 1H), 2.14 (dd, J=4.9, 2.0 Hz, 3H), 1.56 (s, 9H), 1.15 (ddd, J=10.3, 7.2, 3.4 Hz, 6H).

Step 5. Synthesis of methyl 3-[5-(4-fluoro-3-methyl-phenyl)-6-isopropyl-1H-pyrrolo[2,3-f]indazol-7-yl]benzoate (C36)

A mixture of tert-butyl 5-(4-fluoro-3-methyl-phenyl)-7-iodo-6-isopropyl-pyrrolo[2,3-f]indazole-1-carboxylate C35 (75 mg, 0.08 mmol), methyl 3-(4,4,5,5-tetramethyl-1,3,2-dioxaborolan-2-yl)benzoate (30 mg, 0.12 mmol) and Pd(dppf)Cl$_2$ (3 mg, 0.004 mmol) were placed in a vial under nitrogen. DMF (400 μL) and sodium carbonate (115 μL of 2 M, 0.23 mmol) were added and the reaction allowed to stir overnight at 80° C. The mixture was concentrated in vacuo. Water and CH$_2$Cl$_2$ were added, and the phases were separated on a phase separator. Purification on silica gel (Eluent: Ethyl acetate in heptanes) afforded the product (14 mg, 42%). LCMS m/z 442.35 [M+1]$^+$.

Step 6. Synthesis of 3-[5-(4-fluoro-3-methyl-phenyl)-6-isopropyl-1H-pyrrolo[2,3-f]indazol-7-yl]benzoic Acid (11)

To a solution of methyl 3-[5-(4-fluoro-3-methyl-phenyl)-6-isopropyl-1H-pyrrolo[2,3-f]indazol-7-yl]benzoate C36 (10 mg, 0.02 mmol) in MeOH (0.5 mL) and THF (1 mL) was added NaOH (500 μL of 1 M, 0.5 mmol) and the reaction was heated at 50° C. for 1 h. The reaction mixture was concentrated in vacuo. Water was added and the mixture adjusted to pH 2. The mixture was extracted by CH$_2$Cl$_2$. The organic phase was passed through a phase separator, then concentrated in vacuo to afford the product. $^1$H NMR (400 MHz, Methanol-d$_4$) δ 8.16 (s, 1H), 8.06 (d, J=7.8 Hz, 1H), 7.96 (s, 1H), 7.73 (d, J=7.5 Hz, 1H), 7.61 (t, J=7.7 Hz, 1H), 7.38 (d, J=6.9 Hz, 1H), 7.30 (d, J=8.3 Hz, 3H), 7.11 (s, 1H), 3.18 (h, J=7.2 Hz, 1H), 2.39 (d, J=1.9 Hz, 3H), 1.16 (d, J=7.1 Hz, 6H). LCMS m/z 428.31 [M+H]$^+$.

Compound 12

4-[5-(4-fluoro-3-methyl-phenyl)-6-(methoxymethyl)-1H-pyrrolo[2,3-f]indazol-7-yl]benzoic Acid (12)

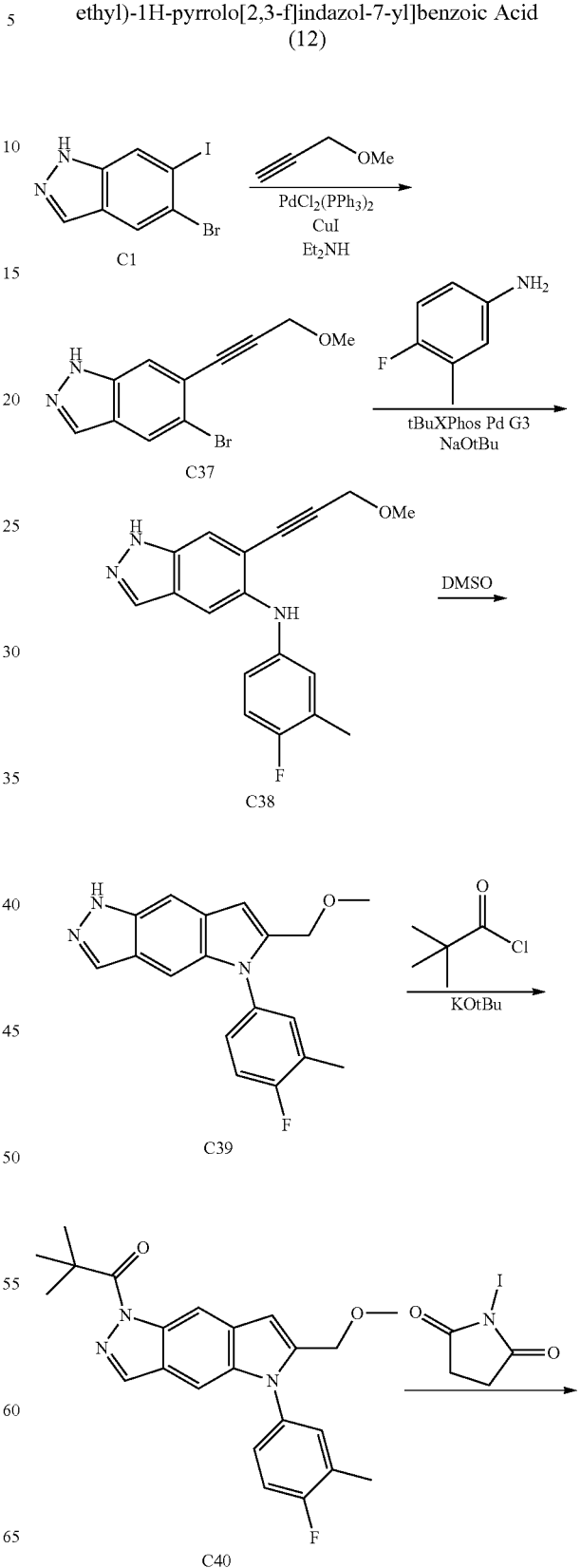

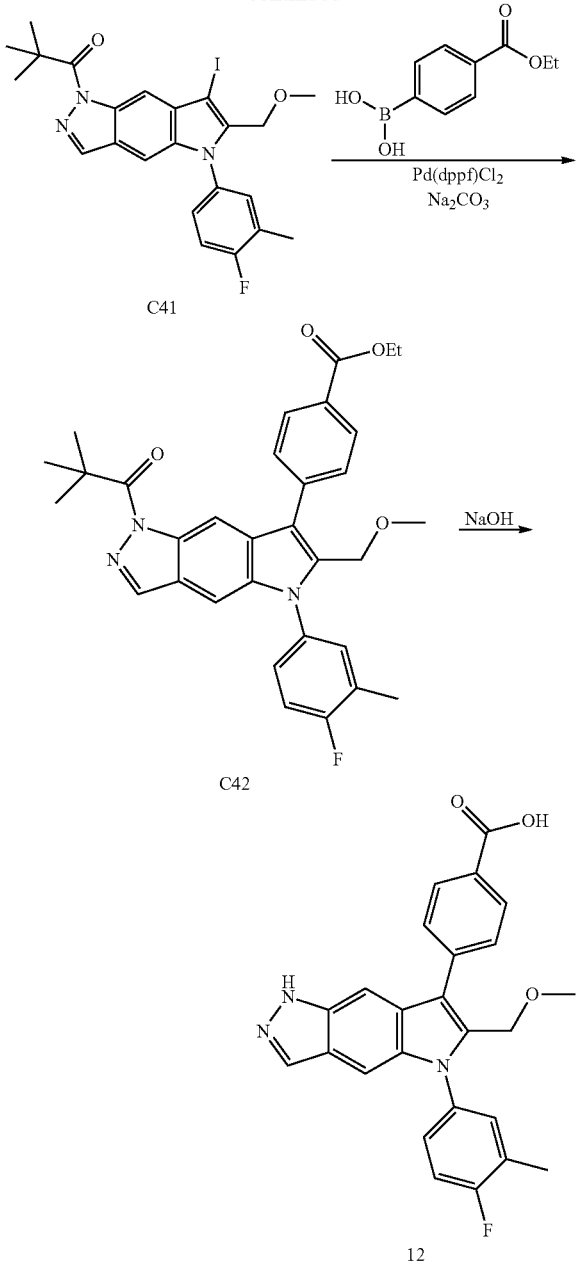

Step 1. Synthesis of 5-bromo-6-(3-methoxyprop-1-ynyl)-1H-indazole (C37)

A solution of 5-bromo-6-iodo-1H-indazole C1 (1 g, 3.1 mmol) in DMF (6.2 mL) was purged with nitrogen. 3-Methoxyprop-1-yne (342 μL, 4.1 mmol), Et$_2$NH (991 μL, 9.6 mmol), PdCl$_2$(PPh$_3$)$_2$ (110 mg, 0.16 mmol) and CuI (44 mg, 0.23 mmol) were added. The reaction mixture was allowed to heat at 90° C. for 4 h. The mixture was concentrated, then water and CH$_2$Cl$_2$ were added. The organic layer was separated by passing through a phase separator. Purification by silica gel chromatography (Eluent: Ethyl acetate/Heptanes) afforded the product (540 mg, 66%). $^1$H NMR (400 MHz, DMSO-d$_6$) δ 13.38 (s, 1H), 8.17 (s, 1H), 8.10-8.08 (m, 1H), 7.79 (s, 1H), 4.41 (s, 2H), 3.40 (s, 3H).

Step 2. Synthesis of N-(4-fluoro-3-methyl-phenyl)-6-(3-methoxyprop-1-ynyl)-1H-indazol-5-amine (C38)

A solution of 5-bromo-6-(3-methoxyprop-1-ynyl)-1H-indazole C37 (1.6 g, 6.03 mmol), 4-fluoro-3-methyl-aniline (1.1 g, 8.8 mmol), NaOtBu (1.0 g, 10.4 mmol) in tert-butanol (25.9 mL) was purged with nitrogen for 10 min at 40° C. tBuXPhos Pd G3 (95.8 mg, 0.12 mmol) was added and the mixture was purged with nitrogen for an additional 10 min. The reaction mixture was heated to 70° C. for 1 h. Additional of tBuXPhos Pd G3 (95.8 mg, 0.12 mmol), NaOtBu (1.0 g, 10.4 mmol) and 4-fluoro-3-methyl-aniline (1.1 g, 8.8 mmol) were added and the mixture was stirred overnight. The mixture was cooled and concentrated in vacuo. CH$_2$Cl$_2$ and NH$_4$Cl were added and the layers were separated and concentrated. The residue was purified by silica gel chromatography (Gradient: 0-100% EtOAc in heptane) to afford the product (640 mg, 32%). LCMS m/z 310.2 [M+H]$^+$.

Step 3. Synthesis of 5-(4-fluoro-3-methyl-phenyl)-6-(methoxymethyl)-1H-pyrrolo[2,3-f]indazole (C39)

A solution of N-(4-fluoro-3-methyl-phenyl)-6-(3-methoxyprop-1-ynyl)-1H-indazol-5-amine C38 (590 mg, 1.76 mmol) in DMSO (2.2 mL) was heated at 150° C. for 30 min. Water and CH$_2$Cl$_2$ were added and the organic layer was separated using phase separator. Purified by silica gel chromatography (Gradient: 0-100% EtOAc in dichloromethane) afforded the product (317 mg, 54%). $^1$H NMR (400 MHz, DMSO-d$_6$) δ 12.68 (s, 1H), 8.01 (s, 1H), 7.63 (s, 1H), 7.45 (d, J=6.9 Hz, 1H), 7.40-7.31 (m, 3H), 6.71 (s, 1H), 4.42 (s, 2H), 3.19 (s, 3H), 2.33 (s, 3H). LCMS m/z 310.3 [M+H]$^+$.

Step 4. 1-[5-(4-fluoro-3-methyl-phenyl)-6-(methoxymethyl)pyrrolo[2,3-f]indazol-1-yl]-2,2-dimethyl-propan-1-one (C40)

To a solution of 5-(4-fluoro-3-methyl-phenyl)-6-(methoxymethyl)-1H-pyrrolo[2,3-f]indazole C39 (318 mg, 1.03 mmol) in THF (7.1 mL) at 0° C. on an ice bath was added KOtBu (283 μL, 2.3 mmol). 2,2-Dimethylpropanoyl chloride (491 μL, 4.0 mmol) was then added dropwise, and the mixture allowed to stir at 0° C. for 1 h. Purification by silica gel chromatography (Gradient: 0-100% EtOAc in dichloromethane) afforded the product (297 mg, 72%). $^1$H NMR (400 MHz, DMSO-d$_6$) δ 8.58 (t, J=0.9 Hz, 1H), 8.43 (d, J=0.8 Hz, 1H), 7.52 (t, J=0.9 Hz, 1H), 7.51-7.47 (m, 1H), 7.41-7.39 (m, 1H), 7.38 (d, J=1.4 Hz, 1H), 6.90-6.88 (m, 1H), 4.47 (s, 2H), 3.21 (s, 3H), 2.34 (d, J=1.5 Hz, 3H), 1.52 (s, 9H). LCMS m/z 394.4 [M+H]$^+$.

Step 5. Synthesis of 1-[5-(4-fluoro-3-methyl-phenyl)-7-iodo-6-(methoxymethyl)pyrrolo[2,3-f]indazol-1-yl]-2,2-dimethyl-propan-1-one (C41)

1-iodopyrrolidine-2,5-dione (218 mg, 0.92 mmol) was added portion wise over 30 min to a solution of 1-[5-(4-fluoro-3-methyl-phenyl)-6-(methoxymethyl)pyrrolo[2,3-f]indazol-1-yl]-2,2-dimethyl-propan-1-one C40 (297 mg, 0.75 mmol) in CH$_2$Cl$_2$ (3.1 mL) at 0° C. and the mixture was allowed to stir for 1 h. The reaction mixture was washed with 1M Na$_2$SO$_3$ and the organic phase was isolated, and passed through a phase separator. Concentration in vacuo afforded the product (350 mg, 80%). $^1$H NMR (300 MHz, Methanol-d$_4$) δ 8.48 (t, J=0.8 Hz, 1H), 8.23 (d, J=0.7 Hz, 1H), 7.41 (d, J=0.9 Hz, 1H), 7.41-7.36 (m, 1H), 7.33-7.23 (m, 2H), 4.54 (s, 2H), 3.29 (s, 3H), 2.37 (d, J=2.0 Hz, 3H), 1.58 (s, 9H). LCMS m/z 520.3 [M+H]$^+$.

Step 6. Synthesis of 4-[1-(2,2-dimethylpropanoyl)-5-(4-fluoro-3-methyl-phenyl)-6-(methoxymethyl)pyrrolo[2,3-f]indazol-7-yl]benzoate (C42)

A mixture of 1-[5-(4-fluoro-3-methyl-phenyl)-7-iodo-6-(methoxymethyl)pyrrolo[2,3-f]indazol-1-yl]-2,2-dimethyl-propan-1-one C41 (50 mg, 0.09 mmol), (4-ethoxycarbonylphenyl)boronic acid (36.8 mg, 0.19 mmol) and Pd(dppf)Cl$_2$ (3.7 mg, 0.005 mmol) in a reaction vial was purged with nitrogen. 1,4-Dioxane (302 μL) and sodium carbonate (147 μL of 2 M, 0.30 mmol) were added and the mixture was allowed to stir at 95° C. for 1 h. Water and CH$_2$Cl$_2$ were added, and the phases were separated on a phase separator. Purification by silica gel chromatography (Gradient: 0-100% CH$_2$Cl$_2$ in heptane) to afford the product (35 mg, 67%). LCMS m/z 542.6 [M+H]$^+$.

Step 7. Synthesis of 4-[5-(4-fluoro-3-methyl-phenyl)-6-(methoxymethyl)-1H-pyrrolo[2,3-f]indazol-7-yl]benzoic Acid (12)

To a solution of ethyl 4-[1-(2,2-dimethylpropanoyl)-5-(4-fluoro-3-methyl-phenyl)-6-(methoxymethyl)pyrrolo[2,3-f]indazol-7-yl]benzoate C42 (35 mg, 0.06 mmol) in THF (778 μL), MeOH (327 μL) was added NaOH (280 μL of 1 M, 0.28 mmol). The mixture was heated at 50° C. for 30 min, then concentrated and re-dissolved in minimal water. The mixture was then acidified by the addition of HCl (280 μL of 1 M, 0.28 mmol). The mixture was filtered and concentrated to afford the product (20.5 mg, 71%). $^1$H NMR (400 MHz, DMSO-d$_6$) δ 12.97 (s, 1H), 12.76 (s, 1H), 8.13 (d, J=7.7 Hz, 2H), 8.09 (s, 1H), 7.79 (d, J=7.7 Hz, 2H), 7.74 (s, 1H), 7.56 (d, J=6.6 Hz, 1H), 7.50-7.40 (m, 3H), 4.33 (s, 2H), 3.17 (s, 3H), 2.36 (s, 3H). LCMS m/z 430.3 [M+H]$^+$.

Compound 13

4-[5-(2-fluorophenyl)-6-isopropyl-1H-pyrrolo[2,3-f]indazol-7-yl]benzoic Acid (13)

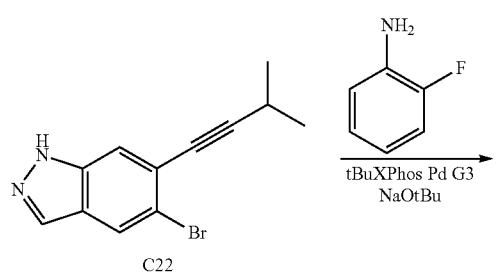

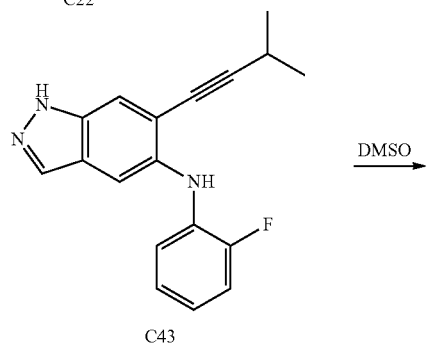

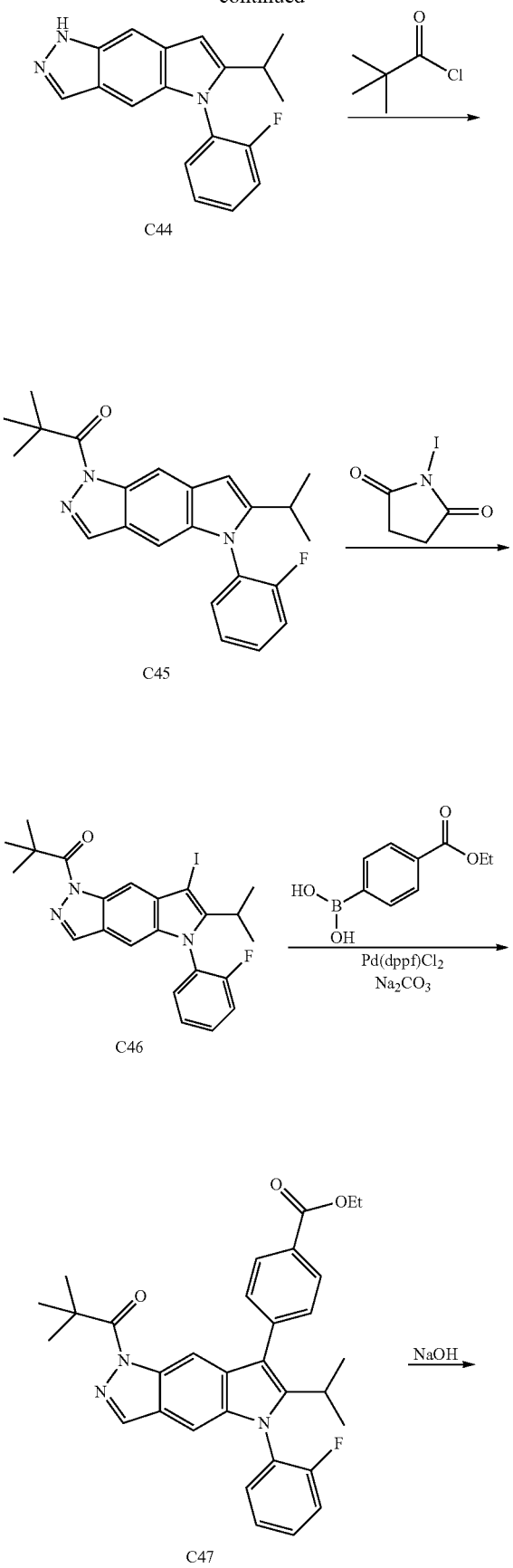

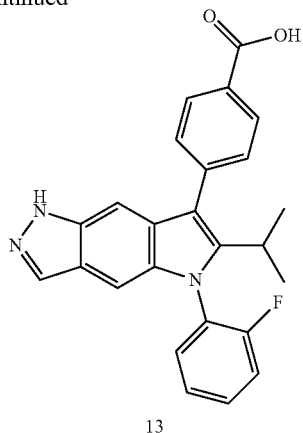

13

Step 1. Synthesis of N-(2-fluorophenyl)-6-(3-methylbut-1-ynyl)-1H-indazol-5-amine (C43)

Compound C43 was prepared from C22 and 2-fluoro aniline as described for the preparation of C38. Purification by silica gel chromatography (Gradient: 0-30% EtOAc in Heptane) afforded the product as a gray solid (399 mg, 67%). $^1$H NMR (400 MHz, Chloroform-d) δ 9.91 (s, 1H), 7.96 (s, 1H), 7.60 (d, J=4.3 Hz, 2H), 7.46 (t, J=8.3 Hz, 1H), 7.19-7.06 (m, 2H), 6.90 (d, J=5.9 Hz, 1H), 6.53 (s, 1H), 2.95-2.84 (m, 1H), 1.33 (dd, J=6.9, 1.5 Hz, 6H). LCMS m/z 294.3 [M+H]$^+$.

Step 2. Synthesis of 5-(2-fluorophenyl)-6-isopropyl-1H-pyrrolo[2,3-f]indazole (C44)

Compound C44 was prepared from C43 using the method described for synthesis of C39 in the preparation of compound 12. Purification by silica gel chromatography (Gradient: 0-40% EtOAc in heptane) provided the product as a light yellow solid (128.2 mg, 35%). $^1$H NMR (400 MHz, Chloroform-d) δ 9.85 (s, 1H), 8.04 (s, 1H), 7.60 (s, 1H), 7.57-7.44 (m, 2H), 7.42-7.33 (m, 2H), 7.21 (s, 1H), 6.52 (s, 1H), 2.89 (hept, J=7.9, 7.1 Hz, 1H), 1.27 (ddd, J=11.6, 6.8, 1.8 Hz, 6H). LCMS m/z 294.3 [M+H]$^+$.

Step 3. 1-[5-(2-fluorophenyl)-6-isopropyl-pyrrolo[2,3-f]indazol-1-yl]-2,2-dimethyl-propan-1-one (C45)

Compound C45 was prepared from C44 as described for the preparation of C40. Purification by silica gel chromatography (Gradient: 0-15% EtOAc in Heptane) afforded the desired product containing ca. 10% Piv-OH (by NMR) impurity. The material was used in the subsequent reaction without further purification (114.7 mg, 71%). $^1$H NMR (400 MHz, Chloroform-d) δ 8.69 (s, 1H), 8.06 (s, 1H), 7.55 (q, J=7.0 Hz, 1H), 7.51-7.44 (m, 1H), 7.42-7.33 (m, 2H), 7.17 (s, 1H), 6.60 (s, 1H), 2.89 (dq, J=12.6, 6.2 Hz, 1H), 1.61 (s, 9H), 1.29-1.25 (m, 6H). LCMS m/z 378.3 [M+H]$^+$.

Step 4. 1-[5-(2-fluorophenyl)-7-iodo-6-isopropyl-pyrrolo[2,3-f]indazol-1-yl]-2,2-dimethyl-propan-1-one (C46)

Compound C46 was prepared by treatment of C45 with 1-iodopyrrolidine-2,5-dione using the method described for the preparation of C41. Silica gel chromatography (Gradient: 0-10% EtOAc in Heptane) afforded the desired product as a white solid (106.2 mg, 72%). $^1$H NMR (400 MHz, Chloroform-d) δ 8.62 (s, 1H), 8.07 (s, 1H), 7.64-7.53 (m, 1H), 7.48-7.33 (m, 3H), 7.06 (s, 1H), 3.14 (dq, J=14.9, 8.0 Hz, 1H), 1.62 (s, 9H), 1.43 (d, J=7.1 Hz, 3H), 1.36 (d, J=7.2 Hz, 3H). LCMS m/z 504.3 [M+H]$^+$.

Step 5. Ethyl 4-[1-(2,2-dimethylpropanoyl)-5-(2-fluorophenyl)-6-isopropyl-pyrrolo[2,3-f]indazol-7-yl]benzoate (C47)

Compound C47 was prepared using the method described for preparation of C42. Silica gel chromatography (Gradient: 0-10% EtOAc in heptane) provided the product as a colorless glassy solid (38.5 mg, 69%). $^1$H NMR (400 MHz, Chloroform-d) δ 8.49 (s, 1H), 8.19 (d, J=7.8 Hz, 2H), 8.07 (s, 1H), 7.65-7.52 (m, 4H), 7.41 (q, J=8.9 Hz, 2H), 7.10 (s, 1H), 4.47 (q, J=7.0 Hz, 2H), 3.24-3.11 (m, 1H), 1.57 (s, 9H), 1.48 (t, J=7.1 Hz, 3H), 1.17 (dd, J=19.4, 7.1 Hz, 6H). LCMS m/z 526.5 [M+H]$^+$.

Step 6. 4-[5-(2-fluorophenyl)-6-isopropyl-1H-pyrrolo[2,3-f]indazol-7-yl]benzoic Acid (13)

Compound 13 was prepared by hydrolysis of C47 using a method analogous to that described in the preparation of compound 12. The crude material was dissolved in minimal DMSO and purified by reversed phase chromatography (C18 column: Gradient: 10-100% acetonitrile in water with 0.2% formic acid modifier) to afford the product as an off-white solid (20.6 mg, 68%). $^1$H NMR (400 MHz, Chloroform-d) δ 8.21-8.12 (m, 2H), 7.98-7.92 (m, 1H), 7.69-7.55 (m, 4H), 7.52-7.39 (m, 2H), 7.35 (s, 1H), 7.04 (d, J=3.3 Hz, 1H), 3.17 (s, 1H), 1.23-1.09 (m, 6H). LCMS m/z 414.3 [M+H]$^+$.

Compound 14

(E)-8-fluoro-20-isopropyl-11,12-dihydro-1H-5,18-(metheno)dibenzo[5,6:11,12][1,4]dioxa[7]azacyclododecino[8,9-f]indazole-15-carboxylic Acid (14)

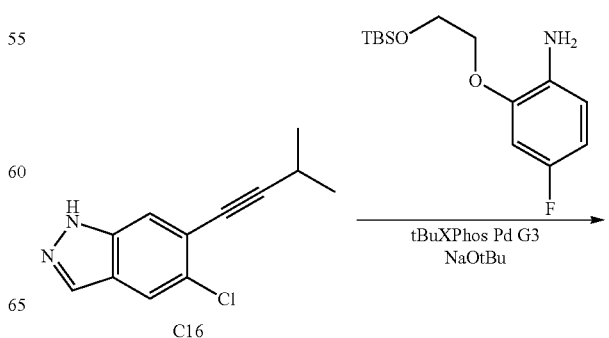

431
-continued
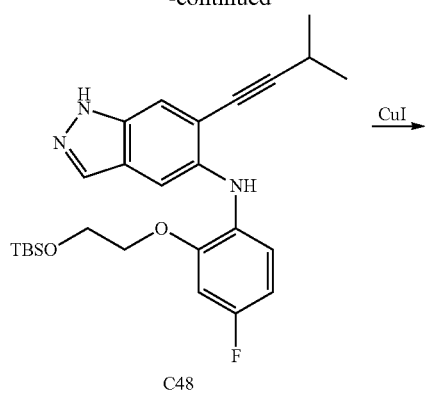
C48
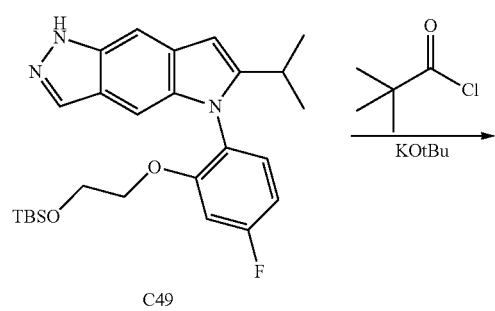
C49
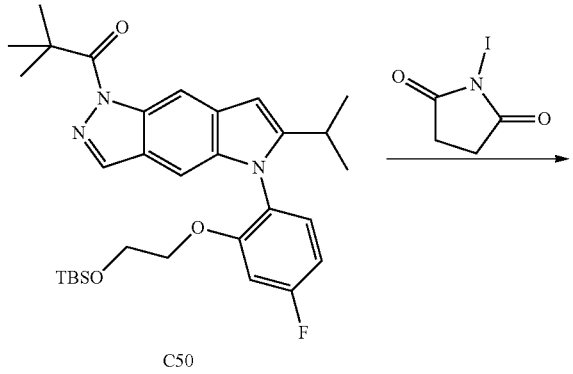
C50
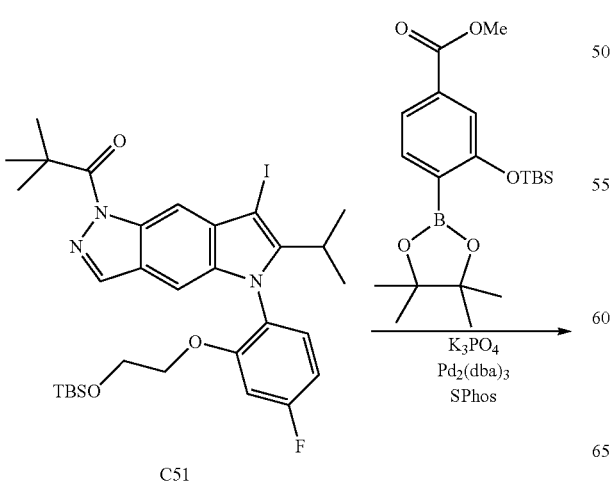
C51
432
-continued
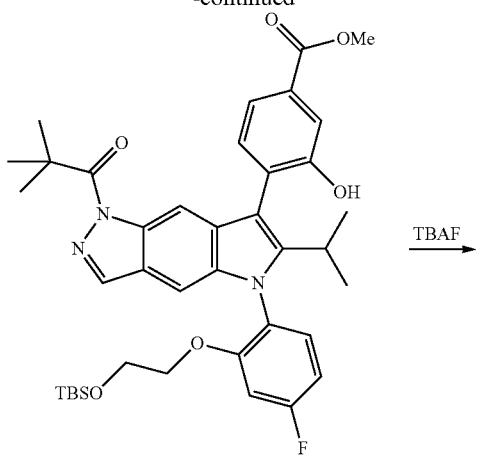
C52
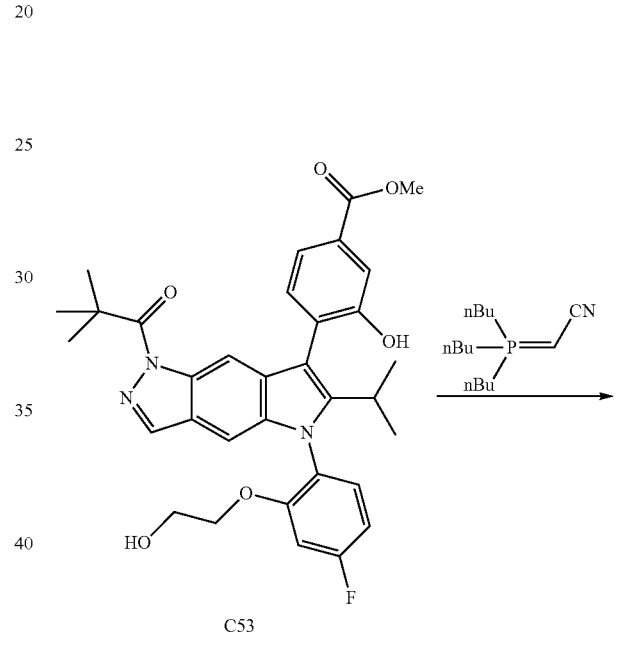
C53
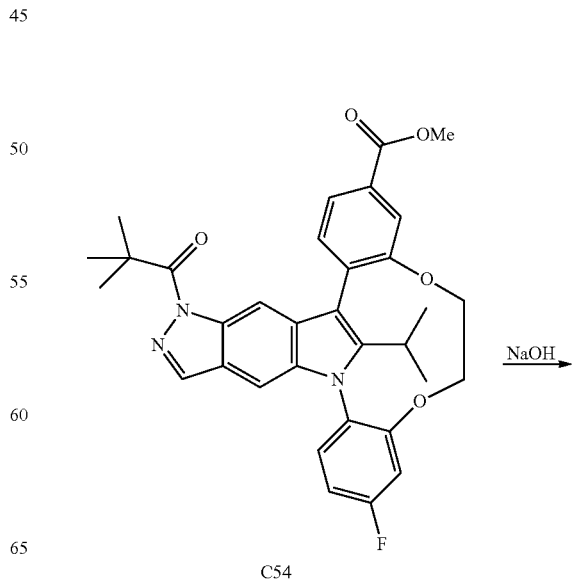
C54

-continued

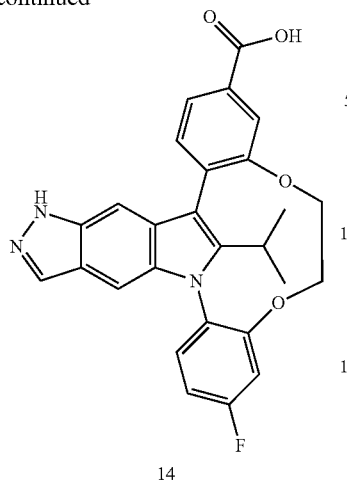

14

Step 1. Synthesis of N-[2-[2-[tert-butyl(dimethyl)silyl]oxyethoxy]-4-fluoro-phenyl]-6-(3-methylbut-1-ynyl)-1H-indazol-5-amine (C48)

tBuOH (1000 μL) was added to a vial containing 5-bromo-6-(3-methylbut-1-ynyl)-1H-indazole C16 (60 mg, 0.2 mmol), 2-[2-[tert-butyl(dimethyl)silyl]oxyethoxy]-4-fluoro-aniline (98 mg, 0.3 mmol), and NaOtBu (62 mg, 0.6 mmol). The mixture was degassed and purged with N₂ for 10 min at 40° C. tBuXphos Pd G3 (22 mg, 0.025 mmol) was added and the reaction heated at 40° C. overnight. The reaction mixture was concentrated in vacuo and purified by silica gel chromatography (Gradient: 0-40% EtOAc in heptane) to afford the product as a light yellow solid (51.6 mg, 50%). ¹H NMR (400 MHz, Chloroform-d) δ 7.84 (s, 1H), 7.50 (s, 1H), 7.39 (s, 1H), 7.25 (dd, J=6.1, 3.9 Hz, 1H), 6.71 (dt, J=10.3, 2.1 Hz, 1H), 6.65-6.58 (m, 1H), 6.41 (s, 1H), 4.07 (t, J=5.7 Hz, 2H), 3.94 (t, J=5.3 Hz, 2H), 2.82 (dq, J=13.8, 6.9, 6.3 Hz, 1H), 1.26 (dd, J=6.9, 1.6 Hz, 6H), 0.82 (s, 9H), 0.04--0.04 (m, 6H). LCMS m/z 468.46 [M+H]⁺.

Step 2. Synthesis of tert-butyl-[2-[5-fluoro-2-(6-isopropyl-1H-pyrrolo[2,3-f]indazol-5-yl)phenoxy]ethoxy]-dimethyl-silane (C49)

A vial containing N-[2-[2-[tert-butyl(dimethyl)silyl]oxyethoxy]-4-fluoro-phenyl]-6-(3-methylbut-1-ynyl)-1H-indazol-5-amine C48 (85 mg, 0.17 mmol) and CuI (13 mg, 0.07 mmol) were purged with nitrogen. DMF (80 μL) was added and the mixture heated at 80° C. for 30 min. The mixture was purified by reversed phase chromatography (C18 g column. Gradient: 10-100% MeCN in water with 0.2% formic acid) to afford the product (62.7 mg, 81%). ¹H NMR (400 MHz, DMSO-d₆) δ 13.10-12.67 (m, 1H), 8.25 (s, 1H), 7.72 (s, 1H), 7.70-7.62 (m, 1H), 7.54-7.47 (m, 1H), 7.26-7.18 (m, 2H), 6.63 (s, 1H), 4.37-4.19 (m, 2H), 3.91-3.79 (m, 2H), 3.02-2.91 (m, 1H), 1.41 (ddd, J=16.9, 6.9, 1.8 Hz, 6H), 0.88 (s, 9H), 0.00 (s, 3H), -0.09 (s, 3H). LCMS m/z 468.4 [M+H]⁺.

Step 3. 1-[5-[2-[2-[tert-butyl(dimethyl)silyl]oxyethoxy]-4-fluoro-phenyl]-6-isopropyl-pyrrolo[2,3-f]indazol-1-yl]-2,2-dimethyl-propan-1-one (C50)

To a solution of tert-butyl-[2-[5-fluoro-2-(6-isopropyl-1H-pyrrolo[2,3-f]indazol-5-yl)phenoxy]ethoxy]-dimethyl-silane C49 (165 mg, 0.35 mmol) in THF (5 mL) at 0° C. was added KOtBu (74 mg, 0.66 mmol), and the mixture was allowed to stir for 5 min. 2,2-dimethylpropanoyl chloride (170 μL, 1.4 mmol) was added and the reaction was stirred 0° C. for 1 h. The reaction mixture was then concentrated in vacuo. Silica gel chromatography (Gradient: 0-10% EtOAc in heptane) afforded the product as a pale yellow oil (139.3 mg, 71%). LCMS m/z 552.31 [M+H]⁺.

Step 4. 1-[5-[2-[2-[tert-butyl(dimethyl)silyl]oxyethoxy]-4-fluoro-phenyl]-7-iodo-6-isopropyl-pyrrolo[2,3-f]indazol-1-yl]-2,2-dimethyl-propan-1-one (C51)

N-iodosuccinimide (64 mg, 0.28 mmol) was added to a solution of 1-[5-[2-[2-[tert-butyl(dimethyl)silyl]oxyethoxy]-4-fluoro-phenyl]-6-isopropyl-pyrrolo[2,3-f]indazol-1-yl]-2,2-dimethyl-propan-1-one C50 (135 mg, 0.24 mmol) in CH₂Cl₂ (2 mL) and the reaction was stirred at room temperature for 30 min. The mixture was concentrated in vacuo, and the crude product purified by silica gel column chromatography (Gradient: 0-5% EtOAc in Heptane) to afford the product as a bright yellow fluorescent viscous oil (119.2 mg, 70%). ¹H NMR (400 MHz, Chloroform-d) δ 8.55 (s, 1H), 8.02 (s, 1H), 7.25-7.22 (m, 1H), 6.97 (s, 1H), 6.91 (d, J=10.1 Hz, 1H), 6.83 (t, J=7.8 Hz, 1H), 3.93 (t, J=4.8 Hz, 2H), 3.62 (t, J=4.9 Hz, 2H), 3.13-3.00 (m, 1H), 1.59 (s, 9H), 1.38 (d, J=6.9 Hz, 3H), 1.28 (d, J=7.2 Hz, 3H), 0.65 (s, 9H), -0.23 (s, 3H), -0.38 (s, 3H). LCMS m/z 678.3 [M+H]⁺.

Step 5. Synthesis of methyl 3-[tert-butyl(dimethyl)silyl]oxy-4-[5-[2-[2-[tert-butyl(dimethyl)silyl]oxyethoxy]-4-fluoro-phenyl]-1-(2,2-dimethylpropanoyl)-6-isopropyl-pyrrolo[2,3-f]indazol-7-yl]benzoate (C52)

THF (6 mL) and water (1.6 mL) were added to a vial containing a mixture of 1-[5-[2-[2-[tert-butyl(dimethyl)silyl]oxyethoxy]-4-fluoro-phenyl]-7-iodo-6-isopropyl-pyrrolo[2,3-f]indazol-1-yl]-2,2-dimethyl-propan-1-one C51 (100 mg, 0.14 mmol), methyl 3-[tert-butyl(dimethyl)silyl]oxy-4-(4,4,5,5-tetramethyl-1,3,2-dioxaborolan-2-yl)benzoate (107 mg, 0.27 mmol), and K₃PO₄ (102 mg, 0.48 mmol). The mixture was purged with nitrogen, then SPhos (16 mg, 0.04 mmol) and Pd₂(dba)₃ (14 mg, 0.015 mmol) were added and the mixture heated to 60° C. for 3 days. The reaction mixture was partitioned between water (10 mL) and dichloromethane (10 mL). The mixture was then passed through a phase separator to collect the organic phase and the solvent was evaporated in vacuo. The mixture was purified by silica gel chromatography (Gradient: 0-20% EtOAc in heptane) to afford two products.

Product 1 (Two TBS groups remain intact). Methyl 3-[tert-butyl(dimethyl)silyl]oxy-4-[5-[2-[2-[tert-butyl(dimethyl)silyl]oxyethoxy]-4-fluoro-phenyl]-1-(2,2-dimethylpropanoyl)-6-isopropyl-pyrrolo[2,3-f]indazol-7-yl]benzoate (17.1 mg, 11%). ¹H NMR (300 MHz, Chloroform-d) δ 8.25 (dt, J=18.1, 0.9 Hz, 1H), 8.01 (dd, J=2.7, 0.8 Hz, 1H), 7.48 (dt, J=7.6, 2.2 Hz, 1H), 7.37-7.29 (m, 2H), 7.29-7.19 (m, 1H), 7.03-6.34 (m, 3H), 4.10-3.93 (m, 5H), 3.76-3.62 (m, 2H), 3.09-2.86 (m, 1H), 1.54 (s, 9H), 1.16-1.02 (m, 6H), 0.87-0.53 (m, 18H), 0.07--0.37 (m, 12H). LCMS m/z 816.48 [M+H]⁺. The NMR spectrum revealed that dba was present as an impurity Product 2 (mono-des-TBS C52). The product mono-des-TBS was obtained as a light yellow viscous oil. Methyl 4-[5-[2-[2-[tert-butyl(dimethyl)silyl]oxyethoxy]-4-fluorophenyl]-1-(2,2-dimethylpropanoyl)-6-isopropyl-pyrrolo[2,3-f]indazol-7-yl]-3-hydroxy-benzoate (77.8 mg, 51%). $^1$H NMR (400 MHz, Chloroform-d) δ 8.24 (s, 1H), 8.03 (s, 1H), 7.75-7.67 (m, 2H), 7.43-7.35 (m, 2H), 7.09 (d, J=6.9 Hz, 1H), 6.97-6.85 (m, 2H), 5.33-5.16 (m, 1H), 4.02-3.95 (m, 5H), 3.72-3.63 (m, 2H), 3.03-2.81 (m, 1H), 1.53 (s, 9H), 1.07 (ddd, J=22.1, 10.7, 7.1 Hz, 6H), 0.70-0.61 (m, 9H), −0.18-0.38 (m, 6H). LCMS m/z 699.78 [M+H]$^+$. The NMR spectrum revealed that the reduced, deprotected boronate was present as an impurity.

Step 6. 4-[1-(2,2-dimethylpropanoyl)-5-[4-fluoro-2-(2-hydroxyethoxy)phenyl]-6-isopropyl-pyrrolo[2,3-f]indazol-7-yl]-3-hydroxy-benzoate (C53)

To a solution of methyl 4-[5-[2-[2-[tert-butyl(dimethyl)silyl]oxyethoxy]-4-fluoro-phenyl]-1-(2,2-dimethylpropanoyl)-6-isopropyl-pyrrolo[2,3-f]indazol-7-yl]-3-hydroxy-benzoate C52 (75 mg, 0.07 mmol) in THF (2 mL) was added TBAF (75 μL of 1 M, 0.08 mmol) and the reaction stirred at room temperature overnight. The reaction mixture was partitioned between water (5 mL) and dichloromethane (5 mL), and passed through a phase separator. The organic phase was collected and the solvent was evaporated in vacuo. The product mixture was purified by silica gel chromatography (Gradient: 0-60% EtOAc in Heptane) to afford the product as a white solid (29.7 mg, 72%). $^1$H NMR (300 MHz, Chloroform-d) δ 8.30-8.23 (m, 1H), 8.04-7.92 (m, 1H), 7.74-7.66 (m, 2H), 7.56-7.41 (m, 1H), 7.40-7.34 (m, 1H), 7.13-7.09 (m, 1H), 7.00-6.83 (m, 2H), 6.12 (s, 1H), 5.25 (s, 1H), 4.04-3.79 (m, 5H), 3.68-3.33 (m, 2H), 3.00-2.77 (m, 1H), 1.53 (s, 9H), 1.07 (ddd, J=14.6, 7.1, 3.8 Hz, 6H). LCMS m/z 588.3 [M+H]$^+$.

Step 7. Synthesis methyl (E)-8-fluoro-20-isopropyl-1-pivaloyl-11,12-dihydro-1H-5,18-(metheno)dibenzo[5,6:11,12][1,4]dioxa[7]azacyclododecino[8,9-f]indazole-15-carboxylate (C54)

To a solution of methyl 4-[1-(2,2-dimethylpropanoyl)-5-[4-fluoro-2-(2-hydroxyethoxy)phenyl]-6-isopropyl-pyrrolo[2,3-f]indazol-7-yl]-3-hydroxy-benzoate (18 mg, 0.03 mmol) in toluene (30 mL) under a nitrogen atmosphere was added 2-(tributyl-λ$^5$-phosphanylidene)acetonitrile (480 μL, 1.83 mmol). The reaction mixture was heated to 100° C. overnight. The solvent was evaporated in vacuo and the mixture was purified by silica gel chromatography (Gradient: 0-10% EtOAc in heptane) to afford the product C54 as a white solid (2.2 mg, 12%). $^1$H NMR (400 MHz, Chloroform-d) δ 8.33 (s, 1H), 8.06-8.01 (m, 2H), 7.88-7.77 (m, 3H), 7.30-7.27 (m, 1H), 6.90 (td, J=8.5, 2.7 Hz, 1H), 6.49 (dd, J=9.3, 2.7 Hz, 1H), 4.16-4.10 (m, 1H), 3.97 (s, 3H), 3.88 (d, J=9.7 Hz, 2H), 3.18 (dd, J=11.0, 8.0 Hz, 1H), 2.88-2.73 (m, 1H), 1.56 (s, 9H), 1.09 (d, J=6.8 Hz, 3H), 0.88-0.83 (m, 3H). LCMS m/z 570.31 [M+H]$^+$.

Step 8. Synthesis of (E)-8-fluoro-20-isopropyl-11,12-dihydro-1H-5,18-(metheno)dibenzo[5,6:11,12][1,4]dioxa[7]azacyclododecino[8,9-f]indazole-15-carboxylic Acid (14)

NaOH (21 μL of 1 M, 0.021 mmol) was added to a solution of methyl 22-(2,2-dimethylpropanoyl)-5-fluoro-28-(propan-2-yl)-8,11-dioxa-1,22,23-triazahexacyclo[16.9.1.0$^{2,7}$.0$^{12,17}$.0$^{19,27}$.0$^{21,25}$]octacosa-2(7),3,5,12,14,16,18(28),19,21(25),23,26-undecaene-14-carboxylate C54 (2 mg, 0.004 mmol) in THF (40 μL) and MeOH (20 μL). The reaction mixture was heated to 50° C. for 50 min. The solvent was evaporated in vacuo and HCl (21 μL of 1 M, 0.021 mmol) was added. A white precipitate formed and the solvent was evaporated in vacuo. The product mixture was dissolved in minimal DMSO, and purified by reverse phase chromatography (C18 column. Gradient: 10-100% MeCN in water with 0.2% formic acid) to afford the desired product as a white solid (1.3 mg, 78%). $^1$H NMR (400 MHz, Methanol-d$_4$) δ 8.19 (s, 1H), 8.04 (d, J=7.8 Hz, 1H), 7.94 (s, 1H), 7.86-7.79 (m, 2H), 7.26 (s, 1H), 7.22 (s, 1H), 6.94 (td, J=8.8, 4.6 Hz, 1H), 6.75-6.68 (m, 1H), 4.18 (d, J=11.0 Hz, 1H), 3.98-3.86 (m, 2H), 3.15 (t, J=9.7 Hz, 1H), 2.84-2.72 (m, 1H), 1.11 (dd, J=6.9, 1.5 Hz, 3H), 0.89 (dd, J=7.2, 1.6 Hz, 3H). LCMS m/z 472.2 [M+H]$^+$.

Compound 15, 16 and 17

2,2,2-trifluoro-1-[4-[5-(4-fluorophenyl)-6-tetrahydropyran-4-yl-1H-pyrrolo[2,3-f]indazol-7-yl]phenyl]ethanol (15), 2,2,2-trifluoro-1-[4-[5-(4-fluorophenyl)-6-tetrahydropyran-4-yl-1H-pyrrolo[2,3-f]indazol-7-yl]phenyl]ethanol (16) ENANT-1 and 2,2,2-trifluoro-1-[4-[5-(4-fluorophenyl)-6-tetrahydropyran-4-yl-1H-pyrrolo[2,3-f]indazol-7-yl]phenyl]ethanol (17) ENANT-2

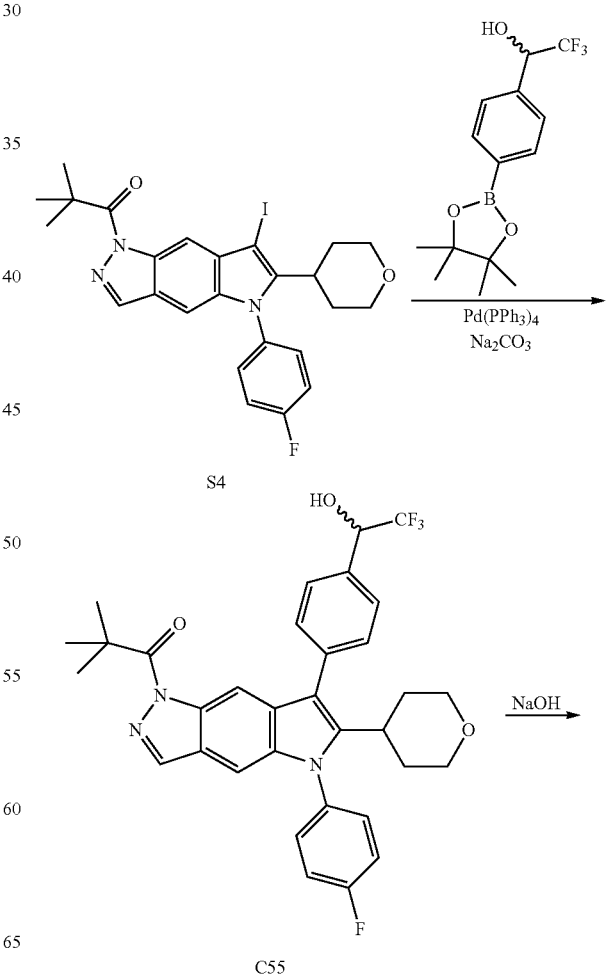

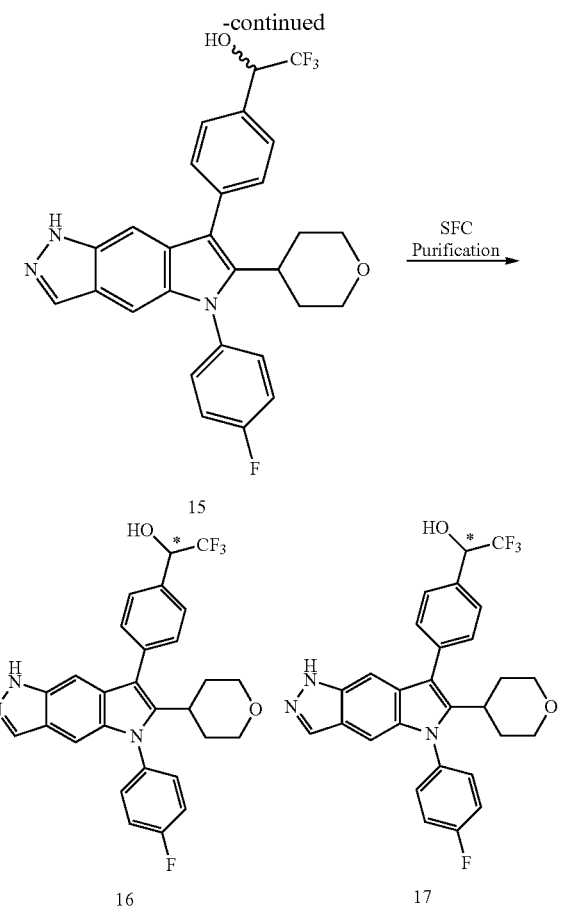

Step 1. Synthesis of 1-[5-(4-fluorophenyl)-6-tetrahydropyran-4-yl-7-[4-(2,2,2-trifluoro-1-hydroxyethyl)phenyl]pyrrolo[2,3-f]indazol-1-yl]-2,2-dimethyl-propan-1-one (C55)

A solution of Na$_2$CO$_3$ (225 μL of 2 M, 0.45 mmol) was added to a solution of 1-[5-(4-fluorophenyl)-7-iodo-6-tetrahydropyran-4-yl-pyrrolo[2,3-f]indazol-1-yl]-2,2-dimethyl-propan-1-one (100 mg, 0.18 mmol) S4, 2,2,2-trifluoro-1-[4-(4,4,5,5-tetramethyl-1,3,2-dioxaborolan-2-yl)phenyl]ethanol (66 mg, 0.22 mmol) and Pd(PPh$_3$)$_4$ (10 mg, 0.009 mmol) in 1,4-dioxane (750 μL) and DMF (750 μL). The reaction was heated at 150° C. for 30 min. Water and CH$_2$Cl$_2$ were added and the mixture was extracted with CH$_2$Cl$_2$ (×3). The organic phases were filtered through a phase separator, combined and concentrated in vacuo to afford the product which was used in the subsequent step without further purification. LCMS m/z 594.4 [M+H]$^+$.

Step 2. Synthesis of 2,2,2-trifluoro-1-[4-[5-(4-fluorophenyl)-6-tetrahydropyran-4-yl-1H-pyrrolo[2,3-f]indazol-7-yl]phenyl]ethanol (15)

NaOH (36 mg, 0.9 mmol) was added to a solution of C55 in THF (750 μL) and water (250 μL). The reaction was heated at 50° C. for 40 h. The pH of the mixture was adjusted to pH 7 by the addition of 1 M HCl. The mixture was extracted with CHCl$_3$:IPA (3:1) (×3). The organic phases were filtered through a phase separator, combined and evaporated in vacuo. The crude was dissolved in DMSO and purified by reversed-phase HPLC (Method: C18 Waters Sunfire column (30×150 mm, 5 micron). Gradient: 10-100% MeCN in H$_2$O with 0.2% formic acid) to afford the product as a white solid.

Step 3. Preparation of 2,2,2-trifluoro-1-[4-[5-(4-fluorophenyl)-6-tetrahydropyran-4-yl-1H-pyrrolo[2,3-f]indazol-7-yl]phenyl]ethanol (16) and 2,2,2-trifluoro-1-[4-[5-(4-fluorophenyl)-6-tetrahydropyran-4-yl-1H-pyrrolo[2,3-f]indazol-7-yl]phenyl]ethanol (17)

Racemic compound 2,2,2-trifluoro-1-[4-[5-(4-fluorophenyl)-6-tetrahydropyran-4-yl-1H-pyrrolo[2,3-f]indazol-7-yl]phenyl]ethanol 15 (30 mg, 0.06 mmol) was separated into its constituent enantiomers by chiral SFC separation. Column: Daicel Chiralpak IB, 10×250 mm. Mobile phase: 20% MeOH (5 mM ammonia), 80% CO$_2$. Flow: 15 m/min. Two products were obtained. Compound 16 was the first eluting enantiomer and compound 17 was the second eluting enantiomer.

2,2,2-trifluoro-1-[4-[5-(4-fluorophenyl)-6-tetrahydropyran-4-yl-1H-pyrrolo[2,3-f]indazol-7-yl]phenyl]ethanol (16) ENANT-1 (10.1 mg, 61%). $^1$H NMR (300 MHz, Methanol-d$_4$) δ 8.34 (s, 1H), 7.68 (d, J=8.0 Hz, 2H), 7.55 (dt, J=8.9, 2.7 Hz, 4H), 7.42 (t, J=8.6 Hz, 2H), 7.34 (t, J=1.1 Hz, 1H), 7.26 (d, J=1.2 Hz, 1H), 5.16 (q, J=7.3 Hz, 1H), 3.79 (dd, J=11.4, 4.1 Hz, 2H), 3.20 (t, J=11.4 Hz, 2H), 3.11-3.02 (m, 1H), 1.88-1.74 (m, 2H), 1.69 (d, J=13.1 Hz, 2H). LCMS m/z 510.2 [M+H]$^+$.

2,2,2-trifluoro-1-[4-[5-(4-fluorophenyl)-6-tetrahydropyran-4-yl-1H-pyrrolo[2,3-f]indazol-7-yl]phenyl]ethanol (17) ENANT-2 (12.1 mg, 74%). $^1$H NMR (300 MHz, Methanol-d$_4$) δ 8.41 (s, 1H), 7.68 (d, J=8.0 Hz, 2H), 7.59-7.50 (m, 4H), 7.43 (t, J=8.6 Hz, 2H), 7.35 (d, J=1.2 Hz, 1H), 7.28 (d, J=1.2 Hz, 1H), 5.17 (q, J=7.1 Hz, 1H), 3.86-3.73 (m, 2H), 3.19 (m, J=11.5 Hz, 2H), 3.06 (m, 1H), 1.88-1.74 (m, 2H), 1.69 (d, J=12.8 Hz, 2H). LCMS m/z 510.2 [M+H]$^+$.

Compound 18

5-(4-fluorophenyl)-7-(4-pyridyl)-6-tetrahydropyran-4-yl-1H-pyrrolo[2,3-f]indazole (18)

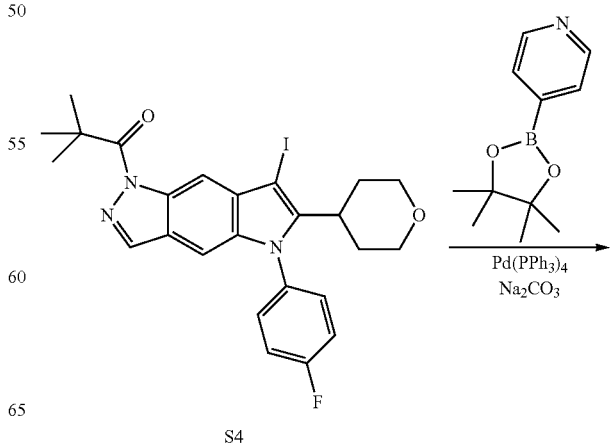

-continued

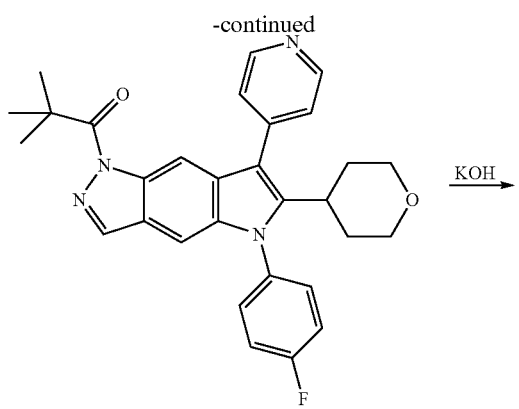

C56

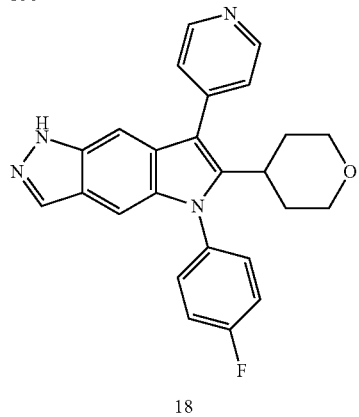

18

Step 1. 1-[5-(4-fluorophenyl)-7-(4-pyridyl)-6-tetra-hydropyran-4-yl-pyrrolo[2,3-f]indazol-1-yl]-2,2-dimethyl-propan-1-one (C56)

1,4-Dioxane (750 μL) and DMF (750 μL) were added to a vial containing 1-[5-(4-fluorophenyl)-7-iodo-6-tetrahydropyran-4-yl-pyrrolo[2,3-f]indazol-1-yl]-2,2-dimethyl-propan-1-one S4 (100 mg, 0.18 mmol), 4-(4,4,5,5-tetramethyl-1,3,2-dioxaborolan-2-yl)pyridine (45 mg, 0.22 mmol), and Pd(PPh$_3$)$_4$ (10 mg, 0.009 mmol) under a nitrogen atmosphere. A solution of Na$_2$CO$_3$ (225 μL of 2 M, 0.45 mmol) was then added and the reaction was heated at 100° C. for 7 h. Water and CH$_2$Cl$_2$ were added, and the mixture was extracted with CH$_2$Cl$_2$ (×3). The organic phases were filtered through a phase separator, and concentrated in vacuo to afford the product which was used without further purification. LCMS m/z 497.2 [M+H]$^+$.

Step 2. Synthesis of 5-(4-fluorophenyl)-7-(4-pyridyl)-6-tetrahydropyran-4-yl-1H-pyrrolo[2,3-f]indazole (18)

KOH (30 mg, 0.5 mmol) was added to a solution of 1-[5-(4-fluorophenyl)-7-(4-pyridyl)-6-tetrahydropyran-4-yl-pyrrolo[2,3-f]indazol-1-yl]-2,2-dimethyl-propan-1-one C56 in EtOH (750 μL) and Water (250 μL). The reaction mixture was heated at 50° C. for 72 h. The pH of the reaction mixture was adjusted to the pH to 7 with 1M HCl. The mixture was then extracted with CHCl$_3$:IPA (3:1) (×3). The organic phases were filtered through a phase separator, combined and concentrated in vacuo. Purification by reversed-phase HPLC (Method: C18 Waters Sunfire column (30×150 mm, 5 micron). Gradient: 10-100% MeCN in H$_2$O with 0.2% formic acid) afforded the product as a white solid (22.6 mg, 29%). $^1$H NMR (400 MHz, DMSO-d$_6$) δ 12.63 (s, 1H), 8.87-8.63 (m, 2H), 8.01 (d, J=1.0 Hz, 1H), 7.68-7.60 (m, 2H), 7.60-7.55 (m, 2H), 7.56-7.48 (m, 2H), 7.34 (t, J=1.1 Hz, 1H), 7.08 (d, J=1.1 Hz, 1H), 3.74 (d, J=11.4 Hz, 2H), 3.20-3.10 (m, 2H), 3.04 (m, 1H), 1.69 (m, 4H). LCMS m/z 413.1 [M+H]$^+$.

Compounds 19-32

Compounds 19-32 were prepared in two steps from S4 according to the method described for the preparation of compound 18 (Suzuki coupling, pivaloyl group deprotection). In some examples, an alternative catalyst is used in the Suzuki coupling step, as noted in the table footnotes.

TABLE 4

Method of preparation structure, physicochemical data for compounds 19-32

| Compound | Method/Product | Boronic acid or ester | $^1$H NMR; LCMS m/z [M + H]$^+$ |
|---|---|---|---|
| 19 | ![structure] Compound 18$^1$ from S4 | ![boronic acid] | $^1$H NMR (400 MHz, DMSO-d$_6$) δ 12.62 (s, 1H), 8.07-7.98 (m, 3H), 7.79-7.70 (m, 2H), 7.67-7.60 (m, 2H), 7.56-7.48 (m, 2H), 7.27 (t, J = 1.1 Hz, 1H), 7.08 (t, J = 0.9 Hz, 1H), 3.73 (d, J = 10.4 Hz, 2H), 3.19-3.06 (m, 2H), 3.07-2.95 (m, 1H), 1.64 (m, 4H). LCMS m/z 436.98 [M + H]$^+$. |

TABLE 4-continued

Method of preparation structure, physicochemical data for compounds 19-32

| Compound | Method/Product | Boronic acid or ester | ¹H NMR; LCMS m/z [M + H]⁺ |
|---|---|---|---|
| 20 | 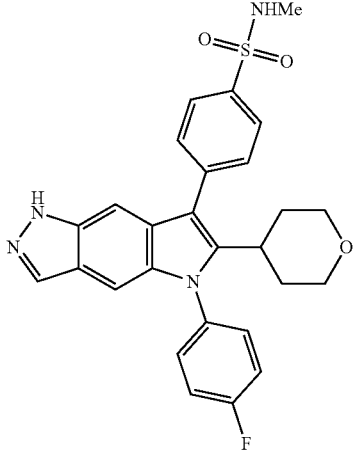<br>Compound 18¹ from S4 | 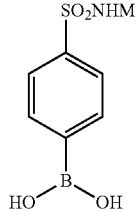<br>SO₂NHMe | ¹H NMR (400 MHz, DMSO-$d_6$) δ 12.59 (br s, 1H), 8.01 (t, J = 1.3 Hz, 1H), 7.98-7.91 (m, 2H), 7.79-7.71 (m, 2H), 7.67-7.59 (m, 2H), 7.59-7.48 (m, 3H), 7.26 (t, J = 1.1 Hz, 1H), 7.08 (tbr s, 1H), 3.73 (d, J = 11.2 Hz, 2H), 3.18-3.06 (m, 2H), 3.07-2.95 (m, 1H), 2.53 (d, J = 5.0 Hz, 3H), 1.67 (m, 4H). LCMS m/z 505.2 [M + H]⁺. |
| 21 | 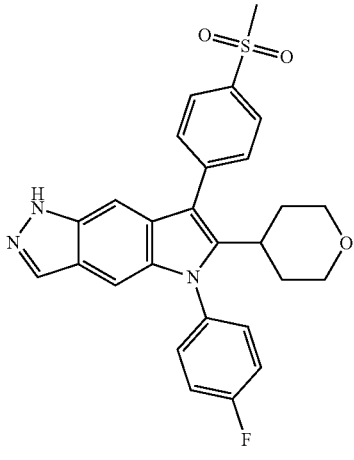<br>Compound 18¹ from S4 | 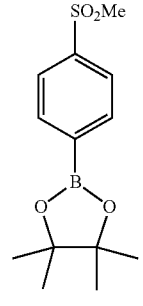<br>SO₂Me | ¹H NMR (400 MHz, DMSO-$d_6$) δ 12.81-12.42 (m, 1H), 8.15-8.06 (m, 2H), 8.01 (t, J = 1.3 Hz, 1H), 7.84-7.75 (m, 2H), 7.68-7.59 (m, 2H), 7.57-7.48 (m, 2H), 7.28 (t, J = 1.1 Hz, 1H), 7.08 (t, J = 0.9 Hz, 1H), 3.80-3.68 (m, 2H), 3.35 (s, 3H), 3.13 (td, J = 11.3, 4.8 Hz, 2H), 3.08-2.97 (m, 1H), 1.75-1.58 (m, 4H). LCMS m/z 490.1 [M + H]⁺. |
| 22 | 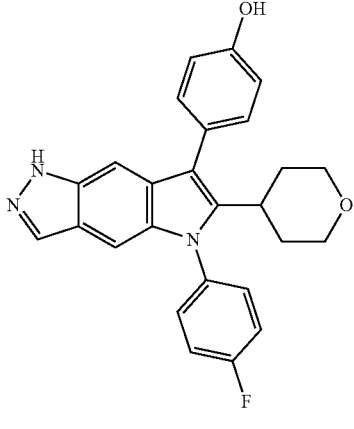<br>Compound 18¹ from S4 | 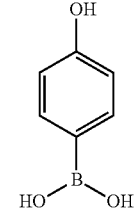 | ¹H NMR (400 MHz, DMSO-$d_6$) δ 12.54 (s, 1H), 9.53 (s, 1H), 7.97 (mz, 1H), 7.61-7.55 (m, 2H), 7.52-7.45 (m, 2H), 7.31-7.23 (m, 2H), 7.16 (m, 1H), 7.05 (m, 1H), 6.96-6.89 (m, 2H), 3.72 (d, J = 10.3 Hz, 2H), 3.08 (t, J = 11.1 Hz, 2H), 2.98-2.83 (m, 1H), 1.77-1.54 (m, 4H). LCMS m/z 428.2 [M + H]⁺. |

TABLE 4-continued

Method of preparation structure, physicochemical data for compounds 19-32

| Compound | Method/Product | Boronic acid or ester | ¹H NMR; LCMS m/z [M + H]⁺ |
|---|---|---|---|
| 23 | 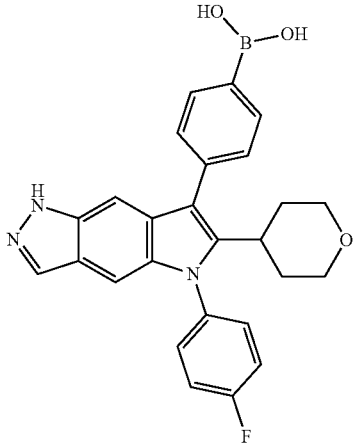  Compound 18² from S4 | 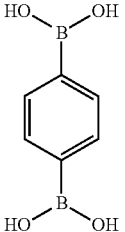 | ¹H NMR (400 MHz, DMSO-d₆) δ 12.56 (d, J = 1.4 Hz, 1H), 8.14 (s, 2H), 7.99 (t, J = 1.3 Hz, 1H), 7.97-7.91 (m, 2H), 7.65-7.58 (m, 2H), 7.55-7.44 (m, 4H), 7.21 (t, J = 1.1 Hz, 1H), 7.06 (t, J = 0.9 Hz, 1H), 3.72 (d, J = 10.7 Hz, 2H), 3.14-3.04 (m, 2H), 3.03-2.93 (m, 1H), 1.74-1.60 (m, 4H). LCMS m/z 456.2 [M + H]⁺. |
| 24 | 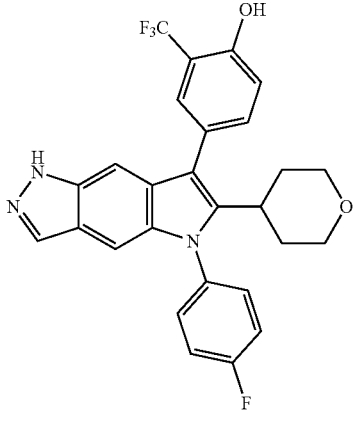  Compound 18³ from S4 | 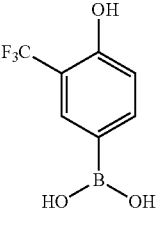 [SMILES: OB(O)c1ccc(O)c(C(F)(F)F)c1] | ¹H NMR (400 MHz, DMSO-d₆) δ 12.56 (s, 1H), 10.76 (s, 1H), 7.99 (s, 1H), 7.65-7.54 (m, 4H), 7.50 (t, J = 8.7 Hz, 2H), 7.22 (d, J = 8.2 Hz, 1H), 7.16 (t, J = 1.2 Hz, 1H), 7.08 (d, J = 1.1 Hz, 1H), 3.74 (d, J = 10.9 Hz, 2H), 3.19-3.02 (m, 2H), 2.98-2.80 (m, 1H), 1.65 (m, 4H). LCMS m/z 496.2 [M + H]⁺. |
| 25 | 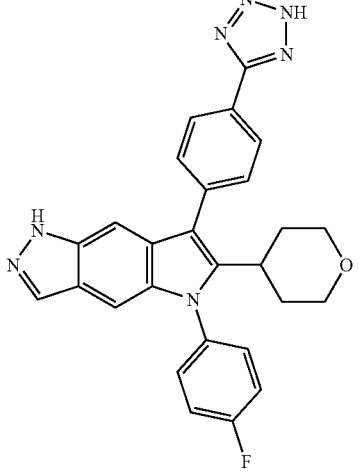  Compound 18³ from S4 | 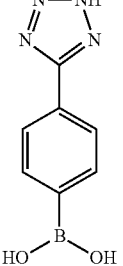 | ¹H NMR (400 MHz, DMSO-d₆) δ 12.60 (s, 1H), 8.26-8.16 (m, 2H), 8.01 (s, 1H), 7.79-7.71 (m, 2H), 7.68-7.60 (m, 2H), 7.57-7.47 (m, 2H), 7.29 (t, J = 1.2 Hz, 1H), 7.09 (d, J = 1.0 Hz, 1H), 3.74 (d, J = 11.3 Hz, 2H), 3.18-3.08 (m, 2H), 3.03 (p, J = 8.6, 8.0 Hz, 1H), 1.77-1.63 (m, 4H). LCMS m/z 480.5 [M + H]⁺. |

TABLE 4-continued

Method of preparation structure, physicochemical data for compounds 19-32

| Compound | Method/Product | Boronic acid or ester | ¹H NMR; LCMS m/z [M + H]⁺ |
|---|---|---|---|
| 26 | 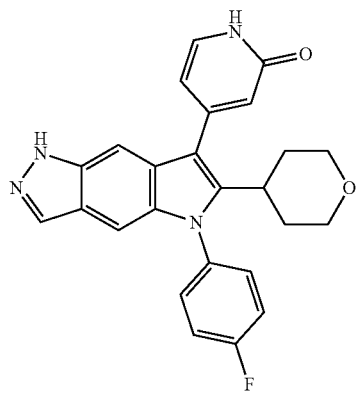<br>Compound 18¹ from S4 | 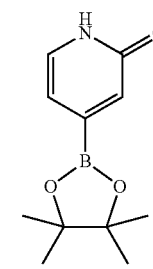 | ¹H NMR (400 MHz, Methanol-d₄) δ 8.05 (d, J = 1.0 Hz, 1H), 7.75-7.66 (m, 1H), 7.58-7.49 (m, 3H), 7.47-7.37 (m, 2H), 7.14 (d, J = 1.1 Hz, 1H), 6.82-6.75 (m, 2H), 3.97-3.76 (m, 2H), 3.29 (m, 2H, behind solvent peak), 3.19 (tt, J = 12.3, 3.4 Hz, 1H), 1.91 (qd, J = 12.5, 4.3 Hz, 2H), 1.73 (d, J = 12.7 Hz, 2H). LCMS m/z 429.2 [M + H]⁺. |
| 27 | 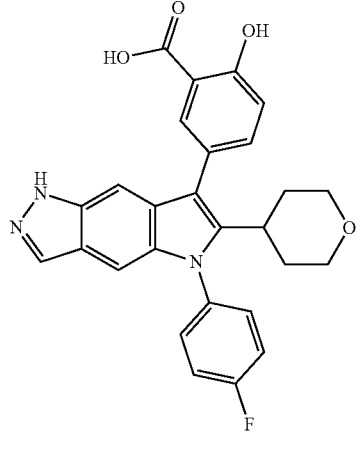<br>From compound 24⁴ | | ¹H NMR (400 MHz, DMSO-d₆) δ 12.56 (s, 1H), 11.37 (s, 1H), 7.99 (s, 1H), 7.88 (d, J = 2.3 Hz, 1H), 7.65-7.59 (m, 3H), 7.54-7.46 (m, 2H), 7.18 (t, J = 1.1 Hz, 1H), 7.14 (d, J = 8.4 Hz, 1H), 7.08 (d, J = 1.1 Hz, 1H), 3.73 (d, J = 11.1 Hz, 2H), 3.09 (dd, J = 14.1, 11.4 Hz, 2H), 2.91 (h, J = 7.8 Hz, 1H), 1.72-1.55 (m, 4H). LCMS m/z 472.2 [M + H]⁺. |
| 28 | <br>Compound 18¹ from S4 | 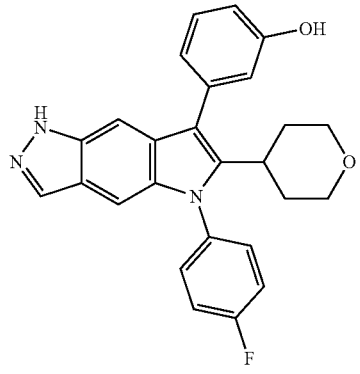 | ¹H NMR (400 MHz, DMSO-d₆) δ 12.55 (d, J = 1.4 Hz, 1H), 9.54 (s, 1H), 7.98 (t, J = 1.3 Hz, 1H), 7.64-7.57 (m, 2H), 7.54-7.46 (m, 2H), 7.36-7.29 (m, 1H), 7.23 (t, J = 1.1 Hz, 1H), 7.05 (m, 1H), 6.91 (m, 2H), 6.84-6.79 (m, 1H), 3.74 (dd, J = 11.3, 3.9 Hz, 2H), 3.10 (t, J = 11.3 Hz, 2H), 3.03-2.90 (m, 1H), 1.72 (qd, J = 12.4, 4.2 Hz, 2H), 1.63 (d, J = 12.7 Hz, 2H). LCMS m/z 428.2 [M + H]⁺. |

TABLE 4-continued

Method of preparation structure, physicochemical data for compounds 19-32

| Compound | Method/Product | Boronic acid or ester | $^1$H NMR; LCMS m/z [M + H]$^+$ |
|---|---|---|---|
| 29 | 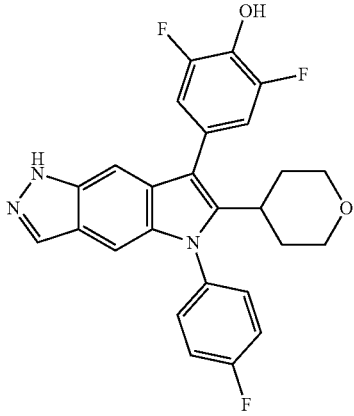<br>Compound 18$^1$ from S4 | 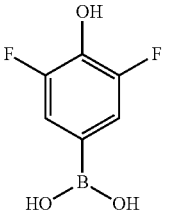 [SMILES: OB(O)c1cc(F)c(O)c(F)c1] | $^1$H NMR (400 MHz, DMSO-d$_6$) δ 12.58 (d, J = 1.4 Hz, 1H), 10.35 (s, 1H), 7.99 (m, 1H), 7.58 (m, 2H), 7.54-7.46 (m, 2H), 7.22 (t, J = 1.1 Hz, 1H), 7.18-7.08 (m, 2H), 7.07 (m, 1H), 3.82-3.66 (m, 2H), 3.17-3.02 (m, 2H), 2.93 (h, J = 8.2 Hz, 1H), 1.65 (m, 4H). LCMS m/z 464.2 [M + H]$^+$. |
| 30 | 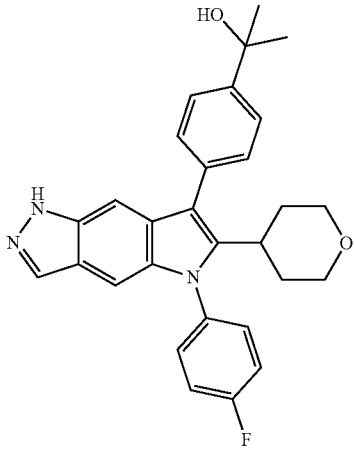<br>Compound 18$^1$ from S4 | 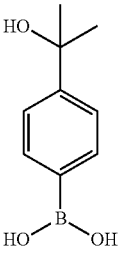 | $^1$H NMR (400 MHz, DMSO-d$_6$) δ 12.51 (d, J = 1.5 Hz, 1H), 7.98 (t, J = 1.3 Hz, 1H), 7.68-7.57 (m, 4H), 7.55-7.46 (m, 2H), 7.46-7.40 (m, 2H), 7.20 (t, J = 1.1 Hz, 1H), 7.05 (d, J = 0.9 Hz, 1H), 5.10 (s, 1H), 3.73 (d, J = 10.9 Hz, 2H), 3.16-3.03 (m, 2H), 3.03-2.91 (m, 1H), 1.69 (m, 4H), 1.53 (s, 6H). LCMS m/z 470.2 [M + H]$^+$. |
| 31 | 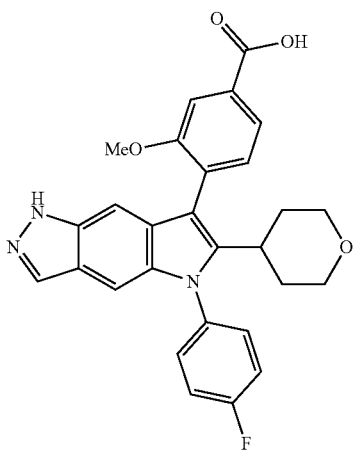<br>Compound 18$^1$ from S4 | 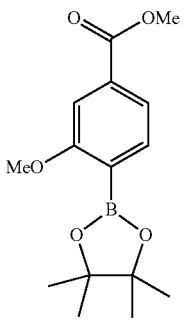 | $^1$H NMR (400 MHz, DMSO-d$_6$) δ 13.08 (s, 1H), 12.52 (s, 1H), 7.98 (s, 1H), 7.72-7.68 (m, 2H), 7.67-7.55 (m, 2H), 7.54-7.45 (m, 3H), 7.08 (s, 1H), 6.98 (s, 1H), 3.80 (s, 3H), 3.70 (t, J = 11.0 Hz, 2H), 3.07 (t, J = 11.6 Hz, 2H), 2.90-2.80 (m, 1H), 1.71-1.48 (m, 4H). LCMS m/z 486.42 [M + H]$^+$. |

TABLE 4-continued

*Method of preparation structure, physicochemical data for compounds 19-32*

| Compound | Method/Product | Boronic acid or ester | ¹H NMR; LCMS m/z [M + H]⁺ |
|---|---|---|---|
| 32 | 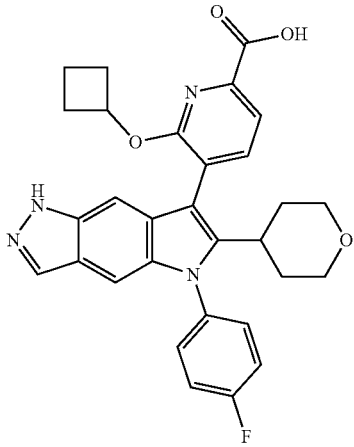<br>from S4 See footnote⁵ | 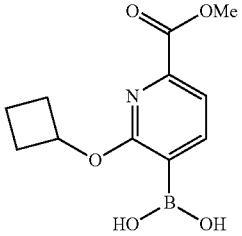 [SMILES: COC(=O)c1ccc(B(O)O)c(OC2CCC2)n1] | ¹H NMR (400 MHz, DMSO-d₆) δ 13.10 (s, 1H), 12.59 (s, 1H), 8.00 (s, 1H), 7.93 (d, J = 7.5 Hz, 1H), 7.81 (d, J = 7.5 Hz, 1H), 7.70-7.63 (m, 1H), 7.62-7.57 (m, 1H), 7.55-7.47 (m, 2H), 7.08 (d, J = 2.7 Hz, 2H), 5.29 (p, J = 8.7 Hz, 1H), 3.73 (t, J = 11.7 Hz, 2H), 3.10 (t, J = 11.3 Hz, 2H), 2.92 (t, J = 13.2 Hz, 1H), 2.45-2.36 (m, 2H), 2.00-1.90 (m, 2H), 1.73-1.53 (m, 6H). LCMS m/z 527.2 [M + H]⁺. |

¹Purification by reversed-phase HPLC. Method: C18 Waters Sunfire column (30 × 150 mm, 5 micron). Gradient: 10-100% MeCN in H₂O with 0.2% formic acid.

²Suzuki coupling reactions with Pd(dppf)Cl₂ and Na₂CO₃ in 1,4-dioxane at 90° C. Purification by reversed-phase HPLC. Method: C18 Waters Sunfire column (30 × 150 mm, 5 micron). Gradient: 10-100% MeCN in H₂O with ammonium formate.

³Purification by reversed-phase HPLC. Method: C18 Waters Sunfire column (30 × 150 mm, 5 micron). Gradient: 10-100% MeCN in H₂O with 0.1% TFA.

⁴Compound 27 was obtained as an additional product of reaction in preparation of compound 24. Purification by reversed-phase HPLC. Method: C18 Waters Sunfire column (30 × 150 mm, 5 micron). Gradient: 10-100% MeCN in H₂O with 0.1% TFA.

⁵Suzuki coupling conditions: Pd(OAc)₂, XPhos, K₃PO₄, 1,4-dioxane 90°C. Hydrolysis: NaOH Compound 33

4-[5-(4-fluorophenyl)-6-tetrahydropyran-4-yl-1H-pyrrolo[2,3-f]indazol-7-yl]benzoic Acid

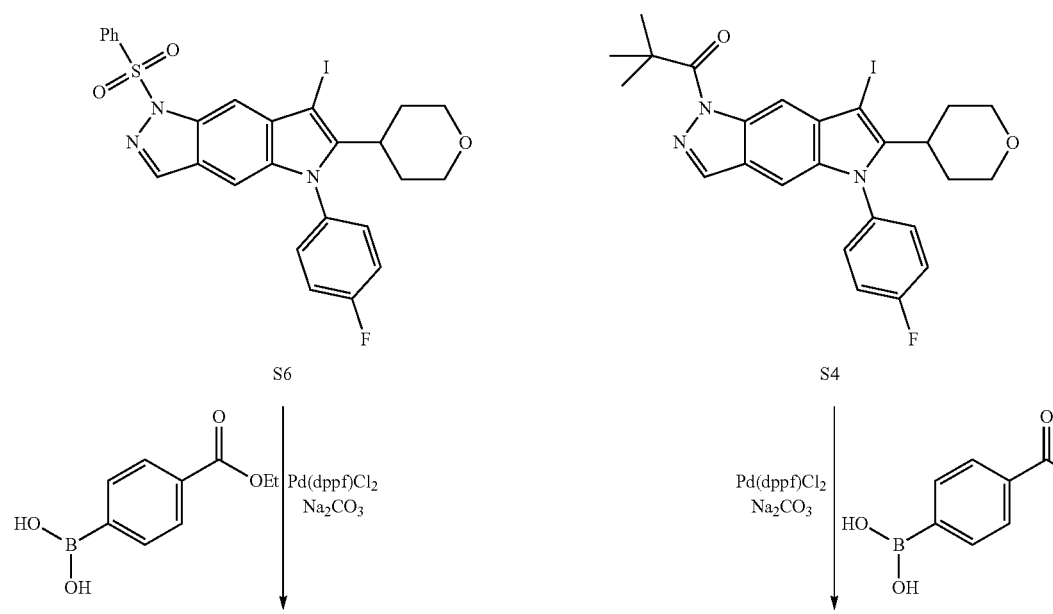

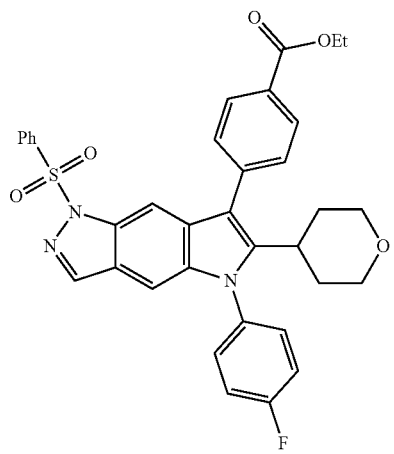

C57

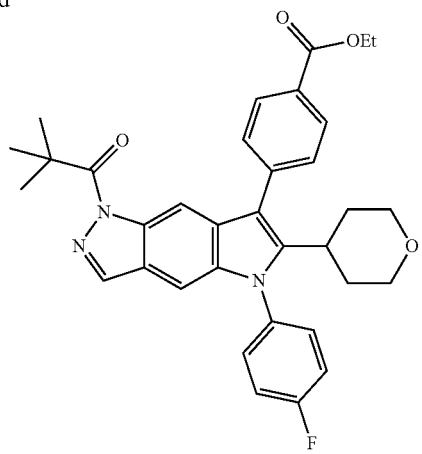

C58

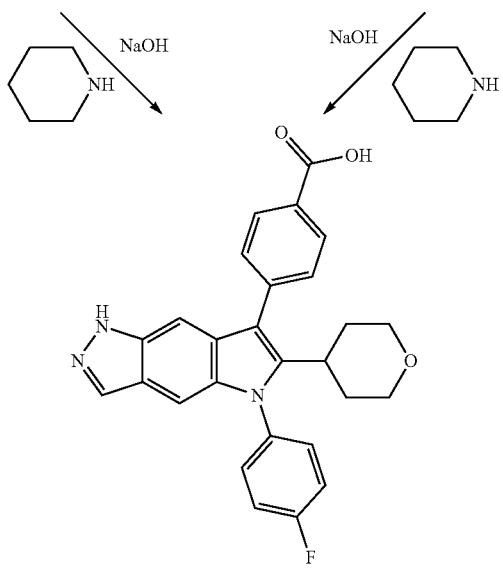

33

Preparation of 4-[5-(4-fluorophenyl)-6-tetrahydro-pyran-4-yl-1H-pyrrolo[2,3-f]indazol-7-yl]benzoic Acid (33) from S6

Step 1. Synthesis of ethyl 4-[1-(benzenesulfonyl)-5-(4-fluorophenyl)-6-tetrahydropyran-4-yl-pyrrolo[2,3-f]indazol-7-yl]benzoate (C57)

A mixture of 1-(benzenesulfonyl)-5-(4-fluorophenyl)-7-iodo-6-tetrahydropyran-4-yl-pyrrolo[2,3-f]indazole S6 (103.8 g, 172.6 mmol), (4-ethoxycarbonylphenyl)boronic acid (67 g, 345.4 mmol), Pd(dppf)Cl$_2$ (6.4 g, 7.8 mmol) and Na$_2$CO$_3$ (270 mL of 2 M, 540 mmol) in 1,4-dioxane (1 L) was purged with nitrogen for 20 min, then heated at 90° C. for 1 h. The mixture was filtered through Celite®, washing with EtOAc (500 mL). The filtrate was concentrated to dryness in vacuo. EtOAc (1 L) and water (300 mL) were added. The organic layer was separated and filtered through Celite®. The organic layer was then washed with 1 M NaOH (300 mL×2), and brine. The organic layer was dried, and concentrated in vacuo. The residue was dissolved in CH$_2$Cl$_2$ (200 mL) and the solution was purified by silica gel chromatography. (Column: 3 kg Silica gel. Gradient: 0-100% EtOAc in heptane) to afford the product as a white, foamy solid (~102 g). TBME (550 mL) was added, and the suspension was allowed to stir at room temperature for 1 h. The solid was filtered (washing with 200 mL MTBE). CH$_2$Cl$_2$ (300 mL) and EtOAc (400 mL) were added to afford a clear solution which was treated with MP-TMT Pd resin (45 g) and allowed to stir overnight. The suspension was filtered, and the filtrate concentrated in vacuo to afford the product as a white solid (96 g, 89%). $^1$H NMR (300 MHz, Chloroform-d) δ 8.33-8.22 (m, 2H), 8.15 (d, J=0.8 Hz, 1H), 8.10 (t, J=0.9 Hz, 1H), 7.91 (dd, J=8.4, 1.3 Hz, 2H), 7.65-7.56 (m, 2H), 7.56-7.46 (m, 1H), 7.46-7.35 (m, 4H), 7.35-7.23 (m, 2H), 7.06 (d, J=1.0 Hz, 1H), 4.49 (q, J=7.1 Hz, 2H), 3.86 (dd, J=11.4, 3.5 Hz, 2H), 3.22 (t, J=11.0 Hz, 2H), 3.05 (ddd, J=12.2, 8.9, 3.3 Hz, 1H), 1.83 (qd, J=12.6, 4.3 Hz, 2H), 1.64 (s, 2H), 1.49 (t, J=7.1 Hz, 3H). LCMS m/z 624.3 [M+H]$^+$.

Step 2. 4-[5-(4-fluorophenyl)-6-tetrahydropyran-4-yl-1H-pyrrolo[2,3-f]indazol-7-yl]benzoic Acid (33)

Piperidine (54 mL, 546.0 mmol) and NaOH (1350 mL of 1 M, 1.350 mol) were added to a solution of ethyl 4-[1-

(benzenesulfonyl)-5-(4-fluorophenyl)-6-tetrahydropyran-4-yl-pyrrolo[2,3-f]indazol-7-yl]benzoate C57 (170 g, 272.6 mmol) in THF (1800 mL) and MeOH (1800 mL) and the mixture was heated to 50° C. for 3.5 h. Upon cooling, HCl (700 mL of 2 M, 1.40 mol) was added to adjust the mixture to pH=2. The solvent volume was reduced (by ~3 L) by concentration in vacuo. The light yellow precipitate was filtered off, washing the filter cake with water (×3), TBME (250 mL×2) and EtOAc (250 mL×2). The solid filter cake was dried under vacuum. The solid was then dissolved in EtOAc (1.2 L) and the solution heated to reflux for 10 min. ~600 mL of solvent was removed by concentration under vacuum. An additional 600 mL of EtOAc was added and the process of refluxing for 10 min followed by removal of 1 L of solvent was repeated. Finally, EtOAc (1 L) was added and the mixture was heated at reflux for 2 h. Upon cooling overnight, the resulting solid was filtered off, washing with EtOAc (1×). This solid was then dried under vacuum at 60° C. for 4 h affording the product as a white solid (97.4 g, 78%). $^1$H NMR (400 MHz, DMSO-$d_6$) δ 13.01 (s, 1H), 12.61 (s, 1H), 8.17-8.05 (m, 2H), 8.01 (d, J=1.0 Hz, 1H), 7.69-7.58 (m, 4H), 7.57-7.45 (m, 2H), 7.31-7.23 (m, 1H), 7.08 (d, J=1.1 Hz, 1H), 3.73 (dt, J=11.2, 3.1 Hz, 2H), 3.20-2.92 (m, 3H), 1.66 (h, J=4.2 Hz, 4H). LCMS m/z 456.0 [M+H]$^+$.

Preparation of 4-[5-(4-fluorophenyl)-6-tetrahydropyran-4-yl-1H-pyrrolo[2,3-f]indazol-7-yl]benzoic Acid (33) from S4

Step 1. Synthesis of ethyl 4-[1-(2,2-dimethylpropanoyl)-5-(4-fluorophenyl)-6-tetrahydropyran-4-yl-pyrrolo[2,3-f]indazol-7-yl]benzoate (C58)

A mixture of 1-[5-(4-fluorophenyl)-7-iodo-6-tetrahydropyran-4-yl-pyrrolo[2,3-f]indazol-1-yl]-2,2-dimethyl-propan-1-one S4 (1.0 g, 1.83 mmol), (4-ethoxycarbonylphenyl)boronic acid (556.9 mg, 2.87 mmol), and Pd(dppf)Cl$_2$ (76.3 mg, 0.09 mmol) was placed under a nitrogen atmosphere. 1,4-dioxane (8.8 mL) and sodium carbonate (3.2 mL of 2 M, 6.4 mmol) were added and the mixture was heated at 90° C. for 30 min. Purification by silica gel chromatography (0-5% EtOAc in CH$_2$Cl$_2$) gave a light tan solid. Minimal Et$_2$O and heptane were added to the solid, and the white solid precipitate was filtered off. The solid was dissolved in dichloromethane (ca. 25 mL). MP-TMT resin (1.1 g) was added and the mixture stirred for 1 h at room temperature. The resin was filtered off and the filtrate concentrated in vacuo to afford the product as a white solid (681.7 mg, 62%). $^1$H NMR (400 MHz, Chloroform-d) δ 8.45 (s, 1H), 8.21 (d, J=7.8 Hz, 2H), 8.08 (s, 1H), 7.58 (d, J=8.0 Hz, 2H), 7.46 (dd, J=8.0, 4.9 Hz, 2H), 7.35 (t, J=8.2 Hz, 2H), 7.12 (s, 1H), 4.48 (q, J=6.9 Hz, 2H), 3.86 (dd, J=11.3, 4.2 Hz, 2H), 3.23 (t, J=11.7 Hz, 2H), 3.09-2.99 (m, 1H), 1.90-1.77 (m, 2H), 1.64 (d, J=13.2 Hz, 2H), 1.58 (s, 9H), 1.48 (t, J=7.1 Hz, 3H). LCMS m/z 568.5 [M+H]$^+$.

Step 2. Synthesis of 4-[5-(4-fluorophenyl)-6-tetrahydropyran-4-yl-1H-pyrrolo[2,3-f]indazol-7-yl]benzoic Acid (33)

NaOH (6 mL of 1 M, 6.0 mmol) and piperidine (260 μL, 2.629 mmol) were added to a solution of ethyl 4-[1-(2,2-dimethylpropanoyl)-5-(4-fluorophenyl)-6-tetrahydropyran-4-yl-pyrrolo[2,3-f]indazol-7-yl]benzoate C58 (682 mg, 1.20 mmol) in THF (14 mL) and MeOH (7 mL). The mixture was heated at 50° C. for 1 h. The solvent was concentrated, and the residue re-dissolved in minimal water. HCl (6 mL of 1 M, 6.0 mmol) was added and a precipitate formed. The solid was filtered off and washed with excess water to afford the product as an off-white solid. (455.7 mg, 83%). $^1$H NMR (400 MHz, DMSO-$d_6$) δ 13.02 (s, 1H), 12.60 (s, 1H), 8.11 (d, J=7.7 Hz, 2H), 8.00 (s, 1H), 7.63 (t, J=7.3 Hz, 4H), 7.51 (t, J=8.4 Hz, 2H), 7.26 (s, 1H), 7.07 (s, 1H), 3.73 (d, J=11.2 Hz, 2H), 3.15-3.07 (m, 2H), 3.05-2.96 (m, 1H), 1.72-1.61 (m, 4H). LCMS m/z 456.4 [M+H]$^+$.

Alternative Preparation of 4-[5-(4-fluorophenyl)-6-tetrahydropyran-4-yl-1H-pyrrolo[2,3-f]indazol-7-yl]benzoic Acid (33) from S4

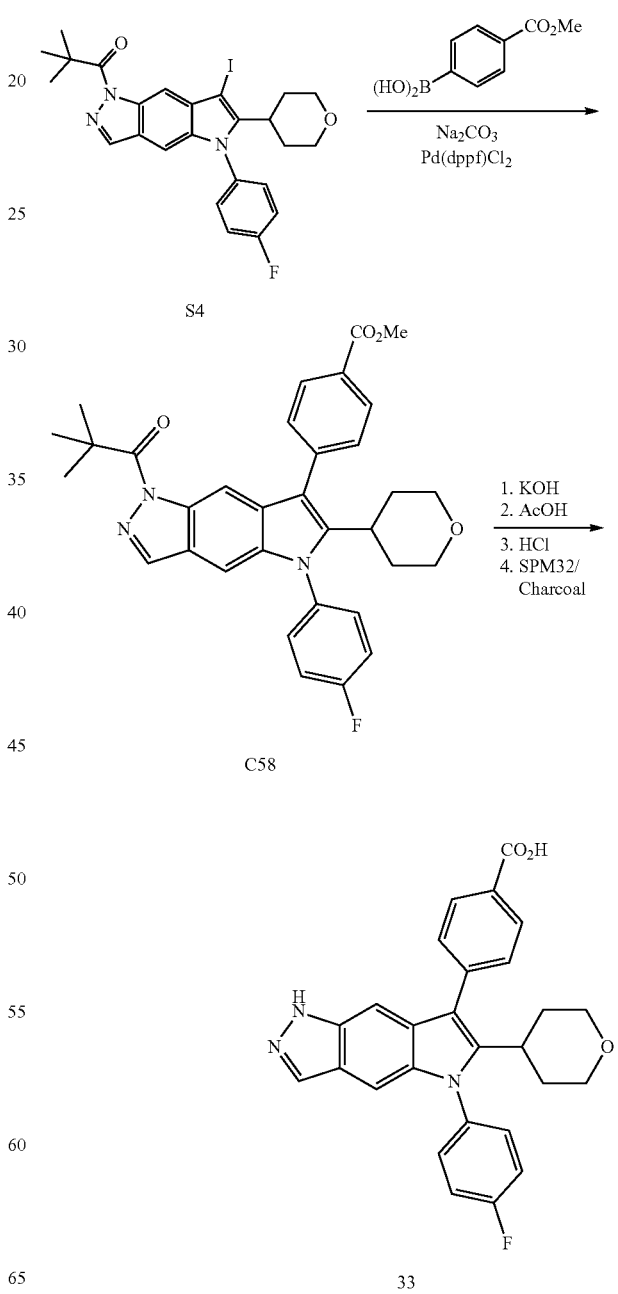

Step 1. Synthesis of ethyl 4-[1-(2,2-dimethylpropanoyl)-5-(4-fluorophenyl)-6-tetrahydropyran-4-yl-pyrrolo[2,3-f]indazol-7-yl]benzoate (C58)

To reactor A under nitrogen was added S4 (5.42 kg), 4-methoxycarbonyl benzene boronic acid (1.786 kg), Na$_2$CO$_3$ (2.986 kg), 1,4-Dioxane (36 L), and potable water (12.5 L). The agitator was started and reactor A was degassed with one vacuum/nitrogen cycle. Nitrogen was bubbled via the bottom of the reaction mixture with stirring at room temperature while venting the nitrogen via the top of the reactor for 1 h. Pd(dppf)Cl$_2$—CH$_2$Cl$_2$ adduct (0.186 kg) was charged as a solid to reactor A. 1,4-Dioxane (1 L) was degassed (nitrogen bubbling for 5 min), and used to rinse the solids off the walls of reactor A. Reactor A was heated to 74° C.-78° C. for 3.5 h. The reaction was then held at 20° C. overnight, and then heated to 38.1° C. Potable water (24 L) was added to reactor A over 18 min, while maintaining the temperature at 36.0° C. to 38.1° C. The slurry was cooled to 20° C. over 2.5 h and filtered (filtration time 25 min). The cake was washed with potable water (2 L×2) and then was deliquored overnight. The wet filter cake solid and CH$_2$Cl$_2$ (25 L) was charged to reactor A. To a container was charged NaCl (1.1 kg) and potable water (9.9 kg). The contents were mixed to dissolve the NaCl. The brine solution was charged to reactor A. The agitator was started and the contents of reactor A were mixed at 22° C. for 15 min. The agitator was stopped and the layers separated for 22 min. The organic layer was removed (no emulsion). The aqueous layer was back extracted by charging CH$_2$Cl$_2$ (5 L) to reactor A. The agitator was started and mixed for 15 min. The agitator was stopped and the phases settled for 15 min. The CH$_2$Cl$_2$ layer was removed and combined with the 1$^{st}$ CH$_2$Cl$_2$ layer. To reactor B was charged charcoal (1 kg) and the solution of product C58 in CH$_2$Cl$_2$. The agitator was started and stirred at room temperature for 23.5 h. A filter was set with Celite® plug and the contents of reactor B were filtered via the Celite® filter. The Celite® cake was washed with CH$_2$Cl$_2$ (6 L). The CH$_2$Cl$_2$ solution was concentrated to 2.5 volumes by vacuum distillation in two separate flasks. Heptanes (7 L) were charged to each flask while rotating, causing the formation of a thick slurry. Both flasks were held at room temperature overnight, and concentrated to 4 volumes. Each flask was cooled to 0-5° C., and rotated for 1 h. The contents of each flask were combined and filtered. The cake was washed with a CH$_2$Cl$_2$: heptanes (1:5) solution. The solids were loaded into trays and dried at 50° C. in a vacuum oven for 3 days, to afford the product C58 as a brown solid (5.3 kg, 88% yield, 8.0 wt % 1,4-dioxane solvate).

Step 2. Synthesis of 4-[5-(4-fluorophenyl)-6-tetrahydropyran-4-yl-1H-pyrrolo[2,3-f]indazol-7-yl]benzoic Acid (33)

Part A. Hydrolysis

To reactor A under nitrogen was added ethyl 4-[1-(2,2-dimethylpropanoyl)-5-(4-fluorophenyl)-6-tetrahydropyran-4-yl-pyrrolo[2,3-f]indazol-7-yl]benzoate (C58) (5.2 kg), ethanol (26 L, 5 vol.), water (14.3 L, 2.7 equiv.), and 45% KOH (6.12 kg, 49.1 mol, 5.2 equiv.). The agitator was started and the reaction mixture was heated to 70-75° C. for 1 h. The reaction was cooled to room temperature and filtered via a plug of Celite®. Reactor A was rinsed with ethanol (5 L, 1 vol.) and used to rinse the Celite®. To reactor A was added acetic acid (2.968 kg, 49.5 mol, 5.2 equiv.) and water 17 L, 3.3 vol.). The acetic acid/water was heated to 46° C. and stirred at 200 rpm. The solution of C58 in ethanol was added over 22 min to the acetic acid/water to give a fine slurry. The temperature was 46.3° C. and the pH was 6.36. Acetic acid (1.176 kg, 19.7 mol, 2 equiv.) was added and the pH was 5.86 measured with a pH probe. The jacket was set with the following profile to hold at 50° C. for 9 h, cool to 20° C., and hold at 20° C. overnight. The slurry was stirred at 20° C. for 6 h before filtering. The slurry was filtered for 24 h. Water was charged to wash the cake (16 L, 3 vol.), which was filtered for an additional day to afford compound 33 as a potassium salt (brown solid, approximately 80% yield).

Part B. Free Acid Formation

To reactor A was added the wet 4-[5-(4-fluorophenyl)-6-tetrahydropyran-4-yl-1H-pyrrolo[2,3-f]indazol-7-yl]benzoic acid (33) potassium salt (3.4 kg). Potable water (44 L) was added to reactor A and the agitator was started. The mixture was stirred slowly at first and then at 133 rpm to give a nice slurry. 1M HCl (7.4 L) (0.1 equivalents excess based on an 80% isolated yield of the potassium salt of compound 33) was charged to reactor A. Stirring was maintained for 3 h at 25° C., and then left overnight. The mixture was filtered on two filters by splitting the batch in half After filtering for 8 h, the cake was washed with potable water (2 L) for each filter. The filtering continued overnight, and the cake was dried with vacuum filtration for 20 h. Compound 33 was dried under vacuum for 2 days at 50° C. and then for 2 days at 30° C. to afford the product (free acid) as a brown solid (3.4 kg, 80% yield).

Part C. Palladium Scavenging

To reactor A under nitrogen was charged compound 33 (3.4 kg, 7.47 mol), MeTHF (34 L), PhosphonicsS SPM32 (0.686 kg) (PhosphonicsS SPM32=3-Mercaptopropyl ethyl sulfide Silica, metal scavenging functionalized silica), and carbon (0.682 kg). The mixture was heated to 68° C. for 17 h with stirring. The mixture was cooled to 43° C. and filtered via a filter lined with a 2 inch silica gel pad. The silica was rinsed with MeTHF (6 L). A 2$^{nd}$ treatment was carried out by charging SPM32 (0.68 kg), carbon (0.681 kg), and the filtrate of compound 33 in MeTHF to a 100 L reactor under nitrogen. MeTHF (4 L) was used to aid in the transfer of the solution of compound 33 in MeTHF back to the reactor. The stirring was initiated and the mixture was heated to 68° C. The mixture was stirred for 23 h, cooled to 50-60° C., and filtered as described above. This process was repeated two additional times. The filtrate was filtered via a 0.2 micron filter into a rotovap flask and concentrated to a wet solid. EtOH (8 L) was added and the vacuum distillation was continued to afford a solid. The solid was dried under vacuum at 50° C. overnight to afford compound 33 (1.95 kg, 8% ethanol solvate).

Part D. Drying Procedure

To a flask containing compound 33 (1.95 kg, 8 wt % ethanol solvate) was added anhydrous CH$_2$Cl$_2$ (10 L). The mixture was distilled under vacuum to viscous slurry. CH$_2$Cl$_2$ (10 L) was added and the mixture was distilled under vacuum again, to give a wet solid. CH$_2$Cl$_2$ (10 L) was added to afford a slurry. The slurry was transferred to reactor A and additional CH$_2$Cl$_2$ (10 L) was used to transfer the residual contents of the flask to reactor A. The agitator was started, and the slurry was heated to 37° C., and held for 2 h at 35-37° C. The slurry was then cooled to 18° C. over 30 min, and held at 18° C. for 30 min. The slurry was filtered and washed with CH$_2$Cl$_2$ (2 L×2) at room temperature over 2 h. The filtered solid material was loaded into trays and dried in a vacuum oven at 70° C. overnight. The solids were broke apart into a fine powder, and dried for an additional 4 h to afford compound 33 as a beige solid (1.36 kg, 72% yield, corrected for EtOH solvate, and 0.4% water).

Alternative Preparation of 4-[5-(4-fluorophenyl)-6-tetrahydropyran-4-yl-1H-pyrrolo[2,3-f]indazol-7-yl]benzoic Acid (33)

Step 1. Synthesis of 5-bromo-6-((tetrahydro-2H-pyran-4-yl)ethynyl)-1H-indazole

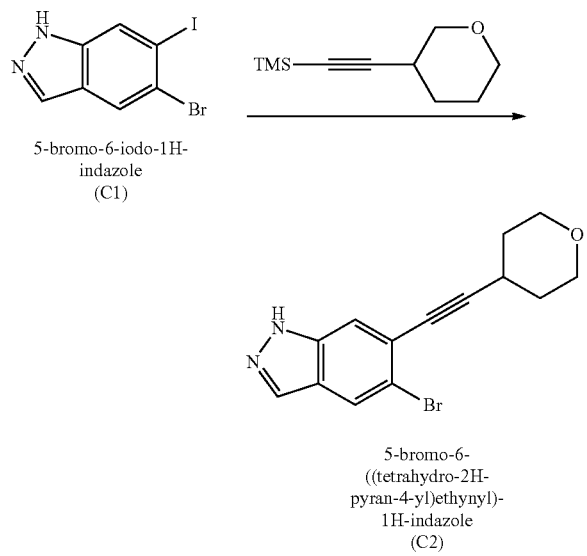

Dispense 5-bromo-6-iodo-1H-indazole (C1) (45.0 g, 139.35 mmol, 1 equiv) in ethanol (270 mL, 6 vol). Charge trimethyl((tetrahydro-2H-pyran-4-yl)ethynyl)silane (27.95 g, 153.28 mmol, 1.1 equiv) and potassium hydroxide 40% w/v solution (41.05 mL, 292.63 mmol, 2.1 equiv).

Evacuate and sparge the reactor with nitrogen multiple times. Add palladium-bis(triphenylphosphine) dichloride (0.978 g, 1.39 mmol, 0.01 equiv) and copper iodide (1.34 g, 6.97 mmol, 0.05 equiv) to the reaction. Evacuate and sparge the reactor with nitrogen multiple times. Heat the reaction to 75° C. Upon reaction completion, cool the reaction and charge DCM (270 ml, 6 vol) followed by an aqueous ammonium chloride solution [9.2 wt %] (270 mL, 6 vol). Stop agitation and separate the layers. Wash the organic layer with an aqueous ammonium chloride [9.2 wt %] solution (270 mL, 6 vol). Charge hydrogen chloride [0.125M] (60 mL, 0.054 equiv) to reactor containing the organic layer to obtain a pH of 5-6 and stir for NLT 30 minutes. Stop agitation and separate layers. Wash the organic layer with an aqueous NaCl solution [8.7 wt %] (270 ml, 6 vol). Distill the organic layer, charge DCM (270 mL, 6 vol) and continue the distillation, repeat twice. Heat the resulting slurry to reflux and add cyclohexane [90 ml, 2 vol]. Cool the reaction to 20° C. over 5 hours. Filter the slurry and rinse the reactor with a 1:1 mixture of DCM/cyclohexane [1 vol]. Dry the wet cake in a vacuum oven at 45° C. with nitrogen bleed. The product, 5-bromo-6-((tetrahydro-2H-pyran-4-yl)ethynyl)-1H-indazole (C2) is isolated in 80% yield.

Examples of alternative reagents and solvents that can be used in Step 1 as described above are as follows:

Solvents: alcoholic solvents like 1-butanol, isopropyl alcohol (IPA), THF/alcohol mixtures, MeTHF/alcohols;

Base: NaOH, $K_2CO_3$, $Na_2CO_3$, $Cs_2CO_3$ NaOtBu, KOtBu;
Catalysts: $Pd(PPh_3)_4$;
Reaction without palladium using CuI or $CuI/PPh_3$ with KOH as base;
Reaction in DMF/with DBU as base with cat $H_2O$.

Step 2. Synthesis of 5-(4-fluorophenyl)-6-(tetrahydro-2H-pyran-4-yl)-1,5-dihydropyrrolo[2,3-f]indazole (C13)

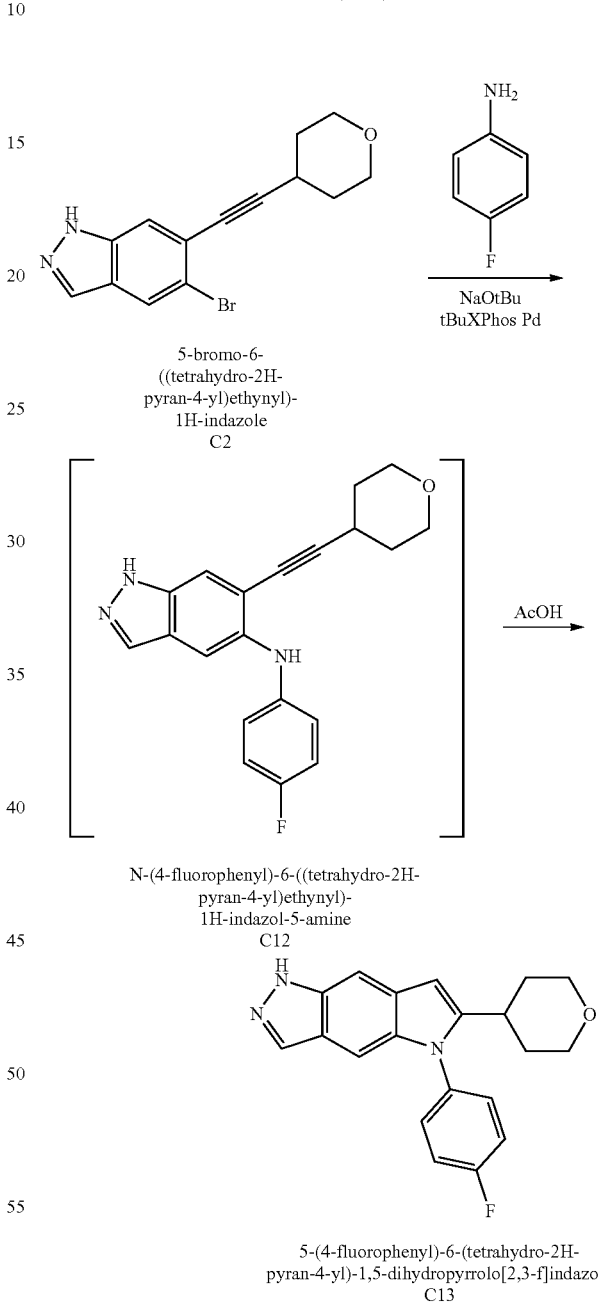

Add sodium tert-butoxide, 97% (99.2 g, 1032.2 mmol, 2.1 equiv) to reactor containing ethanol (900 mL, 6 vol). Degas and sparge solution with nitrogen multiple times. Add 5-bromo-6-((tetrahydro-2H-pyran-4-yl)ethynyl)-1H-indazole (C2) (150 g, 193.99 mmol, 1 equiv) and 4-fluoroaniline (60.08 g, 52.22 mL, 540.67 mmol, 1.1 equiv). Apply vacuum and nitrogen purge cycle 3 times Add chloro(2-di-t-butylphosphino-2',4',6'-tri-i-propyl-1,1'-biphenyl)[2-(2-aminoethyl)phenyl] palladium(II) (11.796 g, 17.203 mmol, 0.035 equiv.) and degas and sparge with nitrogen NLT 3 times. Heat the reactor to 65° C. Upon reaction completion, add acetic acid (140.2 g, 133.65 mL, 2334.7 mmol, 4.75 equiv) at 60° C. and continue to stir for NLT 3 hours. Upon reaction completion, cool the reactor to 20° C. and add NaOH [0.5M] (900 mL, 6 vol) and DCM (600 ml, 4 vol) to reactor. Stop agitation and separate the layers. Back extract the aqueous layer with DCM. Combine the organic layers and distill the organic solution down to 3 volumes. Charge DCM (900 mL, 6 vol) to reactor and continue distillation; repeat the process two more times. Heat the reactor to 38° C. and add n-heptane (450 mL, 3 vol) over 2 hours. Cool the reactor down to 20° C. over 3 hours. Filter the slurry and rinse the wet cake a 1:1 ratio of DCM/n-heptane (1 volume). Dry the wet cake to vacuum oven set to 45° C. The product, 5-(4-fluorophenyl)-6-(tetrahydro-2H-pyran-4-yl)-1,5-dihydropyrrolo[2,3-f]indazole (C13), is isolated in 85% yield.

Examples of alternative reagents and solvents that can be used in Step 2 as described above are as follows:
  Solvents: alcoholic solvents like 1-butanol, tert-butanol, isopropyl alcohol (IPA), tAmOH, THF, MeTHF, CPMe, Toluene, DMF, ACN, DMA, diglyme;
  Base: NaOH, K₃PO₄, K₂CO₃, NaOtBu, KOtBu; NaOEt;
  Catalysts in general all generations of catalysts should work: PdtBuXPhos G1-4 (tested); (PdOAc)₂ Pd(cinnamyl)Cl₂ with ligands: BrettPhos, SPHos, XPHos, XantPhos, dppf, JosiPhos; cataCXium® A (Note: cyclization of N-(4-fluorophenyl)-6-((tetrahydro-2H-pyran-4-yl)ethynyl)-1H-indazol-5-amine to 5-(4-fluorophenyl)-6-(tetrahydro-2H-pyran-4-yl)-1,5-dihydropyrrolo[2,3-f]indazole;
  Reagents: Acids, Lewis acids like copper salts and heat.

Step 3. Synthesis of 1-(5-(4-fluorophenyl)-6-(tetrahydro-2H-pyran-4-yl)pyrrolo[2,3-f]indazol-1(5H)-yl)-2,2-dimethylpropan-1-one

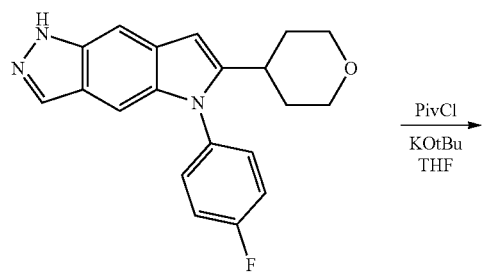

5-(4-fluorophenyl)-6-(tetrahydro-2H-pyran-4-yl)-1,5-dihydropyrrolo[2,3-f]indazole
C13

PivCl
KOtBu
THF

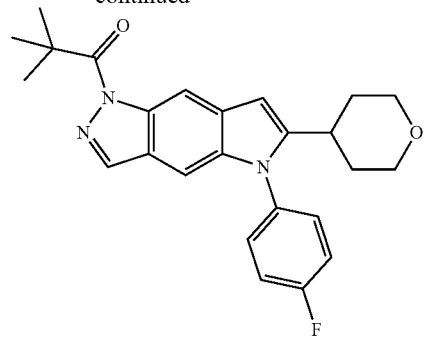

1-(5-(4-fluorophenyl)-6-(tetrahydro-2H-pyran-4-yl)pyrrolo[2,3-f]indazol-1(5H)-yl)-2,2-dimethylpropan-1-one
C14

Dissolve 5-(4-fluorophenyl)-6-(tetrahydro-2H-pyran-4-yl)-1,5-dihydropyrrolo[2,3-f]indazole (C13) (367.5 g, 1.09 mol, 1 equiv) in THF (5.15 L, 14 vol). Cool the reactor to ~6° C. and add KOtBu [2M in THF] (0.71 L, 1.3 equiv). Stir the solution for at NLT 20 minutes. Add trimethylacetyl chloride (0.193 L, 1.43 equiv) to reactor at −6-0° C. and stir the content for 1 hour at 0° C. Upon reaction completion, heat the reactor to 18-20° C. over 1 hour. Add an aqueous solution of NaHCO₃ solution (101 g, 1.1 equiv 1.5 L, 4 vol of water) and MtBE (1.5 L, 4 vol) to reactor. Stir the content for NLT 30 minutes at 20° C. Stop agitation and separate the layers. Prepare an aqueous NaCl solution by mixing NaCl (301 g, 4.7 equiv) in purified water (1.5 L, 4 vol). Add the aqueous NaCl solution to the organic layer and stir for NLT 30 minutes. Stop agitation and separate the layers. Add MP-TMT resin (73.5 g, 20 wt %) to reactor, heat the reactor to 50° C. and stir for NLT 12 hours. Filter the reactor content over a bed of celite and wash the celite with MtBE (0.7 L, 2 vol). Distill the organic filtrate down to 2-3 volumes. Add methanol (0.91 L, 2.5 vol) to reactor and heat the reactor to 60° C. Stir for 1 hour and add methanol (0.184 L, 0.5 vol) to the reactor. Cool the contents to 40° C. Stir the contents for 1 hour at 40° C. Add methanol (1.64 L, 4.5 vol) over 4 hours. Cool the contents to 10° C. over at least 4 hours and age the contents for at least 18 hours at 10° C. Filter the batch and rinse the wet cake with a mixture of methanol (1.38 L, 3.75 vol) and THF (0.46 L, 1.25 vol). Dry the wet cake at 45° C. under vacuum. The product, 1-(5-(4-fluorophenyl)-6-(tetrahydro-2H-pyran-4-yl)pyrrolo[2,3-f]indazol-1(5H)-yl)-2,2-dimethylpropan-1-one (C14), is isolated in 80% yield.

Examples of alternative reagents and solvents that can be used in Step 3 as described above are as follows:
  Solvents: MeTHF, DCM;
  Base: Li/Na/K OtBu, Na/K/LiOtAm.

Step 4. Synthesis of 1-(5-(4-fluorophenyl)-6-(tetrahydro-2H-pyran-4-yl)pyrrolo[2,3-f]indazol-1(5H)-yl)-2,2-dimethylpropan-1-one

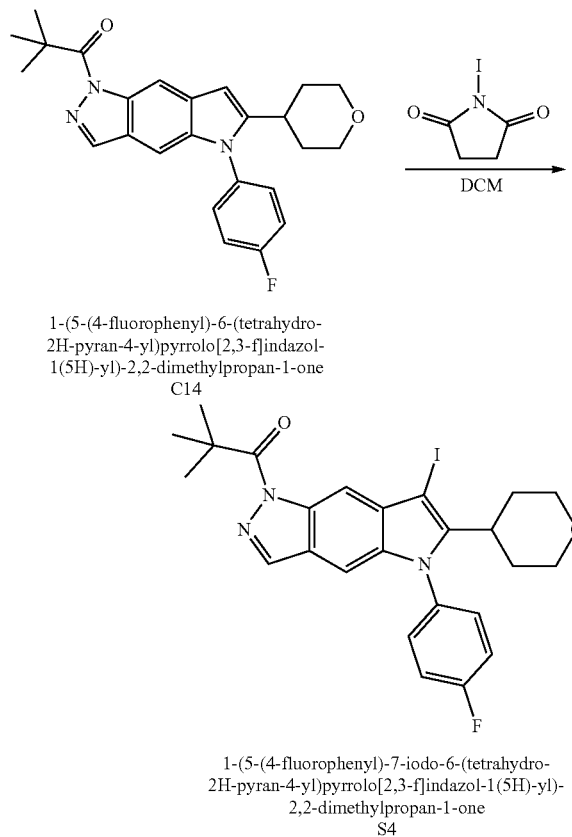

1-(5-(4-fluorophenyl)-6-(tetrahydro-2H-pyran-4-yl)pyrrolo[2,3-f]indazol-1(5H)-yl)-2,2-dimethylpropan-1-one
C14

1-(5-(4-fluorophenyl)-7-iodo-6-(tetrahydro-2H-pyran-4-yl)pyrrolo[2,3-f]indazol-1(5H)-yl)-2,2-dimethylpropan-1-one
S4

Dissolve 1-(5-(4-fluorophenyl)-6-(tetrahydro-2H-pyran-4-yl)pyrrolo[2,3-f]indazol-1(5H)-yl)-2,2-dimethylpropan-1-one (C14) (30.76 g, 73.3 mmol, 1 equiv, limiting reagent) in methylene chloride (307.6 mL, 10 vol). Cool the reactor down to −5° C. and add N-iodosuccinimide (18.23 g, 76.99 mmol, 1.05 equiv.) at −5.0-0° C. Stir reaction at −5° C. for NLT 30 minutes. Upon reaction completion, add an aqueous sodium thiosulfate solution (Na$_2$S$_2$O$_3$·5H$_2$O 9 g, 0.037 mmol, 0.5 equiv in purified water (0.1 L, 2.4 vol) to the reaction at 0° C. Stir the content for NLT 30 minutes at 0° C. followed by warm up to 20° C. Stop agitation and separate layers. Add an aqueous NaHCO$_3$ solution (NaHCO$_3$ 8.7 g, 0.1 mmol, 1.3 equiv dissolved in purified water (0.12 L, 3.7 vol) to the organic layer. Stir for NLT 30 minutes, stop agitation and separate layers. Add an aqueous NaCl solution (NaCl 20 g, 0.34 mmol, 4.7 equiv) in purified water (133 mL, 4.3 vol). Stir for NLT 30 minutes, stop agitation and separate layers. Distill the organic layer down to 2-3 volumes. Add THF (0.15 L, 5 vol) to reactor and distill down to 2-3 volumes, repeat 2-3 times. Add THF (up to 2 volumes) to the reactor to obtain a total of 4 volumes. Heat to slurry to internal temperature of 56-58° C. Add MeOH (0.061 L, 2 vol) at 56° C. over 1 hour to reactor. Cool the reactor content down to 52° C. and stir for NLT 30 minutes. Add MeOH (0.25 L, 8 vol) over 3 hours at 52° C. to reactor. Cool the slurry down to 20° C. at a 5° C./h rate. Stir the reactor content at 20° C. for NLT 30 minutes. Filter the slurry and rinse the wet cake with MeOH (0.03 L, 1 vol)

Dry the wet cake under vacuum at 60° C. The product, 1-(5-(4-fluorophenyl)-7-iodo-6-(tetrahydro-2H-pyran-4-yl)pyrrolo[2,3-f]indazol-1(5H)-yl)-2,2-dimethylpropan-1-one (S4), is isolated in 90% yield.

Examples of alternative solvents that can be used in Step 4 as described above are THF, MeTHF, CAN, EtOAc, DMF, dichloroethane (DCM).

Step 5. Synthesis of methyl 4-(5-(4-fluorophenyl)-1-pivaloyl-6-(tetrahydro-2H-pyran-4-yl)-1,5-dihydropyrrolo[2,3-f]indazol-7-yl)benzoate

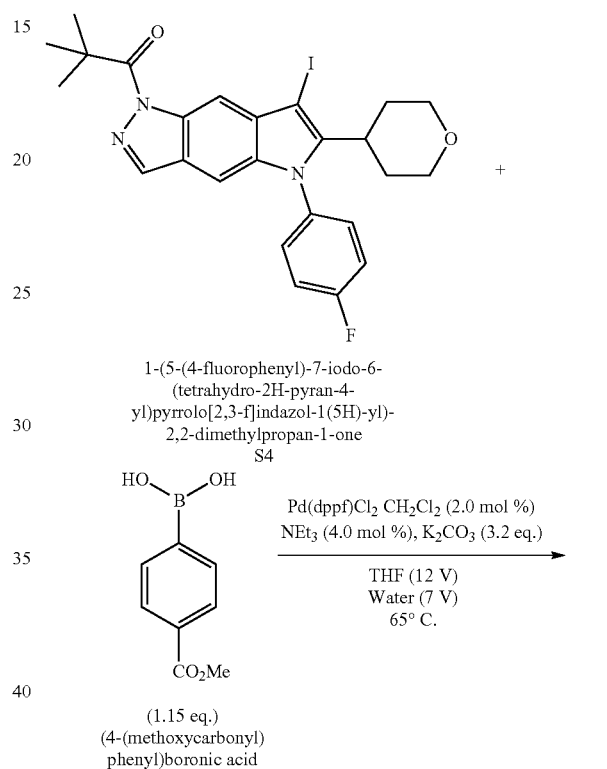

1-(5-(4-fluorophenyl)-7-iodo-6-(tetrahydro-2H-pyran-4-yl)pyrrolo[2,3-f]indazol-1(5H)-yl)-2,2-dimethylpropan-1-one
S4

(1.15 eq.)
(4-(methoxycarbonyl)phenyl)boronic acid

Pd(dppf)Cl$_2$ CH$_2$Cl$_2$ (2.0 mol %)
NEt$_3$ (4.0 mol %), K$_2$CO$_3$ (3.2 eq.)
THF (12 V)
Water (7 V)
65° C.

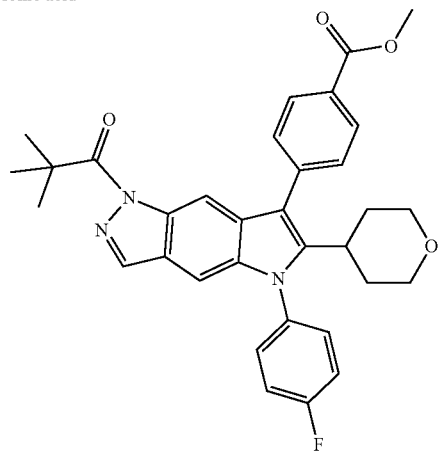

methyl 4-(5-(4-fluorophenyl)-1-pivaloyl-6-(tetrahydro-2H-pyran-4-yl)-1,5-dihydropyrrolo[2,3-f]indazol-7-yl)benzoate
C58

Add 1-(5-(4-fluorophenyl)-7-iodo-6-(tetrahydro-2H-pyran-4-yl)pyrrolo[2,3-f]indazol-1(5H)-yl)-2,2-dimethyl-propan-1-one (S4) (10.0 g, 18.3 mmol, 1.0 eq.), 4-(methoxy-carbonyl)-phenyl)boronic acid (3.80 g, 21.1 mmol, 1.15 eq.), and tetrahydrofuran (100 mL, 10 vol.) to a reactor and begin agitation. Prepare a solution of potassium carbonate in water by adding potassium carbonate (8.11 g, 58.7 mmol, 3.2 eq.) to water (70 mL, 7 vol.) at 25° C. in a separate vessel. Deoxygenate the mixture using three vacuum-nitrogen cycles. Add the aqueous potassium carbonate solution to the reactor. Deoxygenate the resulting biphasic mixture with three successive vacuum-nitrogen cycles. In a separate vessel, add triethylamine (74 mg, 0.73 mmol, 0.04 eq.) to a mixture of Pd(dppf)Cl$_2$ (0.30 g, 0.37 mmol, 0.020 eq.) and tetrahydrofuran (10 mL, 1 vol.). Deoxygenate using three vacuum-nitrogen cycles and the agitate the mixture for ~1-2 h. Add the catalyst slurry to the reactor, rinsing forward with additional tetrahydrofuran (10 mL, 1 vol.) [Total tetrahydrofuran (120 mL, 12 vol) in reaction mixture], and perform an additional three vacuum-nitrogen cycles. Heat the reaction to to 65° C. Upon reaction completion, cool the reactor contents to 55° C. and separate the layers. Add tetrahydrofuran (180 mL, 18 vol.) and Celite (100 wt %, 10.00 g) to the reactor and agitate at 55° C. for 1 hour. Filter the reaction mixture and rinse the cake with tetrahydrofuran (20 mL, 2 vol.). Charge SEM26 (2 g; 20 wt %) to the reactor and heat the mixture to 30-35° C. for NLT 18 hours. Filter the reaction mixture. Distill the filtrate down to 5 volumes. Add THF (150 mL, 15 vol.) and distill down to ~7-8 volumes. Heat the reactor contents to 60-65° C. Cool reactor contents to 50° C. Add ethanol (140 mL, 14 vol.) over 2-3 hours at 50° C. and continue to stir for 30 min. Cool the mixture to 10° C. at a rate of 5° C./h. Stir the slurry at 10° C. for NLT 1 h and filter the mixture. Rinse the wet cake with ethanol (20 ml, 2×1 vol). Dry the solids under vacuum at 65° C. for NLT 12 h. The product, methyl 4-(5-(4-fluorophenyl)-1-pivaloyl-6-(tetrahydro-2H-pyran-4-yl)-1,5-dihydropyrrolo[2,3-f]indazol-7-yl)benzoate (C58), is isolated in 80% yield.

Examples of alternative reagents and solvents that can be used in Step 5 as described above are as follows:
Solvents: Dioxane, MeTHF, IPA, toluene, ACN, DMSO, EtOH;
Catalyst Monodentate ligands: PCy$_3$, P(tBu)$_3$, DavePhos, SPhos Pd(PPh$_3$)$_2$Cl$_2$, Xphos, CataCXium; Pd(AmPhos)Cl$_2$, RuPhos;
Bidentate ligands: Pd(dippf)Cl$_2$, Pd(dtbpf)Cl$_2$, Pd(DPEPhos)Cl$_2$, Pd(dppf)Cl$_2$·CH$_2$Cl$_2$, Pd(Xantphos)Cl$_2$, Pd(dppb)Cl$_2$;
Base: K$_2$CO$_3$, Na$_2$CO$_3$, K$_3$PO$_4$.

Step 6 Optional Recrystallization Procedure to Purge Residual Aryl Dimer

Charge the methyl 4-(5-(4-fluorophenyl)-1-pivaloyl-6-(tetrahydro-2H-pyran-4-yl)-1,5-dihydropyrrolo[2,3-f]indazol-7-yl)benzoate to a reactor. Add THF (9 vol.) and heat the reactor contents to 60° C. Cool reactor contents to 50° C. Add ethanol (18 vol.) over 2-3 hours. Stir the resulting thin slurry at 50° C. for 30 min. Cool the slurry to an internal temp. of 10° C. at a rate of 5° C./h. Stir the slurry at 10° C. for NLT 1 h Filter the mixture
Rinse the wet cake with ethanol (2×1-2 V) 1 (2×1-2 V) Dry the solids under vacuum at 65° C. for NLT 12 h. The product, methyl 4-(5-(4-fluorophenyl)-1-pivaloyl-6-(tetrahydro-2H-pyran-4-yl)-1,5-dihydropyrrolo[2,3-f]indazol-7-yl)benzoate, is isolated in 85% yield

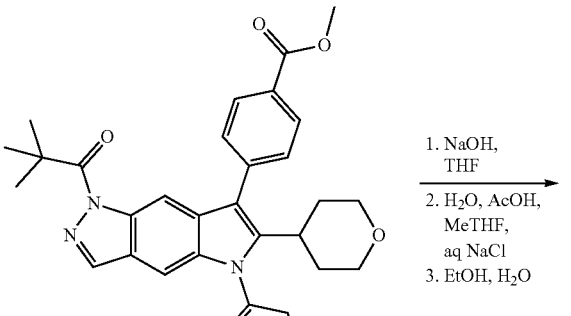

methyl 4-(5-(4-fluorophenyl)-1-pivaloyl-6-(tetrahydro-2H-pyran-4-yl)-1,5-dihydropyrrolo[2,3-f]indazol-7-yl)benzoate
C58

1. NaOH, THF
2. H$_2$O, AcOH, MeTHF, aq NaCl
3. EtOH, H$_2$O

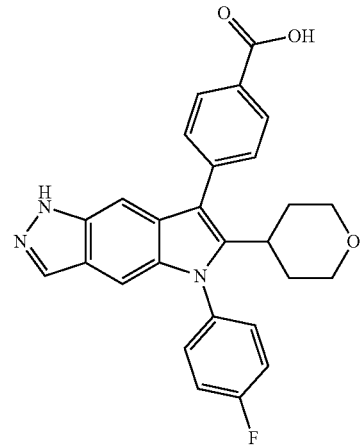

4-(5-(4-fluorophenyl)-6-(tetrahydro-2H-pyran-4-yl)-1,5-dihydropyrrolo[2,3-f]indazol-7-yl)benzoic acid
Compound 33

Add methyl 4-(5-(4-fluorophenyl)-1-pivaloyl-6-(tetrahydro-2H-pyran-4-yl)-1,5-dihydropyrrolo[2,3-f]indazol-7-yl)benzoate (C58) (25.1 g, 45.337 mmol, 1 equiv, limiting reagent) and THF (326.3 mL, 13 vol) to reactor. Add sodium hydroxide [2N] (5.44 g, 68.0 mL, 136.01 mmol, 3 equiv) to reactor and heat to 58° C. Upon reaction completion, cool reactor to 20° C. Add water (75.3 mL, 3 vol), acetic acid (10.89 g, 10.38 mL, 181.35 mmol, 4 equiv.) and 2-MeTHF (251 mL, 10 vols) to reactor and stir for NLT 30 minutes. Stop agitation and separate layers. Add water (75.3 mL, 3 vol) to organic layer and extract. Separate layers and add an aqueous 6.5 wt % sodium chloride solution (NaCl 8.2 g, 0.14 mmol, 3.1 equiv) in water (0.120 L, 4.7 vol) to the organic layer. Stir for NLT 30 minutes, then stop agitation and separate layers. Distill the organic layer down to 2-3 volumes. Add EtOH (0.176 mL, 7 vol) to reactor and continue distillation. Add EtOH (0.150 L, 6 vol) and water (25.1 mL, 1 vol) and distill the slurry down to 2-3 volumes. Add EtOH (0.150 L, 6 vol) and water (25.1 mL, 1 vol) to reactor and continue distillation down to 3 volumes. Add EtOH (0.150 L, 6 vol) and water (25.1 mL, 1 vol) to reactor and stir for NLT 30 minutes at 40° C. Cool the reactor down to 20-25° C. at a 5° C./h rate. Stir the reactor content for at least 30 minutes at 20° C. Filter the slurry and rinse the wet cake with a EtOH/H$_2$O 1:1 mixture (50 ml, 2 vol). Transfer the wet cake to vacuum oven set to 66° C. and dry the material for at NLT 12 hours. The product, 4-(5-(4-fluorophenyl)-6-(tetrahydro-2H-pyran-4-yl)-1,5-dihydropyrrolo[2,3-f]indazol-7-yl)benzoic acid (Compound 33), is isolated in 90% yield.

Examples of alternative reagents and solvents that can be used in Step 5 as described above are as follows:
Solvents: MeTHF, EtOH, MeOH, IPA;
Base: LiOH, NaOH, KOH
Work up: acetic acid, HCL.

Compound 34

(2S,3S,4S,5R)-6-[4-[5-(4-fluorophenyl)-6-tetrahydropyran-4-yl-1H-pyrrolo[2,3-f]indazol-7-yl]benzoyl]oxy-3,4,5-trihydroxy-tetrahydropyran-2-carboxylic Acid (34)

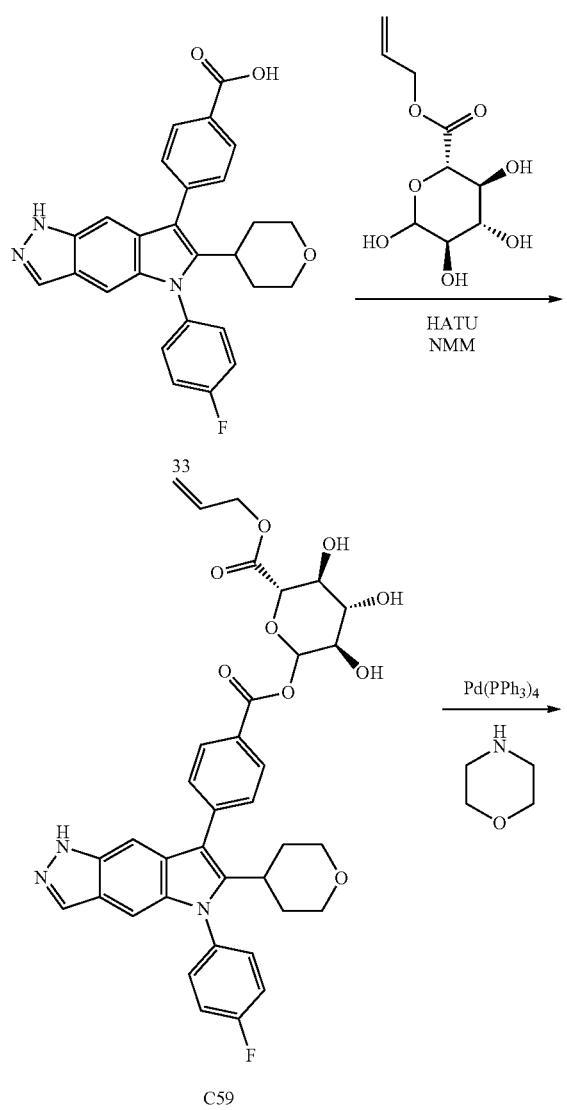

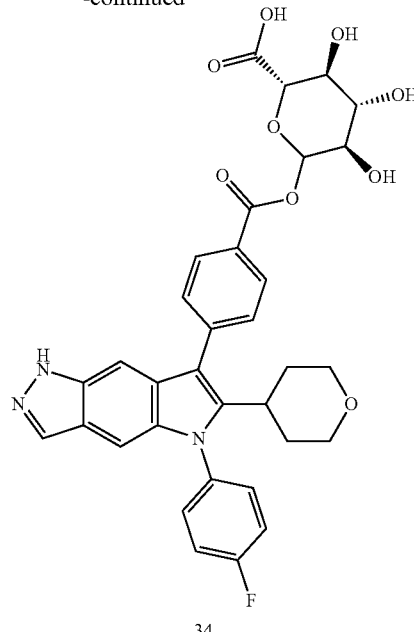

Step 1. Synthesis of Allyl (2S,3S,4S,5R)-6-[4-[5-(4-fluorophenyl)-6-tetrahydropyran-4-yl-1H-pyrrolo[2,3-f]indazol-7-yl]benzoyl]oxy-3,4,5-trihydroxy-tetrahydropyran-2-carboxylate (C59)

MeCN (12 mL) and NMM (210 µL, 1.91 mmol) were added to a mixture of 4-[5-(4-fluorophenyl)-6-tetrahydropyran-4-yl-1H-pyrrolo[2,3-f]indazol-7-yl]benzoic acid 33 (449 mg, 0.96 mmol), allyl (2S,3S,4S,5R)-3,4,5,6-tetrahydroxytetrahydropyran-2-carboxylate (224 mg, 0.96 mmol), and HATU (370 mg, 0.97 mmol). The reaction was allowed to stir overnight at room temperature. The mixture was diluted in CH$_2$Cl$_2$ and washed with 50% saturated sodium bicarbonate. The organic phase was passed through a phase phase separator and concentrated in vacuo. Silica gel chromatography (Gradient: 0-10% methanol in CH$_2$Cl$_2$) afforded the product which was used in the subsequent step without further purification (228 mg, 35%). LCMS m/z 672.5 [M+H]$^+$.

Step 2. Synthesis of (2S,3S,4S,5R)-6-[4-[5-(4-fluorophenyl)-6-tetrahydropyran-4-yl-1H-pyrrolo[2,3-f]indazol-7-yl]benzoyl]oxy-3,4,5-trihydroxy-tetrahydropyran-2-carboxylic Acid (34)

To a solution of allyl (2S,3S,4S,5R)-6-[4-[5-(4-fluorophenyl)-6-tetrahydropyran-4-yl-1H-pyrrolo[2,3-f]indazol-7-yl]benzoyl]oxy-3,4,5-trihydroxy-tetrahydropyran-2-carboxylate (54 mg, 0.08 mmol) in CH$_2$Cl$_2$ (7.2 mL) was added morpholine (14 µL, 0.16 mmol). The solution was purged with nitrogen, then Pd(PPh$_3$)$_4$ (3 mg, 0.003 mmol) was added. The mixture was allowed to stir for 30 min. MP-TMT resin was added and the mixture stirred for an additional 4 h. The mixture was filtered and concentrated. Purification by reversed phase chromatography (Gradient: 0-100% MeCN in water with a 0.2% formic acid modifier) afforded the desired product (20.3 mg, 42%). $^1$H NMR (300 MHz, DMSO-d$_6$) δ 12.55 (s, 1H), 8.16-8.10 (m, 2H), 7.94 (d, J=1.0 Hz, 1H), 7.71-7.61 (m, 2H), 7.60-7.52 (m, 2H), 7.50-7.39

(m, 2H), 7.22 (t, J=1.2 Hz, 1H), 7.01 (d, J=1.1 Hz, 1H), 5.65-5.57 (m, 1H), 5.50 (d, J=4.3 Hz, 1H), 5.31-5.19 (m, 1H), 3.77 (d, J=8.7 Hz, 1H), 3.66 (d, J=10.9 Hz, 2H), 3.40-3.32 (m, 4H), 3.11-2.89 (m, 3H), 1.65-1.48 (m, 4H). LCMS m/z 632.5 [M+H]$^+$.

Compound 35

4-[5-(4-fluorophenyl)-6-tetrahydropyran-4-yl-1H-pyrrolo[2,3-f]indazol-7-yl]-3-methyl-benzoic Acid (35)

12.52 (s, 1H), 8.00 (s, 2H), 7.89 (d, J=7.7 Hz, 1H), 7.67-7.58 (m, 2H), 7.50 (t, J=8.5 Hz, 2H), 7.45 (d, J=7.9 Hz, 1H), 7.16 (s, 1H), 6.83 (s, 1H), 3.74-3.61 (m, 2H), 3.10-2.97 (m, 2H), 2.88-2.73 (m, 1H), 2.18 (s, 3H), 1.76-1.51 (m, 3H), 1.44-1.31 (m, 1H). LCMS m/z 470.44 [M+H]$^+$.

Compound 36

4-[5-(4-fluorophenyl)-6-tetrahydropyran-4-yl-1H-pyrrolo[2,3-f]indazol-7-yl]benzenesulfonic Acid (36)

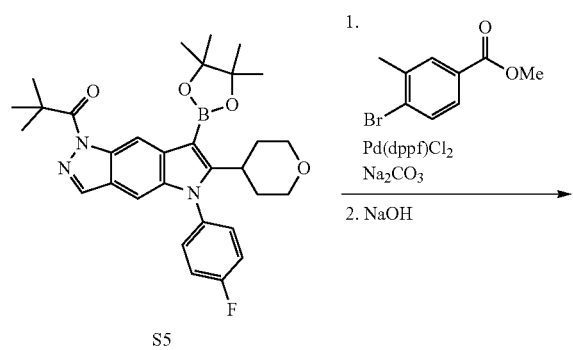

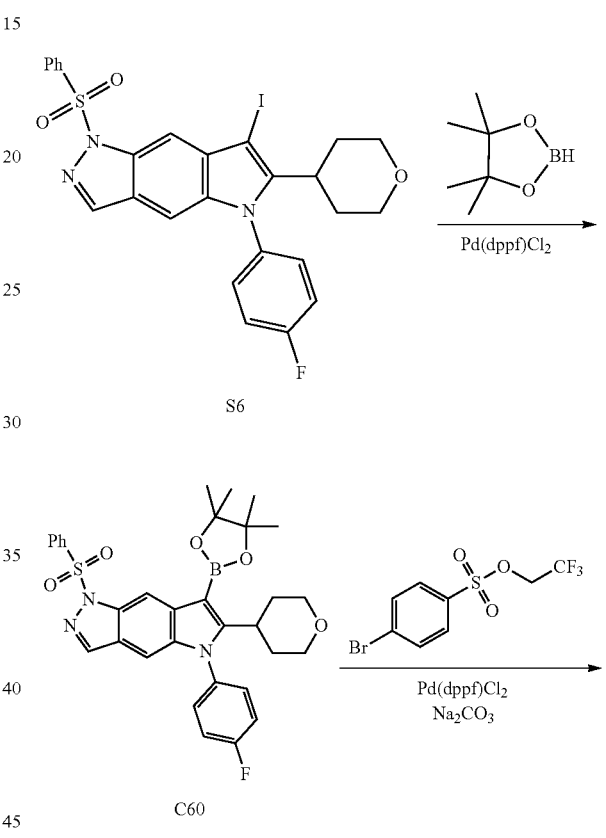

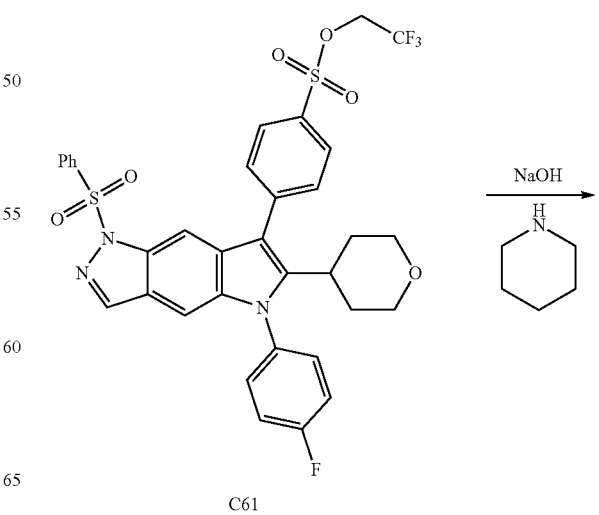

A mixture of 1-[5-(4-fluorophenyl)-6-tetrahydropyran-4-yl-7-(4,4,5,5-tetramethyl-1,3,2-dioxaborolan-2-yl)pyrrolo[2,3-f]indazol-1-yl]-2,2-dimethyl-propan-1-one S5 (257.2 mg, 0.39 mmol), methyl 4-bromo-3-methyl-benzoate (202.3 mg, 0.88 mmol), and Pd(dppf)Cl$_2$ (37.8 mg, 0.05 mmol) was placed under a nitrogen atmosphere (evacuation/nitrogen cycles×3). 1,4-dioxane (1.9 mL) and sodium carbonate (685 µL of 2 M, 1.4 mmol) were added. The mixture was heated at 90° C. for 45 min. Upon cooling, the mixture was diluted with CH$_2$Cl$_2$ (5 mL), filtered through a pad of Celite® and the filtrate was concentrated in vacuo. The residue was dissolved THF (4.2 mL) and MeOH (2.1 mL) and sodium hydroxide (2.3 mL of 1 M, 2.31 mmol) added. The mixture was then heated at 50° C. for 2 h. The solvent was removed under vacuum and re-dissolved in minimal water. HCl (2.3 mL of 1 M, 2.3 mmol) was added and the mixture was concentrated in vacuo. Purification by silica gel chromatography (Gradient: 5-20% EtOAc in CH$_2$Cl$_2$, containing 1% AcOH) afforded the product as a white solid (24.8 mg, 14%). $^1$H NMR (400 MHz, DMSO-d$_6$) δ 12.97 (s, 1H),

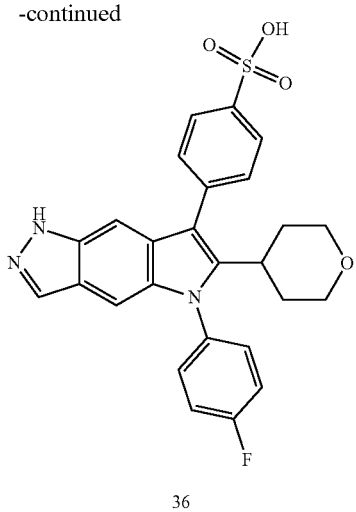

36

Step 1. Synthesis of 1-(benzenesulfonyl)-5-(4-fluorophenyl)-6-tetrahydropyran-4-yl-7-(4,4,5,5-tetramethyl-1,3,2-dioxaborolan-2-yl)pyrrolo[2,3-f]indazole (C60)

A flask containing 1-(benzenesulfonyl)-5-(4-fluorophenyl)-7-iodo-6-tetrahydropyran-4-yl-pyrrolo[2,3-f]indazole S6 (96.7 mg, 0.16 mmol) and Pd(dppf)Cl$_2$ (5.2 mg, 0.007 mmol) was purged with nitrogen. m-Xylene (760 µL) was added and the solution degassed. Et$_3$N (80 µL) followed by 4,4,5,5-tetramethyl-1,3,2-dioxaborolane (36 µL, 0.25 mmol) were added and the mixture was heated at 150° C. for 1 h. The mixture was filtered and concentrated in vacuo. Purification by silica gel chromatography (Gradient: 0-5% EtOAc in CH$_2$Cl$_2$) afforded the product as a light yellow solid, with an 8% impurity from reduced starting material which co-eluted with the product. The product was used in the subsequent step without further purification (67.7 mg, 64%). $^1$H NMR (400 MHz, Chloroform-d) δ 8.93 (s, 1H), 8.13 (s, 1H), 8.00 (d, J=7.9 Hz, 2H), 7.52 (t, J=8.3 Hz, 1H), 7.41 (t, J=7.7 Hz, 2H), 7.01 (s, 1H), 4.02 (dd, J=11.5, 4.1 Hz, 2H), 3.32 (t, J=11.7 Hz, 2H), 3.14-3.03 (m, 1H), 2.49-2.36 (m, 2H), 1.63-1.59 (m, 2H), 1.53 (s, 12H). LCMS m/z 602.4 [M+H]$^+$.

Step 2. Synthesis of 2,2,2-trifluoroethyl 4-[1-(benzenesulfonyl)-5-(4-fluorophenyl)-6-tetrahydropyran-4-yl-pyrrolo[2,3-f]indazol-7-yl]benzenesulfonate (C61)

A solution of 2,2,2-trifluoroethyl 4-bromobenzenesulfonate (24 mg, 0.08 mmol), 1-(benzenesulfonyl)-5-(4-fluorophenyl)-6-tetrahydropyran-4-yl-7-(4,4,5,5-tetramethyl-1,3,2-dioxaborolan-2-yl)pyrrolo[2,3-f]indazole C60 (50 mg, 0.08 mmol), sodium carbonate (112 µL of 2 M, 0.2 mmol) and Pd(dppf)Cl$_2$ (5.9 mg, 0.007 mmol) in 1,4-dioxane (150 µL) was purged with nitrogen, and the reaction was heated at 90° C. for 1.5 h. Upon cooling, water and CH$_2$Cl$_2$ were added and the layers separated using a phase separator. The organic layer was concentrated in vacuo and purified by silica gel chromatography (Gradient: 0-20% EtOAc in dichloromethane) to afford the product (17.5 mg, 26%). LCMS m/z 714.4 [M+H]$^+$.

Step 3. 4-[5-(4-fluorophenyl)-6-tetrahydropyran-4-yl-1H-pyrrolo[2,3-f]indazol-7-yl]benzenesulfonic Acid (36)

Piperidine (4.1 mg, 0.05 mmol) and NaOH (61 µL of 2 M, 0.12 mmol) were added to a solution of 2,2,2-trifluoroethyl 4-[1-(benzenesulfonyl)-5-(4-fluorophenyl)-6-tetrahydropyran-4-yl-pyrrolo[2,3-f]indazol-7-yl]benzenesulfonate C61 (17.5 mg, 0.02 mmol) in MeOH (87.5 µL) and THF (175 µL). The reaction was heated to 55° C. for 1 h, then stirred overnight at room temperature. The mixture was concentrated in vacuo, water (1 mL) was added and the mixture acidified to pH 3 using 1 M HCl. The mixture was then concentrated in vacuo and purified by reversed phase chromatography (C18 column. Gradient: 0-100% MeCN in water with 0.1% formic acid) to afford the product (9.4 mg, 73%). $^1$H NMR (300 MHz, Methanol-d$_4$) δ 8.50 (s, 1H), 8.03-7.96 (m, 2H), 7.63-7.49 (m, 4H), 7.41 (t, J=8.5 Hz, 2H), 7.29 (s, 1H), 7.11 (d, J=1.1 Hz, 1H), 3.86-3.75 (m, 2H), 3.25-3.16 (m, 2H), 3.11-3.04 (m, 1H), 1.88-1.65 (m, 4H). LCMS m/z 492.4 [M+H]$^+$.

Compounds 37-44

Compounds 37-44 were prepared from S6 in two steps according to the method described for compound 33 from S6 (as indicated by Method B). In some examples, alternative Suzuki coupling conditions are used, as indicated by method A. Purification of the final product was performed using HPLC or normal pressure reverse phase chromatography.

Coupling Conditions for Suzuki Coupling Step in Compounds 37-44:

Method A: Step 1. boronic acid or ester, XPhos Pd G3, K$_3$PO$_4$, 1,4-dioxane-water, 85° C., 1 h. Step 2. NaOH, THF-MeOH.

Method B: Step 1. boronic acid or ester, Pd(dppf)Cl$_2$, 2M Na$_2$CO$_3$, 1,4-dioxane, 90° C., 1 h. Step 2. NaOH, THF-MeOH

TABLE 5

Method of preparation, structure, physicochemical data for compounds 37-44

| Compound | Method/Product | Boronic acid or ester | ¹H NMR; LCMS m/z [M + H]⁺ |
|---|---|---|---|
| 37 | 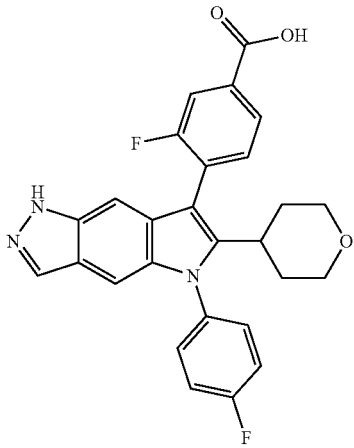<br>Method A from S6 | 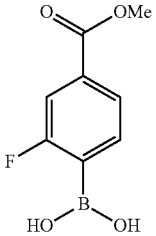 [SMILES: COC(=O)c1ccc(B(O)O)c(F)c1] | NMR (400 MHz, Methanol-d₄) δ 8.00 (d, J = 9.9 Hz, 2H), 7.90 (d, J = 10.0 Hz, 1H), 7.64 (t, J = 7.5 Hz, 1H), 7.60-7.50 (m, 2H), 7.41 (t, J = 8.5 Hz, 2H), 7.16 (s, 2H), 3.85-3.75 (m, 2H), 3.21 (t, J = 11.4 Hz, 2H), 3.04-2.92 (m, 1H), 1.86-1.62 (m, 4H). LCMS m/z 474.7 [M + H]⁺. |
| 38 | 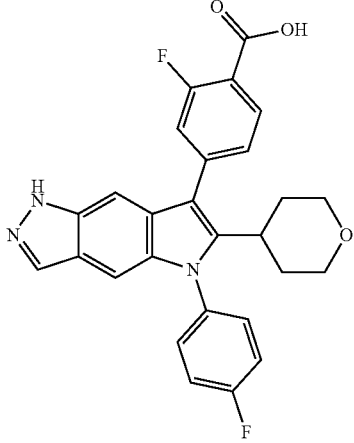<br>Method B from S6 | 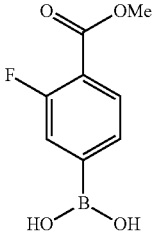 [SMILES: COC(=O)c1ccc(B(O)O)cc1F] | ¹H NMR (400 MHz, Methanol-d₄) δ 8.10 (t, J = 7.9 Hz, 1H), 7.99 (s, 1H), 7.53 (dd, J = 8.6, 4.8 Hz, 2H), 7.47-7.33 (m, 5H), 7.13 (s, 1H), 3.83 (dd, J = 11.4, 3.5 Hz, 2H), 3.24 (t, J = 11.8 Hz, 2H), 3.14-3.04 (m, 1H), 1.83 (qd, J = 13.1, 3.9 Hz, 2H), 1.71 (d, J = 12.6 Hz, 2H). LCMS m/z 474.4 [M + H]⁺. |
| 39 | 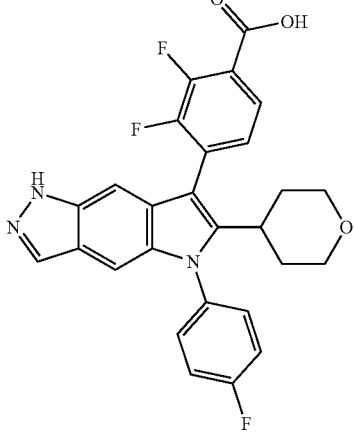<br>Method B from S6 | 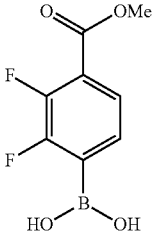 | ¹H NMR (400 MHz, Methanol-d₄) δ 8.00 (s, 1H), 7.88 (t, J = 7.4 Hz, 1H), 7.60-7.50 (m, 2H), 7.47-7.37 (m, 3H), 7.20 (s, 1H), 7.16 (s, 1H), 3.82 (d, J = 11.5 Hz, 2H), 3.28-3.18 (m, 2H), 3.06-2.94 (m, 1H), 1.85-1.64 (m, 4H). LCMS m/z 492.4 [M + H]⁺. |

TABLE 5-continued

Method of preparation, structure, physicochemical data for compounds 37-44

| Compound | Method/Product | Boronic acid or ester | ¹H NMR; LCMS m/z [M + H]⁺ |
|---|---|---|---|
| 40 | Method B¹ from S6 | | ¹H NMR (400 MHz, Methanol-d₄) δ 8.01 (s, 1H), 7.98 (s, 1H), 7.78 (d, J = 8.8 Hz, 1H), 7.54-7.48 (m, 2H), 7.45 (d, J = 8.6 Hz, 1H), 7.38 (t, J = 8.4 Hz, 2H), 7.33 (s, 1H), 7.14 (s, 1H), 3.86 (dd, J = 10.7, 2.8 Hz, 2H), 3.30-3.22 (m, 2H), 3.11-3.00 (m, 1H), 1.90-1.76 (m, 2H), 1.72 (d, J = 12.6 Hz, 2H). LCMS m/z 474.4 [M + H]⁺. |
| 41 | Method A² from S6 | | ¹H NMR (400 MHz, Methanol-d₄) δ 8.15 (s, 1H), 8.10 (d, J = 7.8 Hz, 1H), 7.98 (s, 1H), 7.74 (d, J = 7.5 Hz, 1H), 7.64 (t, J = 7.7 Hz, 1H), 7.54 (dd, J = 7.9, 5.1 Hz, 3H), 7.41 (t, J = 8.5 Hz, 2H), 7.26 (s, 1H), 7.14 (s, 1H), 3.80 (d, J = 11.7 Hz, 2H), 3.21 (t, J = 11.7 Hz, 2H), 3.09-2.98 (m, 1H), 1.87-1.75 (m, 2H), 1.70 (d, J = 12.9 Hz, 2H). LCMS m/z 456.4 [M + H]⁺. |
| 42 | Method B from S6 | | ¹H NMR (400 MHz, Methanol-d₄) δ 8.64 (s, 1H), 8.00 (s, 1H), 7.94 (d, J = 10.9 Hz, 1H), 7.54 (dd, J = 8.5, 4.8 Hz, 2H), 7.46-7.37 (m, 3H), 7.15 (s, 1H), 3.88-3.78 (m, 2H), 3.25 (td, J = 11.2, 3.3 Hz, 2H), 3.09 (tt, J = 11.0, 4.8 Hz, 1H), 1.85-1.70 (m, 4H). LCMS m/z 475.7 [M + H]⁺. |

TABLE 5-continued

Method of preparation, structure, physicochemical data for compounds 37-44

| Compound | Method/Product | Boronic acid or ester | $^1$H NMR; LCMS m/z [M + H]$^+$ |
|---|---|---|---|
| 43 | 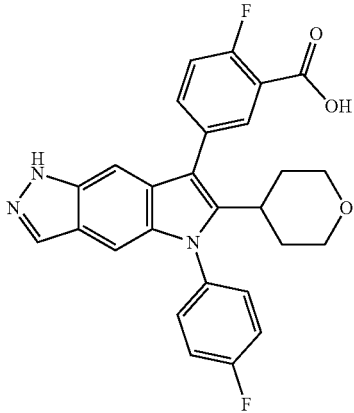<br>Method B from S6 | 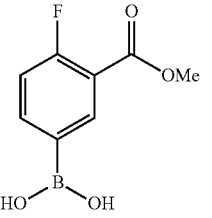 | $^1$H NMR (400 MHz, Methanol-d$_4$) δ 8.01 (d, J = 6.9 Hz, 1H), 7.98 (s, 1H), 7.73-7.68 (m, 1H), 7.53 (dd, J = 8.5, 4.8 Hz, 2H), 7.39 (s, 3H), 7.26 (s, 1H), 7.13 (s, 1H), 3.81 (dd, J = 12.5, 3.3 Hz, 2H), 3.22 (t, J = 11.7 Hz, 2H), 3.07-2.97 (m, 1H), 1.86-1.67 (m, 4H). LCMS m/z 474.4 [M + H]$^+$. |
| 44 | 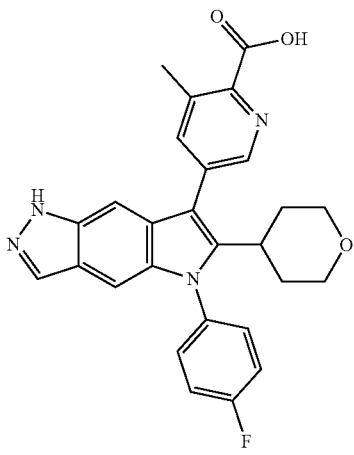<br>Method B from S6 | 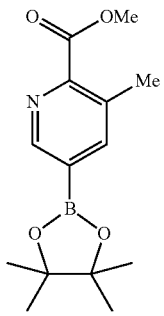 | $^1$H NMR (400 MHz, Methanol-d$_4$) δ 8.61 (s, 1H), 8.02 (s, 1H), 8.00 (s, 1H), 7.55 (dd, J = 8.6, 4.8 Hz, 2H), 7.43 (t, J = 8.4 Hz, 2H), 7.32 (s, 1H), 7.16 (s, 1H), 3.87-3.79 (m, 2H), 3.28-3.19 (m, 2H), 3.06 (dt, J = 11.1, 5.8 Hz, 1H), 2.76 (s, 3H), 1.85-1.68 (m, 4H). LCMS m/z 471.4 [M + H]$^+$. |

$^1$Purification by reversed-phase HPLC. Method: C18 Waters Sunfire column (30x150 mm, 5 micron). Gradient: 10-100% MeCN in H$_2$O with 0.2% formic acid.
$^2$Purification by reversed-phase chromatography on a C18 column. Gradient: 10-100% MeCN in H$_2$O Gradient: 10-100% MeCN in H$_2$O.

Compound 45
4-[8-fluoro-5-(4-fluorophenyl)-6-tetrahydropyran-4-yl-1H-pyrrolo[2,3-f]indazol-7-yl]benzoic Acid (45)
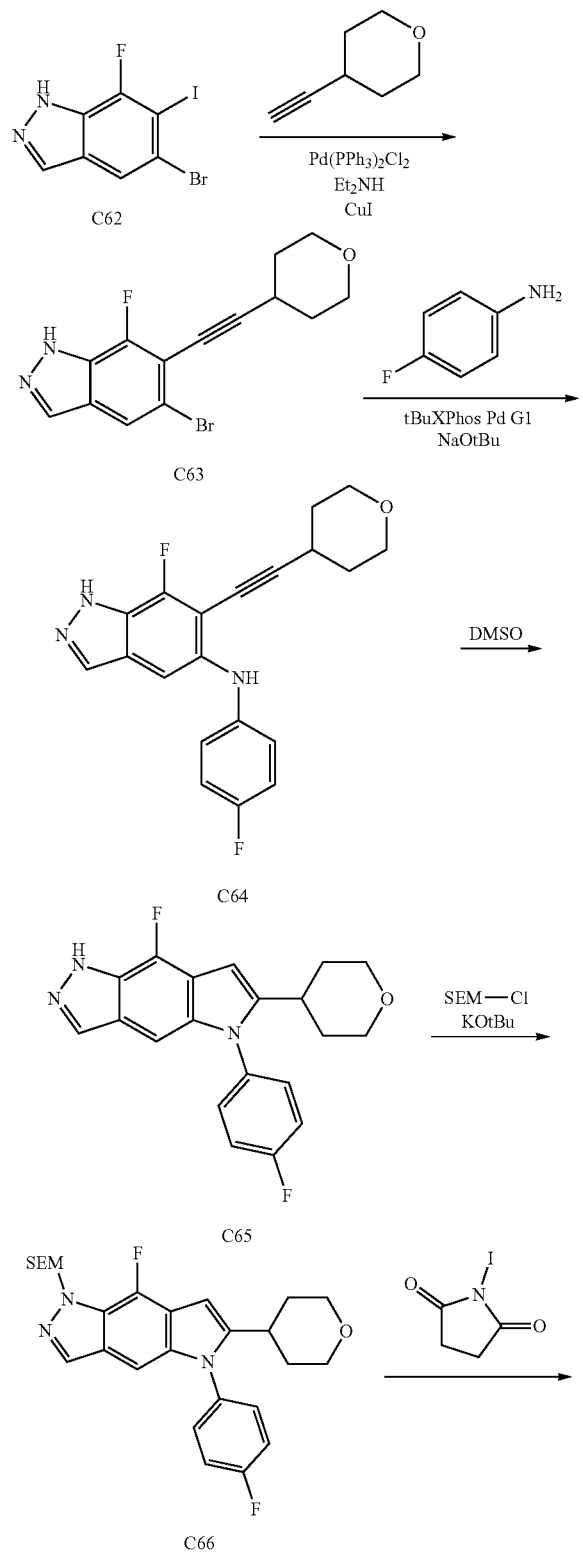
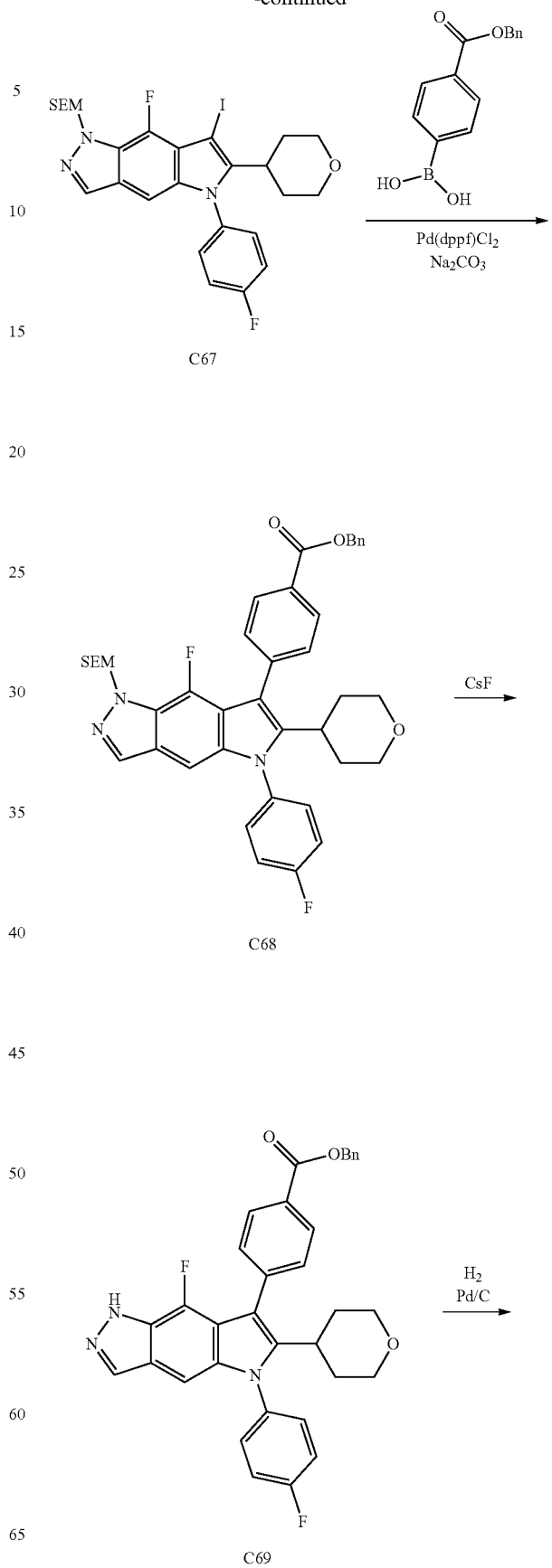

-continued

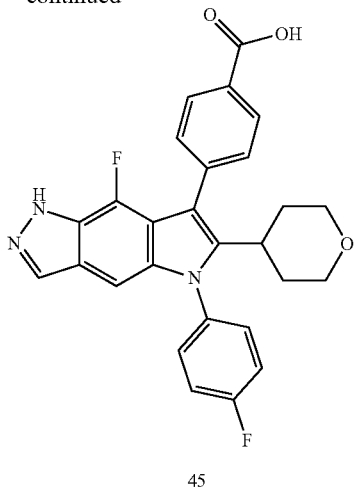

Step 1. Synthesis of 5-bromo-7-fluoro-6-(2-tetrahydropyran-4-ylethynyl)-1H-indazole (C63)

DMF (12 mL) was added to a vial containing 5-bromo-7-fluoro-6-iodo-1H-indazole C62 (2.0 g, 5.87 mmol) under a nitrogen atmosphere. The reaction mixture was purged with nitrogen for an additional 10 min. 4-Ethynyltetrahydropyran (845 mg, 7.67 mmol), $Et_2NH$ (2 mL, 19.3 mmol) $PdCl_2(PPh_3)_2$ (210 mg, 0.30 mmol) and CuI (83 mg, 0.44 mmol) were successively added, and the mixture heated to 90° C. overnight. The mixture was then concentrated to dryness, and then water and $CH_2Cl_2$ were added. The organic phase was separated using a phase separator, then concentrated in vacuo. Purification by silica gel chromatography (Eluent: EtOAc in heptanes) afforded the product 5-bromo-7-fluoro-6-(2-tetrahydropyran-4-ylethynyl)-1H-indazole (1.32 g, 70%). LCMS m/z 323.1 [M+H]$^+$.

Step 2. Synthesis of 7-fluoro-N-(4-fluorophenyl)-6-(2-tetrahydropyran-4-ylethynyl)-1H-indazol-5-amine (C64)

NaOtBu (2.54 g, 26.4 mmol) was added to a solution of 5-bromo-7-fluoro-6-(2-tetrahydropyran-4-ylethynyl)-1H-indazole C63 (4.78 g, 14.8 mmol) and 4-fluoroaniline (2.1 mL, 22.2 mmol) in tBuOH (80 mL). The mixture was purged with nitrogen for 10 min. tBuXPhos Pd G1 (365 mg, 0.53 mmol) was added and the reaction purged with nitrogen for an additional 10 min, then heated to 70° C. for 1 h. Water and $CH_2Cl_2$ were added and the phases were separated on a phase separator. Purification by silica gel chromatography (Eluent: Ethyl acetate in $CH_2Cl_2$) afforded the product (4.48 g, 86%). $^1$H NMR (400 MHz, DMSO-d$_6$) δ 13.55 (s, 1H), 8.11-7.84 (m, 1H), 7.49 (s, 1H), 7.24 (s, 1H), 7.11-7.01 (m, 2H), 7.01-6.88 (m, 2H), 3.70 (dt, J=10.2, 4.5 Hz, 2H), 3.40 (t, J=9.9 Hz, 2H), 2.91 (dt, J=9.2, 4.8 Hz, 1H), 1.75 (dd, J=10.9, 5.6 Hz, 2H), 1.50 (qd, J=12.8, 10.8, 6.0 Hz, 2H).

Step 3. Synthesis of 8-fluoro-5-(4-fluorophenyl)-6-tetrahydropyran-4-yl-1H-pyrrolo[2,3-f]indazole (C65)

A solution of 7-fluoro-N-(4-fluorophenyl)-6-(2-tetrahydropyran-4-ylethynyl)-1H-indazol-5-amine C64 (4200 mg, 11.9 mmol) in DMSO (17 mL) was heated at 150° C. in a microwave for 2 h. Water and EtOAc/Et$_2$O (1:1) were added. The aqueous layer was washed with EtOAc and the organic layers were combined, then dried with $Na_2SO_4$. The organic layer was concentrated in vacuo. Purification by silica gel chromatography (Eluent: Ethyl acetate in $CH_2Cl_2$) afforded the product.
(3750 mg, 89%). $^1$H NMR (400 MHz, DMSO-d$_6$) δ 13.10 (s, 1H), 8.12-8.00 (m, 1H), 7.57 (dd, J=8.5, 5.2 Hz, 2H), 7.48 (t, J=8.4 Hz, 2H), 7.03 (s, 1H), 6.60 (s, 1H), 3.85 (d, J=11.4 Hz, 2H), 3.24 (q, J=10.8, 8.9 Hz, 2H), 2.91-2.76 (m, 1H), 1.70 (dd, J=8.1, 3.2 Hz, 4H).

Step 4. 2-[8-fluoro-5-(4-fluorophenyl)-6-tetrahydropyran-4-yl-pyrrolo[2,3-f]indazol-1-yl]sulfonylethyl-trimethyl-silane (C66)

KOtBu (362 mg, 3.23 mmol) was added to a solution of 8-fluoro-5-(4-fluorophenyl)-6-tetrahydropyran-4-yl-1H-pyrrolo[2,3-f]indazole C65 (922 mg, 2.51 mmol) in THF (10.8 mL) and the reaction was stirred for 10 min. The reaction was then cooled on an ice bath and 2-trimethylsilylethanesulfonyl chloride (473 μL, 2.50 mmol) was added. The reaction was stirred overnight at room temperature. Water and $CH_2Cl_2$ were added, and the layers separated using a phase separator. The organic layer was concentrated in vacuo and purified by silica gel chromatography (Gradient: 0-100% EtOAc in dichloromethane) to afford the product as a mixture of regioisomers, which was used in the subsequent step without separation. (700 mg, 44%). LCMS m/z 518.4 [M+H]$^+$.

Step 5. 2-[8-fluoro-5-(4-fluorophenyl)-7-iodo-6-tetrahydropyran-4-yl-pyrrolo[2,3-f]indazol-1-yl]sulfonylethyl-trimethyl-silane (C67)

1-iodopyrrolidine-2,5-dione (292 mg, 1.30 mmol) was added portion-wise to a solution of 2-[8-fluoro-5-(4-fluorophenyl)-6-tetrahydropyran-4-yl-pyrrolo[2,3-f]indazol-1-yl]sulfonylethyl-trimethyl-silane C66 (700 mg, 1.35 mmol) in $CH_2Cl_2$ (17.6 mL) at 0° C. The reaction was allowed to stir at room temperature for 2 h. The mixture was quenched with 1M $Na_2SO_3$. Water and $CH_2Cl_2$ were added, and the phases were separated on a phase separator. Purification by silica gel chromatography (0-100% EtOAc/dichloromethane) afforded the product 2 (352 mg, 34%). LCMS m/z 644.3 [M+H]$^+$.

Step 6. 4-[8-fluoro-5-(4-fluorophenyl)-6-tetrahydropyran-4-yl-1-(2-trimethylsilylethylsulfonyl)pyrrolo[2,3-f]indazol-7-yl]benzoate (C68)

A mixture of 2-[8-fluoro-5-(4-fluorophenyl)-7-iodo-6-tetrahydropyran-4-yl-pyrrolo[2,3-f]indazol-1-yl]sulfonylethyl-trimethyl-silane C67 (72 mg, 0.08 mmol), (4-benzyloxycarbonylphenyl)boronic acid (41.9 mg, 0.16 mmol), sodium carbonate (122 μL of 2 M, 0.24 mmol) and Pd(dppf)Cl$_2$ (6.2 mg, 0.008 mmol) in 1,4-dioxane (328 μL) was stirred at 90° C. for 1.5 h. Water and $CH_2Cl_2$ were added, and layers separated in a phase separator. The organic layer was concentrated to afford the product, which was used in the subsequent step without further purification (73 mg, 69%). LCMS m/z 728.5 [M+H]$^+$.

Step 7. Synthesis of 4-[8-fluoro-5-(4-fluorophenyl)-6-tetrahydropyran-4-yl-1H-pyrrolo[2,3-f]indazol-7-yl]benzoic Acid (C69)

A solution of benzyl 4-[8-fluoro-5-(4-fluorophenyl)-6-tetrahydropyran-4-yl-1-(2-trimethylsilylethylsulfonyl)pyrrolo[2,3-f]indazol-7-yl]benzoate C68 (73 mg, 0.10 mmol) and CsF (152 mg, 1.0 mmol) were stirred in MeCN (5.0 mL) at 80° C. The reaction mixture was then concentrated in vacuo and purified by silica gel chromatography (0-100% EtOAc in dichloromethane) to afford the product. (22.8 mg, 31%). $^1$H NMR (400 MHz, Methanol-$d_4$) δ 8.15 (d, J=7.9 Hz, 2H), 8.03-8.00 (m, 1H), 7.66 (d, J=7.9 Hz, 2H), 7.57-7.48 (m, 4H), 7.45-7.32 (m, 5H), 6.93 (s, 1H), 5.43 (s, 2H), 3.81-3.75 (m, 2H), 3.19 (t, J=11.6 Hz, 2H), 2.99 (t, J=12.5 Hz, 2H), 1.84-1.63 (m, 6H). LCMS m/z 564.5 [M+H]$^+$.

Step 8. 4-[8-fluoro-5-(4-fluorophenyl)-6-tetrahydropyran-4-yl-1H-pyrrolo[2,3-f]indazol-7-yl]benzoic Acid (45)

A solution of benzyl 4-[8-fluoro-5-(4-fluorophenyl)-6-tetrahydropyran-4-yl-1H-pyrrolo[2,3-f]indazol-7-yl]benzoate C69 (22 mg, 0.04 mmol) in EtOH (330 μL) and THF (330 μL) was added to a flask containing Pd on carbon catalyst (4.1 mg, 0.04 mmol) under an inert atmosphere. The reaction mixture was subjected to hydrogenation conditions under a balloon pressure atmosphere of H$_2$ (3.0 mg, 1.5 mmol) for 90 min. The reaction was filtered through Celite®. The filtrate was purified by reverse phase chromatography (Gradient: 0-100% MeCN in water containing 10 mM ammonium formate) to afford the product (8.2 mg, 40%). $^1$H NMR (400 MHz, Methanol-$d_4$) δ 8.11 (d, J=7.8 Hz, 2H), 8.01 (d, J=3.2 Hz, 1H), 7.62 (d, J=7.9 Hz, 2H), 7.58-7.51 (m, 2H), 7.42 (t, J=8.3 Hz, 2H), 6.93 (s, 1H), 3.83-3.74 (m, 2H), 3.18 (t, J=11.6 Hz, 2H), 3.00 (t, J=12.3 Hz, 1H), 1.84-1.72 (m, 2H), 1.70-1.63 (m, 2H). LCMS m/z 474.4 [M+H]$^+$.

Compound 46

4-[5-(4-fluorophenyl)-6-tetrahydropyran-3-yl-1H-pyrrolo[2,3-f]indazol-7-yl]benzoic Acid (46)

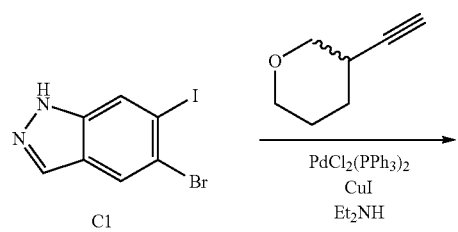

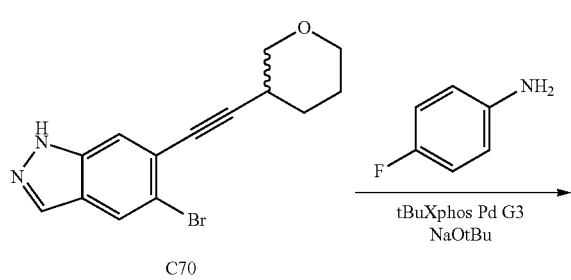

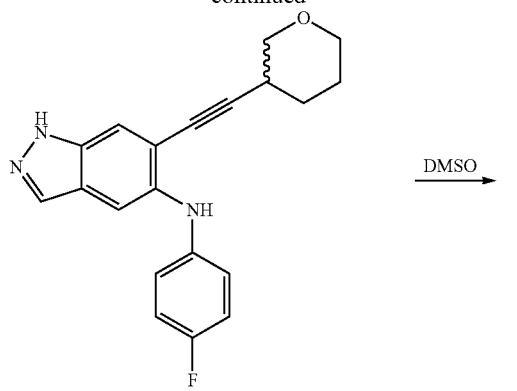

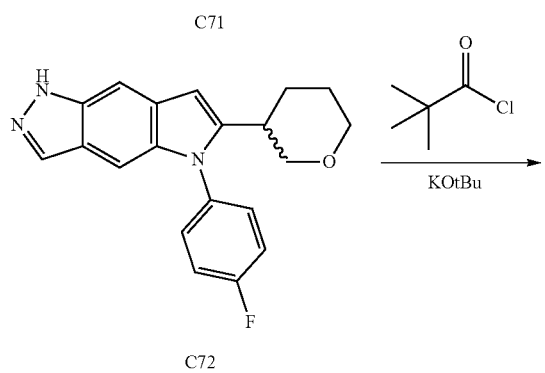

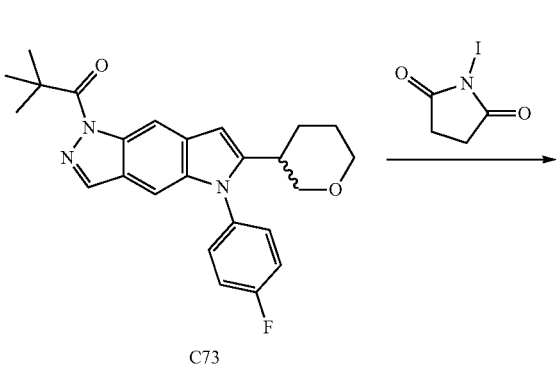

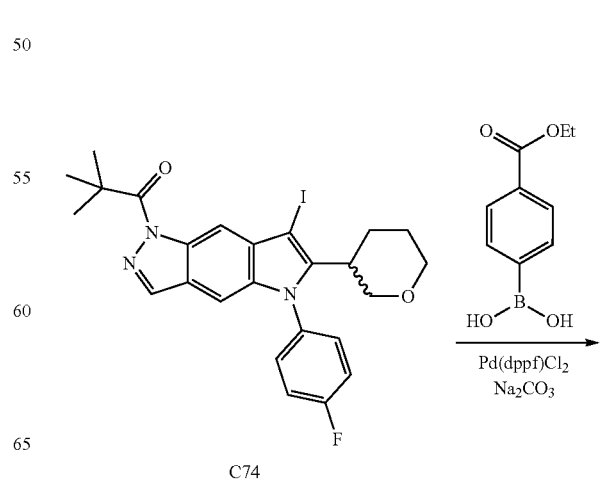

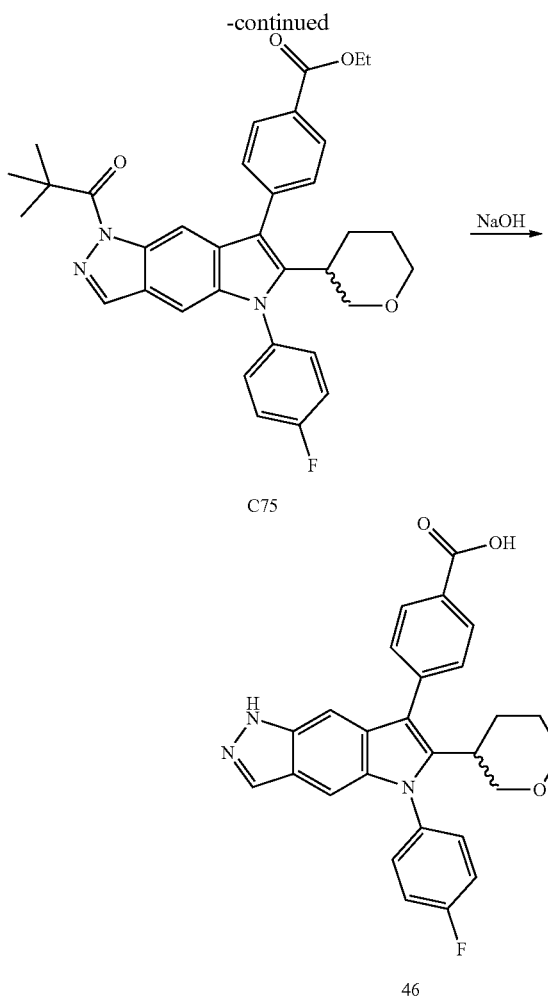

Step 1. Synthesis of 5-bromo-6-(2-tetrahydropyran-3-ylethynyl)-1H-indazole (C70)

To a solution of 5-bromo-6-iodo-1H-indazole C1 (2.5 g, 7.74 mmol) in DMF (15.6 mL) under a nitrogen atmosphere, was added 3-ethynyltetrahydropyran (852 mg, 7.74 mmol), Et$_2$NH (2.4 mL, 23.2 mmol), PdCl$_2$(PPh$_3$)$_2$ (275 mg, 0.4 mmol) and CuI (110 mg, 0.58 mmol). The reaction mixture was heated to 90° C. for 1 h. Water and CH$_2$Cl$_2$ were added and the organic phase was separated on a phase separator. The organic layer was concentrated in vacuo and purified by silica gel chromatography (Eluent: Ethyl acetate in heptanes) to afford the product (1.32 g, 56%). $^1$H NMR (300 MHz, DMSO-d$_6$) δ 13.31 (s, 1H), 8.13 (s, 1H), 8.06 (t, J=1.2 Hz, 1H), 7.69 (s, 1H), 3.90 (ddd, J=10.9, 4.1, 1.3 Hz, 1H), 3.78-3.68 (m, 1H), 3.51-3.41 (m, 2H), 2.90-2.79 (m, 1H), 2.12-2.01 (m, 1H), 1.78-1.47 (m, 3H). LCMS m/z 305.1 [M+H]$^+$.

Step 2. Synthesis of N-(4-fluorophenyl)-6-(2-tetrahydropyran-3-ylethynyl)-1H-indazol-5-amine (C71)

A solution of 5-bromo-6-(2-tetrahydropyran-3-ylethynyl)-1H-indazole C70 (1.27 g, 4.16 mmol), 4-fluoroaniline (562 μL, 5.9 mmol) and NaOtBu (709 mg, 7.4 mmol) in tBuOH (20.6 mL) at 40° C. was purged with nitrogen for 10 min. tBuXPhos Pd G3 was added and the mixture was purged with nitrogen for an additional 10 min. The reaction was then heated to 70° C. for 1 h. Additional 4-fluoroaniline (562 μL, 5.93 mmol), NaOtBu (709 mg, 7.38 mmol) and tBuXPhos Pd G4 (3.3 mg, 0.004 mmol) were added and the reaction stirred for an additional 2 h. One further portion of additional reagents were added, 4-fluoroaniline (562 μL, 5.93 mmol), NaOtBu (709 mg, 7.38 mmol) and tBuXPhos Pd G4 (3.3 mg, 0.004 mmol). The mixture was then heated overnight. Purification by silica gel chromatography (0-100% EtOAc in heptane) afforded the product (535 mg, 36%). LCMS m/z 336.3 [M+H]$^+$.

Step 3. Synthesis of 5-(4-fluorophenyl)-6-tetrahydropyran-3-yl-1H-pyrrolo[2,3-f]indazole (C72)

A solution of N-(4-fluorophenyl)-6-(2-tetrahydropyran-3-ylethynyl)-1H-indazol-5-amine C71 (465 mg, 1.32 mmol) in DMSO (1.8 mL) was heated at 150° C. for 30 min. Water was added and the solid product precipitated out. The solid was filtered and dried to afford the product (345 mg, 66%). $^1$H NMR (400 MHz, DMSO-d$_6$) δ 12.62 (s, 1H), 7.97 (t, J=1.3 Hz, 1H), 7.56 (t, J=1.1 Hz, 1H), 7.48 (t, J=8.9 Hz, 2H), 7.16 (q, J=0.8 Hz, 1H), 6.54 (s, 1H), 3.88-3.75 (m, 2H), 3.41-3.35 (m, 1H), 2.82-2.72 (m, 1H), 2.07-1.95 (m, 1H), 1.81-1.69 (m, 1H), 1.66-1.56 (m, 1H), 1.55-1.42 (m, 1H). LCMS m/z 336.3 [M+H]$^+$.

Step 4. Synthesis of 1-[5-(4-fluorophenyl)-6-tetrahydropyran-3-yl-pyrrolo[2,3-f]indazol-1-yl]-2,2-dimethyl-propan-1-one (C73)

A solution of 5-(4-fluorophenyl)-6-tetrahydropyran-3-yl-1H-pyrrolo[2,3-f]indazole C72 (325 mg, 0.97 mmol) in THF (7.3 mL) was cooled to 0° C. in an ice bath. KOtBu (267 μL, 2.15 mmol) was added and the reaction allowed to stir for 5 min. 2,2-Dimethylpropanoyl chloride (463 μL, 3.76 mmol) was then added and the reaction allowed to stir at 0° C. for 1 h. Purification by silica gel chromatography (0-100% EtOAc/dichloromethane) afforded the product (260 mg, 57%). LCMS m/z 420.4 [M+H]$^+$.

Step 5. Synthesis of 1-[5-(4-fluorophenyl)-7-iodo-6-tetrahydropyran-3-yl-pyrrolo[2,3-f]indazol-1-yl]-2,2-dimethyl-propan-1-one (C74)

1-iodopyrrolidine-2,5-dione (174 mg, 0.73 mmol) was added portion-wise over 30 min to a solution of 1-[5-(4-fluorophenyl)-6-tetrahydropyran-3-yl-pyrrolo[2,3-f]indazol-1-yl]-2,2-dimethyl-propan-1-one C73 (252 mg, 0.60 mmol) in CH$_2$Cl$_2$ (2.6 mL) at 0° C. After 1 h, the mixture was washed with 1M Na$_2$SO$_3$. The organic phase was collected through a phase separator to afford the product (300 mg, 87%). $^1$H NMR (400 MHz, DMSO-d$_6$) δ 8.44 (d, J=0.8 Hz, 1H), 8.39 (t, J=0.9 Hz, 1H), 7.66-7.57 (m, 2H), 7.56-7.50 (m, 2H), 7.29 (d, J=0.9 Hz, 1H), 3.90-3.80 (m, 2H), 3.36-3.27 (m, 1H), 2.97-2.85 (m, 1H), 2.43-2.30 (m, 1H), 1.93 (d, J=13.1 Hz, 1H), 1.64 (d, J=13.5 Hz, 1H), 1.52 (s, 9H), 1.50-1.40 (m, 2H). LCMS m/z 546.4 [M+H]$^+$.

Step 6. Synthesis of ethyl 4-[1-(2,2-dimethylpropanoyl)-5-(4-fluorophenyl)-6-tetrahydropyran-3-yl-pyrrolo[2,3-f]indazol-7-yl]benzoate (C75)

A mixture of 1-[5-(4-fluorophenyl)-7-iodo-6-tetrahydropyran-3-yl-pyrrolo[2,3-f]indazol-1-yl]-2,2-dimethyl-propan-1-one C74 (242 mg, 0.42 mmol), (4-ethoxycarbonylphenyl)boronic acid (169 mg, 0.87 mmol) and Pd(dppf)

Cl₂ (16.9 mg, 0.021 mmol) was placed in a vial and purged with nitrogen. 1,4-Dioxane (1.4 mL) and sodium carbonate (677 μL of 2 M, 1.35 mmol) were added and the reaction was then stirred at 95° C. for 1 h. Water and CH₂Cl₂ were added. The phases were separated on a phase separator. Purification by silica gel chromatography (0-100% CH₂Cl₂/heptane) afforded the product (142 mg, 53%). LCMS m/z 568.5 [M+H]⁺.

Step 7. Synthesis of 4-[5-(4-fluorophenyl)-6-tetrahydropyran-3-yl-1H-pyrrolo[2,3-f]indazol-7-yl]benzoic Acid (46)

NaOH (163 μL of 1 M, 0.16 mmol) was added to a solution of ethyl 4-[1-(2,2-dimethylpropanoyl)-5-(4-fluorophenyl)-6-tetrahydropyran-3-yl-pyrrolo[2,3-f]indazol-7-yl] benzoate C75 (23 mg, 0.04 mmol) in THF (476 μL) and MeOH (202 μL). The reaction was heated at 50° C. for 30 min. The mixture was concentrated in vacuo, and then re-dissolved in minimal water. HCl (163 μL of 1 M, 0.16 mmol) was added and the mixture filtered to afford the product (11.6 mg, 70%). ¹H NMR (400 MHz, DMSO-d₆) δ 13.03 (s, 1H), 12.60 (s, 1H), 8.12 (d, J=7.5 Hz, 2H), 8.01 (s, 1H), 7.70-7.58 (m, 4H), 7.52 (t, J=8.5 Hz, 2H), 7.22 (s, 1H), 7.10 (s, 1H), 3.87 (d, J=10.4 Hz, 1H), 3.69 (d, J=10.9 Hz, 1H), 3.32-3.28 (m, 1H), 3.03-2.87 (m, 2H), 1.88 (d, J=12.8 Hz, 1H), 1.63-1.50 (m, 1H), 1.48-1.30 (m, 2H). LCMS m/z 455.5 [M+H]⁺.

Compound 47 and 48

4-[5-(4-fluorophenyl)-6-tetrahydropyran-3-yl-1H-pyrrolo[2,3-f]indazol-7-yl]benzoic Acid [ENANT-1] (47) and 4-[5-(4-fluorophenyl)-6-tetrahydropyran-3-yl-1H-pyrrolo[2,3-f]indazol-7-yl]benzoic Acid (ENANT-2] (48)

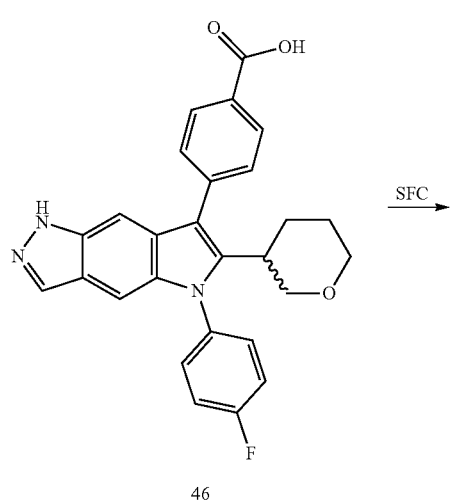

46

SFC →

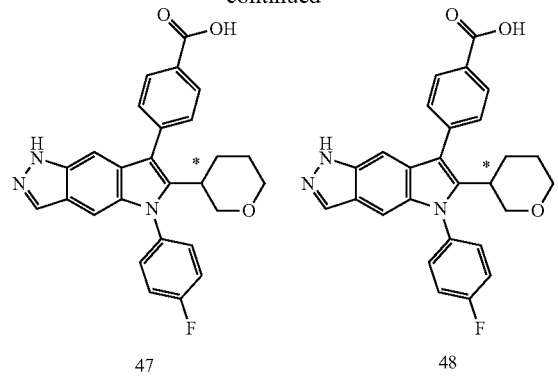

47　　　　48

Racemic 4-[5-(4-fluorophenyl)-6-tetrahydropyran-3-yl-1H-pyrrolo[2,3-f]indazol-7-yl]benzoic acid 46 (54 mg, 0.11 mmol) was separated into its constituent enantiomers 47 and 48 by chiral SFC purification. Column: Daicel Chiralpak AD-H, Mobile phase: 30% IPA (5 mM Ammonia), 70% CO₂. 4-[5-(4-fluorophenyl)-6-tetrahydropyran-3-yl-1H-pyrrolo[2,3-f]indazol-7-yl]benzoic acid [ENANT-1] (47) was the first eluting enantiomer. 4-[5-(4-fluorophenyl)-6-tetrahydropyran-3-yl-1H-pyrrolo[2,3-f]indazol-7-yl]benzoic acid [ENANT-2] (48) was the second eluting enantiomer. Both compounds were further purified by reverse phase chromatography (10-100% MeCN in water containing 0.1% formic acid) to afford the products.

4-[5-(4-fluorophenyl)-6-tetrahydropyran-3-yl-1H-pyrrolo[2,3-f]indazol-7-yl]benzoic acid [ENANT-1] (47) (13 mg, 27%). ¹H NMR (400 MHz, DMSO-d₆) δ 13.01 (s, 1H), 12.60 (s, 1H), 8.17-8.08 (m, 2H), 8.01 (s, 1H), 7.69-7.58 (m, 4H), 7.52 (t, J=8.5 Hz, 2H), 7.22 (s, 1H), 7.10 (s, 1H), 3.91-3.84 (m, 1H), 3.69 (d, J=11.2 Hz, 1H), 3.32-3.27 (m, 1H), 2.95 (q, J=11.7 Hz, 2H), 1.89 (d, J=12.4 Hz, 1H), 1.63-1.50 (m, 1H), 1.48-1.29 (m, 2H). LCMS m/z 456.3 [M+H]⁺.

4-[5-(4-fluorophenyl)-6-tetrahydropyran-3-yl-1H-pyrrolo[2,3-f]indazol-7-yl]benzoic acid [ENANT-2] (48) (13.9 mg, 26%). ¹H NMR (300 MHz, DMSO-d₆) δ 12.59 (s, 1H), 8.11 (d, J=8.1 Hz, 2H), 8.00 (s, 1H), 7.69-7.58 (m, 4H), 7.56-7.47 (m, 2H), 7.22 (s, 1H), 7.10 (s, 1H), 3.92-3.81 (m, 1H), 3.73-3.65 (m, 1H), 3.27 (s, 1H), 3.03-2.88 (m, 2H), 1.94-1.84 (m, 1H), 1.66-1.50 (m, 1H), 1.48-1.29 (m, 2H). LCMS m/z 456.1 [M+H]⁺.

Compound 49

Synthesis of 4-[5-(4-fluorophenyl)-6-isopropyl-1H-pyrrolo[2,3-f]indazol-7-yl]-3-methoxy-benzoic Acid (49)

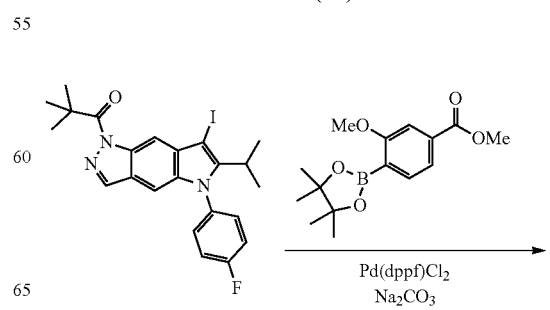

S7

Pd(dppf)Cl₂
Na₂CO₃

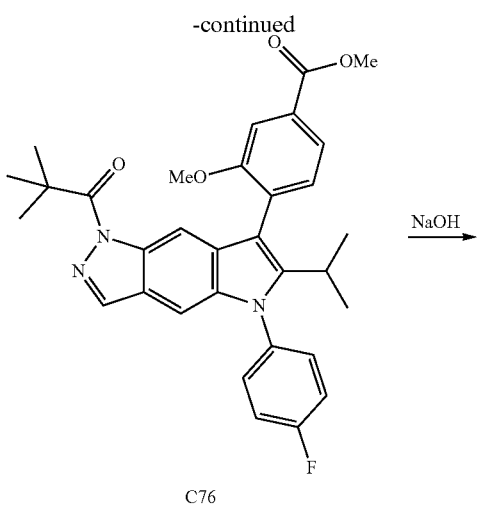

C76

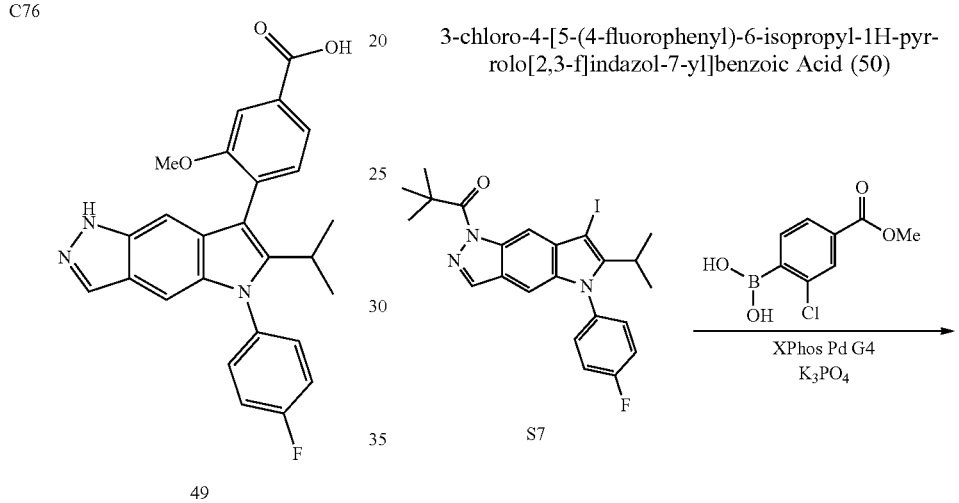

49

Step 1. 4-[1-(2,2-dimethylpropanoyl)-5-(4-fluorophenyl)-6-isopropyl-pyrrolo[2,3-f]indazol-7-yl]-3-methoxy-benzoate (C76)

To a solution of 1-[5-(4-fluorophenyl)-7-iodo-6-isopropyl-pyrrolo[2,3-f]indazol-1-yl]-2,2-dimethyl-propan-1-one S7 (4.90 g, 9.50 mmol), methyl 3-methoxy-4-(4,4,5,5-tetramethyl-1,3,2-dioxaborolan-2-yl)benzoate (5.11 g, 17.5 mmol), and Pd(dppf)Cl$_2$ (604 mg, 0.74 mmol) in 1,4-dioxane (43 mL) was added sodium carbonate (17 mL of 2 M, 34 mmol). The reaction mixture was purged with nitrogen and the solution was stirred at 90° C. for 90 min. Water (100 mL) and dichloromethane (100 mL) were added and the mixture was extracted with dichloromethane (3×100 mL). The organic layers were combined, passed through a phase separator and concentrated in vacuo. Purification by silica gel column chromatography (Eluent: 0-100% dichloromethane in heptane). To a solution of pure material in dichloromethane (150 mL) was added MP-TMT palladium scavenging resin (3.09 g). The suspension was stirred overnight at room temperature. The mixture was filtered, washed with dichloromethane, and concentrated in vacuo to afford the product (2.98 g, 58%). LCMS m/z 542.5 [M+H]$^+$.

Step 2. Synthesis of 4-[5-(4-fluorophenyl)-6-isopropyl-1H-pyrrolo[2,3-f]indazol-7-yl]-3-methoxy-benzoic Acid (49)

To a solution of methyl 4-[1-(2,2-dimethylpropanoyl)-5-(4-fluorophenyl)-6-isopropyl-pyrrolo[2,3-f]indazol-7-yl]-3-methoxy-benzoate C76 (1.2 g, 2.15 mmol) in THF (24 mL) and MeOH (12 mL) was added NaOH (12.84 mL of 1 M, 12.84 mmol). The solution was stirred at 50° C. for 1 h. The solvent was evaporated and the crude material was taken up in minimal water. HCl (12.8 mL of 1 M, 12.8 mmol) was added, forming a precipitate. Minimal DMSO was added to the suspension. Purification by reverse phase column chromatography (Eluent: 10-100% acetonitrile in water with 0.2% formic acid modifier) afforded the desired product (1.29 g, 66%). $^1$H NMR (400 MHz, DMSO-d$_6$) δ 13.04 (s, 1H), 12.51 (s, 1H), 7.97 (s, 1H), 7.71-7.66 (m, 2H), 7.64-7.56 (m, 2H), 7.52-7.42 (m, 3H), 7.06 (s, 1H), 6.99 (s, 1H), 3.80 (s, 3H), 2.99 (hept, J=7.6, 6.9 Hz, 1H), 1.08 (d, J=6.9 Hz, 3H), 1.01 (d, J=6.8 Hz, 3H). LCMS m/z 444.4 [M+H]$^+$.

Compound 50

3-chloro-4-[5-(4-fluorophenyl)-6-isopropyl-1H-pyrrolo[2,3-f]indazol-7-yl]benzoic Acid (50)

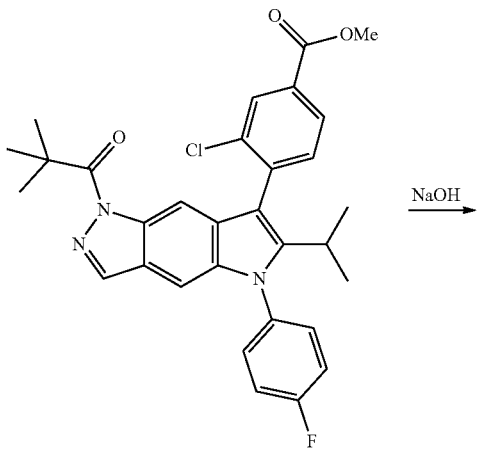

C77

489
-continued

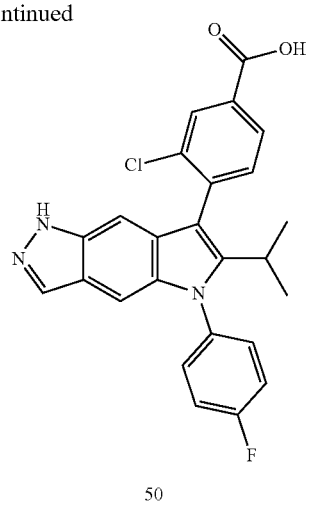

50

Step 1. Synthesis of methyl 3-chloro-4-[1-(2,2-dimethylpropanoyl)-5-(4-fluorophenyl)-6-isopropyl-pyrrolo[2,3-f]indazol-7-yl]benzoate (C77)

1-[5-(4-fluorophenyl)-7-iodo-6-isopropyl-pyrrolo[2,3-f] indazol-1-yl]-2,2-dimethyl-propan-1-one (50 mg, 0.10 mmol) S7, XPhos Pd G4 (84 mg, 0.1 mmol), (2-chloro-4-methoxycarbonyl-phenyl)boronic acid (23 mg, 0.11 mmol) and $K_3PO_4$ (61 mg, 0.3 mmol) were dissolved in 1,4-dioxane (300 μL) and water (30 μL). The mixture was purged with nitrogen, and the solution was stirred at 85° C. for 1 h. Water and dichloromethane were added and the solution was passed through a phase separator. The organic layer was concentrated in vacuo. Purification by silica gel column chromatography (Eluent: 0-80% dichloromethane in heptane) afforded the product (18 mg, 23%). LCMS m/z 545.2 [M+H]$^+$.

Step 2. Synthesis of 3-chloro-4-[5-(4-fluorophenyl)-6-isopropyl-1H-pyrrolo[2,3-f]indazol-7-yl]benzoic Acid (50)

To a solution of 3-chloro-4-[1-(2,2-dimethylpropanoyl)-5-(4-fluorophenyl)-6-isopropyl-pyrrolo[2,3-f]indazol-7-yl] benzoate C77 (52 mg, 0.03 mmol) and piperidine (18.1 μL, 0.18 mmol) (12 mL) in THF (1.0 mL) and MeOH (521 μL), was added NaOH (12.8 mL of 1 M, 12.8 mmol). The solution was stirred at 50° C. for 1 h. The solvent was evaporated and the crude reaction mixture was dissolved in minimal water. HCl (12.8 mL of 1 M, 12.8 mmol) were added, forming a precipitate. Dichloromethane was added and the organic layer was collected using a phase separator. Purification by reverse phase column chromatography (Eluent: MeCN in water with 0.1% Formic acid modifier) afforded the desired product (24 mg, 62%). $^1$H NMR (400 MHz, DMSO-d$_6$) δ 13.39 (s, 1H), 12.54 (s, 1H), 8.16-8.11 (m, 1H), 8.03-7.97 (m, 2H), 7.66 (d, J=7.8 Hz, 1H), 7.64-7.55 (m, 2H), 7.54-7.45 (m, 2H), 7.12 (s, 1H), 6.92 (s, 1H), 2.96 (p, J=7.1 Hz, 1H), 1.11 (d, J=7.0 Hz, 3H), 0.99 (d, J=7.0 Hz, 3H). LCMS m/z 448.3 [M+H]$^+$.

490

Compound 51

3,5-difluoro-4-[5-(4-fluorophenyl)-6-isopropyl-1H-pyrrolo[2,3-f]indazol-7-yl]benzoic Acid (51)

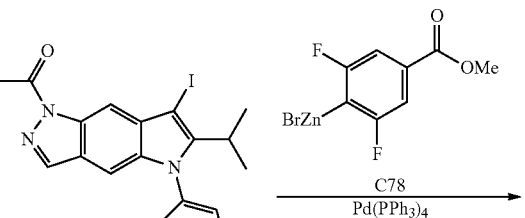

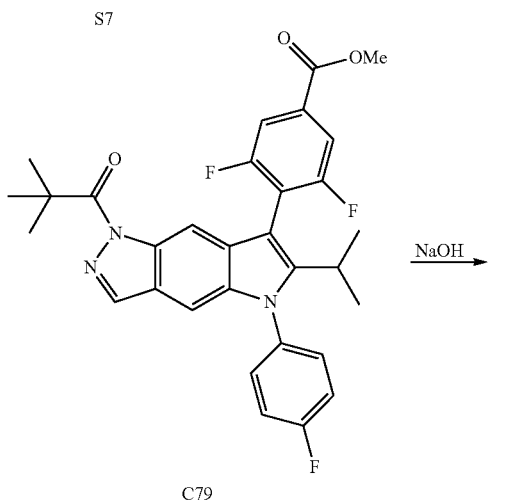

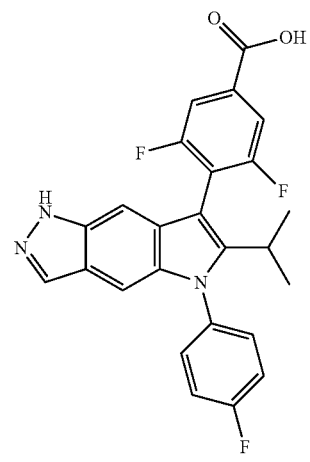

51

Step 1. Synthesis of methyl 4-[1-(2,2-dimethylpropanoyl)-5-(4-fluorophenyl)-6-isopropyl-pyrrolo[2,3-f]indazol-7-yl]-3,5-difluoro-benzoate (C79)

Part A. Preparation of organozinc reagent (C78): To a solution of CoBr$_2$ (15 mg, 0.07 mmol), ZnBr$_2$ (40 mg, 0.18 mmol), and Zn (189 mg, 2.90 mmol) acetonitrile (1000 μL) under nitrogen was added bromobenzene (7 μL, 0.07 mmol) and TFA (2.5 μL, 0.03 mmol). The resulting solution was stirred for 1 h then methyl 4-bromo-3,5-difluoro-benzoate (146 mg, 0.6 mmol) was added. The solution was stirred for an additional 48 h. The reaction was filtered and the supernatant was used immediately in part B of the reaction.

Part B. Coupling of organozinc reagent and S7: The supernatant from part A (C78) was transferred to a flask and degassed for 5 min. 1-[5-(4-fluorophenyl)-7-iodo-6-isopropyl-pyrrolo[2,3-f]indazol-1-yl]-2,2-dimethyl-propan-1-one (76 mg, 0.15 mmol) (S7) and Pd(PPh$_3$)$_4$ (20 mg, 0.02 mmol) were added and the solution was stirred at 50° C. overnight. Solvent was removed in vacuo. Purification by silica gel column chromatography (Eluent: 0-10% ethyl acetate in heptane) afforded the product (8 mg, 9%). $^1$H NMR (400 MHz, Chloroform-d) δ 8.17 (s, 1H), 7.98 (s, 1H), 7.65 (d, J=6.6 Hz, 2H), 7.39 (dd, J=7.4, 5.2 Hz, 2H), 7.23 (t, J=7.9 Hz, 2H), 7.07 (s, 1H), 3.96-3.92 (m, 3H), 3.01-2.90 (m, 1H), 1.46 (s, 9H), 1.10-1.00 (m, 6H). LCMS m/z 548.5 [M+H]$^+$.

Step 2. 3,5-difluoro-4-[5-(4-fluorophenyl)-6-isopropyl-1H-pyrrolo[2,3-f]indazol-7-yl]benzoic Acid (51)

Compound 51 was prepared from C79 by saponification using NaOH as described in the preparation of compound 49 step 2. $^1$H NMR (400 MHz, Chloroform-d) δ 7.99 (s, 1H), 7.74 (d, J=7.0 Hz, 2H), 7.63-7.48 (m, 2H), 7.40 (t, J=8.2 Hz, 2H), 7.16 (d, J=2.0 Hz, 1H), 7.10 (s, 1H), 3.12-3.01 (m, 1H), 1.13 (d, J=6.6 Hz, 6H). LCMS m/z 450.4 [M+H]$^+$.

Compound 52

5-[5-(4-fluorophenyl)-6-isopropyl-1H-pyrrolo[2,3-f]indazol-7-yl]-3-methyl-pyridine-2-carboxylic Acid (52)

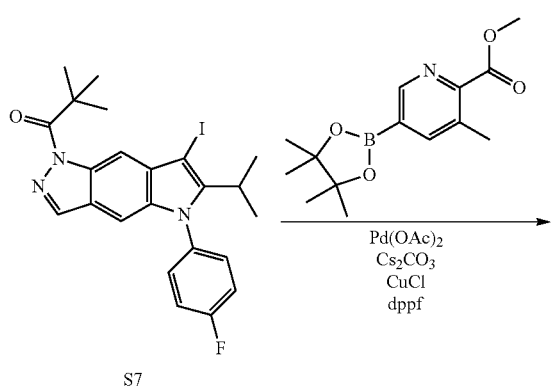

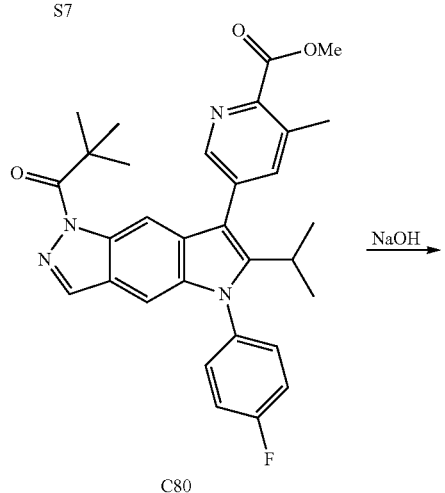

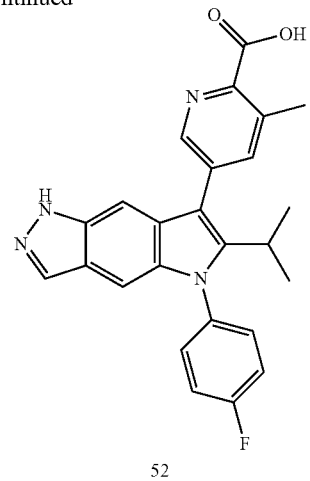

Synthesis of 5-[5-(4-fluorophenyl)-6-isopropyl-1H-pyrrolo[2,3-f]indazol-7-yl]-3-methyl-pyridine-2-carboxylic Acid (52)

A solution of 1-[5-(4-fluorophenyl)-7-iodo-6-isopropyl-pyrrolo[2,3-f]indazol-1-yl]-2,2-dimethyl-propan-1-one (81 mg, 0.2 mmol) (S7), methyl 3-methyl-5-(4,4,5,5-tetramethyl-1,3,2-dioxaborolan-2-yl)pyridine-2-carboxylate (87 mg, 0.30 mmol), Cs$_2$CO$_3$ (95 mg, 0.30 mmol), dppf (16 mg, 0.030 mmol), Pd(OAc)$_2$ (3 mg, 0.02 mmol), and CuCl (43 mg, 0.4 mmol) in DMF (1.6 mL) was purged with nitrogen for 10 min, then heated at 100° C. for 45 min. NaOH (965 μL of 1 M, 0.97 mmol) was added and the reaction was stirred for 30 min. Water (5 mL) and dichloromethane (5 mL) were added. The organic layer was collected and filtered through a Celite® plug, and washed with excess dichloromethane to afford the product (2 mg, 3%). $^1$H NMR (400 MHz, Methanol-d$_4$) δ 8.67 (s, 1H), 8.23 (s, 1H), 8.03 (s, 1H), 7.58-7.50 (m, 2H), 7.45-7.39 (m, 3H), 7.16 (s, 1H), 3.26-3.20 (m, 1H), 2.82 (s, 3H), 1.21 (d, J=7.0 Hz, 6H). LCMS m/z 429.4 [M+H]$^+$.

Compounds 53-65

Compounds 53-67 (see Table 6) were prepared in two steps from intermediate S7 and the appropriate boronic acid or ester reagent, using the cross coupling and saponification methods as described for compounds 49-51. Modifications to these methods are noted in Table 6 and accompanying footnotes.

493                                                                                                494

TABLE 6

Method of preparation, structure, physicochemical data for compounds 53-65

| Compound | Method/Product | Boronic acid or ester | ¹H NMR; LCMS m/z [M + H]⁺ |
|---|---|---|---|
| 53 | 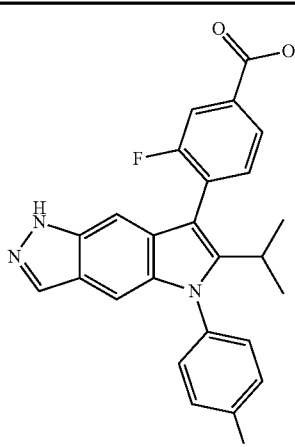<br>Compound 49¹ from S7 | 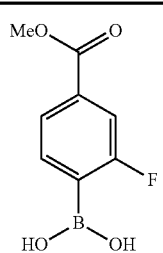 | ¹H NMR (400 MHz, DMSO-d₆) δ 13.32 (s, 1H), 12.58 (s, 1H), 8.00 (s, 1H), 7.93 (d, J = 7.9 Hz, 1H), 7.86 (d, J = 10.1 Hz, 1H), 7.67 (dd, J = 16.0, 8.4 Hz, 3H), 7.50 (t, J = 8.5 Hz, 2H), 7.10 (s, 2H), 3.04 (q, J = 7.1 Hz, 1H), 1.09 (dd, J = 22.3, 7.1 Hz, 5H). LCMS m/z 430.7 [M + H]⁺. |
| 54 | 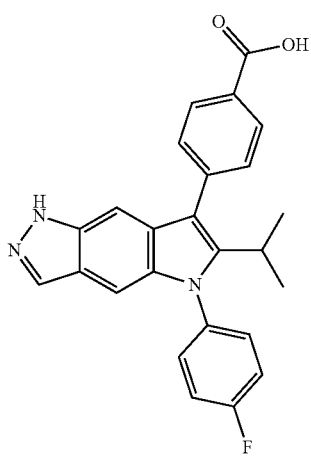<br>Compound 49² from S7 | 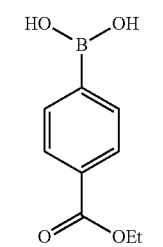 [SMILES: CCOC(=O)c1ccc(B(O)O)cc1] | ¹H NMR (300 MHz, DMSO-d₆) δ 12.90 (s, 1H), 12.67 (s, 1H), 8.18-8.04 (m, 2H), 8.00 (d, J = 1.0 Hz, 1H), 7.71-7.55 (m, 4H), 7.50 (t, J = 8.7 Hz, 2H), 7.31 (t, J = 1.1 Hz, 1H), 7.06 (d, J = 1.1 Hz, 1H), 3.18 (p, J = 7.1 Hz, 1H), 1.13 (d, J = 7.2 Hz, 6H). LCMS m/z 414.2 [M + H]⁺. |
| 55 | 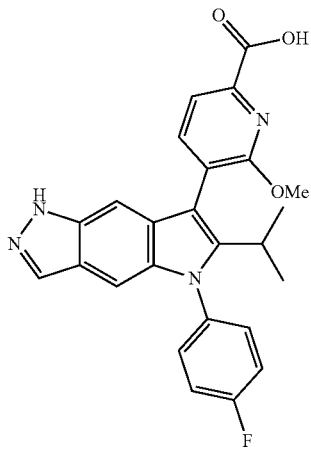<br>Compound 49 from S7 | 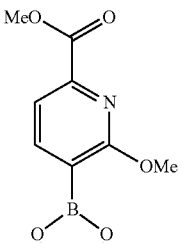 | ¹H NMR (400 MHz, DMSO-d₆) δ 13.01 (s, 1H), 12.55 (s, 1H), 7.99 (s, 1H), 7.93 (d, J = 7.4 Hz, 1H), 7.83 (d, J = 7.4 Hz, 1H), 7.67-7.61 (m, 1H), 7.61-7.54 (m, 1H), 7.53-7.45 (m, 2H), 7.08 (s, 1H), 7.04 (s, 1H), 3.93-3.89 (m, 3H), 2.99 (dq, J = 14.4, 6.8 Hz, 1H), 1.08 (d, J = 7.0 Hz, 3H), 1.02 (d, J = 7.0 Hz, 3H). LCMS m/z 445.4 [M + H]⁺. |

TABLE 6-continued

Method of preparation, structure, physicochemical data for compounds 53-65

| Compound | Method/Product | Boronic acid or ester | $^1$H NMR; LCMS m/z [M + H]$^+$ |
|---|---|---|---|
| 56 | 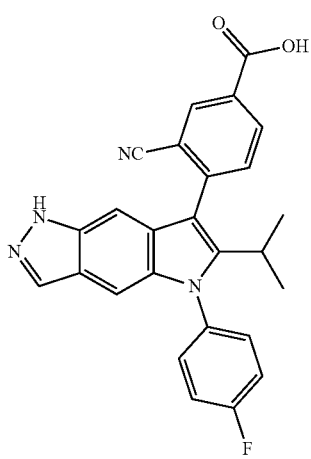<br>Compound 49 from S7 | 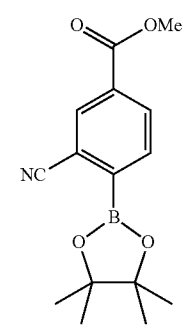 | $^1$H NMR (400 MHz, DMSO-d$_6$) δ 13.59 (s, 1H), 12.62 (s, 1H), 8.47 (s, 1H), 8.34 (d, J = 7.9 Hz, 1H), 8.03 (s, 1H), 7.82 (d, J = 8.1 Hz, 1H), 7.67-7.56 (m, 2H), 7.52 (t, J = 8.7 Hz, 2H), 7.15 (s, 1H), 7.06 (s, 1H), 3.04 (p, J = 7.1 Hz, 1H), 1.12 (d, J = 7.0 Hz, 3H), 1.04 (d, J = 7.0 Hz, 3H). LCMS m/z 439.3 [M + H]$^+$. |
| 57 | 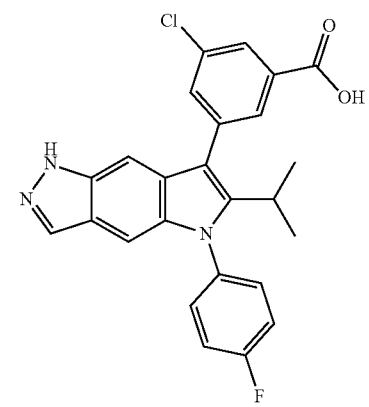<br>Compound 49$^3$ from S7 | 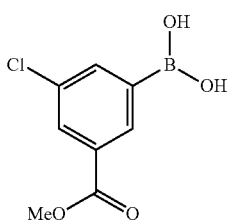 [SMILES: COC(=O)c1cc(Cl)cc(B(O)O)c1] | $^1$H NMR (400 MHz, Methanol-d$_4$) δ 8.07 (s, 1H), 8.02 (s, 1H), 7.98 (s, 1H), 7.72 (s, 1H), 7.56-7.52 (m, 2H), 7.40 (t, J = 8.2 Hz, 2H), 7.32 (s, 1H), 7.12 (s, 1H), 3.21-3.15 (m, 1H), 1.18 (d, J = 7.0 Hz, 6H). LCMS m/z 448.3 [M + H]$^+$. |
| 58 | 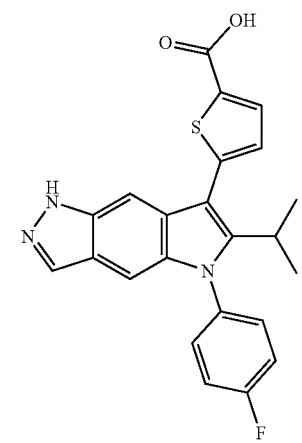<br>Compound 49$^1$ from S7 | 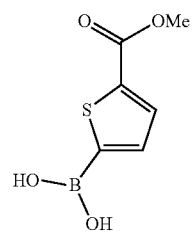 [SMILES: COC(=O)c1ccc(B(O)O)s1] | $^1$H NMR (400 MHz, DMSO-d$_6$) δ 13.08 (s, 1H), 12.67 (s, 1H), 8.02 (s, 1H), 7.84 (d, J = 3.9 Hz, 1H), 7.67-7.61 (m, 2H), 7.53-7.47 (m, 3H), 7.25 (d, J = 3.7 Hz, 1H), 7.07 (s, 1H), 3.30-3.23 (m, 1H), 1.18 (d, J = 7.1 Hz, 6H). LCMS m/z 420.3 [M + H]$^+$. |

TABLE 6-continued

Method of preparation, structure, physicochemical data for compounds 53-65

| Compound | Method/Product | Boronic acid or ester | $^1$H NMR; LCMS m/z [M + H]$^+$ |
|---|---|---|---|
| 59 | 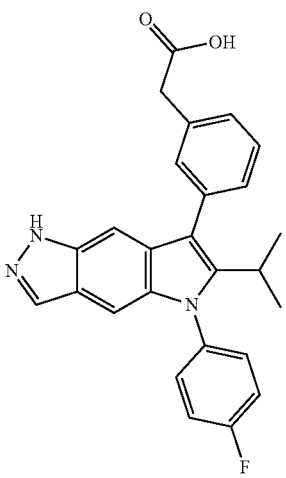<br>Compound 49$^1$ from S7 | 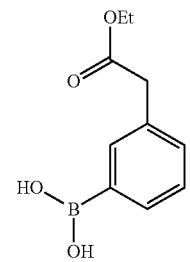 | $^1$H NMR (400 MHz, Methanol-d$_4$) δ 7.95 (s, 1H), 7.52-7.42 (m, 4H), 7.42-7.30 (m, 5H), 7.07 (s, 1H), 3.70 (s, 2H), 3.24-3.10 (m, 1H), 1.15 (d, J = 7.1 Hz, 6H). LCMS m/z 428.4 [M + H]$^+$. |
| 60 | 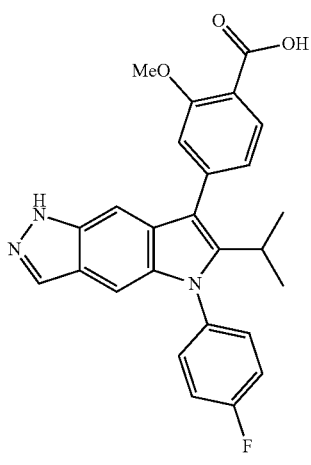<br>Compound 49 from S7 | 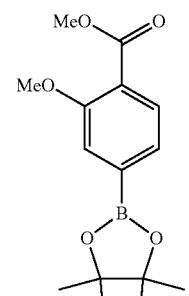 | $^1$H NMR (400 MHz, Methanol-d$_4$) δ 8.01-7.94 (m, 2H), 7.55-7.48 (m, 2H), 7.42-7.36 (m, 3H), 7.25 (s, 1H), 7.19 (d, J = 8.0 Hz, 1H), 7.10 (s, 1H), 3.96 (s, 3H), 3.28-3.18 (m, 1H), 1.21 (d, J = 7.1 Hz, 6H). LCMS m/z 444.3 [M + H]$^+$. |
| 61 | 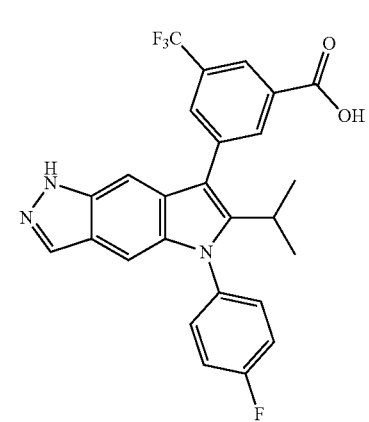<br>Compound 49$^{1,4}$ from S7 | 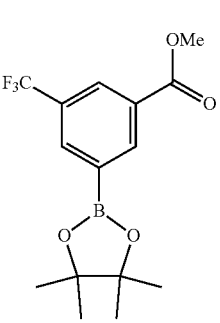 | $^1$H NMR (400 MHz, DMSO-d$_6$) δ 13.69 (s, 1H), 12.60 (s, 1H), 8.32 (s, 1H), 8.22 (s, 1H), 8.06 (s, 1H), 8.01 (s, 1H), 7.67-7.60 (m, 2H), 7.56-7.47 (m, 2H), 7.29 (s, 1H), 7.10 (s, 1H), 3.12 (p, J = 7.0 Hz, 1H), 1.13 (d, J = 7.1 Hz, 6H). LCMS m/z 482.3 [M + H]$^+$. |

TABLE 6-continued

Method of preparation, structure, physicochemical data for compounds 53-65

| Compound | Method/Product | Boronic acid or ester | $^1$H NMR; LCMS m/z [M + H]$^+$ |
|---|---|---|---|
| 62 | 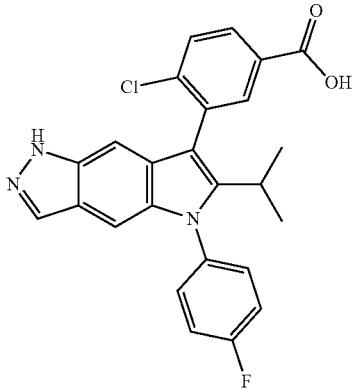<br>Compound 50 from S7 | 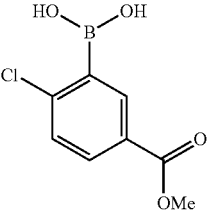 [SMILES: COC(=O)c1ccc(Cl)c(B(O)O)c1] | $^1$H NMR (400 MHz, DMSO-d$_6$) δ 12.52 (s, 1H), 8.05-7.98 (m, 3H), 7.77 (d, J = 8.2 Hz, 1H), 7.68-7.56 (m, 2H), 7.53-7.45 (m, 2H), 7.13 (s, 1H), 6.92 (s, 1H), 2.95 (p, J = 7.0 Hz, 1H), 1.11 (d, J = 7.0 Hz, 3H), 0.99 (d, J = 7.0 Hz, 3H). LCMS m/z 448.3 [M + H]$^+$. |
| 63 | 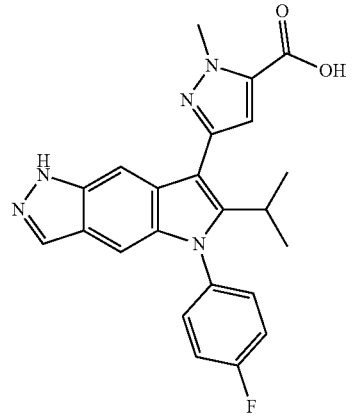<br>Compound 49$^5$ from S7 | 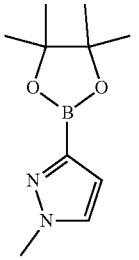 | $^1$H NMR (400 MHz, DMSO-d$_6$) δ 13.48 (s, 1H), 12.60 (s, 1H), 7.98 (s, 1H), 7.66 (s, 1H), 7.61-7.55 (m, 2H), 7.49 (t, J = 8.5 Hz, 2H), 7.02 (s, 1H), 6.96 (s, 1H), 4.20 (d, J = 1.5 Hz, 3H), 3.29-3.25 (m, 1H), 1.20 (d, J = 7.0 Hz, 6H). LCMS m/z 418.3 [M + H]$^+$. |
| 64 | 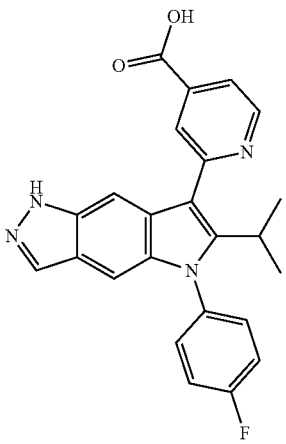<br>Compound 52$^1$ from S7 | 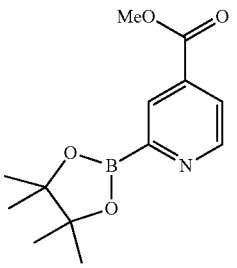 | $^1$H NMR (400 MHz, Methanol-d$_4$) δ 8.85 (d, J = 5.0 Hz, 1H), 8.17 (s, 1H), 7.99 (s, 1H), 7.89 (d, J = 5.1 Hz, 1H), 7.58-7.50 (m, 3H), 7.40 (t, J = 8.3 Hz, 2H), 7.13 (s, 1H), 3.34 (1H obscured by solvent peak), 1.20 (d, J = 7.0 Hz, 6H). LCMS m/z 415.2 [M + H]$^+$. |

TABLE 6-continued

Method of preparation, structure, physicochemical data for compounds 53-65

| Compound | Method/Product | Boronic acid or ester | $^1$H NMR; LCMS m/z [M + H]$^+$ |
|---|---|---|---|
| 65 | 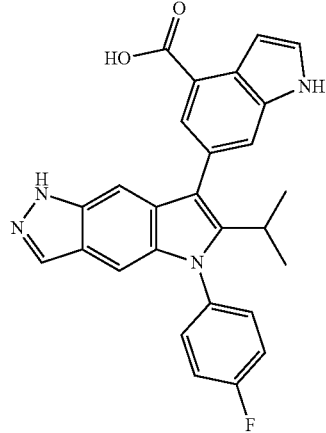<br>Compound 49$^6$ from S7 | 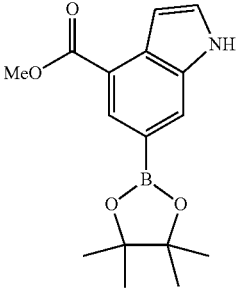 | $^1$H NMR (400 MHz, Methanol-d$_4$) δ 8.00-7.94 (m, 2H), 7.75 (s, 1H), 7.52 (dd, J = 8.3, 4.9 Hz, 2H), 7.46 (d, J = 3.1 Hz, 1H), 7.38 (t, J = 8.4 Hz, 2H), 7.14 (d, J = 3.0 Hz, 1H), 7.11 (s, 1H), 3.18 (dq, J = 15.7, 8.3, 7.6 Hz, 1H), 1.17 (d, J = 7.1 Hz, 6H). LCMS m/z 453.5 [M + H]$^+$. |

$^1$Purification by reversed-phase HPLC. Method: C18 Waters Sunfire column (30x150 mm, 5 micron). Gradient: 10-100% MeCN in H$_2$O with 0.2% formic acid. Compounds 53, 58, 59, 61, 64.

$^2$Compound 54 precipitated upon neutralization with HCl. The product was filtered, washed with water, precipitated in ethyl acetate and dried in vacuo. Then washed with 1N HCl, dried with sodium sulfate, filtered and dried in vacuo. Product was then stirred in NaOH (0.5M), diluted with water and extracted with ethyl acetate. Dried in vacuo and in the oven overnight at 50° C. to afford product.

$^3$Compound 57: Purification of step 1 by reversed-phase HPLC. Method: C18 Waters Sunfire column (30 x 150 mm, 5 micron). Gradient: 10-100% MeCN in H$_2$O.

$^4$Compound 61: Purification by silica gel column chromatography (Gradient: 0-80% dichloromethane in heptane) afforded the product in step 1.

$^5$Compound 63: Purification by reversed-phase chromatography on a C18 column. Gradient: 10-100% MeCN in H$_2$O with 0.1% trifluoroacetic acid.

$^6$Compound 65: Purification by reversed-phase chromatography on a C18 column. Gradient: 10-100% MeCN in H$_2$O with 0.2% formic acid.

Compound 66

(2S,3S,4S,5R)-6-[4-[5-(4-fluorophenyl)-6-isopropyl-1H-pyrrolo[2,3-f]indazol-7-yl]benzoyl]oxy-3,4,5-trihydroxy-tetrahydropyran-2-carboxylic Acid (66)

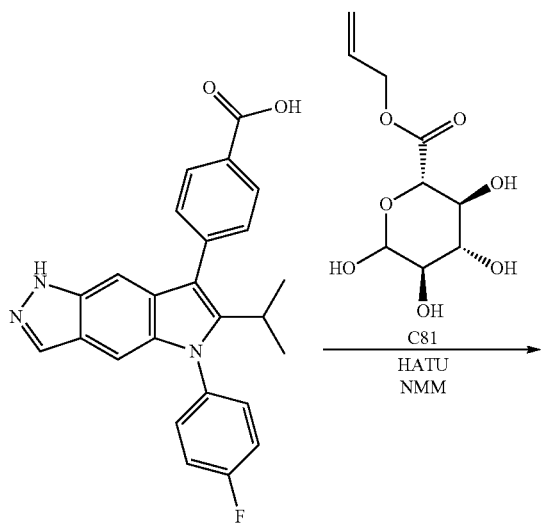

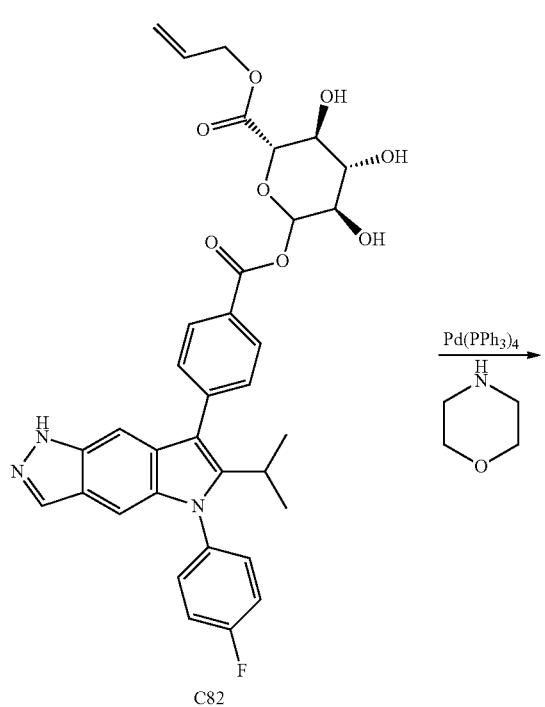

-continued

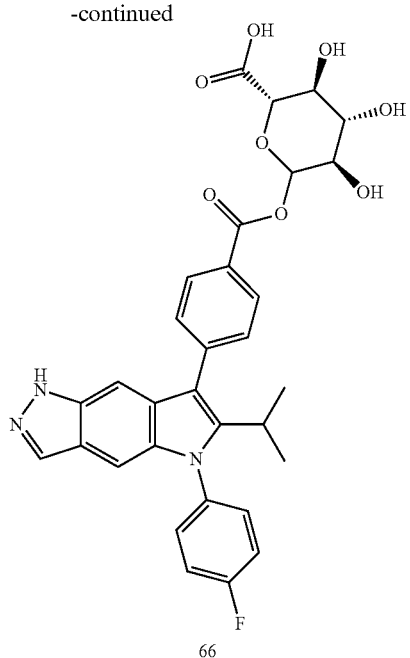

66

Step 1. Allyl (2S,3S,4S,5R)-6-[4-[5-(4-fluorophenyl)-6-isopropyl-1H-pyrrolo[2,3-f]indazol-7-yl]benzoyl]oxy-3,4,5-trihydroxy-tetrahydropyran-2-carboxylate (C82)

To a solution of 4-[5-(4-fluorophenyl)-6-isopropyl-1H-pyrrolo[2,3-f]indazol-7-yl]benzoic acid (54) (368.6 mg, 0.89 mmol), allyl (2S,3S,4S,5R)-3,4,5,6-tetrahydroxytetrahydropyran-2-carboxylate C81 (209 mg, 0.89 mmol), and HATU (338 mg, 0.89 mmol) in MeCN (10 mL) was added NMM (196 μL, 1.78 mmol). The solution was stirred overnight. THF (9 mL) was then added and the solution was stirred for 4 h then N-methyl pyrrolidone (3 mL) was added. The solution was stirred overnight and then further NMM (196 μL, 1.8 mmol) was added. The solvent was removed in vacuo followed by purification by silica gel column chromatography (Eluent: 0-10% methanol in dichloromethane) to afford the product (157 mg, 27%). LCMS m/z 630.5 [M+H]$^+$.

Step 2. (2S,3S,4S,5R)-6-[4-[5-(4-fluorophenyl)-6-isopropyl-1H-pyrrolo[2,3-f]indazol-7-yl]benzoyl]oxy-3,4,5-trihydroxy-tetrahydropyran-2-carboxylic Acid (66)

To a solution of allyl (2S,3S,4S,5R)-6-[4-[5-(4-fluorophenyl)-6-isopropyl-1H-pyrrolo[2,3-f]indazol-7-yl]benzoyl]oxy-3,4,5-trihydroxy-tetrahydropyran-2-carboxylate C82 (155 mg, 0.24 mmol) in CH$_2$Cl$_2$ (20 mL) was added morpholine (44 μL, 0.50 mmol). The mixture was purged with nitrogen for 10 min, and Pd(PPh$_3$)$_4$ (9 mg, 0.008 mmol) was added. After 30 min stirring at room temperature, MP-TMT palladium scavenging resin was added. The solution was stirred for 4 h, filtered and purified by reverse phase column chromatography (Eluent: 10-100% acetonitrile in water with formic acid modifier) to afford the product (21.3 mg, 15%). $^1$H NMR (300 MHz, DMSO-d$_6$) δ 13.04-12.68 (bs, 1H), 12.58 (s, 1H), 8.23-8.14 (m, 2H), 7.99 (d, J=1.0 Hz, 1H), 7.74-7.67 (m, 2H), 7.65-7.57 (m, 2H), 7.49 (t, J=8.7 Hz, 2H), 7.31 (t, J=1.1 Hz, 1H), 7.06 (d, J=1.1 Hz, 1H), 5.68 (d, J=7.4 Hz, 1H), 5.54 (d, J=4.2 Hz, 1H), 5.30 (d, J=4.0 Hz, 1H), 3.88 (d, J=8.9 Hz, 1H), 3.50-3.36 (m, 3H), 3.22-3.12 (m, 1H), 1.13 (dd, J=7.2, 2.1 Hz, 6H). LCMS m/z 590.5 [M+H]$^+$.

Compound 67

4-[5-(4-fluorophenyl)-6-isopropyl-1H-pyrrolo[2,3-f]indazol-7-yl]-3-(oxetan-3-yloxy)benzoic Acid (67)

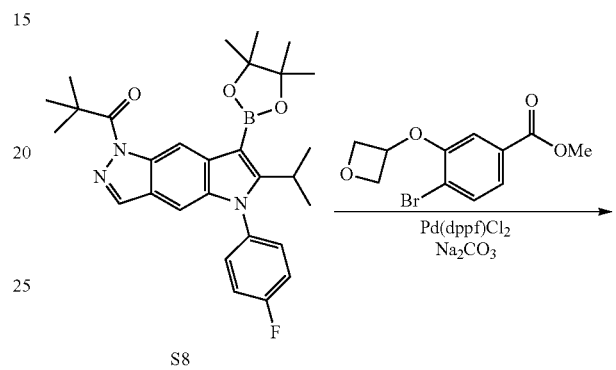

S8

↓ NaOH

67

Step 1. Methyl 4-[1-(2,2-dimethylpropanoyl)-5-(4-fluorophenyl)-6-isopropyl-pyrrolo[2,3-f]indazol-7-yl]-3-(oxetan-3-yloxy)benzoate (C83)

A solution of 1-[5-(4-fluorophenyl)-6-isopropyl-7-(4,4,5,5-tetramethyl-1,3,2-dioxaborolan-2-yl)pyrrolo[2,3-f]indazol-1-yl]-2,2-dimethyl-propan-1-one S8 (320 mg, 0.64 mmol), Pd(dppf)Cl$_2$ (49.1 mg, 0.06 mmol), sodium carbonate (953 μL of 2 M, 1.9 mmol) and methyl 4-bromo-3-(oxetan-3-yloxy)benzoate (182 mg, 0.64 mmol) in 1,4-dioxane (1.9 mL) was stirred at 95° C. for 90 min. Water and dichloromethane (1:1) were added, and the mixture passed through a phase separator and concentrated in vacuo. Purification by silica gel column chromatography (Eluent: 0-100% EtOAc in heptane) afforded the product (202 mg, 47%). LCMS m/z 584.5 [M+H]$^+$.

Step 2. 4-[5-(4-fluorophenyl)-6-isopropyl-1H-pyrrolo[2,3-f]indazol-7-yl]-3-(oxetan-3-yloxy)benzoic Acid (67)

To a solution of methyl 4-[1-(2,2-dimethylpropanoyl)-5-(4-fluorophenyl)-6-isopropyl-pyrrolo[2,3-f]indazol-7-yl]-3-(oxetan-3-yloxy)benzoate C83 (10 mg, 0.02 mmol) in THF (207 μL) and MeOH (87 μL) was added NaOH (69.3 μL of 1 M, 0.07 mmol). The mixture was stirred at 50° C. for 30 min. Solvent was removed in vacuo and the crude was dissolved in minimal water. HCl was added (69.3 μL of 1 M, 0.07 mmol) and the reaction mixture filtered to afford the product (7.0 mg, 91%). $^1$H NMR (400 MHz, DMSO-d$_6$) δ 13.12 (s, 1H), 12.53 (s, 1H), 7.98 (s, 1H), 7.73 (d, J=7.7 Hz, 1H), 7.67-7.57 (m, 2H), 7.55-7.46 (m, 3H), 7.23 (s, 1H), 7.06 (s, 2H), 5.43-5.35 (m, 1H), 4.86 (dt, J=19.5, 6.7 Hz, 2H), 4.49-4.37 (m, 2H), 3.05 (p, J=7.2 Hz, 1H), 1.08 (t, J=7.7 Hz, 6H). LCMS m/z 586.4 [M+H]$^+$.

Compounds 68-96

Compounds 68-95 (see Table 7) were prepared in a single step from intermediate S8 using the appropriate aryl halide reagent, and using the Suzuki and saponification methods as described for compound 67. Modifications to method are noted in Table 7 and accompanying footnotes.

TABLE 7

Method of preparation, structure, physicochemical data for compounds 68-96

| Compound | Method/Product | Aryl Halide | $^1$H NMR; LCMS m/z [M + H]$^+$ |
|---|---|---|---|
| 68 | 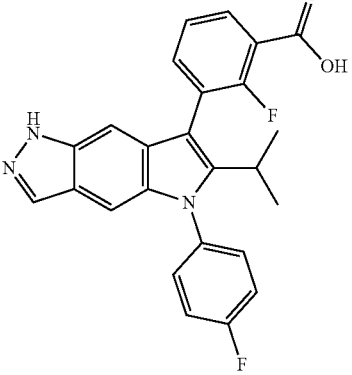<br>Compound 67[4] from S8 | 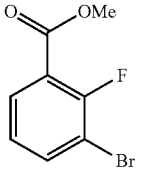 | $^1$H NMR (400 MHz, DMSO-d$_6$) δ 13.34 (s, 1H), 12.55 (s, 1H), 8.00 (s, 1H), 7.94 (t, J = 7.3 Hz, 1H), 7.72 (t, J = 7.1 Hz, 1H), 7.68-7.57 (m, 2H), 7.50 (t, J = 8.5 Hz, 2H), 7.44 (t, J = 7.5 Hz, 1H), 7.10 (s, 1H), 7.05 (s, 1H), 3.01 (p, J = 7.1 Hz, 1H), 1.10 (d, J = 7.1 Hz, 3H), 1.05 (d, J = 7.0 Hz, 3H). LCMS m/z 432.3 [M + H]$^+$. |
| 69 | 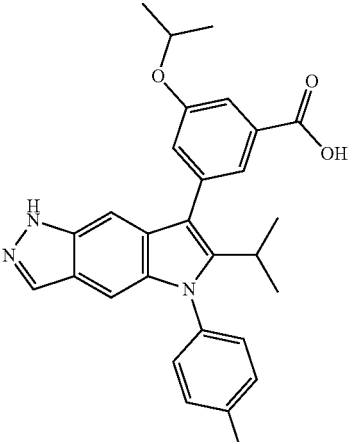<br>Compound 67[4] from S8 | 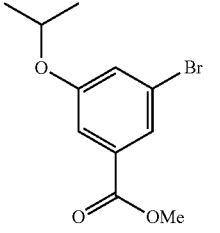 | $^1$H NMR (400 MHz, DMSO-d$_6$) δ 13.10 (s, 1H), 12.56 (s, 1H), 7.99 (s, 1H), 7.66-7.59 (m, 3H), 7.53-7.47 (m, 2H), 7.45 (s, 1H), 7.27 (s, 1H), 7.25-7.21 (m, 1H), 7.06 (s, 1H), 4.74 (p, J = 6.1 Hz, 1H), 3.14 (p, J = 7.1 Hz, 1H), 1.34 (d, J = 5.9, 1.4 Hz, 6H), 1.13 (d, J = 7.1 Hz, 6H). LCMS m/z 472.4 [M + H]$^+$. |

TABLE 7-continued

Method of preparation, structure, physicochemical data for compounds 68-96

| Compound | Method/Product | Aryl Halide | ¹H NMR; LCMS m/z [M + H]⁺ |
|---|---|---|---|
| 70 | 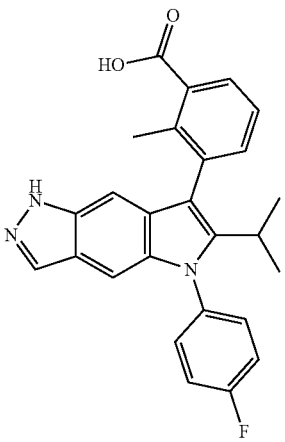<br>Compound 67[1] from S8 | (4-bromo-2-methylbenzoic acid methyl ester) | ¹H NMR (400 MHz, Methanol-d₄) δ 8.06 (s, 1H), 7.98-7.90 (m, 2H), 7.56-7.48 (m, 2H), 7.45 (d, J = 7.8 Hz, 1H), 7.38 (t, J = 8.5 Hz, 2H), 7.16 (s, 1H), 6.97 (s, 1H), 3.00 (hept, J = 6.7, 6.0 Hz, 1H), 2.65 (impurity), 2.23 (s, 3H), 1.17 (dd, J = 7.2, 1.4 Hz, 3H), 1.02 (dd, J = 7.1, 1.4 Hz, 3H). LCMS m/z 428.6 [M + H]⁺. |
| 71 | Compound 67[1,2,3] from S8 | (methyl 3-bromo-2-methylbenzoate) | ¹H NMR (400 MHz, Methanol-d₄) δ 7.96 (s, 1H), 7.92-7.85 (m, 1H), 7.56-7.47 (m, 3H), 7.42-7.34 (m, 3H), 7.15 (s, 1H), 6.97 (s, 1H), 2.99 (dq, J = 15.4, 7.6 Hz, 1H), 2.37 (s, 3H), 1.15 (d, J = 7.0 Hz, 3H), 1.02 (d, J = 7.1 Hz, 3H). LCMS m/z 428.3 [M + H]⁺. |
| 72 | 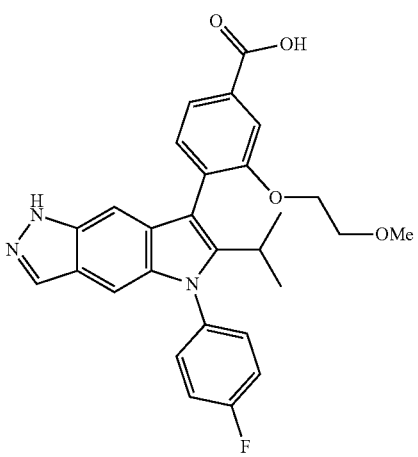<br>Compound 67[3,4,5] from S8 | (methyl 4-bromo-3-(2-methoxyethoxy)benzoate) | ¹H NMR (400 MHz, DMSO-d₆) δ 13.06 (s, 1H), 12.51 (s, 1H), 7.97 (s, 1H), 7.68 (d, J = 7.1 Hz, 2H), 7.63-7.44 (m, 5H), 7.04 (s, 1H), 7.01 (s, 1H), 4.22-4.08 (m, 2H), 3.55-3.43 (m, 2H), 3.09-2.96 (m, 4H), 1.05 (dd, J = 14.7, 7.0 Hz, 6H).LCMS m/z 488.5 [M + H]⁺. |

TABLE 7-continued

Method of preparation, structure, physicochemical data for compounds 68-96

| Compound | Method/Product | Aryl Halide | ¹H NMR; LCMS m/z [M + H]⁺ |
|---|---|---|---|
| 73 | 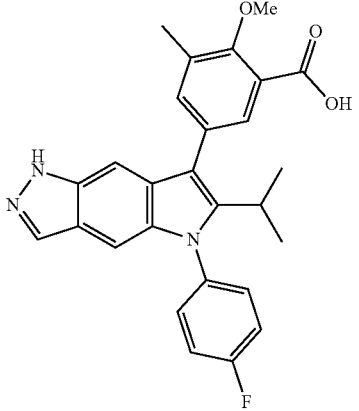<br>Compound 67[6] from S8 | 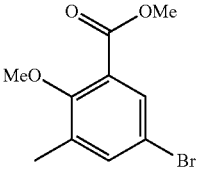 | ¹H NMR (400 MHz, DMSO-d₆) δ 12.94 (s, 1H), 12.55 (s, 1H), 7.98 (s, 1H), 7.64-7.56 (m, 3H), 7.54-7.45 (m, 3H), 7.25 (s, 1H), 7.04 (s, 1H), 3.84 (s, 3H), 3.12 (p, J = 7.2 Hz, 1H), 2.36 (s, 3H), 1.12 (d, J = 7.0 Hz, 6H). LCMS m/z [M + H]⁺ 458.4. |
| 74 | 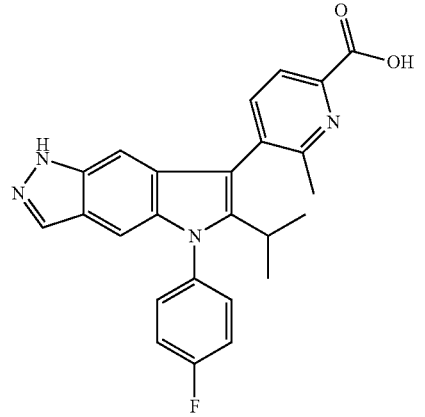<br>Compound 67[12] from S8 | 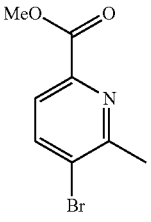 | ¹H NMR (400 MHz, DMSO-d₆) δ 13.14 (s, 1H), 12.57 (s, 1H), 8.02 (d, J = 6.8 Hz, 2H), 7.91 (d, J = 7.8 Hz, 1H), 7.68-7.60 (m, 2H), 7.56-7.46 (m, 2H), 7.16 (s, 1H), 6.90 (s, 1H), 2.93 (hept, J = 8.9, 8.2 Hz, 1H), 2.40 (s, 3H), 1.10 (d, J = 7.0 Hz, 3H), 0.95 (d, J = 7.1 Hz, 3H). LCMS m/z 429.4 [M + H]⁺. |
| 75 | 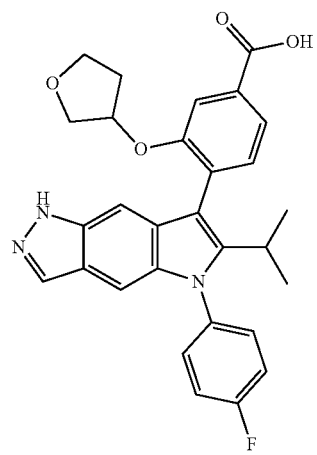<br>Compound 67[7,8] from S8 | 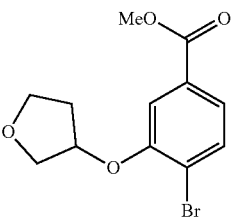 [SMILES: COC(=O)c1ccc(Br)c(OC2CCOC2)c1] | ¹H NMR (400 MHz, DMSO-d₆) δ 12.52 (s, 1H), 7.97 (s, 1H), 7.69 (d, J = 7.7 Hz, 1H), 7.65 (d, J = 4.8 Hz, 1H), 7.62-7.53 (m, 2H), 7.52-7.45 (m, 3H), 7.04 (d, J = 4.6 Hz, 1H), 7.00 (d, J = 8.9 Hz, 1H), 5.14-5.04 (m, 1H), 3.87-3.77 (m, 1H), 3.64-3.49 (m, 3H), 3.07-2.96 (m, 1H), 2.22-2.03 (m, 2H), 1.88-1.74 (m, 1H), 1.12 - 0.99 (m, 6H). LCMS m/z 500.4 [M + H]⁺. |

TABLE 7-continued

Method of preparation, structure, physicochemical data for compounds 68-96

| Compound | Method/Product | Aryl Halide | ¹H NMR; LCMS m/z [M + H]⁺ |
|---|---|---|---|
| 76 | 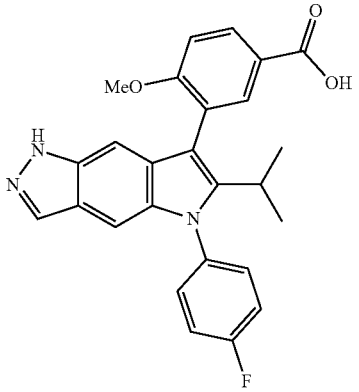<br>Compound 67[1] from S8 | 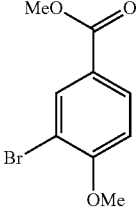 | ¹H NMR (400 MHz, MeOD) δ 7.88-7.78 (m, 2H), 7.65 (s, 1H), 7.24-7.14 (m, 2H), 7.01 (t, J = 8.3 Hz, 2H), 6.88-6.80 (m, 3H), 3.56 (s, 3H), 2.74 (dq, J = 14.0, 7.1 Hz, 1H), 0.83 (d, J = 7.1 Hz, 3H), 0.76 (d, J = 7.1 Hz, 3H). LCMS m/z 444.3 [M + H]⁺. |
| 77 | 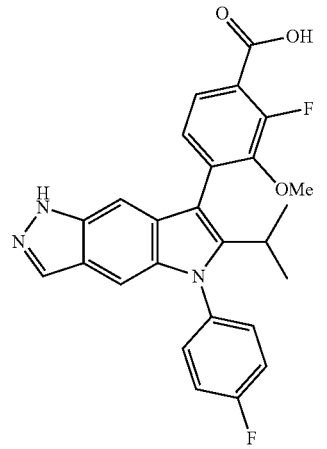<br>Compound 67[3,9] from S8 | 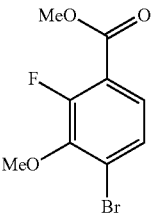 | ¹H NMR (400 MHz, DMSO-d₆) δ 13.17 (s, 1H), 12.56 (s, 1H), 7.99 (s, 1H), 7.68 (t, J = 7.6 Hz, 1H), 7.61 (dd, J = 8.1, 5.0 Hz, 2H), 7.50 (t, J = 8.4 Hz, 2H), 7.29 (d, J = 8.1 Hz, 1H), 7.11 (s, 1H), 7.07 (s, 1H), 3.59 (s, 3H), 3.04 (hept, J = 7.5 Hz, 1H), 1.08 (dd, J = 11.4, 7.1 Hz, 6H). LCMS m/z 462.4 [M + H]⁺. |
| 78 | 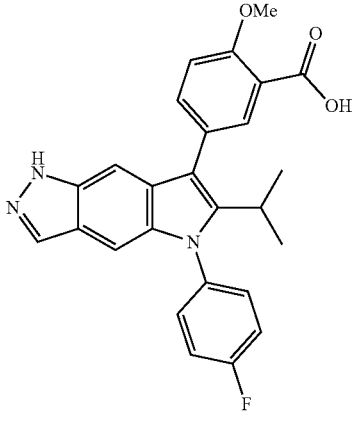<br>Compound 67[8] from S8 | 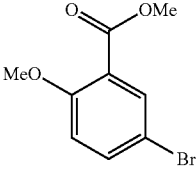 | ¹H NMR (400 MHz, DMSO-d₆) δ 12.56 (s, 1H), 7.98 (s, 1H), 7.74 (s, 1H), 7.65-7.56 (m, 3H), 7.49 (t, J = 8.4 Hz, 2H), 7.28 (d, J = 8.5 Hz, 1H), 7.21 (s, 1H), 7.05 (s, 1H), 3.91 (s, 3H), 3.09 (p, J = 7.3 Hz, 1H), 1.11 (d, J = 7.0 Hz, 6H). LCMS MS m/z 444.4 [M + H]⁺. |

TABLE 7-continued

Method of preparation, structure, physicochemical data for compounds 68-96

| Compound | Method/Product | Aryl Halide | ¹H NMR; LCMS m/z [M + H]⁺ |
|---|---|---|---|
| 79 | 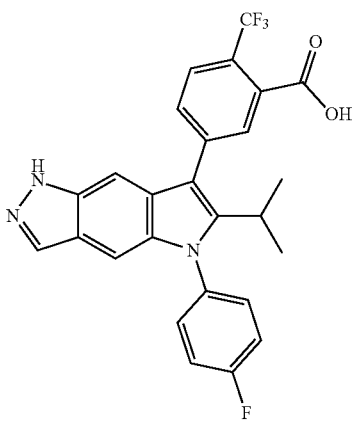<br>Compound 67[7] from S8 | 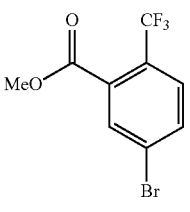 [SMILES: COC(=O)c1cc(Br)ccc1C(F)(F)F] | ¹H NMR (400 MHz, DMSO-d₆) δ 13.72 (s, 1H), 12.62 (s, 1H), 8.03-7.97 (m, 2H), 7.92 (s, 1H), 7.85 (d, J = 8.2 Hz, 1H), 7.67-7.60 (m, 2H), 7.55-7.47 (m, 2H), 7.34 (s, 1H), 7.08 (s, 1H), 3.18 (p, J = 7.2 Hz, 1H), 1.14 (d, J = 7.1 Hz, 6H). LCMS m/z 482.4 [M + H]⁺. |
| 80 | 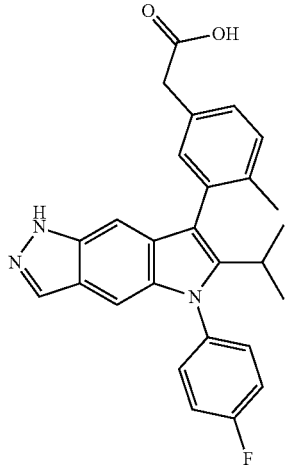<br>Compound 67[1,3] from S8 | 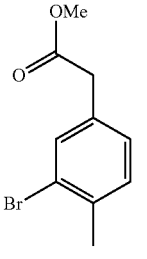 | ¹H NMR (400 MHz, Methanol-d₄) δ 7.96 (s, 1H), 7.54-7.46 (m, 2H), 7.41-7.25 (m, 5H), 7.14 (s, 1H), 6.99 (s, 1H), 3.62 (s, 2H), 2.99 (dq, J = 13.9, 7.2 Hz, 1H), 2.14 (s, 3H), 1.17 (d, J = 7.0 Hz, 3H), 1.00 (d, J = 7.1 Hz, 3H). LCMS m/z 442.4 [M + H]⁺. |
| 81 | 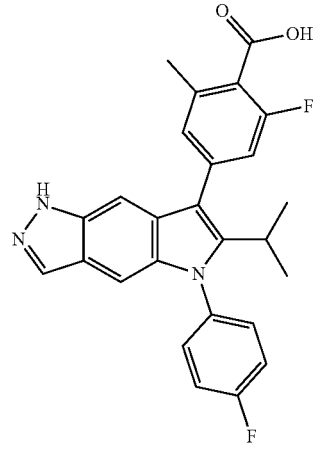<br>Compound 67[5] from S8 | 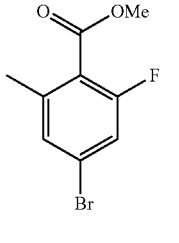 | ¹H NMR (400 MHz, DMSO-d₆) δ 12.58 (s, 1H), 8.27 (d, J = 1.8 Hz, 1H), 7.97 (s, 1H), 7.63-7.56 (m, 2H), 7.48 (t, J = 8.5 Hz, 2H), 7.27 (s, 1H), 7.03 (d, J = 4.5 Hz, 2H), 6.94 (d, J = 9.9 Hz, 1H), 3.16-3.13 (m, 1H), 2.33 (s, 3H), 1.13 (d, J = 7.1 Hz, 6H). LCMS m/z 446.4 [M + H]⁺. |

TABLE 7-continued

Method of preparation, structure, physicochemical data for compounds 68-96

| Compound | Method/Product | Aryl Halide | ¹H NMR; LCMS m/z [M + H]⁺ |
|---|---|---|---|
| 82 | 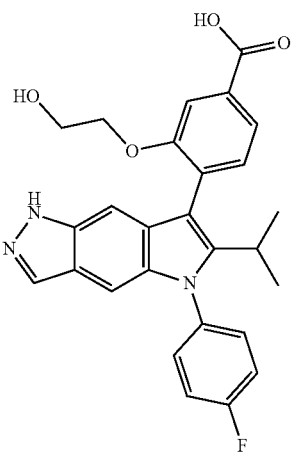<br>Compound 67[3,9] from S8 | 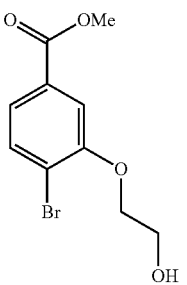 [SMILES: COC(=O)c1ccc(Br)c(OCCO)c1] | ¹H NMR (400 MHz, Chloroform-d) δ 7.98 (s, 1H), 7.95-7.79 (m, 2H), 7.50-7.37 (m, 3H), 7.33-7.17 (m, 3H), 7.09 (s, 1H), 4.20-4.03 (m, 2H), 3.76-3.59 (m, 2H), 3.17-3.02 (m, 1H), 1.09 (dd, J = 15.2, 6.9 Hz, 6H). LCMS m/z 474.4 [M + H]⁺. |
| 83 | 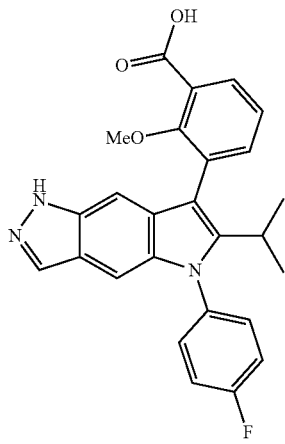<br>Compound 67[6] from S8 | 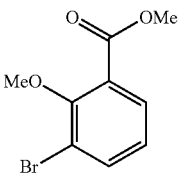 [SMILES: COC(=O)c1cccc(Br)c1OC] | ¹H NMR (400 MHz, DMSO-d₆) δ 12.97 (s, 1H), 12.53 (s, 1H), 7.98 (s, 1H), 7.71 (d, J = 7.6 Hz, 1H), 7.64-7.56 (m, 2H), 7.55-7.46 (m, 3H), 7.31 (t, J = 7.6 Hz, 1H), 7.06 (d, J = 11.2 Hz, 2H), 3.41 (s, 3H), 3.05 (p, J = 7.1 Hz, 1H), 1.11-1.03 (m, 6H). LCMS m/z 444.4 [M + H]⁺. |
| 84 | 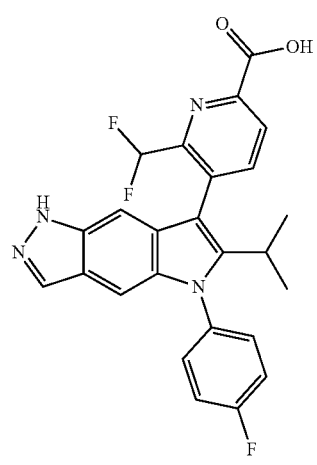<br>Compound 67[3] from S8 | 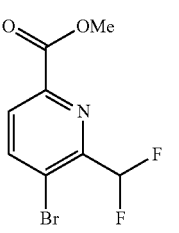 [SMILES: COC(=O)c1ccc(Br)c(C(F)F)n1] | ¹H NMR (400 MHz, Methanol-d₄) δ 8.38 (d, J = 8.0 Hz, 1H), 8.12 (d, J = 8.1 Hz, 1H), 8.00 (s, 1H), 7.61-7.53 (m, 2H), 7.41 (t, J = 8.0 Hz, 2H), 7.19 (s, 1H), 7.03 (s, 1H), 6.69 (t, J = 53.9 Hz, 1H), 3.03 (dq, J = 13.4, 6.6, 6.1 Hz, 1H), 1.09 (dd, J = 44.3, 7.1 Hz, 6H). LCMS m/z 465.2 [M + H]⁺. |

TABLE 7-continued

Method of preparation, structure, physicochemical data for compounds 68-96

| Compound | Method/Product | Aryl Halide | $^1$H NMR; LCMS m/z [M + H]$^+$ |
|---|---|---|---|
| 85 | 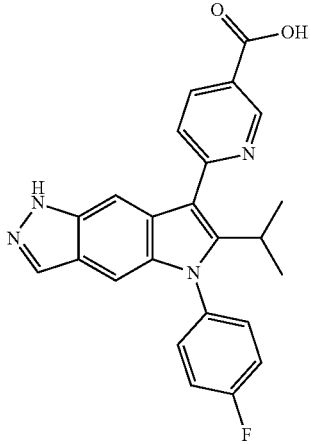<br>Compound 67$^{12}$ from S8 | 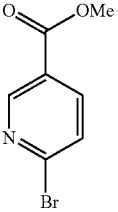 [SMILES: COC(=O)c1ccc(Br)nc1] | $^1$H NMR (400 MHz, DMSO-d$_6$) δ 13.31 (s, 1H), 12.68 (s, 1H), 9.22 (s, 1H), 8.39 (d, J = 8.3 Hz, 1H), 8.01 (s, 1H), 7.83 (d, J = 8.2 Hz, 1H), 7.72 (s, 1H), 7.63 (t, J = 6.0 Hz, 2H), 7.51 (t, J = 8.6 Hz, 3H), 7.06 (s, 1H), 1.21 (d, J = 7.1 Hz, 6H). LCMS m/z 415.3 [M + H]$^+$. |
| 86 | 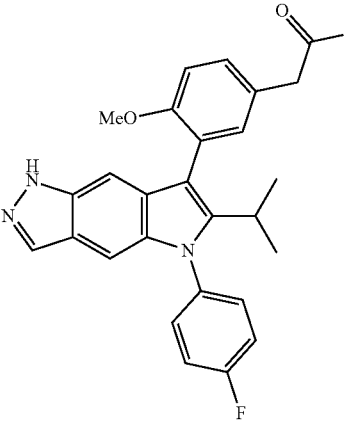<br>Compound 67$^{1,3}$ from S8 | 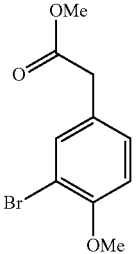 | $^1$H NMR (400 MHz, Methanol-d$_4$) δ 7.72 (s, 1H), 7.49 (s, 2H), 7.37-7.30 (m, 4H), 7.21-7.03 (m, 3H), 3.76 (s, 3H), 3.37 (s, 2H), 3.10-3.02 (m, 1H), 1.13 (d, J = 6.9 Hz, 3H), 1.06 (d, J = 6.9 Hz, 3H). LCMS m/z 458.4 [M + H]$^+$. |
| 87 | 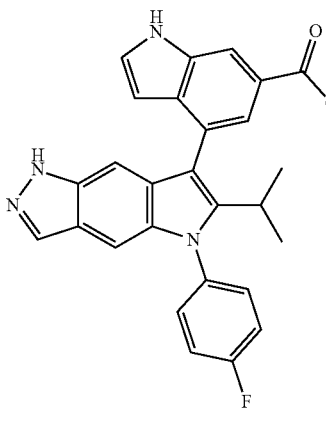<br>Compound 67$^{13}$ from S8 | 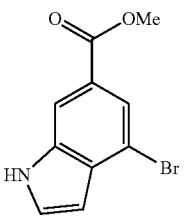 [SMILES: COC(=O)c1cc(Br)c2cc[nH]c2c1] | $^1$H NMR (400 MHz, DMSO-d$_6$) δ 12.63 (s, 1H), 12.44 (s, 1H), 11.58 (s, 1H), 8.11 (t, J = 1.2 Hz, 1H), 7.98 (d, J = 1.0 Hz, 1H), 7.73-7.63 (m, 3H), 7.55 (t, J = 2.8 Hz, 1H), 7.50 (t, J = 8.7 Hz, 2H), 7.09 (d, J = 1.1 Hz, 1H), 6.97 (t, J = 1.1 Hz, 1H), 6.23-6.17 (m, 1H), 3.08 (p, J = 7.1 Hz, 1H), 1.12 (d, J = 7.1 Hz, 3H), 0.98 (d, J = 7.1 Hz, 3H). LCMS m/z 453.4 [M + H]$^+$. |

TABLE 7-continued

Method of preparation, structure, physicochemical data for compounds 68-96

| Compound | Method/Product | Aryl Halide | $^1$H NMR; LCMS m/z [M + H]$^+$ |
|---|---|---|---|
| 88 | 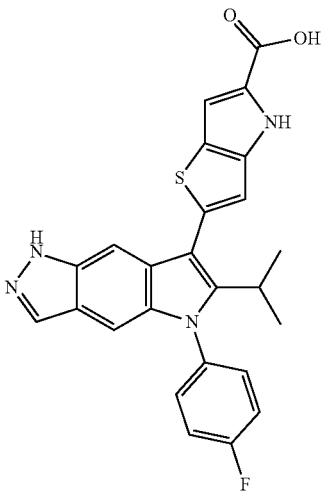<br>Compound 67$^{11}$ from S8 | 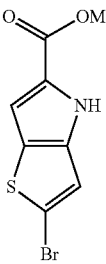 | $^1$H NMR (400 MHz, DMSO-d$_6$) δ 12.64 (s, 1H), 12.55 (br s, 1H), 11.93 (s, 1H), 8.00 (s, 1H), 7.63 (dd, J = 8.8, 5.0 Hz, 2H), 7.54-7.46 (m, 3H), 7.09 (s, 1H), 7.06 (d, J = 1.1 Hz, 1H), 7.01 (d, J = 0.7 Hz, 1H), 3.25 (sept, J = 7.1 Hz, 1H), 1.20 (d, J = 7.2 Hz, 6H). LCMS m/z 473.3 [M + H]$^+$. |
| 89 | 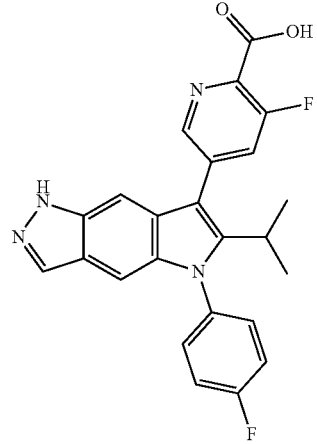<br>Compound 67$^{89}$ from S8 | 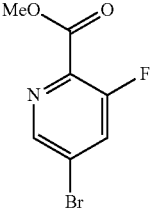 [SMILES: COC(=O)c1ncc(Br)cc1F] | $^1$H NMR (400 MHz, DMSO-d$_6$) δ 13.59 (s, 1H), 12.67 (s, 1H), 8.65 (s, 1H), 8.07-7.96 (m, 2H), 7.67-7.58 (m, 2H), 7.52 (t, J = 8.6 Hz, 2H), 7.38 (s, 1H), 7.09 (s, 1H), 3.23-3.12 (m, 1H), 1.14 (d, J = 7.1 Hz, 6H). LCMS m/z 433.3 [M + H]$^+$. |
| 90 | 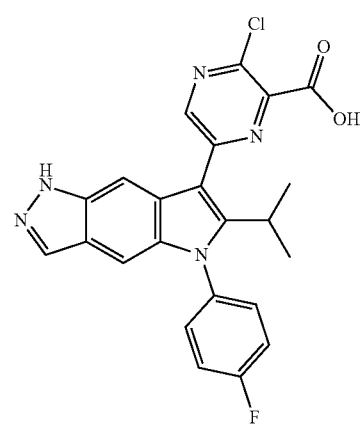<br>Compound 67$^1$ from S8 | 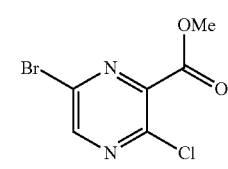 | $^1$H NMR (400 MHz, DMSO-d$_6$) δ 14.34 (s, 1H), 12.76 (s, 1H), 8.92 (s, 1H), 8.03 (s, 1H), 7.78 (s, 1H), 7.67-7.60 (m, 2H), 7.53 (t, J = 8.4 Hz, 2H), 7.10 (s, 1H), 3.30-3.26 (m, 1H), 1.21 (d, J = 7.1 Hz, 6H). LCMS m/z 450.3 [M + H]$^+$. |

TABLE 7-continued

Method of preparation, structure, physicochemical data for compounds 68-96

| Compound | Method/Product | Aryl Halide | 1H NMR; LCMS m/z [M + H]+ |
|---|---|---|---|
| 91 | 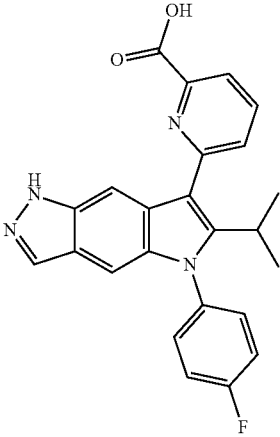<br>Compound 67[12] from S8 | 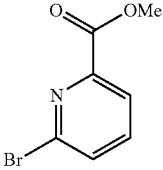 | 1H NMR (400 MHz, DMSO-d6) δ 13.16 (s, 1H), 12.65 (s, 1H), 8.11 (t, J = 7.7 Hz, 1H), 8.05-7.96 (m, 2H), 7.90 (d, 1H), 7.67-7.58 (m, 3H), 7.52 (t, J = 8.5 Hz, 2H), 7.08 (s, 1H), 3.27-3.19 (m, 1H), 1.22 (d, J = 7.1 Hz, 6H). LCMS m/z 415.4 [M + H]+. |
| 92 | 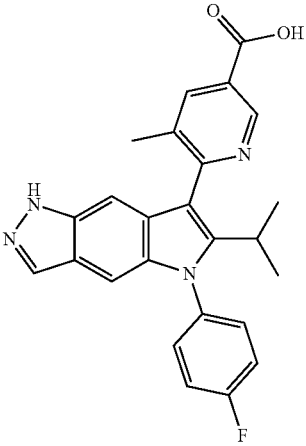<br>Compound 67[8] from S8 | 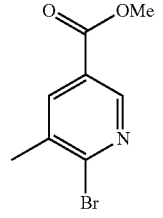 | 1H NMR (400 MHz, DMSO-d6) δ 13.39 (s, 1H), 12.54 (s, 1H), 9.02 (s, 1H), 8.28 (s, 1H), 8.00 (s, 1H), 7.67-7.57 (m, 2H), 7.55-7.45 (m, 2H), 7.15 (s, 1H), 6.92 (s, 1H), 2.93 (p, J = 7.2 Hz, 1H), 2.26 (s, 3H), 1.18 (d, J = 6.9 Hz, 3H), 0.87 (d, J = 7.0 Hz, 3H). LCMS m/z 429.4 [M + H]+. |
| 93 | 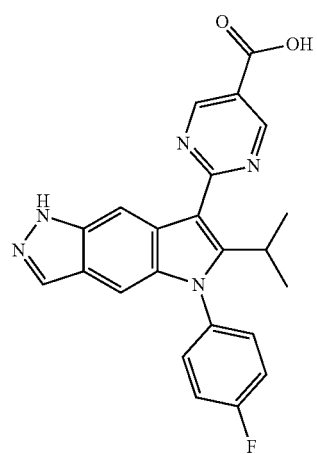<br>Compound 67[8] from S8 | 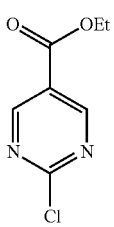 | 1H NMR (400 MHz, Methanol-d4) δ 9.32 (s, 2H), 8.71 (s, 1H), 7.99 (s, 1H), 7.59-7.51 (m, 2H), 7.42 (t, J = 8.1 Hz, 2H), 7.06 (s, 1H), 4.22-4.10 (m, 1H), 1.36 (d, J = 7.1 Hz, 6H). LCMS m/z 416.4 [M + H]+. |

TABLE 7-continued
Method of preparation, structure, physicochemical data for compounds 68-96
| Compound | Method/Product | Aryl Halide | ¹H NMR; LCMS m/z [M + H]⁺ |
|---|---|---|---|
| 94 | 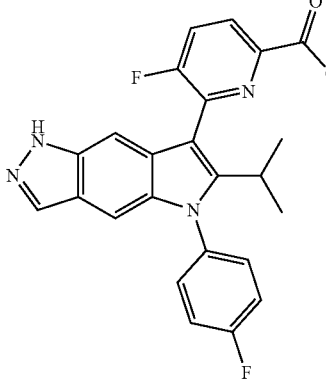<br>Compound 67[12] from S8 | 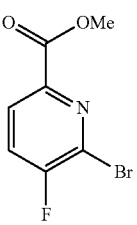 [SMILES: COC(=O)c1ccc(F)c(Br)n1] | ¹H NMR (400 MHz, DMSO-d₆) δ 13.30 (s, 1H), 12.62 (s, 1H), 8.16 (dd, J = 8.6, 3.7 Hz, 1H), 8.05 (d, J = 9.1 Hz, 1H), 8.01 (s, 1H), 7.64 (dd, J = 8.3, 5.0 Hz, 2H), 7.52 (t, J = 8.4 Hz, 2H), 7.27 (s, 1H), 7.12 (s, 1H), 3.04 (hept, J = 6.7, 6.2 Hz, 1H), 1.14 (d, J = 7.0 Hz, 6H). LCMS m/z 433.3 [M + H]⁺. |
| 95 | 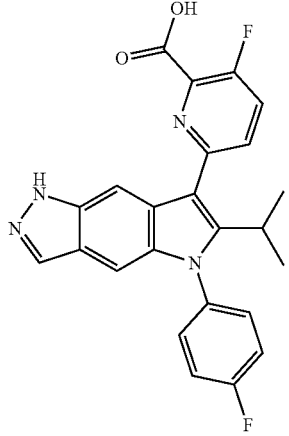<br>Compound 67[12] from S8 | 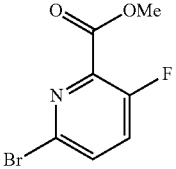 | ¹H NMR (400 MHz, DMSO-d₆) δ 13.59 (s, 1H), 12.67 (s, 1H), 8.05-7.97 (m, 2H), 7.97-7.89 (m, 1H), 7.66-7.56 (m, 3H), 7.51 (t, J = 8.5 Hz, 2H), 7.08 (s, 1H), 3.27-3.13 (m, 1H), 1.20 (d, J = 7.0 Hz, 6H). LCMS m/z 433.5 [M + H]⁺. |

TABLE 7-continued

Method of preparation, structure, physicochemical data for compounds 68-96

| Compound | Method/Product | Aryl Halide | $^1$H NMR; LCMS m/z [M + H]$^+$ |
|---|---|---|---|
| 96 | 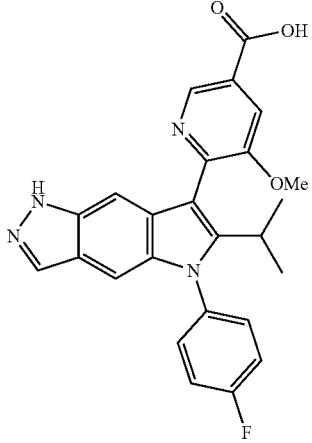Compound 67[8] from S8 | 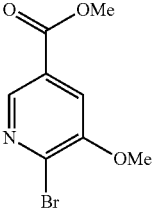 [SMILES: COC(=O)c1cnc(Br)c(OC)c1] | $^1$H NMR (400 MHz, Methanol-d$_4$) δ 8.84 (s, 1H), 8.09 (s, 1H), 7.96 (s, 1H), 7.58-7.50 (m, 2H), 7.39 (t, J = 8.3 Hz, 2H), 7.13 (d, J = 11.7 Hz, 2H), 3.90 (s, 3H), 3.06 (p, J = 7.2 Hz, 1H), 1.10 (d, J = 7.1 Hz, 6H). LCMS m/z 445.4 [M + H]$^+$. |

[1] Compounds 70, 71, 76, 80, 86, 90: Purification by reversed-phase HPLC. Method: C18 Waters Sunfire column (30 x 150 mm, 5 micron). Gradient: 10-100% MeCN in H$_2$O afforded product in step 1.
[2] Compounds 71, 76: A second eq. of NaOH was added and the reaction was run overnight in step 2. Purification by reverse phase column chromatography (Eluent: 10-100% acetonitrile in water with 0.2% Formic Acid modifier) afforded the desired product in step 2.
[3] Compound 72, 76, 77, 80, 81, 82, 84, 86, 88: Purification by reverse phase column chromatography (Eluent: 10-100% acetonitrile in water with 0.2% Formic Acid modifier) afforded the desired product in step 2.
[4] Compounds 70, 72: NMR showed atropisomers.
[5] Compound 72: Purification by silica gel column chromatography of (Eluent: 0-40% ethyl acetate in heptane) afforded the product in step 1.
[6] Compound 73, 83: Purification by silica gel column chromatography (Eluent: 0-80% DCM in heptane) afforded the product in step 1.
[7] Compound 75, 79: Purification by silica gel column chromatography (Eluent: 0-100% CH$_2$Cl$_2$ in heptane) afforded the product in step 1.
[8] Compound 75, 78, 92, 93, 96: Purification by reverse phase column chromatography (Eluent: acetonitrile in water with 0.1% formic acid modifier) afforded the desired product in step 2.
[9] Compound 77, 82: Organics were passed through a silica gel plug, using dichloromethane and ethyl acetate as eluents instead of column chromatography for purification in step 1.
[10] Purification by silica gel column chromatography (Eluent: 0-100% EtOAc:heptane) afforded the product in step 1.
[11] Compound 88: Upon completion of step 2 HCl 1M and CHCl$_3$:IPA (3:1) was added, and the mixture was extracted with CHCl$_3$:IPA (3:1, 3 x). The organic phases were combined, dried with MgSO$_4$, filtered, and the volatiles were evaporated in vacuo to afford the product.
[12] Compound 74, 85, 89, 91, 94, 95: Purification by reversed-phase HPLC. Method: C18 Waters Sunfire column (30 x 150 mm, 5 micron). Gradient: 10-100% MeCN in H$_2$O afforded the product in step 2.
[13] Compound 87: After addition of HCl in step 2 added water and extracted with ethyl acetate. Dried organic layer with sodium sulfate, filtered and removed solvent in vacuo.

Compound 97

2-fluoro-4-[5-(4-fluorophenyl)-6-isopropyl-1H-pyrrolo[2,3-f]indazol-7-yl]benzoic Acid (97)

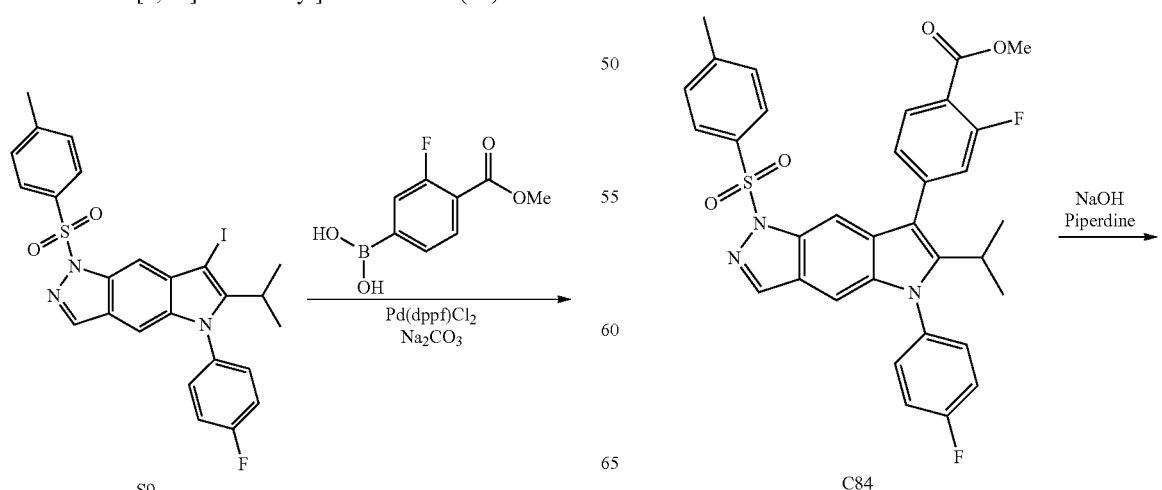

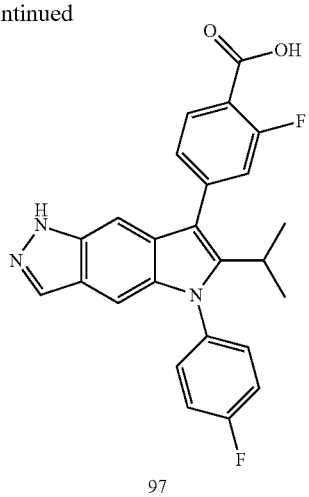

97

Step 1: Methyl 2-fluoro-4-[5-(4-fluorophenyl)-6-isopropyl-1-(p-tolylsulfonyl)pyrrolo[2,3-f]indazol-7-yl]benzoate 5-(4-fluorophenyl)-6-isopropyl-1-(p-tolylsulfonyl)pyrrolo[2,3-f]indazole (C84)

To a solution of 5-(4-fluorophenyl)-7-iodo-6-isopropyl-1-(p-tolylsulfonyl)pyrrolo[2,3-f]indazole (200 mg, 0.34 mmol) S9, and Pd(dppf)Cl$_2$ (15 mg, 0.018 mmol) in 1,4-dioxane (5 mL) under nitrogen was added sodium carbonate (approximately 488.8 μL of 2 M, 0.98 mmol). Nitrogen was run through the reaction mixture for 10 min. The reaction was heated at 100° C. for 60 min in a microwave reactor. Further boronic acid (50 mgs), Pd(dppf)Cl$_2$ (15 mg), and sodium carbonate (approximately 0.3 mL of 2 M solution) were added to the solution and heated to 110° C. for one h in a microwave reactor. Water and EtOAc were added and the mixture was extracted with EtOAc (×3). The organic layer was collected, dried with Na$_2$SO$_4$, filtered, and the solvent was removed in vacuo. Purification by silica gel column chromatography (Gradient: 0-100% dichloromethane in heptane, followed by Gradient: 0-20% EtOAc in dichloromethane) afforded the product (154 mg, 70%). LCMS m/z 600.5 [M+H]$^+$.

Step 2: 2-fluoro-4-[5-(4-fluorophenyl)-6-isopropyl-1H-pyrrolo[2,3-f]indazol-7-yl]benzoic Acid (97)

To a solution of 2-fluoro-4-[5-(4-fluorophenyl)-6-isopropyl-1-(p-tolylsulfonyl)pyrrolo[2,3-f]indazol-7-yl]benzoate C84 (154 mg, 0.26 mmol) in THF (4 mL) and MeOH (2 mL) was added piperidine (51 μL, 0.52 mmol) and NaOH (1.3 mL of 1 M, 1.3 mmol). The solution was heated to 50° C. for 90 min. The solvent was removed in vacuo and 1M HCl (1.6 mL) was added. The solution was extracted with dichloromethane (×3). The organic layer was collected, dried with Na$_2$SO$_4$, filtered, and the solvent was removed in vacuo. Purification by silica gel column chromatography (Eluent: 0-6% methanol in dichloromethane) afforded the product (52 mg, 43%). $^1$H NMR (300 MHz, DMSO-d$_6$) δ 13.21 (s, 1H), 12.61 (s, 1H), 8.16-7.87 (m, 2H), 7.61 (ddt, J=8.5, 5.6, 2.8 Hz, 2H), 7.56-7.37 (m, 4H), 7.35 (t, J=1.1 Hz, 1H), 7.06 (d, J=1.1 Hz, 1H), 3.18 (q, J=7.2 Hz, 1H), 1.14 (d, J=7.2 Hz, 6H). LCMS m/z 432.3 [M+H]$^+$.

Compounds 98-99

Compounds 98-99 (see Table 8) were prepared in two steps from intermediate S9 using the appropriate boronic acid reagent, and using the coupling and deprotection method as described for compound 97. Modifications to method are noted in Table 8 and accompanying footnotes.

TABLE 8

Method of preparation, structure, physicochemical data for compounds 98-99

| Compound | Method/Product | Boronic Acid | $^1$H NMR; LCMS m/z [M + H]$^+$ |
|---|---|---|---|
| 98 | Compound 97[1] from S9 (structure shown) | (structure shown) | $^1$H NMR (300 MHz, DMSO-d$_6$) δ 13.91 (s, 1H), 12.62 (s, 1H), 8.01 (d, J = 1.0 Hz, 1H), 7.63-7.57 (m, 2H), 7.50 (dd, J = 9.9, 7.6 Hz, 2H), 7.37 (t, J = 1.1 Hz, 1H), 7.31 (d, J = 9.2Hz, 2H), 7.06 (d, J = 1.1 Hz, 1H), 3.19 (p, J = 6.9 Hz, 1H), 1.14 (d, J = 7.2 Hz, 6H). LCMS m/z 450.3 [M + H]$^+$. |

TABLE 8-continued

Method of preparation, structure, physicochemical data for compounds 98-99

| Compound | Method/Product | Boronic Acid | $^1$H NMR; LCMS m/z [M + H]$^+$ |
|---|---|---|---|
| 99 | Compound 97$^2$ from S9 | | $^1$H NMR (300 MHz, DMSO-$d_6$) δ 12.66 (s, 1H), 8.78 (dd, J = 2.2, 0.9 Hz, 1H), 8.18 (dd, J = 8.0, 0.8 Hz, 1H), 8.07 (dd, J = 8.0, 2.2 Hz, 1H), 8.01 (d, J = 1.0 Hz, 1H), 7.63 (ddt, J = 8.4, 5.6, 2.8 Hz, 2H), 7.57 – 7.41 (m, 2H), 7.31 (t, J = 1.1 Hz, 1H), 7.09 (d, J = 1.1 Hz, 1H), 3.14 (p, J = 7.1 Hz, 1H), 1.13 (d, J = 7.2 Hz, 6H). LCMS m/z 415.3 [M + H]$^+$. |

$^1$Purification by silica gel column chromatography in step 2 (Gradient: 0-10% methanol: dichloromethane) afforded the product.

$^2$Purification by silica gel column chromatography (Solvent A: 20% MeOH in CH$_2$Cl$_2$ (containing 7 M NH$_3$ in MeOH). Solvent B: MeOH (containing 7 M NH$_3$). Gradient: 0-90% solvent A: solvent B) afforded the product.

Compound 100

2-[4-[5-(4-fluorophenyl)-6-isopropyl-1H-pyrrolo[2,3-f]indazol-7-yl]phenoxy]acetic Acid (100)

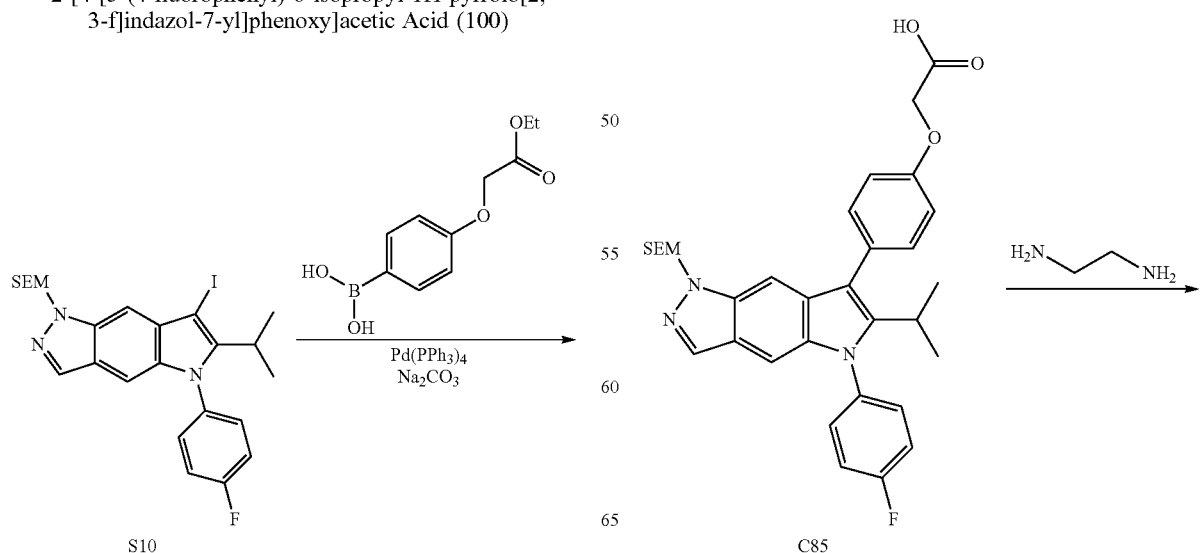

-continued

531
-continued

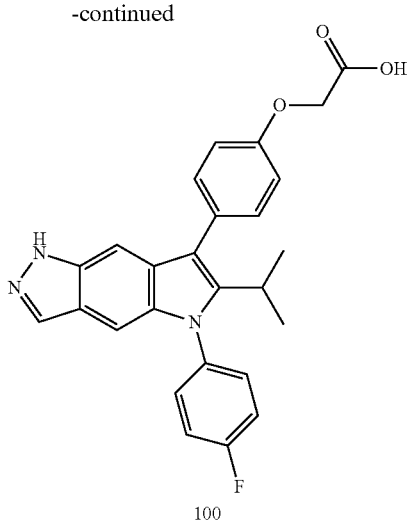

100

Step 1: 2-[4-[5-(4-fluorophenyl)-6-isopropyl-1-(2-trimethylsilylethoxymethyl)pyrrolo[2,3-f]indazol-7-yl]phenoxy]acetic Acid (C85)

To a solution of 2-[[5-(4-fluorophenyl)-7-iodo-6-isopropyl-pyrrolo[2,3-f]indazol-1-yl]methoxy]ethyl-trimethyl-silane S10 (100 mg, 0.18 mmol), [4-(2-ethoxy-2-oxo-ethoxy)phenyl]boronic acid (80 mg, 0.4 mmol), and Pd(PPh$_3$)$_4$ (10 mg, 0.009 mmol) in DMF (1.8 mL) was added Na$_2$CO$_3$ (450 μL of 2 M, 0.9 mmol). The reaction was heated at 125° C. for 60 min. The reaction was diluted in dichloromethane and water, and further extracted with dichloromethane (×3). The organic phase was collected through a phase separator and the solvent was removed in vacuo. Purification by reverse phase column chromatography (Eluent: acetonitrile in water with 0.1% Formic Acid modifier) afforded the desired product along with some of compound 100 (deprotected compound). The mixture was used in the next step without separation. LCMS m/z 574.3 [M+H]$^+$.

Step 2: 2-[4-[5-(4-fluorophenyl)-6-isopropyl-1H-pyrrolo[2,3-f]indazol-7-yl]phenoxy]acetic Acid (100)

To a solution of 2-[4-[5-(4-fluorophenyl)-6-isopropyl-1-(2-trimethylsilylethoxymethyl)pyrrolo[2,3-f]indazol-7-yl]phenoxy]acetic acid (C85 crude from step 1) in THF (1 mL) was added ethane-1,2-diamine (62 μL, 0.93 mmol). The reaction was stirred for 2 h at room temperature. Water and dichloromethane were added and the solution was extracted with dichloromethane (×3). The organic phase was collected through a phase separator and the solvent was removed in vacuo. Purification by reverse phase column chromatography (Eluent: 0%-40% acetonitrile in water with 0.2% formic acid modifier) afforded the product (23.5 mg, 28%). $^1$H NMR (400 MHz, Methanol-d$_4$) δ 7.94 (s, 1H), 7.48 (m, 2H), 7.38 (m, 4H), 7.25 (s, 1H), 7.08 (m, 3H), 4.73 (d, J=1.6 Hz, 2H), 3.13 (septet, J=7.3 Hz, 1H), 1.14 (d, J=7.2 Hz, 6H). LCMS m/z 444.2 [M+H]$^+$.

532

Compound 101

3-fluoro-5-[5-(4-fluorophenyl)-6-isopropyl-1H-pyrrolo[2,3-f]indazol-7-yl]benzoic Acid (101)

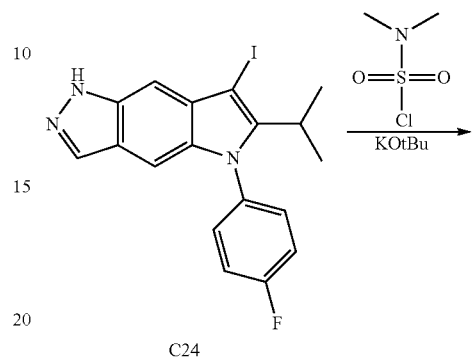

C24

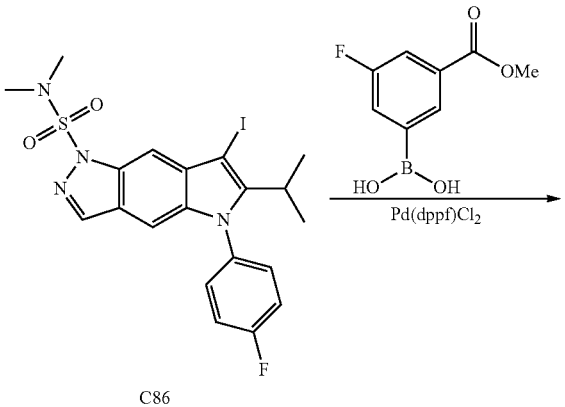

C86

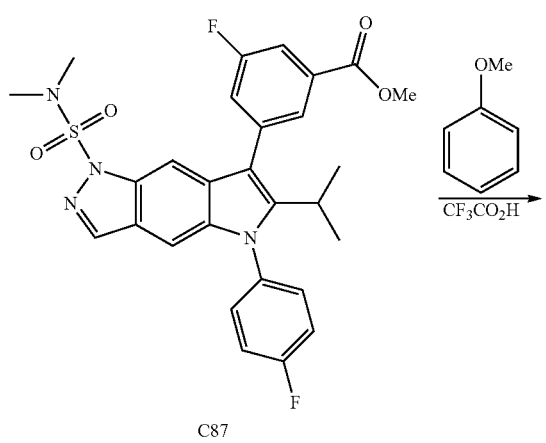

C87

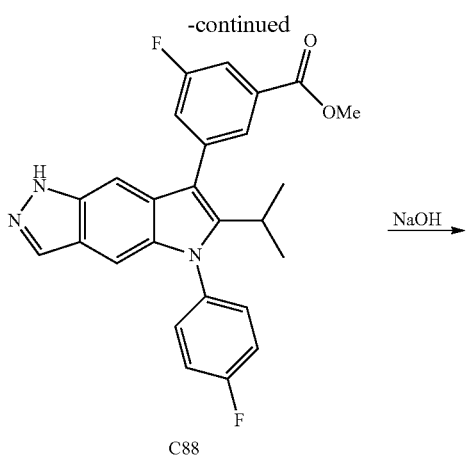

C88

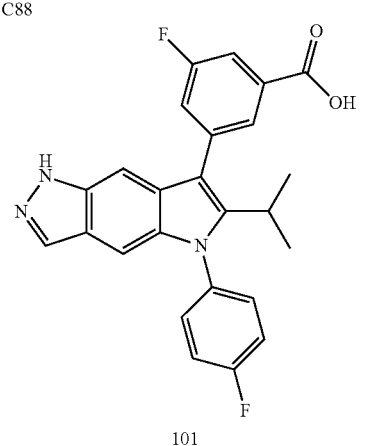

101

Step 1. 5-(4-fluorophenyl)-7-iodo-6-isopropyl-N,N-dimethyl-pyrrolo[2,3-f]indazole-1-sulfonamide (C86)

5-(4-fluorophenyl)-7-iodo-6-isopropyl-1H-pyrrolo[2,3-f]indazole C24 (306 mg, 0.7 mmol) was dissolved in THF (3.6 mL) and cooled in an ice bath. KOtBu (103 mg, 0.92 mmol) was added and the mixture stirred for 5 min. N,N-dimethylsulfamoyl chloride (90 μL, 0.84 mmol) was added and the reaction allowed to stir for 1 h. Aqueous $NH_4Cl_{(sat.)}$ was added, then water and dichloromethane were added. The phases were separated on a phase separator. Purification by silica gel chromatography (Eluent: Ethyl acetate in $CH_2Cl_2$) afforded the product (147 mg, 40%). $^1$H NMR (400 MHz, DMSO) δ 3.00 (p, J=7.0 Hz, 4H), 2.89 (d, J=1.1 Hz, 30H), 1.33 (d, J=7.1 Hz, 30H), 2.80-2.75 (m, 0H), 8.83 (s, 5H), 7.68-7.37 (m, 26H), 7.02 (s, 5H). LC MS m/z 527.2 [M+1]+.

Step 2. methyl 3-[1-(dimethylsulfamoyl)-5-(4-fluorophenyl)-6-isopropyl-pyrrolo[2,3-f]indazol-7-yl]-5-fluoro-benzoate (C87)

A solution of 5-(4-fluorophenyl)-7-iodo-6-isopropyl-N,N-dimethyl-pyrrolo[2,3-f]indazole-1-sulfonamide C86 (54 mg, 0.10 mmol), (3-fluoro-5-methoxycarbonyl-phenyl)boronic acid (30 mg, 0.1515 mmol) and Pd(dppf)Cl$_2$ (8 mg, 0.01 mmol) in DMF (350 μL) was microwaved at 90° C. for 30 min. The reaction was diluted in dichloromethane and water. The organic phase was collected through a phase separator and the solvent was removed in vacuo. Purification by silica gel column chromatography (Eluent: 0-100% EtOAc in dichloromethane) afforded the product (26 mg, 46%). LCMS m/z 553.4 [M+H]+.

Step 3. methyl 3-fluoro-5-[5-(4-fluorophenyl)-6-isopropyl-1H-pyrrolo[2,3-f]indazol-7-yl]benzoate (C88)

To a solution of methyl 3-[1-(dimethylsulfamoyl)-5-(4-fluorophenyl)-6-isopropyl-pyrrolo[2,3-f]indazol-7-yl]-5-fluoro-benzoate C87 (26 mg, 0.05 mmol) in $CH_2Cl_2$ (300 μL), was added anisole (15 μL, 0.14 mmol) and TFA (100 μL). The solution was stirred at room temperature for 48 h. The solvents were removed in vacuo and the crude product used directly in the next step without further purification. LCMS m/z 446.3 [M+H]+.

Step 4. 3-fluoro-5-[5-(4-fluorophenyl)-6-isopropyl-1H-pyrrolo[2,3-f]indazol-7-yl]benzoic Acid (101)

To a solution of methyl 3-fluoro-5-[5-(4-fluorophenyl)-6-isopropyl-1H-pyrrolo[2,3-f]indazol-7-yl]benzoate C88 (25 mg, 0.04 mmol) in MeOH (150 μL) and THF (300 μL) was added sodium hydroxide (175 μL of 2 M, 0.4 mmol). The reaction was stirred at 55° C. for 2 h. Water (1 mL) was added and the organic solvents were removed in vacuo. The pH of the solution was adjusted to pH 3 and the water was removed in vacuo. Purification by reverse phase column chromatography (Eluent: acetonitrile in water with 0.1% Formic Acid modifier) followed by silica gel column chromatography (Eluent: dichloromethane in methanol) afforded the product (8.7 mg, 52%). $^1$H NMR (400 MHz, DMSO-d$_6$) δ 12.59 (s, 1H), 8.00 (s, 1H), 7.91 (s, 1H), 7.79-7.39 (m, 7H), 7.30 (s, 1H), 7.07 (s, 1H), 3.24-2.96 (m, 1H), 1.13 (d, J=7.1 Hz, 6H). LCMS m/z 432.32 [M+H]+.

Compound 102

4-(6-isopropyl-5-phenyl-1H-pyrrolo[2,3-f]indazol-7-yl)benzoic Acid (102)

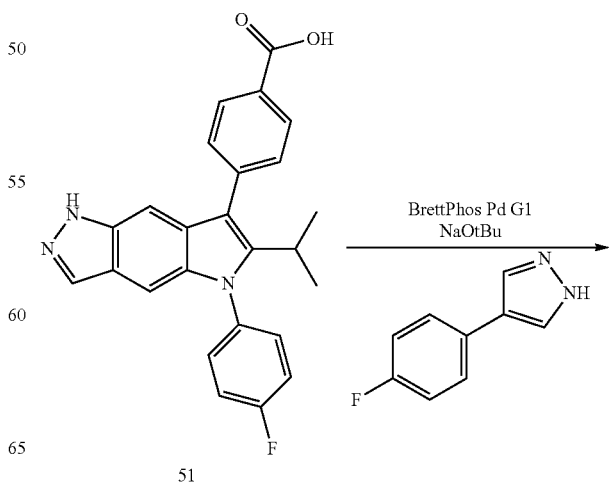

51

-continued

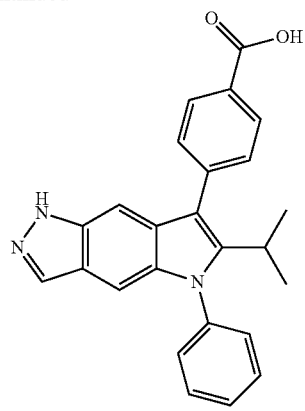
102

NaOtBu (36 mg, 0.37 mmol), BrettPhos Pd G1 (22 mg, 0.03 mmol), 3-(4-fluorophenyl)-1H-pyrazole (18 mg, 0.1 mmol) and 4-[5-(4-fluorophenyl)-6-isopropyl-1H-pyrrolo[2,3-f]indazol-7-yl]benzoic acid 51 (50 mg, 0.12 mmol) were added to a vial under a nitrogen atmosphere. Propan-2-ol (1.5 mL) was added, and the mixture further purged with nitrogen, then heated in a microwave for 180 min at 150° C. The mixture was concentrated to dryness in vacuo. 1M HCl was added and the mixture was extracted with EtOAc. The organic layer was dried over sodium sulfate, and concentrated in vacuo. Purification by reversed phase chromatography (Column: C18. Gradient: 20-100% MeCN in water with a 0.2% formic acid), then HPLC (Gradient: 20-100% MeCN in water with a 0.2% formic acid) to afford the product (23.9 mg, 54%). $^1$H NMR (300 MHz, DMSO-$d_6$) δ 12.96 (s, 1H), 12.57 (s, 1H), 8.13-8.06 (m, 2H), 7.99 (d, J=1.0 Hz, 1H), 7.71-7.58 (m, 5H), 7.58-7.52 (m, 2H), 7.30 (t, J=1.1 Hz, 1H), 7.04 (d, J=1.1 Hz, 1H), 3.19 (p, J=7.0 Hz, 1H), 1.13 (d, J=7.2 Hz, 6H). LCMS m/z 396.3 [M+1]+.

Compound 103 & 104

4-[5-(4-fluorophenyl)-1H-pyrrolo[2,3-f]indazol-7-yl]benzoic Acid (103) and 4-[5-(4-fluorophenyl)-6-trimethylsilyl-1H-pyrrolo[2,3-f]indazol-7-yl]benzoic Acid (104)

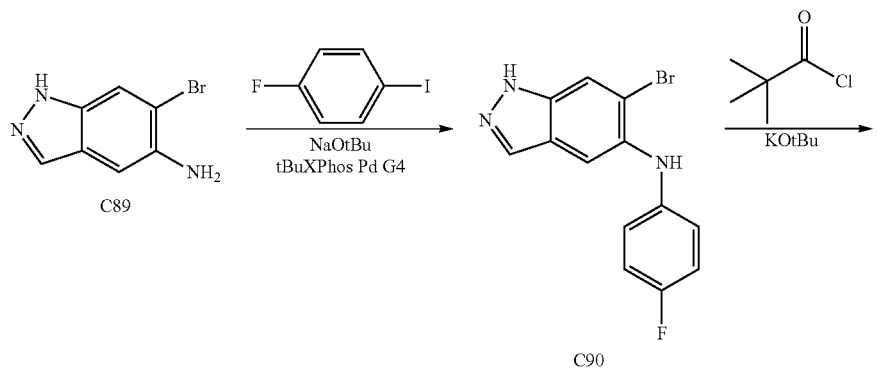

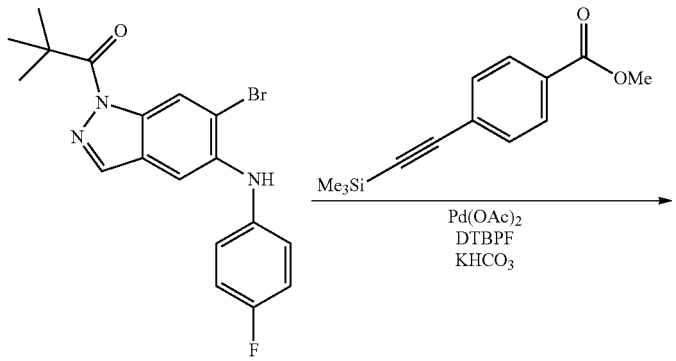

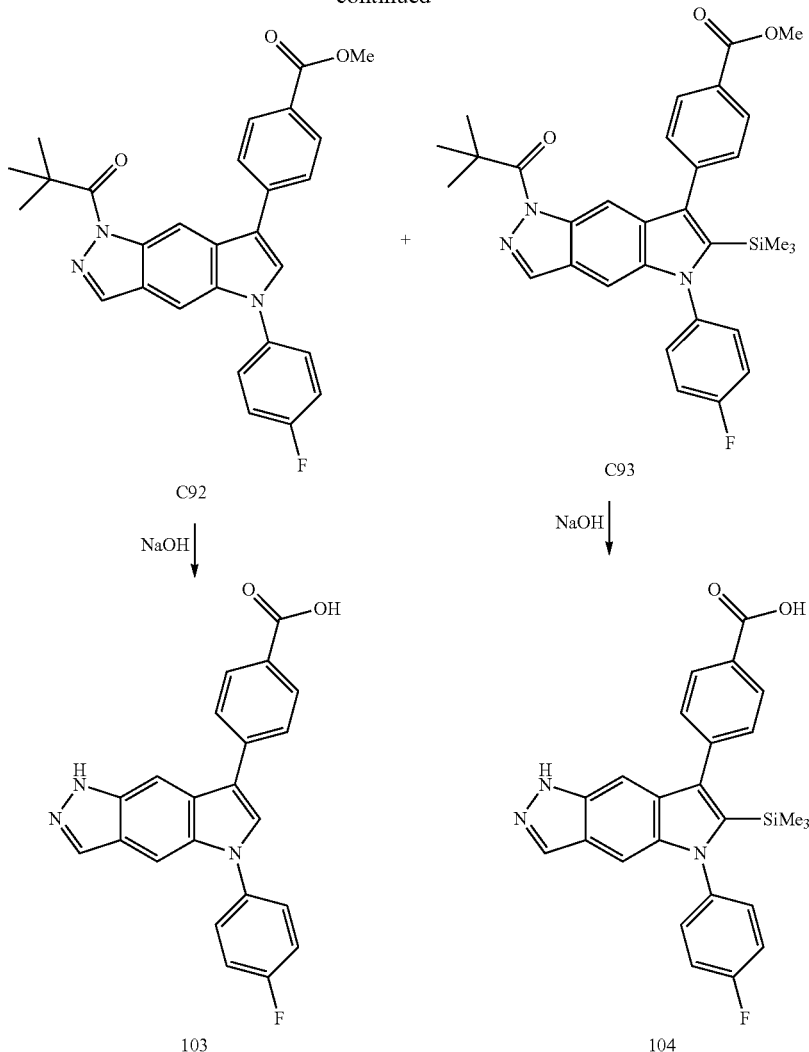

Step 1. Synthesis of 6-bromo-N-(4-fluorophenyl)-1H-indazol-5-amine (C90)

A solution of 1-fluoro-4-iodo-benzene (1.6 mL, 13.9 mmol), 6-bromo-1H-indazol-5-amine C89 (2000 mg, 9.4 mmol), NaOtBu (3.9 g, 40 mmol), and tBuXPhos Pd G4 (432 mg, 0.48 mmol) tBuOH (50 mL) degassed and purged with nitrogen. The mixture was allowed to stir at room temperature for 5 h. The mixture was diluted with ethyl acetate, washed with 50% saturated sodium bicarbonate, and then by brine. The organic layer was dried over with sodium sulfate, filtered and concentrated in vacuo. Silica gel chromatography (Gradient: 0-100% EtOAc in heptane) afforded the product (1.8 g, 62%). $^1$H NMR (400 MHz, DMSO) δ 13.06 (s, 1H), 7.99 (s, 1H), 7.89 (s, 1H), 7.59 (s, 1H), 7.48 (d, J=1.7 Hz, 1H), 7.09-6.88 (m, 2H), 6.80 (dd, J=8.1, 4.7 Hz, 2H). LCMS m/z 305.9 [M+H]$^+$.

Step 2. Synthesis of 1-[6-bromo-5-(4-fluoroanilino)indazol-1-yl]-2,2-dimethyl-propan-1-one (C91)

To a solution of 6-bromo-N-(4-fluorophenyl)-1H-indazol-5-amine C90 (754 mg, 2.4 mmol) in THF (15 mL) at 1° C. (ice-water bath) was added KOtBu (2.6 mL of 1 M, 2.6 mmol) After ~10 min, 2,2-dimethylpropanoyl chloride (340 µL, 2.7 mmol) was added and the mixture stirred for 30 min in cooling bath. An additional 25 µl of 2,2-dimethylpropanoyl chloride was added and the mixture stirred for another ~30 min in the ice bath. The reaction was quenched with water (3 mL), stirred for 5 min and the concentrated to dryness in vacuo. The residue was diluted with CH$_2$Cl$_2$, (20 mL) and washed with water (10 mL). The organic phase was passed through a phase separator and concentrated to dryness in vacuo to afford the product (971 mg, 100%). $^1$H NMR (300 MHz, DMSO-d$_6$) δ 8.61-8.56 (m, 1H), 8.36 (d, J=0.9 Hz, 1H), 7.62 (s, 1H), 7.57 (s, 1H), 7.16-7.04 (m, 4H), 1.49 (s, 9H). LCMS m/z 390.2 [M+H]$^+$.

Step 3. Synthesis of methyl 4-[1-(2,2-dimethylpropanoyl)-5-(4-fluorophenyl)pyrrolo[2,3-f]indazol-7-yl]benzoate (C92)

1-[6-bromo-5-(4-fluoroanilino)indazol-1-yl]-2,2-dimethyl-propan-1-one C91 (511.3 mg, 1.3 mmol), methyl 4-(2-trimethylsilylethynyl)benzoate (362.2 mg, 1.6 mmol), Pd(OAc)$_2$ (17.2 mg, 0.08 mmol), DTBPF (73 mg, 0.15 mmol), and KHCO$_3$ (650 mg, 6.5 mmol) were added to a vial and the mixture degassed and purged with nitrogen.

NMP (2.5 mL) was added and the mixture was flushed with nitrogen. The mixture was heated to 110° C. for 1 h. The reaction mixture was diluted with CH$_2$Cl$_2$, and washed with water. The organic phase was passed through a phase separator, and concentrated in vacuo. Purification by silica gel chromatography (0-100% ethyl acetate in heptane) afforded the product C92 (240 mg, 38%). $^1$H NMR (300 MHz, DMSO-d$_6$) δ 8.98 (s, 1H), 8.57-8.53 (m, 1H), 8.43 (s, 1H), 8.13 (d, J=8.3 Hz, 2H), 8.06 (d, J=1.0 Hz, 1H), 7.97 (d, J=8.4 Hz, 2H), 7.83 (dd, J=8.9, 4.8 Hz, 2H), 7.52 (t, J=8.7 Hz, 2H), 3.90 (s, 3H), 1.54 (s, 9H). LCMS m/z 470.4 [M+1]$^+$. X-ray crystallography confirmed the regiochemistry of the product.

Step 3. Synthesis of methyl 4-[1-(2,2-dimethylpropanoyl)-5-(4-fluorophenyl)-6-trimethylsilyl-pyrrolo[2,3-f]indazol-7-yl]benzoate (C93)

1-[6-bromo-5-(4-fluoroanilino)indazol-1-yl]-2,2-dimethyl-propan-1-one C91 (460 mg, 1.17 mmol), methyl 4-(2-trimethylsilylethynyl)benzoate (325 mg, 1.40 mmol), Pd(OAc)$_2$ (16 mg, 0.07 mmol), DTBPF (66 mg, 0.14 mmol), and KHCO$_3$ (585 mg, 5.8 mmol) were added to a vial and the mixture degassed and purged with nitrogen. NMP (2.5 mL) was added the mixture purged with additional nitrogen. The mixture was heated to 110° C. for 1 h. The reaction mixture was diluted with CH$_2$Cl$_2$, and washed with water. The organic phase was passed through a phase separator, and concentrated in vacuo. The product C93 was obtained as a mixture with des-TMS product C92 and other regioisomers. Purification by silica gel chromatography (Gradient: 0-100% ethyl acetate in heptane) afforded C93. Structure confirmed by x-ray crystallography.
Methyl 4-[1-(2,2-dimethylpropanoyl)-5-(4-fluorophenyl)-6-trimethylsilyl-pyrrolo[2,3-f]indazol-7-yl]benzoate C93 (195 mg). $^1$H NMR (300 MHz, DMSO-d$_6$) δ 8.46 (d, J=0.8 Hz, 1H), 8.35 (t, J=0.9 Hz, 1H), 8.18-8.11 (m, 2H), 7.72-7.62 (m, 4H), 7.57-7.46 (m, 3H), 3.92 (s, 3H), 1.47 (s, 9H), −0.14 (s, 9H). LCMS m/z 542.3 [M+1]$^+$.

Step 4. Synthesis of 4-[5-(4-fluorophenyl)-1H-pyrrolo[2,3-f]indazol-7-yl]benzoic Acid (103)

To a solution of methyl 4-[1-(2,2-dimethylpropanoyl)-5-(4-fluorophenyl)pyrrolo[2,3-f]indazol-7-yl]benzoate C92 (9 mg, 0.02 mmol) in methanol (500 μL) and THF (500 μL) was added aqueous NaOH (200 μL of 1 M, 0.2 mmol) and stirred at 55° C. for 1 h. The mixture was concentrated to dryness in vacuo. EtOAc was added and the mixture was washed with 1M HCl. The organic layer was dried over MgSO$_4$, filtered and concentrated in vacuo. Purification by reversed-phase chromatography (C18 column. Gradient: 10-100% MeCN in water with a formic acid modifier) afforded the product (3.4 mg, 48%). $^1$H NMR (300 MHz, Methanol-d$_4$) δ 8.17-8.09 (m, 3H), 8.08-8.04 (m, 1H), 7.97 (s, 1H), 7.92-7.86 (m, 3H), 7.74-7.66 (m, 2H), 7.41-7.31 (m, 2H). LCMS m/z 372.2 [M+H]$^+$.

Step 5. Synthesis of 4-[5-(4-fluorophenyl)-6-trimethylsilyl-1H-pyrrolo[2,3-f]indazol-7-yl]benzoic Acid (104)

Compound 104 was prepared from C93 using the method described for preparation of 103 from C92. Purification by reversed phase chromatography (C18 column. Gradient: 50-80% MeCN in water with an ammonium formate modifier), afforded the product (12.5 mg, 29%). $^1$H NMR (300 MHz, DMSO-d$_6$) δ 13.4-12.88 (bs, 1H), 12.65 (s, 1H), 8.15-8.02 (m, 3H), 7.70-7.56 (m, 4H), 7.49 (t, J=8.7 Hz, 2H), 7.38 (t, J=1.1 Hz, 1H), 7.36-7.32 (m, 1H), −0.14 (s, 9H). LCMS m/z 444.4 [M+H]$^+$.

Compound 105

4-[5-(4-fluorophenyl)-6-(trifluoromethyl)-1H-pyrrolo[2,3-f]indazol-7-yl]benzoic Acid (105)

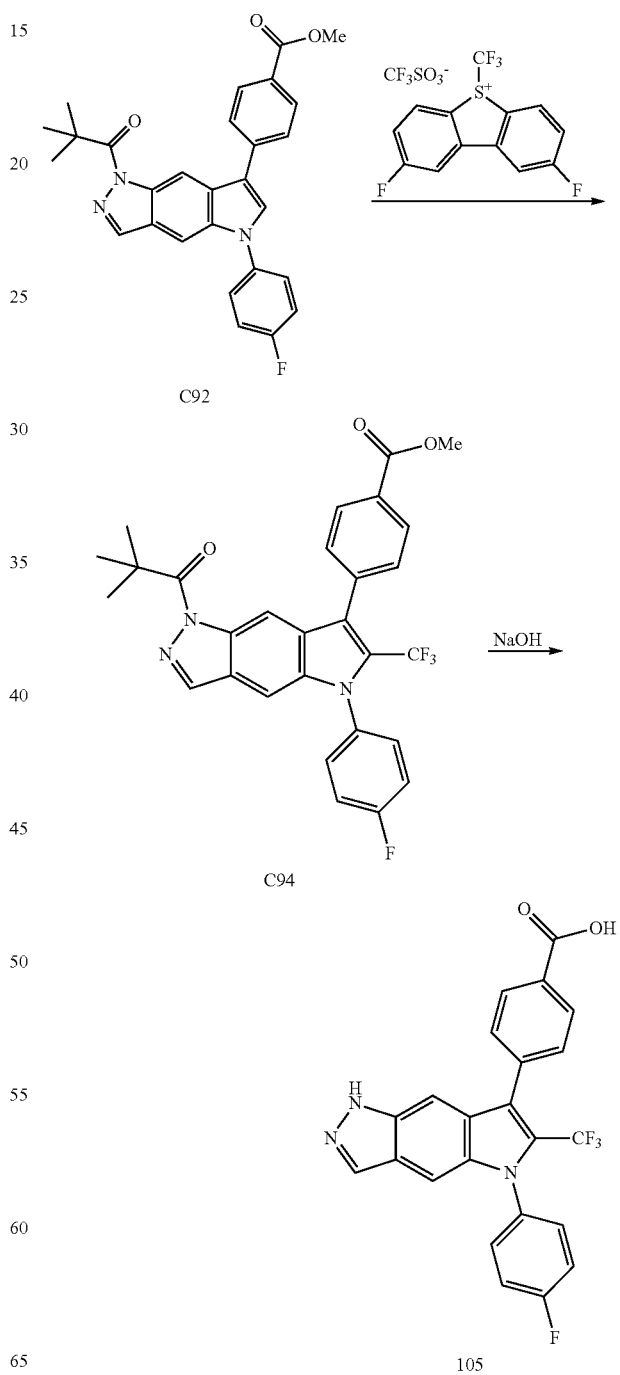

Step 1. Methyl 4-[1-(2,2-dimethylpropanoyl)-5-(4-fluorophenyl)-6-(trifluoromethyl)pyrrolo[2,3-f]indazol-7-yl]benzoate (C94)

A solution of methyl 4-[1-(2,2-dimethylpropanoyl)-5-(4-fluorophenyl)pyrrolo[2,3-f]indazol-7-yl]benzoate C92 (202 mg, 0.4 mmol) and 2,8-difluoro-5-(trifluoromethyl)-4a,9b-dihydrodibenzothiophen-5-ium trifluoromethanesulfonate (365 mg, 0.83 mmol) in DMF (2 mL) and NMM (104 µL, 0.95 mmol) were heated at 50° C. overnight. 1 N HCl (3 mL) was added and the aqueous was extracted with $CH_2Cl_2$ (8 mL×3). The combined organic layers were dried and concentrated in vacuo. Purification by silica gel chromatography (Gradient: 0-100% EtOAc in hexanes) to afford the product (40 mg, 16%). $^1$H NMR (300 MHz, Chloroform-d) δ 8.67-8.62 (m, 1H), 8.23-8.16 (m, 2H), 8.13 (d, J=0.8 Hz, 1H), 7.64 (d, J=8.2 Hz, 2H), 7.51 (dd, J=8.8, 4.7 Hz, 2H), 7.35-7.30 (m, 3H), 3.99 (s, 3H), 1.56 (s, 9H). LCMS m/z 538.4 [M+H]$^+$.

Step 2. 4-[5-(4-fluorophenyl)-6-(trifluoromethyl)-1H-pyrrolo[2,3-f]indazol-7-yl]benzoic Acid (105)

NaOH (500 µL of 1 M, 0.5 mmol) was added to a solution of methyl 4-[1-(2,2-dimethylpropanoyl)-5-(4-fluorophenyl)-6-(trifluoromethyl)pyrrolo[2,3-f]indazol-7-yl]benzoate C94 (30 mg, 0.05 mmol) in methanol (1.5 mL) and THF (1.5 mL). The mixture was allowed to stir for 1 h at 55° C. The mixture was concentrated in vacuo. EtOAc was added and the mixture washed with 1M HCl. The organic layer was dried over MgSO$_4$, filtered and concentrated in vacuo. Purification by reverse phase chromatography (10-100% MeCN in water with a formic acid modifier) afforded the product (4.4 mg, 20%). $^1$H NMR (300 MHz, DMSO-d$_6$) δ 12.88 (s, 1H), 8.16-8.07 (m, 3H), 7.74-7.63 (m, 4H), 7.57-7.46 (m, 3H), 7.38 (d, J=1.2 Hz, 1H). LCMS m/z 440.4 [M+H]$^+$.

Compound 106

4-[5-(4-fluorophenyl)-6-(1-hydroxy-1-methyl-ethyl)-1H-pyrrolo[2,3-f]indazol-7-yl]benzoic Acid (106)

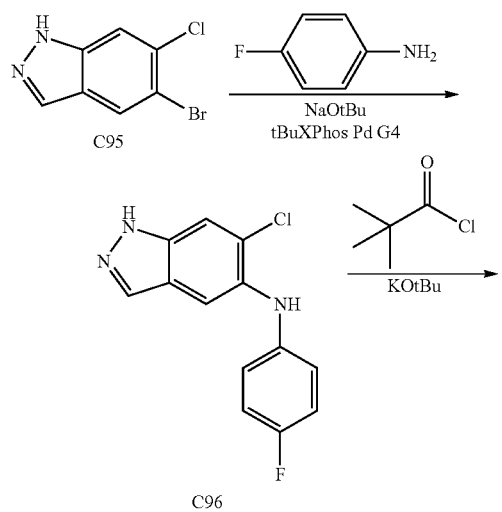

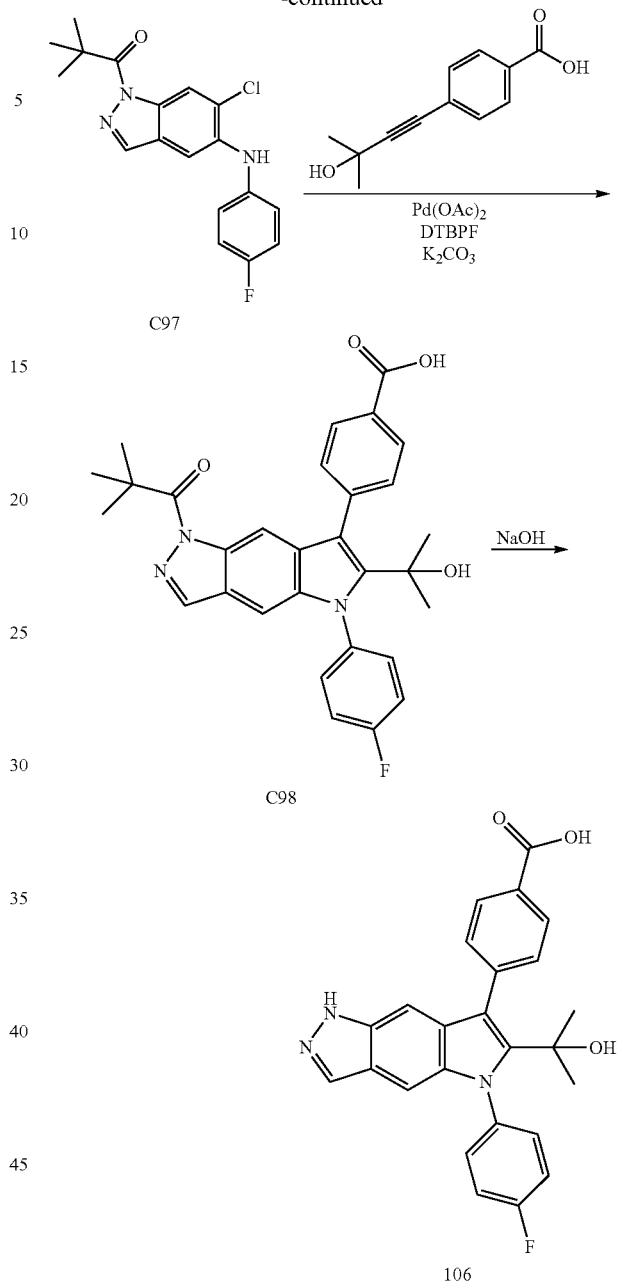

Step 1. Synthesis of 6-chloro-N-(4-fluorophenyl)-1H-indazol-5-amine (C96)

tBuOH (49 mL) (containing 10% m-xylene) was added to a mixture of 5-bromo-6-chloro-1H-indazole C95 (2.05 g, 8.9 mmol), 4-fluoroaniline (940 µL, 9.8 mmol), NaOtBu (2.6 g, 26.6 mmol), and tBuXPhos Pd G4 (410 mg, 0.46 mmol). The mixture was degassed and purged with nitrogen, and the mixture was allowed to stir at room temperature for 4 h. The mixture was concentrated in vacuo, then diluted with $CH_2Cl_2$. The mixture was washed with water and then brine. The organic layer was dried over sodium sulfate, filtered and concentrated in vacuo. Silica gel chromatography (Gradient: 0-100% ethyl acetate in heptane) afforded the product (1.8 g, 79%). $^1$H NMR (300 MHz, DMSO-d$_6$) δ 13.04 (s, 1H), 7.98 (t, J=1.2 Hz, 1H), 7.71 (d, J=0.8 Hz, 1H), 7.58 (s, 1H), 7.53 (s, 1H), 7.08-6.95 (m, 2H), 6.91-6.80 (m, 2H). LCMS m/z 262.1 [M+H]⁺.

Step 2. Synthesis of 1-[6-chloro-5-(4-fluoroanilino)indazol-1-yl]-2,2-dimethyl-propan-1-one (C97)

To a suspension of 6-chloro-N-(4-fluorophenyl)-1H-indazol-5-amine C96 (1.84 g, 6.97 mmol) in THF (36 mL) at 1° C. (ice-water bath) was added KOtBu (7.36 mL of 1 M, 7.4 mmol). After ~10 min, 2,2-dimethylpropanoyl chloride (965 µL, 7.8 mmol) was added and the mixture was stirred for 30 min. The reaction was quenched with water (10 mL), stirred for 5 min then concentrated in vacuo. The mixture was partitioned between CH$_2$Cl$_2$ (100 mL) and water (50 mL). The organic layer was passed through a phase separator, and concentrated to dryness in vacuo. Purification by silica gel chromatography (Gradient: 0-100% ethyl acetate in heptane) afforded the product (2.1 g, 86%). ¹H NMR (300 MHz, DMSO-d$_6$) δ 8.41-8.37 (m, 1H), 8.35 (d, J=0.9 Hz, 1H), 7.76 (s, 1H), 7.57 (s, 1H), 7.15-7.13 (m, 2H), 7.13-7.11 (m, 2H), 1.49 (s, 9H). LCMS m/z 331.7 [M+H]⁺.

Step 3. Synthesis of 4-[1-(2,2-dimethylpropanoyl)-5-(4-fluorophenyl)-6-(1-hydroxy-1-methyl-ethyl)pyrrolo[2,3-f]indazol-7-yl]benzoic Acid (C98)

A mixture of 4-(3-hydroxy-3-methyl-but-1-ynyl)benzoic acid (69 mg, 0.34 mmol), 1-[6-chloro-5-(4-fluoroanilino)indazol-1-yl]-2,2-dimethyl-propan-1-one C97 (98 mg, 0.28 mmol), Pd(OAc)$_2$ (5 mg, 0.02 mmol), DTBPF (16 mg, 0.03 mmol), and K$_2$CO$_3$ (198 mg, 1.43 mmol) were added to a vial and the vessel evacuated and flushed with nitrogen (×3). NMP (1 mL) was added and the mixture flushed with additional nitrogen (×3). The mixture was heated to 110° C. for 1 h. EtOAc was added and the mixture washed with 1 M HCl. The organic layer was dried over Na$_2$SO$_4$, filtered and concentrated. Silica gel chromatography (Gradient: 0-10% methanol in CH$_2$Cl$_2$) afforded the product (72 mg, 50%). ¹H NMR (300 MHz, DMSO-d$_6$) δ 13.00 (s, 1H), 8.39 (d, J=0.8 Hz, 1H), 8.11-8.05 (m, 2H), 8.02-7.99 (m, 1H), 7.61-7.53 (m, 4H), 7.43 (t, J=8.7 Hz, 2H), 7.08 (d, J=1.0 Hz, 1H), 5.01 (s, 1H), 1.44 (s, 9H), 1.33 (s, 6H). LCMS m/z 514.3 [M+H]⁺.

Step 4. 4-[5-(4-fluorophenyl)-6-(1-hydroxy-1-methyl-ethyl)-1H-pyrrolo[2,3-f]indazol-7-yl]benzoic Acid (106)

Aqueous NaOH (1 mL of 1 M, 1.0 mmol) was added to a solution of 4-[1-(2,2-dimethylpropanoyl)-5-(4-fluorophenyl)-6-(1-hydroxy-1-methyl-ethyl)pyrrolo[2,3-f]indazol-7-yl]benzoic acid C98 (71 mg, 0.14 mmol) in methanol (2 mL) and THF (2 mL) and stirred over 1 h at 55° C. The mixture was concentrated to dryness. EtOAc was added and the mixture washed with 1M HCl. The organic layer was dried over MgSO$_4$, filtered and concentrated in vacuo. Purification by silica gel chromatography (Gradient: 0-10% methanol in CH$_2$Cl$_2$) afforded the product (25.2 mg, 41%). ¹H NMR (300 MHz, DMSO-d$_6$) δ 12.98 (s, 1H), 12.51 (s, 1H), 8.09-8.02 (m, 2H), 7.97 (d, J=1.0 Hz, 1H), 7.61-7.50 (m, 4H), 7.40 (t, J=8.8 Hz, 2H), 6.99 (t, J=1.1 Hz, 1H), 6.89 (d, J=1.1 Hz, 1H), 4.92 (s, 1H), 1.32 (s, 6H). LCMS m/z 430.2 [M+H]⁺.

Compound 107

4-[5-(4-fluorophenyl)-6-(3-methyloxetan-3-yl)-1H-pyrrolo[2,3-f]indazol-7-yl]benzoic Acid (107)

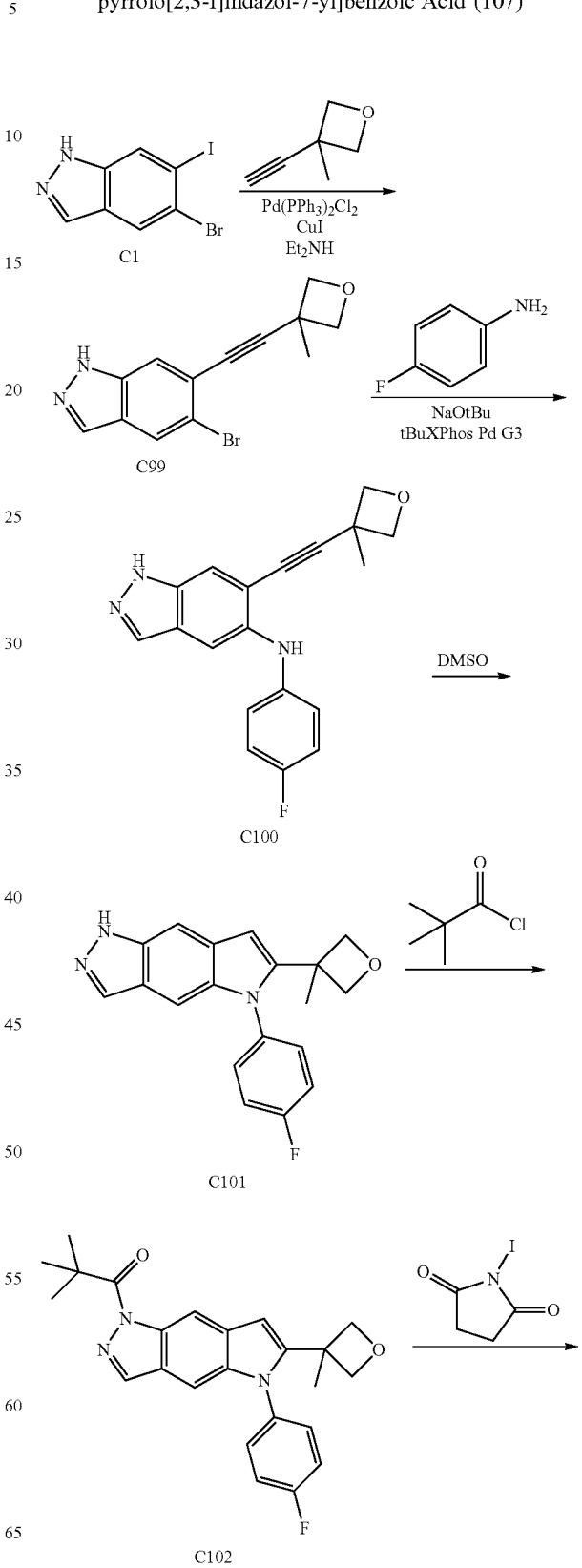

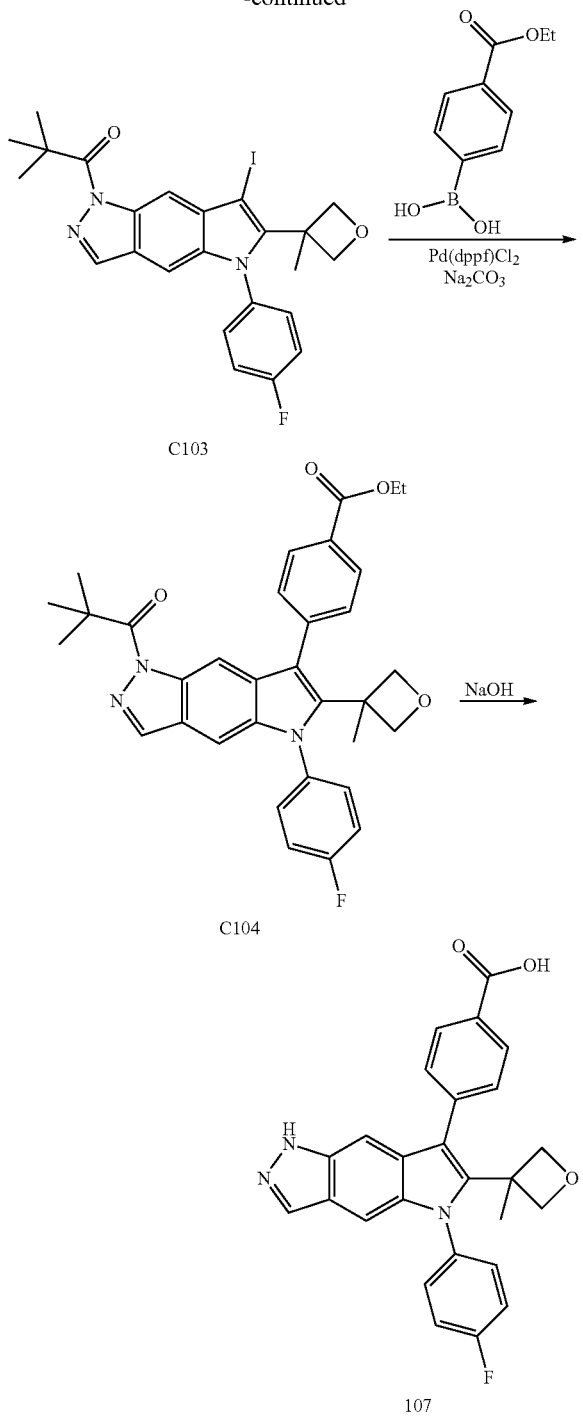

Step 1. Synthesis of 5-bromo-6-[2-(3-methyloxetan-3-yl)ethynyl]-1H-indazole (C99)

To a solution of 5-bromo-6-iodo-1H-indazole C1 (2 g, 6.2 mmol) in DMF (12.5 mL) under nitrogen was added 3-ethynyl-3-methyl-oxetane (626 µL, 6.2 mmol), diethylamine (1.91 mL, 18.5 mmol), PdCl$_2$(PPh$_3$)$_2$ (220 mg, 0.31 mmol) and CuI (88 mg, 0.45 mmol). The reaction mixture was heated to 90° C. for 1 h. The mixture was then concentrated and water and CH$_2$Cl$_2$ were added. The organic layer was concentrated in vacuo. Purification by silica gel chromatography (Eluent: Ethyl acetate in heptanes) afforded the product (1.04 g, 58%). $^1$H NMR (400 MHz, DMSO-d$_6$) δ 13.37 (s, 1H), 8.15 (t, J=0.7 Hz, 1H), 8.08 (t, J=1.3 Hz, 1H), 7.76 (t, J=0.8 Hz, 1H), 4.81 (d, J=5.5 Hz, 2H), 4.48 (d, J=5.5 Hz, 2H), 1.68 (s, 3H). LCMS m/z 291.1 [M+H]$^+$.

Step 2. Synthesis of N-(4-fluorophenyl)-6-[2-(3-methyloxetan-3-yl)ethynyl]-1H-indazol-5-amine (C100)

A solution of 5-bromo-6-[2-(3-methyloxetan-3-yl)ethynyl]-1H-indazole C99 (1.04 g, 3.6 mmol), 4-fluoroaniline (482 µL, 5.10 mmol), NaOtBu (608 mg, 6.33 mmol) in t-butanol (16.8 mL) was purged with N$_2$ for 10 min at 40° C. tBuXPhos Pd G3 (56.7 mg, 0.07 mmol) was added and the mixture was purged with N$_2$ for an additional 10 min. The reaction was heated to 70° C. for 1 h. Additional 4-fluoroaniline (482 µL, 5.1 mmol), NaOtBu (608 mg, 6.3 mmol) and tBuXPhos Pd G3 (56.7 mg, 0.07 mmol) were added and the mixture stirred overnight. Purification by silica gel chromatography (Gradient: 0-100% EtOAc in heptane) afforded the product (568 mg, 48%). $^1$H NMR (400 MHz, Methanol-d$_4$) δ 7.91-7.88 (m, 1H), 7.60 (s, 1H), 7.46-7.41 (m, 1H), 6.96 (d, J=6.6 Hz, 4H), 4.76 (d, J=5.4 Hz, 2H), 4.42 (d, J=5.6 Hz, 2H), 1.62 (s, 3H). LCMS m/z 322.3 [M+H]$^+$.

Step 3. 5-(4-fluorophenyl)-6-(3-methyloxetan-3-yl)-1H-pyrrolo[2,3-f]indazole (C101)

A solution of N-(4-fluorophenyl)-6-[2-(3-methyloxetan-3-yl)ethynyl]-1H-indazol-5-amine (518 mg, 1.5 mmol) in DMSO (2 mL) was heated at 150° C. for 2 h. Water was added and product precipitated out. Filtration of the solid precipitate afforded the product. 5-(4-fluorophenyl)-6-(3-methyloxetan-3-yl)-1H-pyrrolo[2,3-f]indazole (466 mg, 90%). $^1$H NMR (400 MHz, Methanol-d$_4$) δ 7.96 (d, J=1.0 Hz, 1H), 7.59 (t, J=1.0 Hz, 1H), 7.44-7.38 (m, 2H), 7.37-7.29 (m, 2H), 7.11-7.08 (m, 1H), 6.46 (s, 1H), 5.12 (d, J=5.5 Hz, 2H), 4.23 (d, J=5.8 Hz, 2H), 1.64 (s, 3H). LCMS m/z 322.3 [M+H]$^+$.

Step 4. Synthesis of 1-[5-(4-fluorophenyl)-6-(3-methyloxetan-3-yl)pyrrolo[2,3-f]indazol-1-yl]-2,2-dimethyl-propan-1-one (C102)

A solution of 5-(4-fluorophenyl)-6-(3-methyloxetan-3-yl)-1H-pyrrolo[2,3-f]indazole C101 (466 mg, 1.5 mmol) in THF (10.4 mL) was cooled to 0° C. KOtBu (360 mg, 3.21 mmol) was added, and the mixture allowed to stir for 5 min. 2,2-dimethylpropanoyl chloride (692 µL, 5.6 mmol) dropwise, was added and the mixture allowed to stir at 0° C. for 1 h. Purification by silica gel chromatography (Gradient: 0-100% EtOAc in dichloromethane) afforded the product (580 mg, 99%). $^1$H NMR (400 MHz, Methanol-d$_4$) δ 8.57 (s, 1H), 8.14 (s, 1H), 7.45-7.39 (m, 2H), 7.38-7.31 (m, 2H), 7.16 (s, 1H), 6.58 (s, 1H), 5.12 (d, J=5.6 Hz, 2H), 4.24 (d, J=5.7 Hz, 2H), 1.65 (s, 3H), 1.56 (s, 9H). LCMS m/z 406.4 [M+H]$^+$.

Step 5. Synthesis of 1-[5-(4-fluorophenyl)-7-iodo-6-(3-methyloxetan-3-yl)pyrrolo[2,3-f]indazol-1-yl]-2,2-dimethyl-propan-1-one (C103)

1-iodopyrrolidine-2,5-dione (414 mg, 1.75 mmol) was added portionwise to a solution of 1-[5-(4-fluorophenyl)-6-(3-methyloxetan-3-yl)pyrrolo[2,3-f]indazol-1-yl]-2,2-dimethyl-propan-1-one C102 (580 mg, 1.43 mmol) in CH$_2$Cl$_2$ (5.9 mL) at 0° C. and the reaction allowed to stir at room temperature for 1 h. The reaction mixture was washed with 1M Na$_2$SO$_3$ and the organic phase collected through a phase separator to afford the product (513 mg, 68%). $^1$H NMR (400 MHz, DMSO-d$_6$) δ 8.44 (d, J=0.8 Hz, 1H), 8.34 (t, J=0.9 Hz, 1H), 7.68-7.62 (m, 2H), 7.51-7.44 (m, 2H), 7.31 (d, J=0.9 Hz, 1H), 4.86 (d, J=5.7 Hz, 2H), 3.97 (d, J=5.8 Hz, 2H), 1.93 (s, 3H), 1.52 (s, 9H). LCMS m/z 532.4 [M+H]$^+$.

Step 6. Synthesis of ethyl 4-[1-(2,2-dimethylpropanoyl)-5-(4-fluorophenyl)-6-(3-methyloxetan-3-yl)pyrrolo[2,3-f]indazol-7-yl]benzoate (C104)

A mixture of 1-[5-(4-fluorophenyl)-7-iodo-6-(3-methyloxetan-3-yl)pyrrolo[2,3-f]indazol-1-yl]-2,2-dimethyl-propan-1-one C103 (100 mg, 0.18 mmol), (4-ethoxycarbonylphenyl)boronic acid (72 mg, 0.37 mmol) and Pd(dppf)Cl$_2$ (7.1 mg, 0.009 mmol) was placed in a vial. 1,4-dioxane (604 μL) and Na$_2$CO$_3$ (287 μL of 2 M, 0.6 mmol) were added and the reaction stirred at 95° C. for 1 h. Water and CH$_2$Cl$_2$ were added and the phases were separated on a phase separator. Purification by silica gel chromatography (0-100% EtOAc/dichloromethane) afforded the product. (44.6 mg, 45%). LCMS m/z 554.5 [M+H]$^+$.

Step 7. Synthesis of 4-[5-(4-fluorophenyl)-6-(3-methyloxetan-3-yl)-1H-pyrrolo[2,3-f]indazol-7-yl]benzoic Acid (107)

NaOH (332 μL of 1 M, 0.33 mmol) was added to a solution of ethyl 4-[1-(2,2-dimethylpropanoyl)-5-(4-fluorophenyl)-6-(3-methyloxetan-3-yl)pyrrolo[2,3-f]indazol-7-yl]benzoate C104 (45 mg, 0.073 mmol) in THF (918 μL) and MeOH (379 μL). The mixture was heated at 50° C. for 1 h. Concentration in vacuo, followed by reverse phase chromatography (Eluent: MeCN in water containing 0.1% formic acid) afforded (21.1 mg, 63%). $^1$H NMR (400 MHz, DMSO-d$_6$) δ 13.00 (s, 1H), 12.66 (s, 1H), 8.08 (d, J=7.6 Hz, 2H), 8.01 (s, 1H), 7.72-7.65 (m, 2H), 7.60 (d, J=7.8 Hz, 2H), 7.51-7.44 (m, 3H), 7.04 (s, 1H), 4.52 (d, J=5.4 Hz, 2H), 3.65 (d, J=5.2 Hz, 2H), 2.00 (s, 3H). LCMS m/z 442.4 [M+H]$^+$.

Compound 108

4-[5-(4-fluorophenyl)-6-(4-methyltetrahydropyran-4-yl)-1H-pyrrolo[2,3-f]indazol-7-yl]benzoic Acid (108)

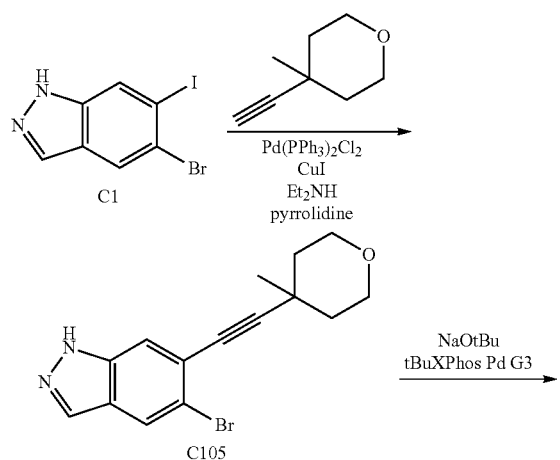

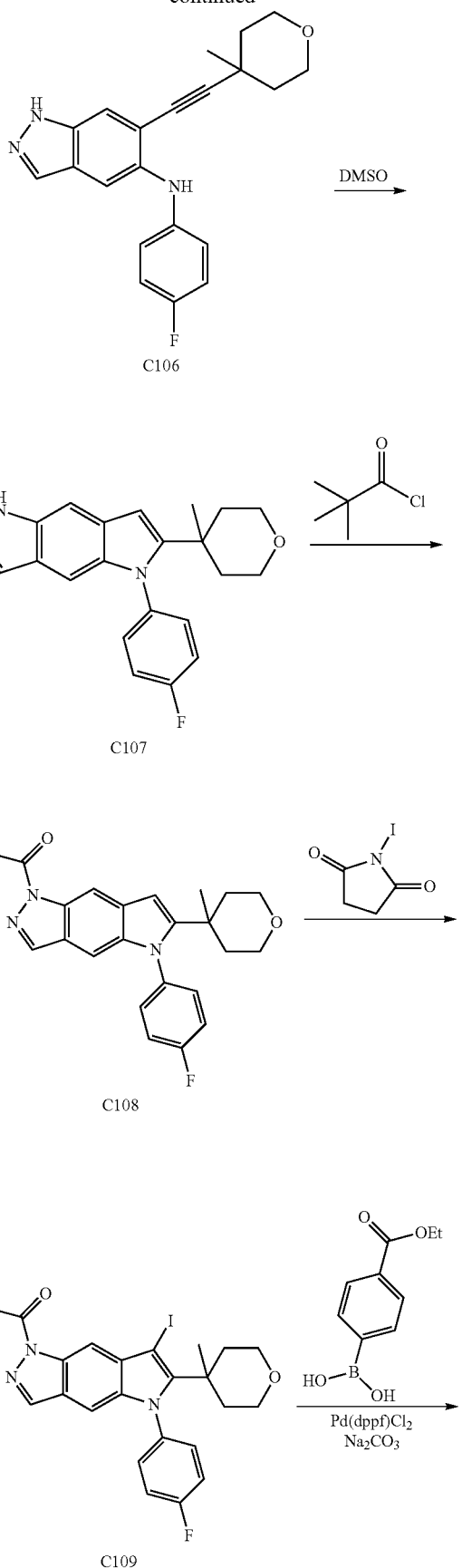

549

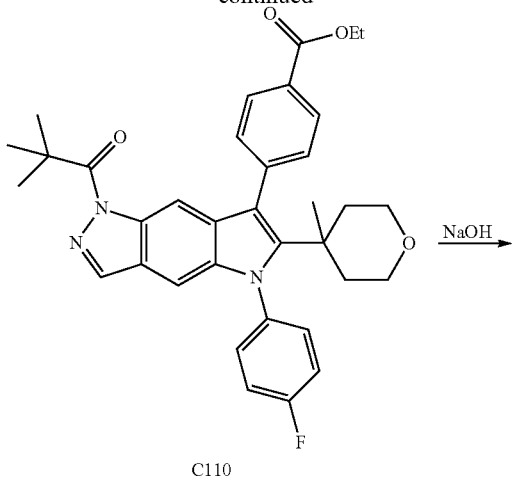

C110

NaOH →

550

Compound 109

4-[5-(4-fluorophenyl)-6-(8-oxabicyclo[3.2.1]octan-3-yl)-1H-pyrrolo[2,3-f]indazol-7-yl]benzoic Acid (109)

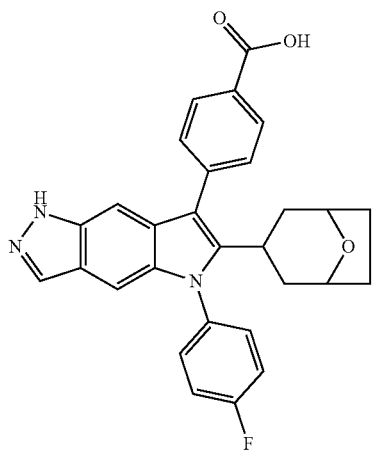 [SMILES: O=C(O)c1ccc(-c2c(C3CC4CCC(C3)O4)n(-c3ccc(F)cc3)c3cc4cn[nH]c4cc23)cc1]

Compound 109 was prepared from C1 and 3-ethynyl-8-oxabicyclo[3.2.1]octane in seven steps using the method described for the preparation of compound 107 and 108. Purification by reverse phase chromatography (C18 column. Gradient: 10-100% acetonitrile in water with 0.2% formic acid) afforded the product was obtained as a white solid (11.9 mg). $^1$H NMR (400 MHz, Methanol-$d_4$) δ 8.18 (d, J=7.8 Hz, 2H), 7.98 (s, 1H), 7.62 (d, J=7.8 Hz, 2H), 7.53 (dd, J=8.3, 4.6 Hz, 2H), 7.42 (t, J=8.3 Hz, 2H), 7.30 (s, 1H), 7.13 (s, 1H), 4.23 (s, 2H), 3.40 (d, J=13.0 Hz, 1H), 1.99 (t, J=13.0 Hz, 2H), 1.84-1.74 (m, 2H), 1.54 (d, J=13.1 Hz, 2H), 1.46-1.36 (m, 2H). LCMS m/z 482.4 [M+H]$^+$.

Compound 110

4-[6-(3-ethyloxetan-3-yl)-5-(4-fluorophenyl)-1H-pyrrolo[2,3-f]indazol-7-yl]-3-fluoro-benzoic Acid (110)

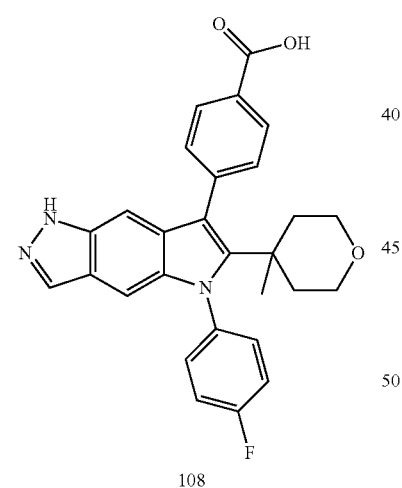

108

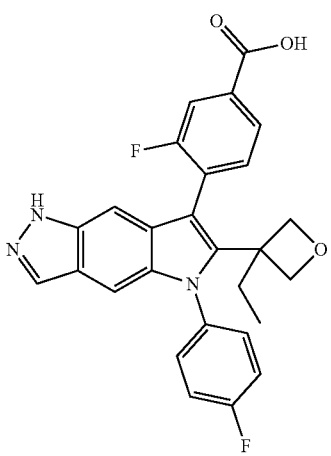 [SMILES: CCC1(c2c(-c3ccc(C(=O)O)cc3F)c3cc4[nH]ncc4cc3n2-c2ccc(F)cc2)COC1]

Compound 108 was prepared from C1 and 4-ethynyl-4-methyl-tetrahydropyran in seven steps, in an analogous manner to the method described for the preparation of compound 107. Purification by reverse phase chromatography (Gradient: 0-100% MeCN in water, containing 10 mM ammonium formate) afforded the product (2.1 mg, 20%). $^1$H NMR (400 MHz, Methanol-$d_4$) δ 8.12 (d, J=7.5 Hz, 2H), 7.94 (s, 1H), 7.57-7.50 (m, 4H), 7.37 (t, J=8.3 Hz, 2H), 7.04 (s, 1H), 6.95 (s, 1H), 3.57-3.39 (m, 4H), 1.92 (d, J=14.8 Hz, 2H), 1.60-1.55 (m, 3H), 1.34-1.24 (m, 2H). LCMS m/z 470.2 [M+H]$^+$.

Compound 110 was prepared from C1 and 3-ethyl-3-ethynyl-oxetane in seven steps using the method described for the preparation of compounds 107 and 108. (2-fluoro-4-methoxycarbonyl-phenyl)boronic acid was used in the Suzuki coupling step. (9.8 mg). $^1$H NMR (400 MHz, DMSO-$d_6$) δ 12.61 (s, 1H), 8.00 (s, 1H), 7.81 (dd, J=21.1, 9.1 Hz, 2H), 7.63 (s, 2H), 7.51-7.39 (m, 3H), 7.11 (s, 1H), 7.01 (s, 1H), 4.86 (d, J=5.7 Hz, 1H), 4.54 (d, J=5.8 Hz, 1H), 3.77 (dd, J=16.1, 5.8 Hz, 2H), 2.12-2.01 (m, 1H), 1.99-1.90 (m, 1H), 1.03 (t, J=7.3 Hz, 3H). LCMS m/z 474.2 [M+H]$^+$.

Compound 111

4-[6-(3-ethyloxetan-3-yl)-5-(4-fluorophenyl)-1H-pyrrolo[2,3-f]indazol-7-yl]benzoic Acid (111)

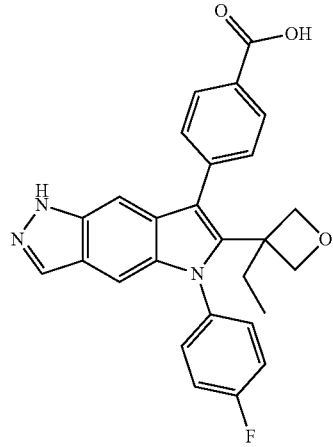

Compound 111 was prepared from C1 and 3-ethyl-3-ethynyl-oxetane in seven steps using the method as described for the preparation of compounds 107 and 108. (4-ethoxycarbonylphenyl)boronic acid was used in the Suzuki coupling step. Purification by reverse phase chromatography (Gradient: 0-100% MeCN in water containing 0.1% formic acid) afforded the product (11.7 mg). $^1$H NMR (400 MHz, DMSO-$d_6$) δ 13.01 (s, 1H), 12.64 (s, 1H), 8.08 (d, J=7.8 Hz, 2H), 8.00 (s, 1H), 7.66-7.60 (m, 2H), 7.57 (d, J=7.9 Hz, 2H), 7.46 (t, J=8.5 Hz, 2H), 7.34 (s, 1H), 6.99 (s, 1H), 4.60 (d, J=5.5 Hz, 2H), 3.80 (d, J=5.5 Hz, 2H), 2.08 (q, J=7.0, 6.1 Hz, 2H), 1.11 (t, J=7.4 Hz, 3H). LCMS m/z 456.2 [M+H]$^+$.

Compound 112

4-[5-(4-fluorophenyl)-6-(2-methoxy-1,1-dimethyl-ethyl)-1H-pyrrolo[2,3-f]indazol-7-yl]benzoic Acid (112)

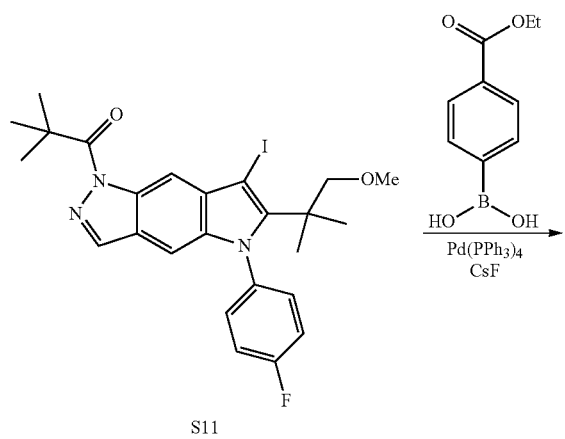

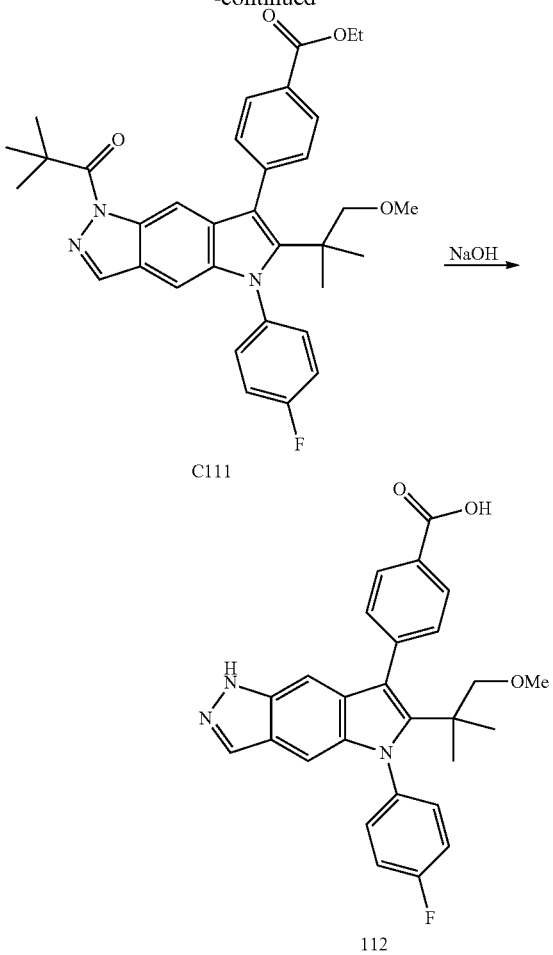

Step 1. Synthesis of ethyl 4-[1-(2,2-dimethylpropanoyl)-5-(4-fluorophenyl)-6-(2-methoxy-1,1-dimethyl-ethyl)pyrrolo[2,3-f]indazol-7-yl]benzoate (C111)

A solution of 1-[5-(4-fluorophenyl)-7-iodo-6-(2-methoxy-1,1-dimethyl-ethyl)pyrrolo[2,3-f]indazol-1-yl]-2,2-dimethyl-propan-1-one S11 (5.7 g, 10.4 mmol), (4-ethoxycarbonylphenyl)boronic acid (4 g, 20.6 mmol) and CsF (6.3 g, 41.5 mmol) in DME (120 mL) was purged with nitrogen. Pd(PPh$_3$)$_4$ (1.2 g, 1.04 mmol) was added and the reaction mixture heated at reflux overnight. The mixture was concentrated and purified twice by silica gel chromatography (Gradient: 0-60% EtOAc in heptane). The product was dissolved in ~100 mL of CH$_2$Cl$_2$:EtOAc (1:1) and then MP-TMT (1.6 g) scavenger resin was added. The mixture was stirred with the resin at room temperature overnight, and then filtered, and concentrated to afford the product, which was used in the subsequent step without further purification (3.5 g, 59%). $^1$H NMR (300 MHz, Chloroform-d) δ 8.21-8.12 (m, 2H), 8.10 (s, 1H), 8.02 (d, J=0.7 Hz, 1H), 7.61-7.53 (m, 2H), 7.53-7.45 (m, 2H), 7.34-7.24 (m, 2H), 6.88 (d, J=0.9 Hz, 1H), 4.47 (q, J=7.1 Hz, 2H), 3.08 (d, J=2.2 Hz, 5H), 1.53 (s, 9H), 1.48 (t, J=7.1 Hz, 3H), 1.17 (s, 6H). LCMS m/z 570.1 [M+H]$^+$. Note: 1.3 g of de-iodinated S11 was recovered in the reaction (33%).

Step 2. Synthesis of 4-[5-(4-fluorophenyl)-6-(2-methoxy-1,1-dimethyl-ethyl)-1H-pyrrolo[2,3-f]indazol-7-yl]benzoic Acid (112)

NaOH (1.32 mL of 1 M, 1.3 mmol) was added to a solution of ethyl 4-[1-(2,2-dimethylpropanoyl)-5-(4-fluorophenyl)-6-(2-methoxy-1,1-dimethyl-ethyl)pyrrolo[2,3-f]indazol-7-yl]benzoate C111 (125 mg, 0.2 mmol) in THF (2.5 mL) and MeOH (1.25 mL). The mixture was heated to 50° C. for 45 min. The mixture was concentrated in vacuo crude and minimal water was added. HCl (1.32 mL of 1 M, 1.32 mmol) was then added, to form a precipitate. Purification by reverse phase chromatography (Column: C18. Gradient: 10-100% acetonitrile in water with 0.2% formic acid) afforded the product as a white crystalline solid. (100 mg, 100%). $^1$H NMR (400 MHz, DMSO-$d_6$) δ 12.91 (d, 1H), 12.49 (s, 1H), 8.10-8.05 (m, 2H), 7.96 (s, 1H), 7.58 (t, J=7.4 Hz, 4H), 7.52-7.46 (m, 2H), 6.83 (d, J=7.4 Hz, 2H), 3.05 (s, 2H), 3.00 (s, 3H), 1.11 (s, 6H). LCMS m/z 458.4 [M+H]$^+$.

Compound 113-116

Compounds 113-116 were prepared in two steps from S11 and the appropriate boronic ester or boronic acid via a Suzuki coupling followed by an ester hydrolysis, as described for the preparation of compound 112. Any modifications to these methods are noted in Table 9 and accompanying footnotes. In some examples, the Suzuki reaction was carried out in the presence of Pd$_2$(dba)$_3$, SPhos, K$_3$PO$_4$, in THF-water at 60° C. In some examples, the reaction was performed with XPhos Pd G3, K$_3$PO$_4$ in 1,4-dioxane-water at 60° C.

TABLE 9

Method of preparation, structure, physicochemical data for compounds 113-116

| Compound | Method/Product | Boronic acid or ester | $^1$H NMR; LCMS m/z [M + H]$^+$ |
|---|---|---|---|
| 113 | Compound 112$^{1,3}$ from S11 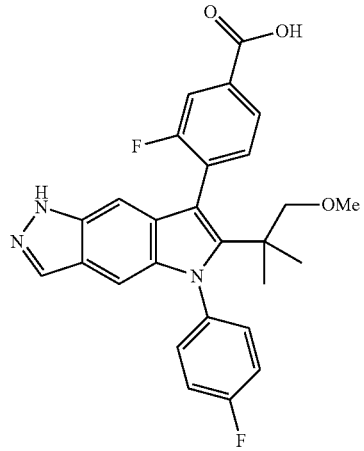 | 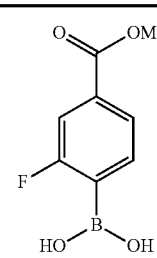 | $^1$H NMR (400 MHz, DMSO-$d_6$) δ 13.33 (s, 1H), 12.50 (s, 1H), 7.98 (s, 1H), 7.92 (d, J = 7.9 Hz, 1H), 7.84 (d, J = 9.8 Hz, 1H), 7.70 – 7.60 (m, 2H), 7.58 – 7.45 (m, 3H), 6.83 (d, J = 10.1 Hz, 2H), 3.13 – 2.97 (m, 5H), 1.12 (s, 6H). LCMS m/z 476.2 [M + H]$^+$. |
| 114 | Compound 112$^{2,3}$ from S11 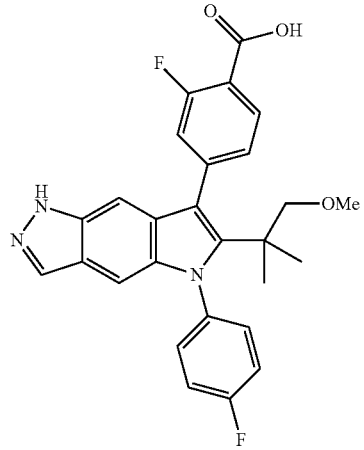 | 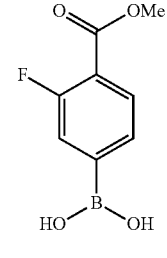 | $^1$H NMR (400 MHz, Methanol-$d_4$) δ 8.03 (t, J = 7.9 Hz, 1H), 7.93 (s, 1H), 7.53 (dd, J = 8.1, 4.9 Hz, 2H), 7.41 – 7.34 (m, 3H), 7.31 (d, J = 11.6 Hz, 1H), 6.98 (s, 1H), 6.87 (s, 1H), 3.17 – 3.09 (m, 5H), 1.18 (s, 6H). LCMS m/z 476.3 [M + H]$^+$. |

TABLE 9-continued

Method of preparation, structure, physicochemical data for compounds 113-116

| Compound | Method/Product | Boronic acid or ester | $^1$H NMR; LCMS m/z [M + H]$^+$ |
|---|---|---|---|
| 115 | Compound 112$^{1,3}$ from S11 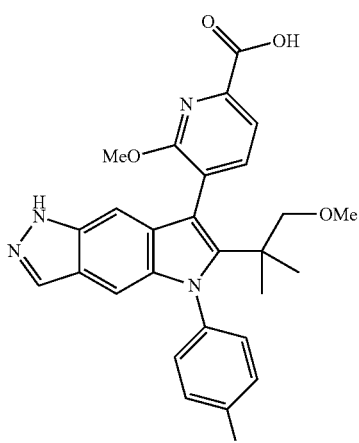 | 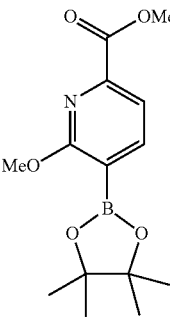 | $^1$H NMR (400 MHz, Methanol-d$_4$) δ 7.95 – 7.80 (m, 3H), 7.57 (dd, J = 8.6, 4.7 Hz, 1H), 7.44 (dd, J = 8.7, 4.7 Hz, 1H), 7.34 (q, J = 7.4 Hz, 2H), 6.83 (d, J = 6.9 Hz, 2H), 3.95 (s, 3H), 3.14 – 2.97 (m, 5H), 1.13 (d, J = 4.8 Hz, 6H). LCMS m/z 489.4 [M + H]$^+$. |
| 116 | Compound 112$^{2,4}$ from S11 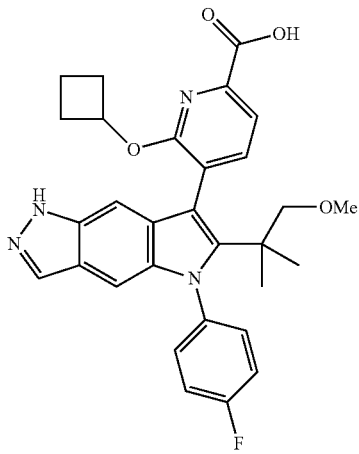 | 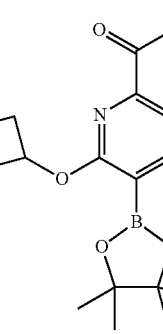 | $^1$H NMR (400 MHz, DMSO-d$_6$) δ 13.07 (s, 1H), 12.48 (s, 1H), 7.96 (s, 1H), 7.84 (d, J = 7.4 Hz, 1H), 7.78 (d, J = 7.3 Hz, 1H), 7.65 – 7.58 (m, 1H), 7.56 – 7.45 (m, 3H), 6.80 (d, J = 11.2 Hz, 2H), 5.29 (p, J = 7.2 Hz, 1H), 3.05 (s, 2H), 2.98 (s, 3H), 2.47 – 2.39 (m, 1H), 2.38 – 2.29 (m, 1H), 1.92 (p, J = 9.9 Hz, 2H), 1.75 – 1.54 (m, 2H), 1.14 (s, 6H). LCMS m/z 529.3 [M + H]$^+$. |

1 Pd$_2$db$_a$3, K$_3$PO$_4$, SPhos, THF-water, 60° C.
2 XPhos Pd G3, K$_3$PO$_4$, 1,4-dioxane-water, 60° C.
3 Purification by reversed-phase chromatography (Column: C18. Gradient: 10-100% MeCN in water with 0.2% formic acid) afforded the product.
4 Purification by reversed-phase chromatography (Column: C18. Gradient: 0-100% MeCN in water with 0.1% trifluoroacetic acid) afforded the product.

Compound 117

4-[5-(4-fluorophenyl)-6-[1-(methoxymethyl)cyclobutyl]-1H-pyrrolo[2,3-f]indazol-7-yl]benzoic Acid (117)

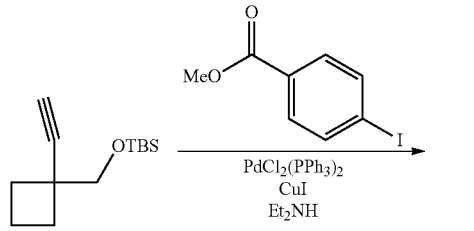

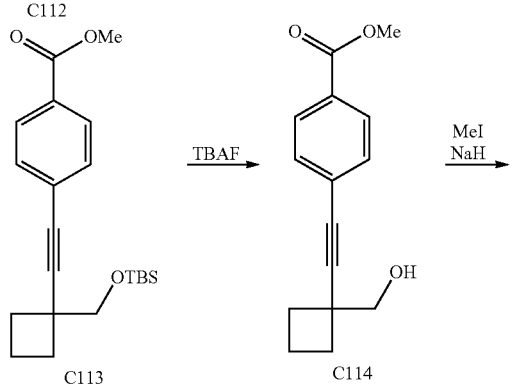

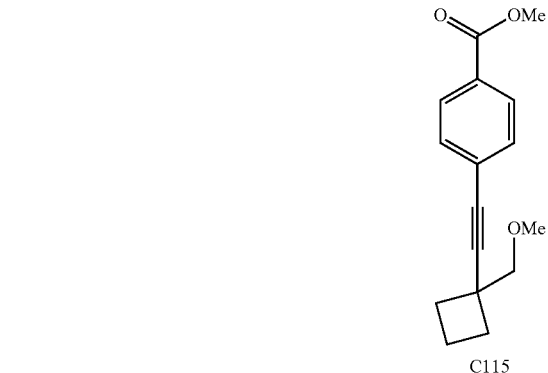

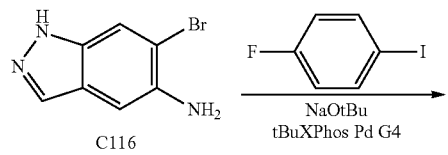

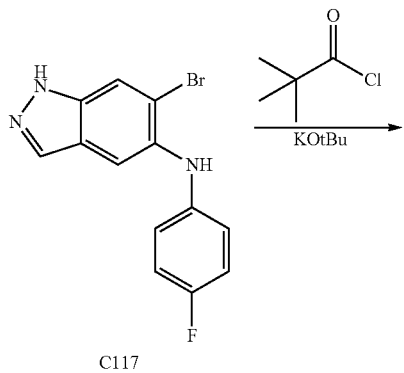

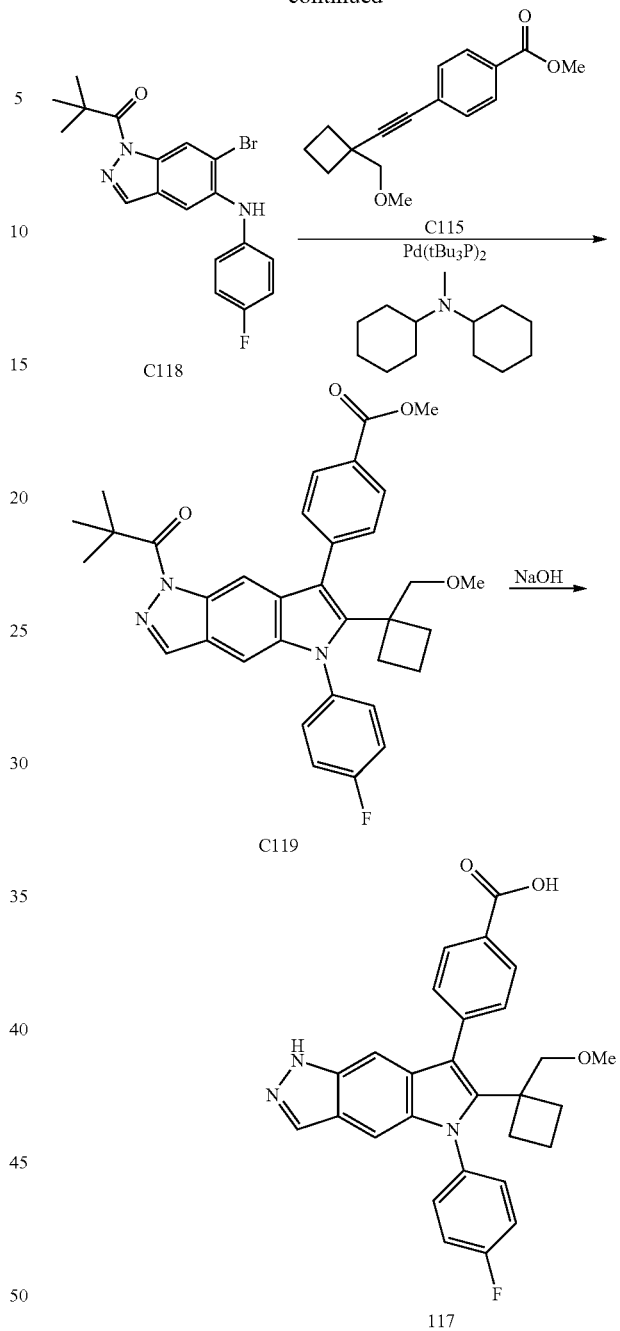

Step 1. Synthesis of methyl 4-[2-[1-[[tert-butyl(dimethyl)silyl]oxymethyl]cyclobutyl]ethynyl] benzoate (C113)

A solution of methyl 4-iodobenzoate (330 mg, 1.26 mmol) in DMF (1.9 mL) was purged with nitrogen for 10 min. Tert-butyl-[(1-ethynylcyclobutyl)methoxy]-dimethylsilane C112 (366 mg, 1.63 mmol), diethylamine (405 μL, 3.9 mmol) were added, followed by PdCl$_2$(PPh$_3$)$_2$ (45.9 mg, 0.07 mmol) and CuI (18.1 mg, 0.10 mmol). The mixture was heated at 90° C. for 90 min under a nitrogen atmosphere. The mixture was then concentrated to dryness, and followed by partitioning between CH$_2$Cl$_2$ and water. The organic layer was passed through a phase separator and concentrated in vacuo. Purification by silica gel chromatography (Gradient: 0-100% EtOAc in heptane) afforded the product (423 mg, 92%). LCMS m/z 359.2 [M+H]⁺.

(C112 was synthesized according to the method described by Chen, G., Zhang, X., Wei, Y., Tang, X. and Shi, M. (2014), Catalyst-Dependent Divergent Synthesis of Pyrroles from 3-Alkynyl Imine Derivatives: A Noncarbonylative and Carbonylative Approach. *Angew. Chem. Int. Ed.*, 53: 8492-8497).

Step 2. Synthesis of methyl 4-[2-[1-(hydroxymethyl)cyclobutyl]ethynyl]benzoate (C114)

To solution of methyl 4-[2-[1-[[tert-butyl(dimethyl)silyl] oxymethyl]cyclobutyl]ethynyl]benzoate C113 (150 mgs) in THF (13.6 mL) was added TBAF (410 µL of 1 M, 0.41 mmol). The reaction mixture was stirred at room temperature for 2 h then concentrated in vacuo. The mixture was then partitioned between CH₂Cl₂ and water. The organic layer was passed through a phase separator, and then concentrated in vacuo to afford the product (60 mg, 59%). LCMS m/z 245.1 [M+H]⁺.

Step 3. Synthesis of methyl 4-[2-[1-(methoxymethyl)cyclobutyl]ethynyl]benzoate (C115)

A solution of methyl 4-[2-[1-(hydroxymethyl)cyclobutyl] ethynyl]benzoate C114 (90 mg, 0.36 mmol) in THF (1.0 mL) was cooled to 0° C. Sodium hydride (8.6 mg, 0.36 mmol) and methyl iodide (22.5 µL, 0.36 mmol) were added. The reaction mixture was stirred at room temperature for 2 h. Further methyl iodide (22.5 µL, 0.36 mmol) and sodium hydride (8.6 mg, 0.36 mmol) were added and the reaction stirred at room temperature for an additional 2 h. The mixture was partitioned between CH₂Cl₂ and water. The organic layer was passed through a phase separator and concentrated in vacuo. Purification by silica gel chromatography (Eluent: 0-100% EtOAc in heptane) afforded the product (423 mg, 92%). LCMS m/z 259.1 [M+H]⁺.

Step 4. Synthesis of 6-bromo-N-(4-fluorophenyl)-1H-indazol-5-amine (C117)

A solution of 1-fluoro-4-iodo-benzene (1.6 mL, 13.9 mmol), 6-bromo-1H-indazol-5-amine C116 (2000 mg, 9.4 mmol), NaOtBu (3.9 g, 40.1 mmol), and tBuXPhos Pd G4 (432 mg, 0.48 mmol) in tBuOH (50 mL) was degassed with nitrogen, then allowed to stir at room temperature for 5 h. The mixture was diluted with EtOAc, washed with saturated sodium bicarbonate solution and then brine. The organic layer was dried over sodium sulfate, filtered, and concentrated in vacuo. Purification by silica gel chromatography (Gradient: 0-100% EtOAc in heptane) afforded the product (1.8 g, 62%). ¹H NMR (400 MHz, DMSO) δ 13.06 (s, 1H), 7.99 (s, 1H), 7.89 (s, 1H), 7.59 (s, 1H), 7.48 (d, J=1.7 Hz, 1H), 7.09-6.88 (m, 2H), 6.80 (dd, J=8.1, 4.7 Hz, 2H). LCMS m/z 305.1 [M+H]⁺.

Step 5. Synthesis of 1-[6-bromo-5-(4-fluoroanilino) indazol-1-yl]-2,2-dimethyl-propan-1-one (C118)

To a suspension of 6-bromo-N-(4-fluorophenyl)-1H-indazol-5-amine C117 (754 mg, 2.46 mmol) in THF (15 mL) at 1° C. (ice-water bath) was added KOtBu (2.6 mL of 1 M, 2.6 mmol). After 10 min, 2,2-dimethylpropanoyl chloride (965 µL, 7.84 mmol) was added. The reaction was stirred for 30 min in cooling bath. Further 2,2-dimethylpropanoyl chloride (25 µL) was added and the mixture stirred for an additional 30 min. The reaction was quenched with water (3 mL), and stirred for 5 min, then concentrated under reduced pressure. The mixture was partitioned between CH₂Cl₂ (20 mL) and water (10 mL). The organic layer was passed through a phase separator and concentrated in vacuo to afford product. (971 mg, 100%). ¹H NMR (300 MHz, DMSO-d₆) δ 8.61-8.56 (m, 1H), 8.36 (d, J=0.9 Hz, 1H), 7.62 (s, 1H), 7.57 (s, 1H), 7.16-7.04 (m, 4H), 1.49 (s, 9H). LCMS m/z 390.2 [M+H]⁺.

Step 6: Synthesis of methyl 4-[1-(2,2-dimethylpropanoyl)-5-(4-fluorophenyl)-6-[1-(methoxymethyl) cyclobutyl]pyrrolo[2,3-f]indazol-7-yl]benzoate (C119)

1-[6-bromo-5-(4-fluoroanilino)indazol-1-yl]-2,2-dimethyl-propan-1-one C118 (40 mg, 0.10 mmol), methyl 4-[2-[1-(methoxymethyl)cyclobutyl]ethynyl]benzoate (39.2 mg, 0.15 mmol) and Pd(PtBu₃)₄ (2.5 mg, 0.005 mmol) were combined in a vial under a nitrogen atmosphere. 1,4-dioxane (506 µL) and N-cyclohexyl-N-methyl-cyclohexanamine (54.1 µL, 0.25 mmol) were added. The reaction mixture was then stirred at 110° C. for 1 h. The reaction was quenched with NH₄Cl and partitioned between CH₂Cl₂ and water. The organic layer was passed through a phase separator and concentrated in vacuo. Purification by silica gel chromatography (Gradient: 0-30% EtOAc in heptane) afforded the product (27 mg, 44%). ¹H NMR (300 MHz, DMSO-d₆) δ 8.61-8.56 (m, 1H), 8.36 (d, J=0.9 Hz, 1H), 7.62 (s, 1H), 7.57 (s, 1H), 7.16-7.04 (m, 4H), 1.49 (s, 9H). LCMS m/z 568.2 [M+H]⁺.

Step 7. Synthesis of 4-[5-(4-fluorophenyl)-6-[1-(methoxymethyl)cyclobutyl]-1H-pyrrolo[2,3-f]indazol-7-yl]benzoic Acid (117)

NaOH (215 µL of 1 M, 0.22 mmol) was added to a solution of methyl 4-[1-(2,2-dimethylpropanoyl)-5-(4-fluorophenyl)-6-[1-(methoxymethyl)cyclobutyl]pyrrolo[2,3-f] indazol-7-yl]benzoate C119 (27 mg, 0.05 mmol) in THF (611 µL) and MeOH (252 µL). The reaction mixture was allowed to stir at 50° C. for 30 min, and then concentrated under reduced pressure. Purification by reverse phase column chromatography (Eluent: MeCN in water with 0.1% formic acid modifier) afforded the desired product (8.5 mg, 37%). ¹H NMR (400 MHz, DMSO-d₆) δ 13.00 (s, 1H), 12.58 (s, 1H), 8.05-7.95 (m, 3H), 7.79 (d, J=7.8 Hz, 2H), 7.65-7.58 (m, 2H), 7.44 (t, J=8.4 Hz, 2H), 7.32 (s, 1H), 6.91 (s, 1H), 3.71 (s, 2H), 3.36 (s, 3H), 2.08 (q, J=9.8 Hz, 2H), 1.55-1.43 (m, 4H). LCMS m/z 470.2 [M+H]⁺.

Compound 118

4-[5-(4-fluorophenyl)-6-[1-(hydroxymethyl)cyclobutyl]-1H-pyrrolo[2,3-f]indazol-7-yl]benzoic Acid (118)

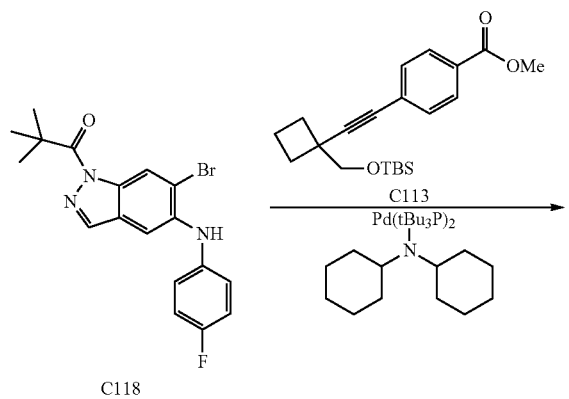

C118

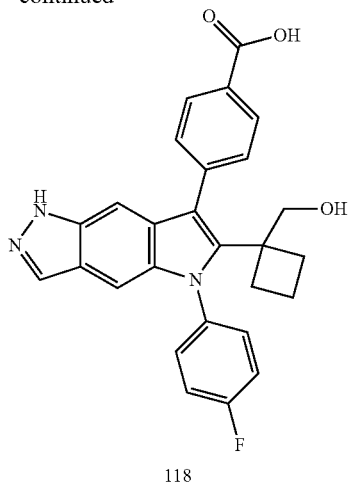

118

Step 1. Synthesis of 4-[6-[1-[[tert-butyl(dimethyl)silyl]oxymethyl]cyclobutyl]-1-(2,2-dimethylpropanoyl)-5-(4-fluorophenyl)pyrrolo[2,3-f]indazol-7-yl]benzoate (C120)

To a mixture of 1-[6-bromo-5-(4-fluoroanilino)indazol-1-yl]-2,2-dimethyl-propan-1-one C118 (60 mg, 0.15 mmol), methyl 4-[2-[1-[[tert-butyl(dimethyl)silyl]oxymethyl]cyclobutyl]ethynyl]benzoate (93 mg, 0.26 mmol) (C113), and Pd(tBu$_3$P)$_2$ (3.8 mg, 0.007 mmol), under a nitrogen atmosphere, was added 1,4-dioxane (760 μL) and N-cyclohexyl-N-methyl-cyclohexanamine (81.4 μL, 0.3 mmol). The mixture was allowed to stir at 110° C. for 1 h. The reaction was quenched with NH$_4$Cl and partitioned between CH$_2$Cl$_2$ and water. The organic layer was passed through a phase separator and concentrated in vacuo. Purification by silica gel chromatography (Gradient: 0-30% EtOAc in heptane) afforded the product (124 mg, 33%). LCMS m/z 668.2 [M+H]$^+$.

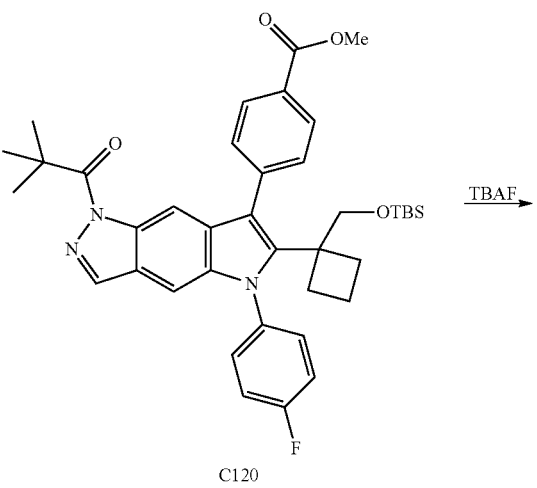

C120

Step 2: Synthesis of 4-[1-(2,2-dimethylpropanoyl)-5-(4-fluorophenyl)-6-[1-(hydroxymethyl)cyclobutyl]pyrrolo[2,3-f]indazol-7-yl]benzoate (C121)

TBAF (185 μL of 1 M, 0.19 mmol) was added to a solution of methyl 4-[6-[1-[[tert-butyl(dimethyl)silyl]oxymethyl]cyclobutyl]-1-(2,2-dimethylpropanoyl)-5-(4-fluorophenyl)pyrrolo[2,3-f]indazol-7-yl]benzoate C120 (124 mg, 0.19 mmol) in THF (6.1 mL). The reaction mixture was allowed to stir at room temperature for 2 h. The mixture was partitioned between CH$_2$Cl$_2$ and water. The organic layer was passed through a phase separator and concentrated to in vacuo to afford the product (97 mg, 94%). LCMS m/z 554.2 [M+H]$^+$.

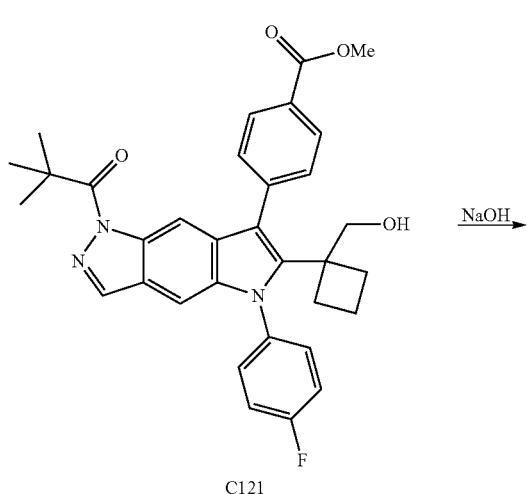

C121

Step 3: 4-[5-(4-fluorophenyl)-6-[1-(hydroxymethyl)cyclobutyl]-1H-pyrrolo[2,3-f]indazol-7-yl]benzoic Acid (118)

NaOH (221 μL of 1 M, 0.22 mmol) was added to a solution of methyl 4-[1-(2,2-dimethylpropanoyl)-5-(4-fluorophenyl)-6-[1-(hydroxymethyl)cyclobutyl]pyrrolo[2,3-f]indazol-7-yl]benzoate (27 mg, 0.05 mmol) in THF (611 μL) and MeOH (252 μL). The reaction mixture was stirred at 50° C. for 30 min, and then concentrated in vacuo. Purification by reverse phase column chromatography (Eluent: MeCN in water with 0.1% formic acid modifier) afforded the product (8.2 mg, 35%). $^1$H NMR (400 MHz, DMSO-$d_6$) δ 12.97 (s, 1H), 12.57 (s, 1H), 8.03-7.96 (m, 3H), 7.87 (d, J=7.5 Hz, 2H), 7.70-7.63 (m, 2H), 7.43 (t, J=8.2 Hz, 2H), 7.35 (s, 1H), 6.89 (s, 1H), 5.34-5.26 (m, 1H), 3.81 (d, J=4.5 Hz, 2H), 2.09-1.98 (m, 2H), 1.55-1.44 (m, 4H). LCMS m/z 456.1 [M+H]$^+$.

Compound 119

4-[5-(4-fluorophenyl)-6-(2-hydroxy-1,1-dimethyl-ethyl)-1H-pyrrolo[2,3-f]indazol-7-yl]benzoic Acid (119)

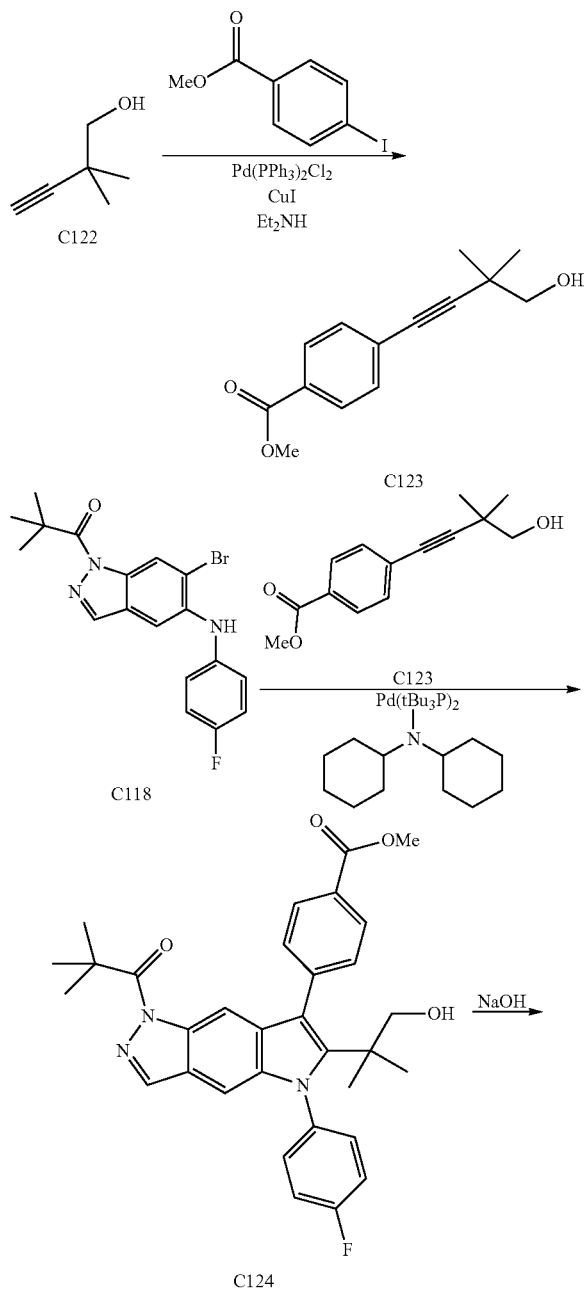

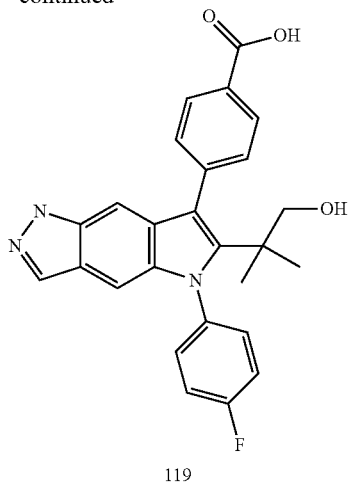

119

Step 1. Synthesis of methyl 4-(4-hydroxy-3,3-dimethyl-but-1-ynyl)benzoate (C123)

A solution of 2,2-dimethylbut-3-yn-1-ol C122 (1 g, 10.2 mmol) and methyl 4-iodobenzoate (4.0 g, 15.3 mmol) in NEt$_3$ (10 mL) and 1,4-dioxane (10 mL) was degassed and purged with nitrogen. CuI (194 mg, 1.0 mmol) and Pd(PPh$_3$)$_2$Cl$_2$ (453 mg, 0.65 mmol) were added, and the reaction stirred under a nitrogen atmosphere at 90° C. for 2 h. The mixture was concentrated to dryness under reduced pressure and partitioned between CH$_2$Cl$_2$ and water. The organic layer was passed through a phase separator and concentrated to dryness under reduced pressure. Purification by silica gel chromatography (Gradient: 0-100% EtOAc in heptane) afforded the product (1.49 g, 58%). $^1$H NMR (400 MHz, Chloroform-d) δ 8.02-7.95 (m, 2H), 7.51-7.46 (m, 2H), 3.94 (s, 3H), 3.54 (d, J=6.9 Hz, 2H), 1.34 (s, 6H). LCMS m/z 233.1 [M+H]$^+$.

Step 2. 4-[1-(2,2-dimethylpropanoyl)-5-(4-fluorophenyl)-6-(2-hydroxy-1,1-dimethyl-ethyl)pyrrolo[2,3-f]indazol-7-yl]benzoate (C124)

To a mixture of 1-[6-bromo-5-(4-fluoroanilino)indazol-1-yl]-2,2-dimethyl-propan-1-one (80 mg, 0.21 mmol) C118, methyl 4-(4-hydroxy-3,3-dimethyl-but-1-ynyl)benzoate (71 mg, 0.31 mmol) and Pd(tBu$_3$P)$_2$ (5.1 mg, 0.01 mmol) under a nitrogen atmosphere was added 1,4-dioxane (1.0 mL), followed by N-cyclohexyl-N-methyl-cyclohexanamine (109 μL, 0.51 mmol). The mixture was stirred at 100° C. for 1 h. The reaction was then quenched with NH$_4$Cl and partitioned between CH$_2$Cl$_2$ and water. The organic layer was passed through a phase separator and concentrated to dryness in vacuo. Purification by silica gel chromatography (Eluent: 0-100% EtOAc in heptane) afforded the product (124 mg, 33%). LCMS m/z 542.1 [M+H]$^+$.

Step 3. 4-[5-(4-fluorophenyl)-6-[1-(hydroxymethyl)cyclobutyl]-1H-pyrrolo[2,3-f]indazol-7-yl]benzoic Acid (119)

NaOH (226 μL of 1 M, 0.23 mmol) was added to a solution of 4-[1-(2,2-dimethylpropanoyl)-5-(4-fluorophenyl)-6-(2-hydroxy-1,1-dimethyl-ethyl)pyrrolo[2,3-f]indazol-7-yl]benzoate C124 (30 mg, 0.05 mmol) in THF (609 μL) and MeOH (252 μL). The mixture was stirred at 50° C. for 30 min then concentrated under reduced pressure. Purification by reverse phase column chromatography (Eluent: MeCN in water with 0.1% formic acid modifier) afforded the product. (15.0 mg, 64%). $^1$H NMR (400 MHz, DMSO-$d_6$) δ 12.99 (s, 1H), 12.47 (s, 1H), 8.06 (d, J=7.6 Hz, 2H), 7.96 (s, 1H), 7.66-7.57 (m, 4H), 7.47 (t, J=8.3 Hz, 2H), 6.82 (d, J=12.9 Hz, 2H), 4.79 (t, J=5.4 Hz, 1H), 3.31 (s, 2H), 1.02 (s, 6H). LCMS m/z 444.1 [M+H]$^+$.

Compound 120

5-[4-[5-(4-fluorophenyl)-6-tetrahydropyran-4-yl-1H-pyrrolo[2,3-f]indazol-7-yl]phenyl]imidazolidine-2,4-dione (120)

Compound 121

5-(4-fluorophenyl)-7-(6-methylsulfonyl-3-pyridyl)-6-tetrahydropyran-4-yl-1H-pyrrolo[2,3-f]indazole (121)

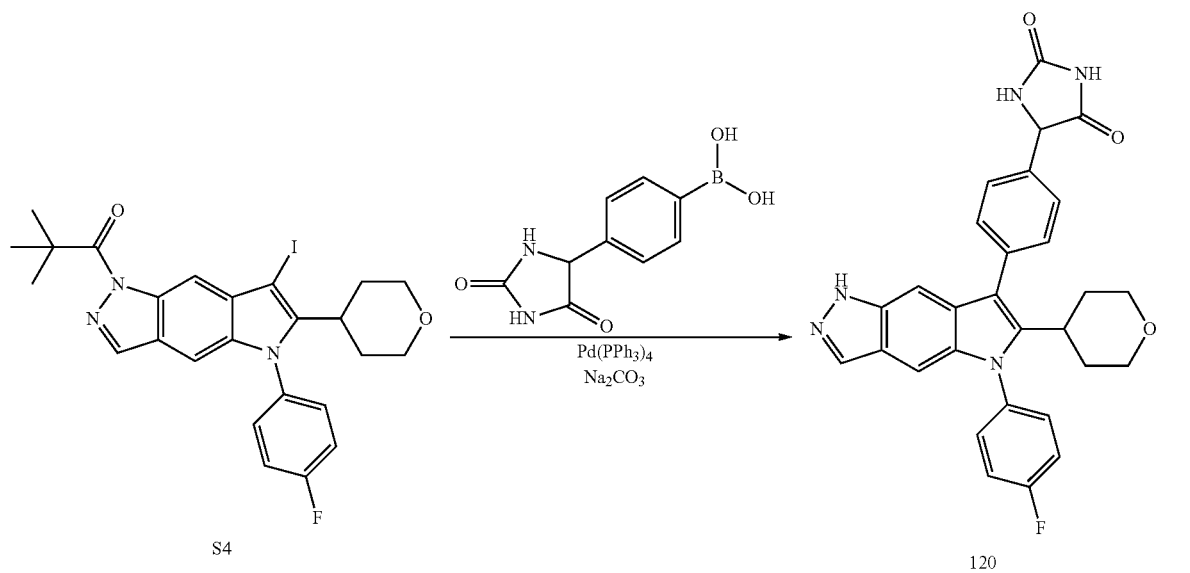

Synthesis of 5-[4-[5-(4-fluorophenyl)-6-tetrahydropyran-4-yl-1H-pyrrolo[2,3-f]indazol-7-yl]phenyl]imidazolidine-2,4-dione (120)

A solution of Na$_2$CO$_3$ (225 μL of 2 M, 0.5 mmol) was added to a solution of 1-[5-(4-fluorophenyl)-7-iodo-6-tetrahydropyran-4-yl-pyrrolo[2,3-f]indazol-1-yl]-2,2-dimethyl-propan-1-one S4 (100 mg, 0.18 mmol), [4-(2,5-dioxoimidazolidin-4-yl)phenyl]boronic acid (50 mg, 0.23 mmol), and Pd(PPh$_3$)$_4$ (10 mg, 0.009 mmol) were dissolved in 1,4-dioxane (750 μL) and DMF (750 μL). The mixture was stirred at 100° C. for 24 h, and then partitioned between CH$_2$Cl$_2$ and water. The organic layer was passed through a phase separator and concentrated to dryness under reduced pressure. Purification by reversed-phase HPLC (Column: C18 Waters Sunfire column 30×150 mm, 5 micron. Gradient: 10-100% MeCN in H$_2$O with 0.1% TFA) afforded the product (3.2 mg, 3%). $^1$H NMR (400 MHz, DMSO-$d_6$) δ 12.55 (s, 1H), 10.89 (s, 1H), 8.51 (s, 1H), 8.00 (s, 1H), 7.63 (dd, J=8.7, 5.0 Hz, 2H), 7.58-7.47 (m, 6H), 7.20 (s, 1H), 7.07 (s, 1H), 5.31 (s, 1H), 3.73 (d, J=11.0 Hz, 2H, overlap from solvent), 3.17-3.04 (m, 2H), 3.01-2.93 (m, 1H), 1.67 (s, 4H). LCMS m/z 510.2 [M+H]$^+$.

-continued

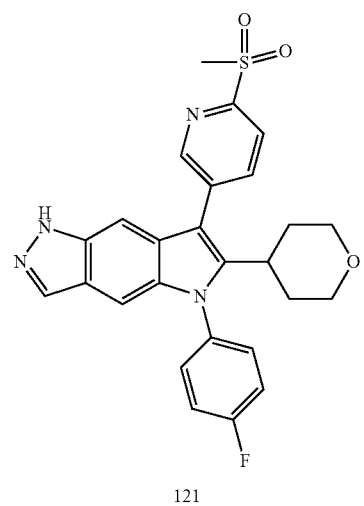

5-(4-fluorophenyl)-7-(6-methylsulfonyl-3-pyridyl)-6-tetrahydropyran-4-yl-1H-pyrrolo[2,3-f]indazole (121)

A solution of Na₂CO₃ (450 µL of 2 M, 0.9 mmol) was added to a solution of 1-[5-(4-fluorophenyl)-7-iodo-6-tetrahydropyran-4-yl-pyrrolo[2,3-f]indazol-1-yl]-2,2-dimethyl-propan-1-one S4 (200 mg, 0.36 mmol), (6-methylsulfonyl-3-pyridyl)boronic acid (88 mg, 0.44 mmol), and Pd(PPh₃)₄ (21 mg, 0.018 mmol) in 1,4-dioxane (1.5 mL) and DMF (1.5 mL). The reaction was stirred at 160° C. for 1 h, then partitioned between CH₂Cl₂ and water. The organic layer was passed through a phase separator, and concentrated to dryness in vacuo. Purification by reverse phase column chromatography (Gradient: 0-40% acetonitrile in water with formic acid modifier) afforded the product (69 mg, 39%). ¹H NMR (400 MHz, DMSO-d₆) δ 12.66 (s, 1H), 8.95 (dd, J=2.2, 0.8 Hz, 1H), 8.31 (dd, J=8.1, 2.2 Hz, 1H), 8.23 (dd, J=8.1, 0.8 Hz, 1H), 8.03 (t, J=1.3 Hz, 1H), 7.70-7.60 (m, 2H), 7.53 (t, J=8.7 Hz, 2H), 7.31 (t, J=1.1 Hz, 1H), 7.11 (d, J=0.9 Hz, 1H), 3.75 (dd, J=11.3, 4.0 Hz, 2H), 3.41 (s, 3H), 3.14 (t, J=11.4 Hz, 2H), 3.02 (m, 1H), 1.72 (d, J=12.6 Hz, 2H), 1.63 (m, 2H). LCMS m/z 491.1 [M+H]⁺.

Compound 122

4-[5-(4-fluorophenyl)-6-(2-methoxy-2-methyl-propyl)-1H-pyrrolo[2,3-f]indazol-7-yl]benzoic Acid (122)

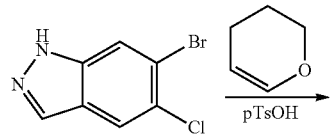
C6

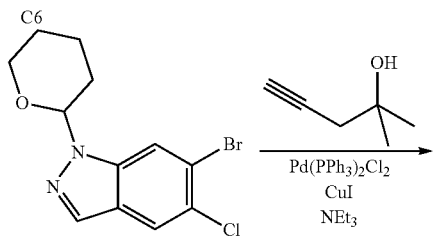
C125

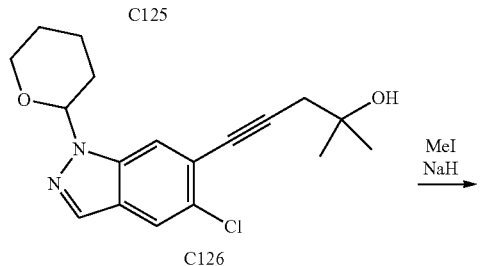
C126

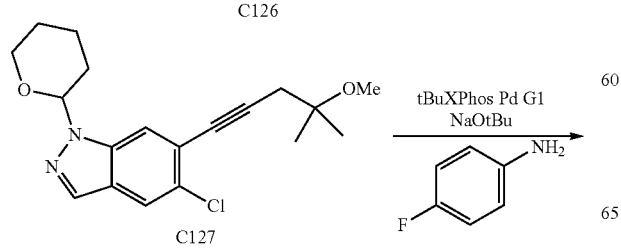
C127

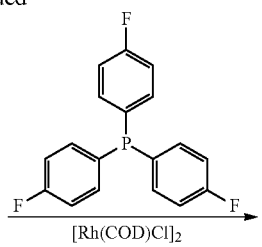

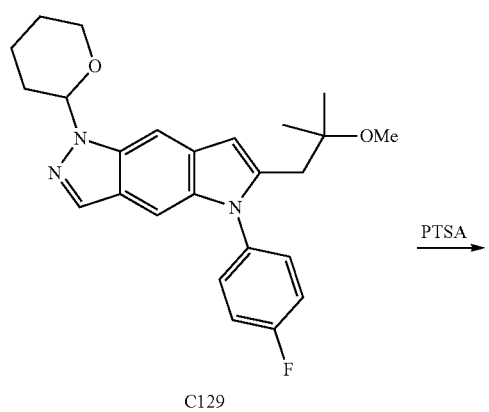
C128

C129

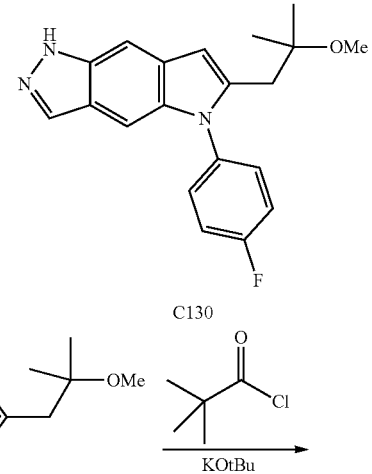
C130

C130

-continued

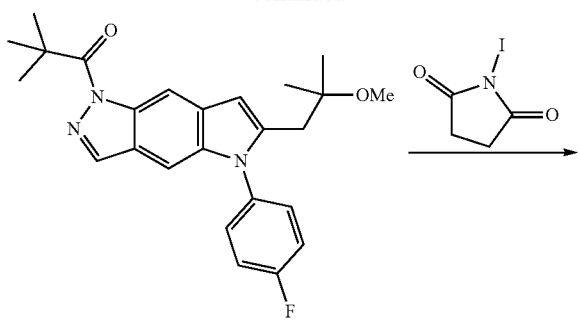

C131

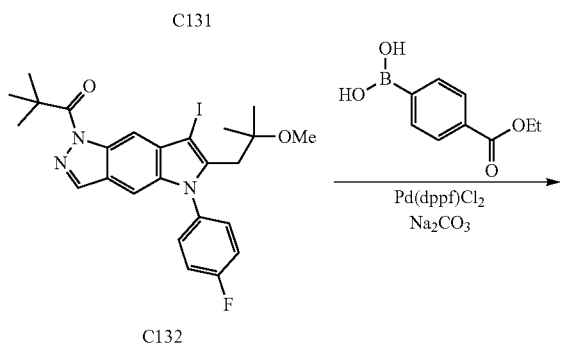

C132

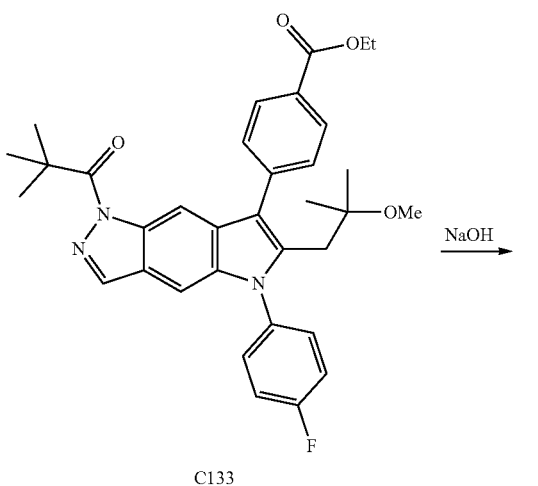

C133

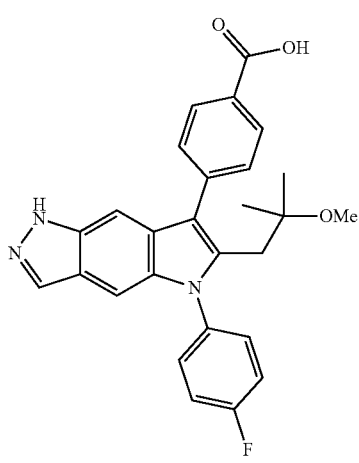

122

Step 1. Synthesis of 6-bromo-5-chloro-1-tetrahydropyran-2-yl-indazole (C125)

To a suspension of 6-bromo-5-chloro-1H-indazole C6 (25 g, 100.4 mmol) and 3,4-dihydro-2H-pyran (28 mL, 306.9 mmol) in $CH_2Cl_2$ (300 mL) was added 4-methylbenzene-sulfonic acid monohydrate (1.8 g, 9.46 mmol). The reaction was allowed to stir at 50° C. for 1 h. The reaction was washed with $NaHCO_3$ and extracted with dichloromethane (×3). The organic layer was dried over sodium sulfate, filtered and concentrated in vacuo. Purification by silica gel chromatography (Eluent: 0-30% EtOAc in heptane) afforded the product (30.8 g, 97%). $^1$H NMR (300 MHz, Chloroform-d) δ 7.87 (d, J=0.8 Hz, 2H), 7.76 (s, 1H), 5.59 (dd, J=9.1, 2.6 Hz, 1H), 4.08-3.86 (m, 1H), 3.77-3.49 (m, 1H), 2.52-2.29 (m, 1H), 2.04 (m, 2H), 1.82-1.53 (m, 3H). LCMS m/z 315.0 $[M+H]^+$.

Step 2. 5-(5-chloro-1-tetrahydropyran-2-yl-indazol-6-yl)-2-methyl-pent-4-yn-2-ol (C126)

To a solution of 6-bromo-5-chloro-1-tetrahydropyran-2-yl-indazole C125 (400 mg, 1.27 mmol), 2-methylpent-4-yn-2-ol (124 mg, 1.26 mmol), and $Et_3N$ (3.3 mL) in 1,4-dioxane (3.2 mL) was purged with nitrogen. CuI (24.1 mg, 0.13 mmol) and $Pd(PPh_3)_2Cl_2$ (56 mg, 0.08 mmol) were added and the reaction was stirred at 100° C. for 1 h. The mixture was partitioned between $CH_2Cl_2$ and water. The organic layer was passed through a phase separator and concentrated to dryness under reduced pressure. Purification by silica gel chromatography (Eluent: 0-100% EtOAc in heptane) afforded the product (264 mg, 59%). $^1$H NMR (400 MHz, Chloroform-d) δ 7.94 (d, J=0.7 Hz, 1H), 7.75 (s, 2H), 5.67 (dd, J=9.3, 2.7 Hz, 1H), 4.06-3.99 (m, 1H), 2.69 (s, 2H), 2.56-2.45 (m, 1H), 2.18-2.03 (m, 3H), 1.80-1.61 (m, 3H), 1.43 (s, 6H). LCMS m/z 333.1 $[M+H]^+$.

Step 3. Synthesis of 5-chloro-6-(4-methoxy-4-methyl-pent-1-ynyl)-1-tetrahydropyran-2-yl-indazole (C127)

To a solution of 5-(5-chloro-1-tetrahydropyran-2-yl-indazol-6-yl)-2-methyl-pent-4-yn-2-ol C126 (720 mg, 2.0 mmol) in THF (9.7 mL) at 0° C. was added NaH (135 mg of 60% w/w, 3.38 mmol). The reaction was warmed to room temperature and stirred for 1 h. Upon cooling to 0° C., methyl iodide (187 μL, 3.0 mmol) was added. The reaction was warmed to room temperature, and stirred for 1 h. Additional NaH (135 mg of 60% w/w, 3.34 mmol) was added. The mixture was stirred for 1 h, and then further methyl iodide (187 μL, 3.0 mmol) was added. The reaction mixture was partitioned between $CH_2Cl_2$ and water. The organic layer was passed through a phase separator and concentrated to dryness under reduced pressure. Purification by silica gel chromatography (Eluent: 0-100% EtOAc in heptane) afforded the product (566 mg, 81%). LCMS m/z 347.1 $[M+H]^+$.

Step 4. Synthesis of N-(4-fluorophenyl)-6-(4-methoxy-4-methyl-pent-1-ynyl)-1-tetrahydropyran-2-yl-indazol-5-amine (C128)

A solution of chloro-6-(4-methoxy-4-methyl-pent-1-ynyl)-1-tetrahydropyran-2-yl-indazole C127 (566 mg, 1.63 mmol), NaOtBu (465 mg, 4.84 mmol), and 4-fluoroaniline (271 mg, 2.44 mmol) in tBuOH (7.3 mL) was degassed with nitrogen for 10 min. tBuXPhos Pd G1 (154 mg, 0.17 mmol) was added. The reaction mixture was stirred at 90° C. for 1 h, and then partitioned between $CH_2Cl_2$ and water. The organic layer was passed through a phase separator and concentrated to dryness under reduced pressure. Purification by silica gel chromatography (Eluent: 0-100% EtOAc in heptane) afforded the product (530 mg, 77%). LCMS m/z 422.2 $[M+H]^+$.

Step 5. Synthesis of 5-(4-fluorophenyl)-6-(2-methoxy-2-methyl-propyl)-1-tetrahydropyran-2-yl-pyrrolo[2,3-f]indazole (C129)

A mixture of N-(4-fluorophenyl)-6-(4-methoxy-4-methyl-pent-1-ynyl)-1-tetrahydropyran-2-yl-indazol-5-amine C128 (530 mg, 1.26 mmol), tris(4-fluorophenyl)phosphane (92.8 mg, 0.3 mmol), and $[Rh(COD)Cl]_2$ (29.3 mg, 0.06 mmol) was purged with nitrogen for 10 min. DMF (5.3 mL) was added and the solution was degassed. The reaction was then allowed to stirred at 100° C. for 24 h, then partitioned between $CH_2Cl_2$ and water. The organic layer was passed through a phase separator and concentrated to dryness under reduced pressure. Purification by silica gel chromatography (Eluent: 0-100% EtOAc in heptane) afforded the product (314 mg, 59%). LCMS m/z 422.2 $[M+H]^+$.

Step 6 Synthesis of 5-(4-fluorophenyl)-6-(2-methoxy-2-methyl-propyl)-1H-pyrrolo[2,3-f]indazole (C130)

To a solution of 5-(4-fluorophenyl)-6-(2-methoxy-2-methyl-propyl)-1-tetrahydropyran-2-yl-pyrrolo[2,3-f]indazole C129 (314 mg, 0.75 mmol) in MeOH (3.1 mL), EtOAc (3.1 mL) and $H_2O$ (1.5 mL) was added 4-methylbenzenesulfonic acid monohydrate (638 μL, 3.6 mmol). The reaction was stirred at 50° C. for 1 h, then partitioned between $CH_2Cl_2$ and saturated sodium bicarbonate. The organic layer was passed through a phase separator and concentrated to dryness under reduced pressure to afford the product (265 mg, 106%). LCMS m/z 338.1 $[M+H]^+$.

Step 7. Synthesis of 1-[5-(4-fluorophenyl)-6-(2-methoxy-2-methyl-propyl)pyrrolo[2,3-f]indazol-1-yl]-2,2-dimethyl-propan-1-one (C131)

To a solution of 5-(4-fluorophenyl)-6-(2-methoxy-2-methyl-propyl)-1H-pyrrolo[2,3-f]indazole C130 (233 mg, 0.69 mmol) in THF (5.2 mL) at 0° C. was added KOtBu (171 mg, 1.5 mmol). After stirring for 10 min, 2,2-dimethylpropanoyl chloride (329 μL, 2.67 mmol) was added and the reaction stirred at 0° C. for 1 h. Purification by silica gel chromatography (Gradient: 0-100% EtOAc in heptane) afforded the product (231 mg, 56%). LCMS m/z 422.2 $[M+H]^+$.

Step 8. Synthesis of 1-[5-(4-fluorophenyl)-7-iodo-6-(2-methoxy-2-methyl-propyl)pyrrolo[2,3-f]indazol-1-yl]-2,2-dimethyl-propan-1-one (C132)

1-iodopyrrolidine-2,5-dione (118 mg, 0.5 mmol) was added portion-wise to a solution of 1-[5-(4-fluorophenyl)-6-(2-methoxy-2-methyl-propyl)pyrrolo[2,3-f]indazol-1-yl]-2,2-dimethyl-propan-1-one C131 (231 mg, 0.38 mmol) in $CH_2Cl_2$ (1.6 mL) at 0° C. The reaction mixture was stirred for 1 h at 0° C. The mixture was then washed with $Na_2SO_3$ (1M). The organic layer was passed through a phase separator and concentrated in vacuo to afford the product (165 mg, 79%). LCMS m/z 548.1 $[M+H]^+$.

Step 9. Synthesis of ethyl 4-[1-(2,2-dimethylpropanoyl)-5-(4-fluorophenyl)-6-(2-methoxy-2-methyl-propyl)pyrrolo[2,3-f]indazol-7-yl]benzoate (C133)

1-[5-(4-fluorophenyl)-7-iodo-6-(2-methoxy-2-methyl-propyl)pyrrolo[2,3-f]indazol-1-yl]-2,2-dimethyl-propan-1-one C132 (50 mg, 0.09 mmol), (4-ethoxycarbonylphenyl)boronic acid (34.9 mg, 0.18 mmol) and $Pd(dppf)Cl_2$ (3.4 mg, 0.004 mmol) were combined in a flask and purged with nitrogen. 1,4-dioxane (302 μL) and sodium carbonate (139 μL of 2 M, 0.28 mmol) were added and the reaction stirred at 95° C. for 1 h. The reaction mixture was then partitioned between $CH_2Cl_2$ and water. Organic layer was passed through a phase separator and concentrated to dryness under reduced pressure. Purification by silica gel chromatography (Eluent: 0-100% EtOAc in heptane) afforded the product (16 mg, 17%). LCMS m/z 570.2 $[M+H]^+$.

Step 10. Synthesis of 4-[5-(4-fluorophenyl)-6-(2-methoxy-2-methyl-propyl)-1H-pyrrolo[2,3-f]indazol-7-yl]benzoic Acid (122)

To a solution of ethyl 4-[1-(2,2-dimethylpropanoyl)-5-(4-fluorophenyl)-6-(2-methoxy-2-methyl-propyl)pyrrolo[2,3-f]indazol-7-yl]benzoate C133 (12 mg, 0.019 mmol), in THF (244 μL) and MeOH (101 μL) was added NaOH (86.0 μL of 1 M, 0.09 mmol). The reaction mixture was stirred at 50° C. for 30 min. The solvent was concentrated to dryness under reduced pressure. Purification by reverse phase column chromatography (Gradient: MeCN in water with 0.1% formic acid modifier) afforded the desired product (5.5 mg, 62%). $^1H$ NMR (400 MHz, DMSO-$d_6$) δ 13.01 (s, 1H), 12.64 (s, 1H), 8.10 (d, J=7.8 Hz, 2H), 8.03 (s, 1H), 7.73 (d, J=7.9 Hz, 2H), 7.62-7.56 (m, 2H), 7.53-7.45 (m, 3H), 7.33 (s, 1H), 3.15 (s, 2H), 2.69 (s, 3H), 0.67 (s, 6H). (16 mg, 17%). LCMS m/z 458.2 $[M+H]^+$.

Compound 123

4-(5-(4-fluorophenyl)-6-(tetrahydro-2H-pyran-4-yl-3,3,4,5,5-d5)-1,5-dihydropyrrolo[2,3-f]indazol-7-yl)benzoic Acid (123)

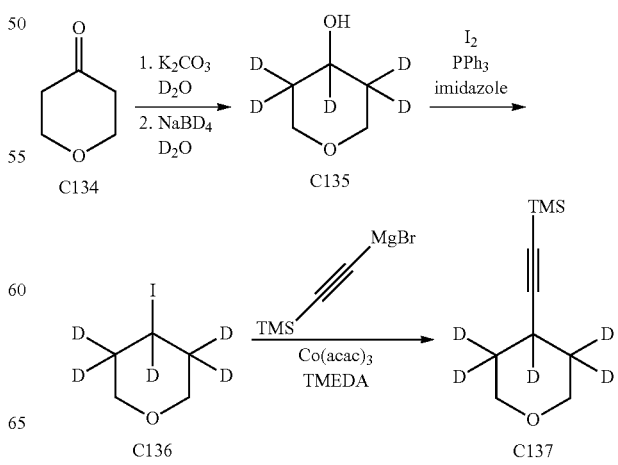

573
-continued

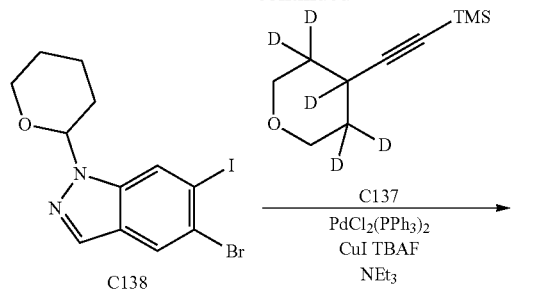

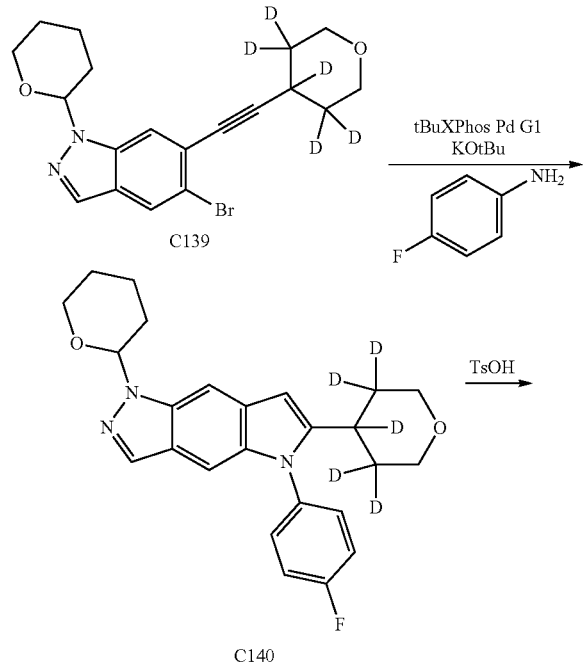

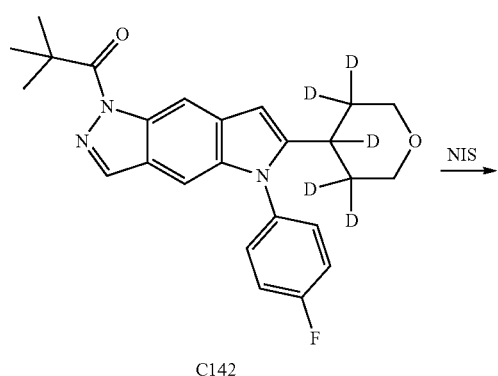

574
-continued

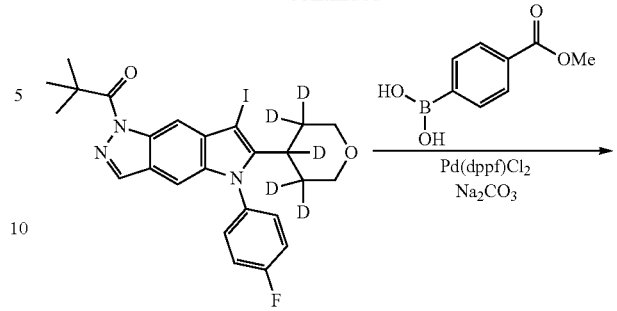

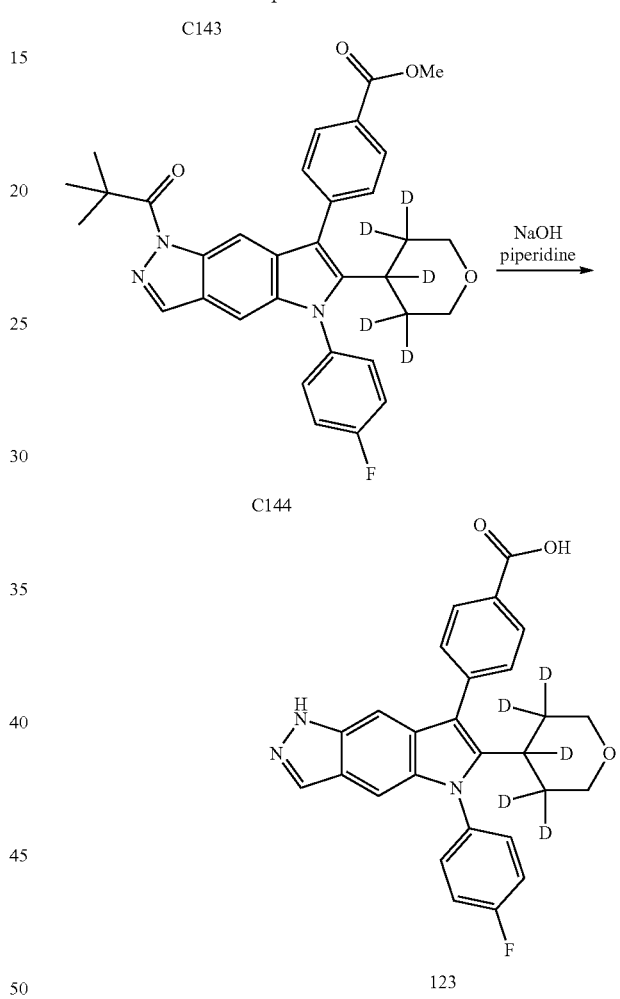

Step 1. Synthesis of
Tetrahydro-2H-pyran-3,3,4,5,5-d$_5$-4-ol (C135)

Tetrahydro-4H-pyran-4-one C134 (50.0 g, 499 mmol) was dissolved in D$_2$O (1 L, 99.8% D) and K$_2$CO$_3$ (6.90 g, 49.9 mmol) was added. The mixture was stirred for 21 h and the obtained solution was used as such in the next step. $^1$H NMR (300 MHz, D$_2$O) δ 4.05 (s, 3H), 3.78 (s, 1H).

NaBD$_4$ (6.27 g, 150 mmol) was added portion-wise over 15 min to a solution of tetrahydro-4H-pyran-4-one-3,3,5,5-d$_4$ (52.0 g, 499 mmol) in D$_2$O (1 L) at 10° C. The mixture was stirred for 1 h at room temperature. The mixture was then quenched with 35% DCl in D$_2$O (20 mL) and concentrated. The residue was dissolved in CH$_2$Cl$_2$ (300 mL), dried over Na$_2$SO$_4$, filtered (sintered glass filter; washed with CH$_2$Cl$_2$) and concentrated to afford the product as a pale-yellow oil which was used in the subsequent step without further purification (46 g, 86% yield). $^1$H NMR (300 MHz, CDCl$_3$) δ 3.95 (d, J=11.7 Hz, 1H), 3.43 (d, J=11.8 Hz, 1H).

Step 2. Synthesis of
4-Iodotetrahydro-2H-pyran-3,3,4,5,5-d$_5$ (C136)

Tetrahydro-2H-pyran-3,3,4,5,5-d$_5$-4-ol C135 (92.7 g, 865.1 mmol) was dissolved in CH$_2$Cl$_2$ (1.5 L) and PPh$_3$ (249.6 g, 951.6 mmol) and 1H-imidazole (64.8 g, 951.6 mmol) were added (clear pale-yellow solution). The mixture was cooled to 0° C. 12 (230.5 g, 908.3 mmol) was added in 8 portions at 0° C. over 1 h (orange suspension). The reaction mixture was stirred overnight. It was quenched with H$_2$O and the phases were separated. The organic phase was washed with 10% Na$_2$S$_2$O$_5$ (2×200 mL), H$_2$O (200 mL), dried over Na$_2$SO$_4$ and concentrated. The pale-yellow solid residue was purified by distillation (liquid product trapped in the solids, which melted at high temperatures). The product distilled at 70-77° C. to afford the product as a colorless liquid (110.7 g, 59% yield),
$^1$H NMR (300 MHz, CDCl$_3$) δ 3.81 (d, J=11.8 Hz, 1H), 3.51 (d, J=11.6 Hz, 1H).

Step 3. Synthesis of Trimethyl((tetrahydro-2H-pyran-4-yl-3,3,4,5,5-d$_5$)ethynyl)silane (C137)

Ethynyltrimethylsilane (31.0 g, 44.6 mL, 315.6 mmol) was dissolved in THF (250 mL) and EtMgBr (3 M, 40.0 g, 99.9 mL, 299.8 mmol) was added slowly drop-wise while being cooled in a water bath. The reaction mixture was heated at 50° C. for 1 h which afforded a brown solution. To a flask containing 4-iodotetrahydro-2H-pyran-3,3,4,5,5-d$_5$ C136 (41.0 g, 188.9 mmol) in THF (100 mL) cooled on an ice-water bath, was added TMEDA (32.9 g, 42.4 mL, 283.3 mmol) and cobalt(III) (Z)-4-oxopent-2-en-2-olate (7.4 g, 20.8 mmol). ((Trimethylsilyl)ethynyl)-magnesium bromide (60.9 g, 302.2 mmol, still at 50° C.) was added drop-wise over 20 min while the mixture was cooled in an ice-water bath. The cooling bath was removed and the reaction mixture was stirred for 3 h at room temperature. The mixture was quenched with 1M aq. citric acid (300 mL) while being cooled in an ice bath. TBME was added and the phases were separated. The organic phase was washed with 1M aq. citric acid (200 mL) and brine, dried over Na$_2$SO$_4$, filtered, and concentrated to a black oil containing some solids (48.3 g). The crude was dissolved in CH$_2$Cl$_2$ and stirred with charcoal for 1 h. The mixture was filtered through a Celite® plug, washed with CH$_2$Cl$_2$ (×4), and concentrated to give a black oil (43.77 g). Purification by distillation (Heating at 125-150° C.; vapor temperature at 72-84° C.; pressure at 17-21 mbar) afforded the product as a yellow oil: 21.6 g (61% yield). $^1$H NMR (300 MHz, CDCl$_3$) δ 3.87 (d, J=11.6 Hz, 1H), 3.47 (d, J=11.6 Hz, 1H), 0.15 (s, 5H).

Step 4. Synthesis of 5-Bromo-1-(tetrahydro-2H-pyran-2-yl)-6-((tetrahydro-2H-pyran-4-yl-3,3,4,5,5-d$_5$)ethynyl)-1H-indazole (C139)

Under N$_2$ atmosphere, trimethyl((tetrahydro-2H-pyran-4-yl-3,3,4,5,5-d$_5$)ethynyl)silane C137 (27.6 g, 147.4 mmol) and 5-bromo-6-iodo-1-(tetrahydro-2H-pyran-2-yl)-1H-indazole C138 (50.0 g, 122.8 mmol) were dissolved in water (4.4 mL, 245.7 mmol), 1,4-dioxane (370 mL) and Et$_3$N (261 g, 358 mL, 2579.5 mmol). Nitrogen was bubbled through the mixture vigorously for 30 min. CuI (93.6 mg, 491.3 µmol), PdCl$_2$(PPh$_3$)$_2$ (344.9 mg, 491.3 µmol) and TBAF (3.8 g, 14.7 mL, 14.7 mmol) were added while degassing. The reaction mixture was degassed with nitrogen gas for and additional 5 min and stirred at room temperature (brown suspension). After 4 h and 20 min, the reaction mixture was filtered (yellow solid removed), washed with THF (4×90 mL) and concentrated. The crude (black viscous oil) was dissolved in MeOH (200 mL) and H$_2$O (1 L). A viscous black oil precipitated together with a fine emulsion and the mixture was left standing to settle overnight. The H$_2$O/MeOH mixture was decanted and the remaining black oil with orange solid was dissolved in CH$_2$Cl$_2$ (300 mL) and dried over Na$_2$SO$_4$. The mixture was filtered, washed with CH$_2$Cl$_2$ (4×80 mL) and concentrated to give a black oil (58.7 g). Silica gel chromatography (Gradient: 0-30% EtOAc/heptanes), afforded an orange solid (40.8 g) which was dissolved in EtOAc (170 mL) and left stirring at room temperature overnight. A white solid was collected by filtration, washed with EtOAc (50 mL), TBME (2×75 mL), and heptanes (2×100 mL), and then dried in vacuo at 50° C. 30.71 g (63.4% yield). The mother liquor was concentrated (orange solid 9.9 g), dissolved in EtOAc (50 mL) at reflux and then TBME (50 mL) and heptanes (20 mL) were added. The mixture was stirred at room temperature over the weekend, filtered and washed with TBME (4×30 mL). Drying in vacuo at 50° C. afforded the product as an off-white solid (6.2 g, 13% yield).
Total yield: 36.9 g (76% yield). $^1$H NMR (300 MHz, CDCl$_3$) δ 7.94 (s, 1H), 7.93 (s, 1H), 7.73 (s, 1H), 5.67 (dd, J=9.2, 2.7 Hz, 1H), 4.01 (d, J=11.7 Hz, 3H), 3.75 (ddd, J=12.8, 10.0, 3.4 Hz, 1H), 3.61 (d, J=11.6 Hz, 2H), 2.61-2.43 (m, 1H), 2.19-2.01 (m, 2H), 1.80-1.63 (m, 3H).

Step 5. Synthesis of 5-(4-Fluoro-3-methylphenyl)-1-(tetrahydro-2H-pyran-2-yl)-6-(tetrahydro-2H-pyran-4-yl-3,3,4,5,5-d$_5$)-1,5-dihydropyrrolo[2,3-f]indazole (C140)

A mixture of 5-bromo-1-(tetrahydro-2H-pyran-2-yl)-6-((tetrahydro-2H-pyran-4-yl-3,3,4,5,5-d$_5$)ethynyl)-1H-indazole C139 (42.7 g, 108.3 mmol), tBuXPhos Pd G1 (4.3 g, 5.4 mmol) and tBuXPhos (459.7 mg, 1.1 mmol) were suspended in 1,4-dioxane (110 mL) and tBuOH (330 mL). The reaction mixture was heated to 60° C. and nitrogen gas was bubbled through the solution for 30 min. 4-Fluoroaniline (18.5 g, 15.4 mL, 162.4 mmol) and KOtBu (36.4 g, 324.8 mmol) were added (exotherm from 62 to 80° C. observed; brown suspension) and nitrogen gas was bubbled through the suspension for an additional 10 min. The reaction mixture was stirred at 73-75° C. for ~3 h. Water (300 mL), sat. aq. NH$_4$Cl (150 mL) and CH$_2$Cl$_2$ (300 mL) were added and the phases separated. The aqueous layer was extracted with CH$_2$Cl$_2$ (2×300 mL). The combined organic phases were washed with sat. aq. NH$_4$Cl (2×100 mL), dried over Na$_2$SO$_4$ and concentrated to a brown solid (61.4 g). The crude product was dissolved in CH$_2$Cl$_2$ (450 mL) and stirred with charcoal (22 g) and SiliaMetS-DMT (8 g) for 1 h. The mixture was filtered through a Celite® plug and washed with CH$_2$Cl$_2$ (4×80 mL), giving a clear yellow-brown solution, which was concentrated to a brown solid 43.6 g. The crude product was dissolved in CH$_2$Cl$_2$ (60 mL) and iPrOH (350 mL) was added. The CH$_2$Cl$_2$ was removed under reduced pressure, resulting in heavy precipitation. TBME (100 mL) was added and the suspension stirred overnight at room temperature. A yellow solid was collected by filtration, washed with iPrOH (3×50 mL) and dried in vacuo at 50° C. affording the product (26.7 g, 58% yield). The mother liquor was concentrated to about 120 mL and left stirring overnight. The solid was filtered and washed with iPrOH (3×40 mL) and TBME (2×40 mL). Drying in vacuo at 50° C. afforded additional product as a beige solid 2.25 g (4.9% yield). Total yield: 28.95 g (63% yield). $^1$H NMR (300 MHz, CDCl$_3$) δ 7.97 (s, 1H), 7.67 (s, 1H), 7.42-7.22 (m, 4H), 7.19 (s, 1H), 6.49 (s, 1H), 5.76 (dd, J=9.3, 2.6 Hz, 1H), 4.15-3.91 (m, 3H), 3.85-3.69 (m, 1H), 3.34 (d, J=11.6 Hz, 2H), 2.75-2.51 (m, 1H), 2.14 (dd, J=21.8, 10.5 Hz, 2H), 1.93-1.61 (m, 3H).

Step 6 Synthesis of 5-(4-Fluorophenyl)-6-(tetrahydro-2H-pyran-4-yl-3,3,4,5,5-d$_5$)-1,5-dihydropyrrolo[2,3-f]indazole·pTsOH (C141)

5-(4-fluorophenyl)-1-(tetrahydro-2H-pyran-2-yl)-6-(tetrahydro-2H-pyran-4-yl-3,3,4,5,5-d$_5$)-1,5-dihydropyrrolo[2,3-f]indazole C140 (67.9 g, 160 mmol) was suspended in MeOH (600 mL), EtOAc (600 mL) and H$_2$O (300 mL). TsOH·H$_2$O (152 g, 800 mmol) was added and the mixture, a yellow suspension, was stirred at 55±5° C. for 1 h (color changes to black-brown). Full conversion was determined by HPLC. The reaction mixture was concentrated to a yellow solid, suspended in H$_2$O (~1.4 L), stirred for 10 min, filtered, and washed with H$_2$O (3×200 mL). The wet yellow solid obtained was again suspended in 1.75 L H$_2$O with 5.5 mL NaOH (10 M) added and stirred for 45 min (pH>12). The suspension was filtered, washed with H$_2$O (4×150 mL) and heptanes (2×150 mL), and dried in vacuo at 50° C. for 3.45 h to afford the product as a pale-yellow solid: 77.2 g (97.6% yield).
$^1$H NMR (300 MHz, CDCl$_3$) δ 8.53 (s, 1H), 7.95-7.83 (m, 3H), 7.8-7.26 (m, 5H), 7.17 (d, J=8.0 Hz, 2H), 6.53 (s, 1H), 3.98 (d, J=11.7 Hz, 2H), 3.33 (d, J=11.6 Hz, 2H), 2.34 (s, 3H).

Step 7. 1-(5-(4-Fluorophenyl)-6-(tetrahydro-2H-pyran-4-yl-3,3,4,5,5-d$_5$)pyrrolo[2,3-f]indazol-1(5H)-yl)-2,2-dimethylpropan-1-one (C142)

5-(4-fluorophenyl)-6-(tetrahydro-2H-pyran-4-yl-3,3,4,5,5-d)-1-tosyl-1,5-dihydropyrrolo[2,3-f]indazole C141 (77.2 g, 156.09 mmol) was suspended in THF (1.60 L) and cooled to 8° C. (ice bath). KOtBu (43.79 g, 390.2 mmol) was added and stirred for 5 min (small exotherm to 14° C., brown suspension). At 10° C., pivaloyl chloride (75.3 g, 76.8 mL, 624.3 mmol) was added drop-wise, and the mixture was stirred at 10-20° C. for 15 min, then warmed to room temperature for 1.5 h. The reaction was quenched with water, EtOAc, and sat. aq. NaHCO$_3$. The layers were separated. The organic phase washed with sat. aq. NaHCO$_3$ (3×100 mL), dried over Na$_2$SO$_4$, filtered and concentrated to a yellow-brown solid. The crude was suspended at reflux in EtOH (400 mL) and H$_2$O (800 mL) was added. The mixture was cooled to room temperature while stirring, and the solid was filtered, then washed with H$_2$O (150 mL, yellow filtrate) and heptanes (200 mL, dark orange filtrate). The wet product (85 grams) was dissolved in CH$_2$Cl$_2$ (1 L), washed with brine (100 mL) and dried over Na$_2$SO$_4$ to afford the product (58.6 g, 88%). $^1$H NMR (299 MHz, CDCl$_3$) δ 8.67 (d, J=1.0 Hz, 1H), 8.04 (d, J=0.9 Hz, 1H), 7.45-7.23 (m, 4H), 7.18 (d, J=1.0 Hz, 1H), 6.56 (d, J=0.9 Hz, 1H), 3.98 (d, J=11.6 Hz, 2H), 3.33 (d, J=11.6 Hz, 2H), 1.58 (d, J=1.2 Hz, 9H).

Step 8. 1-(5-(4-Fluorophenyl)-7-iodo-6-(tetrahydro-2H-pyran-4-yl-3,3,4,5,5-d$_5$)pyrrolo[2,3-f]indazol-1(5H)-yl)-2,2-dimethylpropan-1-one (C143)

A solution of 1-(5-(4-fluorophenyl)-6-(tetrahydro-2H-pyran-4-yl-3,3,4,5,5-d$_5$)pyrrolo[2,3-f]indazol-1(5H)-yl)-2,2-dimethylpropan-1-one C142 (58.6 g, 138 mmol) in CH$_2$Cl$_2$ (750 mL) (dark-brown solution) was treated with N-iodosuccinimide (34.2 g, 1.1 eq, 152 mmol) over 40 min (orange suspension). The reaction mixture was stirred at room temperature for 30 min. The mixture was washed with water (2×150 mL), 10% aq. Na$_2$S$_2$O$_5$ (200 mL) and brine (100 mL) and dried over Na$_2$SO$_4$ and concentrated affording 76 gram of the product. Purification by silica gel chromatography (Eluent: CH$_2$Cl$_2$, then a gradient of 1-5% EtOAc in CH$_2$Cl$_2$) afforded the product as an off-white solid. 1-(5-(4-fluorophenyl)-7-iodo-6-(tetrahydro-2H-pyran-4-yl-3,3,4,5,5-d$_5$)pyrrolo[2,3-f]indazol-1(5H)-yl)-2,2-dimethylpropan-1-one (66.0 g, 86.9% yield)$^1$H NMR (300 MHz, CDCl$_3$) δ 8.59 (s, 1H), 8.05 (s, 1H), 7.38-7.27 (m, 4H), 7.06 (s, 1H), 4.01 (d, J=11.7 Hz, 2H), 3.34 (d, J=11.6 Hz, 2H), 1.59 (s, 9H). $^{19}$F NMR (282 MHz, CDCl$_3$) δ −110.96.

Step 9. 4-(5-(4-Fluorophenyl)-1-pivaloyl-6-(tetrahydro-2H-pyran-4-yl-3,3,4,5,5-d$_5$)-1,5-dihydropyrrolo[2,3-f]indazol-7-yl)benzoate (C144)

A mixture of 1-(5-(4-Fluorophenyl)-7-iodo-6-(tetrahydro-2H-pyran-4-yl-3,3,4,5,5-d$_5$)pyrrolo[2,3-J]indazol-1(5H)-yl)-2,2-dimethylpropan-1-one C143 (56.9 g, 0.10 mol) and (4-(methoxycarbonyl)phenyl)boronic acid (31 g, 1.7 eq, 0.17 mol) were suspended in 1,4-dioxane (750 mL) (yellow suspension) and purged with nitrogen for 30 min. 2M aq. Na$_2$CO$_3$ (0.18 L, 3.6 eq, 0.36 mol) was added and the mixture purged with nitrogen for an additional 5 min. Pd(dppf)Cl$_2$ (4.0 g, 0.05 eq, 5.2 mmol) was added and the reaction mixture was stirred for 60 min at 60-65° C. (dark-red suspension). The mixture was concentrated, water (500 mL) was added and the mixture was extracted with CH$_2$Cl$_2$ (2×200 mL). The combined organic layers were washed with brine (150 mL) and flushed over a plug of silica gel. The product was further eluted from the silica plug with 10% EtOAc in CH$_2$Cl$_2$. The product fractions were concentrated to ~1 L. Scavenger resin (25 g, SiliaMetS DMT, 40-63 μm, 60 Å) was added to the mixture and stirred for 1 h. The mixture was then filtered and concentrated. Purification by silica gel chromatography (Gradient: 1-3% EtOAc in CH$_2$Cl$_2$) afforded the product as a white solid (49.1 g, 88% yield). Methyl 4-(5-(4-fluorophenyl)-1-pivaloyl-6-(tetrahydro-2H-pyran-4-yl-3,3,4,5,5-d$_5$)-1,5-dihydropyrrolo[2,3-f]indazol-7-yl)benzoate.
$^1$H NMR (300 MHz, CDCl$_3$) δ 8.42 (s, 1H), 8.22-8.12 (m, 2H), 8.04 (d, J=0.7 Hz, 1H), 7.56 (d, J=8.4 Hz, 2H), 7.43 (ddt, J=8.1, 5.3, 2.7 Hz, 2H), 7.38-7.26 (m, 2H), 7.09 (d, J=1.0 Hz, 1H), 3.99 (s, 3H), 3.83 (d, J=11.6 Hz, 2H), 3.18 (d, J=11.6 Hz, 2H), 1.54 (s, 9H).

Step 10. 4-(5-(4-Fluorophenyl)-6-(tetrahydro-2H-pyran-4-yl-3,3,4,5,5-d$_5$)-1,5-dihydropyrrolo[2,3-f]indazol-7-yl)benzoic Acid (123)

To a solution of methyl 4-(5-(4-fluorophenyl)-1-pivaloyl-6-(tetrahydro-2H-pyran-4-yl-3,3,4,5,5-d$_5$)-1,5-dihydropyrrolo[2,3-f]indazol-7-yl)benzoate C144 (21.0 g, 37.6 mmol) was dissolved in THF (200 mL) and MeOH (100 mL) was added 2M aq. NaOH (75.2 mL, 4 eq, 150 mmol). The mixture was heated to 60° C. for 1 h. The organic solvents were evaporated, the residue was diluted with water (350 mL) and washed with EtOAc (2×150 mL). The aqueous solution was acidified with 3N aq. HCl to pH 1 and the precipitate was taken up EtOAc/MeOH (97:3). The organic layer was washed with brine (150 mL), dried over Na$_2$SO$_4$ and concentrated. The residue was refluxed in CH$_3$CN (200 mL) and stirred for 30 min. The solid was filtered off after cooling to room temperature, and then dried in vacuo. The material was partially taken up in refluxing IPA (200 mL) and filtered hot. The filtrate was allowed to crystallize and the crystals were collected by filtration. The product was dissolved in DMSO (60 mL, warm) and slowly added to water (1 L, HPLC-grade). The milky solution was heated to approximately 80° C. until the morphology of the precipitate had changed (10 min). The solid was then collected by filtration, and washed with water (2×100 mL). The product was dried overnight in a circulation oven at 45° C. to afford the product as a white solid. (10.4 g, 60.1% yield). 4-(5-(4-fluorophenyl)-6-(tetrahydro-2H-pyran-4-yl-3,3,4,5,5-$d_5$)-1,5-dihydropyrrolo[2,3-f]indazol-7-yl)benzoic acid $^1$H NMR (300 MHz, DMSO-$d_6$) δ 8.10 (d, J=8.3 Hz, 2H); 7.98 (s, 1H); 7.67-7.58 (m, 4H); 7.58-7.42 (m, 2H); 7.25 (d, J=1.1 Hz, 1H); 7.06 (d, J=1.1 Hz, 1H); 3.70 (d, J=11.5 Hz, 2H); 3.07 (d, J=11.5 Hz, 2H).

$^{19}$F NMR (282 MHz, DMSO-$d_6$) δ −112.57.

Compound 124

4-[6-[2-(difluoromethoxy)-1,1-dimethyl-ethyl]-5-(4-fluorophenyl)-1H-pyrrolo[2,3-f]indazol-7-yl]benzoic Acid (124)

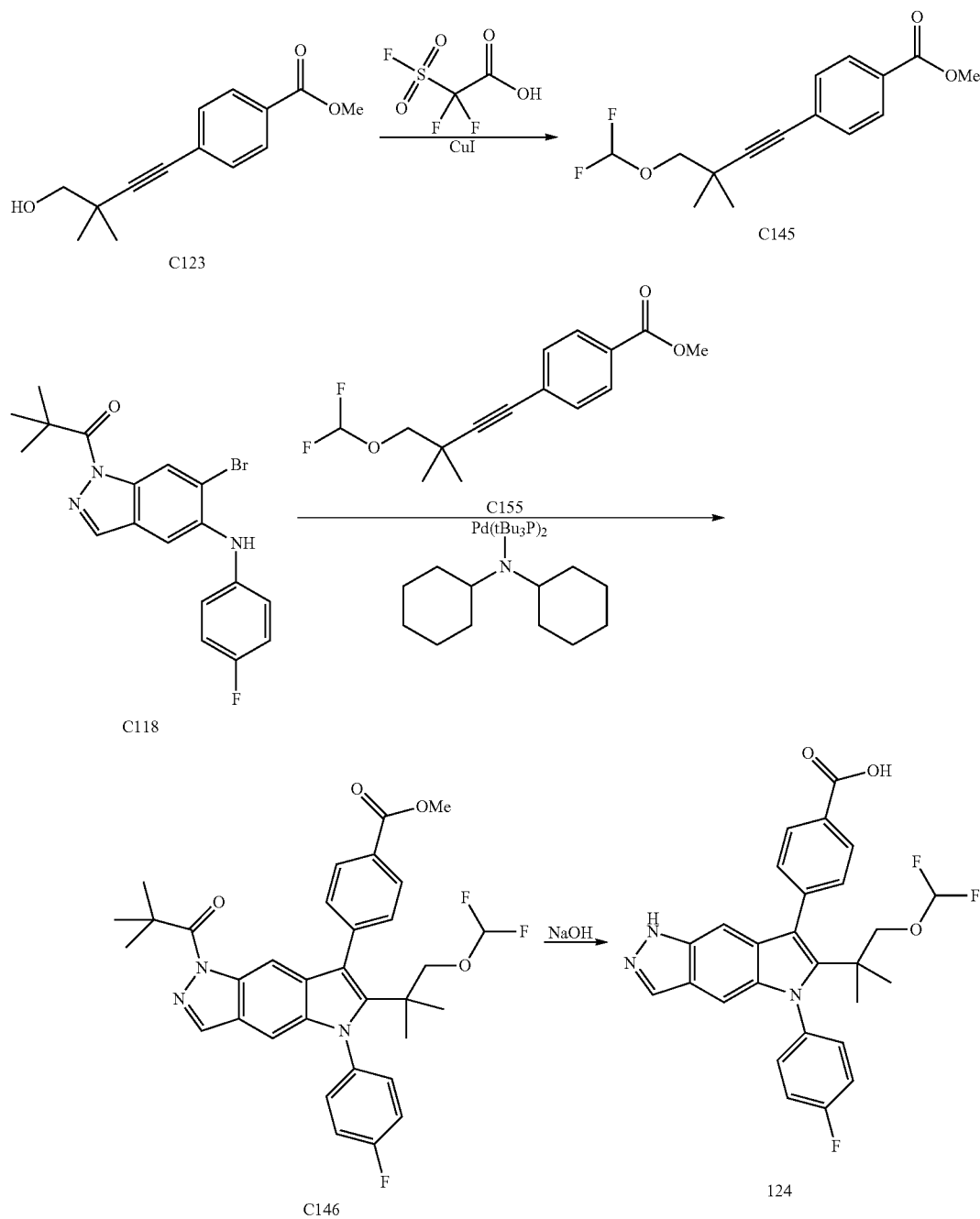

Step 1. Synthesis of methyl 4-[4-(difluoromethoxy)-3,3-dimethyl-but-1-ynyl]benzoate (C145)

To a solution of methyl 4-(4-hydroxy-3,3-dimethyl-but-1-ynyl)benzoate C123 (190 mg, 0.82 mmol) and CuI (25.3 mg, 0.13 mmol) in MeCN (2.3 mL) was added 2,2-difluoro-2-fluorosulfonyl-acetic acid (68.8 µL, 0.67 mmol). The reaction mixture was allowed to stir for 2 h at 50° C. Water and CH$_2$Cl$_2$ were added, and the organic layer was collected through a phase separator. Purification by reversed-phase chromatography (Column: C18. Gradient: 0-100% MeCN in water with 0.1% formic acid) afforded the product (38 mg, 19%). LCMS m/z 283.1 [M+1]$^+$.

Step 2. Synthesis of methyl 4-[6-[2-(difluoromethoxy)-1,1-dimethyl-ethyl]-1-(2,2-dimethylpropanoyl)-5-(4-fluorophenyl)pyrrolo[2,3-f]indazol-7-yl]benzoate (C146)

Compound C146 was prepared from C118 (45 mg, 0.12 mmol) and C145 using the method described for the preparation of C119 in the synthesis of compound 117. Purification by silica gel chromatography (Gradient: 0-100% EtOAc in heptane) afforded the product (41 mg, 48%). LCMS m/z 592.1 [M+1]$^+$.

Step 3. Synthesis of 4-[6-[2-(difluoromethoxy)-1,1-dimethyl-ethyl]-5-(4-fluorophenyl)-1H-pyrrolo[2,3-f]indazol-7-yl]benzoic Acid (124)

Compound 124 was prepared from C146 (41 mg, 0.07 mmol) by hydrolysis with sodium hydroxide as described for the synthesis of compound 117 from C119. Purification by reversed-phase chromatography (Column: C18. Gradient: 0-100% MeCN in water with 0.1% formic acid) afforded the product (21 mg, 59%). $^1$H NMR (400 MHz, DMSO-d$_6$) δ 13.03 (s, 1H), 12.51 (s, 1H), 8.07 (d, J=7.7 Hz, 2H), 7.97 (s, 1H), 7.63-7.55 (m, 4H), 7.49 (t, J=8.4 Hz, 2H), 6.85 (s, 2H), 6.58-6.55 (m, 1H), 3.67 (s, 2H), 1.12 (s, 6H). LCMS m/z 494.1 [M+1]$^+$.

Compound 125

4-[6-(2-cyano-1,1-dimethyl-ethyl)-5-(4-fluorophenyl)-1H-pyrrolo[2,3-f]indazol-7-yl]benzoic Acid (125)

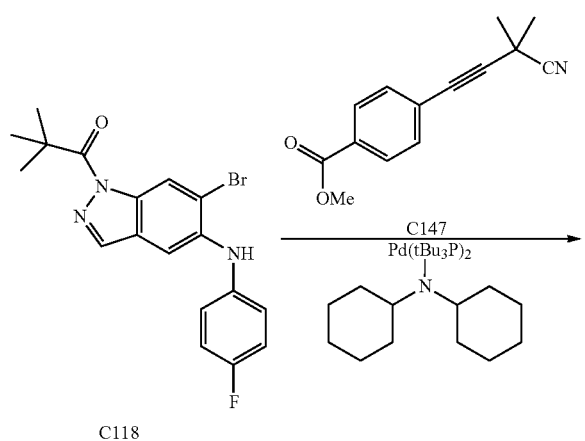

C118

C147

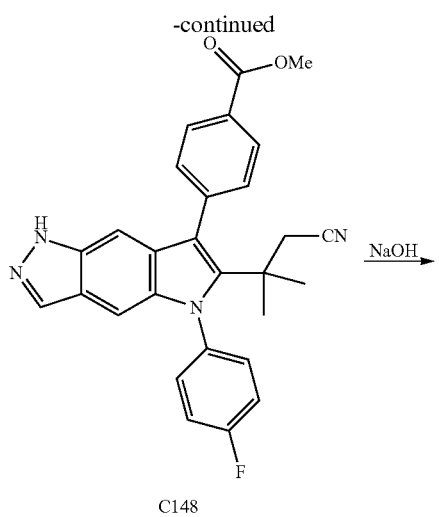

C148

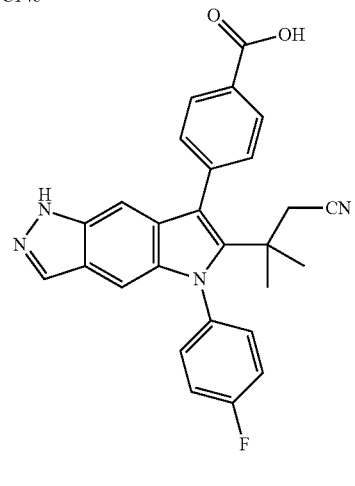

125

Step 1. Synthesis of methyl 4-[6-(2-cyano-1,1-dimethyl-ethyl)-1-(2,2-dimethylpropanoyl)-5-(4-fluorophenyl)pyrrolo[2,3-f]indazol-7-yl]benzoate Compound C148 was prepared from C118 (50 mg, 0.13 mmol) and C147 as described for C146. Silica gel chromatography (Gradient: 0-100% EtOAc/heptane) afforded the product (42 mg, 44%). LCMS m/z 551.1 [M+1]$^+$.

Step 2. Synthesis of 4-[6-(2-cyano-1,1-dimethyl-ethyl)-5-(4-fluorophenyl)-1H-pyrrolo[2,3-f]indazol-7-yl]benzoic Acid (125)

Compound 125 was prepared from C148 by hydrolysis with sodium hydroxide as described for the synthesis of compound 117 from C119. Purification by reversed-phase chromatography (Column: C18. Gradient: 0-100% MeCN in water with 0.1% formic acid) afforded the product (4.8 mg, 13%). $^1$H NMR (300 MHz, DMSO-d$_6$) δ 13.04 (s, 1H), 12.54 (s, 1H), 8.10 (d, J=8.2 Hz, 2H), 7.99 (s, 1H), 7.69-7.60 (m, 4H), 7.58-7.48 (m, 2H), 6.88 (s, 2H), 2.63 (s, 2H), 1.25 (s, 6H). LCMS m/z 453.1 [M+1]$^+$.

Compound 126

4-[5-(4-fluorophenyl)-6-methylsulfonyl-1H-pyrrolo[2,3-f]indazol-7-yl]benzoic Acid

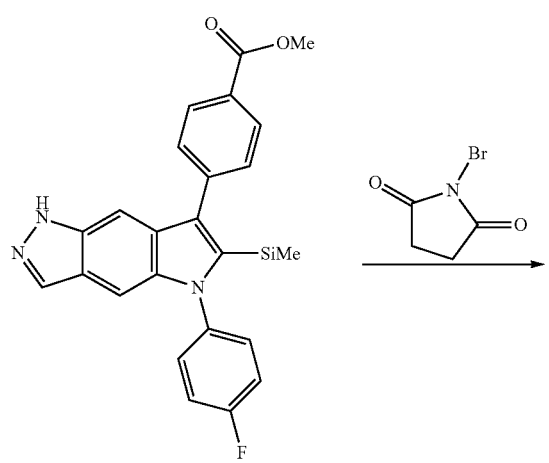

C93

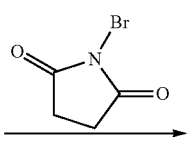

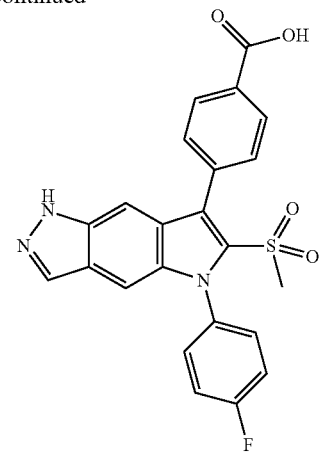

126

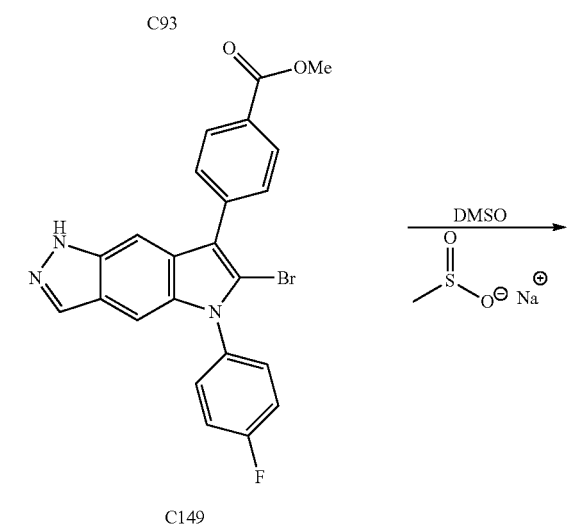

C149

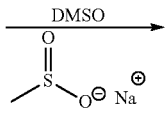

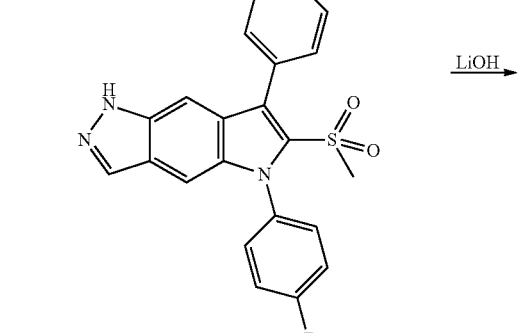

C150

Step 1. Synthesis of methyl 4-[6-bromo-1-(2,2-dimethylpropanoyl)-5-(4-fluorophenyl)pyrrolo[2,3-f]indazol-7-yl]benzoate (C149)

To a solution of methyl 4-[1-(2,2-dimethylpropanoyl)-5-(4-fluorophenyl)-6-trimethylsilyl-pyrrolo[2,3-f]indazol-7-yl]benzoate C93 (76.6 mg, 0.14 mmol) in $CH_2Cl_2$ (3.9 mL) was added N-bromosuccinimide (25 mg, 0.14 mmol). The mixture was allowed to stir at room temperature overnight. The mixture was diluted with dichloromethane and washed with water. The organic phase was passed through a phase separator and concentrated to dryness under reduced pressure to give methyl 4-[6-bromo-1-(2,2-dimethylpropanoyl)-5-(4-fluorophenyl)pyrrolo[2,3-f]indazol-7-yl]benzoate (74 mg, 95%). $^1$H NMR (300 MHz, DMSO-$d_6$) δ 8.62 (t, J=0.9 Hz, 1H), 8.48 (d, J=0.8 Hz, 1H), 8.21-8.15 (m, 2H), 7.88-7.81 (m, 2H), 7.72-7.66 (m, 2H), 7.58 (d, J=1.0 Hz, 1H), 7.57-7.49 (m, 2H), 3.91 (s, 3H), 1.49 (s, 9H). LCMS m/z 548.1 [M+1]$^+$.

Step 2. Synthesis of methyl 4-[1-(2,2-dimethylpropanoyl)-5-(4-fluorophenyl)-6-methylsulfonyl-pyrrolo[2,3-f]indazol-7-yl]benzoate (C150)

A solution of methyl 4-[6-bromo-1-(2,2-dimethylpropanoyl)-5-(4-fluorophenyl)pyrrolo[2,3-f]indazol-7-yl]benzoate C149 (53 mg, 0.09 mmol), and sodium methanesulfinate (58 mg, 0.57 mmol) in DMSO (1 mL) was heated to 110° C. overnight. Additional sodium methanesulfinate (58 mg, 0.57 mmol) was added and the mixture was heated overnight at the 110° C. Water (10 mL) was added, and the mixture washed with Ethyl Acetate. The organic layer was dried over sodium sulfate. The water layer was washed with additional Ethyl Acetate (10 mL) and then over sodium sulfate. The combined organic layers were purified by silica gel chromatography (Gradient: 0-100% ethyl acetate in heptane) to afford the product (15.5 mg, 30%). $^1$H NMR (300 MHz, Chloroform-d) δ 8.66-8.62 (m, 1H), 8.27-8.21 (m, 2H), 8.16-8.13 (m, 1H), 7.76-7.70 (m, 2H), 7.61-7.54 (m, 2H), 7.38-7.30 (m, 3H), 4.01 (s, 3H), 2.87 (s, 3H), 1.58 (s, 9H). LCMS m/z 548.2 [M+1]$^+$.

Step 3. Synthesis of 4-[5-(4-fluorophenyl)-6-methylsulfonyl-1H-pyrrolo[2,3-f]indazol-7-yl]benzoic Acid (126)

Compound 126 was prepared from C150 (15.5 mg, 0.03 mmol) by hydrolysis with LiOH was in methanol (1 mL) and THF (1 mL). Purification by reversed phase chromatography (C18 column. Gradient: 10-100% MeCN in water with 0.1% formic acid modifier) afforded the product (6.6 mg, 47%). $^1$H NMR (300 MHz, Methanol-d$_4$) δ 8.21-8.15 (m, 2H), 8.09 (d, J=1.1 Hz, 1H), 7.74-7.68 (m, 2H), 7.65-7.58 (m, 2H), 7.54 (t, J=1.2 Hz, 1H), 7.41-7.34 (m, 3H), 2.99 (s, 3H). LCMS m/z 450.1 [M+1]$^+$.

Compound 127

5-(4-fluorophenyl)-6-(2-methoxy-1,1-dimethyl-ethyl)-7-(6-methylsulfonyl-3-pyridyl)-1H-pyrrolo[2,3-f]indazole (127)

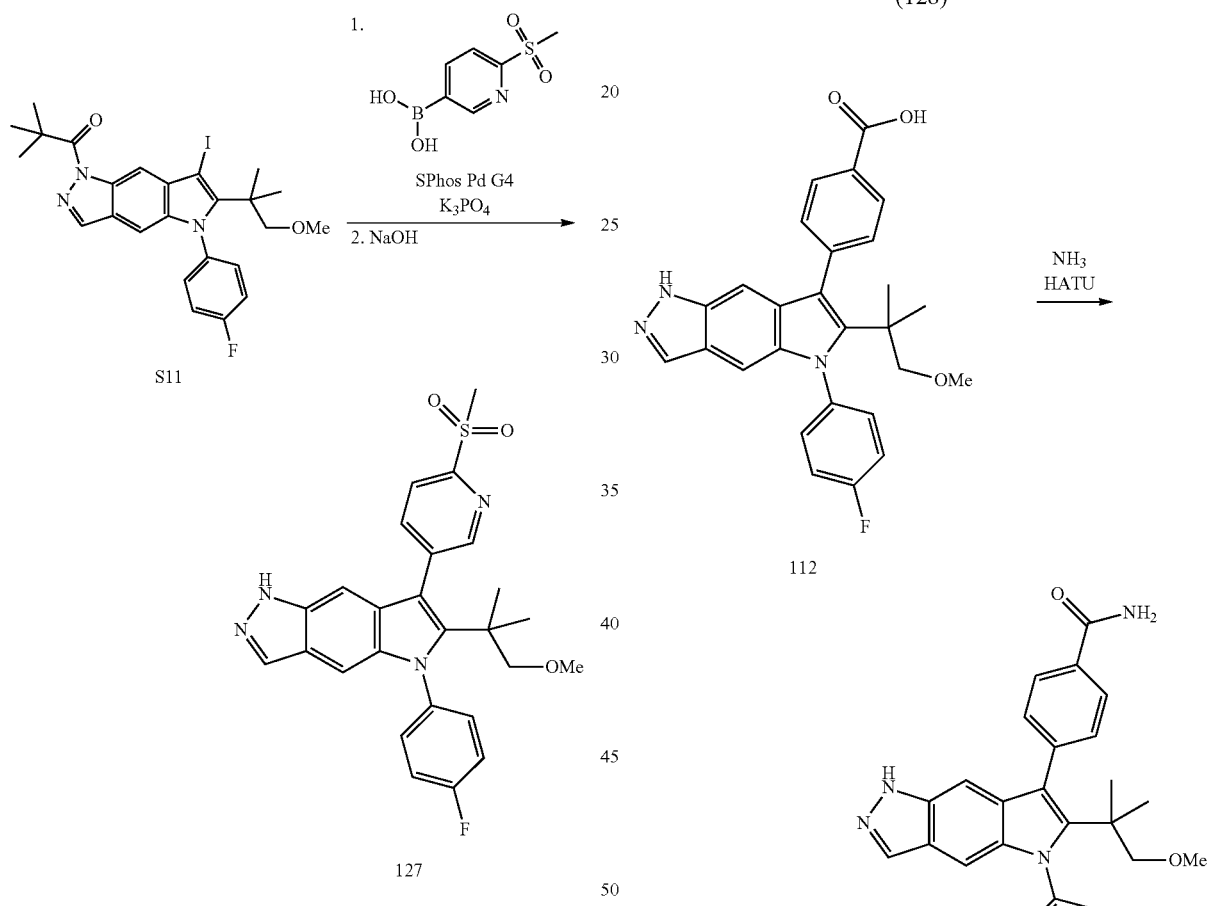

To a mixture of 1-[5-(4-fluorophenyl)-7-iodo-6-(2-methoxy-1,1-dimethyl-ethyl)pyrrolo[2,3-f]indazol-1-yl]-2,2-dimethyl-propan-1-one S11 (50 mg, 0.09 mmol), (6-methylsulfonyl-3-pyridyl)boronic acid (57 mg, 0.28 mmol), and K$_3$PO$_4$ (68 mg, 0.32 mmol) in 1,4-dioxane (720 μL) and water (140 μL) were added SPhos Pd G4 (10 mg, 0.013 mmol) was then added, and the reaction was heated to 60° C. overnight. Additional (6-methylsulfonyl-3-pyridyl)boronic acid (50 mg, 0.25 mmol) was added and the mixture degassed with N$_2$ for 10 min. Additional SPhos Pd G4 (11 mg, 0.02 mmol) was added and the mixture and heated to 80° C. The mixture was allowed to stir over 3 days. The reaction was diluted with water (5 mL) and dichloromethane (5 mL), and passed through a phase separator. The organic phase was collected and concentrated in vacuo. This residue was dissolved in THF (1 μL) and MeOH (500 μL), and then NaOH (544 μL of 1 M, 0.54 mmol) was added. The solution was stirred at 50° C. for 1 h. The solvent was evaporated, and the residue was suspended in water, and neutralized with HCl (544 μL of 1 M, 0.54 mmol). Purification by SFC chromatography afforded the product as a light yellow solid (11.8 mg, 27%). $^1$H NMR (400 MHz, Methanol-d$_4$) δ 8.84 (s, 1H), 8.22 (s, 2H), 7.95 (s, 1H), 7.54 (dd, J=8.5, 4.9 Hz, 2H), 7.39 (t, J=8.4 Hz, 2H), 6.95 (s, 1H), 6.91 (s, 1H), 3.35 (s, 3H), 3.16-3.07 (m, 5H), 1.16 (s, 6H). LCMS m/z 493.1 [M+1]$^+$.

Compound 128

4-[5-(4-fluorophenyl)-6-(2-methoxy-1,1-dimethyl-ethyl)-1H-pyrrolo[2,3-f]indazol-7-yl]benzamide (128)

Synthesis of 4-[5-(4-fluorophenyl)-6-(2-methoxy-1,1-dimethyl-ethyl)-1H-pyrrolo[2,3-f]indazol-7-yl]benzamide (128)

To a solution of 4-[5-(4-fluorophenyl)-6-(2-methoxy-1,1-dimethyl-ethyl)-1H-pyrrolo[2,3-f]indazol-7-yl]benzoic acid 112 (10 mg, 0.02 mmol) and HATU (10 mg, 0.03 mmol) dissolved in DMF (200 μL). DIPEA (14 μL, 0.08 mmol) was added and the reaction was stirred at room temperature for 5 min. Ammonia (5 μL of 30% w/w, 0.08 mmol) was added and the reaction stirred for 10 min. Purification by reversed-phase HPLC (Method: C18 Waters Sunfire column (30×150 mm, 5 micron). Gradient: MeCN in H$_2$O with 0.2% formic acid) afforded the product as a white solid (8.1 mg, 80%). $^1$H NMR (400 MHz, DMSO-d$_6$) δ 12.49 (s, 1H), 8.07 (s, 1H), 8.00 (d, J=8.2 Hz, 2H), 7.96 (s, 1H), 7.63-7.54 (m, 2H), 7.55-7.40 (m, 5H), 6.83 (d, J=7.8 Hz, 2H), 3.06 (s, 2H), 3.01 (s, 3H), 1.11 (s, 6H). LCMS m/z 457.2 [M+1]$^+$.

Compound 129

4-[5-(4-fluorophenyl)-6-(2-methoxy-1,1-dimethyl-ethyl)-3-methyl-1H-pyrrolo[2,3-f]indazol-7-yl]benzoic Acid (129)

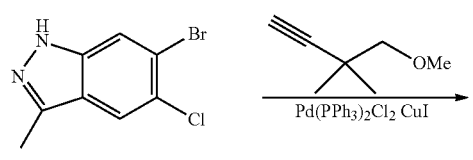

C151

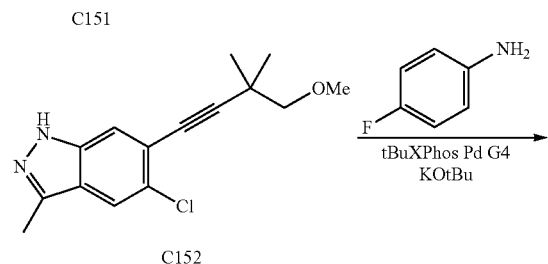

C152

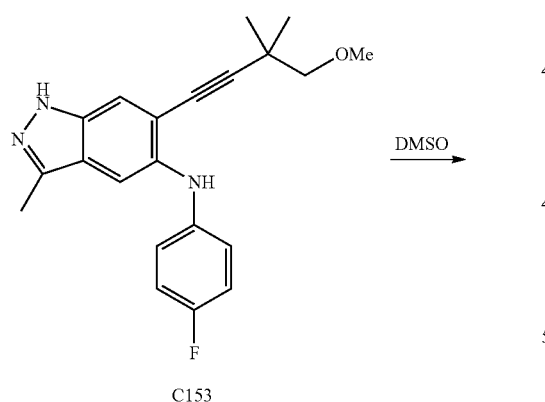

C153

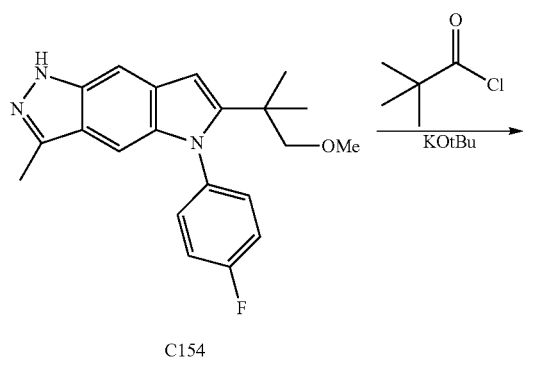

C154

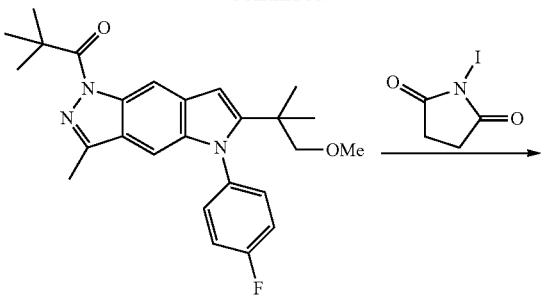

C155

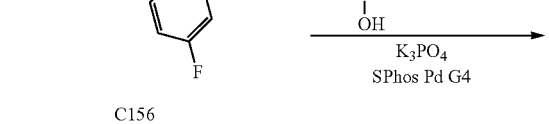

C156

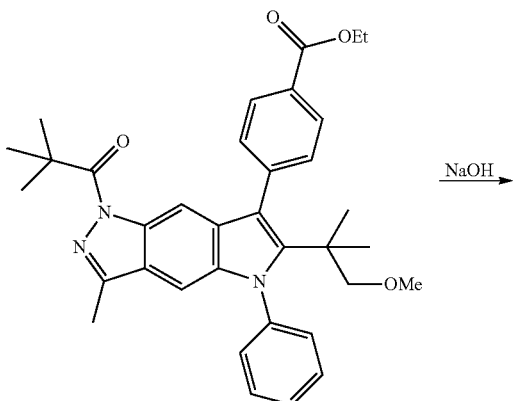

C157

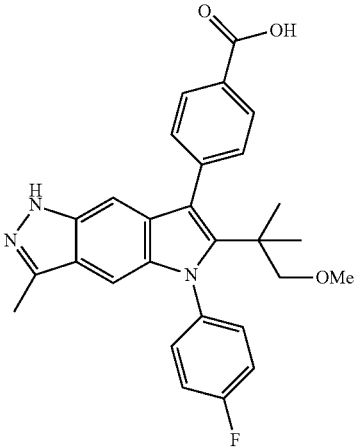

129

Preparation of 1-[5-(4-fluorophenyl)-7-iodo-6-(2-methoxy-1,1-dimethyl-ethyl)-3-methyl-pyrrolo[2,3-f]indazol-1-yl]-2,2-dimethyl-propan-1-one (C156)

C156 was prepared in five steps from C151 according to the method described for the preparation of S11. $^1$H NMR (400 MHz, DMSO-d$_6$) δ 8.44 (s, 1H), 7.54-7.42 (m, 4H), 6.84 (s, 1H), 3.56 (s, 2H), 3.15 (s, 3H), 2.46 (s, 3H), 1.51 (s, 9H), 1.36 (s, 6H). LCMS m/z 562.0 [M+1]$^+$.

Preparation of 4-[5-(4-fluorophenyl)-6-(2-methoxy-1,1-dimethyl-ethyl)-3-methyl-1H-pyrrolo[2,3-f]indazol-7-yl]benzoic Acid (129)

Compound 129 was prepared in two steps from compound C156 using the method described for the preparation of compound 127. Reversed phase chromatography (C18 column. Gradient: 10-100% acetonitrile in water with 0.2% formic acid) afforded the product as a white solid (9.1 mg, 45%). $^1$H NMR (400 MHz, DMSO-d$_6$) δ 13.05 (s, 1H), 12.05 (s, 1H), 8.14-8.02 (m, 2H), 7.58 (td, J=8.8, 7.7, 4.6 Hz, 4H), 7.49 (t, J=8.1 Hz, 2H), 6.77 (s, 1H), 6.70 (s, 1H), 3.04 (s, 2H), 3.00 (s, 3H), 2.37 (s, 3H), 1.10 (s, 6H). LCMS m/z 472.1 [M+1]$^+$.

Compound 130

5-(4-fluorophenyl)-6-(2-methoxy-1,1-dimethyl-ethyl)-3-methyl-7-(6-methylsulfonyl-3-pyridyl)-1H-pyrrolo[2,3-f]indazole (130)

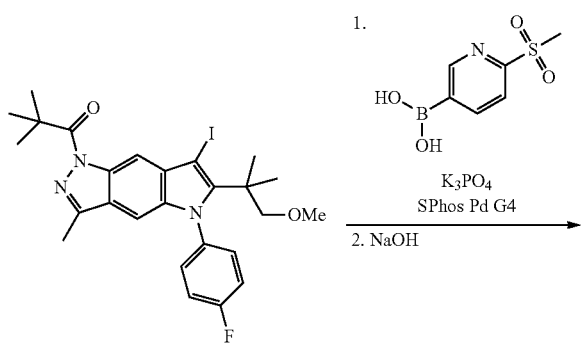

C156

Step 1. Synthesis of 1-(5-(4-fluorophenyl)-6-(1-methoxy-2-methylpropan-2-yl)-3-methyl-7-(6-(methylsulfonyl)pyridin-3-yl)pyrrolo[2,3-f]indazol-1(5H)-yl)-2,2-dimethylpropan-1-one A solution of 1-[5-(4-fluorophenyl)-7-iodo-6-(2-methoxy-1,1-dimethyl-ethyl)-3-methyl-pyrrolo[2,3-f]indazol-1-yl]-2,2-dimethyl-propan-1-one C156 (58 mg, 0.10 mmol), (6-methylsulfonyl-3-pyridyl)boronic acid (40 mg, 0.20 mmol), and K$_3$PO$_4$ (96 mg, 0.45 mmol) 1,4-dioxane (500 μL) and water (100 μL) was purged with N$_2$ for 10 min. SPhos Pd G4 (9 mg, 0.012 mmol) was added, and the reaction was heated to 80° C. After 6 hours, the reaction was purged with N$_2$, and added additional (6-methylsulfonyl-3-pyridyl)boronic acid (37 mg, 0.18 mmol) and SPhos Pd G4 (9 mg, 0.012 mmol) were added. Heating at 80° C. was continued over 3 days. Water (5 mL) and dichloromethane (5 mL) were added, and the mixture was passed through a phase separator. The organic phase was collected, the solvent evaporated and the product used directly in the subsequent step.

Step 2. Synthesis of 5-(4-fluorophenyl)-6-(2-methoxy-1,1-dimethyl-ethyl)-3-methyl-7-(6-methylsulfonyl-3-pyridyl)-1H-pyrrolo[2,3-f]indazole (130)

The product from step 1 dissolved in THF (2 mL) and MeOH (1000 μL), and NaOH (605 μL of 1 M, 0.61 mmol) was added. The reaction was heated to 50° C. for 30 min. The solvent was evaporated, and the crude material was suspended in water (2 mL). HCl (605 μL of 1 M, 0.61 mmol) was added to neutralize the mixture. Purification by SFC afforded the product as a light yellow solid. 5-(4-fluorophenyl)-6-(2-methoxy-1,1-dimethyl-ethyl)-3-methyl-7-(6-methylsulfonyl-3-pyridyl)-1H-pyrrolo[2,3-f]indazole (4.3 mg, 8%). LCMS m/z 507.1 [M+1]$^+$.

Compound 131

4-[5-(5-fluoro-2-pyridyl)-6-(4-hydroxytetrahydropyran-4-yl)-1H-pyrrolo[2,3-f]indazol-7-yl]benzoic Acid (131)

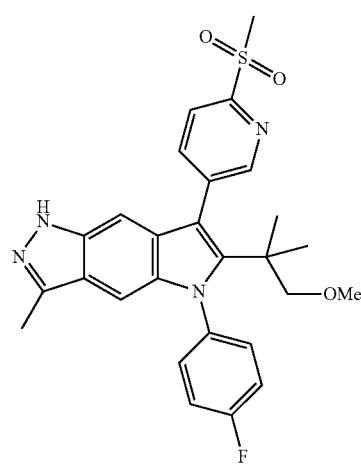

130

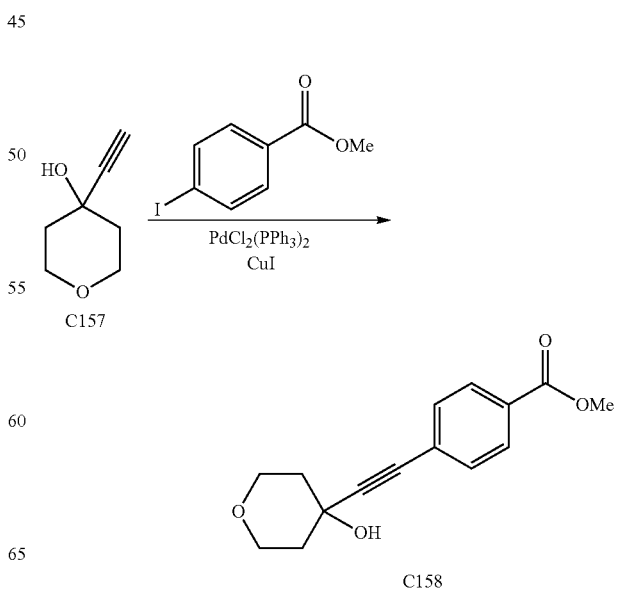

C157

C158

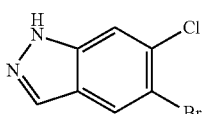
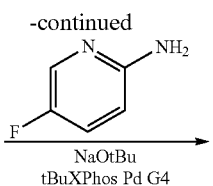

C95

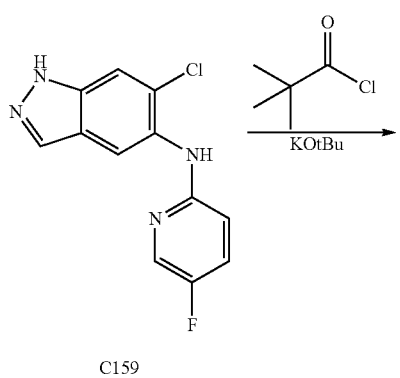

C159

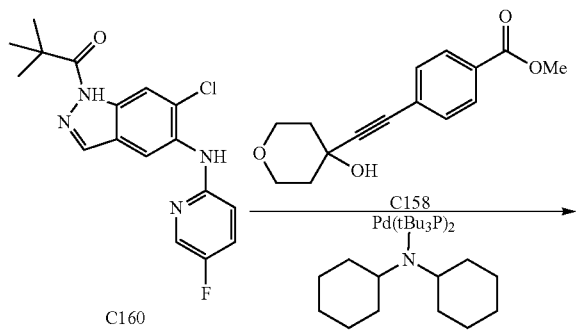

C160

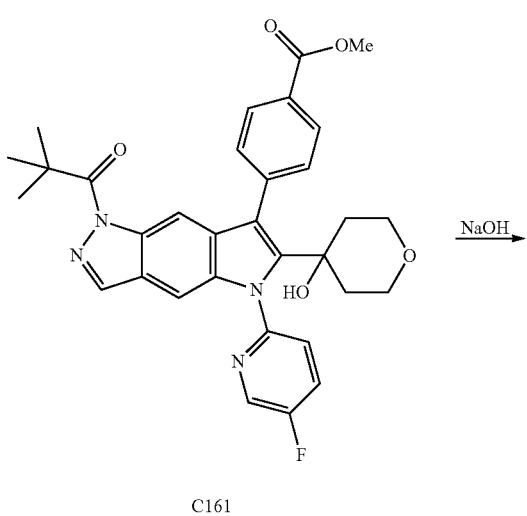

C161

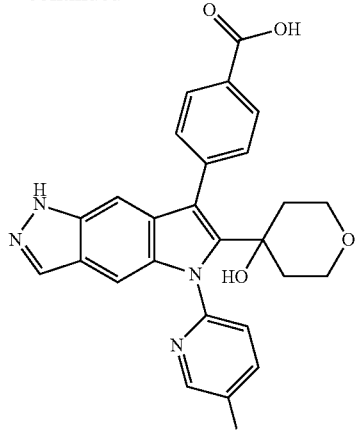

131

Step 1. Synthesis of methyl 4-[2-(4-hydroxytetrahydropyran-4-yl)ethynyl]benzoate (C158)

C158 was prepared from C157 using the method described for the preparation of compound C123 (NEt$_3$ was substituted for Et$_2$NH). Purification by silica gel chromatography (Gradient: 0-100% EtOAc in heptane) afforded the product. (0.92 g, 92%). $^1$H NMR (300 MHz, DMSO-d$_6$) δ 8.01-7.89 (m, 2H), 7.63-7.51 (m, 2H), 5.83 (s, 1H), 3.86 (s, 3H), 3.79 (dt, J=11.7, 4.6 Hz, 2H), 3.57 (ddd, J=11.6, 8.6, 3.1 Hz, 2H), 1.94-1.89 (m, 1H), 1.89-1.83 (m, 1H), 1.71 (ddd, J=12.8, 8.6, 3.8 Hz, 2H). LCMS m/z 261.0 [M+1]$^+$.

Step 2. 6-chloro-N-(5-fluoro-2-pyridyl)-1H-indazol-5-amine (C159)

Compound C159 was prepared from 5-bromo-6-chloro-1H-indazole C95 (0.42 g, 1.80 mmol) and 5-fluoropyridin-2-amine (230 mg, 2.05 mmol) using the method described for the preparation of C96 in the synthesis of compound 106. Purification by silica gel chromatography (Gradient: 0-100% ethyl acetate in heptane) afforded the product. 6-chloro-N-(5-fluoro-2-pyridyl)-1H-indazol-5-amine (327 mg, 68%). $^1$H NMR (300 MHz, DMSO-d$_6$) δ 13.08 (s, 1H), 8.39 (s, 1H), 8.08-8.03 (m, 2H), 8.01 (d, J=3.1 Hz, 1H), 7.75-7.63 (m, 1H), 7.50 (ddd, J=9.2, 8.4, 3.1 Hz, 1H), 6.79 (dd, J=9.2, 3.7 Hz, 1H). LCMS m/z 263.0 [M+1]$^+$.

Step 3. 1-[6-chloro-5-[(5-fluoro-2-pyridyl)amino]indazol-1-yl]-2,2-dimethyl-propan-1-one (C160)

C160 was prepared from C159 as described for the synthesis of C97 in the preparation of compound 106. 1-[6-chloro-5-[(5-fluoro-2-pyridyl)amino]indazol-1-yl]-2,2-dimethyl-propan-1-one (220 mg, 52%). LCMS m/z 347.1 [M+1]$^+$.

Steps 4 & 5. 4-[5-(5-fluoro-2-pyridyl)-6-(4-hydroxytetrahydropyran-4-yl)-1H-pyrrolo[2,3-f]indazol-7-yl]benzoic Acid (131)

Compound 131 was prepared in two steps from compound C160 using the method described for the preparation of 117. Purification by silica gel chromatography (Gradient: 0-10% methanol in dichloromethane) afforded the product.

4-[5-(5-fluoro-2-pyridyl)-6-(4-hydroxytetrahydropyran-4-yl)-1H-pyrrolo[2,3-f]indazol-7-yl]benzoic acid (8.3 mg, 58%). $^1$H NMR (300 MHz, DMSO-d$_6$) δ 13.1 (bs, 1H), 12.56 (s, 1H), 8.63 (d, J=3.1 Hz, 1H), 8.13-8.07 (m, 2H), 8.03 (td, J=8.5, 3.1 Hz, 1H), 7.99 (d, J=1.0 Hz, 1H), 7.70 (dd, J=8.7, 4.1 Hz, 1H), 7.63-7.55 (m, 2H), 7.09 (d, J=1.1 Hz, 1H), 6.97 (t, J=1.1 Hz, 1H), 5.10 (s, 1H), 3.48 (d, J=12.6 Hz, 4H), 1.90 (td, J=12.2, 11.2, 5.3 Hz, 2H), 1.77 (d, J=13.3 Hz, 2H). LCMS m/z 473.2 [M+1]$^+$.
Compound 132
2,6-difluoro-4-[5-(4-fluorophenyl)-3-methyl-6-tetrahydropyran-4-yl-1H-pyrrolo[2,3-f]indazol-7-yl]phenol (132)
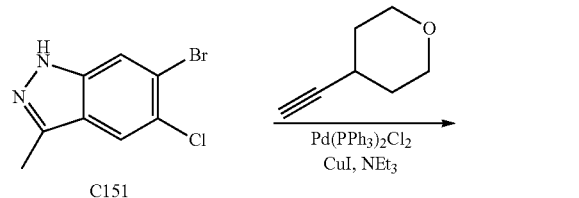
C151
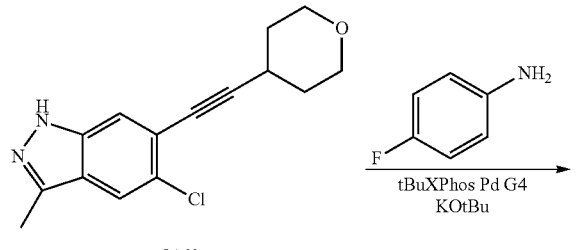
C162
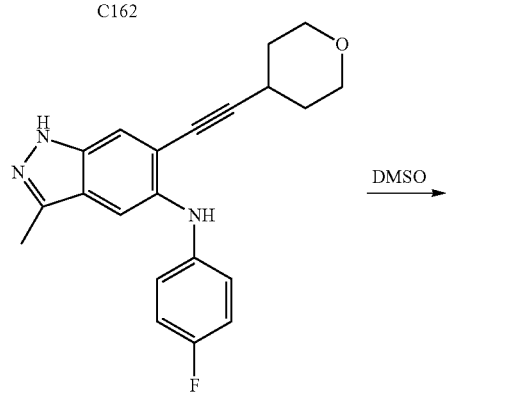
C163
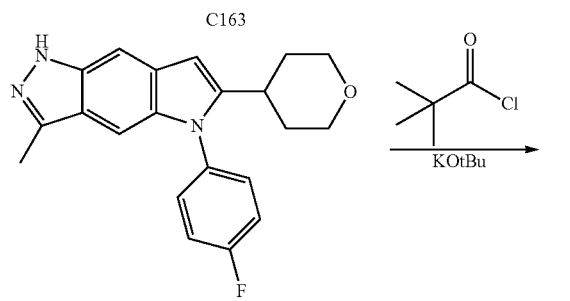
C164
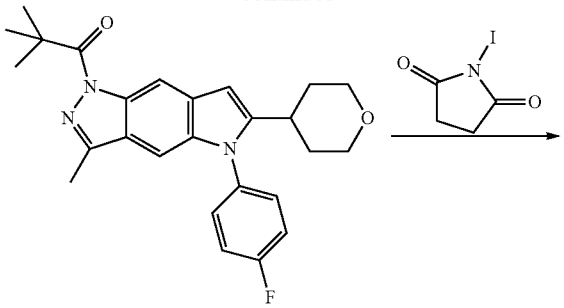
C165
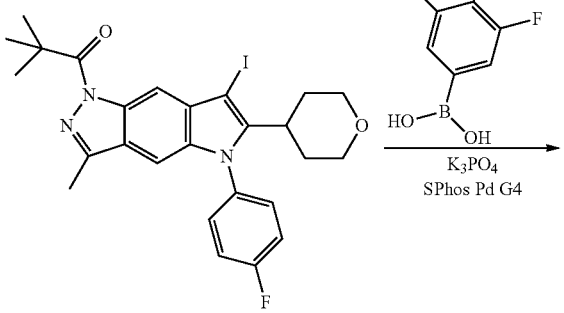
C166
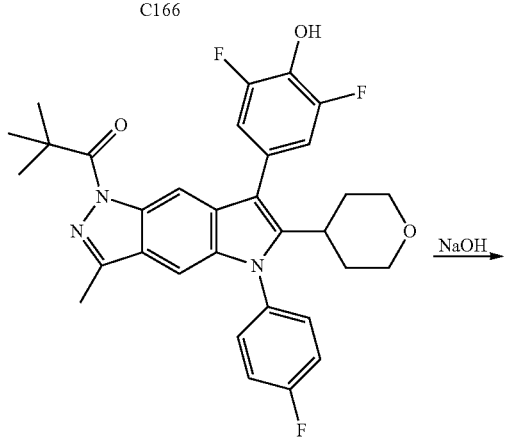
C167
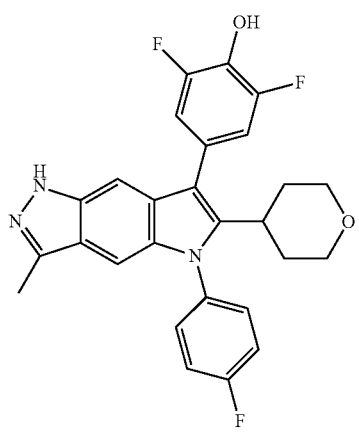
132

Preparation of 1-[5-(4-fluorophenyl)-7-iodo-3-methyl-6-tetrahydropyran-4-yl-pyrrolo[2,3-f]indazol-1-yl]-2,2-dimethyl-propan-1-one (C166)

Intermediate C166 was prepared from C151 according to the method described for the preparation of S11. $^1$H NMR (400 MHz, DMSO-$d_6$) δ 8.37 (s, 1H), 7.62-7.56 (m, 2H), 7.55-7.49 (m, 2H), 7.18 (s, 1H), 3.90 (dd, J=11.6, 4.1 Hz, 2H), 3.22 (t, J=11.7 Hz, 2H), 2.98-2.85 (m, 1H), 2.55-2.51 (m, 3H), 2.30 (tt, J=13.8, 6.9 Hz, 2H), 1.70-1.60 (m, 2H), 1.51 (s, 9H). LCMS m/z 559.96 [M+1]$^+$.

Synthesis of 2,6-difluoro-4-[5-(4-fluorophenyl)-3-methyl-6-tetrahydropyran-4-yl-1H-pyrrolo[2,3-f]indazol-7-yl]phenol (132)

Compound 132 was prepared from C166 in two steps using the method described for the preparation of compound 129. Reversed phase HPLC afforded the product as an off-white solid. 2,6-difluoro-4-[5-(4-fluorophenyl)-3-methyl-6-tetrahydropyran-4-yl-1H-pyrrolo[2,3-f]indazol-7-yl]phenol (6.1 mg, 13%). LCMS m/z 478.1 [M+1]$^+$.

Compounds 133-136

Compounds 133-136 (see Table 10) were prepared in two steps from intermediate C172 and the appropriate boronic acid or ester via a Suzuki coupling then hydrolysis, according to the method described for the preparation of compounds 129 and 130. SPhos Pd G4 was used as catalyst and $K_3PO_4$ was used as base in the Suzuki coupling step. Sodium hydroxide was used in the final deprotection or deprotection/ester hydrolysis step.

TABLE 10

Method of preparation, structure, physicochemical data for compounds 133-136

| Compound | Method/Product | Boronic acid or ester | $^1$H NMR; LCMS m/z [M + H]$^+$ |
| --- | --- | --- | --- |
| 133 | Compound 132 from C172[1] | [structure] | LCMS m/z 505.1 [M + 1]$^+$ |
| 134 | Compound 132 from C172[1] | [structure] | $^1$H NMR (400 MHz, DMSO-$d_6$) δ 12.14 (s, 1H), 7.93 (d, J = 7.9 Hz, 2H), 7.74 (d, J = 7.9 Hz, 2H), 7.63 (dd, J = 8.7, 5.0 Hz, 2H), 7.53 (q, J = 8.6, 6.6 Hz, 3H), 7.18 (s, 1H), 6.96 (s, 1H), 3.73 (d, J = 10.5 Hz, 2H), 3.17 – 3.06 (m, 2H), 3.04 – 2.94 (m, 1H), 2.56 – 2.51 (m, 3H), 2.41 (s, 3H), 1.73 – 1.56 (m, 4H). LCMS m/z 519.1 [M + 1]$^+$. |

TABLE 10-continued

Method of preparation, structure, physicochemical data for compounds 133-136

| Compound | Method/Product | Boronic acid or ester | ¹H NMR; LCMS m/z [M + H]⁺ |
|---|---|---|---|
| 135 | Compound 132 from C172[1] 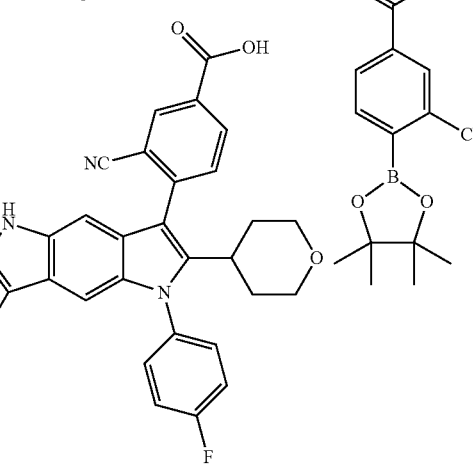 | 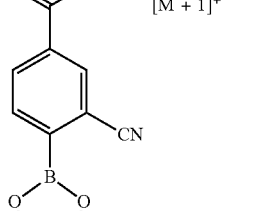 | LCMS m/z 495.1 [M + 1]⁺ |
| 136 | Compound 132 from C172[2] 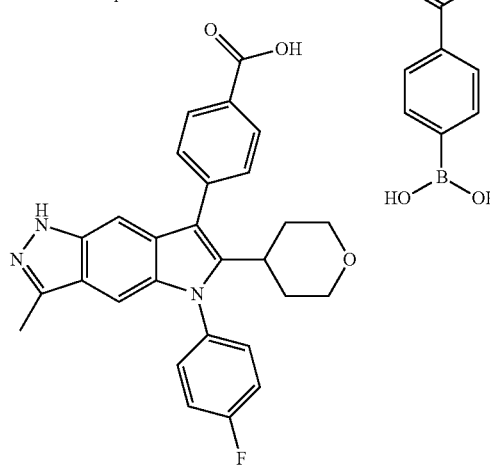 | 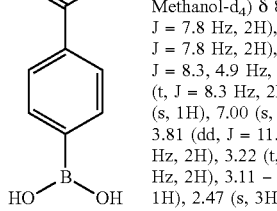 | ¹H NMR (400 MHz, Methanol-d₄) δ 8.17 (d, J = 7.8 Hz, 2H), 7.61 (d, J = 7.8 Hz, 2H), 7.53 (dd, J = 8.3, 4.9 Hz, 2H), 7.41 (t, J = 8.3 Hz, 2H), 7.24 (s, 1H), 7.00 (s, 1H), 3.81 (dd, J = 11.4, 3.9 Hz, 2H), 3.22 (t, J = 11.7 Hz, 2H), 3.11 – 3.00 (m, 1H), 2.47 (s, 3H), 1.82 (tt, J = 12.5, 6.6 Hz, 2H), 1.72 – 1.64 (m, 2H). LCMS m/z 470.1 [M + 1]⁺ |

[1]Purification by reversed-phase HPLC. Method: C18 Waters Sunfire column (30 × 150 mm, 5 micron). Gradient: MeCN in H₂O with 0.2% formic acid.
[2]Purification by reversed-phase chromatography (Column: C18. Gradient: 10-100% MeCN in water with 0.1% formic acid) afforded the product.

Compound 137

5-(4-fluorophenyl)-7-(5-methylsulfonyl-2-pyridyl)-6-tetrahydropyran-4-yl-1H-pyrrolo[2,3-f]indazole (137)

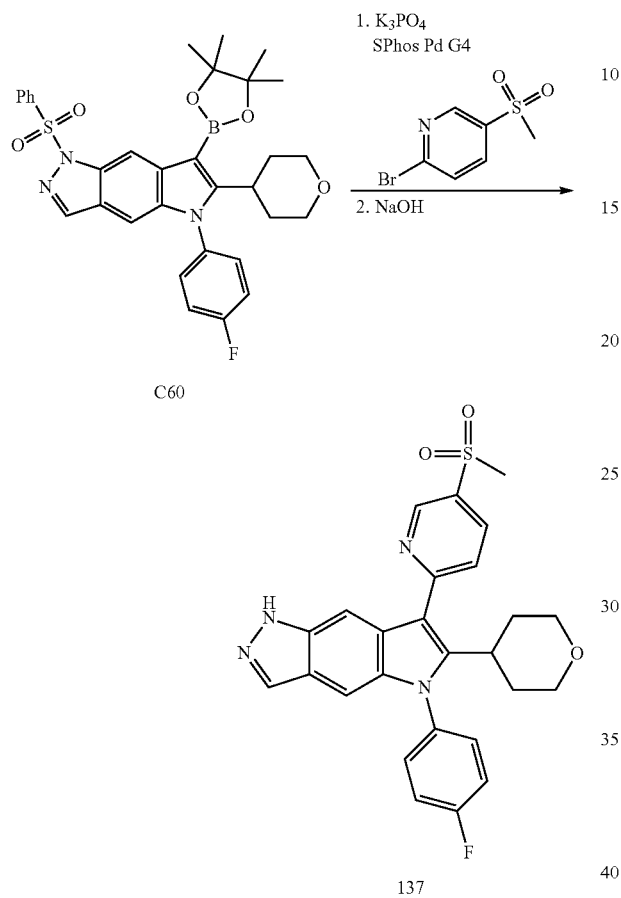

Synthesis of 5-(4-fluorophenyl)-7-(5-methylsulfonyl-2-pyridyl)-6-tetrahydropyran-4-yl-1H-pyrrolo[2,3-f]indazole Compound 137 was synthesized in two steps from C60 (50 mg, 0.07 mmol), according to the method described for compound 129. Purification by reversed-phase HPLC. Method: C18 Waters Sunfire column (30×150 mm, 5 micron). Gradient: MeCN in $H_2O$ with 0.1% trifluoroacetic acid (5.7 mg, 14%). $^1$H NMR (400 MHz, DMSO-$d_6$) δ 12.74 (s, 1H), 9.21 (d, J=2.5 Hz, 1H), 8.43 (dd, J=8.4, 2.5 Hz, 1H), 8.04 (s, 1H), 7.99 (d, J=8.4 Hz, 1H), 7.75 (s, 1H), 7.65 (dd, J=8.7, 5.0 Hz, 2H), 7.54 (t, J=8.7 Hz, 2H), 7.08 (s, 1H), 3.81-3.76 (m, 2H, overlap with water), 3.44 (s, 3H), 3.34 (t, J=12.2 Hz, 1H), 3.19 (t, J=11.5 Hz, 2H), 1.99-1.80 (m, 2H), 1.69 (d, J=12.5 Hz, 2H). LCMS m/z 491.1 [M+1]$^+$.

Compound 138-143

Compounds 138-143 (see Table 11) were prepared in two steps from S4 and the appropriate boronic acid or ester via a Suzuki coupling then hydrolysis, according to the method described for the preparation of compounds 131 and 132. Any modifications to the methods are noted in the footnotes.

TABLE 11

Method of preparation, structure, physicochemical data for compounds 138-143

| Compound | Method/Product | Boronic acid or ester | ¹H NMR; LCMS m/z [M + H]⁺ |
|---|---|---|---|
| 138 | Compound 132 from S4[1] 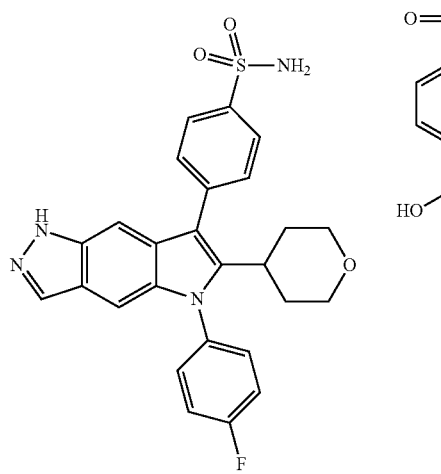 | 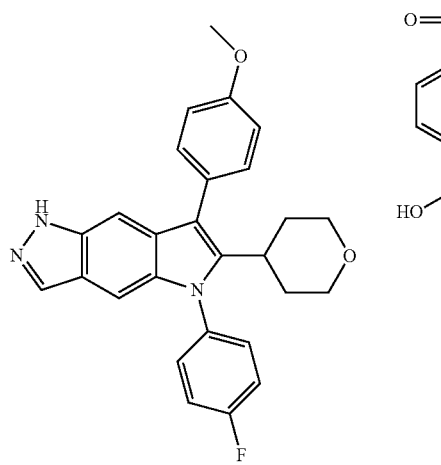 | LCMS m/z 491.1 [M + 1]⁺. |
| 139 | Compound 132 from S4[1,2] | | ¹H NMR (400 MHz, DMSO-d₆) δ 12.58 (d, J = 1.4 Hz, 1H), 8.27 (dd, J = 2.4, 0.7 Hz, 1H), 8.00 (t, J = 1.2 Hz, 1H), 7.83 (dd, J = 8.4, 2.4 Hz, 1H), 7.65 – 7.56 (m, 2H), 7.55 – 7.46 (m, 2H), 7.14 (t, J = 1.1 Hz, 1H), 7.09 (t, J = 0.8 Hz, 1H), 7.02 (dd, J = 8.4, 0.8 Hz, 1H), 3.96 (s, 3H), 3.73 (d, J = 10.4 Hz, 2H), 3.09 (td, J = 11.2, 3.8 Hz, 2H), 2.90 (m, 1H), 1.73 – 1.56 (m, 4H). LCMS m/z 443.2 [M + 1]⁺. |
| 140 | Compound 132 from S4[3] | 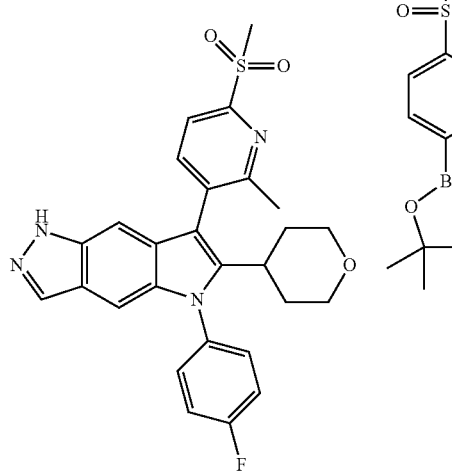 | ¹H NMR (400 MHz, DMSO-d₆) δ 12.57 (s, 1H), 8.17 – 8.08 (m, 1H), 8.07 – 7.99 (m, 2H), 7.71 – 7.61 (m, 2H), 7.58 – 7.48 (m, 2H), 7.19 (s, 1H), 6.90 (s, 1H), 3.82 – 3.60 (m, 2H), 3.41 (s, 3H), 3.07 (q, J = 10.8 Hz, 2H), 2.84 (t, J = 12.4 Hz, 1H), 2.44 (s, 3H), 1.80 – 1.27 (m, 4H). LCMS m/z 505.1 [M + 1]⁺. |

TABLE 11-continued
Method of preparation, structure, physicochemical data for compounds 138-143
| Compound | Method/Product | Boronic acid or ester | 1H NMR; LCMS m/z [M + H]+ |
|---|---|---|---|
| 141 | Compound 132 from S4[3] 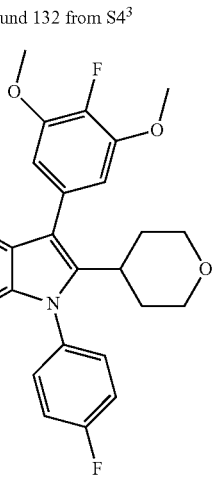 | 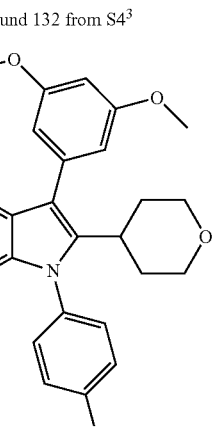 | 1H NMR (400 MHz, DMSO-d6) δ 12.57 (s, 1H), 7.99 (s, 1H), 7.63 – 7.47 (m, 4H), 7.31 (s, 1H), 7.06 (s, 1H), 6.90 – 6.83 (m, 2H), 3.87 (d, J = 1.6 Hz, 6H), 3.75 (d, J = 11.2 Hz, 2H), 3.19 – 3.07 (m, 2H), 3.06 – 2.96 (m, 1H), 1.75 – 1.64 (m, 4H). LCMS m/z 490.1 [M + 1]+. |
| 142 | Compound 132 from S4[3] | | 1H NMR (400 MHz, DMSO-d6) δ 12.55 (s, 1H), 7.99 (s, 1H), 7.60 (dd, J = 8.3, 5.0 Hz, 2H), 7.53 – 7.47 (m, 2H), 7.28 (s, 1H), 7.05 (s, 1H), 6.63 (s, 2H), 6.59 (s, 1H), 3.82 (s, 6H), 3.78 – 3.71 (m, 2H), 3.10 (t, J = 11.4 Hz, 2H), 3.04 – 2.95 (m, 1H), 1.80 – 1.60 (m, 4H). LCMS m/z 472.1 [M + 1]+. |

TABLE 11-continued

Method of preparation, structure, physicochemical data for compounds 138-143

| Compound | Method/Product | Boronic acid or ester | $^{1}$H NMR; LCMS m/z [M + H]$^{+}$ |
|---|---|---|---|
| 143 | from S4-see footnotes[1,4] | 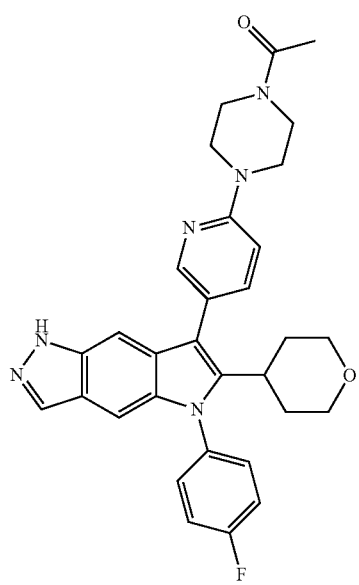 | $^{1}$H NMR (400 MHz, DMSO-d$_{6}$) δ 12.57 (s, 1H), 8.23 (d, J = 2.4 Hz, 1H), 7.99 (s, 1H), 7.68 (dd, J = 8.6, 2.5 Hz, 1H), 7.59 (dd, J = 8.7, 5.1 Hz, 2H), 7.50 (t, J = 8.7 Hz, 2H), 7.16 (s, 1H), 7.08 (s, 1H), 7.03 (d, J = 8.7 Hz, 1H), 3.74 (d, J = 11.1 Hz, 2H), 3.62 (m, 8H), 3.09 (m, 2H), 2.88 (tm, 1H), 2.08 (s, 3H), 1.68 (m, 4H). LCMS m/z 539.1 [M + 1]$^{+}$. |

[1]Purification by reversed-phase HPLC. Method: C18 Waters Sunfire column (30 × 150 mm, 5 micron). Gradient: MeCN in H$_{2}$O with 0.2% formic acid.

[2]The methoxy substituted by-product 139 5-(4-fluorophenyl)-7-(6-methoxy-3-pyridyl)-6-tetrahydropyran-4-yl-1H-pyrrolo[2,3-f]indazole was isolated from the two step Suzuki coupling/ pivaloyl group deprotection in addition to compound 138.

[3]Purification by reversed-phase chromatography (Column: C18. Gradient: 10-100% MeCN in water with 0.1% formic acid) afforded the product.

[4]The Suzuki coupling step was carried out using Pd(PPh$_{3}$)$_{4}$ and Na$_{2}$CO$_{3}$ in DMF and 1,4-dioxane at 150° C.

Compound 144

4-[1-(4-fluorophenyl)-2-tetrahydropyran-4-yl-5H-pyrrolo[2,3-f]indol-3-yl]benzoic Acid (144)

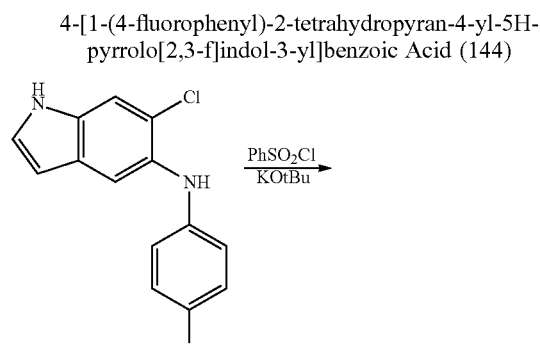

C168

-continued

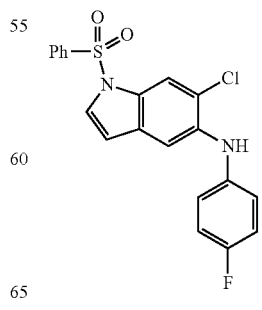

C169

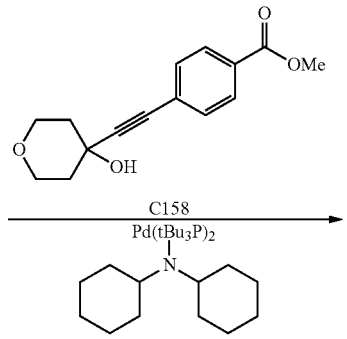

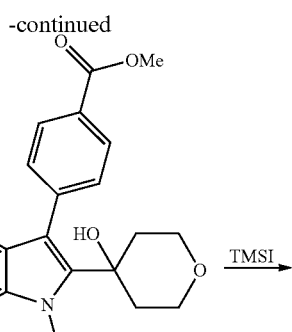

C170

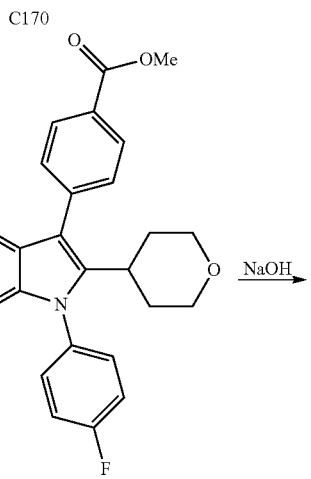

C171

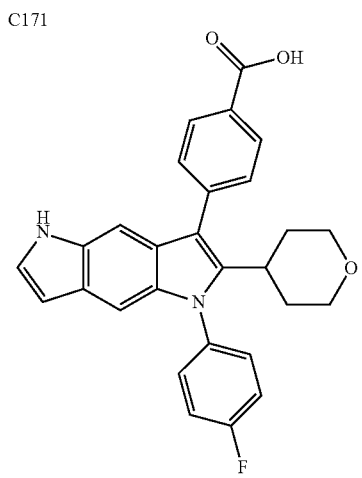

144

Step 1. Synthesis of 1-(benzenesulfonyl)-6-chloro-N-(4-fluorophenyl)indol-5-amine (C169)

To a solution of 6-chloro-N-(4-fluorophenyl)-1H-indol-5-amine C168 (448 mg, 1.68 mmol) in THF (12 mL) at −0° C. (ice-water bath) was added KOtBu (1.9 mL of 1 M, 1.9 mmol). After ~10 min, benzenesulfonyl chloride (287 µL, 2.25 mmol) was added and the reaction stirred for 60 min in an ice bath. The reaction was quenched with water (10 mL), and stirred for 5 min. 50% saturated brine (40 mL) was added and the mixture extracted with EtOAc (100 mL). The organic layer was dried with sodium sulfate, filtered and concentrated. Purification by silica gel chromatography (0-100% ethyl acetate in heptane) afforded the product (305 mg, 43%). $^1$H NMR (300 MHz, DMSO-$d_6$) δ 8.03-7.92 (m, 3H), 7.78 (d, J=3.6 Hz, 1H), 7.76-7.68 (m, 1H), 7.66-7.59 (m, 2H), 7.57 (s, 1H), 7.34 (s, 1H), 7.11-6.98 (m, 4H), 6.75 (dd, J=3.7, 0.9 Hz, 1H). LCMS m/z 401.1 [M+1]$^+$.

Step 2. Methyl 4-[5-(benzenesulfonyl)-1-(4-fluorophenyl)-2-(4-hydroxytetrahydropyran-4-yl)pyrrolo[2,3-f]indol-3-yl]benzoate (C170)

Compound C169 was prepared from C170 1-(benzenesulfonyl)-6-chloro-N-(4-fluorophenyl)indol-5-amine (99.5 mg, 0.24 mmol) and C175 methyl 4-[2-(4-hydroxytetrahydropyran-4-yl)ethynyl]benzoate (112 mg, 0.43 mmol) using the method described for the preparation of compound C156. Purification by silica gel chromatography (0-100% ethyl acetate in heptane) afforded the product (121 mg, 80%). $^1$H NMR (300 MHz, DMSO-$d_6$) δ 8.21-8.15 (m, 2H), 7.72-7.46 (m, 11H), 7.37 (t, J=8.7 Hz, 2H), 6.82-6.74 (m, 2H), 5.12 (s, 1H), 3.94 (s, 3H), 3.52-3.35 (m, 4H), 1.81 (td, J=12.9, 5.3 Hz, 2H), 1.55 (d, J=13.0 Hz, 2H). LCMS m/z 624.1 [M+1]$^+$.

Step 3. Synthesis of methyl 4-[5-(benzenesulfonyl)-1-(4-fluorophenyl)-2-tetrahydropyran-4-yl-pyrrolo[2,3-f]indol-3-yl]benzoate (C171)

To a solution of methyl 4-[5-(benzenesulfonyl)-1-(4-fluorophenyl)-2-(4-hydroxytetrahydropyran-4-yl)pyrrolo[2,3-f]indol-3-yl]benzoate C170 (95 mg, 0.15 mmol) in MeCN (2 mL) at room temperature was added iodo(trimethyl)silane (100 µL, 0.70 mmol). The reaction was heated at 50° C. for 10 min. The reaction was quenched with water and extracted by CH$_2$Cl$_2$. The combined organic layer was dried over MgSO$_4$, filtered and concentrated. Purification by silica gel chromatography (0 to 100% ethyl acetate in heptane) afforded the product cartridge (41 mg, 44%). $^1$H NMR (300 MHz, DMSO-$d_6$) δ 8.24-8.18 (m, 2H), 7.81-7.75 (m, 3H), 7.70-7.53 (m, 8H), 7.48 (t, J=8.7 Hz, 2H), 6.94 (d, J=0.8 Hz, 1H), 6.82 (d, J=3.9 Hz, 1H), 3.94 (s, 3H), 3.71 (d, J=11.0 Hz, 2H), 3.14-3.03 (m, 2H), 3.02-2.91 (m, 1H), 1.69-1.55 (m, 4H). LCMS m/z 609.1 [M+1]+.

Step 5. Synthesis of 4-[1-(4-fluorophenyl)-2-tetrahydropyran-4-yl-5H-pyrrolo[2,3-f]indol-3-yl]benzoic Acid (144)

Compound 144 was prepared from compound methyl 4-[5-(benzenesulfonyl)-1-(4-fluorophenyl)-2-tetrahydropyran-4-yl-pyrrolo[2,3-f]indol-3-yl]benzoate C171 (40 mg, 0.063 mmol) by hydrolysis with NaOH at 80° C. as described in the preparation of compound 129. Purification by reversed-phase HPLC (Method: C18 Waters Sunfire column (30×150 mm, 5 micron). Gradient: MeCN in H$_2$O with 0.2% formic acid) afforded the product (10.8 mg, 37%). $^1$H NMR (300 MHz, DMSO-$d_6$) δ 13.01 (s, 1H), 10.63 (s, 1H), 8.13-8.04 (m, 2H), 7.65-7.54 (m, 4H), 7.49 (t, J=8.7 Hz, 2H), 7.29 (t, J=2.8 Hz, 1H), 7.26-7.19 (m, 1H), 6.85 (s, 1H), 6.35-6.28 (m, 1H), 3.73 (d, J=11.3 Hz, 2H), 3.17-2.93 (m, 3H), 1.71-1.60 (m, 4H). LCMS m/z 455.1 [M+1]$^+$.

Compound 145

4-[5-(4-fluorophenyl)-6-tetrahydropyran-4-yl-1H-pyrrolo[2,3-f]indazol-7-yl]benzamide (145)

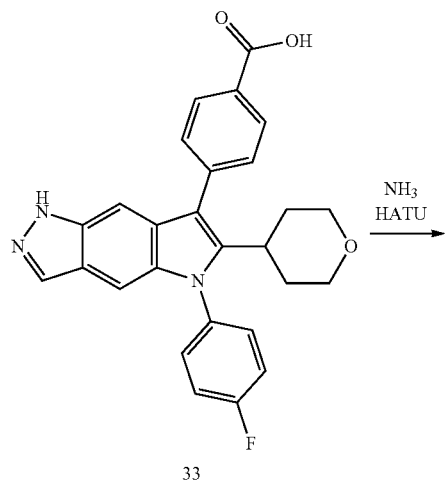

33

NH₃
HATU

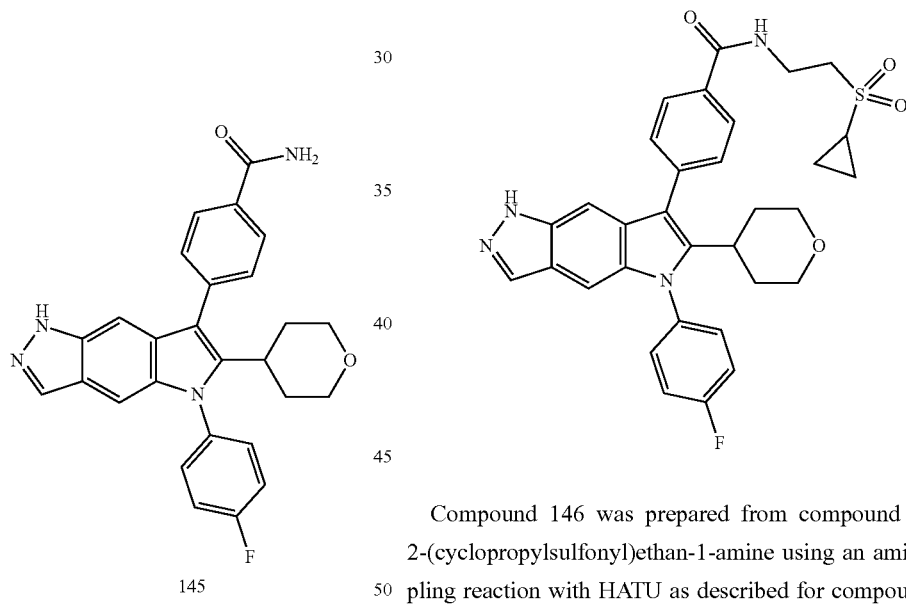

145

Preparation of 4-[5-(4-fluorophenyl)-6-tetrahydropyran-4-yl-1H-pyrrolo[2,3-f]indazol-7-yl]benzamide (145)

To a solution of 4-[5-(4-fluorophenyl)-6-tetrahydropyran-4-yl-1H-pyrrolo[2,3-f]indazol-7-yl]benzoic acid (10 mg, 0.02 mmol) and HATU (10 mg, 0.03 mmol) in DMF (250 μL) was added DIPEA (12 μL, 0.07 mmol) was added, and the reaction was stirred at room temperature for 5 min. Ammonia (10 μL of 30% w/w) was added and the reaction was stirred at room temperature for 5 min. The reaction was worked up by addition of water and dichloromethane. The mixture was extracted with dichloromethane (×3). The organic phases were filtered through a phase separator, combined and the volatiles were evaporated in vacuo. Purification by reversed-phase HPLC (Method: C18 Waters Sunfire column (30×150 mm, 5 micron). Gradient: MeCN in H₂O with 0.2% formic acid) afforded the product as a white solid (8.4 mg, 82%). $^1$H NMR (400 MHz, DMSO-d$_6$) δ 12.59 (s, 1H), 8.08 (s, 1H), 8.04 (d, J=8.3 Hz, 2H), 8.00 (t, J=1.3 Hz, 1H), 7.62 (m, 2H), 7.60-7.57 (m, 2H), 7.51 (m, 2H), 7.44 (s, 1H), 7.23 (t, J=1.1 Hz, 1H), 7.07 (s, 1H), 3.73 (d, J=11.3 Hz, 2H), 3.16-3.05 (m, 2H), 2.99 (m, 1H), 1.67 (m, 4H). LCMS m/z 455.2 [M+1]$^+$.

Compound 146

N-(2-(cyclopropylsulfonyl)ethyl)-4-(5-(4-fluorophenyl)-6-(tetrahydro-2H-pyran-4-yl)-1,5-dihydropyrrolo[2,3-f]indazol-7-yl)benzamide (146)

Compound 146 was prepared from compound 33 and 2-(cyclopropylsulfonyl)ethan-1-amine using an amide coupling reaction with HATU as described for compound 145. N-(2-cyclopropylsulfonylethyl)-4-[5-(4-fluorophenyl)-6-tetrahydropyran-4-yl-1H-pyrrolo[2,3-f]indazol-7-yl]benzamide (24.7 mg, 35%). $^1$H NMR (400 MHz, Chloroform-d) δ 8.03 (s, 1H), 7.93 (d, J=8.1 Hz, 2H), 7.56 (d, J=8.0 Hz, 2H), 7.51-7.37 (m, 2H), 7.37-7.20 (m, 4H), 7.16-7.06 (m, 1H), 4.19-4.04 (m, 2H), 3.83 (dd, J=11.5, 4.1 Hz, 2H), 3.47-3.38 (m, 2H), 3.20 (td, J=11.9, 1.9 Hz, 2H), 3.00 (ddt, J=15.0, 9.2, 4.8 Hz, 1H), 2.51 (tt, J=7.9, 4.8 Hz, 1H), 1.80 (qd, J=12.5, 4.2 Hz, 2H), 1.63 (s, 2H), 1.32 (qd, J=5.8, 1.3 Hz, 2H), 1.26 (t, J=7.1 Hz, 1H), 1.13 (tt, J=7.0, 3.0 Hz, 2H). $^{19}$F NMR (376 MHz, Chloroform-d) δ −111.64. LCMS m/z 587.2 [M+H]$^+$.

Compound 147

N-(2-acetamidoethyl)-4-(5-(4-fluorophenyl)-6-(tetrahydro-2H-pyran-4-yl)-1,5-dihydropyrrolo[2,3-f]indazol-7-yl)benzamide (147)

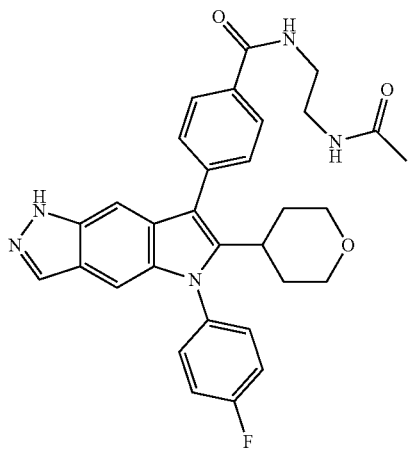 [SMILES: CC(=O)NCCNC(=O)c1ccc(-c2c(C3CCOCC3)n(-c3ccc(F)cc3)c3cc4cn[nH]c4cc23)cc1]

Compound 147 was prepared from compound 33 and N-(2-aminoethyl)acetamide using an amide coupling reaction with HATU as described for compound 145. N-(2-acetamidoethyl)-4-[5-(4-fluorophenyl)-6-tetrahydropyran-4-yl-1H-pyrrolo[2,3-f]indazol-7-yl]benzamide (12.9 mg, 21%). $^1$H NMR (400 MHz, DMSO-d$_6$) δ 12.60 (s, 1H), 8.64 (d, J=6.2 Hz, 1H), 8.01 (d, J=7.8 Hz, 4H), 7.73-7.41 (m, 6H), 7.22 (s, 1H), 7.08 (s, 1H), 3.73 (d, J=11.2 Hz, 2H), 3.35 (m, 3H) 3.13 (d, J=30.7 Hz, 3H), 2.98 (s, 1H), 1.84 (s, 3H), 1.67 (s, 4H). $^{19}$F NMR (376 MHz, Chloroform-d) δ −112.6 LCMS m/z 540.2 [M+H]$^+$.

Compound 148

4-[5-(4-fluorophenyl)-6-tetrahydropyran-4-yl-1H-pyrrolo[2,3-f]indazol-7-yl]-N-[2-(2-oxooxazolidin-3-yl)ethyl]benzamide (148)

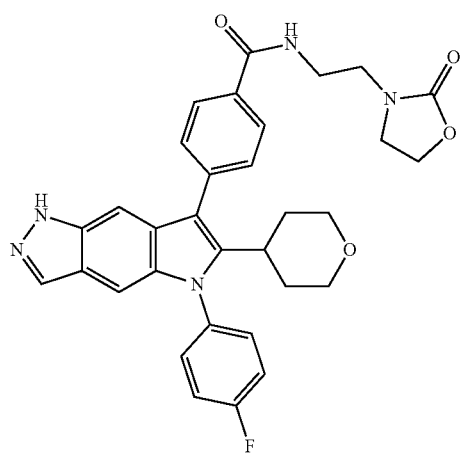 [SMILES: O=C(NCCN1CCOC1=O)c1ccc(-c2c(C3CCOCC3)n(-c3ccc(F)cc3)c3cc4cn[nH]c4cc23)cc1]

Compound 148 was prepared from compound 33 and 3-(2-aminoethyl)oxazolidin-2-one using an amide coupling reaction with HATU as described for compound 145. 4-[5-(4-fluorophenyl)-6-tetrahydropyran-4-yl-1H-pyrrolo[2,3-f]indazol-7-yl]-N-[2-(2-oxooxazolidin-3-yl)ethyl]benzamide (5.9 mg, 8%). $^1$H NMR (400 MHz, DMSO-d$_6$) δ 12.58 (s, 1H), 8.71 (s, 1H), 8.05-7.92 (m, 3H), 7.65-7.47 (m, 6H), 7.23 (s, 1H), 7.07 (s, 1H), 4.27 (s, 2H), 3.71 (dd, J=19.9, 9.6 Hz, 3H), 3.55-3.46 (m, 2H), 3.36 (d, J=20.5 Hz, 3H), 3.10 (s, 2H), 3.00 (s, 1H), 1.67 (s, 4H). LCMS m/z 568.2 [M+1]$^+$.

Compound 149

4-[5-(4-fluorophenyl)-6-tetrahydropyran-4-yl-1H-pyrrolo[2,3-f]indazol-7-yl]-N-(3-methylsulfonylcyclobutyl)benzamide (149)

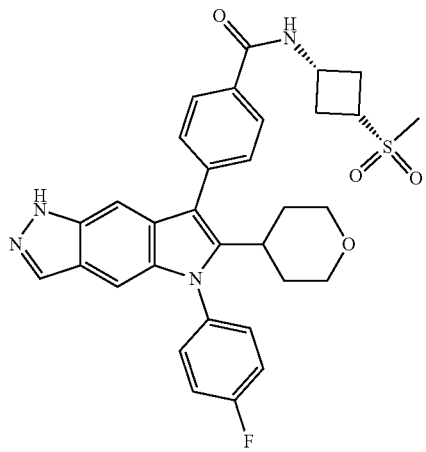

Compound 149 was prepared from compound 33 and 3-methylsulfonylcyclobutanamine hydrochloride salt by an amide coupling reaction with HATU as described for compound 145. 4-[5-(4-fluorophenyl)-6-tetrahydropyran-4-yl-1H-pyrrolo[2,3-f]indazol-7-yl]-N-(3-methylsulfonylcyclobutyl)benzamide (3.1 mg, 3%). $^1$H NMR (400 MHz, DMSO-d$_6$) δ 12.61 (s, 1H), 8.97 (d, J=7.5 Hz, 1H), 8.13-7.92 (m, 3H), 7.56 (dt, J=40.4, 8.5 Hz, 7H), 7.23 (s, 1H), 7.08 (s, 1H), 4.57-4.40 (m, 1H), 3.76 (m, 4H), 3.34 (s, 1H), 3.09 (s, 3H), 2.92 (m, 4H), 1.65 (m, 4H). LCMS m/z 587.1 [M+1]$^+$.

Compounds 150-159

Compounds 150-159 (see Table 12) were prepared from S4 using the method described for the preparation of compound 132. SPhos Pd G4 or Pd(PPh$_3$)$_4$ was used as the catalyst in the Suzuki reaction step. Any modifications to these conditions are noted in the table and accompanying footnotes.

TABLE 12

Method of preparation, structure, physicochemical data for compounds 148-156

| Compound | Method/Product | Boronic acid or ester | $^1$H NMR; LCMS m/z. [M + H]$^+$ |
|---|---|---|---|
| 150 | Compound 132 from S4$^1$ 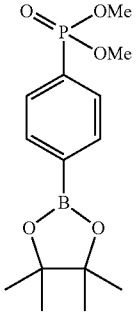 | 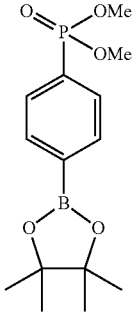 | $^1$H NMR (400 MHz, Methanol-d$_4$) δ 8.28 (s, 1H), 8.02 – 7.85 (m, 3H), 7.72 (ddt, J = 7.8, 4.1, 1.1 Hz, 2H), 7.58 – 7.46 (m, 2H), 7.47 – 7.35 (m, 2H), 7.30 (t, J = 1.1 Hz, 1H), 7.12 (d, J = 1.2 Hz, 1H), 3.86 (d, J = 11.1 Hz, 8H), 3.22 (td, J = 11.8, 2.1 Hz, 2H), 3.15 – 2.99 (m, 1H), 1.81 (qd, J = 12.4, 4.3 Hz, 2H), 1.69 (d, J = 13.0 Hz, 2H). LCMS m/z 520.0 [M + 1]$^+$. |
| 151 | Compound 132 from S4$^1$ | | $^1$H NMR (400 MHz, Methanol-d$_4$) δ 8.05 – 7.89 (m, 3H), 7.73 – 7.61 (m, 2H), 7.58 – 7.47 (m, 2H), 7.46 – 7.36 (m, 2H), 7.29 (t, J = 1.1 Hz, 1H), 7.13 (d, J = 1.1 Hz, 1H), 3.87 – 3.71 (m, 5H), 3.29 – 3.12 (m, 2H), 3.12 – 2.95 (m, 1H), 1.82 (qd, J = 12.5, 4.3 Hz, 2H), 1.69 (d, J = 12.9 Hz, 2H). LCMS m/z 506.0 [M + 1]+ |
| 152 | Compound 132 from S4$^2$ 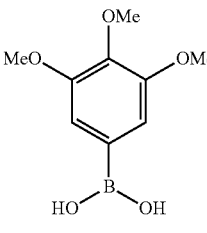 | | $^1$H NMR (400 MHz, DMSO-d$_6$) δ 12.53 (s, 1H), 7.99 (d, J = 1.0 Hz, 1H), 7.58 (ddt, J = 8.4, 5.6, 2.8 Hz, 2H), 7.55 – 7.47 (m, 2H), 7.32 (t, J = 1.1 Hz, 1H), 7.04 (d, J = 1.1 Hz, 1H), 6.77 (s, 2H), 3.82 (s, 6H), 3.78 (s, 3H), 3.77 – 3.69 (m, 2H), 3.18 – 2.97 (m, 3H), 1.80 – 1.64 (m, 4H). LCMS m/z 502.1 [M + 1]$^+$. |

TABLE 12-continued

Method of preparation, structure, physicochemical data for compounds 148-156

| Compound | Method/Product | Boronic acid or ester | ¹H NMR; LCMS m/z. [M + H]⁺ |
|---|---|---|---|
| 153 | From S4-See footnote[3] | | ¹H NMR (400 MHz, DMSO-$d_6$) δ 12.61 (s, 1H), 8.84 – 8.60 (m, 1H), 8.08 (s, 1H), 8.01 (s, 1H), 7.75 (d, J = 9.2 Hz, 1H), 7.70 (s, 1H), 7.63 (dd, J = 8.7, 5.0 Hz, 2H), 7.52 (t, J = 8.6 Hz, 2H), 7.38 (d, J = 9.3 Hz, 1H), 7.25 (s, 1H), 7.12 (s, 1H), 3.73 (d, J = 11.2 Hz, 2H), 3.20 – 3.04 (m, 2H), 2.98 (m, 1H), 1.70 (m, 4H). LCMS m/z 452.2 |
| 154 | Compound 132 from S4[2] | | ¹H NMR (400 MHz, DMSO-$d_6$) δ 12.56 (s, 1H), 7.99 (s, 1H), 7.63 – 7.57 (m, 2H), 7.50 (t, J = 8.5 Hz, 2H), 7.37 – 7.29 (m, 2H), 7.26 (d, J = 8.4 Hz, 1H), 7.18 (s, 1H), 7.07 (s, 1H), 3.95 (s, 3H), 3.74 (d, J= 11.4 Hz, 2H), 3.17 – 3.04 (m, 2H), 2.98 – 2.88 (m, 1H), 1.72 – 1.61 (m, 4H). LCMS m/z 460.1 [M + 1]⁺. |
| 155 | From S4-See footnote[3] | | ¹H NMR (400 MHz, DMSO-$d_6$) δ 12.57 (s, 1H), 8.23 (d, J = 2.4 Hz, 1H), 7.99 (s, 1H), 7.68 (dd, J = 8.7, 2.4 Hz, 1H), 7.65 – 7.56 (m, 2H), 7.50 (t, J = 8.7 Hz, 2H), 7.16 (s, 1H), 7.08 (s, 1H), 7.01 (d, J = 8.7 Hz, 1H), 3.83 – 3.67 (m, 6H), 3.55 (m, 4H), 3.10 (m, 2H), 2.89 (m, 1H), 1.68 (m, 4H). LCMS m/z 498.1 [M + 1]⁺ |

TABLE 12-continued

Method of preparation, structure, physicochemical data for compounds 148-156

| Compound | Method/Product | Boronic acid or ester | $^1$H NMR; LCMS m/z. [M + H]$^+$ |
|---|---|---|---|
| 156 | From S4-See footnote$^3$ 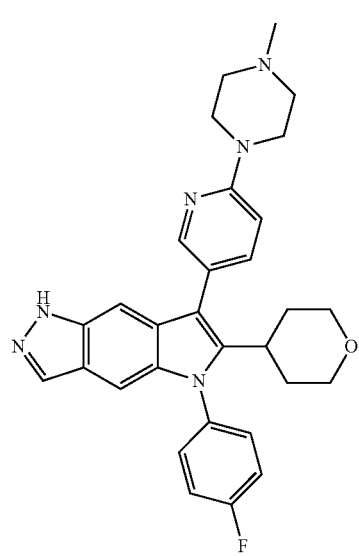 | 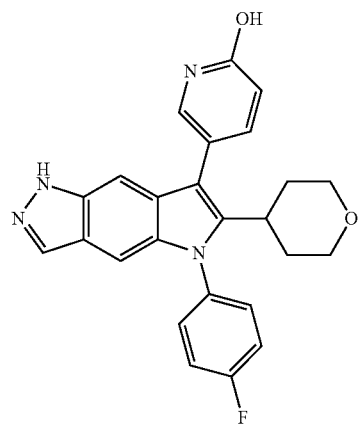 | $^1$H NMR (400 MHz, DMSO-d$_6$) δ 12.57 (s, 1H), 8.22 (d, J = 2.4 Hz, 1H), 7.99 (s, 1H), 7.66 (dd, J = 8.7, 2.5 Hz, 1H), 7.59 (dd, J = 8.7, 5.0 Hz, 2H), 7.50 (t, J = 8.7 Hz, 2H), 7.15 (s, 1H), 7.08 (s, 1H), 7.02 (d, J = 8.8 Hz, 1H), 3.74 (d, J = 10.9 Hz, 2H), 3.61 (m, 4H), 3.10 (m, 2H), 2.90 (m, 1H), 2.64-2.56 (m, 4H), 2.34 (s, 3H), 1.68 (m, 4H). LCMS m/z 511.2 [M + 1]$^+$. |
| 157 | From S4-See footnote$^3$ | | $^1$H NMR (400 MHz, DMSO-d$_6$) δ 12.61 (s, 1H), 11.80 (s, 1H), 7.99 (s, 1H), 7.63 – 7.45 (m, 5H), 7.42 (s, 1H), 7.22 (s, 1H), 7.08 (s, 1H), 6.51 (d, J = 9.3 Hz, 1H), 3.77 (d, J = 11.3 Hz, 2H), 3.21 – 3.05 (m, 2H), 2.88 (m, 1H), 1.69 (m, 4H). LCMS m/z 429.2 [M + 1]$^+$. |

TABLE 12-continued

Method of preparation, structure, physicochemical data for compounds 148-156

| Compound | Method/Product | Boronic acid or ester | $^1$H NMR; LCMS m/z. [M + H]$^+$ |
|---|---|---|---|
| 158 | From S4-See footnote[3] | | $^1$H NMR (400 MHz, DMSO-d$_6$) δ 12.58 (s, 1H), 8.25 (d, J = 2.4 Hz, 1H), 8.00 (s, 1H), 7.82 (dd, J = 8.4, 2.5 Hz, 1H), 7.60 (dd, J = 8.7, 5.0 Hz, 2H), 7.51 (t, J = 8.6 Hz, 2H), 7.16 (s, 1H), 7.09 (s, 1H), 6.99 (d, J = 8.4 Hz, 1H), 5.30 (m, 1H), 3.92 (m, 2H), 3.73 (d, J = 11.2 Hz, 2H), 3.58 – 3.49 (m, 2H), 3.18 – 3.04 (m, 2H), 2.98 – 2.85 (m, 1H), 2.10 (m, 2H), 1.79 – 1.55 (m, 6H). LCMS m/z 513.2 |
| 159 | From S4-See footnote[3,4] | | $^1$H NMR (400 MHz, Methanol-d$_4$) δ 8.13 – 7.92 (m, 2H), 7.82 (s, 1H), 7.49 (m, 2H), 7.44 – 7.33 (m, 3H), 7.13 (d, J = 1.2 Hz, 1H), 5.72 (s, 2H), 3.84 (dd, J = 11.5, 4.3 Hz, 2H), 3.25 (m, 2H), 3.05 (s, 4H), 1.98 – 1.84 (m, 2H), 1.68 (d, J = 13.2 Hz, 2H). LCMS m/z 494.2 [M + 1]$^+$. |
| 160 | From S4-See footnote[3,4] | | $^1$H NMR (400 MHz, Methanol-d$_4$) δ 8.04 (d, J = 1.1 Hz, 1H), 7.92 (d, J = 0.7 Hz, 1H), 7.72 (d, J = 0.8 Hz, 1H), 7.47 (m, 2H), 7.43 – 7.38 (m, 2H), 7.37 (m, 1H), 7.13 (d, J = 1.1 Hz, 1H), 4.82 – 4.74 (m, 2H), 3.83 (m, 4H), 3.25 (d, J = 11.7 Hz, 2H), 3.10 – 2.95 (m, 1H), 2.86 (d, J = 0.7 Hz, 3H), 1.91 (qd, J = 12.7, 4.4 Hz, 2H), 1.67 (d, J = 12.5 Hz, 2H). LCMS m/z 507.0 M + 1]$^+$. |

TABLE 12-continued

Method of preparation, structure, physicochemical data for compounds 148-156

| Compound | Method/Product | Boronic acid or ester | $^1$H NMR; LCMS m/z. [M + H]$^+$ |
|---|---|---|---|
| 161 | From S4-See footnote[5] | | $^1$H NMR (400 MHz, Methanol-d$_4$) δ 8.02 – 7.90 (m, 3H), 7.76 – 7.66 (m, 2H), 7.57 – 7.47 (m, 2H), 7.45 – 7.35 (m, 2H), 7.29 (t, J = 1.1 Hz, 1H), 7.12 (d, J = 1.2 Hz, 1H), 3.87 – 3.75 (m, 2H), 3.21 (td, J = 11.8, 2.0 Hz, 2H), 3.06 (tt, J = 12.2, 3.5 Hz, 1H), 1.89 (d, J = 13.4 Hz, 6H), 1.86 – 1.55 (m, 4H). LCMS m/z 488.0 [M + 1]$^+$. |
| 162 | From S4-See footnote[3,4] | | $^1$H NMR (400 MHz, DMSO-d$_6$) δ 12.60 (s, 1H), 7.98 (d, J = 1.2 Hz, 1H), 7.93 (d, J = 0.8 Hz, 1H), 7.63 (d, J = 0.8 Hz, 1H), 7.56 (m, 2H), 7.53 – 7.46 (m, 2H), 7.36 (t, J = 1.1 Hz, 1H), 7.02 (d, J = 1.0 Hz, 1H), 5.00 (m, 1H), 4.28 (t, J = 5.7 Hz, 2H), 3.85 (m, 2H), 3.81 – 3.72 (m, 2H), 3.16 (td, J = 11.7, 2.0 Hz, 2H), 3.08 – 2.94 (m, 1H), 1.75 (qd, J = 12.5, 4.2 Hz, 2H), 1.63 (d, J = 12.9 Hz, 2H). LCMS m/z 446.2 [M + 1]$^+$. |
| 163 | From S4-See footnote[3,4] | | $^1$H NMR (400 MHz, DMSO-d$_6$) δ 12.59 (d, J = 1.3 Hz, 1H), 7.98 (t, J = 1.3 Hz, 1H), 7.88 (d, J = 0.8 Hz, 1H), 7.62 (d, J = 0.7 Hz, 1H), 7.60 – 7.53 (m, 2H), 7.49 (m, 2H), 7.32 (t, J = 1.1 Hz, 1H), 7.04 (t, J = 0.9 Hz, 1H), 4.79 (s, 1H), 4.16 (s, 2H), 3.76 (dd, J = 11.4, 4.0 Hz, 2H), 3.14 (t, J = 11.6 Hz, 2H), 3.07 – 2.90 (m, 1H), 1.88 – 1.68 (m, 2H), 1.63 (d, J = 12.9 Hz, 2H), 1.15 (s, 6H). LCMS m/z 558.3 [M + 1]$^+$. |

TABLE 12-continued

Method of preparation, structure, physicochemical data for compounds 148-156

| Compound | Method/Product | Boronic acid or ester | ¹H NMR; LCMS m/z. [M + H]⁺ |
|---|---|---|---|
| 164 | From S4-See footnote[2,3] | | ¹H NMR (400 MHz, Methanol-d₄) δ 7.96 (mz, 2H), 7.77 (d, J = 0.7 Hz, 1H), 7.47 (m, 2H), 7.42 – 7.36 (m, 2H), 7.35 (t, J = 1.1 Hz, 1H), 7.10 (d, J = 1.2 Hz, 1H), 5.79 – 5.64 (m, 1H), 5.23 – 5.09 (m, 4H), 3.84 (dd, J = 11.5, 4.2 Hz, 2H), 3.29 – 3.21 (m, 2H), 3.02 (tt, J = 12.5, 3.5 Hz, 1H), 1.90 (qd, J = 12.5, 4.4 Hz, 2H), 1.68 (d, J = 12.8 Hz, 2H). LCMS m/z 542.14 [M + 1]⁺. |
| 165 | From S4-See footnote[2,3] | | ¹H NMR (400 MHz, Methanol-d₄) δ 7.96 (d, J = 1.1 Hz, 1H), 7.87 (d, J = 0.7 Hz, 1H), 7.68 (d, J = 0.7 Hz, 1H), 7.48 (m, 2H), 7.42 (t, J = 1.1 Hz, 1H), 7.41 – 7.35 (m, 2H), 7.09 (d, J = 1.2 Hz, 1H), 5.10 (s, 2H), 3.84 (dd, J = 11.6, 4.2 Hz, 2H), 3.29 – 3.20 (m, 2H), 3.05 (ddd, J = 12.4, 8.9, 3.5 Hz, 1H), 1.93 (qd, J = 12.6, 4.3 Hz, 2H), 1.67 (d, J = 12.8 Hz, 2H). LCMS m/z 544.17 [M + 1]⁺. |
| 166 | From S4-See footnote[2,3] | | ¹H NMR (400 MHz, Methanol-d₄) δ 7.96 (d, J = 1.1 Hz, 1H), 7.83 (d, J = 0.8 Hz, 1H), 7.64 (d, J = 0.8 Hz, 1H), 7.50 – 7.44 (m, 2H), 7.39 (m, 2H), 7.32 (t, J = 1.1 Hz, 1H), 7.11 (d, J = 1.1 Hz, 1H), 4.53 – 4.41 (m, 2H), 3.89 – 3.77 (m, 4H), 3.35 (t, J = 7.1 Hz, 2H), 3.24 (t, J = 11.3 Hz, 2H), 3.06 – 2.92 (m, 1H), 2.35 (t, J = 8.1 Hz, 2H), 2.02 (m, 2H), 1.98 – 1.83 (m, 2H), 1.68 (d, J = 13.2 Hz, 2H). LC MS m/z 597.22 [M + 1]⁺. |

TABLE 12-continued

Method of preparation, structure, physicochemical data for compounds 148-156

| Compound | Method/Product | Boronic acid or ester | $^1$H NMR; LCMS m/z. [M + H]$^+$ |
|---|---|---|---|
| 167 | From S4-See footnote[6] | | $^1$H NMR (400 MHz, Methanol-d$_4$) δ 7.95 (s, 1H), 7.90 (s, 1H), 7.66 (s, 1H), 7.46 (m, 2H), 7.42 – 7.33 (m, 3H), 7.08 (m, 1H), 3.90 – 3.80 (m, 4H), 3.29 – 3.19 (m, 2H), 3.10 – 2.97 (m, 1H), 1.90 (qd, J = 12.6, 4.2 Hz, 2H), 1.66 (m, 8H). LCMS m/z 474.1 [M + 1]$^+$. |

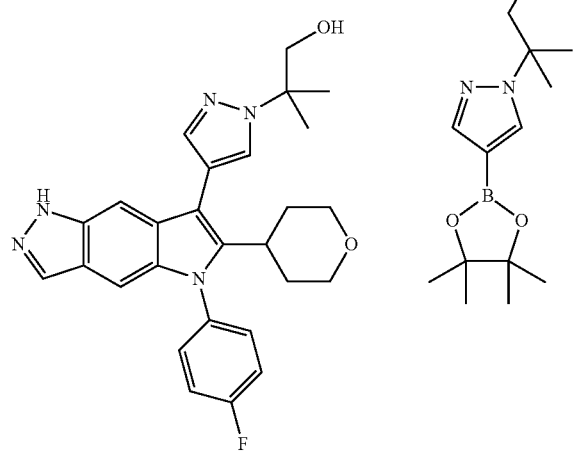

[1]Two products were obtained in the hydrolysis step. Purification by reversed-phase chromatography (Column: C18. Gradient: 10-100% MeCN in water) afforded compounds 148 and 149.

[2]Purification by reversed-phase chromatography (Column: C18. Gradient: 10-100% MeCN in water with 0.2% formic acid) afforded the product.

[3]The Suzuki coupling step was performed by reaction of S4 and the appropriate boronic ester or boronic acid with Pd(PPh$_3$)$_4$ catalyst and Na$_2$CO$_3$. The reaction was performed in a mixture of DMF and 1,4-dioxane at 140° C. under microwave conditions.

[4]Purification by reversed-phase HPLC. Method: C18 Waters Sunfire column (30 × 150 mm, 5 micron). Gradient: MeCN in H$_2$O with 0.1% trifluoroacetic acid

[5]The Suzuki coupling step was performed using SPhos Pd G3 and K$_3$PO$_4$. 2-(4-dimethylphosphorylphenyl)-4,4,5,5-tetramethyl-1,3,2-dioxaborolane was prepared by coupling 2-(4-iodophenyl)-4,4,5,5-tetramethyl-1,3,2-dioxaborolane and methylphosphonoylmethane using Pd$_2$(dba)$_3$, xantphos and NEt$_3$.

[6]The Suzuki coupling step was performed using Pd(PPh$_3$)$_4$ and Na$_2$CO$_3$, heating in a microwave at 125° C. μW for 1 hour. Pivaloyl group deprotection was performed using NaOH in ethanol heating at 50° C. Purification by reversed-phase HPLC. Method: C18 Waters Sunfire column (30 × 150 mm, 5 micron). Gradient: MeCN in H$_2$O with 0.1% trifluoroacetic acid. The product was then triturated with heptane:dichloromethane (8:2) to afford the product 167 2-[4-[5-(4-fluorophenyl)-6-tetrahydropyran-4-yl-1H-pyrrolo[2,3-f]indazol-7-yl]pyrazol-1-yl]-2-methyl-propan-1-ol.

Compound 168

7-(6-dimethylphosphoryl-3-pyridyl)-5-(4-fluorophenyl)-6-tetrahydropyran-4-yl-1H-pyrrolo[2,3-f]indazole (168)

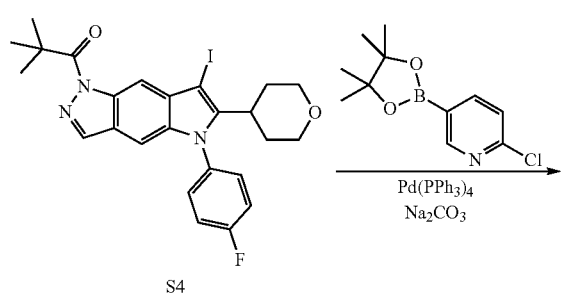

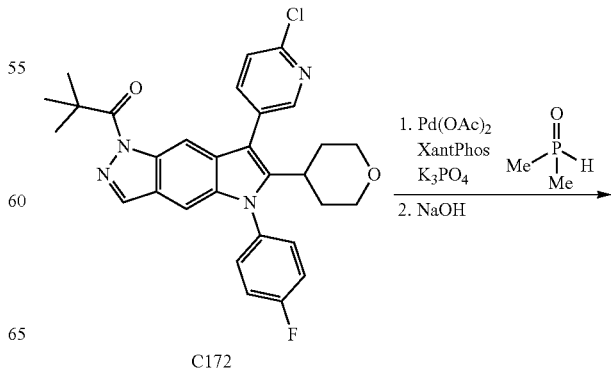

-continued

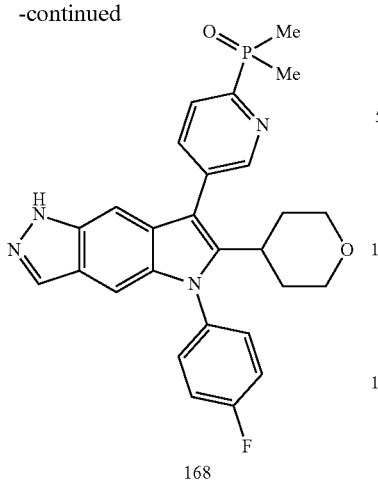

168

Step 1. Synthesis of 7-(6-chloro-3-pyridyl)-5-(4-fluorophenyl)-6-tetrahydropyran-4-yl-1H-pyrrolo[2,3-f]indazole (C172)

To a mixture of 1-[5-(4-fluorophenyl)-7-iodo-6-tetrahydropyran-4-yl-pyrrolo[2,3-f]indazol-1-yl]-2,2-dimethyl-propan-1-one (50 mg, 0.09 mmol), 2-chloro-5-(4,4,5,5-tetramethyl-1,3,2-dioxaborolan-2-yl)pyridine (26 mg, 0.11 mmol), and Pd(PPh$_3$)$_4$ (5 mg, 0.004 mmol) in 1,4-dioxane (0.6 mL) and DMF (0.6 mL) was added a solution of Na$_2$CO$_3$ (136 µL of 2 M, 0.3 mmol). The reaction was heated at 100° C. for 18 hours. Water and dichloromethane were added. The mixture was extracted with dichloromethane (×3). The organic phases were filtered through a phase separator, combined and the volatiles were evaporated in vacuo. Purification by reversed phase chromatography (C18 column. Gradient: 0-40% of CH$_3$CN in water containing formic acid) afforded the product as a white solid. 1-[7-(6-chloro-3-pyridyl)-5-(4-fluorophenyl)-6-tetrahydropyran-4-yl-pyrrolo[2,3-f]indazol-1-yl]-2,2-dimethyl-propan-1-one (19.4 mg, 40%). $^1$H NMR (400 MHz, Chloroform-d) δ 8.48 (dd, J=2.4, 0.8 Hz, 1H), 8.36 (d, J=1.0 Hz, 1H), 8.07 (d, J=0.8 Hz, 1H), 7.80 (dd, J=8.1, 2.4 Hz, 1H), 7.49 (dd, J=8.1, 0.8 Hz, 1H), 7.44 (ddd, J=8.8, 5.0, 2.6 Hz, 2H), 7.37-7.31 (m, 2H), 7.13 (d, J=1.0 Hz, 1H), 3.92-3.80 (m, 2H), 3.22 (td, J=11.8, 2.0 Hz, 2H), 2.97 (tt, J=12.3, 3.5 Hz, 1H), 1.85-1.69 (m, 2H), 1.69-1.59 (m, 2H), 1.55 (s, 9H). LCMS m/z 531.1 [M+1]$^+$.

Step 2. Synthesis of 7-(6-dimethylphosphoryl-3-pyridyl)-5-(4-fluorophenyl)-6-tetrahydropyran-4-yl-1H-pyrrolo[2,3-f]indazole (168)

Part A. To a mixture of 1-[7-(6-chloro-3-pyridyl)-5-(4-fluorophenyl)-6-tetrahydropyran-4-yl-pyrrolo[2,3-f]indazol-1-yl]-2,2-dimethyl-propan-1-one (20 mg, 0.037 mmol), K$_3$PO$_4$ (25 mg, 0.12 mmol), Xantphos (5 mg, 0.009 mmol) and Pd(OAc)$_2$ (2 mg, 0.009 mmol) in DMF (500 µL) was added methylphosphonoylmethane (9 mg, 0.12 mmol). The mixture was heated at 150° C. for 20 minutes. Water and dichloromethane were added. The mixture was extracted with CH$_2$Cl$_2$ (×3). The organic phases were filtered through a phase separator, combined and the volatiles were evaporated in vacuo. The crude was used as is in the next step, 1-[7-(6-dimethylphosphoryl-3-pyridyl)-5-(4-fluorophenyl)-6-tetrahydropyran-4-yl-pyrrolo[2,3-f]indazol-1-yl]-2,2-dimethyl-propan-1-one.

Part B. To a solution of 1-[7-(6-dimethylphosphoryl-3-pyridyl)-5-(4-fluorophenyl)-6-tetrahydropyran-4-yl-pyrrolo[2,3-f]indazol-1-yl]-2,2-dimethyl-propan-1-one (from part A) in Ethanol (1 mL) was added NaOH (150 µL of 1 M, 0.15 mmol). The reaction was heated at 50° C. for 18 hours. Water and dichloromethane was added. The mixture was extracted with dichloromethane (×3). The organic phases were filtered through a phase separator, combined and the volatiles were evaporated in vacuo. Purification by reversed-phase HPLC (Method: C18 Waters Sunfire column (30×150 mm, 5 micron). Gradient: MeCN in H$_2$O with 0.2% formic acid) afforded the product as a white solid. 7-(6-dimethylphosphoryl-3-pyridyl)-5-(4-fluorophenyl)-6-tetrahydropyran-4-yl-1H-pyrrolo[2,3-f]indazole (11 mg, 60%). $^1$H NMR (400 MHz, Methanol-d$_4$) δ 9.03-8.81 (m, 1H), 8.19 (ddd, J=7.9, 5.3, 1.0 Hz, 1H), 8.14 (ddd, J=7.8, 3.6, 2.0 Hz, 1H), 7.99 (d, J=1.0 Hz, 1H), 7.59-7.49 (m, 2H), 7.46-7.37 (m, 2H), 7.31 (t, J=1.1 Hz, 1H), 7.15 (d, J=1.1 Hz, 1H), 3.81 (dd, J=10.9, 3.6 Hz, 2H), 3.23 (td, J=11.3, 3.4 Hz, 2H), 3.07 (tt, J=11.0, 4.9 Hz, 1H), 1.93 (s, 3H), 1.90 (s, 3H), 1.85-1.67 (m, 4H). LCMS m/z 489.1 [M+1]$^+$.

Compound 169

4-[5-(4-fluorophenyl)-6-(4-hydroxytetrahydropyran-4-yl)pyrrolo[2,3-f][1,3]benzothiazol-7-yl]benzoic Acid (169)

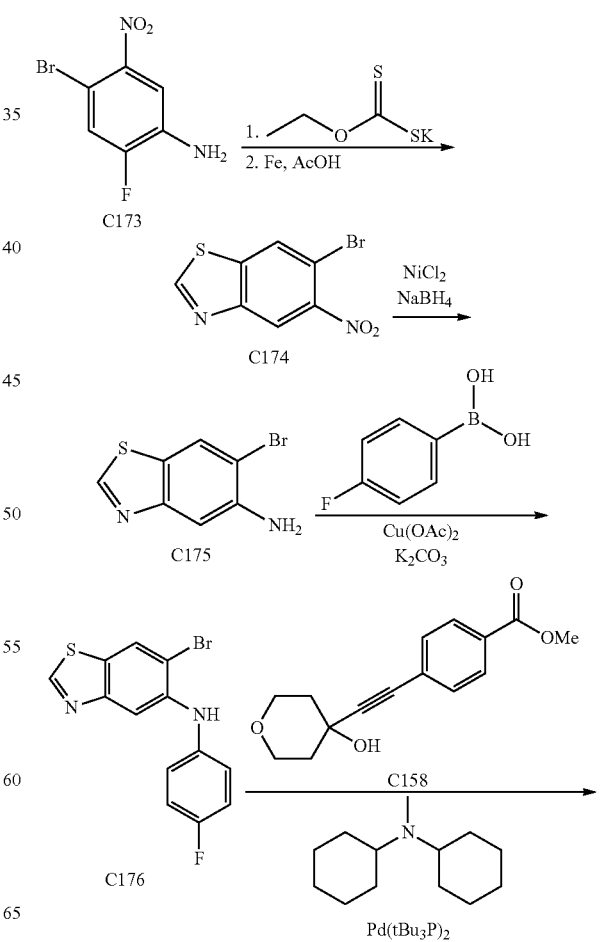

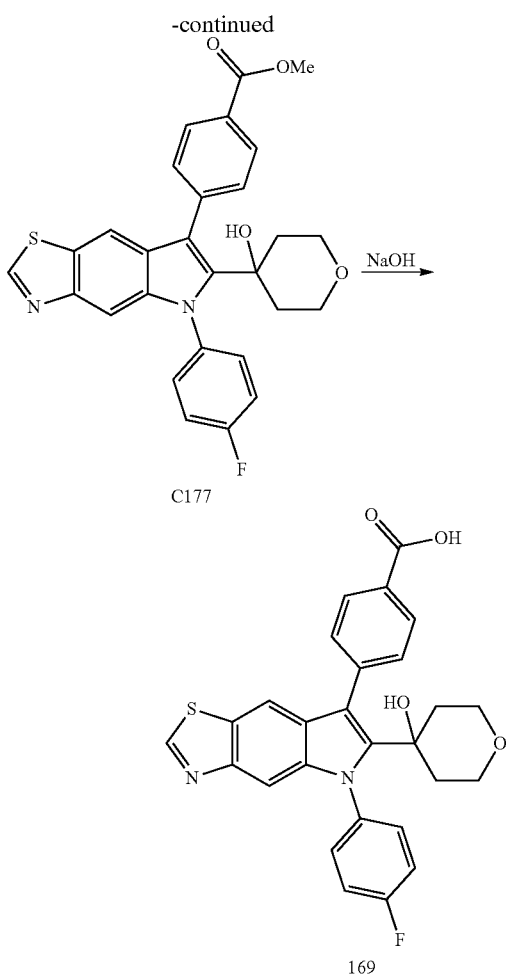

Step 1. Synthesis of 6-bromo-5-nitro-1,3-benzothiazole (C174)

Part A. A mixture of 4-bromo-2-fluoro-5-nitro-aniline C173 (5 g, 21.3 mmol) and potassium ethoxycarbothioylsulfanyl (7 g, 43.7 mmol) in DMF (60 mL) was stirred for 18 h at 110° C. Upon cooling to room temperature, the mixture was diluted with water (200 mL) and concentrated HCl (10 mL). The resulting solid precipitates were collected by vacuum filtration, and washed with water to afford 6-bromo-5-nitro-3H-1,3-benzothiazole-2-thione (6 g, 97%) which was used directly in part B. LCMS m/z 290.0 [M+1]$^+$.

Part B. To a solution of 6-bromo-5-nitro-3H-1,3-benzothiazole-2-thione (6 g, 97%) in AcOH (60 mL), EtOH (15 mL), THF (15 mL) and water (15 mL) was added Fe (6.6 g, 118.2 mmol). The reaction mixture was heated at 110° C. for 4 h. The reaction mixture was cooled to room temperature, diluted with EtOAc, and filtered through a layer of Celite®. The filtrate was dried over Na$_2$SO$_4$, and concentrated to afford the product. 6-bromo-5-nitro-1,3-benzothiazole (3.8 g, 69%). LCMS m/z 260.0 [M+1]$^+$.

Step 2. Synthesis of 6-bromo-1,3-benzothiazol-5-amine (C175)

A solution of 6-bromo-5-nitro-1,3-benzothiazole C174 (3.8 g, 14.7 mmol) in MeOH (30 mL) and THF (10 mL) was cooled to 0° C. NiCl$_2$ (2.5 g, 19.3 mmol) and sodium borohydride (1.6 g, 42.3 mmol) were added to the solution in portions. An additional portion of sodium borohydride (3 g, 79.3 mmol) was added and the mixture stirred for 30 minutes. The reaction was quenched with water, diluted with CH$_2$Cl$_2$, and filtered through a layer of Celite®. The organic layer was dried over Na$_2$SO$_4$, and concentrated. Purification by silica gel chromatography (Gradient: 0-40% EtOAc in heptane) to afford the product. 6-bromo-1,3-benzothiazol-5-amine (850 mg, 25%). LCMS m/z 230.0 [M+1]$^+$.

Step 3. Synthesis of 6-bromo-N-(4-fluorophenyl)-1,3-benzothiazol-5-amine (C176)

A mixture of 6-bromo-1,3-benzothiazol-5-amine (170 mg, 0.74 mmol), (4-fluorophenyl)boronic acid (200 mg, 1.4 mmol), copper (II) acetate (270 mg, 1.49 mmol) and K$_2$CO$_3$ (210 mg, 1.52 mmol) in DMSO (5 mL) was stirred for 2 days. The mixture was diluted with EtOAc, filtered through a layer of Celite®. The organic layer was then washed with water, dried over Na$_2$SO$_4$, and concentrated. Purification by silica gel chromatography (Gradient: 0-30% EtOAc in heptane) afforded the product. 6-bromo-N-(4-fluorophenyl)-1,3-benzothiazol-5-amine (60 mg, 25%). LCMS m/z 323.0 [M+1]$^+$.

Step 4. Synthesis of 4-[5-(4-fluorophenyl)-6-(4-hydroxytetrahydropyran-4-yl)pyrrolo[2,3-f][1,3]benzothiazol-7-yl]benzoic Acid (169)

To a mixture of 6-bromo-N-(4-fluorophenyl)-1,3-benzothiazol-5-amine C176 (50 mg, 0.15 mmol), methyl 4-[2-(4-hydroxytetrahydropyran-4-yl)ethynyl]benzoate (73 mg, 0.28 mmol), and N-cyclohexyl-N-methyl-cyclohexanamine (85 μL, 0.40 mmol) was added 1,4-dioxane (1.0 mL) and the mixture purged with nitrogen for 5 minutes. Pd(tBu$_3$P)$_2$ (8.5 mg, 0.02 mmol) was added and the reaction flushed with nitrogen. The mixture was heated to 110° C. overnight. The mixture was concentrated to dryness under reduced pressure, diluted with CH$_2$Cl$_2$ (10 mL) and washed with water (8 mL) and brine (8 mL). The organic layer was passed through a phase separator and concentrated under reduced pressure. Purification by silica gel chromatography (Gradient: 0-80% ethyl acetate in heptane) afforded the product which was used in the subsequent hydrolysis step. methyl 4-[5-(4-fluorophenyl)-6-(4-hydroxytetrahydropyran-4-yl)pyrrolo[2,3-f][1,3]benzothiazol-7-yl]benzoate (28 mg, 36%). LCMS m/z 503.0 [M+1]$^+$.

To a solution of methyl 4-[5-(4-fluorophenyl)-6-(4-hydroxytetrahydropyran-4-yl)pyrrolo[2,3-f][1,3]benzothiazol-7-yl]benzoate C177 (28 mg, 36%) in THF (1 mL) and MeOH (1 mL) was added NaOH (1 mL of 1 M, 1.0 mmol). The mixture was stirred for 2 h at room temperature. The reaction mixture was adjusted to pH=3, then concentrated. Purification by silica gel chromatography (Gradient: 0-5% MeOH in dichloromethane), and then by reversed phase chromatography (C18 column. Gradient: 10-100% CH$_3$CN in H$_2$O containing 0.2% formic acid) afforded the product. 4-[5-(4-fluorophenyl)-6-(4-hydroxytetrahydropyran-4-yl)pyrrolo[2,3-f][1,3]benzothiazol-7-yl]benzoic acid (7.2 mg, 9%). $^1$H NMR (400 MHz, Methanol-d$_4$) δ 9.07 (s, 1H), 8.24-8.07 (m, 2H), 7.65-7.49 (m, 6H), 7.39-7.28 (m, 3H), 3.66 (td, J=11.8, 2.0 Hz, 2H), 3.57-3.45 (m, 2H), 2.09-1.92 (m, 2H), 1.77-1.62 (m, 2H). LCMS m/z 489.0 [M+1]$^+$.

Compound 170

4-[6-(3,6-dihydro-2H-pyran-4-yl)-5-(4-fluorophenyl)pyrrolo[2,3-f][1,3]benzothiazol-7-yl]benzoic Acid (170)

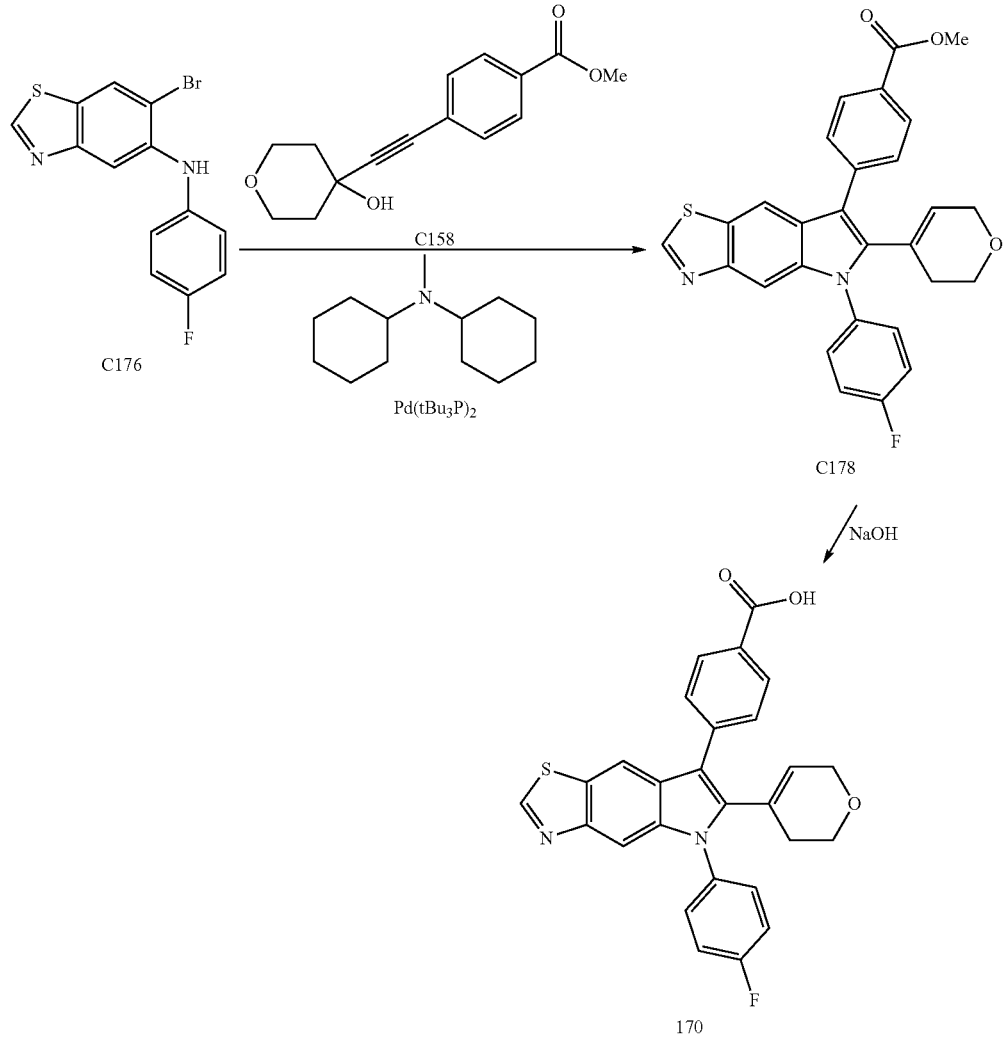

Step 1. Synthesis of methyl 4-[6-(3,6-dihydro-2H-pyran-4-yl)-5-(4-fluorophenyl)pyrrolo[2,3-f][1,3]benzothiazol-7-yl]benzoate (C178)

A mixture of 6-bromo-N-(4-fluorophenyl)-1,3-benzothiazol-5-amine C176 (60 mg, 0.19 mmol), methyl 4-[2-(4-hydroxytetrahydropyran-4-yl)ethynyl]benzoate C158 (75 mg, 0.29 mmol), and N-cyclohexyl-N-methyl-cyclohexanamine (110 µL, 0.51 mmol) in 1,4-dioxane (1.2 mL) was purged with nitrogen for 5 min. Pd(tBu$_3$P)$_2$ (10 mg, 0.02 mmol) was added, and the mixture was flushed with further nitrogen. The reaction vial was sealed and the mixture heated to 110° C. overnight. The reaction was then concentrated to near dryness under reduced pressure. The mixture was diluted with CH$_2$Cl$_2$ (10 mL) and washed with water/brine (8 mL). The organic layer was passed through a phase separator and concentrated under reduced pressure. Silica gel chromatography (Gradient: 0-80% ethyl acetate in heptane) afforded two products C177 methyl 4-[5-(4-fluorophenyl)-6-(4-hydroxytetrahydropyran-4-yl)pyrrolo[2,3-f][1,3]benzothiazol-7-yl]benzoate (57 mg, 61%), LCMS m/z 503.0 [M+1]$^+$ and methyl 4-[6-(3,6-dihydro-2H-pyran-4-yl)-5-(4-fluorophenyl)pyrrolo[2,3-f][1,3]benzothiazol-7-yl]benzoate C178 (20 mg, 22%), LCMS m/z 485.0 [M+1]$^+$. C178 was used in the subsequent step without further purification.

Step 2. Synthesis of 4-[6-(3,6-dihydro-2H-pyran-4-yl)-5-(4-fluorophenyl)pyrrolo[2,3-f][1,3]benzothiazol-7-yl]benzoic Acid (170)

To a solution of methyl 4-[6-(3,6-dihydro-2H-pyran-4-yl)-5-(4-fluorophenyl)pyrrolo[2,3-f][1,3]benzothiazol-7-yl]benzoate C178 (15 mg, 0.031 mmol) in MeOH (2 mL) was added NaOH (300 µL of 1 M, 0.30 mmol). The reaction was stirred for 1 h, then the mixture was adjusted to pH=2. Purification by reversed phase chromatography (C18 column. Gradient: 10-90% CH$_3$CN in H$_2$O contain in 0.2% formic acid) afforded 4-[6-(3,6-dihydro-2H-pyran-4-yl)-5-(4-fluorophenyl)pyrrolo[2,3-f][1,3]benzothiazol-7-yl]benzoic acid 170 (5.1 mg, 33%). $^1$H NMR (400 MHz, DMSO-d$_6$) δ 9.20 (s, 1H), 8.07 (d, J=8.0 Hz, 2H), 7.71 (s, 1H), 7.65-7.52 (m, 7H), 7.19 (s, 1H), 5.17 (s, 1H), 3.49 (t, J=11.4 Hz, 2H), 1.93-1.78 (m, 2H), 1.61 (d, J=13.1 Hz, 2H). LCMS m/z 471.8 [M+1]$^+$.

Compound 171

N-(1,1-dimethyl-2-methylsulfonyl-ethyl)-4-[5-(4-fluorophenyl)-6-tetrahydropyran-4-yl-1H-pyrrolo[2,3-f]indazol-7-yl]benzamide (171)

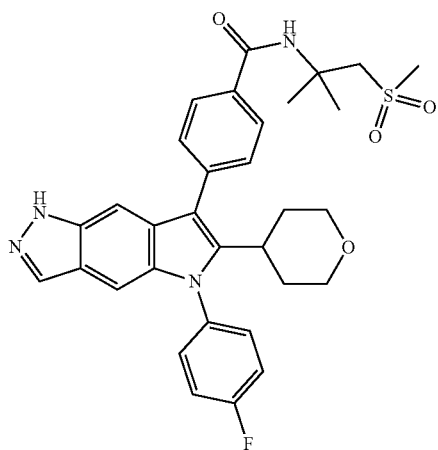 [SMILES: CC(C)(CS(C)(=O)=O)NC(=O)c1ccc(-c2c(C3CCOCC3)n(-c3ccc(F)cc3)c3cc4cn[nH]c4cc23)cc1]

Compound 171 was prepared from compound 33 and 2-methyl-1-(methylsulfonyl)propan-2-amine by an amide coupling reaction with HATU and DIPEA as described for compound 145. $^1$H NMR (400 MHz, DMSO-d$_6$) δ 12.60 (s, 1H), 8.25 (s, 1H), 8.03-7.91 (m, 2H), 7.66-7.56 (m, 4H), 7.51 (t, J=8.7 Hz, 2H), 7.21 (t, J=1.1 Hz, 1H), 7.08 (d, J=1.1 Hz, 1H), 3.87 (s, 2H), 3.77-3.67 (m, 1H), 3.37 (s, 3H), 3.09 (td, J=11.3, 4.4 Hz, 2H), 3.00 (s, 3H), 1.68 (td, J=9.7, 8.4, 3.4 Hz, 4H), 1.61 (s, 6H). LCMS m/z 589.2 [M+H]$^+$.

Compound 172

4-[5-(4-fluorophenyl)-6-tetrahydropyran-4-yl-1H-pyrrolo[2,3-f]indazol-7-yl]-N-(2-methylsulfonyl-ethyl)benzamide (172)

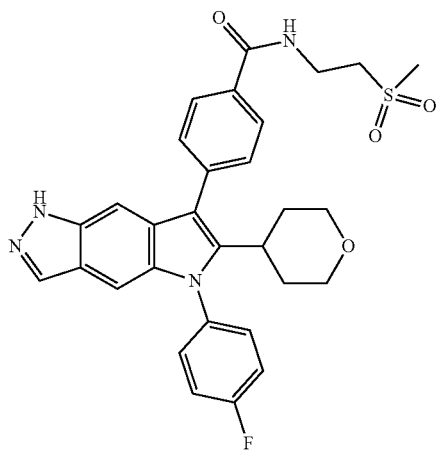 [SMILES: CS(=O)(=O)CCNC(=O)c1ccc(-c2c(C3CCOCC3)n(-c3ccc(F)cc3)c3cc4cn[nH]c4cc23)cc1]

Compound 172 was prepared from compound 33 and 2-(methylsulfonyl)ethan-1-amine by an amide coupling reaction with HATU and DIPEA as described for compound 145.

$^1$H NMR (400 MHz, DMSO-d$_6$) δ 12.59 (s, 1H), 8.84 (t, J=5.6 Hz, 1H), 8.09-7.91 (m, 2H), 7.62 (d, J=8.4 Hz, 4H), 7.51 (t, J=8.7 Hz, 2H), 7.23 (s, 1H), 7.08 (d, J=1.1 Hz, 1H), 3.81-3.67 (m, 6H), 3.44 (d, J=6.8 Hz, 2H), 3.09 (s, 4H), 2.99 (s, 1H), 1.66 (d, J=3.1 Hz, 4H). LCMS m/z 561.1 [M+H]$^+$.

Compound 173

[4-[5-(4-fluorophenyl)-6-tetrahydropyran-4-yl-1H-pyrrolo[2,3-f]indazol-7-yl]phenyl]-(3-methylsulfonylazetidin-1-yl)methanone (173)

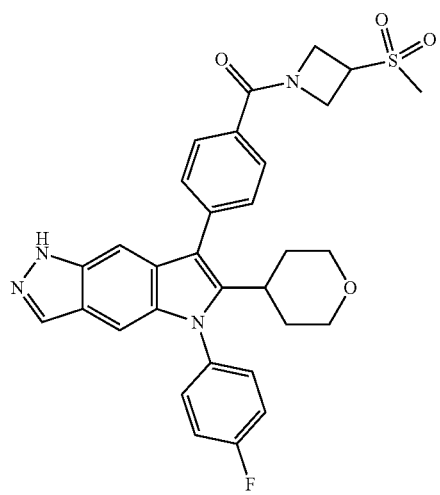 [SMILES: CS(=O)(=O)C1CN(C(=O)c2ccc(-c3c(C4CCOCC4)n(-c4ccc(F)cc4)c4cc5cn[nH]c5cc34)cc2)C1]

Compound 173 was prepared from compound 33 and 3-(methylsulfonyl)azetidine by an amide coupling reaction with HATU and DIPEA as described for compound 145.

$^1$H NMR (400 MHz, DMSO-d$_6$) δ 12.59 (s, 1H), 8.00 (d, J=1.1 Hz, 1H), 7.85 (d, J=8.3 Hz, 2H), 7.63 (d, J=8.2 Hz, 4H), 7.51 (t, J=8.7 Hz, 2H), 7.27 (s, 1H), 7.07 (d, J=1.1 Hz, 1H), 4.79 (s, 1H), 4.59 (d, J=9.5 Hz, 1H), 4.40 (d, J=6.3 Hz, 2H), 4.31 (s, 1H), 3.83-3.70 (m, 2H), 3.11 (s, 5H), 3.02 (s, 1H), 1.77-1.59 (m, 4H). LCMS m/z 573.2 [M+H]$^+$.

Compound 174 & Compound 175

7-[4-[ethoxy(methyl)phosphoryl]phenyl]-5-(4-fluorophenyl)-6-tetrahydropyran-4-yl-1H-pyrrolo[2,3-f]indazole (174) and [4-[5-(4-fluorophenyl)-6-tetrahydropyran-4-yl-1H-pyrrolo[2,3-f]indazol-7-yl]phenyl]-methyl-phosphinic Acid (175)

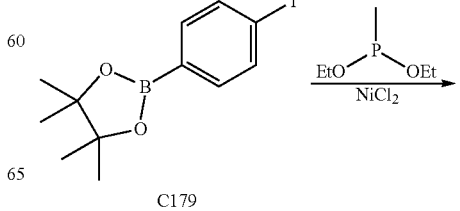

C179

-continued

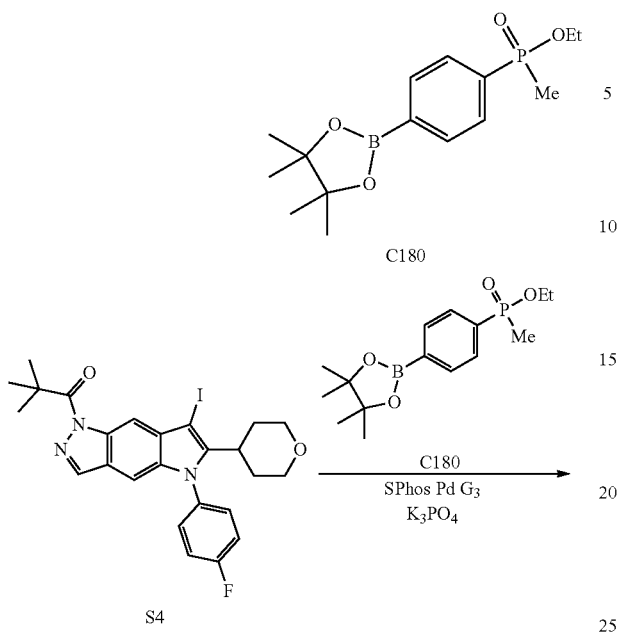

-continued

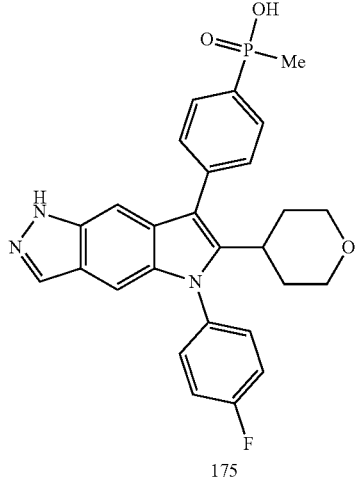

Synthesis of 2-[4-[ethoxy(methyl)phosphoryl]phenyl]-4,4,5,5-tetramethyl-1,3,2-dioxaborolane (C180)

Diethoxy(methyl)phosphane (180 mg, 1.32 mmol) was added to a mixture of 2-(4-iodophenyl)-4,4,5,5-tetramethyl-1,3,2-dioxaborolane (330 mg, 1.0 mmol) and NiCl$_2$ (13 mg, 0.10 mmol). The mixture was purged with nitrogen for 5 min. The reaction mixture was stirred at 170° C. for 2 h. Purification by silica gel chromatography (Gradient: 0-8% MeOH in dichloromethane) afforded the product as a colorless oil 2-[4-[ethoxy(methyl)phosphoryl]phenyl]-4,4,5,5-tetramethyl-1,3,2-dioxaborolane C180 (70 mg, 23%), LCMS m/z 331.0 [M+1]$^+$. The boronic acid product [4-[ethoxy(methyl)phosphoryl]phenyl]boronic acid (70 mg, 31%) was also obtained. C181 was used in the subsequent step without further purification.

Synthesis of 7-[4-[ethoxy(methyl)phosphoryl]phenyl]-5-(4-fluorophenyl)-6-tetrahydropyran-4-yl-1H-pyrrolo[2,3-f]indazole (174)

Part A. 1,4-dioxane (500 µL) and water (100 µL) were added to a vial charged with 1-[5-(4-fluorophenyl)-7-iodo-6-tetrahydropyran-4-yl-pyrrolo[2,3-f]indazol-1-yl]-2,2-dimethyl-propan-1-one S4 (57 mg, 0.10 mmol), 2-[4-[ethoxy(methyl)phosphoryl]phenyl]-4,4,5,5-tetramethyl-1,3,2-dioxaborolane C180 (48 mg, 0.15 mmol), and K$_3$PO$_4$ (70 mg, 0.33 mmol). The solution was purged with N$_2$ for 10 min. SPhos Pd G3 (10 mg, 0.013 mmol) was added and the reaction was heated to 80° C. for 30 min. Water (5 mL) and dichloromethane (5 mL) were added, and the mixture was passed through a phase separator. The organic phase was concentrated and purified by silica gel chromatography (Gradient: 0-5% MeOH in dichloromethane) to afford the product C181 as a white solid. 1-[7-[4-[ethoxy(methyl)phosphoryl]phenyl]-5-(4-fluorophenyl)-6-tetrahydropyran-4-yl-pyrrolo[2,3-f]indazol-1-yl]-2,2-dimethyl-propan-1-one (55 mg, 88%). LCMS m/z 602.0 [M+1]+.

Part B. To a solution of 1-[7-[4-[ethoxy(methyl)phosphoryl]phenyl]-5-(4-fluorophenyl)-6-tetrahydropyran-4-yl-pyrrolo[2,3-f]indazol-1-yl]-2,2-dimethyl-propan-1-one C181 (55 mg) in MeOH (1.5 mL) and THF (1.5 mL) was added NaOH (750 µL of 1 M, 0.75 mmol) and the mixture stirred for 1 h. The reaction was then concentrated and adjusted to pH=2. The mixture contained both compound 174 and compound 175. The solution was extracted with dichloromethane and separated on a phase separator. The organic phase was purified by silica gel chromatography (Gradient: 0-10% MeOH in dichloromethane) to afford the product 7-[4-[ethoxy(methyl)phosphoryl]phenyl]-5-(4-fluorophenyl)-6-tetrahydropyran-4-yl-1H-pyrrolo[2,3-f]indazole 174 (4.2 mg, 8%), LMS m/z 518.14 [M+1]+. $^1$H NMR (400 MHz, Chloroform-d) δ 10.04 (s, 1H), 8.06 (d, J=1.1 Hz, 1H), 8.01-7.90 (m, 2H), 7.72-7.63 (m, 2H), 7.52-7.44 (m, 2H), 7.40 (t, J=1.1 Hz, 1H), 7.37-7.30 (m, 2H), 7.15 (d, J=1.1 Hz, 1H), 4.22 (m, 1H), 4.11-3.96 (m, 1H), 3.88 (dd, J=11.6, 4.1 Hz, 2H), 3.25 (t, J=11.7 Hz, 2H), 3.05 (ddd, J=12.4, 8.9, 3.4 Hz, 1H), 1.99-1.71 (m, 5H), 1.66 (d, J=11.9 Hz, 2H), 1.41 (t, J=7.1 Hz, 3H). An unseparated mixture of compound 174 and 175 was also obtained, and used in the subsequent step without further purification.

Synthesis of [4-[5-(4-fluorophenyl)-6-tetrahydropyran-4-yl-1H-pyrrolo[2,3-f]indazol-7-yl]phenyl]-methyl-phosphinic Acid (175)

To a mixture of compound 174 and 175 in dichloromethane (2 mL) was added trimethylsilyl bromide (100 μL, 0.76 mmol). The reaction was allowed to stir at room temperature for 1 h. The mixture was concentrated and purified by reversed phase chromatography (C18 column. Gradient: 10-90% MeCN in water containing 0.2% formic acid) to afford the product 175. $^1$H NMR (400 MHz, Chloroform-d) δ 8.15-7.89 (m, 4H), 7.58 (d, J=7.5 Hz, 2H), 7.41 (d, J=10.4 Hz, 3H), 7.29 (m, 2H), 7.11 (d, J=1.1 Hz, 1H), 3.83 (d, J=10.9 Hz, 2H), 3.21 (t, J=11.6 Hz, 2H), 3.09-2.90 (m, 2H), 1.82 (d, J=14.5 Hz, 4H), 1.59 (d, J=12.9 Hz, 2H). LCMS m/z 490.0 [M+1]+.

Compound 176

4-(5-(4-fluorophenyl)-6-(4-hydroxytetrahydro-2H-pyran-4-yl)-1,5-dihydropyrrolo[2,3-f]indazol-7-yl) benzoic Acid (176)

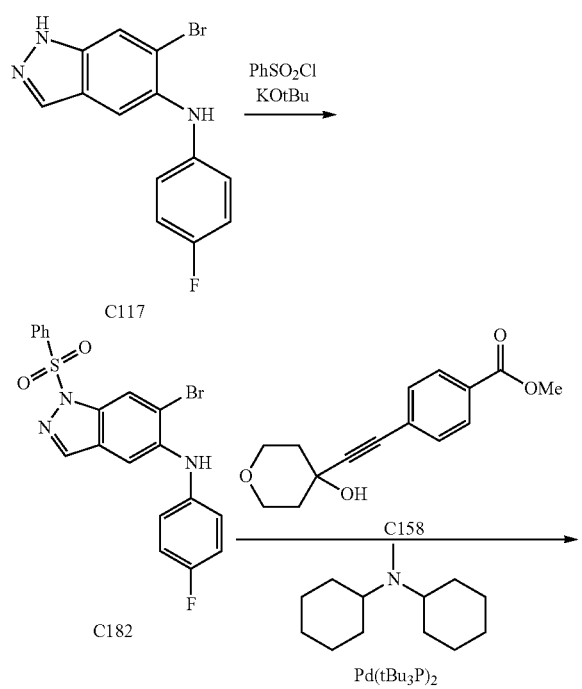

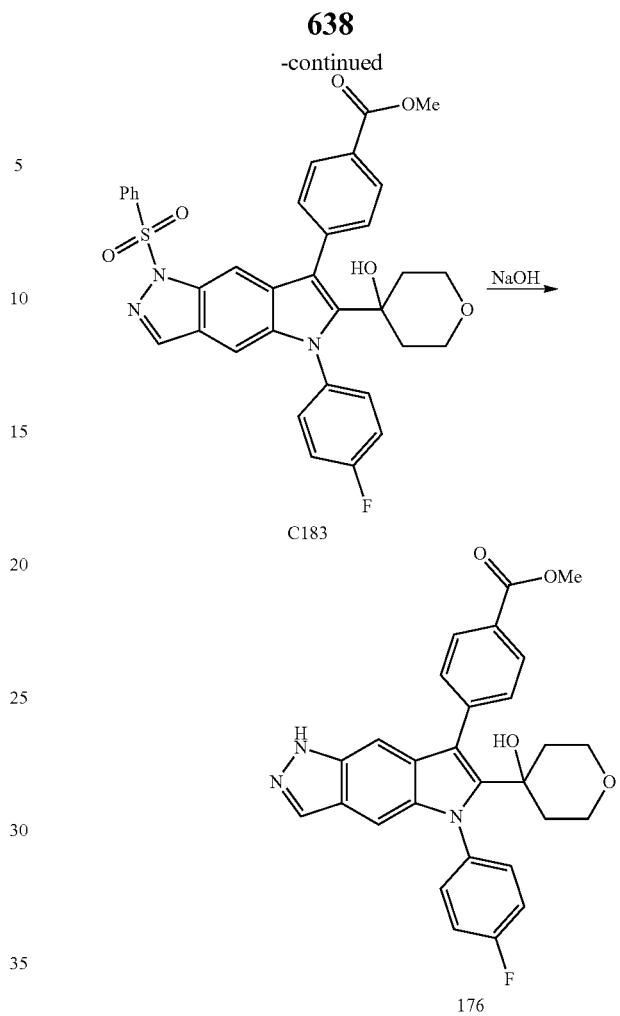

Step 1. Synthesis of 1-(benzenesulfonyl)-6-bromo-N-(4-fluorophenyl)indazol-5-amine (C182)

To a suspension of 6-bromo-N-(4-fluorophenyl)-1H-indazol-5-amine C117 (2 g, 6.5 mmol) in THF (55 mL) at 1° C. (ice-water bath) was added KOtBu (7.2 mL of 1 M, 7.2 mmol). After ~10 min, benzenesulfonyl chloride (1.11 mL, 8.7 mmol) was added and the mixture stirred for 60 min in cooling bath. The reaction was quenched with water (10 mL), stirred for 5 min. The mixture was then extracted with ethyl acetate (100 mL) and the organic layer dried over with sodium sulfate. Purification by silica gel chromatography (0-100% ethyl acetate in heptane) afforded the product C182 1-(benzenesulfonyl)-6-bromo-N-(4-fluorophenyl)indazol-5-amine (2.36 g, 81%). LCMS m/z 446.1 [M+1]+. $^1$H NMR showed the product contained a mixture of the two indazole regiosiomers with the phenyl sulfonyl group on N1 and N$_2$.

Step 2. Synthesis of methyl 4-[1-(benzenesulfonyl)-5-(4-fluorophenyl)-6-(4-hydroxytetrahydropyran-4-yl)pyrrolo[2,3-f]indazol-7-yl]benzoate (C183)

1,4-Dioxane (8.2 mL) was added to a mixture of 1-(benzenesulfonyl)-6-bromo-N-(4-fluorophenyl)indazol-5-amine (394.6 mg, 0.88 mmol) C182, methyl 4-[2-(4-hydroxytetrahydropyran-4-yl)ethynyl]benzoate C183 (420 mg, 1.6 mmol), and N-cyclohexyl-N-methyl-cyclohexanamine (478 μL, 2.2 mmol). The mixture was evacuated and flushed with nitrogen. Pd(PtBu$_3$)$_2$ (49 mg, 0.096 mmol) was added and the reaction evacuated and flushed with nitrogen an additional time. The reaction vial was sealed and heated to 80° C. overnight. The mixture was concentrated to dryness, diluted with dichloromethane (10 mL) and washed with water/brine (8 mL). The organic phase was passed through a phase separator and concentrated to dryness under reduced pressure. Purification by silica gel chromatography (Gradient: 0-100% ethyl acetate in heptane) afforded the product C183 (531.8 mg, 94%). $^1$H NMR (300 MHz, DMSO-d$_6$) δ 8.47 (d, J=0.8 Hz, 1H), 8.18 (d, J=8.3 Hz, 2H), 7.72-7.61 (m, 6H), 7.59-7.49 (m, 4H), 7.40 (t, J=8.7 Hz, 2H), 7.06 (d, J=1.0 Hz, 1H), 5.22 (s, 1H), 3.94 (s, 3H), 3.51-3.39 (m, 4H), 1.90-1.78 (m, 2H), 1.58 (d, J=12.9 Hz, 2H). LCMS m/z 626.2 [M+1]$^+$.

Step 3. Synthesis of 4-(5-(4-fluorophenyl)-6-(4-hydroxytetrahydro-2H-pyran-4-yl)-1,5-dihydropyrrolo[2,3-f]indazol-7-yl)benzoic Acid (176)

To a solution of methyl 4-[1-(benzenesulfonyl)-5-(4-fluorophenyl)-6-(4-hydroxytetrahydropyran-4-yl)pyrrolo[2,3-f]indazol-7-yl]benzoate (44 mg, 0.07 mmol) in methanol (1 mL) and THF (1 mL) was added NaOH (700 μL of 1 M, 0.7 mmol) and the mixture was stirred for 2 hours at 65° C. The mixture was Concentrated to dryness under reduced pressure. EtOAc was added and the mixture washed with 1M HCl. The organic layers were dried over MgSO$_4$, filtered and concentrated under reduced pressure. Purification by silica gel chromatography (Gradient: 0-10% MeOH in dichloromethane) afforded the product (14.4 mg, 44%).

$^1$H NMR (300 MHz, DMSO-d$_6$) δ 13.03 (s, 1H), 12.51 (s, 1H), 8.13-8.03 (m, 2H), 7.98 (d, J=1.0 Hz, 1H), 7.64-7.52 (m, 4H), 7.40 (t, J=8.8 Hz, 2H), 6.97-6.88 (m, 2H), 5.13 (s, 1H), 3.54-3.37 (m, 4H), 1.85 (td, J=12.7, 12.2, 5.2 Hz, 2H), 1.59 (d, J=13.0 Hz, 2H). LCMS m/z 472.2 [M+1]$^+$.

Compound 177

4-(6-(1-cyano-2-methylpropan-2-yl)-5-(2-methylpyridin-4-yl)-1,5-dihydropyrrolo[2,3-f]indazol-7-yl)benzoic Acid (177)

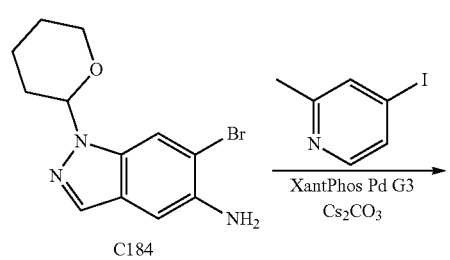

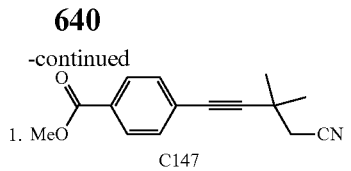

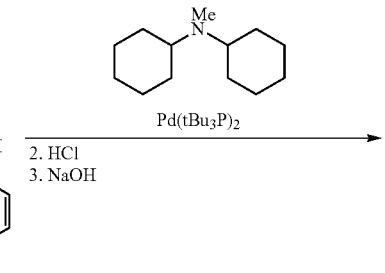

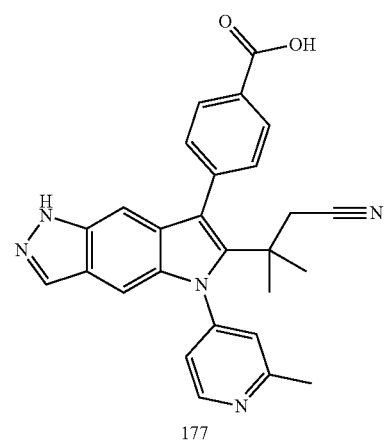

Compound 177 was prepared in two steps from C184 by N-arylation with 2-methyl 4-iodopyridine, then Larock cyclization with C147 as described for the preparation of compound 125. $^1$H NMR (400 MHz, Methanol-d$_4$) δ 8.74 (d, J=5.3 Hz, 1H), 8.23-8.14 (m, 2H), 7.98 (s, 1H), 7.69-7.62 (m, 2H), 7.58 (d, J=1.9 Hz, 1H), 7.52-7.46 (m, 1H), 7.07-7.00 (m, 2H), 2.71 (s, 3H), 2.59 (s, 2H), 1.36 (s, 6H). LCMS m/z 450.28 [M+H]$^+$.

Compounds 178-182

Compounds 178-182 (Table 13) were prepared from alkyne C147 and the appropriate aryl aniline in two steps using the method described for the preparation of compound 125. Aryl anilines were prepared from C184 or C89 and the appropriate aryl halide by N-arylation using Buchwald conditions. Alternatively, aryl anilines were prepared from C95 as described for the preparation of compound C96.

TABLE 13

*Method of preparation, structure, physicochemical data for compounds 178-183*

| Compound | Structure | Aryl Iodide or Aniline | ¹H NMR; LCMS m/z [M + H]⁺ |
|---|---|---|---|
| 178[1] | 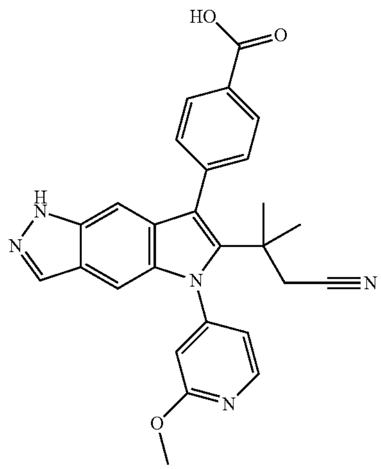 [SMILES: COc1cc(-n2c(C(C)(C)CC#N)c(-c3ccc(C(=O)O)cc3)c3cc4[nH]ncc4cc32)ccn1] | | ¹H NMR (400 MHz, Methanol-d₄) δ 8.43 (dd, J = 5.4, 0.6 Hz, 1H), 8.23 – 8.13 (m, 2H), 7.98 (d, J = 1.2 Hz, 1H), 7.65 (d, J = 7.6 Hz, 2H), 7.16 (dd, J = 5.4, 1.8 Hz, 1H), 7.07 (d, J = 1.1 Hz, 1H), 7.05 (dd, J = 1.8, 0.6 Hz, 1H), 7.00 (t, J = 1.1 Hz, 1H), 4.05 (s, 3H), 2.61 (s, 2H), 1.37 (mz, 6H). LCMS m/z 466.22 [M + H]⁺. |
| 179[2] | 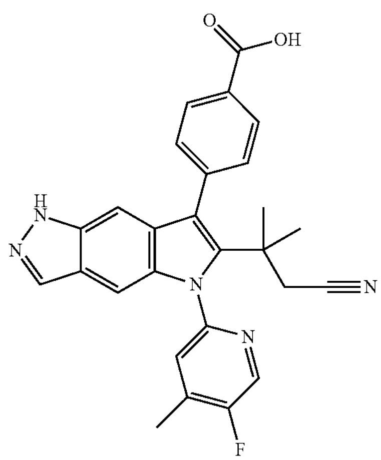 [SMILES: Cc1cc(-n2c(C(C)(C)CC#N)c(-c3ccc(C(=O)O)cc3)c3cc4[nH]ncc4cc32)ncc1F] | | ¹H NMR (300 MHz, DMSO-d₆) δ 13.25-12.84 (bs, 1H), 12.59 (s, 1H), 8.64 (d, J = 1.1 Hz, 1H), 8.11 (d, J = 8.4 Hz, 2H), 8.01 (d, J = 1.0 Hz, 1H), 7.84 (d, J = 5.6 Hz, 1H), 7.70 – 7.58 (m, 2H), 7.18 (d, J = 1.1 Hz, 1H), 6.94 – 6.85 (m, 1H), 2.88 (s, 2H), 2.47 (d, J = 1.6 Hz, 3H), 1.18 (s, 6H). LCMS m/z 468.21 [M + H]⁺. |
| 180[1] | 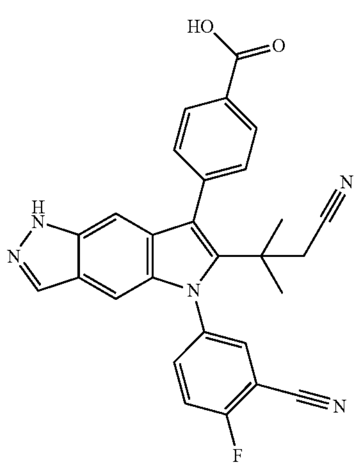 [SMILES: CC(C)(CC#N)c1c(-c2ccc(C(=O)O)cc2)c2cc3[nH]ncc3cc2n1-c1ccc(F)c(C#N)c1] | | ¹H NMR (400 MHz, Methanol-d₄) δ 8.15 (d, J = 8.5 Hz, 2H), 8.10 (dd, J = 5.6, 2.7 Hz, 1H), 7.97 (d, J = 1.0 Hz, 1H), 7.96 – 7.89 (m, 1H), 7.67 (t, J = 8.8 Hz, 1H), 7.64 – 7.57 (m, 2H), 7.00 (t, J = 1.1 Hz, 1H), 6.97 (d, J = 1.2 Hz, 1H), 2.59 (s, 2H), 1.33 (s, 6H). LCMS m/z 478.32 [M + H]⁺. |

TABLE 13-continued

Method of preparation, structure, physicochemical data for compounds 178-183

| Compound | Structure | Aryl Iodide or Aniline | $^1$H NMR; LCMS m/z [M + H]$^+$ |
|---|---|---|---|
| 181[1] | 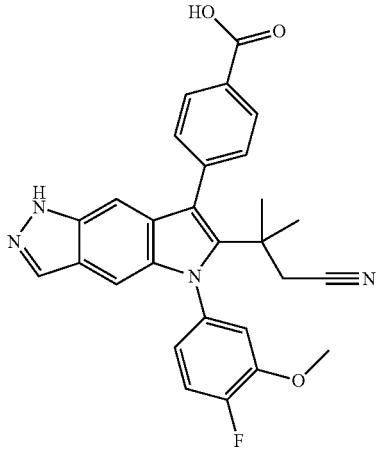 [SMILES: COc1cc(-n2c(C(C)(C)CC#N)c(-c3ccc(C(=O)O)cc3)c3cc4[nH]ncc4cc32)ccc1F] | 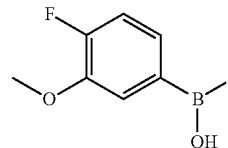 | $^1$H NMR (400 MHz, Methanol-d$_4$) δ 8.22 – 8.13 (m, 2H), 8.01 (d, J = 1.1 Hz, 1H), 7.67 – 7.58 (m, 2H), 7.39 (dd, J = 11.1, 8.5 Hz, 1H), 7.29 (dd, J = 7.6, 2.4 Hz, 1H), 7.16 (ddd, J = 8.5, 3.9, 2.4 Hz, 1H), 7.01 (d, J = 1.1 Hz, 1H), 6.98 (t, J = 1.1 Hz, 1H), 3.90 (s, 3H), 2.69 – 2.49 (m, 2H), 1.36 (d, J = 6.9 Hz, 6H). LCMS m/z 483.37 [M + H]$^+$. |
| 182[3] | 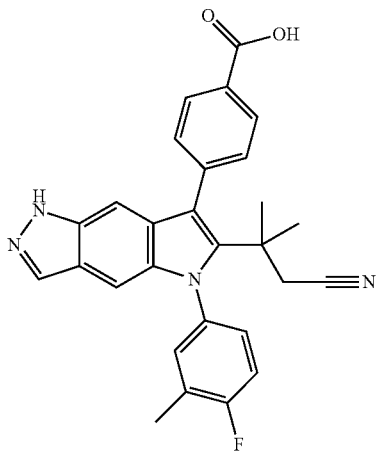 [SMILES: Cc1cc(-n2c(C(C)(C)CC#N)c(-c3ccc(C(=O)O)cc3)c3cc4[nH]ncc4cc32)ccc1F] | 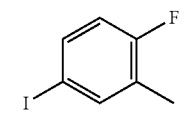 | $^1$H NMR (300 MHz, DMSO-d$_6$) δ 13.06 (s, 1H), 12.52 (s, 1H), 8.15 – 8.05 (m, 2H), 7.99 (d, J = 1.0 Hz, 1H), 7.67 – 7.58 (m, 2H), 7.54 (d, J = 7.2 Hz, 1H), 7.48 – 7.40 (m, 2H), 6.95 – 6.81 (m, 2H), 2.63 (s, 2H), 2.36 (d, J = 1.9 Hz, 3H), 1.26 (d, J = 2.0 Hz, 6H). LCMS m/z 467.36 [M + H]$^+$. |

[1]Prepared from C184.
[2]Prepared from C95.
[3]Prepared from C89.

Compound 183

3-(7-(6-(dimethylphosphoryl)-5-methylpyridin-3-yl)-5-(4-fluoro-3-methoxyphenyl)-1,5-dihydropyrrolo[2,3-f]indazol-6-yl)-3-methylbutanenitrile (183)

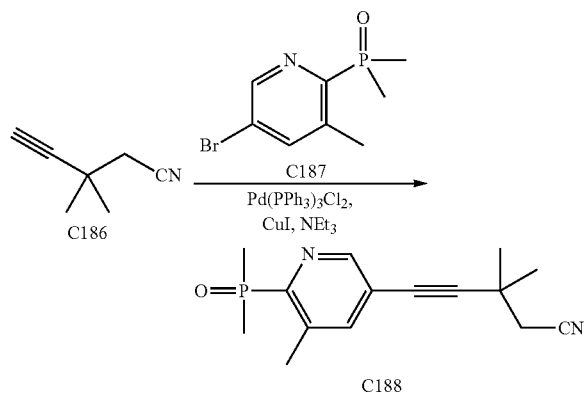

Compound 183 was prepared from C189 and C188 using the method described for the preparation of compound 125. LCMS m/z 530.16 [M+H]⁺.

Compound 184

4-[6-(2-methoxy-1,1-dimethyl-ethyl)-5-phenyl-1H-pyrrolo[2,3-f]indazol-7-yl]benzoic Acid (184)

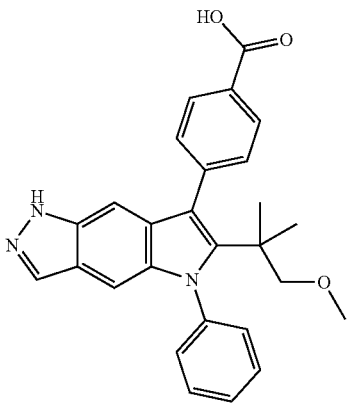 [SMILES: COCC(C)(C)c1c(-c2ccc(C(=O)O)cc2)c2cc3[nH]ncc3cc2n1-c1ccccc1]

Compound 184 was prepared by reduction of compound 112 using the method described for the preparation of compound 102. ¹H NMR (300 MHz, DMSO-d₆) δ 12.99 (s, 1H), 12.46 (s, 1H), 8.12-8.01 (m, 2H), 7.95 (d, J=1.0 Hz, 1H), 7.70-7.49 (m, 7H), 6.88-6.82 (m, 1H), 6.79 (d, J=1.1 Hz, 1H), 3.05 (s, 2H), 3.00 (s, 3H), 1.11 (s, 6H). LCMS m/z 440.25 [M+H]⁺.

Compound 185

4-(5-phenyl-6-tetrahydropyran-4-yl-1H-pyrrolo[2,3-f]indazol-7-yl)benzoic Acid (185)

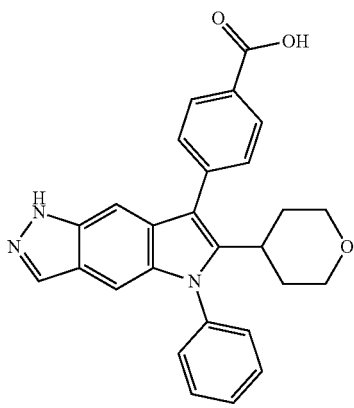 [SMILES: O=C(O)c1ccc(-c2c(C3CCOCC3)n(-c3ccccc3)c3cc4cn[nH]c4cc23)cc1]

Compound 185 was prepared from compound 33 using the reduction method described for the preparation of compound 102. ¹H NMR (300 MHz, DMSO-d₆) δ 12.99 (s, 1H), 12.58 (s, 1H), 8.16-8.08 (m, 2H), 8.00 (d, J=1.0 Hz, 1H), 7.75-7.60 (m, 5H), 7.60-7.52 (m, 2H), 7.29-7.24 (m, 1H), 7.06 (d, J=1.1 Hz, 1H), 3.77-3.67 (m, 2H), 3.14-2.96 (m, 3H), 1.77-1.59 (m, 4H). LCMS m/z 438.27 [M+H]⁺.

Compounds 186-202

Compounds 186-202 (Table 14) were prepared from C118 or C117 and the appropriate alkyne, as described for the preparation of compound 125 (Larock cyclization method). Alkynes were prepared from C186 and the appropriate aryl halide as described for the preparation of compound C188. In some examples, compounds were prepared by Suzuki coupling from 3-[1-(2,2-dimethylpropanoyl)-5-(4-fluorophenyl)-7-iodo-pyrrolo[2,3-f]indazol-6-yl]-3-methyl-butanenitrile (see examples 189 and 192 and 195).

TABLE 14

Method of preparation, structure and physicochemical data for compounds 186-202

| Compound | Method/Product | ¹H NMR; LCMS m/z [M + H]⁺ |
|---|---|---|
| 186 | As for compound 125 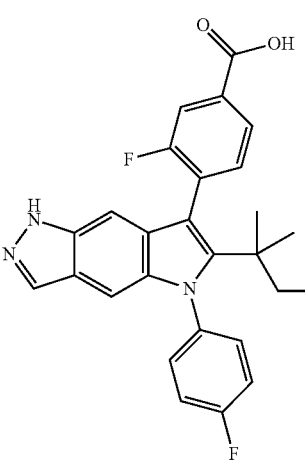 | NMR (400 MHz, DMSO-$d_6$) δ 13.40 (s, 1H), 12.57 (s, 1H), 8.01 (d, J = 1.0 Hz, 1H), 7.95 (dd, J = 7.9, 1.6 Hz, 1H), 7.87 (dd, J = 9.8, 1.6 Hz, 1H), 7.74 – 7.65 (m, 2H), 7.65 – 7.58 (m, 1H), 7.54 (tt, J = 8.9, 3.1 Hz, 2H), 6.89 (d, J = 1.1 Hz, 1H), 6.88 – 6.86 (m, 1H), 2.64 (d, J = 2.7 Hz, 2H), 1.26 (d, J = 3.4 Hz, 6H). LCMS m/z 471.275 [M + H]⁺. |
| 187 | As for compound 125 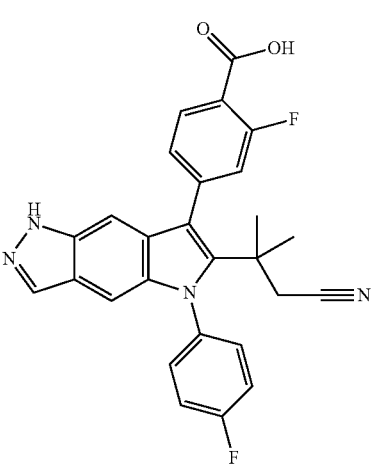 | ¹H NMR (400 MHz, DMSO-$d_6$) δ 13.37 (s, 1H), 12.57 (s, 1H), 8.06 – 7.97 (m, 2H), 7.68 – 7.58 (m, 2H), 7.58 – 7.48 (m, 2H), 7.48 – 7.36 (m, 2H), 6.93 (t, J = 1.1 Hz, 1H), 6.89 (d, J = 1.1 Hz, 1H), 2.66 (s, 2H), 1.26 (s, 6H). LCMS m/z 471.23 [M + H]⁺. |
| 188 | As for compound 125 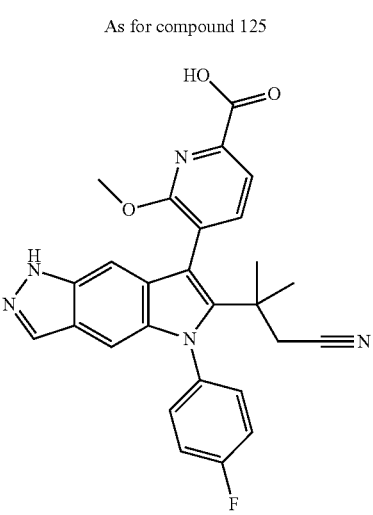 [SMILES: COc1nc(C(=O)O)ccc1-c1c(C(C)(C)CC#N)n(-c2ccc(F)cc2)c2cc3cn[nH]c3cc12] | ¹H NMR (300 MHz, DMSO-$d_6$) δ 13.18 (s, 1H), 12.54 (s, 1H), 7.99 (d, J = 1.0 Hz, 1H), 7.96 – 7.83 (m, 2H), 7.74 – 7.65 (m, 1H), 7.63 – 7.47 (m, 3H), 6.86 (d, J = 1.1 Hz, 1H), 6.83 (t, J = 1.1 Hz, 1H), 3.90 (s, 3H), 2.62 (s, 2H), 1.24 (d, J = 6.8 Hz, 6H). LCMS m/z 484.28 [M + H]⁺. |

TABLE 14-continued

Method of preparation, structure and physicochemical data for compounds 186-202

| Compound | Method/Product | ¹H NMR; LCMS m/z [M + H]⁺ |
|---|---|---|
| 189[1] | Suzuki coupling as for compound 6 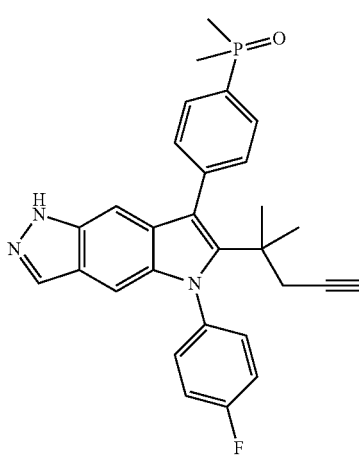 | ¹H NMR (400 MHz, Methanol-d₄) δ 8.01 – 7.91 (m, 3H), 7.77 – 7.71 (m, 2H), 7.59 (m, 2H), 7.42 (m, 2H), 6.96 (t, J = 1.1 Hz, 1H), 6.92 (d, J = 1.2 Hz, 1H), 2.58 (s, 2H), 1.90 (d, J = 13.4 Hz, 6H), 1.32 (s, 6H); ¹H NMR (400 MHz, Methanol-d₄) δ 8.02 – 7.90 (m, 3H), 7.74 (dd, J = 8.2, 2.6 Hz, 2H), 7.65 – 7.55 (m, 2H), 7.42 (m, 2H), 6.96 (t, J = 1.2 Hz, 1H), 6.92 (d, J = 1.2 Hz, 1H), 2.58 (s, 2H), 1.91 (s, 3H), 1.88 (s, 3H), 1.32 (s, 6H). LCMS m/z 485.335 [M + H]⁺. |
| 190 | As for compound 125 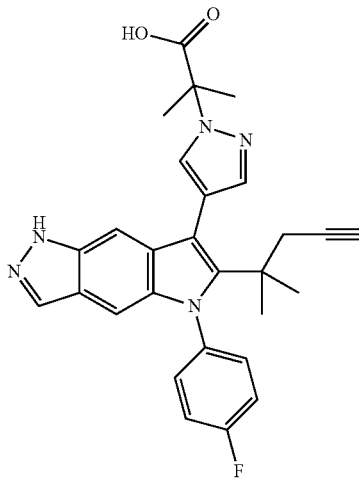 | ¹H NMR (400 MHz, Methanol-d₄) δ 7.99 (d, J = 0.7 Hz, 1H), 7.94 (d, J = 1.1 Hz, 1H), 7.66 (d, J = 0.7 Hz, 1H), 7.57 – 7.48 (m, 2H), 7.43 – 7.34 (m, 2H), 7.18 (t, J = 1.1 Hz, 1H), 6.91 (d, J = 1.1 Hz, 1H), 2.68 (s, 2H), 1.95 (s, 6H), 1.35 (s, 6H). LCMS m/z 485.4 [M + H]⁺. |
| 191 | As for compound 125 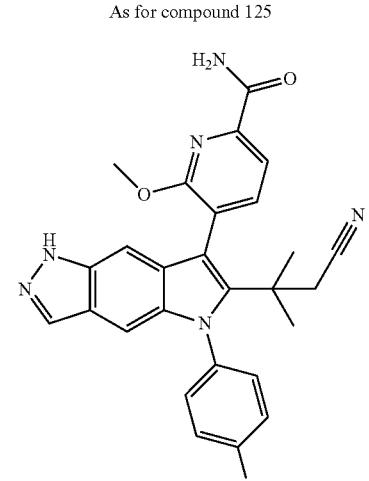 | ¹H NMR (400 MHz, DMSO-d₆) δ 12.54 (s, 1H), 8.14 (s, 1H), 7.99 (s, 1H), 7.93 (d, J = 7.4 Hz, 1H), 7.81 (d, J = 7.4 Hz, 1H), 7.76 (s, 1H), 7.69 (t, J = 6.5 Hz, 1H), 7.62 – 7.48 (m, 3H), 6.86 (s, 1H), 6.83 (s, 1H), 3.95 (s, 3H), 2.62 (s, 2H), 1.24 (d, J = 8.6 Hz, 6H). LCMS m/z 483.37 [M + H]⁺. |

TABLE 14-continued

Method of preparation, structure and physicochemical data for compounds 186-202

| Compound | Method/Product | $^1$H NMR; LCMS m/z [M + H]$^+$ |
|---|---|---|
| 192[1] | Suzuki coupling as for compound 6 | $^1$H NMR (400 MHz, Methanol-d$_4$) δ 8.98 – 8.87 (m, 1H), 8.23 – 8.11 (m, 2H), 7.97 (d, J = 1.0 Hz, 1H), 7.61 (m, 2H), 7.44 (m, 2H), 6.96 (t, J = 1.1 Hz, 1H), 6.95 (d, J = 1.2 Hz, 1H), 2.61 (s, 2H), 1.92 (dd, J = 13.7, 6.0 Hz, 6H), 1.31 (s, 6H). LCMS m/z 486.25 [M + H]$^+$. |
| 193 | Suzuki coupling as for compound 6 | $^1$H NMR (400 MHz, Methanol-d$_4$) δ 7.93 (d, J = 1.1 Hz, 1H), 7.81 (d, J = 0.7 Hz, 1H), 7.62 (d, J = 0.7 Hz, 1H), 7.57 – 7.48 (m, 2H), 7.46 – 7.33 (m, 2H), 7.26 (t, J = 1.1 Hz, 1H), 6.90 (d, J = 1.2 Hz, 1H), 4.96 (s, 2H), 2.72 (s, 2H), 1.37 (s, 6H). LCMS m/z 457.36 [M + H]$^+$. |
| 194 | Compound 125[2] | $^1$H NMR (400 MHz, Methanol-d$_4$) δ 7.97 (d, J = 1.0 Hz, 1H), 7.87 (d, J = 3.7 Hz, 1H), 7.64 – 7.51 (m, 2H), 7.49 – 7.35 (m, 2H), 7.25 (d, J = 3.7 Hz, 1H), 7.19 (t, J = 1.1 Hz, 1H), 6.94 (d, J = 1.1 Hz, 1H), 2.67 (s, 2H), 1.41 (s, 6H). LCMS m/z 459.31 [M + H]$^+$. |

TABLE 14-continued

Method of preparation, structure and physicochemical data for compounds 186-202

| Compound | Method/Product | ¹H NMR; LCMS m/z [M + H]⁺ |
|---|---|---|
| 195[1] | Suzuki coupling as for compound 6 | ¹H NMR (400 MHz, Methanol-$d_4$) δ 7.94 (d, J = 1.1 Hz, 1H), 7.84 (s, 1H), 7.63 (ddd, J = 11.3, 4.9, 2.6 Hz, 1H), 7.47 (ddd, J = 7.6, 4.9, 2.6 Hz, 1H), 7.44 – 7.34 (m, 2H), 7.09 (t, J = 1.1 Hz, 1H), 6.91 (d, J = 1.2 Hz, 1H), 2.76 (d, J = 17.0 Hz, 1H), 2.62 (d, J = 16.9 Hz, 1H), 2.15 (s, 3H), 1.91 (d, J = 8.6 Hz, 6H), 1.38 (s, 3H), 1.33 (s, 3H). LCMS m/z 499.4 [M + H]⁺. |
| 196 | As for compound 125 | ¹H NMR (400 MHz, Methanol-$d_4$) δ 8.76 (s, 1H), 8.07 (d, J = 5.8 Hz, 1H), 8.01 (d, J = 1.0 Hz, 1H), 7.74 – 7.66 (m, 1H), 7.60 (m, 1H), 7.44 (m, 2H), 6.96 (d, J = 1.1 Hz, 1H), 6.85 (d, J = 1.1 Hz, 1H), 2.59 (m, 2H), 2.37 (s, 3H), 1.90 (dd, J = 13.7, 6.3 Hz, 6H), 1.29 (s, 6H). LCMS m/z 500.35 [M + H]⁺. |
| 197 | As for compound 125 | ¹H NMR (400 MHz, Methanol-$d_4$) δ 8.74 – 8.64 (m, 1H), 7.99 (d, J = 1.1 Hz, 1H), 7.93 – 7.87 (m, 1H), 7.67 – 7.54 (m, 2H), 7.52 – 7.35 (m, 2H), 6.97 (t, J = 1.1 Hz, 1H), 6.95 (d, J = 1.1 Hz, 1H), 2.88 – 2.76 (m, 3H), 2.60 (s, 2H), 1.96 (dd, J = 13.5, 6.0 Hz, 6H), 1.31 (s, 6H). LCMS m/z 500.34 [M + H]⁺. |

TABLE 14-continued

Method of preparation, structure and physicochemical data for compounds 186-202

| Compound | Method/Product | ¹H NMR; LCMS m/z [M + H]⁺ |
|---|---|---|
| 198 | As for compound 125 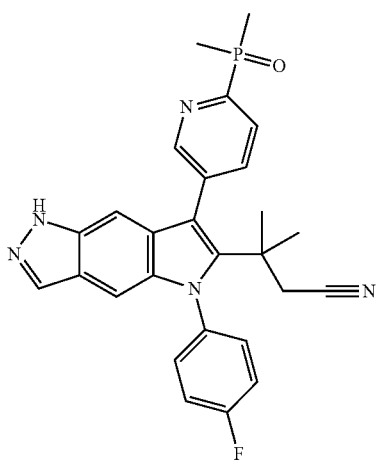 | ¹H NMR (400 MHz, Methanol-$d_4$) δ 9.12 (d, J = 5.9 Hz, 1H), 8.53 – 8.40 (m, 1H), 8.00 (m, 2H), 7.68 – 7.56 (m, 2H), 7.47 – 7.41 (m, 2H), 7.15 (s, 1H), 7.00 (d, J = 1.2 Hz, 1H), 2.77 (s, 2H), 1.98 (d, J = 13.6 Hz, 6H), 1.33 (s, 6H). LCMS m/z 486.39 [M + H]⁺. |
| 199 | As for compound 125 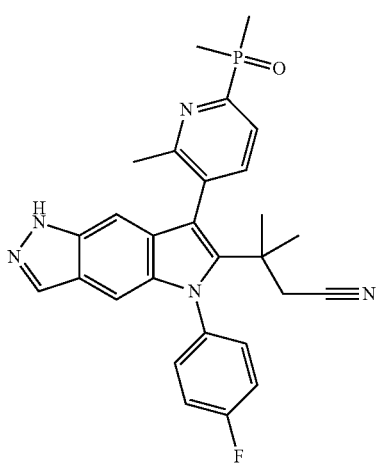 | ¹H NMR (400 MHz, Methanol-$d_4$) δ 8.01 (m, 2H), 7.86 – 7.78 (m, 0.5H), 7.70 (m, 1H), 7.59 (m, 1H), 7.52 – 7.36 (m, 2.5H), 6.98 (d, J = 1.2 Hz, 1H), 6.87 (s, 1H), 2.59 (d, J = 4.6 Hz, 2H), 2.51 (s, 3H), 1.91 (dd, J = 13.7, 9.9 Hz, 6H), 1.29 (d, J = 1.8 Hz, 6H). LCMS m/z 500.35 [M + H]⁺. |
| 200 | As for compound 125 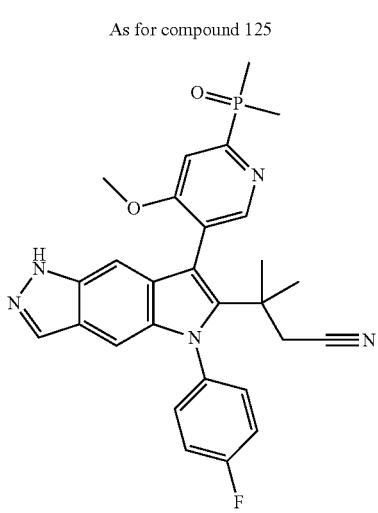 [SMILES: COc1cc(P(C)(C)=O)ncc1-c1c(C(C)(C)CC#N)n(-c2ccc(F)cc2)c2cc3cn[nH]c3cc12] | ¹H NMR (400 MHz, Methanol-$d_4$) δ 8.67 (s, 1H), 7.98 (d, J = 1.1 Hz, 1H), 7.85 (d, J = 6.9 Hz, 1H), 7.71 – 7.61 (m, 1H), 7.56 (m, 1H), 7.50 – 7.35 (m, 2H), 6.92 (m, 2H), 3.98 (s, 3H), 2.70 – 2.49 (m, 2H), 1.92 (dd, J = 13.8, 7.4 Hz, 6H), 1.32 (d, J = 11.4 Hz, 6H). LCMS m/z 516.42 [M + H]⁺. |

TABLE 14-continued

Method of preparation, structure and physicochemical data for compounds 186-202

| Compound | Method/Product | $^1$H NMR; LCMS m/z [M + H]$^+$ |
| --- | --- | --- |
| 201 | As for compound 125 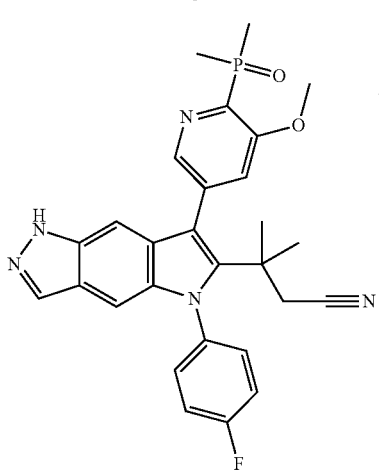 | $^1$H NMR (400 MHz, Methanol-d$_4$) δ 8.48 (s, 1H), 7.97 (d, J = 1.0 Hz, 1H), 7.80 (m, 1H), 7.59 (qd, J = 6.4, 3.1 Hz, 2H), 7.49 – 7.37 (m, 2H), 7.01 (d, J = 1.1 Hz, 1H), 6.94 (d, J = 1.2 Hz, 1H), 4.02 (s, 3H), 2.75 – 2.52 (m, 2H), 1.98 (d, J = 13.7 Hz, 6H), 1.32 (m, 6H). LCMS m/z 516.33 [M + H]$^+$. |
| 202 | As for compound 125 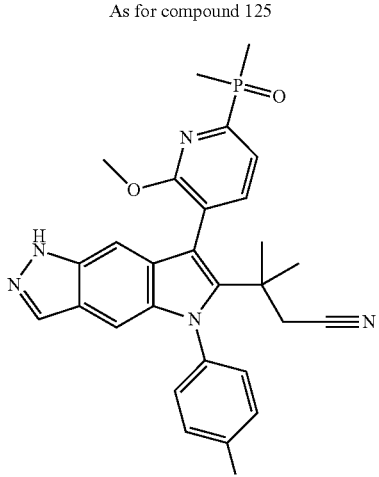 | $^1$H NMR (400 MHz, Methanol-d$_4$) δ 8.01 (s, 1H), 7.97 (m, 1H), 7.77 (m, 1H), 7.68 – 7.61 (m, 1H), 7.60 – 7.53 (m, 1H), 7.48 – 7.38 (m, 2H), 6.96 – 6.88 (m, 2H), 3.96 (s, 3H), 2.70 – 2.50 (m, 2H), 1.91 (dd, J = 13.7, 7.2 Hz, 6H), 1.32 (d, J = 12.8 Hz, 6H). LCMS m/z 516.25 [M + H]$^+$. |

[1]Prepared by Suzuki coupling from 3-[1-(2,2-dimethylpropanoyl)-5-(4-fluorophenyl)-7-iodo-pyrrolo[2,3-f]indazol-6-yl]-3-methyl-butanenitrile.
[2]Tosyl protected intermediate. Methyl 5-(4-cyano-3,3-dimethyl-but-1-ynyl)thiophene-2-carboxylate.

Compounds 203-254

Compounds 203-254 (Table 15) were prepared from compound 112 by amide coupling with the appropriate amine as described for the preparation of compound 128. In some examples, compounds are prepared by Suzuki coupling of the appropriate boronic acid with S11 as described for the preparation of compound 127. In some examples, compounds were prepared by Larock indole formation according to the method described for compound 119.

TABLE 15

Method of preparation, structure, physicochemical data for compounds 203-254

| Compound | Method/Product | ¹H NMR; LCMS m/z [M + H]⁺ |
|---|---|---|
| 203 | As for Compound 128 from 112 | ¹H NMR (400 MHz, DMSO-d$_6$) δ 12.52 (s, 1H), 8.87 (d, J = 6.7 Hz, 1H), 8.00 (d, J = 7.8 Hz, 2H), 7.97 (s, 1H), 7.71 (s, 1H), 7.57 (m, 4H), 7.49 (t, J = 8.5 Hz, 2H), 6.88-6.78 (m, 2H), 4.66 (m, 1H), 3.64 (dd, J = 10.0, 7.3 Hz, 1H), 3.23 (dd, J = 10.1, 4.6 Hz, 1H), 3.06 (s, 2H), 3.02 (s, 3H), 2.59 (m, 1H), 2.33 (dd, J = 16.8, 5.5 Hz, 1H), 1.11 (s, 6H). LCMS m/z 540.4 [M + H]⁺. |
| 204 | As for Compound 127 from S11 | ¹H NMR (400 MHz, Methanol-d$_4$) δ 7.91 (d, J = 1.0 Hz, 1H), 7.88 (d, J = 0.7 Hz, 1H), 7.68 (d, J = 0.7 Hz, 1H), 7.52-7.44 (m, 2H), 7.40-7.29 (m, 2H), 7.09 (t, J = 1.1 Hz, 1H), 6.84 (d, J = 1.2 Hz, 1H), 5.76-5.62 (m, 1H), 5.14 (m, 4H), 3.18 (s, 2H), 3.13 (s, 3H), 1.20 (s, 6H). LCMS m/z 460.3 [M + H]⁺. |
| 205 | As for Compound 128 from 112 | ¹H NMR (400 MHz, DMSO-d$_6$) δ 13.84 (s, 1H), 12.52 (s, 1H), 8.32 (d, J = 7.9 Hz, 2H), 7.98 (s, 1H), 7.69 (d, J = 7.9 Hz, 2H), 7.60 (m, 2H), 7.50 (m, 2H), 6.87 (t, J = 1.1 Hz, 1H), 6.85 (d, J = 1.3 Hz, 1H), 3.62 (s, 3H), 3.08 (s, 2H), 3.03 (s, 3H), 1.13 (s, 6H). LCMS m/z 619.28 [M + H]⁺. |

TABLE 15-continued

Method of preparation, structure, physicochemical data for compounds 203-254

| Compound | Method/Product | ¹H NMR; LCMS m/z [M + H]⁺ |
|---|---|---|
| 206 | As for Compound 128 from 112 | ¹H NMR (400 MHz, DMSO-d$_6$) δ 12.50 (s, 1H), 8.62 (t, J = 5.6 Hz, 1H), 8.04 (t, J = 5.7 Hz, 1H), 7.98 (m, 3H), 7.58 (dd, J = 8.6, 5.0 Hz, 2H), 7.54 (d, J = 7.8 Hz, 2H), 7.49 (m, 2H), 6.83 (m, 2H), 3.26 (m, 2H), 3.06 (s, 2H), 3.02 (s, 3H), 1.85 (s, 3H), 1.11 (s, 6H). LCMS m/z 542.43 [M + H]⁺. |
| 207 | As for Compound 128 from 112 | ¹H NMR (400 MHz, DMSO-d$_6$) δ 12.49 (s, 1H), 8.72 (t, J = 6.1 Hz, 1H), 7.99 (dm, 3H), 7.63-7.52 (m, 4H), 7.49 (dd, J = 9.9, 7.6 Hz, 2H), 6.89-6.76 (m, 2H), 4.57 (d, J = 6.3 Hz, 1H), 4.44 (d, J = 6.3 Hz, 1H), 3.63 (d, J = 6.1 Hz, 1H), 3.12-2.97 (m, 6H), 1.11 (d, J = 3.6 Hz, 6H). Methylene from NH$_2$CH$_2$ overlaps with water LCMS m/z 543.38 [M + H]⁺. |
| 208 | As for Compound 128 from 112 | ¹H NMR (400 MHz, DMSO-d$_6$) δ 12.47 (s, 1H), 8.69 (t, J = 5.9 Hz, 1H), 7.96 (s, 1H), 7.93 (d, J = 7.8 Hz, 2H), 7.58 (m, 2H), 7.54 (d, J = 7.8 Hz, 2H), 7.48 (t, J = 8.5 Hz, 2H), 6.84 (d, J = 1.3 Hz, 1H), 6.82 (d, J = 1.2 Hz, 1H), 4.27 (dd, J = 9.0, 7.0 Hz, 2H), 3.67 (dd, J = 8.9, 7.1 Hz, 2H), 3.49 (m, 2H), 3.06 (s, 2H), 3.02 (s, 3H), 1.11 (s, 6H). 2H overlapping with water signal. LCMS m/z 570.42 [M + H]⁺. |

TABLE 15-continued

Method of preparation, structure, physicochemical data for compounds 203-254

| Compound | Method/Product | $^1$H NMR; LCMS m/z [M + H]$^+$ |
|---|---|---|
| 209 | As for Compound 128 from 112 | $^1$H NMR (400 MHz, DMSO-d$_6$) δ 12.49 (s, 1H), 7.97 (d, J = 1.1 Hz, 1H), 7.65 (m 2H), 7.59 (m, 2H), 7.56-7.43 (m, 4H), 6.88 (m, 1H), 6.83 (t, J = 1.2 Hz, 1H), 4.07 (m, 1H), 3.95 (m, 2H), 3.70 (m, 2H), 3.12 (s, 2H), 3.07 (s, 3H), 3.01 (s, 3H), 2.37 (m, 2H), 1.12 (s, 6H). LCMS m/z 589.39 [M + H]$^+$. |
| 210 | As for Compound 128 from 112 | $^1$H NMR (400 MHz, DMSO-d$_6$) δ 12.49 (s, 1H), 7.97 (s, 1H), 7.65 (d, J = 7.6 Hz, 2H), 7.58 (m, 2H), 7.54-7.43 (m, 4H), 6.88 (s, 1H), 6.83 (s, 1H), 4.03 (d, J = 4.3 Hz, 1H), 3.97 (m, 1H), 3.83 (dd, J = 11.1, 3.8 Hz, 1H), 3.74 (dd, J = 12.8, 4.4 Hz, 1H), 3.07 (s, 2H), 3.01 (d, J = 4.2 Hz, 3H), 1.12 (s, 6H). 2H likely behinf the water peak. LCMS m/z 543.38 [M + H]$^+$. |
| 211 | As for Compound 128 from 112 | $^1$H NMR (400 MHz, DMSO-d$_6$) δ 12.49 (s, 1H), 8.51 (t, J = 5.6 Hz, 1H), 8.02-7.96 (m, 2H), 7.95 (s, 1H), 7.58 (m, 2H), 7.54 (d, J = 7.8 Hz, 2H), 7.49 (t, J = 8.5 Hz, 2H), 6.84 (d, J = 1.3 Hz, 1H), 6.83 (d, J = 1.3 Hz, 1H), 3.06 (s, 2H), 3.02 (d, J = 1.2 Hz, 3H), 2.25 (s, 3H), 1.11 (s, 6H). There 12H from methylenes that are likely behind the water and DMSO signals. LCMS m/z 583.47 [M + H]$^+$. |

TABLE 15-continued

Method of preparation, structure, physicochemical data for compounds 203-254

| Compound | Method/Product | $^1$H NMR; LCMS m/z [M + H]$^+$ |
|---|---|---|
| 212 | As for Compound 128 from 112 | $^1$H NMR (400 MHz, DMSO-d$_6$) δ 12.49 (s, 1H), 8.50 (t, J = 5.7 Hz, 1H), 8.04-7.92 (m, 3H), 7.58 (dd, J = 8.7, 4.9 Hz, 2H), 7.55-7.44 (m, 4H), 6.83 (dt, J = 5.1, 1.2 Hz, 2H), 3.69 (q, J = 5.7 Hz, 1H), 3.45 (dd, J = 11.9, 6.5 Hz, 2H; overlaps with water), 3.26 (dt, J = 12.9, 6.1 Hz, 2H), 3.06 (s, 2H), 3.02 (d, J = 1.1 Hz, 3H), 1.11 (s, 6H). LCMS m/z 531.37 [M + H]$^+$. |
| 213 | As for Compound 128 from 112 | $^1$H NMR (400 MHz, DMSO-d$_6$) δ 12.49 (s, 1H), 8.55 (t, J = 5.9 Hz, 1H), 8.05-7.90 (m, 3H), 7.57 (m, 4H), 7.49 (t, J = 8.5 Hz, 2H), 6.84 (d, J = 1.2 Hz, 1H), 6.82 (d, J = 1.2 Hz, 1H), 3.89-3.74 (m, 3H), 3.71 (d, J = 9.0 Hz, 2H), 3.06 (s, 2H), 3.03 (d, J = 1.2 Hz, 3H), 2.01 (dt, J = 12.6, 8.6 Hz, 1H), 1.87-1.73 (m, 1H), 1.11 (s, 6H). *1H overlaps with water. LCMS m/z 557.42 [M + H]$^+$. |
| 214 | As for Compound 128 from 112 | $^1$H NMR (400 MHz, DMSO-d$_6$) δ 12.48 (s, 1H), 8.81 (t, J = 5.5 Hz, 1H), 7.98 (s, 1H), 7.96 (m, 2H), 7.63-7.53 (m, 4H), 7.49 (t, J = 8.5 Hz, 2H), 6.87-6.77 (m, 2H), 3.77 (q, J = 6.6 Hz, 2H), 3.48 (t, J = 7.0 Hz, 2H), 3.06 (s, 2H), 3.02 (s, 3H), 2.85 (p, J = 6.4 Hz, 1H), 1.11 (s, 6H), 1.05 (m, 4H). LCMS m/z 589.39 [M + H]$^+$. |

TABLE 15-continued

Method of preparation, structure, physicochemical data for compounds 203-254

| Compound | Method/Product | $^1$H NMR; LCMS m/z [M + H]$^+$ |
|---|---|---|
| 215 | As for Compound 128 from 112 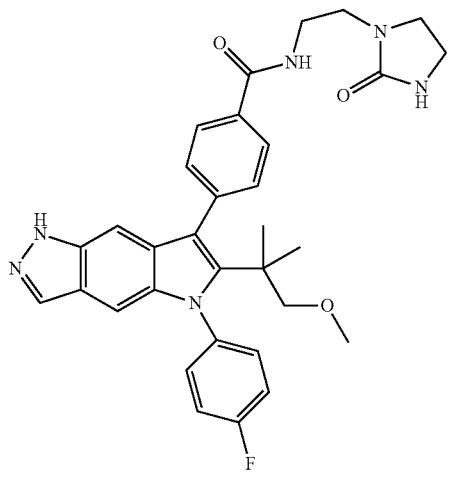 | $^1$H NMR (400 MHz, DMSO-d$_6$) δ 12.48 (s, 1H), 8.64 (t, J = 5.7 Hz, 1H), 8.04-7.85 (m, 3H), 7.58 (m, 2H), 7.53 (d, J = 7.9 Hz, 2H), 7.49 (t, J = 8.5 Hz, 2H), 6.84 (s, 1H), 6.83 (s, 1H), 3.47 (m, 4H), 3.31-3.23 (m, 4H), 3.06 (s, 2H), 3.02 (s, 3H), 1.11 (s, 6H). LCMS m/z 569.47 [M + H]$^+$. |
| 216 | As for Compound 128 from 112 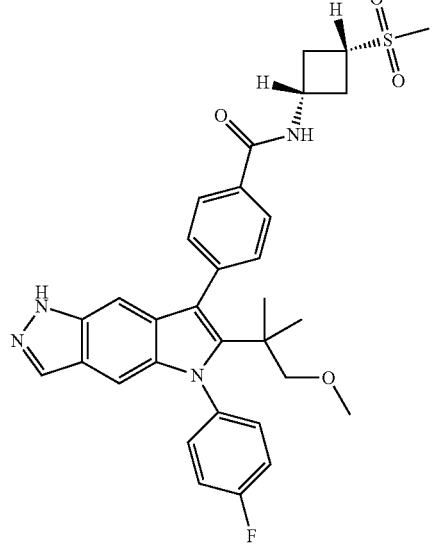 | $^1$H NMR (400 MHz, DMSO-d$_6$) δ 12.51 (s, 1H), 8.96 (d, J = 7.3 Hz, 1H), 8.00 (d, J = 7.8 Hz, 2H), 7.97 (s, 1H), 7.58 (m, 2H), 7.54 (d, J = 7.8 Hz, 2H), 7.49 (t, J = 8.5 Hz, 2H), 6.83 (m, 2H), 4.49 (p, J = 8.2 Hz, 1H), 3.79 (p, J = 8.8 Hz, 1H), 3.06 (s, 2H), 3.02 (s, 3H), 2.93 (s, 3H), 2.64-2.57 (m, 2H), 2.49-2.41 (m, 2H), 1.11 (s, 6H). LCMS m/z 589.34 [M + H]$^+$. |

TABLE 15-continued

Method of preparation, structure, physicochemical data for compounds 203-254

| Compound | Method/Product | ¹H NMR; LCMS m/z [M + H]⁺ |
|---|---|---|
| 217 | As for Compound 128 from 112 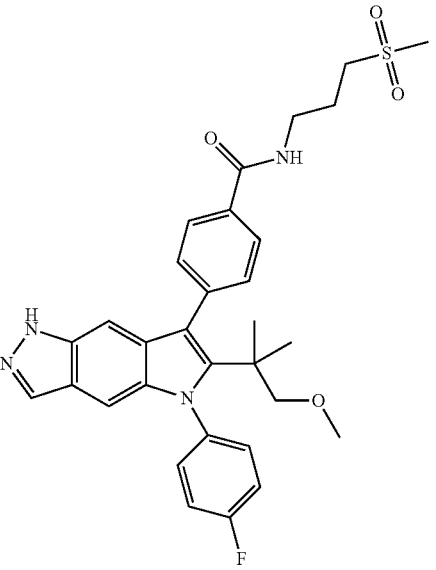 | ¹H NMR (400 MHz, DMSO-d₆) δ 12.52 (s, 1H), 8.69 (t, J = 5.7 Hz, 1H), 8.04-7.91 (m, 3H), 7.58 (m, 2H), 7.54 (d, J = 7.6 Hz, 2H), 7.49 (t, J = 8.5 Hz, 2H), 6.84 (s, 1H), 6.83 (s, 1H), 3.23 (dd, J = 9.8, 6.1 Hz, 2H), 3.06 (s, 2H), 3.02 (m, 6H), 2.01 (p, J = 6.9 Hz, 2H), 1.11 (s, 6H). 2H from CH₂ behind the water peak. LCMS m/z 577.38 [M + H]⁺. |
| 218 | As for Compound 127 from S11 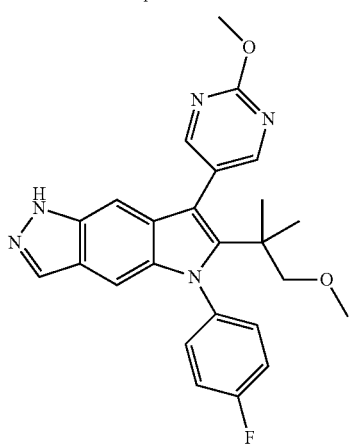 | ¹H NMR (400 MHz, Methanol-d₄) δ 8.62 (s, 2H), 7.94 (d, J = 1.0 Hz, 1H), 7.59-7.46 (m, 2H), 7.44-7.28 (m, 2H), 7.00 (t, J = 1.1 Hz, 1H), 6.88 (d, J = 1.1 Hz, 1H), 4.11 (s, 3H), 3.13 (s, 3H), 3.12 (s, 2H), 1.16 (s, 6H). LCMS m/z 446.26 [M + H]⁺. |
| 219 | As for Compound 127 from S11 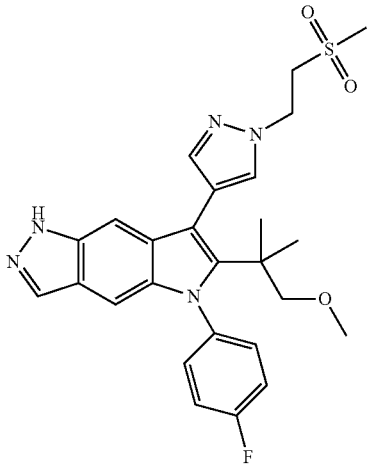 | ¹H NMR (400 MHz, Methanol-d₄) δ 8.09 (s, 1H), 7.91 (d, J = 1.1 Hz, 1H), 7.83 (d, J = 0.7 Hz, 1H), 7.62 (d, J = 0.7 Hz, 1H), 7.53-7.44 (m, 2H), 7.39-7.29 (m, 2H), 7.10 (t, J = 1.1 Hz, 1H), 6.83 (d, J = 1.1 Hz, 1H), 4.77 (dd, J = 6.9, 5.9 Hz, 2H), 3.81 (t, J = 6.3 Hz, 2H), 3.19 (s, 2H), 3.15 (s, 3H), 2.91 (m, 3H), 1.20 (s, 6H). LCMS m/z 510.28 [M + H]⁺. |

TABLE 15-continued

Method of preparation, structure, physicochemical data for compounds 203-254

| Compound | Method/Product | ¹H NMR; LCMS m/z [M + H]⁺ |
|---|---|---|
| 220 | As for Compound 127 from S11 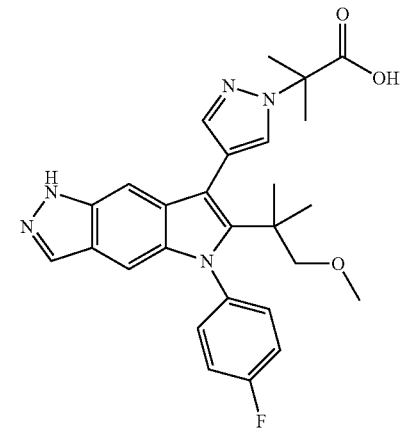 | ¹H NMR (400 MHz, Methanol-$d_4$) δ 7.91 (d, J = 1.1 Hz, 1H), 7.88 (d, J = 0.7 Hz, 1H), 7.58 (d, J = 0.7 Hz, 1H), 7.51-7.43 (m, 2H), 7.39-7.28 (m, 2H), 7.14 (t, J = 1.1 Hz, 1H), 6.84 (d, J = 1.1 Hz, 1H), 3.21 (s, 2H), 3.13 (s, 3H), 1.94 (s, 6H), 1.20 (s, 6H). LCMS m/z 490.33 [M + H]⁺. |
| 221 | As for Compound 127 from S11 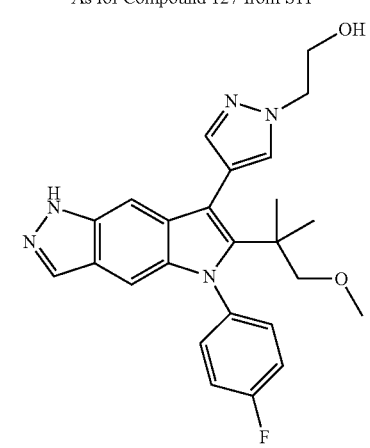 | ¹H NMR (400 MHz, Methanol-$d_4$) δ 7.90 (d, J = 1.1 Hz, 1H), 7.74 (d, J = 0.8 Hz, 1H), 7.57 (d, J = 0.7 Hz, 1H), 7.50-7.43 (m, 2H), 7.38-7.29 (m, 2H), 7.14 (t, J = 1.1 Hz, 1H), 6.83 (d, J = 1.1 Hz, 1H), 4.35 (t, J = 5.5 Hz, 2H), 3.99 (t, J = 5.5 Hz, 2H), 3.19 (s, 2H), 3.13 (s, 3H), 1.20 (s, 6H). LCMS m/z 448.29 [M + H]⁺. |
| 222 | As for Compound 127 from S11 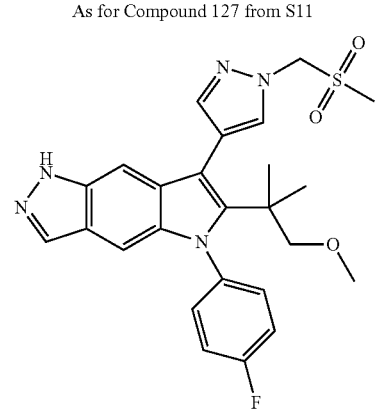 [SMILES: COCC(C)(C)c1c(-c2cnn(CS(C)(=O)=O)c2)c2cc3[nH]ncc3cc2n1-c1ccc(F)cc1] | ¹H NMR (400 MHz, Methanol-$d_4$) δ 7.92 (d, J = 0.7 Hz, 1H), 7.91 (d, J = 1.1 Hz, 1H), 7.72 (d, J = 0.7 Hz, 1H), 7.56-7.42 (m, 2H), 7.35 (m, 2H), 7.12 (t, J = 1.1 Hz, 1H), 6.85 (d, J = 1.2 Hz, 1H), 5.71 (d, J = 0.8 Hz, 2H), 3.20 (s, 2H), 3.15 (s, 3H), 3.06 (d, J = 0.8 Hz, 3H), 1.21 (s, 6H). LCMS m/z 496.29 [M + H]⁺. |

TABLE 15-continued

Method of preparation, structure, physicochemical data for compounds 203-254

| Compound | Method/Product | ¹H NMR; LCMS m/z [M + H]⁺ |
|---|---|---|
| 223 | As for Compound 127 from S11 | ¹H NMR (400 MHz, Methanol-d₄) δ 8.01 (d, J = 1.1 Hz, 1H), 7.93 (d, J = 0.7 Hz, 1H), 7.69 (d, J = 0.7 Hz, 1H), 7.63-7.51 (m, 2H), 7.51-7.36 (m, 2H), 7.25 (t, J = 1.1 Hz, 1H), 6.94 (d, J = 1.1 Hz, 1H), 3.96 (s, 2H), 3.30 (s, 2H), 3.24 (s, 3H), 1.76 (s, 6H), 1.30 (s, 6H). LCMS m/z 476.33 [M + H]⁺. |
| 224 | As for Compound 127 from S11 | ¹H NMR (400 MHz, Methanol-d₄) δ 7.90 (d, J = 1.1 Hz, 1H), 7.74 (s, 1H), 7.55 (s, 1H), 7.52-7.44 (m, 2H), 7.34 (m, 2H), 7.22 (t, J = 1.1 Hz, 1H), 6.83 (d, J = 1.1 Hz, 1H), 4.97 (s, 2H), 3.22 (s, 2H), 3.14 (s, 3H), 1.21 (s, 6H). LCMS m/z 462.24 [M + H]⁺. |
| 225 | As for Compound 128 from 112 | ¹H NMR (400 MHz, DMSO-d₆) δ 12.48 (s, 1H), 7.97 (d, J = 1.4 Hz, 1H), 7.81 (d, J = 7.7 Hz, 2H), 7.64-7.53 (m, 4H), 7.49 (t, J = 8.5 Hz, 2H), 6.87 (d, J = 1.2 Hz, 1H), 6.83 (s, 1H), 4.78 (m, 1H), 4.58 (m, 1H), 4.36 (m, 3H), 3.11 (s, 3H), 3.06 (s, 2H), 3.01 (s, 3H), 1.12 (s, 6H). LCMS m/z 575.26 [M + H]⁺. |

TABLE 15-continued
Method of preparation, structure, physicochemical data for compounds 203-254
| Compound | Method/Product | $^1$H NMR; LCMS m/z [M + H]$^+$ |
|---|---|---|
| 226 | As for Compound 128 from 112 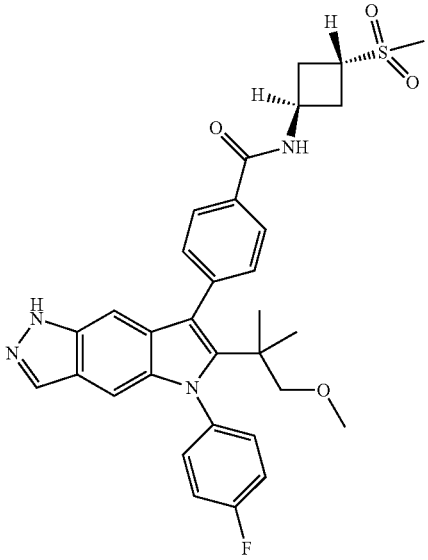 | $^1$H NMR (400 MHz, DMSO-d$_6$) δ 12.50 (s, 1H), 8.89 (d, J = 7.4 Hz, 1H), 8.04-7.91 (m, 3H), 7.63-7.52 (m, 4H), 7.49 (t, J = 8.5 Hz, 2H), 6.83 (m, 2H), 4.66 (p, J = 7.9 Hz, 1H), 3.98-3.78 (m, 1H), 3.06 (s, 2H), 3.02 (s, 3H), 2.99 (s, 3H), 2.79-2.68 (m, 2H), 2.61 (m, 2H), 1.10 (s, 6H). LCMS m/z 589.35 [M + H]$^+$. |
| 227 | As for Compound 128 from 112 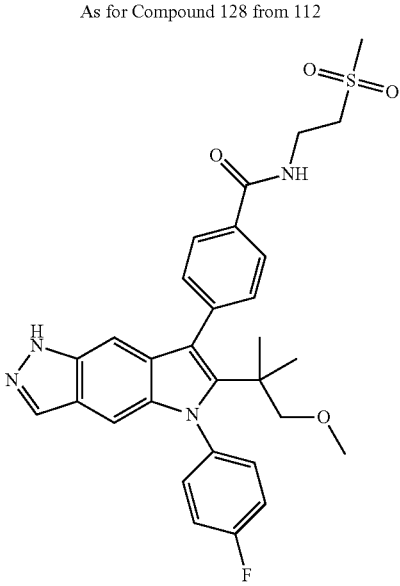 [SMILES: COCC(C)(C)c1c(-c2ccc(C(=O)NCCS(C)(=O)=O)cc2)c2cc3[nH]ncc3cc2n1-c1ccc(F)cc1] | $^1$H NMR (400 MHz, DMSO-d$_6$) δ 12.49 (s, 1H), 8.83 (t, J = 5.7 Hz, 1H), 8.01-7.93 (m, 3H), 7.62-7.53 (m, 4H), 7.49 (t, J = 8.5 Hz, 2H), 6.87-6.80 (m, 2H), 3.75 (q, J = 6.5 Hz, 2H), 3.44 (t, J = 6.9 Hz, 2H), 3.09 (s, 3H), 3.06 (s, 2H), 3.02 (s, 3H), 1.11 (s, 6H). LCMS m/z 563.29 [M + H]$^+$. |

TABLE 15-continued

Method of preparation, structure, physicochemical data for compounds 203-254

| Compound | Method/Product | $^1$H NMR; LCMS m/z [M + H]$^+$ |
|---|---|---|
| 228 | As for Compound 128 from 112 | $^1$H NMR (400 MHz, DMSO-d$_6$) δ 12.48 (s, 1H), 8.71 (t, J = 5.4 Hz, 1H), 8.57 (s, 1H), 8.02 (d, J = 1.2 Hz, 1H), 7.96 (d, J = 1.3 Hz, 1H), 7.92 (d, J = 7.8 Hz, 2H), 7.58 (m, 2H), 7.54 (d, J = 7.9 Hz, 2H), 7.49 (t, J = 8.5 Hz, 2H), 6.83 (m, 2H), 4.43 (t, J = 6.0 Hz, 2H), 3.72 (q, J = 5.9 Hz, 2H), 3.06 (s, 2H), 3.02 (m, 3H), 1.11 (s, 6H). LCMS m/z 552.27 [M + H]$^+$. |
| 229 | As for Compound 128 from 112 | $^1$H NMR (400 MHz, DMSO-d$_6$) δ 12.50 (s, 1H), 8.45 (t, J = 6.1 Hz, 1H), 8.00 (d, J = 7.8 Hz, 2H), 7.97 (d, J = 1.3 Hz, 1H), 7.59 (m, 2H), 7.55 (d, J = 7.6 Hz, 2H), 7.49 (t, J = 8.5 Hz, 2H), 6.85 (s, 1H), 6.83 (s, 1H), 4.76 (s, 1H), 4.65 (s, 1H), 3.42 m, 2H), 3.28 (m, 2H), 3.07 (s, 2H), 3.03 (s, 3H), 1.11 (m, 9H). LCMS m/z 545.34 [M + H]$^+$. |
| 230 | As for Compound 127 from S11 | $^1$H NMR (400 MHz, Methanol-d$_4$) δ 7.90 (d, J = 1.1 Hz, 1H), 7.74 (d, J = 0.8 Hz, 1H), 7.56 (d, J = 0.8 Hz, 1H), 7.51-7.43 (m, 2H), 7.38-7.29 (m, 2H), 7.13 (t, J = 1.1 Hz, 1H), 6.83 (d, J = 1.1 Hz, 1H), 4.42 (dd, J = 14.0, 4.6 Hz, 1H), 4.26 (dd, J = 14.0, 7.2 Hz, 1H), 4.09 (dq, J = 7.2, 5.1 Hz, 1H), 3.65-3.48 (m, 2H), 3.20 (s, 2H), 3.14 (s, 3H), 1.20 (s, 6H). LCMS m/z 478.29 [M + H]$^+$. |

TABLE 15-continued

Method of preparation, structure, physicochemical data for compounds 203-254

| Compound | Method/Product | $^1$H NMR; LCMS m/z [M + H]$^+$ |
|---|---|---|
| 231 | As for Compound 127 from S11 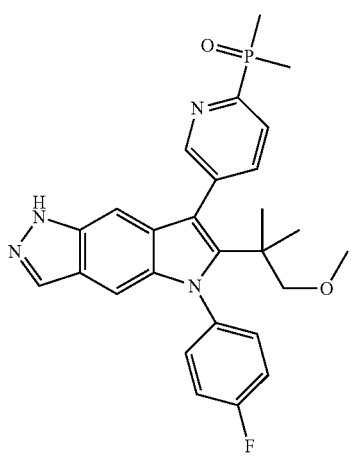 | $^1$H NMR (400 MHz, Methanol-d$_4$) δ 8.87 (dd, J = 2.1, 0.9 Hz, 1H), 8.15 (ddd, J = 7.8, 5.3, 0.9 Hz, 1H), 8.09 (ddd, J = 7.8, 3.6, 2.0 Hz, 1H), 7.94 (d, J = 1.0 Hz, 1H), 7.61-7.48 (m, 2H), 7.44-7.33 (m, 2H), 6.93 (t, J = 1.1 Hz, 1H), 6.89 (d, J = 1.2 Hz, 1H), 3.10 (s, 2H), 3.10 (s, 3H), 1.90 (m, 6H), 1.15 (s, 6H). LCMS m/z 491.32 [M + H]$^+$. |
| 232 | As for Compound 127 from S11 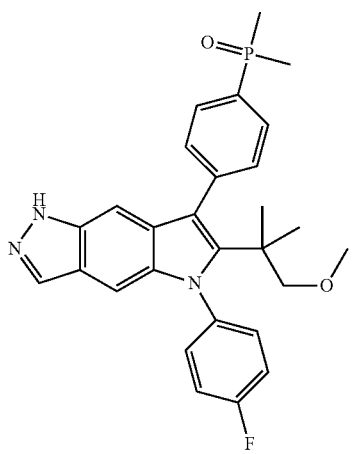 | $^1$H NMR (400 MHz, Methanol-d$_4$) δ 7.94 (d, J = 1.1 Hz, 1H), 7.93-7.87 (m, 2H), 7.70-7.65 (m, 2H), 7.56-7.50 (m, 2H), 7.37 (m, 2H), 6.92 (t, J = 1.1 Hz, 1H), 6.87 (d, J = 1.1 Hz, 1H), 3.10 (s, 2H), 3.09 (s, 3H), 1.90 (s, 3H), 1.87 (s, 3H), 1.16 (s, 6H). LCMS m/z 490.33 [M + H]$^+$. |
| 233 | As for Compound 128 from 112 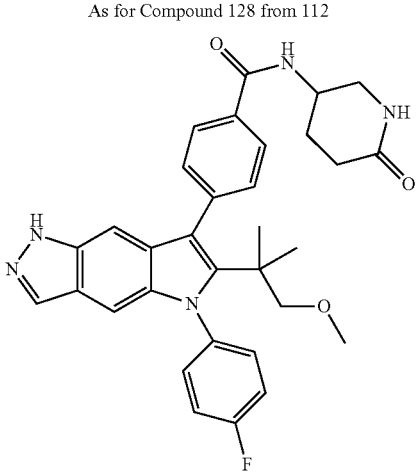 [SMILES: COCC(C)(C)c1c(-c2ccc(C(=O)NC3CCC(=O)NC3)cc2)c2cc3[nH]ncc3cc2n1-c1ccc(F)cc1] | $^1$H NMR (400 MHz, DMSO-d$_6$) δ 12.51 (s, 1H), 8.54 (d, J = 7.3 Hz, 1H), 8.02-7.92 (m, 3H), 7.62-7.52 (m, 4H), 7.53-7.44 (m, 3H), 6.83 (m, 2H), 4.23 (s, 1H), 3.19 (m, 1H), 3.07 (s, 2H), 3.03 (s, 3H), 2.41-2.27 (m, 2H), 1.95 (m, 2H), 1.11 (s, 6H). One CH likely overlaps with the water peak LCMS m/z 554.44 [M + H]$^+$. |

TABLE 15-continued

Method of preparation, structure, physicochemical data for compounds 203-254

| Compound | Method/Product | $^1$H NMR; LCMS m/z [M + H]$^+$ |
|---|---|---|
| 234 | As for Compound 128 from 112 | $^1$H NMR (400 MHz, DMSO-d$_6$) δ 12.50 (s, 1H), 8.75 (d, J = 8.4 Hz, 1H), 8.00 (d, J = 7.9 Hz, 2H), 7.95 (d, J = 10.8 Hz, 2H), 7.62-7.52 (m, 4H), 7.49 (t, J = 8.7 Hz, 2H), 6.85 (s, 1H), 6.83 (s, 1H), 4.99 (br s, 1H), 4.72 (q, J = 9.3 Hz, 1H), 3.57 (m, 1H), 3.43 (m, 2H), 3.06 (s, 2H), 3.03 (s, 3H), 2.27 (t, J = 10.9 Hz, 1H), 2.22-2.09 (m, 1H), 1.11 (s, 6H). LCMS m/z 570.46 [M + H]$^+$. |
| 235 | As for Compound 128 from 112 | $^1$H NMR (400 MHz, DMSO-d$_6$) δ 12.49 (s, 1H), 8.78 (d, J = 8.4 Hz, 1H), 8.01 (d, J = 7.9 Hz, 2H), 7.96 (s, 1H), 7.89 (s, 1H), 7.63-7.53 (m, 4H), 7.49 (t, J = 8.6 Hz, 2H), 6.85 (s, 1H), 6.83 (s, 1H), 4.63 (q, J = 9.2 Hz, 1H), 3.27 (m, 2H), 3.07 (s, 2H), 3.03 (s, 3H), 2.39 (m, 1H), 2.08 (p, J = 9.6 Hz, 1H), 1.12 (s, 6H). LCMS m/z 540.4 [M + H]$^+$. |

TABLE 15-continued

Method of preparation, structure, physicochemical data for compounds 203-254

| Compound | Method/Product | $^1$H NMR; LCMS m/z [M + H]$^+$ |
|---|---|---|
| 236 | As for Compound 128 from 112 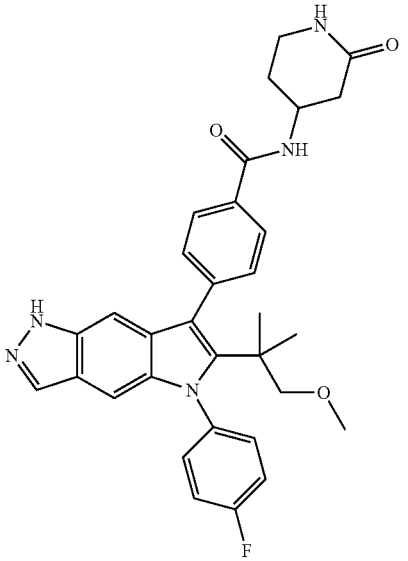 | $^1$H NMR (400 MHz, DMSO-d$_6$) δ 12.50 (s, 1H), 8.56 (d, J = 7.2 Hz, 1H), 8.03-7.95 (m, 3H), 7.66-7.52 (m, 5H), 7.49 (t, J = 8.6 Hz, 2H), 6.83 (m, 2H), 4.26 (m, 1H), 3.23 (m, 2H), 3.07 (s, 2H), 3.03 (s, 3H), 2.40-2.24 (m, 2H), 2.00 (m, 1H), 1.77 (m, 1H), 1.11 (s, 6H). LCMS m/z 554.44 [M + H]$^+$. |
| 237 | As for Compound 128 from 112 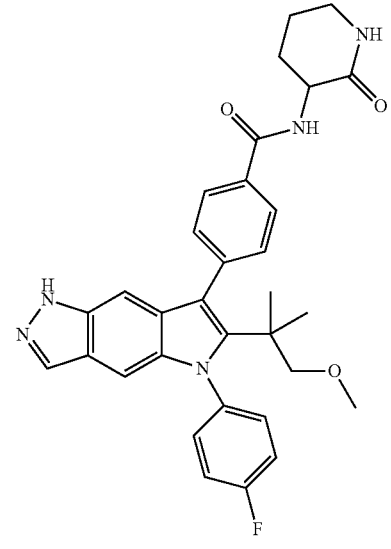 | $^1$H NMR (400 MHz, DMSO-d$_6$) δ 12.48 (s, 1H), 8.72 (d, J = 8.3 Hz, 1H), 8.00 (d, J = 7.9 Hz, 2H), 7.96 (s, 1H), 7.68 (s, 1H), 7.59 (m, 2H), 7.55 (d, J = 7.9 Hz, 2H), 7.49 (t, J = 8.5 Hz, 2H), 6.85 (s, 1H), 6.83 (s, 1H), 4.43 (m, 1H), 3.27-3.16 (m, 2H), 3.07 (s, 2H), 3.03 (s, 3H), 2.06 (m, 1H), 1.87 (m, 3H), 1.12 (s, 6H). LCMS m/z 554.39 [M + H]$^+$. |

TABLE 15-continued

Method of preparation, structure, physicochemical data for compounds 203-254

| Compound | Method/Product | ¹H NMR; LCMS m/z [M + H]⁺ |
|---|---|---|
| 238 | As for Compound 128 from 112 | ¹H NMR (400 MHz, DMSO-$d_6$) δ 12.51 (s, 1H), 9.20 (d, J = 8.3 Hz, 1H), 8.24 (s, 1H), 8.01 (d, J = 7.9 Hz, 2H), 7.97 (s, 1H), 7.58 (m, 4H), 7.49 (t, J = 8.5 Hz, 2H), 6.84 (s, 1H), 6.83 (s, 1H), 4.60 (dd, J = 8.4, 2.3 Hz, 1H), 3.74 (m, 1H), 3.06 (s, 2H), 3.02 (s, 3H), 1.35 (d, J = 6.1 Hz, 3H), 1.11 (s, 6H). LCMS m/z 540.44 [M + H]⁺. |
| 239 | As for Compound 128 from 112 | ¹H NMR (400 MHz, DMSO-$d_6$) δ 12.48 (s, 1H), 7.96 (s, 1H), 7.59 (m, 2H), 7.49 (m, 6H), 6.89 (s, 1H), 6.83 (s, 1H), 4.70 (m, 1H), 4.46 (m, 1H), 4.06 (m, 1H), 3.30-3.11 (m, 3H), 3.07 (s, 2H), 3.00 (s, 3H), 1.93-1.64 (m, 2H), 1.53 (m, 2H), 1.12 (s, 6H). LCMS m/z 571.41 [M + H]⁺. |

TABLE 15-continued

Method of preparation, structure, physicochemical data for compounds 203-254

| Compound | Method/Product | $^1$H NMR; LCMS m/z [M + H]$^+$ |
|---|---|---|
| 240[1] | As for Compound 128 from 112 | $^1$H NMR (400 MHz, DMSO-d$_6$) δ 12.47 (s, 1H), 7.96 (s, 1H), 7.64 (m, 2H), 7.58 (m, 2H), 7.54-7.42 (m, 4H), 6.87 (s, 1H), 6.82 (s, 1H), 5.01-4.82 (m, 2H), 3.66 (m, 3H), 3.51-3.41 (m, 1H), 3.29 (m, 1H), 3.06 (s, 2H), 3.01 (s, 3H), 2.02 (m, 1H), 1.74 (m, 1H), 1.12 (s, 6H). LCMS m/z 557.42 [M + H]$^+$. |
| 241 | As for Compound 128 from 112 | $^1$H NMR (400 MHz, DMSO-d$_6$) δ 12.47 (s, 1H), 7.96 (s, 1H), 7.63-7.39 (m, 8H), 6.87 (s, 1H), 6.82 (s, 1H), 3.84 (m, 2H), 3.55 (t, J = 7.1 Hz, 2H), 3.11 (s, 2H), 3.06 (s, 5H), 3.01 (s, 3H), 2.91 (m, 1H), 1.11 (s, 6H). NMR shows conformers. LCMS m/z 577.42 [M + H]$^+$. |

TABLE 15-continued

Method of preparation, structure, physicochemical data for compounds 203-254

| Compound | Method/Product | ¹H NMR; LCMS m/z [M + H]⁺ |
|---|---|---|
| 242 | As for Compound 128 from 112 | ¹H NMR (400 MHz, DMSO-d$_6$) δ 12.50 (s, 1H), 9.20 (d, J = 8.5 Hz, 1H), 8.09 (s, 1H), 8.01 (d, J = 7.9 Hz, 2H), 7.97 (s, 1H), 7.58 (m, 4H), 7.49 (t, J = 8.6 Hz, 2H), 6.85 (s, 1H), 6.83 (s, 1H), 5.12 (m, 1H), 3.52 (t, J = 5.4 Hz, 1H), 3.06 (s, 2H), 3.02 (s, 3H), 1.11 (s, 6H). There is likely a C—H behind the water peak. LCMS m/z 526.4 [M + H]⁺. |
| 243 | As for Compound 128 from 112 | ¹H NMR (400 MHz, DMSO-d$_6$) δ 12.48 (s, 1H), 8.21 (s, 1H), 7.97 (s, 1H), 7.64-7.56 (m, 4H), 7.54 (d, J = 7.9 Hz, 2H), 7.49 (t, J = 8.6 Hz, 2H), 6.89 (s, 1H), 6.83 (s, 1H), 4.09 (m, 2H), 3.74 (m, 2H), 3.07 (s, 2H), 3.02 (s, 3H), 1.12 (s, 6H). A CH$_2$ multiplet is likely behind the water peak. LCMS m/z 540.44 [M + H]⁺. |

TABLE 15-continued

Method of preparation, structure, physicochemical data for compounds 203-254

| Compound | Method/Product | ¹H NMR; LCMS m/z [M + H]⁺ |
| --- | --- | --- |
| 244 | As for Compound 128 from 112 | ¹H NMR (400 MHz, DMSO-d$_6$) δ 12.49 (s, 1H), 8.77 (d, J = 8.4 Hz, 1H), 8.01 (d, J = 7.9 Hz, 2H), 7.96 (s, 1H), 7.93 (s, 1H), 7.64-7.53 (m, 4H), 7.49 (t, J = 8.6 Hz, 2H), 6.85 (s, 1H), 6.83 (s, 1H), 4.90 (t, J = 5.4 Hz, 1H), 4.69 (q, J = 9.3 Hz, 1H), 3.59 (m, 1H), 3.45 (m, 2H), 3.06 (s, 2H), 3.02 (s, 3H), 2.47-2.37 (m, 1H), 1.75 (q, J = 10.4 Hz, 1H), 1.12 (s, 6H). LCMS m/z 570.51 [M + H]⁺. |
| 245 | As for Compound 128 from 112 | ¹H NMR (400 MHz, Methanol-d$_4$) δ 8.01-7.94 (m, 2H), 7.92 (d, J = 1.1 Hz, 1H), 7.61-7.55 (m, 2H), 7.55-7.49 (m, 2H), 7.37 (m, 2H), 6.92 (t, J = 1.2 Hz, 1H), 6.86 (d, J = 1.2 Hz, 1H), 4.85-4.80 (m, 1H), 3.85 (dd, J = 10.5, 7.4 Hz, 1H), 3.42 (dd, J = 10.5, 4.5 Hz, 1H), 3.10 (s, 2H), 3.09 (s, 3H), 2.80 (dd, J = 17.3, 8.6 Hz, 1H), 2.50 (dd, J = 17.3, 5.5 Hz, 1H), 1.16 (s, 6H). LCMS m/z 540.34 [M + H]⁺. |
| 246 | As for Compound 128 from 112 | ¹H NMR (400 MHz, Methanol-d$_4$) δ 8.01-7.94 (m, 2H), 7.94-7.89 (m, 1H), 7.62-7.55 (m, 2H), 7.55-7.48 (m, 2H), 7.42-7.32 (m, 2H), 6.92 (m, 1H), 6.86 (d, J = 1.1 Hz, 1H), 4.85-4.79 (m, 1H), 3.85 (dd, J = 10.5, 7.3 Hz, 1H), 3.42 (dd, J = 10.5, 4.6 Hz, 1H), 3.10 (s, 2H), 3.09 (s, 3H), 2.80 (dd, J = 17.2, 8.6 Hz, 1H), 2.50 (dd, J = 17.2, 5.5 Hz, 1H), 1.16 (s, 6H). LCMS m/z 540.39 [M + H]⁺. |

TABLE 15-continued

Method of preparation, structure, physicochemical data for compounds 203-254

| Compound | Method/Product | $^1$H NMR; LCMS m/z [M + H]$^+$ |
|---|---|---|
| 247 | As for Compound 127 from S11 | $^1$H NMR (400 MHz, DMSO-d$_6$) δ 12.53 (s, 1H), 7.94 (s, 1H), 7.91 (s, 1H), 7.58 (s, 1H), 7.56-7.41 (m, 4H), 7.31 (s, 1H), 7.07 (d, J = 1.2 Hz, 1H), 6.84 (s, 1H), 6.78 (d, J = 1.1 Hz, 1H), 3.14 (s, 2H), 3.05 (s, 3H), 1.81 (s, 6H), 1.13 (s, 6H). LCMS m/z 489.42 [M + H]$^+$. |
| 248 | As for Compound 127 from S11 | $^1$H NMR (400 MHz, DMSO-d$_6$) δ 12.49 (s, 1H), 8.18-8.07 (m, 1H), 7.97 (s, 1H), 7.87 (d, J = 7.4 Hz, 1H), 7.78 (d, J = 7.4 Hz, 1H), 7.73 (s, 1H), 7.65 (m, 1H), 7.57-7.43 (m, 3H), 6.82 (s, 1H), 6.77 (s, 1H), 3.95 (s, 3H), 3.05-3.00 (m, 2H), 2.98 (s, 3H), 1.10 (s, 6H). LCMS m/z 488.38 [M + H]$^+$. |
| 249 | As for Compound 127 from S11 | $^1$H NMR (400 MHz, Methanol-d$_4$) δ 8.12 (d, J = 1.1 Hz, 1H), 7.59-7.52 (m, 2H), 7.51-7.43 (m, 1H), 7.36 (m, 2H), 7.08 (m, 1H), 6.93 (m, 1.1 Hz, 1H), 5.05 (s, 2H), 3.20 (m, 2H), 3.13 (m, 3H), 2.14 (s, 3H), 1.20 (m, 6H). LCMS m/z 476.41 [M + H]$^+$. |

TABLE 15-continued

Method of preparation, structure, physicochemical data for compounds 203-254

| Compound | Method/Product | ¹H NMR; LCMS m/z [M + H]⁺ |
|---|---|---|
| 250 | As for Compound 127 from S11 | ¹H NMR (400 MHz, Methanol-d₄) δ 8.11 (s, 1H), 7.83 (s, 1H), 7.57 (m, 1H), 7.48-7.41 (m, 1H), 7.41-7.31 (m, 2H), 7.07 (t, J = 1.1 Hz, 1H), 6.92 (s, 1H), 3.24 (d, J = 9.0 Hz, 1H), 3.15 (d, J = 9.0 Hz, 1H), 3.13 (s, 3H), 2.13 (s, 3H), 1.92 (d, J = 7.0 Hz, 6H), 1.20 (d, J = 11.5 Hz, 6H). LCMS m/z 504.41 [M + H]⁺. |
| 251 | As for Compound 127 from S11 | ¹H NMR (400 MHz, Methanol-d₄) δ 8.12 (d, J = 1.1 Hz, 1H), 7.55-7.47 (m, 2H), 7.41-7.31 (m, 2H), 7.20 (t, J = 1.2 Hz, 1H), 7.00 (s, 1H), 6.94 (d, J = 1.1 Hz, 1H), 4.27 (s, 3H), 3.19 (s, 2H), 3.11 (s, 3H), 1.21 (s, 6H). LCMS m/z 462.37 [M + H]⁺. |
| 252 | As for Compound 127 from S11 | ¹H NMR (400 MHz, Methanol-d₄) δ 7.93 (d, J = 1.0 Hz, 1H), 7.84 (d, J = 3.7 Hz, 1H), 7.56-7.48 (m, 2H), 7.42-7.32 (m, 2H), 7.16-7.11 (m, 2H), 6.87 (d, J = 1.1 Hz, 1H), 3.18 (s, 2H), 3.14 (s, 3H), 1.24 (s, 6H). LCMS m/z 464.32 [M + H]⁺. |

TABLE 15-continued

Method of preparation, structure, physicochemical data for compounds 203-254

| Compound | Method/Product | $^1$H NMR; LCMS m/z [M + H]+ |
|---|---|---|
| 253 | As for Compound 128 from 119 | $^1$H NMR (400 MHz, Methanol-$d_4$) δ 8.04-7.96 (m, 2H), 7.92 (d, J = 1.1 Hz, 1H), 7.63-7.58 (m, 2H), 7.59-7.54 (m, 2H), 7.39-7.31 (m, 2H), 6.92 (t, J = 1.1 Hz, 1H), 6.85 (d, J = 1.2 Hz, 1H), 3.45 (s, 2H), 1.11 (s, 6H). LCMS m/z 443.36 [M + H]+. |
| 254 | Larock method as for compound 119 | $^1$H NMR (400 MHz, Methanol-$d_4$) δ 8.67 (s, 1H), 7.91 (s, 1H), 7.86 (s, 1H), 7.58 (m, 2H), 7.37 (t, J = 8.6 Hz, 2H), 6.92 (s, 1H), 6.88 (s, 1H), 3.44 (s, 2H), 2.79 (s, 3H), 2.03-1.88 (m, 6H), 1.10 (s, 6H). LCMS m/z 491.23 [M + H]+. |

[1]Protected boronic acid

Compound 255

4-[6-(1,1-dimethyl-2-methylsulfonyl-ethyl)-5-(4-fluorophenyl)-1H-pyrrolo[2,3-f]indazol-7-yl]benzoic Acid (255)

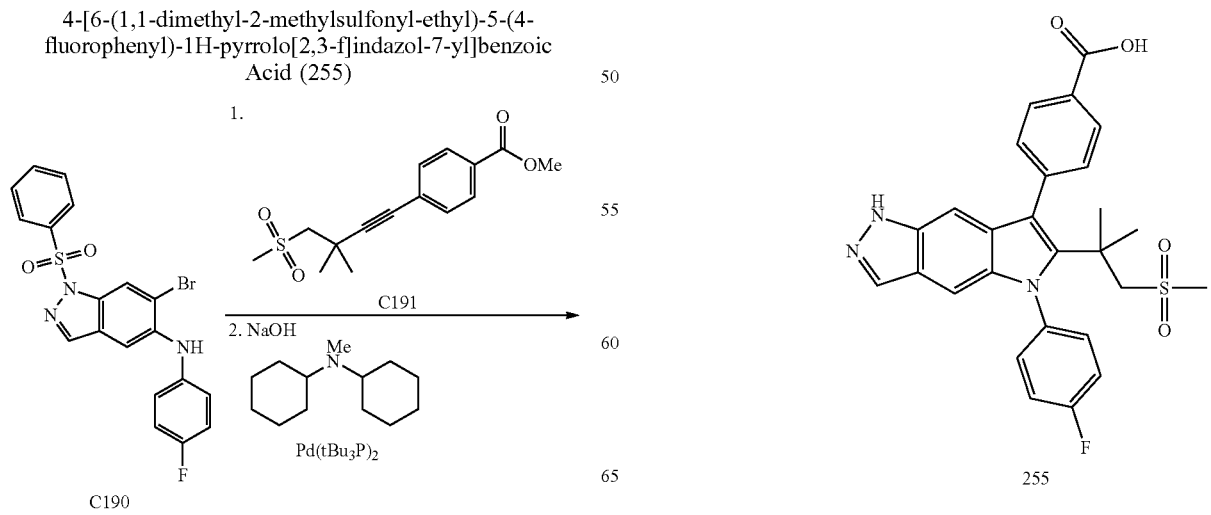

Compound 255-258 (Table 16) were prepared from C190 and C191 by Larock indole cyclization, followed by removal of the N-tosyl group and methyl ester by hydrolysis as described for compound 125.

1H NMR (400 MHz, Methanol-d4) δ 8.18-8.10 (m, 2H), 7.93 (d, J=1.1 Hz, 1H), 7.71-7.66 (m, 2H), 7.66-7.63 (m, 2H), 7.41 (m, 2H), 6.92 (t, J=1.1 Hz, 1H), 6.84 (d, J=1.2 Hz, 1H), 3.39 (s, 2H), 2.81 (s, 3H), 1.40 (s, 6H). LCMS m/z 506.31 [M+H]⁺.

Compounds 256-258

TABLE 16

Method of preparation, structure, physicochemical data for compounds 256-258

| Compound | Structure | Method | ¹H NMR; LCMS m/z [M + H]⁺ |
|---|---|---|---|
| 256 | 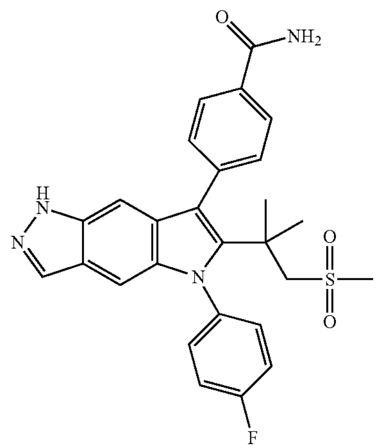 [SMILES: CC(C)(CS(C)(=O)=O)c1c(-c2ccc(C(N)=O)cc2)c2cc3[nH]ncc3cc2n1-c1ccc(F)cc1] | As for compound 255 | ¹H NMR (400 MHz, DMSO-d₆) δ 12.51 (s, 1H), 8.09 (s, 1H), 8.01 (d, J = 7.9 Hz, 2H), 7.97 (s, 1H), 7.69 (dd, J = 8.7, 5.0 Hz, 2H), 7.61-7.50 (m, 4H), 7.46 (s, 1H), 6.81 (s, 1H), 6.80 (s, 1H), 2.86 (s, 3H), 1.32 (s, 6H). CH₂ overlapps with water peak LCMS m/z 505.36 [M + H]⁺. |
| 257 | 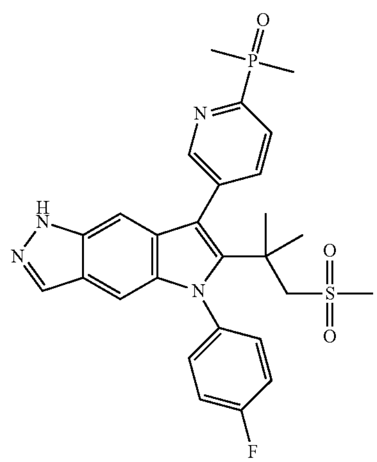 [SMILES: CC(C)(CS(C)(=O)=O)c1c(-c2ccc(P(C)(C)=O)nc2)c2cc3[nH]ncc3cc2n1-c1ccc(F)cc1] | As for compound 255 | ¹H NMR (400 MHz, Methanol-d₄) δ 8.93 (t, J = 1.5 Hz, 1H), 8.20-8.09 (m, 2H), 7.95 (d, J = 1.1 Hz, 1H), 7.76-7.66 (m, 2H), 7.49-7.37 (m, 2H), 6.90 (t, J = 1.1 Hz, 1H), 6.87 (d, J = 1.1 Hz, 1H), 3.38 (s, 2H), 2.84 (s, 3H), 1.91 (dd, J = 13.7, 6.9 Hz, 6H), 1.38 (s, 6H). LCMS m/z 539.4 [M + H]⁺. |
| 258 | 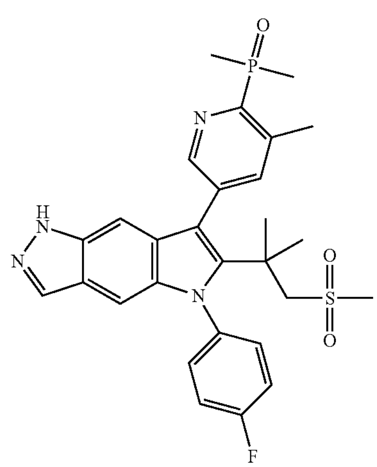 [SMILES: Cc1cc(-c2c(C(C)(C)CS(C)(=O)=O)n(-c3ccc(F)cc3)c3cc4cn[nH]c4cc23)cnc1P(C)(C)=O] | As for compound 255 | ¹H NMR (400 MHz, Methanol-d₄) δ 8.76-8.63 (m, 1H), 7.94 (d, J = 1.1 Hz, 1H), 7.90 (m, 1H), 7.70 (m, 2H), 7.43 (m, 2H), 6.90 (t, J = 1.1 Hz, 1H), 6.86 (d, J = 1.1 Hz, 1H), 3.38 (d, J = 1.8 Hz, 2H), 2.84 (s, 3H), 2.78 (br s, 3H), 1.94 (dd, J = 13.5, 7.8 Hz, 6H), 1.38 (s, 6H). LCMS m/z 553.18 [M + H]⁺. |

Compound 259

4-[5-(4-fluorophenyl)-6-(1-hydroxy-2-methoxy-1-methyl-ethyl)-1H-pyrrolo[2,3-f]indazol-7-yl]benzoic Acid (259)

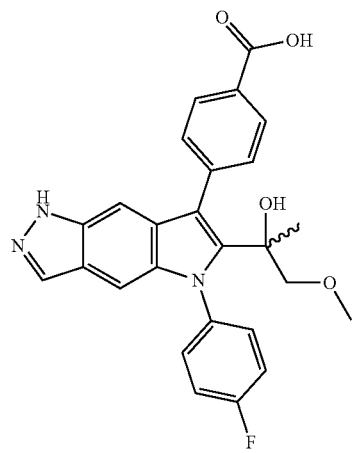 [SMILES: COCC(C)(O)c1c(-c2ccc(C(=O)O)cc2)c2cc3[nH]ncc3cc2n1-c1ccc(F)cc1]

Compound 259 was prepared from C190 and methyl 4-(3-hydroxy-4-methoxy-3-methyl-but-1-ynyl)benzoate using the method described for the preparation of compound 255.

Compounds 260-277

Compounds 260-277 (Table 17) were prepared from C1 and the appropriate alkyne using the routes described for compounds 107-111. In some examples, compounds were prepared from C117 or C190 using the Larock indole method as described for compound 125.

$^1$H NMR (300 MHz, DMSO-d$_6$) δ 12.52 (s, 1H), 8.00-7.89 (m, 3H), 7.60-7.45 (m, 2H), 7.45-7.30 (m, 4H), 6.97 (t, J=1.1 Hz, 1H), 6.86 (d, J=1.0 Hz, 1H), 4.95 (s, 1H), 3.22 (d, J=3.2 Hz, 2H), 3.03 (s, 3H), 1.26 (s, 3H). LCMS m/z 460.34 [M+H]$^+$.

TABLE 17

Method of preparation, structure, physicochemical data for compounds 260-277

| Compound | Structure | Method | $^1$H NMR; LCMS m/z [M + H]$^+$ |
|---|---|---|---|
| 260 | 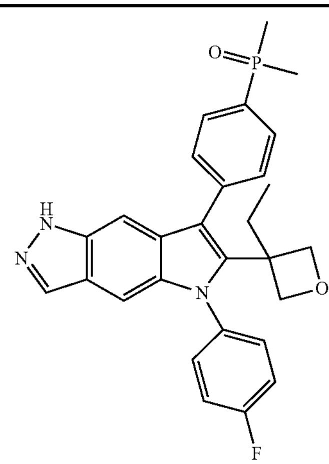 | Suzuki Method. As for compounds 107-111. | $^1$H NMR (400 MHz, Methanol-d$_4$) δ 7.98 (d, J = 1.1 Hz, 1H), 7.97-7.89 (m, 2H), 7.68 (dd, J = 8.2, 2.6 Hz, 2H), 7.55-7.47 (m, 2H), 7.42-7.32 (m, 3H), 7.05 (d, J = 1.1 Hz, 1H), 4.72 (d, J = 5.9 Hz, 2H), 3.92-3.82 (m, 2H), 2.19 (q, J = 7.4 Hz, 2H), 1.89 (s, 3H), 1.86 (s, 3H), 1.18 (t, J = 7.5 Hz, 3H). LCMS m/z 488.34 [M + H]$^+$. |
| 261 | 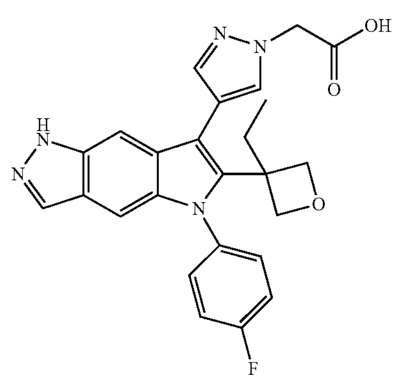 [SMILES: CCC1(c2c(-c3cnn(CC(=O)O)c3)c3cc4[nH]ncc4cc3n2-c2ccc(F)cc2)COC1] | Suzuki Method. As for compounds 107-111. | $^1$H NMR (400 MHz, Methanol-d$_4$) δ 7.96 (d, J = 1.0 Hz, 1H), 7.80 (d, J = 0.8 Hz, 1H), 7.65 (d, J = 0.8 Hz, 1H), 7.52-7.44 (m, 2H), 7.43 (m, 1H), 7.39-7.31 (m, 2H), 7.03 (d, J = 1.2 Hz, 1H), 5.08 (s, 2H), 4.86 (m, 2H), 3.93 (d, J = 5.9 Hz, 2H), 2.15 (q, J = 7.4 Hz, 2H), 1.13 (t, J = 7.4 Hz, 3H). LCMS m/z 460.34 [M + H]$^+$. |

TABLE 17-continued

Method of preparation, structure, physicochemical data for compounds 260-277

| Compound | Structure | Method | ¹H NMR; LCMS m/z [M + H]⁺ |
|---|---|---|---|
| 262 | 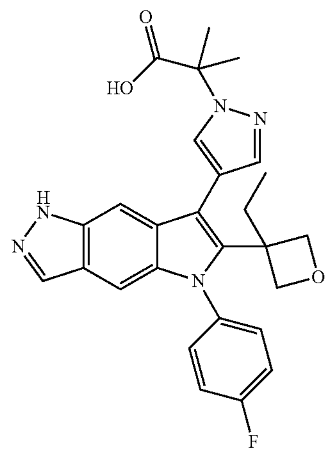 [SMILES: CCC1(c2c(-c3cnn(C(C)(C)C(=O)O)c3)c3cc4[nH]ncc4cc3n2-c2ccc(F)cc2)COC1] | Suzuki Method. As for compounds 107-111. | ¹H NMR (400 MHz, Methanol-d₄) δ 7.96 (d, J = 1.1 Hz, 1H), 7.88 (d, J = 0.8 Hz, 1H), 7.64 (d, J = 0.7 Hz, 1H), 7.49-7.43 (m, 2H), 7.40 (t, J = 1.1 Hz, 1H), 7.34 (m, 2H), 7.02 (d, J = 1.2 Hz, 1H), 4.86 (d, J = 6.1 Hz, 2H), 3.89 (d, J = 5.9 Hz, 2H), 2.15 (q, J = 7.5 Hz, 2H), 1.93 (s, 6H), 1.12 (t, J = 7.4 Hz, 3H). LCMS m/z 488.38 [M + H]⁺. |
| 263 | 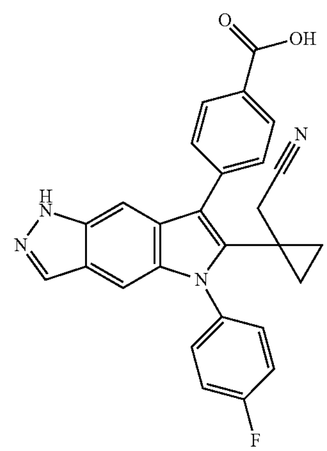 [SMILES: N#CCC1(c2c(-c3ccc(C(=O)O)cc3)c3cc4[nH]ncc4cc3n2-c2ccc(F)cc2)CC1] | As from compound 125. Larock Method from C117 | ¹H NMR (300 MHz, DMSO-d₆) δ 13.33-12.91 (bs, 1H), 12.81 (s, 1H), 8.07 (d, J = 1.0 Hz, 1H), 7.92-7.83 (m, 3H), 7.56-7.49 (m, 2H), 7.46 (d, J = 1.1 Hz, 1H), 7.37-7.22 (m, 4H), 3.13 (s, 2H), 0.96-0.87 (m, 2H), 0.59-0.51 (m, 2H); ¹H NMR (400 MHz, DMSO-d₆) δ 13.10 (s, 1H), 12.83 (s, 1H), 8.08 (d, J = 1.0 Hz, 1H), 7.92-7.90 (m, 1H), 7.90-7.87 (m, 2H), 7.58-7.52 (m, 2H), 7.47 (d, J = 1.1 Hz, 1H), 7.36-7.25 (m, 4H), 3.14 (s, 2H), 0.96-0.88 (m, 2H), 0.58-0.49 (m, 2H). LCMS m/z 451.28 [M + H]⁺. |
| 264 | 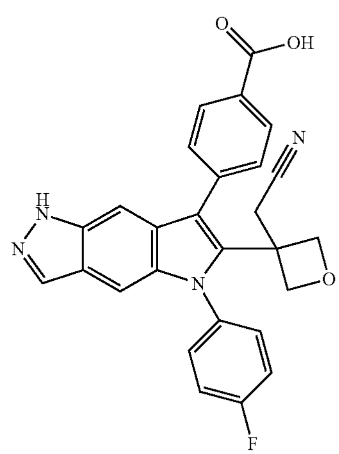 [SMILES: N#CCC1(c2c(-c3ccc(C(=O)O)cc3)c3cc4[nH]ncc4cc3n2-c2ccc(F)cc2)COC1] | As from compound 125. Larock Method from C117 | ¹H NMR (300 MHz, DMSO-d₆) δ 13.06 (s, 1H), 12.71 (s, 1H), 8.13-8.06 (m, 2H), 8.04 (d, J = 1.0 Hz, 1H), 7.75-7.66 (m, 4H), 7.50 (t, J = 8.7 Hz, 2H), 7.42 (t, J = 1.1 Hz, 1H), 7.07 (d, J = 1.1 Hz, 1H), 4.65 (d, J = 6.4 Hz, 2H), 3.87 (d, J = 6.3 Hz, 2H), 3.46 (s, 2H). LCMS m/z 467.31 [M + H]⁺. |

TABLE 17-continued

Method of preparation, structure, physicochemical data for compounds 260-277

| Compound | Structure | Method | ¹H NMR; LCMS m/z [M + H]⁺ |
|---|---|---|---|
| 265 | 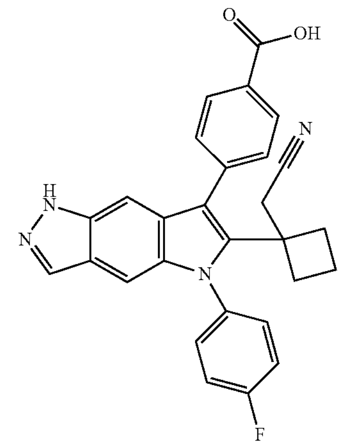 [SMILES: N#CCC1(c2c(-c3ccc(C(=O)O)cc3)c3cc4[nH]ncc4cc3n2-c2ccc(F)cc2)CCC1] | As from compound 125. Larock Method from C117 | ¹H NMR (300 MHz, DMSO-d₆) δ 13.01 (s, 1H), 12.62 (s, 1H), 8.10-8.03 (m, 2H), 8.00 (d, J = 1.0 Hz, 1H), 7.80-7.72 (m, 2H), 7.72-7.62 (m, 2H), 7.48 (t, J = 8.7 Hz, 2H), 7.26 (t, J = 1.1 Hz, 1H), 6.98 (d, J = 1.1 Hz, 1H), 3.18 (s, 2H), 2.36-2.21 (m, 2H), 2.04-1.87 (m, 1H), 1.61-1.44 (m, 3H). LCMS m/z 465.33 [M + H]⁺. |
| 266 | 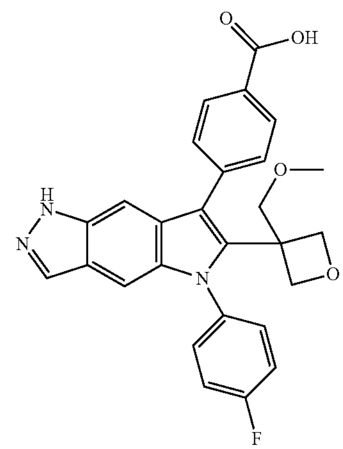 [SMILES: COCC1(c2c(-c3ccc(C(=O)O)cc3)c3cc4[nH]ncc4cc3n2-c2ccc(F)cc2)COC1] | As from compound 125. Larock Method from C117 | ¹H NMR (300 MHz, DMSO-d₆) δ 12.96 (s, 1H), 12.66 (s, 1H), 8.11-7.97 (m, 3H), 7.81-7.73 (m, 2H), 7.69-7.59 (m, 2H), 7.53-7.41 (m, 3H), 7.00 (d, J = 1.1 Hz, 1H), 4.52 (d, J = 5.9 Hz, 2H), 3.91 (s, 2H), 3.82 (d, J = 5.8 Hz, 2H), 3.40 (s, 3H). LCMS m/z 472.31 [M + H]⁺. |
| 267 | 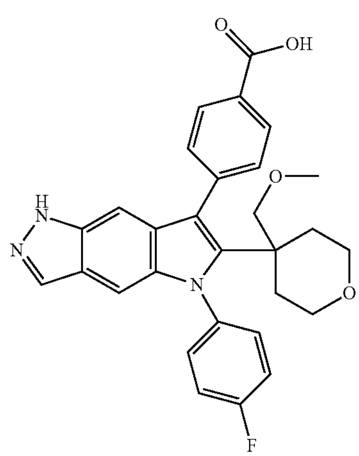 [SMILES: COCC1(c2c(-c3ccc(C(=O)O)cc3)c3cc4[nH]ncc4cc3n2-c2ccc(F)cc2)CCOCC1] | As from compound 125. Larock Method from C117 | ¹H NMR (300 MHz, Acetone-d₆) δ 12.19-11.18 (bs, 2H), 8.24-8.09 (m, 2H), 7.97 (d, J = 1.0 Hz, 1H), 7.73 (d, J = 8.0 Hz, 2H), 7.68-7.56 (m, 2H), 7.50-7.37 (m, 2H), 7.07 (t, J = 1.1 Hz, 1H), 6.93 (d, J = 1.1 Hz, 1H), 3.62 (s, 2H), 3.54-3.39 (m, 4H), 3.38 (s, 3H), 1.96-1.85 (m, 2H), 1.51-1.39 (m, 2H). LCMS m/z 500.43 [M + H]⁺. |

TABLE 17-continued

Method of preparation, structure, physicochemical data for compounds 260-277

| Compound | Structure | Method | ¹H NMR; LCMS m/z [M + H]⁺ |
|---|---|---|---|
| 268[1] | 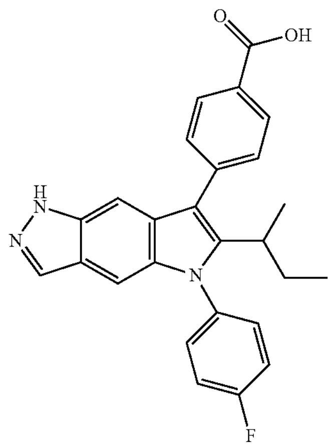 [SMILES: CCC(C)c1c(-c2ccc(C(=O)O)cc2)c2cc3[nH]ncc3cc2n1-c1ccc(F)cc1] | As from compound 125. Larock Method from C190 | ¹H NMR (300 MHz, DMSO-d$_6$) δ 12.97 (s, 1H), 12.58 (s, 1H), 8.14-8.07 (m, 2H), 8.00 (d, J = 1.0 Hz, 1H), 7.66-7.55 (m, 4H), 7.55-7.44 (m, 2H), 7.28 (t, J = 1.1 Hz, 1H), 7.06 (d, J = 1.1 Hz, 1H), 2.94-2.82 (m, 1H), 1.52-1.27 (m, 2H), 1.18 (d, J = 7.1 Hz, 3H), 0.67 (t, J = 7.3 Hz, 3H). LCMS m/z 428.33 [M + H]⁺. |
| 269 | 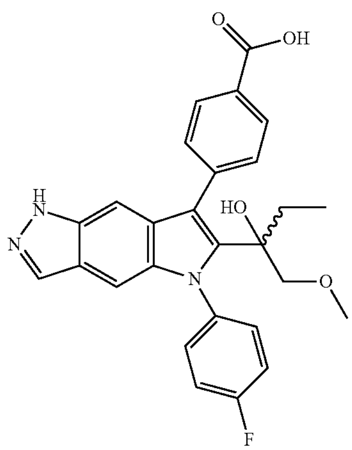 [SMILES: CCC(O)(COC)c1c(-c2ccc(C(=O)O)cc2)c2cc3[nH]ncc3cc2n1-c1ccc(F)cc1] | As from compound 125. Larock Method from C190 | ¹H NMR (300 MHz, DMSO-d$_6$) δ 12.51 (s, 1H), 8.01-7.88 (m, 3H), 7.58-7.49 (m, 1H), 7.49-7.41 (m, 1H), 7.41-7.28 (m, 4H), 6.91 (t, J = 1.1 Hz, 1H), 6.82 (d, J = 1.0 Hz, 1H), 4.49 (s, 1H), 3.23 (d, J = 9.7 Hz, 2H), 3.09 (s, 3H), 1.60-1.41 (m, 2H), 0.70 (t, J = 7.3 Hz, 3H). LCMS m/z 474.38 [M + H]⁺. |
| 270 | 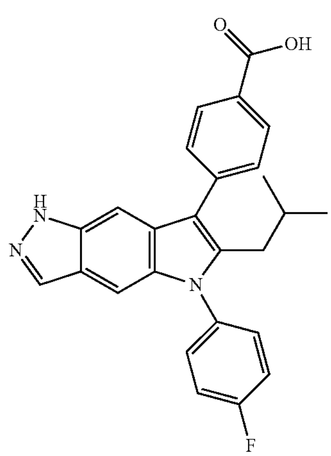 [SMILES: CC(C)Cc1c(-c2ccc(C(=O)O)cc2)c2cc3[nH]ncc3cc2n1-c1ccc(F)cc1] | As from compound 125. Larock Method from C190 | ¹H NMR (300 MHz, DMSO-d$_6$) δ 12.90 (s, 1H), 12.64 (s, 1H), 8.17-8.06 (m, 2H), 8.02 (d, J = 1.0 Hz, 1H), 7.78-7.68 (m, 2H), 7.68-7.56 (m, 2H), 7.56-7.45 (m, 3H), 7.30 (d, J = 1.1 Hz, 1H), 2.77 (d, J = 7.3 Hz, 2H), 1.48-1.35 (m, 1H), 0.57 (d, J = 6.6 Hz, 6H). LCMS m/z 428.29 [M + H]⁺. |

TABLE 17-continued

Method of preparation, structure, physicochemical data for compounds 260-277

| Compound | Structure | Method | $^1$H NMR; LCMS m/z [M + H]$^+$ |
|---|---|---|---|
| 271 | 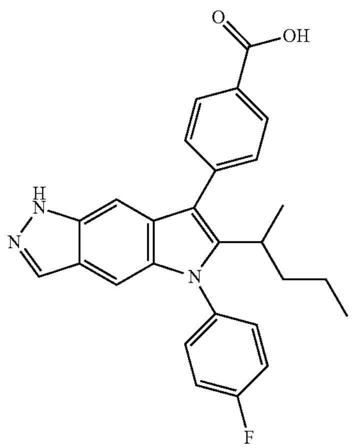 [SMILES: CCCC(C)c1c(-c2ccc(C(=O)O)cc2)c2cc3[nH]ncc3cc2n1-c1ccc(F)cc1] | As from compound 125. Larock Method from C117 | $^1$H NMR (300 MHz, DMSO-d$_6$) δ 12.95 (s, 1H), 12.57 (s, 1H), 8.16-8.04 (m, 2H), 7.99 (d, J = 1.0 Hz, 1H), 7.66-7.45 (m, 6H), 7.28 (t, J = 1.1 Hz, 1H), 7.06 (d, J = 1.1 Hz, 1H), 3.07-2.91 (m, 1H), 1.45-1.22 (m, 2H), 1.19 (d, J = 7.2 Hz, 3H), 1.06 (p, J = 7.2 Hz, 2H), 0.61 (t, J = 7.3 Hz, 3H). LCMS m/z 442.33 [M + H]$^+$. |
| 272 | 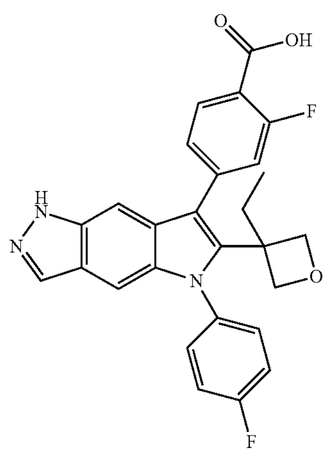 [SMILES: CCC1(c2c(-c3ccc(C(=O)O)c(F)c3)c3cc4[nH]ncc4cc3n2-c2ccc(F)cc2)COC1] | Suzuki Method. As for compounds 107-111. | $^1$H NMR (400 MHz, Methanol-d$_4$) δ 8.05 (t, J = 7.9 Hz, 1H), 7.97 (d, J = 1.1 Hz, 1H), 7.50 (m, 2H), 7.42 (t, J = 1.1 Hz, 1H), 7.40-7.33 (m, 3H), 7.30 (m, 1H), 7.04 (d, J = 1.1 Hz, 1H), 4.74 (d, J = 5.8 Hz, 2H), 3.90 (d, J = 5.8 Hz, 2H), 2.18 (q, J = 7.4 Hz, 2H), 1.17 (t, J = 7.4 Hz, 3H). LCMS m/z 474.24 [M + H]$^+$. |
| 273 | 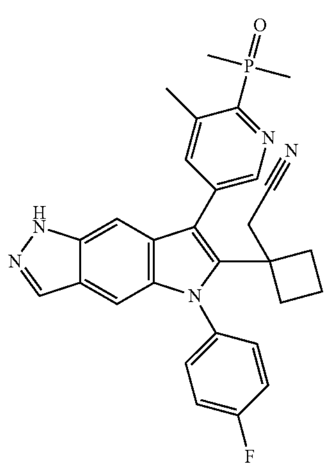 [SMILES: Cc1cc(-c2c(C3(CC#N)CCC3)n(-c3ccc(F)cc3)c3cc4cn[nH]c4cc23)cnc1P(C)(C)=O] | As from compound 125. Larock Method from C117 | $^1$H NMR (400 MHz, Methanol-d$_4$) δ 8.84 (m, 1H), 8.05 (d, J = 4.3 Hz, 1H), 7.98 (s, 1H), 7.63-7.51 (m, 2H), 7.44-7.34 (m, 2H), 7.30 (s, 1H), 7.04 (m, 1H), 3.11 (s, 2H), 2.85-2.73 (m, 3H), 2.36 (q, J = 10.8, 10.4 Hz, 2H), 2.01 (q, J = 8.0, 6.4 Hz, 1H), 1.96-1.89 (m, 6H), 1.67 (m, 1H), 1.58 (m, 2H). LCMS m/z 512.24 [M + H]$^+$. |

TABLE 17-continued

Method of preparation, structure, physicochemical data for compounds 260-277

| Compound | Structure | Method | ¹H NMR; LCMS m/z [M + H]⁺ |
|---|---|---|---|
| 274 | 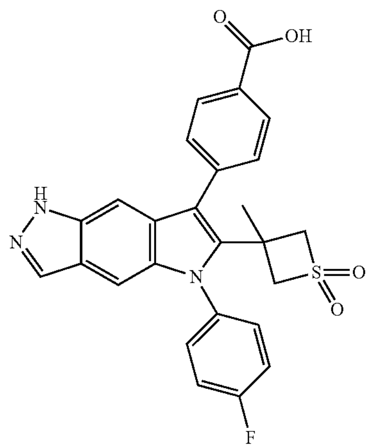 [SMILES: CC1(c2c(-c3ccc(C(=O)O)cc3)c3cc4[nH]ncc4cc3n2-c2ccc(F)cc2)CS(=O)(=O)C1] | As from compound 125. Larock Method from C117 | ¹H NMR (400 MHz, Methanol-d₄) δ 8.29-8.13 (m, 2H), 8.01 (s, 1H), 7.70-7.58 (m, 4H), 7.42 (m, 2H), 7.37 (s, 1H), 7.08 (m, 1H), 4.35-4.22 (m, 2H), 3.44-3.34 (m, 2H), 2.09 (s, 3H). LCMS m/z 490.33 [M + H]⁺. |
| 275 | 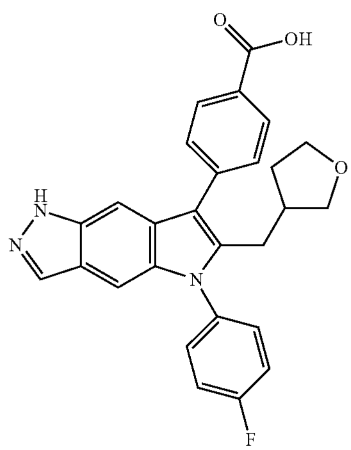 [SMILES: O=C(O)c1ccc(-c2c(CC3CCOC3)n(-c3ccc(F)cc3)c3cc4cn[nH]c4cc23)cc1] | Photoredox method² See footnote | ¹H NMR (300 MHz, DMSO-d₆) δ 12.68 (s, 2H), 8.16-8.07 (m, 2H), 8.04 (d, J = 1.0 Hz, 1H), 7.77-7.70 (m, 2H), 7.70-7.61 (m, 2H), 7.56-7.47 (m, 3H), 7.31 (d, J = 1.1 Hz, 1H), 3.43-3.30 (m, 3H), 3.03-2.91 (m, 3H), 2.05-1.92 (m, 1H), 1.69-1.54 (m, 1H), 1.26-1.13 (m, 1H). LCMS m/z 456.28 [M + H]⁺. |
| 276 | 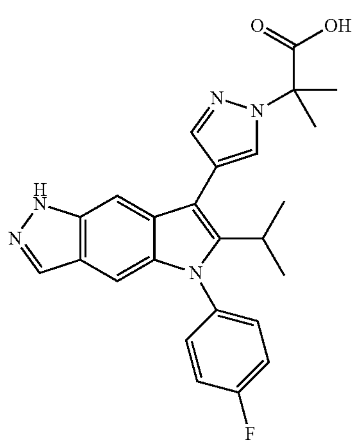 [SMILES: CC(C)c1c(-c2cnn(C(C)(C)C(=O)O)c2)c2cc3[nH]ncc3cc2n1-c1ccc(F)cc1] | Suzuki Method. As for compounds 107-111. | ¹H NMR (400 MHz, Methanol-d₄) δ 7.97-7.93 (m, 1H), 7.92 (m, 1H), 7.65 (m, 1H), 7.45 (m, 2H), 7.40-7.38 (m, 1H), 7.38-7.32 (m, 2H), 7.07 (d, J = 1.2 Hz, 1H), 3.15 (heptet, J = 7.1 Hz, 1H), 1.94 (s, 6H), 1.20 (d, J = 7.1 Hz, 6H). LCMS m/z 446.17 [M + H]⁺. |

TABLE 17-continued

Method of preparation, structure, physicochemical data for compounds 260-277

| Compound | Structure | Method | $^1$H NMR; LCMS m/z [M + H]$^+$ |
|---|---|---|---|
| 277[3] | 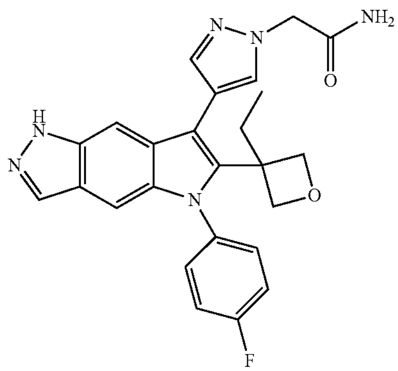 [SMILES: CCC1(c2c(-c3cnn(CC(N)=O)c3)c3cc4[nH]ncc4cc3n2-c2ccc(F)cc2)COC1] | From compound 261. Amide coupling with ammonia. | $^1$H NMR (400 MHz, Methanol-d$_4$) δ 7.96 (d, J = 1.0 Hz, 1H), 7.80 (d, J = 0.7 Hz, 1H), 7.66 (d, J = 0.7 Hz, 1H), 7.50-7.44 (m, 3H), 7.39-7.29 (m, 2H), 7.02 (d, J = 1.1 Hz, 1H), 4.99 (s, 2H), 4.86 (m, 2H), 3.94 (d, J = 5.9 Hz, 2H), 2.15 (q, J = 7.4 Hz, 2H), 1.13 (t, J = 7.5 Hz, 3H). LCMS m/z 459.22 [M + H]$^+$. |

[1]Methyl 4-(3-hydroxy-4-methyl-pent-1-ynyl)benzoate is used as the alkyne in the coupling partner. Route involves an elimination step.
[2]Compound 275 was prepared from methyl 4-[1-(benzenesulfonyl)-6-bromo-5-(4-fluorophenyl)pyrrolo[2,3-f]indazol-7-yl]benzoate and 3-(bromomethyl)tetrahydrofuran by a photoredox coupling reaction, followed by simultaneous removal of the tosyl protecting group and the ester group by treatment with NaOH, Piperidine in THF. Photoredox coupling conditions: Added Bis [2-(2,4-difluorophenyl)-5-trifluoromethylpyridine] iridium hexafluorophosphate (2 mg, 0.002 mmol), 4-tert-butyl-2-(4-tert-butyl-2-pyridyl)pyridine (5 mg, 0.019 mmol) and dichloronickel 1,2-dimethoxyethane (4 mg, 0.01820 mmol) to a vial in a dry box. A mixture of bis(trimethylsilyl)silyl-trimethyl-silane (49 μL, 0.1588 mmol), 2,6-dimethylpyridine (37 μL, 0.3194 mmol), 3-(bromomethyl)tetrahydrofuran (250 mg, 1.515 mmol) and methyl 4-[1-(benzenesulfonyl)-6-bromo-5-(4-fluorophenyl)pyrrolo[2,3-f]indazol-7-yl]benzoate (91 mg, 0.1484 mmol) dissolved in 1,2-dimethoxyethane (2.5 mL) were added to the first vial via syringe under nitrogen. The mixture was irradiated in a Merck Photoreactor at 100% LED power, 4700 RPM fan for 18 hours, then concentrated to dryness under reduced pressure.
[3]HATU reagent was used.

Compounds 278-292

Compounds 278-292 (Table 18) were prepared from S4 as described for the preparation of compounds 18-45.

TABLE 18

Method of preparation, structure and physicochemical data for compounds 278-292

| Compound | Structure | Boronate Reagent | $^1$H NMR; LCMS m/z [M + H]$^+$ |
|---|---|---|---|
| 278 | 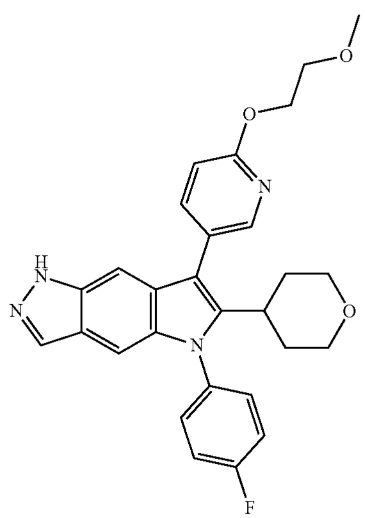 [SMILES: COCCOc1ccc(-c2c(C3CCOCC3)n(-c3ccc(F)cc3)c3cc4cn[nH]c4cc23)cn1] | | $^1$H NMR (400 MHz, Methanol-d$_4$) δ 8.20 (dd, J = 2.4, 0.8 Hz, 1H), 7.97 (d, J = 1.0 Hz, 1H), 7.79 (dd, J = 8.5, 2.4 Hz, 1H), 7.49 (ddt, J = 8.2, 5.6, 2.8 Hz, 2H), 7.45-7.33 (m, 2H), 7.22 (t, J = 1.1 Hz, 1H), 7.13 (d, J = 1.2 Hz, 1H), 6.99 (dd, J = 8.4, 0.8 Hz, 1H), 4.60-4.46 (m, 2H), 3.89-3.73 (m, 4H), 3.46 (s, 3H), 3.20 (td, J = 11.8, 2.2 Hz, 2H), 2.97 (tt, J = 12.0, 3.7 Hz, 1H), 1.77 (qd, J = 12.4, 12.0, 4.3 Hz, 2H), 1.67 (d, J = 12.4 Hz, 2H). LCMS m/z 487.21 [M + H]$^+$. |

TABLE 18-continued

Method of preparation, structure and physicochemical data for compounds 278-292

| Compound | Structure | Boronate Reagent | ¹H NMR; LCMS m/z [M + H]⁺ |
|---|---|---|---|
| 279 | 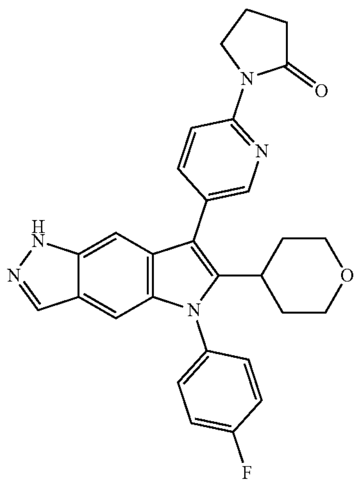 | | ¹H NMR (400 MHz, Methanol-$d_4$) δ 8.48 (dd, J = 8.6, 0.8 Hz, 1H), 8.46 (dd, J = 2.3, 0.8 Hz, 1H), 7.95 (d, J = 1.1 Hz, 1H), 7.90 (dd, J = 8.6, 2.4 Hz, 1H), 7.53-7.46 (m, 2H), 7.37 (m, 2H), 7.25 (t, J = 1.1 Hz, 1H), 7.13 (d, J = 1.1 Hz, 1H), 4.26-4.18 (m, 2H), 3.81 (dd, J = 11.5, 4.0 Hz, 2H), 3.27-3.15 (m, 2H), 3.07-2.90 (m, 1H), 2.72 (m, 2H), 2.22 (p, J = 7.7 Hz, 2H), 1.78 (m, 2H), 1.69 (d, J = 12.9 Hz, 2H). LCMS m/z 496.2 [M + H]⁺. |
| 280 | 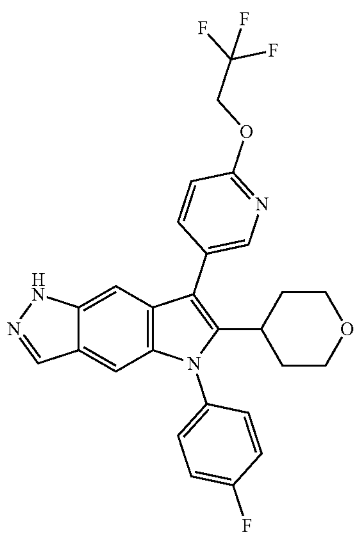 [SMILES: Fc1ccc(-n2c(C3CCOCC3)c(-c3ccc(OCC(F)(F)F)nc3)c3cc4[nH]ncc4cc32)cc1] | | ¹H NMR (400 MHz, Methanol-$d_4$) δ 8.26 (dd, J = 2.4, 0.8 Hz, 1H), 7.97 (d, J = 1.1 Hz, 1H), 7.86 (dd, J = 8.4, 2.4 Hz, 1H), 7.55-7.46 (m, 2H), 7.43-7.35 (m, 2H), 7.22 (t, J = 1.1 Hz, 1H), 7.13 (d, J = 1.1 Hz, 1H), 7.08 (dd, J = 8.4, 0.8 Hz, 1H), 4.96 (q, J = 8.8 Hz, 2H), 3.89-3.70 (m, 2H), 3.20 (td, J = 11.7, 2.3 Hz, 2H), 2.97 (tt, J = 12.0, 3.8 Hz, 1H), 1.76 (gd, J = 12.2, 11.7, 4.2 Hz, 2H), 1.68 (d, J = 13.1 Hz, 2H). LCMS m/z 511.19 [M + H]⁺. |
| 281 | 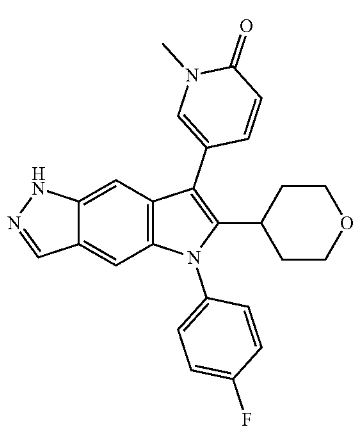 | | ¹H NMR (400 MHz, Methanol-$d_4$) δ 7.97 (d, J = 1.1 Hz, 1H), 7.79 (d, J = 2.4 Hz, 1H), 7.65 (dd, J = 9.1, 2.5 Hz, 1H), 7.48 (m, 2H), 7.43-7.36 (m, 2H), 7.30 (t, J = 1.1 Hz, 1H), 7.13 (d, J = 1.1 Hz, 1H), 6.73 (dd, J = 9.2, 0.6 Hz, 1H), 3.95-3.78 (m, 2H), 3.70 (s, 3H), 3.24 (td, J = 11.8, 2.0 Hz, 2H), 2.97 (tt, J = 12.1, 3.6 Hz, 1H), 1.84 (qd, J = 12.5, 4.3 Hz, 2H), 1.76- |

TABLE 18-continued

Method of preparation, structure and physicochemical data for compounds 278-292

| Compound | Structure | Boronate Reagent | ¹H NMR; LCMS m/z [M + H]⁺ |
|---|---|---|---|
| | | | 1.63 (m, 2H). LCMS m/z 443.19 [M + H]⁺. |
| 282 | 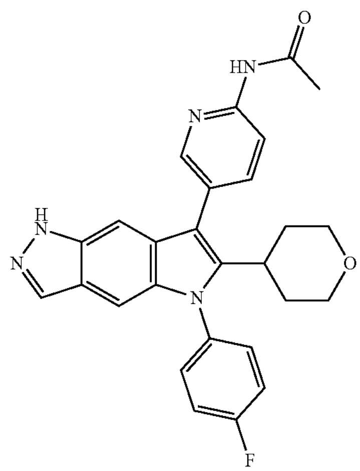 [SMILES: CC(=O)Nc1ccc(-c2c(C3CCOCC3)n(-c3ccc(F)cc3)c3cc4cn[nH]c4cc23)cn1] | | ¹H NMR (400 MHz, Methanol-d₄) δ 8.40 (dd, J = 2.3, 0.8 Hz, 1H), 8.26 (d, J = 8.5 Hz, 1H), 7.98 (d, J = 1.1 Hz, 1H), 7.89 (dd, J = 8.5, 2.3 Hz, 1H), 7.57-7.47 (m, 2H), 7.40 (t, J = 8.6 Hz, 2H), 7.25 (t, J = 1.1 Hz, 1H), 7.14 (d, J = 1.1 Hz, 1H), 3.81 (dd, J = 11.3, 4.1 Hz, 2H), 3.26-3.16 (m, 2H), 3.07-2.90 (m, 1H), 2.24 (s, 3H), 1.79 (qd, J = 12.3, 11.7, 4.2 Hz, 2H), 1.70 (d, J = 12.9 Hz, 2H). LCMS m/z 470.19 [M + H]⁺. |
| 283 | 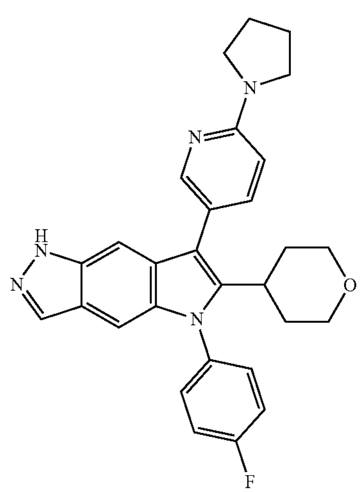 [SMILES: Fc1ccc(-n2c(C3CCOCC3)c(-c3ccc(N4CCCC4)nc3)c3cc4[nH]ncc4cc32)cc1] | | ¹H NMR (400 MHz, Chloroform-d) δ 8.20 (dd, J = 2.4, 0.8 Hz, 1H), 7.94 (d, J = 1.2 Hz, 1H), 7.49 (dd, J = 8.6, 2.3 Hz, 1H), 7.39-7.30 (m, 2H), 7.27 (t, J = 1.1 Hz, 1H), 7.25-7.19 (m, 2H), 7.05 (d, J = 1.1 Hz, 1H), 6.47 (dd, J = 8.7, 0.8 Hz, 1H), 3.88-3.68 (m, 2H), 3.61-3.39 (m, 4H), 3.15 (td, J = 11.8, 1.8 Hz, 2H), 2.86 (tt, J = 12.3, 3.5 Hz, 1H), 2.07-1.91 (m, 4H), 1.79 (qd, J = 12.5, 4.3 Hz, 3H), 1.62-1.45 (m, 2H). LCMS m/z 482.25 [M + H]⁺. |

TABLE 18-continued

Method of preparation, structure and physicochemical data for compounds 278-292

| Compound | Structure | Boronate Reagent | ¹H NMR; LCMS m/z [M + H]⁺ |
|---|---|---|---|
| 284 | 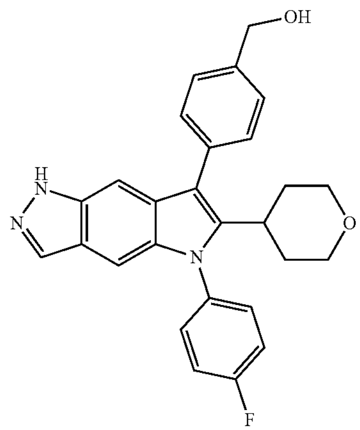 [SMILES: OCc1ccc(-c2c(C3CCOCC3)n(-c3ccc(F)cc3)c3cc4cn[nH]c4cc23)cc1] | | ¹H NMR (400 MHz, Methanol-d₄) δ 7.96 (d, J = 1.1 Hz, 1H), 7.59-7.44 (m, 7H), 7.44-7.33 (m, 2H), 7.23 (t, J = 1.1 Hz, 1H), 7.11 (d, J = 1.2 Hz, 1H), 4.73 (s, 2H), 3.78 (dd, J = 11.6, 4.1 Hz, 2H), 3.23-3.12 (m, 2H), 3.01 (tt, J = 12.2, 3.5 Hz, 1H), 1.83 (dd, J = 12.8, 4.3 Hz, 2H), 1.66 (d, J = 13.0 Hz, 2H). LCMS m/z 442 [M + H]⁺. |
| 285 | 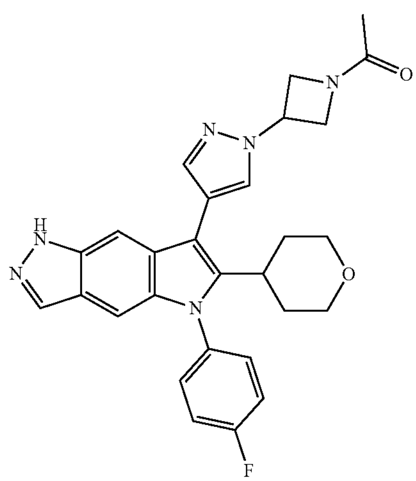 [SMILES: CC(=O)N1CC(n2cc(-c3c(C4CCOCC4)n(-c4ccc(F)cc4)c4cc5cn[nH]c5cc34)cn2)C1] | | ¹H NMR (400 MHz, Methanol-d₄ + CDCl3) δ 7.94 (d, J = 1.0 Hz, 1H), 7.89 (s, 1H), 7.44 (m, 2H), 7.39-7.31 (m, 3H), 7.09 (d, J = 1.2 Hz, 1H), 5.38 (m, 1H), 4.78-4.70 (m, 2H), 4.59-4.50 (m, 1H), 4.46 (dd, J = 10.6, 5.5 Hz, 1H), 3.85 (dd, J = 11.7, 4.1 Hz, 2H), 3.25 (m, 2H), 3.01 (m, 1H), 1.98 (s, 3H), 1.96-1.82 (m, 2H), 1.67 (d, J = 13.1 Hz, 2H). LCMS m/z 499.31 [M + H]⁺. |
| 286 | 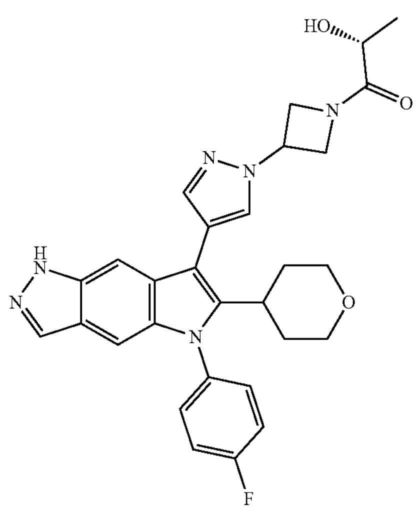 [SMILES: C[C@@H](O)C(=O)N1CC(n2cc(-c3c(C4CCOCC4)n(-c4ccc(F)cc4)c4cc5cn[nH]c5cc34)cn2)C1] | | ¹H NMR (400 MHz, Methanol-d₄) δ 7.96 (d, J = 1.0 Hz, 1H), 7.94 (d, J = 0.9 Hz, 1H), 7.78 (d, J = 0.8 Hz, 1H), 7.50-7.43 (m, 2H), 7.42-7.33 (m, 3H), 7.10 (d, J = 1.2 Hz, 1H), 5.43 (tq, J = 8.1, 5.3 Hz, 1H), 4.94 (m, 1H), 4.87-4.79 (m, 1H), 4.63-4.43 (m, 2H), 4.41-4.30 (m, 1H), 3.92-3.76 (m, 2H), 3.28-3.19 (m, 2H), 3.02 (tt, J = 12.3, 3.5 Hz, 1H), 1.90 (qd, J = 12.6, 4.3 Hz, 2H), 1.68 (d, J = 12.9 Hz, 2H), 1.40 (d, J = 6.8 Hz, 3H). LCMS m/z 529.38 [M + H]⁺. |

TABLE 18-continued

Method of preparation, structure and physicochemical data for compounds 278-292

| Compound | Structure | Boronate Reagent | $^1$H NMR; LCMS m/z [M + H]$^+$ |
|---|---|---|---|
| 287 | 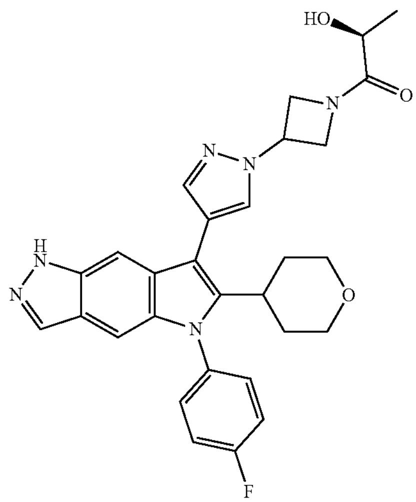 [SMILES: C[C@H](O)C(=O)N1CC(n2cc(-c3c(C4CCOCC4)n(-c4ccc(F)cc4)c4cc5cn[nH]c5cc34)cn2)C1] | | $^1$H NMR (400 MHz, Methanol-d$_4$) δ 7.96 (d, J = 1.1 Hz, 1H), 7.95 (d, J = 0.8 Hz, 1H), 7.78 (d, J = 1.1 Hz, 1H), 7.47 (m, 2H), 7.42-7.33 (m, 3H), 7.10 (d, J = 1.1 Hz, 1H), 5.51-5.35 (m, 1H), 4.94 (m, 1H), 4.83 (m, 1H), 4.65-4.43 (m, 2H), 4.36 (q, J = 6.8 Hz, 1H), 3.84 (dd, J = 11.6, 4.0 Hz, 2H), 3.28-3.21 (m, 2H), 3.02 (m, 1H), 1.90 (qd, J = 12.6, 4.3 Hz, 2H), 1.68 (d, J = 12.4 Hz, 2H), 1.40 (d, J = 6.8 Hz, 3H). LCMS m/z 529.38 [M + H]$^+$. |
| 288 | 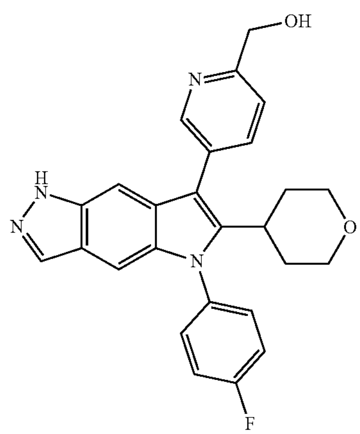 [SMILES: OCc1ccc(-c2c(C3CCOCC3)n(-c3ccc(F)cc3)c3cc4cn[nH]c4cc23)cn1] | | $^1$H NMR (400 MHz, Methanol-d$_4$) δ 8.63-8.56 (m, 1H), 8.06-7.95 (m, 2H), 7.75 (d, J = 7.9 Hz, 1H), 7.58-7.49 (m, 2H), 7.41 (dd, J = 9.3, 8.0 Hz, 2H), 7.24 (t, J = 1.1 Hz, 1H), 7.15 (d, J = 1.1 Hz, 1H), 4.84 (s, 2H), 3.80 (dd, J = 11.1, 3.8 Hz, 2H), 3.35 (s, 1H), 3.21 (td, J = 11.5, 2.8 Hz, 2H), 3.01 (tt, J = 11.4, 4.2 Hz, 1H), 1.74 (dd, J = 11.3, 3.8 Hz, 3H). LCMS m/z 443 [M + H]$^+$. |
| 289 | 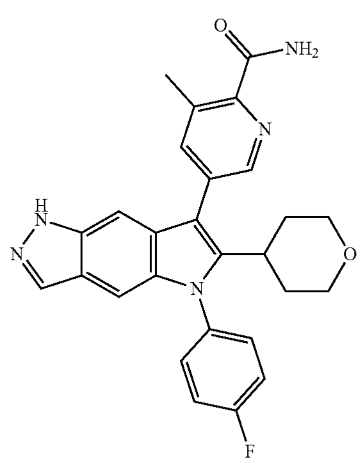 [SMILES: Cc1cc(-c2c(C3CCOCC3)n(-c3ccc(F)cc3)c3cc4cn[nH]c4cc23)cnc1C(N)=O] | | $^1$H NMR (400 MHz, DMSO-d$_6$) δ 12.62 (s, 1H), 8.55 (d, J = 2.0 Hz, 1H), 8.19-8.08 (m, 1H), 8.02 (s, 1H), 7.89 (d, J = 2.0 Hz, 1H), 7.62 (m, 2H), 7.58-7.47 (m, 3H), 7.24 (s, 1H), 7.10 (s, 1H), 3.83-3.67 (m, 2H), 3.18-3.06 (m, 2H), 2.99 (m, 1H), 2.67 (s, 3H), 1.66 (m, 4H). LCMS m/z 470.37 [M + H]$^+$. |

TABLE 18-continued

Method of preparation, structure and physicochemical data for compounds 278-292

| Compound | Structure | Boronate Reagent | ¹H NMR; LCMS m/z [M + H]⁺ |
|---|---|---|---|
| 290 | 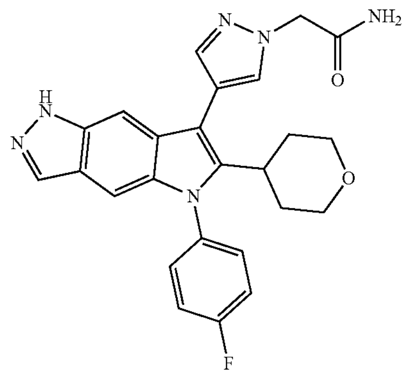 [SMILES: NC(=O)Cn1cc(-c2c(C3CCOCC3)n(-c3ccc(F)cc3)c3cc4cn[nH]c4cc23)cn1] | | ¹H NMR (400 MHz, DMSO-d$_6$) δ 12.64 (s, 1H), 7.98 (s, 1H), 7.94 (s, 1H), 7.64 (s, 1H), 7.60-7.53 (m, 3H), 7.49 (t, J = 8.6 Hz, 2H), 7.38 (s, 1H), 7.32 (s, 1H), 7.03 (s, 1H), 3.86-3.66 (m, 2H), 3.17 (t, J = 11.5 Hz, 2H), 3.10-2.95 (m, 1H), 1.74 (dd, J = 14.1, 10.1 Hz, 2H), 1.63 (d, J = 12.8 Hz, 2H). LCMS m/z 459.35 [M + H]⁺. |
| 291[1] | 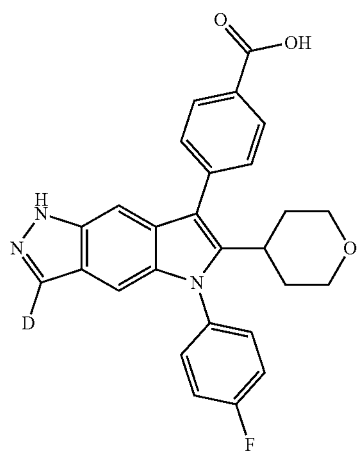 [SMILES: [2H]c1n[nH]c2cc3c(-c4ccc(C(=O)O)cc4)c(C4CCOCC4)n(-c4ccc(F)cc4)c3cc12] | See footnote 1 | ¹H NMR (300 MHz, DMSO-d$_6$) δ 13.12-12.82 (bs, 1H), 12.57 (s, 1H), 8.17-8.05 (m, 2H), 7.71-7.57 (m, 4H), 7.57-7.44 (m, 2H), 7.26 (d, J = 1.2 Hz, 1H), 7.07 (d, J = 1.1 Hz, 1H), 3.73 (d, J = 11.0 Hz, 2H), 3.18-2.93 (m, 3H), 1.77-1.56 (m, 4H). LCMS m/z 457.36 [M + H]⁺. |
| 292 | 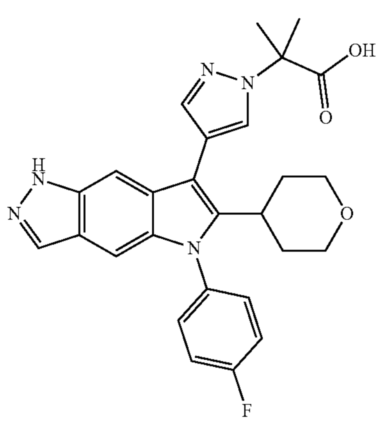 [SMILES: CC(C)(C(=O)O)n1cc(-c2c(C3CCOCC3)n(-c3ccc(F)cc3)c3cc4cn[nH]c4cc23)cn1] | | ¹H NMR (400 MHz, Methanol-d$_4$) δ 7.93 (d, J = 1.0 Hz, 1H), 7.84 (m, 1H), 7.65 (m, 1H), 7.42 (m, 2H), 7.39 (t, J = 1.1 Hz, 1H), 7.36-7.29 (m, 2H), 7.08 (d, J = 1.1 Hz, 1H), 3.85 (dd, J = 11.5, 4.1 Hz, 2H), 3.29-3.18 (m, 2H), 3.00 (tt, J = 12.3, 3.5 Hz, 1H), 1.95 (s, 6H), 1.88 (qd, J = 12.6, 4.3 Hz, 2H), 1.66 (d, J = 12.6 Hz, 2H). LCMS m/z 488.21 [M + H]⁺. |

[1]Compound 291 was prepared from compound 33. A solution of compound 33 (100 mg) in MeOD (14 mL) was treated with NaH. The mixture was sealed in a vial and heated at 70° C. for 3 days. The mixture was concentrated, diluted with DMSO-D6 (3 mL) and D$_2$O (0.25 mL) and injected on a C18 column. Purification by reversed-phase chromatography (Column: C18. Gradient: 1 0-100% MeCN in water with 0.1% formic acid) afforded the product.

Compounds 293 and 294

(2S,3S,4S,5R)-6-(7-(4-carboxyphenyl)-5-(4-fluorophenyl)-6-(tetrahydro-2H-pyran-4-yl)pyrrolo[2,3-f]indazol-2(5H)-yl)-3,4,5-trihydroxytetrahydro-2H-6l3-pyran-2-carboxylic Acid (293) and (2S,3S,4S,5R)-6-(7-(4-carboxyphenyl)-5-(4-fluorophenyl)-6-(tetrahydro-2H-pyran-4-yl)pyrrolo[2,3-f]indazol-1(5H)-yl)-3,4,5-trihydroxytetrahydro-2H-6l3-pyran-2-carboxylic Acid (294)

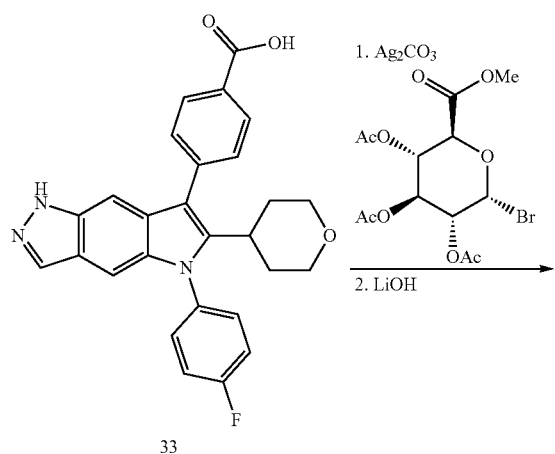

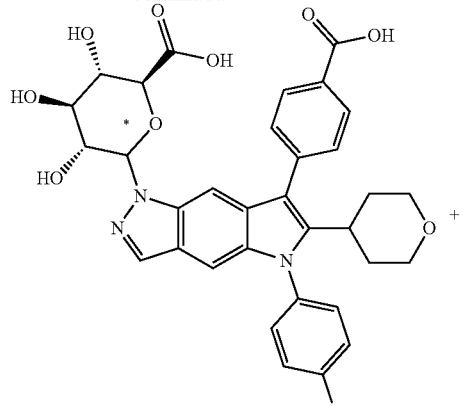

294
Minor

Benzene (11 mL) was added to a mixture of methyl (2S,3S,4S,5R,6R)-3,4,5-triacetoxy-6-bromo-tetrahydropyran-2-carboxylate (1.13 g, 2.845 mmol), 4-[5-(4-fluorophenyl)-6-tetrahydropyran-4-yl-1H-pyrrolo[2,3-f]indazol-7-yl]benzoic acid 33 (281 mg, 0.62 mmol), and Ag₂O₃ (851 mg, 3.09 mmol). The mixture was stirred overnight at 70° C. in a sealed vial under nitrogen. The mixture was concentrated to dryness. Methanol (11 mL) and THF (11 mL) were added and then a solution of LiOH (3.1 mL of 2 M, 6.2 mmol). The mixture was stirred overnight at room temperature. The mixture was filtered through a pad of Celite® and washed the plug with additional THF and Methanol. The reaction mixture was concentrated to dryness under reduced pressure.

The mixture was diluted with ~8 mL of DMSO:water (3:1) and injected on a C18 150 g column. Purification by reversed-phase chromatography (Column: C18. Gradient: 10-45% acetonitrile in water, then isocratic at 45% MeCN in water until the compound elutes and finally 100% ACN all with 0.1% formic acid) afforded two peaks. The first eluting peak corresponded to compound 293 and the second eluting peak corresponded to compound 294.

Compound 293 (peak 1) (2S,3S,4S,5R)-6-(7-(4-carboxyphenyl)-5-(4-fluorophenyl)-6-(tetrahydro-2H-pyran-4-yl)pyrrolo[2,3-f]indazol-2(5H)-yl)-3,4,5-trihydroxytetrahydro-2H-6l3-pyran-2-carboxylic acid 293 (167.0 mg, 42%). $^1$H NMR (300 MHz, DMSO-$d_6$) δ 12.94 (s, 2H), 8.45 (s, 1H), 8.18-8.05 (m, 2H), 7.72-7.58 (m, 4H), 7.52 (t, J=8.7 Hz, 2H), 7.46-7.38 (m, 1H), 6.97 (d, J=1.3 Hz, 1H), 5.60 (d, J=9.2 Hz, 1H), 5.53-5.21 (m, 3H), 4.06-3.84 (m, 2H), 3.82-3.64 (m, 2H), 3.59-3.37 (m, 2H), 3.20-3.05 (m, 2H), 3.05-2.91 (m, 1H), 1.77-1.53 (m, 4H). LCMS m/z 632.36 [M+H]⁺.

Compound 294 (peak 2) (2S,3S,4S,5R)-6-(7-(4-carboxyphenyl)-5-(4-fluorophenyl)-6-(tetrahydro-2H-pyran-4-yl)pyrrolo[2,3-f]indazol-1(5H)-yl)-3,4,5-trihydroxytetrahydro-2H-6l3-pyran-2-carboxylic acid 294 (7.1 mg, 2%). $^1$H NMR (300 MHz, DMSO-$d_6$) δ 13.12-12.7 (bs, 2H), 8.18-8.07 (m, 3H), 7.70-7.57 (m, 4H), 7.57-7.46 (m, 3H), 7.13-7.08 (m, 1H), 5.79 (d, J=8.9 Hz, 1H), 5.25-4.96 (m, 3H), 4.03 (d, J=8.0 Hz, 2H), 3.72 (d, J=10.9 Hz, 2H), 3.45 (s, 2H), 3.10 (s, 3H), 1.65 (s, 4H). LCMS m/z 632.36 [M+H]⁺.

Compounds 295-297

Compounds 295-297 were prepared as described in Table 19 with modifications noted in the footnotes.

TABLE 19

Method of preparation, structure and physicochemical data for compounds 295-297

| Compound | Structure | Method | $^1$H NMR; LCMS m/z [M + H]$^+$ |
|---|---|---|---|
| 295[1] | 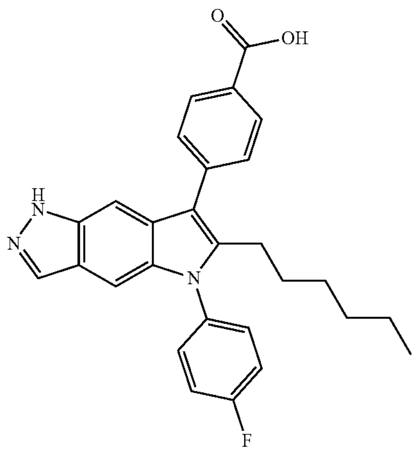 [SMILES: CCCCCCc1c(-c2ccc(C(=O)O)cc2)c2cc3[nH]ncc3cc2n1-c1ccc(F)cc1] | As for compound 255. Larock method from C190. | $^1$H NMR (300 MHz, DMSO-d$_6$) δ 12.90 (s, 1H), 12.64 (s, 1H), 8.17-8.06 (m, 2H), 8.02 (d, J = 1.0 Hz, 1H), 7.73-7.67 (m, 2H), 7.67-7.59 (m, 2H), 7.58-7.55 (m, 1H), 7.50 (t, J = 8.7 Hz, 2H), 7.27 (d, J = 1.1 Hz, 1H), 2.80 (t, J = 7.8 Hz, 2H), 1.35-1.20 (m, 2H), 1.09-0.87 (m, 6H), 0.74-0.64 (m, 3H). LCMS m/z 456.33 [M + H]$^+$. |
| 296 | 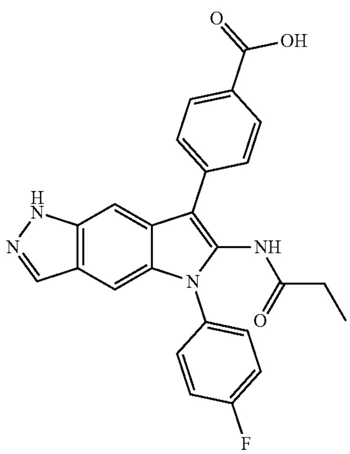 [SMILES: CCC(=O)Nc1c(-c2ccc(C(=O)O)cc2)c2cc3[nH]ncc3cc2n1-c1ccc(F)cc1] | See footnote 2 | $^1$H NMR (300 MHz, DMSO-d$_6$) δ 12.77 (s, 2H), 9.98 (s, 1H), 8.13-8.01 (m, 3H), 7.84-7.70 (m, 3H), 7.57-7.39 (m, 5H), 2.12 (q, J = 7.6 Hz, 2H), 0.89 (t, J = 7.6 Hz, 3H). LCMS m/z 443.28 [M + H]$^+$. |
| 297 | 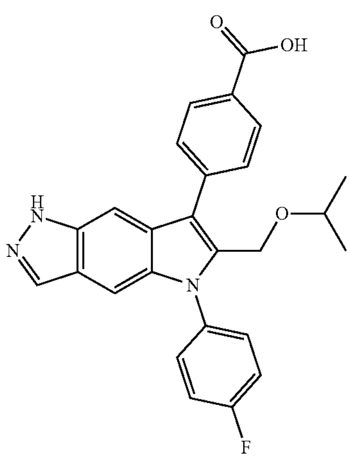 [SMILES: CC(C)OCc1c(-c2ccc(C(=O)O)cc2)c2cc3[nH]ncc3cc2n1-c1ccc(F)cc1] | See footnote 3 | LCMS m/z 444.19 [M + H]$^+$. |

[1] Methyl 4-(3-hydroxyoct-1-ynyl)benzoate was used as the alkyne in the Larock indole cyclization. A reduction step using Et$_3$SiH and NaI was applied prior to treatment with NaOH. See compound 176 for an analogous method.
[2] Prepared from Buchwald amination of methyl 4-[1-(benzenesulfonyl)-6-bromo-5-(4-fluorophenyl)pyrrolo[2,3-f]indazol-7-yl]benzoate with propenamide. Conditions: XantPhos Pd G3, Cs$_2$CO$_3$ in 1,4-dioxane at 110° C. Methyl 4-[1-(benzenesulfonyl)-6-bromo-5-(4-fluorophenyl)pyrrolo[2,3-f]indazol-7-yl]benzoate was prepared in an analogous fashion to C149.
[3] Compound 297 was prepared by Larock cyclization between 6-bromo-N-(4-fluorophenyl)-1-tetrahydropyran-2-yl-indazol-5-amine and ethyl 4-(3-hydroxyprop-1-ynyl)benzoate. The resulting intermediate ethyl 4-[5-(4-fluorophenyl)-6-(hydroxymethyl)-1-tetrahydropyran-2-yl-pyrrolo[2,3-f]indazol-7-yl]benzoate was alkylated with iodopropane. Ester hydrolysis with NaOH, followed by treatment with HCl to remove the THP protecting group afford compound 297.

Compound 298

4-[5-benzyl-6-(2-cyano-1,1-dimethyl-ethyl)-1H-pyrrolo[2,3-f]indazol-7-yl]benzoic Acid (298)

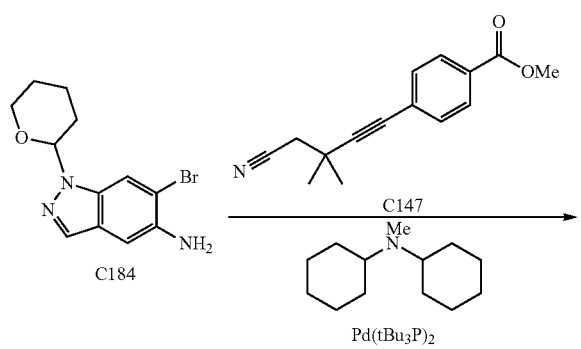

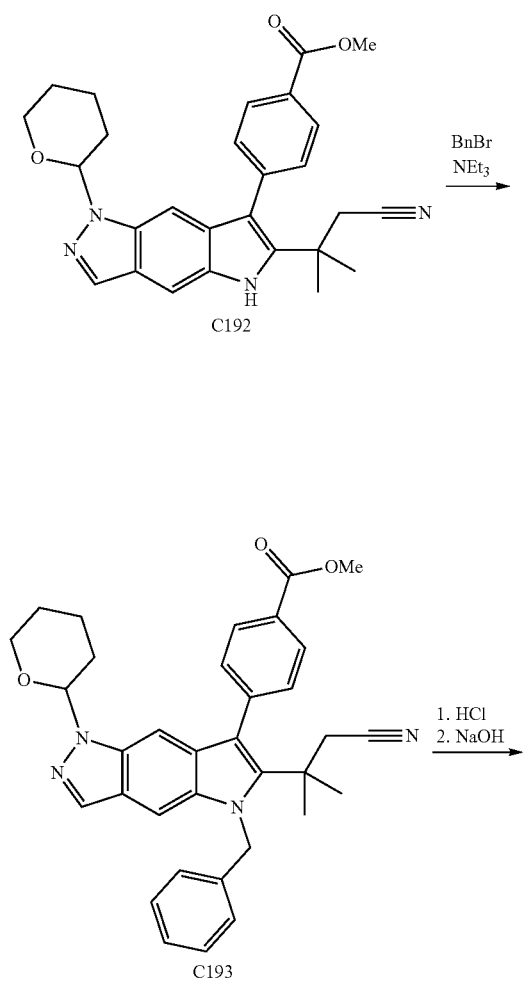

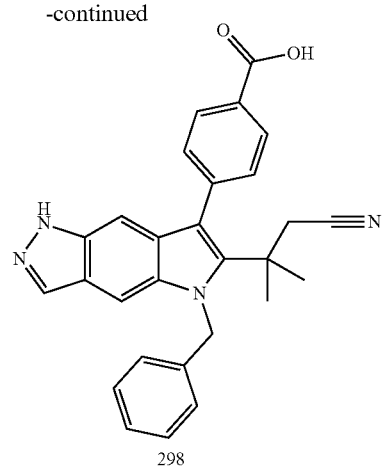

Step 1. Methyl 4-[6-(2-cyano-1,1-dimethyl-ethyl)-1-tetrahydropyran-2-yl-5H-pyrrolo[2,3-f]indazol-7-yl]benzoate (C192)

6-bromo-1-tetrahydropyran-2-yl-indazol-5-amine (674 mg, 2.119 mmol), methyl 4-(4-cyano-3,3-dimethyl-but-1-ynyl)benzoate (1.00 g, 4.1 mmol), Pd(PtBu$_3$)$_2$ (110 mg, 0.22 mmol) were suspended in 1,4-dioxane (13 mL). Then, N-cyclohexyl-N-methyl-cyclohexanamine (1.2 mL, 5.6 mmol) was added. The reaction was heated at 85° C. for 18 h and under nitrogen. Water and CH$_2$Cl$_2$ were added. The mixture was extracted with CH$_2$Cl$_2$ (3×). The organic phases were passed through a phase separator, combined and concentrated in vacuo. The crude was purified by flash column chromatography (12 g silica gel, 0-3% of MeOH in CH$_2$Cl$_2$). A light brown solid was obtained, methyl 4-[6-(2-cyano-1,1-dimethyl-ethyl)-1-tetrahydropyran-2-yl-5H-pyrrolo[2,3-f]indazol-7-yl]benzoate (776.0 mg, 76%). $^1$H NMR (400 MHz, DMSO-d$_6$) δ 11.01 (s, 1H), 8.11 (d, J=0.9 Hz, 1H), 8.10-8.06 (m, 2H), 7.69 (d, J=1.1 Hz, 1H), 7.64-7.50 (m, 2H), 7.04 (s, 1H), 5.70 (m, 1H), 3.91 (s, 3H), 3.74 (m, 1H), 3.59 (m, 1H), 2.90 (s, 2H), 2.40 (m, 1H), 1.98 (m, 1H), 1.87 (m, 1H), 1.71 (m, 1H), 1.49 (m, 2H), 1.38 (m, 6H). LCMS m/z 457.28 [M+H]$^+$.

Step 2. methyl 4-[5-benzyl-6-(2-cyano-1,1-dimethyl-ethyl)-1-tetrahydropyran-2-yl-pyrrolo[2,3-f]indazol-7-yl]benzoate (C193)

Methyl 4-[6-(2-cyano-1,1-dimethyl-ethyl)-1-tetrahydropyran-2-yl-5H-pyrrolo[2,3-f]indazol-7-yl]benzoate (20 mg, 0.042 mmol) was dissolved in DMF (208.1 μL). Then, Et$_3$N (9 μL, 0.065 mmol) was added, followed by benzyl bromide (7.5 μL, 0.063 mmol) and the reaction was stirred for 90 minutes at room temperature. This mixture was advanced to the next step without further purification.

Step 3. Synthesis of 4-[5-benzyl-6-(2-cyano-1,1-dimethyl-ethyl)-1H-pyrrolo[2,3-f]indazol-7-yl]benzoic Acid (298)

Part A: To a solution of methyl 4-[5-benzyl-6-(2-cyano-1,1-dimethyl-ethyl)-1-tetrahydropyran-2-yl-pyrrolo[2,3-f]indazol-7-yl]benzoate C193 (40 mg, 0.073 mmol) in DMF (0.4 mL) was added a solution of HCl (200 μL of 4 M, 0.8 mmol) in dioxane. The mixture was stirred for approximately two weeks. Water and CH₂Cl₂ were added. The mixture was extracted with CH₂Cl₂ (3×). The organic phases were passed through a phase separator, combined and concentrated in vacuo to afford methyl 4-[5-benzyl-6-(2-cyano-1,1-dimethyl-ethyl)-1H-pyrrolo[2,3-f]indazol-7-yl]benzoate. LCMS m/z 463.35 [M+H]⁺.

Part B: Methyl 4-[5-benzyl-6-(2-cyano-1,1-dimethyl-ethyl)-1H-pyrrolo[2,3-f]indazol-7-yl]benzoate was suspended in EtOH (0.3 mL) and an aqueous solution of NaOH (100 μL of 2 M, 0.20 mmol) was added. The mixture was heated at 60° C. for 48 h. Aqueous HCl 1.0 M and CH₂Cl₂ were added. The mixture was extracted with CH₂Cl₂ (3×). The organic phases were passed through a phase separator, combined, and concentrated in vacuo. Purification by reversed-phase HPLC. Method: C18 Waters Sunfire column (30×150 mm, 5 micron). Gradient: MeCN in H₂O with 0.1% trifluoroacetic acid afford the products as a white solid. 4-[5-benzyl-6-(2-cyano-1,1-dimethyl-ethyl)-1H-pyrrolo[2,3-f]indazol-7-yl]benzoic acid (Trifluoroacetate salt) (6.1 mg, 15%). ¹H NMR (400 MHz, Methanol-d₄) δ 8.20-8.10 (m, 2H), 8.04 (d, J=1.1 Hz, 1H), 7.66-7.55 (m, 2H), 7.40 (d, J=1.2 Hz, 1H), 7.34-7.25 (m, 2H), 7.26-7.18 (m, 1H), 7.04-6.93 (m, 3H), 5.80 (s, 2H), 2.86 (s, 2H), 1.47 (s, 6H). LCMS m/z 449.33 [M+H]⁺.

Compounds 299-305

Compounds 299-305 (Table 20) were made according to the route described for compound 298 using various alkylating agents for alkylation of intermediate C192.

TABLE 20

Method of preparation, structure and physicochemical data for compounds 299-305

| Compound | Structure | Alkylating Agent | ¹H NMR; LCMS m/z [M + H]⁺ |
|---|---|---|---|
| 299 | 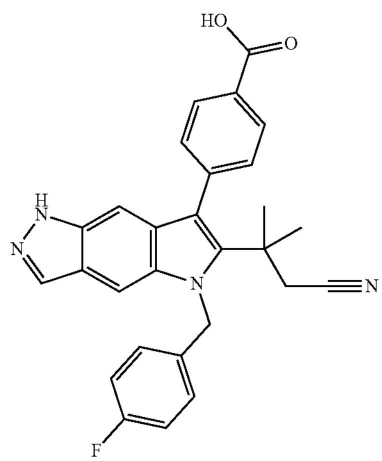 [SMILES: CC(C)(CC#N)c1c(-c2ccc(C(=O)O)cc2)c2cc3[nH]ncc3cc2n1Cc1ccc(F)cc1] | | ¹H NMR (400 MHz, Methanol-d₄) δ 8.18-8.12 (m, 2H), 8.03 (d, J = 1.1 Hz, 1H), 7.64-7.57 (m, 2H), 7.40 (d, J = 1.2 Hz, 1H), 7.11-6.92 (m, 5H), 5.79 (s, 2H), 2.87 (s, 2H), 1.47 (s, 6H). LCMS m/z 467.3 [M + H]⁺. |
| 300 | 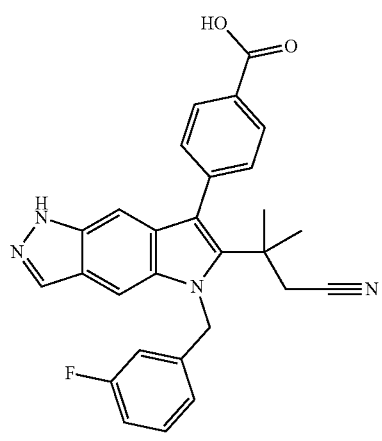 [SMILES: CC(C)(CC#N)c1c(-c2ccc(C(=O)O)cc2)c2cc3[nH]ncc3cc2n1Cc1cccc(F)c1] | | ¹H NMR (400 MHz, Methanol-d₄) δ 8.21-8.07 (m, 2H), 7.98 (d, J = 1.1 Hz, 1H), 7.66-7.58 (m, 2H), 7.38 (d, J = 1.2 Hz, 1H), 7.30 (m, 1H), 7.01-6.92 (m, 2H), 6.80 (d, J = 7.9 Hz, 1H), 6.73 (d, J = 9.8 Hz, 1H), 5.81 (s, 2H), 2.87 (s, 2H), 1.47 (s, 6H). LCMS m/z 467.34 [M + H]⁺. |

TABLE 20-continued

Method of preparation, structure and physicochemical data for compounds 299-305

| Compound | Structure | Alkylating Agent | ¹H NMR; LCMS m/z [M + H]⁺ |
|---|---|---|---|
| 301 | 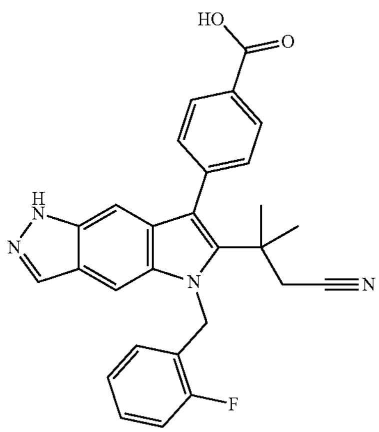 [SMILES: CC(C)(CC#N)c1c(-c2ccc(C(=O)O)cc2)c2cc3[nH]ncc3cc2n1Cc1ccccc1F] | 2-fluorobenzyl bromide | ¹H NMR (400 MHz, Methanol-d₄) δ 8.22-8.10 (m, 2H), 7.96 (d, J = 1.0 Hz, 1H), 7.66-7.55 (m, 2H), 7.38 (d, J = 1.1 Hz, 1H), 7.27 (m, 1H), 7.20 (m, z 1H), 6.97 (t, J = 1.2 Hz, 1H), 6.97-6.90 (m, 1H), 6.41 (td, J = 7.8, 1.6 Hz, 1H), 5.80 (s, 2H), 2.85 (s, 2H), 1.46 (s, 6H); ¹H NMR (400 MHz, Methanol-d₄) δ 8.20-8.10 (m, 2H), 7.98 (d, J = 1.1 Hz, 1H), 7.68-7.57 (m, 2H), 7.40 (d, J = 1.2 Hz, 1H), 7.33-7.24 (m, 1H), 7.20 (ddd, J = 10.5, 8.3, 1.2 Hz, 1H), 6.99-6.92 (m, 2H), 6.46-6.37 (m, 1H), 5.82 (s, 2H), 2.86 (s, 2H), 1.47 (s, 6H). LCMS m/z 467.315 [M + H]⁺. |
| 302 | 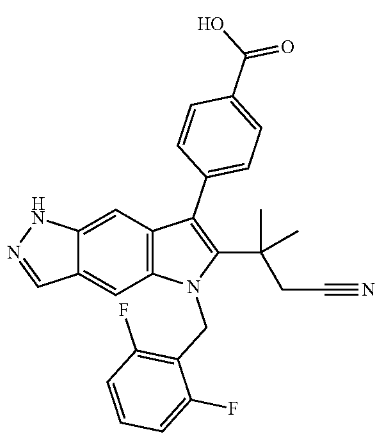 [SMILES: CC(C)(CC#N)c1c(-c2ccc(C(=O)O)cc2)c2cc3[nH]ncc3cc2n1Cc1c(F)cccc1F] | 2,6-difluorobenzyl bromide | ¹H NMR (400 MHz, Methanol-d₄) δ 8.21-8.09 (m, 2H), 7.96 (d, J = 1.1 Hz, 1H), 7.63-7.54 (m, 2H), 7.38-7.25 (m, 2H), 6.99-6.88 (m, 3H), 5.87 (s, 2H), 2.99 (s, 2H), 1.55 (s, 6H). LCMS m/z 485.44 [M + H]⁺. |
| 303 | 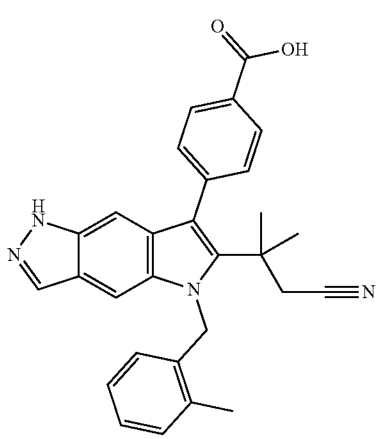 [SMILES: Cc1ccccc1Cn1c(C(C)(C)CC#N)c(-c2ccc(C(=O)O)cc2)c2cc3[nH]ncc3cc21] | 2-methylbenzyl bromide | ¹H NMR (400 MHz, Methanol-d₄) δ 8.19-8.10 (m, 2H), 7.96 (d, J = 1.1 Hz, 1H), 7.67-7.57 (m, 2H), 7.31 (d, J = 1.1 Hz, 1H), 7.27 (d, J = 7.5 Hz, 1H), 7.13 (td, J = 7.5, 1.3 Hz, 1H), 6.97 (t, J = 1.1 Hz, 1H), 6.94 (dd, J = 8.1, 6.9 Hz, 1H), 6.29-6.19 (m, 1H), 5.68 (s, 2H), 2.84 (s, 2H), 2.54 (s, 3H), 1.45 (s, 6H). LCMS m/z 463.41 [M + H]⁺. |

TABLE 20-continued

Method of preparation, structure and physicochemical data for compounds 299-305

| Compound | Structure | Alkylating Agent | ¹H NMR; LCMS m/z [M + H]⁺ |
|---|---|---|---|
| 304 | 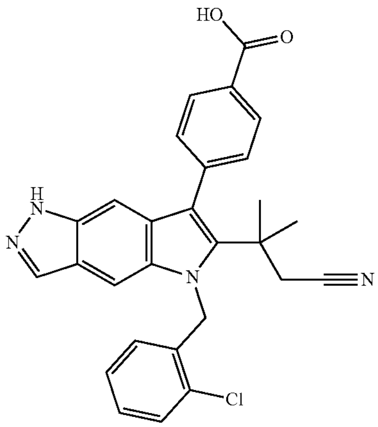 [SMILES: CC(C)(CC#N)c1c(-c2ccc(C(=O)O)cc2)c2cc3[nH]ncc3cc2n1Cc1ccccc1Cl] | | ¹H NMR (400 MHz, Methanol-d₄) δ 8.21-8.09 (m, 2H), 7.97 (d, J = 1.1 Hz, 1H), 7.67-7.57 (m, 2H), 7.51 (dd, J = 8.0, 1.2 Hz, 1H), 7.34 (d, J = 1.2 Hz, 1H), 7.25 (td, J = 7.7, 1.6 Hz, 1H), 7.09 (td, J = 7.6, 1.2 Hz, 1H), 6.98 (t, J = 1.1 Hz, 1H), 6.38 (dd, J = 7.8, 1.6 Hz, 1H), 5.77 (s, 2H), 2.82 (s, 2H), 1.45 (s, 6H); ¹H NMR (400 MHz, Methanol-d₄) δ 8.25-8.09 (m, 2H), 7.99 (d, J = 1.1 Hz, 1H), 7.72-7.58 (m, 2H), 7.52 (dd, J = 8.0, 1.2 Hz, 1H), 7.35 (d, J = 1.2 Hz, 1H), 7.26 (td, J = 7.7, 1.6 Hz, 1H), 7.10 (td, J = 7.5, 1.2 Hz, 1H), 6.98 (t, J = 1.1 Hz, 1H), 6.38 (dd, J = 7.8, 1.5 Hz, 1H), 5.78 (s, 2H), 2.83 (s, 2H), 1.46 (s, 6H). LCMS m/z 483.34 [M + H]⁺. |
| 305 | 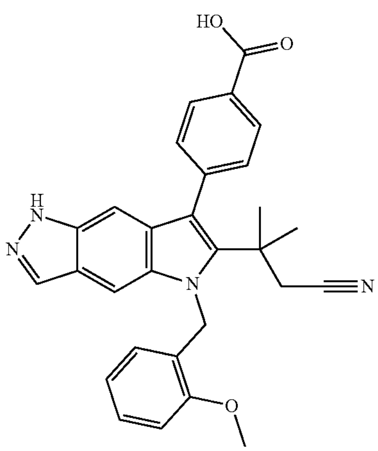 [SMILES: COc1ccccc1Cn1c(C(C)(C)CC#N)c(-c2ccc(C(=O)O)cc2)c2cc3[nH]ncc3cc21] | | ¹H NMR (400 MHz, Methanol-d₄) δ 8.23-8.08 (m, 2H), 7.98 (d, J = 1.1 Hz, 1H), 7.67-7.57 (m, 2H), 7.35 (d, J = 1.1 Hz, 1H), 7.23 (ddd, J = 9.0, 7.4, 1.7 Hz, 1H), 7.07 (dd, J = 8.3, 1.1 Hz, 1H), 6.97 (t, J = 1.1 Hz, 1H), 6.72 (td, J = 7.5, 1.1 Hz, 1H), 6.28 (dd, J = 7.6, 1.6 Hz, 1H), 5.68 (s, 2H), 4.01 (s, 3H), 2.81 (s, 2H), 1.45 (s, 6H). LCMS m/z 479.44 [M + H]⁺. |

Compound 306

4-(6-(1-cyano-2-methylpropan-2-yl)-5-(thiophen-2-ylmethyl)-1,5-dihydropyrrolo[2,3-f]indazol-7-yl)benzoic Acid (306)

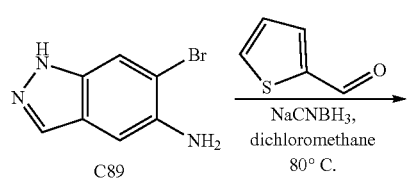

-continued

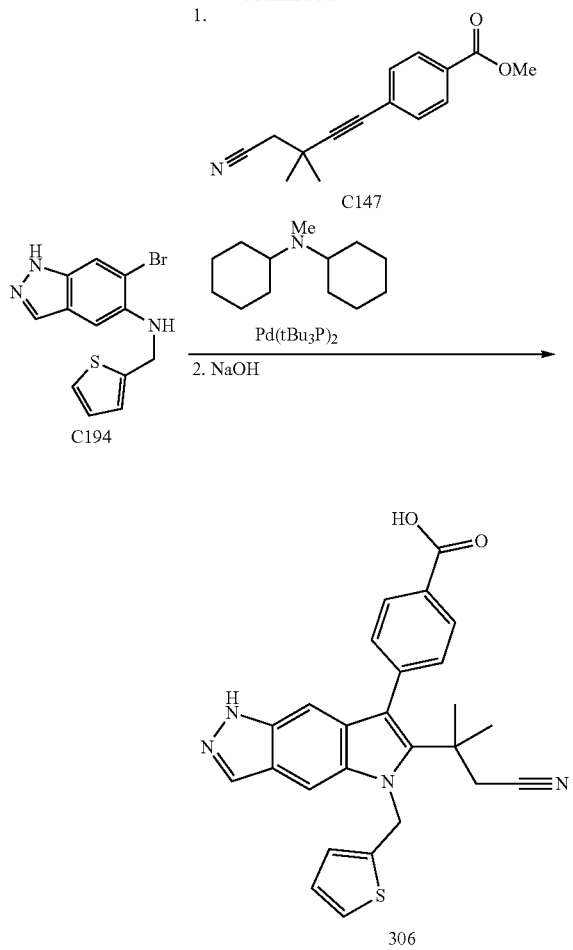

Part A: 6-bromo-1H-indazol-5-amine (20 mg, 0.094 mmol), thiophene-2-carbaldehyde (approximately 12.70 mg, 0.11 mmol), Pd(tBu₃P)₂ (5 mg, 0.01 mmol), polymer supported acetic acid (10 µL, 0.18 mmol) were suspended in DCE (0.3 mL). The reactions were heated at 80° C. for 18 h. The reaction mixture was filtered, and the beads washed with methanol. The mixture was concentrated in vacuo and the crude product C194 was advanced to the next step without further purification.

Part B: The crude product C194 and methyl 4-(4-cyano-3,3-dimethyl-but-1-ynyl)benzoate (35 mg, 0.15 mmol) were suspended in Dioxane (0.4 mL), then NaOH (200 µL of 1 M, 0.20 mmol) was added. A current of nitrogen was blown through the reaction vial, and N-cyclohexyl-N-methyl-cyclohexanamine (50 µL, 0.23 mmol) was added. The reaction was heated at 110° C. for 24 h.

Part C: An aqueous solution of NaOH (200 µL of 1 M) was added to the reactions and the mixtures were heated at 60° C. for 5 h. After this time LC-MS chromatogram was obtained to confirm the formation of product. Water and CHCl₃:IPA (3:1) were added. The mixture was extracted with CHCl₃:IPA (3:1) (3×). The organic phases were passed through a phase separator, combined and concentrated in vacuo. Purification by reversed-phase HPLC. Method: C18 Waters Sunfire column (30×150 mm, 5 micron). Gradient: MeCN in H₂O with 0.2% formic acid afford the product. $^1$H NMR (400 MHz, Methanol-d₄) δ 8.10-8.01 (m, 2H), 7.99 (d, J=1.1 Hz, 1H), 7.53 (d, J=1.2 Hz, 1H), 7.49-7.42 (m, 2H), 7.27 (dd, J=5.1, 1.2 Hz, 1H), 6.96 (t, J=1.1 Hz, 1H), 6.92 (dd, J=5.1, 3.5 Hz, 1H), 6.72 (dd, J=3.5, 1.3 Hz, 1H), 5.90 (s, 2H), 2.87 (s, 2H), 1.51 (s, 6H). LCMS m/z 455.29 [M+H]⁺.

Compounds 307-319

Compounds 307-319 (Table 21) were prepared using the method described for the preparation of compound 306.

TABLE 21

Method of preparation, structure, physicochemical data for compounds 307-319

| Compound | Structure | Aldehyde or ketone reagent/Method | $^1$H NMR; LCMS m/z [M + H]⁺ |
|---|---|---|---|
| 307 | (structure shown) | As for compound 306 | $^1$H NMR (400 MHz, Chloroform-d) δ 8.20 (d, J = 7.9 Hz, 2H), 8.18-8.14 (m, 1H), 7.62 (d, J = 1.0 Hz, 1H), 7.53 (d, J = 7.9 Hz, 2H), 7.03 (s, 1H), 4.31 (d, J = 7.4 Hz, 2H), 3.98 (dd, J = 11.2, 4.0 Hz, 2H), 3.33 (dd, J = 12.5, 10.2 Hz, 2H), 2.72 (s, 2H), 2.51-2.33 (m, 1H), 1.59 (s, 6H), 1.57-1.39 (m, 4H). LCMS m/z 457.45 [M + H]⁺. |

TABLE 21-continued

Method of preparation, structure, physicochemical data for compounds 307-319

| Compound | Structure | Aldehyde or ketone reagent/Method | $^1$H NMR; LCMS m/z [M + H]$^+$ |
|---|---|---|---|
| 308 | 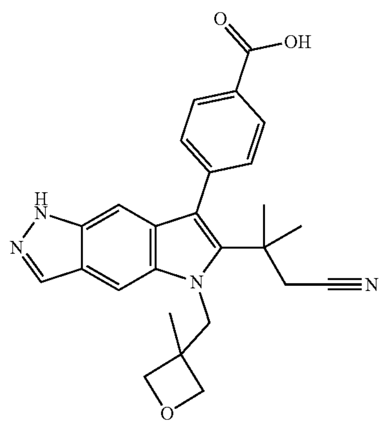 [SMILES: CC1(Cn2c(C(C)(C)CC#N)c(-c3ccc(C(=O)O)cc3)c3cc4[nH]ncc4cc32)COC1] | As for compound 306 | $^1$H NMR (400 MHz, Methanol-d$_4$) δ 8.15-8.11 (m, 2H), 8.11 (d, J = 1.1 Hz, 1H), 7.59-7.51 (m, 3H), 6.96 (t, J = 1.1 Hz, 1H), 4.63 (s, 2H), 4.29-4.15 (m, 2H), 3.70-3.49 (m, 2H), 2.86 (s, 2H), 1.46 (s, 6H), 1.29 (s, 3H). LCMS m/z 443.19 [M + H]$^+$. |
| 309 | 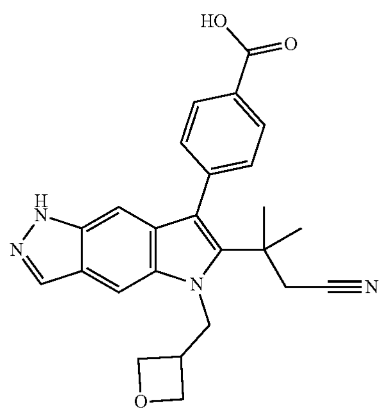 [SMILES: CC(C)(CC#N)c1c(-c2ccc(C(=O)O)cc2)c2cc3[nH]ncc3cc2n1CC1COC1] | As for compound 306 | $^1$H NMR (400 MHz, Methanol-d$_4$) δ 8.14 (d, J = 1.0 Hz, 1H), 8.13-8.08 (m, 2H), 7.73 (d, J = 1.2 Hz, 1H), 7.56-7.46 (m, 2H), 6.91 (t, J = 1.1 Hz, 1H), 4.83 (d, J = 6.4 Hz, 2H), 4.73 (dd, J = 7.5, 1.6 Hz, 4H), 3.62-3.54 (m, 1H), 2.94 (s, 2H), 1.52 (s, 6H). LCMS m/z 429.32 [M + H]$^+$. |
| 310 | 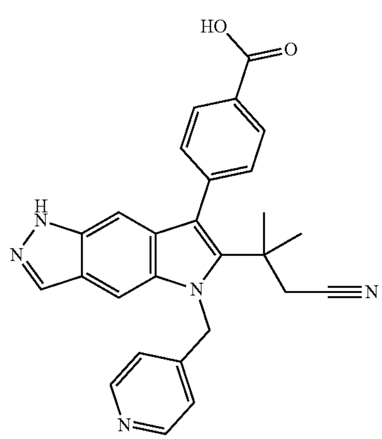 [SMILES: CC(C)(CC#N)c1c(-c2ccc(C(=O)O)cc2)c2cc3[nH]ncc3cc2n1Cc1ccncc1] | As for compound 306 | $^1$H NMR (400 MHz, Methanol-d$_4$) δ 8.50-8.42 (m, 2H), 8.15 (d, J = 8.4, 2H), 7.97 (d, J = 1.1 Hz, 1H), 7.65-7.59 (m, 2H), 7.37 (d, J = 1.2 Hz, 1H), 7.10-7.02 (m, 2H), 6.98 (t, J = 1.1 Hz, 1H), 5.87 (s, 2H), 2.87 (s, 2H), 1.46 (s, 6H). LCMS m/z 450.28 [M + H]$^+$. |

TABLE 21-continued

Method of preparation, structure, physicochemical data for compounds 307-319

| Compound | Structure | Aldehyde or ketone reagent/Method | $^1$H NMR; LCMS m/z [M + H]$^+$ |
|---|---|---|---|
| 311 | 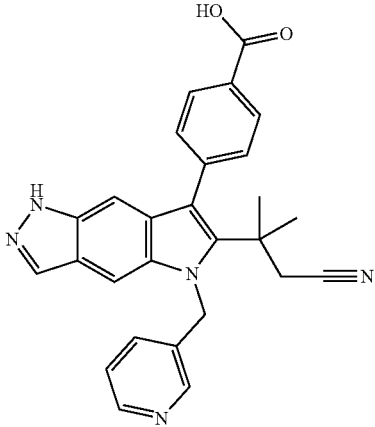 [SMILES: CC(C)(CC#N)c1c(-c2ccc(C(=O)O)cc2)c2cc3[nH]ncc3cc2n1Cc1cccnc1] | 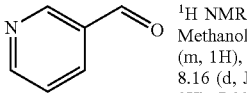 As for compound 306 | $^1$H NMR (400 MHz, Methanol-d$_4$) δ 8.62 (m, 1H), 8.30 (m, 1H), 8.16 (d, J = 8.3 Hz, 2H), 7.98 (s, 1H), 7.85 (m, 1H), 7.76 (m, 1H), 7.63 (d, J = 8.2 Hz, 2H), 7.44 (s, 1H), 7.00 (s, 1H), 6.01 (s, 2H), 2.90 (s, 2H), 1.48 (s, 6H). LCMS m/z 450.29 [M + H]$^+$. |
| 312$^1$ | 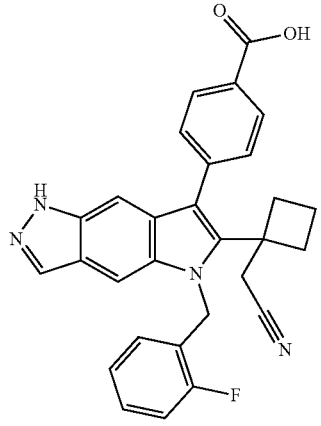 [SMILES: N#CCC1(c2c(-c3ccc(C(=O)O)cc3)c3cc4[nH]ncc4cc3n2Cc2ccccc2F)CCC1] | See table footnote | $^1$H NMR (400 MHz, Methanol-d$_4$) δ 8.17-8.09 (m, 2H), 7.98 (d, J = 1.1 Hz, 1H), 7.77-7.68 (m, 2H), 7.40 (d, J = 1.1 Hz, 1H), 7.33 (t, J = 1.1 Hz, 1H), 7.27 (m, 1H), 7.20 (m, 1H), 6.97 (td, J = 7.5, 1.2 Hz, 1H), 6.46-6.35 (m, 1H), 5.52 (s, 2H), 3.21 (s, 2H), 2.49-2.34 (m, 2H), 2.19-2.02 (m, 3H), 1.71 (m, 1H). LCMS m/z 479.35 [M + H]$^+$. |
| 313 | 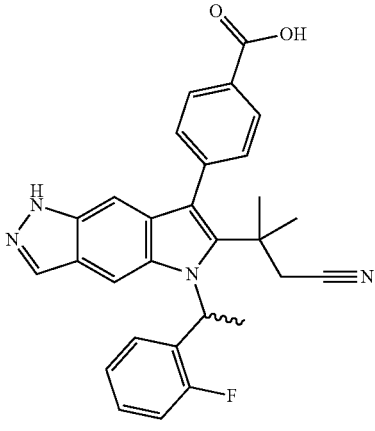 | 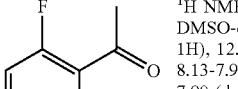 As for compound 306 | $^1$H NMR (300 MHz, DMSO-d$_6$) δ 12.99 (s, 1H), 12.40 (s, 1H), 8.13-7.99 (m, 2H), 7.90 (d, J = 1.0 Hz, 1H), 7.62-7.51 (m, 2H), 7.43-7.27 (m, 2H), 7.27-7.12 (m, 3H), 6.84-6.68 (m, 1H), 6.40-6.23 (m, 1H), 3.15-2.94 (m, 2H), 2.13-1.99 (m, 3H), 1.46 (d, J = 12.6 Hz, 6H). LCMS m/z 481.34 [M + H]$^+$. |

TABLE 21-continued

Method of preparation, structure, physicochemical data for compounds 307-319

| Compound | Structure | Aldehyde or ketone reagent/Method | $^1$H NMR; LCMS m/z [M + H]$^+$ |
|---|---|---|---|
| 314 | 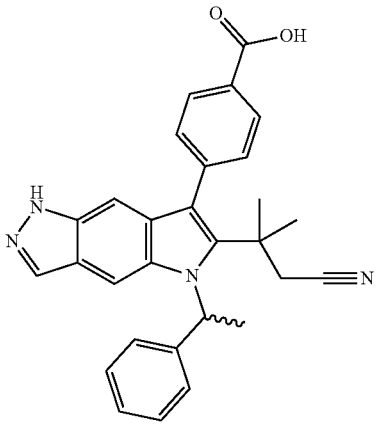 [SMILES: CC(c1ccccc1)n1c(C(C)(C)CC#N)c(-c2ccc(C(=O)O)cc2)c2cc3[nH]ncc3cc21] | As for compound 306 | $^1$H NMR (300 MHz, DMSO-d$_6$) δ 13.02 (s, 1H), 12.39 (s, 1H), 8.11-8.01 (m, 2H), 7.87 (d, J = 1.0 Hz, 1H), 7.66-7.52 (m, 2H), 7.45-7.34 (m, 2H), 7.34-7.22 (m, 3H), 6.93 (d, J = 1.1 Hz, 1H), 6.78-6.71 (m, 1H), 6.30-6.16 (m, 1H), 3.21-2.98 (m, 2H), 2.00 (d, J = 6.6 Hz, 3H), 1.47 (d, J = 2.1 Hz, 6H). LCMS m/z 463.26 [M + H]$^+$. |
| 315 | 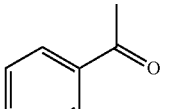 | Larock indole method with C188[2] | $^1$H NMR (400 MHz, Methanol-d$_4$) δ 8.68 (d, J = 1.8 Hz, 1H), 8.01 (s, 1H), 7.93-7.84 (m, 1H), 7.52 (dd, J = 8.1, 1.2 Hz, 1H), 7.39 (d, J = 1.2 Hz, 1H), 7.26 (td, J = 7.7, 1.6 Hz, 1H), 7.09 (td, J = 7.6, 1.2 Hz, 1H), 6.97 (d, J = 1.2 Hz, 1H), 6.35 (d, J = 7.9 Hz, 1H), 5.81 (s, 2H), 2.86 (s, 2H), 2.79 (m, 3H), 2.00-1.91 (m, 6H), 1.44 (s, 6H). LCMS m/z 530.29 [M + H]$^+$. |
| 316 | 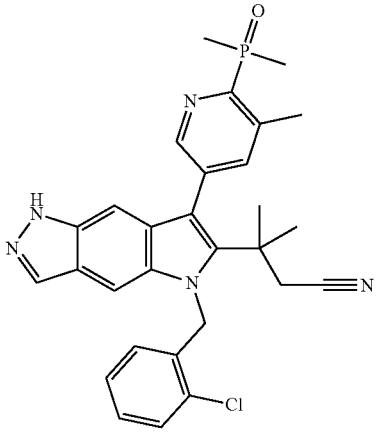 | Larock indole method with C188[3] | $^1$H NMR (400 MHz, Methanol-d$_4$) δ 8.72-8.64 (m, 1H), 8.00 (d, J = 1.1 Hz, 1H), 7.88 (m, 1H), 7.43 (d, J = 1.2 Hz, 1H), 7.35-7.25 (m, 1H), 7.21 (m, 1H), 7.01-6.89 (m, 2H), 6.43-6.34 (m, 1H), 5.84 (s, 2H), 2.90 (s, 2H), 2.83-2.75 (m, 3H), 1.95 (dd, J = 13.5, 6.9 Hz, 6H), 1.45 (s, 6H). LCMS m/z 514.3 [M + H]$^+$. |

TABLE 21-continued

Method of preparation, structure, physicochemical data for compounds 307-319

| Compound | Structure | Aldehyde or ketone reagent/Method | $^1$H NMR; LCMS m/z [M + H]$^+$ |
|---|---|---|---|
| 317 | 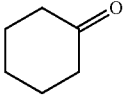 | As for compound 306 | $^1$H NMR (400 MHz, Methanol-d$_4$) δ 8.16-8.05 (m, 3H), 7.99 (d, J = 1.2 Hz, 1H), 7.57-7.45 (m, 2H), 6.84 (t, J = 1.1 Hz, 1H), 4.64-4.42 (m, 1H), 2.92 (s, 2H), 2.75 (q, J = 12.2 Hz, 2H), 2.09-2.01 (m, 2H), 1.95 (d, J = 13.0 Hz, 2H), 1.85 (d, J = 9.4 Hz, 1H), 1.59 (dd, J = 23.4, 9.2 Hz, 3H), 1.52 (s, 6H). LCMS m/z 441.29 [M + H]$^+$. |
| 318 | 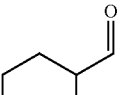 | As for compound 306 | $^1$H NMR (400 MHz, Methanol-d$_4$) δ 8.13-8.09 (m, 2H), 8.08 (d, J = 1.0 Hz, 1H), 7.72 (d, J = 1.1 Hz, 1H), 7.58-7.49 (m, 2H), 6.92 (t, J = 1.1 Hz, 1H), 4.31 (d, J = 7.6 Hz, 2H), 2.89 (s, 2H), 2.17 (m, 1H), 1.83-1.60 (m, 3H), 1.52 (m, 8H), 1.18 (m, 5H). LCMS m/z 455.29 [M + H]$^+$. |
| 319 | 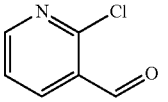 | As for compound 306 | $^1$H NMR (400 MHz, Methanol-d$_4$) δ 8.29 (dd, J = 4.8, 1.9 Hz, 1H), 8.18-8.11 (m, 2H), 7.99 (d, J = 1.1 Hz, 1H), 7.65-7.57 (m, 2H), 7.37 (d, J = 1.2 Hz, 1H), 7.20 (dd, J = 7.7, 4.8 Hz, 1H), 6.99 (t, J = 1.1 Hz, 1H), 6.76 (dd, J = 7.7, 1.8 Hz, 1H), 5.78 (s, 2H), 2.85 (s, 2H), 1.46 (s, 6H). LCMS m/z 484.15 [M + H]$^+$. |

[1]Prepared by Larock indole cyclization between 6-bromo-N-[(2-fluorophenyl)methyl]-1H-indazol-5-amine and methyl 4-[2-[1-(cyanomethyl)cyclobutyl]ethynyl]benzoate C196.

[2]6-bromo-N-[(2-chlorophenyl)methyl]-1-tetrahydropyran-2-yl-indazol-5-amine.

[3]6-bromo-N-[(2-fluorophenyl)methyl]-1-tetrahydropyran-2-yl-indazol-5-amine.

Compound 320

4-[6-[1-(cyanomethyl)cyclobutyl]-5-(4-fluoro-3-methyl-phenyl)-1H-pyrrolo[2,3-f]indazol-7-yl]benzoic Acid (320)

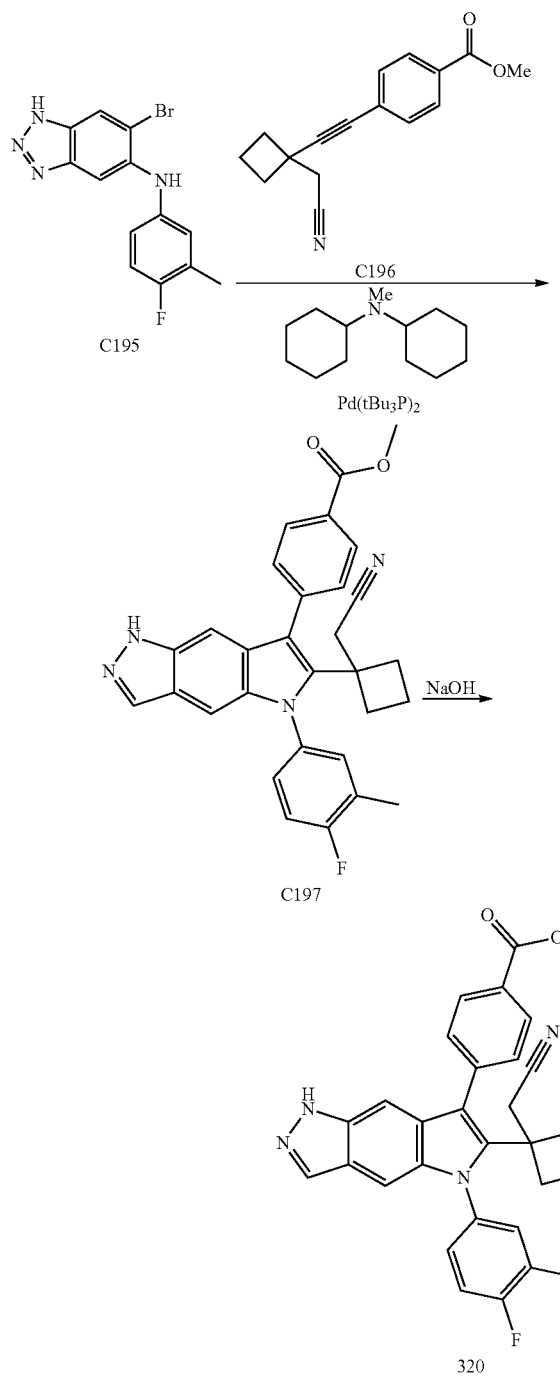

Compound 320 was prepared from C195 and alkyne C196 according to the method described for the preparation of compound 125. C195 was prepared from C116 and 1-fluoro-4-iodo-2-methyl-benzene to afford 4-[6-[1-(cyanomethyl)cyclobutyl]-5-(4-fluoro-3-methyl-phenyl)-1H-pyrrolo[2,3-f]indazol-7-yl]benzoic acid.

$^1$H NMR (300 MHz, DMSO-d$_6$) δ 12.99 (s, 1H), 12.61 (s, 1H), 8.09-8.03 (m, 2H), 8.03-7.97 (m, 1H), 7.79-7.69 (m, 2H), 7.61-7.53 (m, 1H), 7.51-7.44 (m, 1H), 7.40 (t, J=8.9 Hz, 1H), 7.28-7.21 (m, 1H), 6.99 (d, J=1.1 Hz, 1H), 3.19 (s, 2H), 2.39-2.32 (m, 3H), 2.32-2.2 (m, 2H), 2.02-1.88 (m, 1H), 1.61-1.45 (m, 3H). LCMS m/z 479.28 [M+H]$^+$.

Compound 321

4-(5-(4-fluorophenyl-1,2,3,4,5,6-13C6)-6-(tetrahydro-2H-pyran-4-yl)-1,5-dihydropyrrolo[2,3-f]indazol-7-yl)benzoic-2,3,5,6-d$_4$ Acid (321)

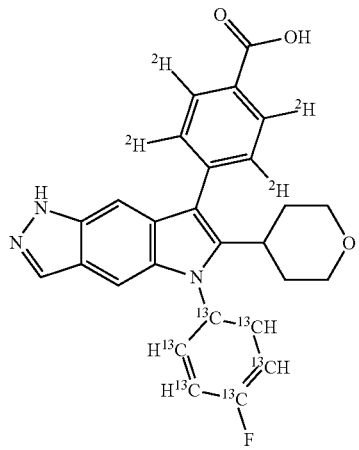

Compound 321 was prepared from C2 using 4-fluoro-2λ3,3λ3,5λ3,6λ3-benzenamine-$^{13}$C$_6$ and (4-(ethoxycarbonyl)phenyl-2,3,5,6-d$_4$)boronic acid using the procedures described for the preparation of compound S4 and compound 33. $^1$H NMR (300 MHz, DMSO-d$_6$) δ 12.99 (s, 1H), 12.60 (s, 1H), 8.00 (d, J=1.0 Hz, 1H), 7.97-7.72 (m, 2H), 7.44-7.30 (m, 1H), 7.30-7.18 (m, 2H), 7.07 (d, J=1.1 Hz, 1H), 3.73 (d, J=11.1 Hz, 2H), 3.17-2.95 (m, 3H), 1.72-1.61 (m, 4H). LCMS m/z 466.37 [M+H]$^+$.

Compound 322

4-[6-(2-cyano-1,1-dimethyl-ethyl)-5-(4-fluorophenyl)-1H-pyrrolo[2,3-f]benzotriazol-7-yl]benzoic Acid (322)

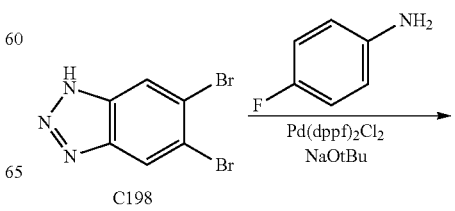

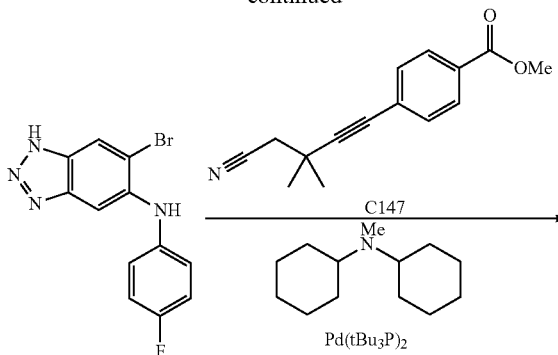

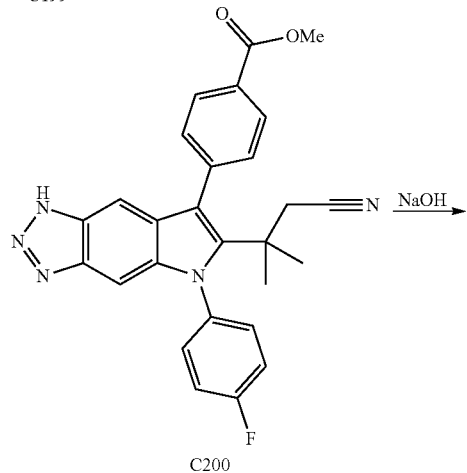

323

Step 1. Synthesis of 6-bromo-N-(4-fluorophenyl)-1H-benzotriazol-5-amine (C199)

Josiphos Pd G3 and Pd(dppf)Cl₂ (185 mg, 0.2002 mmol) was added to a degassed solution of 5,6-dibromo-1H-benzotriazole (557 mg, 2.011 mmol), 4-fluoroaniline (231 µL, 2.407 mmol), and sodium t-butoxide (590 mg, 6.14 mmol) in tetrahydrofuran (11 mL). A nitrogen atmosphere was maintained through the set-up and the vial sealed. The reaction mixture was stirred under a nitrogen atmosphere at room temperature overnight. The mixture was diluted with ethyl acetate and washed with water. The organics were absorbed onto Celite® and purified on a 40 g Si gold cartridge. Purification by silica gel chromatography (Gradient: 0-100% EtOAc in heptane) yielded 6-bromo-N-(4-fluorophenyl)-1H-benzotriazol-5-amine (338 mg, 54%). $^1$H NMR (300 MHz, DMSO-$d_6$) δ 15.35 (s, 1H), 8.32 (s, 1H), 7.63 (s, 1H), 7.29-7.07 (m, 5H). LCMS m/z 307.0 [M+H]⁺.

Step 2-3. Synthesis of 4-[6-(2-cyano-1,1-dimethyl-ethyl)-5-(4-fluorophenyl)-1H-pyrrolo[2,3-f]benzotriazol-7-yl]benzoic Acid (322)

Compound 322 was prepared in two steps from C199 using the method described for the preparation of compound 125. Purification by reversed-phase chromatography (Column: C18. Gradient: 10-100% MeCN in water with 0.1% formic acid) afforded the desired product. Concentrated the desired fractions to dryness under reduced pressure to give 4-[6-(2-cyano-1,1-dimethyl-ethyl)-5-(4-fluorophenyl)-1H-pyrrolo[2,3-f]benzotriazol-7-yl]benzoic acid (Trifluoroacetic Acid (0.5)) (18.7 mg, 58%). $^1$H NMR (300 MHz, DMSO-$d_6$) δ 15.42-15.00 (bs, 1H), 13.09 (s, 1H), 8.17-8.09 (m, 2H), 7.76-7.62 (m, 4H), 7.62-7.50 (m, 2H), 7.34-6.73 (m, 2H), 2.64 (s, 2H), 1.25 (s, 6H). LCMS m/z 454.3 [M+H]⁺.

Compound 323

4-[6-(2-cyano-1,1-dimethyl-ethyl)-7-(4-fluorophenyl)-1H-pyrrolo[3,2-f]indazol-5-yl]benzoic Acid (323)

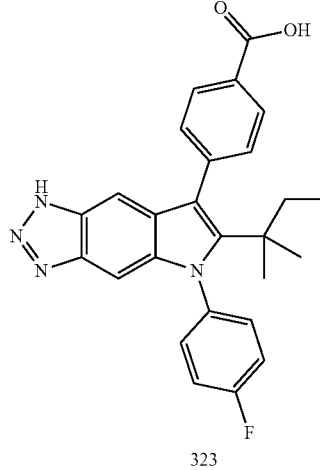

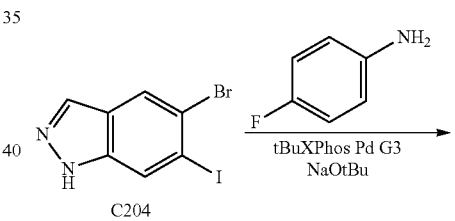

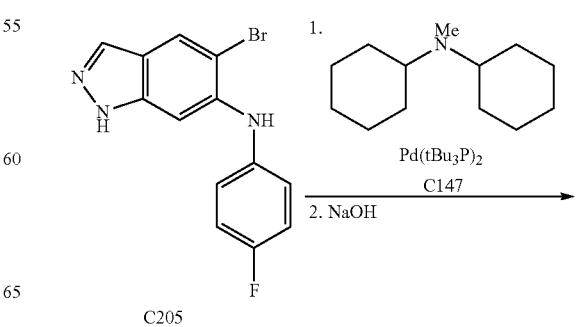

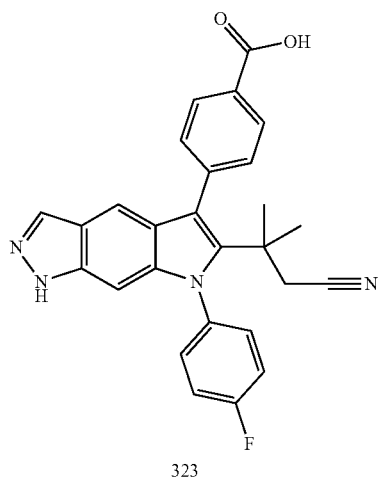

323

Synthesis of 4-[6-(2-cyano-1,1-dimethyl-ethyl)-7-(4-fluorophenyl)-1H-pyrrolo[3,2-f]indazol-5-yl]benzoic Acid (323)

Compound 323 was prepared from compound C204 using the method described for the preparation of compound 324. In this example, the addition of tosyl protecting group was omitted. 4-[6-(2-cyano-1,1-dimethyl-ethyl)-7-(4-fluorophenyl)-1H-pyrrolo[3,2-f]indazol-5-yl]benzoic acid (29.5 mg, 67%). $^1$H NMR (300 MHz, DMSO-$d_6$) δ 13.06 (s, 1H), 12.49 (s, 1H), 8.12-8.05 (m, 2H), 8.00 (d, J=1.0 Hz, 1H), 7.70-7.49 (m, 6H), 7.25 (d, J=1.1 Hz, 1H), 6.50 (t, J=1.2 Hz, 1H), 2.62 (s, 2H), 1.24 (s, 6H). LCMS m/z 453.31 [M+H]$^+$.

Compound 324

4-[6-(2-cyano-1,1-dimethyl-ethyl)-7-(4-fluorophenyl)-1H-pyrrolo[3,2-f]indazol-5-yl]benzoic Acid (324)

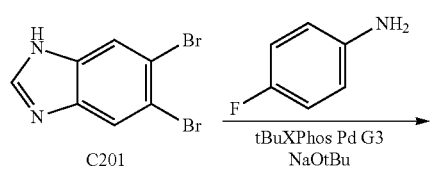

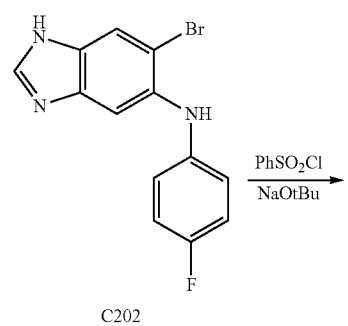

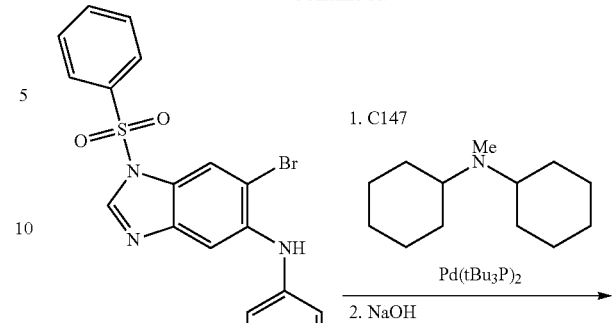

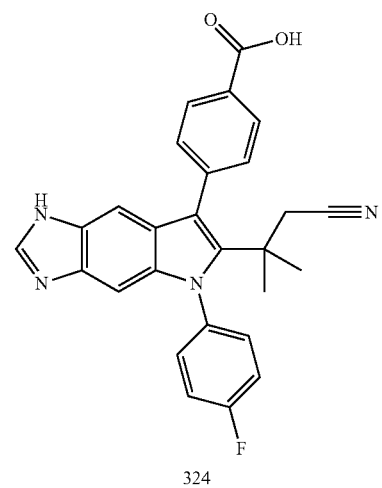

324

Step 1. Synthesis of 6-bromo-N-(4-fluorophenyl)-1H-benzimidazol-5-amine (C202)

Compound 202 was prepared by amination of C201 using tBuXPhosPd G3, using the method described for the preparation of compound C199. Purification by silica gel chromatography (Gradient: 0-100% EtOAc in heptane) yielded 6-bromo-N-(4-fluorophenyl)-1H-benzimidazol-5-amine (270 mg, 39%). LCMS m/z 306.01 [M+H]$^+$.

Step 2. Synthesis of 1-(benzenesulfonyl)-6-bromo-N-(4-fluorophenyl)benzimidazol-5-amine (C203)

Compound 203 was prepared from C202 using the method described for the preparation of compound C5 from C4. Purified on a Si 40 g gold cartridge and eluted with 0-100% ethyl acetate in heptane to give a mixture of N-1 and N-2 indazole protected desired product, 1-(benzenesulfonyl)-6-bromo-N-(4-fluorophenyl)benzimidazol-5-amine (100 mg, 41%). LCMS m/z 446.11 [M+H]$^+$.

Step 3. Synthesis of methyl 4-[1-(benzenesulfonyl)-6-(2-cyano-1,1-dimethyl-ethyl)-5-(4-fluorophenyl)pyrrolo[2,3-f]benzimidazol-7-yl]benzoate (323)

Compound 324 was prepared from C203 and C147 using the method described for the preparation of compound 125. 4-[6-(2-cyano-1,1-dimethyl-ethyl)-5-(4-fluorophenyl)-1H- pyrrolo[2,3-f]benzimidazol-7-yl]benzoic acid (8.5 mg, 20%). ¹H NMR (300 MHz, DMSO-d₆) δ 12.10 (s, 2H), 8.11 (s, 1H), 8.11-8.05 (m, 2H), 7.69-7.58 (m, 4H), 7.58-7.46 (m, 2H), 6.99 (s, 1H), 6.66 (s, 1H), 2.62 (s, 2H), 1.24 (s, 6H). LCMS m/z 453.22 [M+H]⁺.

Compound 325

4-[4-(4-fluorophenyl)-5-(2-methoxy-1,1-dimethyl-ethyl)-2,4,10,11-tetrazatricyclo[7.3.0.0³,⁷]dodeca-1,3(7),5,8,11-pentaen-6-yl]benzoic Acid (325)

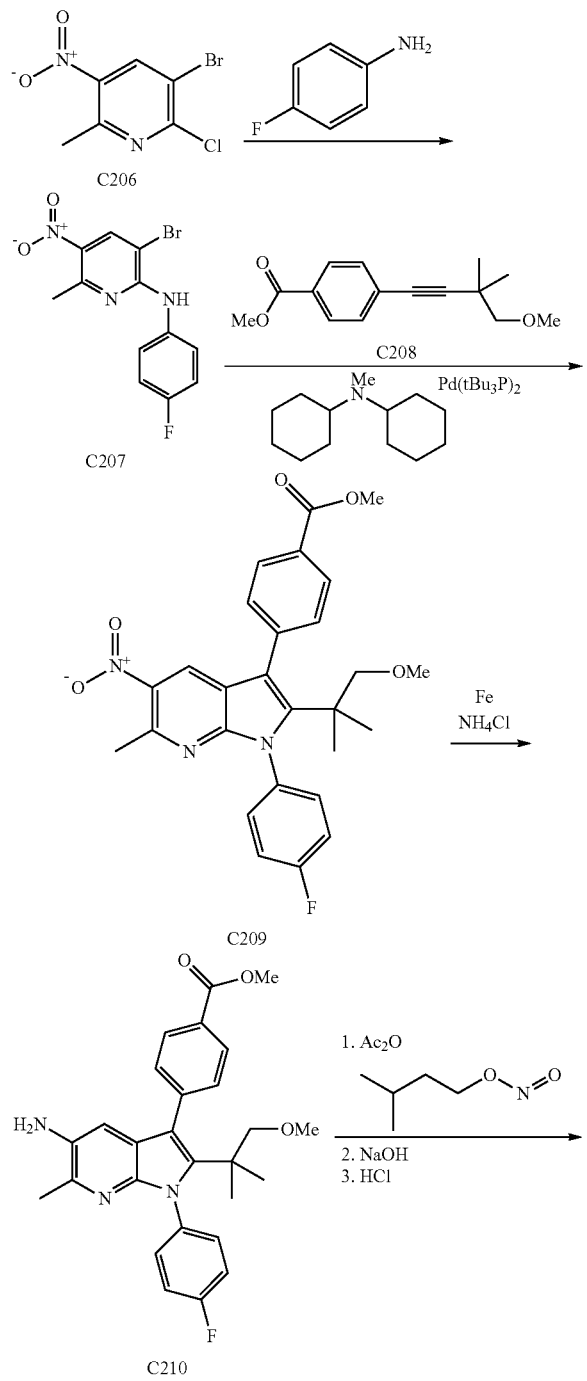

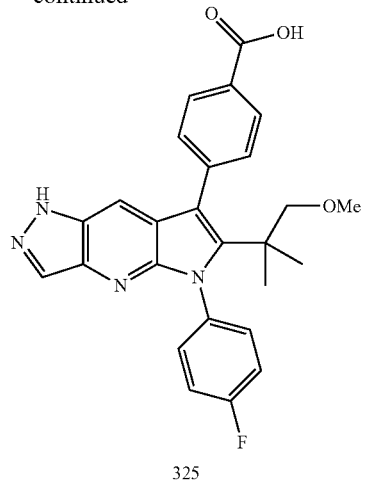

Step 1. Synthesis of 3-bromo-N-(4-fluorophenyl)-6-methyl-5-nitro-pyridin-2-amine (C207)

A 100 mL round bottom flask was charged with 3-bromo-2-chloro-6-methyl-5-nitro-pyridine (2.69 g, 10.70 mmol) and DMSO (22 mL) was added. 4-Fluoroaniline (3 mL, 31.67 mmol) was added and the reaction was heated to 120° C. After 30 minutes, The reaction mixture was allowed to cool to room temperature, and was poured into water (500 mL), forming a green precipitate. This precipitate was collected by vacuum filtration and washed with excess water. The crude material was purified by column chromatography using an 80 g silica gel gold column with 0-20% EtOAc in Heptane as eluent. The desired product was obtained as a mustard yellow solid. 3-bromo-N-(4-fluorophenyl)-6-methyl-5-nitro-pyridin-2-amine (3.1888 g, 89%). ¹H NMR (400 MHz, DMSO-d₆) δ 9.14 (s, 1H), 8.56 (s, 1H), 7.66 (ddd, J=9.1, 5.0, 1.7 Hz, 2H), 7.21 (td, J=8.8, 1.7 Hz, 2H), 2.61 (s, 3H). LCMS m/z 325.9 [M+H]⁺.

Step 2. Synthesis of methyl 4-[1-(4-fluorophenyl)-2-(2-methoxy-1,1-dimethyl-ethyl)-6-methyl-5-nitro-pyrrolo[2,3-b]pyridin-3-yl]benzoate (C209)

Compound C209 was prepared from C207 and C208 using Larock indole cyclization as described for the preparation of compound 125. Methyl 4-[1-(4-fluorophenyl)-2-(2-methoxy-1,1-dimethyl-ethyl)-6-methyl-5-nitro-pyrrolo[2,3-b]pyridin-3-yl]benzoate (369.2 mg, 51%). ¹H NMR (400 MHz, Chloroform-d) δ 8.17 (d, J=7.8 Hz, 2H), 8.09 (s, 1H), 7.54 (d, J=7.7 Hz, 2H), 7.48-7.41 (m, 2H), 7.30-7.25 (m, 2H), 4.01 (s, 3H), 3.08 (s, 3H), 3.04 (s, 2H), 2.77 (s, 3H), 1.16 (s, 6H). LCMS m/z 492.15 [M+H]⁺.

Step 3. Synthesis of methyl 4-[5-amino-1-(4-fluorophenyl)-2-(2-methoxy-1,1-dimethyl-ethyl)-6-methyl-pyrrolo[2,3-b]pyridin-3-yl]benzoate (C210)

A 0.5-2 mL microwave vial was charged with methyl 4-[1-(4-fluorophenyl)-2-(2-methoxy-1,1-dimethyl-ethyl)-6-methyl-5-nitro-pyrrolo[2,3-b]pyridin-3-yl]benzoate C209 (30 mg, 0.06057 mmol), NH₄Cl (18 mg, 0.3365 mmol), and iron (21 mg, 0.3760 mmol). MeOH (250 µL) was added and the reaction was heated to 80° C. over the weekend. Upon returning, all starting material had been consumed. Water (5 mL) and dichloromethane (5 mL) were added, and the mixture was passed through a phase separator. The solvent was evaporated and the crude material was taken up in minimal DMSO and purified by reverse phase chromatography using a gradient of 10-100% acetonitrile in water with 0.2% formic acid on a 15.5 g gold C18 column. The desired product was obtained as a white solid. Methyl 4-[5-amino-1-(4-fluorophenyl)-2-(2-methoxy-1,1-dimethyl-ethyl)-6-methyl-pyrrolo[2,3-b]pyridin-3-yl]benzoate (13.0 mg, 41%). $^1$H NMR (400 MHz, Chloroform-d) δ 8.12 (dd, J=8.0, 1.7 Hz, 2H), 7.57-7.49 (m, 2H), 7.45 (dt, J=6.6, 3.4 Hz, 2H), 7.23 (t, J=8.1 Hz, 2H), 6.72 (s, 1H), 3.99 (s, 3H), 3.07 (s, 3H), 3.03 (s, 2H), 2.39 (s, 3H), 1.12 (s, 6H). LCMS m/z 462.14 [M+H]$^+$.

4-[4-(4-fluorophenyl)-5-(2-methoxy-1,1-dimethyl-ethyl)-2,4,10,11-tetrazatricyclo[7.3.0.03,7]dodeca-1,3(7),5,8,11-pentaen-6-yl]benzoic Acid (325)

A 1-dram vial was charged with methyl 4-[5-amino-1-(4-fluorophenyl)-2-(2-methoxy-1,1-dimethyl-ethyl)-6-methyl-pyrrolo[2,3-b]pyridin-3-yl]benzoate (13 mg, 0.02481 mmol) and KOAc (3 mg, 0.03057 mmol). Chloroform (250 µL) was added and the mixture was stirred at 65° C. for 30 minutes. Then, acetic anhydride (7 µL, 0.07419 mmol) was added dropwise, followed by isoamyl nitrite (4 µL). The mixture was allowed to stir for 3 h. 1,4,7,10,13,16-hexaoxacyclooctadecane (1 mg, 0.003783 mmol) was added and the mixture stirred overnight at 65° C. The reaction mixture was washed with water (5 mL) and passed through a phase separator. The organic phase was collected and the solvent was evaporated. The crude material was taken up in THF (240 µL) and MeOH (120 µL), and NaOH (149 µL of 1 M, 0.1490 mmol) was added. The reaction was heated to 50° C. After 30 minutes, the reaction was complete by LCMS. The solvent was evaporated and the crude material was taken up in minimal water. HCl (149 µL of 1 M, 0.1490 mmol) was added, forming a precipitate. The solvent was evaporated and the crude material was taken up in minimal DMSO. Purification by reverse phase chromatography using a gradient of 10-100% acetonitrile in water with 0.2% formic acid on a 15.5 g gold C18 column afforded the desired product was obtained as an off-white solid. 4-[4-(4-fluorophenyl)-5-(2-methoxy-1,1-dimethyl-ethyl)-2,4,10,11-tetrazatricyclo[7.3.0.03,7]dodeca-1,3(7),5,8,11-pentaen-6-yl]benzoic acid (3.3 mg, 26%). $^1$H NMR (400 MHz, Methanol-d$_4$) δ 8.15 (d, J=7.6 Hz, 2H), 8.02 (s, 1H), 7.59 (d, J=7.6 Hz, 2H), 7.54 (dt, J=9.3, 3.2 Hz, 2H), 7.45 (s, 1H), 7.37 (t, J=8.2 Hz, 2H), 3.11-3.02 (m, 5H), 1.19 (s, 6H). LCMS m/z 459.12 [M+H]$^+$.

Compound 326

4-[4-(4-fluorophenyl)-5-tetrahydropyran-4-yl-2,4,10,11-tetrazatricyclo[7.3.0.03,7]dodeca-1,3(7),5,8,11-pentaen-6-yl]benzoic Acid (326)

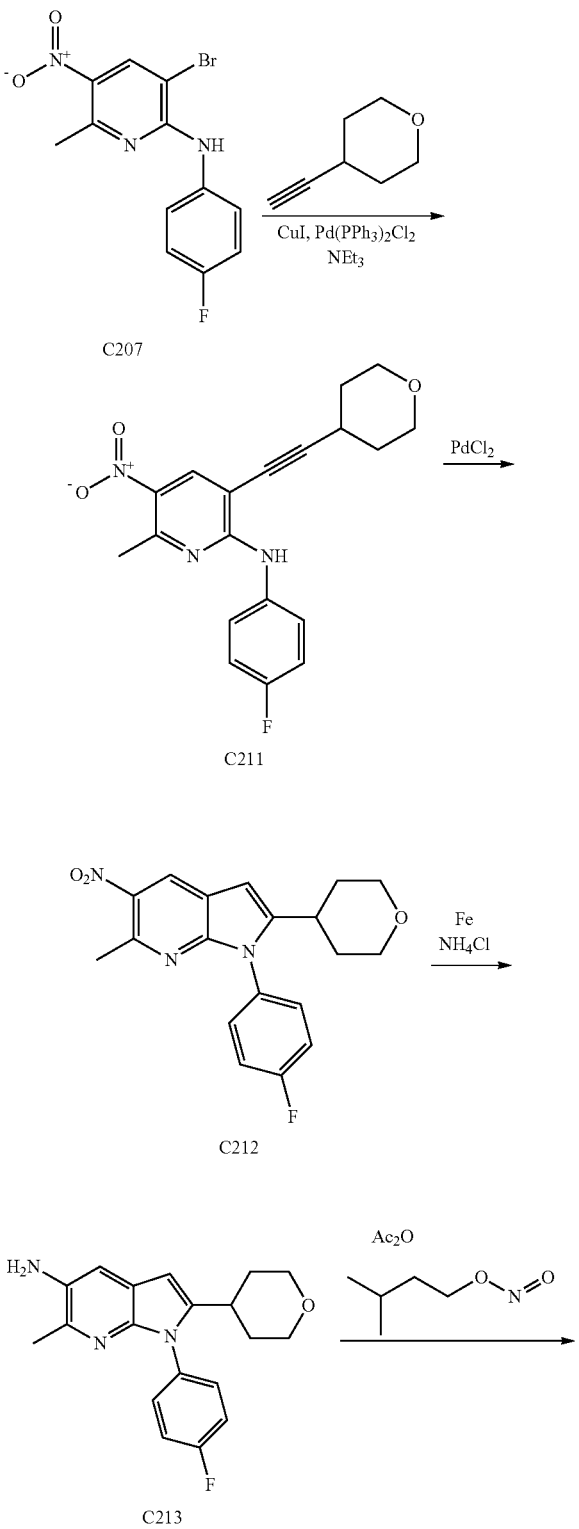

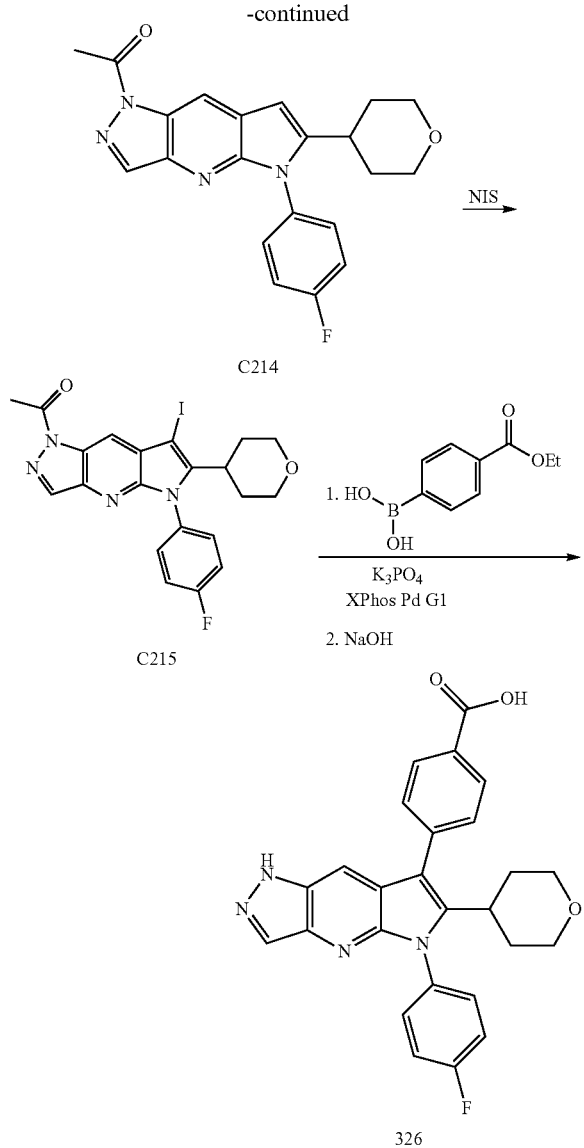

Step 1. N-(4-fluorophenyl)-6-methyl-5-nitro-3-(2-tetrahydropyran-4-ylethynyl)pyridin-2-amine (C211)

Compound 211 was prepared from C207 by Sonogashira coupling according to the method described for preparation of C2. N-(4-fluorophenyl)-6-methyl-5-nitro-3-(2-tetrahydropyran-4-ylethynyl)pyridin-2-amine (1.0132 g, 65%). $^1$H NMR (400 MHz, DMSO-$d_6$) δ 8.90 (s, 1H), 8.27 (s, 1H), 7.68 (dd, J=8.7, 5.1 Hz, 2H), 7.26-7.15 (m, 2H), 3.83 (dt, J=11.3, 4.2 Hz, 2H), 3.46 (t, J=10.6 Hz, 2H), 3.05-2.94 (m, 1H), 2.65 (s, 3H), 1.95-1.85 (m, 2H), 1.79-1.62 (m, 2H). LCMS m/z 356.04 [M+H]$^+$.

Step 2. Synthesis of 1-(4-fluorophenyl)-6-methyl-5-nitro-2-tetrahydropyran-4-yl-pyrrolo[2,3-b]pyridine (C212)

A 100 mL round bottom flask was charged with N-(4-fluorophenyl)-6-methyl-5-nitro-3-(2-tetrahydropyran-4-ylethynyl)pyridin-2-amine (957 mg, 2.649 mmol) and PdCl$_2$ (160 mg, 0.9023 mmol). MeCN (31 mL) was added, and the reaction was heated to 50° C. After 24 h, the reaction was complete by LCMS. The solvent was evaporated, and the crude material was purified by column chromatography using a 40 g silica gel gold column with 0-30% EtOAc in Heptane as eluent. The product was obtained as a light orange solid. 1-(4-fluorophenyl)-6-methyl-5-nitro-2-tetrahydropyran-4-yl-pyrrolo[2,3-b]pyridine (534.4 mg, 54%). $^1$H NMR (400 MHz, DMSO-$d_6$) δ 8.72 (s, 1H), 7.60-7.53 (m, 2H), 7.45 (td, J=8.6, 1.7 Hz, 2H), 6.68 (s, 1H), 3.84 (d, J=11.2 Hz, 2H), 3.28-3.17 (m, 2H), 2.85 (p, J=7.7 Hz, 1H), 2.68 (s, 3H), 1.78-1.58 (m, 4H). LCMS m/z 356.04 [M+H]$^+$.

Step 3. Synthesis of 1-(4-fluorophenyl)-6-methyl-2-tetrahydropyran-4-yl-pyrrolo[2,3-b]pyridin-5-amine (C213)

A 10-20 mL microwave vial was charged with 1-(4-fluorophenyl)-6-methyl-5-nitro-2-tetrahydropyran-4-yl-pyrrolo[2,3-b]pyridine (530 mg, 1.423 mmol), NH$_4$Cl (1030 mg, 19.26 mmol), and iron (850 mg, 15.22 mmol). MeOH (8 mL) was added and the reaction was heated to 80° C. over 36 h. The reaction was filtered, and the solid washed with excess MeOH and CH$_2$Cl$_2$. The filtrate was evaporated, and the crude material was taken up in minimal DMSO and purified by reverse phase chromatography using a gradient of 10-100% acetonitrile in water with 0.2% formic acid on a 50 g gold C18 column. The desired product was obtained as a light brown solid. 1-(4-fluorophenyl)-6-methyl-2-tetrahydropyran-4-yl-pyrrolo[2,3-b]pyridin-5-amine (125.5 mg, 24%). LCMS m/z 326.08 [M+H]$^+$.

Step 4. Synthesis of 1-[4-(4-fluorophenyl)-5-tetrahydropyran-4-yl-2,4,10,11-tetrazatricyclo[7.3.0.03,7]dodeca-1(9),2,5,7,11-pentaen-10-yl]ethenone (C214)

1-(4-fluorophenyl)-6-methyl-2-tetrahydropyran-4-yl-pyrrolo[2,3-b]pyridin-5-amine (125 mg, 0.3842 mmol), KOAc (116 mg, 1.182 mmol), and 1,4,7,10,13,16-hexaoxacyclooctadecane (217 mg, 0.8210 mmol). chloroform (5 mL) was added, followed by acetic anhydride (110 µL, 1.166 mmol) and isoamyl nitrite (110 µL, 0.8188 mmol). The reaction was heated to 60° C. After 6 days, the solution was washed with sat. NaHCO$_3$, and the mixture was passed through a phase separator. The organic phase was collected, and the solvent was evaporated. The crude material was purified by column chromatography using a 24 g silica gel gold column with 0-40% EtOAc in Heptane as eluent. The desired product was obtained as a light yellow solid. 1-[4-(4-fluorophenyl)-5-tetrahydropyran-4-yl-2,4,10,11-tetrazatricyclo[7.3.0.03,7]dodeca-1(9),2,5,7,11-pentaen-10-yl]ethanone (26.3 mg, 18%). $^1$H NMR (400 MHz, DMSO-$d_6$) δ 8.81 (d, J=0.8 Hz, 1H), 8.56 (d, J=0.8 Hz, 1H), 7.63-7.55 (m, 2H), 7.51-7.43 (m, 2H), 6.77 (d, J=0.8 Hz, 1H), 3.90-3.79 (m, 2H), 3.29-3.21 (m, 2H), 3.00-2.86 (m, 1H), 2.74 (s, 3H), 1.76-1.66 (m, 4H). LCMS m/z 379.03 [M+H]$^+$.

Step 5. Synthesis of 4-[4-(4-fluorophenyl)-5-tetrahydropyran-4-yl-2,4,10,11-tetrazatricyclo[7.3.0.03,7]dodeca-1,3(7),5,8,11-pentaen-6-yl]benzoic Acid (326)

A 20 mL scintillation vial was charged with 1-[4-(4-fluorophenyl)-5-tetrahydropyran-4-yl-2,4,10,11-tetrazatricyclo[7.3.0.03,7]dodeca-1(9),2,5,7,11-pentaen-10-yl]ethanone (25 mg, 0.06607 mmol) and NIS (45 mg, 0.2000 mmol). DCM (2000 µL) was added, and the reaction was stirred at room temperature. The solvent was evaporated, and the crude material was purified by column chromatography using a 12 g silica gel gold column with 0-40% EtOAc in Heptane as eluent. The product C215 was used in the subsequent step without further purification.

A 0.5-2 mL microwave vial was charged with 1-[4-(4-fluorophenyl)-6-iodo-5-tetrahydropyran-4-yl-2,4,10,11-tetrazatricyclo[7.3.0.03,7]dodeca-1(9),2,5,7,11-pentaen-10-yl]ethenone, (4-ethoxycarbonylphenyl)boronic acid (30 mg, 0.1546 mmol), and $K_3PO_4$ (65 mg, 0.3062 mmol). dioxane (250 μL) and water (50 μL) were added, and the solution was degassed with $N_2$ for 10 minutes. Then, XPhos Pd G1 (5 mg, 0.0064 mmol) was added, and the reaction was heated to 80° C. After 2.5 h, water (5 mL) and dichloromethane (5 mL) were added, and the mixture was passed through a phase separator. The organic phase was collected, and the solvent was evaporated. The crude material was directly subjected to the next reaction.

A 20 mL scintillation vial was charged with the crude reaction mixture and dissolved in THF (1000 μL) and MeOH (500 μL). NaOH (396 μL of 1 M, 0.3960 mmol) was added and the reaction was heated to 50° C. After 30 minutes, the reaction was complete by LCMS. The solvent was evaporated, and the crude material was taken up in minimal water. HCl (396 μL of 1 M, 0.3960 mmol) was added, forming a precipitate. The solvent was evaporated, and the crude material was taken up in minimal DMSO and purified by reverse phase chromatography using a gradient of 10-100% acetonitrile in water with 0.2% formic acid modifier on a 15.5 g gold C18 column. The desired product was obtained as a white solid. 4-[4-(4-fluorophenyl)-5-tetrahydropyran-4-yl-2,4,10,11-tetrazatricyclo[7.3.0.03,7]dodeca-1,3(7),5,8,11-pentaen-6-yl]benzoic acid (2.5 mg, 8%). LCMS m/z 457.1 [M+H]$^+$.

Compound 327

4-[10-(4-fluorophenyl)-11-(2-methoxy-1,1-dimethylethyl)-2,4,5,10-tetrazatricyclo[7.3.0.03,7]dodeca-1,3(7),5,8,11-pentaen-12-yl]benzoic Acid (327)

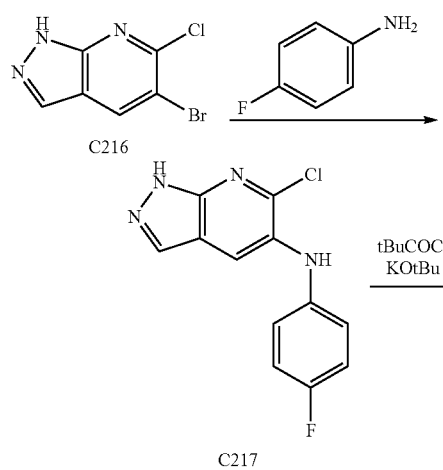

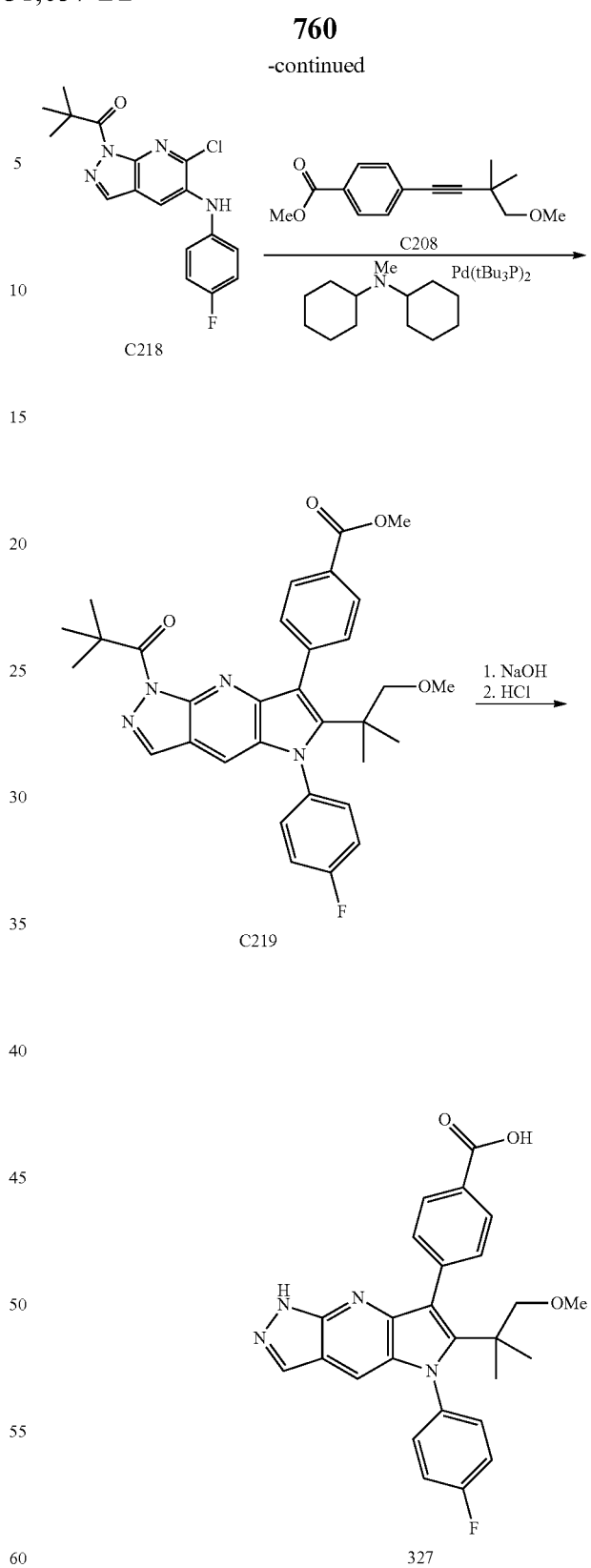

Compound 327 was prepared from C218 using the method described for the preparation of compound 125. $^1$H NMR (400 MHz, Methanol-d$_4$) δ 8.14 (d, J=7.7 Hz, 2H), 8.00 (s, 1H), 7.65-7.52 (m, 4H), 7.43-7.34 (m, 3H), 3.39-3.27 (m, 5H), 1.20 (s, 6H). LCMS m/z 459.12 [M+H]$^+$.

Compound 328
4-[10-(4-fluorophenyl)-11-tetrahydropyran-4-yl-2,4,5,10-tetrazatricyclo[7.3.0.0³,⁷]dodeca-1,3(7),5,8,11-pentaen-12-yl]benzoic Acid (328)
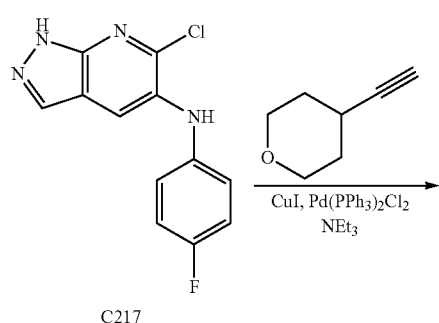
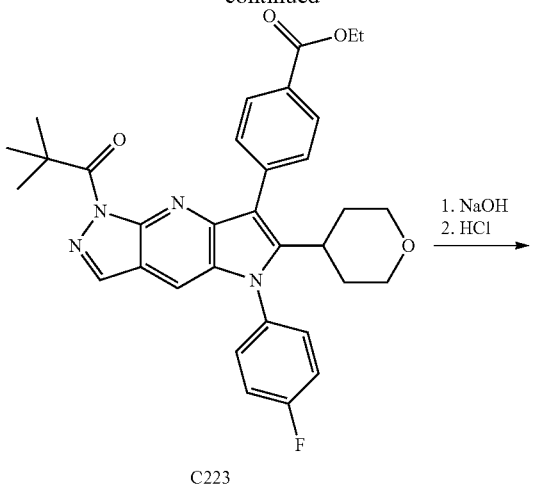
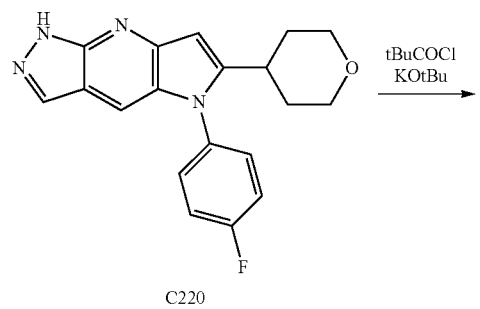
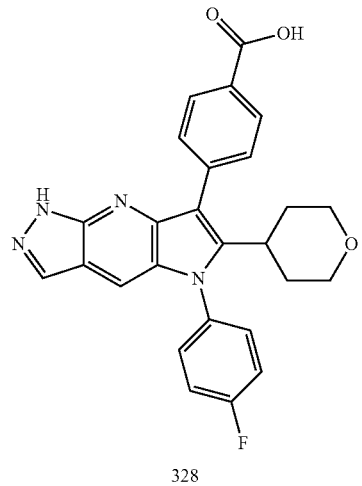
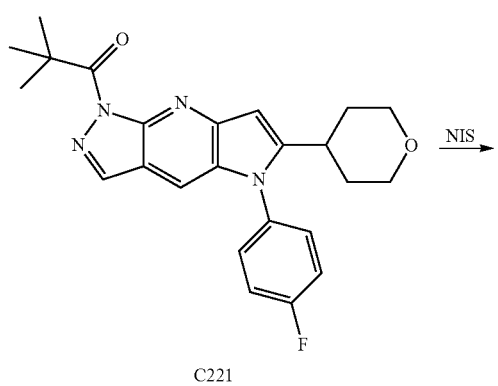
Compound 328 was prepared from C217 using the method described for the preparation of compound 108. ¹H NMR (400 MHz, DMSO-$d_6$) δ 13.14 (s, 1H), 12.97 (s, 1H), 8.06 (d, J=8.4 Hz, 3H), 7.68 (dd, J=8.5, 4.9 Hz, 4H), 7.57 (s, 1H), 7.53 (t, J=8.5 Hz, 2H), 3.74 (d, J=11.2 Hz, 2H), 3.18-3.04 (m, 3H), 1.77-1.65 (m, 4H). LCMS m/z 457.1 [M+H]⁺.
Compound 329
4-[10-(4-fluorophenyl)-11-isopropyl-2,4,5,8,10-pentazatricyclo[7.3.0.0³,⁷]dodeca-1,3(7),5,8,11-pentaen-12-yl]benzoic Acid (329)
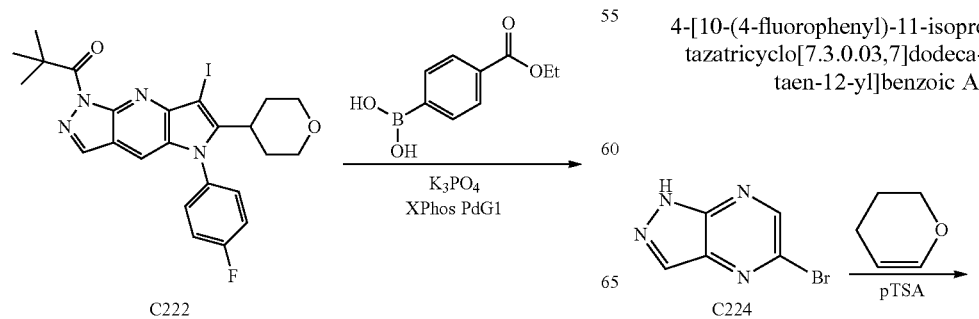

-continued

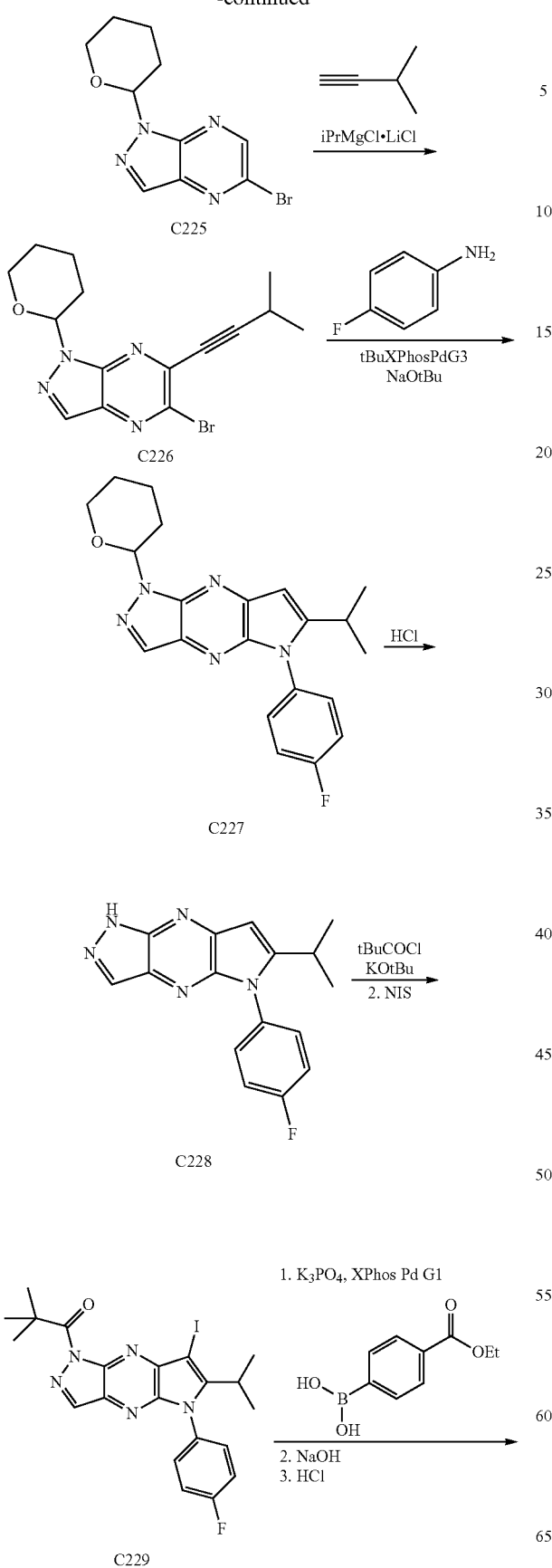

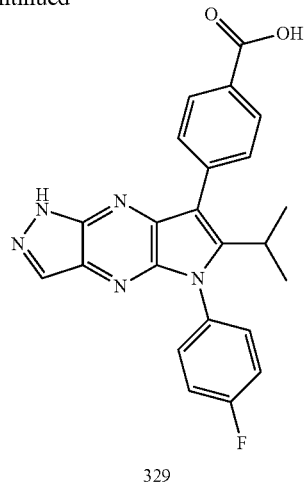

329

Step 1. Synthesis of 5-bromo-1-tetrahydropyran-2-yl-pyrazolo[3,4-b]pyrazine (C225)

To a solution of 5-bromo-1H-pyrazolo[3,4-b]pyrazine (1.315 g, 6.608 mmol) and 3,4-dihydro-2H-pyran (1.8 mL, 19.73 mmol) in dichloromethane (22 mL) was added p-TsOH (Water (1)) (126 mg, 0.6624 mmol).

The reaction was stirred overnight at room temperature and was quenched with a saturated solution of sodium bicarbonate. The phases were separated, and the aqueous phase was extracted twice with dichloromethane. The combined organic layers were dried over $Na_2SO_4$, filtered and evaporated. Purification by silica gel cartridge (40 g column) eluting with EtOAc/Heptane 100:0 to 50:50 gave 5-bromo-1-tetrahydropyran-2-yl-pyrazolo[3,4-b]pyrazine (1.67 g, 87%). $^1$H NMR (400 MHz, Chloroform-d) δ 8.55 (s, 1H), 8.26 (s, 1H), 6.02 (dd, J=10.3, 2.6 Hz, 1H), 4.15-4.06 (m, 1H), 3.85-3.74 (m, 1H), 2.72-2.60 (m, 1H), 2.21-2.15 (m, 1H), 2.05-1.96 (m, 1H), 1.85-1.75 (m, 2H), 1.69-1.64 (m, 1H). LCMS m/z 296.25 [M+H]$^+$.

Step 2: Synthesis of 5-bromo-6-(3-methylbut-1-ynyl)-1-tetrahydropyran-2-yl-4,7-dihydropyrazolo[3,4-b]pyrazine (C226)

5-bromo-6-(3-methylbut-1-ynyl)-1-tetrahydropyran-2-yl-pyrazolo[3,4-b]pyrazine

At rt, to a solution of 3-methylbut-1-yne (72 mg, 1.057 mmol) in THF (1.0 mL) was slowly added chloro(isopropyl) magnesium chlorolithium (598 µL of 1.3 M, 0.7774 mmol). After stirring the mixture for 15 min, the reaction was heated at 40° C. for 45 min and cooled down to −78° C. A solution of 5-bromo-1-tetrahydropyran-2-yl-pyrazolo[3,4-b]pyrazine (100 mg, 0.3532 mmol) in THF (1.0 mL) was added dropwise. The reaction was stirred 30 min at −78° C., then warmed up to 0° C., stirred for 30 min. The mixture was warmed to room temperature, stirred 1 h, then heated at 65° C. for 45 min. The product was using immediately in the subsequent reaction. 5-bromo-6-(3-methylbut-1-ynyl)-1-tetrahydropyran-2-yl-4,7-dihydropyrazolo[3,4-b]pyrazine (124 mg, 80%) LCMS m/z 351.05 [M+H]$^+$.

Steps 3-9. Synthesis of 4-[10-(4-fluorophenyl)-11-isopropyl-2,4,5,8,10-pentazatricyclo[7.3.0.03,7]dodeca-1,3(7),5,8,11-pentaen-12-yl]benzoic Acid (329)

Compound 329 was prepared from C226 as described for the preparation of S3 from C2, and then the preparation of compound 107. An additional step for the remove of the THP protecting group by treatment with HCl was performed. 4-[10-(4-fluorophenyl)-11-isopropyl-2,4,5,8,10-pentazatricyclo[7.3.0.03,7]dodeca-1,3(7),5,8,11-pentaen-12-yl]benzoic acid (5.3 mg, 13%). $^1$H NMR (400 MHz, DMSO-$d_6$) δ 13.61 (s, 1H), 8.27 (s, 1H), 8.08 (d, J=8.4 Hz, 2H), 7.72-7.65 (m, 4H), 7.53-7.44 (m, 2H), 3.34-3.27 (overlap water peak, m, 1H), 1.17 (d, J=7.1 Hz, 6H). LCMS m/z 416.15 [M+H]$^+$.

Compound 330

4-[10-(4-fluorophenyl)-11-tetrahydropyran-4-yl-2,4,5,10-tetrazatricyclo[7.3.0.03,7]dodeca-1,3(7),5,8,11-pentaen-12-yl]benzamide (330)

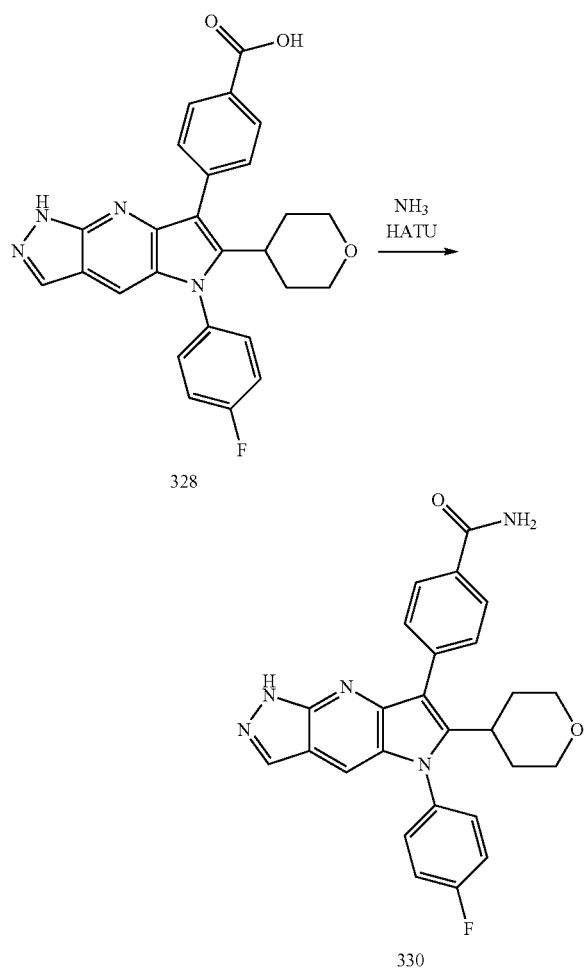

Compound 330 was prepared from compound 328 using the method described for the preparation of compound 128. $^1$H NMR (400 MHz, Methanol-$d_4$) δ 8.39 (s, 1H), 8.20 (s, 1H), 8.12-8.03 (m, 2H), 7.72-7.61 (m, 4H), 7.54-7.43 (m, 2H), 3.79 (dd, J=11.3, 3.9 Hz, 2H), 3.19 (td, J=11.6, 2.6 Hz, 2H), 3.15-3.04 (m, 1H), 1.86-1.65 (m, 4H). LCMS m/z 456.37 [M+H]$^+$.

Compound 331

4-[5-(4-fluorophenyl)-6-tetrahydropyran-4-yl-1H-pyrrolo[3,2-f]indazol-7-yl]benzoic Acid (331)

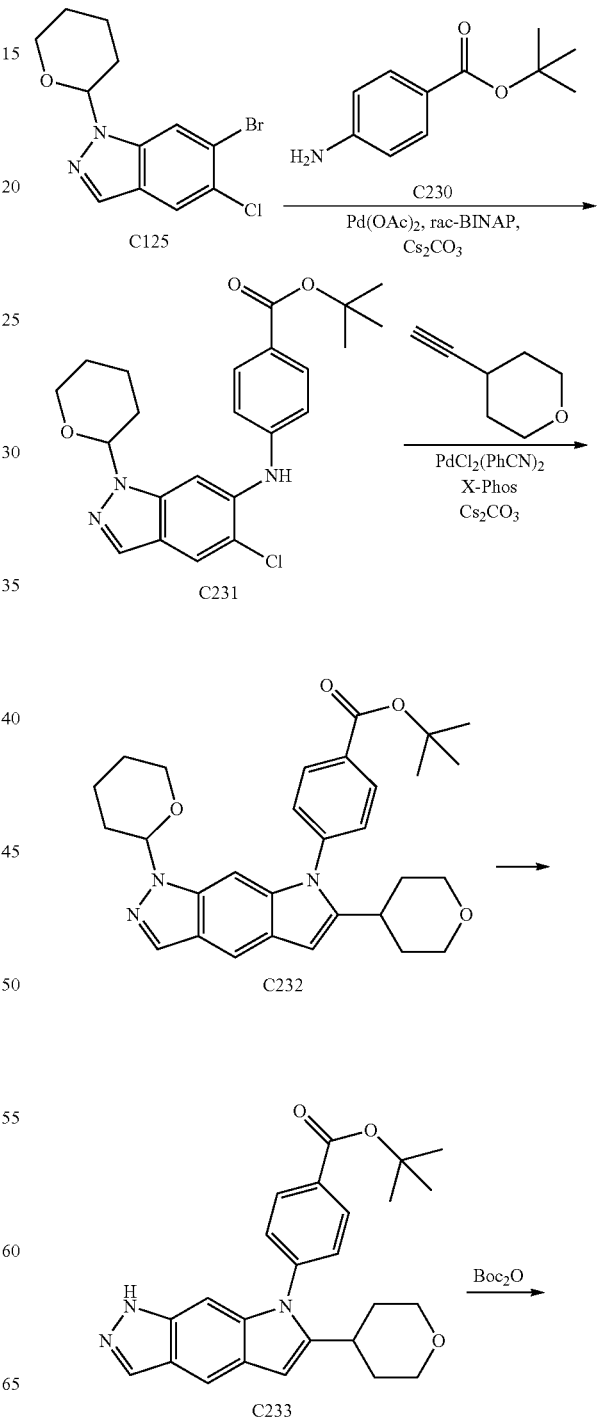

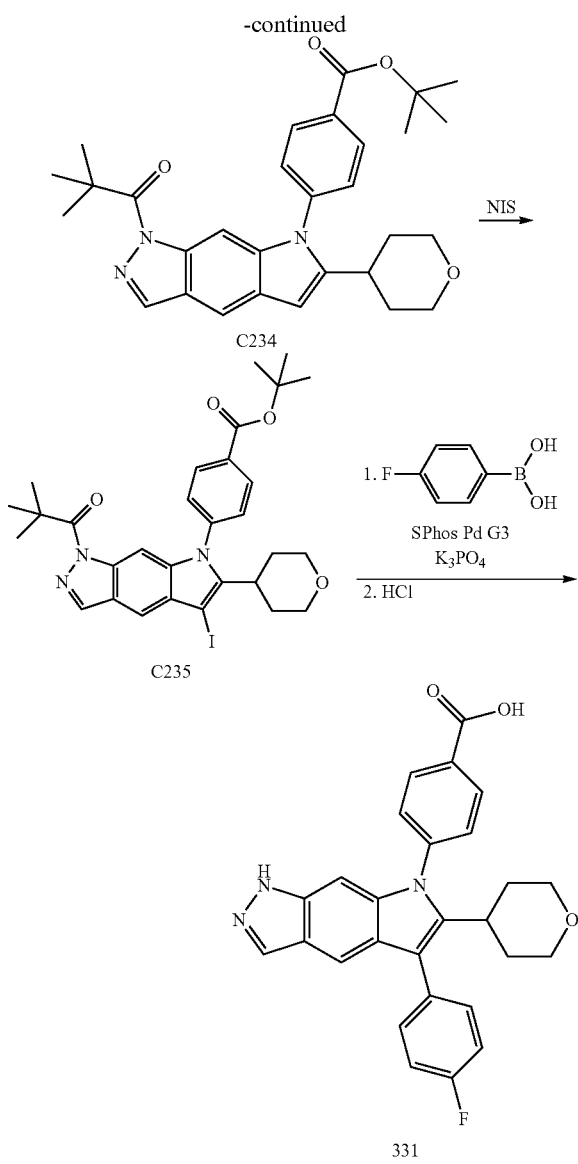

Step 1. Synthesis of tert-butyl 4-[(5-chloro-1-tetrahydropyran-2-yl-indazol-6-yl)amino]benzoate (C231)

In a 30 mL microwave vial was loaded 6-bromo-5-chloro-1-tetrahydropyran-2-yl-indazole (1 g, 3.169 mmol), tert-butyl 4-aminobenzoate (748 mg, 3.871 mmol), Pd$_2$(dba)$_3$, (142 mg, 0.1551 mmol), rac-BINAP (120 mg, 0.19 mmol) and Cs$_2$CO$_3$ (1.63 g, 5.03 mmol). tert-butyl 4-aminobenzoate (748 mg, 3.871 mmol) in THF (20 mL) was added. The mixture was bubbled with N$_2$. The vial was sealed and heated at 80° C. for 10 h. The mixture was cooled to rt, partitioned in EtOAc and water, extracted with EtOAc (3×). The organic phase was dried over Na$_2$SO$_4$, filtered and evaporated. Purification by silica gel chromatography (24 g silica gel, EtOAc/heptane 0-50%) and then a second time (24 g silica gel, EtOAc/DCM 0-30%) afforded the product. tert-butyl 4-[(5-chloro-1-tetrahydropyran-2-yl-indazol-6-yl)amino]benzoate (948 mg, 70%). $^1$H NMR (300 MHz, Chloroform-d) δ 7.99 (d, J=8.8 Hz, 2H), 7.91 (d, J=0.9 Hz, 1H), 7.78 (s, 1H), 7.56 (t, J=0.7 Hz, 1H), 7.23 (d, J=8.7 Hz, 2H), 6.46 (s, 1H), 5.58 (dd, J=9.2, 2.6 Hz, 1H), 4.08-3.89 (m, 1H), 3.83-3.53 (m, 1H), 2.52 (ddd, J=13.3, 10.1, 6.8 Hz, 1H), 2.24-2.07 (m, 2H), 1.82-1.60 (m, 3H), 1.62 (s, 9H). LCMS m/z 428.2 [M+H]$^+$.

Step 2. Synthesis of tert-butyl 4-(1-tetrahydropyran-2-yl-6-tetrahydropyran-4-yl-pyrrolo[3,2-f]indazol-7-yl)benzoate (C232)

In a 30 mL microwave tube was loaded PdCl$_2$(PhCN)$_2$ (42 mg, 0.1095 mmol), X-Phos (157 mg, 0.3293 mmol), Cs$_2$CO$_3$ (1.8 g, 5.525 mmol) and acetonitrile (5 mL). The mixture was bubbled with N$_2$. tert-butyl 4-[(5-chloro-1-tetrahydropyran-2-yl-indazol-6-yl)amino]benzoate (940 mg, 2.197 mmol) in acetonitrile (15 mL) was added. After 5 min, tert-butyl 4-[(5-chloro-1-tetrahydropyran-2-yl-indazol-6-yl)amino]benzoate (940 mg, 2.197 mmol) in acetonitrile (4 mL) was added. The vial was sealed and heated at 80° C. for 3 h. The mixture was concentrated. The residue was suspended in water and 8 mL 1N HCl was added. The mixture was extracted with DCM (3×). The organic phase was dried over Na$_2$SO$_4$, filtered and evaporated. Silica gel chromatography (40 g silica gel, EtOAc/heptane 0-50%) afforded the product. tert-butyl 4-(1-tetrahydropyran-2-yl-6-tetrahydropyran-4-yl-pyrrolo[3,2-f]indazol-7-yl)benzoate (448 mg, 37%). $^1$H NMR (300 MHz, Chloroform-d) δ 8.25 (d, J=8.7 Hz, 2H), 8.12 (d, J=0.8 Hz, 1H), 7.88 (d, J=1.0 Hz, 1H), 7.50 (d, J=8.3 Hz, 2H), 7.03 (d, J=1.0 Hz, 1H), 6.54 (d, J=0.9 Hz, 1H), 5.60 (dd, J=9.2, 2.8 Hz, 1H), 4.10-3.85 (m, 3H), 3.77-3.54 (m, 2H), 3.35 (tt, J=11.6, 2.6 Hz, 2H), 2.87 (td, J=11.2, 5.6 Hz, 1H), 2.62 (m, 1H), 2.26-1.73 (m, 8H), 1.68 (s, 9H). LCMS m/z 502.28 [M+H]$^+$.

Step 3. Synthesis of tert-butyl 4-(6-tetrahydropyran-4-yl-1H-pyrrolo[3,2-f]indazol-7-yl)benzoate (C233)

To a solution of tert-butyl 4-(1-tetrahydropyran-2-yl-6-tetrahydropyran-4-yl-pyrrolo[3,2-f]indazol-7-yl)benzoate (222 mg, 0.4049 mmol) in MeOH (10 mL) was added methanol (Hydrochloride salt) (3 mL of 1.25 M, 3.750 mmol) (HCl in MeOH). The mixture was in a sealed vial and stirred at 50° C. for 3 h. The mixture was cooled with dry ice, 2-methylpropan-2-olate (Potassium Ion (1)) (1.3 mL of 1 M, 1.300 mmol) was added to neutralized (pH ca 9). The mixture was evaporated. The residue was dissolved in DCM, brine was added. The mixture was extracted with DCM (3×). The organic phase was dried over Na$_2$SO$_4$, filtered and evaporated. Purification by silica gel chromatography (4 g silica gel, EtOAc/heptane 0-50%) afforded the product. White solid. tert-butyl 4-(6-tetrahydropyran-4-yl-1H-pyrrolo[3,2-f]indazol-7-yl)benzoate (131 mg, 67%). $^1$H NMR (300 MHz, Chloroform-d) δ 10.11 (s, 1H), 8.23 (d, J=8.4 Hz, 2H), 8.15 (d, J=1.1 Hz, 1H), 7.91 (d, J=1.1 Hz, 1H), 7.55-7.41 (m, 2H), 7.02 (q, J=1.0 Hz, 1H), 6.55 (d, J=0.8 Hz, 1H), 3.99 (ddd, J=11.6, 4.2, 2.0 Hz, 2H), 3.49-3.26 (m, 2H), 2.89 (ddt, J=15.3, 11.0, 4.2 Hz, 1H), 1.94-1.70 (m, 4H), 1.67 (s, 9H). LCMS m/z 418.26 [M+H]$^+$.

Step 4. Synthesis of tert-butyl 4-[1-(2,2-dimethylpropanoyl)-6-tetrahydropyran-4-yl-pyrrolo[3,2-f]indazol-7-yl]benzoate (C234)

A mixture of tert-butyl 4-(6-tetrahydropyran-4-yl-1H-pyrrolo[3,2-f]indazol-7-yl)benzoate (50 mg, 0.1061 mmol) and 2,2-dimethylpropanoyl 2,2-dimethylpropanoate (2 mL, 9.858 mmol) was heated at 80° C. for 90 min. The mixture was evaporated in vacuum at 70° C. The residue was suspended in aqueous sodium bicarbonate, extracted with DCM (3×). The organic phase was dried over $Na_2SO_4$, filtered and evaporated. Silica gel chromatography (2×4 g silica gel, 0-30%) afforded the product as a white solid. tert-butyl 4-[1-(2,2-dimethylpropanoyl)-6-tetrahydropyran-4-yl-pyrrolo[3,2-f]indazol-7-yl]benzoate (57 mg, 107%). $^1$H NMR (300 MHz, Chloroform-d) δ 8.21-8.10 (m, 2H), 8.08 (d, J=0.8 Hz, 1H), 8.04 (d, J=0.9 Hz, 1H), 7.79 (d, J=1.0 Hz, 1H), 7.43-7.29 (m, 2H), 6.50 (d, J=0.8 Hz, 1H), 3.89 (dd, J=10.8, 3.7 Hz, 2H), 3.26 (td, J=11.6, 2.7 Hz, 2H), 2.88-2.72 (m, 1H), 1.84-1.63 (m, 4H), 1.59 (s, 9H), 1.47 (s, 9H). LCMS m/z 502.3 [M+H]$^+$.

Step 5. Synthesis of tert-butyl 4-[1-(2,2-dimethylpropanoyl)-5-iodo-6-tetrahydropyran-4-yl-pyrrolo[3,2-f]indazol-7-yl]benzoate (C235)

To a solution of tert-butyl 4-[1-(2,2-dimethylpropanoyl)-6-tetrahydropyran-4-yl-pyrrolo[3,2-f]indazol-7-yl]benzoate (124 mg, 0.2472 mmol) in DCM (15 mL) was added NIS (115 mg, 0.5111 mmol), After 10 minutes, the reaction was complete by LCMS. After 30 min, the mixture was loaded onto 2×4 g silica gel, and eluted with 0-30% EtOAc in heptane as eluent. tert-butyl 4-[1-(2,2-dimethylpropanoyl)-5-iodo-6-tetrahydropyran-4-yl-pyrrolo[3,2-f]indazol-7-yl]benzoate (154 mg, 99%). $^1$H NMR (300 MHz, Chloroform-d) δ 8.34-8.16 (m, 3H), 7.97 (d, J=0.9 Hz, 1H), 7.81 (d, J=0.9 Hz, 1H), 7.39 (d, J=8.5 Hz, 2H), 4.03 (dd, J=11.5, 4.2 Hz, 2H), 3.34 (td, J=11.8, 1.8 Hz, 2H), 3.02 (tt, J=12.4, 3.6 Hz, 1H), 2.48 (qd, J=12.6, 4.4 Hz, 2H), 1.69 (s, 9H), 1.65-1.57 (m, 2H), 1.55 (s, 9H). LCMS m/z 628.28 [M+H]$^+$.

Step 6. Synthesis of tert-butyl 4-[1-(2,2-dimethylpropanoyl)-5-(4-fluorophenyl)-6-tetrahydropyran-4-yl-pyrrolo[3,2-f]indazol-7-yl]benzoate In a 30 mL microwave vial was charged with tert-butyl 4-[1-(2,2-dimethylpropanoyl)-5-iodo-6-tetrahydropyran-4-yl-pyrrolo[3,2-f]indazol-7-yl]benzoate (63 mg, 0.1004 mmol), (4-fluorophenyl)boronic acid (37 mg, 0.26 mmol), $K_3PO_4$ (74 mg, 0.35 mmol) and SPhos Pd G3 (6 mg, 0.007670 mmol). Dioxane (7 mL) and water (200 μL) were added. The suspension was bubbled with $N_2$. The vial was sealed and heated at 100° C. under microwave for 2 h, cooled to room temperature, and evaporated. The residue was suspended in water, extracted with DCM (3×). The organic phase was dried over $Na_2SO_4$, filtered and evaporated. Silica gel chromatography (4 g silica gel, EtOAc/heptane 0-30%) afforded the product. tert-butyl 4-[1-(2,2-dimethylpropanoyl)-5-(4-fluorophenyl)-6-tetrahydropyran-4-yl-pyrrolo[3,2-f]indazol-7-yl]benzoate (58.7 mg, 98%). $^1$H NMR (300 MHz, Chloroform-d) δ 8.25 (d, J=8.4 Hz, 2H), 8.10 (d, J=0.8 Hz, 1H), 8.01 (t, J=0.9 Hz, 1H), 7.58 (d, J=1.0 Hz, 1H), 7.54-7.42 (m, 4H), 7.23 (t, J=8.7 Hz, 2H), 3.90-3.79 (m, 2H), 3.20 (td, J=11.8, 1.9 Hz, 2H), 2.97 (tt, J=12.3, 3.5 Hz, 1H), 1.93-1.73 (m, 2H), 1.70 (s, 9H), 1.65 (m, 2H), 1.55 (s, 9H). LCMS m/z 595.42 [M+H]$^+$.

Step 7. Synthesis of 4-[5-(4-fluorophenyl)-6-tetrahydropyran-4-yl-1H-pyrrolo[3,2-f]indazol-7-yl]benzoic Acid (331)

A solution of tert-butyl 4-[1-(2,2-dimethylpropanoyl)-5-(4-fluorophenyl)-6-tetrahydropyran-4-yl-pyrrolo[3,2-f]indazol-7-yl]benzoate (58.7 mg, 0.099 mmol) in THF (2 mL) and $H_2O$ (0.5 mL) was treated with LiOH (200 μL of 5 M, 1.0 mmol) for 18 h. The mixture was concentrated. The residue was dissolved in MeOH (1 mL), acidified with 6 N HCl, diluted with DMSO (1 mL), filtered through cotton plug. The filtrate was purified by reverse HPLC (Waters, acetonitrile/water/0.1% TFA 0-90%). The pure fractions were collected and lyophilized to afford the product. 4-[5-(4-fluorophenyl)-6-tetrahydropyran-4-yl-1H-pyrrolo[3,2-f]indazol-7-yl]benzoic acid (Trifluoroacetate salt) (27.9 mg, 40%). $^1$H NMR (300 MHz, DMSO-d$_6$) δ 12.53 (s, 1H), 8.31-8.14 (m, 2H), 8.03 (d, J=1.0 Hz, 1H), 7.77-7.62 (m, 2H), 7.62-7.47 (m, 3H), 7.46-7.30 (m, 2H), 6.79 (s, 1H), 3.83-3.49 (m, 2H), 3.08 (td, J=11.2, 4.3 Hz, 2H), 2.93 (p, J=8.4, 7.6 Hz, 1H), 1.65 (dd, J=8.0, 3.3 Hz, 4H). LCMS m/z 456.24 [M+H]$^+$.

Compound 332

4-[5-(4-chlorophenyl)-6-tetrahydropyran-4-yl-1H-pyrrolo[3,2-f]indazol-7-yl]benzoic Acid (332)

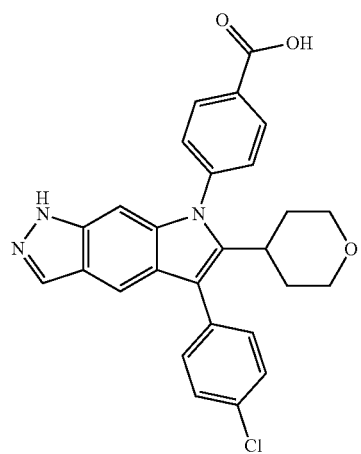

Compound 332 was prepared from C232 according to the method described for the preparation of compound 331. $^1$H NMR (300 MHz, DMSO-d$_6$) δ 12.53 (s, 1H), 8.23 (d, J=8.5 Hz, 2H), 8.04 (d, J=1.0 Hz, 1H), 7.70 (d, J=8.5 Hz, 2H), 7.60 (d, J=8.5 Hz, 2H), 7.56-7.49 (m, 3H), 6.79 (t, J=1.1 Hz, 1H), 3.88-3.60 (m, 2H), 3.09 (dq, J=11.2, 6.2 Hz, 2H), 2.94 (q, J=7.4, 6.9 Hz, 1H), 1.65 (dd, J=8.2, 3.2 Hz, 4H). LCMS m/z 472.13 [M+H]$^+$.

Compound 333

4-[5-(2-methyl-4-pyridyl)-6-tetrahydropyran-4-yl-1H-pyrrolo[3,2-f]indazol-7-yl]benzoic Acid (333)

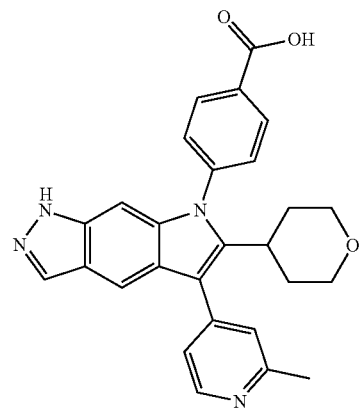

Compound 333 was prepared from C232 according to the method described for the preparation of compound 331. $^1$H NMR (300 MHz, DMSO-$d_6$) δ 13.39 (s, 1H), 12.63 (s, 1H), 8.77 (d, J=5.9 Hz, 1H), 8.31-8.17 (m, 2H), 8.12 (d, J=1.0 Hz, 1H), 7.91 (d, J=5.3 Hz, 2H), 7.82 (d, J=5.7 Hz, 1H), 7.72 (d, J=8.5 Hz, 2H), 6.74 (t, J=1.1 Hz, 1H), 3.75 (d, J=11.0 Hz, 2H), 3.26-3.04 (m, 3H), 2.77 (s, 3H), 1.70 (q, J=12.1, 11.5 Hz, 4H). LCMS m/z 453.22 [M+H]$^+$.

Compound 334

4-(5-(2-methylpyridin-4-yl)-6-(tetrahydro-2H-pyran-4-yl)pyrrolo[3,2-f]indazol-7(1H)-yl)benzamide (334)

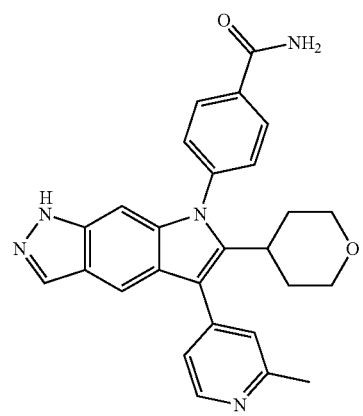

Compound 334 was prepared from compound 333 according to the method described for the preparation of compound 128. $^1$H NMR (400 MHz, Methanol-$d_4$) δ 8.63 (d, J=5.8 Hz, 1H), 8.24-8.15 (m, 2H), 8.12-8.04 (m, 1H), 7.87 (m, 1H), 7.82 (m, 1H), 7.75 (d, J=5.8 Hz, 1H), 7.67-7.60 (m, 2H), 6.84 (t, J=1.1 Hz, 1H), 3.83 (dd, J=11.6, 4.0 Hz, 2H), 3.25 (m, 2H), 3.18 (m, 1H), 2.78 (s, 3H), 1.84 (qd, J=12.2, 11.5, 4.1 Hz, 2H), 1.76 (d, J=13.0 Hz, 2H). LCMS m/z 452.35 [M+H]$^+$.

Compound 335

4-(5-(2-methylpyridin-4-yl)-6-(tetrahydro-2H-pyran-4-yl)pyrrolo[3,2-f]indazol-7(1H)-yl)-N-(5-oxopyrrolidin-3-yl)benzamide (335)

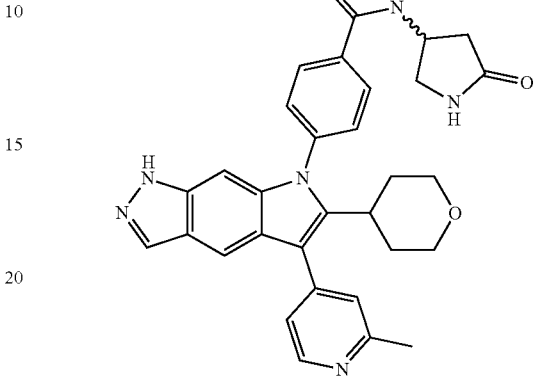

Compound 335 was prepared from compound 333 and 4-aminopyrrolidin-2-one by HATU coupling using the method described for the preparation of compound 128. $^1$H NMR (400 MHz, Methanol-$d_4$) δ 8.56 (d, J=5.3 Hz, 1H), 8.18-8.13 (m, 2H), 8.05 (d, J=1.1 Hz, 1H), 7.72 (d, J=1.2 Hz, 1H), 7.67-7.59 (m, 2H), 7.56 (br s, 1H), 7.49 (dd, J=5.5, 1.6 Hz, 1H), 6.83 (t, J=1.1 Hz, 1H), 4.82 (m, 1H), 3.86 (dd, J=10.6, 7.3 Hz, 1H), 3.80 (dd, J=11.5, 3.9 Hz, 2H), 3.43 (dd, J=10.5, 4.4 Hz, 1H), 3.27-3.17 (m, 2H), 3.17-3.04 (m, 1H), 2.88-2.81 (m, 1H), 2.68 (s, 3H), 2.49 (dd, J=17.3, 5.3 Hz, 1H), 1.81 (qd, J=12.3, 11.9, 4.2 Hz, 2H), 1.72 (d, J=12.9 Hz, 2H). LCMS m/z 535.38 [M+H]$^+$.

Compounds 336 and 337

4-[5-(4-fluorophenyl)-1-methyl-6-tetrahydropyran-4-yl-pyrrolo[2,3-f]indazol-7-yl]benzoic Acid (336) and 4-[5-(4-fluorophenyl)-2-methyl-6-tetrahydropyran-4-yl-pyrrolo[2,3-f]indazol-7-yl]benzoic Acid (337)

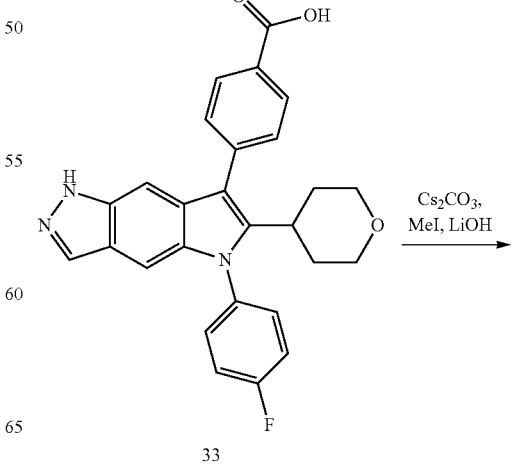

33

-continued

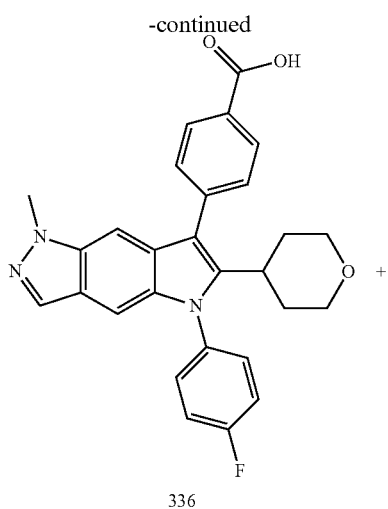

336

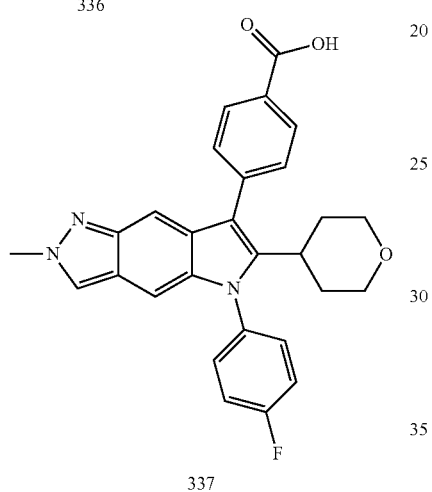

337

To a solution of 33 (50 mg, 0.11 mmol) and Cs$_2$CO$_3$ (108 mg, 0.33 mmol) in tetrahydrofuran (1 mL) was added methyl iodide (17 µL, 0.27 mmol). The reaction mixture was flushed with nitrogen and stirred at 65° C. for 15 h. Methanol (1 mL) and LiOH (500 µL of 2 M, 1.0 mmol) were added and further stirring was continued for 4 h at 65° C. and the mixture was concentrated to dryness, diluted with a mixture of DMSO/water, and injected on a C18 50 g cartridge. Purification by reversed-phase chromatography (Column: C18. Gradient: 10-100% MeCN in water with 0.1% formic acid) afforded 336 (13.5 mg, 49%). $^1$H NMR (300 MHz, DMSO-d$_6$) δ 13.25-12.68 (bs, 1H), 8.16-8.07 (m, 2H), 7.97 (d, J=0.9 Hz, 1H), 7.71-7.57 (m, 4H), 7.57-7.44 (m, 2H), 7.38-7.29 (m, 1H), 7.07 (d, J=1.1 Hz, 1H), 3.97 (s, 3H), 3.78-3.65 (m, 2H), 3.17-2.94 (m, 3H), 1.74-1.56 (m, 4H). LCMS m/z 470.3 [M+H]$^+$ and 337 (12.5 mg, 36%). $^1$H NMR (300 MHz, DMSO-d$_6$) δ 13.35-12.5 (bs, 1H), 8.26 (s, 1H), 8.18-8.05 (m, 2H), 7.70-7.56 (m, 4H), 7.56-7.44 (m, 2H), 7.39 (s, 1H), 6.96 (d, J=1.2 Hz, 1H), 4.17 (s, 3H), 3.73 (d, J=11.0 Hz, 2H), 3.18-2.91 (m, 3H), 1.76-1.54 (m, 4H). LCMS m/z 470.25 [M+H]$^+$.

Compound 338

4-[5-(3,4-difluorophenyl)-6-(2-methoxy-1,1-dimethyl-ethyl)-1H-pyrrolo[2,3-f]indazol-7-yl]-3,5-dimethoxy-benzoic Acid (338)

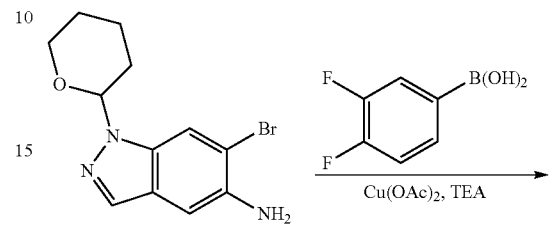

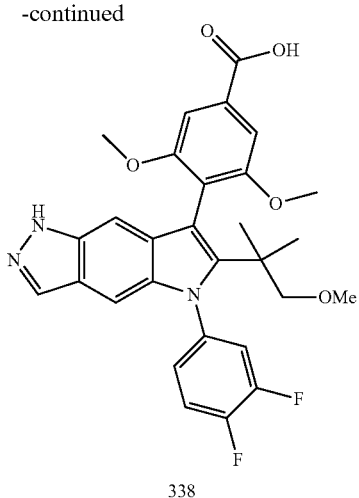

338

Step 1: Synthesis of 6-bromo-N-(3,4-difluorophenyl)-1-tetrahydropyran-2-yl-indazol-5-amine (C236)

To a solution of C184 (20.4 g, 68.88 mmol) and 3,4-difluorophenyl)boronic acid (35.15 g, 222.6 mmol) in dichloromethane (300 mL) was added TEA (32 mL, 229.6 mmol), then 57 g of 3 Å sieves were added followed by Cu(OAc)$_2$ (25.32 g, 204.9 mmol). The blue-green reaction was stirred at room temperature for 15 h. The reaction was filtered, and the filtrate was diluted with dichloromethane (200 mL) and washed with sat. aq. NH$_4$Cl (500 mL) to which a NH$_4$OH solution (120 mL) had been added. The organic layer was washed with water, separated, dried (MgSO$_4$), filtered, and evaporated in vacuo to afford a dark brown oil. The oil was dissolved in dichloromethane and filtered over a plug of silica gel. The plug was eluted with 10% EtOAc/dichloromethane until all of the product had eluted. The filtrate was evaporated in vacuo to afford C236 (15.5 g, 55%). $^1$H NMR (300 MHz, Chloroform-d) δ 7.98-7.73 (m, 2H), 7.48 (s, 1H), 7.05 (dt, J=10.1, 8.9 Hz, 1H), 6.83 (ddd, J=12.1, 6.8, 2.8 Hz, 1H), 6.69 (dtd, J=8.6, 3.3, 1.6 Hz, 1H), 5.79 (s, 1H), 5.64 (dd, J=9.2, 2.5 Hz, 1H), 4.03 (ddt, J=11.7, 3.5, 2.1 Hz, 1H), 3.87-3.61 (m, 1H), 2.67-2.37 (m, 1H), 2.11 (dddd, J=19.4, 13.2, 6.0, 3.4 Hz, 2H), 1.86-1.57 (m, 3H). $^{19}$F NMR (282 MHz, Chloroform-d) δ −136.07 (d, J=22.0 Hz), −147.19 (d, J=22.0 Hz) ppm. LCMS m/z 408.23 [M+H]$^+$;

Step 2: Synthesis of 6-bromo-N-(3,4-difluorophenyl)-1H-indazol-5-amine (C237)

To a solution of C236 (1.21 g, 2.96 mmol) in MeOH (20 mL) was added TsOH (Water (1)) (820 mg, 4.31 mmol). The reaction mixture was refluxed for 2 h and was poured into approx. 100 mL of sat. aq. NaHCO$_3$ (caution: gas evolution was observed). An off-white solid precipitated that was filtered and washed with water. The filter cake was dissolved in EtOAc (50 mL), dried with MgSO$_4$, and filtered over a plug of silica gel. The plug was eluted with EtOAc and the filtrate was evaporated in vacuo to afford an off-white solid. The solid was triturated with dichloromethane and the solvent evaporated. This was repeated once more and the resulting solid was dried in vacuo to afford C237 (900 mg, 94%). $^1$H NMR (300 MHz, DMSO-d$_6$) δ 13.14 (s, 1H), 8.10-7.86 (m, 2H), 7.76 (d, J=30.4 Hz, 2H), 7.18 (dt, J=10.7, 9.1 Hz, 1H), 6.64 (ddd, J=13.3, 7.0, 2.7 Hz, 1H), 6.50 (dq, J=9.6, 2.6, 2.1 Hz, 1H). $^{19}$F NMR (282 MHz, DMSO-d$_6$) δ −138.14 (d, J=23.2 Hz), −152.57 (d, J=23.1 Hz) ppm. LCMS m/z 324.06 [M+H]$^+$;

Step 3: Synthesis of methyl 4-[5-(3,4-difluorophenyl)-6-(2-methoxy-1,1-dimethyl-ethyl)-1H-pyrrolo[2,3-f]indazol-7-yl]-3,5-dimethoxy-benzoate (C239)

A solution of C237 (50 mg, 0.15 mmol), C238 (60 mg, 0.18 mmol) and N-cyclohexyl-N-methyl-cyclohexanamine (100 μL, 0.47 mmol) in 1,4-dioxane (1 mL) was degassed with nitrogen for 10 min. Then, Pd(t-Bu$_3$P)$_2$ (6 mg, 0.012 mmol) was added and the reaction was degassed for an additional 5 min, then heated at 105° C. and stirred for 15 h. The reaction was cooled to room temperature, diluted with water, and extracted with EtOAc. The organic layer was passed through a phase separator and concentrated. The crude material was purified by silica gel chromatography (24 g column, 0-30% EtOAc/Heptane) to afford C239 (38 mg, 45%) LCMS m/z 550.32 [M+H]+;

Step 4: Synthesis of 4-[5-(3,4-difluorophenyl)-6-(2-methoxy-1,1-dimethyl-ethyl)-1H-pyrrolo[2,3-f]indazol-7-yl]-3,5-dimethoxy-benzoic Acid (338)

To a solution of C239 (38 mg, 0.07 mmol) in THF (1 mL), MeOH (0.5 mL) and water (0.5 mL) was added LiOH (16.56 mg, 0.7 mmol). The reaction was stirred at room temperature for 45 min. The reaction was then acidified with 1M HCl, extracted with EtOAc, and concentrated. The crude material was purified by reversed-phase HPLC. Method: C18 Waters Sunfire column (30×150 mm, 5 micron). Gradient: MeCN in water with 0.1% trifluoroacetic acid to afford 338 (13.2 mg, 33%). $^1$H NMR (400 MHz, DMSO-d$_6$) δ 12.38 (s, 1H), 7.94 (d, J=1.0 Hz, 1H), 7.76-7.63 (m, 2H), 7.36 (s, 3H), 6.86 (d, J=1.1 Hz, 1H), 6.68 (t, J=1.1 Hz, 1H), 3.74 (s, 6H), 3.07 (d, J=2.7 Hz, 2H), 3.00 (s, 3H), 1.08 (s, 7H). LCMS m/z 536.21 [M+H]$^+$;

Compound 339

Methyl 5-[5-(4-fluoro-3-methyl-phenyl)-6-tetrahydropyran-3-yl-1H-pyrrolo[2,3-f]indazol-7-yl]-6-methoxy-pyridine-2-carboxylate (339)

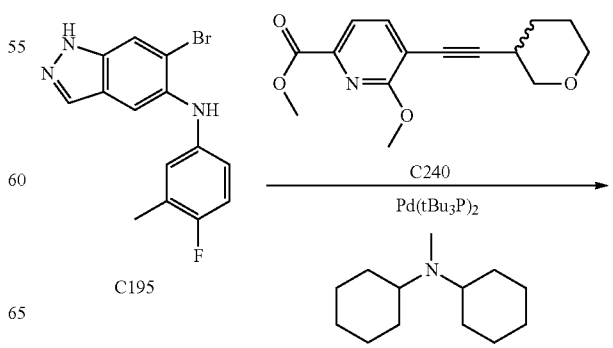

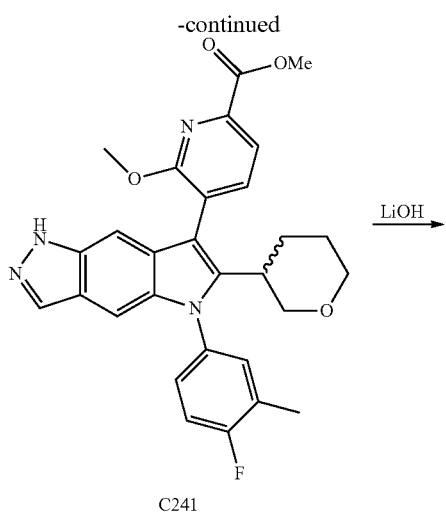

C241

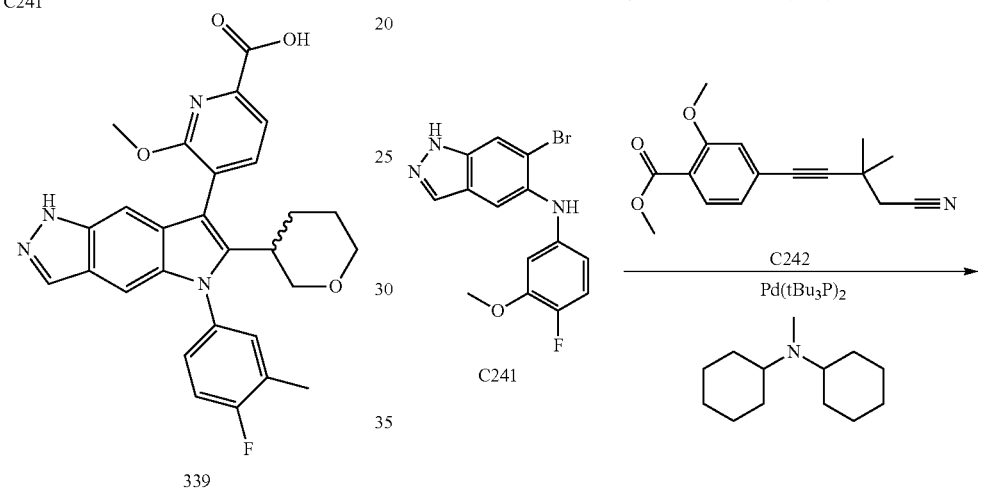

339

Step 1: Synthesis of methyl 5-[5-(4-fluoro-3-methyl-phenyl)-6-tetrahydropyran-3-yl-1H-pyrrolo[2,3-f]indazol-7-yl]-6-methoxy-pyridine-2-carboxylate (C241)

A solution of C240 (300 mg, 1.09 mmol), C195 (351 mg, 1.096 mmol), Pd(t-Bu$_3$P)$_2$ (60 mg, 0.12 mmol) and N-cyclohexyl-N-methyl-cyclohexanamine (912 mg, 4.7 mmol) were mixed in dioxane (5 mL) and the reaction was degassed with nitrogen for 1 min. The reaction was heated at 120° C. for 15 h. The reaction was cooled to room temperature and was diluted with EtOAc and washed with water and brine. The organic layer was dried and concentrated and the residue was purified by silica gel chromatography (40 g silica gel, 10-90% EtOAc in hexanes) to afford C241 (180 mg, 29%). LCMS m/z 515.35 [M+H]$^+$;

Step 2: Synthesis of 5-[5-(4-fluoro-3-methyl-phenyl)-6-tetrahydropyran-3-yl-1H-pyrrolo[2,3-f]indazol-7-yl]-6-methoxy-pyridine-2-carboxylic Acid (339)

To a solution of C241 (160 mg, 0.31 mmol) in THF (8 mL), MeOH (4 mL) and water (4 mL) was added LiOH·H$_2$O (158 mg, 3.8 mmol). The reaction was stirred at 60° C. for 15 h. Then, after cooling to room temperature, 1M HCl was added to carefully adjust the pH to 5, and the reaction was extracted with dichloromethane (10 mL). The organic layer was dried over sodium sulfate and concentrated. The residue was purified by reversed-phase chromatography (10-90% water-acetonitrile, 0.1% formic acid) to afford 339 (130 mg, 79%). $^1$H NMR (400 MHz, DMSO-d$_6$) δ 13.20 (s, 1H), 12.68 (s, 1H), 8.05 (s, 1H), 7.94-7.80 (m, 2H), 7.70 (dd, J=7.4, 1.0 Hz, 1H), 7.42 (dd, J=3.6, 1.0 Hz, 1H), 7.26 (s, 1H), 7.15 (t, J=9.1 Hz, 1H), 7.01 (s, 1H), 4.01-3.78 (m, 3H), 3.54-3.29 (m, 2H), 2.97-2.75 (m, 1H), 2.20 (s, 3H), 1.92 (q, J=14.4, 13.6 Hz, 1H), 1.63 (d, J=20.6 Hz, 2H). LCMS m/z 501.22 [M+H]$^+$;

Compound 340

4-[6-(2-cyano-1,1-dimethyl-ethyl)-5-(4-fluoro-3-methoxy-phenyl)-1H-pyrrolo[2,3-f]indazol-7-yl]-2-methoxy-benzoic Acid (340)

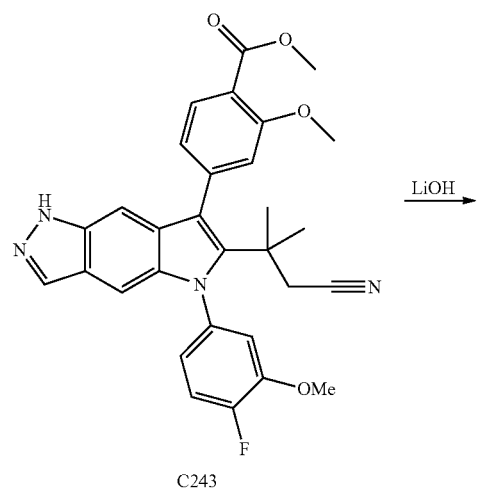

C243

-continued

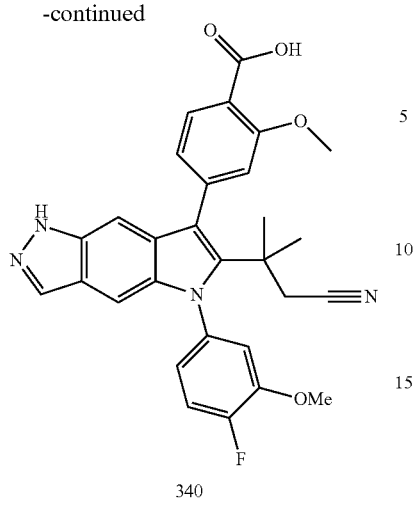

340

Compound 340 was prepared from intermediate C184 using the proper reagents to generate C241 and C242 using the same procedures as for compound 338. $^1$H NMR (400 MHz, Methanol-$d_4$) δ 8.05-7.93 (m, 2H), 7.40 (dd, J=11.1, 8.5 Hz, 1H), 7.33 (d, J=1.4 Hz, 1H), 7.31-7.23 (m, 1H), 7.18 (td, J=9.3, 8.6, 2.4 Hz, 2H), 7.04 (dt, J=15.2, 1.2 Hz, 2H), 3.95 (d, J=1.1 Hz, 3H), 3.91 (s, 3H), 2.72-2.52 (m, 2H), 1.38 (t, J=6.2 Hz, 6H). LCMS m/z 513.27 [M+H]$^+$.

Compound 341

4-[6-[1-(cyanomethyl)cyclobutyl]-8-fluoro-5-(3-fluoro-5-methoxy-phenyl)-1H-pyrrolo[2,3-f]indazol-7-yl]benzoic Acid (341)

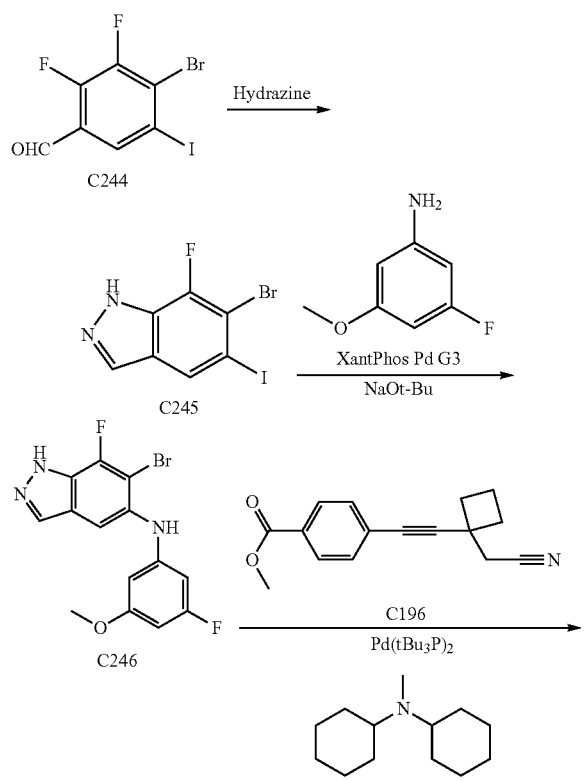

-continued

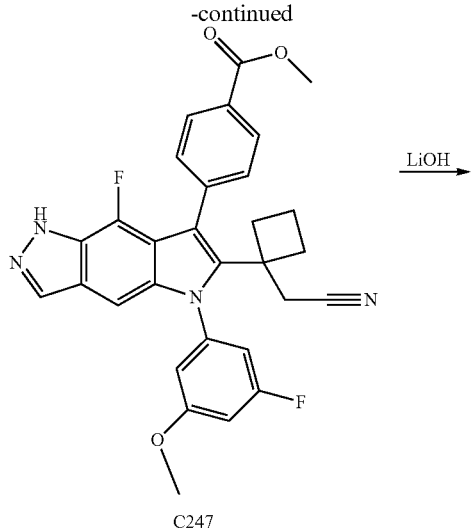

Step 1: Synthesis of 6-bromo-7-fluoro-5-iodo-1H-indazole (C245)

To a solution of C244 (114.7 g, 330.6 mmol) in 2-MeTHF (700 mL) was added hydrazine·H$_2$O (100 mL, 2.040 mol) and the reaction was refluxed for 4 days. The reaction was poured into water (500 mL) and extracted with MTBE (500 mL). The organic layer was separated, dried over MgSO$_4$ and evaporated in vacuo. The solid that remained was triturated with heptane and dried in vacuo to afford C235 (60 g, 53%). $^1$H NMR (300 MHz, DMSO-$d_6$) δ 13.92 (s, 1H), 8.26 (s, 1H), 8.16 (d, J=3.4 Hz, 1H). $^{19}$F NMR (282 MHz, DMSO-$d_6$) δ -113.46. LCMS m/z 340.72 [M+H]+;

Step 2: Synthesis of 6-bromo-7-fluoro-N-(3-fluoro-5-methoxy-phenyl)-1H-indazol-5-amine (C246)

A solution of C245 (1 g, 2.933 mmol), 3-fluoro-5-methoxy-aniline (493 µL, 4.108 mmol) and NaOt-Bu (705 mg, 7.336 mmol) in dioxane (11.75 mL) was purged with nitrogen for 10 min. Then, XantPhos Pd G3 (279 mg, 0.2942 mmol) was added and the reaction was purged with nitrogen for another 5 min. The reaction was then stirred at 90° C. for 15 h. The reaction was cooled down and EtOAc (120 mL) was added followed by aq. sat. NH$_4$Cl and 6M HCl to adjust the pH to ~2. The two layers were separated, and the organic layer was washed with 1M HCl, concentrated to dryness. The residue was purified by silica gel chromatography (Gradient: 0-100% EtOAc in heptane) to afford C247 (357 mg, 34%). ¹H NMR (400 MHz, DMSO-d$_6$) δ 13.76 (s, 1H), 8.17 (s, 1H), 7.99 (s, 1H), 7.59 (s, 1H), 6.18-6.12 (m, 2H), 6.08 (dt, J=11.4, 2.1 Hz, 1H), 3.67 (s, 3H). LCMS m/z 354.01 [M+H]⁺;

Steps 3 and 4: Synthesis of 4-[6-[1-(cyanomethyl) cyclobutyl]-8-fluoro-5-(3-fluoro-5-methoxy-phenyl)-1H-pyrrolo[2,3-f]indazol-7-yl]benzoic Acid (341)

A solution of C246 (59 mg, 0.16 mmol) and C196 (85 mg, 0.34 mmol) in dioxane (865 μL) was bubbled with nitrogen for 2 min. Then, N-cyclohexyl-N-methyl-cyclohexanamine (89 μL, 0.41 mmol) was added and nitrogen was bubbled through for 5 min. Then, Pd(tBu$_3$P)$_2$ (9 mg, 0.018 mmol) was added and nitrogen was bubbled through for another 5 min. The reaction was stirred at 80° C. for 15 h. Then, additional Pd(tBu$_3$P)$_2$ (9 mg, 0.01761 mmol) was added and the reaction was stirred at 100° C. for 2 h and cooled down to 50° C. Methanol (1.2 mL), THF (1.2 mL) and LiOH (650 μL of 2.5M, 1.63 mmol) were successively added and the reaction was stirred at 50° C. for 1 h. The reaction mixture was concentrated to dryness and diluted with a DMSO/water (2:1, 2 mL) and purified by reversed-phase chromatography (Column: C18. Gradient: 0-100% acetonitrile in water with 0.1% formic acid) to afford 341 (22.9 mg, 26%). ¹H NMR (400 MHz, DMSO-d6) δ 13.10 (s, 1H), 12.99 (s, 1H), 8.09 (d, J=3.3 Hz, 1H), 8.03-7.95 (m, 2H), 7.74 (dd, J=8.3, 1.5 Hz, 2H), 7.18 (dt, J=9.1, 2.1 Hz, 1H), 7.16-7.12 (m, 1H), 7.12-7.09 (m, 1H), 6.94 (s, 1H), 3.85 (s, 3H), 3.23 (s, 2H), 2.35-2.23 (m, 2H), 1.94 (p, J=9.4 Hz, 1H), 1.58-1.42 (m, 3H). LCMS m/z 513.22 [M+H]⁺;

Compound 342

4-[6-[1-(cyanomethyl)cyclobutyl]-3-fluoro-5-(4-fluorophenyl)-1H-pyrrolo[2,3-f]indazol-7-yl]benzoic Acid (342)

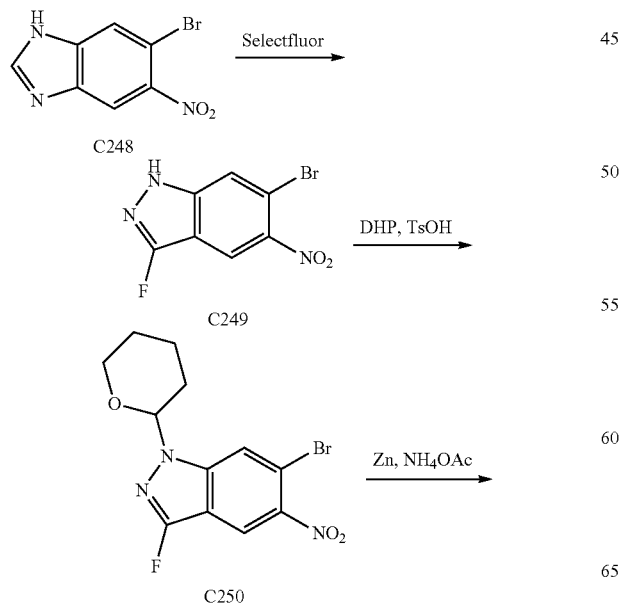

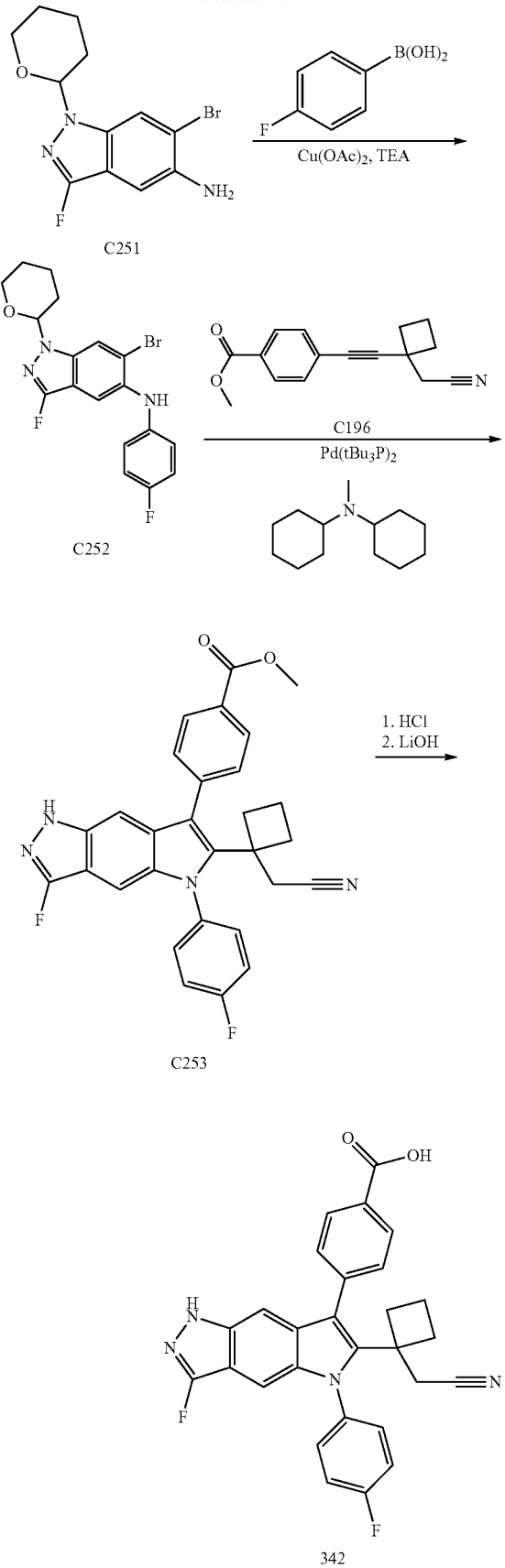

Step 1: Synthesis of 6-bromo-3-fluoro-5-nitro-1H-indazole (C250)

To a solution of C249 (2.41 g, 10 mmol) in acetonitrile (20 mL) and AcOH (20 mL) was added Selectfluor® (3.53 g, 11 mmol). The mixture was stirred at 100° C. for 16 h. After cooling down, the salts were filtered out, the resulting filtrate was concentrated to give C250 (1.14 g, 44%). LCMS m/z (M+1)$^+$: 260.0.

Step 2: Synthesis of 6-bromo-3-fluoro-5-nitro-1-(tetrahydro-2H-pyran-2-yl)-1H-indazole (C251)

To a solution of C250 (2 g, 7.7 mmol) in dichloromethane (20 mL), was added TsOH (1.46 g, 8.47 mmol). The mixture was stirred at room temperature for 24 h and then poured into water (50 mL) and extracted by EA (50 mL×3). The organic layer was concentrated under vacuum and purified by silica gel chromatography (gradient: EtOAc 50% in heptane) to give C251 (1.3 g, 50%). LCMS m/z (M+H)$^+$: 344.0

Step 3: Synthesis of 6-bromo-3-fluoro-1-(tetrahydro-2H-pyran-2-yl)-1H-indazol-5-amine (C252)

To a mixture of C251 (1.3 g, 3.8 mmol) in methanol (30 mL), was added zinc powder (1.23 g, 19 mmol, 5 eq) and NH4OAc (0.45 g, 5.7 mmol, 1.5 eq). The mixture was stirred at rt for 16 h. The reaction mixture was filtered and concentrated under reduced pressure. The residue was purified by silica gel chromatography (gradient: EtOAc 50% in heptane) to give C252 (350 mg, 29%). $^1$H NMR (400 MHz, DMSO-d$_6$) δ: 7.95 (s, 1H), 6.92 (s, 1H), 5.57 (d, J=7.2 Hz, 1H), 5.20 (s, 2H), 3.85-3.81 (m, 1H), 3.72-3.68 (m, 1H), 2.20-2.15 (m, 1H), 1.98-1.94 (m, 1H), 1.89-1.85 (m, 1H), 1.68-1.65 (m, 1H), 1.55-1.49 (m, 2H). LCMS m/z (M+H)$^+$: 314.1.

Step 4: Synthesis of 6-bromo-3-fluoro-N-(4-fluorophenyl)-1-tetrahydropyran-2-yl-indazol-5-amine (C252)

To a suspension of 1 g of 3 Å molecular sieves, C251 (1 g, 3.18 mmol) and (4-fluorophenyl)boronic acid (1.44 g, 10.3 mmol) in dichloromethane (15 mL) was added TEA (1.5 mL, 10.8 mmol) and Cu(OAc)$_2$ (1.75 g, 9.64 mmol). The reaction was stirred at 4 h and Celite® was added and the mixture was concentrated to dryness. The residue was dry loaded on an 80-gram Si gold cartridge. (Gradient: 0-100% EtOAc in heptane) to afford C252 (860 mg, 62%). $^1$H NMR (400 MHz, DMSO-d$_6$) δ 8.21 (d, J=2.0 Hz, 1H), 7.55 (s, 1H), 7.39 (s, 1H), 7.09-7.00 (m, 2H), 6.96-6.88 (m, 2H), 5.80 (dt, J=9.7, 2.6 Hz, 1H), 3.92-3.83 (m, 1H), 3.79-3.69 (m, 1H), 2.26-2.16 (m, 1H), 2.04-1.96 (m, 1H), 1.96-1.88 (m, 1H), 1.76-1.64 (m, 1H), 1.59-1.50 (m, 2H). LCMS m/z 408.15 [M+H]+;

Steps 5-7: Synthesis of 4-[6-[1-(cyanomethyl)cyclobutyl]-3-fluoro-5-(4-fluorophenyl)-1H-pyrrolo[2,3-f]indazol-7-yl]benzoic Acid (342)

To a solution of C196 (63 mg, 0.2483 mmol) and C252 (53 mg, 0.1215 mmol) in dioxane (745 μL) was added N-cyclohexyl-N-methyl-cyclohexanamine (67 μL, 0.3128 mmol) and the mixture was bubbled nitrogen for 5 min. Then, Pd(tBu$_3$P)$_2$ (6.5 mg, 0.013 mmol) was added and nitrogen through the mixture for an additional 5 min. The reaction was stirred at 80° C. for 15 h. The reaction mixture was concentrated to dryness and afford crude C253 which was taken directly to the next step.

A solution of the crude from the previous step in MeOH (1 mL) and HCl (203 μL of 6M, 1.218 mmol) was stirred at 50° C. for 1 h. LCMS showed the desired product and THF (1 mL) was added to the solution. Then, LiOH (975 μL of 2.5M, 2.44 mmol) was added and the mixture was stirred for 15 min at 50° C. and concentrated to dryness. The residue was purified by silica gel chromatography on a Si gold 12-gram column. (Gradient: 0-10% methanol in dichloromethane) to yield 342 (12.6 mg, 20%). $^1$H NMR (400 MHz, DMSO-d$_6$) δ 13.05 (s, 1H), 12.02 (s, 1H), 8.13-8.01 (m, 2H), 7.79-7.72 (m, 2H), 7.72-7.63 (m, 2H), 7.55-7.41 (m, 2H), 7.24-7.12 (m, 1H), 6.85 (s, 1H), 3.19 (s, 2H), 2.36-2.22 (m, 2H), 1.99-1.88 (m, 1H), 1.60-1.45 (m, 3H). LCMS m/z 483.22 [M+H]$^+$

Example 2. Assays for Detecting and Measuring AAT Modulator Properties of Compounds A. AAT Function Assay (MSD Assay NL20-SI Cell Line)

Alpha-1 antitrypsin (AAT) is a SERPIN (serine protease inhibitor) that inactivates enzymes by binding to them covalently. This assay measured the amount of functionally active AAT in a sample in the presence of the disclosed compounds 1-342 by determining the ability of AAT to form an irreversible complex with human neutrophil Elastase (hNE). In practice, the sample (cell supernatant, blood sample, or other) was incubated with excess hNE to allow AAT-Elastase complex to be formed with all functional AAT in the sample. This complex was then captured to a microplate coated with an anti-AAT antibody. The complex captured to the plate was detected with a labeled anti-Elastase antibody and quantitated using a set of AAT standards spanning the concentration range present in the sample. Meso Scale Discovery (MSD) plate reader, Sulfo-tag labeling, and microplates were used to provide high sensitivity and wide dynamic range.

Materials:

| Reagents/Plates | Concentration |
| --- | --- |
| Goat anti-human Alpha-1-Antitrypsin Polyclonal Antibody Use at 5 μg/mL in phosphate buffered saline (PBS) | 1 mL @ 1 mg/mL |
| Human Neutrophil Elastase Stock at 3.4 μM (0.1 mg + 1 mL PBS) Working at 1 μg/mL (34 nm) in MSD Assay buffer (1% bovine serum albumin (BSA)) | 100 μg lyophilized |
| Mouse anti-human Neutrophil Elastase Monoclonal Antibody Sulfo-tagged @ 12:1 using MSD Gold Sulfo-tag N-hydroxysuccinimide (NHS) ester; use at 0.45 μg/mL in MSD Assay buffer (1% BSA) | 900 μg/mL |
| M-AAT (Alpha-1-Antitrypsin) | 5 mg lyophilized |
| MSD Blocker A (BSA) 5% solution in PBS for blocking 1% solution in PBS for assay buffer | 250 mL |
| MSD Read Buffer T (4×) with Surfactant | 1 L or 250 mL |
| MSD 384 high bind plates | |
| Polypropylene for dilution 384 well plate | |
| Tissue culture treated black well 384 well plate | |

Instrument(s):
  Meso Sector S600
  Bravo
  Washer dispenser
  Multidrop Combi

Assay Protocol
Day 1 Cell Culture
1. Harvest NL20 human bronchial epithelial cells expressing human Z-AAT in OptiMEM™ containing Pen/Strep (P/S)
2. Seed at 16,000 cells/well in 30 µL (384 well plate)
3. Centrifuge plates briefly up to speed (1200 rpm) and place into 37° C. incubator overnight Day 2: Compound Addition and Coating Plates with Capture Antibody Compound Addition:
1. Dispense 40 µL of OptiMEM™ (P/S) with doxycycline (1:1000 stock=0.1 µM final) to each well of the compound plate using a multidrop Combi in hood
2. Remove cell plate from incubator, flip/blot and take immediately to Bravo to transfer compounds
3. Return plates to incubator overnight Coat MSD Plates
1. Dilute capture antibody (Polyclonal Goat anti-AAT) to 5 µg/mL (1:200) in PBS (no BSA).
2. Dispense 25 µL of diluted capture antibody into all wells of MSD 384-well High Bind plate using the Multidrop equipped with a standard cassette.
3. Incubate overnight at 4° C.

Prepare Blocker A (BSA) Solutions
1. Prepare solution of 5% MSD Blocker A (BSA) following the manufacturer's instructions.
2. Further dilute the 5% MSD Blocker A in PBS to 1% (Blocker A) as needed.

Day 3: Run MSD Assay
Block Plates
1. Wash plate 1× with 50 µL Wash buffer (PBS+0.5% Tween 20), and adds 35 µL 5% Block A buffer to block non-specific binding on washer dispenser
2. Rotate plates on shaker for 1 hour at 600 rpm Prepare M-AAT Standards
1. Dilute M-AAT stock to 1.6 µg/mL in 1% BSA Blocker A (Stock in −70° C.); then prepare 12×1:2 serial dilutions in 1% Blocker A
2. The top starting final concentration on MSD plate is 320 ng/mL. These dilutions correspond to a final concentration of 320, 160, 80, 40, 20, 10, 5, 2.5, 1.25, 0.625, 0.312, 0.156 ng/mL.

Dilution Plate
1. Add 80 µL of 1% Assay buffer to all wells except columns 1/24 (standards) with Multidrop Combi
2. Add diluted standards to columns 1 and 24
3. Centrifuge dilution plates 1200 rpm briefly Cell Plate
1. Aspirate columns which will have the standards from the cell plates in the hood using 16-pin aspirator Prepare Human Neutrophil Elastase (hNE)
1. Prepare 1 µg/mL Human Neutrophil Elastase by diluting in 1% Blocker A.
   a. Small 100 µg vial—add 1 mL PBS (100 µg/mL)
      i. This can then be diluted 1:100 in 1% Assay Buffer for a final 1 µg/mL concentration MSD—Add hNE (20 µL/Well)
1. After the MSD plate has blocked for at least 1 hour, wash plate 1× with 50 µL Wash buffer (PBS+0.5% Tween 20) and then add 20 µL hNE to each well Bravo—Cell Plate—Dilution Plate—MSD Plate
Using the Bravo aspirate 10 µL from the cell plate, transfer to the dilution plate (9-fold dilution)
1. Mix 25 µL 3×, then aspirate 5 µL, transfer to MSD plate (5-fold dilution)
2. Mix 10 µL 3×. Total dilution is 45-fold.
3. Shake plates at 600 rpm for 1.5 hours Add Functional Detection hNE Antibody
1. Wash plate 1× with wash buffer
2. Add 25 µL Sulfo-tagged anti-Elastase Monoclonal Mouse anti-Elastase) diluted to 0.45 µg/mL (1:2000) in 1% Blocker A into all wells of the functional activity MSD plates using the washer/dispenser
   Note: The dilution required for sufficient signal must be determined for each new lot of labeled antibody.
3. Incubate at RT shaking at 600 rpm for 1 hour.

Final Wash and MSD Imager Read
1. Wash the plate 1×, and add 25 µL of Wash Buffer to the plate.
2. Make 2× Read buffer
3. Remove wash buffer from MSD plate
4. Transfer 35 µL 2× Read Buffer to MSD plate using Bravo and take to MSD to read immediately Data analysis in MSD Discovery Workbench 4.0 software and $EC_{50}$ values were determined using Genedata. See Table 22 for data.

B. Biochemical Assay (Z-AAT Elastase Activity Assay)
This assay measured the modulation of compounds 1-342 on Z-AAT SERPIN activity using purified Z-AAT protein and purified human neutrophil elastase (hNE). Normally, when active monomeric Z-AAT encounters a protease such as trypsin or elastase, it forms a 1:1 covalent "suicide" complex in which both the AAT and protease are irreversibly inactivated. However, compounds binding to Z-AAT can lead to a decrease in SERPIN activity. In such cases, when a protease encounters compound-bound Z-AAT, the protease cleaves and inactivates Z-AAT without itself being inactivated.

Materials
Reagents
  PBS buffer (media prep)+0.01% BRIJ35 detergent (Calbiochem catalog #203728)
  Opti-MEM media (Fisher 11058-021)
  Human neutrophil elastase (hNE, Athens Research #16-14-051200)
    3.4 µM stock (0.1 mg/mL) prepared in 50 mM Na Acetate, pH 5.5, 150 mM NaCl, stored at −80° C.
  Elastase substrate V (ES V, fluorescent peptide substrate MeOSuc-Ala-Ala-Pro-Val-AMC, Calbiochem catalog #324740)
    20 mM stock in DMSO, stored at −20° C.
  Purified Z-AAT protein from human plasma;
    12.9 µM (0.67 mg/mL) Z-AAT Vertex Cambridge Sample 4942, from patient #061-SSN, stored at −80 C Plates
  Corning 4511 (384 well black low volume)
Instruments
  PerkinElmer® EnVision™

Assay Protocol
Pre-Incubation of Z-AAT with Compounds
1. 7.5 µL of Z-AAT (20 nM) was incubated with compounds 1-342 in a GCA plate for 1 hour at room temperature Addition of hNE
1. 7.5 µl of HNE solution (3 nM in PBS+0.01% BRIJ35) added into GCA plate
2. Incubate plate for 30 minutes to allow Z-AAT/HNE suicide complex formation Addition of Substrate and Read Plate on PE Envision
1. 7.5 µL of substrate (300 µM solution of elastase substrate (ES V) in PBS+0.01% BRIJ35) dispensed per well into GCA plate
2. Immediately read on Envision.

C. IC$_{50}$ and EC$_{50}$ Data for Compounds 1-342

The compounds of formula (I) are useful as modulators of AAT activity. Table 22 below illustrates the IC$_{50}$ and EC$_{50}$ of the compounds 1-342 using procedures described above (assays described above in Example 2A). In Table 22 below, the following meanings apply. For IC$_{50}$ and EC$_{50}$: "+++" means <0.4 μM; "++" means 0.4 μM to 1.0 μM; "+" means greater than 1.0 μM; and "N/A" means activity not assessed. For IC$_{50}$, "N.D." means activity not detected up to 30 μm.

TABLE 22

IC$_{50}$ and EC$_{50}$ data for Compounds 1-342

| Compound | Z-AAT Elastase Activity (IC$_{50}$) | NL20 Func. (EC$_{50}$) |
|---|---|---|
| 1 | + | +++ |
| 2 | + | +++ |
| 3 | N.D. | ++ |
| 4 | + | ++ |
| 5 | N.D. | + |
| 6 | N.D. | + |
| 7 | + | +++ |
| 8 | + | ++ |
| 9 | N.D. | ++ |
| 10 | + | +++ |
| 11 | + | +++ |
| 12 | N.D. | + |
| 13 | + | +++ |
| 14 | N.D. | + |
| 15 | N.D. | ++ |
| 16 | N.D. | + |
| 17 | N.D. | ++ |
| 18 | N.D. | + |
| 19 | N.D. | + |
| 20 | N.D. | +++ |
| 21 | N.D. | ++ |
| 22 | N.D. | + |
| 23 | N.D. | + |
| 24 | N.D. | + |
| 25 | + | + |
| 26 | N.D. | + |
| 27 | + | + |
| 28 | N.D. | + |
| 29 | N.D. | +++ |
| 30 | N.D. | ++ |
| 31 | + | ++ |
| 32 | + | ++ |
| 33 | + | +++ |
| 34 | + | + |
| 35 | + | +++ |
| 36 | + | + |
| 37 | + | +++ |
| 38 | + | ++ |
| 39 | + | ++ |
| 40 | N.D. | ++ |
| 41 | N.D. | ++ |
| 42 | N.D. | + |
| 43 | N.D. | + |
| 44 | N.D. | + |
| 45 | + | +++ |
| 46 | N.D. | +++ |
| 47 | + | +++ |
| 48 | + | ++ |
| 49 | + | +++ |
| 50 | + | +++ |
| 51 | + | +++ |
| 52 | + | ++ |
| 53 | + | +++ |
| 54 | + | +++ |
| 55 | + | +++ |
| 56 | +++ | +++ |
| 57 | + | +++ |
| 58 | + | +++ |
| 59 | + | ++ |
| 60 | + | ++ |
| 61 | N.D. | ++ |
| 62 | N.D. | + |
| 63 | N.D. | + |
| 64 | N.D. | + |
| 65 | N.D. | ++ |
| 66 | + | + |
| 67 | + | +++ |
| 68 | + | +++ |
| 69 | + | +++ |
| 70 | + | +++ |
| 71 | + | +++ |
| 72 | + | +++ |
| 73 | N.D. | +++ |
| 74 | + | +++ |
| 75 | + | +++ |
| 76 | N.D. | +++ |
| 77 | + | +++ |
| 78 | N.D. | ++ |
| 79 | + | ++ |
| 80 | + | ++ |
| 81 | + | ++ |
| 82 | + | ++ |
| 83 | + | ++ |
| 84 | + | ++ |
| 85 | + | ++ |
| 86 | N.D. | + |
| 87 | + | + |
| 88 | N/A | + |
| 89 | + | + |
| 90 | N.D. | + |
| 91 | N.D. | + |
| 92 | + | + |
| 93 | N.D. | + |
| 94 | N.D. | + |
| 95 | N.D. | + |
| 96 | N.D. | + |
| 97 | + | +++ |
| 98 | + | ++ |
| 99 | N.D. | + |
| 100 | + | + |
| 101 | N.D. | +++ |
| 102 | ++ | +++ |
| 103 | N.D. | + |
| 104 | ++ | +++ |
| 105 | + | +++ |
| 106 | + | ++ |
| 107 | N.D. | + |
| 108 | ++ | +++ |
| 109 | + | +++ |
| 110 | + | +++ |
| 111 | + | +++ |
| 112 | + | +++ |
| 113 | + | +++ |
| 114 | + | +++ |
| 115 | N.D. | ++ |
| 116 | + | +++ |
| 117 | + | +++ |
| 118 | + | + |
| 119 | + | ++ |
| 120 | + | + |
| 121 | N.D. | ++ |
| 122 | N.D. | + |
| 123 | + | +++ |
| 124 | + | +++ |
| 125 | ++ | +++ |
| 126 | + | + |
| 127 | N.D. | +++ |
| 128 | + | +++ |
| 129 | + | +++ |
| 130 | N.D. | ++ |
| 131 | N.D. | + |
| 132 | N.D. | ++ |
| 133 | N.D. | + |
| 134 | N.D. | + |
| 135 | + | + |
| 136 | + | +++ |
| 137 | N.D. | + |
| 138 | N.D. | ++ |

TABLE 22-continued

IC$_{50}$ and EC$_{50}$ data for Compounds 1-342

| Compound | Z-AAT Elastase Activity (IC$_{50}$) | NL20 Func. (EC$_{50}$) |
|---|---|---|
| 139 | N.D. | ++ |
| 140 | N.D. | + |
| 141 | N.D. | + |
| 142 | N/A | + |
| 143 | N.D. | + |
| 144 | N.D. | +++ |
| 145 | N.D. | ++ |
| 146 | N.D. | + |
| 147 | N.D. | + |
| 148 | N.D. | + |
| 149 | + | + |
| 150 | N.D. | +++ |
| 151 | N.D. | + |
| 152 | N.D. | + |
| 153 | N.D. | ++ |
| 154 | N.D. | + |
| 155 | N/A | + |
| 156 | N.D. | + |
| 157 | N.D. | + |
| 158 | N.D. | + |
| 159 | + | + |
| 160 | + | + |
| 161 | N.D. | + |
| 162 | + | + |
| 163 | N.D. | + |
| 164 | + | ++ |
| 165 | N/A. | + |
| 166 | + | + |
| 167 | + | + |
| 168 | + | + |
| 169 | N.D. | + |
| 170 | + | + |
| 171 | N.D. | + |
| 172 | + | + |
| 173 | + | + |
| 174 | N.D. | +++ |
| 175 | N.D. | + |
| 176 | + | + |
| 177 | N/A | + |
| 178 | + | + |
| 179 | N.D. | + |
| 180 | N.D. | + |
| 181 | +++ | N/A |
| 182 | +++ | +++ |
| 183 | ++ | +++ |
| 184 | + | +++ |
| 185 | + | +++ |
| 186 | ++ | +++ |
| 187 | ++ | ++ |
| 188 | + | + |
| 189 | ++ | +++ |
| 190 | ++ | ++ |
| 191 | + | +++ |
| 192 | + | ++ |
| 193 | + | + |
| 194 | + | + |
| 195 | N/A | + |
| 196 | + | ++ |
| 197 | ++ | +++ |
| 198 | + | + |
| 199 | + | + |
| 200 | + | + |
| 201 | + | + |
| 202 | + | ++ |
| 203 | + | ++ |
| 204 | N.D. | ++ |
| 205 | N.D. | ++ |
| 206 | N.D. | + |
| 207 | + | + |
| 208 | N.D. | + |
| 209 | N.D. | + |
| 210 | N.D. | + |
| 211 | N.D. | + |
| 212 | + | + |
| 213 | N.D. | + |
| 214 | + | + |
| 215 | N.D. | + |
| 216 | N.D. | + |
| 217 | + | + |
| 218 | + | ++ |
| 219 | N.D. | + |
| 220 | + | ++ |
| 221 | N.D. | + |
| 222 | + | + |
| 223 | + | + |
| 224 | N.D. | + |
| 225 | N.D. | ++ |
| 226 | N.D. | + |
| 227 | N.D. | + |
| 228 | + | + |
| 229 | N.D. | + |
| 230 | + | + |
| 231 | + | ++ |
| 232 | + | ++ |
| 233 | + | + |
| 234 | + | + |
| 235 | + | + |
| 236 | N.D. | + |
| 237 | + | + |
| 238 | + | ++ |
| 239 | N.D. | + |
| 240 | N.D. | + |
| 241 | N.D. | + |
| 242 | + | ++ |
| 243 | + | + |
| 244 | + | + |
| 245 | + | ++ |
| 246 | + | ++ |
| 247 | + | ++ |
| 248 | N.D. | + |
| 249 | N.D. | + |
| 250 | N.D. | + |
| 251 | N.D. | + |
| 252 | + | +++ |
| 253 | +++ | +++ |
| 254 | + | ++ |
| 255 | + | + |
| 256 | + | +++ |
| 257 | N.D. | + |
| 258 | N.D. | ++ |
| 259 | N.D. | + |
| 260 | N.D. | + |
| 261 | N.D. | + |
| 262 | + | + |
| 263 | N.D. | + |
| 264 | N.D. | + |
| 265 | + | +++ |
| 266 | N.D. | + |
| 267 | + | +++ |
| 268 | ++ | +++ |
| 269 | + | +++ |
| 270 | + | +++ |
| 271 | ++ | +++ |
| 272 | + | + |
| 273 | N.D. | ++ |
| 274 | N.D. | + |
| 275 | + | + |
| 276 | N.D. | + |
| 277 | + | + |
| 278 | + | ++ |
| 279 | N.D. | + |
| 280 | N.D. | + |
| 281 | N.D. | + |
| 282 | N.D. | + |
| 283 | N.D. | + |
| 284 | + | +++ |
| 285 | N.D. | + |
| 286 | + | + |
| 287 | N.D. | + |
| 288 | N.D. | + |

TABLE 22-continued

IC$_{50}$ and EC$_{50}$ data for Compounds 1-342

| Compound | Z-AAT Elastase Activity (IC$_{50}$) | NL20 Func. (EC$_{50}$) |
|---|---|---|
| 289 | N.D. | ++ |
| 290 | + | + |
| 291 | + | +++ |
| 292 | N.D. | + |
| 293 | N.D. | + |
| 294 | N.D. | + |
| 295 | N.D. | + |
| 296 | + | + |
| 297 | N.D. | + |
| 298 | + | + |
| 299 | + | + |
| 300 | N.D. | + |
| 301 | + | ++ |
| 302 | N.D. | + |
| 303 | + | + |
| 304 | + | +++ |
| 305 | N.D. | + |
| 306 | + | + |
| 307 | N.D. | + |
| 308 | N.D. | + |
| 309 | N.D. | + |
| 310 | N.D. | + |
| 311 | N.D. | + |
| 312 | N.D. | + |
| 313 | + | + |
| 314 | + | + |
| 315 | N.D. | + |
| 316 | N.D. | + |
| 317 | + | ++ |
| 318 | N.D. | + |
| 319 | + | + |
| 320 | ++ | +++ |
| 321 | + | +++ |
| 322 | N.D. | + |
| 323 | N.D. | + |
| 324 | N.D. | + |
| 325 | N.D. | + |
| 326 | N/A | + |
| 327 | + | + |
| 328 | + | + |
| 329 | N.D. | + |
| 330 | + | + |
| 331 | + | +++ |
| 332 | + | ++ |
| 333 | N.D. | + |
| 334 | N.D. | + |
| 335 | N.D. | + |
| 336 | N.D. | + |
| 337 | N.D. | + |
| 338 | + | N/A |
| 339 | N.D. | + |
| 340 | N/A | N/A |
| 341 | N/A | N/A |
| 342 | ++ | N/A |

Example 3: Solid Forms of Compound 33

Bruker-Biospin 400 MHz wide-bore spectrometer equipped with Bruker-Biospin 4 mm HFX probe was used. Samples were packed into 4 mm ZrO$_2$ rotors and spun under Magic Angle Spinning (MAS) condition with spinning speed typically set to 12.5 kHz. The proton relaxation time was measured using $^1$H MAS T$_1$ saturation recovery relaxation experiment in order to set up proper recycle delay of the $^{13}$C cross-polarization (CP) MAS experiment. The fluorine relaxation time was measured using $^{19}$F MAS T$_1$ saturation recovery relaxation experiment in order to set up proper recycle delay of the $^{19}$F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

1. Compound 33 Form A

A. Synthetic Procedure

Methyl 4-(5-(4-fluorophenyl)-1-pivaloyl-6-(tetrahydro-2H-pyran-4-yl)-1,5-dihydropyrrolo[2,3-f]indazol-7-yl)benzoate (25.1 g, 45.337 mmol) was dissolved in THF (326.3 mL, 13 vol). Sodium hydroxide [2N] (5.44 g, 68.0 mL, 136.01 mmol, 3 equiv) was added and the mixture was heated to 55-60° C. Upon reaction completion, the reaction mixture was cooled to 20° C. and water (75.3 mL, 3 vol) and acetic acid (10.89 g, 10.38 mL, 181.35 mmol, 4 equiv.) was added thereto. 2-MeTHF (251 mL, 10 vols) was added aqueous work up was performed. The organic layer was washed with water (75.3 mL, 3 vol) followed by a 6.5 wt % sodium chloride solution by dissolving NaCl (8.2 g, 0.14 mmol, 3.1 equiv) in water (0.120 L, 4.7 vol). The organic layer and solvent swap were distilled into ethanol. A mixture of EtOH (0.150 L, 6 vol) and water (25.1 mL, 1 vol) was added and distillation was continued, and this step was repeat once. EtOH (0.150 L, 6 vol) and water (25.1 mL, 1 vol) were added to the reactor and the mixture was stirred at 40° C. The mixture was cooled to 20-25° C. and the product was isolated by filtration. Compound 33 was dried under vacuum at 66° C. with nitrogen bleed. Compound 33 was isolated in 90% yield with >99.8% area.

B. X-Ray Powder Diffraction

X-ray powder diffraction (XRPD) spectra were recorded at room temperature in reflection mode using a PANalytical Empyrean system equipped with a sealed tube source and a PIXcel 1D Medipix-2 detector (Malvern PANalytical Inc, Westborough, Massachusetts). The X-Ray generator operated at a voltage of 45 kV and a current of 40 mA with copper radiation (1.54060 Å). The powder sample was placed in a back filled sample holder and loaded into the instrument. The sample was scanned over the range of about 3° to about 40° 2θ with a step size of 0.0131303° and 49.725 s per step. The XRPD diffractogram is shown in FIG. 1A and XRPD data are summarized in Table 23.

TABLE 23

XRPD Peaks for Compound 33 Form A

| Peak # | Angle (Degrees 2-Theta ± 0.2) | Intensity % |
|---|---|---|
| 1 | 19.2 | 100.0 |
| 2 | 16.0 | 26.8 |
| 3 | 19.5 | 25.1 |
| 4 | 14.2 | 24.3 |
| 5 | 16.2 | 20.9 |
| 6 | 15.5 | 20.8 |
| 7 | 21.8 | 20.2 |
| 8 | 11.0 | 20.0 |
| 9 | 21.3 | 17.1 |
| 10 | 20.9 | 14.7 |
| 11 | 17.5 | 13.4 |
| 12 | 25.5 | 10.4 |

C. Solid State NMR (1) $^{13}$C CPMAS Analysis

Figure 1B:
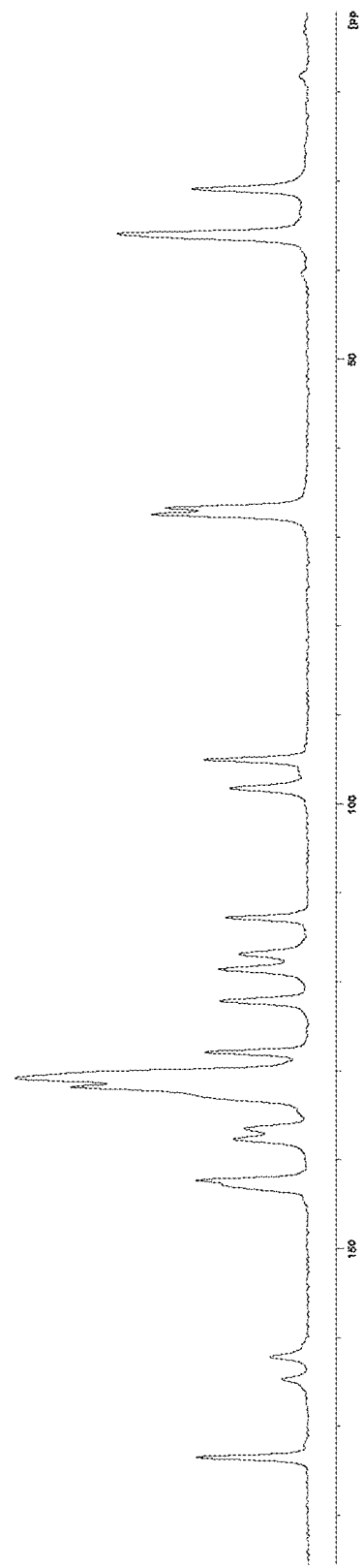
FIG. 1B shows a solid state $^{13}C$ NMR spectrum of Compound 33 Form A.

Solid state $^{13}$C NMR data for Compound 33 Form A is provided in FIG. 1B and summarized in Table 24 below.

TABLE 24

Solid State NMR of Compound 33 Form A

| Peak # | Chem Shift [ppm] | Intensity [rel] |
|---|---|---|
| 1 | 173.5 | 38.2 |
| 2 | 164.7 | 8.8 |
| 3 | 162.1 | 12.9 |
| 4 | 142.9 | 29.0 |
| 5 | 142.3 | 38.2 |
| 6 | 137.6 | 25.4 |
| 7 | 136.5 | 21.6 |
| 8 | 132.8 | 37.1 |
| 9 | 131.8 | 81.1 |
| 10 | 130.8 | 100.0 |
| 11 | 127.9 | 35.4 |
| 12 | 122.1 | 30.1 |
| 13 | 118.6 | 30.6 |
| 14 | 116.8 | 23.4 |
| 15 | 112.8 | 28.1 |
| 16 | 98.2 | 26.9 |
| 17 | 95.0 | 35.4 |
| 18 | 67.4 | 53.6 |
| 19 | 66.7 | 48.7 |
| 20 | 35.9 | 65.3 |
| 21 | 30.8 | 39.5 |

(2) $^{19}$F MAS Analysis

Figure 1C:
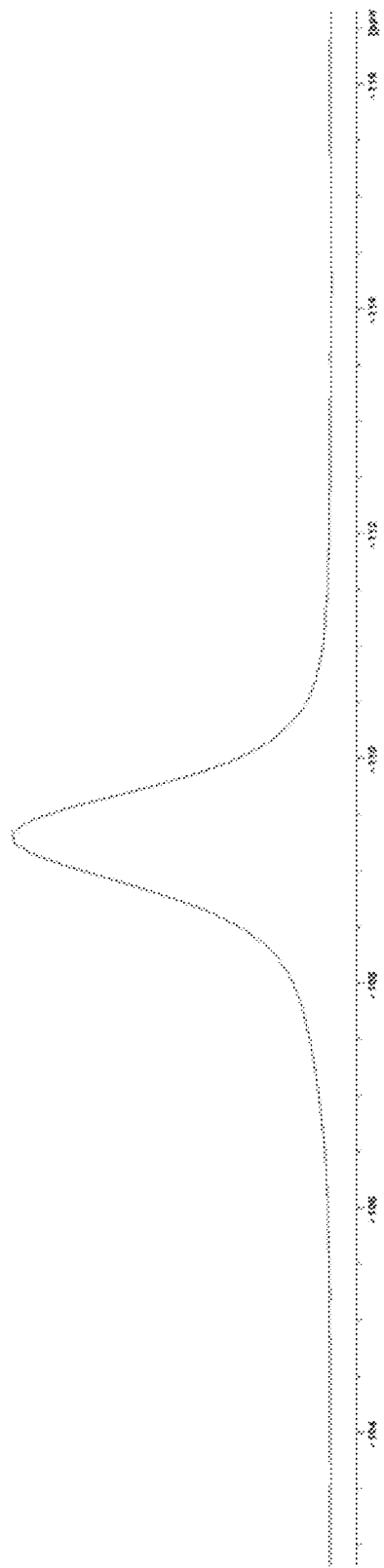
FIG. 1C shows a solid state $^{19}$F NMR spectrum of Compound 33 Form A.

Solid state $^{19}$F NMR data for Compound 33 Form A is provided in FIG. 1C and summarized in Table 25 below.

TABLE 25

Solid State NMR of Compound 33 Form A

| Peak # | Chem Shift [ppm] | Intensity [rel] |
|---|---|---|
| 1 | −109.3 | 12.5 |

D. Thermogravimetric Analysis

Figure 1D:
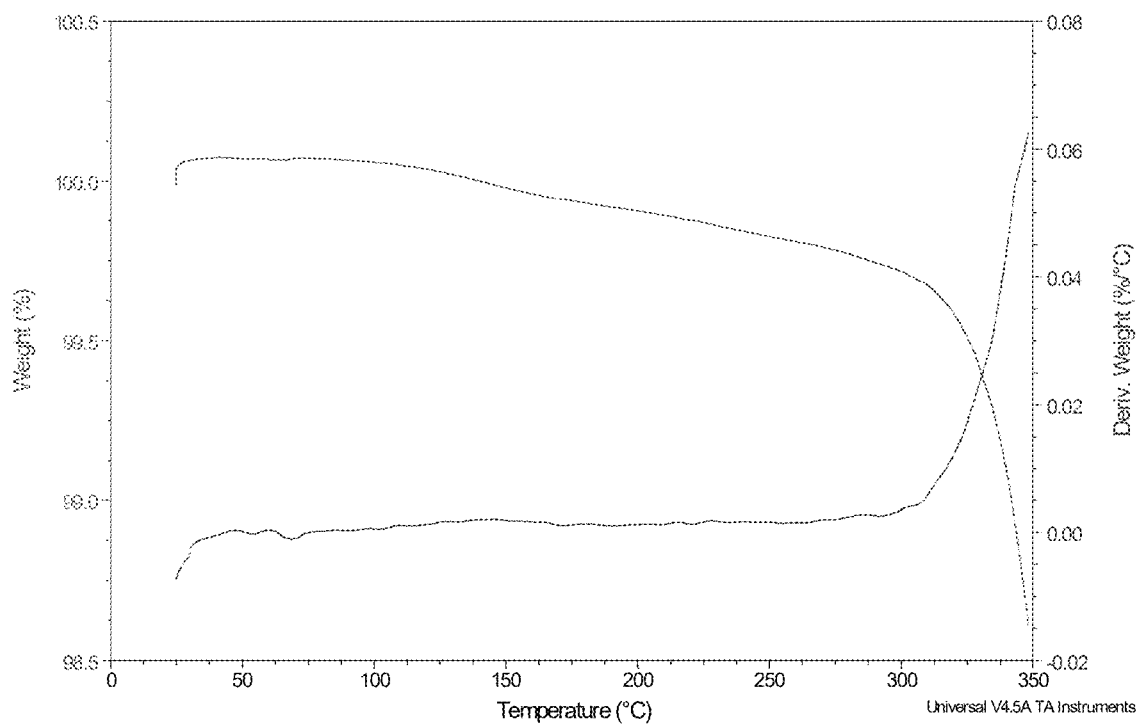
FIG. 1D shows a TGA thermogram of Compound 33 Form A.

Thermal gravimetric analysis of Compound 33 Form A was measured using the TA Instruments TGA Q5000. The thermogram showed 0.1% weight loss from ambient temperature up to 150° C. The TGA thermogram for Compound 33 Form A is provided in FIG. 1D.

E. Differential Scanning Calorimetry Analysis

Figure 1E:
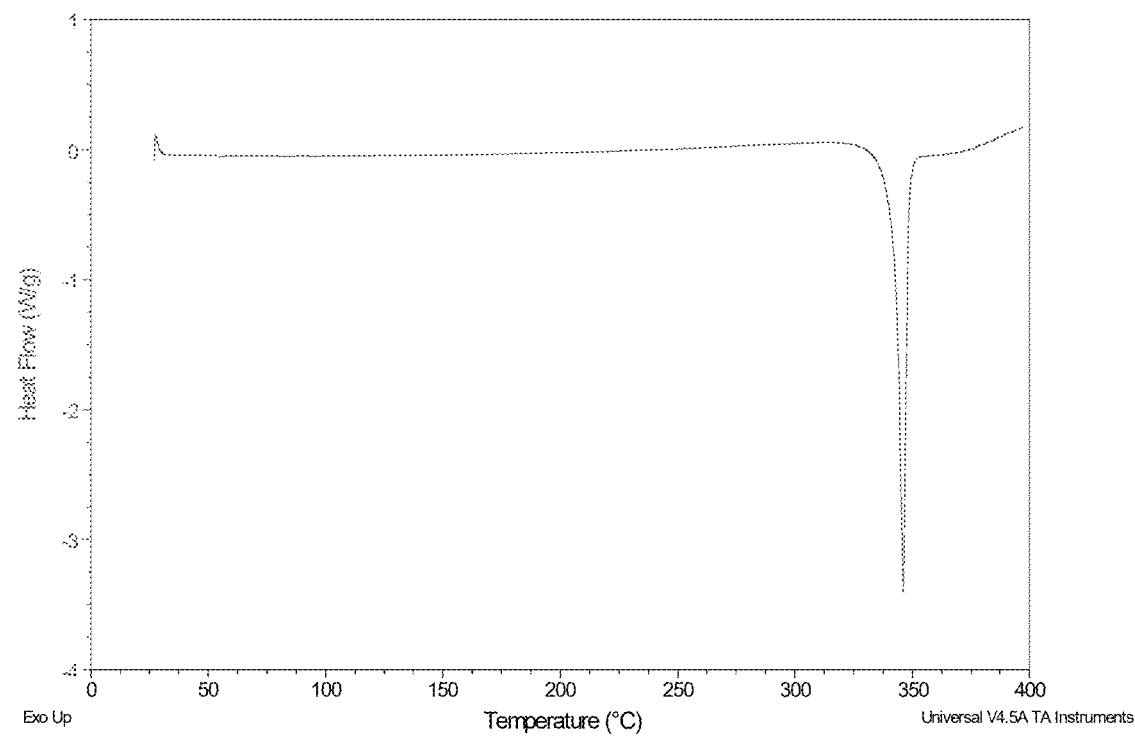
FIG. 1E shows a DSC thermogram of Compound 33 Form A.

DSC of Compound 33 Form A was measured using the TA Instruments Q2000 DSC. The DSC thermogram is provided at FIG. 1E and shows an endothermic peak at 346° C.

F. IR Spectroscopy

Figure 1F:
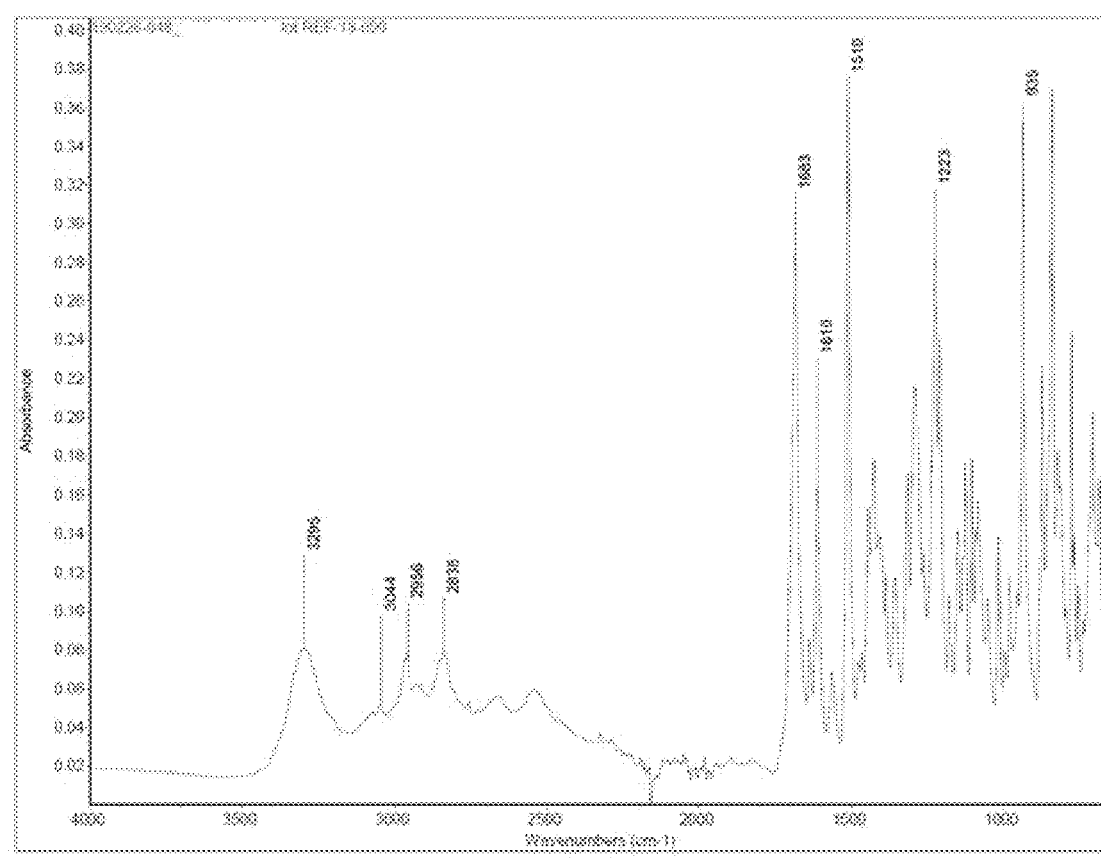
FIG. 1F shows an IR spectrum of Compound 33 Form A.

The IR spectrum of Compound 33 Form A was collected using the Thermo Scientific Nicolet iS50 Spectrometer equipped with a diamond ATR sampling accessory. The IR spectrum of Compound 33 Form A is shown at FIG. 1F and the interpretation of the IR data is summarized in Table 26 below.

TABLE 26

Interpretation of IR Spectrum for Compound 33 Form A

| Frequency (cm$^{-1}$) | Moiety | Vibration |
|---|---|---|
| 3295 | O—H | Stretch |
| 3044 | Aromatic C—H | Stretch |
| 2956, 2838 | Aliphatic C—H | Stretch |
| 1683 | Acid C=O | Stretch |
| 1610, 1510 | Aromatic Ring C—C/C=C | Stretch |
| 1223 | Aromatic C—F | Stretch |
| 935 | Heteroaromatic Ring | Ring deformation |

2. Compound 33 Form B

A. Synthetic Procedure:

15 mg of Compound 33 Form A was suspended in 0.3 mL DCM in a glass vial and stirred with a magnetic starring bar at RT for 3 days. The air dried solids were isolated as Compound 33 Form B.

B. X-Ray Powder Diffraction:

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ 7 with a step size of 0.0131303° and 49 s per step. The XRPD diffractogram is shown in FIG. 2A and XRPD data are summarized in Table 27.

TABLE 27

XRPD Peaks for Compound 33 Form B

| Peak # | Angle (Degrees 2-Theta ± 0.2) | Intensity % |
|---|---|---|
| 1 | 18.1 | 100.0 |
| 2 | 18.4 | 80.1 |
| 3 | 20.2 | 73.8 |
| 4 | 19.8 | 60.3 |
| 5 | 11.0 | 55.9 |
| 6 | 20.6 | 40.3 |
| 7 | 22.3 | 33.9 |
| 8 | 14.3 | 28.4 |
| 9 | 17.1 | 26.1 |
| 10 | 9.2 | 24.3 |
| 11 | 24.7 | 22.9 |
| 12 | 16.2 | 22.7 |
| 13 | 9.9 | 20.8 |
| 14 | 4.5 | 20.6 |
| 15 | 28.9 | 15.5 |
| 16 | 12.7 | 14.5 |
| 17 | 15.1 | 12.8 |
| 18 | 16.8 | 11.8 |
| 19 | 21.4 | 11.6 |
| 20 | 27.4 | 10.6 |
| 21 | 23.6 | 10.4 |
| 22 | 26.6 | 10.3 |

C. Solid State NMR (1) $^{13}$C CPMAS Analysis

Figure 2B:
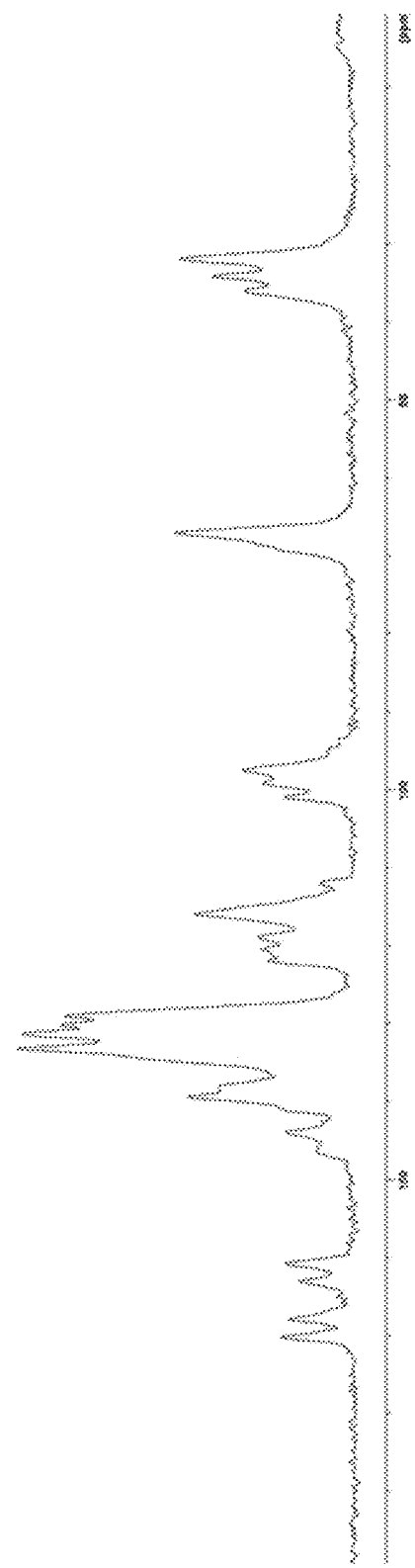
FIG. 2B shows a solid state $^{13}$C NMR spectrum of Compound 33 Form B.

Solid state $^{13}$C NMR data for Compound 33 Form B is provided in FIG. 2B and summarized in Table 28 below.

TABLE 28

Solid State NMR of Compound 33 Form B

| Peak # | Chem Shift [ppm] | Intensity [rel] |
|---|---|---|
| 1 | 170.1 | 21.76 |
| 2 | 167.9 | 19.7 |
| 3 | 163.0 | 16.48 |
| 4 | 160.7 | 20.7 |
| 5 | 146.3 | 11.3 |
| 6 | 143.9 | 20.6 |
| 7 | 139.3 | 49.5 |
| 8 | 138.3 | 40.3 |
| 9 | 133.1 | 100.0 |
| 10 | 131.2 | 98.5 |
| 11 | 130.1 | 87.1 |
| 12 | 128.9 | 86.0 |
| 13 | 121.8 | 25.6 |
| 14 | 120.4 | 27.7 |
| 15 | 118.8 | 28.8 |

TABLE 28-continued

Solid State NMR of Compound 33 Form B

| Peak # | Chem Shift [ppm] | Intensity [rel] |
|---|---|---|
| 16 | 115.9 | 47.4 |
| 17 | 112.0 | 10.4 |
| 18 | 100.9 | 21.1 |
| 19 | 99.1 | 27.5 |
| 20 | 97.4 | 33.2 |
| 21 | 68.8 | 24.2 |
| 22 | 67.0 | 53.4 |
| 23 | 35.9 | 32.5 |
| 24 | 34.1 | 42.3 |
| 25 | 31.9 | 52.0 |

(2) $^{19}$F MAS Analysis

Figure 2C:
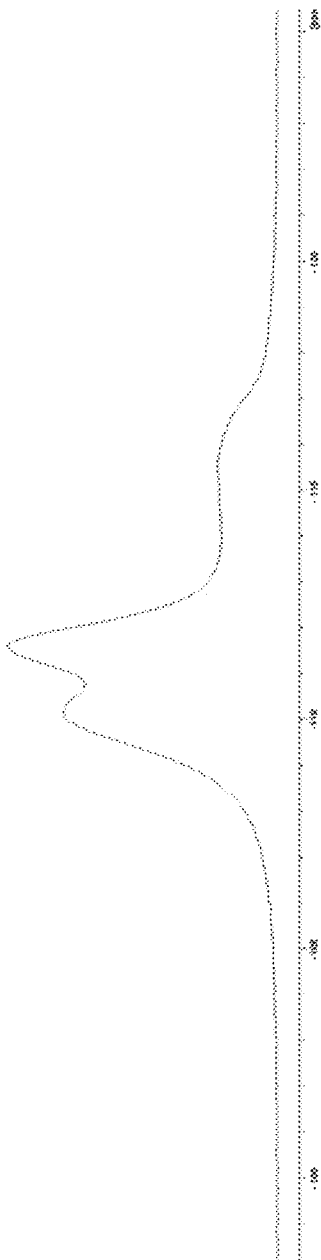
FIG. 2C shows a solid state $^{19}$F NMR spectrum of Compound 33 Form B.

Solid state $^{19}$F NMR data for Compound 33 Form B is provided in FIG. 2C and summarized in Table 29 below.

TABLE 29

Solid State NMR of Compound 33 Form B

| Peak # | Chem Shift [ppm] | Intensity [rel] |
|---|---|---|
| 1 | −110.2 | 9.9 |
| 2 | −111.6 | 12.5 |
| 3 | −115.6 | 2.76 |

D. Thermogravimetric Analysis

Figure 2D:
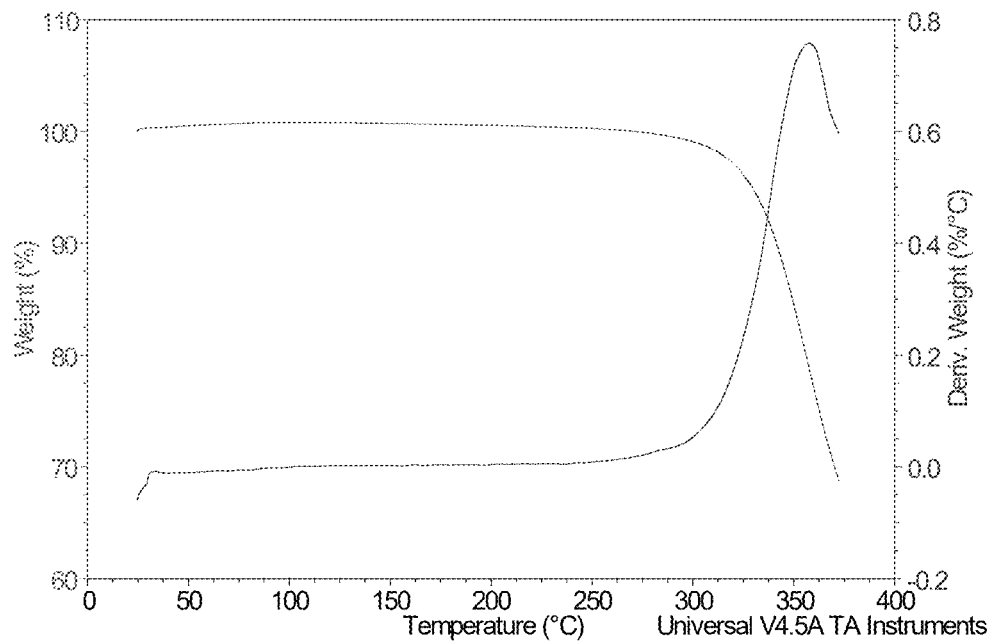
FIG. 2D shows a TGA thermogram of Compound 33 Form B.

Thermal gravimetric analysis of Compound 33 Form B was measured using TA Discovery 550 TGA from TA Instrument. A sample with weight of approximately 1-5 mg was scanned from 25° C. to 375° C. at a heating rate of 10° C./min with nitrogen purge. Data were collected by Thermal Advantage Q Series™ software and analyzed by Trios and/or Universal Analysis software (TA Instruments, New Castle, DE). The thermogram showed minimum weight loss from ambient temperature up to 250° C. The TGA thermogram for Compound 33 Form B is provided in FIG. 2D.

Figure 2E:
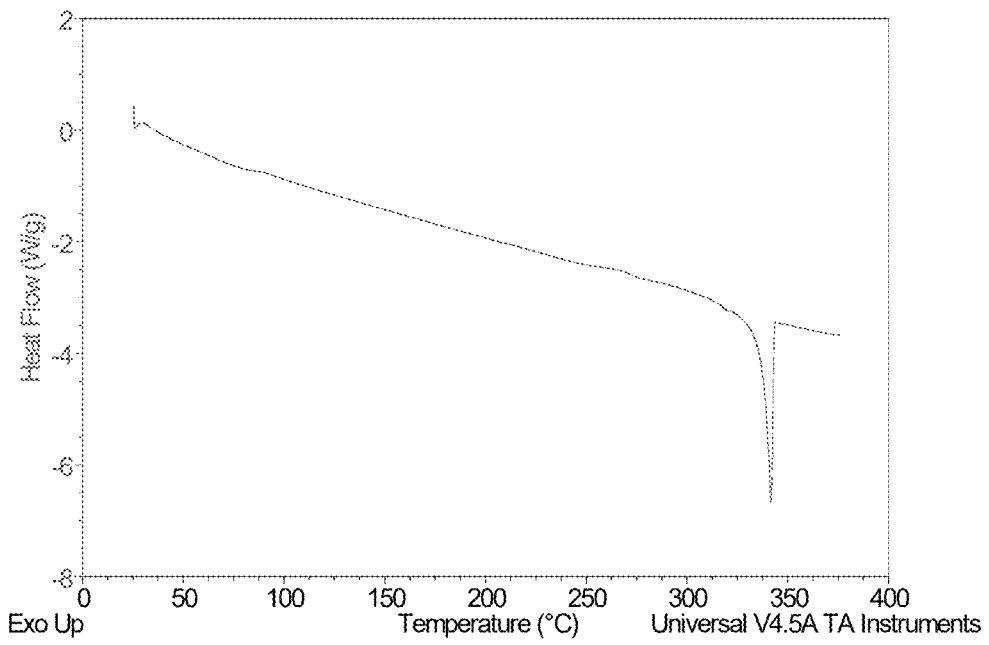
FIG. 2E shows a DSC thermogram of Compound 33 Form B.

E. Differential Scanning Calorimetry Analysis:

DSC of Compound 33 Form B was measured using the TA Q2000 DSC from TA Instrument. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 380° C. When the run was completed, the data were analyzed by Trios and/or Universal Analysis software (TA Instruments, New Castle, DE). The thermogram showed an endothermic peak around 342° C. The DSC thermogram is provided at FIG. 2E and shows an endothermic peak at 346° C.

3. Compound 33 DCM Solvate Form A

A. Synthetic Procedure 50 mg Compound 33 Form A was suspended in 1 ml solvent mixture of DCM, EtOH, and THF (54:36:10 by volume), and the vial was stirred with a magnetic stir bar at RT for one day. The solid was isolated as Compound 33 DCM solvate Form A.

B. X-Ray Powder Diffraction:

The XRPD patterns are acquired at room temperature in reflection mode using a Bruker Advance equipped with Vantec-1 detector. Sample was analyzed on a silicon sample holder from 3-40° 2-theta on continuous mode with step size of 0.01445310 and time per step of 0.25 seconds. Sample was spinning at 15 rpm. The XRPD diffractogram is shown in FIG. 3A and XRPD data are summarized in Table 30.

TABLE 30

XRPD Peaks for Compound 33 DCM Solvate Form A

| Peak # | Angle (Degrees 2-Theta ± 0.2) | Relative Intensity % |
|---|---|---|
| 1 | 20.9 | 100.0 |
| 2 | 18.3 | 87.8 |
| 3 | 14.4 | 59.5 |
| 4 | 17.2 | 59.4 |
| 5 | 20.3 | 43.2 |
| 6 | 22.8 | 28.3 |
| 7 | 22.6 | 24.1 |
| 8 | 27.7 | 23.9 |
| 9 | 8.8 | 23.3 |
| 10 | 7.1 | 23.3 |
| 11 | 28.3 | 21.6 |
| 12 | 9.0 | 18.8 |
| 13 | 26.6 | 17.4 |
| 14 | 10.1 | 14.7 |
| 15 | 13.9 | 14.3 |
| 16 | 23.4 | 12.9 |
| 17 | 27.1 | 12.3 |
| 18 | 13.3 | 11.7 |
| 19 | 21.7 | 10.7 |
| 20 | 24.0 | 10.0 |

C. Thermogravimetric Analysis

Figure 3B:
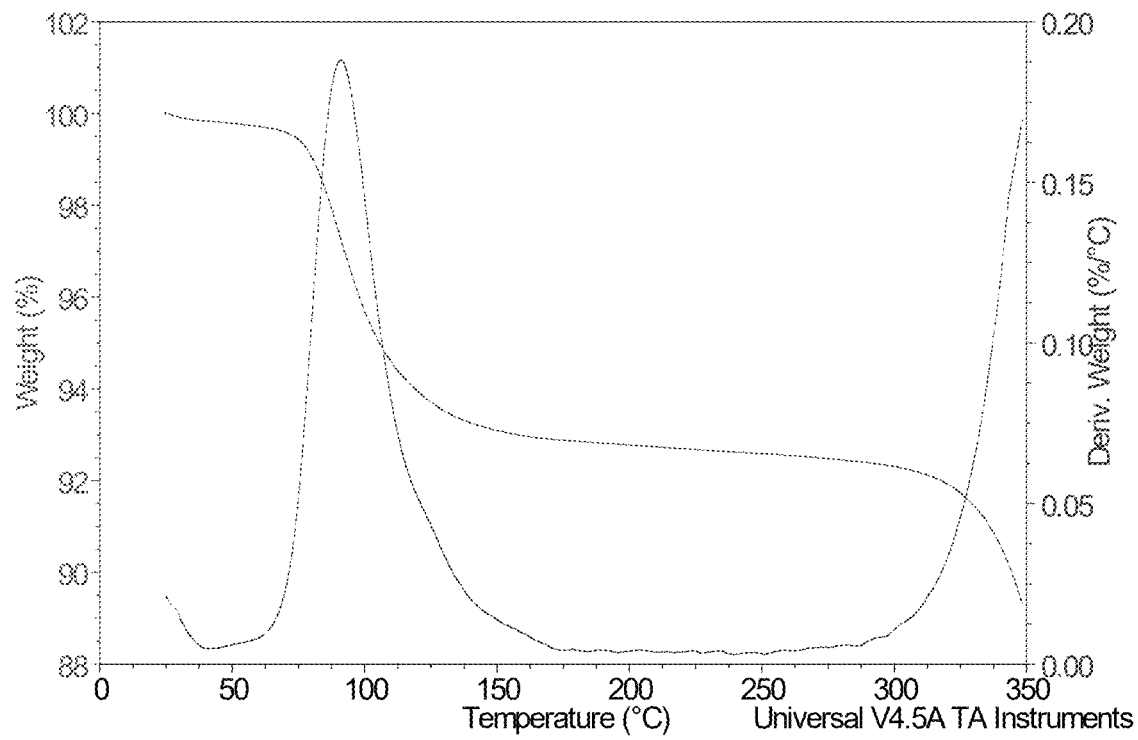
FIG. 3B shows a TGA thermogram of Compound 33 DCM solvate Form A.

Thermal gravimetric analysis of Compound 33 DCM solvate Form A was measured using the TA Instruments TGA Q5000. A sample with weight of approximately 1-5 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The thermogram showed ~7% weight loss from ambient temperature up to 175° C. The TGA thermogram for Compound 33 DCM solvate Form A is provided in FIG. 3B.

D. Differential Scanning Calorimetry Analysis

Figure 3C:
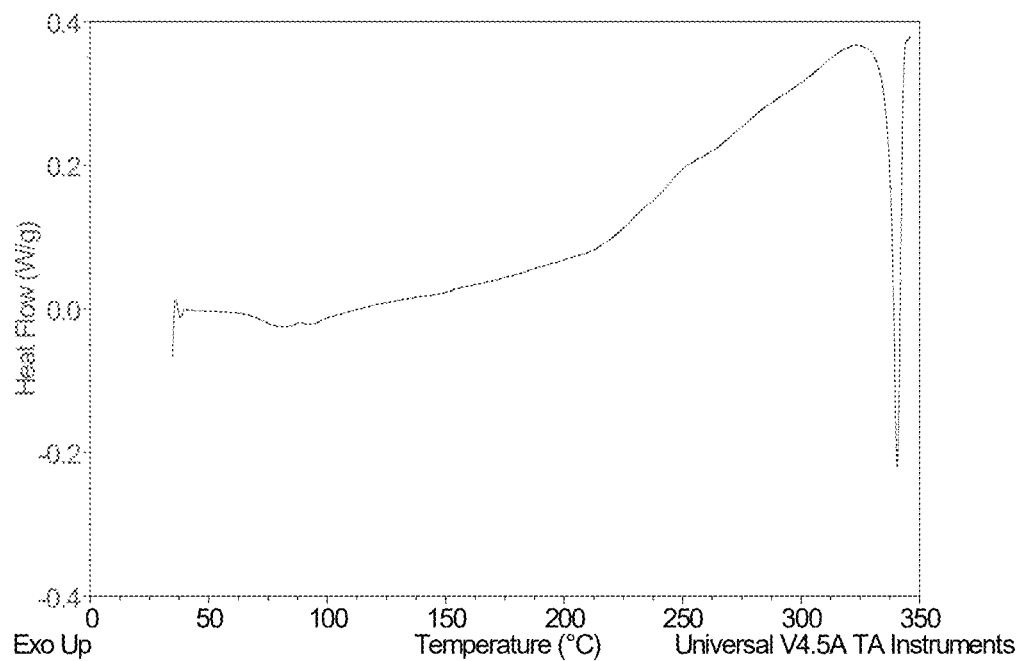
FIG. 3C shows a DSC thermogram of Compound 33 DCM solvate Form A.

DSC of Compound 33 DCM solvate Form A was measured using the TA Instruments Q2000 DSC. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 2° C./min (modulate±0.32° C. every 60 s) to a temperature of 350° C. When the run was completed, the data were analyzed by Trios and/or Universal Analysis software (TA Instruments, New Castle, DE). The DSC thermogram is provided in FIG. 3C and shows an endothermic peak around 341° C.

4. Compound 33 Hydrate Form A

A. Synthetic Procedure 10 mg of Compound 33 Form A were weighed in 2 ml glass vial and 200-300 µl of water was added along with a small magnetic stir bar. The sample was stirred at RT for two weeks. Then the solid was isolated as Compound 33 hydrate Form A.

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The XRPD diffractogram is shown in FIG. 4A and XRPD data are summarized in Table 31.

TABLE 31

XRPD Peaks for Compound 33 Hydrate Form A

| Peak # | Angle (Degrees 2-Theta ± 0.2) | Relative Intensity % |
|---|---|---|
| 1 | 19.5 | 100.0 |
| 2 | 10.4 | 79.9 |
| 3 | 16.6 | 32.7 |
| 4 | 13.6 | 25.6 |
| 5 | 18.4 | 24.4 |
| 6 | 21.6 | 20.8 |
| 7 | 17.5 | 18.9 |
| 8 | 21.1 | 17.6 |
| 9 | 18.9 | 17.6 |
| 10 | 21.8 | 12.3 |
| 11 | 20.8 | 11.5 |
| 12 | 24.8 | 10.5 |
| 13 | 21.4 | 10.1 |

C. Single Crystal Elucidation

Single crystals having the hydrate structure were grown from ethanol/water. X-ray diffraction data were acquired at 100K on a Bruker diffractometer equipped with Cu $K_\alpha$ radiation (λ=1.54178 Å) and a CMOS detector. The structure was solved and refined using SHELX programs (Sheldrick, G. M., Acta Cryst., (2008) A64, 112-122) and results are summarized in Table 32 below.

TABLE 32

Single crystal elucidation of Compound 33 hydrate Form A

| Crystal System | Triclinic |
|---|---|
| Space Group | P-1 |
| a (Å) | 9.9750 (16) |
| b (Å) | 10.4232 (8) |
| c (Å) | 11.3003 (5) |
| α (°) | 74.060 (6) |
| β (°) | 78.914 (7) |
| γ (°) | 84.141 (11) |
| V (Å³) | 1107.1 (2) |
| Z/Z' | 2/1 |
| Temperature | 100 K |

D. Solid State NMR
(1) $^{13}C$ CPMAS Analysis

Figure 4B:
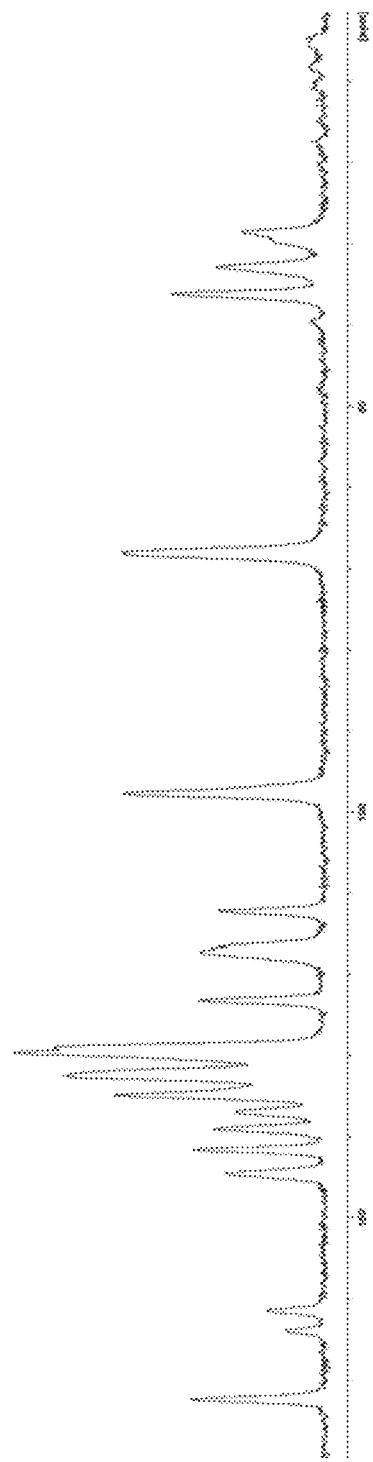
FIG. 4B shows a solid state $^{13}$C NMR spectrum of Compound 33 hydrate Form A.

Solid state $^{13}C$ NMR data for Compound 33 hydrate Form A is provided in FIG. 4B and summarized in Table 33 below.

TABLE 33

Solid State NMR of Compound 33 Hydrate Form A

| Peak # | Chem Shift [ppm] | Intensity [rel] |
|---|---|---|
| 1 | 172.3 | 42.8 |
| 2 | 163.8 | 11.7 |
| 3 | 161.3 | 17.8 |
| 4 | 144.4 | 31.8 |
| 5 | 141.6 | 41.7 |
| 6 | 139.0 | 35.4 |
| 7 | 136.8 | 28.6 |

TABLE 33-continued

Solid State NMR of Compound 33 Hydrate Form A

| Peak # | Chem Shift [ppm] | Intensity [rel] |
|---|---|---|
| 8 | 134.8 | 67.3 |
| 9 | 132.4 | 84.0 |
| 10 | 129.6 | 100.0 |
| 11 | 128.9 | 87.3 |
| 12 | 123.1 | 39.9 |
| 13 | 117.2 | 40.0 |
| 14 | 116.5 | 33.5 |
| 15 | 112.1 | 33.7 |
| 16 | 97.7 | 64.8 |
| 17 | 67.9 | 64.7 |
| 18 | 36.1 | 48.8 |
| 19 | 32.8 | 34.3 |
| 20 | 29.4 | 16.9 |
| 21 | 28.4 | 25.8 |

(2) $^{19}F$ MAS Analysis

Figure 4C:
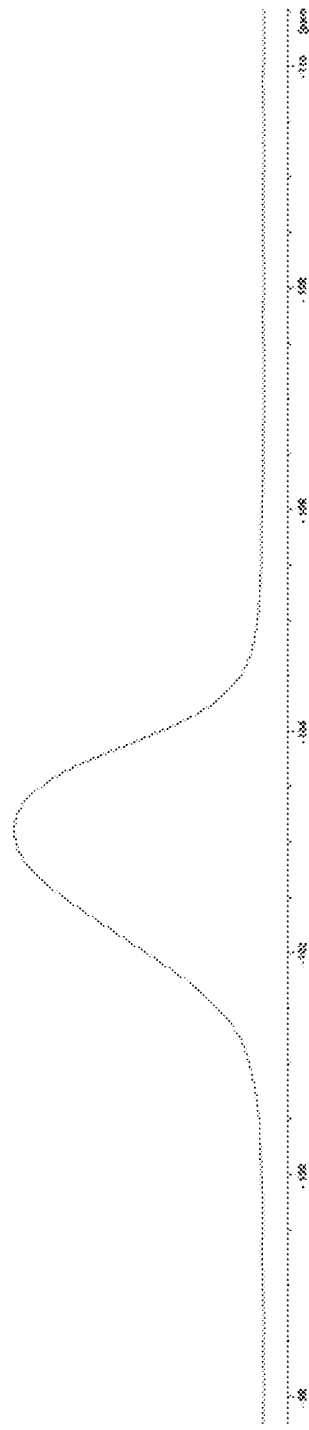
FIG. 4C shows a solid state $^{19}$F NMR spectrum of Compound 33 hydrate Form A.

Solid state $^{19}F$ NMR data for Compound 33 hydrate Form A is provided in FIG. 4C and summarized in Table 34 below.

TABLE 34

Solid State NMR of Compound 33 Hydrate Form A

| Peak # | Chem Shift [ppm] | Intensity [rel] |
|---|---|---|
| 1 | −103.1 | 12.5 |

E. Thermogravimetric Analysis

Figure 4D:
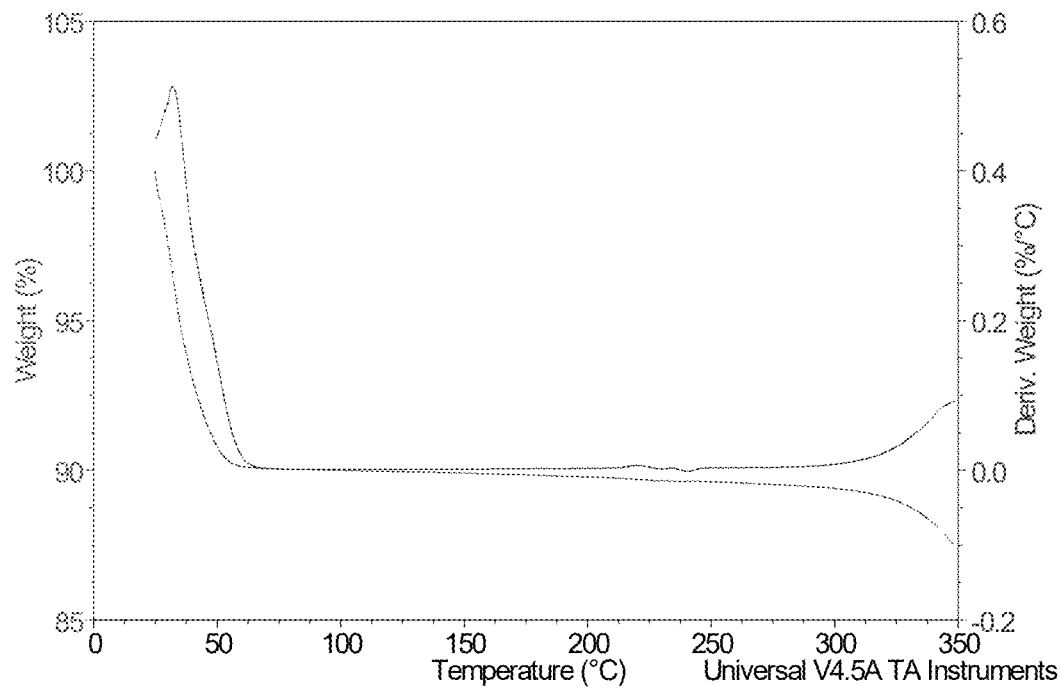
FIG. 4D shows a TGA thermogram of Compound 33 hydrate Form A.

Thermal gravimetric analysis of Compound 33 hydrate Form A was measured using the TA Instruments TGA Q5000. A sample with weight of approximately 1-5 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The thermogram showed ~10% weight loss from ambient temperature up to 60° C. The TGA thermogram for Compound 33 hydrate Form A is provided in FIG. 4D.

F. Differential Scanning Calorimetry Analysis

Figure 4E:
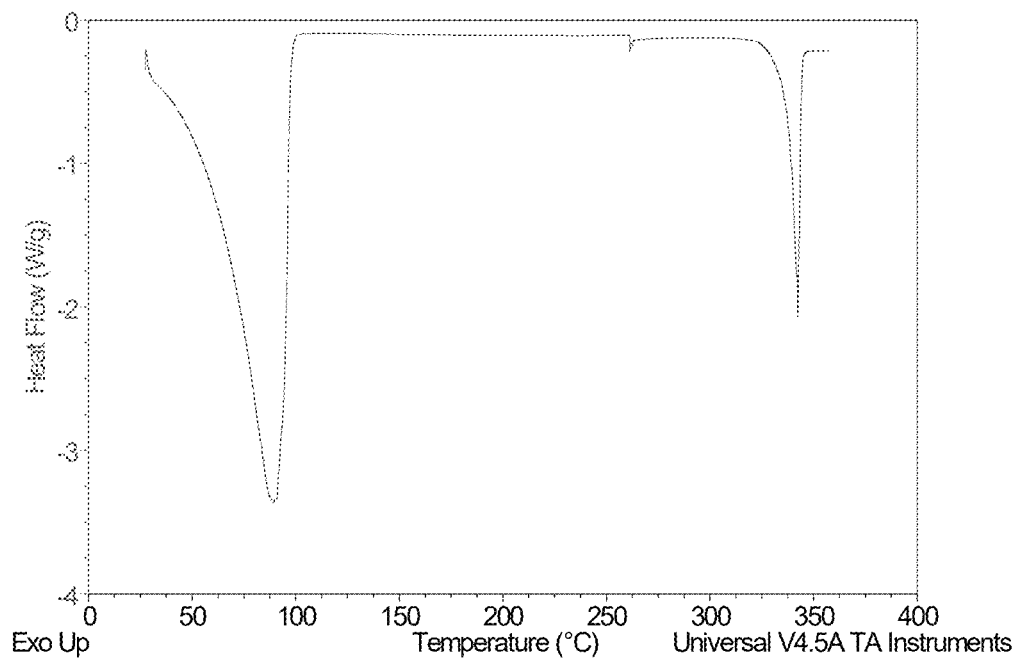
FIG. 4E shows a DSC thermogram of Compound 33 hydrate Form A.

DSC of Compound 33 hydrate Form A was measured using the TA Instruments Q2000 DSC. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./mm to a temperature of 360° C. When the run was completed, the data were analyzed by Trios and/or Universal Analysis software (TA Instruments, New Castle, DE). The DSC thermogram provided in FIG. 4E shows two endothermic peaks around 89 and 342° C.

5. Compound 33 MeOH/H$_2$O Solvate/Hydrate Form A

A group of Compound 33 isostructural MeOH/H$_2$O solvate/hydrate with different API/solvent/water ratios, one of which has a similar PXRD pattern as the MeOH/H$_2$O solvate.

A. Synthetic Procedure 10 mg of Compound 33 Form A were weighed in 2 ml glass vial and 200-300 μl of MeOH was added along with a small magnetic stir bar. The sample was stirred at RT for two weeks. Then the solid was isolated as Compound MeOH/H$_2$O Solvate/Hydrate Form A.

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The XRPD diffractogram is shown in FIG. 5A and XRPD data are summarized in Table 35.

TABLE 35

XRPD Peaks for Compound 33 MeOH/H$_2$O Solvate/Hydrate Form

| Peak # | Angle (Degrees 2-Theta ± 0.2) | Relative Intensity % |
|---|---|---|
| 1 | 19.4 | 100.0 |
| 2 | 10.4 | 55.6 |
| 3 | 18.2 | 28.7 |
| 4 | 16.6 | 25.0 |
| 5 | 13.5 | 20.2 |
| 6 | 21.0 | 19.1 |
| 7 | 21.6 | 18.1 |
| 8 | 18.8 | 17.9 |
| 9 | 17.4 | 13.0 |
| 10 | 21.3 | 10.0 |
| 11 | 21.7 | 10.7 |
| 12 | 24.0 | 10.0 |

C. Single Crystal Elucidation

Single crystals having the MeOH/H$_2$O structure were grown from methanol. X-ray diffraction data were acquired at 100K on a Bruker diffractometer equipped with Cu K$_\alpha$ radiation (λ=1.54178 Å) and a CMOS detector. The structure was solved and refined using SHELX programs (Sheldrick, G. M., Acta Cryst., (2008) A64, 112-122) and results are summarized in Table 36 below.

TABLE 36

Single crystal elucidation of Compound 33 MeOH/H$_2$O Solvate/Hydrate Form A

| Crystal System | Triclinic |
|---|---|
| Space Group | P-1 |
| a (Å) | 10.0229 (3) |
| b (Å) | 10.4254 (3) |
| c (Å) | 11.2467 (4) |
| α (°) | 74.4963 (9) |
| β (°) | 79.6241 (9) |
| γ (°) | 84.9826 (9) |
| V (Å$^3$) | 1112.96 (6) |
| Z/Z' | 2/1 |
| Temperature | 100 K |

D. Thermogravimetric Analysis

Figure 5B:
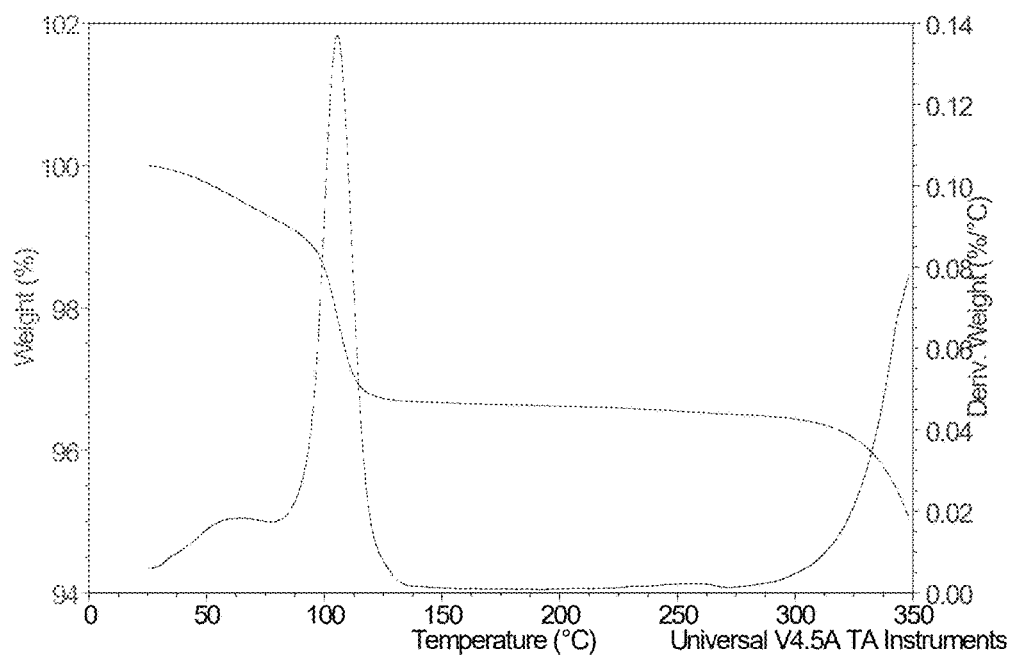
FIG. 5B shows a TGA thermogram of Compound 33 MeOH/H$_2$O solvate/hydrate Form A.

Thermal gravimetric analysis of Compound 33 MeOH/H$_2$O Solvate/Hydrate Form A was measured using the TA Instruments TGA Q5000. A sample with weight of approximately 1-5 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram as provided in FIG. 5B shows 3.3% weight loss from ambient temperature up to 150° C.

E. Differential Scanning Calorimetry Analysis

Figure 5C:
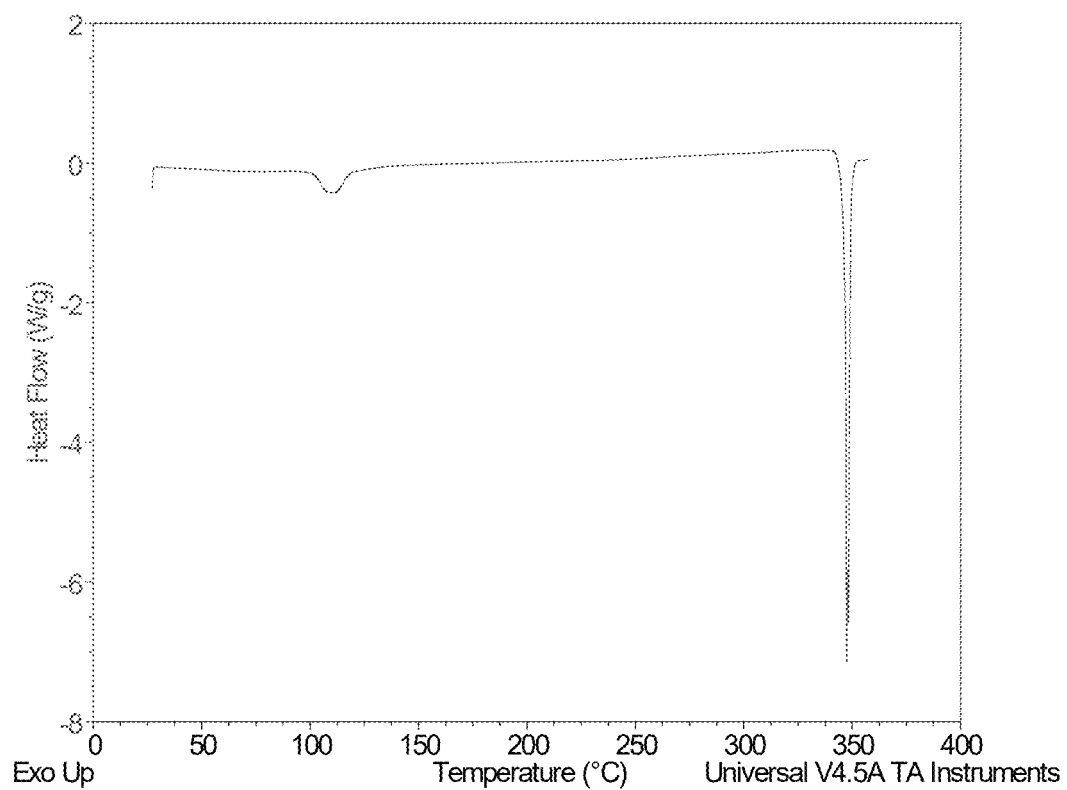
FIG. 5C shows a DSC thermogram of Compound 33 MeOH/H$_2$O solvate/hydrate Form A.

DSC of Compound 33 MeOH/H$_2$O Solvate/Hydrate Form A was measured using the TA Instruments Q2000 DSC. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 357° C. When the run was completed, the data were analyzed by Trios and/or Universal Analysis software (TA Instruments, New Castle, DE). The DSC thermogram as provided in FIG. 5C shows two endothermic peaks around 111 and 348° C.

6. Compound 33 Form C

A. Synthetic Procedure 210.9 mg of Compound 33 Form A was weighed and dissolved in 42 mL of MeOH, after the sample was warmed to 45° C. for 10 min followed by 50° C. for 5 minutes. It was used as the stock solution after cooling to room temperature. Compound 33 was stirred in MeOH/water at 2/1 (vol.), prepared by mixing 6 mL of stock solution and 3 mL water, at 45° C. for 3 days. Then the solid was isolated as Compound 33 Form C.

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The XRPD diffractogram is shown in FIG. 6A and XRPD data are summarized in Table 37.

TABLE 37

XRPD Peaks for Compound 33 Form C

| Peak # | Angle (Degrees 2-Theta ± 0.2) | Relative Intensity % |
|---|---|---|
| 1 | 19.0 | 100.0 |
| 2 | 21.0 | 42.4 |
| 3 | 9.4 | 20.2 |
| 4 | 18.2 | 15.4 |
| 5 | 15.4 | 15.3 |
| 6 | 21.5 | 14.8 |
| 7 | 20.2 | 14.5 |
| 8 | 19.6 | 10.5 |

7. Compound 33 Form D

A. Synthetic Procedure

Approximately 15 mg of Compound 33 THF solvate Form A was weighed into a 4-mL vial, which was placed into a 20-mL vial with 2 mL of MeOH. The 20-mL vial was sealed with a cap and kept at RT for ten days allowing solvent vapor to interact with the solid sample. Then the solid was taken out as Compound 33 Form D.

B. X-Ray Powder Diffraction

XRPD was performed with a Panalytical X'Pert$^3$ Powder XRPD on a Si zero-background holder. The 2θ position was calibrated against a Panalytical Si reference standard disc.

The parameters used are listed in the Table 38. The XRPD diffractogram is shown in FIG. 7A and XRPD data are summarized in Table 39.

TABLE 38

Parameters for XRPD test of Compound 33 Form D

| Parameters | Reflection Mode |
|---|---|
| X-Ray wavelength | Cu, kα<br>Kα1 (Å): 1.540598,<br>Kα1 (A): 1.544426,<br>Kα2/Kα1 intensity ratio: 0.50 |
| X-Ray tube setting | 45 kV, 40 mA |
| Divergence slit | Fixed 1/8° |
| Scan mode | Continuous |
| Scan range (°2TH) | 3-40 |
| Scan step time [s] | 18.87 |
| Step size (°2TH) | 0.0131 |
| Test Time | 4 min 15 s |

TABLE 39

XRPD Peaks for Compound 33 Form D

| Peak # | Angle (Degrees 2-Theta ± 0.2) | Relative Intensity % |
|---|---|---|
| 1 | 10.4 | 100.0 |
| 2 | 20.5 | 75.3 |
| 3 | 14.4 | 54.1 |
| 4 | 20.1 | 51.1 |
| 5 | 7.8 | 39.9 |
| 6 | 8.2 | 34.5 |
| 7 | 8.6 | 26.3 |
| 8 | 15.3 | 25.1 |
| 9 | 24.0 | 18.5 |
| 10 | 18.9 | 17.6 |
| 11 | 24.3 | 17.1 |
| 12 | 18.6 | 15.6 |
| 13 | 13.7 | 15.5 |
| 14 | 21.9 | 12.9 |

C. Thermogravimetric Analysis

Figure 7B:
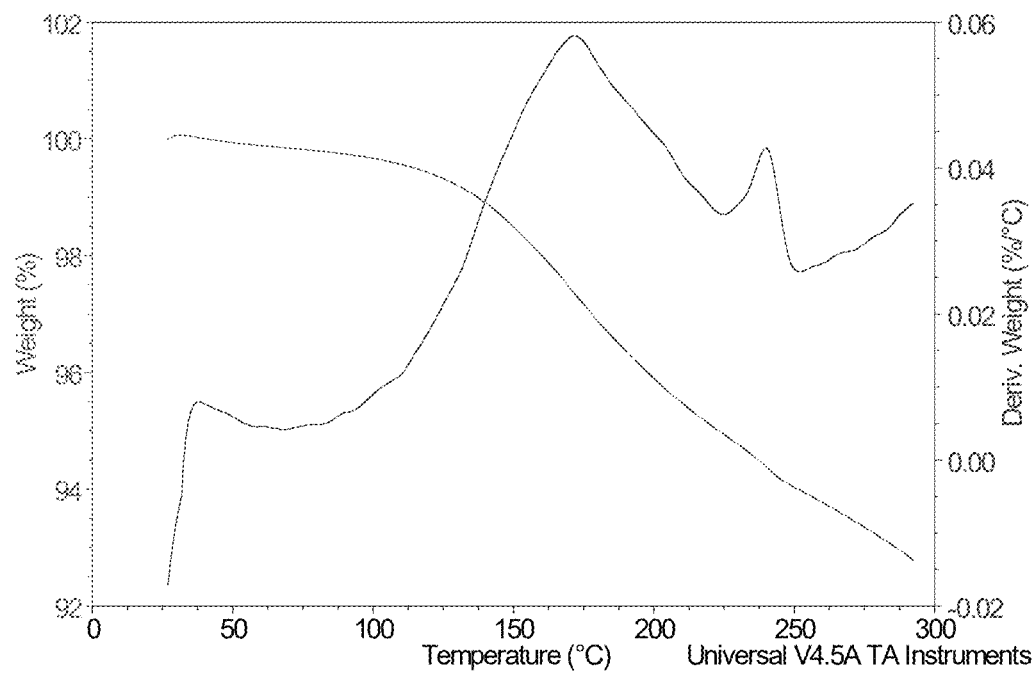
FIG. 7B shows a TGA thermogram of Compound 33 Form D.

Thermal gravimetric analysis of Compound 33 Form D was measured using TA Discovery 550 TGA from TA Instrument. A sample with weight of approximately 1-5 mg was scanned from 25° C. to 290° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram as provided in FIG. 7B shows around 5% weight loss from ambient temperature up to around 220° C.

D. Differential Scanning Calorimetry Analysis

Figure 7C:
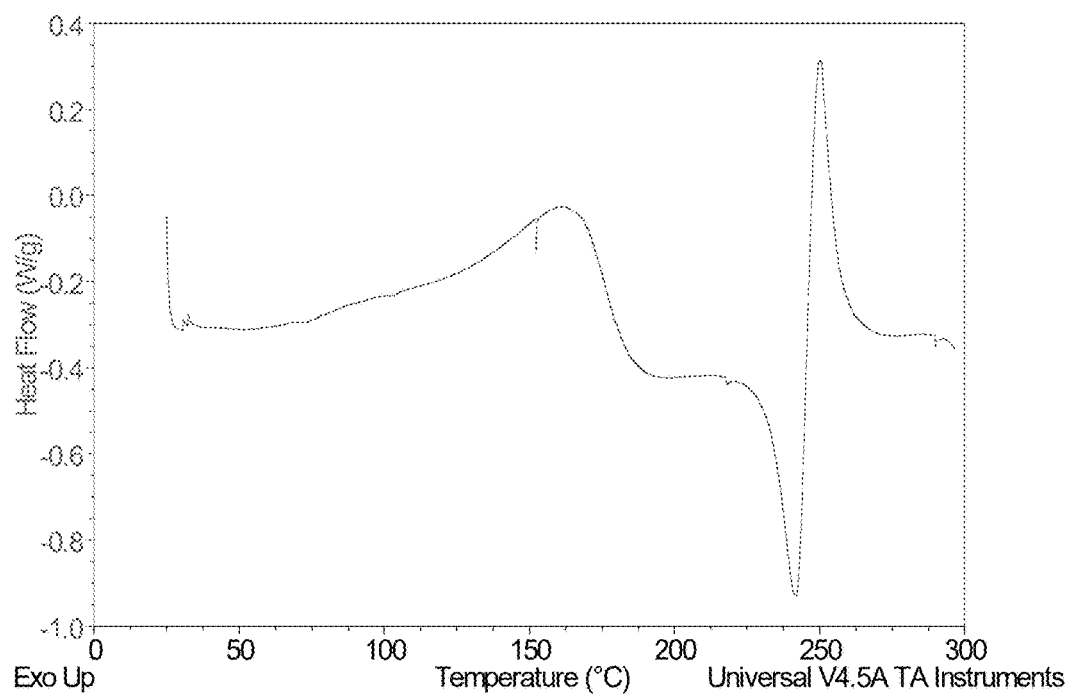
FIG. 7C shows a DSC thermogram of Compound 33 Form D.

DSC of Compound 33 Form D was measured using the TA Q2000 DSC from TA Instrument. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 300° C. When the run was completed, the data were analyzed by Trios and/or Universal Analysis software (TA Instruments, New Castle, DE). The DSC thermogram in FIG. 7C shows multiple exothermic and endothermic peaks around 162, 240, and 250° C.

8. Compound 33 Form E

A. Synthetic Procedure 210.9 mg of Compound 33 Form A was weighed and dissolved in 42 mL of MeOH, after the sample was warmed to 45° C. for 10 min followed by 50° C. for 5 minutes. It was used as the stock solution after cooling to room temperature. 6 mL of the stock solution was moved to the cold room and stirred for 3 days. Then the solid was isolated as Compound 33 Form E.

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step. The XRPD diffractogram is shown in FIG. 8A and XRPD data are summarized in Table 40.

TABLE 40

XRPD Peaks for Compound 33 Form E

| Peak # | Angle (Degrees 2-Theta ± 0.2) | Relative Intensity % |
|---|---|---|
| 1 | 20.7 | 100.0 |
| 2 | 12.6 | 65.2 |
| 3 | 17.9 | 46.6 |
| 4 | 11.2 | 45.0 |
| 5 | 7.9 | 42.7 |
| 6 | 16.2 | 31.2 |
| 7 | 22.8 | 24.9 |
| 8 | 21.1 | 24.4 |
| 9 | 12.8 | 21.2 |
| 10 | 19.9 | 19.1 |
| 11 | 13.7 | 19.0 |
| 12 | 27.0 | 16.3 |
| 13 | 22.5 | 15.1 |
| 14 | 15.3 | 14.5 |
| 15 | 28.9 | 13.1 |
| 16 | 25.0 | 12.9 |
| 17 | 24.1 | 11.1 |

9. Compound 33 Form F

A. Synthetic Procedure 0.2 g Compound A THF solvate Form A and 2 ml of EtOH were added in a vial with a magnetic stir bar, and slurrifying at 20° C. for overnight. Then the solid was isolated as Compound 33 Form F.

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The XRPD diffractogram is shown in FIG. 9A and XRPD data are summarized in Table 41.

TABLE 41

XRPD Peaks for Compound 33 Form F

| Peak # | Angle (Degrees 2-Theta ± 0.2) | Relative Intensity % |
|---|---|---|
| 1 | 19.2 | 100.0 |
| 2 | 18.4 | 84.7 |
| 3 | 15.1 | 40.6 |
| 4 | 18.3 | 37.6 |
| 5 | 22.8 | 37.5 |
| 6 | 11.6 | 35.6 |
| 7 | 17.8 | 33.5 |
| 8 | 21.4 | 28.1 |
| 9 | 24.9 | 23.7 |
| 10 | 23.0 | 21.9 |
| 11 | 14.2 | 21.2 |
| 12 | 19.0 | 20.5 |
| 13 | 14.9 | 19.4 |
| 14 | 20.4 | 17.0 |
| 15 | 12.2 | 16.9 |
| 16 | 23.3 | 14.3 |
| 17 | 8.6 | 13.4 |
| 18 | 21.6 | 12.6 |
| 19 | 13.0 | 12.5 |
| 20 | 25.8 | 12.2 |
| 21 | 17.4 | 12.1 |
| 22 | 17.3 | 11.9 |
| 23 | 11.4 | 11.8 |
| 24 | 26.4 | 11.0 |
| 25 | 7.7 | 11.0 |
| 26 | 24.0 | 10.9 |
| 27 | 24.2 | 10.8 |
| 28 | 22.6 | 10.6 |

C. Thermogravimetric Analysis

Figure 9B:
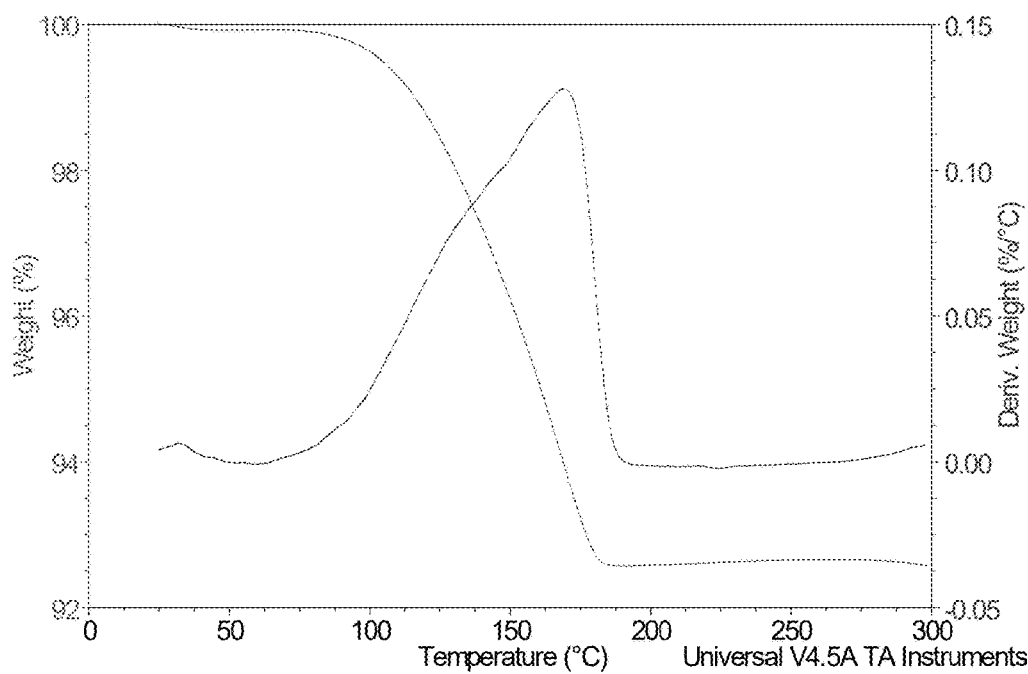
FIG. 9B shows a TGA thermogram of Compound 33 Form F.

Thermal gravimetric analysis of Compound 33 Form F was measured using TA Discovery TGA from TA Instrument. A sample with weight of approximately 1-10 mg was scanned from 25° C. to 300° C. at a heating rate of 10° C./min with nitrogen purge. Data were collected by Thermal Advantage Q Series™ software and analyzed by Trios and/or Universal Analysis software (TA Instruments, New Castle, DE). The TSC thermogram of FIG. 9B shows 7.4% weight loss from ambient temperature up to 200° C.

D. Differential Scanning Calorimetry Analysis

Figure 9C:
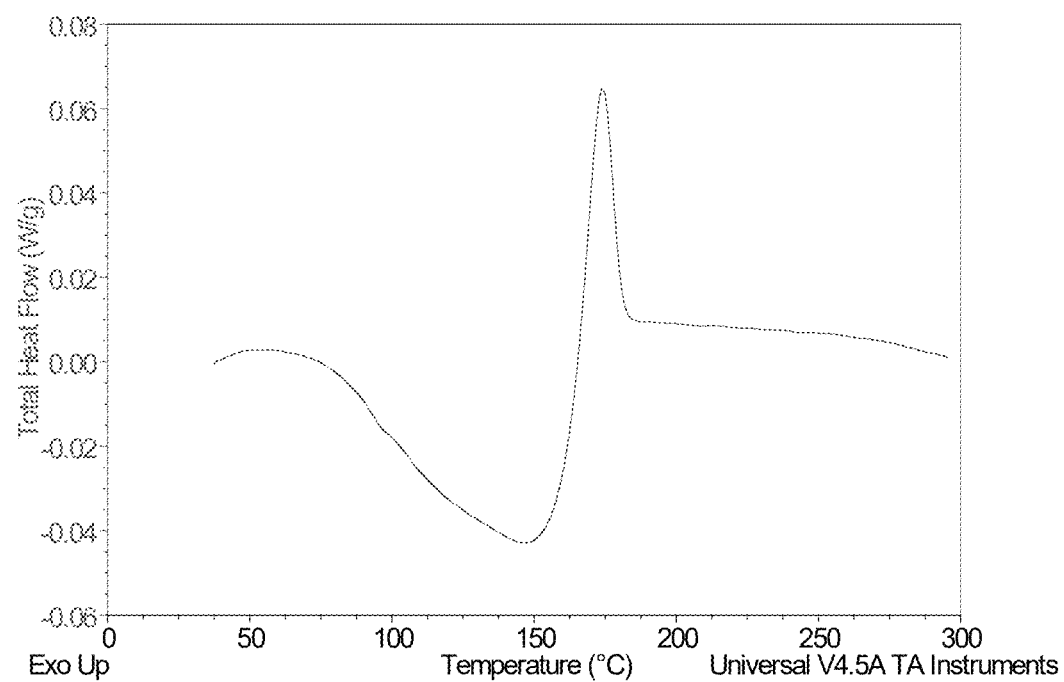
FIG. 9C shows a DSC thermogram of Compound 33 Form F.

DSC of Compound 33 Form F was measured using the TA Discovery DSC from TA Instrument. A sample with a weight between 1-5 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 300° C. When the run was completed, the data were analyzed by Trios and/or Universal Analysis software (TA Instruments, New Castle, DE). The DSC thermogram provided in FIG. 9C shows an endothermic peak around 147° C. and an exothermic peak around 174° C.

10. Compound 33 Form G

A. Synthetic Procedure

About 20 mg of Compound 33 Form A was suspended in 0.2 mL of EtOH in a 2-mL glass vial, and the slurry was stirred magnetically for one day at 5° C. Then the solids were isolated as Compound 33 Form G.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 42. The XRPD diffractogram is shown in FIG. 10A and XRPD data are summarized in Table 43.

TABLE 42

Parameters for XRPD test of Compound 33 Form G

| Parameters | Reflection Mode |
|---|---|
| X-Ray wavelength | Cu, kα |
|  | Kα1 (Å): 1.540598, |
|  | Kα2 (Å): 1.544426, |
|  | Kα2/Kα1 intensity ratio: 0.50 |
| X-Ray tube setting | 45 kV, |
|  | 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 43

XRPD Peaks for Compound 33 Form G

| Peak # | Angle (Degrees 2-Theta ± 0.2) | Relative Intensity % |
|---|---|---|
| 1 | 20.2 | 100.0 |
| 2 | 19.8 | 67.7 |
| 3 | 20.8 | 52.4 |
| 4 | 9.3 | 40.1 |
| 5 | 10.8 | 35.8 |
| 6 | 24.2 | 35.6 |
| 7 | 21.6 | 32.6 |
| 8 | 18.4 | 27.0 |
| 9 | 11.5 | 20.5 |
| 10 | 23.4 | 16.3 |
| 11 | 22.6 | 15.3 |
| 12 | 19.1 | 14.9 |
| 13 | 17.5 | 14.8 |
| 14 | 12.6 | 11.4 |
| 15 | 25.5 | 10.9 |

C. Thermogravimetric Analysis

Figure 10B:
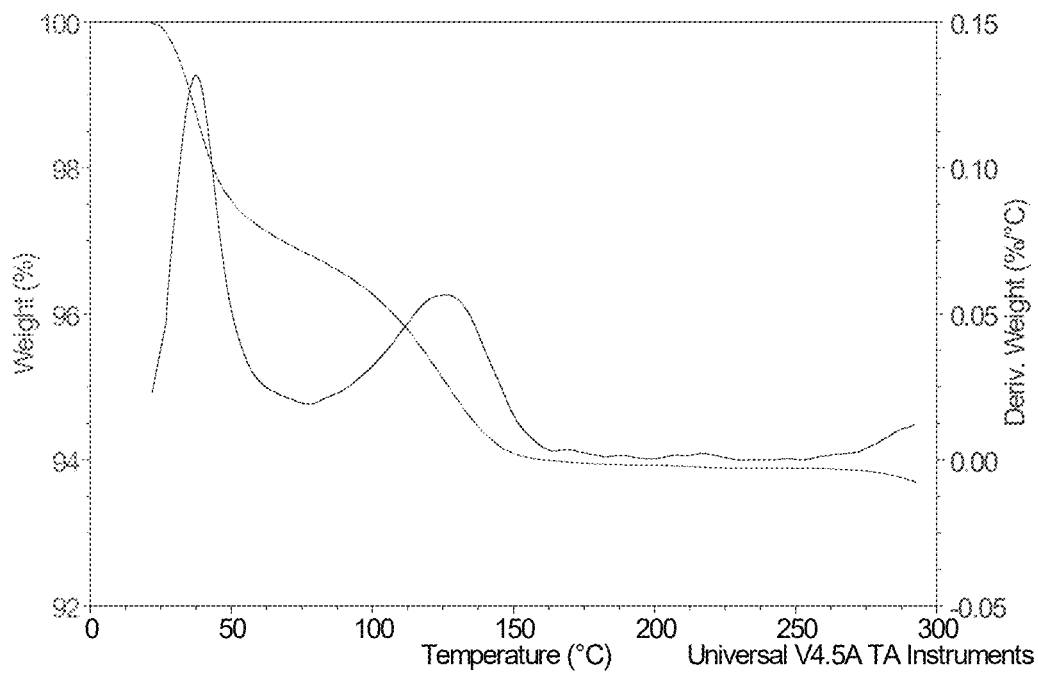
FIG. 10B shows a TGA thermogram of Compound 33 Form G.

Thermal gravimetric analysis of Compound 33 Form G was measured using TA Discovery 550 TGA from TA Instrument. A sample with weight of approximately 1-5 mg was scanned from 25° C. to 290° C. at a heating rate of 10° C./min with nitrogen purge. Data were collected by Thermal Advantage Q Series™ software and analyzed by Trios and/or Universal Analysis software (TA Instruments, New Castle, DE). The TSC thermogram provided in FIG. 10B shows 3% weight loss from ambient temperature up to 75° C. and another 3% weight loss from 75 to 180° C.

D. Differential Scanning Calorimetry Analysis

Figure 10C:
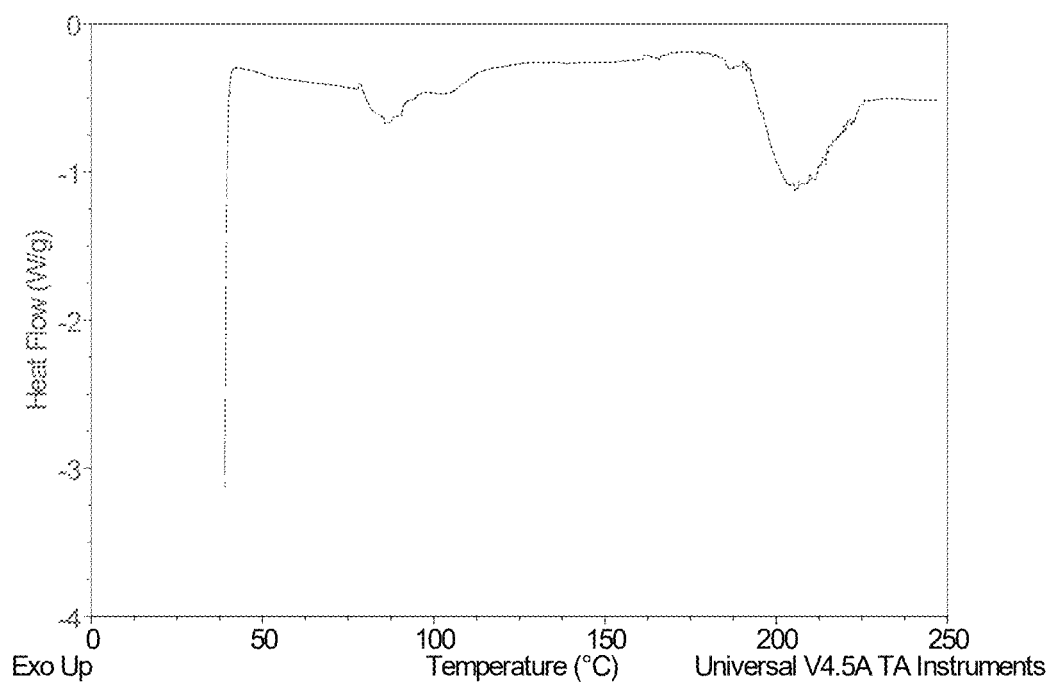
FIG. 10C shows a DSC thermogram of Compound 33 Form G.

DSC of Compound 33 Form G was measured using the TA Q2000 DSC from TA Instrument. A sample with a weight between 1-10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 250° C. When the run was completed, the data were analyzed by Trios and/or Universal Analysis software (TA Instruments, New Castle, DE). The DSC thermogram provided in FIG. 10C shows endothermic peaks around 86 and 205° C.

11. Compound 33 Form H

A. Synthetic Procedure

Approximately 15 mg of Compound 33 Form A was dissolved in 0.1~0.2 mL EtOH to obtain a clear solution in a 3-mL vial. This solution was then placed into a 20-mL vial with 3 mL of water. The 20-mL vial was sealed with a cap and kept at RT allowing enough time for the water vapor to interact with the solution. The precipitates were isolated as Compound 33 Form H.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 44. The XRPD diffractogram is shown in FIG. 11A and XRPD data are summarized in Table 45.

TABLE 44

Parameters for XRPD test of Compound 33 Form H

| Parameters | Reflection Mode |
|---|---|
| X-Ray wavelength | Cu, kα |
|  | Kα1 (Å): 1.540598, |
|  | Kα2 (Å): 1.544426, |
|  | Kα2/Kα1 intensity ratio: 0.50 |
| X-Ray tube setting | 45 kV, |
|  | 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 45

XRPD Peaks for Compound 33 Form H

| Peak # | Angle (Degrees 2-Theta ± 0.2) | Relative Intensity % |
|---|---|---|
| 1 | 5.0 | 100.0 |
| 2 | 19.5 | 86.2 |
| 3 | 18.3 | 36.8 |
| 4 | 18.9 | 20.6 |
| 5 | 20.7 | 13.2 |
| 6 | 15.0 | 10.8 |
| 7 | 17.6 | 10.7 |
| 8 | 8.8 | 10.3 |

C. Thermogravimetric Analysis

Figure 11B:
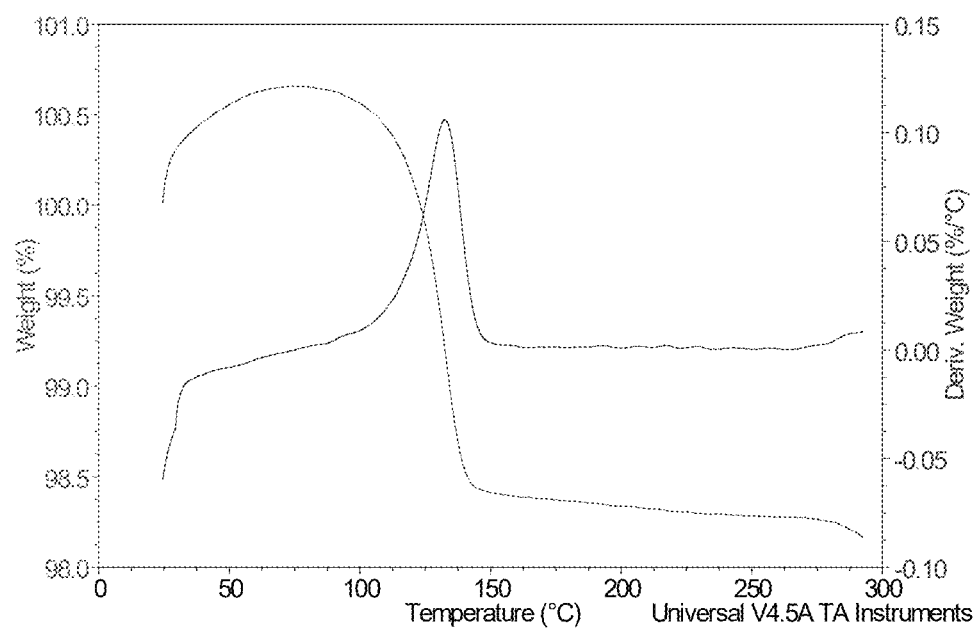
FIG. 11B shows a TGA thermogram of Compound 33 Form H.

Thermal gravimetric analysis of Compound 33 Form H was measured using TA Discovery 550 TGA from TA Instrument. A sample with weight of approximately 1-5 mg was scanned from 25° C. to 290° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram provided in FIG. 11B shows 1.6% weight loss from ambient temperature up to 150° C.

D. Differential Scanning Calorimetry Analysis

Figure 11C:
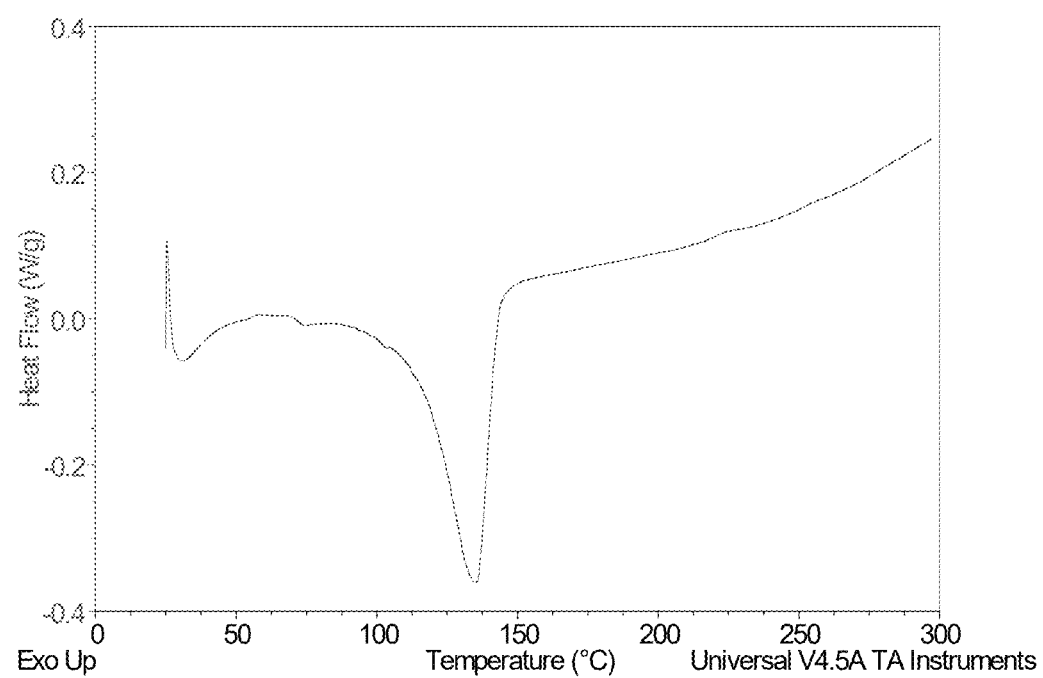
FIG. 11C shows a DSC thermogram of Compound 33 Form H.

DSC of Compound 33 Form H was measured using the TA Q2000 DSC from TA Instrument. A sample with a weight between 1-10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 300° C. When the run was completed, the data were analyzed by Trios and/or Universal Analysis software (TA Instruments, New Castle, DE). The DSC thermogram provided in FIG. 11C shows an endothermic peak around 135° C.

12. Compound 33 Form I

A. Synthetic Procedure

The solid form was observed after the distillative crystallization of raw Compound 33 from 2 Me-THF/THF to EtOH/water. Specifically, EtOH-reacted Compound 33 (see FIG. 12A for XRPD diffractogram and Table 46 for XRPD diffraction data) was initially sampled after adding 50 ml of EtOH, which was previously washed by water followed by 2 cycles of adding 50 ml EtOH and distillation. After Compound 33 was added with 100 ml of EtOH/water (3:1) and stirred at ambient temperature overnight, the crude product (see FIG. 12B for XRPD diffractogram and Table 47 for XRPD diffraction data) sampled was a wet cake. Compound 33 Form I was the solid after drying in vacuum oven with nitrogen bleed at 66° C. overnight (see FIG. 12C for XRPD diffractogram and Table 48 for XRPD diffraction data).

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

TABLE 46

XRPD Peaks for EtOH-Reacted Compound 33 (Initial Sampling)

| Peak # | Angle (Degrees 2-Theta ± 0.2) | Relative Intensity % |
|---|---|---|
| 1 | 19.6 | 100.0 |
| 2 | 20.2 | 67.9 |
| 3 | 19.2 | 63.9 |
| 4 | 10.6 | 49.1 |
| 5 | 17.1 | 47.7 |
| 6 | 9.7 | 29.7 |
| 7 | 12.8 | 22.9 |
| 8 | 20.8 | 20.8 |
| 9 | 11.1 | 20.0 |
| 10 | 18.5 | 19.4 |
| 11 | 23.3 | 13.7 |
| 12 | 13.8 | 10.5 |

TABLE 47

XRPD Peaks for Compound 33 Reacted with EtOH Ovenight

| Peak # | Angle (Degrees 2-Theta ± 0.2) | Relative Intensity % |
|---|---|---|
| 1 | 4.9 | 100.0 |
| 2 | 19.1 | 75.0 |
| 3 | 19.0 | 62.2 |
| 4 | 18.5 | 55.9 |
| 5 | 20.1 | 45.3 |
| 6 | 18.7 | 42.9 |
| 7 | 20.4 | 42.4 |
| 8 | 19.4 | 34.2 |
| 9 | 9.7 | 31.4 |
| 10 | 17.0 | 28.2 |
| 11 | 12.0 | 21.2 |
| 12 | 21.0 | 18.4 |
| 13 | 22.7 | 18.4 |

TABLE 47-continued

XRPD Peaks for Compound 33
Reacted with EtOH Ovenight

| Peak # | Angle (Degrees 2-Theta ± 0.2) | Relative Intensity % |
|---|---|---|
| 14 | 15.6 | 14.0 |
| 15 | 21.9 | 13.6 |
| 16 | 13.9 | 12.1 |
| 17 | 10.5 | 11.6 |
| 18 | 21.5 | 11.1 |
| 19 | 14.2 | 10.9 |
| 20 | 9.3 | 10.8 |
| 21 | 14.8 | 10.7 |

TABLE 48

XRPD Peaks for Compound 33 Form I

| Peak # | Angle (Degrees 2-Theta ± 0.2) | Relative Intensity % |
|---|---|---|
| 1 | 19.0 | 100.0 |
| 2 | 9.3 | 19.2 |
| 3 | 21.0 | 15.9 |
| 4 | 18.3 | 13.8 |
| 5 | 20.2 | 13.6 |
| 6 | 15.4 | 13.3 |
| 7 | 18.6 | 10.8 |

C. Thermogravimetric Analysis

Figure 12D:
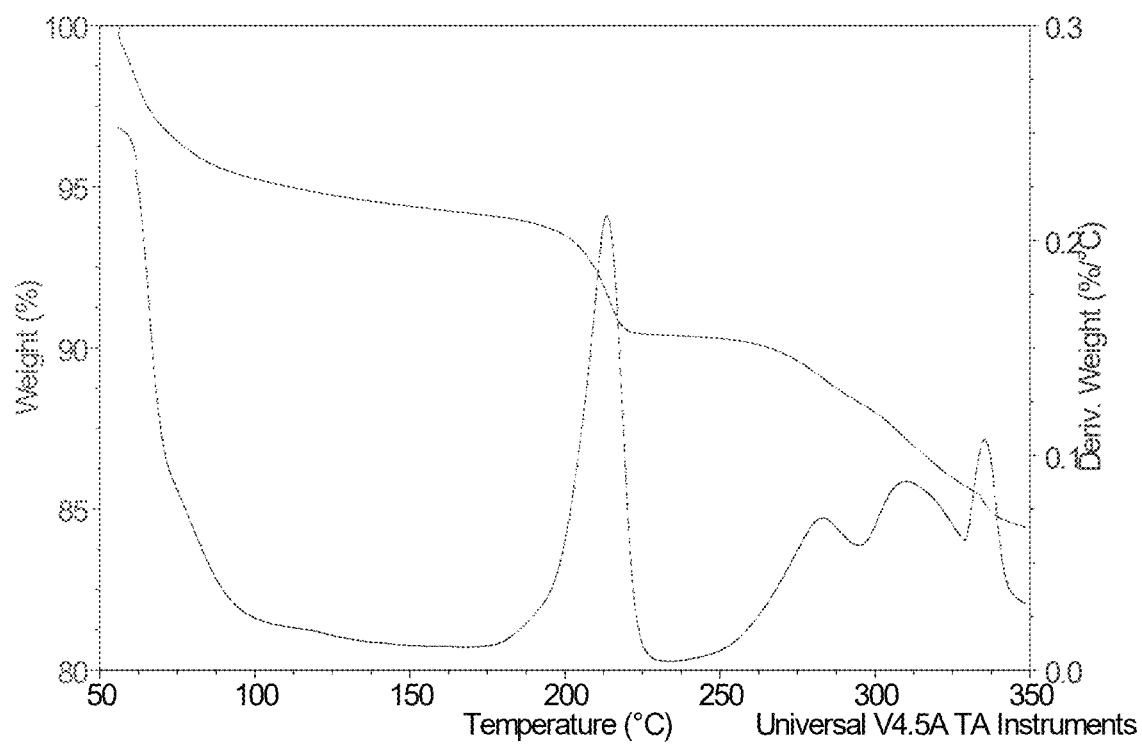
FIG. 12D shows a TGA thermogram of Compound 33 Form I.

Thermal gravimetric analysis of Compound 33 Form I was measured using the TA Instruments TGA Q5000. A sample with weight of approximately 1-5 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram provided in FIG. 12D showed 9.4% weight loss from ambient temperature up to 230° C. and another 6.0% weight loss from 230 to 350° C.

Figure 12E:
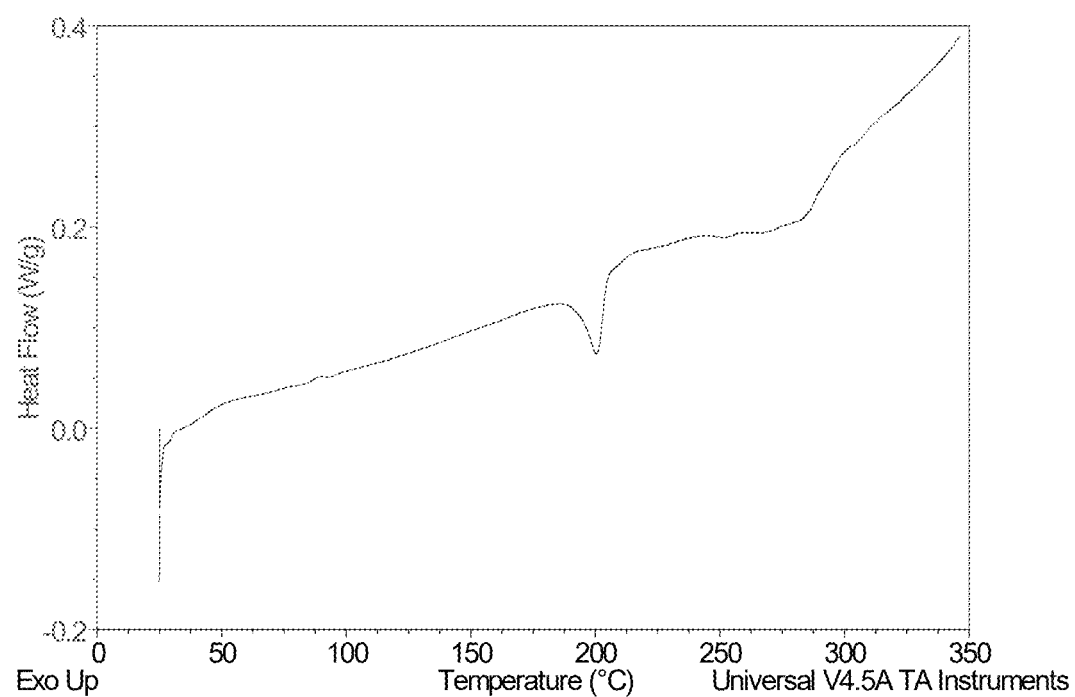
FIG. 12E shows a DSC thermogram of Compound 33 Form I.

D. Differential Scanning Calorimetry Analysis:

DSC of Compound 33 Form I was measured using the TA Instruments Q2000 DSC. A sample with a weight between 1-10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 2° C./min (modulate±0.32° C. every 60 s) to a temperature of 350° C. When the run was completed, the data were analyzed by Trios and/or Universal Analysis software (TA Instruments, New Castle, DE). The DSC thermogram in FIG. 12E shows two endothermic peaks around 200 and 283° C.

13. Compound 33 THF Solvate Form A

A. Synthetic Procedure:

Compound 33 Form A (10.4 g, 22.833 mmol, 1 equiv.) was dissolved in THF/$H_2O$ 9:1 (100.4 mL, 10 Vols) and the reaction mixture was heated to 60° C. Water (18.72 mL, 1.8 Vols) was added the the heating at 60° C. was continued for over 15 minutes. The reaction was cooled down to 53° C. The reaction was further cooled down to 20° C. and water (74.88 mL, 7.2 Vols) was at 20° C. over 1 hour. The reaction mixture was then stirred for another hour. The product was isolated by filtration and dried in vacuum oven at 64° C. with nitrogen bleed. Compound 33 THF Solvate Form A was isolated in 95% yield. Exemplary alternative solvent combinations to make the Compound 33 THF Solvate Form A include THF/Water 9:1 vol/vol with 20 vol IPA, THF/Water 9:10.5 vol/vol with 1 vol MeOH, and THF/Water 10:9.5 vol/vol with 0.1 vol IPA.

Alternatively, 10 mg of Compound 33 Form A can be weighed in 2 ml glass vial and 200-300 μl of THF added along with a small magnetic stir bar. The sample is stirred at RT for two weeks. Then the solid can be isolated as Compound 33 THF Solvate Form A.

B. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The XRPD diffractogram is shown in FIG. 13A and XRPD data are summarized in Table 49.

TABLE 49

XRPD Peaks for Compound 33 THF Solvate Form A

| Peak # | Angle (Degrees 2-Theta ± 0.2) | Relative Intensity % |
|---|---|---|
| 1 | 19.4 | 100.0 |
| 2 | 19.1 | 58.0 |
| 3 | 21.5 | 37.4 |
| 4 | 8.5 | 23.7 |
| 5 | 11.3 | 18.4 |
| 6 | 20.5 | 17.2 |
| 7 | 21.2 | 15.1 |
| 8 | 17.1 | 14.9 |
| 9 | 9.5 | 14.7 |
| 10 | 21.1 | 13.8 |
| 11 | 23.1 | 12.6 |
| 12 | 22.9 | 12.3 |
| 13 | 8.2 | 10.9 |
| 14 | 17.8 | 10.4 |

C. Single Crystal Elucidation

Single crystals having the THF solvate structure were grown from ethanol/water. X-ray diffraction data were acquired at 100K on a Bruker diffractometer equipped with Cu $K_\alpha$ radiation (λ=1.54178 Å) and a CMOS detector. The structure was solved and refined using SHELX programs (Sheldrick, G. M., Acta Cryst., (2008) A64, 112-122) and results are summarized in Table 50 below.

TABLE 50

Single crystal elucidation of
Compound 33 THF solvate Form A

| Crystal System | Orthorhombic |
|---|---|
| Space Group | $Pca2_1$ |
| a (Å) | 25.1154(5) |
| b (Å) | 11.9769(2) |
| c (Å) | 17.7368(4) |
| α (°) | 90 |
| β (°) | 90 |
| γ (°) | 90 |
| V (Å$^3$) | 5335.31 |
| Z/Z' | 4/2 |
| Temperature | 100 K. |

D. Solid State NMR (1) $^{13}$C CPMAS Analysis

Figure 13B:
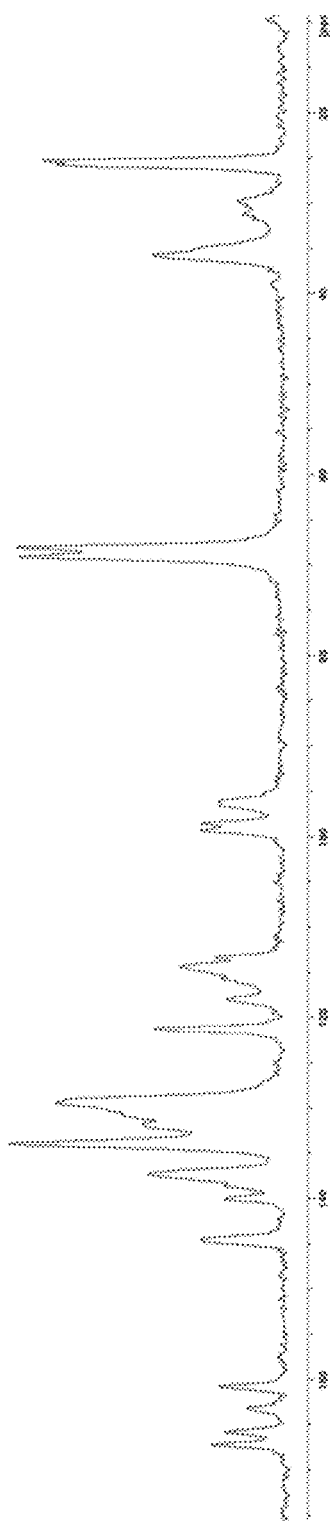
FIG. 13B shows a solid state $^{13}$C NMR spectrum of Compound 33 THF solvate Form A.

Solid state $^{13}$C NMR data for Compound 33 THF solvate Form A is provided in FIG. 13B and summarized in Table 51 below.

TABLE 51

Solid State NMR of Compound 33 Solvate Form A

| Peak # | Chem Shift [ppm] | Intensity [rel] |
|---|---|---|
| 1 | 167.2 | 25.2 |
| 2 | 165.8 | 20.5 |
| 3 | 163.1 | 12.6 |
| 4 | 160.7 | 22.7 |
| 5 | 144.5 | 29.2 |
| 6 | 140.0 | 20.7 |
| 7 | 138.5 | 20.8 |
| 8 | 137.2 | 48.6 |
| 9 | 133.9 | 100.0 |
| 10 | 131.7 | 50.5 |
| 11 | 129.4 | 82.4 |
| 12 | 121.2 | 46.9 |
| 13 | 117.9 | 19.6 |
| 14 | 115.6 | 22.0 |
| 15 | 114.3 | 36.9 |
| 16 | 113.3 | 24.4 |
| 17 | 99.3 | 29.4 |
| 18 | 98.5 | 29.3 |
| 19 | 96.5 | 22.6 |
| 20 | 96.1 | 23.0 |
| 21 | 69.0 | 95.8 |
| 22 | 68.0 | 96.8 |
| 23 | 35.7 | 47.2 |
| 24 | 31.1 | 13.8 |
| 25 | 29.8 | 15.9 |
| 26 | 25.7 | 82.3 |
| 27 | 25.3 | 87.5 |

(2) $^{19}$F MAS Analysis

Figure 13C:
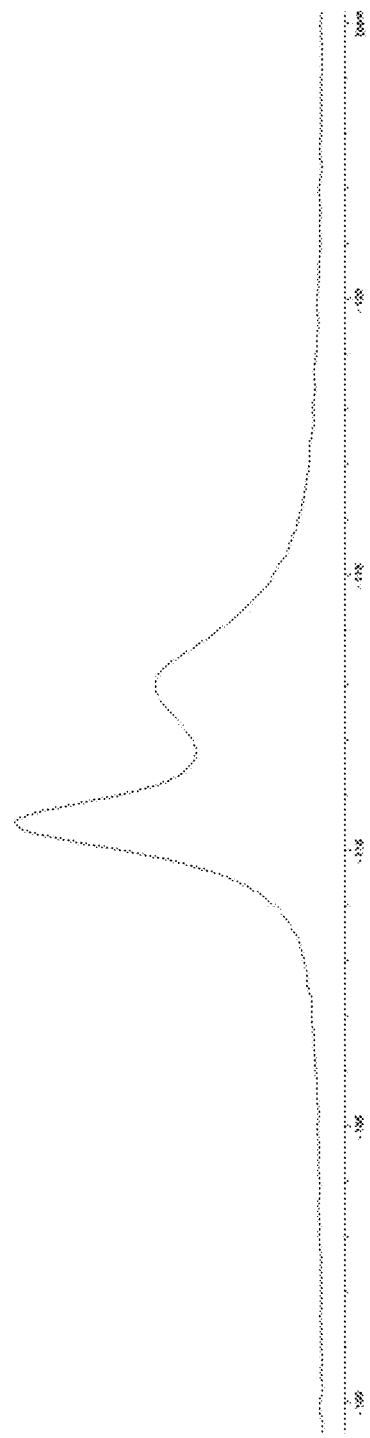
FIG. 13C shows a solid state $^{19}$F NMR spectrum of Compound 33 THF solvate Form A.

Solid state $^{19}$F NMR data for Compound 33 THF solvate Form A is provided in FIG. 13C and summarized in Table 52 below.

TABLE 52

Solid State NMR of Compound 33 THF Solvate Form A

| Peak # | Chem Shift [ppm] | Intensity [rel] |
|---|---|---|
| 1 | −110.5 | 12.5 |
| 2 | −113.0 | 6.8 |

E. Thermogravimetric Analysis

Figure 13D:
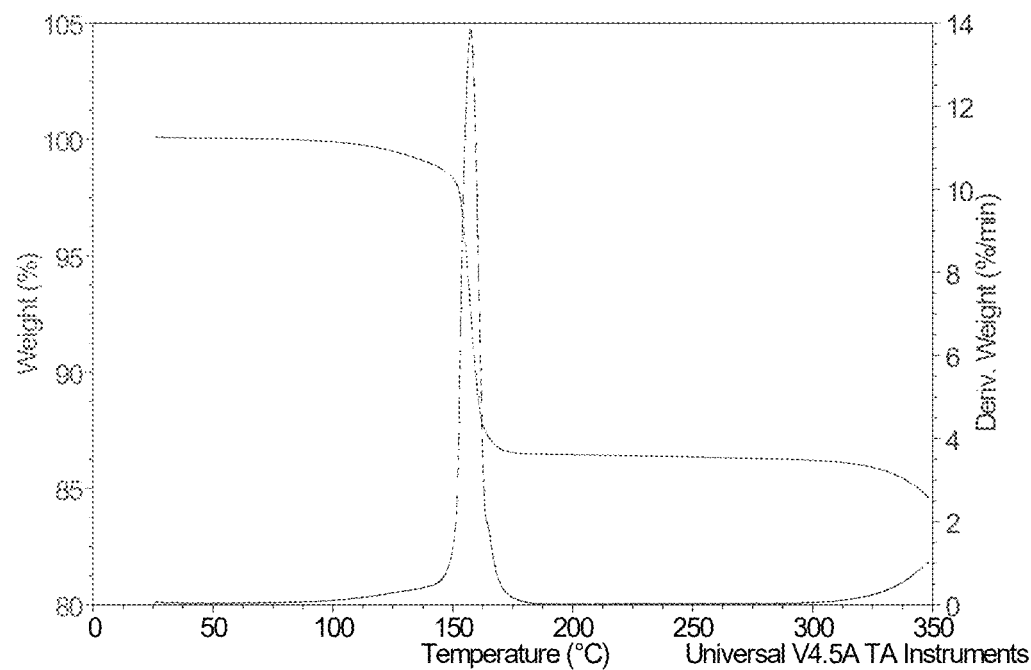
FIG. 13D shows a TGA thermogram of Compound 33 THF solvate Form A.

Thermal gravimetric analysis of Compound 33 THF solvate Form A was measured using the TA Instruments TGA Q5000. A sample with weight of approximately 1-5 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram as provided in FIG. 13D shows 13.4% weight loss from ambient temperature up to 170° C.

F. Differential Scanning Calorimetry Analysis

Figure 13E:
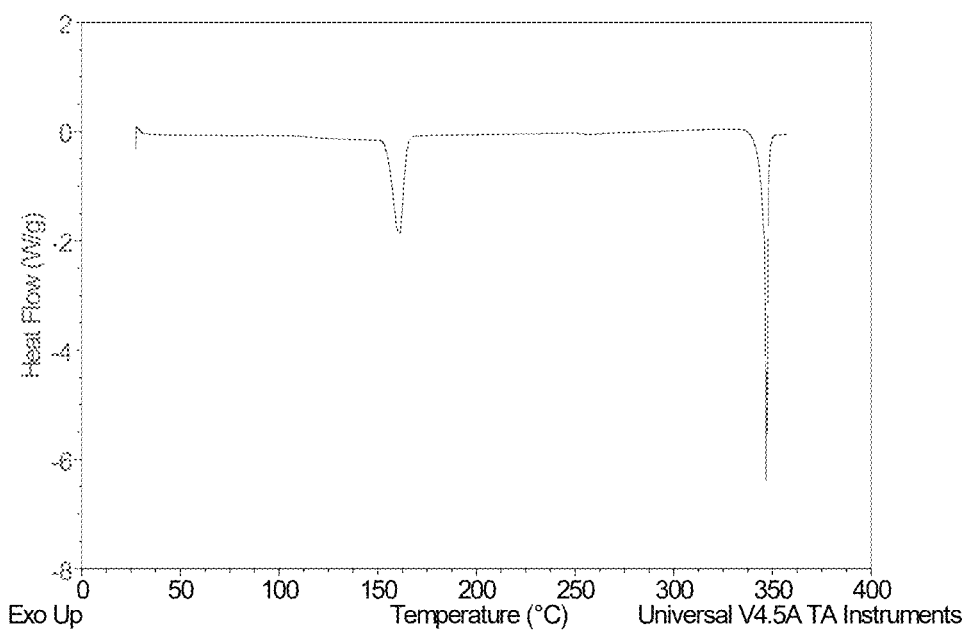
FIG. 13E shows a DSC thermogram of Compound 33 THF solvate Form A.

DSC of Compound 33 THF solvate Form A was measured using the TA Instruments Q2000 DSC. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 360° C. When the run was completed, the data were analyzed by Trios and/or Universal Analysis software (TA Instruments, New Castle, DE). The DSC thermogram as provided in FIG. 13E shows two endothermic peaks around 161 and 347° C.

14. Compound 33 Form J

A. Synthetic Procedure

~16.2 mg of Compound 33 Form A was weighed into a 3-mL glass vial. Then the 0.5 mL solvent, THF:EtOH:Water 6:1:1 (v/v/v), was added to get a saturated solution at RT. This sample was slurried for 1 hour and was then filtered using a Nylon membrane with the pore size of 0.22 μm into a new vial. Then ~2 mg of a pre-prepared polymer mixture (polyvinyl pyrrolidone (PVP), polyvinyl alcohol (PVA), polyvinylchloride (PVC), hypromellose (HPMC), methyl cellulose (MC) (mass ratio of 1:1:1:1:1)) was added into the filtrate and stirred at RT to induce precipitation for a day. No precipitation occurred, so the clear solution was then transferred to slow evaporation (vial covered with parafilm that had a hole poked through it) to induce precipitation. The precipitated solid was isolated as Compound 33 Form J.

B. X-Ray Powder Diffraction

XRPD was performed with a Panalytical X'Pert$^3$ Powder XRPD on a Si zero-background holder. The 2θ position was calibrated against a Panalytical Si reference standard disc. The parameters used are listed in the Table 53. The XRPD diffractogram is shown in FIG. 14A and XRPD data are summarized in Table 54.

TABLE 53

Parameters for XRPD test of Compound 33 Form J

| Parameters | Reflection Mode |
|---|---|
| X-Ray wavelength | Cu, kα<br>Kα1 (Å): 1.540598,<br>Kα2 (Å): 1.544426,<br>Kα2/Kα1 intensity ratio: 0.50 |
| X-Ray tube setting | 45 kV,<br>40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 54

XRPD Peaks for Compound 33 Form J

| Peak # | Angle (Degrees) 2-Theta ± 0.2 | Relative Intensity % |
|---|---|---|
| 1 | 6.6 | 100.0 |
| 2 | 15.0 | 77.0 |
| 3 | 19.4 | 74.8 |
| 4 | 10.3 | 55.8 |
| 5 | 16.0 | 44.3 |
| 6 | 19.9 | 41.2 |
| 7 | 16.8 | 39.2 |
| 8 | 20.6 | 35.3 |
| 9 | 20.8 | 27.4 |
| 10 | 15.6 | 20.6 |
| 11 | 21.4 | 19.7 |
| 12 | 22.5 | 16.1 |
| 13 | 7.5 | 15.6 |

TABLE 54-continued

XRPD Peaks for Compound 33 Form J

| Peak # | Angle (Degrees 2-Theta ± 0.2) | Relative Intensity % |
|---|---|---|
| 14 | 20.1 | 14.0 |
| 15 | 21.7 | 12.0 |
| 16 | 17.9 | 11.0 |

C. Thermogravimetric Analysis

Figure 14B:
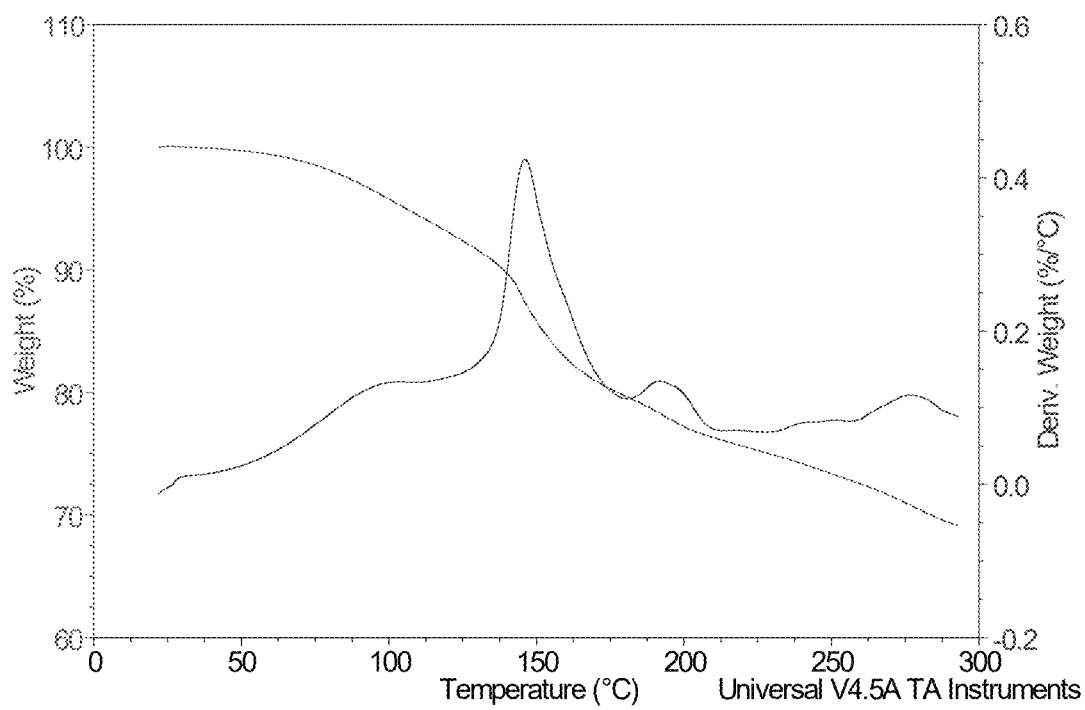
FIG. 14B shows a TGA thermogram of Compound 33 Form J.

Thermal gravimetric analysis of Compound 33 Form J was measured using TA Discovery 550 TGA from TA Instrument. A sample with weight of approximately 1-5 mg was scanned from 25° C. to 290° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram as provided in FIG. 14B shows 20.3% weight loss from ambient temperature up to 180° C.

15. Compound 33 Form K

A. Synthetic Procedure

Approximately 15 mg of Compound 33 Form A was dissolved in 0.1-0.2 mL THF to obtain a clear solution in a 3-mL vial. This solution was then placed into a 20-mL vial with 3 mL of water. The 20-mL vial was sealed with a cap and kept at RT allowing enough time for the water vapor to interact with the solution. The precipitate was isolated for as Compound 33 Form K.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 55. The XRPD diffractogram is shown in FIG. 15A and XRPD data are summarized in Table 56.

TABLE 55

Parameters for XRPD test of Compound 33 Form K

| Parameters | Reflection Mode |
|---|---|
| X-Ray wavelength | Cu, kα<br>Kα1 (Å): 1.540598,<br>Kα2 (Å): 1.544426,<br>Kα2/Kα1 intensity ratio: 0.50 |
| X-Ray tube setting | 45 kV,<br>40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 56

XRPD Peaks for Compound 33 Form K

| Peak # | Angle (Degrees 2-Theta ± 0.2) | Relative Intensity % |
|---|---|---|
| 1 | 9.7 | 100.0 |
| 2 | 20.5 | 68.2 |
| 3 | 19.7 | 59.2 |
| 4 | 19.4 | 58.1 |
| 5 | 19.1 | 45.9 |

TABLE 56-continued

XRPD Peaks for Compound 33 Form K

| Peak # | Angle (Degrees 2-Theta ± 0.2) | Relative Intensity % |
|---|---|---|
| 6 | 11.2 | 26.1 |
| 7 | 21.0 | 23.7 |
| 8 | 17.0 | 20.0 |
| 9 | 14.5 | 19.0 |
| 10 | 24.4 | 12.6 |

C. Thermogravimetric Analysis

Figure 15B:
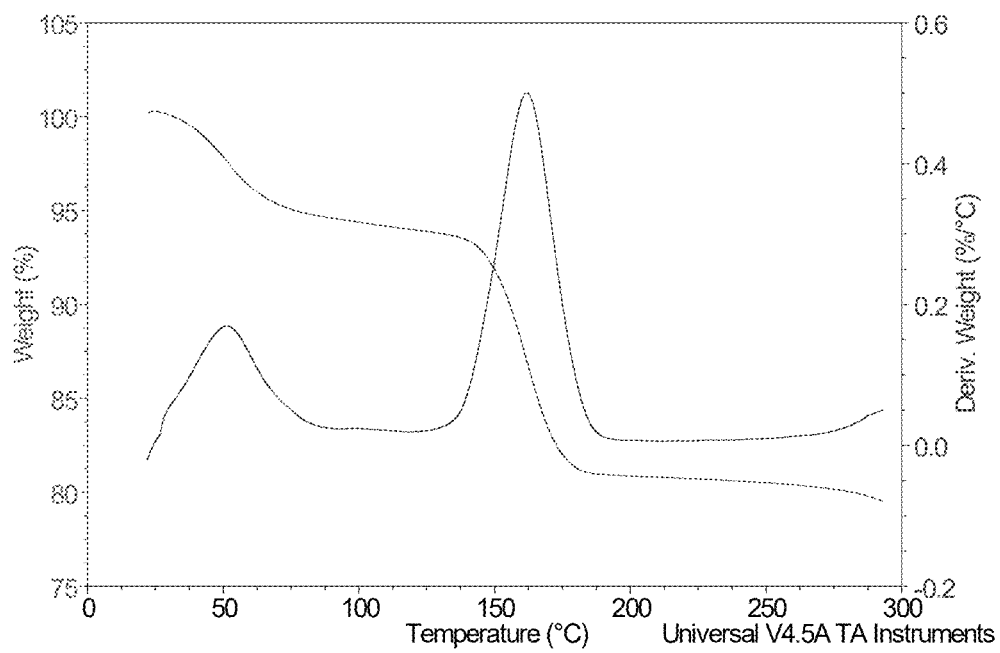
FIG. 15B shows a TGA thermogram of Compound 33 Form K.

Thermal gravimetric analysis of Compound 33 THF Form K was measured using TA Discovery 550 TGA from TA Instrument. A sample with weight of approximately 1-5 mg was scanned from 25° C. to 290° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram as provided in FIG. 15B shows 5.8% weight loss from ambient temperature up to 100° C. and additional 14.8% weight loss from 100° C. up to 290° C.

D. Differential Scanning Calorimetry Analysis

Figure 15C:
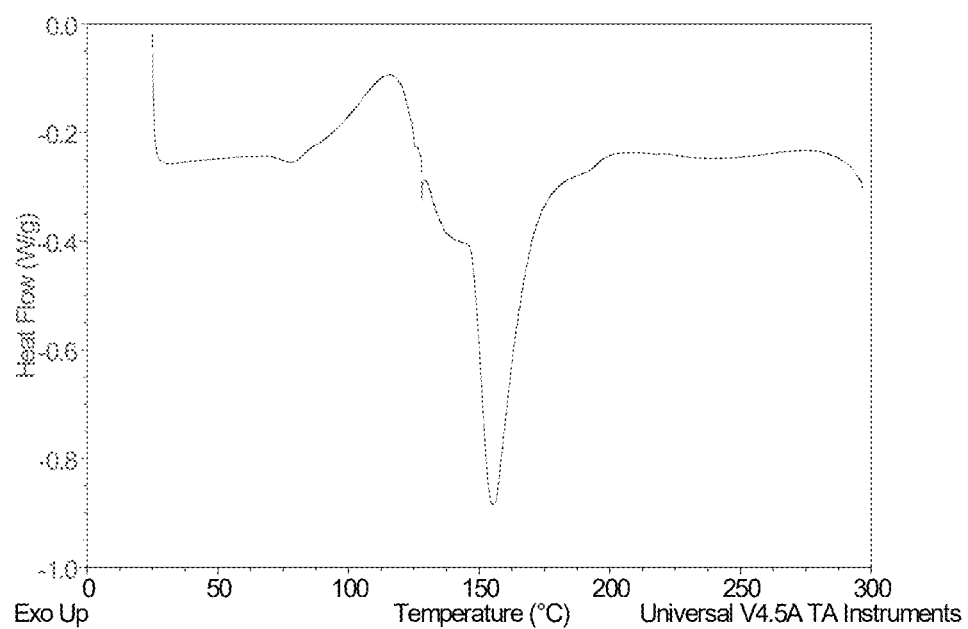
FIG. 15C shows a DSC thermogram of Compound 33 Form K.

DSC of Compound 33 Form K was measured using the TA Q2000 DSC from TA Instrument. A sample with a weight between 1-10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to around temperature of 300° C. When the run was completed, the data were analyzed by Trios and/or Universal Analysis software (TA Instruments, New Castle, DE). The DSC thermogram as provided in FIG. 15C shows an exothermic peak around 116° C. and endothermic peak around 156° C.

16. Compound 33 2-MeTHF Solvate Form A

A. Synthetic Procedure

About 20 mg of Compound 33 Form A was suspended in 0.2 mL of 2-MeTHF in a 2-mL glass vial, and the slurry was stirred magnetically for two days at RT or one day at 5° C. Then the solids were isolated as Compound 33 2-MeTHF Solvate Form A.

B. X-Ray Powder Diffraction

XRPD was performed with a Panalytical X'Pert Powder XRPD on a Si zero-background holder. The 2θ position was calibrated against a Panalytical Si reference standard disc. The parameters used are listed in the Table 57. The XRPD diffractogram is shown in FIG. 16A and XRPD data are summarized in Table 58.

TABLE 57

Parameters for XRPD test of Compound 33 2-MeTHF Solvate Form A

| Parameters | Reflection Mode |
|---|---|
| X-Ray wavelength | Cu, kα<br>Kα1 (Å): 1.540598,<br>Kα2 (Å): 1.544426,<br>Kα2/Kα1 intensity ratio: 0.50 |
| X-Ray tube setting | 45 kV,<br>40 mA |
| Divergence slit | Fixed 1/8° |
| Scan mode | Continuous |
| Scan range (° 2TH) | 3-40 |

TABLE 57-continued

Parameters for XRPD test of Compound 33
2-MeTHF Solvate Form A

| Parameters | Reflection Mode |
|---|---|
| Scan step time [s] | 18.87 |
| Step size (° 2TH) | 0.0131 |
| Test Time | 4 min 15 s |

TABLE 58

XRPD Peaks for Compound 33 2-MeTHF Solvate Form A

| Peak # | Angle (Degrees 2-Theta ± 0.2) | Relative Intensity % |
|---|---|---|
| 1 | 18.1 | 100.0 |
| 2 | 19.0 | 24.3 |
| 3 | 21.3 | 22.6 |
| 4 | 20.8 | 13.3 |
| 5 | 20.0 | 13.0 |
| 6 | 18.7 | 12.2 |
| 7 | 13.8 | 10.4 |

C. Thermogravimetric Analysis

Figure 16B:
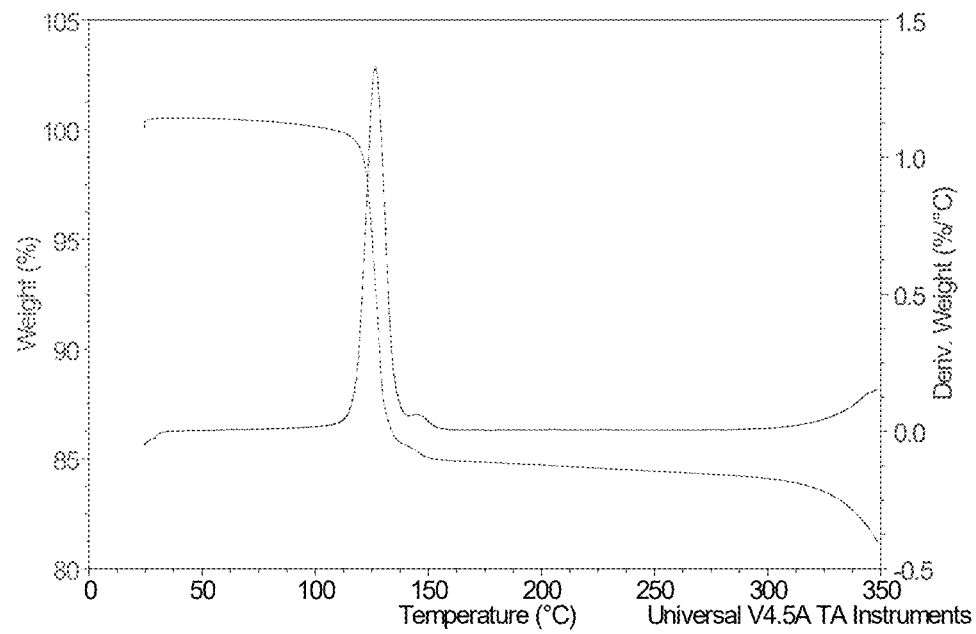
FIG. 16B shows a TGA thermogram of Compound 33 2-MeTHF solvate Form A.

Thermal gravimetric analysis of Compound 33 2-MeTHF Solvate Form A was measured using the TA Instruments TGA Q5000. A sample with weight of approximately 1-5 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram provided in FIG. 16B shows 15% weight loss from ambient temperature up to 160° C.

D. Differential Scanning Calorimetry Analysis

Figure 16C:
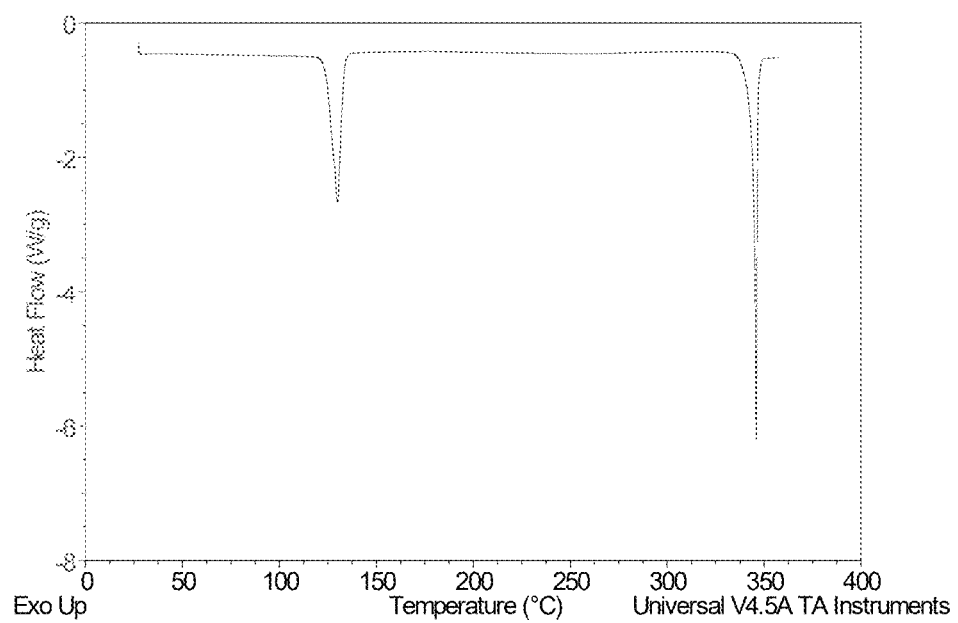
FIG. 16C shows a DSC thermogram of Compound 33 2-MeTHF solvate Form A.

DSC of Compound 33 2-MeTHF Solvate Form A was measured using the TA Instruments Q2000 DSC. A sample with a weight between 1-5 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to around 357° C. When the run was completed, the data were analyzed by Trios and/or Universal Analysis software (TA Instruments, New Castle, DE). The DSC thermogram provided in FIG. 16C shows two endothermic peaks around 130 and 346° C.

17. Compound 33 Form L

A. Synthetic Procedure

Approximately 15 mg of Compound 33 Form A was dissolved in 1-2 mL of 2-MeTHF in a 3-mL glass vial. The visually clear solution was allowed a slow evaporation at RT. The solids were isolated as Compound 33 Form L.

In an alternative procedure, approximate 15 mg of Compound 33 Form A was added with 0.2 mL of 2-MeTHF/Heptane (1:1, v:v). The mixture was then heated to 50° C. with magnetic stirring and equilibrated for two hours, and then filtered using a PTFE membrane (pore size of 0.20 µm). The filtrate was slowly cooled down to 5° C. at a rate of 0.1° C./min, and the precipitated solids were isolated as Compound 33 Form L.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 59. The XRPD diffractogram is shown in FIG. 17A and XRPD data are summarized in Table 60.

TABLE 59

Parameters for XRPD test of Compound 33
2-MeTHF solvate Form A

| Parameters | Reflection Mode |
|---|---|
| X-Ray wavelength | Cu, kα |
| | Kα1 (Å): 1.540598, |
| | Kα2 (Å): 1.544426, |
| | Kα2/Kα1 intensity ratio: 0.50 |
| X-Ray tube setting | 45 kV, 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 60

XRPD Peaks for Compound 33
2-MeTHF solvate Form A

| Peak # | Angle (Degrees 2-Theta ± 0.2) | Relative Intensity % |
|---|---|---|
| 1 | 14.6 | 100.0 |
| 2 | 18.6 | 86.7 |
| 3 | 14.5 | 73.2 |
| 4 | 7.0 | 49.7 |
| 5 | 7.0 | 46.4 |
| 6 | 21.0 | 40.2 |
| 7 | 20.9 | 38.4 |
| 8 | 18.8 | 36.2 |
| 9 | 17.3 | 26.5 |
| 10 | 22.2 | 22.2 |
| 11 | 20.2 | 21.4 |
| 12 | 20.4 | 17.4 |
| 13 | 31.7 | 16.8 |
| 14 | 9.9 | 16.0 |
| 15 | 28.6 | 15.6 |
| 16 | 16.3 | 15.2 |
| 17 | 23.1 | 15.1 |
| 18 | 19.7 | 13.4 |
| 19 | 8.8 | 13.2 |
| 20 | 22.7 | 13.0 |
| 21 | 27.1 | 12.8 |
| 22 | 13.7 | 12.6 |
| 23 | 17.9 | 12.5 |
| 24 | 17.6 | 12.2 |
| 25 | 23.6 | 10.4 |
| 26 | 21.9 | 10.4 |

C. Thermogravimetric Analysis

Figure 17B:
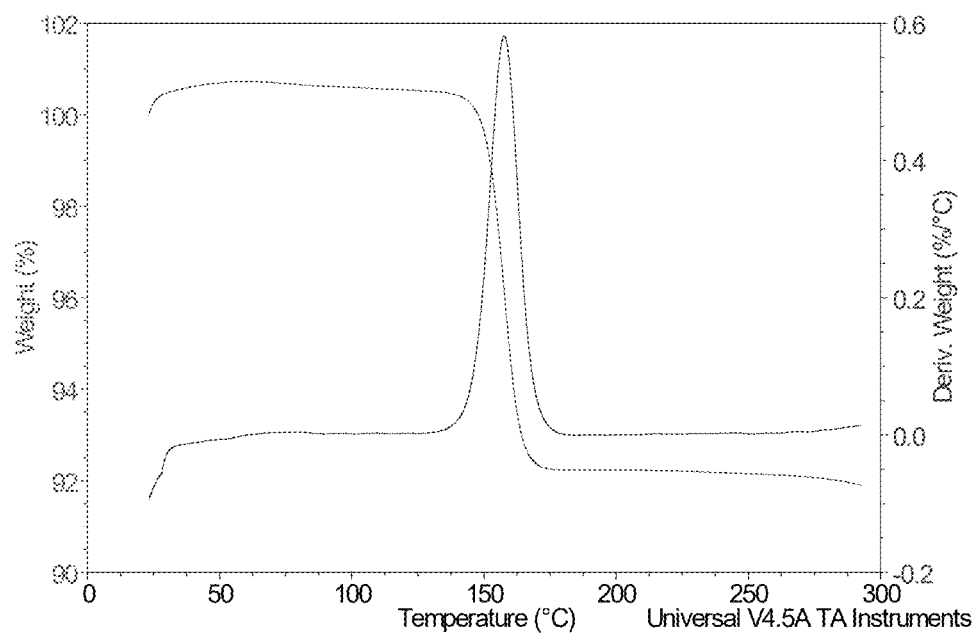
FIG. 17B shows a TGA thermogram of Compound 33 Form L.

Thermal gravimetric analysis of Compound 33 Form L was measured using TA Discovery 550 TGA from TA Instrument. A sample with weight of approximately 1-5 mg was scanned from 25° C. to around 290° C. at a heating rate of 10° C./min with nitrogen purge. Data were collected by Thermal Advantage Q Series™ software and analyzed by Trios and/or Universal Analysis software (TA Instruments, New Castle, DE). The TGA thermogram as provided in FIG. 17B shows 7.8% weight loss from ambient temperature up to 200° C.

D. Differential Scanning Calorimetry Analysis

Figure 17C:
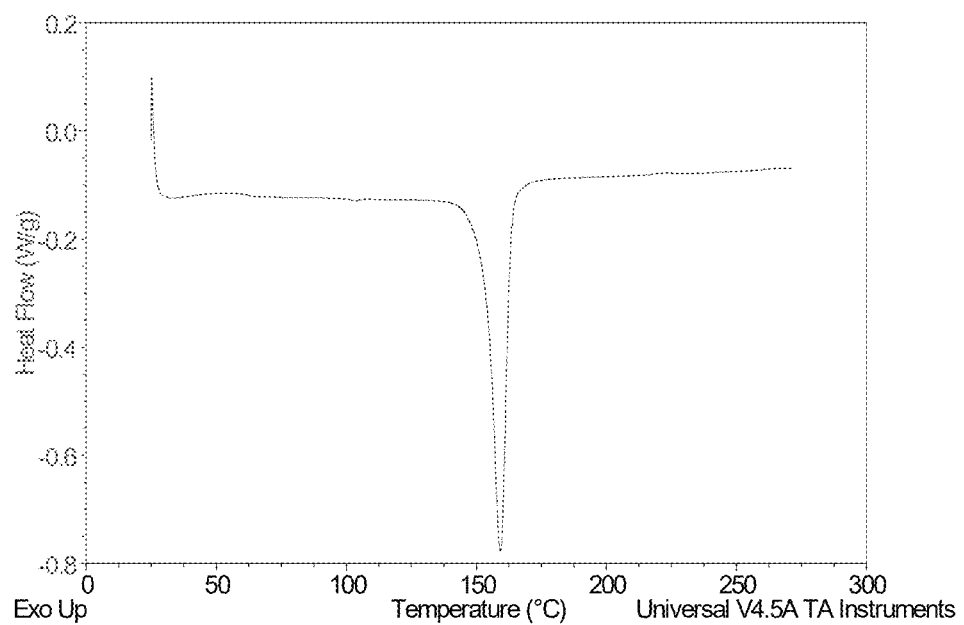
FIG. 17C shows a DSC thermogram of Compound 33 Form L.

DSC of Compound 33 Form L was measured using the TA Q2000 DSC from TA Instrument. A sample with a weight between 1-10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min around 270° C. When the run was completed, the data were analyzed by Trios and/or Universal Analysis software (TA Instruments, New Castle, DE). The DSC thermogram as provided in FIG. 17C shows an endothermic peak around 159° C.

18. Compound 33 Form M

A. Synthetic Procedure

About 15 mg of Compound 33 Form M was weighed into a 4 mL vial, which was placed into a 20 mL vial with 2 mL of MTBE. The 20 mL vial was sealed with a cap and kept at RT for ten days allowing solvent vapor to interact with the solid sample.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 61. The XRPD diffractogram is shown in FIG. 18A and XRPD data are summarized in Table 62.

TABLE 61

Parameters for XRPD test of Compound 33 Form M

| Parameters | Reflection Mode |
|---|---|
| X-Ray wavelength | Cu, kα |
| | Kα1 (Å): 1.540598, |
| | Kα2 (Å): 1.544426 |
| | Kα2/Kα1 intensity ratio: 0.50 |
| X-Ray tube setting | 45 kV, |
| | 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 62

XRPD Peaks for Compound 33 Form M

| Peak # | Angle (Degrees 2-Theta ± 0.2) | Intensity % |
|---|---|---|
| 1 | 18.3 | 100.0 |
| 2 | 18.9 | 35.4 |
| 3 | 21.2 | 30.0 |
| 4 | 8.4 | 15.9 |
| 5 | 11.3 | 15.4 |
| 6 | 20.6 | 15.2 |
| 7 | 21.7 | 15.1 |
| 8 | 16.0 | 14.9 |
| 9 | 7.0 | 14.8 |
| 10 | 17.2 | 12.8 |
| 11 | 9.4 | 11.4 |
| 12 | 13.8 | 10.1 |

C. Thermogravimetric Analysis

Figure 18B:
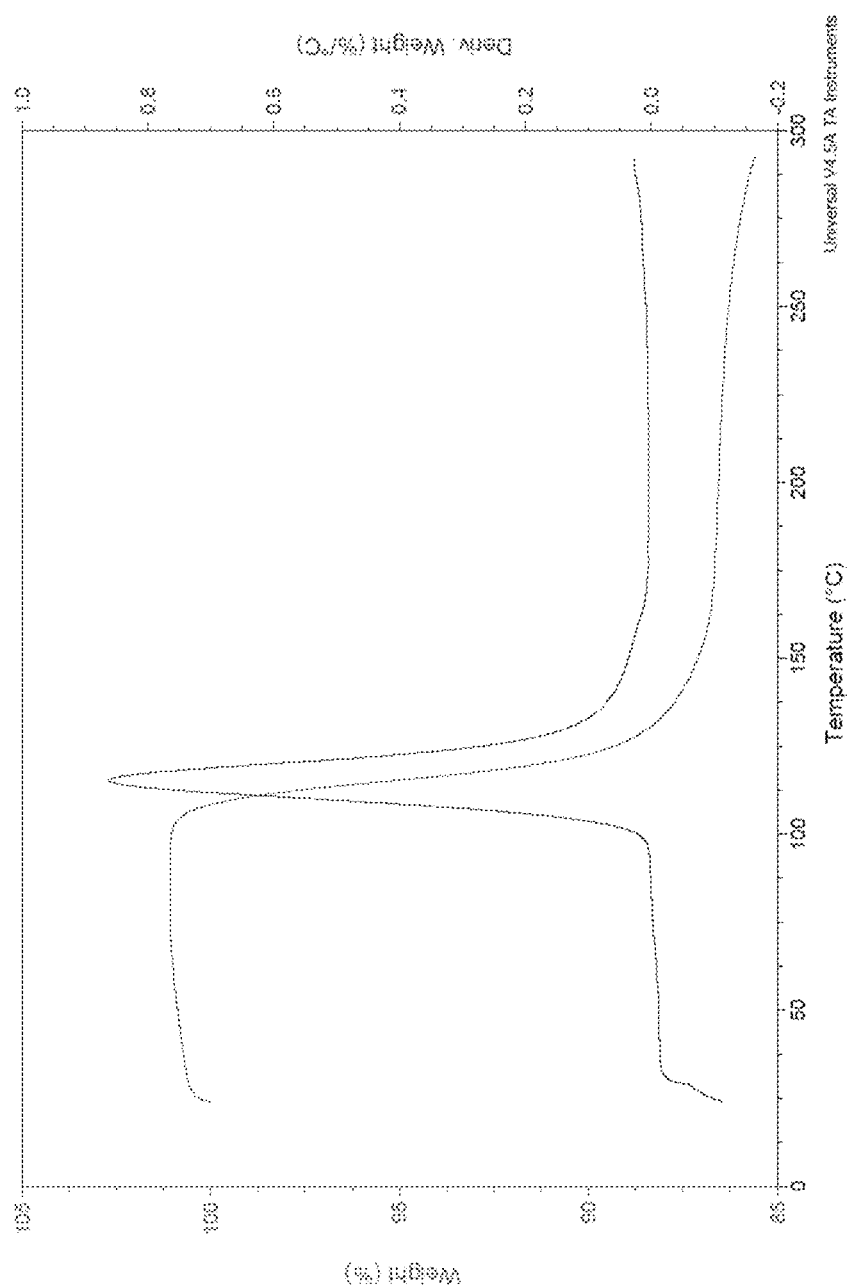
FIG. 18B shows a TGA thermogram of Compound 33 Form M.

TGA data was collected using a TA Discovery 550 TGA from TA Instrument. TGA was calibrated using nickel reference standard. Detailed parameters used are listed in Table 63. The TSC thermogram as provided in FIG. 18B shows ~15% weight loss from ambient temperature up to ~200° C.

TABLE 63

Parameters used for TGA and DSC analyses

| Parameters | TGA | DSC |
|---|---|---|
| Method | Ramp | Ramp |
| Sample pan | Platinum, open | Aluminum, crimped |
| Temperature | | RT-300° C. |
| Heating rate | | 10° C./min |
| Purge gas | | N₂ |

D. Differential Scanning Calorimetry Analysis

Figure 18C:
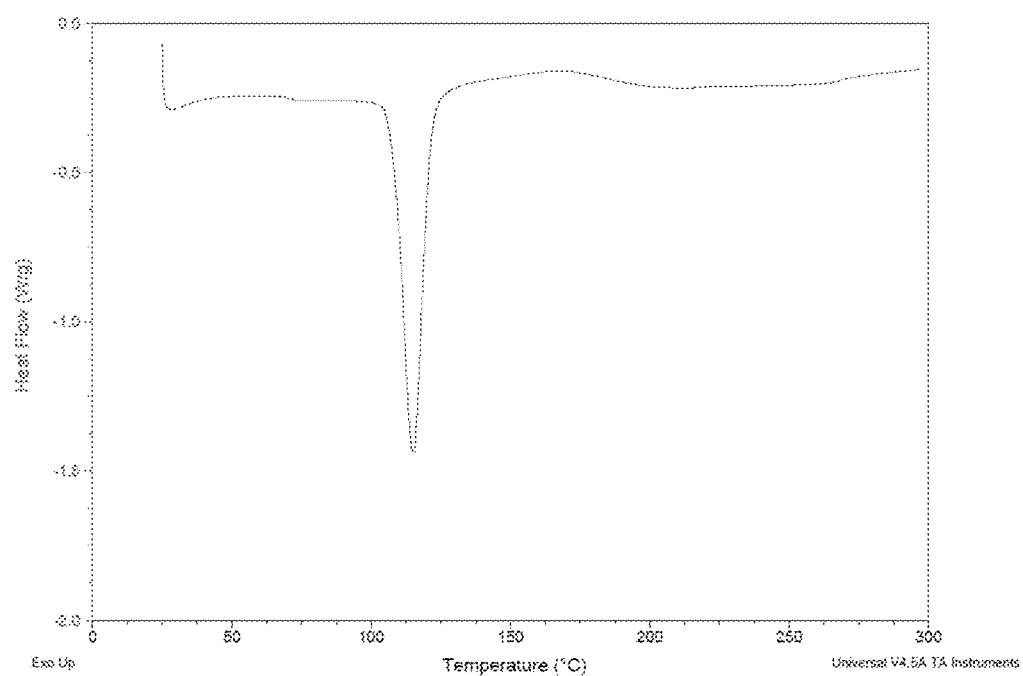
FIG. 18C shows a DSC thermogram of Compound 33 Form M.

DSC was performed using a TA Q2000 DSC from TA Instrument. DSC was calibrated with Indium reference standard. Detailed parameters used are listed in Table 63. The thermogram as provided in FIG. 18C shows an endothermic peak at ~115° C.

19. Compound 33 Form N

A. Synthetic Procedure

About 15 mg of Compound 33 Form A was suspended in 0.3 mL of EtOAc in a glass vial. After the suspension was stirred magnetically at room temperature, the remaining solids were isolated.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 64. The XRPD diffractogram is shown in FIG. 19A and XRPD data are summarized in Table 65.

TABLE 64

Parameters for XRPD test of Compound 33 Form N

| Parameters | Reflection Mode |
|---|---|
| X-Ray wavelength | Cu, kα |
| | Kα1 (Å): 1.540598, |
| | Kα2 (Å): 1.544426 |
| | Kα2/Kα1 intensity ratio: 0.50 |
| X-Ray tube setting | 45 kV, |
| | 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TABLE 65

XRPD Peaks for Compound 33 Form N

| Peak # | Angle (Degrees 2-Theta ± 0.2) | Intensity % |
|---|---|---|
| 1 | 19.6 | 100.0 |
| 2 | 20.5 | 71.2 |
| 3 | 18.7 | 69.6 |
| 4 | 15.6 | 66.0 |
| 5 | 18.2 | 63.6 |
| 6 | 21.8 | 43.0 |
| 7 | 23.1 | 39.0 |
| 8 | 25.6 | 36.4 |
| 9 | 21.5 | 34.9 |
| 10 | 11.7 | 33.0 |
| 11 | 14.3 | 31.3 |
| 12 | 24.0 | 28.8 |
| 13 | 26.1 | 25.3 |
| 14 | 12.3 | 24.7 |
| 15 | 13.0 | 23.9 |

TABLE 65-continued

XRPD Peaks for Compound 33 Form N

| Peak # | Angle (Degrees 2-Theta ± 0.2) | Intensity % |
|---|---|---|
| 16 | 19.2 | 21.7 |
| 17 | 17.6 | 19.9 |
| 18 | 17.1 | 18.0 |
| 19 | 22.2 | 15.0 |
| 20 | 8.8 | 14.6 |
| 21 | 26.8 | 14.3 |
| 22 | 4.2 | 13.9 |
| 23 | 22.7 | 13.7 |
| 24 | 28.4 | 12.5 |
| 25 | 12.6 | 11.1 |
| 26 | 28.0 | 10.4 |

C. Thermogravimetric Analysis

Figure 19B:
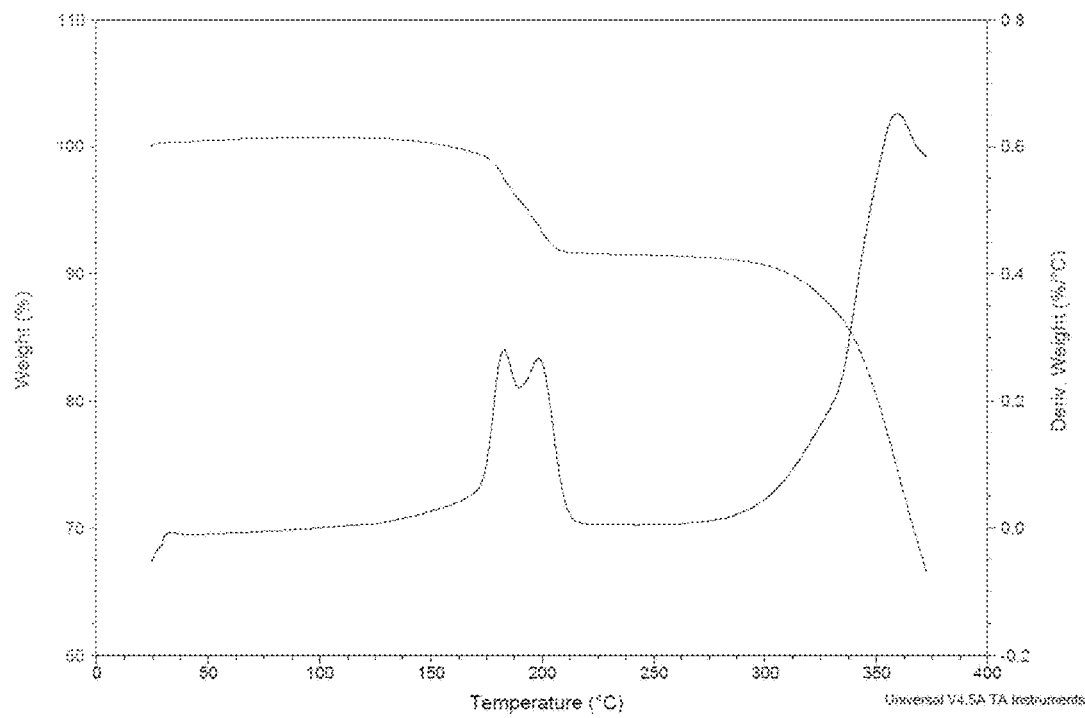
FIG. 19B shows a TGA thermogram of Compound 33 Form N.

TGA data was collected using a TA Discovery 550 TGA from TA Instrument. TGA was calibrated using nickel reference standard. Detailed parameters used are listed in Table 66. The TGA thermogram as provided in FIG. 19B shows ~9% weight loss from ambient temperature up to ~217° C.

TABLE 66

Parameters used for TGA and DSC analyses

| Parameters | TGA | DSC |
|---|---|---|
| Method | Ramp | Ramp |
| Sample pan | Platinum, open | Aluminum, crimped |
| Temperature | | RT-300° C. |
| Heating rate | | 10° C./min |
| Purge gas | | N₂ |

D. Differential Scanning Calorimetry Analysis

Figure 19C:
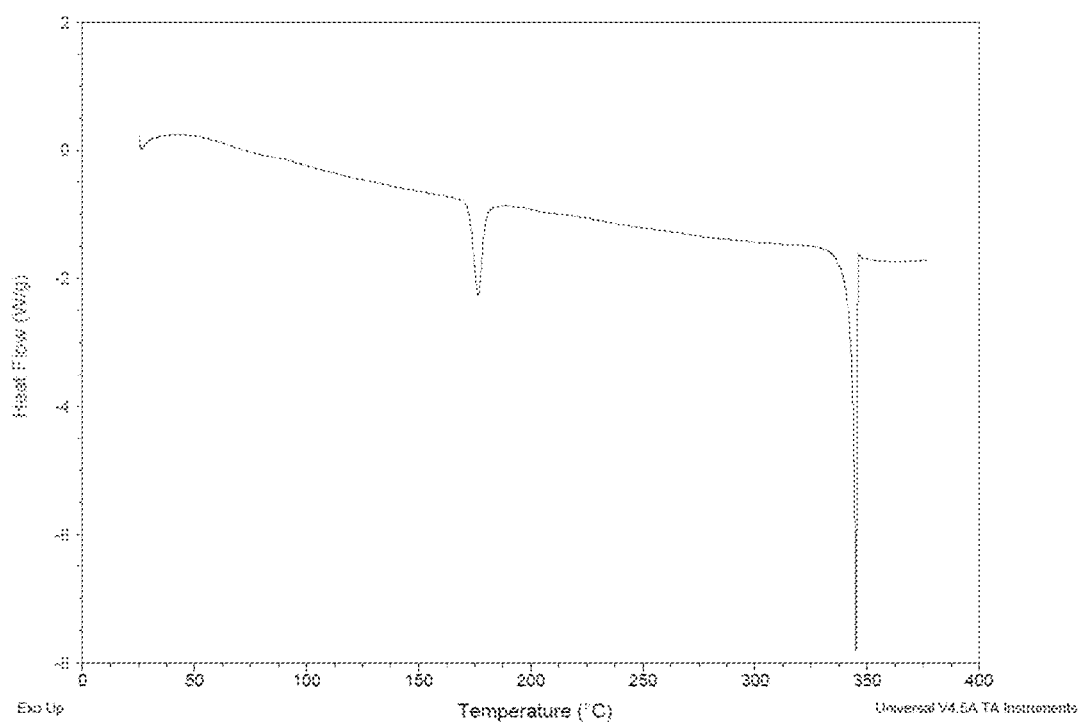
FIG. 19C shows a DSC thermogram of Compound 33 Form N.

DSC was performed using a TA Q2000 DSC from TA Instrument. DSC was calibrated with Indium reference standard. Detailed parameters used are listed in Table 66. The DSC thermogram provided in FIG. 19C shows endothermic peaks at ~177, 345° C.

20. Compound 33 Form O

A. Synthetic Procedure:

About ~20 mg of Compound 33 THF solvate Form A was suspended in 0.1~0.3 mL of EtOAc in a 2 mL glass vial. After the suspension was stirred magnetically for two days at room temperature (RT), the remaining solids were isolated.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 67. The XRPD diffractogram is shown in FIG. 20A and XRPD data are summarized in Table 68.

TABLE 67

Parameters for XRPD test of Compound 33 Form O

| Parameters | Reflection Mode |
|---|---|
| X-Ray wavelength | Cu, kα Kα1 (Å): 1.540598, Kα2 (Å): 1.544426 Kα2/Kα1 intensity ratio: 0.50 |
| X-Ray tube setting | 45 kV, 40 mA |
| Divergence slit | Fixed 1/8° |
| Scan mode | Continuous |

TABLE 67-continued

Parameters for XRPD test of Compound 33 Form O

| Parameters | Reflection Mode |
|---|---|
| Scan range (° 2TH) | 3-40 |
| Scan step time [s] | 18.87 |
| Step size (° 2TH) | 0.0131 |
| Test Time | 4 min 15 s |

TABLE 68

XRPD Peaks for Compound 33 Form O

| Peak # | Angle (Degrees 2-Theta ± 0.2) | Intensity % |
|---|---|---|
| 1 | 7.0 | 100.0 |
| 2 | 21.2 | 70.6 |
| 3 | 17.4 | 64.5 |
| 4 | 10.4 | 41.3 |
| 5 | 19.5 | 38.5 |
| 6 | 18.8 | 31.8 |
| 7 | 16.9 | 31.3 |
| 8 | 22.9 | 28.2 |
| 9 | 20.4 | 28.1 |
| 10 | 21.6 | 22.3 |
| 11 | 23.3 | 19.6 |
| 12 | 8.8 | 16.0 |
| 13 | 16.6 | 14.6 |
| 14 | 22.3 | 13.7 |
| 15 | 15.5 | 13.1 |
| 16 | 8.3 | 11.5 |

C. Thermogravimetric Analysis

Figure 20B:
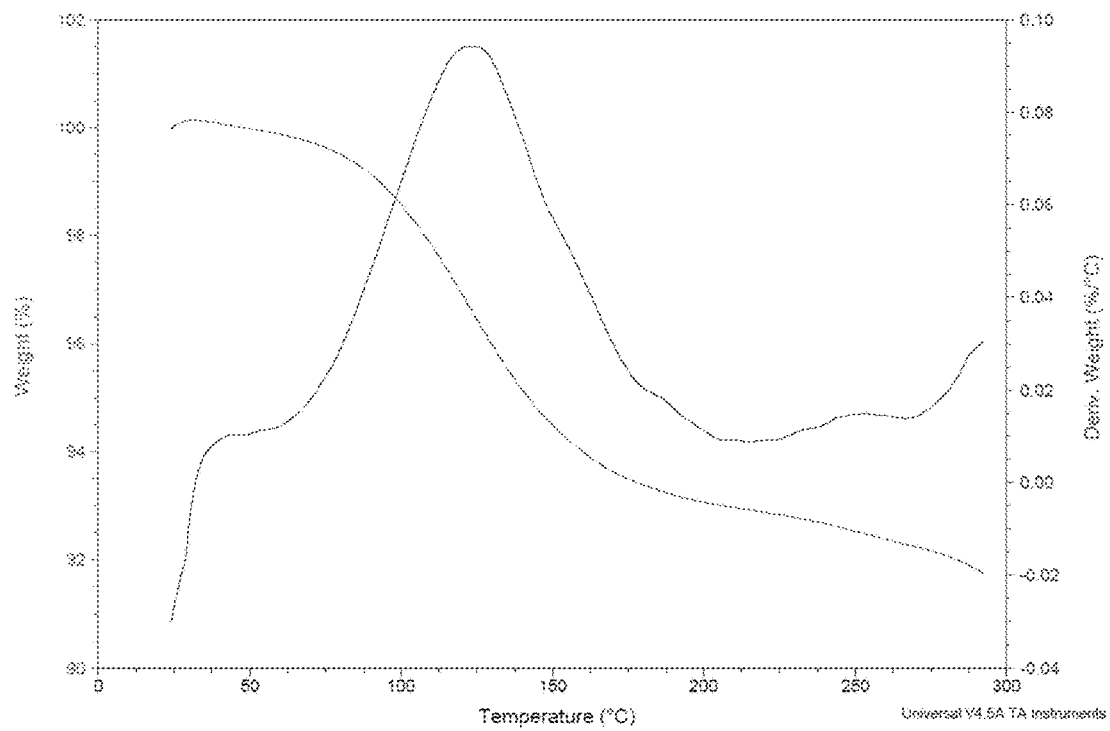
FIG. 20B shows a TGA thermogram of Compound 33 Form O.

TGA data was collected using a TA Discovery 550 TGA from TA Instrument. TGA was calibrated using nickel reference standard. Detailed parameters used are listed in Table 69. The TGA thermogram as provided in FIG. 20B shows ~7% weight loss from ambient temperature up to ~200° C.

TABLE 69

Parameters used for TGA and DSC analyses

| Parameters | TGA | DSC |
|---|---|---|
| Method | Ramp | Ramp |
| Sample pan | Platinum, open | Aluminum, crimped |
| Temperature | | RT - 300° C. |
| Heating rate | | 10° C./min |
| Purge gas | | N₂ |

21. Compound 33 Potassium Salt Form A

A. Synthetic Procedure 401 mg Compound 33 Form A was dissolved into 60 mL acetone at 50° C. to get clear solution. And 74 mg KOH was dissolved into 3 mL water for KOH aqueous solution. 3 mL Compound 33 acetone solution was dispensed in a glass vial at room temperature and 0.1 mL KOH aqueous solution was added into it. Compound 33 K salt A was obtained via evaporation at room temperature.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 70. The XRPD diffractogram is shown in FIG. 21A and XRPD data are summarized in Table 71.

TABLE 70

Parameters for XRPD test of Compound 33 K salt Form A

| Parameters | Reflection Mode |
|---|---|
| X-Ray wavelength | Cu, kα |
|  | Kα1 (Å): 1.540598, Kα2 (Å): 1.544426 |
|  | Kα2/Kα1 intensity ratio: 0.50 |
| X-Ray tube setting | 45 kV, 40 mA |
| Divergence slit | Fixed 1/8° |
| Scan mode | Continuous |
| Scan range (°2TH) | 3-40 |
| Scan step time [s] | 18.87 |
| Step size (°2TH) | 0.0131 |
| Test Time | 4 min 15 s |

TABLE 71

XRPD Peaks for Compound 33 K Salt Form A

| Peak # | Angle (Degrees 2-Theta ± 0.2) | Intensity % |
|---|---|---|
| 1 | 20.7 | 100.0 |
| 2 | 11.7 | 85.9 |
| 3 | 18.0 | 53.9 |

C. Thermogravimetric Analysis

Figure 21B:
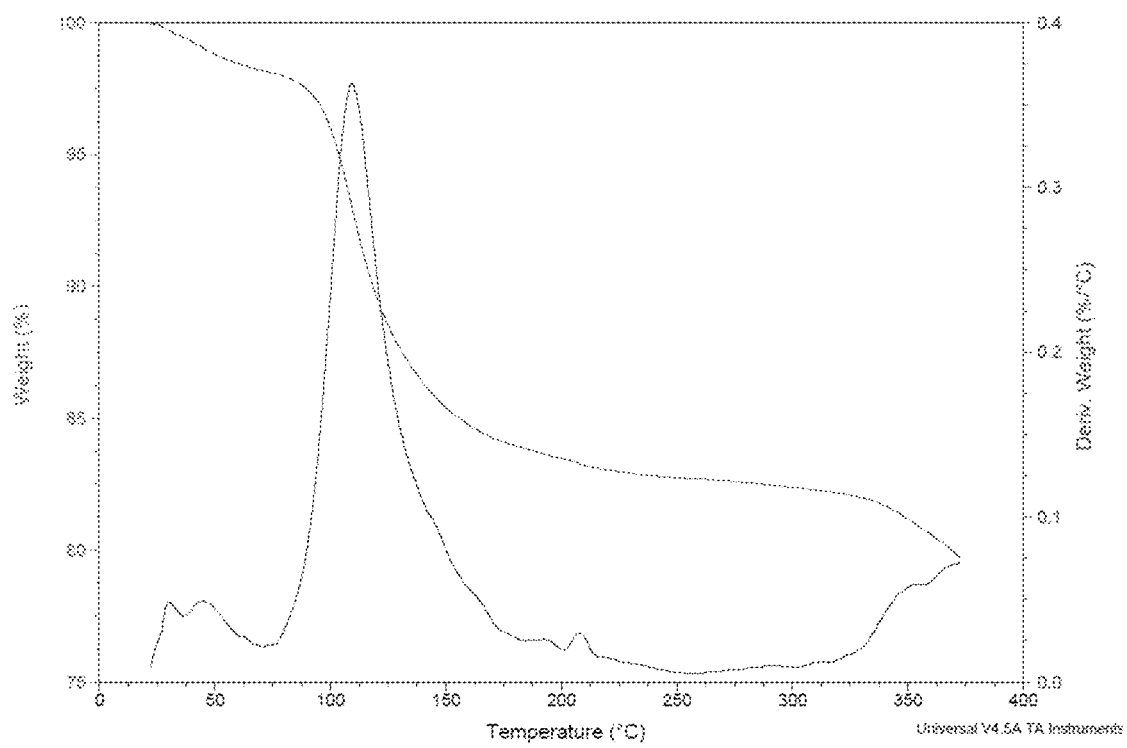
FIG. 21B shows a TGA thermogram of Compound 33 K salt Form A.

TGA data was collected using a TA Discovery 550 TGA from TA Instrument. TGA was calibrated using nickel reference standard. Detailed parameters used are listed in Table 72. The TGA thermogram provided in FIG. 21B shows ~16% weight loss from ambient temperature up to ~190° C.

D. Differential Scanning Calorimetry Analysis

Figure 21C:
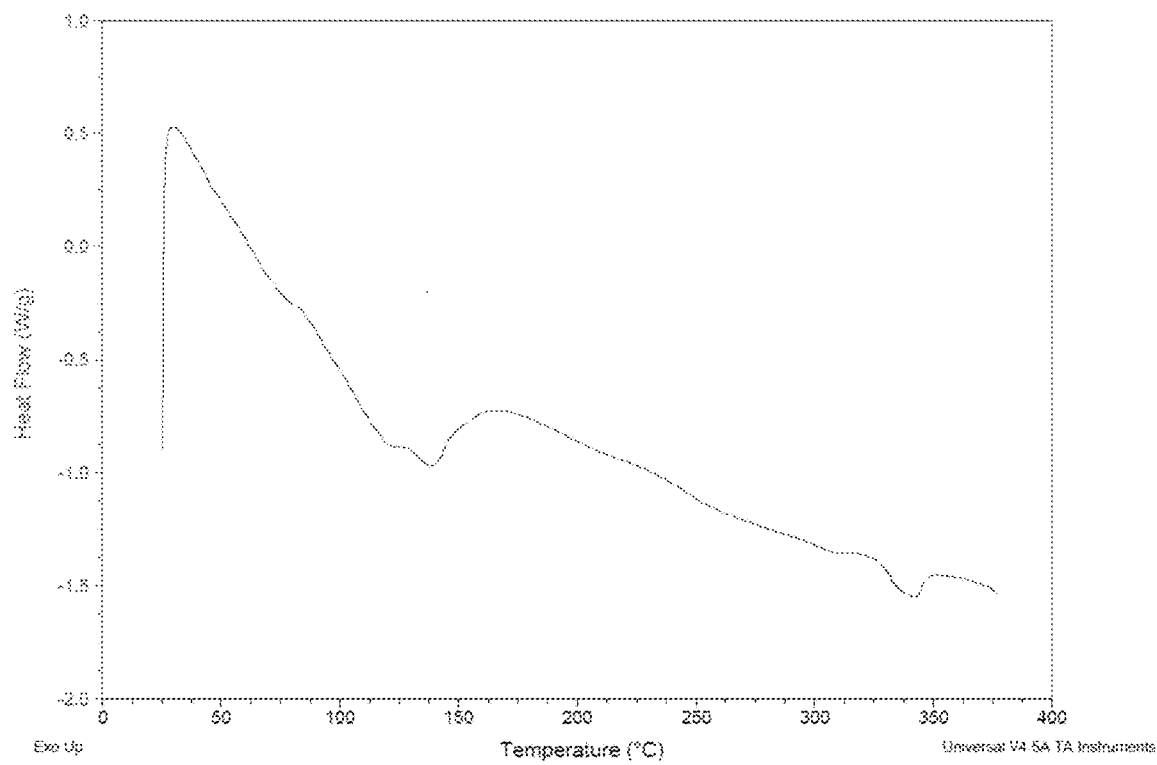
FIG. 21C shows a DSC thermogram of Compound 33 K salt Form A.

DSC was performed using a TA Q2000 DSC from TA Instrument. DSC was calibrated with Indium reference standard. Detailed parameters used are listed in Table 72. The DSC thermogram provided in FIG. 21C shows endothermic peaks at ~140 and 342° C.

22. Compound 33 Potassium Salt Form B

A. Synthetic Procedure 399 mg Compound 33 Form A was dissolved into 10 mL 1,4-dioxane at 50° C. with sonication to get clear solution. And 74 mg KOH was dissolved into 3 mL water for KOH aqueous solution. 0.5 mL Compound 1,4-dioxane solution was dispensed in a glass vial at room temperature and 0.1 mL KOH aqueous solution was added into it. Compound 33 K salt B was isolated at room temperature.

B. X-Ray Powder Diffraction

Figure 22A:
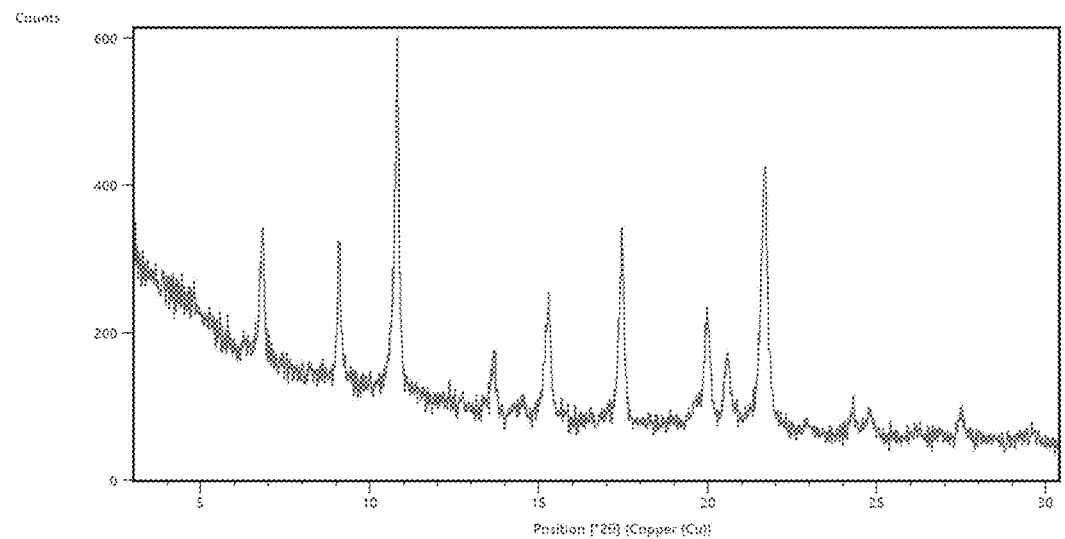
FIG. 22A shows an XRPD diffractogram of Compound 33 K salt Form B.

XRPD was performed with a Panalytical X'Pert³ Powder XRPD on a Si zero-background holder. The 2θ position was calibrated against a Panalytical Si reference standard disc. The parameters used are listed in the Table 73. The XRPD diffractogram is shown in FIG. 22A and XRPD data are summarized in Table 74.

TABLE 73

Parameters for XRPD test of Compound 33 K salt Form B

| Parameters | Reflection Mode |
|---|---|
| X-Ray wavelength | Cu, kα |
|  | Kα1 (Å): 1.540598, Kα2 (Å): 1.544426 |
|  | Kα2/Kα1 intensity ratio: 0.50 |
| X-Ray tube setting | 45 kV, 40 mA |
| Divergence slit | Fixed 1/8° |
| Scan mode | Continuous |
| Scan range (°2TH) | 3-40 |
| Scan step time [s] | 18.87 |
| Step size (°2TH) | 0.0131 |
| Test Time | 4 min 15 s |

TABLE 74

XRPD Peaks for Compound 33 K Salt Form B

| Peak # | Angle (Degrees 2-Theta ± 0.2) | Intensity % |
|---|---|---|
| 1 | 10.8 | 100.0 |
| 2 | 21.7 | 74.8 |
| 3 | 17.5 | 58.1 |
| 4 | 9.1 | 40.4 |
| 5 | 6.9 | 34.6 |
| 6 | 15.3 | 33.2 |
| 7 | 20.0 | 32.3 |
| 8 | 20.6 | 21.0 |
| 9 | 13.7 | 18.0 |

C. Thermogravimetric Analysis

Figure 22B:
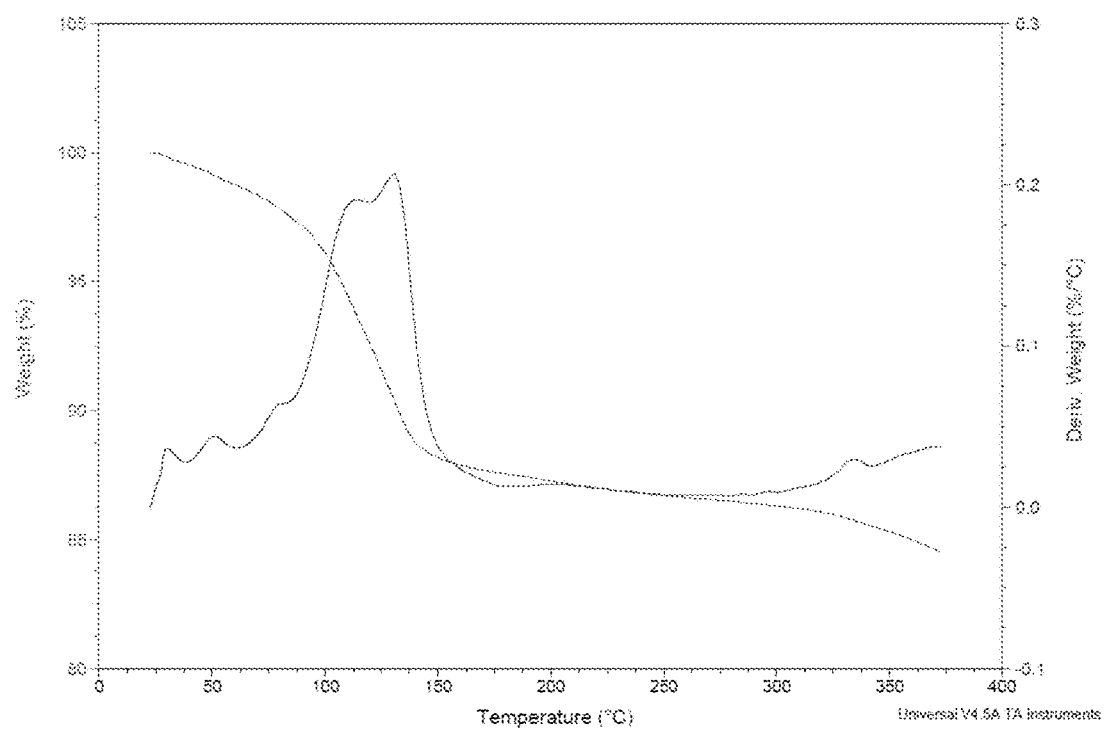
FIG. 22B shows a TGA thermogram of Compound 33 K salt Form B.

TGA data was collected using a TA Discovery 550 TGA from TA Instrument. TGA was calibrated using nickel reference standard. Detailed parameters used are listed in Table 75. The TGA thermogram provided in FIG. 22B shows ~12% weight loss from ambient temperature up to ~170° C.

TABLE 75

Parameters used for TGA and DSC analyses

| Parameters | TGA | DSC |
|---|---|---|
| Method | Ramp | Ramp |
| Sample pan | Platinum, open | Aluminum, crimped |
| Temperature |  | RT-300° C. |
| Heating rate |  | 10° C./min |
| Purge gas |  | $N_2$ |

D. Differential Scanning Calorimetry Analysis

Figure 22C:
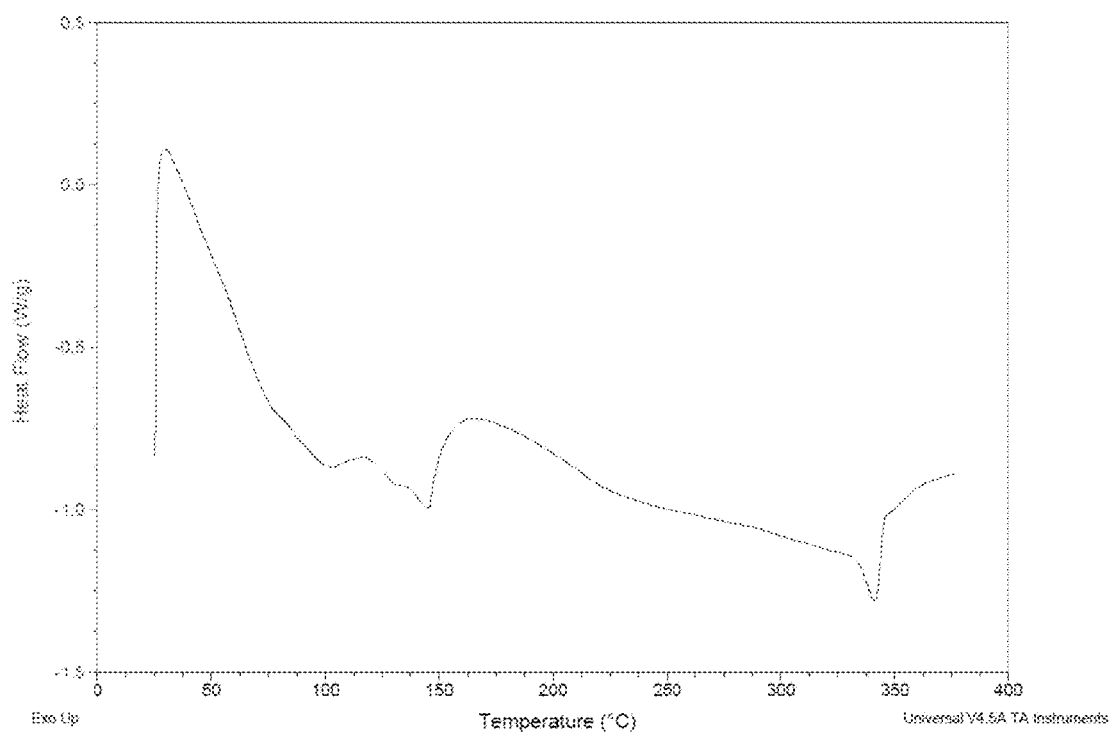
FIG. 22C shows a DSC thermogram of Compound 33 K salt Form B.

DSC was performed using a TA Q2000 DSC from TA Instrument. DSC was calibrated with Indium reference standard. Detailed parameters used are listed in Table 75. The DSC thermogram provided in FIG. 22C shows endothermic peaks at ~98, 146 and 342° C.

23. Compound 33 Potassium Salt Form C

A. Synthetic Procedure 402 mg Compound 33 Form A was dissolved into 60 mL acetone/water (v/v, 9:1) at 50° C. to get clear solution. And 74 mg KOH was dissolved into 3 mL water for KOH aqueous solution. 3 mL Compound 33 acetone/water solution was dispensed in a glass vial at room temperature and 0.1 mL KOH aqueous solution was added into it. Compound 33 K salt C was obtained via evaporation at room temperature.

B. X-Ray Powder Diffraction

XRPD was performed with a Panalytical X'Pert³ Powder XRPD on a Si zero-background holder. The 2θ position was calibrated against a Panalytical Si reference standard disc. The parameters used are listed in the Table 76. The XRPD diffractogram is shown in FIG. 23A and XRPD data are summarized in Table 77.

TABLE 76

Parameters for XRPD test of Compound 33 K salt Form C

| Parameters | Reflection Mode |
|---|---|
| X-Ray wavelength | Cu, Kα |
| | Kα1 (Å): 1.540598, Kα2 (Å): 1.544426 |
| | Kα2/Kα1 intensity ratio: 0.50 |
| X-Ray tube setting | 45 kV, 40 mA |
| Divergence slit | Fixed 1/8° |
| Scan mode | Continuous |
| Scan range (°2TH) | 3-40 |
| Scan step time [s] | 18.87 |
| Step size (°2TH) | 0.0131 |
| Test Time | 4 min 15 s |

TABLE 77

XRPD Peaks for Compound 33 K Salt Form C

| Peak # | Angle (Degrees 2-Theta ± 0.2) | Intensity % |
|---|---|---|
| 1 | 16.8 | 100.0 |
| 2 | 6.7 | 77.7 |
| 3 | 19.3 | 74.1 |
| 4 | 10.5 | 46.2 |

C. Thermogravimetric Analysis

Figure 23B:
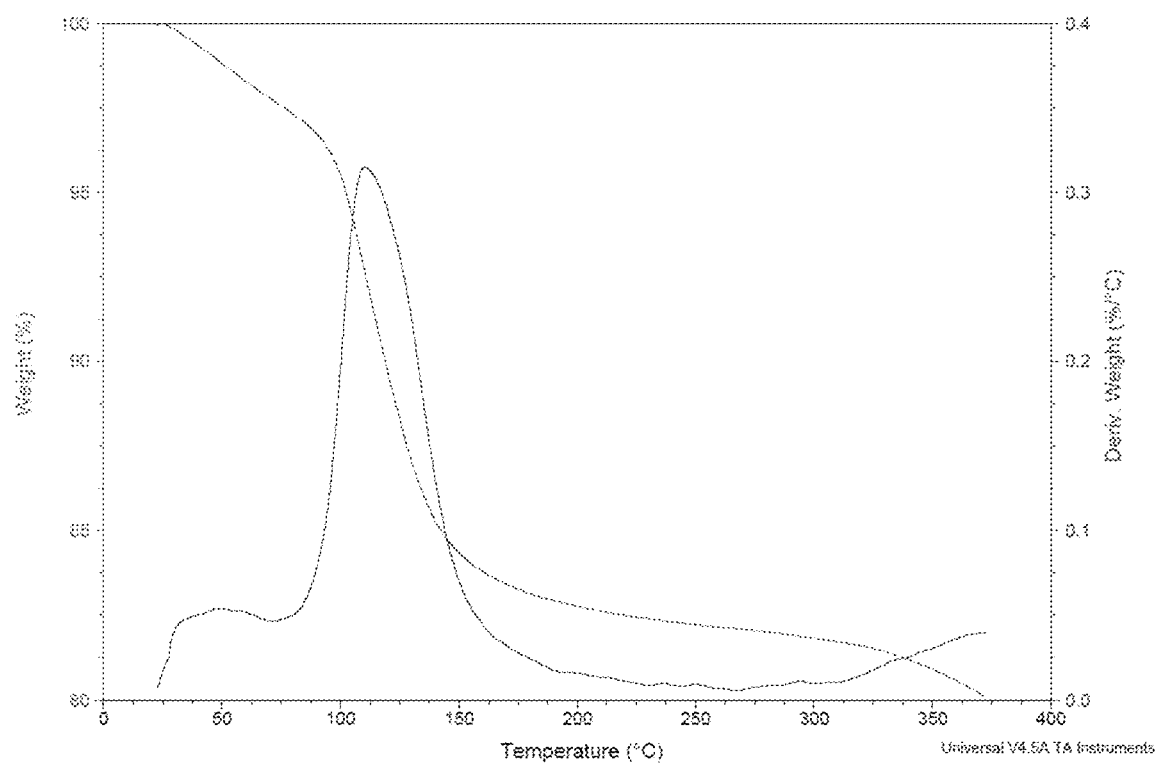
FIG. 23B shows a TGA thermogram of Compound 33 K salt Form C.

TGA data was collected using a TA Discovery 550 TGA from TA Instrument. TGA was calibrated using nickel reference standard. Detailed parameters used are listed in Table 78. The TGA thermogram provided in FIG. 23B shows ~17% weight loss from ambient temperature up to ~190° C.

TABLE 78

Parameters used for TGA and DSC analyses

| Parameters | TGA | DSC |
|---|---|---|
| Method | Ramp | Ramp |
| Sample pan | Platinum, open | Aluminum, crimped |
| Temperature | | RT-300° C. |
| Heating rate | | 10° C./min |
| Purge gas | | $N_2$ |

D. Differential Scanning Calorimetry Analysis

Figure 23C:
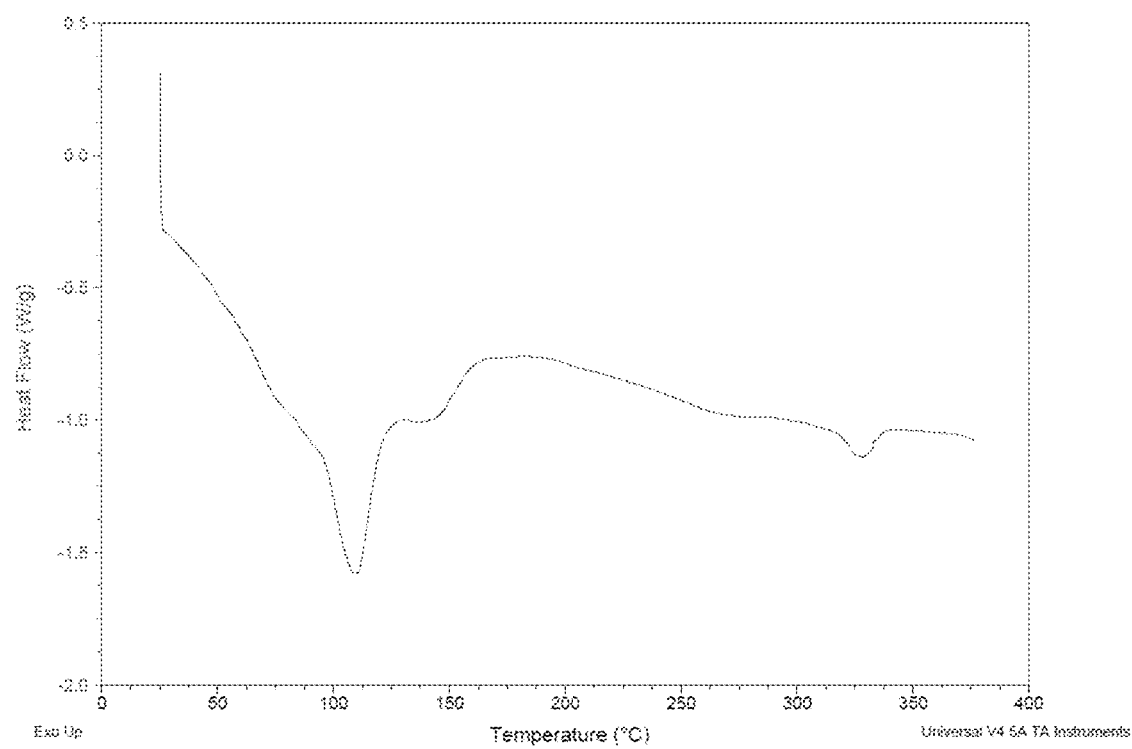
FIG. 23C shows a DSC thermogram of Compound 33 K salt Form C.

DSC was performed using a TA Q2000 DSC from TA Instrument. DSC was calibrated with Indium reference standard. Detailed parameters used are listed in Table 78. The DSC thermogram provided in FIG. 23C shows endothermic peaks at ~110, 145 and 328° C.

Example 4: Spray Dried Dispersions (SDD) of Amorphous Forms of Compound 33

Various spray dried dispersions (SDD) of amorphous forms of Compound 33 were prepared using either 50% or 80% drug loading (DL) and with different polymers (e.g., HPMCAS-H, PVPVA, HPMC E15), different organic solvent systems (e.g., DCM, EtOH, THF, Me-THF) and at different amounts of water.

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

For ssNMN analysis, Bruker-Biospin 400 MHz wide-bore spectrometer equipped with Bruker-Biospin 4 mm HFX probe was used. Samples were packed into 4 mm $ZrO_2$ rotors and spun under Magic Angle Spinning (MAS) condition with spinning speed typically set to 12.5 kHz. The proton relaxation time was measured using $^1$H MAS $T_1$ saturation recovery relaxation experiment in order to set up proper recycle delay of the $^{13}$C cross-polarization (CP) MAS experiment. The fluorine relaxation time was measured using $^{19}$F MAS $T_1$ saturation recovery relaxation experiment in order to set up proper recycle delay of the $^{19}$F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

1. Compound 33 50% DL Amorphous Spray Dried Dispersion [DCM/EtOH/10% Water with HPMCAS-H] (Composition Used in Clinical Suspension in Phase I)

A. Synthetic Procedure 125 g of Compound 33 was weighed into a bottle. 2875 g of 56.8/33.7/9.5 DCM/EtOH/Water was added. The bottle was capped and the contents were stirred for ~1 h at ambient temperature when a clear solution resulted. 125 g of hydroxypropylmethylcellulose acetate succinate H grade (HPMCAS-H) was added. The bottle was capped and the contents were stirred for ~2 hrs at ambient temperature when a clear solution resulted. This solution was then spray dried to make amorphous Compound 33.

B. X-Ray Powder Diffraction

Figure 24A:
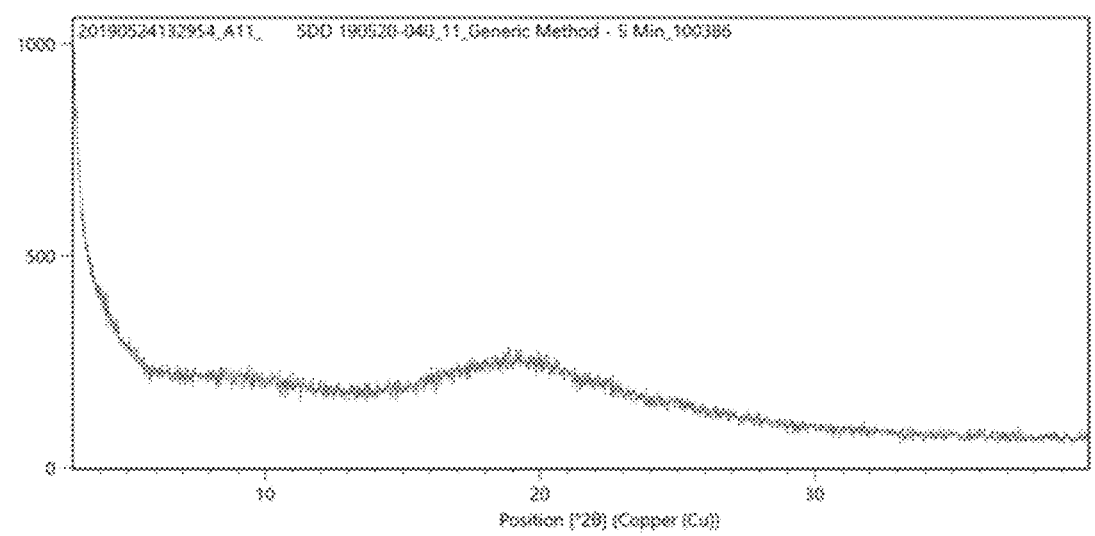
FIG. 24A shows an XRPD diffractogram of Compound 33 50% DL Amorphous Spray Dried Dispersion [DCM/EtOH/10% Water with HPMCAS-H].

X-ray powder diffraction (XRPD) spectra were recorded at room temperature in transmission mode using a PANalytical Empyrean system. The XRPD diffractogram is shown in FIG. 24A.

B. Differential Scanning Calorimetry

Figure 24B:
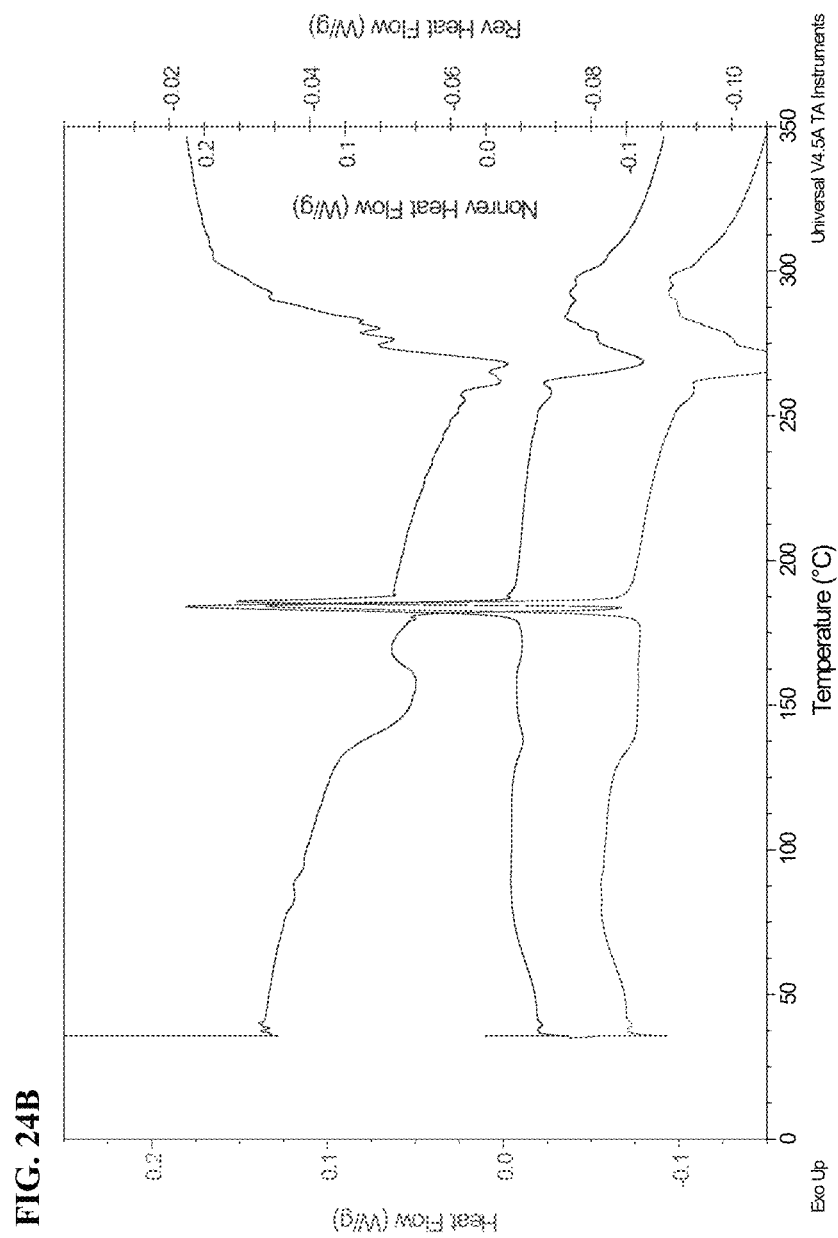
FIG. 24B shows a DSC thermogram of Compound 33 50% DL Amorphous Spray Dried Dispersion [DCM/EtOH/10% Water with HPMCAS-H].

Modulated Differential Scanning Calorimetry Analysis of Compound 33 amorphous form was carried out using the TA Instruments Discovery DSC. The thermogram as provided in FIG. 24B shows a glass transition at ~140° C., a recrystallization at ~175° C. and a melt endotherm at ~215° C.

C. Thermal Gravimetric Analysis

Figure 24C:
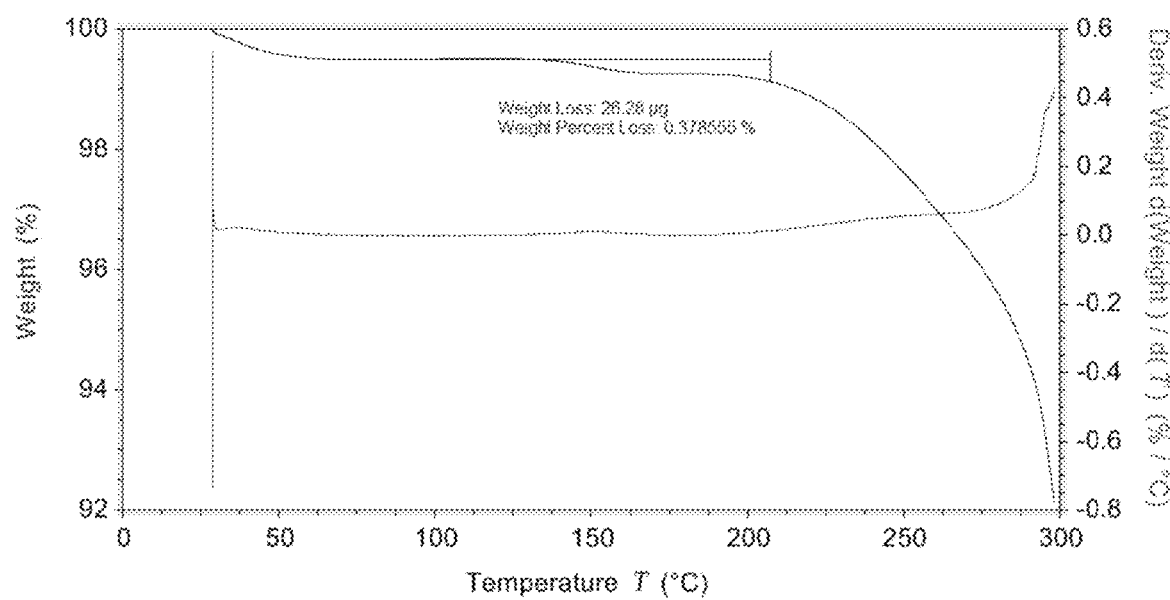
FIG. 24C shows a TGA thermogram of Compound 33 50% DL Amorphous Spray Dried Dispersion [DCM/EtOH/10% Water with HPMCAS-H].

Thermal Gravimetric Analysis of Compound 33 amorphous form was carried out using the TA Instruments Discovery TGA. The thermogram as provided in FIG. 24C shows a weight loss of ~0.37.

2. 50% DL Amorphous Spray Dried Dispersion [DCM/EtOH/10% Water with PVPVA]

A. Synthetic Procedure 1 g of Compound 33 was weighed into a bottle. 23 g of 56.8/33.7/9.5 DCM/EtOH/Water was added. The bottle was capped and the contents were stirred for ~1 h at ambient temperature when a clear solution resulted. 1 g of polyvinylpyrrolidone/vinyl acetate PVPVA was added. The bottle was capped and the contents were stirred for ~2 h at ambient temperature when a clear solution resulted. This solution was then spray dried to make amorphous Compound 33.

B. X-Ray Powder Diffraction

Figure 25A:
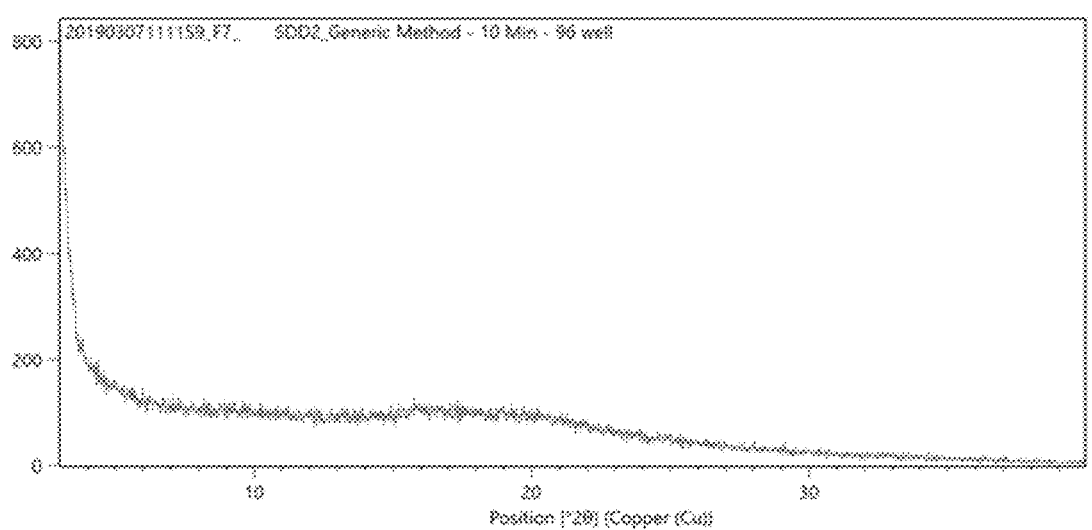
FIG. 25A shows an XRPD diffractogram of Compound 33 50% DL Amorphous Spray Dried Dispersion [DCM/EtOH/10% Water with PVPVA].

X-ray powder diffraction (XRPD) spectra were recorded at room temperature in transmission mode using a PANalytical Empyrean system. The XRPD diffractogram is shown in FIG. 25A.

C. Differential Scanning Calorimetry

Figure 25B:
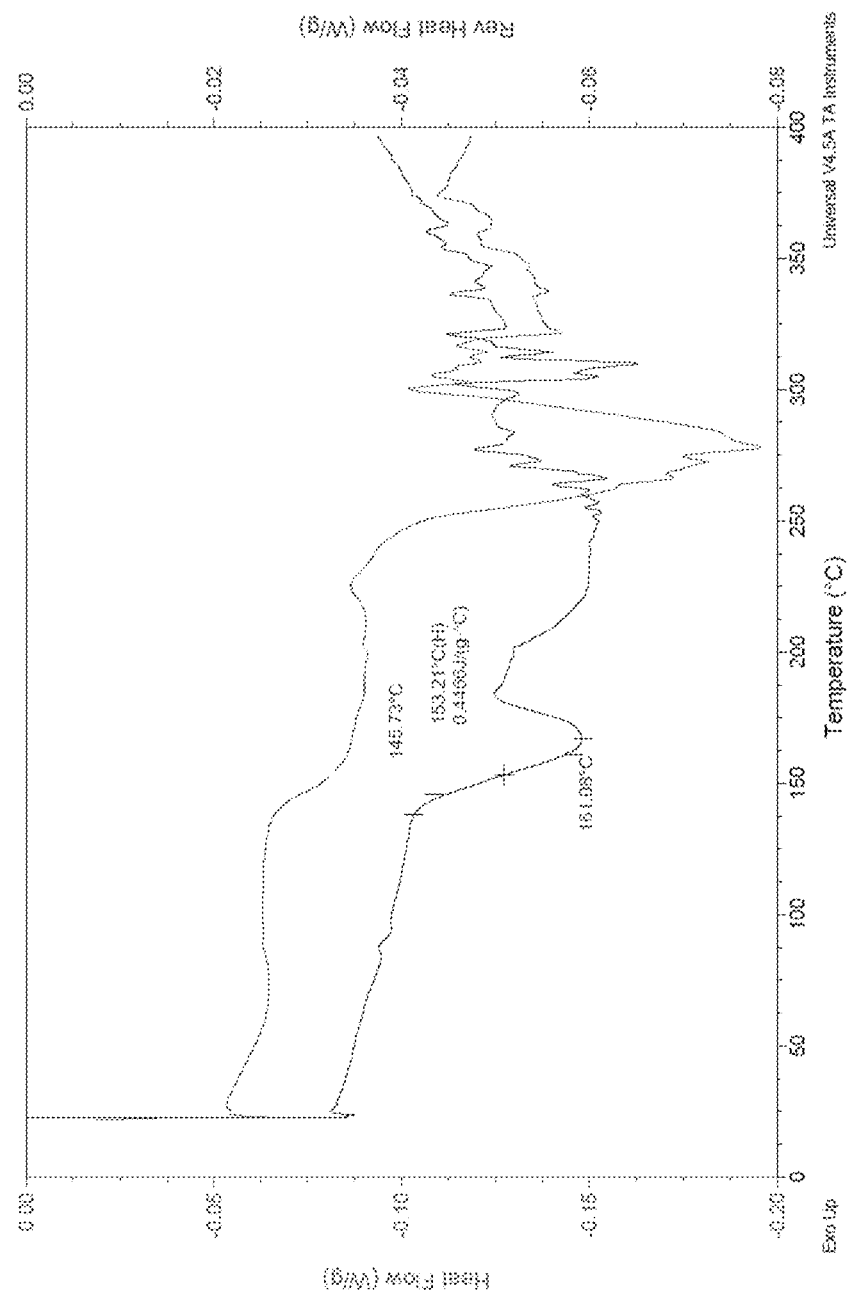
FIG. 25B shows a DSC thermogram of Compound 33 50% DL Amorphous Spray Dried Dispersion [DCM/EtOH/10% Water with PVPVA].

Modulated Differential Scanning Calorimetry Analysis of Compound 33 amorphous form was carried out using the TA Instruments Discovery DSC. The thermogram as provided in FIG. 25B shows a glass transition at ~153° C.

3. Compound 33 50% DL Amorphous Spray Dried Dispersion [DCM/EtOH/10% Water with HPMC E15]

A. Synthetic Procedure 1 g of Compound 33 was weighed into a bottle. 23 g of 56.8/33.7/9.5 DCM/EtOH/Water was added. The bottle was capped and the contents were stirred for ~1 h at ambient temperature when a clear solution resulted. 1 g of hydroxypropylmethylcellulose (HPMC) E15 was added. The bottle was capped and the contents were stirred for ~2 h at ambient temperature when a clear solution resulted. This solution was then spray dried to make amorphous Compound 33.

B. X-Ray Powder Diffraction

Figure 26A:
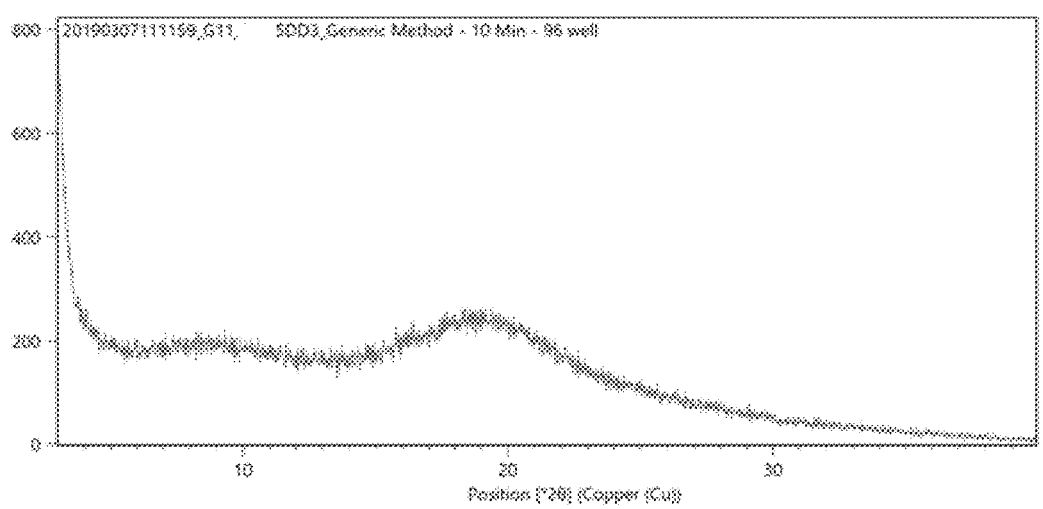
FIG. 26A shows an XRPD diffractogram of Compound 33 50% DL Amorphous Spray Dried Dispersion [DCM/EtOH/10% Water with HPMC E15].

X-ray powder diffraction (XRPD) spectra were recorded at room temperature in transmission mode using a PANalytical Empyrean system. The XRPD diffractogram is shown in FIG. 26A.

C. Differential Scanning Calorimetry

Figure 26B:
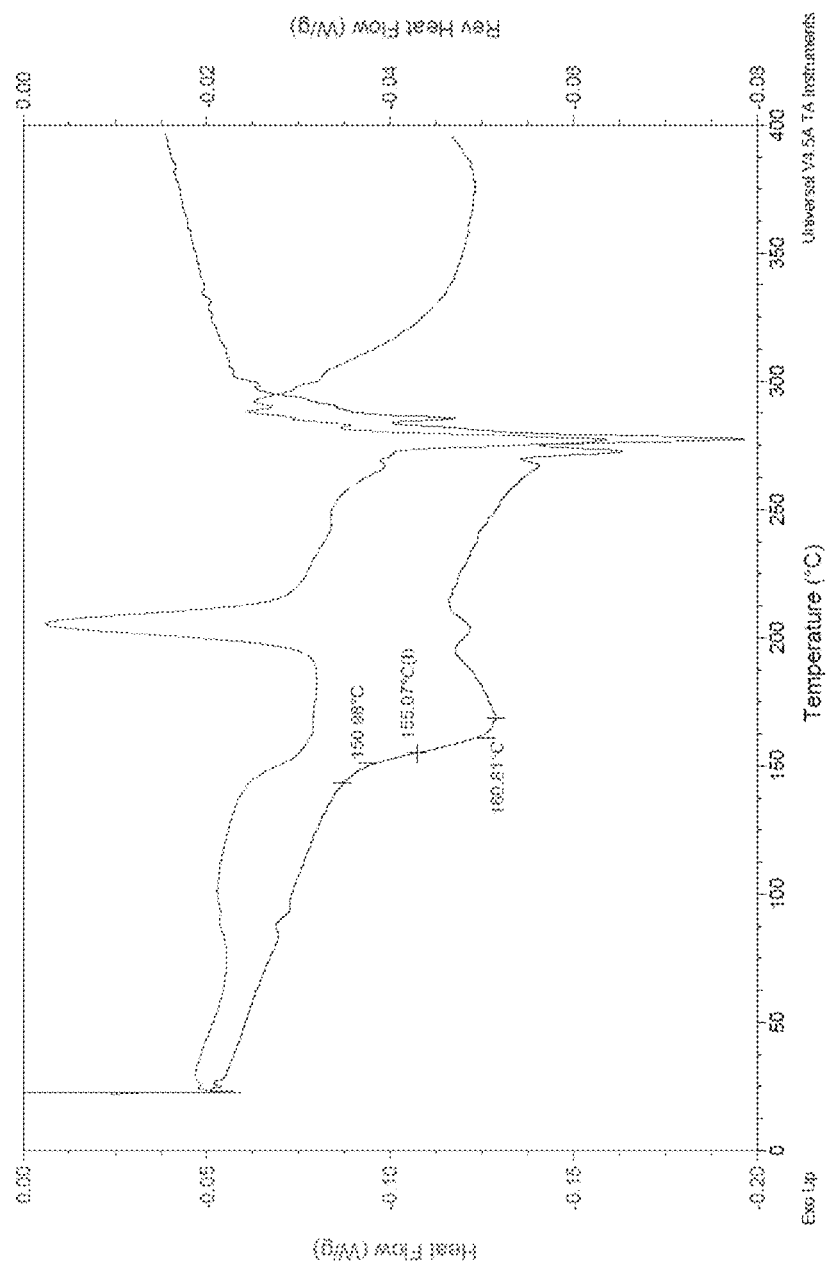
FIG. 26B shows a DSC thermogram of Compound 33 50% DL Amorphous Spray Dried Dispersion [DCM/EtOH/10% Water with HPMC E15].

Modulated Differential Scanning Calorimetry Analysis of Compound 33 amorphous form was carried out using the TA Instruments Discovery DSC. The thermogram as provided in FIG. 26B shows a glass transition at ~155° C.

4. Compound 33 50% DL Amorphous Spray Dried Dispersion [DCM/EtOH/1% Water with HPMCAS-H]

A. Synthetic Procedure 125 g of Compound 33 was weighed into a bottle. 4750 g of 70/29/1 DCM/EtOH/Water was added. The bottle was capped and the contents were stirred for ~1 h at ambient temperature when a clear solution resulted. 125 g of HPMCAS-H was added. The bottle was capped and the contents were stirred for ~2 h at ambient temperature when a clear solution resulted. This solution was then spray dried to make amorphous Compound 33.

B. X-Ray Powder Diffraction

Figure 27A:
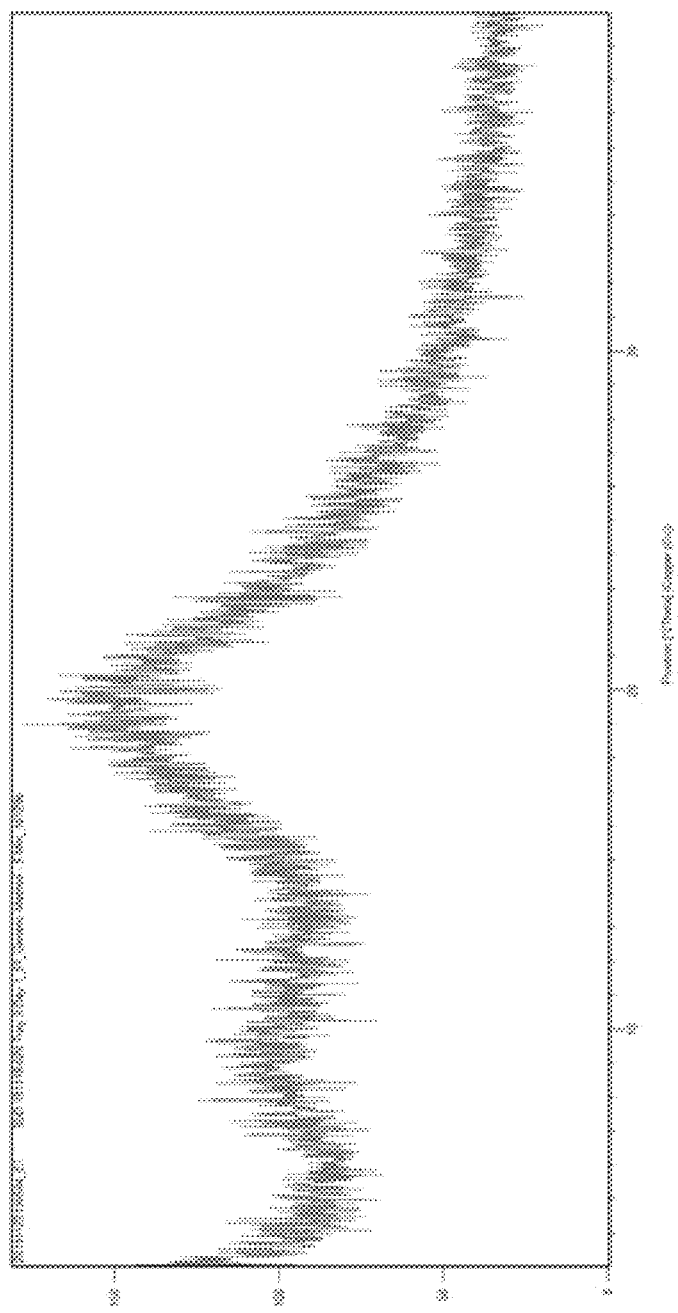
FIG. 27A shows an XRPD diffractogram of Compound 33 50% DL Amorphous Spray Dried Dispersion [DCM/EtOH/1% Water with HPMCAS-H].

X-ray powder diffraction (XRPD) spectra were recorded at room temperature in transmission mode using a PANalytical Empyrean system. The XRPD diffractogram is shown in FIG. 27A.

C. Differential Scanning Calorimetry

Figure 27B:
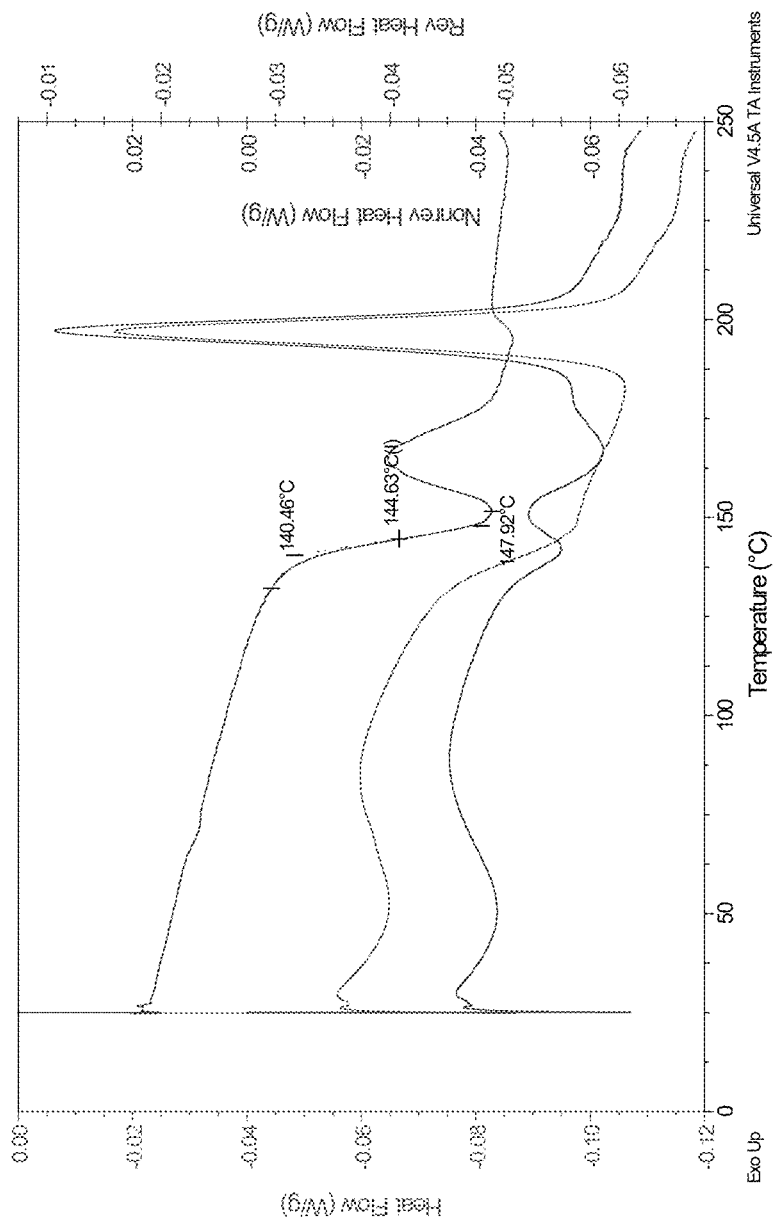
FIG. 27B shows a DSC thermogram of Compound 33 50% DL Amorphous Spray Dried Dispersion [DCM/EtOH/1% Water with HPMCAS-H].

Modulated Differential Scanning Calorimetry Analysis of Compound 33 amorphous form was carried out using the TA Instruments Discovery DSC. The thermogram as provided in FIG. 27B shows a glass transition at ~145° C. and a recrystallization at ~195° C.

D. Thermal Gravimetric Analysis

Figure 27C:
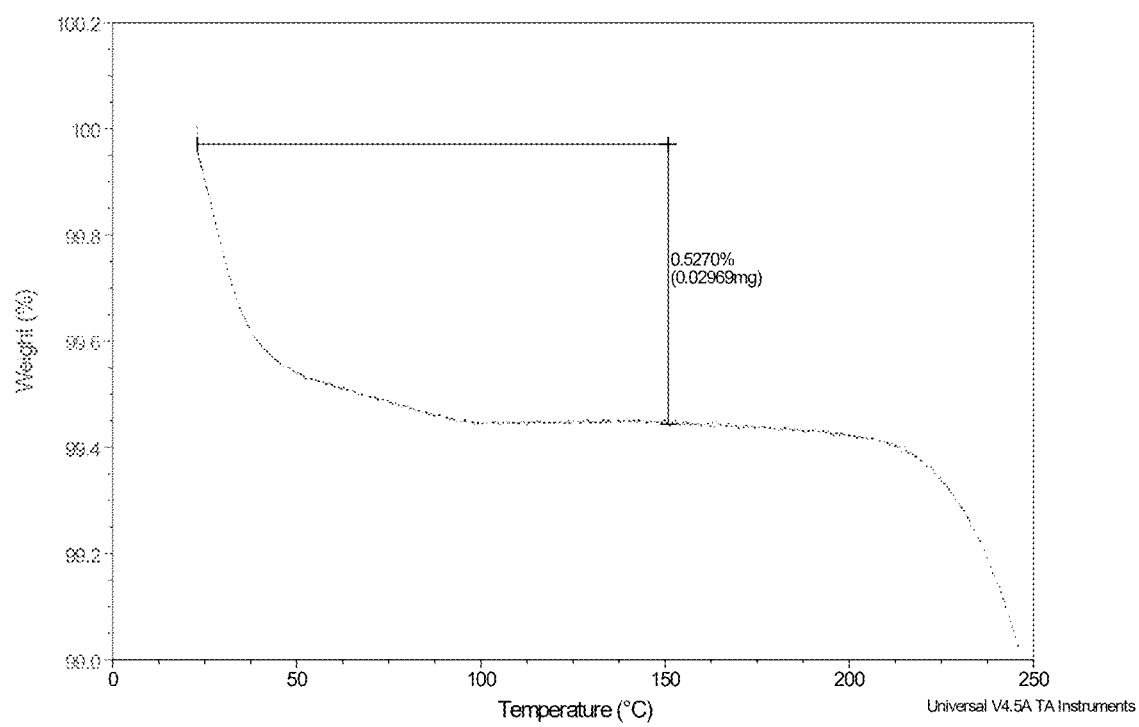
FIG. 27C shows a TGA thermogram of Compound 33 50% DL Amorphous Spray Dried Dispersion [DCM/EtOH/1% Water with HPMCAS-H].

Thermal Gravimetric Analysis of Compound 33 amorphous form was carried out using the TA Instruments Discovery TGA. The thermogram as provided in FIG. 27C shows a weight loss of ~0.53.

5. Compound 33 50% DL Amorphous Spray Dried Dispersion [DCM/EtOH/1% Water with HPMCAS-H]

A. Synthetic Procedure 360 g of Compound 33 was weighed into a bottle. 11.288 g of 65.98/27.17/0.87 DCM/EtOH/Water was added. The bottle was capped and the contents were stirred for ~1 h at ambient temperature when a clear solution resulted. 360 g of HPMCAS-H was added. The bottle was capped and the contents were stirred for ~2 h at ambient temperature when a clear solution resulted. This solution was then spray dried to make amorphous Compound 33.

B. X-Ray Powder Diffraction

Figure 28A:
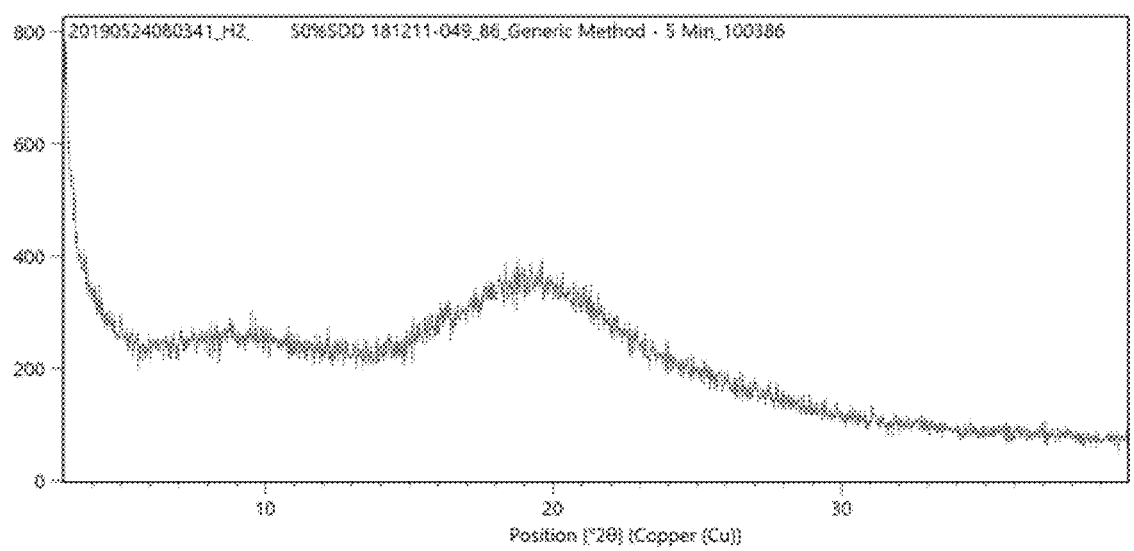
FIG. 28A shows an XRPD diffractogram of Compound 33 50% DL Amorphous Spray Dried Dispersion [DCM/EtOH/1% Water with HPMCAS-H].

X-ray powder diffraction (XRPD) spectra were recorded at room temperature in transmission mode using a PANalytical Empyrean system (ELN 190524-009). The XRPD diffractogram is shown in FIG. 28A.

C. Differential Scanning Calorimetry

Figure 28B:
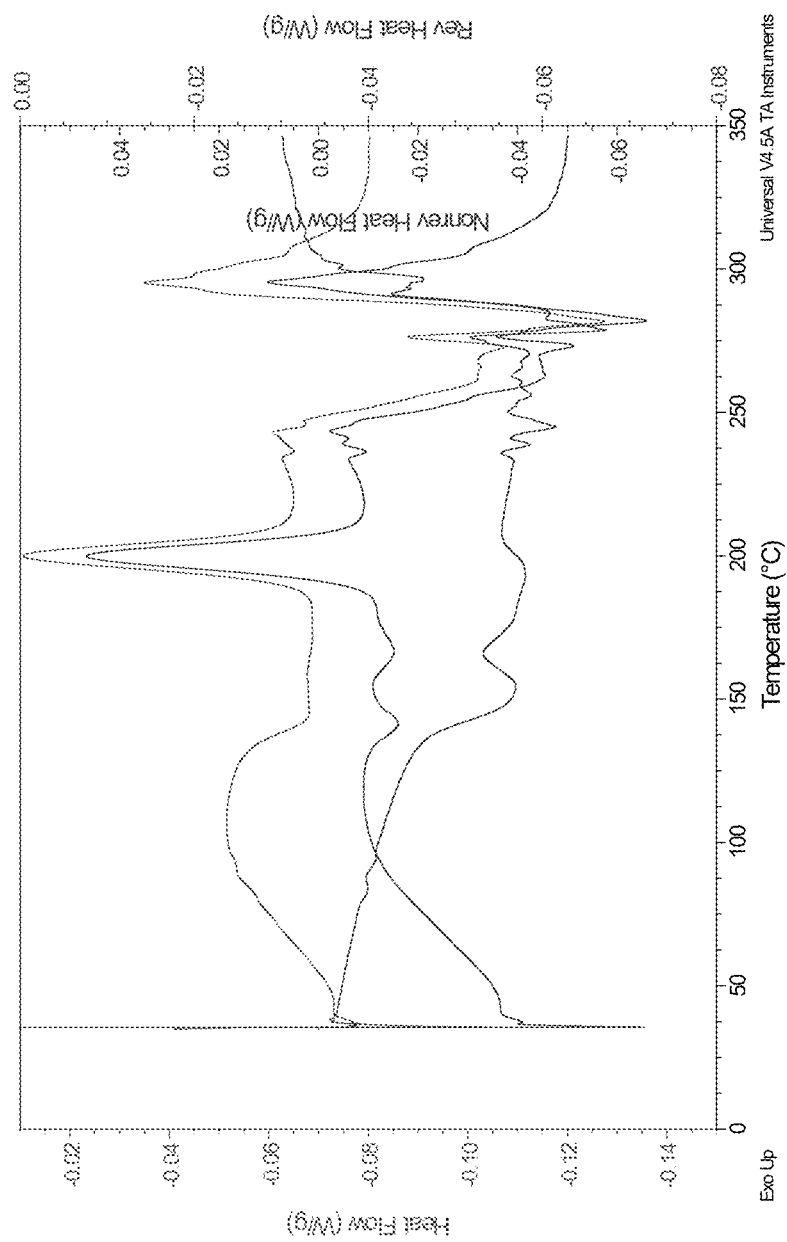
FIG. 28B shows a DSC thermogram of Compound 33 50% DL Amorphous Spray Dried Dispersion [DCM/EtOH/1% Water with HPMCAS-H].

Modulated Differential Scanning Calorimetry Analysis of Compound 33 amorphous form was carried out using the TA Instruments Discovery DSC. The thermogram as provided in FIG. 28B shows a glass transition at ~145° C., a recrystallization at ~200° C. and a melt endotherm at ~275° C.

D. Thermal Gravimetric Analysis

Figure 28C:
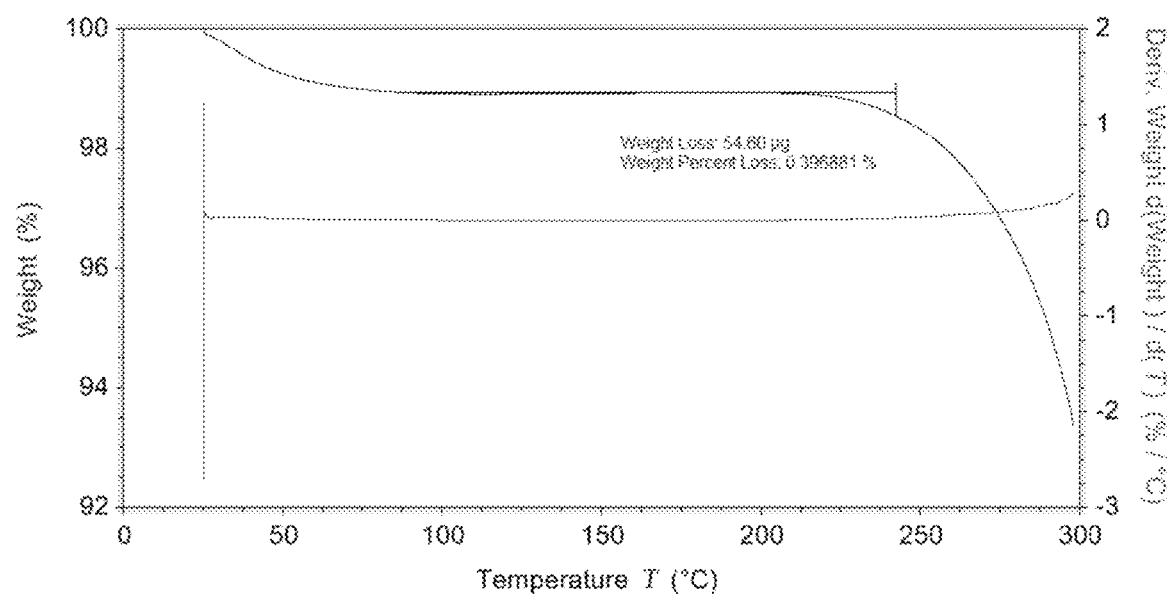
FIG. 28C shows a TGA thermogram of Compound 33 50% DL Amorphous Spray Dried Dispersion [DCM/EtOH/1% Water with HPMCAS-H].

Thermal Gravimetric Analysis of Compound 33 amorphous form was carried out using the TA Instruments Discovery TGA. The thermogram as provided in FIG. 28C shows a weight loss of ~0.40.

6. Compound 33 50% DL Amorphous Spray Dried Dispersion [DCM/EtOH/1% Water with HPMCAS-H])

A. Synthetic Procedure 47 g of Compound 33 was weighed into a bottle. 1450 mL of 59/40/1 DCM/EtOH/Water was added. The bottle was capped and the contents were stirred for ~1 h at ambient temperature when a clear solution resulted. 47 g of HPMCAS-H was added. The bottle was capped and the contents were stirred for ~2 h at ambient temperature when a clear solution resulted. This solution was then spray dried to make amorphous Compound 33.

B. X-Ray Powder Diffraction

Figure 29A:
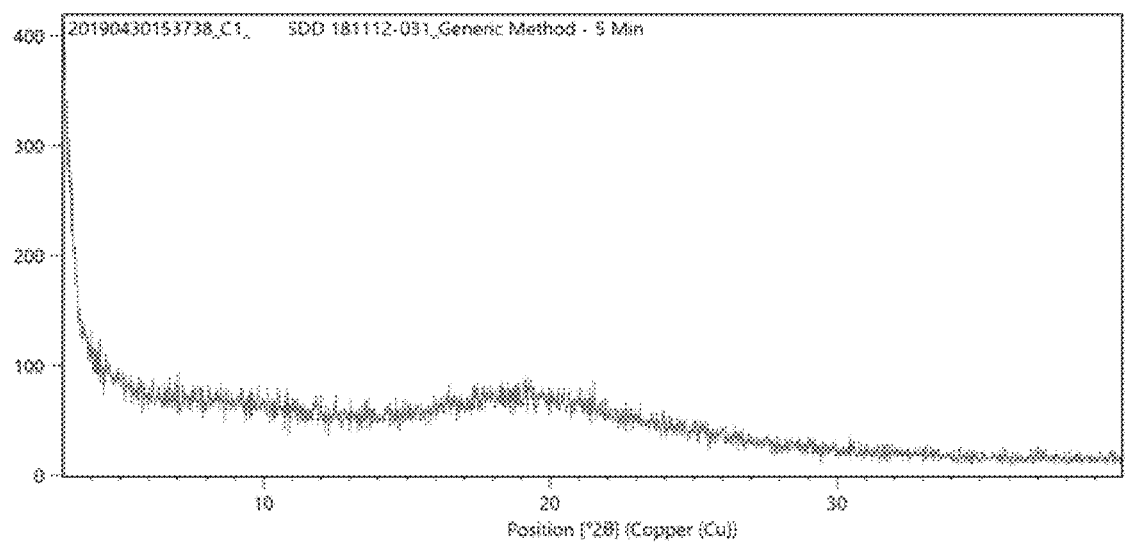
FIG. 29A shows an XRPD diffractogram of Compound 33 50% DL Amorphous Spray Dried Dispersion [DCM/EtOH/1% Water with HPMCAS-H].

X-ray powder diffraction (XRPD) spectra were recorded at room temperature in transmission mode using a PANalytical Empyrean system. The XRPD diffractogram is shown in FIG. 29A.

C. Differential Scanning Calorimetry

Figure 29B:
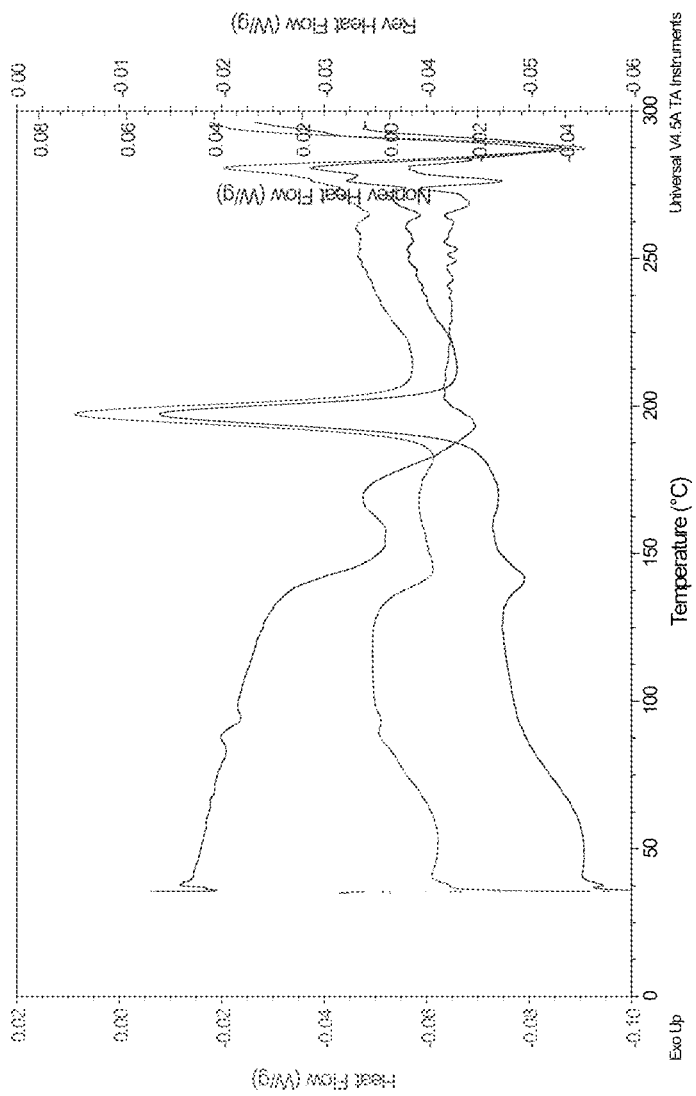
FIG. 29B shows a DSC thermogram of Compound 33 50% DL Amorphous Spray Dried Dispersion [DCM/EtOH/1% Water with HPMCAS-H].

Modulated Differential Scanning Calorimetry Analysis of Compound 33 amorphous form was carried out using the TA Instruments Discovery DSC. The thermogram as provided in FIG. 29B shows a glass transition at ~144° C. and a recrystallization at ~213° C.

7. Compound 33 50% DL Amorphous Spray Dried Dispersion [THF/Water with HPMCAS-H]

A. Synthetic Procedure 16 g of 50% DL Compound 33 (with HPMCAS-H) was weighed into a bottle. 144 g of 90/10 THF/Water was added. The bottle was capped and the contents were stirred for ~2 h at ambient temperature when a clear solution resulted. This solution was then spray dried to make amorphous Compound 33.

B. X-Ray Powder Diffraction

Figure 30A:
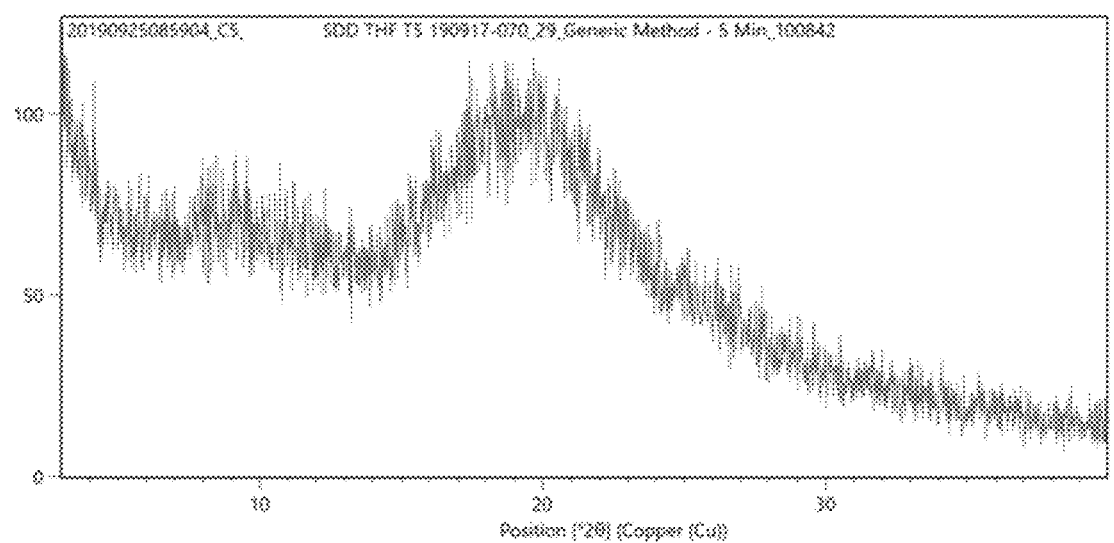
FIG. 30A shows an XRPD diffractogram of Compound 33 50% DL Amorphous Spray Dried Dispersion [THF/Water with HPMCAS-H].

X-ray powder diffraction (XRPD) spectra were recorded at room temperature in transmission mode using a PANalytical Empyrean system. The XRPD diffractogram is shown in FIG. 30A.

C. Differential Scanning Calorimetry

Figure 30B:
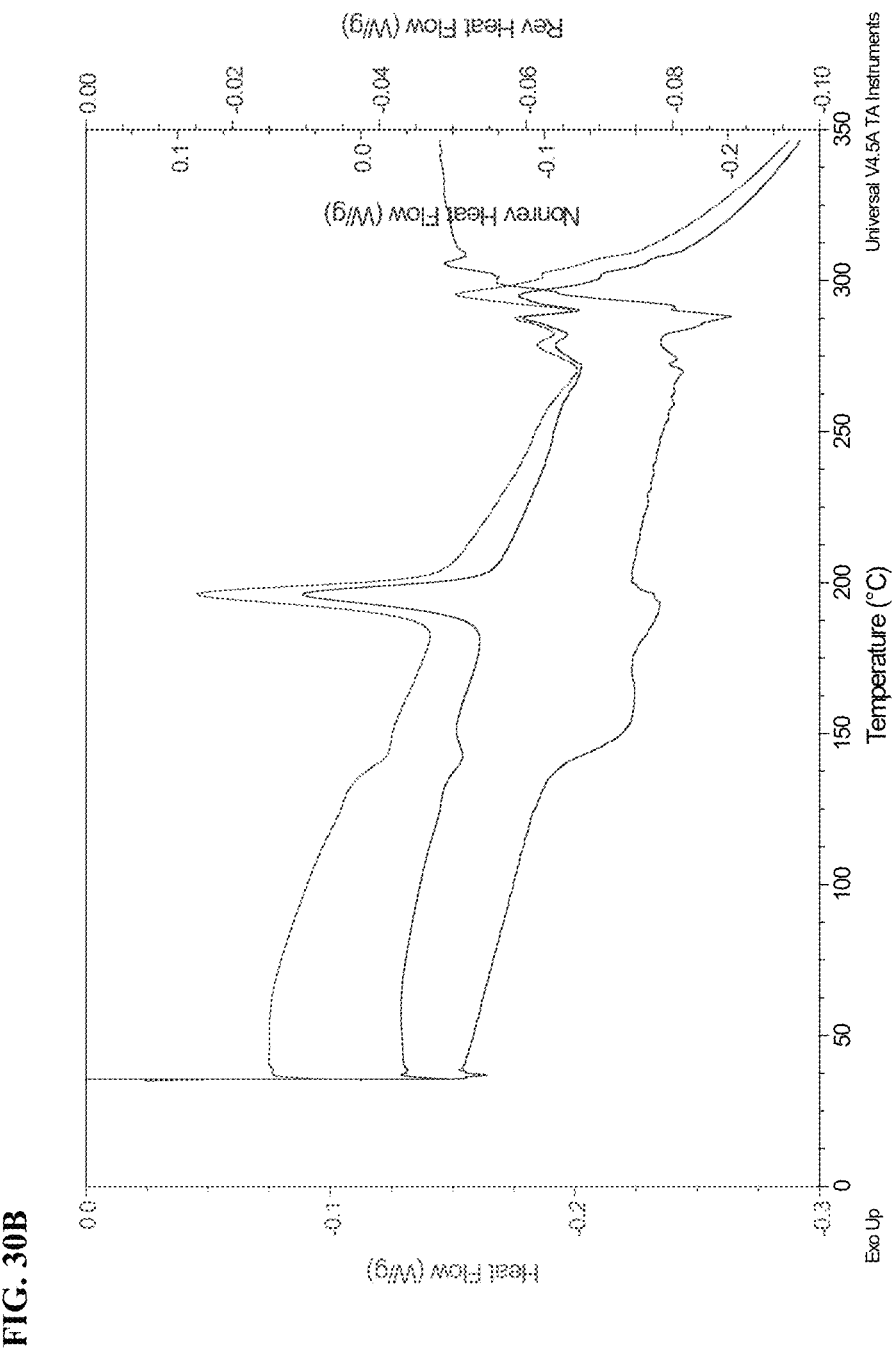
FIG. 30B shows a DSC thermogram of Compound 33 50% DL Amorphous Spray Dried Dispersion [THF/Water with HPMCAS-H].

Modulated Differential Scanning Calorimetry Analysis of Compound 33 amorphous form was carried out using the TA Instruments Discovery DSC. The thermogram as provided in FIG. 30B shows a glass transition at ~140° C. and a recrystallization at ~195° C.

D. Thermal Gravimetric Analysis

Figure 30C:
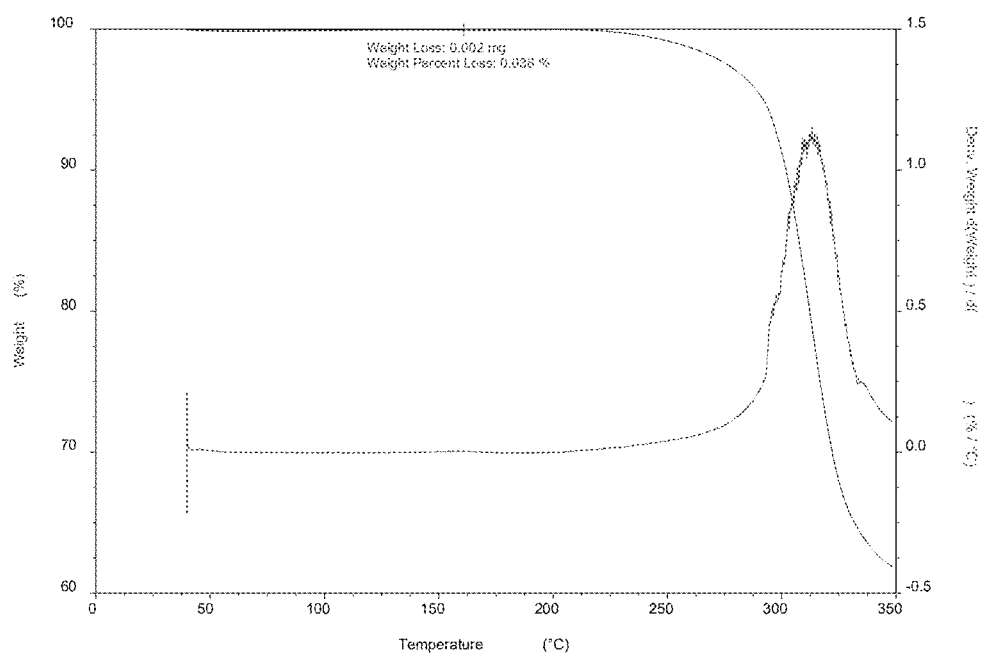
FIG. 30C shows a TGA thermogram of Compound 33 50% DL Amorphous Spray Dried Dispersion [THF/Water with HPMCAS-H].
Figure 30D:
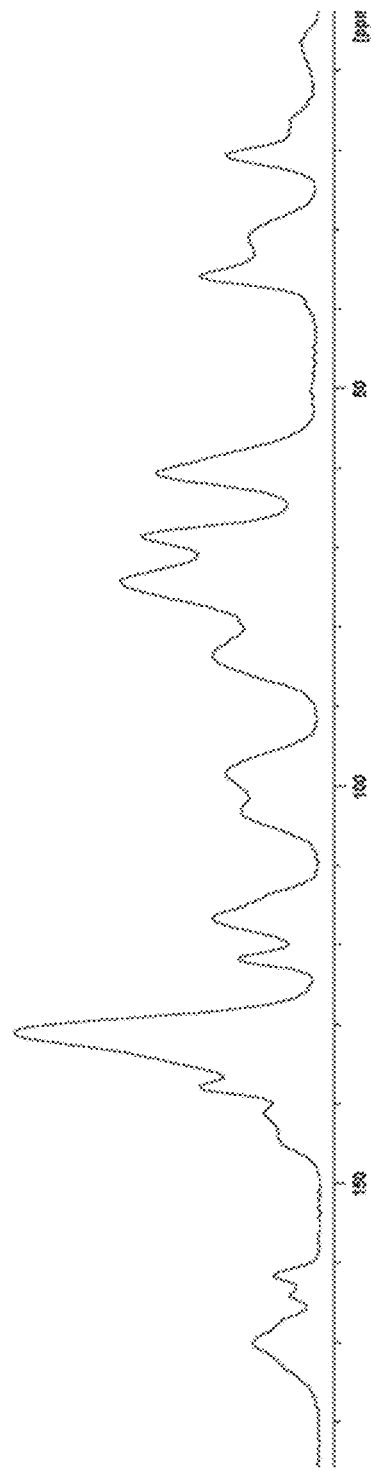
FIG. 30D shows a solid state $^{13}$C NMR spectrum of a spray dried dispersion of 50% Compound 33 with HPMCAS.

Thermal Gravimetric Analysis of Compound 33 amorphous form was carried out using the TA Instruments Discovery TGA. The thermogram as provided in FIG. 30C shows a weight loss of ~0.40.

E. Solid State NMR Analysis $^{13}$C ssNMR data for a spray dried dispersion of 50% DL Compound 33 with HPMCAS-from THF is provided in FIG. 30D and summarized in Table 79A below.

TABLE 79A 13C ssNMR for SDD of 50% Compound 33/HPCMAS

| Peak # | Chem Shift [ppm] | Intensity [rel] |
|---|---|---|
| 1 | 173.1 | 11.4 |
| 2 | 170.0 | 22.2 |
| 3 | 167.2 | 12.6 |
| 4 | 163.9 | 9.8 |
| 5 | 161.5 | 15.1 |
| 6 | 144.4 | 13.1 |
| 7 | 141.2 | 18.3 |
| 8 | 137.8 | 39.3 |
| 9 | 130.9 | 100.0 |
| 10 | 121.7 | 26.6 |
| 11 | 116.5 | 34.9 |
| 12 | 103.0 | 25.7 |
| 13 | 98.4 | 30.6 |
| 14 | 83.5 | 35.2 |
| 15 | 74.1 | 65.1 |
| 16 | 68.5 | 58.2 |
| 17 | 60.5 | 53.4 |
| 18 | 35.8 | 39.2 |
| 19 | 30.7 | 23.3 |
| 20 | 20.6 | 30.8 |
| 21 | 16.5 | 9.6 |

Figure 30E:
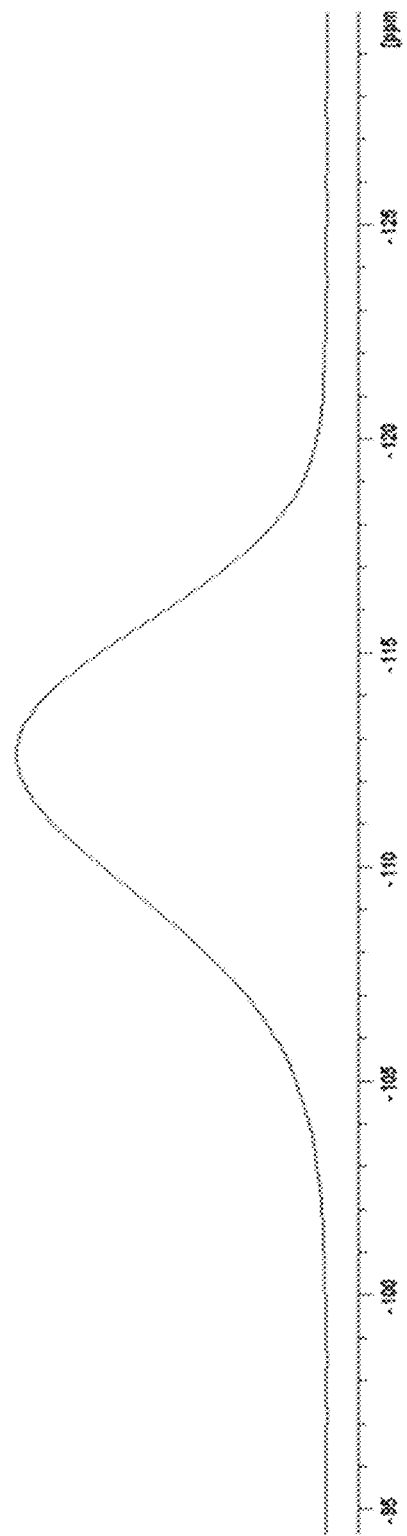
FIG. 30E shows a solid state $^{19}$F NMR spectrum of a spray dried dispersion of 50% Compound 33 with HPMCAS.

$^{19}$F ssNMR data for a spray dried dispersion of 50% DL Compound 33 with HPCMAS-from THF is provided in FIG. 30E and summarized in Table 79B.

| Peak # | Chem Shift [ppm] | Intensity [rel] |
|---|---|---|
| 1 | −112.6 | 12.5 |

Figure 31A:
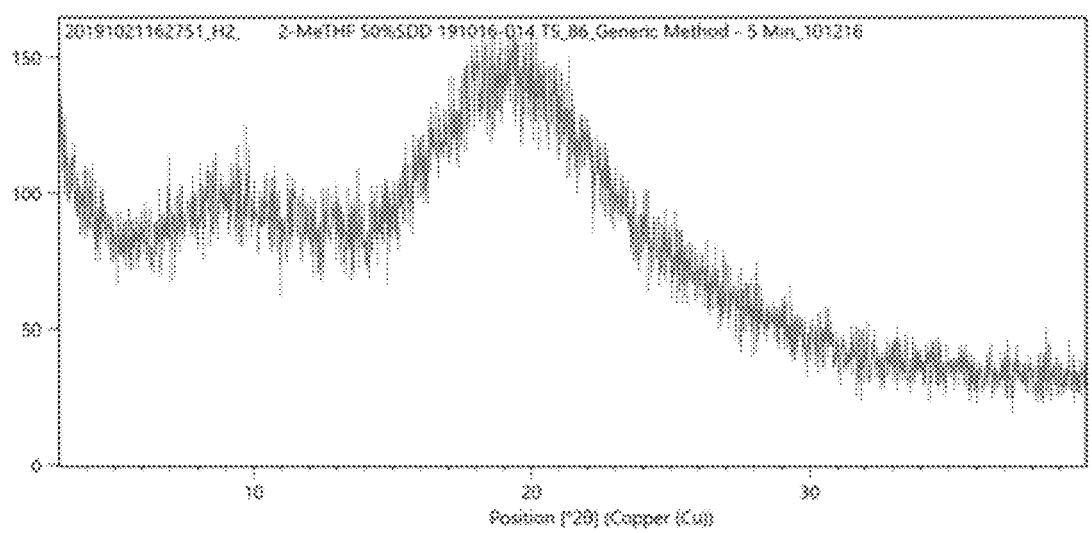
FIG. 31A shows an XRPD diffractogram of Compound 33 50% DL Amorphous Spray Dried Dispersion [2-MeTHF/EtOH/Water with HPMCAS-H].
Figure 31B:
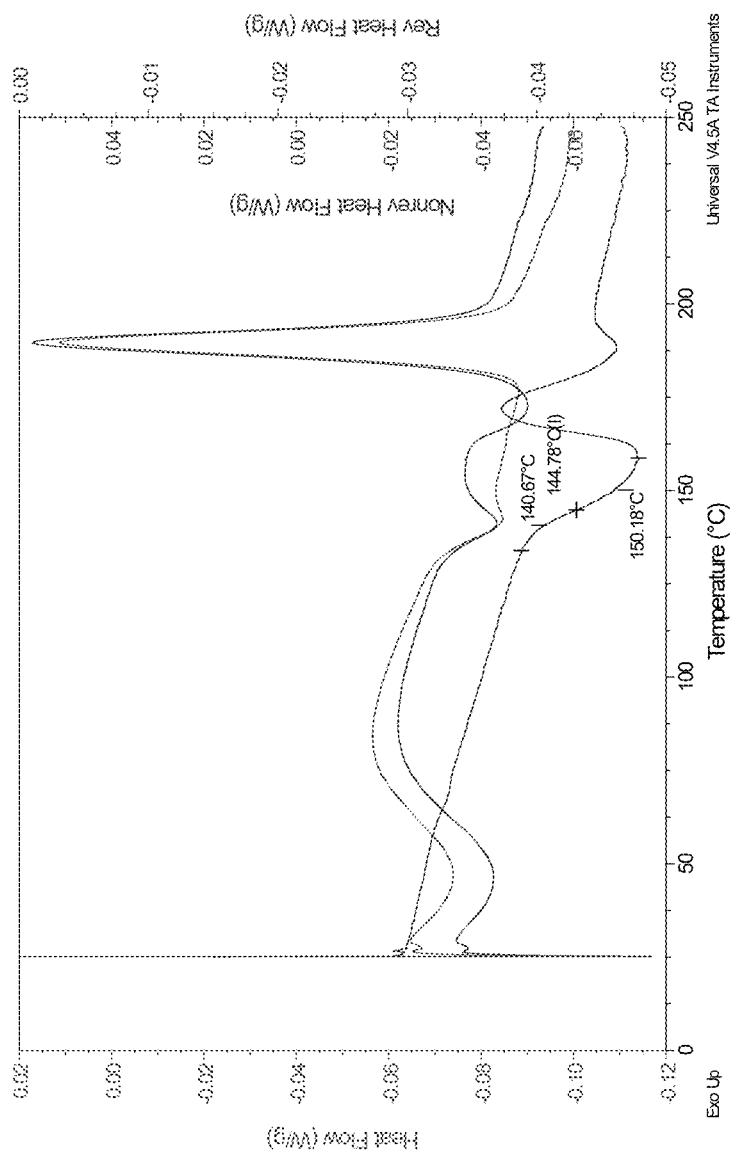
FIG. 31B shows a DSC thermogram of Compound 33 50% DL Amorphous Spray Dried Dispersion [2-MeTHF/EtOH/Water with HPMCAS-H].
Figure 31C:
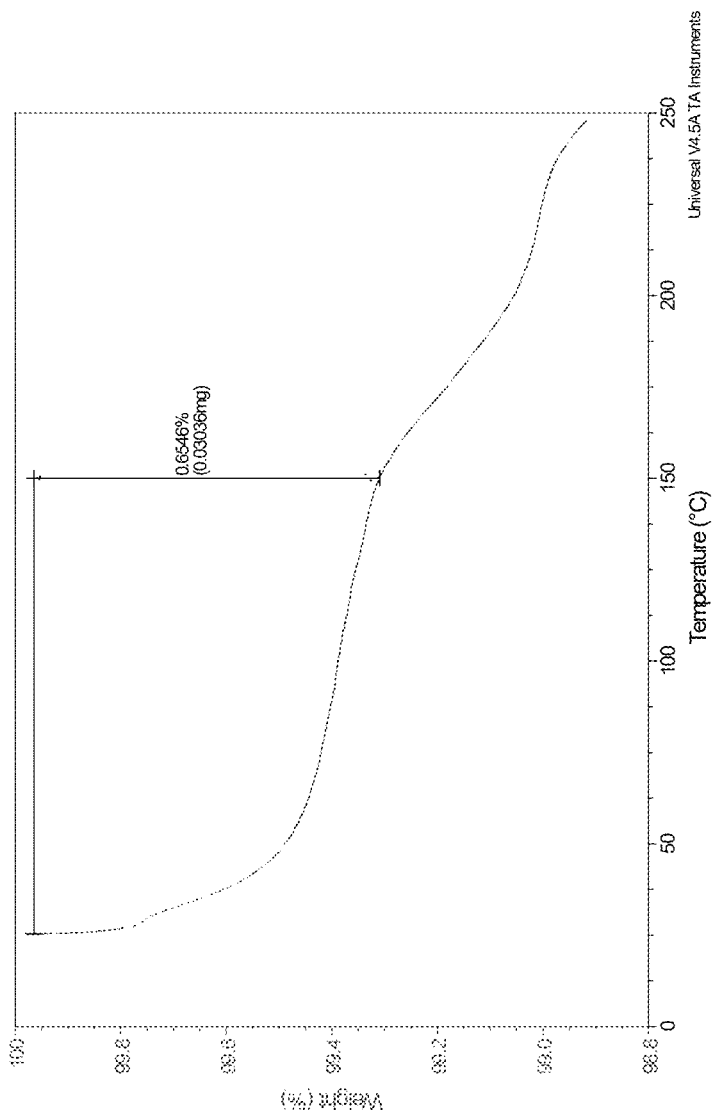
FIG. 31C shows a TGA thermogram of Compound 33 50% DL Amorphous Spray Dried Dispersion [2-MeTHF/EtOH/Water with HPMCAS-H].

8. Compound 33 50% DL Amorphous Spray Dried Dispersion [2-MeTHF/EtOH/Water with HPMCAS-H]
A. Synthetic Procedure 6 g of Compound 33 was weighed into a bottle. 108 g of 80/13/7 2-MeTHF/EtOH/Water was added. The bottle was capped and the contents were stirred for ~1 h at ambient temperature when a clear solution resulted. 6 g of HPMCAS-H was added. The bottle was capped and the contents were stirred for ~2 h at ambient temperature when a clear solution resulted. This solution was then spray dried to make amorphous Compound 33.
B. X-Ray Powder Diffraction X-ray powder diffraction (XRPD) spectra were recorded at room temperature in transmission mode using a PANalytical Empyrean system The XRPD diffractogram is shown in FIG. 31A.
C. Differential Scanning Calorimetry Modulated Differential Scanning Calorimetry Analysis of Compound 33 amorphous form was carried out using the TA Instruments Discovery DSC. The thermogram as provided in FIG. 31B shows a glass transition at ~145° C. and a recrystallization at ~180° C.
D. Thermal Gravimetric Analysis Thermal Gravimetric Analysis of Compound 33 amorphous form was carried out using the TA Instruments Discovery TGA. The thermogram as provided in FIG. 31C shows a weight loss of ~0.65.

Figure 32A:
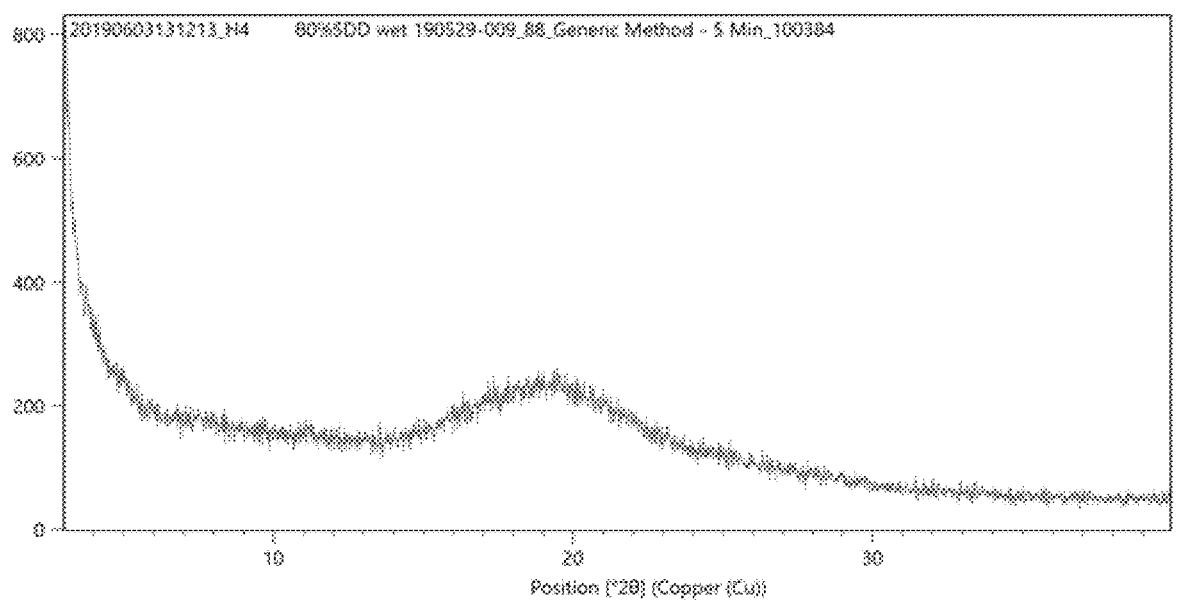
FIG. 32A shows an XRPD diffractogram of Compound 33 80% DL Amorphous Spray Dried Dispersion [DCM/EtOH/Water with HPMCAS-H].
Figure 32B:
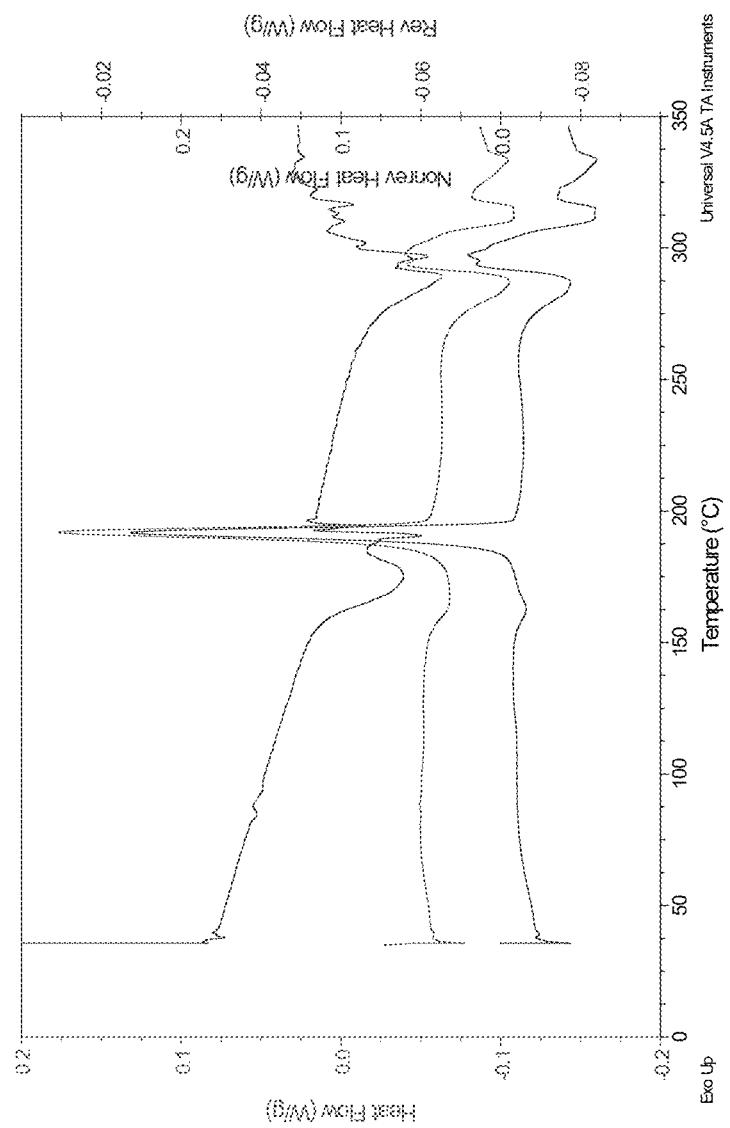
FIG. 32B shows a DSC thermogram of Compound 33 80% DL Amorphous Spray Dried Dispersion [DCM/EtOH/Water with HPMCAS-H].
Figure 32C:
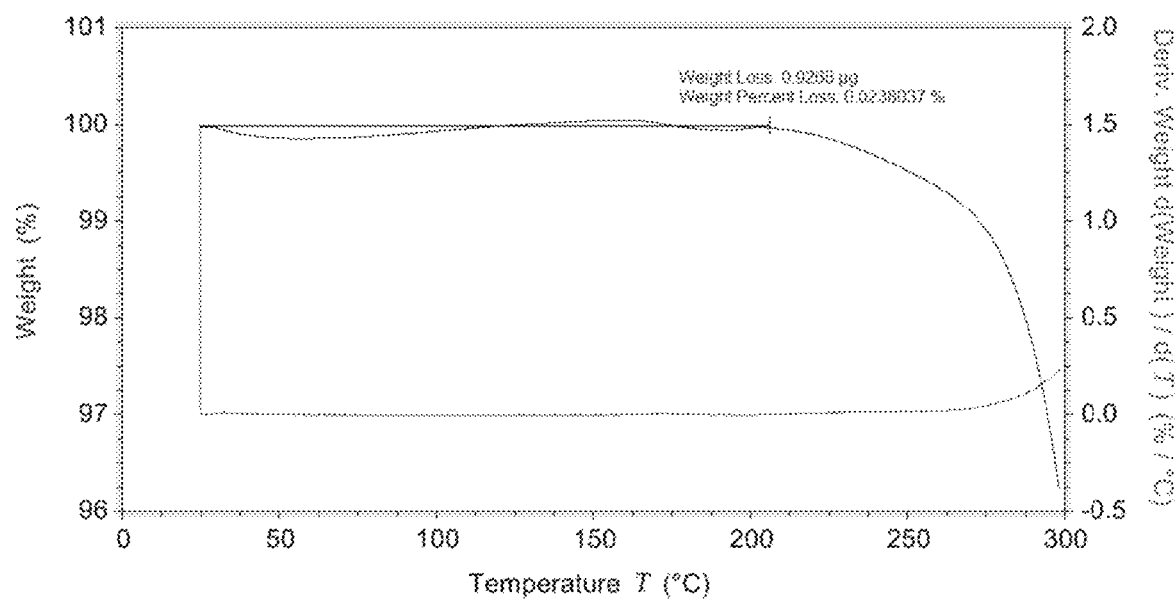
FIG. 32C shows a TGA thermogram of Compound 33 80% DL Amorphous Spray Dried Dispersion [DCM/EtOH/Water with HPMCAS-H].

9. Compound 33 80% DL Amorphous Spray Dried Dispersion [DCM/EtOH/Water with HPMCAS-H]
A. Synthetic Procedure 160 g of Compound 33 was weighed into a bottle. 3800 g of 56.8/33.7/9.5 DCM/EtOH/Water was added. The bottle was capped and the contents were stirred for ~1 h at ambient temperature when a clear solution resulted. 40 g of HPMCAS-H was added. The bottle was capped and the contents were stirred for ~2 h at ambient temperature when a clear solution resulted. This solution was then spray dried to make amorphous Compound 33.
B. X-Ray Powder Diffraction X-ray powder diffraction (XRPD) spectra were recorded at room temperature in transmission mode using a PANalytical Empyrean system. The XRPD diffractogram is shown in FIG. 32A.
C. Differential Scanning Calorimetry Modulated Differential Scanning Calorimetry Analysis of Compound 33 amorphous form was carried out using the TA Instruments Discovery DSC. The thermogram as provided in FIG. 32B shows a glass transition at ~164° C. and a recrystallization at ~180° C.
D. Thermal Gravimetric Analysis Thermal Gravimetric Analysis of Compound 33 amorphous form was carried out using the TA Instruments Discovery TGA. The thermogram as provided in FIG. 32C shows a weight loss of ~0.02.

Figure 33A:
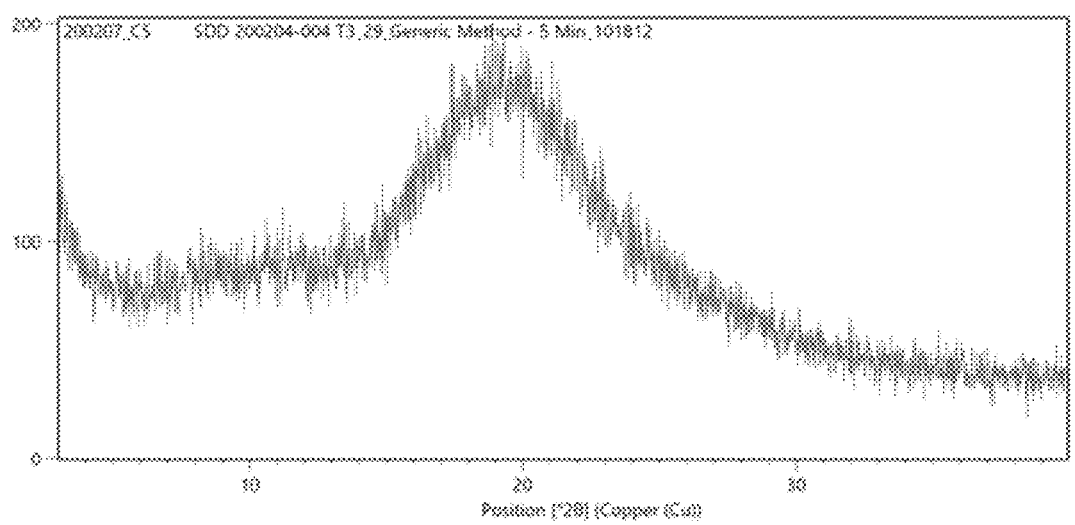
FIG. 33A shows an XRPD diffractogram of Compound 33 80% DL Amorphous Spray Dried Dispersion [DCM/EtOH/Water with HPMCAS-H, starting with THF Solvate DS].
Figure 33B:
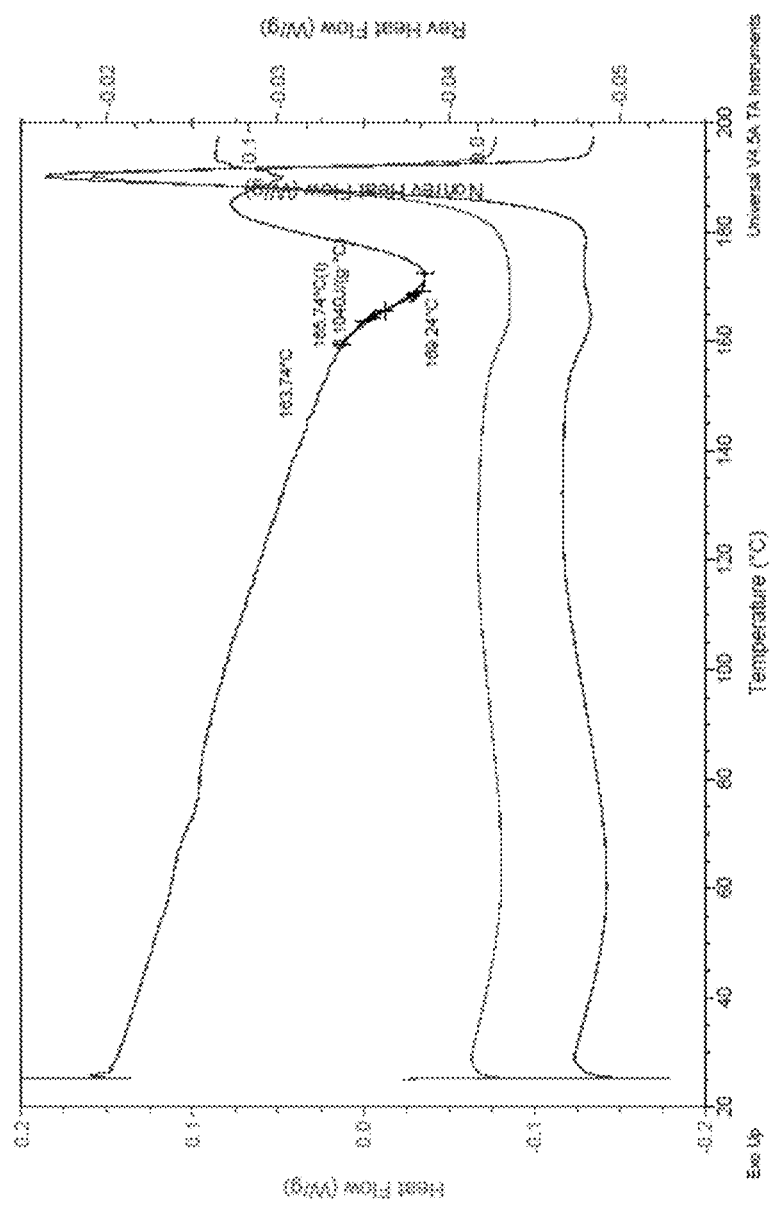
FIG. 33B shows a DSC thermogram of Compound 33 80% DL Amorphous Spray Dried Dispersion [DCM/EtOH/Water with HPMCAS-H, starting with THF Solvate DS].

11. Compound 33 80% DL Amorphous Spray Dried Dispersion [DCM/EtOH/Water with HPMCAS-H, starting with THF Solvate DS]
A. Synthetic Procedure 7.9 g of Compound 33 THF Solvate was weighed into a bottle. 500 g of 56.8/33.7/9.5 DCM/EtOH/Water was added. The bottle was capped and the contents were stirred for ~1 h at ambient temperature when a clear solution resulted. 2.0 g of HPMCAS-H was added. The bottle was capped and the contents were stirred for ~2 h at ambient temperature when a clear solution resulted. This solution was then spray dried to make amorphous Compound 33.
B. X-Ray Powder Diffraction X-ray powder diffraction (XRPD) spectra were recorded at room temperature in transmission mode using a PANalytical Empyrean system. The XRPD diffractogram is shown in FIG. 33A.
C. Differential Scanning Calorimetry Modulated Differential Scanning Calorimetry Analysis of Compound 33 amorphous form was carried out using the TA Instruments Discovery DSC. The thermogram provided in FIG. 33B shows a glass transition at −165° C.

Figure 34A:
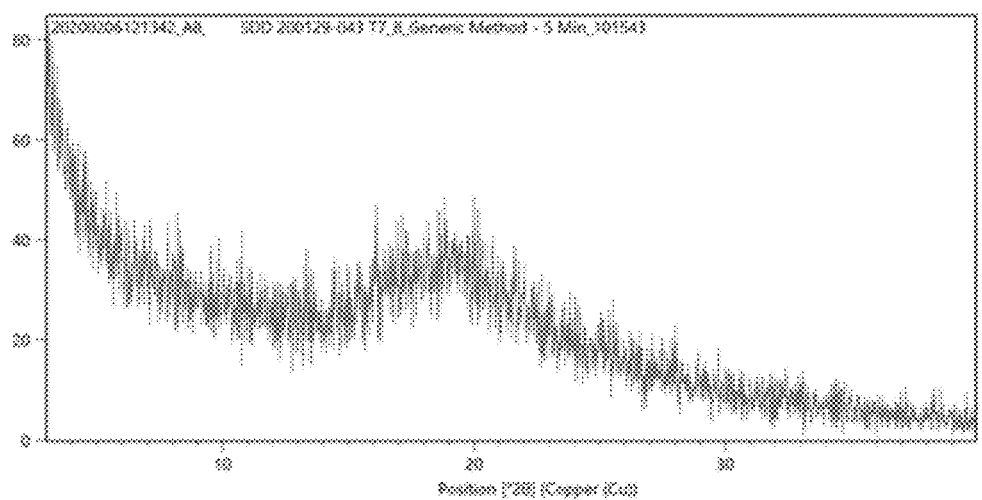
FIG. 34A shows an XRPD diffractogram of Compound 33 80% DL Amorphous Spray Dried Dispersion [THF/Water with HPMCAS-H].
Figure 34B:
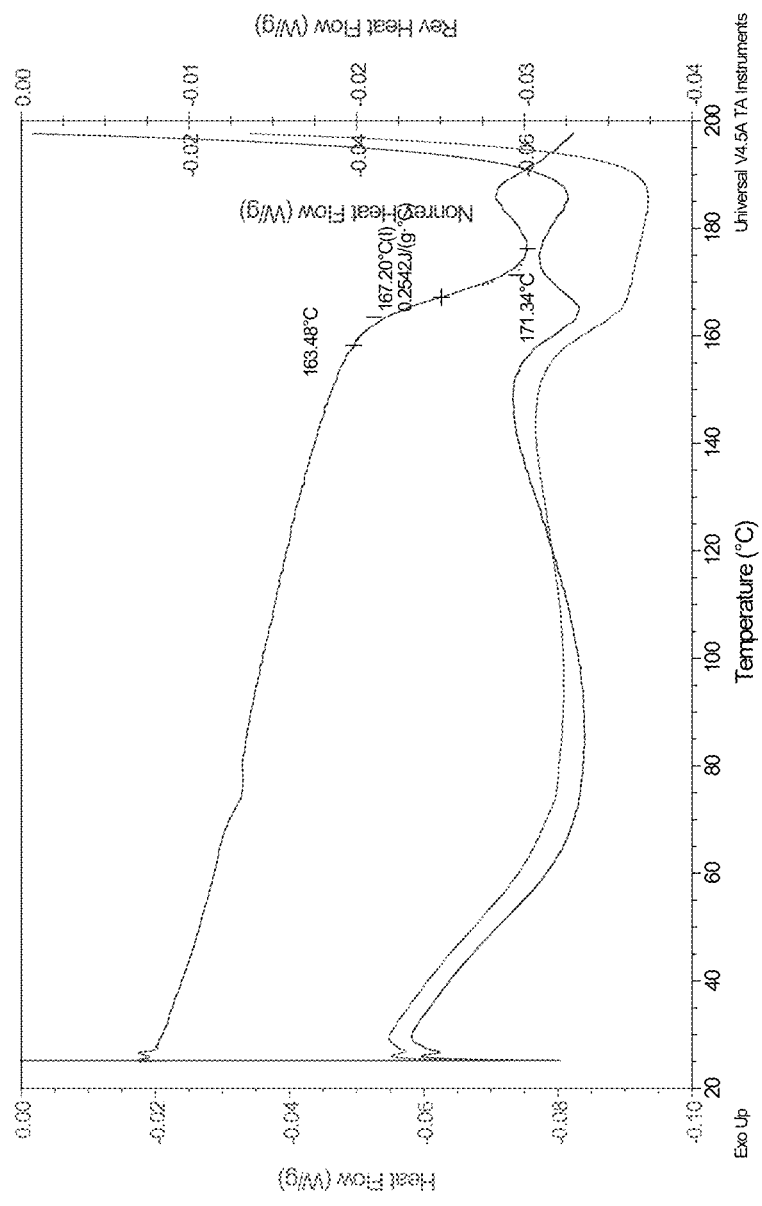
FIG. 34B shows a DSC thermogram of Compound 33 80% DL Amorphous Spray Dried Dispersion [THF/Water with HPMCAS-H].
Figure 34C:
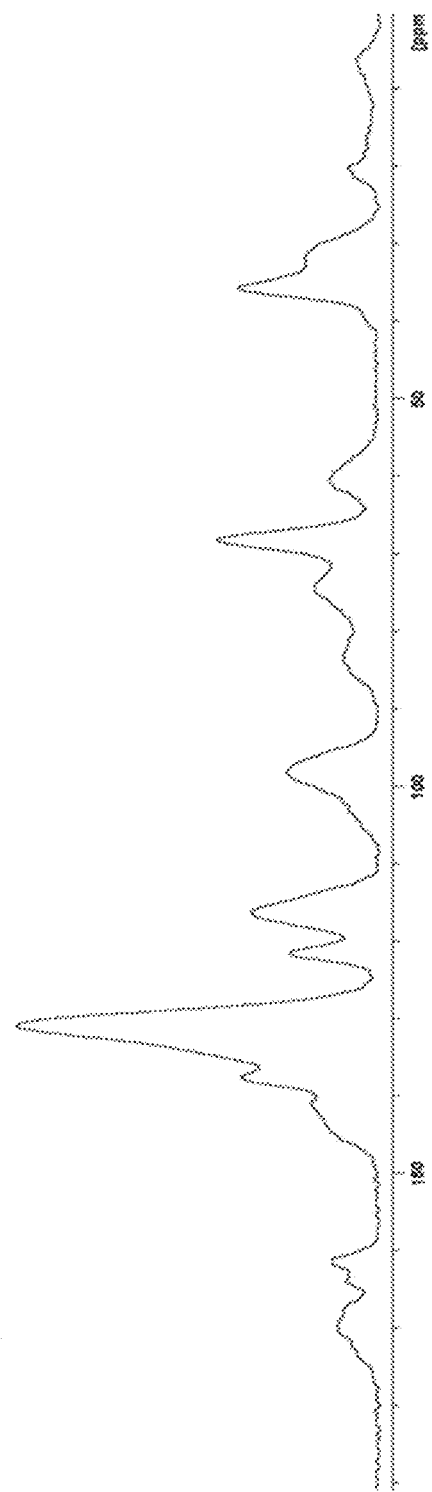
FIG. 34C shows a solid state $^{13}$C NMR spectrum of a spray dried dispersion of 80% Compound 33 with HPMCAS.

11. Compound 33 80% DL Amorphous Spray Dried Dispersion [THF/Water with HPMCAS-H]
A. Synthetic Procedure 200 g of Compound 33 was weighed into a bottle. 2875 g of 90/10 THF/Water was added. The bottle was capped and the contents were stirred for ~1 h at ambient temperature when a clear solution resulted. 50 g of HPMCAS-H was added. The bottle was capped and the contents were stirred for ~2 h at ambient temperature when a clear solution resulted. This solution was then spray dried to make amorphous Compound 33.
B. X-Ray Powder Diffraction X-ray powder diffraction (XRPD) spectra were recorded at room temperature in transmission mode using a PANalytical Empyrean system. The XRPD diffractogram is shown in FIG. 34A.
C. Differential Scanning Calorimetry Modulated Differential Scanning Calorimetry Analysis of Compound 33 amorphous form was carried out using the TA Instruments Discovery DSC. The thermogram as provided in FIG. 34B shows a glass transition at ~167° C.
D. Solid State NMR Analysis $^{13}$C ssNMR data for a spray dried dispersion of 80% Compound 33 with HPMCAS-from THF is provided in FIG. 34C and summarized in Table 80A below.

TABLE 80A 13C ssNMR for SDD of 80% Compound 33/HPCMAS

| Peak # | Chem Shift [ppm] | Intensity [rel] |
|---|---|---|
| 1 | 173.0 | 5.7 |
| 2 | 169.6 | 11.1 |
| 3 | 163.8 | 8.7 |
| 4 | 161.2 | 12.7 |
| 5 | 144.1 | 13.6 |
| 6 | 140.9 | 18.3 |
| 7 | 137.6 | 37.9 |
| 8 | 130.9 | 100.0 |
| 9 | 121.6 | 24.2 |
| 10 | 116.3 | 35.0 |
| 11 | 103.2 | 8.1 |
| 12 | 98.1 | 25.1 |
| 13 | 82.9 | 9.4 |
| 14 | 74.6 | 17.6 |
| 15 | 68.2 | 44.3 |
| 16 | 60.5 | 13.4 |
| 17 | 35.6 | 38.6 |
| 18 | 31.5 | 20.0 |
| 19 | 20.1 | 8.3 |

Figure 34D:
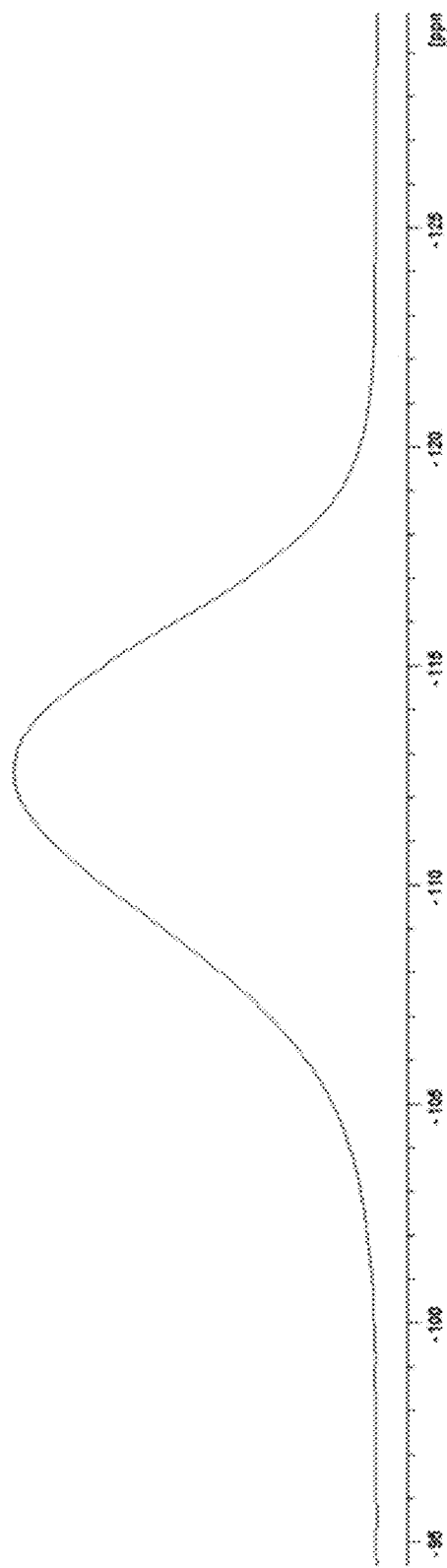
FIG. 34D shows a solid state $^{19}$F NMR spectrum of a spray dried dispersion of 80% Compound 33 with HPMCAS.

$^{19}$F ssNMR data for a spray dried dispersion of 80% DL Compound 33 with HPCMAS-from THF is provided in FIG. 34D and summarized in Table 80B.

TABLE 80B $^{19}$F ssNMR for SDD of 80% Compound 33/HPCMAS

| Peak # | Chem Shift [ppm] | Intensity [rel] |
|---|---|---|
| 1 | −112.6 | 12.5 |

12. Compound 33 80% DL Amorphous Spray Dried Dispersion [THF/Water with PVPVA]

A. Synthetic Procedure 1.6 g of Compound 33 was weighed into a bottle. 18 g of 90/10 THF/Water was added. The bottle was capped and the contents were stirred for ~1 h at ambient temperature when a clear solution resulted. 0.4 g of PVPVA was added. The bottle was capped and the contents were stirred for ~2 h at ambient temperature when a clear solution resulted. This solution was then spray dried to make amorphous Compound 33.

B. X-Ray Powder Diffraction

Figure 35A:
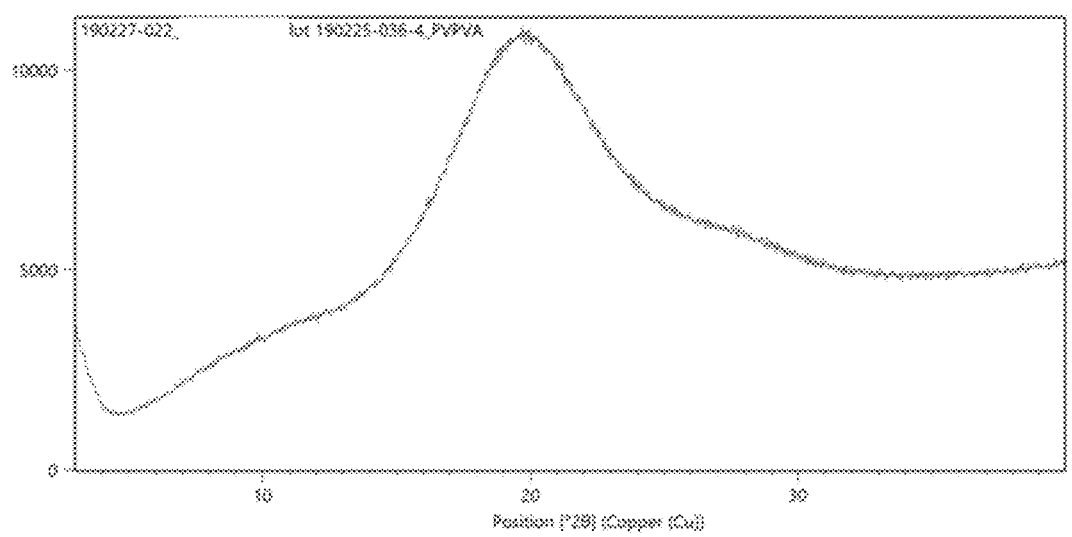
FIG. 35A shows an XRPD diffractogram of Compound 33 80% DL Amorphous Spray Dried Dispersion [THF/Water with PVPVA].

X-ray powder diffraction (XRPD) spectra were recorded at room temperature in transmission mode using a PANalytical Empyrean system. The XRPD diffractogram is shown in FIG. 35A.

C. Differential Scanning Calorimetry

Figure 35B:
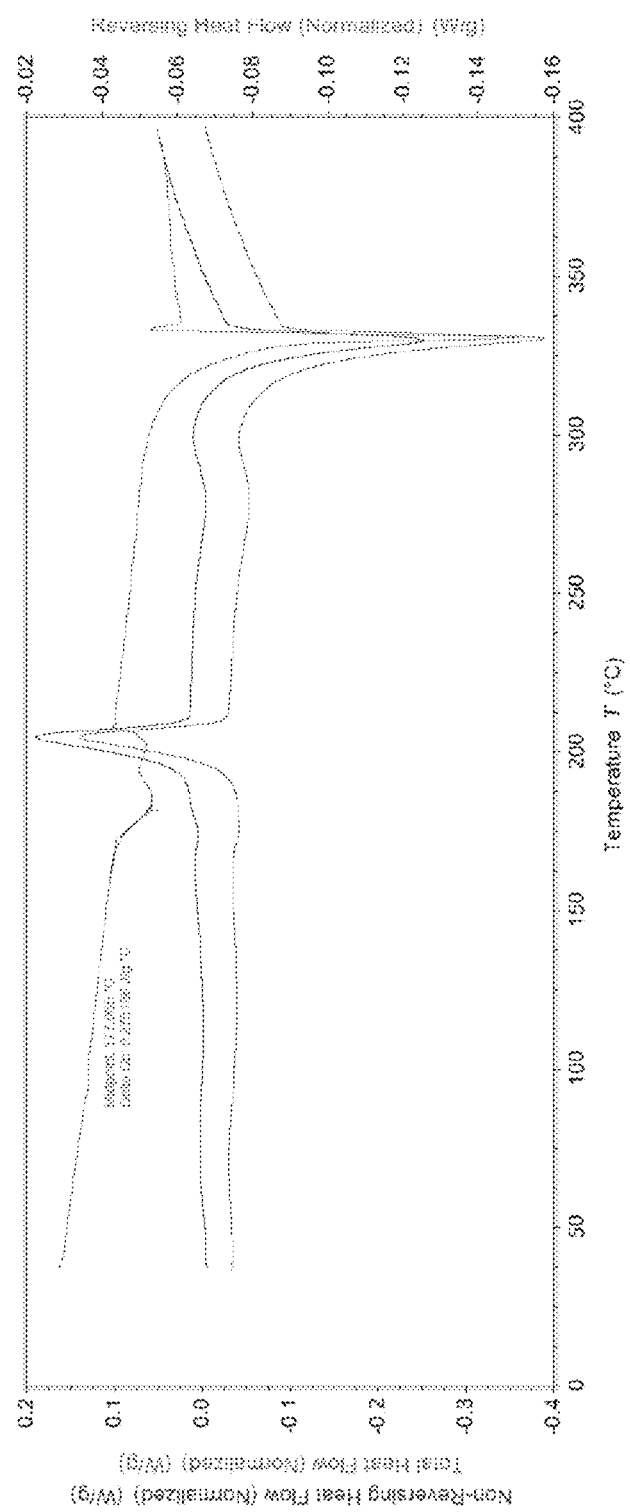
FIG. 35B shows a DSC thermogram of Compound 33 80% DL Amorphous Spray Dried Dispersion [THF/Water with PVPVA].

Modulated Differential Scanning Calorimetry Analysis of Compound 33 amorphous form was carried out using the TA Instruments Discovery DSC. The thermogram provided in FIG. 35B shows a glass transition at ~177° C., a recrystallization at ~205° C. and a melt endotherm at ~230° C.

13. Compound 33 80% DL Amorphous Spray Dried Dispersion [THF/Water with HPMC E15]

A. Synthetic Procedure 1.6 g of Compound 33 was weighed into a bottle. 18 g of 90/10 THF/Water was added. The bottle was capped and the contents were stirred for ~1 h at ambient temperature when a clear solution resulted. 0.4 g of HPMC E15 was added. The bottle was capped and the contents were stirred for ~2 h at ambient temperature when a clear solution resulted. This solution was then spray dried to make amorphous Compound 33.

B. X-Ray Powder Diffraction

Figure 36A:
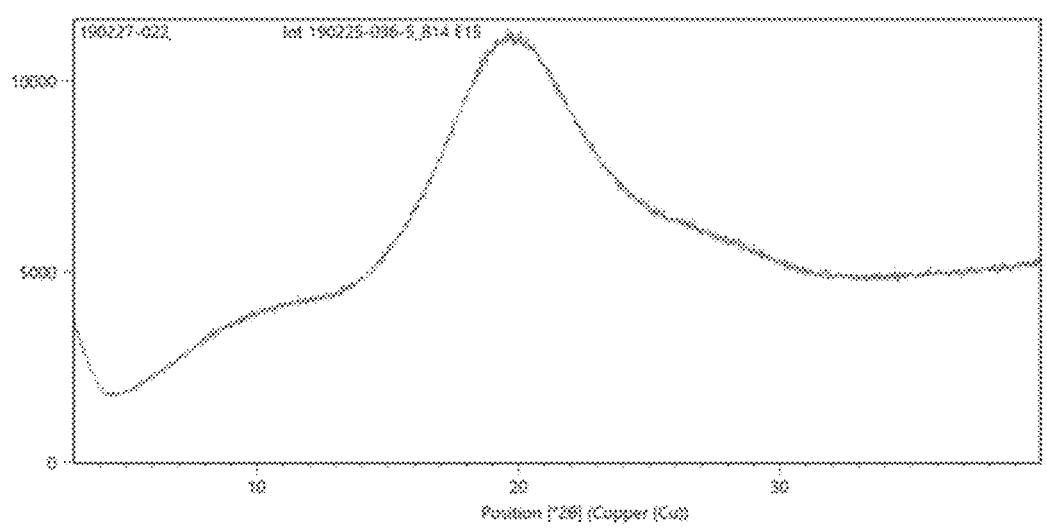
FIG. 36A shows an XRPD diffractogram of Compound 33 80% DL Amorphous Spray Dried Dispersion [THF/Water with HPMC E15].

X-ray powder diffraction (XRPD) spectra were recorded at room temperature in transmission mode using a PANalytical Empyrean system. The XRPD diffractogram is shown in FIG. 36A.

C. Differential Scanning Calorimetry

Figure 36B:
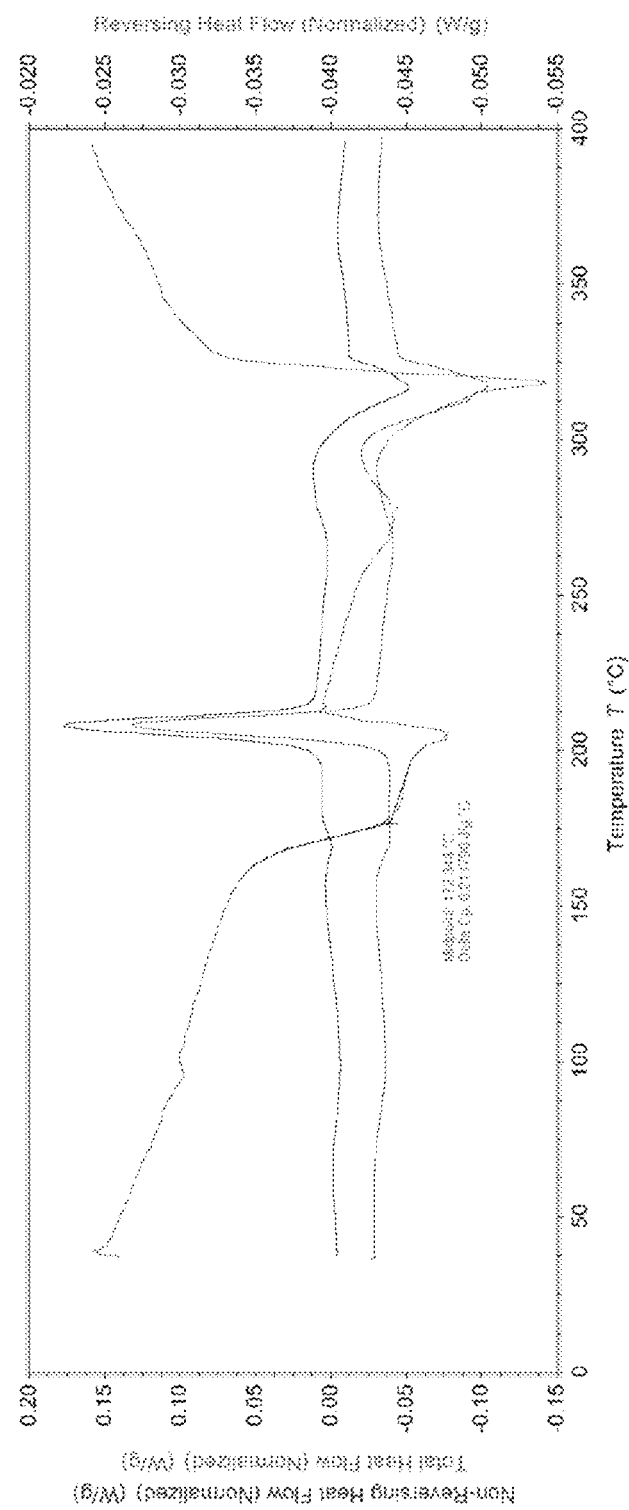
FIG. 36B shows a DSC thermogram of Compound 33 80% DL Amorphous Spray Dried Dispersion [THF/Water with HPMC E15].

Modulated Differential Scanning Calorimetry Analysis of Compound 33 amorphous form was carried out using the TA Instruments Discovery DSC. The thermogram as provided in FIG. 36B shows a glass transition at ~172° C., a recrystallization at ~210° C. and a melt endotherm at ~320° C.

14. Compound 33 80% DL Amorphous Spray Dried Dispersion [2-MeTHF/EtOH/Water with HPMCAS-H]

A. Synthetic Procedure 16 g of Compound 33 was weighed into a bottle. 180 g of 80/13/7 2-MeTHF/EtOH/Water was added. The bottle was capped and the contents were stirred for ~1 h at ambient temperature when a clear solution resulted. 4 g of HPMCAS-H was added. The bottle was capped and the contents were stirred for ~2 h at ambient temperature when a clear solution resulted. This solution was then spray dried to make amorphous Compound 33.

B. X-Ray Powder Diffraction

Figure 37A:
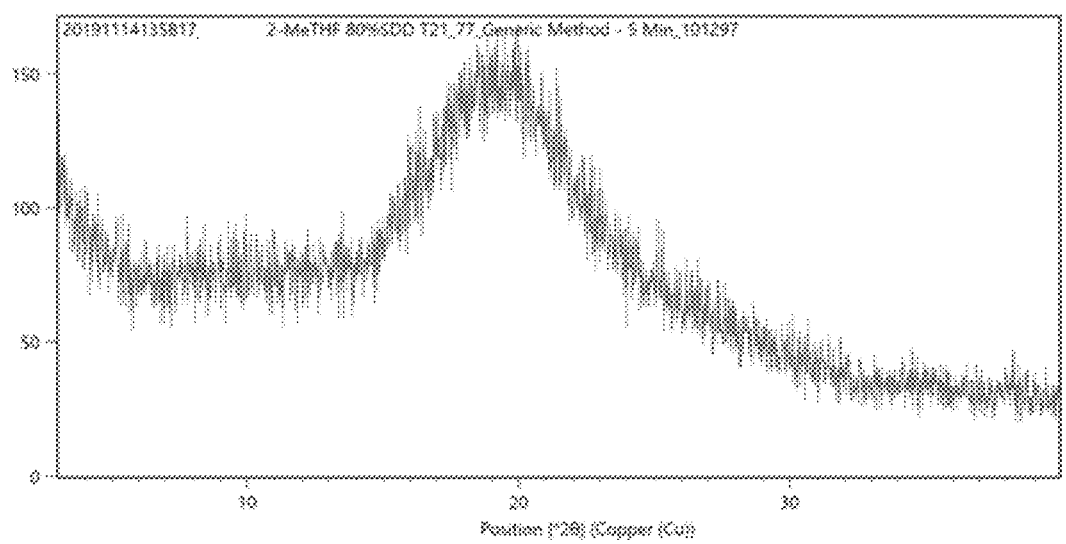
FIG. 37A shows an XRPD diffractogram of Compound 33 80% DL Amorphous Spray Dried Dispersion [2-MeTHF/EtOH/Water with HPMCAS-H].

X-ray powder diffraction (XRPD) spectra were recorded at room temperature in transmission mode using a PANalytical Empyrean system. The XRPD diffractogram is shown in FIG. 37A.

C. Differential Scanning Calorimetry

Figure 37B:
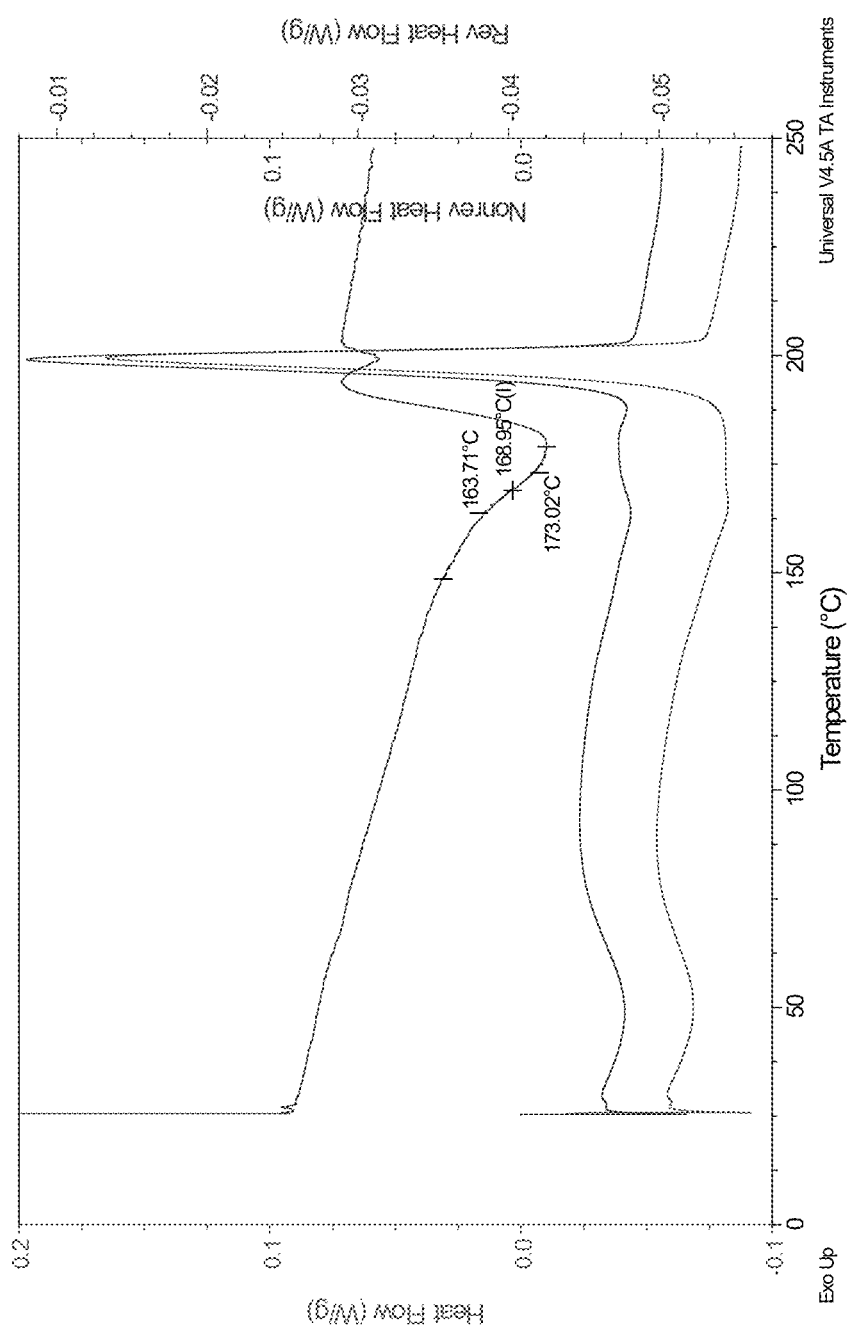
FIG. 37B shows a DSC thermogram of Compound 33 80% DL Amorphous Spray Dried Dispersion [2-MeTHF/EtOH/Water with HPMCAS-H].

Modulated Differential Scanning Calorimetry Analysis of Compound 33 amorphous form was carried out using the TA Instruments Discovery DSC. The thermogram in FIG. 37B shows a glass transition at ~169° C. and a recrystallization at ~200° C.

D. Thermal Gravimetric Analysis

Figure 37C:
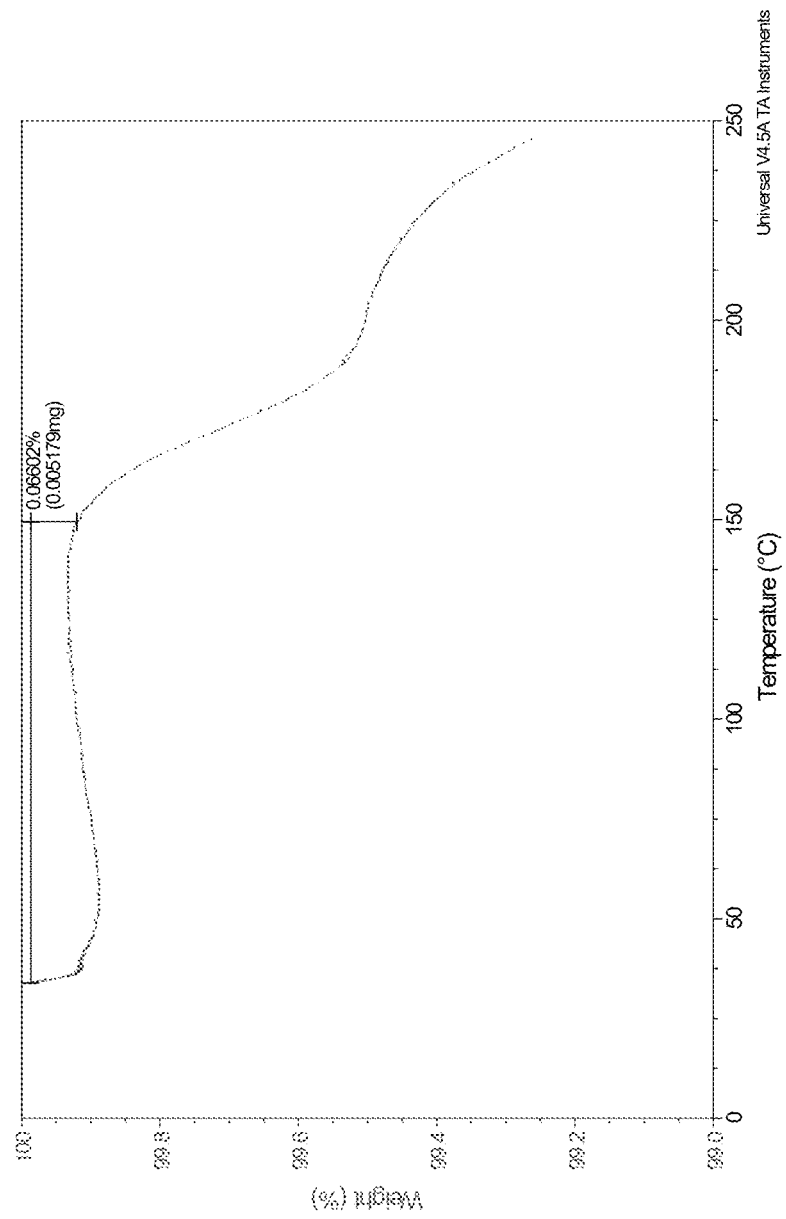
FIG. 37C shows a TGA thermogram of Compound 33 80% DL Amorphous Spray Dried Dispersion [2-MeTHF/EtOH/Water with HPMCAS-H].

Thermal Gravimetric Analysis of Compound 33 amorphous form was carried out using the TA Instruments Discovery TGA. The thermogram of FIG. 37C shows a weight loss of ~0.07.

15. Compound 33 Neat Amorphous Spray Dried Material [DCM/EtOH/Water without Polymer]

A. Synthetic Procedure 3.5 g of Compound 33 was weighed into a bottle. 100 mL of 60/39/1 DCM/EtOH/Water was added. The bottle was capped and the contents were stirred for approximately 1 hour at ambient temperature to provide a clear solution. This solution was then spray dried to make neat amorphous Compound 33.

Figure 38A:
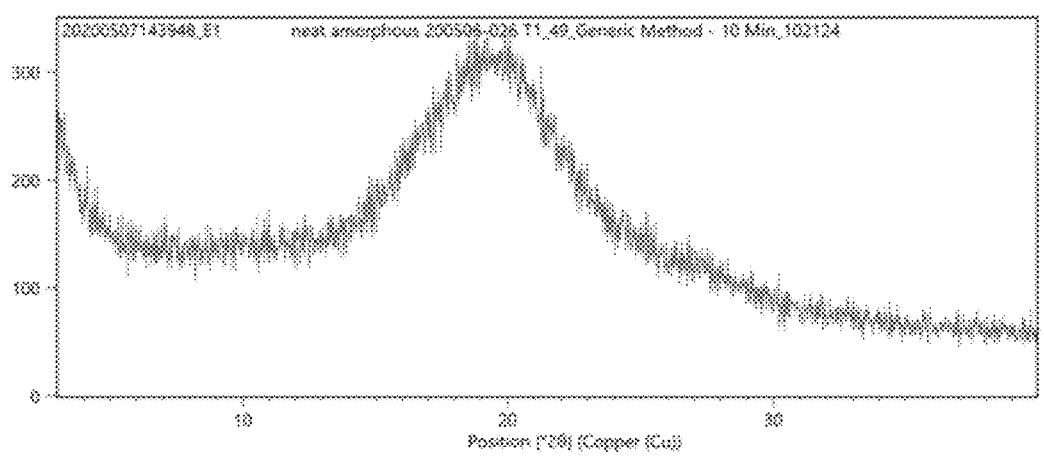
FIG. 38A shows an XRPD diffractogram of Spray-Dried Neat Amorphous Compound 33 [DCM/EtOH/Water without polymer].

B. X-Ray Powder Diffraction:

X-ray powder diffraction (XRPD) spectra were recorded at room temperature in transmission mode using a PANalytical Empyrean system. The XRPD diffractogram is shown in FIG. 38A.

C. Differential Scanning Calorimetry

Figure 38B:
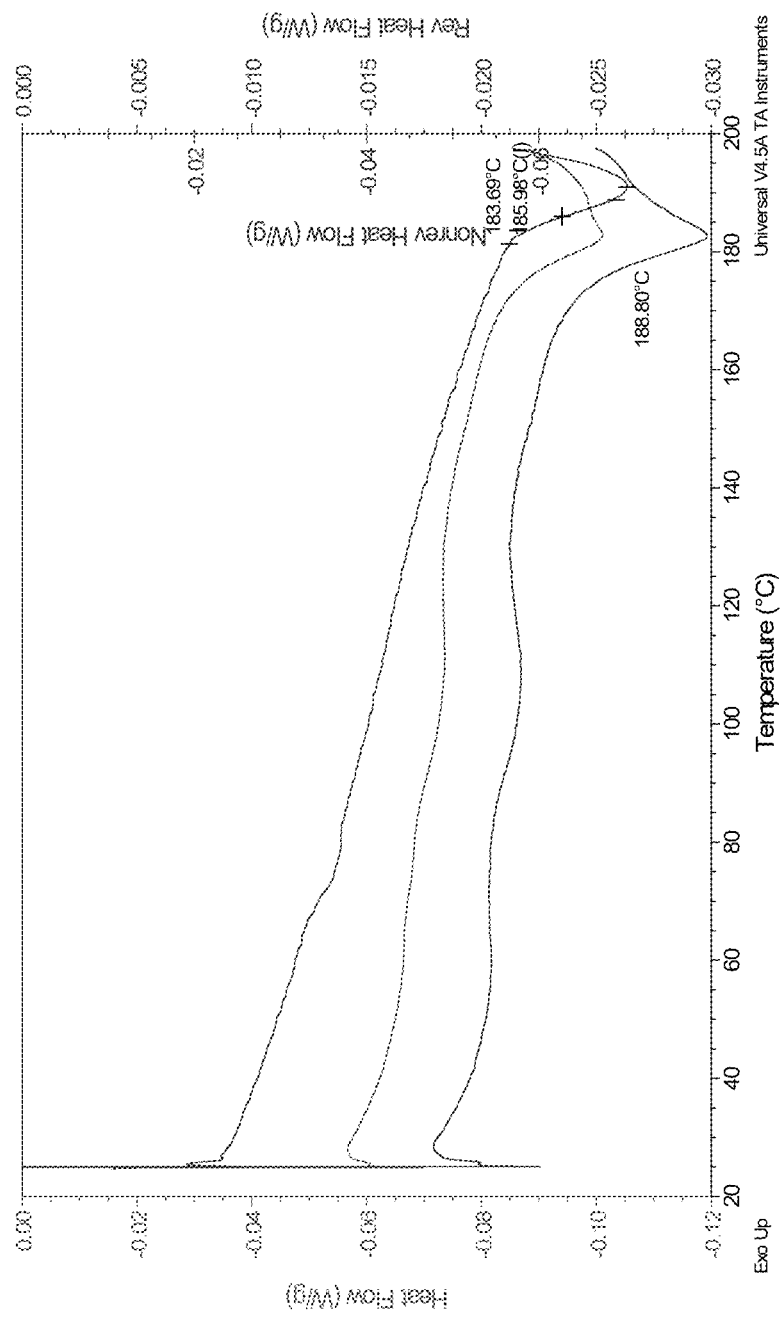
FIG. 38B shows a DSC thermogram of Spray-Dried Neat Amorphous Compound 33 [DCM/EtOH/Water without polymer].

Modulated Differential Scanning Calorimetry Analysis of Compound 33 neat amorphous form was carried out using the TA Instruments Discovery DSC. The thermogram in FIG. 38B shows a glass transition at ~186° C.

D. SSNMR on Neat Amorphous Compound 33

Figure 38C:
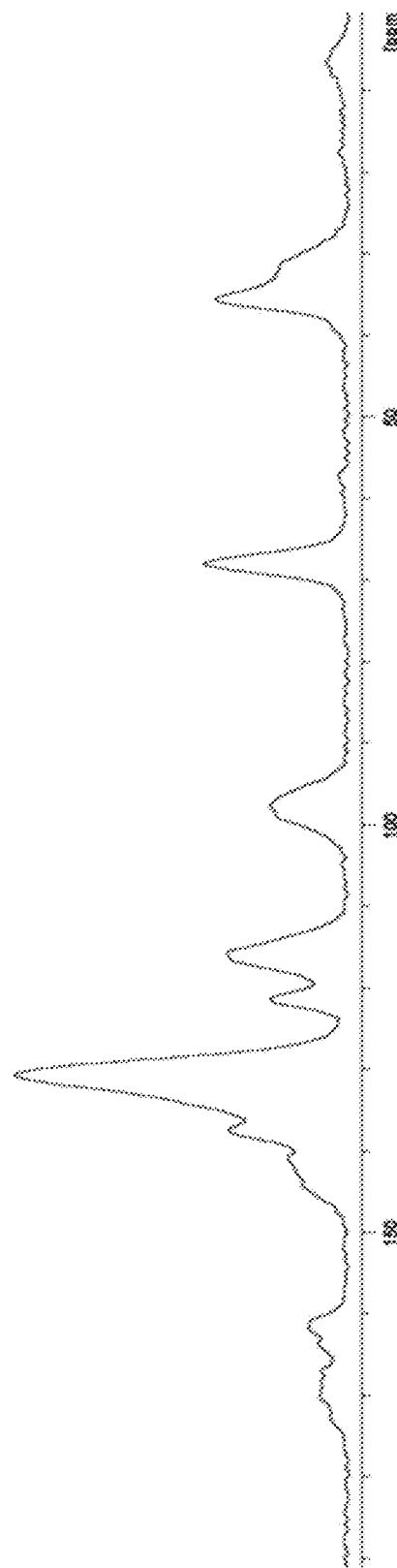
FIG. 38C shows a solid state $^{13}$C NMR spectrum of neat amorphous Compound 33.

Solid state $^{13}$C NMR data for neat amorphous Compound 33 is provided in FIG. 38C and summarized in Table 79 below.

TABLE 81A

| 13C ss NMR for Neat Amorphous Compound 33 | | |
|---|---|---|
| Peak # | Chem Shift [ppm] | Intensity [rel] |
| 1 | 172.5 | 4.9 |
| 2 | 170.1 | 8.2 |
| 3 | 167.0 | 7.6 |
| 4 | 163.7 | 8.4 |
| 5 | 161.6 | 11.3 |
| 6 | 144.5 | 12.4 |
| 7 | 140.8 | 17.7 |
| 8 | 137.4 | 35.3 |
| 9 | 130.7 | 100.0 |
| 10 | 121.4 | 22.8 |
| 11 | 115.7 | 35.8 |
| 12 | 97.6 | 23.0 |
| 13 | 67.9 | 42.9 |
| 14 | 35.5 | 39.3 |
| 15 | 31.5 | 20.0 |

Figure 38D:
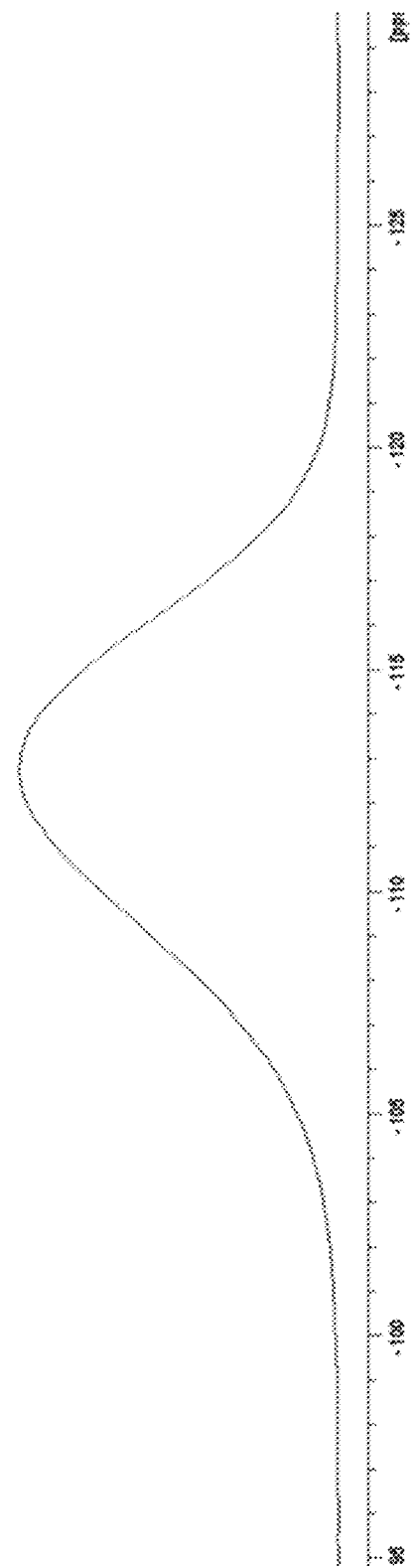
FIG. 38D shows a solid state $^{19}$F NMR spectrum of neat amorphous Compound.

Solid state $^{19}$F ssNMR data for neat amorphous Compound 33 is provided in FIG. 38D and summarized in Table 80.

TABLE 81B

| 19F ssNMR for Neat Amorphous Compound 33 | | |
|---|---|---|
| Peak # | Chem Shift [ppm] | Intensity [rel] |
| 1 | −112.8 | 12.5 |

Other Embodiments

This disclosure provides merely exemplary embodiments of the invention. One skilled in the art will readily recognize from the disclosure and accompanying figures and claims, that various changes, modifications and variations can be made therein without departing from the spirit and scope of the invention as defined in the following claims.

The invention claimed is:
1. A compound of formula (I):

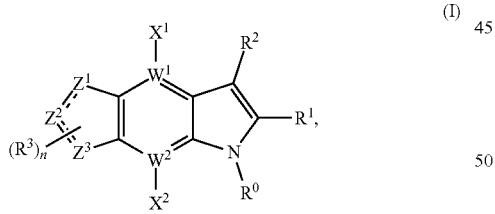

(I)

a tautomer, a pharmaceutically acceptable salt, or a deuterated derivative thereof;
wherein:
(i) $R^0$ is
(a) a $C_1$-$C_8$ linear, branched, or cyclic alkyl group, wherein the alkyl group is optionally substituted with 1-4 $R^A$; or
(b) a 5- to 14-membered aromatic ring optionally substituted with 1-4 $R^A$;
wherein each $R^A$ is independently a halogen, cyano, hydroxy, thiol, sulfonic acid, sulfonamide, sulfinamide, amino, amide, carboxylic acid, 5- to 10-membered aromatic ring, or a $C_1$-$C_6$ linear, branched, or cyclic group, wherein the amide nitrogen atom in the amide of $R^A$ is optionally substituted with a heterocyclyl group that is optionally further substituted with oxo,
wherein each $C_1$-$C_6$ linear, branched, or cyclic group is, independently, an alkyl, alkoxy, thioalkyl, alkylsulfoxide, alkylsulfonyl, alkylsulfonamide, alkylsulfinamide, aminoalkyl, or alkylamide,
wherein each 5- to 10-membered aromatic ring or $C_1$-$C_6$ linear, branched, or cyclic group, independently, is optionally substituted with 1-4 substituents, wherein each substituent, independently, is a halogen, a $C_1$-$C_6$ linear, branched, or cyclic group, or a methoxy, or
wherein an $R^A$ group is optionally linked to an $R^B$ group or to an $R^2$ group;
(ii) $R^1$ is
(a) a hydrogen,
(b) a $C_1$-$C_8$ linear, branched, or cyclic alkyl group, wherein the alkyl group is optionally substituted with 1-4 substituents, wherein each substituent, independently, is a
halogen,
cyano,
cyanoalkyl,
hydroxy,
alkylsulfonyl, or
$C_1$-$C_6$ linear, branched, or cyclic group, wherein the $C_1$-$C_6$ linear, branched, or cyclic group is an alkyl or alkoxy group, and wherein the $C_1$-$C_6$ linear, branched, or cyclic group is optionally substituted with 1-4 substituents, wherein each substituent, independently, is a
halogen,
hydroxy, or
$C_1$-$C_6$ linear, branched, or cyclic alkoxy group,
(c) a $C_1$-$C_8$ linear, branched, or cyclic alkoxy or cyclic thioalkyl group optionally substituted with 1-4 substituents, wherein each substituent, independently, is a
halogen,
cyano,
cyanoalkyl,
sulfone,
sulfonamide,
hydroxy, or
$C_1$-$C_6$ linear, branched, or cyclic alkyl group optionally substituted with 1-4 halogens or alkoxy groups;
(d) a $C_1$-$C_6$ linear, branched, or cyclic alkylsulfonyl group optionally substituted with a $C_1$-$C_6$ linear or branched alkyl group;
(e) an aminosulfonyl group, optionally substituted with 1 or 2 substituents, wherein each substituent, independently, is a
$C_1$-$C_6$ linear, branched, or cyclic alkyl group;
(f) a $C_1$-$C_6$ linear, branched, or cyclic alkylsulfonyl amino group;
(g) a phosphine oxide group, optionally substituted with 1 or 2 substituents, wherein each substituent, independently, is a
$C_1$-$C_6$ linear, branched, or cyclic alkyl group;
(h) a $C_1$-$C_6$ linear, branched, or cyclic trialkylsilyl group; or
(i) a $C_1$-$C_6$ alkylamide;

(iii) $R^2$ is a 5- to 6-membered aromatic ring comprising 0-4 heteroatoms, wherein each heteroatom, when present, independently, is an O, N, or S, wherein the 5-membered aromatic ring is optionally substituted with 1-4 $R^B$ groups and the 6-membered aromatic ring is optionally substituted with 1-5 $R^B$ groups, wherein each $R^B$ group, independently, is a(n)
(a) amide, optionally substituted with 1-3 groups, wherein each group, independently, is a $C_1$-$C_6$ linear, branched, or cyclic alkyl group (optionally substituted with a heteroaryl group), or 4- to 6-membered heterocyclyl (optionally substituted with oxo, $C_1$-$C_6$ linear, branched, or cyclic alkyl group, hydroxyalkyl, amide, alkylsulfonyl, or acetamide); or wherein the amide nitrogen atom forms part of a 3- to 8-membered heterocyclyl ring (optionally substituted with an alkylsulfonyl or $C_1$-$C_6$ linear, branched, or cyclic alkyl group),
(b) imidazolidine-2,4-dione,
(c) heterocyclyl, optionally substituted with one or more groups, wherein each group, independently, is an oxo, acyl, or $C_1$-$C_6$ linear, branched, or cyclic alkyl group (which is optionally further substituted with 1-3 groups, wherein each group, independently, is an oxo, hydroxy, or acyl),
(d) phosphorous acid optionally esterified with a $C_1$-$C_6$ linear, branched, or cyclic alkyl group,
(e) di($C_1$-$C_6$)alkylphosphine oxide,
(f) ($C_1$-$C_6$)alkylphosphinic acid optionally esterified with a $C_1$-$C_6$ linear, branched, or cyclic alkyl group,
(g) halogen,
(h) cyano,
(i) hydroxy,
(j) carboxylic acid optionally esterified with a uronic acid or a $C_1$-$C_6$ linear, branched, or cyclic alkyl group,
(k) oxo,
(l) dihydroxylboryl,
(m) 5- or 6-membered aromatic ring comprising 0-4 heteroatoms, wherein each heteroatom, when present, independently, is an O, N, or S, wherein the 5- or 6-membered aromatic ring is optionally substituted with 1 or 2 substituents, wherein each substituent, independently, is a $C_1$-$C_6$ linear, branched, or cyclic alkyl group that is optionally substituted with 1-4 substituents, wherein each substituent, independently, is a
hydroxy,
carboxylic acid,
pyrrolidin-2-one,
$C_1$-$C_6$ linear, branched, or cyclic alkyl group, or
$C_1$-$C_6$ linear, branched, or cyclic alkylsulfonyl group, or
(n) $C_1$-$C_6$ linear, branched, or cyclic alkoxy group,
(o) sulfonic acid,
(p) alkylsulfonamide,
(q) $C_1$-$C_6$ linear, branched, or cyclic alkylsulfonyl group, or
aminosulfonyl group, optionally substituted with 1 or 2 substituents, wherein each substituent, independently, is a
$C_1$-$C_6$ linear, branched, or cyclic alkyl group,
(r) $C_1$-$C_6$ linear, branched, or cyclic alkyl group that is optionally substituted with 1-4 substituents, wherein each substituent, independently, is a
halogen,
hydroxy,
carboxylic acid,
$C_1$-$C_6$ linear, branched, or cyclic alkoxy group,
heterocyclyl optionally substituted with oxo, or
amide,
(s) $C_1$-$C_6$ linear, branched, or cyclic alkoxy group that is optionally substituted with 1-4 substituents, wherein each substituent, independently, is a
halogen,
hydroxy,
carboxylic acid,
$C_1$-$C_6$ linear, branched, or cyclic alkyl group, or
$C_1$-$C_6$ linear, branched, or cyclic alkoxy group, or
(t) tetrazolyl group that is optionally substituted with a
halogen,
hydroxy,
carboxylic acid,
$C_1$-$C_6$ linear, branched, or cyclic alkyl group, or
$C_1$-$C_6$ linear, branched, or cyclic alkoxy group,
wherein 2 adjacent hydrogens on the 5- or 6-membered aromatic ring can be replaced by attachments to a second 5- or 6-membered aromatic ring comprising 0-4 heteroatoms, wherein each heteroatom, when present, independently, is an O, N, or S, to form a bicyclic $R^2$ group that is optionally substituted with 1-6 $R^B$ groups;
(iv) each of $X^1$ and $X^2$, independently, is a hydrogen, halogen, cyano, hydroxy, or $C_1$-$C_6$ linear, branched, or cyclic group, wherein each $C_1$-$C_6$ linear, branched, or cyclic group, independently, is an alkyl, alkoxy, thioalkyl, or aminoalkyl group, and wherein each $C_1$-$C_6$ linear, branched, or cyclic group is optionally substituted with 1-4 independently chosen halogens;
(v) each of $W^1$ and $W^2$, independently, is a C or N;
(vi) each ═══ is a single or double bond, provided that no more than one ═══ is a double bond;
(vii) each $R^3$, independently, is a hydrogen, halogen, cyano, $C_1$-$C_6$ linear, branched, or cyclic alkyl group, or $C_1$-$C_6$ linear, branched, or cyclic alkoxy group, wherein the $C_1$-$C_6$ linear, branched, or cyclic alkyl group and the $C_1$-$C_6$ linear, branched, or cyclic alkoxy group are each optionally substituted with 1-4 substituents, wherein each substituent, independently, is a halogen, hydroxy, or carboxylic acid;
(viii) n is 0, 1, 2, or 3; and
(ix) two of $Z^1$, $Z^2$, and $Z^3$ are nitrogen, and the third one is carbon or nitrogen, wherein the valences of carbon and nitrogen are completed with hydrogen, halogen, $C_1$-$C_6$ linear, branched, or cyclic alkyl group, or $C_1$-$C_6$ linear, branched, or cyclic alkoxy group, wherein the $C_1$-$C_6$ linear, branched, or cyclic alkyl group and the $C_1$-$C_6$ linear, branched, or cyclic alkoxy group are each optionally substituted with 1-4 substituents, wherein each substituent, independently, is a halogen, hydroxy, or carboxylic acid.

2. The compound, tautomer, salt, or deuterated derivative according to claim 1, wherein $R^0$ is:

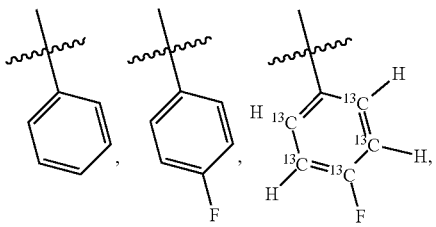

833
-continued
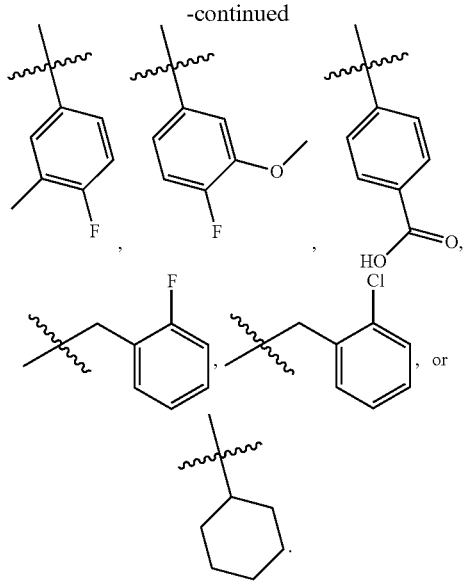
3. The compound, tautomer, salt, or deuterated derivative according to claim 1, wherein $R^1$ is:
hydrogen, methyl, trimethylsilyl, trifluoromethyl,
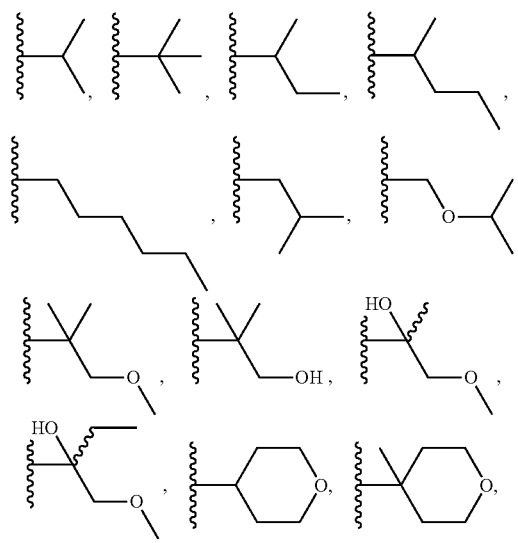
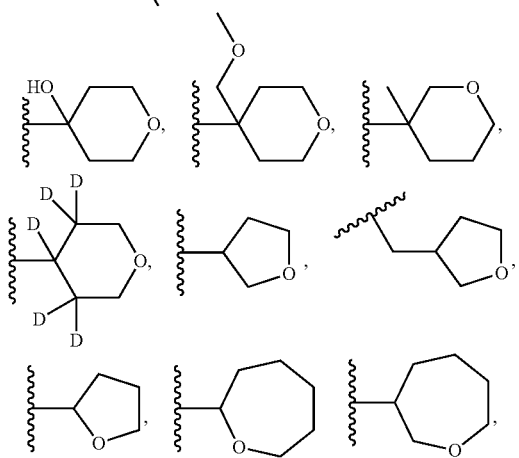
834
-continued
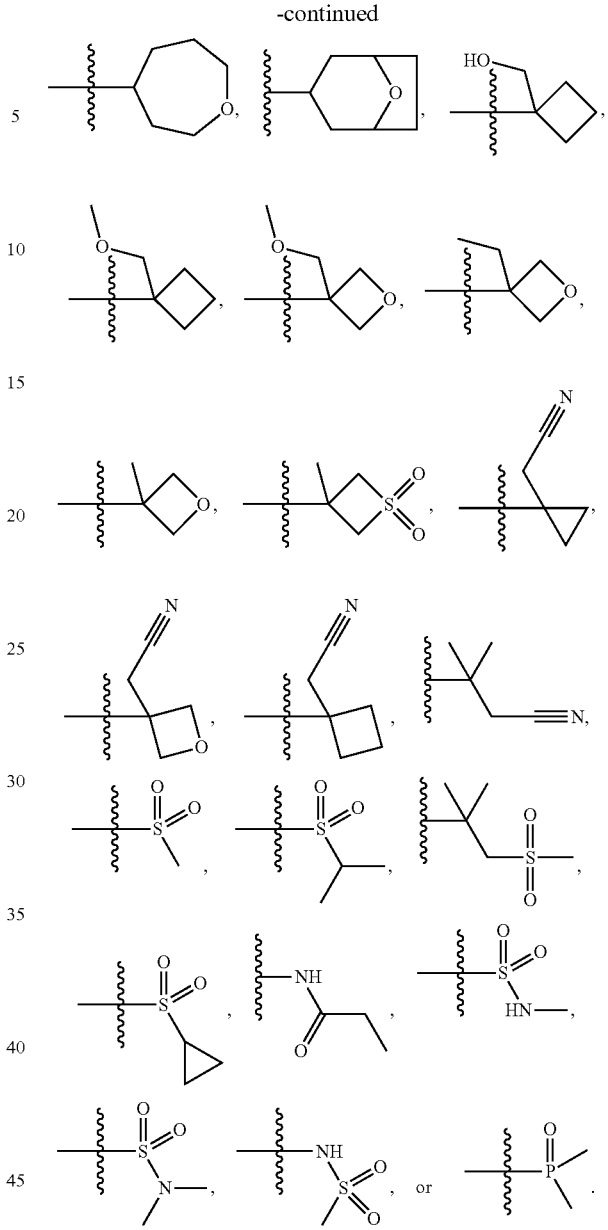
4. The compound, tautomer, salt, or deuterated derivative according to claim 1, wherein $R^2$ is:
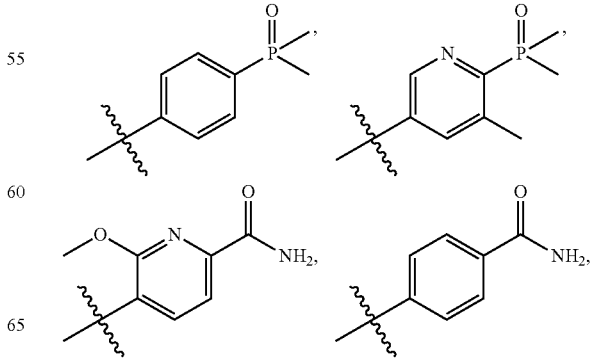

-continued
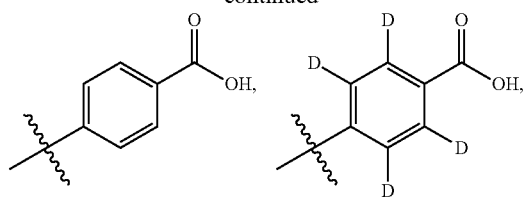
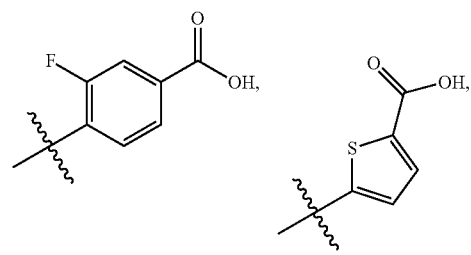
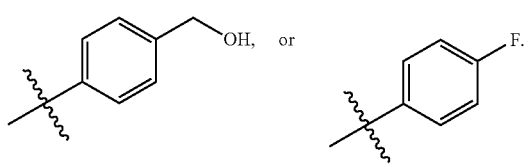
5. The compound, tautomer, salt, or deuterated derivative according to claim 1, wherein the Formula I is Formula (I-A), (I-B), (I-C), (I-D), (I-E), (I-F), (I-G), or (I-H):
(I-A)
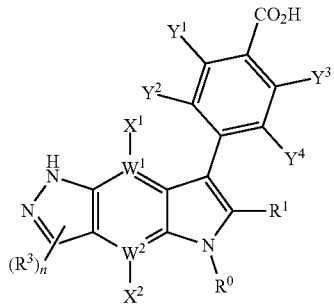
(I-B)
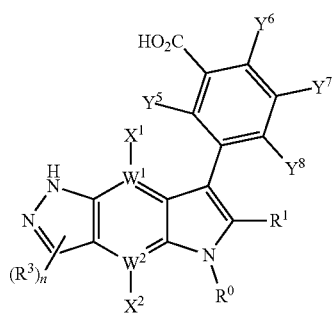
-continued
(I-C)
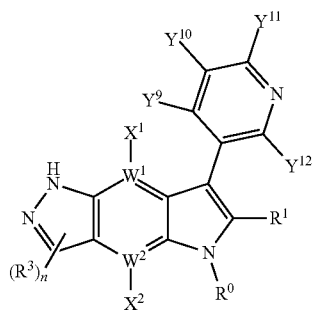
(I-D)
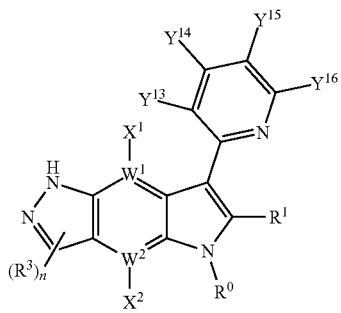
(I-E)
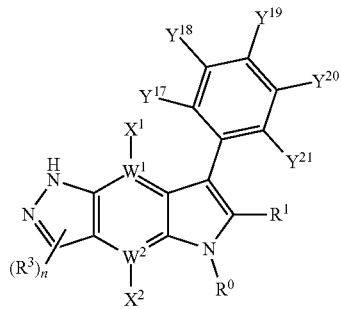
(I-F)
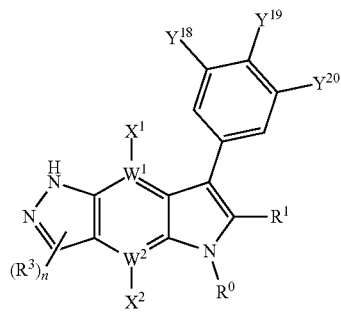
(I-G)
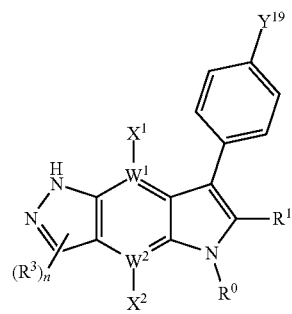

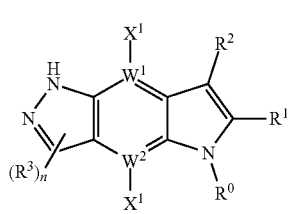

wherein:

$R^0$, $R^1$, $R^2$, $R^3$, and n are defined in claim 1, each of $X^1$ and $X^2$, independently, is hydrogen or fluorine, or $X^1$ is fluorine and $X^2$ is hydrogen, or $X^2$ is fluorine and $X^1$ is hydrogen, or $X^1$ and $X^2$ are each hydrogen, each of $W^1$ and $W^2$, independently, is C or N, each of $Y^1$, $Y^2$, $Y^3$, and $Y^4$, independently, is a
- hydrogen,
- cyano,
- halogen,
- $C_1$-$C_6$ linear, branched, or cyclic alkyl group, or
- $C_1$-$C_6$ linear, branched, or cyclic alkoxy group optionally substituted with 1-4 substituents, wherein each substituent, independently, is a hydroxy,
- $C_1$-$C_6$ linear, branched, or cyclic alkyl group, or
- $C_1$-$C_6$ linear, branched, or cyclic alkoxy group;

each of $Y^5$, $Y^6$, $Y^7$, and $Y^8$, independently, is a
- hydrogen,
- halogen,
- hydroxy,
- $C_1$-$C_6$ linear, branched, or cyclic alkyl group optionally substituted with 1-4 independently chosen halogens, or
- $C_1$-$C_6$ linear, branched, or cyclic alkoxy group, each of $Y^9$, $Y^{10}$, $Y^{11}$, $Y^{12}$, $Y^{13}$, $Y^{14}$, $Y^{15}$, and $Y^{16}$, independently, is a
- carboxylic acid,
- hydrogen,
- halogen,
- $C_1$-$C_6$ linear, branched, or cyclic alkylsulfonyl group,
- $C_1$-$C_6$ linear, branched, or cyclic alkyl group optionally substituted with 1-4 independently chosen halogens, or
- $C_1$-$C_6$ linear, branched, or cyclic alkoxy group, each of $Y^{17}$, $Y^{18}$, $Y^{19}$, $Y^{20}$, and $Y^{21}$, independently, is a
- hydrogen,
- carboxylic acid,
- halogen,
- cyano,
- hydroxy,
- $C_1$-$C_6$ linear, branched, or cyclic alkyl group optionally substituted with 1-4 substituents, wherein each substituent, independently, is a
  - halogen,
  - hydroxy, or
  - carboxylic acid,
- $C_1$-$C_6$ linear, branched, or cyclic alkoxy group optionally substituted with a carboxylic acid group,
- dihydroxyboryl,
- sulfonic acid,
- carboxylic acid optionally esterified with a uronic acid,
- tetrazolyl group,
- aminosulfonyl group, optionally substituted with 1 or 2 substituents, wherein each substituent, independently, is a
  - $C_1$-$C_6$ linear, branched, or cyclic alkyl group, or
  - $C_1$-$C_6$ linear, branched, or cyclic alkylsulfonyl group, with the proviso that, in Formula (I-E), at least one of $Y^{17}$, $Y^{18}$, $Y^{19}$, $Y^{20}$, and $Y^{21}$ is hydrogen.

6. The compound, tautomer, salt, or deuterated derivative according to claim 5, wherein one or more of $Y^{17}$, $Y^{18}$, $Y^{19}$, $Y^{20}$, and $Y^{21}$ is methyl, methoxy, cyano, fluorine, hydroxy, —$CF_3$, —$B(OH)_2$, —$SO_2NHMe$, —$SO_2Me$, —$SO_2H$, —$CH_2CO_2H$,

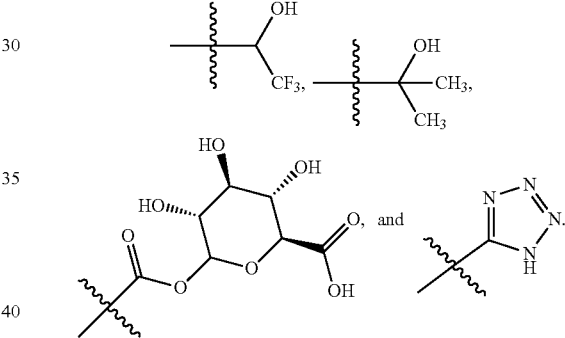

7. A pharmaceutical composition comprising the compound, tautomer, salt, or deuterated derivative according to claim 1 and at least one pharmaceutically acceptable carrier.

8. A method of treating alpha-1 antitrypsin deficiency comprising administering to a patient in need thereof at least one compound, tautomer, pharmaceutically acceptable salt, or deuterated derivative according to claim 1.

9. The method according to claim 8, wherein the patient has a Z mutation in alpha-1 antitrypsin.

10. The method according to claim 8, wherein the patient has an SZ mutation in alpha-1 antitrypsin.

11. The method according to claim 8, wherein the patient is homozygous for Z mutations in alpha-1 antitrypsin.

* * * * *